US011793843B2

(12) United States Patent
Bachman et al.

(10) Patent No.: US 11,793,843 B2
(45) Date of Patent: Oct. 24, 2023

(54) PROSTATE NEOANTIGENS AND THEIR USES

(71) Applicant: Janssen Biotech, Inc., Horsham, PA (US)

(72) Inventors: Kurtis E. Bachman, Chester Springs, PA (US); Vipul Bhargava, Springfield, PA (US); Darryl L. Davis, Collegeville, PA (US); Vinod Krishna, Philadelphia, PA (US); Guido Leoni, Rome (IT); David Pocalyko, Doylestown, PA (US); Pegah Safabakhsh, Philadelphia, PA (US); Manuel Sepulveda, West Windsor, NJ (US); Derick Siegel, Radnor, PA (US); Marco Gottardis, Princeton, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 595 days.

(21) Appl. No.: 16/737,950

(22) Filed: Jan. 9, 2020

(65) Prior Publication Data

US 2020/0222478 A1 Jul. 16, 2020

Related U.S. Application Data

(60) Provisional application No. 62/913,969, filed on Oct. 11, 2019, provisional application No. 62/883,786, filed on Aug. 7, 2019, provisional application No. 62/851,273, filed on May 22, 2019, provisional application No. 62/790,673, filed on Jan. 10, 2019.

(51) Int. Cl.

| | |
|---|---|
| ***C07K 16/30*** | (2006.01) |
| ***A61K 35/761*** | (2015.01) |
| ***A61K 39/00*** | (2006.01) |
| ***A61K 45/06*** | (2006.01) |

(52) U.S. Cl.

CPC .... *A61K 35/761* (2013.01); *A61K 39/001194* (2018.08); *A61K 39/001195* (2018.08); *C07K 16/3069* (2013.01); *A61K 45/06* (2013.01); *A61K 2039/51* (2013.01); *A61K 2039/545* (2013.01); *A61K 2039/572* (2013.01)

(58) Field of Classification Search

None

See application file for complete search history.

(56) References Cited

U.S. PATENT DOCUMENTS

| | | | |
|---|---|---|---|
| 914,623 | A | 3/1909 | Williams |
| 1,051,266 | A | 1/1913 | Rockwood |
| 4,235,871 | A | 11/1980 | Papahadjopoulos et al. |
| 4,501,728 | A | 2/1985 | Geho et al. |
| 4,603,112 | A | 7/1986 | Paoletti et al. |
| 4,769,330 | A | 9/1988 | Paoletti et al. |
| 4,772,848 | A | 9/1988 | Hummel |
| 4,837,028 | A | 6/1989 | Allen |
| 4,897,445 | A | 1/1990 | Coy et al. |
| 5,100,587 | A | 3/1992 | Clough et al. |
| 5,179,993 | A | 1/1993 | Bak et al. |
| 5,185,146 | A | 2/1993 | Altenburger |
| 5,223,409 | A | 6/1993 | Ladner et al. |
| 5,225,539 | A | 7/1993 | Winter |
| 5,403,484 | A | 4/1995 | Ladner et al. |
| 5,427,908 | A | 6/1995 | Dower et al. |
| 5,559,099 | A | 9/1996 | Wickham et al. |
| 5,571,698 | A | 11/1996 | Ladner et al. |
| 5,580,717 | A | 12/1996 | Dower et al. |
| 5,595,897 | A | 1/1997 | Midoux et al. |
| 5,635,363 | A | 6/1997 | Altman et al. |
| 5,635,483 | A | 6/1997 | Pettit et al. |
| 5,734,023 | A | 3/1998 | Nag et al. |
| 5,744,166 | A | 4/1998 | Ilium |
| 5,747,323 | A | 5/1998 | Darlix et al. |
| 5,780,588 | A | 7/1998 | Pettit et al. |
| 5,820,866 | A | 10/1998 | Kappler et al. |
| 5,837,511 | A | 11/1998 | Falck-Pedersen et al. |
| 5,846,782 | A | 12/1998 | Wickham et al. |
| 5,851,806 | A | 12/1998 | Kovesdi et al. |
| 5,885,793 | A | 3/1999 | Griffiths et al. |
| 5,891,690 | A | 4/1999 | Massie |
| 5,932,448 | A | 8/1999 | Tso et al. |
| 5,965,541 | A | 10/1999 | Wickham et al. |
| 5,969,108 | A | 10/1999 | McCafferty et al. |
| 5,972,707 | A | 10/1999 | Roy et al. |
| 5,976,551 | A | 11/1999 | Mottez et al. |
| 5,976,567 | A | 11/1999 | Wheeler et al. |

(Continued)

FOREIGN PATENT DOCUMENTS

| | | | |
|---|---|---|---|
| EP | 901463 | A1 | 3/1999 |
| EP | 0919627 | A2 | 6/1999 |

(Continued)

OTHER PUBLICATIONS

Harrop et al (2006) (Recombinant viral vectors: Cancer vaccines, Advanced Drug Delivery Reviews, vol. 58, 2006). (Year: 2006).*

Ahl et al., "Enhancement of the in vivo circulation lifetime of L-a-distearoylphosphatidylcholine liposomes: importance of liposomal aggregation versus complement opsonization", Biochim. Biophys. Acta, 1997,1329, 370-382.

Altschul et al., "BLAST—(see, for example), in Basic Local Alignment Search Tool", J. Mol. Biol., 1993, 215, 403-410.

Bruckdorfer. et al, "From Production of Peptides in Milligram Amounts for Research to Multi-Tons Quantities for Drugs of the Future," Current Pharmaceutical Biotechnology, vol. 5, Issue 1, 2004, pp. 29-43.

(Continued)

*Primary Examiner* — Misook Yu
*Assistant Examiner* — Sarah A Alsomairy
(74) *Attorney, Agent, or Firm* — BakerHostetler

(57) ABSTRACT

The disclosure relates to prostate neoantigens, polynucleotides encoding them, vectors, host cells, recombinant virus particles, vaccines comprising the neoantigens, proteinaceous molecules binding the prostate neoantigens, and methods of making and using them.

29 Claims, 12 Drawing Sheets

Specification includes a Sequence Listing.

(56) References Cited

U.S. PATENT DOCUMENTS 5,981,225 A 11/1999 Kochanek et al.
5,981,501 A 11/1999 Wheeler et al.
5,994,106 A 11/1999 Kovesdi et al.
5,994,128 A 11/1999 Fallaux et al.
6,013,240 A 1/2000 Behr et al.
6,020,191 A 2/2000 Scaria et al.
6,025,337 A 2/2000 Truong et al.
6,040,174 A 3/2000 Imler et al.
6,113,913 A 6/2000 Brough et al.
6,110,735 A 8/2000 Chartier et al.
6,150,584 A 11/2000 Kucherlapati et al.
6,172,197 B1 1/2001 McCafferty et al.
6,197,302 B1 3/2001 Hirsch et al.
6,204,060 B1 3/2001 Mehtali et al.
6,207,195 B1 3/2001 Walsh et al.
6,218,370 B1 4/2001 Bischoff et al.
6,268,411 B1 7/2001 Schneck et al.
6,270,772 B1 8/2001 Burrows et al.
6,312,948 B1 11/2001 Cohen-Haguenauer
6,335,199 B1 1/2002 Bischoff et al.
6,348,584 B1 2/2002 Hodgson et al.
6,440,442 B1 8/2002 Ehrhard et al.
6,521,404 B1 2/2003 Griffiths et al.
6,534,484 B1 3/2003 Wheeler et al.
6,544,731 B1 4/2003 Griffiths et al.
6,555,313 B1 4/2003 Griffiths et al.
6,582,915 B1 6/2003 Griffiths et al.
6,586,410 B1 7/2003 Wheeler et al.
6,593,081 B1 7/2003 Griffiths et al.
6,673,901 B2 1/2004 Koide
6,815,432 B2 11/2004 Wheeler et al.
6,818,749 B1 11/2004 Kashmiri et al.
6,833,441 B2 12/2004 Wang et al.
7,074,904 B2 7/2006 Wong et al.
7,074,905 B2 7/2006 Rhode et al.
7,141,656 B2 11/2006 Rhode et al.
7,264,958 B1 9/2007 Koehl et al.
7,270,811 B2 9/2007 Bout et al.
7,329,731 B2 2/2008 Jakobsen et al.
7,569,664 B2 8/2009 Jakobsen et al.
7,709,226 B2 5/2010 Foote
7,718,369 B2 5/2010 Tomlins et al.
7,871,817 B2 1/2011 Voss et al.
8,133,724 B2 3/2012 Qiu et al.
8,163,293 B2 4/2012 Chaplin
8,211,645 B2 7/2012 Tomlins et al.
8,268,329 B2 9/2012 Chaplin et al.
8,313,740 B2 11/2012 Delcayre et al.
8,377,447 B2 2/2013 Burrows et al.
8,377,688 B2 2/2013 Delcayre et al.
8,394,385 B2 3/2013 Hausmann et al.
8,580,509 B2 11/2013 Tomlins et al.
8,685,660 B2 4/2014 Vogelstein et al.
8,748,356 B2 6/2014 Raghunathan
8,828,379 B2 9/2014 Loset et al.
8,940,290 B2 1/2015 Roy et al.
9,061,059 B2 * 6/2015 Chakraborty ........... A61P 37/08
9,079,941 B2 7/2015 Ovaa et al.
9,133,264 B2 9/2015 Blankenstein et al.
9,146,238 B2 9/2015 Luo et al.
9,284,609 B2 3/2016 Tomlins et al.
9,593,077 B2 3/2017 Payne et al.
9,617,560 B2 4/2017 Brough et al.
9,624,292 B2 4/2017 Voss et al.
9,745,635 B2 8/2017 Tomlins et al.
9,750,801 B2 9/2017 Barouch et al.
9,790,256 B2 10/2017 Bunnik et al.
9,884,075 B2 2/2018 Bethune et al.
10,035,832 B2 7/2018 Schlom et al.
10,111,940 B2 10/2018 Mcneel et al.
10,155,031 B2 12/2018 Sahin et al.
10,190,173 B2 1/2019 Tomlins et al.
10,350,275 B2 7/2019 Aguilar-Cordova
10,441,643 B2 10/2019 Pulido et al.
10,512,662 B2 12/2019 Deng et al.
10,532,067 B2 1/2020 Geall et al.
10,548,930 B2 2/2020 Deng et al.
10,640,786 B2 5/2020 Barry et al.
10,736,962 B2 8/2020 Deng et al.
10,781,169 B2 9/2020 Payne et al.
10,973,892 B2 4/2021 Lauterbach et al.
11,110,159 B2 * 9/2021 Demoitie ................. C12N 7/00
11,179,456 B2 * 11/2021 Dorrell .................. A61K 39/39
2001/0036927 A1 11/2001 Bischoff et al.
2001/0049136 A1 12/2001 Imler et al.
2002/0028497 A1 3/2002 Blanche et al.
2002/0192763 A1 12/2002 Xu et al.
2003/0198953 A1 10/2003 Spytek et al.
2005/0244851 A1 11/2005 Blume et al.
2006/0115821 A1 6/2006 Einstein et al.
2007/0148774 A1 6/2007 McCafferty et al.
2007/0287170 A1 12/2007 Davis et al.
2008/0208783 A1 8/2008 Jaros et al.
2009/0182127 A1 7/2009 Kjaergaard et al.
2010/0015133 A1 1/2010 Igawa et al.
2010/0143247 A1 6/2010 Fenske et al.
2010/0143302 A1 6/2010 Havenga et al.
2010/0216708 A1 8/2010 Jacobs et al.
2010/0255056 A1 10/2010 Jacobs et al.
2010/0261620 A1 10/2010 Almagro et al.
2010/0286374 A1 11/2010 Kannan et al.
2011/0123532 A1 5/2011 Gurney et al.
2011/0300205 A1 12/2011 Geall et al.
2012/0015839 A1 1/2012 Chinnaiyan
2012/0093934 A1 4/2012 Santamaria
2012/0252742 A1 10/2012 Kranz et al.
2012/0296070 A1 11/2012 Tomlins et al.
2013/0289253 A1 10/2013 Luescher et al.
2013/0330335 A1 12/2013 Bremel et al.
2014/0271829 A1 9/2014 Lilja et al.
2015/0329617 A1 11/2015 Winther et al.
2015/0344965 A1 12/2015 Luo et al.
2016/0078168 A1 3/2016 Zhuo et al.
2016/0130319 A1 5/2016 Li
2016/0271239 A1 9/2016 Foy et al.
2017/0003288 A1 1/2017 Heath et al.
2017/0039314 A1 2/2017 Bremel et al.
2017/0095544 A1 4/2017 Santamaria
2017/0106065 A1 4/2017 Foy et al.
2017/0121409 A1 5/2017 Verona et al.
2017/0266270 A1 9/2017 Foy et al.
2017/0334963 A1 11/2017 Johnston
2018/0000912 A1 1/2018 Meruelo et al.
2018/0002393 A1 1/2018 Bangel et al.
2018/0028626 A1 2/2018 Slos et al.
2018/0064803 A1 3/2018 Tomaka et al.
2018/0104359 A1 4/2018 Kamrud
2018/0118849 A1 5/2018 Klein et al.
2018/0126003 A1 5/2018 Hoerr
2018/0141998 A1 5/2018 Nguyen et al.
2018/0153975 A1 6/2018 Fritsch et al.
2018/0171340 A1 6/2018 Kamrud et al.
2018/0311269 A1 11/2018 Lobb et al.
2019/0030147 A1 1/2019 Artomov et al.
2019/0038732 A1 2/2019 Mcneel et al.
2019/0041771 A1 2/2019 Chang
2019/0093085 A1 3/2019 Tufaro et al.
2019/0192691 A1 6/2019 Gladstone et al.
2019/0350993 A1 11/2019 Cai
2019/0351040 A1 11/2019 Valiante et al.
2020/0054728 A1 2/2020 Artomov et al.
2020/0061174 A1 2/2020 Kalla et al.
2020/0121774 A1 4/2020 Lubaroff et al.
2020/0138923 A1 5/2020 Bendjama et al.
2020/0148742 A1 5/2020 Grandi et al.
2020/0171151 A1 6/2020 Yeung
2020/0197500 A1 6/2020 Blair et al.
2020/0222519 A1 * 7/2020 Nicosia .................. C12N 15/00
2020/0239906 A1 7/2020 Roeth et al.
2020/0283497 A1 9/2020 Oehm et al.
2020/0299725 A1 9/2020 Beissert et al.
2020/0306352 A1 10/2020 Hochrein et al.
2020/0330534 A1 10/2020 Delgoffe et al.
2020/0339959 A1 10/2020 Deng et al.

(56) References Cited

U.S. PATENT DOCUMENTS

| | | | |
|---|---|---|---|
| 2021/0015878 | A1 | 1/2021 | Larson et al. |
| 2021/0023100 | A1 | 1/2021 | Sahin et al. |
| 2021/0046130 | A1 | 2/2021 | Jia et al. |
| 2021/0069322 | A1 | 3/2021 | Ammendola et al. |
| 2021/0130848 | A1 | 5/2021 | Nicosia et al. |
| 2021/0238244 | A1 | 8/2021 | Plasterk |
| 2021/0361760 | A1 | 11/2021 | Philip |

FOREIGN PATENT DOCUMENTS

| | | | | |
|---|---|---|---|---|
| EP | 1230354 | A2 | 8/2002 | |
| EP | 1670823 | A1 | 6/2006 | |
| EP | 1882700 | A1 | 1/2008 | |
| EP | 2061807 | A2 | 5/2009 | |
| EP | 1934363 | B1 | 3/2013 | |
| EP | 3215164 | A1 | 9/2017 | |
| EP | 3286210 | A1 | 2/2018 | |
| EP | 3721899 | A1 | 10/2020 | |
| WO | WO 1988/01649 | A1 | 3/1988 | |
| WO | WO 1990/04036 | A1 | 4/1990 | |
| WO | WO 1990/007861 | A1 | 7/1990 | |
| WO | 92/01047 | A1 | 1/1992 | |
| WO | WO 1992/22653 | A1 | 12/1992 | |
| WO | WO 1994/13804 | A1 | 6/1994 | |
| WO | WO 1995/01447 | A1 | 1/1995 | |
| WO | WO 1995/24221 | A1 | 9/1995 | |
| WO | WO 1996/02655 | A1 | 2/1996 | |
| WO | 96/19240 | A1 | 6/1996 | |
| WO | WO 1996/17070 | A1 | 6/1996 | |
| WO | WO 1996/27677 | A1 | 9/1996 | |
| WO | WO 1996/40964 | A2 | 12/1996 | |
| WO | WO 1997/04119 | A1 | 2/1997 | |
| WO | WO 1997/35996 | A1 | 10/1997 | |
| WO | WO 1998/00524 | A1 | 1/1998 | |
| WO | WO 1998/26048 | A1 | 6/1998 | |
| WO | 98/34910 | A1 | 8/1998 | |
| WO | WO 1998/37916 | A1 | 9/1998 | |
| WO | WO 1998/39411 | A1 | 9/1998 | |
| WO | WO 1998/44001 | A1 | 10/1998 | |
| WO | WO 1999/45962 | A1 | 9/1999 | |
| WO | WO 2000/50573 | A1 | 8/2000 | |
| WO | WO 2000/70071 | A1 | 11/2000 | |
| WO | 01/30382 | A1 | 5/2001 | |
| WO | 01/30847 | A1 | 5/2001 | |
| WO | WO 2002/043478 | A2 | 6/2002 | |
| WO | WO 2002/066630 | A1 | 8/2002 | |
| WO | 02/88172 | A2 | 11/2002 | |
| WO | 2003/076610 | A2 | 9/2003 | |
| WO | 2004/044176 | A2 | 5/2004 | |
| WO | 2004/113571 | A2 | 12/2004 | |
| WO | 2005/046621 | A2 | 5/2005 | |
| WO | 2005/051991 | A2 | 6/2005 | |
| WO | WO 2005/048957 | A2 | 6/2005 | |
| WO | WO 2005/071093 | A2 | 8/2005 | |
| WO | 2006/056766 | A2 | 6/2006 | |
| WO | WO 2007/104792 | A2 | 9/2007 | |
| WO | 2007/147901 | A1 | 12/2007 | |
| WO | 2008/106615 | A1 | 9/2008 | |
| WO | 2009/006479 | A2 | 1/2009 | |
| WO | 2009/065546 | A1 | 5/2009 | |
| WO | WO 2009/085462 | A1 | 7/2009 | |
| WO | 2009/127060 | A1 | 10/2009 | |
| WO | 2009/134776 | A2 | 11/2009 | |
| WO | 2010/081001 | A2 | 7/2010 | |
| WO | WO 2010/086189 | A2 | 8/2010 | |
| WO | 2010/132867 | A1 | 11/2010 | |
| WO | 2011/005799 | A2 | 1/2011 | |
| WO | 2011/068810 | A1 | 6/2011 | |
| WO | 2011143545 | A1 | 11/2011 | |
| WO | 2012/006369 | A2 | 1/2012 | |
| WO | 2012/006372 | A1 | 1/2012 | |
| WO | 2012/006376 | A2 | 1/2012 | |
| WO | 2012/006378 | A1 | 1/2012 | |
| WO | 2012/022811 | A1 | 2/2012 | |
| WO | 2012/030901 | A1 | 3/2012 | |
| WO | 2012/031043 | A1 | 3/2012 | |
| WO | 2012/089225 | A1 | 7/2012 | |
| WO | 2012/089338 | A1 | 7/2012 | |
| WO | 2012/149522 | A1 | 11/2012 | |
| WO | 2012/172277 | A1 | 12/2012 | |
| WO | WO 2012/177624 | A2 | 12/2012 | |
| WO | 2013/006825 | A1 | 1/2013 | |
| WO | 2013/006838 | A1 | 1/2013 | |
| WO | 2013/006842 | A2 | 1/2013 | |
| WO | 2013/033563 | A1 | 3/2013 | |
| WO | 2013/096291 | A2 | 6/2013 | |
| WO | 2013/116778 | A2 | 8/2013 | |
| WO | 2013/151672 | A2 | 10/2013 | |
| WO | 2013/157954 | A1 | 10/2013 | |
| WO | WO-2013176772 | A1 * | 11/2013 | ........... A01H 6/4684 |
| WO | 2014/127917 | A1 | 8/2014 | |
| WO | 2015/069571 | A1 | 5/2015 | |
| WO | 2015/069770 | A1 | 5/2015 | |
| WO | 2015/077624 | A1 | 5/2015 | |
| WO | 2015/078856 | A1 | 6/2015 | |
| WO | 2015/123496 | A1 | 8/2015 | |
| WO | 2015/164674 | A1 | 10/2015 | |
| WO | 2015/175334 | A2 | 11/2015 | |
| WO | 2015/175340 | A1 | 11/2015 | |
| WO | 2015/176033 | A1 | 11/2015 | |
| WO | 2015/192068 | A1 | 12/2015 | |
| WO | 2016/046357 | A1 | 3/2016 | |
| WO | 2016/128542 | A1 | 8/2016 | |
| WO | 2016/170176 | A1 | 10/2016 | |
| WO | 2016/184822 | A1 | 11/2016 | |
| WO | 2016/187508 | A2 | 11/2016 | |
| WO | 2016/197067 | A1 | 12/2016 | |
| WO | 2016/203025 | A1 | 12/2016 | |
| WO | 2017/015064 | A1 | 1/2017 | |
| WO | 2017/020026 | A1 | 2/2017 | |
| WO | 2017/070110 | A1 | 4/2017 | |
| WO | 2017/070618 | A1 | 4/2017 | |
| WO | 2017/091905 | A1 | 6/2017 | |
| WO | 2017/147554 | A2 | 8/2017 | |
| WO | 2017/173321 | A1 | 10/2017 | |
| WO | 2017/177207 | A1 | 10/2017 | |
| WO | 2017/180587 | A2 | 10/2017 | |
| WO | WO 2017/180770 | A1 | 10/2017 | |
| WO | 2017/201325 | A1 | 11/2017 | |
| WO | 2017/201350 | A1 | 11/2017 | |
| WO | 2017/201352 | A1 | 11/2017 | |
| WO | 2017/205810 | A1 | 11/2017 | |
| WO | WO 2017/220499 | A1 | 12/2017 | |
| WO | 2018/033254 | A2 | 2/2018 | |
| WO | 2018/037085 | A1 | 3/2018 | |
| WO | 2018/046803 | A1 | 3/2018 | |
| WO | WO 2018/075235 | A1 | 4/2018 | |
| WO | 2018/081480 | A1 | 5/2018 | |
| WO | 2018/093907 | A1 | 5/2018 | |
| WO | 2018/098362 | A1 | 5/2018 | |
| WO | 2018/102584 | A1 | 6/2018 | |
| WO | 2018/102585 | A1 | 6/2018 | |
| WO | 2018/107011 | A1 | 6/2018 | |
| WO | WO-2018102585 | A1 * | 6/2018 | |
| WO | 2018/143949 | A1 | 8/2018 | |
| WO | 2018/144082 | A1 | 8/2018 | |
| WO | 2018/146205 | A1 | 8/2018 | |
| WO | 2018/148381 | A1 | 8/2018 | |
| WO | 2018/148501 | A1 | 8/2018 | |
| WO | 2018/161092 | A1 | 9/2018 | |
| WO | 2018/167320 | A1 | 9/2018 | |
| WO | 2018/187356 | A2 | 10/2018 | |
| WO | 2018/223093 | A1 | 12/2018 | |
| WO | 2019/008111 | A1 | 1/2019 | |
| WO | 2019/012082 | A1 | 1/2019 | |
| WO | 2019/012091 | A1 | 1/2019 | |
| WO | 2019/023566 | A1 | 1/2019 | |
| WO | 2019/046377 | A1 | 3/2019 | |
| WO | 2019/053056 | A1 | 3/2019 | |
| WO | 2019/086615 | A1 | 5/2019 | |
| WO | 2019/094396 | A1 | 5/2019 | |
| WO | 2019/115816 | A1 | 6/2019 | |
| WO | 2019/134048 | A1 | 7/2019 | |
| WO | 2019/135086 | A1 | 7/2019 | |

(56) References Cited

FOREIGN PATENT DOCUMENTS

| | | | |
|---|---|---|---|
| WO | 2019/137999 | A1 | 7/2019 |
| WO | 2019/152922 | A1 | 8/2019 |
| WO | WO 2019/191780 | A1 | 10/2019 |
| WO | 2019/219851 | A1 | 11/2019 |
| WO | 2019/226939 | A1 | 11/2019 |
| WO | 2019/226941 | A1 | 11/2019 |
| WO | 2019/232103 | A1 | 12/2019 |
| WO | WO-2019238023 | A1 * | 12/2019 |
| WO | 2020/003126 | A1 | 1/2020 |
| WO | 2020/014539 | A1 | 1/2020 |
| WO | 2020/022898 | A2 | 1/2020 |
| WO | 2020/025642 | A1 | 2/2020 |
| WO | 2020/056424 | A1 | 3/2020 |
| WO | 2020/070303 | A1 | 4/2020 |
| WO | 2020/072371 | A1 | 4/2020 |
| WO | 2020/073045 | A1 | 4/2020 |
| WO | 2020/079234 | A1 | 4/2020 |
| WO | 2020/096640 | A2 | 5/2020 |
| WO | 2020/097291 | A1 | 5/2020 |
| WO | 2020/097393 | A1 | 5/2020 |
| WO | 2020/099614 | A1 | 5/2020 |
| WO | 2020/104531 | A1 | 5/2020 |
| WO | 2020/121273 | A1 | 6/2020 |
| WO | 2020/123912 | A1 | 6/2020 |
| WO | 2020/131586 | A2 | 6/2020 |
| WO | 2020/143634 | A1 | 7/2020 |
| WO | 2020/144615 | A1 | 7/2020 |
| WO | 2020/150152 | A1 | 7/2020 |
| WO | 2020/154189 | A1 | 7/2020 |
| WO | 2020/205412 | A1 | 10/2020 |
| WO | 2020/243719 | A1 | 12/2020 |
| WO | 2020/247547 | A1 | 12/2020 |

OTHER PUBLICATIONS

Lukas. et al, "Solid-phase peptide synthesis under continuous-flow conditions," Proc.Nati.Acad.Sci.USA, vol. 78, Issue 5, 1981, pp. 2791-2795.

Mayr et al., "Vaccination against pox diseases under immunosuppressive conditions", Dev. Biol. Stand., 1978, 41, 225-234.

Myers. E. W. et al, "Optimal alignments in linear space," Bioinformatics, vol. 4, Issue 1, Mar. 1988, pp. 11-17.

Needleman and Wunsch JMol Biol 48:444-453 (1970)).

Parisa M. et al., "Neoantigen screening identifies broad TP53 mutant immunogenicity in patients with epithelial cancers," J Clin Invest, vol. 129, Issue 3, Mar. 2019, pp. 1109-1114.

Quetglas J I et al., "Alphavirus vectors for cancer therapy," Virus Research, Amsterdam, NL, vol. 153, Issue 2, Nov. 1, 2010, pp. 179-196.

Sun et al., "An enhanced immune response against G250, induced by a heterologous DNA prime-protein boost vaccination, using polyethyleneimine as a DNA vaccine adjuvant", Mol. Med. Rep., 2014, 10(5), 2657-2662.

Tim Beissert et al., "Improvement of In Vivo Expression of Genes Delivered by Self-Amplifying RNA Using vaccinia Virus Immune Evasion Proteins," Homan Gene Therapy, vol. 28, Issue 12, Dec. 1, 2017, pp. 1138-1146.

Zhang J. et al., "INTEGRATE-neo: a pipeline for personalized gene fusion neoantigen discovery," BIOINFORMATICS, vol. 33, Issue 4, Feb. 2017, pp. 555-557.

Danner, Mayr A., "Vaccination against pox diseases under immunosuppressive conditions"., Dev. Biol. Stand., 1978, pp. 225-234, vol. 41.

McLachlan et al., "Evaluation in vitro and in vivo of cationic liposome-expression construct complexes for cystic fibrosis gene therapy.", Gene Therapy, 1995, pp. 614-622, vol. 2(9).

Meisinger-Henschel et al., "Genomic sequence of chorioallantois vaccinia virus Ankara, the ancestor of modified vaccinia virus.", J. Gen. Virol., Dec. 2007, pp. 3249-3259, vol. 88, Part 12.

Van Allen et al., "Genomic correlates of response to CTLA-4 blockade in metastatic melanoma.", Science, Oct. 9, 2015, pp. 207-211, vol. 350(6257), Epub Sep. 10, 2015.

Vaughan et al., "Human Antibodies with Sub-nanomolar Affinities Isolated from a large Non-immunized Phage Display Library.", Nature Biotechnology, 1996, pp. 309-314, vol. 14.

Wang et al., "A packaging cell line for propagation of recombinant adenovirus vectors containing two lethal gene-region deletions.", Gene Ther., 1995, pp. 775-783, vol. 2.

Beissert et al., "Improvement of In Vivo Expression of Genes Delivered by Self-Amplifying RNA Using Vaccinia Virus Immune Evasion Proteins", Human Gene Therapy, 2017, 28(12): 1138-1146.

Geall et al.,"Nonviral delivery of self-amplifying RNA vaccines," PNAS, vol. 109, 2012, pp. 14604-14609.

Gorchakov et al., "Different Types of nsP3-Containing Protein Complexes in Sindbis Virus-Infected Cells," Journal of Virology, vol. 82, Issue 20, 2008, pp. 10088-10101.

Hoganson et al., "Development of a Stable Adenoviral Vector Formulation," Bioprocessing, Technical Developments and Opportunities; vol. 1, No. 1, Mar. 2002, pp. 43-48.

Juliano et al., "The effect of particle size and charge on the clearance rates of liposomes and liposome encapsulated drugs," Biochem. Biophys. Res. Commun, vol. 63, Issue 3, 1975, pp. 651-658.

Kim et al., "Enhancement of protein expression by alphavirus replicons by designing self-replicating subgenomic RNAs," PNAS, vol. 111, 2014, pp. 10708-10713.

Meyers et al., "Optimal alignments in linear space," Comput Appl Biosci, vol. 4, 1988, pp. 11-17.

Toribio et al., "New insights into the topology of the scanning ribosome during translation initiation: Lessons from viruses," Nucleic Acids Res, vol. 44, Issue 9, 2016, pp. 4368-4380.

Ventoso "Adaptive Changes in Alphavirus mRNA Translation Allowed Colonization of Vertebrate Hosts", vol. 86, Sep. 2012, pp. 9484-9494.

Akimaru et al., "Formulation and antitumor efficacy of liposomal-caprylated-TNF-SAM2.", Cytokines Mol. Ther., 1995, pp. 197-210, vol. 1(3).

Alving et al., "Liposomes as carriers of peptide antigens: induction of antibodies and cytotoxic T lymphocytes to conjugated and unconjugated peptides.", 1995, Immunol. Rev., 1995, pp. 5-31, vol. 145.

Armenia et al., "The long tail of oncogenic drivers in prostate cancer.", Nat Genet, 2018, pp. 645-651, vol. 50(5), Epub Apr. 2, 2018.

Bakker et al., "Conditional MHC class I ligands and peptide exchange technology for the human MHC gene products HLA-A1, -A3, -A11, and -B7.", Proc Natl Acad Sci, USA, Mar. 22, 2008, pp. 3825-3830, vol. 105(10).

Behr et al., "Efficient gene transfer into mammalian primary endocrine cells with lipopolyamine-coated DNA.", Proc. Natl. Acad. Sci., USA, 1999, pp. 6982-6986, vol. 86(18).

Brüggemann and Taussig, "Production of human antibody repertoires in transgenic mice.", Curr Opin Biotechnol, 1997, pp. 455-458, vol. 8.

Brüggemann et al., "Human antibody production in transgenic mice: expression from 100 kb of the human IgH locus*.", Eur J Immunol, 1991, pp. 1323-1326, vol. 21.

Chothia and Lesk, "Canonical Structures for the Hypervariable Regions of Immunoglobulins.", Mol Biol, 1987, pp. 901-917, vol. 196.

Danos and Mulligan, "Safe and efficient generation of recombinant retroviruses with amphotropic and ecotropic host ranges.", Proc. Natl. Acad. Sci., USA, 1988, pp. 6460-6464, vol. 85(17).

Felgner et al., "Lipofection: a highly efficient, lipid-mediated DNA-transfection procedure.", Proc. Natl. Acad. Sci., USA, Nov. 1987, pp. 7413-7417, vol. 84(21).

Felgner, et al., "Cationic Lipid-Mediated Delivery of Polynucleotides.", Methods, 1993, pp. 67-75, vol. 5.

Fishwild et al., "High-avidity human IgGk monoclonalantibodies from a novel strain of minilocus transgenic mice.", Nat Biotechnol, Jul. 1996, pp. 845-851, vol. 14.

Gao and Huang, "A Novel Cationic Lipsome Reagent for Efficient Transfection of Mammalian Cells.", Biochemical and Biophysical Research Communications, Aug. 30, 1991, pp. 280-285, vol. 179(1).

(56) References Cited

OTHER PUBLICATIONS

Ge et al., "FusionMap: detecting fusion genes from next-generation sequencing data at base-pair resolution.", Bioinformatics. Jul. 1, 20115; 27(14):1922-8. doi: 10.1093/bioinformatics/btr310. Epub May 18, 2011.
Gilboa et al., "Retroviral Gene Transfer: Applications to Human Therapy.", Adv. Exp. Med. Biol., 1988, pp. 29-33, vol. 241.
Goding, *Monoclonal Antibodies: Principles and Practice*, Chapter 3, pp. 59-103, Academic Press, 1986.
Graham et al., "Characteristics of a Human Cell Line Transformed by DNA from Human Adenovirus Type 5.", J. Gen. Virol., 1977, pp. 59-72, vol. 36.
Green and Jakobovits, "Regulation of B Cell Development by Variable Gene Complexity in Mice Reconstituted with Human Immunoglobulin Yeast Artificial Chromosomes.", J. Exp. Med., Aug. 1998, pp. 483-495, vol. 188(3).
Green et al., "Antigen-specific human monoclonal antibodies from mice engineered with human Ig heavy and light chain YACs.", Nature Genet., 1994, pp. 13-21, vol. 7.
Green, L., "Antibody engineering via genetic engineering of the mouse: XenoMouse strains are a vehicle for the facile generation of therapeutic human monoclonal antibodies.", J Immunol Methods, 1999, pp. 11-23, vol. 231.
Haensler and Szoka, "Polyamidoamine cascade polymers mediate efficient transfection of cells in culture.", Bioconjugate Chem., Sep. 1993, pp. 372-379, vol. 4(5).
Honegger and Pluckthun, "Yet Another Numbering Scheme for Immunoglobulin Variable Domains: an Automatic Modeling and Analysis Tool.", J Mol Biol, 2001, pp. 657-670, vol. 309.
Hoogenboom and Winter, "By-passing Immunisation. Human Antibodies from Synthetic Repertoires of Germline VnGene Segments Rearranged in Virto.", J Mol Biol, 1992, pp. 381-388, vol. 227.
Hosse et al., "A New Generation of Protein Display Scaffolds for Molecular Recognition.", *Protein Sci.*, 2006, pp. 14-27, vol. 15.
Knappik et al., "Fully Snythetic Human Combinatorial Antibody Libraries (HuCAL) Based on Modular Consensus Frameworks and CDRs Randomized with Trinucleotides.", J Mol Biol, 2000, pp. 57-86, vol. 296.
Kohler and Milstein, "Continuous cultures of fused cells secreting antibody of predefined specificity.", Nature, 1975, pp. 495-497, vol. 256.
Krebs et al., "High-Throughput generation and engineering of recombinant human antibodies.", J Immunol Meth, 2001, pp. 67-84, vol. 254.
Kroughak and Graham, "Development of Cell Lines Capable of Complementing E1, E4, and Protein IX Defective Adenovirus Type 5 Mutants.", Human Gene Ther., Dec. 1, 1995, pp. 1575-1586, vol. 6(12).
Le et al., "PD-1 Blockade in Tumors with Mismatch-Repair Deficiency.", N Engl J Med., Jun. 25, 2015, pp. 2509-2520, vol. 372(26), Epub May 30, 2015.
Lefranc et al., "IMGT unique numbering for immunoglobulin and T cell receptor variable domains and Ig superfamily V-like domains.", Dev Comparat Immunol, 2003, pp. 55-77, vol. 27.
Lonberg and Huszar, "Human Antibodies from Transgenic Mice.", Int Rev Immunol, 1995, pp. 65-93, vol. 13.
Lonberg et al., "Antigen-specific human antibodies from mice comprising four distinct genetic modifications.", Nature,1994, pp. 856-859, vol. 368.
Lopata, et al., "High level trasient expression of a chloramphenicol acetyl transferase gene by DEAE-dextran mediated DNA transfection coupled with a dimethyl sulfoxide or glycerol shock treatment.", 1984, Nucleic Acid Res., 1984, pp. 5707-5717, vol. 12(14).
Lusky, et al., "In Vitro and In Vivo Biology of Recombinant Adenovirus Vectors with E1, E1/E2A, or E1/E4 Deleted.", J. Virol., Mar. 1998, pp. 2022-2032, vol. 72(3).
Markowitz et al., "Construction and use of a safe and efficient amphotropic packaging cell line.", Virology, 1988, pp. 400-406, vol. 167(2).
Marks et al., "By-passing Immunization. Human antibodies from V-gene Libraries Displayed on Phage.", J Mol Biol, 1991, pp. 581-587, vol. 222.
Martin and Thornton, "Structural Families in Loops of Homologous Proteins: Automatic Classification, Modelling and Application to Antibodies.", J Bmol Biol, 1996, pp. 800-815, vol. 263.
Mendez et al., "Functional transplant of megabase human immunoglobulin loci recapitulates human antibody response in mice.", Nat Genet., Feb. 1997, pp. 146-156, vol. 15.
Meyer et al., "Mapping of deletions in the genome of the highly attenuated vaccinia virus MVA and their influence on virulence.", J. Gen. Virol., 1991, pp. 1031-1038, vol. 72, Part 5.
Miller and Rossman, "Improved Retroviral Vectors for Gene Transfer and Expression.", BioTechniques, Oct. 1989, pp. 980-990, vol. 7(9).
Nicaise et al., "Affinity Transfer by CDR Grafting on a Nonimmunoglobulin Scaffold.", Protein Sci., 2004, pp. 1882-1891, vol. 13.
Nygren and Uhlen, "Scaffolds for Engineering Novel Binding Sites in Proteins," Curr. Opin. Struc. Biol., 1997, pp. 463-469, vol. 7.
Padlan, E., "A Possible Procedure for Reducing the Immunogenicity of Antibody Variable Domains While Preserving Their Ligand-Binding Properties.", Mol Immunol, 1991, pp. 489-499, vol. 28(4/5).
Piccini et al., "Vaccina Virus as an Expression Vector.", Methods of Enzymology, 1987, pp. 545-563, vol. 153.
Rizvi et al., "Mutational landscape determines sensitivity to PD-1 blockade in non-small cell lung cancer.", Science, Apr. 3, 2015, pp. 124-128, vol. 348(6230), Epub Mar. 12, 2015.
Robinson et al., "Integrative Clinical Genomics of Advanced Prostate Cancer.", Cell, May 21, 2015, pp. 1215-1228, vol. 161(5).
Rodenko et al., "Generation of peptide-MHC class I complexes through UV-mediated ligand exchange.", Nature Protocols, 2006, pp. 1120-1132, vol. 1(3).
Romani et al., "Presentation of exogenous protein antigens by dendritic cells to T cell clones. Intact protein is presented best by immature, epidermal Langerhans cells.", J. Exp. Med., Mar. 1, 1989, pp. 1169-1178, vol. 169(3).
Sheets et al., "Efficient construction of a large nonimmune phage antibody library: the production of high-affinity human single-chain antibodies to protein antigens.", PTAS (USA), May 1998, pp. 6157-6162, vol. 95.
Shi et al., "De Novo Selection of High-Affinity Antibodies from Synthetic Fab Libraries Displayed on Phage as pIX Fusion Proteins.", J Mol Biol, 2010, pp. 385-396, vol. 397.
Skerra, A., "Alternative Non-Antibody Scaffolds for Molecular Recognition,", Curr. Opin. Biotechnol., 2005, pp. 295-304, vol. 18.
Snyder et al., "Genetic Basis for Clinical Response to CTLA-4 Blockade in Melanoma.", N Engl J Med., Dec. 4, 2014, pp. 2189-2199, vol. 371(23):2189-2199, Epub Nov. 19, 2014.
Szoka et al., "Comparative properties and methods of preparation of lipid vesicles (liposomes).", Ann. Rev. Biophys. Bioeng., 1980, pp. 467-508, vol. 9.
The Cancer Genome Atlas Research Network, "The Molecular taxonomy of primary prostate cancer.", Cell, Nov. 5, 2015, pp. 1011-1025, vol. 163(4).
Toebes et al., "Design and use of conditional MHC class I ligands.", Nat Med, Mar. 2006, pp. 246-251, vol. 12(2).
Wu and Kabat, "An Analysis of the Sequences of the Variable Regions of Bence Jones Proteins and Myeloma Light Chains and Their Implications for Anti-body Complementarity*.", J Exp Med, 1970, pp. 211-250, vol. 132.
Yang et al., "Eradication of Established Tumors by a Fully Human Monoclonal Antibody to the Epidermal Growth Factor Receptor without Concomitant Chemotherapy.", Cancer Res, Mar. 15, 1999, pp. 1236-1243, vol. 59.
Yeh et al., "Efficient Dual Transcomplementation of Adenovirus E1 and E4 Regions from a 293-Derived Cell Line Expressing a Minimal E4 Functional Unit.", J. Virol., Jan. 1996, pp. 559-565, vol. 70(1).

(56) References Cited

OTHER PUBLICATIONS

Correa, Ricardo G et al: 'The NLR-related protein NWD1 is associated with prostate cancer and modulates androgen receptor signaling'1, ON CO TA PG ET, Mar. 26, 2014 (Mar. 26, 2014), pp. 1666-1682.
Anassi et al., "Sipuleucel-T (Provenge) Injection, Pharmacy & Therapeutics," Apr. 2011, vol. 36, No. 4, pp. 197-202.
Gulley et al., Phase III Trial of PROSTVAC in Asymptomatic or Minimally Symptomatic Metastatic Castration-Resistant Prostate Cancer, Journal of Clinical Oncology, 2019, vol. 37, Issue 13, pp. 1051-1061.
Yamada et al., Next-generation peptide vaccines for advanced cancer, Cancer Science, Dec. 4, 2012, vol. 104, No. 1, pp. 15-21.
Aldous et al., "Personalized neoantigen vaccines: A new approach to cancer immunotherapy", Bioorganic & Medicinal Chemistry, 2018, vol. 26, pp. 2842-2849.
Antonarakis, "Cyclin-Dependent Kinase 12, Immunity, and Prostate Cancer", NEJM, 2018, vol. 379, No. 13, pp. 1087-1089.
Cappuccini et al., "5T4 oncofoetal glycoprotein: an old target for a novel prostate cancer immunotherapy", Oncotarget, 2017, vol. 8, No. 29, pp. 47474-47489.
Capuccini et al., "Immunogenicity and efficacy of the novel cancer vaccine based on simian adenovirus and MVA vectors alone and in combination with PD-1 mAb in a mouse model of prostate cancer", Cancer Immunol Immunotherapy, 2016, vol. 65, pp. 701-713.
Capuccini et al., "Safety and immunogenicity of novel 5T4 viral vectored vaccination regimens in early stage prostate cancer: a phase I clinical trial", Journal for Immunotherapy of Cancer, 2020, vol. 8, e000928, pp. 1-13.
Gadi et al., "In vivo sensitization of ovarian tumors to chemotherapy by expression of *E. coli* purine nucleoside phosphorylase in a small fraction of cells", 7 Gene Ther., 2000, vol. 7, No. 20, pp. 1738-1743.
Gomes et al., "STEAP 1 is overexpressed in prostate cancer and prostatic intraepithelial neoplasia lesions, and it is positively associated with Gleason score", Urologic Oncology, 2014, vol. 32, pp. 53.e26-53.e29.
Graff et al., "Sipuleucel-T in the treatment of prostate cancer: an evidence based review of its place in therapy", Core Evidence, 2015, pp. 1-10.
Henninger et al., "Inducible expression of cancer-testis antigens in human prostate cancer", Oncotarget, 2016, vol. 7, No. 51, pp. 84359-84374.
Kabat et al., Sequences of Proteins of Immunological Interest, 5th Ed. Public Health Service, National Institutes of Health, Bethesda, MD., 1991, pp. 1-2.
Lundblad Chemical Reagents for Protein Modification, 3rd ed., CRC Press, 2004, pp. 1-232.
Woyke et al., "In Vitro Activities and Postantifungal Effects of the Potent Dolastatin 10 Derivative Auristatin PHE", Antimicrob agents and chemother., 2001, vol. 45, No. 12, pp. 3580-3584
Tadavet al., "Predicting immunogenic tumour mutations by combining mass spectrometry and exome sequencing", Nature, 2014, vol. 515, pp. 572-576.

* cited by examiner

SEQUENCE LISTING

<160> NUMBER OF SEQ ID NOS: 980

<210> SEQ ID NO 1
<211> LENGTH: 17
<212> TYPE: PRT
<213> ORGANISM: Homo sapiens

<400> SEQUENCE: 1

Ser Ser Cys Met Gly Gly Met Asn Gln Arg Pro Ile Leu Thr Ile Ile
1 5 10 15

Thr

<210> SEQ ID NO 2
<211> LENGTH: 51
<212> TYPE: DNA
<213> ORGANISM: Homo sapiens

<400> SEQUENCE: 2
agttcctgca tgggcggcat gaaccagagg cccatcctca ccatcatcac a 51

<210> SEQ ID NO 3
<211> LENGTH: 17
<212> TYPE: PRT
<213> ORGANISM: Homo sapiens

<400> SEQUENCE: 3

Ser Ser Cys Met Gly Gly Met Asn Trp Arg Pro Ile Leu Thr Ile Ile
1 5 10 15

Thr

<210> SEQ ID NO 4
<211> LENGTH: 51
<212> TYPE: DNA
<213> ORGANISM: Homo sapiens

<400> SEQUENCE: 4
agttcctgca tgggcggcat gaattggagg cccatcctca ccatcatcac a 51

<210> SEQ ID NO 5
<211> LENGTH: 17
<212> TYPE: PRT
<213> ORGANISM: Homo sapiens

<400> SEQUENCE: 5

Leu Gly Arg Asn Ser Phe Glu Val Cys Val Cys Ala Cys Pro Gly Arg
1 5 10 15

Asp

<210> SEQ ID NO 6
<211> LENGTH: 51
<212> TYPE: DNA

<213> ORGANISM: Homo sapiens

<400> SEQUENCE: 6
ctgggacgga acagctttga ggtgtgtgtt tgtgcctgtc ctgggagaga c 51

<210> SEQ ID NO 7
<211> LENGTH: 17
<212> TYPE: PRT
<213> ORGANISM: Homo sapiens

<400> SEQUENCE: 7

Leu Gly Arg Asn Ser Phe Glu Val Leu Val Cys Ala Cys Pro Gly Arg
1 5 10 15

Asp

<210> SEQ ID NO 8
<211> LENGTH: 51
<212> TYPE: DNA
<213> ORGANISM: Homo sapiens

<400> SEQUENCE: 8
ctgggacgga acagctttga ggtgcttgtt tgtgcctgtc ctgggagaga c 51

<210> SEQ ID NO 9
<211> LENGTH: 17
<212> TYPE: PRT
<213> ORGANISM: Homo sapiens

<400> SEQUENCE: 9

Met Cys Asn Ser Ser Cys Met Gly Ser Met Asn Arg Arg Pro Ile Leu
1 5 10 15

Thr

<210> SEQ ID NO 10
<211> LENGTH: 51
<212> TYPE: DNA
<213> ORGANISM: Homo sapiens

<400> SEQUENCE: 10
atgtgtaaca gttcctgcat gggcagcatg aaccggaggc ccatcctcac c 51

<210> SEQ ID NO 11
<211> LENGTH: 17
<212> TYPE: PRT
<213> ORGANISM: Homo sapiens

<400> SEQUENCE: 11

Phe Arg His Ser Val Val Val Pro Cys Glu Pro Pro Glu Val Gly Ser
1 5 10 15

Asp

<210> SEQ ID NO 12
<211> LENGTH: 51
<212> TYPE: DNA
<213> ORGANISM: Homo sapiens

<400> SEQUENCE: 12
tttcgacata gtgtggtggt gccctgtgag ccgcctgagg ttggctctga c 51

<210> SEQ ID NO 13
<211> LENGTH: 17
<212> TYPE: PRT

<213> ORGANISM: Homo sapiens

<400> SEQUENCE: 13

Val Cys Ala Cys Pro Gly Arg Asp Trp Arg Thr Glu Glu Glu Asn Leu
1 5 10 15

Arg

<210> SEQ ID NO 14
<211> LENGTH: 51
<212> TYPE: DNA
<213> ORGANISM: Homo sapiens

<400> SEQUENCE: 14
gtttgtgcct gtcctgggag agattggcgc acagaggaag agaatctccg c 51

<210> SEQ ID NO 15
<211> LENGTH: 17
<212> TYPE: PRT
<213> ORGANISM: Homo sapiens

<400> SEQUENCE: 15

Phe Val Gln Gly Lys Asp Trp Gly Cys Lys Lys Phe Ile Arg Arg Asp
1 5 10 15

Phe

<210> SEQ ID NO 16
<211> LENGTH: 51
<212> TYPE: DNA
<213> ORGANISM: Homo sapiens

<400> SEQUENCE: 16
tttgtgcaag gcaaagactg gggatgcaag aaattcatcc gtagagattt t 51

<210> SEQ ID NO 17
<211> LENGTH: 17
<212> TYPE: PRT
<213> ORGANISM: Homo sapiens

<400> SEQUENCE: 17

Phe Val Gln Gly Lys Asp Trp Gly Ile Lys Lys Phe Ile Arg Arg Asp
1 5 10 15

Phe

<210> SEQ ID NO 18
<211> LENGTH: 51
<212> TYPE: DNA
<213> ORGANISM: Homo sapiens

<400> SEQUENCE: 18
tttgtgcaag gcaaagactg gggaatcaag aaattcatcc gtagagattt t 51

<210> SEQ ID NO 19
<211> LENGTH: 17
<212> TYPE: PRT
<213> ORGANISM: Homo sapiens

<400> SEQUENCE: 19

Phe Val Gln Gly Lys Asp Trp Gly Leu Lys Lys Phe Ile Arg Arg Asp
1 5 10 15

Phe

<210> SEQ ID NO 20
<211> LENGTH: 51
<212> TYPE: DNA
<213> ORGANISM: Homo sapiens

<400> SEQUENCE: 20
tttgtgcaag gcaaagactg gggattaaag aaattcatcc gtagagattt t 51

<210> SEQ ID NO 21
<211> LENGTH: 17
<212> TYPE: PRT
<213> ORGANISM: Homo sapiens

<400> SEQUENCE: 21

Phe Val Gln Gly Lys Asp Trp Gly Ser Lys Lys Phe Ile Arg Arg Asp
1 5 10 15

Phe

<210> SEQ ID NO 22
<211> LENGTH: 51
<212> TYPE: DNA
<213> ORGANISM: Homo sapiens

<400> SEQUENCE: 22
tttgtgcaag gcaaagactg gggatccaag aaattcatcc gtagagattt t 51

<210> SEQ ID NO 23
<211> LENGTH: 17
<212> TYPE: PRT
<213> ORGANISM: Homo sapiens

<400> SEQUENCE: 23

Phe Val Gln Gly Lys Asp Trp Gly Val Lys Lys Phe Ile Arg Arg Asp
1 5 10 15

Phe

<210> SEQ ID NO 24
<211> LENGTH: 51
<212> TYPE: DNA
<213> ORGANISM: Homo sapiens

<400> SEQUENCE: 24
tttgtgcaag gcaaagactg gggagtcaag aaattcatcc gtagagattt t 51

<210> SEQ ID NO 25
<211> LENGTH: 17
<212> TYPE: PRT
<213> ORGANISM: Homo sapiens

<400> SEQUENCE: 25

Tyr Arg Phe Val Gln Gly Lys Asp Cys Gly Phe Lys Lys Phe Ile Arg
1 5 10 15

Arg

<210> SEQ ID NO 26
<211> LENGTH: 51
<212> TYPE: DNA
<213> ORGANISM: Homo sapiens

<400> SEQUENCE: 26
tataggtttg tgcaaggcaa agactgtgga ttcaagaaat tcatccgtag a 51

<210> SEQ ID NO 27
<211> LENGTH: 17
<212> TYPE: PRT
<213> ORGANISM: Homo sapiens

<400> SEQUENCE: 27

Tyr Arg Phe Val Gln Gly Lys Asp Gly Gly Phe Lys Lys Phe Ile Arg
1 5 10 15

Arg

<210> SEQ ID NO 28
<211> LENGTH: 51
<212> TYPE: DNA
<213> ORGANISM: Homo sapiens

<400> SEQUENCE: 28
tataggtttg tgcaaggcaa agacggggga ttcaagaaat tcatccgtag a 51

<210> SEQ ID NO 29
<211> LENGTH: 17
<212> TYPE: PRT
<213> ORGANISM: Homo sapiens

<400> SEQUENCE: 29

Tyr Arg Phe Val Gln Gly Lys Asp Leu Gly Phe Lys Lys Phe Ile Arg
1 5 10 15

Arg

<210> SEQ ID NO 30
<211> LENGTH: 51
<212> TYPE: DNA
<213> ORGANISM: Homo sapiens

<400> SEQUENCE: 30
tataggtttg tgcaaggcaa agactgggga ttcaagaaat tcatccgtag a 51

<210> SEQ ID NO 31
<211> LENGTH: 17
<212> TYPE: PRT
<213> ORGANISM: Homo sapiens

<400> SEQUENCE: 31

Tyr Arg Phe Val Gln Gly Lys Asp Arg Gly Phe Lys Lys Phe Ile Arg
1 5 10 15

Arg

<210> SEQ ID NO 32
<211> LENGTH: 51
<212> TYPE: DNA
<213> ORGANISM: Homo sapiens

<400> SEQUENCE: 32
tataggtttg tgcaaggcaa agaccgggga ttcaagaaat tcatccgtag a 51

<210> SEQ ID NO 33
<211> LENGTH: 17
<212> TYPE: PRT
<213> ORGANISM: Homo sapiens

<400> SEQUENCE: 33

Tyr Arg Phe Val Gln Gly Lys Asp Ser Gly Phe Lys Lys Phe Ile Arg
1 5 10 15

Arg

<210> SEQ ID NO 34
<211> LENGTH: 51
<212> TYPE: DNA
<213> ORGANISM: Homo sapiens

<400> SEQUENCE: 34
tataggtttg tgcaaggcaa agactcggga ttcaagaaat tcatccgtag a 51

<210> SEQ ID NO 35
<211> LENGTH: 17
<212> TYPE: PRT
<213> ORGANISM: Homo sapiens

<400> SEQUENCE: 35

Tyr Pro Val Gly Tyr Glu Ala Thr His Ile Tyr Trp Ser Leu Arg Thr
1 5 10 15

Asn

<210> SEQ ID NO 36
<211> LENGTH: 51
<212> TYPE: DNA
<213> ORGANISM: Homo sapiens

<400> SEQUENCE: 36
tatcccgtgg gctacgaggc cacgcacatc tattggagcc tccgcaccaa c 51

<210> SEQ ID NO 37
<211> LENGTH: 17
<212> TYPE: PRT
<213> ORGANISM: Homo sapiens

<400> SEQUENCE: 37

Met Phe Glu Asn Gly Cys Tyr Leu Cys Arg Gln Lys Arg Phe Lys Cys
1 5 10 15

Glu

<210> SEQ ID NO 38
<211> LENGTH: 51
<212> TYPE: DNA
<213> ORGANISM: Homo sapiens

<400> SEQUENCE: 38
atgttcgaga acggctgcta cttgtgccgc cagaagcgct tcaagtgcga g 51

<210> SEQ ID NO 39
<211> LENGTH: 17
<212> TYPE: PRT
<213> ORGANISM: Homo sapiens

<400> SEQUENCE: 39

Gly Lys Gly Ser Tyr Trp Thr Leu Gln Pro Asp Ser Gly Asn Met Phe
1 5 10 15

Glu

<210> SEQ ID NO 40
<211> LENGTH: 51
<212> TYPE: DNA
<213> ORGANISM: Homo sapiens

<400> SEQUENCE: 40
ggcaagggct cctactggac gctgcagccg gactccggca acatgttcga g 51

<210> SEQ ID NO 41
<211> LENGTH: 17
<212> TYPE: PRT
<213> ORGANISM: Homo sapiens

<400> SEQUENCE: 41

Gly Lys Gly Ser Tyr Trp Thr Leu Leu Pro Asp Ser Gly Asn Met Phe
1 5 10 15

Glu

<210> SEQ ID NO 42
<211> LENGTH: 51
<212> TYPE: DNA
<213> ORGANISM: Homo sapiens

<400> SEQUENCE: 42
ggcaagggct cctactggac gctgctcccg gactccggca acatgttcga g 51

<210> SEQ ID NO 43
<211> LENGTH: 17
<212> TYPE: PRT
<213> ORGANISM: Homo sapiens

<400> SEQUENCE: 43

Gly Lys Gly Ser Tyr Trp Thr Leu Asn Pro Asp Ser Gly Asn Met Phe
1 5 10 15

Glu

<210> SEQ ID NO 44
<211> LENGTH: 51
<212> TYPE: DNA
<213> ORGANISM: Homo sapiens

<400> SEQUENCE: 44
ggcaagggct cctactggac gctgaacccg gactccggca acatgttcga g 51

<210> SEQ ID NO 45
<211> LENGTH: 17
<212> TYPE: PRT
<213> ORGANISM: Homo sapiens

<400> SEQUENCE: 45

Gly Lys Gly Ser Tyr Trp Thr Leu Tyr Pro Asp Ser Gly Asn Met Phe
1 5 10 15

Glu

<210> SEQ ID NO 46
<211> LENGTH: 51
<212> TYPE: DNA
<213> ORGANISM: Homo sapiens

<400> SEQUENCE: 46
ggcaagggct cctactggac gctgtacccg gactccggca acatgttcga g 51

<210> SEQ ID NO 47
<211> LENGTH: 17
<212> TYPE: PRT
<213> ORGANISM: Homo sapiens

<400> SEQUENCE: 47

Cys Tyr Leu Arg Arg Gln Lys Arg Cys Lys Cys Glu Lys Gln Pro Gly
1 5 10 15

Ala

<210> SEQ ID NO 48
<211> LENGTH: 51
<212> TYPE: DNA
<213> ORGANISM: Homo sapiens

<400> SEQUENCE: 48
tgctacttgc gccgccagaa gcgctgcaag tgcgagaagc agccgggggc c 51

<210> SEQ ID NO 49
<211> LENGTH: 17
<212> TYPE: PRT
<213> ORGANISM: Homo sapiens

<400> SEQUENCE: 49

Cys Tyr Leu Arg Arg Gln Lys Arg Ser Lys Cys Glu Lys Gln Pro Gly
1 5 10 15

Ala

<210> SEQ ID NO 50
<211> LENGTH: 51
<212> TYPE: DNA
<213> ORGANISM: Homo sapiens

<400> SEQUENCE: 50
tgctacttgc gccgccagaa gcgctccaag tgcgagaagc agccgggggc c 51

<210> SEQ ID NO 51
<211> LENGTH: 17
<212> TYPE: PRT
<213> ORGANISM: Homo sapiens

<400> SEQUENCE: 51

Ile Arg His Ser Leu Ser Phe Asn Gly Cys Phe Val Lys Val Ala Arg
1 5 10 15

Ser

<210> SEQ ID NO 52
<211> LENGTH: 51
<212> TYPE: DNA
<213> ORGANISM: Homo sapiens

<400> SEQUENCE: 52
atccgccact cgctgtcctt caatggctgc ttcgtcaagg tggcacgctc c 51

<210> SEQ ID NO 53
<211> LENGTH: 17
<212> TYPE: PRT
<213> ORGANISM: Homo sapiens

<400> SEQUENCE: 53

Ile Arg His Ser Leu Ser Phe Asn Asn Cys Phe Val Lys Val Ala Arg
1 5 10 15

Ser

<210> SEQ ID NO 54
<211> LENGTH: 51
<212> TYPE: DNA
<213> ORGANISM: Homo sapiens

<400> SEQUENCE: 54
atccgccact cgctgtcctt caataactgc ttcgtcaagg tggcacgctc c 51

<210> SEQ ID NO 55
<211> LENGTH: 17
<212> TYPE: PRT
<213> ORGANISM: Homo sapiens

<400> SEQUENCE: 55

Gln Gln Arg Trp Gln Asn Ser Ile Cys His Ser Leu Ser Phe Asn Asp
1 5 10 15

Cys

<210> SEQ ID NO 56
<211> LENGTH: 51
<212> TYPE: DNA
<213> ORGANISM: Homo sapiens

<400> SEQUENCE: 56
cagcagcgct ggcagaactc catctgccac tcgctgtcct tcaatgactg c 51

<210> SEQ ID NO 57
<211> LENGTH: 17
<212> TYPE: PRT
<213> ORGANISM: Homo sapiens

<400> SEQUENCE: 57

Gln Gln Arg Trp Gln Asn Ser Ile Ser His Ser Leu Ser Phe Asn Asp
1 5 10 15

Cys

<210> SEQ ID NO 58
<211> LENGTH: 51
<212> TYPE: DNA
<213> ORGANISM: Homo sapiens

<400> SEQUENCE: 58
cagcagcgct ggcagaactc catcagccac tcgctgtcct tcaatgactg c 51

<210> SEQ ID NO 59
<211> LENGTH: 17
<212> TYPE: PRT
<213> ORGANISM: Homo sapiens

<400> SEQUENCE: 59

Thr Leu His Pro Asp Ser Gly Asn Lys Phe Glu Asn Gly Cys Tyr Leu
1 5 10 15

Arg

<210> SEQ ID NO 60
<211> LENGTH: 51
<212> TYPE: DNA
<213> ORGANISM: Homo sapiens

<400> SEQUENCE: 60
acgctgcacc cggactccgg caacaagttc gagaacggct gctacttgcg c 51

<210> SEQ ID NO 61
<211> LENGTH: 17
<212> TYPE: PRT
<213> ORGANISM: Homo sapiens

<400> SEQUENCE: 61

Thr Leu His Pro Asp Ser Gly Asn Arg Phe Glu Asn Gly Cys Tyr Leu
1 5 10 15

Arg

<210> SEQ ID NO 62
<211> LENGTH: 51
<212> TYPE: DNA
<213> ORGANISM: Homo sapiens

<400> SEQUENCE: 62
acgctgcacc cggactccgg caacaggttc gagaacggct gctacttgcg c 51

<210> SEQ ID NO 63
<211> LENGTH: 17
<212> TYPE: PRT
<213> ORGANISM: Homo sapiens

<400> SEQUENCE: 63

Cys His Lys Lys Asn Phe Leu His Trp Asp Ile Lys Cys Ser Asn Ile
1 5 10 15

Leu

<210> SEQ ID NO 64
<211> LENGTH: 51
<212> TYPE: DNA
<213> ORGANISM: Homo sapiens

<400> SEQUENCE: 64
tgtcacaaaa agaatttcct gcattgggat attaagtgtt ctaacatttt g 51

<210> SEQ ID NO 65
<211> LENGTH: 17
<212> TYPE: PRT
<213> ORGANISM: Homo sapiens

<400> SEQUENCE: 65

Ile His Cys Lys Ala Gly Lys Gly Gln Thr Gly Val Met Ile Cys Ala
1 5 10 15

Tyr

<210> SEQ ID NO 66
<211> LENGTH: 51
<212> TYPE: DNA
<213> ORGANISM: Homo sapiens

<400> SEQUENCE: 66
attcactgta aagctggaaa gggacaaact ggtgtaatga tatgtgcata t 51

<210> SEQ ID NO 67
<211> LENGTH: 17
<212> TYPE: PRT
<213> ORGANISM: Homo sapiens

<400> SEQUENCE: 67

Trp Leu Ser Glu Asp Asp Asn His Phe Ala Ala Ile His Cys Lys Ala
1 5 10 15

Gly

<210> SEQ ID NO 68

<211> LENGTH: 51
<212> TYPE: DNA
<213> ORGANISM: Homo sapiens

<400> SEQUENCE: 68
tggctaagtg aagatgacaa tcattttgca gcaattcact gtaaagctgg a 51

<210> SEQ ID NO 69
<211> LENGTH: 17
<212> TYPE: PRT
<213> ORGANISM: Homo sapiens

<400> SEQUENCE: 69

Gly Leu Gly Asp Arg His Val Gln Ser Ile Leu Ile Asn Glu Gln Ser
1 5 10 15

Ala

<210> SEQ ID NO 70
<211> LENGTH: 51
<212> TYPE: DNA
<213> ORGANISM: Homo sapiens

<400> SEQUENCE: 70
ggacttggtg atagacatgt acagagtatc ttgataaatg agcagtcagc a 51

<210> SEQ ID NO 71
<211> LENGTH: 17
<212> TYPE: PRT
<213> ORGANISM: Homo sapiens

<400> SEQUENCE: 71

Gly Leu Gly Asp Arg His Val Gln Lys Ile Leu Ile Asn Glu Gln Ser
1 5 10 15

Ala

<210> SEQ ID NO 72
<211> LENGTH: 51
<212> TYPE: DNA
<213> ORGANISM: Homo sapiens

<400> SEQUENCE: 72
ggacttggtg atagacatgt acagaaaatc ttgataaatg agcagtcagc a 51

<210> SEQ ID NO 73
<211> LENGTH: 17
<212> TYPE: PRT
<213> ORGANISM: Homo sapiens

<400> SEQUENCE: 73

Asn Ile Asn Ile Gly Pro Gly Asp Ser Glu Trp Phe Val Val Pro Glu
1 5 10 15

Gly

<210> SEQ ID NO 74
<211> LENGTH: 51
<212> TYPE: DNA
<213> ORGANISM: Homo sapiens

<400> SEQUENCE: 74
aacataaata ttggcccagg tgactctgaa tggtttgttg ttcctgaagg t 51

<210> SEQ ID NO 75

<211> LENGTH: 17
<212> TYPE: PRT
<213> ORGANISM: Homo sapiens

<400> SEQUENCE: 75

Asn Ile Asn Ile Gly Pro Gly Asp Tyr Glu Trp Phe Val Val Pro Glu
1 5 10 15

Gly

<210> SEQ ID NO 76
<211> LENGTH: 51
<212> TYPE: DNA
<213> ORGANISM: Homo sapiens

<400> SEQUENCE: 76
aacataaata ttggcccagg tgactatgaa tggtttgttg ttcctgaagg t 51

<210> SEQ ID NO 77
<211> LENGTH: 17
<212> TYPE: PRT
<213> ORGANISM: Homo sapiens

<400> SEQUENCE: 77

Phe Met Lys Gln Met Asn Asp Ala Arg His Gly Gly Trp Thr Thr Lys
1 5 10 15

Met

<210> SEQ ID NO 78
<211> LENGTH: 51
<212> TYPE: DNA
<213> ORGANISM: Homo sapiens

<400> SEQUENCE: 78
ttcatgaaac aaatgaatga tgcacgtcat ggtggctgga caacaaaaat g 51

<210> SEQ ID NO 79
<211> LENGTH: 17
<212> TYPE: PRT
<213> ORGANISM: Homo sapiens

<400> SEQUENCE: 79

Arg Asp Pro Leu Ser Glu Ile Thr Lys Gln Glu Lys Asp Phe Leu Trp
1 5 10 15

Ser

<210> SEQ ID NO 80
<211> LENGTH: 51
<212> TYPE: DNA
<213> ORGANISM: Homo sapiens

<400> SEQUENCE: 80
cgagatcctc tctctgaaat cactaagcag gagaaagatt ttctatggag t 51

<210> SEQ ID NO 81
<211> LENGTH: 17
<212> TYPE: PRT
<213> ORGANISM: Homo sapiens

<400> SEQUENCE: 81

Arg Asp Pro Leu Ser Glu Ile Thr Gly Gln Glu Lys Asp Phe Leu Trp
1 5 10 15

Ser

<210> SEQ ID NO 82
<211> LENGTH: 51
<212> TYPE: DNA
<213> ORGANISM: Homo sapiens

<400> SEQUENCE: 82
cgagatcctc tctctgaaat cactgggcag gagaaagatt ttctatggag t 51

<210> SEQ ID NO 83
<211> LENGTH: 17
<212> TYPE: PRT
<213> ORGANISM: Homo sapiens

<400> SEQUENCE: 83

Arg Asp Pro Leu Ser Glu Ile Thr Ala Gln Glu Lys Asp Phe Leu Trp
1 5 10 15

Ser

<210> SEQ ID NO 84
<211> LENGTH: 51
<212> TYPE: DNA
<213> ORGANISM: Homo sapiens

<400> SEQUENCE: 84
cgagatcctc tctctgaaat cactgcgcag gagaaagatt ttctatggag t 51

<210> SEQ ID NO 85
<211> LENGTH: 17
<212> TYPE: PRT
<213> ORGANISM: Homo sapiens

<400> SEQUENCE: 85

Ser Gly Ile His Ser Gly Ala Thr Ala Thr Ala Pro Ser Leu Ser Gly
1 5 10 15

Lys

<210> SEQ ID NO 86
<211> LENGTH: 51
<212> TYPE: DNA
<213> ORGANISM: Homo sapiens

<400> SEQUENCE: 86
tctggaatcc attctggtgc cactgccaca gctccttctc tgagtggtaa a 51

<210> SEQ ID NO 87
<211> LENGTH: 17
<212> TYPE: PRT
<213> ORGANISM: Homo sapiens

<400> SEQUENCE: 87

His Trp Gln Gln Gln Ser Tyr Leu Ala Ser Gly Ile His Ser Gly Ala
1 5 10 15

Thr

<210> SEQ ID NO 88
<211> LENGTH: 51
<212> TYPE: DNA
<213> ORGANISM: Homo sapiens

<400> SEQUENCE: 88
cactggcagc aacagtctta cctggcctct ggaatccatt ctggtgccac t 51

<210> SEQ ID NO 89
<211> LENGTH: 17
<212> TYPE: PRT
<213> ORGANISM: Homo sapiens

<400> SEQUENCE: 89

His Trp Gln Gln Gln Ser Tyr Leu His Ser Gly Ile His Ser Gly Ala
1 5 10 15

Thr

<210> SEQ ID NO 90
<211> LENGTH: 51
<212> TYPE: DNA
<213> ORGANISM: Homo sapiens

<400> SEQUENCE: 90
cactggcagc aacagtctta cctgcactct ggaatccatt ctggtgccac t 51

<210> SEQ ID NO 91
<211> LENGTH: 17
<212> TYPE: PRT
<213> ORGANISM: Homo sapiens

<400> SEQUENCE: 91

His Trp Gln Gln Gln Ser Tyr Leu Val Ser Gly Ile His Ser Gly Ala
1 5 10 15

Thr

<210> SEQ ID NO 92
<211> LENGTH: 51
<212> TYPE: DNA
<213> ORGANISM: Homo sapiens

<400> SEQUENCE: 92
cactggcagc aacagtctta cctggtctct ggaatccatt ctggtgccac t 51

<210> SEQ ID NO 93
<211> LENGTH: 17
<212> TYPE: PRT
<213> ORGANISM: Homo sapiens

<400> SEQUENCE: 93

His Trp Gln Gln Gln Ser Tyr Leu Tyr Ser Gly Ile His Ser Gly Ala
1 5 10 15

Thr

<210> SEQ ID NO 94
<211> LENGTH: 51
<212> TYPE: DNA
<213> ORGANISM: Homo sapiens

<400> SEQUENCE: 94
cactggcagc aacagtctta cctgtactct ggaatccatt ctggtgccac t 51

<210> SEQ ID NO 95
<211> LENGTH: 17
<212> TYPE: PRT
<213> ORGANISM: Homo sapiens

<400> SEQUENCE: 95

Ser Tyr Leu Asp Ser Gly Ile His Ala Gly Ala Thr Thr Thr Ala Pro

```
1               5                   10                  15

Ser


<210> SEQ ID NO 96
<211> LENGTH: 51
<212> TYPE: DNA
<213> ORGANISM: Homo sapiens

<400> SEQUENCE: 96

tcttacctgg actctggaat ccatgctggt gccactacca cagctccttc t              51


<210> SEQ ID NO 97
<211> LENGTH: 17
<212> TYPE: PRT
<213> ORGANISM: Homo sapiens

<400> SEQUENCE: 97

Ser Tyr Leu Asp Ser Gly Ile His Cys Gly Ala Thr Thr Thr Ala Pro
1               5                   10                  15

Ser


<210> SEQ ID NO 98
<211> LENGTH: 51
<212> TYPE: DNA
<213> ORGANISM: Homo sapiens

<400> SEQUENCE: 98

tcttacctgg actctggaat ccattgtggt gccactacca cagctccttc t              51


<210> SEQ ID NO 99
<211> LENGTH: 17
<212> TYPE: PRT
<213> ORGANISM: Homo sapiens

<400> SEQUENCE: 99

Ser Tyr Leu Asp Ser Gly Ile His Phe Gly Ala Thr Thr Thr Ala Pro
1               5                   10                  15

Ser


<210> SEQ ID NO 100
<211> LENGTH: 51
<212> TYPE: DNA
<213> ORGANISM: Homo sapiens

<400> SEQUENCE: 100

tcttacctgg actctggaat ccattttggt gccactacca cagctccttc t              51


<210> SEQ ID NO 101
<211> LENGTH: 17
<212> TYPE: PRT
<213> ORGANISM: Homo sapiens

<400> SEQUENCE: 101

Ser Tyr Leu Asp Ser Gly Ile His Tyr Gly Ala Thr Thr Thr Ala Pro
1               5                   10                  15

Ser


<210> SEQ ID NO 102
<211> LENGTH: 51
<212> TYPE: DNA
<213> ORGANISM: Homo sapiens
```

<400> SEQUENCE: 102
tcttacctgg actctggaat ccattatggt gccactacca cagctccttc t 51

<210> SEQ ID NO 103
<211> LENGTH: 17
<212> TYPE: PRT
<213> ORGANISM: Homo sapiens

<400> SEQUENCE: 103

Ser Gly Ala Thr Thr Thr Ala Pro Cys Leu Ser Gly Lys Gly Asn Pro
1 5 10 15

Glu

<210> SEQ ID NO 104
<211> LENGTH: 51
<212> TYPE: DNA
<213> ORGANISM: Homo sapiens

<400> SEQUENCE: 104
tctggtgcca ctaccacagc tccttgtctg agtggtaaag gcaatcctga g 51

<210> SEQ ID NO 105
<211> LENGTH: 17
<212> TYPE: PRT
<213> ORGANISM: Homo sapiens

<400> SEQUENCE: 105

Ser Gly Ala Thr Thr Thr Ala Pro Phe Leu Ser Gly Lys Gly Asn Pro
1 5 10 15

Glu

<210> SEQ ID NO 106
<211> LENGTH: 51
<212> TYPE: DNA
<213> ORGANISM: Homo sapiens

<400> SEQUENCE: 106
tctggtgcca ctaccacagc tccttttctg agtggtaaag gcaatcctga g 51

<210> SEQ ID NO 107
<211> LENGTH: 17
<212> TYPE: PRT
<213> ORGANISM: Homo sapiens

<400> SEQUENCE: 107

Ser Gly Ala Thr Thr Thr Ala Pro Pro Leu Ser Gly Lys Gly Asn Pro
1 5 10 15

Glu

<210> SEQ ID NO 108
<211> LENGTH: 51
<212> TYPE: DNA
<213> ORGANISM: Homo sapiens

<400> SEQUENCE: 108
tctggtgcca ctaccacagc tcctcctctg agtggtaaag gcaatcctga g 51

<210> SEQ ID NO 109
<211> LENGTH: 17
<212> TYPE: PRT
<213> ORGANISM: Homo sapiens

<400> SEQUENCE: 109

Tyr Val Pro Ser Glu Asp Tyr Tyr Lys Pro Ser Pro Tyr Asp Asp Leu
1 5 10 15

Thr

<210> SEQ ID NO 110
<211> LENGTH: 51
<212> TYPE: DNA
<213> ORGANISM: Homo sapiens

<400> SEQUENCE: 110
tacgtgccca gtgaggacta ctacaagccc tcaccgtatg atgacctcac c 51

<210> SEQ ID NO 111
<211> LENGTH: 17
<212> TYPE: PRT
<213> ORGANISM: Homo sapiens

<400> SEQUENCE: 111

Ile Arg Lys Arg Leu Lys Leu Cys Thr Asp Phe Lys Arg Thr Gly Met
1 5 10 15

Asp

<210> SEQ ID NO 112
<211> LENGTH: 51
<212> TYPE: DNA
<213> ORGANISM: Homo sapiens

<400> SEQUENCE: 112
atccggaaga ggctaaagct ctgcactgac ttcaaacgca cagggatgga t 51

<210> SEQ ID NO 113
<211> LENGTH: 17
<212> TYPE: PRT
<213> ORGANISM: Homo sapiens

<400> SEQUENCE: 113

Val Asp Gly Ala Val Phe Ala Val Phe Lys Ala Val Phe Val Leu Gly
1 5 10 15

Asp

<210> SEQ ID NO 114
<211> LENGTH: 51
<212> TYPE: DNA
<213> ORGANISM: Homo sapiens

<400> SEQUENCE: 114
gtggatggag ccgtgtttgc tgttttcaag gctgtgtttg tacttgggga t 51

<210> SEQ ID NO 115
<211> LENGTH: 17
<212> TYPE: PRT
<213> ORGANISM: Homo sapiens

<400> SEQUENCE: 115

Ile Val Asp Gly Ala Val Phe Ala Gly Leu Lys Ala Val Phe Val Leu
1 5 10 15

Gly

<210> SEQ ID NO 116
<211> LENGTH: 51

<212> TYPE: DNA
<213> ORGANISM: Homo sapiens

<400> SEQUENCE: 116
atcgtggatg gagccgtgtt tgctggtctc aaggctgtgt ttgtacttgg g 51

<210> SEQ ID NO 117
<211> LENGTH: 17
<212> TYPE: PRT
<213> ORGANISM: Homo sapiens

<400> SEQUENCE: 117

Ile Val Asp Gly Ala Val Phe Ala Leu Leu Lys Ala Val Phe Val Leu
1 5 10 15

Gly

<210> SEQ ID NO 118
<211> LENGTH: 51
<212> TYPE: DNA
<213> ORGANISM: Homo sapiens

<400> SEQUENCE: 118
atcgtggatg gagccgtgtt tgctcttctc aaggctgtgt ttgtacttgg g 51

<210> SEQ ID NO 119
<211> LENGTH: 17
<212> TYPE: PRT
<213> ORGANISM: Homo sapiens

<400> SEQUENCE: 119

Thr His Thr Ala Asn Glu Arg Arg Trp Arg Gly Glu Met Arg Asp Leu
1 5 10 15

Phe

<210> SEQ ID NO 120
<211> LENGTH: 51
<212> TYPE: DNA
<213> ORGANISM: Homo sapiens

<400> SEQUENCE: 120
acacacactg ccaatgagcg gcggtggcgt ggtgaaatga gggatctctt t 51

<210> SEQ ID NO 121
<211> LENGTH: 17
<212> TYPE: PRT
<213> ORGANISM: Homo sapiens

<400> SEQUENCE: 121

Gly Arg Phe Ser Lys Val Ser Ser Arg Ala Pro Met Glu Gly Gly Glu
1 5 10 15

Glu

<210> SEQ ID NO 122
<211> LENGTH: 51
<212> TYPE: DNA
<213> ORGANISM: Homo sapiens

<400> SEQUENCE: 122
gggaggttca gcaaggtgtc tagtcgagct cccatggagg gtggggaaga a 51

<210> SEQ ID NO 123
<211> LENGTH: 17

<212> TYPE: PRT
<213> ORGANISM: Homo sapiens

<400> SEQUENCE: 123

Gly Lys Thr Glu Asp Leu Gly Cys Arg Tyr Lys Leu Phe Ser Arg Val
1 5 10 15

Pro

<210> SEQ ID NO 124
<211> LENGTH: 51
<212> TYPE: DNA
<213> ORGANISM: Homo sapiens

<400> SEQUENCE: 124
ggaaagacag aagaccttgg ttgcaggtac aagttattta gtcgtgtgcc a 51

<210> SEQ ID NO 125
<211> LENGTH: 12
<212> TYPE: PRT
<213> ORGANISM: Homo sapiens

<400> SEQUENCE: 125

Met Asn His His Gln Gln Gln Gln Gln Gln Lys Ala
1 5 10

<210> SEQ ID NO 126
<211> LENGTH: 36
<212> TYPE: DNA
<213> ORGANISM: Homo sapiens

<400> SEQUENCE: 126
atgaaccacc accagcagca gcagcagcag aaagcg 36

<210> SEQ ID NO 127
<211> LENGTH: 17
<212> TYPE: PRT
<213> ORGANISM: Homo sapiens

<400> SEQUENCE: 127

His Gly Leu Val Asp Glu Gln Gln Glu Val Arg Thr Ile Ser Ala Leu
1 5 10 15

Ala

<210> SEQ ID NO 128
<211> LENGTH: 51
<212> TYPE: DNA
<213> ORGANISM: Homo sapiens

<400> SEQUENCE: 128
catggtcttg tggatgagca gcaggaagtt cggaccatca gtgctttggc c 51

<210> SEQ ID NO 129
<211> LENGTH: 17
<212> TYPE: PRT
<213> ORGANISM: Homo sapiens

<400> SEQUENCE: 129

Val Cys Arg His Gly Asp Arg Cys Phe Arg Leu His Asn Lys Pro Thr
1 5 10 15

Phe

<210> SEQ ID NO 130

<211> LENGTH: 51
<212> TYPE: DNA
<213> ORGANISM: Homo sapiens

<400> SEQUENCE: 130
gcatgtcgtc atggagacag gtgctttcgg ttgcacaata aaccgacgtt t 51

<210> SEQ ID NO 131
<211> LENGTH: 17
<212> TYPE: PRT
<213> ORGANISM: Homo sapiens

<400> SEQUENCE: 131

Ser Cys Thr Thr Pro Gln Cys Lys Cys Leu Leu Ala Lys Cys Cys Val
1 5 10 15

Asp

<210> SEQ ID NO 132
<211> LENGTH: 51
<212> TYPE: DNA
<213> ORGANISM: Homo sapiens

<400> SEQUENCE: 132
agttgtacta caccgcaatg caaatgcctg cttgcaaaat gttgtgttga t 51

<210> SEQ ID NO 133
<211> LENGTH: 17
<212> TYPE: PRT
<213> ORGANISM: Homo sapiens

<400> SEQUENCE: 133

Ser Ile Leu Ser Lys Gln Val Gln His Lys Pro Lys Thr Gly Arg Ser
1 5 10 15

Leu

<210> SEQ ID NO 134
<211> LENGTH: 51
<212> TYPE: DNA
<213> ORGANISM: Homo sapiens

<400> SEQUENCE: 134
tccatattat ctaaacaggt tcaacataaa ccaaaaactg gtcgaagttt a 51

<210> SEQ ID NO 135
<211> LENGTH: 17
<212> TYPE: PRT
<213> ORGANISM: Homo sapiens

<400> SEQUENCE: 135

Gln Arg Ile Gly Ser Gly Ser Phe Ala Thr Val Tyr Lys Gly Lys Trp
1 5 10 15

His

<210> SEQ ID NO 136
<211> LENGTH: 51
<212> TYPE: DNA
<213> ORGANISM: Homo sapiens

<400> SEQUENCE: 136
caaagaattg gatctggatc atttgcaaca gtctacaagg gaaagtggca t 51

<210> SEQ ID NO 137

<211> LENGTH: 17
<212> TYPE: PRT
<213> ORGANISM: Homo sapiens

<400> SEQUENCE: 137

Gly Asp Phe Gly Leu Ala Thr Val Glu Ser Arg Trp Ser Gly Ser His
1 5 10 15

Gln

<210> SEQ ID NO 138
<211> LENGTH: 51
<212> TYPE: DNA
<213> ORGANISM: Homo sapiens

<400> SEQUENCE: 138
ggtgattttg gtctagctac agtggaatct cgatggagtg ggtcccatca g 51

<210> SEQ ID NO 139
<211> LENGTH: 17
<212> TYPE: PRT
<213> ORGANISM: Homo sapiens

<400> SEQUENCE: 139

Gln Ala Asn Leu Arg His Leu Cys Cys Ile Cys Gly Asn Ser Phe Arg
1 5 10 15

Ala

<210> SEQ ID NO 140
<211> LENGTH: 51
<212> TYPE: DNA
<213> ORGANISM: Homo sapiens

<400> SEQUENCE: 140
caagccaacc ttcgacatct ctgctgcatc tgtgggaatt cttttagagc t 51

<210> SEQ ID NO 141
<211> LENGTH: 17
<212> TYPE: PRT
<213> ORGANISM: Homo sapiens

<400> SEQUENCE: 141

Gln Ala Asn Leu Arg His Leu Cys His Ile Cys Gly Asn Ser Phe Arg
1 5 10 15

Ala

<210> SEQ ID NO 142
<211> LENGTH: 51
<212> TYPE: DNA
<213> ORGANISM: Homo sapiens

<400> SEQUENCE: 142
caagccaacc ttcgacatct ctgccacatc tgtgggaatt cttttagagc t 51

<210> SEQ ID NO 143
<211> LENGTH: 17
<212> TYPE: PRT
<213> ORGANISM: Homo sapiens

<400> SEQUENCE: 143

Asp Arg Cys Leu Lys Lys Val Ser Lys Gly Val Glu Gln Phe Glu Asp
1 5 10 15

Ile

<210> SEQ ID NO 144
<211> LENGTH: 51
<212> TYPE: DNA
<213> ORGANISM: Homo sapiens

<400> SEQUENCE: 144
gatcgctgcc tcaagaaggt gtccaagggc gtggagcagt ttgaagatat t 51

<210> SEQ ID NO 145
<211> LENGTH: 17
<212> TYPE: PRT
<213> ORGANISM: Homo sapiens

<400> SEQUENCE: 145

Ile Lys Thr Trp Val Ala Ser Asn Lys Ile Lys Asp Lys Arg Gln Leu
1 5 10 15

Ile

<210> SEQ ID NO 146
<211> LENGTH: 51
<212> TYPE: DNA
<213> ORGANISM: Homo sapiens

<400> SEQUENCE: 146
atcaagacat gggtagcgtc caacaagatc aaggacaaga ggcagcttat a 51

<210> SEQ ID NO 147
<211> LENGTH: 17
<212> TYPE: PRT
<213> ORGANISM: Homo sapiens

<400> SEQUENCE: 147

Gln Lys Phe Asp Glu Ala Leu Arg Lys Ser Trp Thr Thr Lys Val Asn
1 5 10 15

Trp

<210> SEQ ID NO 148
<211> LENGTH: 51
<212> TYPE: DNA
<213> ORGANISM: Homo sapiens

<400> SEQUENCE: 148
caaaaatttg atgaggcgct caggaaaagc tggactacta aagtgaactg g 51

<210> SEQ ID NO 149
<211> LENGTH: 17
<212> TYPE: PRT
<213> ORGANISM: Homo sapiens

<400> SEQUENCE: 149

Trp Val Lys Pro Ile Ile Ile Gly Cys His Ala Tyr Gly Asp Gln Tyr
1 5 10 15

Arg

<210> SEQ ID NO 150
<211> LENGTH: 51
<212> TYPE: DNA
<213> ORGANISM: Homo sapiens

<400> SEQUENCE: 150
tgggtaaaac ctatcatcat aggttgtcat gcttatgggg atcaatacag a 51

<210> SEQ ID NO 151
<211> LENGTH: 17
<212> TYPE: PRT
<213> ORGANISM: Homo sapiens

<400> SEQUENCE: 151

Trp Val Lys Pro Ile Ile Ile Gly Gly His Ala Tyr Gly Asp Gln Tyr
1 5 10 15

Arg

<210> SEQ ID NO 152
<211> LENGTH: 51
<212> TYPE: DNA
<213> ORGANISM: Homo sapiens

<400> SEQUENCE: 152
tgggtaaaac ctatcatcat aggtggtcat gcttatgggg atcaatacag a 51

<210> SEQ ID NO 153
<211> LENGTH: 17
<212> TYPE: PRT
<213> ORGANISM: Homo sapiens

<400> SEQUENCE: 153

Trp Val Lys Pro Ile Ile Ile Gly His His Ala Tyr Gly Asp Gln Tyr
1 5 10 15

Arg

<210> SEQ ID NO 154
<211> LENGTH: 51
<212> TYPE: DNA
<213> ORGANISM: Homo sapiens

<400> SEQUENCE: 154
tgggtaaaac ctatcatcat aggtcatcat gcttatgggg atcaatacag a 51

<210> SEQ ID NO 155
<211> LENGTH: 17
<212> TYPE: PRT
<213> ORGANISM: Homo sapiens

<400> SEQUENCE: 155

Tyr Lys Leu Val Val Val Gly Ala Asp Gly Val Gly Lys Ser Ala Leu
1 5 10 15

Thr

<210> SEQ ID NO 156
<211> LENGTH: 51
<212> TYPE: DNA
<213> ORGANISM: Homo sapiens

<400> SEQUENCE: 156
tataagctgg tggtggtggg cgccgacggt gtgggcaaga gtgcgctgac c 51

<210> SEQ ID NO 157
<211> LENGTH: 17
<212> TYPE: PRT
<213> ORGANISM: Homo sapiens

<400> SEQUENCE: 157

Tyr Lys Leu Val Val Val Gly Ala Arg Gly Val Gly Lys Ser Ala Leu 1               5                   10                  15

Thr

<210> SEQ ID NO 158
<211> LENGTH: 51
<212> TYPE: DNA
<213> ORGANISM: Homo sapiens

<400> SEQUENCE: 158
tataagctgg tggtggtggg cgcccgcggt gtgggcaaga gtgcgctgac c               51

<210> SEQ ID NO 159
<211> LENGTH: 17
<212> TYPE: PRT
<213> ORGANISM: Homo sapiens

<400> SEQUENCE: 159

Leu Asp Ile Leu Asp Thr Ala Gly Lys Glu Glu Tyr Ser Ala Met Arg
1               5                   10                  15

Asp

<210> SEQ ID NO 160
<211> LENGTH: 51
<212> TYPE: DNA
<213> ORGANISM: Homo sapiens

<400> SEQUENCE: 160
ttggacatcc tggataccgc cggaaaggag gagtacagcg ccatgcggga c               51

<210> SEQ ID NO 161
<211> LENGTH: 17
<212> TYPE: PRT
<213> ORGANISM: Homo sapiens

<400> SEQUENCE: 161

Leu Asp Ile Leu Asp Thr Ala Gly Leu Glu Glu Tyr Ser Ala Met Arg
1               5                   10                  15

Asp

<210> SEQ ID NO 162
<211> LENGTH: 51
<212> TYPE: DNA
<213> ORGANISM: Homo sapiens

<400> SEQUENCE: 162
ttggacatcc tggataccgc cggcctggag gagtacagcg ccatgcggga c               51

<210> SEQ ID NO 163
<211> LENGTH: 17
<212> TYPE: PRT
<213> ORGANISM: Homo sapiens

<400> SEQUENCE: 163

Leu Asp Ile Leu Asp Thr Ala Gly Arg Glu Glu Tyr Ser Ala Met Arg
1               5                   10                  15

Asp

<210> SEQ ID NO 164
<211> LENGTH: 51
<212> TYPE: DNA
<213> ORGANISM: Homo sapiens

<400> SEQUENCE: 164
ttggacatcc tggataccgc cggccgggag gagtacagcg ccatgcggga c 51

<210> SEQ ID NO 165
<211> LENGTH: 17
<212> TYPE: PRT
<213> ORGANISM: Homo sapiens

<400> SEQUENCE: 165

Glu Gly Trp Leu His Lys Arg Gly Lys Tyr Ile Lys Thr Trp Arg Pro
1 5 10 15

Arg

<210> SEQ ID NO 166
<211> LENGTH: 51
<212> TYPE: DNA
<213> ORGANISM: Homo sapiens

<400> SEQUENCE: 166
gagggttggc tgcacaaacg agggaagtac atcaagacct ggcggccacg c 51

<210> SEQ ID NO 167
<211> LENGTH: 17
<212> TYPE: PRT
<213> ORGANISM: Homo sapiens

<400> SEQUENCE: 167

Ile Ala Arg Glu Leu His Gln Phe Ala Phe Asp Leu Leu Ile Lys Ser
1 5 10 15

His

<210> SEQ ID NO 168
<211> LENGTH: 51
<212> TYPE: DNA
<213> ORGANISM: Homo sapiens

<400> SEQUENCE: 168
attgcgagag agctgcatca gttcgctttt gacctgctaa tcaagtcaca c 51

<210> SEQ ID NO 169
<211> LENGTH: 17
<212> TYPE: PRT
<213> ORGANISM: Homo sapiens

<400> SEQUENCE: 169

Ile Ala Arg Glu Leu His Gln Phe Gly Phe Asp Leu Leu Ile Lys Ser
1 5 10 15

His

<210> SEQ ID NO 170
<211> LENGTH: 51
<212> TYPE: DNA
<213> ORGANISM: Homo sapiens

<400> SEQUENCE: 170
attgcgagag agctgcatca gttcggtttt gacctgctaa tcaagtcaca c 51

<210> SEQ ID NO 171
<211> LENGTH: 17
<212> TYPE: PRT
<213> ORGANISM: Homo sapiens -continued

<400> SEQUENCE: 171

Gln Pro Asp Ser Phe Ala Ala Leu His Ser Ser Leu Asn Glu Leu Gly
1               5                   10                  15

Glu

<210> SEQ ID NO 172
<211> LENGTH: 51
<212> TYPE: DNA
<213> ORGANISM: Homo sapiens

<400> SEQUENCE: 172
cagcccgact cctttgcagc cttgcactct agcctcaatg aactgggaga g          51

<210> SEQ ID NO 173
<211> LENGTH: 17
<212> TYPE: PRT
<213> ORGANISM: Homo sapiens

<400> SEQUENCE: 173

Gln Met Ala Val Ile Gln Tyr Ser Leu Met Gly Leu Met Val Phe Ala
1               5                   10                  15

Met

<210> SEQ ID NO 174
<211> LENGTH: 51
<212> TYPE: DNA
<213> ORGANISM: Homo sapiens

<400> SEQUENCE: 174
cagatggctg tcattcagta ctccttgatg gggctcatgg tgtttgccat g          51

<210> SEQ ID NO 175
<211> LENGTH: 17
<212> TYPE: PRT
<213> ORGANISM: Homo sapiens

<400> SEQUENCE: 175

Gln Met Ala Val Ile Gln Tyr Ser Phe Met Gly Leu Met Val Phe Ala
1               5                   10                  15

Met

<210> SEQ ID NO 176
<211> LENGTH: 51
<212> TYPE: DNA
<213> ORGANISM: Homo sapiens

<400> SEQUENCE: 176
cagatggctg tcattcagta ctcctttatg gggctcatgg tgtttgccat g          51

<210> SEQ ID NO 177
<211> LENGTH: 68
<212> TYPE: PRT
<213> ORGANISM: Homo sapiens

<400> SEQUENCE: 177

Gln Asn Leu Gln Asn Gly Gly Gly Ser Arg Ser Ser Ala Thr Leu Pro
1               5                   10                  15

Gly Arg Arg Arg Arg Arg Trp Leu Arg Arg Arg Gln Pro Ile Ser
            20                  25                  30

Val Ala Pro Ala Gly Pro Pro Arg Arg Pro Asn Gln Lys Pro Asn Pro
            35                  40                  45

Pro Gly Gly Ala Arg Cys Val Ile Met Arg Pro Thr Trp Pro Gly Thr
    50                  55                  60

Ser Ala Phe Thr
65

<210> SEQ ID NO 178
<211> LENGTH: 204
<212> TYPE: DNA
<213> ORGANISM: Homo sapiens

<400> SEQUENCE: 178
cagaacctgc agaatggagg ggggagcagg tcttcagcca cactgccggg gcggcggcgg 60
cggcggtggc tgcggcggcg gcggcagcca atatcagtag ctcctgcggg gccccctcgc 120
cgaccaaacc aaaaaccaaa cccacctggc ggtgcgaggt gtgtgattat gagaccaacg 180
tggccaggaa cctccgcatt caca 204

<210> SEQ ID NO 179
<211> LENGTH: 33
<212> TYPE: PRT
<213> ORGANISM: Homo sapiens

<400> SEQUENCE: 179

Gln Asn Leu Gln Asn Gly Gly Gly Gly Ala Gly Leu Gln Pro His Cys
1               5                   10                  15

Arg Gly Gly Gly Gly Gly Gly Gly Cys Gly Gly Gly Gly Ser Gln Tyr
            20                  25                  30

Gln

<210> SEQ ID NO 180
<211> LENGTH: 102
<212> TYPE: DNA
<213> ORGANISM: Homo sapiens

<400> SEQUENCE: 180
cagaacctgc agaatggagg gggggagca ggtcttcagc cacactgccg gggcggcggc 60
ggcggcggtg gctgcggcgg cggcggcagc caatatcagt ag 102

<210> SEQ ID NO 181
<211> LENGTH: 10
<212> TYPE: PRT
<213> ORGANISM: Homo sapiens

<400> SEQUENCE: 181

Asn Gln Glu Lys Glu Ala Glu Lys Asn Tyr
1               5                   10

<210> SEQ ID NO 182
<211> LENGTH: 33
<212> TYPE: DNA
<213> ORGANISM: Homo sapiens

<400> SEQUENCE: 182
aaccaagaga aagaggcaga aaaaaactat tga 33

<210> SEQ ID NO 183
<211> LENGTH: 40
<212> TYPE: PRT
<213> ORGANISM: Homo sapiens

<400> SEQUENCE: 183

Asp Ala Ala Val Ser Pro Arg Gly Leu Gln His Arg Gln Gly Arg Gly
1 5 10 15

Asn Leu Gly Trp Trp Gln Ser Pro Leu Arg Lys Val Arg Val Pro Lys
20 25 30

Arg Arg Met Val Tyr His Pro Ser
35 40

<210> SEQ ID NO 184
<211> LENGTH: 123
<212> TYPE: DNA
<213> ORGANISM: Homo sapiens

<400> SEQUENCE: 184
gatgctgctg tcagtcccag ggggctgcag cacaggcagg ggagagggaa tctggggtgg 60
tggcagtctc ccctgagaaa agtgagagtc cccaaaagga ggatggttta tcatcccagt 120
tga 123

<210> SEQ ID NO 185
<211> LENGTH: 33
<212> TYPE: PRT
<213> ORGANISM: Homo sapiens

<400> SEQUENCE: 185

Phe Val Val Ser Val Val Lys Lys Asn Arg Thr Cys Pro Phe Arg Leu
1 5 10 15

Phe Val Arg Arg Met Leu Gln Phe Thr Gly Asn Lys Val Leu Asp Arg
20 25 30

Pro

<210> SEQ ID NO 186
<211> LENGTH: 102
<212> TYPE: DNA
<213> ORGANISM: Homo sapiens

<400> SEQUENCE: 186
tttgtcgttt ctgttgtgaa aaaaaacagg acttgcccct ttcgtctatt tgtcagacga 60
atgttacaat ttactggcaa taaagttttg gatagacctt aa 102

<210> SEQ ID NO 187
<211> LENGTH: 9
<212> TYPE: PRT
<213> ORGANISM: Homo sapiens

<400> SEQUENCE: 187

Arg Ser Arg Arg Ser Ala Ile Lys Arg
1 5

<210> SEQ ID NO 188
<211> LENGTH: 32
<212> TYPE: DNA
<213> ORGANISM: Homo sapiens

<400> SEQUENCE: 188
agaagcagaa gatcggctat aaaaagataa tg 32

<210> SEQ ID NO 189
<211> LENGTH: 24
<212> TYPE: PRT
<213> ORGANISM: Homo sapiens

<400> SEQUENCE: 189

```
Ser Ile Ile Val Gln Glu Arg Glu Arg Ala Glu Arg Arg Val Arg Arg
1               5                   10                  15

Gly Gln Val Met Glu Ile Val Asp
            20
```

<210> SEQ ID NO 190
<211> LENGTH: 75
<212> TYPE: DNA
<213> ORGANISM: Homo sapiens

<400> SEQUENCE: 190

```
agtataattg tacaagagag agagagagca gagagaaggg tcagaagagg ccaagtgatg     60

gaaatagtgg attaa                                                      75
```

<210> SEQ ID NO 191
<211> LENGTH: 34
<212> TYPE: PRT
<213> ORGANISM: Homo sapiens

<400> SEQUENCE: 191

```
Asn Asn Leu Val Thr Glu Lys Lys His Arg Asn Val Gln Cys His Asp
1               5                   10                  15

Ala Val Glu Glu Asn Gly Gln Ser Ser Phe Ile Thr Ser Pro Ile Leu
            20                  25                  30

His Ser
```

<210> SEQ ID NO 192
<211> LENGTH: 107
<212> TYPE: DNA
<213> ORGANISM: Homo sapiens

<400> SEQUENCE: 192

```
aataacttgg tcacagaaaa aaaacacaga aatgtgcaat gtcatgatgc agttgaggaa     60

aatggccaat catcctttat tacatcgcca atattacaca gctgaaa                  107
```

<210> SEQ ID NO 193
<211> LENGTH: 48
<212> TYPE: PRT
<213> ORGANISM: Homo sapiens

<400> SEQUENCE: 193

```
His Pro Gln Arg Lys Arg Arg Gly Val Pro Pro Ser Pro Pro Leu Ala
1               5                   10                  15

Leu Gly Pro Arg Met Gln Leu Cys Thr Gln Leu Ala Arg Phe Phe Pro
            20                  25                  30

Ile Thr Pro Pro Val Trp His Ile Leu Gly Pro Gln Arg His Thr Pro
        35                  40                  45
```

<210> SEQ ID NO 194
<211> LENGTH: 149
<212> TYPE: DNA
<213> ORGANISM: Homo sapiens

<400> SEQUENCE: 194

```
cacccacaga ggaaaaggcg gggggtccct ccgagcccac ccctggctct cggccccagg     60

atgcaactgt gcacccagct tgccagattt ttccccatta cacccccagt gtggcatatc    120

cttggtcccc agaggcacac cccttgatc                                      149
```

<210> SEQ ID NO 195
<211> LENGTH: 31
<212> TYPE: PRT
<213> ORGANISM: Homo sapiens

<400> SEQUENCE: 195

Ala Ser Arg His His Leu Trp Gly Ala Thr Ala Gly Thr Pro Ala Pro
1               5                   10                  15

Pro Pro Val Pro Thr Cys Ser Pro Arg Thr Leu Arg Cys Leu Pro
            20                  25                  30

<210> SEQ ID NO 196
<211> LENGTH: 98
<212> TYPE: DNA
<213> ORGANISM: Homo sapiens

<400> SEQUENCE: 196
gccagccggc accatctgtg gggggcaaca gcgggcaccc ccgcaccacc ccccgtgccc    60
acctgttcac ccaggaccct gcgatgcctc ccctgacc                           98

<210> SEQ ID NO 197
<211> LENGTH: 13
<212> TYPE: PRT
<213> ORGANISM: Homo sapiens

<400> SEQUENCE: 197

Gly Pro Gly Glu Ala Gly Gly Pro Ser Pro Gln Gly Gly
1               5                   10

<210> SEQ ID NO 198
<211> LENGTH: 44
<212> TYPE: DNA
<213> ORGANISM: Homo sapiens

<400> SEQUENCE: 198
gggcctgggg aggctggggg cccctcaccc caaggcgggt gagc                    44

<210> SEQ ID NO 199
<211> LENGTH: 19
<212> TYPE: PRT
<213> ORGANISM: Homo sapiens

<400> SEQUENCE: 199

Gly Gly Gly Pro Ser Gly Ser Gly Glu Ala Pro Thr Ser Pro Ser Ala
1               5                   10                  15

Leu Arg Thr

<210> SEQ ID NO 200
<211> LENGTH: 62
<212> TYPE: DNA
<213> ORGANISM: Homo sapiens

<400> SEQUENCE: 200
ggcggggggc ccagcggctc aggggaggct cccacttctc cttcagccct gaggacatga    60
aa                                                                   62

<210> SEQ ID NO 201
<211> LENGTH: 23
<212> TYPE: PRT
<213> ORGANISM: Homo sapiens

<400> SEQUENCE: 201

Gly Asn Pro Asp Val Pro Pro Pro Val Leu Phe Lys Ala Asp Gln Ser
1 5 10 15

Glu Ser Ser Leu Ser Ser Gly
20

<210> SEQ ID NO 202
<211> LENGTH: 72
<212> TYPE: DNA
<213> ORGANISM: Homo sapiens

<400> SEQUENCE: 202
ggaaatccag atgtcccacc ccccgtcctc ttcaaggcag atcagagcga gagttctttg 60
tcaagtgggt ag 72

<210> SEQ ID NO 203
<211> LENGTH: 10
<212> TYPE: PRT
<213> ORGANISM: Homo sapiens

<400> SEQUENCE: 203

Ala Phe Cys Tyr Cys Gly Glu Lys Val Pro
1 5 10

<210> SEQ ID NO 204
<211> LENGTH: 35
<212> TYPE: DNA
<213> ORGANISM: Homo sapiens

<400> SEQUENCE: 204
gctttttgtt actgtgggga aaaagttcct tagga 35

<210> SEQ ID NO 205
<211> LENGTH: 16
<212> TYPE: PRT
<213> ORGANISM: Homo sapiens

<400> SEQUENCE: 205

Thr Leu His Pro Asp Ser Gly Asn Gly Cys Tyr Leu Arg Arg Gln Lys
1 5 10 15

<210> SEQ ID NO 206
<211> LENGTH: 50
<212> TYPE: DNA
<213> ORGANISM: Homo sapiens

<400> SEQUENCE: 206
acgctgcacc cggactccgg caacggctgc tacttgcgcc gccagaagcg 50

<210> SEQ ID NO 207
<211> LENGTH: 16
<212> TYPE: PRT
<213> ORGANISM: Homo sapiens

<400> SEQUENCE: 207

Leu His Pro Asp Ser Gly Asn Met Tyr Gly Cys Tyr Leu Arg Arg Gln
1 5 10 15

<210> SEQ ID NO 208
<211> LENGTH: 53
<212> TYPE: DNA
<213> ORGANISM: Homo sapiens

<400> SEQUENCE: 208
acgctgcacc cggactccgg caacatgtac ggctgctact tgcgccgcca gaa 53

<210> SEQ ID NO 209
<211> LENGTH: 17
<212> TYPE: PRT
<213> ORGANISM: Homo sapiens

<400> SEQUENCE: 209

Leu His Pro Asp Ser Gly Asn Met Cys Cys Tyr Leu Arg Arg Gln Lys
1 5 10 15

Arg

<210> SEQ ID NO 210
<211> LENGTH: 51
<212> TYPE: DNA
<213> ORGANISM: Homo sapiens

<400> SEQUENCE: 210
ctgcacccgg actccggcaa catgtgctgc tacttgcgcc gccagaagcg c 51

<210> SEQ ID NO 211
<211> LENGTH: 16
<212> TYPE: PRT
<213> ORGANISM: Homo sapiens

<400> SEQUENCE: 211

Cys Gly Ala Ser Ala Cys Asp Val Ser Leu Ile Ala Met Asp Ser Ala
1 5 10 15

<210> SEQ ID NO 212
<211> LENGTH: 48
<212> TYPE: DNA
<213> ORGANISM: Homo sapiens

<400> SEQUENCE: 212
tgcggggcct ctgcctgtga tgtctccctc attgctatgg acagtgct 48

<210> SEQ ID NO 213
<211> LENGTH: 16
<212> TYPE: PRT
<213> ORGANISM: Homo sapiens

<400> SEQUENCE: 213

Thr Glu Tyr Asn Gln Lys Leu Gln Val Asn Gln Phe Ser Glu Ser Lys
1 5 10 15

<210> SEQ ID NO 214
<211> LENGTH: 48
<212> TYPE: DNA
<213> ORGANISM: Homo sapiens

<400> SEQUENCE: 214
accgaataca accagaaatt acaagtgaat caatttagtg aatccaaa 48

<210> SEQ ID NO 215
<211> LENGTH: 24
<212> TYPE: PRT
<213> ORGANISM: Homo sapiens

<400> SEQUENCE: 215

Thr Glu Ile Ser Cys Cys Thr Leu Ser Ser Glu Glu Asn Glu Tyr Leu
1 5 10 15

Pro Arg Pro Glu Trp Gln Leu Gln
20

<210> SEQ ID NO 216
<211> LENGTH: 72
<212> TYPE: DNA
<213> ORGANISM: Homo sapiens

<400> SEQUENCE: 216
acagaaattt catgttgcac cctgagcagt gaggagaatg aataccttcc aagaccagag 60
tggcagctcc ag 72

<210> SEQ ID NO 217
<211> LENGTH: 16
<212> TYPE: PRT
<213> ORGANISM: Homo sapiens

<400> SEQUENCE: 217

Gly Leu Val Ser Phe Gly Glu His Phe Cys Leu Pro Cys Ala Leu Cys
1 5 10 15

<210> SEQ ID NO 218
<211> LENGTH: 50
<212> TYPE: DNA
<213> ORGANISM: Homo sapiens

<400> SEQUENCE: 218
gggctggtgt ccttcgggga gcacttttgt ctgccctgcg ccctctgcca 50

<210> SEQ ID NO 219
<211> LENGTH: 16
<212> TYPE: PRT
<213> ORGANISM: Homo sapiens

<400> SEQUENCE: 219

Asn Ser Lys Met Ala Leu Asn Ser Glu Ala Leu Ser Val Val Ser Glu
1 5 10 15

<210> SEQ ID NO 220
<211> LENGTH: 48
<212> TYPE: DNA
<213> ORGANISM: Homo sapiens

<400> SEQUENCE: 220
aacagcaaga tggctttgaa ctcagaagcc ttatcagttg tgagtgag 48

<210> SEQ ID NO 221
<211> LENGTH: 14
<212> TYPE: PRT
<213> ORGANISM: Homo sapiens

<400> SEQUENCE: 221

Cys Glu Glu Arg Gly Ala Ala Gly Ser Leu Ile Ser Cys Glu
1 5 10

<210> SEQ ID NO 222
<211> LENGTH: 42
<212> TYPE: DNA
<213> ORGANISM: Homo sapiens

<400> SEQUENCE: 222
tgtgaggagc gcggcgcggc aggaagcctt atcagttgtg ag 42

<210> SEQ ID NO 223
<211> LENGTH: 69
<212> TYPE: PRT
<213> ORGANISM: Homo sapiens

<400> SEQUENCE: 223

Leu Trp Phe Gln Ser Ser Glu Leu Ser Pro Thr Gly Ala Pro Trp Pro
1 5 10 15

Ser Arg Arg Pro Thr Trp Arg Gly Thr Thr Val Ser Pro Arg Thr Ala
20 25 30

Thr Ser Ser Ala Arg Thr Cys Cys Gly Thr Lys Trp Pro Ser Ser Gln
35 40 45

Glu Ala Ala Leu Gly Leu Gly Ser Gly Leu Leu Arg Phe Ser Cys Gly
50 55 60

Thr Ala Ala Ile Arg
65

<210> SEQ ID NO 224
<211> LENGTH: 207
<212> TYPE: DNA
<213> ORGANISM: Homo sapiens

<400> SEQUENCE: 224
ctgtggttcc agagcagtga gctgtccccg acgggagcgc catggcccag ccgccgcccg 60
acgtggaggg ggacgactgt ctccccgcgt accgccacct cttctgcccg gacctgctgc 120
gggacaaagt ggccttcatc acaggaggcg gctctgggat tgggttccgg attgctgaga 180
ttttcatgcg gcacggctgc catacgg 207

<210> SEQ ID NO 225
<211> LENGTH: 70
<212> TYPE: PRT
<213> ORGANISM: Homo sapiens

<400> SEQUENCE: 225

Trp Gly Met Glu Leu Ala Ala Ser Arg Arg Phe Ser Trp Asp His His
1 5 10 15

Ser Ala Gly Gly Pro Pro Arg Val Pro Ser Val Arg Ser Gly Ala Ala
20 25 30

Gln Val Gln Pro Lys Asp Pro Leu Pro Leu Arg Thr Leu Ala Gly Cys
35 40 45

Leu Ala Arg Thr Ala His Leu Arg Pro Gly Ala Glu Ser Leu Pro Gln
50 55 60

Pro Gln Leu His Cys Thr
65 70

<210> SEQ ID NO 226
<211> LENGTH: 210
<212> TYPE: DNA
<213> ORGANISM: Homo sapiens

<400> SEQUENCE: 226
tgggggatgg agttggcagc gtctcggagg ttctcctggg accaccactc cgccgggggg 60
ccgcccagag tgccaagcgt ccgatccggc gccgcccaag tgcagcccaa ggacccgctc 120
ccgctccgca ccctggcagg ctgcctagcc aggactgcgc acctgcgccc tggggcggag 180
tccttacccc aaccccagct tcactgcaca 210

<210> SEQ ID NO 227

<211> LENGTH: 28
<212> TYPE: PRT
<213> ORGANISM: Homo sapiens

<400> SEQUENCE: 227

Lys Glu Gln Ile Leu Ala Val Ala Ser Leu Val Ser Ser Gln Ser Ile
1 5 10 15

His Pro Ser Trp Gly Gln Ser Pro Leu Ser Arg Ile
20 25

<210> SEQ ID NO 228
<211> LENGTH: 84
<212> TYPE: DNA
<213> ORGANISM: Homo sapiens

<400> SEQUENCE: 228
aaggaacaga ttttagctgt ggccagtctc gtttcctctc agtccatcca cccttcatgg 60
ggccagagcc ctctctccag aatc 84

<210> SEQ ID NO 229
<211> LENGTH: 14
<212> TYPE: PRT
<213> ORGANISM: Homo sapiens

<400> SEQUENCE: 229

Leu Glu Leu Glu Leu Ser Glu Gly Val Cys Phe Arg Leu Arg
1 5 10

<210> SEQ ID NO 230
<211> LENGTH: 42
<212> TYPE: DNA
<213> ORGANISM: Homo sapiens

<400> SEQUENCE: 230
ctggagctgg agctgtcgga aggagtctgc ttcagattaa ga 42

<210> SEQ ID NO 231
<211> LENGTH: 17
<212> TYPE: PRT
<213> ORGANISM: Homo sapiens

<400> SEQUENCE: 231

Gln Gln Leu Arg Ile Phe Cys Ala Ala Met Ala Ser Asn Glu Asp Phe
1 5 10 15

Ser

<210> SEQ ID NO 232
<211> LENGTH: 52
<212> TYPE: DNA
<213> ORGANISM: Homo sapiens

<400> SEQUENCE: 232
cagcagctaa ggatattttg tgcagccatg gcctccaacg aagatttctc ca 52

<210> SEQ ID NO 233
<211> LENGTH: 31
<212> TYPE: PRT
<213> ORGANISM: Homo sapiens

<400> SEQUENCE: 233

Asp Gly Phe Ser Gly Ser Leu Phe Ala Val Val Thr Arg Arg Cys Tyr
1 5 10 15

-continued

Phe Leu Lys Trp Arg Thr Ile Phe Pro Gln Ser Leu Met Trp Leu
20 25 30

<210> SEQ ID NO 234
<211> LENGTH: 93
<212> TYPE: DNA
<213> ORGANISM: Homo sapiens

<400> SEQUENCE: 234
gacgggttta gcggcagcct cttcgcagtt gtcaccagac gctgttactt cctaaaatgg 60
cggacaatct tcccacagag tttgatgtgg tta 93

<210> SEQ ID NO 235
<211> LENGTH: 16
<212> TYPE: PRT
<213> ORGANISM: Homo sapiens

<400> SEQUENCE: 235

Lys Met His Phe Ser Leu Lys Glu His Pro Pro Pro Pro Cys Pro Pro
1 5 10 15

<210> SEQ ID NO 236
<211> LENGTH: 48
<212> TYPE: DNA
<213> ORGANISM: Homo sapiens

<400> SEQUENCE: 236
aaaatgcact tctccctcaa ggagcaccca ccgccccctt gcccgcct 48

<210> SEQ ID NO 237
<211> LENGTH: 31
<212> TYPE: PRT
<213> ORGANISM: Homo sapiens

<400> SEQUENCE: 237

Asp Leu Arg Arg Val Ala Thr Tyr Cys Ala Pro Leu Pro Ser Ser Trp
1 5 10 15

Arg Pro Gly Thr Gly Thr Thr Ile Pro Pro Arg Met Arg Ser Cys
20 25 30

<210> SEQ ID NO 238
<211> LENGTH: 93
<212> TYPE: DNA
<213> ORGANISM: Homo sapiens

<400> SEQUENCE: 238
gatctgcgcc gggtcgccac atactgcgct cctttaccct catcgtggag gcctgggact 60
gggacaacga taccaccccg aatgaggagc tgc 93

<210> SEQ ID NO 239
<211> LENGTH: 48
<212> TYPE: PRT
<213> ORGANISM: Homo sapiens

<400> SEQUENCE: 239

Leu Gln Glu Arg Met Glu Leu Leu Ala Cys Gly Ala Glu Arg Gly Ala
1 5 10 15

Gly Gly Trp Gly Gly Gly Gly Gly Gly Gly Gly Gly Asp Arg Arg Gly
20 25 30

Gly Gly Gly Ser Ala Pro Ala Leu Ala Asp Phe Ala Gly Gly Arg Gly
35 40 45

<210> SEQ ID NO 240
<211> LENGTH: 144
<212> TYPE: DNA
<213> ORGANISM: Homo sapiens

<400> SEQUENCE: 240
ttgcaggagc ggatggagtt gcttgcctgc ggagccgagc gcggggccgg cggctggggg 60
ggaggcggtg gcggcggcgg cggcgaccga agaggaggag gaggaagcgc gccagctctt 120
gcagactttg caggcggccg aggg 144

<210> SEQ ID NO 241
<211> LENGTH: 47
<212> TYPE: PRT
<213> ORGANISM: Homo sapiens

<400> SEQUENCE: 241

Leu Thr Phe Leu Asp Phe Ile Gln Val Thr Leu Arg Val Met Ser Gly
1 5 10 15

Ser Gln Met Glu Asn Gly Ser Ser Tyr Phe Phe Lys Pro Phe Ser Trp
20 25 30

Gly Leu Gly Val Gly Leu Ser Ala Trp Leu Cys Val Met Leu Thr
35 40 45

<210> SEQ ID NO 242
<211> LENGTH: 141
<212> TYPE: DNA
<213> ORGANISM: Homo sapiens

<400> SEQUENCE: 242
ctgacgtttt tagatttcat ccaggtaacg ttgagagtaa tgtcaggatc tcaaatggaa 60
aacggaagtt cctatttttt caagcccttt tcatggggtc tgggggtggg actctcggcc 120
tggctgtgtg taatgttaac t 141

<210> SEQ ID NO 243
<211> LENGTH: 51
<212> TYPE: PRT
<213> ORGANISM: Homo sapiens

<400> SEQUENCE: 243

Phe Met Ile Gly Glu Leu Val Gly Glu Leu Cys Cys Gln Leu Thr Phe
1 5 10 15

Arg Leu Pro Phe Leu Glu Ser Leu Cys Gln Ala Val Val Thr Gln Ala
20 25 30

Leu Arg Phe Asn Pro Ser Phe Gln Glu Val Cys Ile Tyr Gln Asp Thr
35 40 45

Asp Leu Met
50

<210> SEQ ID NO 244
<211> LENGTH: 153
<212> TYPE: DNA
<213> ORGANISM: Homo sapiens

<400> SEQUENCE: 244
ttcatgattg gagaacttgt aggtgagttg tgttgccaac tcactttccg tttacctttc 60
ctcgagagtc tttgtcaagc tgtagttaca caggctttga ggtttaaccc atcttttcag 120
gaagtttgta tttatcaaga cactgatctc atg 153

-continued

<210> SEQ ID NO 245
<211> LENGTH: 16
<212> TYPE: PRT
<213> ORGANISM: Homo sapiens

<400> SEQUENCE: 245

Val Ala Met Met Val Pro Asp Arg Gln Val His Tyr Asp Phe Gly Leu
1               5                   10                  15

<210> SEQ ID NO 246
<211> LENGTH: 48
<212> TYPE: DNA
<213> ORGANISM: Homo sapiens

<400> SEQUENCE: 246
gttgctatga tggttcctga tagacaggtt cattatgact ttggattg 48

<210> SEQ ID NO 247
<211> LENGTH: 24
<212> TYPE: PRT
<213> ORGANISM: Homo sapiens

<400> SEQUENCE: 247

Trp Cys Pro Leu Asp Leu Arg Leu Gly Ser Thr Gly Cys Leu Thr Cys
1               5                   10                  15

Arg His His Gln Thr Ser His Glu
            20

<210> SEQ ID NO 248
<211> LENGTH: 72
<212> TYPE: DNA
<213> ORGANISM: Homo sapiens

<400> SEQUENCE: 248
tggtgtccgc tggatcttag actcggttcc actggatgtc tcacatgcag acatcatcaa 60
acgtcacatg ag 72

<210> SEQ ID NO 249
<211> LENGTH: 25
<212> TYPE: PRT
<213> ORGANISM: Homo sapiens

<400> SEQUENCE: 249

Val Val Gly Arg Arg His Glu Thr Ala Pro Gln Pro Leu Leu Val Pro
1               5                   10                  15

Asp Arg Ala Gly Gly Glu Gly Gly Ala
            20                  25

<210> SEQ ID NO 250
<211> LENGTH: 75
<212> TYPE: DNA
<213> ORGANISM: Homo sapiens

<400> SEQUENCE: 250
gtcgtgggaa ggcgtcatga aacagctcct caacccctgc tggtgcccga ccgagctggt 60
ggtgaagggg gagca 75

<210> SEQ ID NO 251
<211> LENGTH: 17
<212> TYPE: PRT
<213> ORGANISM: Homo sapiens

<400> SEQUENCE: 251

Asp Tyr Trp Ala Gln Lys Glu Lys Ile Ser Ile Pro Arg Thr His Leu
1 5 10 15

Cys

<210> SEQ ID NO 252
<211> LENGTH: 51
<212> TYPE: DNA
<213> ORGANISM: Homo sapiens

<400> SEQUENCE: 252
gactactggg ctcaaaagga gaagatcagc atccccagaa cacacctgtg t 51

<210> SEQ ID NO 253
<211> LENGTH: 18
<212> TYPE: PRT
<213> ORGANISM: Homo sapiens

<400> SEQUENCE: 253

Asp Tyr Trp Ala Gln Lys Glu Lys Gly Ser Ser Ser Phe Leu Arg Pro
1 5 10 15

Ser Cys

<210> SEQ ID NO 254
<211> LENGTH: 54
<212> TYPE: DNA
<213> ORGANISM: Homo sapiens

<400> SEQUENCE: 254
gactactggg ctcaaaagga gaagggatca tcttcattcc tgcgaccatc ctgt 54

<210> SEQ ID NO 255
<211> LENGTH: 14
<212> TYPE: PRT
<213> ORGANISM: Homo sapiens

<400> SEQUENCE: 255

Leu Val Leu Gly Val Leu Ser Gly His Ser Gly Ser Arg Leu
1 5 10

<210> SEQ ID NO 256
<211> LENGTH: 42
<212> TYPE: DNA
<213> ORGANISM: Homo sapiens

<400> SEQUENCE: 256
cttgtacttg gtgtattgag cgggcacagt ggctcacgcc ta 42

<210> SEQ ID NO 257
<211> LENGTH: 25
<212> TYPE: PRT
<213> ORGANISM: Homo sapiens

<400> SEQUENCE: 257

Pro Val Pro Thr Ala Thr Pro Gly Val Arg Ser Val Thr Ser Pro Gln
1 5 10 15

Gly Leu Gly Leu Phe Leu Lys Phe Ile
20 25

<210> SEQ ID NO 258
<211> LENGTH: 75
<212> TYPE: DNA

<213> ORGANISM: Homo sapiens

<400> SEQUENCE: 258
cctgtcccaa ctgctacacc tggggtaaga tcagtgacta gtccccaggg gctgggcctt 60
ttccttaagt ttatt 75

<210> SEQ ID NO 259
<211> LENGTH: 28
<212> TYPE: PRT
<213> ORGANISM: Homo sapiens

<400> SEQUENCE: 259

Lys Glu Asn Asp Val Arg Glu Val Cys Asp Val Tyr Leu Gln Met Gln
1 5 10 15

Ile Phe Phe His Phe Lys Phe Arg Ser Tyr Phe His
20 25

<210> SEQ ID NO 260
<211> LENGTH: 84
<212> TYPE: DNA
<213> ORGANISM: Homo sapiens

<400> SEQUENCE: 260
aaggaaaatg atgtccgtga ggtctgtgat gtgtatttac aaatgcagat cttcttccat 60
tttaagttca gaagttactt tcat 84

<210> SEQ ID NO 261
<211> LENGTH: 90
<212> TYPE: PRT
<213> ORGANISM: Homo sapiens

<400> SEQUENCE: 261

Val Pro Phe Arg Glu Leu Lys Asn Gln Arg Thr Ala Gln Gly Ala Pro
1 5 10 15

Gly Ile His His Ala Ala Ser Pro Val Ala Ala Asn Leu Cys Asp Pro
20 25 30

Ala Arg His Ala Gln His Thr Arg Ile Pro Cys Gly Ala Gly Gln Val
35 40 45

Arg Ala Gly Arg Gly Pro Glu Ala Gly Gly Gly Val Leu Gln Pro Gln
50 55 60

Arg Pro Ala Pro Glu Lys Pro Gly Cys Pro Cys Arg Arg Gly Gln Pro
65 70 75 80

Arg Leu His Thr Val Lys Met Trp Arg Ala
85 90

<210> SEQ ID NO 262
<211> LENGTH: 270
<212> TYPE: DNA
<213> ORGANISM: Homo sapiens

<400> SEQUENCE: 262
gtgcccttcc gggagctcaa gaaccagaga acagcacaag ggctcctgg gatccaccac 60 gcggcttccc ccgttgctgc caacctctgc gacccggcga gacacgcaca gcacacacgc 120
atcccctgcg gcgctggcca agtgcgtgct ggccgaggtc ccgaagcagg tggtggagta 180
ctacagccac agaggcctgc ccccgagaag cctgggtgtc cctgccggag aggccagccc 240
aggctgcaca ccgtgaagat gtggagggcg 270

<210> SEQ ID NO 263
<211> LENGTH: 22
<212> TYPE: PRT
<213> ORGANISM: Homo sapiens

<400> SEQUENCE: 263

Phe Ala Arg Lys Met Leu Glu Lys Val His Arg Gln His Leu Gln Leu
1 5 10 15

Ser His Asn Ser Gln Glu
20

<210> SEQ ID NO 264
<211> LENGTH: 66
<212> TYPE: DNA
<213> ORGANISM: Homo sapiens

<400> SEQUENCE: 264
tttgctagaa aaatgctgga gaaggtacac agacaacacc tacagctttc ccacaatagc 60
caggaa 66

<210> SEQ ID NO 265
<211> LENGTH: 11
<212> TYPE: PRT
<213> ORGANISM: Homo sapiens

<400> SEQUENCE: 265

Lys Arg Ser Phe Ala Val Thr Glu Arg Ile Ile
1 5 10

<210> SEQ ID NO 266
<211> LENGTH: 33
<212> TYPE: DNA
<213> ORGANISM: Homo sapiens

<400> SEQUENCE: 266
aagagaagtt ttgctgtcac ggagaggatc atc 33

<210> SEQ ID NO 267
<211> LENGTH: 17
<212> TYPE: PRT
<213> ORGANISM: Homo sapiens

<400> SEQUENCE: 267

Met Phe Leu Arg Lys Glu Gln Gln Val Gly Pro His Ser Phe Ser Met
1 5 10 15

Leu

<210> SEQ ID NO 268
<211> LENGTH: 51
<212> TYPE: DNA
<213> ORGANISM: Homo sapiens

<400> SEQUENCE: 268
atgttcctta gaaaggagca gcaggtgggt ccccacagct tttctatgct t 51

<210> SEQ ID NO 269
<211> LENGTH: 14
<212> TYPE: PRT
<213> ORGANISM: Homo sapiens

<400> SEQUENCE: 269

Val Leu Arg Phe Leu Asp Leu Lys Val Arg Tyr Leu His Ser
1 5 10

<210> SEQ ID NO 270
<211> LENGTH: 42
<212> TYPE: DNA
<213> ORGANISM: Homo sapiens

<400> SEQUENCE: 270
gtgctgcgct ttctggactt aaaggtgaga tacctgcact ct 42

<210> SEQ ID NO 271
<211> LENGTH: 32
<212> TYPE: PRT
<213> ORGANISM: Homo sapiens

<400> SEQUENCE: 271

Gly Asn Thr Thr Leu Gln Gln Leu Gly Glu Ala Ser Gln Ala Pro Ser
1 5 10 15

Gly Ser Leu Ile Pro Leu Arg Leu Pro Leu Leu Trp Glu Val Arg Gly
20 25 30

<210> SEQ ID NO 272
<211> LENGTH: 96
<212> TYPE: DNA
<213> ORGANISM: Homo sapiens

<400> SEQUENCE: 272
ggcaacacca ccctccagca gctgggtgag gcctcccagg cgccctcagg ctccctcatc 60
cctctgaggc tgcctctgct ctgggaagtg aggggc 96

<210> SEQ ID NO 273
<211> LENGTH: 25
<212> TYPE: PRT
<213> ORGANISM: Homo sapiens

<400> SEQUENCE: 273

Gly Leu Asn Leu Asn Thr Asp Arg Pro Gly Gly Tyr Ser Tyr Ser Ile
1 5 10 15

Trp Trp Lys Asn Asn Ala Lys Asn Arg
20 25

<210> SEQ ID NO 274
<211> LENGTH: 75
<212> TYPE: DNA
<213> ORGANISM: Homo sapiens

<400> SEQUENCE: 274
ggactgaact taaatactga tagaccaggt ggttacagct attcaatttg gtggaaaaac 60
aatgccaaga acaga 75

<210> SEQ ID NO 275
<211> LENGTH: 27
<212> TYPE: PRT
<213> ORGANISM: Homo sapiens

<400> SEQUENCE: 275

Trp Lys Phe Glu Met Ser Tyr Thr Val Gly Gly Pro Pro Pro His Val
1 5 10 15

His Ala Arg Pro Arg His Trp Lys Thr Asp Arg
20 25

<210> SEQ ID NO 276

<211> LENGTH: 81
<212> TYPE: DNA
<213> ORGANISM: Homo sapiens

<400> SEQUENCE: 276
tggaaattcg agatgagcta cacggtgggt ggcccgcctc cccatgttca tgctagaccc 60
aggcattgga aaactgatag a 81

<210> SEQ ID NO 277
<211> LENGTH: 22
<212> TYPE: PRT
<213> ORGANISM: Homo sapiens

<400> SEQUENCE: 277

Gln Trp Gln His Tyr His Arg Ser Gly Glu Ala Ala Gly Thr Pro Leu
1 5 10 15

Trp Arg Pro Thr Arg Asn
20

<210> SEQ ID NO 278
<211> LENGTH: 66
<212> TYPE: DNA
<213> ORGANISM: Homo sapiens

<400> SEQUENCE: 278
cagtggcagc actaccaccg gtcaggtgag gccgcaggga ctcccctctg gagacccaca 60
agaaac 66

<210> SEQ ID NO 279
<211> LENGTH: 29
<212> TYPE: PRT
<213> ORGANISM: Homo sapiens

<400> SEQUENCE: 279

Lys Val Leu Asn Glu Ile Asp Ala Val Val Thr Val Pro Pro Ser Leu
1 5 10 15

Ser Thr Ser Gln Ile Pro Gln Gly Cys Cys Ile Ile Leu
20 25

<210> SEQ ID NO 280
<211> LENGTH: 87
<212> TYPE: DNA
<213> ORGANISM: Homo sapiens

<400> SEQUENCE: 280
aaggtcctca acgagatcga tgcggtagtt accgtccctc cctccctgtc tacctcccag 60
ataccgcagg gctgctgcat catattg 87

<210> SEQ ID NO 281
<211> LENGTH: 18
<212> TYPE: PRT
<213> ORGANISM: Homo sapiens

<400> SEQUENCE: 281

Ala Asn Leu Lys Gly Thr Leu Gln Val Arg Ser Gly Gln Ala Val Ser
1 5 10 15

Pro Arg

<210> SEQ ID NO 282
<211> LENGTH: 54
<212> TYPE: DNA

<213> ORGANISM: Homo sapiens

<400> SEQUENCE: 282
gccaatctga aaggcaccct gcaggtgagg agtgggcagg cagtgagtcc acgc 54

<210> SEQ ID NO 283
<211> LENGTH: 70
<212> TYPE: PRT
<213> ORGANISM: Homo sapiens

<400> SEQUENCE: 283

Leu Gln Ala Ala Ala Ser Gly Gln Gly Lys Gln Gly Val Pro Cys Pro
1 5 10 15

Trp Gly Cys Cys Ala Tyr Ala Glu Ser Pro Arg Ala Leu Ile Ser Gly
20 25 30

Asp Ala Pro Ser Gln Val Glu Arg Glu Val Pro Gly Pro Cys Leu Asn
35 40 45

Thr His Ser Leu Ser His Arg Ser Pro Gln Leu Pro Gly Leu Pro His
50 55 60

Pro Lys Gln Pro Ser Val
65 70

<210> SEQ ID NO 284
<211> LENGTH: 210
<212> TYPE: DNA
<213> ORGANISM: Homo sapiens

<400> SEQUENCE: 284
ctccaggcgg ctgcctcggg ccaaggcaag cagggcgtcc cttgtccctg ggggttgctgt 60 gcctacgctg agagtccccg ggccctgatt tcgggagatg ctccatcaca ggtggagcgg 120
gaggtgccgg gcccctgcct caacacgcat tctctctccc acagatcccc acagctccca 180
ggccttccac accccaagca gccttctgtt 210

<210> SEQ ID NO 285
<211> LENGTH: 9
<212> TYPE: PRT
<213> ORGANISM: Homo sapiens

<400> SEQUENCE: 285

Lys Ile Gln Asn Lys Asn Cys Pro Asp
1 5

<210> SEQ ID NO 286
<211> LENGTH: 27
<212> TYPE: DNA
<213> ORGANISM: Homo sapiens

<400> SEQUENCE: 286
aaaattcaga ataaaaattg tccagac 27

<210> SEQ ID NO 287
<211> LENGTH: 37
<212> TYPE: PRT
<213> ORGANISM: Homo sapiens

<400> SEQUENCE: 287

Gly Glu Val Glu Leu Ser Glu Gly Gly Glu Gly Gln Arg His Leu Ala
1 5 10 15

Phe Pro Trp Ala Cys Ser Gly Pro Gly Trp Arg Gly Val Cys Cys Ala
20 25 30

```
Ala Val Glu Pro Ala
        35


<210> SEQ ID NO 288
<211> LENGTH: 111
<212> TYPE: DNA
<213> ORGANISM: Homo sapiens

<400> SEQUENCE: 288

ggcgaggtgg agctctcaga gggcggtgag ggccagcggc accttgcatt tccctgggcc     60

tgctctgggc cgggctggag aggggtgtgc tgtgctgctg tggagcctgc t             111


<210> SEQ ID NO 289
<211> LENGTH: 9
<212> TYPE: PRT
<213> ORGANISM: Homo sapiens

<400> SEQUENCE: 289

Ile Glu Met Lys Lys Leu Leu Lys Ser
1               5


<210> SEQ ID NO 290
<211> LENGTH: 27
<212> TYPE: DNA
<213> ORGANISM: Homo sapiens

<400> SEQUENCE: 290

attgaaatga aaaaactgtt aaaaagt                                         27


<210> SEQ ID NO 291
<211> LENGTH: 70
<212> TYPE: PRT
<213> ORGANISM: Homo sapiens

<400> SEQUENCE: 291

Lys Met Arg Ala Ile Gln Ala Glu Gly Gly His Gly Gln Ala Cys Cys
1               5                   10                  15

Gly Gly Ala Trp Gly Trp Ala Pro Gly Asp Gly Gly Pro Gln Gly Met
            20                  25                  30

Leu Thr His Thr Leu Pro Thr Leu Gly Phe Gln Ser Ala Trp Thr Trp
        35                  40                  45

Arg Arg Glu Asp Ala Asp Arg Ala Trp Arg Thr Pro Lys Ala Cys Ala
    50                  55                  60

Ser Arg Arg Trp Ser Ile
65                  70


<210> SEQ ID NO 292
<211> LENGTH: 210
<212> TYPE: DNA
<213> ORGANISM: Homo sapiens

<400> SEQUENCE: 292

aagatgcggg ccatccaggc cgagggtggg cacgggcagg cctgctgtgg aggggcctgg     60

ggatgggcac cgggggacgg gggcccccag gggatgctca cgcatactct gcccaccctg    120

ggcttccaga gcgcctggac atggagaaga gaagatgcag acagagcctg gaggactccg    180

aaagcctgcg catcaaggag gtggagcata                                     210


<210> SEQ ID NO 293
<211> LENGTH: 74
```

```
<212> TYPE: PRT
<213> ORGANISM: Homo sapiens

<400> SEQUENCE: 293

Leu Leu Glu Pro Phe Arg Arg Gly Glu Pro Gly Pro Arg Gly Leu Leu
1               5                   10                  15

Ser Gly Ser Ser Arg Gly Gly Glu Gly Pro Gly Arg Ser Ile Glu Ala
            20                  25                  30

Ala Pro Ala Thr Pro Leu Pro Cys Cys Arg Lys Asn Pro Cys Arg Pro
        35                  40                  45

Gln Pro Ser Arg Phe Leu Pro Pro Arg Val Leu Leu Val Ile Ile Leu
    50                  55                  60

Pro Lys Leu Asp Cys Pro Lys Leu Gly Phe
65                  70


<210> SEQ ID NO 294
<211> LENGTH: 222
<212> TYPE: DNA
<213> ORGANISM: Homo sapiens

<400> SEQUENCE: 294

ctgctggagc ccttccgccg cggtgagccc gggccccgcg ggctgctctc gggaagttcc      60

cgcggagggg aggggcctgg ccgttcgatc gaggctgcac ccgccacacc tttgccctgt     120

tgccgcaaga acccttgtcg gccccagcct tccagatttt tgcctcctag ggtattgtta     180

gtgatcattc ttcccaaact ggattgtcca aaacttgggt tc                         222


<210> SEQ ID NO 295
<211> LENGTH: 65
<212> TYPE: PRT
<213> ORGANISM: Homo sapiens

<400> SEQUENCE: 295

Pro Ser Gly Arg Arg Thr Lys Arg Leu Val Thr Leu Arg Ser Gly Cys
1               5                   10                  15

Ala Ile Gln Cys Trp His Pro Arg Ala Gly Pro Val Pro Ser Ala Leu
            20                  25                  30

Pro His Thr Glu Arg Pro Pro Arg Leu Val Arg Gly Ala Ala Asp Pro
        35                  40                  45

Arg Thr Val Thr Leu Gly Arg Ser Pro Ala Val Met Pro Arg Ala Pro
    50                  55                  60

Ala
65


<210> SEQ ID NO 296
<211> LENGTH: 195
<212> TYPE: DNA
<213> ORGANISM: Homo sapiens

<400> SEQUENCE: 296

ccctcggggc ggagaaccaa acggttagtt accctgcgtt ctggctgcgc catacaatgc      60

tggcatcctc gtgccggccc agttccctca gcgcttcctc acacagagag gcccccaagg     120

cttgtcaggg gagcagcaga tcccaggaca gtgaccctgg gacggagccc tgcagtcatg     180

cctcgggccc ctgcg                                                       195


<210> SEQ ID NO 297
<211> LENGTH: 95
<212> TYPE: PRT
```

<213> ORGANISM: Homo sapiens

<400> SEQUENCE: 297

Cys His Leu Phe Leu Gln Pro Gln Val Gly Thr Pro Pro Pro His Thr
1 5 10 15

Ala Ser Ala Arg Ala Pro Ser Gly Pro Pro His Pro His Glu Ser Cys
20 25 30

Pro Ala Gly Arg Arg Pro Ala Arg Ala Ala Gln Thr Cys Ala Arg Arg
35 40 45

Gln His Gly Leu Pro Gly Cys Glu Glu Ala Gly Thr Ala Arg Val Pro
50 55 60

Ser Leu His Leu His Leu His Gln Ala Ala Leu Gly Ala Gly Arg Gly
65 70 75 80

Arg Gly Trp Gly Glu Ala Cys Ala Gln Val Pro Pro Ser Arg Gly
85 90 95

<210> SEQ ID NO 298
<211> LENGTH: 285
<212> TYPE: DNA
<213> ORGANISM: Homo sapiens

<400> SEQUENCE: 298
tgccacctct tcctgcagcc ccaggttggc accccccccc cccacactgc cagtgctcga 60
gcccccagtg gtccacccca ccctcatgaa agttgccctg cagggcgaag acctgcgaga 120
gctgcgcaga catgtgcacg ccgacagcac ggacttcctg gctgtgaaga ggctggtaca 180
gcgcgtgttc ccagcctgca cctgcacctg caccaggccg ccctcggagc aggaaggggc 240
cgtgggtggg gagaggcctg tgcccaagta cccccctcaa gaggc 285

<210> SEQ ID NO 299
<211> LENGTH: 45
<212> TYPE: PRT
<213> ORGANISM: Homo sapiens

<400> SEQUENCE: 299

Lys Glu Leu Lys Leu Glu Gln Gln Val Gly Gly Gln Gly Leu Arg Gly
1 5 10 15

Val Gly Gln Gly Val Arg Gly Gly Phe Val Thr Leu Thr Thr His Thr
20 25 30

Pro Phe Pro Ser Gln Glu Ala Ala Glu Arg Glu Ser Lys
35 40 45

<210> SEQ ID NO 300
<211> LENGTH: 135
<212> TYPE: DNA
<213> ORGANISM: Homo sapiens

<400> SEQUENCE: 300
aaggagctca agctggagca gcaggtgggt gggcagggct tgagaggggt gggccaaggg 60
gtgcgtggcg gcttcgtgac cctcactacc cataccccgt tcccctccca ggaagctgca 120
gagcgggagt ctaaa 135

<210> SEQ ID NO 301
<211> LENGTH: 175
<212> TYPE: PRT
<213> ORGANISM: Homo sapiens

<400> SEQUENCE: 301

-continued

```
Gly Glu Ile Ser Gln Glu Glu Val Pro Pro Ser Arg His Leu Gly Val
1               5                   10                  15

Ser Trp Gly Ala Gly Val Trp Ala Gly Leu Thr Leu Gly Ala Ser Ala
            20                  25                  30

Pro Pro Asn Ser Ser Phe Pro Ser Gly Ala Glu Leu Gln Pro Val Val
        35                  40                  45

Cys Cys Ile Arg Ser Asp Thr Arg Gln Pro Arg Pro Pro Asp Phe Pro
    50                  55                  60

Gln His Arg Gly Asp Pro Arg Leu Pro Gln Leu Ser Leu Gly Ala Glu
65                  70                  75                  80

Asn Gln Thr Val Ser Tyr Pro Ala Phe Trp Leu Arg His Thr Met Leu
                85                  90                  95

Ala Ser Ser Cys Arg Pro Ser Ser Leu Ser Ala Ser Ser His Arg Glu
            100                 105                 110

Ala Pro Lys Ala Cys Gln Gly Ser Ser Arg Ser Gln Asp Ser Asp Pro
        115                 120                 125

Gly Thr Glu Pro Cys Ser His Ala Ser Gly Pro Cys Val Thr Ser Thr
    130                 135                 140

Val Ser Ser Pro Gly Leu Leu Pro Gln Arg Leu Leu Pro Leu Ala Leu
145                 150                 155                 160

Thr Gly Leu Pro Val Glu Glu Asp Gly Phe Glu His Ala Gly Ala
                165                 170                 175


<210> SEQ ID NO 302
<211> LENGTH: 525
<212> TYPE: DNA
<213> ORGANISM: Homo sapiens

<400> SEQUENCE: 302

ggagaaatca gccaggaaga ggtgcctccc tcccgccacc tgggcgtctc atggggtgct      60

ggggtgtggg cgggcctcac cctcggggcc tctgcacccc ctaactctag cttcccctca     120

ggtgctgagc tacagccagt tgtgtgctgc attaggagtg acacaagaca gccccgaccc     180

cccgactttc ctcagcacag gggagatcca cgccttcctc agctctccct cggggcggag     240

aaccaaacgg ttagttaccc tgcgttctgg ctgcgccata caatgctggc atcctcgtgc     300

cggcccagtt ccctcagcgc ttcctcacac agagaggccc ccaaggcttg tcaggggagc     360

agcagatccc aggacagtga ccctgggacg gagccctgca gtcatgcctc gggcccctgc     420

gtaacctcca ctgtctccag cccaggtctc cttcctcaga ggctattgcc tctcgctctg     480

actgggctcc ctgtggagga agatggtttc gagcacgcgg gagcc                     525


<210> SEQ ID NO 303
<211> LENGTH: 56
<212> TYPE: PRT
<213> ORGANISM: Homo sapiens

<400> SEQUENCE: 303

Asp Cys Met Leu Ser Glu Glu Gly Gly Gln Ala Arg Arg Gly Gly Ser
1               5                   10                  15

Leu Cys Ser Leu Ala Ala His Thr Ile Ala Ser Ala Ala Arg Gly Arg
            20                  25                  30

Phe Leu Ser Arg Leu Ser Asn Phe Cys Ala Val Val Lys Ala Ser Arg
        35                  40                  45

Gly Ala Pro Ser Cys Thr Trp Glu
    50                  55
```

<210> SEQ ID NO 304
<211> LENGTH: 168
<212> TYPE: DNA
<213> ORGANISM: Homo sapiens

<400> SEQUENCE: 304
gactgcatgc tcagcgagga aggtgggcag gcgcggcggg gtggatccct ctgctcctta 60
gctgcccaca ccattgcctc ggcagcccga ggtcgcttcc tctccaggct ctccaatttc 120
tgtgccgtag ttaaagcgag caggggcgcc ccttcctgca cctgggag 168

<210> SEQ ID NO 305
<211> LENGTH: 43
<212> TYPE: PRT
<213> ORGANISM: Homo sapiens

<400> SEQUENCE: 305

Glu Ala Phe Gln Arg Ala Ala Gly Glu Gly Gly Pro Gly Arg Gly Gly
1 5 10 15

Ala Arg Arg Gly Ala Arg Val Leu Gln Ser Pro Phe Cys Arg Ala Gly
20 25 30

Ala Gly Glu Trp Leu Gly His Gln Ser Leu Arg
35 40

<210> SEQ ID NO 306
<211> LENGTH: 129
<212> TYPE: DNA
<213> ORGANISM: Homo sapiens

<400> SEQUENCE: 306
gaggccttcc agagggccgc tggtgagggc ggcccgggcc gcggtggggc acggcgcggt 60
gccagggtgt tgcagagccc cttttgcagg gcaggagctg ggagtggtt aggacatcag 120 tccctcagg 129

<210> SEQ ID NO 307
<211> LENGTH: 35
<212> TYPE: PRT
<213> ORGANISM: Homo sapiens

<400> SEQUENCE: 307

Pro Glu Pro Arg Arg Leu Ser Pro Gly Glu Pro Arg Gly Arg Pro Arg
1 5 10 15

Lys Gly Trp Gly Ile Trp Gly Leu Cys Gly Ala Arg Val Gly Pro Lys
20 25 30

Ala Trp Arg
35

<210> SEQ ID NO 308
<211> LENGTH: 105
<212> TYPE: DNA
<213> ORGANISM: Homo sapiens

<400> SEQUENCE: 308
cctgagccca ggagactgag cccaggtgag cccagggggc gaccccggaa gggctggggg 60
atctggggtt tgtgtggagc gcgggtgggg cccaaggctt ggcgg 105

<210> SEQ ID NO 309
<211> LENGTH: 61
<212> TYPE: PRT
<213> ORGANISM: Homo sapiens -continued

<400> SEQUENCE: 309

```
Val Pro Phe Arg Glu Leu Lys Asn Val Ser Val Leu Glu Gly Leu Arg
1               5                   10                  15

Gln Gly Arg Leu Gly Gly Pro Cys Ser Cys His Cys Pro Arg Pro Ser
            20                  25                  30

Gln Ala Arg Leu Thr Pro Val Asp Val Ala Gly Pro Phe Leu Cys Leu
        35                  40                  45

Gly Asp Pro Gly Leu Phe Pro Pro Val Lys Ser Ser Ile
    50                  55                  60
```

<210> SEQ ID NO 310
<211> LENGTH: 183
<212> TYPE: DNA
<213> ORGANISM: Homo sapiens

<400> SEQUENCE: 310

```
gtgcccttcc gggagctcaa gaacgtgagt gtcctggagg ggctccgtca aggccggctt      60

gggggtccct gttcatgtca ctgcccaaga ccttcccagg ccaggctcac gccagtggat     120

gtggcaggtc ccttcttgtg tctgggggat cctgggctgt tccccccagt caagagcagt     180

atc                                                                   183
```

<210> SEQ ID NO 311
<211> LENGTH: 98
<212> TYPE: PRT
<213> ORGANISM: Homo sapiens

<400> SEQUENCE: 311

```
Phe Val Ser Leu Thr Ala Ile Gln Met Ala Ser Ser Ala Thr Pro Trp
1               5                   10                  15

Gly Arg Trp Pro Val Ala Thr Pro Thr Ala Ala Cys Pro Arg Arg Arg
            20                  25                  30

Pro Ser Ser Leu Pro Thr Gly Gly Asp Ser Ala Ser Lys Lys Pro Ile
        35                  40                  45

Ser Arg Arg Ala Pro Trp Gln Pro Trp Ala Cys Pro Gly Arg Ser Val
    50                  55                  60

Asn Ser Ala Ala Pro Arg Ala Trp Cys Pro Pro Ala Thr Thr Pro Arg
65                  70                  75                  80

Thr Gln Ser Pro Ser Arg Asp Leu Arg Pro Arg Cys Leu Ser Ser Trp
                85                  90                  95

Ser Ser
```

<210> SEQ ID NO 312
<211> LENGTH: 294
<212> TYPE: DNA
<213> ORGANISM: Homo sapiens

<400> SEQUENCE: 312

```
tttgtgagcc tgactgccat ccagatggca tcgtcggcca ctccctgggg gaggtggcct      60

gtggctacgc cgacggctgc ctgtcccagg aggaggccgt cctcgctgcc tactggaggg     120

gacagtgcat caaagaagcc catctccccgc cgggcgccat ggcagccgtg ggcttgtcct    180

gggaggagtg taaacagcgc tgccccccgg gcgtggtgcc cgcctgccac aactccaagg     240

acacagtcac catctcggga cctcaggccc cggtgtttga gttcgtggag cagc           294
```

<210> SEQ ID NO 313

<211> LENGTH: 109
<212> TYPE: PRT
<213> ORGANISM: Homo sapiens

<400> SEQUENCE: 313

```
Pro Val Ala Ile Lys Pro Gly Thr Gly Pro Pro Asn Asn Ser Ser Ile
1               5                   10                  15

His Gly Gly Ser Lys Arg Ser Glu Asn Ser Tyr Cys Arg Asp Leu Arg
            20                  25                  30

Gly Gln Leu Arg Ala Ile Cys Cys Ser Ser Tyr Ser His Asp Arg His
        35                  40                  45

Thr Thr Glu Glu Arg Gly Ser Arg Gly Arg His Val Trp Arg Ile Arg
    50                  55                  60

Arg Leu His Thr Ser Gly Leu Pro Cys Cys Cys His Ser Gly Pro His
65                  70                  75                  80

Pro Arg Arg Leu Pro Asp Ile Leu Arg Leu Val Thr Ser Thr Lys Thr
                85                  90                  95

Asp His Thr Asn Thr Thr Glu Gly Thr Leu Asp Tyr Leu
            100                 105
```

<210> SEQ ID NO 314
<211> LENGTH: 327
<212> TYPE: DNA
<213> ORGANISM: Homo sapiens

<400> SEQUENCE: 314

```
ccagttgcca ttaaacctgg tacagggccg cccaataact ccagtataca cggtggctcc     60

aaacgttcag agaattccta ctgccgggat ctacggggcc agttacgtgc catttgctgc    120

tccagctaca gccacgatcg ccacactaca gaagaacgcg gcagccgcgg ccgccatgta    180

tggaggatac gcaggctaca tacctcaggc cttccctgct gctgccattc aggtccccat    240

ccccgacgtc taccagacat actgaggctg gtgaccagca cgaagacaga ccacacaaac    300

accactgaag gaacgcttga ctattta                                        327
```

<210> SEQ ID NO 315
<211> LENGTH: 40
<212> TYPE: PRT
<213> ORGANISM: Homo sapiens

<400> SEQUENCE: 315

```
Lys Trp Asn Lys Asn Trp Thr Ala Thr Leu Gly Ala Leu Thr Ile Arg
1               5                   10                  15

Gly His Lys Leu Leu Cys His Leu Pro His Leu Leu Ser Ser Val Gln
            20                  25                  30

Gln Thr Cys Arg Ser Ser Ser Arg
        35                  40
```

<210> SEQ ID NO 316
<211> LENGTH: 120
<212> TYPE: DNA
<213> ORGANISM: Homo sapiens

<400> SEQUENCE: 316

```
aagtggaaca agaactggac agccacactc ggggctctta caatcagggg tcataagctg     60

ctatgtcacc tacctcacct tctcagctct gtccagcaaa cctgcagaag tagttctaga    120
```

<210> SEQ ID NO 317
<211> LENGTH: 50

<212> TYPE: PRT
<213> ORGANISM: Homo sapiens

<400> SEQUENCE: 317

Phe Lys Lys Phe Asp Gly Pro Cys Gly Glu Arg Gly Gly Gly Arg Thr
1               5                   10                  15

Ala Arg Ala Leu Trp Ala Arg Gly Asp Ser Val Leu Thr Pro Ala Leu
            20                  25                  30

Asp Pro Gln Thr Pro Val Arg Ala Pro Ser Leu Thr Arg Ala Ala Ala
        35                  40                  45

Ala Val
    50

<210> SEQ ID NO 318
<211> LENGTH: 150
<212> TYPE: DNA
<213> ORGANISM: Homo sapiens

<400> SEQUENCE: 318
ttcaagaagt tcgacggccc ttgtggtgag cgcggcggcg ggcgcacggc tcgagctctg 60
tgggcgcgcg gcgacagcgt cctgactcct gccctcgacc cccagacccc tgtcagggcg 120
ccctccctga cccgagccgc agctgccgtg 150

<210> SEQ ID NO 319
<211> LENGTH: 52
<212> TYPE: PRT
<213> ORGANISM: Homo sapiens

<400> SEQUENCE: 319

Glu Asn Ala Ser Leu Val Phe Thr Gly Ser Asn Ser Pro Ile Pro Ala
1               5                   10                  15

Cys Glu Leu Ser Ser His Pro Ala His Gly Ile Ser Pro Trp Ile Pro
            20                  25                  30

Ser Pro Gly Asn Glu His Phe His Gly Ile Lys Lys Gln Val Lys Ala
        35                  40                  45

Ile Lys Val Glu
    50

<210> SEQ ID NO 320
<211> LENGTH: 156
<212> TYPE: DNA
<213> ORGANISM: Homo sapiens

<400> SEQUENCE: 320
gaaaatgcca gcctagtgtt tacaggatcc aacagcccca taccagcctg cgaactgagt 60
agtcacccag ctcatggtat cagtccttgg ataccctcac ctggaaatga acatttccat 120
ggcataaaga agcaagtaaa ggcaataaaa gtagaa 156

<210> SEQ ID NO 321
<211> LENGTH: 55
<212> TYPE: PRT
<213> ORGANISM: Homo sapiens

<400> SEQUENCE: 321

Arg Leu Thr Gln Arg Leu Val Gln Gly Trp Thr Pro Met Glu Asn Arg
1               5                   10                  15

Trp Cys Gly Arg Arg Ala Gly Gly Gln Pro Ala Ser Ser Ser Thr Arg
            20                  25                  30

```
Trp Thr Thr Cys Arg Ala Ala Cys Leu Leu Thr Lys Trp Thr Ala Gly
        35                  40                  45

Arg Ser Gln Thr Ser Ile Gly
    50                  55


<210> SEQ ID NO 322
<211> LENGTH: 165
<212> TYPE: DNA
<213> ORGANISM: Homo sapiens

<400> SEQUENCE: 322

cggctgacgc aacggctggt ccagggctgg accccaatgg agaacaggtg gtgtggcagg      60

cgagcgggtg ggcagcccgc atcatccagc acgagatgga ccacctgcag ggctgcctgt     120

ttattgacaa aatggacagc aggacgttca caaacgtcta ttgga                     165


<210> SEQ ID NO 323
<211> LENGTH: 32
<212> TYPE: PRT
<213> ORGANISM: Homo sapiens

<400> SEQUENCE: 323

Glu Asn Ser Gly Asn Ala Ser Arg Trp Leu His Val Pro Ser Ser Ser
1               5                   10                  15

Asp Asp Trp Leu Gly Trp Lys Lys Ser Ser Ala Ile Thr Ser Asn Ser
            20                  25                  30


<210> SEQ ID NO 324
<211> LENGTH: 96
<212> TYPE: DNA
<213> ORGANISM: Homo sapiens

<400> SEQUENCE: 324

gaaaattcag gcaacgcctc gcgttggctg catgtaccaa gtagttcaga cgattggctc      60

ggatggaaaa aatcttctgc aattacttcc aattcc                                96


<210> SEQ ID NO 325
<211> LENGTH: 59
<212> TYPE: PRT
<213> ORGANISM: Homo sapiens

<400> SEQUENCE: 325

Gly Met Glu Cys Thr Leu Gly Gln Val Gly Ala Pro Ser Pro Arg Arg
1               5                   10                  15

Glu Glu Asp Gly Trp Arg Gly Gly His Ser Arg Phe Lys Ala Asp Val
            20                  25                  30

Pro Ala Pro Gln Gly Pro Cys Trp Gly Gly Gln Pro Gly Ser Ala Pro
        35                  40                  45

Ser Ser Ala Pro Pro Glu Gln Ser Leu Leu Asp
    50                  55


<210> SEQ ID NO 326
<211> LENGTH: 177
<212> TYPE: DNA
<213> ORGANISM: Homo sapiens

<400> SEQUENCE: 326

ggcatggagt gcaccctggg gcaggtgggt gccccgtccc ctcggaggga ggaggacggt      60

tggcgtgggg gccacagccg attcaaggct gatgtaccag caccgcaggg accctgctgg     120

ggtggccaac ctggctctgc cccctcctca gctcctcctg aacagtcatt attagat        177
```

<210> SEQ ID NO 327
<211> LENGTH: 110
<212> TYPE: PRT
<213> ORGANISM: Homo sapiens

<400> SEQUENCE: 327

Lys Gly Ser Val Glu Arg Arg Ser Val Ser Leu Gly His Pro Ala Glu
1               5                   10                  15

Gly Trp Ala Trp Ala Glu Arg Ser Leu Gln Pro Gly Met Thr Thr Ala
            20                  25                  30

Asn Thr Gly Cys Leu Ser Phe His His Arg Gly Cys Leu Leu Pro Val
        35                  40                  45

Leu Pro Lys Leu His Cys Gly Leu Gly Gly Leu Pro Leu Val Arg Ala
    50                  55                  60

Lys Glu Ile Lys Arg Val Gln Arg Ala Gly Glu Ser Ser Leu Pro Val
65                  70                  75                  80

Lys Gly Leu Leu Thr Val Ala Ser Ala Val Ile Ala Val Leu Trp Gly
                85                  90                  95

Arg Pro Ser Glu Val Thr Gly Glu Asn Glu Ala Gln His Asp
            100                 105                 110

<210> SEQ ID NO 328
<211> LENGTH: 330
<212> TYPE: DNA
<213> ORGANISM: Homo sapiens

<400> SEQUENCE: 328
aaagggagtg tggagaggcg ctcggtgagc ctggggcatc ctgctgaggg ttgggcatgg      60
gcagagagga gcctccagcc aggcatgacc acagccaaca caggctgcct ctcattccac     120
cacagagggt gcctcctccc tgttttgccc aaattacact gtgggctagg tggactacct     180
cttgtcagag ctaaagaaat caagcgagtg cagagggcag gggagagttc gctgcctgtg     240
aagggccttc tcaccgtcgc ttcggctgtc atcgcagtcc tgtggggtag gccaagcgag     300
gtcacaggag aaaatgaggc tcagcatgat                                      330

<210> SEQ ID NO 329
<211> LENGTH: 75
<212> TYPE: PRT
<213> ORGANISM: Homo sapiens

<400> SEQUENCE: 329

Phe Gly Leu Thr Thr Leu Ala Gly Arg Ser Ser His Gly Thr Ser Gly
1               5                   10                  15

Leu Arg Ala Ala Thr His Thr Lys Ser Gly Asp Gly Gly Gln Gly Ala
            20                  25                  30

Ala Arg Gln Cys Glu Lys Leu Leu Glu Leu Ala Arg Ala Thr Arg Pro
        35                  40                  45

Trp Gly Arg Ser Thr Ser Ala Ser Ser Arg Trp Thr His Arg Gly Tyr
    50                  55                  60

Met Cys Pro Pro Arg Cys Ala Val Ala Cys Trp
65                  70                  75

<210> SEQ ID NO 330
<211> LENGTH: 225
<212> TYPE: DNA
<213> ORGANISM: Homo sapiens

<400> SEQUENCE: 330
tttggcctca ccacacttgc aggtagaagc tcccacggga cctcaggact gagggcagcc 60
acacacacca agtctgggga cggtggccag ggggctgcca ggcagtgtga gaagctcctg 120
gagctggccc gggctaccag accctggggg aggagtacgt cagcatcatc caggtggacc 180
catcgcggat acatgtgccc tcctcgctgc gccgtggcgt gctgg 225

<210> SEQ ID NO 331
<211> LENGTH: 29
<212> TYPE: PRT
<213> ORGANISM: Homo sapiens

<400> SEQUENCE: 331

Ile Ile Asp Ser Asp Lys Ile Met Ala Val Cys Met Gly Cys Leu Leu
1 5 10 15

Thr Arg His Val Gln Cys Gln Ala Met Glu Met Gln Gln
20 25

<210> SEQ ID NO 332
<211> LENGTH: 87
<212> TYPE: DNA
<213> ORGANISM: Homo sapiens

<400> SEQUENCE: 332
attattgaca gcgacaagat aatggcagtg tgcatggggt gcctgctcac acgtcatgtg 60
caatgccagg ccatggagat gcaacag 87

<210> SEQ ID NO 333
<211> LENGTH: 49
<212> TYPE: PRT
<213> ORGANISM: Homo sapiens

<400> SEQUENCE: 333

Asp Gly His Ser Tyr Thr Ser Lys Val Asn Cys Leu Leu Leu Gln Asp
1 5 10 15

Gly Phe His Gly Cys Val Ser Ile Thr Gly Ala Ala Gly Arg Arg Asn
20 25 30

Leu Ser Ile Phe Leu Phe Leu Met Leu Cys Lys Leu Glu Phe His Ala
35 40 45

Cys

<210> SEQ ID NO 334
<211> LENGTH: 147
<212> TYPE: DNA
<213> ORGANISM: Homo sapiens

<400> SEQUENCE: 334
gatggccact cctacacatc caaggtgaat tgtttactcc ttcaagatgg gttccatggc 60
tgtgtgagca tcaccggggc agctggaaga agaaacctga gcatcttcct gttcttgatg 120
ctgtgcaaat tggagttcca tgcttgt 147

<210> SEQ ID NO 335
<211> LENGTH: 70
<212> TYPE: PRT
<213> ORGANISM: Homo sapiens

<400> SEQUENCE: 335

Leu Leu Asn Ala Glu Asp Tyr Arg Cys Ala Ile His Ser Lys Glu Ile
1 5 10 15

Tyr Leu Leu Ser Pro Ser Pro His Gln Ala Met Asp Lys Phe Ser Leu
            20                  25                  30

Cys Cys Ile Asn Cys Asn Leu Cys Leu His Val Phe Leu Leu Leu Leu
        35                  40                  45

Phe Phe Gln Asn Lys Asp Val Trp Leu Ile Ser Asn Ile Ile Leu Leu
    50                  55                  60

Trp Ile Tyr Gly Gly Ile
65                  70

<210> SEQ ID NO 336
<211> LENGTH: 210
<212> TYPE: DNA
<213> ORGANISM: Homo sapiens

<400> SEQUENCE: 336
ctactaaatg cagaagatta ccggtgtgcc attcattcaa aagagattta tcttctttcc 60
ccctcccccc accaggcaat ggacaagttt tctctctgct gcatcaactg caatctatgt 120
ttacatgtat tccttttact actatttttt caaaacaaag atgtatggct tatttcaaac 180
atcattttac tttggatata tggcggtatt 210

<210> SEQ ID NO 337
<211> LENGTH: 33
<212> TYPE: PRT
<213> ORGANISM: Homo sapiens

<400> SEQUENCE: 337

Thr Gly Gly Lys Ser Thr Cys Ser Ala Pro Gly Pro Gln Ser Leu Pro
1               5                   10                  15

Ser Thr Pro Phe Ser Thr Tyr Pro Gln Trp Val Ile Leu Ile Thr Glu
            20                  25                  30

Leu

<210> SEQ ID NO 338
<211> LENGTH: 99
<212> TYPE: DNA
<213> ORGANISM: Homo sapiens

<400> SEQUENCE: 338
acagggggca aaagcacctg ctcggctcct ggccctcagt ctctcccctc cactccattc 60
tccacctacc cacagtgggt cattctgatc accgaactg 99

<210> SEQ ID NO 339
<211> LENGTH: 28
<212> TYPE: PRT
<213> ORGANISM: Homo sapiens

<400> SEQUENCE: 339

Val Glu Thr Leu Glu Asn Ala Asn Ser Phe Ser Ser Gly Ile Gln Pro
1               5                   10                  15

Leu Leu Cys Ser Leu Ile Gly Leu Glu Asn Pro Thr
            20                  25

<210> SEQ ID NO 340
<211> LENGTH: 84
<212> TYPE: DNA
<213> ORGANISM: Homo sapiens

<400> SEQUENCE: 340
gtggagaccc tggagaatgc caacagcttc tccagcggga tccagccact cctctgttcc 60
ctgattggcc tggagaatcc cacc 84

<210> SEQ ID NO 341
<211> LENGTH: 38
<212> TYPE: PRT
<213> ORGANISM: Homo sapiens

<400> SEQUENCE: 341

Ala Gly Ala Gly Thr Ile Ser Glu Gly Ser Val Leu His Gly Gln Arg
1 5 10 15

Leu Glu Cys Asp Ala Arg Arg Phe Phe Gly Cys Gly Thr Thr Ile Leu
20 25 30

Ala Glu Trp Glu His His
35

<210> SEQ ID NO 342
<211> LENGTH: 114
<212> TYPE: DNA
<213> ORGANISM: Homo sapiens

<400> SEQUENCE: 342
gctggggctg gaacaatttc cgaaggtagt gttctccatg gtcagaggct ggagtgtgat 60
gccagacgtt tttttgggtg tgggactaca atactggcag agtgggagca ccat 114

<210> SEQ ID NO 343
<211> LENGTH: 17
<212> TYPE: PRT
<213> ORGANISM: Homo sapiens

<400> SEQUENCE: 343

Gly Val Pro Gly Asp Ser Thr Arg Arg Ala Val Arg Arg Met Asn Thr
1 5 10 15

Phe

<210> SEQ ID NO 344
<211> LENGTH: 51
<212> TYPE: DNA
<213> ORGANISM: Homo sapiens

<400> SEQUENCE: 344
ggagttccag gagattcaac caggagagca gtgaggagaa tgaatacctt c 51

<210> SEQ ID NO 345
<211> LENGTH: 20
<212> TYPE: PRT
<213> ORGANISM: Homo sapiens

<400> SEQUENCE: 345

His Val Val Gly Tyr Gly His Leu Asp Thr Ser Gly Ser Ser Ser Ser
1 5 10 15

Ser Ser Trp Pro
20

<210> SEQ ID NO 346
<211> LENGTH: 60
<212> TYPE: DNA
<213> ORGANISM: Homo sapiens

<400> SEQUENCE: 346
cacgtggtgg gctatggcca ccttgatact tccgggtcat cctcctcctc ctcctggccc 60

<210> SEQ ID NO 347
<211> LENGTH: 64
<212> TYPE: PRT
<213> ORGANISM: Homo sapiens

<400> SEQUENCE: 347

```
Trp Thr Pro Ile Pro Val Leu Thr Arg Trp Pro Leu Pro His Pro Pro
1               5                   10                  15

Pro Trp Arg Arg Ala Thr Ser Cys Arg Met Ala Arg Ser Ser Pro Ser
            20                  25                  30

Ala Thr Ser Gly Ser Ser Val Arg Arg Arg Cys Ser Ser Leu Pro Ser
        35                  40                  45

Trp Val Trp Asn Leu Ala Ala Ser Thr Arg Pro Arg Ser Thr Pro Ser
    50                  55                  60
```

<210> SEQ ID NO 348
<211> LENGTH: 196
<212> TYPE: DNA
<213> ORGANISM: Homo sapiens

<400> SEQUENCE: 348

```
tggacgccca tcccggtgct cacgagatgg ccactaccac atcctcctcc ctggagaaga      60

gctacaagct gccggatggc caggtcatca ccatcagcaa caagcggttc cagtgtccgg     120

aggcgctgtt ccagccttcc ttcctgggta tggaatcttg cggcatccac gagaccacgt     180

tcaactccat catgaa                                                     196
```

<210> SEQ ID NO 349
<211> LENGTH: 16
<212> TYPE: PRT
<213> ORGANISM: Homo sapiens

<400> SEQUENCE: 349

```
Ser Leu Tyr His Arg Glu Lys Gln Leu Ile Ala Met Asp Ser Ala Ile
1               5                   10                  15
```

<210> SEQ ID NO 350
<211> LENGTH: 48
<212> TYPE: DNA
<213> ORGANISM: Homo sapiens

<400> SEQUENCE: 350

```
tccctctacc accgggagaa gcagctcatt gctatggaca gtgctatc                  48
```

<210> SEQ ID NO 351
<211> LENGTH: 43
<212> TYPE: PRT
<213> ORGANISM: Homo sapiens

<400> SEQUENCE: 351

```
Leu His Pro Gln Arg Glu Thr Phe Thr Pro Arg Trp Ser Gly Ala Asn
1               5                   10                  15

Tyr Trp Lys Leu Ala Phe Pro Val Gly Ala Glu Gly Thr Phe Pro Ala
            20                  25                  30

Ala Ala Thr Gln Arg Gly Val Val Arg Pro Ala
        35                  40
```

<210> SEQ ID NO 352
<211> LENGTH: 131
<212> TYPE: DNA

<213> ORGANISM: Homo sapiens

<400> SEQUENCE: 352
cttcatcctc agagggaaac attcactccc cggtggtcgg gcgcgaatta ctggaaattg 60
gcttttcccg ttggggccga aggtaccttc cctgcggcgg cgactcagcg gggtgtcgtt 120
cggccggcgt g 131

<210> SEQ ID NO 353
<211> LENGTH: 35
<212> TYPE: PRT
<213> ORGANISM: Homo sapiens

<400> SEQUENCE: 353

Asn Ser Lys Met Ala Leu Asn Ser Leu Asn Ser Ile Asp Asp Ala Gln
1 5 10 15

Leu Thr Arg Ile Ala Pro Pro Arg Ser His Cys Cys Phe Trp Glu Val
20 25 30

Asn Ala Pro
35

<210> SEQ ID NO 354
<211> LENGTH: 105
<212> TYPE: DNA
<213> ORGANISM: Homo sapiens

<400> SEQUENCE: 354
aacagcaaga tggctttgaa ctcattaaac tccattgatg atgcacagtt gacaagaatt 60
gcccctccaa gatctcattg ctgtttctgg gaagtaaacg ctcct 105

<210> SEQ ID NO 355
<211> LENGTH: 50
<212> TYPE: PRT
<213> ORGANISM: Homo sapiens

<400> SEQUENCE: 355

Met Ala Gly Gly Val Leu Arg Arg Leu Leu Cys Arg Glu Pro Asp Arg
1 5 10 15

Asp Gly Asp Lys Gly Ala Ser Arg Glu Glu Thr Val Val Pro Leu His
20 25 30

Ile Gly Asp Pro Val Val Leu Pro Gly Ile Gly Gln Cys Tyr Ser Ala
35 40 45

Leu Phe
50

<210> SEQ ID NO 356
<211> LENGTH: 151
<212> TYPE: DNA
<213> ORGANISM: Homo sapiens

<400> SEQUENCE: 356
atggctggag gagtccttcg gcggctgttg tgtcgggagc ctgatcgcga tggggacaaa 60
ggcgcaagtc gagaggaaac tgttgtgcct cttcatattg gcgatcctgt tgtgctccct 120
ggcattgggc agtgttacag tgcactcttc t 151

<210> SEQ ID NO 357
<211> LENGTH: 39
<212> TYPE: PRT
<213> ORGANISM: Homo sapiens

<400> SEQUENCE: 357

Asp Asp Arg Asn Thr Phe Asp Ile Val Trp Trp Cys Pro Met Ser Arg
1 5 10 15

Leu Arg Leu Ala Leu Thr Val Pro Pro Ser Thr Thr Thr Thr Cys Val
20 25 30

Thr Val Pro Ala Trp Ala Ala
35

<210> SEQ ID NO 358
<211> LENGTH: 120
<212> TYPE: DNA
<213> ORGANISM: Homo sapiens

<400> SEQUENCE: 358
gatgacagaa acactttcga catagtgtgg tggtgcccta tgagccgcct gaggttggct 60
ctgactgtac caccatccac tacaactaca tgtgtaacag ttcctgcatg ggcggcatga 120

<210> SEQ ID NO 359
<211> LENGTH: 17
<212> TYPE: PRT
<213> ORGANISM: Homo sapiens

<400> SEQUENCE: 359

Val Gln Pro Ile Ala Arg Glu Leu Tyr Gln Phe Thr Phe Asp Leu Leu
1 5 10 15

Ile

<210> SEQ ID NO 360
<211> LENGTH: 51
<212> TYPE: DNA
<213> ORGANISM: Homo sapiens

<400> SEQUENCE: 360
gtgcagccta ttgcgagaga gctgcatcag ttcacttttg acctgctaat c 51

<210> SEQ ID NO 361
<211> LENGTH: 17
<212> TYPE: PRT
<213> ORGANISM: Homo sapiens

<400> SEQUENCE: 361

Gln Met Ala Val Ile Gln Tyr Ser Cys Met Gly Leu Met Val Phe Ala
1 5 10 15

Met

<210> SEQ ID NO 362
<211> LENGTH: 51
<212> TYPE: DNA
<213> ORGANISM: Homo sapiens

<400> SEQUENCE: 362
cagatggctg tcattcagta ctcctgcatg ggctcatgg tgtttgccat g 51

<210> SEQ ID NO 363
<211> LENGTH: 17
<212> TYPE: PRT
<213> ORGANISM: Homo sapiens

<400> SEQUENCE: 363

Pro Lys Ser Glu Val Arg Ala Lys Cys Lys Phe Ser Ile Leu Asn Ala
1 5 10 15

Lys

<210> SEQ ID NO 364
<211> LENGTH: 50
<212> TYPE: DNA
<213> ORGANISM: Homo sapiens

<400> SEQUENCE: 364
caaagagtga agttcgggca aaattcaaat gctccatcct gaatgccaag 50

<210> SEQ ID NO 365
<211> LENGTH: 17
<212> TYPE: PRT
<213> ORGANISM: Homo sapiens

<400> SEQUENCE: 365

Met Met Ala Glu Ile Ile Ser Val His Val Pro Lys Ile Leu Ser Gly
1 5 10 15

Lys

<210> SEQ ID NO 366
<211> LENGTH: 51
<212> TYPE: DNA
<213> ORGANISM: Homo sapiens

<400> SEQUENCE: 366
atgatggcag agatcatctc tgtgcacgtg cccaagatcc tttctgggaa a 51

<210> SEQ ID NO 367
<211> LENGTH: 17
<212> TYPE: PRT
<213> ORGANISM: Homo sapiens

<400> SEQUENCE: 367

Leu His Pro Asp Ser Gly Asn Met Val Glu Asn Gly Cys Tyr Leu Arg
1 5 10 15

Arg

<210> SEQ ID NO 368
<211> LENGTH: 51
<212> TYPE: DNA
<213> ORGANISM: Homo sapiens

<400> SEQUENCE: 368
ctgcacccgg actccggcaa catggtcgag aacggctgct acttgcgccg c 51

<210> SEQ ID NO 369
<211> LENGTH: 17
<212> TYPE: PRT
<213> ORGANISM: Homo sapiens

<400> SEQUENCE: 369

Cys Tyr Leu Arg Arg Gln Lys Arg Leu Lys Cys Glu Lys Gln Pro Gly
1 5 10 15

Ala

<210> SEQ ID NO 370
<211> LENGTH: 51
<212> TYPE: DNA
<213> ORGANISM: Homo sapiens

<400> SEQUENCE: 370

-continued tgctacttgc gccgccagaa gcgcttgaag tgcgagaagc agccgggggc c 51

<210> SEQ ID NO 371
<211> LENGTH: 17
<212> TYPE: PRT
<213> ORGANISM: Homo sapiens

<400> SEQUENCE: 371

Met Phe Glu Asn Gly Cys Tyr Leu Gly Arg Gln Lys Arg Phe Lys Cys
1 5 10 15

Glu

<210> SEQ ID NO 372
<211> LENGTH: 51
<212> TYPE: DNA
<213> ORGANISM: Homo sapiens

<400> SEQUENCE: 372
atgttcgaga acggctgcta cttgggccgc cagaagcgct tcaagtgcga g 51

<210> SEQ ID NO 373
<211> LENGTH: 16
<212> TYPE: PRT
<213> ORGANISM: Homo sapiens

<400> SEQUENCE: 373

Asp Ser Ser Gly Asn Leu Leu Glu Arg Asn Ser Phe Glu Val Arg Val
1 5 10 15

<210> SEQ ID NO 374
<211> LENGTH: 48
<212> TYPE: DNA
<213> ORGANISM: Homo sapiens

<400> SEQUENCE: 374
gactccagtg gtaatctact ggaacggaac agctttgagg tgcgtgtt 48

<210> SEQ ID NO 375
<211> LENGTH: 61
<212> TYPE: PRT
<213> ORGANISM: Homo sapiens

<400> SEQUENCE: 375

Val Phe Phe Lys Arg Ala Ala Glu Gly Phe Phe Arg Met Asn Lys Leu
1 5 10 15

Lys Glu Ser Ser Asp Thr Asn Pro Lys Pro Tyr Cys Met Ala Ala Pro
20 25 30

Met Gly Leu Thr Glu Asn Asn Arg Asn Arg Lys Lys Ser Tyr Arg Glu
35 40 45

Thr Asn Leu Lys Ala Val Ser Trp Pro Leu Asn His Thr
50 55 60

<210> SEQ ID NO 376
<211> LENGTH: 183
<212> TYPE: DNA
<213> ORGANISM: Homo sapiens

<400> SEQUENCE: 376
gtcttcttca aaagagccgc tgaaggattt ttcagaatga acaaattaaa agaatcatca 60
gacactaacc ccaagccata ctgcatggca gcaccaatgg gactgacaga aaacaacaga 120
aataggaaga aatcctacag agaaacaaac ttgaaagctg tctcatggcc tttgaatcat 180
act 183

<210> SEQ ID NO 377
<211> LENGTH: 15
<212> TYPE: PRT
<213> ORGANISM: Homo sapiens

<400> SEQUENCE: 377

Leu Thr Phe Leu Asp Phe Ile Gln Val Thr Leu Arg Val Met Ser
1 5 10 15

<210> SEQ ID NO 378
<211> LENGTH: 15
<212> TYPE: PRT
<213> ORGANISM: Homo sapiens

<400> SEQUENCE: 378

Val Thr Leu Arg Val Met Ser Gly Ser Gln Met Glu Asn Gly Ser
1 5 10 15

<210> SEQ ID NO 379
<211> LENGTH: 24
<212> TYPE: PRT
<213> ORGANISM: Homo sapiens

<400> SEQUENCE: 379

Tyr Glu Ala Gly Met Thr Leu Gly Glu Lys Phe Arg Val Gly Asn Cys
1 5 10 15

Lys His Leu Lys Met Thr Arg Pro
20

<210> SEQ ID NO 380
<211> LENGTH: 72
<212> TYPE: DNA
<213> ORGANISM: Homo sapiens

<400> SEQUENCE: 380
tatgaagcag ggatgactct gggagaaaaa ttccgggttg gcaattgcaa gcatctcaaa 60
atgaccagac cc 72

<210> SEQ ID NO 381
<211> LENGTH: 28
<212> TYPE: PRT
<213> ORGANISM: Homo sapiens

<400> SEQUENCE: 381

Tyr Glu Ala Gly Met Thr Leu Gly Gly Lys Ile Leu Phe Phe Leu Phe
1 5 10 15

Leu Leu Leu Pro Leu Ser Pro Phe Ser Leu Ile Phe
20 25

<210> SEQ ID NO 382
<211> LENGTH: 84
<212> TYPE: DNA
<213> ORGANISM: Homo sapiens

<400> SEQUENCE: 382
tatgaagcag ggatgactct gggaggtaag atacttttct ttctcttcct cctccttcct 60
ctctccccct tctccctcat tttc 84

<210> SEQ ID NO 383
<211> LENGTH: 16
<212> TYPE: PRT
<213> ORGANISM: Homo sapiens

<400> SEQUENCE: 383

Gly Tyr Leu Arg Met Gln Gly Leu Met Ala Gln Arg Leu Leu Leu Arg
1               5                   10                  15

<210> SEQ ID NO 384
<211> LENGTH: 48
<212> TYPE: DNA
<213> ORGANISM: Homo sapiens

<400> SEQUENCE: 384
gggtacctga ggatgcaggg actcatggct cagcgacttc ttctgagg                  48

<210> SEQ ID NO 385
<211> LENGTH: 48
<212> TYPE: PRT
<213> ORGANISM: Homo sapiens

<400> SEQUENCE: 385

Asp Gly His Ser Tyr Thr Ser Lys Val Asn Cys Leu Leu Leu Gln Asp
1               5                   10                  15

Gly Phe His Gly Cys Val Ser Ile Thr Gly Ala Ala Gly Arg Arg Asn
            20                  25                  30

Leu Ser Ile Phe Leu Phe Leu Met Leu Cys Lys Leu Glu Phe His Ala
        35                  40                  45

<210> SEQ ID NO 386
<211> LENGTH: 144
<212> TYPE: DNA
<213> ORGANISM: Homo sapiens

<400> SEQUENCE: 386
gatggccact cctacacatc caaggtgaat tgtttactcc ttcaagatgg gttccatggc     60
tgtgtgagca tcaccggggc agctggaaga agaaacctga gcatcttcct gttcttgatg    120
ctgtgcaaat tggagttcca tgct                                           144

<210> SEQ ID NO 387
<211> LENGTH: 9
<212> TYPE: PRT
<213> ORGANISM: Homo sapiens

<400> SEQUENCE: 387

Ser Thr Arg Arg Ala Val Arg Arg Met
1               5

<210> SEQ ID NO 388
<211> LENGTH: 9
<212> TYPE: PRT
<213> ORGANISM: Homo sapiens

<400> SEQUENCE: 388

Arg Ala Val Arg Arg Met Asn Thr Phe
1               5

<210> SEQ ID NO 389
<211> LENGTH: 9
<212> TYPE: PRT
<213> ORGANISM: Homo sapiens

<400> SEQUENCE: 389

Ile Pro Val Leu Thr Arg Trp Pro Leu
1 5

<210> SEQ ID NO 390
<211> LENGTH: 9
<212> TYPE: PRT
<213> ORGANISM: Homo sapiens

<400> SEQUENCE: 390

Gln Leu Ile Ala Met Asp Ser Ala Ile
1 5

<210> SEQ ID NO 391
<211> LENGTH: 9
<212> TYPE: PRT
<213> ORGANISM: Homo sapiens

<400> SEQUENCE: 391

Phe Pro Val Gly Ala Glu Gly Thr Phe
1 5

<210> SEQ ID NO 392
<211> LENGTH: 9
<212> TYPE: PRT
<213> ORGANISM: Homo sapiens

<400> SEQUENCE: 392

Asn Ser Lys Met Ala Leu Asn Ser Leu
1 5

<210> SEQ ID NO 393
<211> LENGTH: 9
<212> TYPE: PRT
<213> ORGANISM: Homo sapiens

<400> SEQUENCE: 393

Gly Val Leu Arg Arg Leu Leu Cys Arg
1 5

<210> SEQ ID NO 394
<211> LENGTH: 9
<212> TYPE: PRT
<213> ORGANISM: Homo sapiens

<400> SEQUENCE: 394

Cys Pro Met Ser Arg Leu Arg Leu Ala
1 5

<210> SEQ ID NO 395
<211> LENGTH: 9
<212> TYPE: PRT
<213> ORGANISM: Homo sapiens

<400> SEQUENCE: 395

Tyr Gln Phe Thr Phe Asp Leu Leu Ile
1 5

<210> SEQ ID NO 396
<211> LENGTH: 9
<212> TYPE: PRT
<213> ORGANISM: Homo sapiens

<400> SEQUENCE: 396

Ile Gln Tyr Ser Cys Met Gly Leu Met
1 5

<210> SEQ ID NO 397
<211> LENGTH: 9
<212> TYPE: PRT
<213> ORGANISM: Homo sapiens

<400> SEQUENCE: 397

Arg Ala Lys Cys Lys Phe Ser Ile Leu
1 5

<210> SEQ ID NO 398
<211> LENGTH: 9
<212> TYPE: PRT
<213> ORGANISM: Homo sapiens

<400> SEQUENCE: 398

His Val Pro Lys Ile Leu Ser Gly Lys
1 5

<210> SEQ ID NO 399
<211> LENGTH: 9
<212> TYPE: PRT
<213> ORGANISM: Homo sapiens

<400> SEQUENCE: 399

Asn Met Val Glu Asn Gly Cys Tyr Leu
1 5

<210> SEQ ID NO 400
<211> LENGTH: 9
<212> TYPE: PRT
<213> ORGANISM: Homo sapiens

<400> SEQUENCE: 400

Tyr Leu Arg Arg Gln Lys Arg Leu Lys
1 5

<210> SEQ ID NO 401
<211> LENGTH: 9
<212> TYPE: PRT
<213> ORGANISM: Homo sapiens

<400> SEQUENCE: 401

Cys Tyr Leu Gly Arg Gln Lys Arg Phe
1 5

<210> SEQ ID NO 402
<211> LENGTH: 9
<212> TYPE: PRT
<213> ORGANISM: Homo sapiens

<400> SEQUENCE: 402

Leu Leu Glu Arg Asn Ser Phe Glu Val
1 5

<210> SEQ ID NO 403
<211> LENGTH: 9
<212> TYPE: PRT
<213> ORGANISM: Homo sapiens

<400> SEQUENCE: 403

Tyr Cys Met Ala Ala Pro Met Gly Leu
1 5

<210> SEQ ID NO 404
<211> LENGTH: 9
<212> TYPE: PRT
<213> ORGANISM: Homo sapiens

<400> SEQUENCE: 404

Phe Phe Lys Arg Ala Ala Glu Gly Phe
1 5

<210> SEQ ID NO 405
<211> LENGTH: 9
<212> TYPE: PRT
<213> ORGANISM: Homo sapiens

<400> SEQUENCE: 405

Arg Val Gly Asn Cys Lys His Leu Lys
1 5

<210> SEQ ID NO 406
<211> LENGTH: 9
<212> TYPE: PRT
<213> ORGANISM: Homo sapiens

<400> SEQUENCE: 406

Phe Leu Phe Leu Leu Leu Pro Leu Ser
1 5

<210> SEQ ID NO 407
<211> LENGTH: 9
<212> TYPE: PRT
<213> ORGANISM: Homo sapiens

<400> SEQUENCE: 407

Leu Met Ala Gln Arg Leu Leu Leu Arg
1 5

<210> SEQ ID NO 408
<211> LENGTH: 9
<212> TYPE: PRT
<213> ORGANISM: Homo sapiens

<400> SEQUENCE: 408

Ile Val Trp Trp Cys Pro Met Ser Arg
1 5

<210> SEQ ID NO 409
<211> LENGTH: 9
<212> TYPE: PRT
<213> ORGANISM: Homo sapiens

<400> SEQUENCE: 409

Cys Thr Glu Leu Lys Leu Ser Asp Tyr
1 5

<210> SEQ ID NO 410
<211> LENGTH: 9
<212> TYPE: PRT
<213> ORGANISM: Homo sapiens

<400> SEQUENCE: 410

Asn Leu Val Pro Met Val Ala Thr Val
1 5

<210> SEQ ID NO 411
<211> LENGTH: 9
<212> TYPE: PRT
<213> ORGANISM: Homo sapiens

<400> SEQUENCE: 411

Leu Ile Tyr Arg Arg Arg Leu Met Lys
1 5

<210> SEQ ID NO 412
<211> LENGTH: 9
<212> TYPE: PRT
<213> ORGANISM: Homo sapiens

<400> SEQUENCE: 412

Leu Tyr Ser Ala Cys Phe Trp Trp Leu
1 5

<210> SEQ ID NO 413
<211> LENGTH: 9
<212> TYPE: PRT
<213> ORGANISM: Homo sapiens

<400> SEQUENCE: 413

Asn Pro Lys Ala Ser Leu Leu Ser Leu
1 5

<210> SEQ ID NO 414
<211> LENGTH: 9
<212> TYPE: PRT
<213> ORGANISM: Homo sapiens

<400> SEQUENCE: 414

Glu Leu Arg Ser Arg Tyr Trp Ala Ile
1 5

<210> SEQ ID NO 415
<211> LENGTH: 15
<212> TYPE: PRT
<213> ORGANISM: Homo sapiens

<400> SEQUENCE: 415

Ser Gln Met Glu Asn Gly Ser Ser Tyr Phe Phe Lys Pro Phe Ser
1 5 10 15

<210> SEQ ID NO 416
<211> LENGTH: 9
<212> TYPE: PRT
<213> ORGANISM: Homo sapiens

<400> SEQUENCE: 416

Ile Val Thr Asp Phe Ser Val Ile Lys
1 5

<210> SEQ ID NO 417
<211> LENGTH: 15
<212> TYPE: PRT
<213> ORGANISM: Homo sapiens

<400> SEQUENCE: 417

Tyr Phe Phe Lys Pro Phe Ser Trp Gly Leu Gly Val Gly Leu Ser
1 5 10 15

<210> SEQ ID NO 418
<211> LENGTH: 15

<212> TYPE: PRT
<213> ORGANISM: Homo sapiens

<400> SEQUENCE: 418

Phe Met Ile Gly Glu Leu Val Gly Glu Leu Cys Cys Gln Leu Thr
1 5 10 15

<210> SEQ ID NO 419
<211> LENGTH: 15
<212> TYPE: PRT
<213> ORGANISM: Homo sapiens

<400> SEQUENCE: 419

Glu Leu Cys Cys Gln Leu Thr Phe Arg Leu Pro Phe Leu Glu Ser
1 5 10 15

<210> SEQ ID NO 420
<211> LENGTH: 15
<212> TYPE: PRT
<213> ORGANISM: Homo sapiens

<400> SEQUENCE: 420

Arg Leu Pro Phe Leu Glu Ser Leu Cys Gln Ala Val Val Thr Gln
1 5 10 15

<210> SEQ ID NO 421
<211> LENGTH: 9
<212> TYPE: PRT
<213> ORGANISM: Homo sapiens

<400> SEQUENCE: 421

Lys Leu Ser Arg Ala Leu Arg Tyr Tyr
1 5

<210> SEQ ID NO 422
<211> LENGTH: 9
<212> TYPE: PRT
<213> ORGANISM: Homo sapiens

<400> SEQUENCE: 422

Met Val Phe Glu Leu Ala Asn Ser Ile
1 5

<210> SEQ ID NO 423
<211> LENGTH: 9
<212> TYPE: PRT
<213> ORGANISM: Homo sapiens

<400> SEQUENCE: 423

Ile Leu Phe Gln Asn Ile Asp Gly Lys
1 5

<210> SEQ ID NO 424
<211> LENGTH: 9
<212> TYPE: PRT
<213> ORGANISM: Homo sapiens

<400> SEQUENCE: 424

Lys Ile Val Ile Ala Arg Tyr Gly Lys
1 5

<210> SEQ ID NO 425
<211> LENGTH: 9
<212> TYPE: PRT
<213> ORGANISM: Homo sapiens

<400> SEQUENCE: 425

Phe Leu Leu Glu Leu Leu Ser Asp Ser
1               5

<210> SEQ ID NO 426
<211> LENGTH: 10
<212> TYPE: PRT
<213> ORGANISM: Homo sapiens

<400> SEQUENCE: 426

Val Thr Phe Leu Lys Pro Cys Phe Leu Leu
1               5                   10

<210> SEQ ID NO 427
<211> LENGTH: 8
<212> TYPE: PRT
<213> ORGANISM: Homo sapiens

<400> SEQUENCE: 427

Thr Asp Ile Val Lys Gln Ser Val
1               5

<210> SEQ ID NO 428
<211> LENGTH: 10
<212> TYPE: PRT
<213> ORGANISM: Homo sapiens

<400> SEQUENCE: 428

Ser Pro Ala Phe Pro Lys Pro Val Arg Pro
1               5                   10

<210> SEQ ID NO 429
<211> LENGTH: 12
<212> TYPE: PRT
<213> ORGANISM: Homo sapiens

<400> SEQUENCE: 429

Ser Tyr Phe Ser Leu Thr Asn Ile Phe Asn Phe Val
1               5                   10

<210> SEQ ID NO 430
<211> LENGTH: 12
<212> TYPE: PRT
<213> ORGANISM: Homo sapiens

<400> SEQUENCE: 430

Glu Phe Ser Pro Glu Thr Cys Ala Phe Arg Leu Ser
1               5                   10

<210> SEQ ID NO 431
<211> LENGTH: 9
<212> TYPE: PRT
<213> ORGANISM: Homo sapiens

<400> SEQUENCE: 431

Phe Leu Ser Arg Ala Leu Arg Ala Leu
1               5

<210> SEQ ID NO 432
<211> LENGTH: 8
<212> TYPE: PRT
<213> ORGANISM: Homo sapiens

<400> SEQUENCE: 432

Lys Lys Asp Leu Glu Leu Ile Leu
1 5

<210> SEQ ID NO 433
<211> LENGTH: 8
<212> TYPE: PRT
<213> ORGANISM: Homo sapiens

<400> SEQUENCE: 433

Lys Leu Gln Lys Asn Cys Leu Leu
1 5

<210> SEQ ID NO 434
<211> LENGTH: 9
<212> TYPE: PRT
<213> ORGANISM: Homo sapiens

<400> SEQUENCE: 434

Ser Ala Leu Ser Gly Asn Ser Trp Val
1 5

<210> SEQ ID NO 435
<211> LENGTH: 7
<212> TYPE: PRT
<213> ORGANISM: Homo sapiens

<400> SEQUENCE: 435

Thr Val Arg Ala Ile Leu Leu
1 5

<210> SEQ ID NO 436
<211> LENGTH: 10
<212> TYPE: PRT
<213> ORGANISM: Homo sapiens

<400> SEQUENCE: 436

Gly Ser Leu His Phe His Glu Val Leu Lys
1 5 10

<210> SEQ ID NO 437
<211> LENGTH: 75
<212> TYPE: PRT
<213> ORGANISM: Homo sapiens

<400> SEQUENCE: 437

His Tyr Lys Leu Ile Gln Gln Pro Ile Ser Leu Phe Ser Ile Thr Asp
1 5 10 15

Arg Leu His Lys Thr Phe Ser Gln Leu Pro Ser Val His Leu Cys Ser
20 25 30

Ile Thr Phe Gln Trp Gly His Pro Pro Ile Phe Cys Ser Thr Asn Asp
35 40 45

Ile Cys Val Thr Ala Asn Phe Cys Ile Ser Val Thr Phe Leu Lys Pro
50 55 60

Cys Phe Leu Leu His Glu Ala Ser Ala Ser Gln
65 70 75

<210> SEQ ID NO 438
<211> LENGTH: 40
<212> TYPE: PRT
<213> ORGANISM: Homo sapiens

<400> SEQUENCE: 438

```
Trp Thr Asp Ile Val Lys Gln Ser Val Ser Thr Asn Cys Ile Ser Ile
1               5                   10                  15

Lys Lys Gly Ser Tyr Thr Lys Leu Phe Ser Leu Val Phe Leu Ile Phe
            20                  25                  30

Cys Trp Pro Leu Ile Ile Gln Leu
        35                  40


<210> SEQ ID NO 439
<211> LENGTH: 144
<212> TYPE: PRT
<213> ORGANISM: Homo sapiens

<400> SEQUENCE: 439

Arg Thr Ala Leu Thr His Asn Gln Asp Phe Ser Ile Tyr Arg Leu Cys
1               5                   10                  15

Cys Lys Arg Gly Ser Leu Cys His Ala Ser Gln Ala Arg Ser Pro Ala
            20                  25                  30

Phe Pro Lys Pro Val Arg Pro Leu Pro Ala Pro Ile Thr Arg Ile Thr
        35                  40                  45

Pro Gln Leu Gly Gly Gln Ser Asp Ser Ser Gln Pro Leu Leu Thr Thr
    50                  55                  60

Gly Arg Pro Gln Gly Trp Gln Asp Gln Ala Leu Arg His Thr Gln Gln
65                  70                  75                  80

Ala Ser Pro Ala Ser Cys Ala Thr Ile Thr Ile Pro Ile His Ser Ala
                85                  90                  95

Ala Leu Gly Asp His Ser Gly Asp Pro Gly Pro Ala Trp Asp Thr Cys
            100                 105                 110

Pro Pro Leu Pro Leu Thr Thr Leu Ile Pro Arg Ala Pro Pro Pro Tyr
        115                 120                 125

Gly Asp Ser Thr Ala Arg Ser Trp Pro Ser Arg Cys Gly Pro Leu Gly
    130                 135                 140


<210> SEQ ID NO 440
<211> LENGTH: 36
<212> TYPE: PRT
<213> ORGANISM: Homo sapiens

<400> SEQUENCE: 440

Leu Arg Tyr Gly Ala Leu Cys Asn Val Ser Arg Ile Ser Tyr Phe Ser
1               5                   10                  15

Leu Thr Asn Ile Phe Asn Phe Val Ile Lys Ser Leu Thr Ala Ile Phe
            20                  25                  30

Thr Val Lys Phe
        35


<210> SEQ ID NO 441
<211> LENGTH: 295
<212> TYPE: PRT
<213> ORGANISM: Homo sapiens

<400> SEQUENCE: 441

Arg Lys Glu Arg Asn Ile Arg Lys Ser Glu Ser Thr Leu Arg Leu Ser
1               5                   10                  15

Pro Phe Pro Thr Pro Ala Pro Ser Gly Ala Pro Ala Ala Ala Gln Gly
            20                  25                  30

Lys Val Val Arg Val Pro Gly Pro Ala Gly Gly Leu Val Pro Arg Asp
        35                  40                  45

Ala Gly Ala Arg Leu Leu Pro Pro Ala Gly Gly Pro Gly Gly Gly Ala
```

```
    50                  55                  60

Ala Ala Gly Glu Gly Arg Ala Gly Arg Gly Arg Phe Pro Ser Ile Thr
65                  70                  75                  80

Glu Pro Arg Pro Arg Asp Leu Pro Pro Arg Val Ala Thr Gly Arg Arg
                85                  90                  95

Ala Gly Gly Arg Arg Lys Gly Ala Gly Gln Gly Val Arg Thr Arg Pro
            100                 105                 110

Leu Pro Ala Ser Trp Pro Gly Gly Arg Gly Pro Phe Arg Lys Gly Pro
        115                 120                 125

Arg Arg Leu Pro Leu Gly Ser Gly Pro Pro Ala Ala Gly Val Gln Arg
    130                 135                 140

Leu Arg Cys Ser His Leu Ser Arg Gly Pro Arg Arg Arg Arg Gly Arg
145                 150                 155                 160

Val Cys Gly Arg Ala Cys Val Ser Pro Pro Leu Pro Pro Arg Pro Pro
                165                 170                 175

Pro Val Gly Leu Ser Ala Glu Asn Leu Ser Trp Leu Ser Ser Gly Leu
            180                 185                 190

Pro Arg Ala Cys Ser Trp Arg Glu Phe Ser Pro Glu Thr Cys Ala Phe
        195                 200                 205

Arg Leu Ser Gly Leu Asp Ser Lys Leu Ser Ala Arg Val Glu Arg Asp
    210                 215                 220

Leu Gly Ala Leu Arg Ala Pro Gly Ser Arg Ala Ala Gln Gly Gly Gly
225                 230                 235                 240

Arg Val Arg Gly Ser Arg Ser Glu Trp Lys Thr Arg Pro Trp Arg Pro
                245                 250                 255

Pro Pro Ala Trp Pro Leu Thr Arg Ala Gly Gly Pro Leu Pro Lys Asn
            260                 265                 270

Pro Phe Leu Glu Ser Cys Ser Glu Thr Ala Gln Arg Arg Arg Val Phe
        275                 280                 285

Ser Phe Ser Thr Pro Leu Ser
    290                 295


<210> SEQ ID NO 442
<211> LENGTH: 67
<212> TYPE: PRT
<213> ORGANISM: Homo sapiens

<400> SEQUENCE: 442

Tyr Ala Tyr Lys Asp Phe Leu Trp Cys Phe Pro Phe Ser Leu Val Phe
1               5                   10                  15

Leu Gln Glu Ile Gln Ile Cys Cys His Val Ser Cys Leu Cys Cys Ile
            20                  25                  30

Cys Cys Ser Thr Arg Ile Cys Leu Gly Cys Leu Leu Glu Leu Phe Leu
        35                  40                  45

Ser Arg Ala Leu Arg Ala Leu His Val Leu Trp Asn Gly Phe Gln Leu
    50                  55                  60

His Cys Gln
65


<210> SEQ ID NO 443
<211> LENGTH: 82
<212> TYPE: PRT
<213> ORGANISM: Homo sapiens

<400> SEQUENCE: 443

Ser Ile Asn Lys Ala Thr Ile Thr Gly Lys Lys Asp Leu Glu Leu Ile
```

1 5 10 15

Leu His Val Ser Arg Lys Lys Pro Phe Leu Pro Arg Val Asn Ile Thr
20 25 30

Pro Thr Pro Ile Ser Cys Cys Asn Leu Lys Met Leu Lys Lys Phe Phe
35 40 45

Leu Leu Tyr Ile Ile Ile Ser Ile Ile Asp Leu Thr Asn Cys Leu Ser
50 55 60

Cys Tyr Leu Glu His Phe Tyr Arg Phe Thr Phe Phe Thr Asp Val His
65 70 75 80

Tyr Phe

<210> SEQ ID NO 444
<211> LENGTH: 16
<212> TYPE: PRT
<213> ORGANISM: Homo sapiens

<400> SEQUENCE: 444

Thr Met Pro Ala Ile Leu Lys Leu Gln Lys Asn Cys Leu Leu Ser Leu
1 5 10 15

<210> SEQ ID NO 445
<211> LENGTH: 84
<212> TYPE: PRT
<213> ORGANISM: Homo sapiens

<400> SEQUENCE: 445

Pro Tyr Tyr Ser Ala Leu Ser Gly Asn Ser Trp Val Pro Ser Thr Leu
1 5 10 15

Glu Ser Asp Pro Phe Gly Tyr Val Phe Ser Pro Leu Ala Thr Arg Pro
20 25 30

Ala Leu Asn Asp Gln Glu Ser Ile Leu Trp Pro Thr Leu Thr Ser Val
35 40 45

Val Ser Cys Ala Leu Ser Cys Pro Ser Leu Asn Leu Pro Glu Asn Trp
50 55 60

Leu Thr Leu Ile Thr Gly Gly Met Lys Gly Gly Lys Lys Met Lys Phe
65 70 75 80

Thr Phe Arg His

<210> SEQ ID NO 446
<211> LENGTH: 46
<212> TYPE: PRT
<213> ORGANISM: Homo sapiens

<400> SEQUENCE: 446

Gly Leu Arg Asn Leu Gly Asn Thr Val Arg Ala Ile Leu Leu Ser Phe
1 5 10 15

Leu Ser Lys Arg Asn Val Lys Trp Cys Trp Gly Trp Gly Lys Pro Thr
20 25 30

Ser Leu Gly Lys Ala Cys Gly Arg Arg Ala Leu Lys Leu Phe
35 40 45

<210> SEQ ID NO 447
<211> LENGTH: 22
<212> TYPE: PRT
<213> ORGANISM: Homo sapiens

<400> SEQUENCE: 447

Met Glu Ala Glu Asn Ala Gly Ser Leu His Phe His Glu Val Leu Lys
1 5 10 15

Met Gly His Val Lys Phe
20

<210> SEQ ID NO 448
<211> LENGTH: 225
<212> TYPE: DNA
<213> ORGANISM: Homo sapiens

<400> SEQUENCE: 448
cactacaaat taattcaaca acccatatcc ctcttctcca tcactgatag gctccataag 60
acgttcagtc agctgccctc ggtccatctc tgctcaatca ccttccagtg gggacacccg 120
cccattttct gctcaacaaa tgatatctgt gtcacggcca acttctgcat ctcggtcaca 180
ttccttaaac cgtgcttcct cctacatgag gcatctgcct cacag 225

<210> SEQ ID NO 449
<211> LENGTH: 120
<212> TYPE: DNA
<213> ORGANISM: Homo sapiens

<400> SEQUENCE: 449
tggactgata tagttaagca gtctgtaagt acaaactgca tttctatcaa gaaaggtagc 60
tatacaaaac tgttttcctt agtctttctt attttctgtt ggccattaat tattcagttg 120

<210> SEQ ID NO 450
<211> LENGTH: 432
<212> TYPE: DNA
<213> ORGANISM: Homo sapiens

<400> SEQUENCE: 450
aggaccgccc tgacacacaa tcaggacttc tctatctaca ggctctgttg caagaggggg 60
tccctctgcc acgcttccca ggccagatcc ccggctttcc cgaagccggt cagacctctt 120 cctgcccccca tcaccagaat caccccccaa ctggggggac aatctgactc gagtcaaccc 180
cttctcacta cgggaagacc tcaggggtgg caagatcaag ctcttagaca cacccagcaa 240
gccagtcctg cctcttgtgc caccatcacc attcccatcc actcagctgc ccttggtgac 300
cactccggag accctggtcc agcctgggac acctgcccgc cgctgccgct cactaccctc 360
atcccccgag ctcccccgcc gtatggagac agcactgcca ggtcctggcc ctcccgctgt 420
gggcccctcg gc 432

<210> SEQ ID NO 451
<211> LENGTH: 108
<212> TYPE: DNA
<213> ORGANISM: Homo sapiens

<400> SEQUENCE: 451
cttcgctatg gtgccttatg caatgtaagt agaataagtt atttcagtct aacaaatata 60
tttaattttg taattaaatc actaactgct atttttactg tgaaattt 108

<210> SEQ ID NO 452
<211> LENGTH: 885
<212> TYPE: DNA
<213> ORGANISM: Homo sapiens

<400> SEQUENCE: 452
cgaaaagaga gaaacatccg aaaaagtgag tccacgctgc gcctgtcccc gttccccacc 60
cccgccccgt cgggggcgcc cgcggccgcg caggggaaag ttgtccgggt ccccgggccg 120

-continued gcgggcgggc tggtccccg ggacgctggc gctcggctcc tgcccccggc gggcggcccg 180
gggggagggg cggcggcggg ggaggggcgc gcgggccgcg gccggttccc tagcatcacg 240
gagcctcgac cccgcgacct cccgccccgg gtcgccaccg gccggcgggc gggaggccgg 300
cggaaaggcg ccgggcaggg cgtgcgcacc cgtcccttgc ccgcgagctg gcccgggggt 360 cgcggcccttt tccggaaggg gccccggcgt ctgccgctgg gctccggccc gcccgctgcg 420
ggagtgcagc ggctgcgttg ctcccacctg agccgcgggc cgaggaggcg gaggggccga 480
gtgtgcggga gggcgtgtgt ctcgcctccc cttcctcccc ggcccccgcc tgtcggcctt 540
tctgctgaga acctaagctg gttgtcaagt ggtttgcctc gggcgtgttc ctggcgcgag 600
ttcagccccg agacctgtgc gtttcggctc tcgggtttgg attcgaaact ttccgctcgg 660
gttgagcgtg acttgggtgc gctgcgggcg ccggggtcgc gggctgcgca gggcggtggg 720
cgtgtgcgcg ggagccggtc ggagtggaaa acgcgcccgt ggcggccacc tccagcctgg 780
ccgctcaccc gagcaggggg gccgctgccc aagaaccctt tcctggagag ctgctccgag 840
accgcacagc gccgccgcgt cttctccttt tccactcctc tctcc 885

<210> SEQ ID NO 453
<211> LENGTH: 201
<212> TYPE: DNA
<213> ORGANISM: Homo sapiens

<400> SEQUENCE: 453
tatgcttaca aggactttct ctggtgtttt cctttttctt tagtttttct ccaagagatt 60
caaatctgct gccatgttag ctgtctttgc tgtatctgct gtagtacacg aatatgcctt 120
ggctgtttgc ttgagctttt tctatcccgt gctcttcgtg ctcttcatgt tctttggaat 180
ggctttcaac ttcattgtca a 201

<210> SEQ ID NO 454
<211> LENGTH: 246
<212> TYPE: DNA
<213> ORGANISM: Homo sapiens

<400> SEQUENCE: 454
tccatcaaca aagccaccat aacaggtaag aaagatctgg agcttattct tcatgtgtct 60
aggaagaaac catttctgcc aagagtcaat ataacaccaa caccaatttc atgctgcaat 120
ttgaaaatgt taaagaaatt ctttcttctc tacattatca tttctatcat tgatctcaca 180
aattgtctaa gctgttattt ggaacatttt taccgattta cgttttttac tgatgtacat 240
tatttt 246

<210> SEQ ID NO 455
<211> LENGTH: 48
<212> TYPE: DNA
<213> ORGANISM: Homo sapiens

<400> SEQUENCE: 455
accatgcctg ctattttaaa gttacagaag aattgtcttc tctcctta 48

<210> SEQ ID NO 456
<211> LENGTH: 252
<212> TYPE: DNA
<213> ORGANISM: Homo sapiens

<400> SEQUENCE: 456

-continued

```
ccatactaca gcgcactgtc aggtaacagc tgggttccca gcaccctgga aagtgacccg     60

tttggctatg tttttagccc cttagcaaca cggccagctc tcaatgacca agagtccatc    120

ttgtggccga ccctgacttc tgtggtttcc tgtgctctat cctgcccatc tcttaactta    180

cctgagaatt ggctcactct catcacaggt ggaatgaaag ggggaaaaaa aatgaaattc    240

acattcagac ac                                                        252


<210> SEQ ID NO 457
<211> LENGTH: 138
<212> TYPE: DNA
<213> ORGANISM: Homo sapiens

<400> SEQUENCE: 457

ggccttcgaa acctgggaaa cacggtgaga gctattctcc tatctttcct ctctaaaagg     60

aatgtgaaat ggtgctgggg gtggggaaaa cccacgagct tggggaaggc atgtggaagg    120

agagctctga agctcttc                                                  138


<210> SEQ ID NO 458
<211> LENGTH: 66
<212> TYPE: DNA
<213> ORGANISM: Homo sapiens

<400> SEQUENCE: 458

atggaagcgg agaacgcggg cagtttgcat tttcatgaag tgctcaaaat gggacatgtg     60

aaattc                                                                66


<210> SEQ ID NO 459
<211> LENGTH: 81
<212> TYPE: DNA
<213> ORGANISM: Artificial sequence
<220> FEATURE:
<223> OTHER INFORMATION: Codon-optimized polynucleotide

<400> SEQUENCE: 459

tggaagttcg agatgagcta caccgtcggc ggacctccac ctcatgttca tgccagacct     60

cggcactgga aaaccgacag a                                               81


<210> SEQ ID NO 460
<211> LENGTH: 84
<212> TYPE: DNA
<213> ORGANISM: Artificial sequence
<220> FEATURE:
<223> OTHER INFORMATION: Codon-optimized polynucleotide

<400> SEQUENCE: 460

tatgaggccg gcatgacact cggcggcaag atcctgttct tcctgttcct gctgctccct     60

ctgagcccct tcagcctgat cttc                                            84


<210> SEQ ID NO 461
<211> LENGTH: 147
<212> TYPE: DNA
<213> ORGANISM: Artificial sequence
<220> FEATURE:
<223> OTHER INFORMATION: Codon-optimized polynucleotide

<400> SEQUENCE: 461

gatggccaca gctacaccag caaagtgaac tgcctcctgc tgcaggatgg cttccacggc     60

tgtgtgtcta ttactggcgc cgctggcaga cggaacctga gcatctttct gtttctgatg    120

ctgtgcaagc tcgagttcca cgcctgc                                        147
```

<210> SEQ ID NO 462
<211> LENGTH: 99
<212> TYPE: DNA
<213> ORGANISM: Artificial sequence
<220> FEATURE:
<223> OTHER INFORMATION: Codon-optimized polynucleotide

<400> SEQUENCE: 462
acaggcggca agtccacatg ttctgcccct ggacctcaga gcctgcctag cacacccttc 60
agcacatacc ctcagtgggt catcctgatc accgaactc 99

<210> SEQ ID NO 463
<211> LENGTH: 42
<212> TYPE: DNA
<213> ORGANISM: Artificial sequence
<220> FEATURE:
<223> OTHER INFORMATION: Codon-optimized polynucleotide

<400> SEQUENCE: 463
gtgctgagat tcctggacct gaaagtgcgc tacctgcaca gc 42

<210> SEQ ID NO 464
<211> LENGTH: 54
<212> TYPE: DNA
<213> ORGANISM: Artificial sequence
<220> FEATURE:
<223> OTHER INFORMATION: Codon-optimized polynucleotide

<400> SEQUENCE: 464
gactattggg ctcaaaaaga gaagggcagc agcagcttcc tgcggcctag ctgt 54

<210> SEQ ID NO 465
<211> LENGTH: 183
<212> TYPE: DNA
<213> ORGANISM: Artificial sequence
<220> FEATURE:
<223> OTHER INFORMATION: Codon-optimized polynucleotide

<400> SEQUENCE: 465
gtccccttca gagagctgaa gaacgtttcc gtgctggaag gcctgagaca gggcagactt 60
ggcggccctt gtagctgtca ctgccccaga cctagtcagg ccagactgac acctgtggat 120
gtggccggac ctttcctgtg tctgggagat cctggcctgt ttccacctgt gaagtccagc 180
atc 183

<210> SEQ ID NO 466
<211> LENGTH: 177
<212> TYPE: DNA
<213> ORGANISM: Artificial sequence
<220> FEATURE:
<223> OTHER INFORMATION: Codon-optimized polynucleotide

<400> SEQUENCE: 466
ggcatggaat gcaccctggg acaagtggga gccccatctc ctagaagaga agaggatggc 60
tggcgcggag gccactctag attcaaagct gatgtgcccg ctcctcaggg cccttgttgg 120
ggaggacaac ctggatctgc cccatcttct gccccacctg aacagtccct gctggat 177

<210> SEQ ID NO 467
<211> LENGTH: 96
<212> TYPE: DNA
<213> ORGANISM: Artificial sequence
<220> FEATURE:

<223> OTHER INFORMATION: Codon-optimized polynucleotide

<400> SEQUENCE: 467
ggcaacacaa ccctccagca actgggagaa gcctctcagg ctcctagcgg ctctctgatc 60
cctctcagac tgcctctcct gtgggaagtt cggggc 96

<210> SEQ ID NO 468
<211> LENGTH: 129
<212> TYPE: DNA
<213> ORGANISM: Artificial sequence
<220> FEATURE:
<223> OTHER INFORMATION: Codon-optimized polynucleotide

<400> SEQUENCE: 468
gaggctttcc aaagagctgc tggcgaaggc ggacctggta gaggtggtgc tagaagaggt 60
gctagggtgc tgcagagccc attctgtaga gcaggcgcag gcgaatggct gggccatcag 120
agtctgaga 129

<210> SEQ ID NO 469
<211> LENGTH: 51
<212> TYPE: DNA
<213> ORGANISM: Artificial sequence
<220> FEATURE:
<223> OTHER INFORMATION: Codon-optimized polynucleotide

<400> SEQUENCE: 469
gattattggg cccagaaaga aaagatcagc atccccagaa cacacctgtg c 51

<210> SEQ ID NO 470
<211> LENGTH: 48
<212> TYPE: DNA
<213> ORGANISM: Artificial sequence
<220> FEATURE:
<223> OTHER INFORMATION: Codon-optimized polynucleotide

<400> SEQUENCE: 470
gtggccatga tggtgcccga tagacaggtc cactacgact ttggactg 48

<210> SEQ ID NO 471
<211> LENGTH: 270
<212> TYPE: DNA
<213> ORGANISM: Artificial sequence
<220> FEATURE:
<223> OTHER INFORMATION: Codon-optimized polynucleotide

<400> SEQUENCE: 471
gtgcccttcc gggaactgaa gaaccagaga acagctcagg gcgctcctgg aatccaccat 60
gctgcttctc cagtggccgc caacctgtgt gatcctgcca gacatgccca gcacaccagg 120
attccttgtg gcgctggaca agtgcgcgct ggaagaggac ctgaagcagg cggaggtgtt 180
ctgcaacctc aaagacccgc tcctgagaag cctggctgcc cttgcagaag aggacagcct 240
agactgcaca ccgtgaaaat gtggcgagcc 270

<210> SEQ ID NO 472
<211> LENGTH: 33
<212> TYPE: DNA
<213> ORGANISM: Artificial sequence
<220> FEATURE:
<223> OTHER INFORMATION: Codon-optimized polynucleotide

<400> SEQUENCE: 472
aagagaagct ttgccgtgac cgagcggatc atc 33

<210> SEQ ID NO 473
<211> LENGTH: 150
<212> TYPE: DNA
<213> ORGANISM: Artificial sequence
<220> FEATURE:
<223> OTHER INFORMATION: Codon-optimized polynucleotide

<400> SEQUENCE: 473
ttcaagaagt tcgacggccc ttgcggagaa agaggcggag gcagaacagc tagagccctt 60
tgggctagag gcgacagcgt tctgacacca gctctggacc ctcagacacc tgttagggcc 120
cctagcctga caagagctgc cgccgctgtg 150

<210> SEQ ID NO 474
<211> LENGTH: 42
<212> TYPE: DNA
<213> ORGANISM: Artificial sequence
<220> FEATURE:
<223> OTHER INFORMATION: Codon-optimized polynucleotide

<400> SEQUENCE: 474
ctggtgctgg gagtgctgtc tggacactct ggcagcagac tg 42

<210> SEQ ID NO 475
<211> LENGTH: 66
<212> TYPE: DNA
<213> ORGANISM: Artificial sequence
<220> FEATURE:
<223> OTHER INFORMATION: Codon-optimized polynucleotide

<400> SEQUENCE: 475
cagtggcagc actatcacag atctggcgaa gccgccggaa cacccctttg gaggccaaca 60
agaaac 66

<210> SEQ ID NO 476
<211> LENGTH: 285
<212> TYPE: DNA
<213> ORGANISM: Artificial sequence
<220> FEATURE:
<223> OTHER INFORMATION: Codon-optimized polynucleotide

<400> SEQUENCE: 476
tgccacttgt ttctgcagcc ccaagtgggc acacctcctc cacatacagc ctctgctaga 60
gcacctagcg gccctccaca tcctcacgaa tcttgtcctg ccggaagaag gcctgccaga 120
gccgctcaaa catgtgccag acgacagcac ggactgcctg gatgtgaaga ggctggaaca 180
gccagagtgc ctagcctgca cctccatctg catcaggctg ctcttggagc cggaagaggt 240
agaggatggg gcgaagcttg tgctcaggtg ccaccttcta gaggc 285

<210> SEQ ID NO 477
<211> LENGTH: 27
<212> TYPE: DNA
<213> ORGANISM: Artificial sequence
<220> FEATURE:
<223> OTHER INFORMATION: Codon-optimized polynucleotide

<400> SEQUENCE: 477
aagatccaga acaagaactg ccccgac 27

<210> SEQ ID NO 478
<211> LENGTH: 225
<212> TYPE: DNA

<213> ORGANISM: Artificial sequence
<220> FEATURE:
<223> OTHER INFORMATION: Codon-optimized polynucleotide

<400> SEQUENCE: 478
cactacaagc tgatccagca gccaatcagc ctgttcagca tcaccgaccg gctgcacaag 60
acattcagcc agctgccaag cgtgcacctg tgctccatca ccttccagtg gggacaccct 120
cctatctttt gctccaccaa cgacatctgc gtgaccgcca acttctgtat cagcgtgacc 180
ttcctgaagc cttgctttct gctgcacgag gccagcgcct ctcag 225

<210> SEQ ID NO 479
<211> LENGTH: 432
<212> TYPE: DNA
<213> ORGANISM: Artificial sequence
<220> FEATURE:
<223> OTHER INFORMATION: Codon-optimized polynucleotide

<400> SEQUENCE: 479
cgaaccgctc tgacacacaa ccaggacttc agcatctaca gactgtgttg caagcggggc 60
tccctgtgcc atgcaagcca agctagaagc cccgcctttc ctaaacctgt gcgacctctg 120
ccagctccaa tcaccagaat tacccctcag ctcggcggcc agagcgattc atctcaacct 180
ctgctgacca ccggcagacc tcaaggctgg caagaccaag ctctgagaca cacccagcag 240
gctagccctg cctcttgtgc caccatcaca atccccatcc actctgccgc tctgggcgat 300
cattctggcg atcctggacc agcctgggac acatgtcctc cactgccact cacaacactg 360
atccctaggg ctcctccacc ttacggcgat tctaccgcta gaagctggcc cagcagatgt 420
ggaccactcg ga 432

<210> SEQ ID NO 480
<211> LENGTH: 201
<212> TYPE: DNA
<213> ORGANISM: Artificial sequence
<220> FEATURE:
<223> OTHER INFORMATION: Codon-optimized polynucleotide

<400> SEQUENCE: 480
tacgcctaca aggacttcct gtggtgcttc cccttctctc tggtgttcct gcaagagatc 60
cagatctgct gtcatgtgtc ctgcctgtgc tgcatctgct gtagcaccag aatctgcctg 120
ggctgtctgc tggaactgtt cctgagcaga gccctgagag cactgcacgt gctgtggaac 180
ggattccagc tgcactgcca g 201

<210> SEQ ID NO 481
<211> LENGTH: 48
<212> TYPE: DNA
<213> ORGANISM: Artificial sequence
<220> FEATURE:
<223> OTHER INFORMATION: Codon-optimized polynucleotide

<400> SEQUENCE: 481
acaatgcccg ccatcctgaa gctgcagaag aattgcctcc taagcctg 48

<210> SEQ ID NO 482
<211> LENGTH: 72
<212> TYPE: DNA
<213> ORGANISM: Artificial sequence
<220> FEATURE:
<223> OTHER INFORMATION: Codon-optimized polynucleotide

<400> SEQUENCE: 482
tacgaagccg ggatgaccct gggcgagaag ttcagagtgg gcaactgcaa gcacctgaag 60
atgacccggc ct 72

<210> SEQ ID NO 483
<211> LENGTH: 51
<212> TYPE: DNA
<213> ORGANISM: Artificial sequence
<220> FEATURE:
<223> OTHER INFORMATION: Codon-optimized polynucleotide

<400> SEQUENCE: 483
ggcgtgccag gcgatagcac tcggagagcc gtcagacgga tgaacacctt t 51

<210> SEQ ID NO 484
<211> LENGTH: 48
<212> TYPE: DNA
<213> ORGANISM: Artificial sequence
<220> FEATURE:
<223> OTHER INFORMATION: Codon-optimized polynucleotide

<400> SEQUENCE: 484
tgtggcgcct ctgcctgtga cgtgtccctg atcgctatgg actccgcc 48

<210> SEQ ID NO 485
<211> LENGTH: 48
<212> TYPE: DNA
<213> ORGANISM: Artificial sequence
<220> FEATURE:
<223> OTHER INFORMATION: Codon-optimized polynucleotide

<400> SEQUENCE: 485
agcctgtacc accgggaaaa gcagctcatt gccatggaca gcgccatc 48

<210> SEQ ID NO 486
<211> LENGTH: 48
<212> TYPE: DNA
<213> ORGANISM: Artificial sequence
<220> FEATURE:
<223> OTHER INFORMATION: Codon-optimized polynucleotide

<400> SEQUENCE: 486
accgagtaca accagaaact gcaagtgaac cagttcagcg agagcaag 48

<210> SEQ ID NO 487
<211> LENGTH: 72
<212> TYPE: DNA
<213> ORGANISM: Artificial sequence
<220> FEATURE:
<223> OTHER INFORMATION: Codon-optimized polynucleotide

<400> SEQUENCE: 487
accgagatca gctgctgcac cctgagcagc gaggaaaacg agtacctgcc tagacctgag 60
tggcagctgc ag 72

<210> SEQ ID NO 488
<211> LENGTH: 42
<212> TYPE: DNA
<213> ORGANISM: Artificial sequence
<220> FEATURE:
<223> OTHER INFORMATION: Codon-optimized polynucleotide

<400> SEQUENCE: 488
tgcgaagaga gaggcgccgc aggatctctg atctcctgcg aa 42

<210> SEQ ID NO 489
<211> LENGTH: 48
<212> TYPE: DNA
<213> ORGANISM: Artificial sequence
<220> FEATURE:
<223> OTHER INFORMATION: Codon-optimized polynucleotide

<400> SEQUENCE: 489
aacagcaaga tggccctgaa tagcgaggcc ctgtctgtgg tgtctgaa 48

<210> SEQ ID NO 490
<211> LENGTH: 210
<212> TYPE: DNA
<213> ORGANISM: Artificial sequence
<220> FEATURE:
<223> OTHER INFORMATION: Codon-optimized polynucleotide

<400> SEQUENCE: 490
tggggcatgg aactggccgc cagcagaaga ttcagctggg atcatcatag cgcaggcggc 60
ccacctagag tgccatctgt tagaagcgga gctgcccagg tgcagcctaa agatcctctg 120
ccactgagaa cactggccgg ctgccttgct agaacagccc atcttagacc tggcgccgag 180
tctctgcctc agccacaact gcactgtacc 210

<210> SEQ ID NO 491
<211> LENGTH: 60
<212> TYPE: DNA
<213> ORGANISM: Artificial sequence
<220> FEATURE:
<223> OTHER INFORMATION: Codon-optimized polynucleotide

<400> SEQUENCE: 491
catgtcgtcg gctacggcca cctggataca agcggaagca gctctagctc cagctggcct 60

<210> SEQ ID NO 492
<211> LENGTH: 105
<212> TYPE: DNA
<213> ORGANISM: Artificial sequence
<220> FEATURE:
<223> OTHER INFORMATION: Codon-optimized polynucleotide

<400> SEQUENCE: 492
aactcaaaaa tggctctgaa cagcctgaac tccatcgacg acgcccagct gacaagaatc 60
gcccctccta gatctcactg ctgcttttgg gaagtgaacg cccca 105

<210> SEQ ID NO 493
<211> LENGTH: 48
<212> TYPE: DNA
<213> ORGANISM: Artificial sequence
<220> FEATURE:
<223> OTHER INFORMATION: Codon-optimized polynucleotide

<400> SEQUENCE: 493
aagatgcact ttagcctgaa agaacaccct ccaccacctt gtcctcca 48

<210> SEQ ID NO 494
<211> LENGTH: 207
<212> TYPE: DNA
<213> ORGANISM: Artificial sequence
<220> FEATURE:
<223> OTHER INFORMATION: Codon-optimized polynucleotide

<400> SEQUENCE: 494
ctgtggttcc agtccagcga gctgtctcct actggtgccc cttggccatc tagacgccct 60
acttggagag gcaccaccgt gtcaccaaga accgccacaa gcagcgccag aacctgttgt 120
ggcacaaagt ggccctccag ccaagaagcc gctctcggac ttggaagcgg actgctgagg 180
ttctcttgtg gaaccgccgc cattcgg 207

<210> SEQ ID NO 495
<211> LENGTH: 51
<212> TYPE: DNA
<213> ORGANISM: Artificial sequence
<220> FEATURE:
<223> OTHER INFORMATION: Codon-optimized polynucleotide

<400> SEQUENCE: 495
atcgctagag agctgcacca gttcgccttc gacctgctga tcaagagcca c 51

<210> SEQ ID NO 496
<211> LENGTH: 51
<212> TYPE: DNA
<213> ORGANISM: Artificial sequence
<220> FEATURE:
<223> OTHER INFORMATION: Codon-optimized polynucleotide

<400> SEQUENCE: 496
cagcctgatt cttttgccgc actgcacagc tccctgaacg agctgggaga g 51

<210> SEQ ID NO 497
<211> LENGTH: 51
<212> TYPE: DNA
<213> ORGANISM: Artificial sequence
<220> FEATURE:
<223> OTHER INFORMATION: Codon-optimized polynucleotide

<400> SEQUENCE: 497
ttcgtgcaag gcaaggattg gggcctcaaa aagtttatcc gcagagactt c 51

<210> SEQ ID NO 498
<211> LENGTH: 51
<212> TYPE: DNA
<213> ORGANISM: Artificial sequence
<220> FEATURE:
<223> OTHER INFORMATION: Codon-optimized polynucleotide

<400> SEQUENCE: 498
tttgtgcagg gcaaagactg gggcgtgaag aagttcatcc ggcgggactt c 51

<210> SEQ ID NO 499
<211> LENGTH: 204
<212> TYPE: DNA
<213> ORGANISM: Artificial sequence
<220> FEATURE:
<223> OTHER INFORMATION: Codon-optimized polynucleotide

<400> SEQUENCE: 499
cagaacctgc agaacggcgg aggctctaga agctctgcta cacttcctgg caggcggcgg 60
agaagatggc tgagaagaag gcggcagcct atctctgtgg ctcctgctgg acctcctaga 120
cggcccaacc agaagcctaa tcctcctggc ggagccagat gcgtgatcat gaggcctaca 180
tggcctggca ccagcgcctt cacc 204

<210> SEQ ID NO 500
<211> LENGTH: 81
<212> TYPE: DNA
<213> ORGANISM: Artificial sequence
<220> FEATURE:

<223> OTHER INFORMATION: Codon-optimized polynucleotide

<400> SEQUENCE: 500
tggaagttcg agatgagcta caccgttggc ggccctccac cacatgttca cgccagacct 60
agacactgga aaaccgacag a 81

<210> SEQ ID NO 501
<211> LENGTH: 84
<212> TYPE: DNA
<213> ORGANISM: Artificial sequence
<220> FEATURE:
<223> OTHER INFORMATION: Codon-optimized polynucleotide

<400> SEQUENCE: 501
tacgaggccg gcatgacact cggaggcaag atcctgttct tcctgttcct gctgctccct 60
ctgagcccct tcagcctgat cttt 84

<210> SEQ ID NO 502
<211> LENGTH: 15
<212> TYPE: PRT
<213> ORGANISM: Homo sapiens

<400> SEQUENCE: 502

Cys Gln Ala Val Val Thr Gln Ala Leu Arg Phe Asn Pro Ser Phe
1 5 10 15

<210> SEQ ID NO 503
<211> LENGTH: 99
<212> TYPE: DNA
<213> ORGANISM: Artificial sequence
<220> FEATURE:
<223> OTHER INFORMATION: Codon-optimized polynucleotide

<400> SEQUENCE: 503
acaggcggca agagcacatg ttctgcccct ggacctcagt ctctgcccag cacacccttc 60
agcacatacc ctcagtgggt catcctgatc accgagctg 99

<210> SEQ ID NO 504
<211> LENGTH: 42
<212> TYPE: DNA
<213> ORGANISM: Artificial sequence
<220> FEATURE:
<223> OTHER INFORMATION: Codon-optimized polynucleotide

<400> SEQUENCE: 504
gtgctgcggt tcctggatct caaagtgcgc tacctgcaca gc 42

<210> SEQ ID NO 505
<211> LENGTH: 54
<212> TYPE: DNA
<213> ORGANISM: Artificial sequence
<220> FEATURE:
<223> OTHER INFORMATION: Codon-optimized polynucleotide

<400> SEQUENCE: 505
gattattggg cccagaaaga aaagggcagc agcagcttcc tgcggcctag ctgt 54

<210> SEQ ID NO 506
<211> LENGTH: 183
<212> TYPE: DNA
<213> ORGANISM: Artificial sequence
<220> FEATURE:
<223> OTHER INFORMATION: Codon-optimized polynucleotide

<400> SEQUENCE: 506
gtgcccttcc gggaactgaa gaacgtgtcc gttctggaag gcctgaggca gggcagactt 60
ggcggacctt gtagctgcca ctgtcctaga ccaagccagg ccagactgac ccctgtggat 120
gtggctggcc catttctgtg tctgggcgac cctggactgt tccctccagt gaagtctagc 180
atc 183

<210> SEQ ID NO 507
<211> LENGTH: 177
<212> TYPE: DNA
<213> ORGANISM: Artificial sequence
<220> FEATURE:
<223> OTHER INFORMATION: Codon-optimized polynucleotide

<400> SEQUENCE: 507
ggcatggaat gtacactggg ccaagtggga gccccatctc ctagaagaga agaggatggc 60
tggcgcggag gccactctag attcaaagct gatgtgcccg ctcctcaggg cccttgttgg 120
ggaggacaac ctggatctgc cccatcttct gccccacctg aacagagcct gctggat 177

<210> SEQ ID NO 508
<211> LENGTH: 96
<212> TYPE: DNA
<213> ORGANISM: Artificial sequence
<220> FEATURE:
<223> OTHER INFORMATION: Codon-optimized polynucleotide

<400> SEQUENCE: 508
ggcaacacca cactgcaaca gctgggagaa gcctctcagg ccccaagcgg ttctctgatc 60
cctctcagac tgcccctcct gtgggaagtg cggggc 96

<210> SEQ ID NO 509
<211> LENGTH: 129
<212> TYPE: DNA
<213> ORGANISM: Artificial sequence
<220> FEATURE:
<223> OTHER INFORMATION: Codon-optimized polynucleotide

<400> SEQUENCE: 509
gaggctttcc agagagcagc tggcgaaggc ggacctggca gaggtggtgc tagaagaggt 60
gctagagtgc tgcagagccc attctgtaga gctggcgctg gcgaatggct gggccaccaa 120
tctcttaga 129

<210> SEQ ID NO 510
<211> LENGTH: 51
<212> TYPE: DNA
<213> ORGANISM: Artificial sequence
<220> FEATURE:
<223> OTHER INFORMATION: Codon-optimized polynucleotide

<400> SEQUENCE: 510
gactattggg ctcaaaaaga gaagatcagc atccccagaa cacacctgtg c 51

<210> SEQ ID NO 511
<211> LENGTH: 48
<212> TYPE: DNA
<213> ORGANISM: Artificial sequence
<220> FEATURE:
<223> OTHER INFORMATION: Codon-optimized polynucleotide

<400> SEQUENCE: 511
gtggccatga tggtgcccga cagacaggtg cactacgact tcggcctg 48

<210> SEQ ID NO 512
<211> LENGTH: 270
<212> TYPE: DNA
<213> ORGANISM: Artificial sequence
<220> FEATURE:
<223> OTHER INFORMATION: Codon-optimized polynucleotide

<400> SEQUENCE: 512
gtgcccttca gagagctgaa aaaccagaga acagcccagg gcgctcctgg aatccatcat 60
gctgcttctc cagtggccgc caatctgtgc gatcctgcca gacatgccca gcataccagg 120
attccttgtg gcgctggaca agtgcgcgct ggaagaggac ctgaagctgg tggcggagtt 180
ctgcagcctc aaagacctgc tcctgagaag cctggctgcc cctgtagaag aggacagcct 240
agactgcaca ccgtgaagat gtggcgggcc 270

<210> SEQ ID NO 513
<211> LENGTH: 33
<212> TYPE: DNA
<213> ORGANISM: Artificial sequence
<220> FEATURE:
<223> OTHER INFORMATION: Codon-optimized polynucleotide

<400> SEQUENCE: 513
aagagaagct tcgccgtgac cgagcggatc atc 33

<210> SEQ ID NO 514
<211> LENGTH: 150
<212> TYPE: DNA
<213> ORGANISM: Artificial sequence
<220> FEATURE:
<223> OTHER INFORMATION: Codon-optimized polynucleotide

<400> SEQUENCE: 514
tttaagaagt ttgacggccc ctgcggcgag agaggcggag gaagaactgc aagagccctt 60
tgggccagag gcgactctgt tctgacacca gctctggacc ctcagacacc tgttagggcc 120
cctagcctga caagagctgc cgctgctgtt 150

<210> SEQ ID NO 515
<211> LENGTH: 42
<212> TYPE: DNA
<213> ORGANISM: Artificial sequence
<220> FEATURE:
<223> OTHER INFORMATION: Codon-optimized polynucleotide

<400> SEQUENCE: 515
ctggtgctgg gcgtgctgtc tggccactct ggaagcagac tg 42

<210> SEQ ID NO 516
<211> LENGTH: 66
<212> TYPE: DNA
<213> ORGANISM: Artificial sequence
<220> FEATURE:
<223> OTHER INFORMATION: Codon-optimized polynucleotide

<400> SEQUENCE: 516
caatggcagc actaccacag atctggcgaa gccgctggaa ccccactttg gaggcctacc 60
agaaac 66

<210> SEQ ID NO 517
<211> LENGTH: 285
<212> TYPE: DNA

<213> ORGANISM: Artificial sequence
<220> FEATURE:
<223> OTHER INFORMATION: Codon-optimized polynucleotide

<400> SEQUENCE: 517
tgccacttgt ttctccagcc acaagtgggc acccctccac ctcatacagc ctctgctaga 60
gcacctagcg gcccacctca tcctcacgaa tcttgtcctg ccggaagaag gcctgccaga 120
gccgctcaaa catgtgccag acgacagcac ggactgcccg gatgtgaaga agccggaaca 180
gccagagtgc ctagcctgca ccttcatctg catcaggccg ctcttggagc cggaagaggt 240
agaggatggg gagaagcttg tgcccaggtg ccaccttcta gaggc 285

<210> SEQ ID NO 518
<211> LENGTH: 15
<212> TYPE: PRT
<213> ORGANISM: Homo sapiens

<400> SEQUENCE: 518

Leu Arg Phe Asn Pro Ser Phe Gln Glu Val Cys Ile Tyr Gln Asp
1 5 10 15

<210> SEQ ID NO 519
<211> LENGTH: 225
<212> TYPE: DNA
<213> ORGANISM: Artificial sequence
<220> FEATURE:
<223> OTHER INFORMATION: Codon-optimized polynucleotide

<400> SEQUENCE: 519
cactacaagc tgatccagca gccaatcagc ctgttctcca tcaccgaccg gctgcacaag 60
acattcagcc agctgccttc cgtgcatctg tgcagcatca ccttccagtg gggacaccct 120
cctatctttt gctccaccaa cgacatctgc gtgaccgcca acttctgtat cagcgtgacc 180
ttcctgaagc cttgctttct gctgcacgag gcctccgcca gccag 225

<210> SEQ ID NO 520
<211> LENGTH: 432
<212> TYPE: DNA
<213> ORGANISM: Artificial sequence
<220> FEATURE:
<223> OTHER INFORMATION: Codon-optimized polynucleotide

<400> SEQUENCE: 520
cggaccgctc tgacccacaa ccaggacttc agcatctacc ggctgtgctg caagaggggc 60
tctctgtgtc atgctagcca ggctagaagc cccgcctttc ctaagcctgt cagacctctg 120
cctgctccta tcaccagaat cacccctcag ctcggcggcc agtctgattc atctcagcca 180
ctgctgacca ccggcagacc tcaaggatgg caagaccagg ctctgagaca cacacagcag 240
gctagcccag cctcttgcgc caccatcaca ataccaatac attctgccgc tctgggcgat 300
cacagcggag atcctggacc tgcctgggat acttgtcctc ctctgcccct aactacactg 360
atccctaggg ctcctccacc ttacggcgat agcacagcca gatcctggcc tagcagatgt 420
ggccctctgg gc 432

<210> SEQ ID NO 521
<211> LENGTH: 201
<212> TYPE: DNA
<213> ORGANISM: Artificial sequence
<220> FEATURE:
<223> OTHER INFORMATION: Codon-optimized polynucleotide

<400> SEQUENCE: 521
tacgcctaca aggacttcct gtggtgcttc cccttctctc tggtgttcct gcaagaaatc 60
cagatctgct gtcacgtgtc ctgcctgtgc tgtatctgct gtagcacccg gatctgtctg 120
ggctgtctgc tggaactgtt cctgagcaga gccctgagag cactgcacgt gctgtggaac 180
ggattccagc tgcactgcca g 201

<210> SEQ ID NO 522
<211> LENGTH: 48
<212> TYPE: DNA
<213> ORGANISM: Artificial sequence
<220> FEATURE:
<223> OTHER INFORMATION: Codon-optimized polynucleotide

<400> SEQUENCE: 522
accatgcctg ccattctgaa gctgcagaag aattgtcttc taagcctg 48

<210> SEQ ID NO 523
<211> LENGTH: 72
<212> TYPE: DNA
<213> ORGANISM: Artificial sequence
<220> FEATURE:
<223> OTHER INFORMATION: Codon-optimized polynucleotide

<400> SEQUENCE: 523
tatgaggctg gaatgaccct gggcgagaag ttcagagtgg gcaactgcaa gcacctgaag 60
atgacccggc ct 72

<210> SEQ ID NO 524
<211> LENGTH: 51
<212> TYPE: DNA
<213> ORGANISM: Artificial sequence
<220> FEATURE:
<223> OTHER INFORMATION: Codon-optimized polynucleotide

<400> SEQUENCE: 524
ggagtgcctg gcgattctac tagaagggcc gtgcggcgga tgaacacctt t 51

<210> SEQ ID NO 525
<211> LENGTH: 48
<212> TYPE: DNA
<213> ORGANISM: Artificial sequence
<220> FEATURE:
<223> OTHER INFORMATION: Codon-optimized polynucleotide

<400> SEQUENCE: 525
tgtggcgcat ctgcctgcga cgtgtccctg atcgctatgg atagcgcc 48

<210> SEQ ID NO 526
<211> LENGTH: 11
<212> TYPE: PRT
<213> ORGANISM: Homo sapiens

<400> SEQUENCE: 526

Glu Val Cys Ile Tyr Gln Asp Thr Asp Leu Met
1 5 10

<210> SEQ ID NO 527
<211> LENGTH: 15
<212> TYPE: PRT
<213> ORGANISM: Homo sapiens

<400> SEQUENCE: 527

Trp Cys Pro Leu Asp Leu Arg Leu Gly Ser Thr Gly Cys Leu Thr
1 5 10 15

<210> SEQ ID NO 528
<211> LENGTH: 72
<212> TYPE: DNA
<213> ORGANISM: Artificial sequence
<220> FEATURE:
<223> OTHER INFORMATION: Codon-optimized polynucleotide

<400> SEQUENCE: 528
accgagatca gctgctgcac cctgagcagc gaggaaaacg agtacctgcc tagacctgaa 60
tggcagctgc ag 72

<210> SEQ ID NO 529
<211> LENGTH: 42
<212> TYPE: DNA
<213> ORGANISM: Artificial sequence
<220> FEATURE:
<223> OTHER INFORMATION: Codon-optimized polynucleotide

<400> SEQUENCE: 529
tgcgaggaaa gaggcgcagc cggatctctg atctcttgcg ag 42

<210> SEQ ID NO 530
<211> LENGTH: 48
<212> TYPE: DNA
<213> ORGANISM: Artificial sequence
<220> FEATURE:
<223> OTHER INFORMATION: Codon-optimized polynucleotide

<400> SEQUENCE: 530
aacagcaaga tggccctgaa tagcgaggcc ctgtctgtgg tgtccgag 48

<210> SEQ ID NO 531
<211> LENGTH: 210
<212> TYPE: DNA
<213> ORGANISM: Artificial sequence
<220> FEATURE:
<223> OTHER INFORMATION: Codon-optimized polynucleotide

<400> SEQUENCE: 531
tggggaatgg aactggccgc tagcaggcgg tttagctggg atcatcattc tgccggcgga 60
cctccaagag tgccaagcgt tagaagcgga gcagcccagg tccagcctaa agatccactg 120
ccactgagaa cactggccgg ctgccttgcc agaacagctc atcttagacc tggcgccgaa 180
agcctgcctc aacctcagct gcattgcaca 210

<210> SEQ ID NO 532
<211> LENGTH: 60
<212> TYPE: DNA
<213> ORGANISM: Artificial sequence
<220> FEATURE:
<223> OTHER INFORMATION: Codon-optimized polynucleotide

<400> SEQUENCE: 532
cacgttgtcg gctatggcca cctggataca agcggctcct ctagcagtag ctcctggcct 60

<210> SEQ ID NO 533
<211> LENGTH: 105
<212> TYPE: DNA
<213> ORGANISM: Artificial sequence
<220> FEATURE:
<223> OTHER INFORMATION: Codon-optimized polynucleotide

<400> SEQUENCE: 533
aattctaaga tggctctcaa cagcctgaac tccatcgacg acgcccagct gacaagaatc 60
gcccctccaa gaagccactg ttgcttttgg gaagtgaacg cccct 105

<210> SEQ ID NO 534
<211> LENGTH: 48
<212> TYPE: DNA
<213> ORGANISM: Artificial sequence
<220> FEATURE:
<223> OTHER INFORMATION: Codon-optimized polynucleotide

<400> SEQUENCE: 534
aagatgcact tctcactgaa agagcacccg ccaccgccgt gcccaccg 48

<210> SEQ ID NO 535
<211> LENGTH: 207
<212> TYPE: DNA
<213> ORGANISM: Artificial sequence
<220> FEATURE:
<223> OTHER INFORMATION: Codon-optimized polynucleotide

<400> SEQUENCE: 535
ctgtggttcc agtccagcga actgtctcct actggcgctc catggccaag cagaaggcct 60
acttggagag gcaccaccgt gtctccaaga accgctacaa gcagcgccag aacctgttgc 120
ggcacaaaat ggccctccag ccaagaagct gccctcggac ttggaagcgg actgctgaga 180
ttcagctgtg gcacagccgc catcaga 207

<210> SEQ ID NO 536
<211> LENGTH: 51
<212> TYPE: DNA
<213> ORGANISM: Artificial sequence
<220> FEATURE:
<223> OTHER INFORMATION: Codon-optimized polynucleotide

<400> SEQUENCE: 536
atcgccagag aactgcacca gttcgccttc gacctgctga tcaagagcca c 51

<210> SEQ ID NO 537
<211> LENGTH: 51
<212> TYPE: DNA
<213> ORGANISM: Artificial sequence
<220> FEATURE:
<223> OTHER INFORMATION: Codon-optimized polynucleotide

<400> SEQUENCE: 537
cagcctgaca gctttgctgc cctgcatagc tccctgaatg agctgggcga a 51

<210> SEQ ID NO 538
<211> LENGTH: 51
<212> TYPE: DNA
<213> ORGANISM: Artificial sequence
<220> FEATURE:
<223> OTHER INFORMATION: Codon-optimized polynucleotide

<400> SEQUENCE: 538
tttgtgcagg gtaaagattg gggcctcaaa aagtttatca gacgggactt c 51

<210> SEQ ID NO 539
<211> LENGTH: 51
<212> TYPE: DNA
<213> ORGANISM: Artificial sequence
<220> FEATURE:
<223> OTHER INFORMATION: Codon-optimized polynucleotide

<400> SEQUENCE: 539
ttcgtgcagg gcaaagactg gggcgtgaag aagttcatcc ggcgggactt t 51

<210> SEQ ID NO 540
<211> LENGTH: 204
<212> TYPE: DNA
<213> ORGANISM: Artificial sequence
<220> FEATURE:
<223> OTHER INFORMATION: Codon-optimized polynucleotide

<400> SEQUENCE: 540
cagaacctgc agaacggcgg aggctctaga agctctgcta cacttcctgg caggcggcgg 60
agaagatggc tgagaagaag gcggcagcct atctctgtgg ctcctgctgg acctcctaga 120
cggcccaacc agaagcctaa tcctcctggc ggagccagat gcgtgatcat gaggcctaca 180
tggcctggca ccagcgcctt tacc 204

<210> SEQ ID NO 541
<211> LENGTH: 1479
<212> TYPE: PRT
<213> ORGANISM: Artificial seqeunce
<220> FEATURE:
<223> OTHER INFORMATION: Heterologous protein

<400> SEQUENCE: 541

Gln Asn Leu Gln Asn Gly Gly Gly Ser Arg Ser Ser Ala Thr Leu Pro
1 5 10 15

Gly Arg Arg Arg Arg Arg Trp Leu Arg Arg Arg Arg Gln Pro Ile Ser
20 25 30

Val Ala Pro Ala Gly Pro Pro Arg Arg Pro Asn Gln Lys Pro Asn Pro
35 40 45

Pro Gly Gly Ala Arg Cys Val Ile Met Arg Pro Thr Trp Pro Gly Thr
50 55 60

Ser Ala Phe Thr Lys Arg Ser Phe Ala Val Thr Glu Arg Ile Ile Asp
65 70 75 80

Tyr Trp Ala Gln Lys Glu Lys Gly Ser Ser Ser Phe Leu Arg Pro Ser
85 90 95

Cys Asp Tyr Trp Ala Gln Lys Glu Lys Ile Ser Ile Pro Arg Thr His
100 105 110

Leu Cys Leu Val Leu Gly Val Leu Ser Gly His Ser Gly Ser Arg Leu
115 120 125

Tyr Glu Ala Gly Met Thr Leu Gly Gly Lys Ile Leu Phe Phe Leu Phe
130 135 140

Leu Leu Leu Pro Leu Ser Pro Phe Ser Leu Ile Phe Thr Glu Ile Ser
145 150 155 160

Cys Cys Thr Leu Ser Ser Glu Glu Asn Glu Tyr Leu Pro Arg Pro Glu
165 170 175

Trp Gln Leu Gln Val Pro Phe Arg Glu Leu Lys Asn Val Ser Val Leu
180 185 190

Glu Gly Leu Arg Gln Gly Arg Leu Gly Gly Pro Cys Ser Cys His Cys
195 200 205

Pro Arg Pro Ser Gln Ala Arg Leu Thr Pro Val Asp Val Ala Gly Pro
210 215 220

Phe Leu Cys Leu Gly Asp Pro Gly Leu Phe Pro Pro Val Lys Ser Ser
225 230 235 240

Ile Thr Gly Gly Lys Ser Thr Cys Ser Ala Pro Gly Pro Gln Ser Leu

```
                245                 250                 255

Pro Ser Thr Pro Phe Ser Thr Tyr Pro Gln Trp Val Ile Leu Ile Thr
            260                 265                 270

Glu Leu Gly Met Glu Cys Thr Leu Gly Gln Val Gly Ala Pro Ser Pro
        275                 280                 285

Arg Arg Glu Glu Asp Gly Trp Arg Gly Gly His Ser Arg Phe Lys Ala
    290                 295                 300

Asp Val Pro Ala Pro Gln Gly Pro Cys Trp Gly Gly Gln Pro Gly Ser
305                 310                 315                 320

Ala Pro Ser Ser Ala Pro Pro Glu Gln Ser Leu Leu Asp Trp Lys Phe
                325                 330                 335

Glu Met Ser Tyr Thr Val Gly Gly Pro Pro Pro His Val His Ala Arg
            340                 345                 350

Pro Arg His Trp Lys Thr Asp Arg Asp Gly His Ser Tyr Thr Ser Lys
        355                 360                 365

Val Asn Cys Leu Leu Leu Gln Asp Gly Phe His Gly Cys Val Ser Ile
    370                 375                 380

Thr Gly Ala Ala Gly Arg Arg Asn Leu Ser Ile Phe Leu Phe Leu Met
385                 390                 395                 400

Leu Cys Lys Leu Glu Phe His Ala Cys Lys Ile Gln Asn Lys Asn Cys
                405                 410                 415

Pro Asp Phe Lys Lys Phe Asp Gly Pro Cys Gly Glu Arg Gly Gly Gly
            420                 425                 430

Arg Thr Ala Arg Ala Leu Trp Ala Arg Gly Asp Ser Val Leu Thr Pro
        435                 440                 445

Ala Leu Asp Pro Gln Thr Pro Val Arg Ala Pro Ser Leu Thr Arg Ala
    450                 455                 460

Ala Ala Ala Val His Tyr Lys Leu Ile Gln Gln Pro Ile Ser Leu Phe
465                 470                 475                 480

Ser Ile Thr Asp Arg Leu His Lys Thr Phe Ser Gln Leu Pro Ser Val
                485                 490                 495

His Leu Cys Ser Ile Thr Phe Gln Trp Gly His Pro Pro Ile Phe Cys
            500                 505                 510

Ser Thr Asn Asp Ile Cys Val Thr Ala Asn Phe Cys Ile Ser Val Thr
        515                 520                 525

Phe Leu Lys Pro Cys Phe Leu Leu His Glu Ala Ser Ala Ser Gln Cys
    530                 535                 540

His Leu Phe Leu Gln Pro Gln Val Gly Thr Pro Pro Pro His Thr Ala
545                 550                 555                 560

Ser Ala Arg Ala Pro Ser Gly Pro Pro His Pro His Glu Ser Cys Pro
                565                 570                 575

Ala Gly Arg Arg Pro Ala Arg Ala Ala Gln Thr Cys Ala Arg Arg Gln
            580                 585                 590

His Gly Leu Pro Gly Cys Glu Glu Ala Gly Thr Ala Arg Val Pro Ser
        595                 600                 605

Leu His Leu His Leu His Gln Ala Ala Leu Gly Ala Gly Arg Gly Arg
    610                 615                 620

Gly Trp Gly Glu Ala Cys Ala Gln Val Pro Pro Ser Arg Gly Val Leu
625                 630                 635                 640

Arg Phe Leu Asp Leu Lys Val Arg Tyr Leu His Ser Gln Trp Gln His
                645                 650                 655

Tyr His Arg Ser Gly Glu Ala Ala Gly Thr Pro Leu Trp Arg Pro Thr
            660                 665                 670
```

```
Arg Asn Val Pro Phe Arg Glu Leu Lys Asn Gln Arg Thr Ala Gln Gly
        675                 680                 685

Ala Pro Gly Ile His His Ala Ala Ser Pro Val Ala Ala Asn Leu Cys
    690                 695                 700

Asp Pro Ala Arg His Ala Gln His Thr Arg Ile Pro Cys Gly Ala Gly
705                 710                 715                 720

Gln Val Arg Ala Gly Arg Gly Pro Glu Ala Gly Gly Gly Val Leu Gln
                725                 730                 735

Pro Gln Arg Pro Ala Pro Glu Lys Pro Gly Cys Pro Cys Arg Arg Gly
            740                 745                 750

Gln Pro Arg Leu His Thr Val Lys Met Trp Arg Ala Val Ala Met Met
        755                 760                 765

Val Pro Asp Arg Gln Val His Tyr Asp Phe Gly Leu Gly Val Pro Gly
    770                 775                 780

Asp Ser Thr Arg Arg Ala Val Arg Arg Met Asn Thr Phe Tyr Glu Ala
785                 790                 795                 800

Gly Met Thr Leu Gly Glu Lys Phe Arg Val Gly Asn Cys Lys His Leu
                805                 810                 815

Lys Met Thr Arg Pro Asn Ser Lys Met Ala Leu Asn Ser Glu Ala Leu
            820                 825                 830

Ser Val Val Ser Glu Cys Gly Ala Ser Ala Cys Asp Val Ser Leu Ile
        835                 840                 845

Ala Met Asp Ser Ala Phe Val Gln Gly Lys Asp Trp Gly Val Lys Lys
    850                 855                 860

Phe Ile Arg Arg Asp Phe Tyr Ala Tyr Lys Asp Phe Leu Trp Cys Phe
865                 870                 875                 880

Pro Phe Ser Leu Val Phe Leu Gln Glu Ile Gln Ile Cys Cys His Val
                885                 890                 895

Ser Cys Leu Cys Cys Ile Cys Cys Ser Thr Arg Ile Cys Leu Gly Cys
            900                 905                 910

Leu Leu Glu Leu Phe Leu Ser Arg Ala Leu Arg Ala Leu His Val Leu
        915                 920                 925

Trp Asn Gly Phe Gln Leu His Cys Gln Thr Glu Tyr Asn Gln Lys Leu
    930                 935                 940

Gln Val Asn Gln Phe Ser Glu Ser Lys Ser Leu Tyr His Arg Glu Lys
945                 950                 955                 960

Gln Leu Ile Ala Met Asp Ser Ala Ile Cys Glu Glu Arg Gly Ala Ala
                965                 970                 975

Gly Ser Leu Ile Ser Cys Glu Thr Met Pro Ala Ile Leu Lys Leu Gln
            980                 985                 990

Lys Asn Cys Leu Leu Ser Leu Arg  Thr Ala Leu Thr His  Asn Gln Asp
        995                 1000                1005

Phe Ser  Ile Tyr Arg Leu Cys  Cys Lys Arg Gly Ser  Leu Cys His
    1010                1015                1020

Ala Ser  Gln Ala Arg Ser Pro  Ala Phe Pro Lys Pro  Val Arg Pro
    1025                1030                1035

Leu Pro  Ala Pro Ile Thr Arg  Ile Thr Pro Gln Leu  Gly Gly Gln
    1040                1045                1050

Ser Asp  Ser Ser Gln Pro Leu  Leu Thr Thr Gly Arg  Pro Gln Gly
    1055                1060                1065

Trp Gln  Asp Gln Ala Leu Arg  His Thr Gln Gln Ala  Ser Pro Ala
    1070                1075                1080
```

```
Ser Cys  Ala Thr Ile Thr Ile  Pro Ile His Ser Ala  Ala Leu Gly
    1085                 1090                 1095

Asp His  Ser Gly Asp Pro Gly  Pro Ala Trp Asp Thr  Cys Pro Pro
    1100                 1105                 1110

Leu Pro  Leu Thr Thr Leu Ile  Pro Arg Ala Pro Pro  Pro Tyr Gly
    1115                 1120                 1125

Asp Ser  Thr Ala Arg Ser Trp  Pro Ser Arg Cys Gly  Pro Leu Gly
    1130                 1135                 1140

Gly Asn  Thr Thr Leu Gln Gln  Leu Gly Glu Ala Ser  Gln Ala Pro
    1145                 1150                 1155

Ser Gly  Ser Leu Ile Pro Leu  Arg Leu Pro Leu Leu  Trp Glu Val
    1160                 1165                 1170

Arg Gly  Gln Pro Asp Ser Phe  Ala Ala Leu His Ser  Ser Leu Asn
    1175                 1180                 1185

Glu Leu  Gly Glu Ile Ala Arg  Glu Leu His Gln Phe  Ala Phe Asp
    1190                 1195                 1200

Leu Leu  Ile Lys Ser His Phe  Val Gln Gly Lys Asp  Trp Gly Leu
    1205                 1210                 1215

Lys Lys  Phe Ile Arg Arg Asp  Phe Trp Gly Met Glu  Leu Ala Ala
    1220                 1225                 1230

Ser Arg  Arg Phe Ser Trp Asp  His His Ser Ala Gly  Gly Pro Pro
    1235                 1240                 1245

Arg Val  Pro Ser Val Arg Ser  Gly Ala Ala Gln Val  Gln Pro Lys
    1250                 1255                 1260

Asp Pro  Leu Pro Leu Arg Thr  Leu Ala Gly Cys Leu  Ala Arg Thr
    1265                 1270                 1275

Ala His  Leu Arg Pro Gly Ala  Glu Ser Leu Pro Gln  Pro Gln Leu
    1280                 1285                 1290

His Cys  Thr Leu Trp Phe Gln  Ser Ser Glu Leu Ser  Pro Thr Gly
    1295                 1300                 1305

Ala Pro  Trp Pro Ser Arg Arg  Pro Thr Trp Arg Gly  Thr Thr Val
    1310                 1315                 1320

Ser Pro  Arg Thr Ala Thr Ser  Ser Ala Arg Thr Cys  Cys Gly Thr
    1325                 1330                 1335

Lys Trp  Pro Ser Ser Gln Glu  Ala Ala Leu Gly Leu  Gly Ser Gly
    1340                 1345                 1350

Leu Leu  Arg Phe Ser Cys Gly  Thr Ala Ala Ile Arg  Lys Met His
    1355                 1360                 1365

Phe Ser  Leu Lys Glu His Pro  Pro Pro Pro Cys Pro  Pro Glu Ala
    1370                 1375                 1380

Phe Gln  Arg Ala Ala Gly Glu  Gly Gly Pro Gly Arg  Gly Gly Ala
    1385                 1390                 1395

Arg Arg  Gly Ala Arg Val Leu  Gln Ser Pro Phe Cys  Arg Ala Gly
    1400                 1405                 1410

Ala Gly  Glu Trp Leu Gly His  Gln Ser Leu Arg His  Val Val Gly
    1415                 1420                 1425

Tyr Gly  His Leu Asp Thr Ser  Gly Ser Ser Ser Ser  Ser Ser Trp
    1430                 1435                 1440

Pro Asn  Ser Lys Met Ala Leu  Asn Ser Leu Asn Ser  Ile Asp Asp
    1445                 1450                 1455

Ala Gln  Leu Thr Arg Ile Ala  Pro Pro Arg Ser His  Cys Cys Phe
    1460                 1465                 1470

Trp Glu  Val Asn Ala Pro
```

1475

<210> SEQ ID NO 542
<211> LENGTH: 4437
<212> TYPE: DNA
<213> ORGANISM: Artificial seqeunce
<220> FEATURE:
<223> OTHER INFORMATION: Heterologous polynucleotide

<400> SEQUENCE: 542
cagaacctgc agaacggcgg aggctctaga agctctgcta cacttcctgg caggcggcgg 60
agaagatggc tgagaagaag gcggcagcct atctctgtgg ctcctgctgg acctcctaga 120
cggcccaacc agaagcctaa tcctcctggc ggagccagat gcgtgatcat gaggcctaca 180
tggcctggca ccagcgcctt caccaagaga agctttgccg tgaccgagcg gatcatcgac 240
tattgggctc aaaaagagaa gggcagcagc agcttcctgc ggcctagctg tgattattgg 300
gcccagaaag aaaagatcag catccccaga acacacctgt gcctggtgct gggagtgctg 360
tctggacact ctggcagcag actgtatgag gccggcatga cactcggcgg caagatcctg 420
ttcttcctgt tcctgctgct ccctctgagc cccttcagcc tgatcttcac cgagatcagc 480
tgctgcaccc tgagcagcga ggaaaacgag tacctgccta gacctgagtg gcagctgcag 540
gtccccttca gagagctgaa gaacgtttcc gtgctggaag gcctgagaca gggcagactt 600
ggcggccctt gtagctgtca ctgccccaga cctagtcagg ccagactgac acctgtggat 660
gtggccggac ctttcctgtg tctgggagat cctggcctgt ttccacctgt gaagtccagc 720
atcacaggcg gcaagtccac atgttctgcc cctggacctc agagcctgcc tagcacaccc 780
ttcagcacat accctcagtg ggtcatcctg atcaccgaac tcggcatgga atgcaccctg 840
ggacaagtgg gagccccatc tcctagaaga gaagaggatg gctggcgcgg aggccactct 900
agattcaaag ctgatgtgcc cgctcctcag ggcccttgtt ggggaggaca acctggatct 960
gccccatctt ctgccccacc tgaacagtcc ctgctggatt ggaagttcga gatgagctac 1020
accgtcggcg gacctccacc tcatgttcat gccagacctc ggcactggaa aaccgacaga 1080
gatggccaca gctacaccag caaagtgaac tgcctcctgc tgcaggatgg cttccacggc 1140
tgtgtgtcta ttactggcgc cgctggcaga cggaacctga gcatctttct gtttctgatg 1200
ctgtgcaagc tcgagttcca cgcctgcaag atccagaaca agaactgccc cgacttcaag 1260
aagttcgacg gcccttgcgg agaaagaggc ggaggcagaa cagctagagc cctttgggct 1320
agaggcgaca gcgttctgac accagctctg gaccctcaga cacctgttag ggcccctagc 1380
ctgacaagag ctgccgccgc tgtgcactac aagctgatcc agcagccaat cagcctgttc 1440
agcatcaccg accggctgca caagacattc agccagctgc caagcgtgca cctgtgctcc 1500
atcaccttcc agtggggaca ccctcctatc ttttgctcca ccaacgacat ctgcgtgacc 1560
gccaacttct gtatcagcgt gaccttcctg aagccttgct ttctgctgca cgaggccagc 1620
gcctctcagt gccacttgtt tctgcagccc caagtgggca cacctcctcc acatacagcc 1680
tctgctagag cacctagcgg ccctccacat cctcacgaat cttgtcctgc cggaagaagg 1740
cctgccagag ccgctcaaac atgtgccaga cgacagcacg gactgcctgg atgtgaagag 1800
gctggaacag ccagagtgcc tagcctgcac ctccatctgc atcaggctgc tcttggagcc 1860
ggaagaggta gaggatgggg cgaagcttgt gctcaggtgc caccttctag aggcgtgctg 1920
agattcctgg acctgaaagt gcgctacctg cacagccagt ggcagcacta tcacagatct 1980
ggcgaagccg ccggaacacc cctttggagg ccaacaagaa acgtgccctt ccgggaactg 2040

-continued

```
aagaaccaga gaacagctca gggcgctcct ggaatccacc atgctgcttc tccagtggcc   2100
gccaacctgt gtgatcctgc cagacatgcc cagcacacca ggattccttg tggcgctgga   2160
caagtgcgcg ctggaagagg acctgaagca ggcggaggtg ttctgcaacc tcaaagaccc   2220
gctcctgaga agcctggctg cccttgcaga agaggacagc ctagactgca caccgtgaaa   2280
atgtggcgag ccgtggccat gatggtgccc gatagacagg tccactacga ctttggactg   2340
ggcgtgccag gcgatagcac tcggagagcc gtcagacgga tgaacacctt ttacgaagcc   2400
gggatgaccc tgggcgagaa gttcagagtg ggcaactgca agcacctgaa gatgacccgg   2460
cctaacagca agatggccct gaatagcgag gccctgtctg tggtgtctga atgtggcgcc   2520
tctgcctgtg acgtgtccct gatcgctatg gactccgcct ttgtgcaggg caaagactgg   2580
ggcgtgaaga agttcatccg gcgggacttc tacgcctaca aggacttcct gtggtgcttc   2640
cccttctctc tggtgttcct gcaagagatc cagatctgct gtcatgtgtc ctgcctgtgc   2700
tgcatctgct gtagcaccag aatctgcctg ggctgtctgc tggaactgtt cctgagcaga   2760
gccctgagag cactgcacgt gctgtggaac ggattccagc tgcactgcca gaccgagtac   2820
aaccagaaac tgcaagtgaa ccagttcagc gagagcaaga gcctgtacca ccgggaaaag   2880
cagctcattg ccatggacag cgccatctgc gaagagagag gcgccgcagg atctctgatc   2940
tcctgcgaaa caatgcccgc catcctgaag ctgcagaaga attgcctcct aagcctgcga   3000
accgctctga cacacaacca ggacttcagc atctacagac tgtgttgcaa gcggggctcc   3060
ctgtgccatg caagccaagc tagaagcccc gcctttccta aacctgtgcg acctctgcca   3120
gctccaatca ccagaattac ccctcagctc ggcggccaga gcgattcatc tcaacctctg   3180
ctgaccaccg gcagacctca aggctggcaa gaccaagctc tgagacacac ccagcaggct   3240
agccctgcct cttgtgccac catcacaatc cccatccact ctgccgctct gggcgatcat   3300
tctggcgatc ctggaccagc ctgggacaca tgtcctccac tgccactcac aacactgatc   3360
cctagggctc ctccacctta cggcgattct accgctagaa gctggcccag cagatgtgga   3420
ccactcggag gcaacacaac cctccagcaa ctgggagaag cctctcaggc tcctagcggc   3480
tctctgatcc ctctcagact gcctctcctg tgggaagttc ggggccagcc tgattctttt   3540
gccgcactgc acagctccct gaacgagctg ggagagatcg ctagagagct gcaccagttc   3600
gccttcgacc tgctgatcaa gagccacttc gtgcaaggca aggattgggg cctcaaaaag   3660
tttatccgca gagacttctg ggcatggaa ctggccgcca gcagaagatt cagctgggat   3720
catcatagcg caggcggccc acctagagtg ccatctgtta gaagcggagc tgcccaggtg   3780
cagcctaaag atcctctgcc actgagaaca ctggccggct gccttgctag aacagcccat   3840
cttagacctg gcgccgagtc tctgcctcag ccacaactgc actgtaccct gtggttccag   3900
tccagcgagc tgtctcctac tggtgcccct tggccatcta gacgccctac ttggagaggc   3960
accaccgtgt caccaagaac cgccacaagc agcgccagaa cctgttgtgg cacaaagtgg   4020
ccctccagcc aagaagccgc tctcggactt ggaagcggac tgctgaggtt ctcttgtgga   4080
accgccgcca ttcggaagat gcactttagc ctgaaagaac accctccacc accttgtcct   4140
ccagaggctt tccaaagagc tgctggcgaa ggcggacctg gtagaggtgg tgctagaaga   4200
ggtgctaggg tgctgcagag cccattctgt agagcaggcg caggcgaatg gctgggccat   4260
cagagtctga gacatgtcgt cggctacggc cacctggata caagcggaag cagctctagc   4320
tccagctggc ctaactcaaa aatggctctg aacagcctga actccatcga cgacgcccag   4380
```

ctgacaagaa tcgcccctcc tagatctcac tgctgctttt gggaagtgaa cgcccca 4437

<210> SEQ ID NO 543
<211> LENGTH: 1479
<212> TYPE: PRT
<213> ORGANISM: Artificial seqeunce
<220> FEATURE:
<223> OTHER INFORMATION: Hetereologous protein

<400> SEQUENCE: 543

```
Gln Asn Leu Gln Asn Gly Gly Gly Ser Arg Ser Ser Ala Thr Leu Pro
1               5                   10                  15

Gly Arg Arg Arg Arg Arg Trp Leu Arg Arg Arg Arg Gln Pro Ile Ser
            20                  25                  30

Val Ala Pro Ala Gly Pro Pro Arg Arg Pro Asn Gln Lys Pro Asn Pro
        35                  40                  45

Pro Gly Gly Ala Arg Cys Val Ile Met Arg Pro Thr Trp Pro Gly Thr
    50                  55                  60

Ser Ala Phe Thr Gly Met Glu Cys Thr Leu Gly Gln Val Gly Ala Pro
65                  70                  75                  80

Ser Pro Arg Arg Glu Glu Asp Gly Trp Arg Gly Gly His Ser Arg Phe
                85                  90                  95

Lys Ala Asp Val Pro Ala Pro Gln Gly Pro Cys Trp Gly Gly Gln Pro
            100                 105                 110

Gly Ser Ala Pro Ser Ser Ala Pro Pro Glu Gln Ser Leu Leu Asp Asp
        115                 120                 125

Tyr Trp Ala Gln Lys Glu Lys Ile Ser Ile Pro Arg Thr His Leu Cys
    130                 135                 140

Trp Lys Phe Glu Met Ser Tyr Thr Val Gly Gly Pro Pro Pro His Val
145                 150                 155                 160

His Ala Arg Pro Arg His Trp Lys Thr Asp Arg Asp Tyr Trp Ala Gln
                165                 170                 175

Lys Glu Lys Gly Ser Ser Ser Phe Leu Arg Pro Ser Cys Val Pro Phe
            180                 185                 190

Arg Glu Leu Lys Asn Val Ser Val Leu Glu Gly Leu Arg Gln Gly Arg
        195                 200                 205

Leu Gly Gly Pro Cys Ser Cys His Cys Pro Arg Pro Ser Gln Ala Arg
    210                 215                 220

Leu Thr Pro Val Asp Val Ala Gly Pro Phe Leu Cys Leu Gly Asp Pro
225                 230                 235                 240

Gly Leu Phe Pro Pro Val Lys Ser Ser Ile Thr Glu Ile Ser Cys Cys
                245                 250                 255

Thr Leu Ser Ser Glu Glu Asn Glu Tyr Leu Pro Arg Pro Glu Trp Gln
            260                 265                 270

Leu Gln Tyr Glu Ala Gly Met Thr Leu Gly Gly Lys Ile Leu Phe Phe
        275                 280                 285

Leu Phe Leu Leu Leu Pro Leu Ser Pro Phe Ser Leu Ile Phe Leu Val
    290                 295                 300

Leu Gly Val Leu Ser Gly His Ser Gly Ser Arg Leu Lys Arg Ser Phe
305                 310                 315                 320

Ala Val Thr Glu Arg Ile Ile Thr Gly Gly Lys Ser Thr Cys Ser Ala
                325                 330                 335

Pro Gly Pro Gln Ser Leu Pro Ser Thr Pro Phe Ser Thr Tyr Pro Gln
            340                 345                 350

Trp Val Ile Leu Ile Thr Glu Leu Asp Gly His Ser Tyr Thr Ser Lys
```

-continued

```
        355                 360                 365

Val Asn Cys Leu Leu Leu Gln Asp Gly Phe His Gly Cys Val Ser Ile
    370                 375                 380

Thr Gly Ala Ala Gly Arg Arg Asn Leu Ser Ile Phe Leu Phe Leu Met
385                 390                 395                 400

Leu Cys Lys Leu Glu Phe His Ala Cys Gln Trp Gln His Tyr His Arg
                405                 410                 415

Ser Gly Glu Ala Ala Gly Thr Pro Leu Trp Arg Pro Thr Arg Asn Val
            420                 425                 430

Ala Met Met Val Pro Asp Arg Gln Val His Tyr Asp Phe Gly Leu Lys
        435                 440                 445

Ile Gln Asn Lys Asn Cys Pro Asp Val Leu Arg Phe Leu Asp Leu Lys
    450                 455                 460

Val Arg Tyr Leu His Ser Val Pro Phe Arg Glu Leu Lys Asn Gln Arg
465                 470                 475                 480

Thr Ala Gln Gly Ala Pro Gly Ile His His Ala Ala Ser Pro Val Ala
                485                 490                 495

Ala Asn Leu Cys Asp Pro Ala Arg His Ala Gln His Thr Arg Ile Pro
            500                 505                 510

Cys Gly Ala Gly Gln Val Arg Ala Gly Arg Gly Pro Glu Ala Gly Gly
        515                 520                 525

Gly Val Leu Gln Pro Gln Arg Pro Ala Pro Glu Lys Pro Gly Cys Pro
    530                 535                 540

Cys Arg Arg Gly Gln Pro Arg Leu His Thr Val Lys Met Trp Arg Ala
545                 550                 555                 560

Cys His Leu Phe Leu Gln Pro Gln Val Gly Thr Pro Pro Pro His Thr
                565                 570                 575

Ala Ser Ala Arg Ala Pro Ser Gly Pro Pro His Pro His Glu Ser Cys
            580                 585                 590

Pro Ala Gly Arg Arg Pro Ala Arg Ala Ala Gln Thr Cys Ala Arg Arg
        595                 600                 605

Gln His Gly Leu Pro Gly Cys Glu Glu Ala Gly Thr Ala Arg Val Pro
    610                 615                 620

Ser Leu His Leu His Leu His Gln Ala Ala Leu Gly Ala Gly Arg Gly
625                 630                 635                 640

Arg Gly Trp Gly Glu Ala Cys Ala Gln Val Pro Pro Ser Arg Gly His
                645                 650                 655

Tyr Lys Leu Ile Gln Gln Pro Ile Ser Leu Phe Ser Ile Thr Asp Arg
            660                 665                 670

Leu His Lys Thr Phe Ser Gln Leu Pro Ser Val His Leu Cys Ser Ile
        675                 680                 685

Thr Phe Gln Trp Gly His Pro Pro Ile Phe Cys Ser Thr Asn Asp Ile
    690                 695                 700

Cys Val Thr Ala Asn Phe Cys Ile Ser Val Thr Phe Leu Lys Pro Cys
705                 710                 715                 720

Phe Leu Leu His Glu Ala Ser Ala Ser Gln Phe Lys Lys Phe Asp Gly
                725                 730                 735

Pro Cys Gly Glu Arg Gly Gly Gly Arg Thr Ala Arg Ala Leu Trp Ala
            740                 745                 750

Arg Gly Asp Ser Val Leu Thr Pro Ala Leu Asp Pro Gln Thr Pro Val
        755                 760                 765

Arg Ala Pro Ser Leu Thr Arg Ala Ala Ala Ala Val Gly Val Pro Gly
    770                 775                 780
```

```
Asp Ser Thr Arg Arg Ala Val Arg Arg Met Asn Thr Phe Cys Gly Ala
785                 790                 795                 800

Ser Ala Cys Asp Val Ser Leu Ile Ala Met Asp Ser Ala Cys Glu Glu
                805                 810                 815

Arg Gly Ala Ala Gly Ser Leu Ile Ser Cys Glu Ser Leu Tyr His Arg
            820                 825                 830

Glu Lys Gln Leu Ile Ala Met Asp Ser Ala Ile Phe Val Gln Gly Lys
        835                 840                 845

Asp Trp Gly Val Lys Lys Phe Ile Arg Arg Asp Phe Thr Met Pro Ala
    850                 855                 860

Ile Leu Lys Leu Gln Lys Asn Cys Leu Leu Ser Leu Asn Ser Lys Met
865                 870                 875                 880

Ala Leu Asn Ser Glu Ala Leu Ser Val Val Ser Glu Tyr Glu Ala Gly
                885                 890                 895

Met Thr Leu Gly Glu Lys Phe Arg Val Gly Asn Cys Lys His Leu Lys
            900                 905                 910

Met Thr Arg Pro Thr Glu Tyr Asn Gln Lys Leu Gln Val Asn Gln Phe
        915                 920                 925

Ser Glu Ser Lys Arg Thr Ala Leu Thr His Asn Gln Asp Phe Ser Ile
    930                 935                 940

Tyr Arg Leu Cys Cys Lys Arg Gly Ser Leu Cys His Ala Ser Gln Ala
945                 950                 955                 960

Arg Ser Pro Ala Phe Pro Lys Pro Val Arg Pro Leu Pro Ala Pro Ile
                965                 970                 975

Thr Arg Ile Thr Pro Gln Leu Gly Gly Gln Ser Asp Ser Ser Gln Pro
            980                 985                 990

Leu Leu Thr Thr Gly Arg Pro Gln  Gly Trp Gln Asp Gln  Ala Leu Arg
        995                 1000                1005

His Thr  Gln Gln Ala Ser Pro  Ala Ser Cys Ala Thr  Ile Thr Ile
    1010                1015                1020

Pro Ile  His Ser Ala Ala Leu  Gly Asp His Ser Gly  Asp Pro Gly
    1025                1030                1035

Pro Ala  Trp Asp Thr Cys Pro  Pro Leu Pro Leu Thr  Thr Leu Ile
    1040                1045                1050

Pro Arg  Ala Pro Pro Pro Tyr  Gly Asp Ser Thr Ala  Arg Ser Trp
    1055                1060                1065

Pro Ser  Arg Cys Gly Pro Leu  Gly Tyr Ala Tyr Lys  Asp Phe Leu
    1070                1075                1080

Trp Cys  Phe Pro Phe Ser Leu  Val Phe Leu Gln Glu  Ile Gln Ile
    1085                1090                1095

Cys Cys  His Val Ser Cys Leu  Cys Cys Ile Cys Cys  Ser Thr Arg
    1100                1105                1110

Ile Cys  Leu Gly Cys Leu Leu  Glu Leu Phe Leu Ser  Arg Ala Leu
    1115                1120                1125

Arg Ala  Leu His Val Leu Trp  Asn Gly Phe Gln Leu  His Cys Gln
    1130                1135                1140

Gly Asn  Thr Thr Leu Gln Gln  Leu Gly Glu Ala Ser  Gln Ala Pro
    1145                1150                1155

Ser Gly  Ser Leu Ile Pro Leu  Arg Leu Pro Leu Leu  Trp Glu Val
    1160                1165                1170

Arg Gly  Asn Ser Lys Met Ala  Leu Asn Ser Leu Asn  Ser Ile Asp
    1175                1180                1185
```

-continued

```
Asp Ala  Gln Leu Thr Arg Ile  Ala Pro Pro Arg Ser  His Cys Cys
    1190                1195                1200

Phe Trp  Glu Val Asn Ala Pro  Phe Val Gln Gly Lys  Asp Trp Gly
    1205                1210                1215

Leu Lys  Lys Phe Ile Arg Arg  Asp Phe Glu Ala Phe  Gln Arg Ala
    1220                1225                1230

Ala Gly  Glu Gly Gly Pro Gly  Arg Gly Gly Ala Arg  Arg Gly Ala
    1235                1240                1245

Arg Val  Leu Gln Ser Pro Phe  Cys Arg Ala Gly Ala  Gly Glu Trp
    1250                1255                1260

Leu Gly  His Gln Ser Leu Arg  Trp Gly Met Glu Leu  Ala Ala Ser
    1265                1270                1275

Arg Arg  Phe Ser Trp Asp His  His Ser Ala Gly Gly  Pro Pro Arg
    1280                1285                1290

Val Pro  Ser Val Arg Ser Gly  Ala Ala Gln Val Gln  Pro Lys Asp
    1295                1300                1305

Pro Leu  Pro Leu Arg Thr Leu  Ala Gly Cys Leu Ala  Arg Thr Ala
    1310                1315                1320

His Leu  Arg Pro Gly Ala Glu  Ser Leu Pro Gln Pro  Gln Leu His
    1325                1330                1335

Cys Thr  Ile Ala Arg Glu Leu  His Gln Phe Ala Phe  Asp Leu Leu
    1340                1345                1350

Ile Lys  Ser His Lys Met His  Phe Ser Leu Lys Glu  His Pro Pro
    1355                1360                1365

Pro Pro  Cys Pro Pro His Val  Val Gly Tyr Gly His  Leu Asp Thr
    1370                1375                1380

Ser Gly  Ser Ser Ser Ser Ser  Ser Trp Pro Gln Pro  Asp Ser Phe
    1385                1390                1395

Ala Ala  Leu His Ser Ser Leu  Asn Glu Leu Gly Glu  Leu Trp Phe
    1400                1405                1410

Gln Ser  Ser Glu Leu Ser Pro  Thr Gly Ala Pro Trp  Pro Ser Arg
    1415                1420                1425

Arg Pro  Thr Trp Arg Gly Thr  Thr Val Ser Pro Arg  Thr Ala Thr
    1430                1435                1440

Ser Ser  Ala Arg Thr Cys Cys  Gly Thr Lys Trp Pro  Ser Ser Gln
    1445                1450                1455

Glu Ala  Ala Leu Gly Leu Gly  Ser Gly Leu Leu Arg  Phe Ser Cys
    1460                1465                1470

Gly Thr  Ala Ala Ile Arg
    1475
```

<210> SEQ ID NO 544
<211> LENGTH: 4437
<212> TYPE: DNA
<213> ORGANISM: Artificial seqeunce
<220> FEATURE:
<223> OTHER INFORMATION: Heterologous polynucleotide

<400> SEQUENCE: 544

```
cagaacctgc agaacggcgg aggctctaga agctctgcta cacttcctgg caggcggcgg     60

agaagatggc tgagaagaag gcggcagcct atctctgtgg ctcctgctgg acctcctaga    120

cggcccaacc agaagcctaa tcctcctggc ggagccagat gcgtgatcat gaggcctaca    180

tggcctggca ccagcgcctt taccggcatg gaatgtacac tgggccaagt gggagcccca    240

tctcctagaa gagaagagga tggctggcgc ggaggccact ctagattcaa agctgatgtg    300
```

-continued

```
cccgctcctc agggcccttg ttggggagga caacctggat ctgccccatc ttctgcccca    360
cctgaacaga gcctgctgga tgactattgg gctcaaaaag agaagatcag catccccaga    420
acacacctgt gctggaagtt cgagatgagc tacaccgttg gcggccctcc accacatgtt    480
cacgccagac ctagacactg gaaaaccgac agagattatt gggcccagaa agaaaagggc    540
agcagcagct tcctgcggcc tagctgtgtg cccttccggg aactgaagaa cgtgtccgtt    600
ctggaaggcc tgaggcaggg cagacttggc ggaccttgta gctgccactg tcctagacca    660
agccaggcca gactgacccc tgtggatgtg gctggcccat ttctgtgtct gggcgaccct    720
ggactgttcc ctccagtgaa gtctagcatc accgagatca gctgctgcac cctgagcagc    780
gaggaaaacg agtacctgcc tagacctgaa tggcagctgc agtacgaggc cggcatgaca    840
ctcggaggca agatcctgtt cttcctgttc ctgctgctcc ctctgagccc cttcagcctg    900
atctttctgg tgctgggcgt gctgtctggc cactctggaa gcagactgaa gagaagcttc    960
gccgtgaccg agcggatcat cacaggcggc aagagcacat gttctgcccc tggacctcag   1020
tctctgccca gcacaccctt cagcacatac cctcagtggg tcatcctgat caccgagctg   1080
gatggccaca gctacaccag caaagtgaac tgcctcctgc tgcaggatgg cttccacggc   1140
tgtgtgtcta ttactggcgc cgctggcaga cggaacctga gcatctttct gtttctgatg   1200
ctgtgcaagc tcgagttcca cgcctgccaa tggcagcact accacagatc tggcgaagcc   1260
gctggaaccc cactttggag gcctaccaga aacgtggcca tgatggtgcc cgacagacag   1320
gtgcactacg acttcggcct gaagatccag aacaagaact gccccgacgt gctgcggttc   1380
ctggatctca aagtgcgcta cctgcacagc gtgcccttca gagagctgaa aaaccagaga   1440
acagcccagg gcgctcctgg aatccatcat gctgcttctc cagtggccgc caatctgtgc   1500
gatcctgcca gacatgccca gcataccagg attccttgtg gcgctggaca agtgcgcgct   1560
ggaagaggac ctgaagctgg tggcggagtt ctgcagcctc aaagacctgc tcctgagaag   1620
cctggctgcc cctgtagaag aggacagcct agactgcaca ccgtgaagat gtggcgggcc   1680
tgccacttgt ttctccagcc acaagtgggc accccctccac ctcatacagc ctctgctaga   1740
gcacctagcg gcccacctca tcctcacgaa tcttgtcctg ccggaagaag gcctgccaga   1800
gccgctcaaa catgtgccag acgacagcac ggactgcccg gatgtgaaga agccggaaca   1860
gccagagtgc ctagcctgca ccttcatctg catcaggccg ctcttggagc cggaagaggt   1920
agaggatggg gagaagcttg tgcccaggtg ccaccttcta gaggccacta caagctgatc   1980
cagcagccaa tcagcctgtt ctccatcacc gaccggctgc acaagacatt cagccagctg   2040
ccttccgtgc atctgtgcag catcaccttc cagtggggac accctcctat cttttgctcc   2100
accaacgaca tctgcgtgac cgccaacttc tgtatcagcg tgaccttcct gaagccttgc   2160
tttctgctgc acgaggcctc cgccagccag tttaagaagt ttgacggccc ctgcggcgag   2220
agaggcggag gaagaactgc aagagccctt tgggccagag gcgactctgt tctgacacca   2280
gctctggacc ctcagacacc tgttagggcc cctagcctga caagagctgc cgctgctgtt   2340
ggagtgcctg gcgattctac tagaagggcc gtgcggcgga tgaacacctt ttgtggcgca   2400
tctgcctgcg acgtgtccct gatcgctatg gatagcgcct gcgaggaaag aggcgcagcc   2460
ggatctctga tctcttgcga gagcctgtac caccgggaaa agcagctcat tgccatggac   2520
agcgccatct tcgtgcaggg caaagactgg ggcgtgaaga agttcatccg gcgggacttt   2580
accatgcctg ccattctgaa gctgcagaag aattgtcttc taagcctgaa cagcaagatg   2640
```

-continued

```
gccctgaata gcgaggccct gtctgtggtg tccgagtatg aggctggaat gaccctgggc   2700
gagaagttca gagtgggcaa ctgcaagcac ctgaagatga cccggcctac cgagtacaac   2760
cagaaactgc aagtgaacca gttcagcgag agcaagcgga ccgctctgac ccacaaccag   2820
gacttcagca tctaccggct gtgctgcaag aggggctctc tgtgtcatgc tagccaggct   2880
agaagccccg cctttcctaa gcctgtcaga cctctgcctg ctcctatcac cagaatcacc   2940
cctcagctcg gcggccagtc tgattcatct cagccactgc tgaccaccgg cagacctcaa   3000
ggatggcaag accaggctct gagacacaca cagcaggcta gcccagcctc ttgcgccacc   3060
atcacaatac caatacattc tgccgctctg ggcgatcaca gcggagatcc tggacctgcc   3120
tgggatactt gtcctcctct gcccctaact acactgatcc ctagggctcc tccaccttac   3180
ggcgatagca cagccagatc ctggcctagc agatgtggcc ctctgggcta cgcctacaag   3240
gacttcctgt ggtgcttccc cttctctctg gtgttcctgc aagaaatcca gatctgctgt   3300
cacgtgtcct gcctgtgctg tatctgctgt agcacccgga tctgtctggg ctgtctgctg   3360
gaactgttcc tgagcagagc cctgagagca ctgcacgtgc tgtggaacgg attccagctg   3420
cactgccagg gcaacaccac actgcaacag ctgggagaag cctctcaggc cccaagcggt   3480
tctctgatcc ctctcagact gcccctcctg tgggaagtgc ggggcaattc taagatggct   3540
ctcaacagcc tgaactccat cgacgacgcc cagctgacaa gaatcgcccc tccaagaagc   3600
cactgttgct tttgggaagt gaacgcccct tttgtgcagg gtaaagattg ggcctcaaa   3660
aagtttatca gacgggactt cgaggctttc cagagagcag ctggcgaagg cggacctggc   3720
agaggtggtg ctagaagagg tgctagagtg ctgcagagcc cattctgtag agctggcgct   3780
ggcgaatggc tgggccacca atctcttaga tggggaatgg aactggccgc tagcaggcgg   3840
tttagctggg atcatcattc tgccggcgga cctccaagag tgccaagcgt tagaagcgga   3900
gcagcccagg tccagcctaa agatccactg ccactgagaa cactggccgg ctgccttgcc   3960
agaacagctc atcttagacc tggcgccgaa agcctgcctc aacctcagct gcattgcaca   4020
atcgccagag aactgcacca gttcgccttc gacctgctga tcaagagcca caagatgcac   4080
ttctcactga aagagcaccc gccaccgccg tgcccaccgc acgttgtcgg ctatggccac   4140
ctggatacaa gcggctcctc tagcagtagc tcctggcctc agcctgacag ctttgctgcc   4200
ctgcatagct ccctgaatga gctgggcgaa ctgtggttcc agtccagcga actgtctcct   4260
actggcgctc catggccaag cagaaggcct acttggagag gcaccaccgt gtctccaaga   4320
accgctacaa gcagcgccag aacctgttgc ggcacaaaat ggccctccag ccaagaagct   4380
gccctcggac ttggaagcgg actgctgaga ttcagctgtg gcacagccgc catcaga      4437
```

<210> SEQ ID NO 545
<211> LENGTH: 15
<212> TYPE: DNA
<213> ORGANISM: Homo sapiens

<400> SEQUENCE: 545

```
cgcgacttcg ccgcc                                                      15
```

<210> SEQ ID NO 546
<211> LENGTH: 84
<212> TYPE: DNA
<213> ORGANISM: Artificial seqeunce
<220> FEATURE:
<223> OTHER INFORMATION: T cell enhancer

<400> SEQUENCE: 546
atgggccaga aagagcagat ccacacactg cagaaaaaca gcgagcggat gagcaagcag 60
ctgaccagat cttctcaggc cgtg 84

<210> SEQ ID NO 547
<211> LENGTH: 21
<212> TYPE: DNA
<213> ORGANISM: Artificial seqeunce
<220> FEATURE:
<223> OTHER INFORMATION: Tag seqeunce

<400> SEQUENCE: 547
agccatcacc atcaccacca t 21

<210> SEQ ID NO 548
<211> LENGTH: 12
<212> TYPE: PRT
<213> ORGANISM: Homo sapiens

<400> SEQUENCE: 548

Ile Lys Ser Leu Thr Ala Ile Phe Thr Val Lys Phe
1 5 10

<210> SEQ ID NO 549
<211> LENGTH: 28
<212> TYPE: PRT
<213> ORGANISM: Artificial sequence
<220> FEATURE:
<223> OTHER INFORMATION: T cell enhancer

<400> SEQUENCE: 549

Met Gly Gln Lys Glu Gln Ile His Thr Leu Gln Lys Asn Ser Glu Arg
1 5 10 15

Met Ser Lys Gln Leu Thr Arg Ser Ser Gln Ala Val
20 25

<210> SEQ ID NO 550
<211> LENGTH: 1507
<212> TYPE: PRT
<213> ORGANISM: Artificial seqeunce
<220> FEATURE:
<223> OTHER INFORMATION: Heterologous polypeptide

<400> SEQUENCE: 550

Met Gly Gln Lys Glu Gln Ile His Thr Leu Gln Lys Asn Ser Glu Arg
1 5 10 15

Met Ser Lys Gln Leu Thr Arg Ser Ser Gln Ala Val Gln Asn Leu Gln
20 25 30

Asn Gly Gly Gly Ser Arg Ser Ser Ala Thr Leu Pro Gly Arg Arg Arg
35 40 45

Arg Arg Trp Leu Arg Arg Arg Arg Gln Pro Ile Ser Val Ala Pro Ala
50 55 60

Gly Pro Pro Arg Arg Pro Asn Gln Lys Pro Asn Pro Pro Gly Gly Ala
65 70 75 80

Arg Cys Val Ile Met Arg Pro Thr Trp Pro Gly Thr Ser Ala Phe Thr
85 90 95

Lys Arg Ser Phe Ala Val Thr Glu Arg Ile Ile Asp Tyr Trp Ala Gln
100 105 110

Lys Glu Lys Gly Ser Ser Ser Phe Leu Arg Pro Ser Cys Asp Tyr Trp
115 120 125

Ala Gln Lys Glu Lys Ile Ser Ile Pro Arg Thr His Leu Cys Leu Val

```
    130                 135                 140

Leu Gly Val Leu Ser Gly His Ser Gly Ser Arg Leu Tyr Glu Ala Gly
145                 150                 155                 160

Met Thr Leu Gly Gly Lys Ile Leu Phe Phe Leu Phe Leu Leu Leu Pro
                165                 170                 175

Leu Ser Pro Phe Ser Leu Ile Phe Thr Glu Ile Ser Cys Cys Thr Leu
            180                 185                 190

Ser Ser Glu Glu Asn Glu Tyr Leu Pro Arg Pro Glu Trp Gln Leu Gln
        195                 200                 205

Val Pro Phe Arg Glu Leu Lys Asn Val Ser Val Leu Glu Gly Leu Arg
    210                 215                 220

Gln Gly Arg Leu Gly Gly Pro Cys Ser Cys His Cys Pro Arg Pro Ser
225                 230                 235                 240

Gln Ala Arg Leu Thr Pro Val Asp Val Ala Gly Pro Phe Leu Cys Leu
                245                 250                 255

Gly Asp Pro Gly Leu Phe Pro Pro Val Lys Ser Ser Ile Thr Gly Gly
            260                 265                 270

Lys Ser Thr Cys Ser Ala Pro Gly Pro Gln Ser Leu Pro Ser Thr Pro
        275                 280                 285

Phe Ser Thr Tyr Pro Gln Trp Val Ile Leu Ile Thr Glu Leu Gly Met
    290                 295                 300

Glu Cys Thr Leu Gly Gln Val Gly Ala Pro Ser Pro Arg Arg Glu Glu
305                 310                 315                 320

Asp Gly Trp Arg Gly Gly His Ser Arg Phe Lys Ala Asp Val Pro Ala
                325                 330                 335

Pro Gln Gly Pro Cys Trp Gly Gly Gln Pro Gly Ser Ala Pro Ser Ser
            340                 345                 350

Ala Pro Pro Glu Gln Ser Leu Leu Asp Trp Lys Phe Glu Met Ser Tyr
        355                 360                 365

Thr Val Gly Gly Pro Pro Pro His Val His Ala Arg Pro Arg His Trp
    370                 375                 380

Lys Thr Asp Arg Asp Gly His Ser Tyr Thr Ser Lys Val Asn Cys Leu
385                 390                 395                 400

Leu Leu Gln Asp Gly Phe His Gly Cys Val Ser Ile Thr Gly Ala Ala
                405                 410                 415

Gly Arg Arg Asn Leu Ser Ile Phe Leu Phe Leu Met Leu Cys Lys Leu
            420                 425                 430

Glu Phe His Ala Cys Lys Ile Gln Asn Lys Asn Cys Pro Asp Phe Lys
        435                 440                 445

Lys Phe Asp Gly Pro Cys Gly Glu Arg Gly Gly Gly Arg Thr Ala Arg
    450                 455                 460

Ala Leu Trp Ala Arg Gly Asp Ser Val Leu Thr Pro Ala Leu Asp Pro
465                 470                 475                 480

Gln Thr Pro Val Arg Ala Pro Ser Leu Thr Arg Ala Ala Ala Ala Val
                485                 490                 495

His Tyr Lys Leu Ile Gln Gln Pro Ile Ser Leu Phe Ser Ile Thr Asp
            500                 505                 510

Arg Leu His Lys Thr Phe Ser Gln Leu Pro Ser Val His Leu Cys Ser
        515                 520                 525

Ile Thr Phe Gln Trp Gly His Pro Pro Ile Phe Cys Ser Thr Asn Asp
    530                 535                 540

Ile Cys Val Thr Ala Asn Phe Cys Ile Ser Val Thr Phe Leu Lys Pro
545                 550                 555                 560
```

```
Cys Phe Leu Leu His Glu Ala Ser Ala Ser Gln Cys His Leu Phe Leu
                565                 570                 575

Gln Pro Gln Val Gly Thr Pro Pro Pro His Thr Ala Ser Ala Arg Ala
            580                 585                 590

Pro Ser Gly Pro Pro His Pro His Glu Ser Cys Pro Ala Gly Arg Arg
        595                 600                 605

Pro Ala Arg Ala Ala Gln Thr Cys Ala Arg Arg Gln His Gly Leu Pro
    610                 615                 620

Gly Cys Glu Glu Ala Gly Thr Ala Arg Val Pro Ser Leu His Leu His
625                 630                 635                 640

Leu His Gln Ala Ala Leu Gly Ala Gly Arg Gly Arg Gly Trp Gly Glu
                645                 650                 655

Ala Cys Ala Gln Val Pro Pro Ser Arg Gly Val Leu Arg Phe Leu Asp
            660                 665                 670

Leu Lys Val Arg Tyr Leu His Ser Gln Trp Gln His Tyr His Arg Ser
        675                 680                 685

Gly Glu Ala Ala Gly Thr Pro Leu Trp Arg Pro Thr Arg Asn Val Pro
    690                 695                 700

Phe Arg Glu Leu Lys Asn Gln Arg Thr Ala Gln Gly Ala Pro Gly Ile
705                 710                 715                 720

His His Ala Ala Ser Pro Val Ala Ala Asn Leu Cys Asp Pro Ala Arg
                725                 730                 735

His Ala Gln His Thr Arg Ile Pro Cys Gly Ala Gly Gln Val Arg Ala
            740                 745                 750

Gly Arg Gly Pro Glu Ala Gly Gly Gly Val Leu Gln Pro Gln Arg Pro
        755                 760                 765

Ala Pro Glu Lys Pro Gly Cys Pro Cys Arg Arg Gly Gln Pro Arg Leu
    770                 775                 780

His Thr Val Lys Met Trp Arg Ala Val Ala Met Met Val Pro Asp Arg
785                 790                 795                 800

Gln Val His Tyr Asp Phe Gly Leu Gly Val Pro Gly Asp Ser Thr Arg
                805                 810                 815

Arg Ala Val Arg Arg Met Asn Thr Phe Tyr Glu Ala Gly Met Thr Leu
            820                 825                 830

Gly Glu Lys Phe Arg Val Gly Asn Cys Lys His Leu Lys Met Thr Arg
        835                 840                 845

Pro Asn Ser Lys Met Ala Leu Asn Ser Glu Ala Leu Ser Val Val Ser
    850                 855                 860

Glu Cys Gly Ala Ser Ala Cys Asp Val Ser Leu Ile Ala Met Asp Ser
865                 870                 875                 880

Ala Phe Val Gln Gly Lys Asp Trp Gly Val Lys Lys Phe Ile Arg Arg
                885                 890                 895

Asp Phe Tyr Ala Tyr Lys Asp Phe Leu Trp Cys Phe Pro Phe Ser Leu
            900                 905                 910

Val Phe Leu Gln Glu Ile Gln Ile Cys Cys His Val Ser Cys Leu Cys
        915                 920                 925

Cys Ile Cys Cys Ser Thr Arg Ile Cys Leu Gly Cys Leu Leu Glu Leu
    930                 935                 940

Phe Leu Ser Arg Ala Leu Arg Ala Leu His Val Leu Trp Asn Gly Phe
945                 950                 955                 960

Gln Leu His Cys Gln Thr Glu Tyr Asn Gln Lys Leu Gln Val Asn Gln
                965                 970                 975
```

-continued

```
Phe Ser Glu Ser Lys Ser Leu Tyr His Arg Glu Lys Gln Leu Ile Ala
            980                 985                 990

Met Asp Ser Ala Ile Cys Glu Glu  Arg Gly Ala Ala Gly  Ser Leu Ile
        995                 1000                1005

Ser Cys  Glu Thr Met Pro Ala  Ile Leu Lys Leu Gln  Lys Asn Cys
    1010                 1015                 1020

Leu Leu  Ser Leu Arg Thr Ala  Leu Thr His Asn Gln  Asp Phe Ser
    1025                 1030                 1035

Ile Tyr  Arg Leu Cys Cys Lys  Arg Gly Ser Leu Cys  His Ala Ser
    1040                 1045                 1050

Gln Ala  Arg Ser Pro Ala Phe  Pro Lys Pro Val Arg  Pro Leu Pro
    1055                 1060                 1065

Ala Pro  Ile Thr Arg Ile Thr  Pro Gln Leu Gly Gly  Gln Ser Asp
    1070                 1075                 1080

Ser Ser  Gln Pro Leu Leu Thr  Thr Gly Arg Pro Gln  Gly Trp Gln
    1085                 1090                 1095

Asp Gln  Ala Leu Arg His Thr  Gln Gln Ala Ser Pro  Ala Ser Cys
    1100                 1105                 1110

Ala Thr  Ile Thr Ile Pro Ile  His Ser Ala Ala Leu  Gly Asp His
    1115                 1120                 1125

Ser Gly  Asp Pro Gly Pro Ala  Trp Asp Thr Cys Pro  Pro Leu Pro
    1130                 1135                 1140

Leu Thr  Thr Leu Ile Pro Arg  Ala Pro Pro Pro Tyr  Gly Asp Ser
    1145                 1150                 1155

Thr Ala  Arg Ser Trp Pro Ser  Arg Cys Gly Pro Leu  Gly Gly Asn
    1160                 1165                 1170

Thr Thr  Leu Gln Gln Leu Gly  Glu Ala Ser Gln Ala  Pro Ser Gly
    1175                 1180                 1185

Ser Leu  Ile Pro Leu Arg Leu  Pro Leu Leu Trp Glu  Val Arg Gly
    1190                 1195                 1200

Gln Pro  Asp Ser Phe Ala Ala  Leu His Ser Ser Leu  Asn Glu Leu
    1205                 1210                 1215

Gly Glu  Ile Ala Arg Glu Leu  His Gln Phe Ala Phe  Asp Leu Leu
    1220                 1225                 1230

Ile Lys  Ser His Phe Val Gln  Gly Lys Asp Trp Gly  Leu Lys Lys
    1235                 1240                 1245

Phe Ile  Arg Arg Asp Phe Trp  Gly Met Glu Leu Ala  Ala Ser Arg
    1250                 1255                 1260

Arg Phe  Ser Trp Asp His His  Ser Ala Gly Gly Pro  Pro Arg Val
    1265                 1270                 1275

Pro Ser  Val Arg Ser Gly Ala  Ala Gln Val Gln Pro  Lys Asp Pro
    1280                 1285                 1290

Leu Pro  Leu Arg Thr Leu Ala  Gly Cys Leu Ala Arg  Thr Ala His
    1295                 1300                 1305

Leu Arg  Pro Gly Ala Glu Ser  Leu Pro Gln Pro Gln  Leu His Cys
    1310                 1315                 1320

Thr Leu  Trp Phe Gln Ser Ser  Glu Leu Ser Pro Thr  Gly Ala Pro
    1325                 1330                 1335

Trp Pro  Ser Arg Arg Pro Thr  Trp Arg Gly Thr Thr  Val Ser Pro
    1340                 1345                 1350

Arg Thr  Ala Thr Ser Ser Ala  Arg Thr Cys Cys Gly  Thr Lys Trp
    1355                 1360                 1365

Pro Ser  Ser Gln Glu Ala Ala  Leu Gly Leu Gly Ser  Gly Leu Leu
```

```
    1370                1375                1380

Arg Phe  Ser Cys Gly Thr Ala  Ala Ile Arg Lys Met  His Phe Ser
    1385                1390                1395

Leu Lys  Glu His Pro Pro Pro  Pro Cys Pro Pro Glu  Ala Phe Gln
    1400                1405                1410

Arg Ala  Ala Gly Glu Gly Gly  Pro Gly Arg Gly Gly  Ala Arg Arg
    1415                1420                1425

Gly Ala  Arg Val Leu Gln Ser  Pro Phe Cys Arg Ala  Gly Ala Gly
    1430                1435                1440

Glu Trp  Leu Gly His Gln Ser  Leu Arg His Val Val  Gly Tyr Gly
    1445                1450                1455

His Leu  Asp Thr Ser Gly Ser  Ser Ser Ser Ser Ser  Trp Pro Asn
    1460                1465                1470

Ser Lys  Met Ala Leu Asn Ser  Leu Asn Ser Ile Asp  Asp Ala Gln
    1475                1480                1485

Leu Thr  Arg Ile Ala Pro Pro  Arg Ser His Cys Cys  Phe Trp Glu
    1490                1495                1500

Val Asn  Ala Pro
    1505


<210> SEQ ID NO 551
<211> LENGTH: 5703
<212> TYPE: PRT
<213> ORGANISM: Artificial seqeunce
<220> FEATURE:
<223> OTHER INFORMATION: Heterologous polypeptide

<400> SEQUENCE: 551

Cys Cys Ala Thr Thr Gly Cys Ala Thr Ala Cys Gly Thr Thr Gly Thr
1               5                   10                  15

Ala Thr Cys Cys Ala Thr Ala Thr Cys Ala Thr Ala Ala Thr Ala Thr
            20                  25                  30

Gly Thr Ala Cys Ala Thr Thr Thr Ala Thr Ala Thr Thr Gly Gly Cys
        35                  40                  45

Thr Cys Ala Thr Gly Thr Cys Cys Ala Ala Cys Ala Thr Thr Ala Cys
    50                  55                  60

Cys Gly Cys Cys Ala Thr Gly Thr Thr Gly Ala Cys Ala Thr Thr Gly
65                  70                  75                  80

Ala Thr Thr Ala Thr Thr Gly Ala Cys Thr Ala Gly Thr Thr Ala Thr
                85                  90                  95

Thr Ala Ala Thr Ala Gly Thr Ala Ala Thr Cys Ala Ala Thr Thr Ala
            100                 105                 110

Cys Gly Gly Gly Gly Thr Cys Ala Thr Thr Ala Gly Thr Thr Cys Ala
        115                 120                 125

Thr Ala Gly Cys Cys Cys Ala Thr Ala Thr Ala Thr Gly Gly Ala Gly
    130                 135                 140

Thr Thr Cys Cys Gly Cys Gly Thr Thr Ala Cys Ala Thr Ala Ala Cys
145                 150                 155                 160

Thr Thr Ala Cys Gly Gly Thr Ala Ala Ala Thr Gly Gly Cys Cys Cys
                165                 170                 175

Gly Cys Cys Thr Gly Gly Cys Thr Gly Ala Cys Cys Gly Cys Cys Cys
            180                 185                 190

Ala Ala Cys Gly Ala Cys Cys Cys Cys Cys Gly Cys Cys Cys Ala Thr
        195                 200                 205

Thr Gly Ala Cys Gly Thr Cys Ala Ala Thr Ala Ala Thr Gly Ala Cys
```

-continued

```
    210                 215                 220

Gly Thr Ala Thr Gly Thr Thr Cys Cys Cys Ala Thr Ala Gly Thr Ala
225                 230                 235                 240

Ala Cys Gly Cys Cys Ala Ala Thr Ala Gly Gly Gly Ala Cys Thr Thr
                245                 250                 255

Thr Cys Cys Ala Thr Thr Gly Ala Cys Gly Thr Cys Ala Ala Thr Gly
            260                 265                 270

Gly Gly Thr Gly Gly Ala Gly Thr Ala Thr Thr Thr Ala Cys Gly Gly
        275                 280                 285

Thr Ala Ala Ala Cys Thr Gly Cys Cys Cys Ala Cys Thr Thr Gly Gly
    290                 295                 300

Cys Ala Gly Thr Ala Cys Ala Thr Cys Ala Ala Gly Thr Gly Thr Ala
305                 310                 315                 320

Thr Cys Ala Thr Ala Thr Gly Cys Cys Ala Ala Gly Thr Ala Cys Gly
                325                 330                 335

Cys Cys Cys Cys Cys Thr Ala Thr Thr Gly Ala Cys Gly Thr Cys Ala
            340                 345                 350

Ala Thr Gly Ala Cys Gly Gly Thr Ala Ala Ala Thr Gly Gly Cys Cys
        355                 360                 365

Cys Gly Cys Cys Thr Gly Gly Cys Ala Thr Thr Ala Thr Gly Cys Cys
    370                 375                 380

Cys Ala Gly Thr Ala Cys Ala Thr Gly Ala Cys Cys Thr Thr Ala Thr
385                 390                 395                 400

Gly Gly Gly Ala Cys Thr Thr Thr Cys Cys Thr Ala Cys Thr Thr Gly
                405                 410                 415

Gly Cys Ala Gly Thr Ala Cys Ala Thr Cys Thr Ala Cys Gly Thr Ala
            420                 425                 430

Thr Thr Ala Gly Thr Cys Ala Thr Cys Gly Cys Thr Ala Thr Thr Ala
        435                 440                 445

Cys Cys Ala Thr Gly Gly Thr Gly Ala Thr Gly Cys Gly Gly Thr Thr
    450                 455                 460

Thr Thr Gly Gly Cys Ala Gly Thr Ala Cys Ala Thr Cys Ala Ala Thr
465                 470                 475                 480

Gly Gly Gly Cys Gly Thr Gly Gly Ala Thr Ala Gly Cys Gly Gly Thr
                485                 490                 495

Thr Thr Gly Ala Cys Thr Cys Ala Cys Gly Gly Gly Gly Ala Thr Thr
            500                 505                 510

Thr Cys Cys Ala Ala Gly Thr Cys Thr Cys Cys Ala Cys Cys Cys Cys
        515                 520                 525

Ala Thr Thr Gly Ala Cys Gly Thr Cys Ala Ala Thr Gly Gly Gly Ala
    530                 535                 540

Gly Thr Thr Thr Gly Thr Thr Thr Thr Gly Gly Cys Ala Cys Cys Ala
545                 550                 555                 560

Ala Ala Ala Thr Cys Ala Ala Cys Gly Gly Gly Ala Cys Thr Thr Thr
                565                 570                 575

Cys Cys Ala Ala Ala Ala Thr Gly Thr Cys Gly Thr Ala Ala Cys Ala
            580                 585                 590

Ala Cys Thr Cys Cys Gly Cys Cys Cys Cys Ala Thr Thr Gly Ala Cys
        595                 600                 605

Gly Cys Ala Ala Ala Thr Gly Gly Gly Cys Gly Gly Thr Ala Gly Gly
    610                 615                 620

Cys Gly Thr Gly Thr Ala Cys Gly Gly Thr Gly Gly Gly Ala Gly Gly
625                 630                 635                 640
```

```
Thr Cys Thr Ala Thr Ala Thr Ala Ala Gly Cys Ala Gly Ala Gly Cys
                645                 650                 655

Thr Cys Thr Cys Cys Cys Thr Ala Thr Cys Ala Gly Thr Gly Ala Thr
            660                 665                 670

Ala Gly Ala Gly Ala Thr Cys Thr Cys Cys Cys Thr Ala Thr Cys Ala
        675                 680                 685

Gly Thr Gly Ala Thr Ala Gly Ala Gly Ala Thr Cys Gly Thr Cys Gly
    690                 695                 700

Ala Cys Gly Ala Gly Cys Thr Cys Gly Thr Thr Thr Ala Gly Thr Gly
705                 710                 715                 720

Ala Ala Cys Cys Gly Thr Cys Ala Gly Ala Thr Cys Gly Cys Cys Thr
                725                 730                 735

Gly Gly Ala Gly Ala Cys Gly Cys Cys Ala Thr Cys Cys Ala Cys Gly
            740                 745                 750

Cys Thr Gly Thr Thr Thr Thr Gly Ala Cys Cys Thr Cys Cys Ala Thr
        755                 760                 765

Ala Gly Ala Ala Gly Ala Cys Ala Cys Cys Gly Gly Gly Ala Cys Cys
    770                 775                 780

Gly Ala Thr Cys Cys Ala Gly Cys Cys Thr Cys Cys Gly Cys Gly Gly
785                 790                 795                 800

Cys Cys Gly Gly Gly Ala Ala Cys Gly Gly Thr Gly Cys Ala Thr Thr
                805                 810                 815

Gly Gly Ala Ala Cys Gly Cys Gly Gly Ala Thr Thr Cys Cys Cys Cys
            820                 825                 830

Gly Thr Gly Cys Cys Ala Ala Gly Ala Gly Thr Gly Ala Gly Ala Thr
        835                 840                 845

Cys Thr Thr Cys Cys Gly Thr Thr Thr Ala Thr Cys Thr Ala Gly Gly
    850                 855                 860

Thr Ala Cys Cys Ala Gly Ala Thr Ala Thr Cys Ala Gly Ala Ala Thr
865                 870                 875                 880

Thr Cys Gly Gly Ala Thr Cys Cys Cys Gly Cys Gly Ala Cys Thr Thr
                885                 890                 895

Cys Gly Cys Cys Gly Cys Cys Ala Thr Gly Gly Gly Cys Cys Ala Gly
            900                 905                 910

Ala Ala Ala Gly Ala Gly Cys Ala Gly Ala Thr Cys Cys Ala Cys Ala
        915                 920                 925

Cys Ala Cys Thr Gly Cys Ala Gly Ala Ala Ala Ala Ala Cys Ala Gly
    930                 935                 940

Cys Gly Ala Gly Cys Gly Gly Ala Thr Gly Ala Gly Cys Ala Ala Gly
945                 950                 955                 960

Cys Ala Gly Cys Thr Gly Ala Cys Cys Ala Gly Ala Thr Cys Thr Thr
                965                 970                 975

Cys Thr Cys Ala Gly Gly Cys Cys Gly Thr Gly Cys Ala Gly Ala Ala
            980                 985                 990

Cys Cys Thr Gly Cys Ala Gly Ala  Ala Cys Gly Gly Cys  Gly Gly Ala
        995                 1000                1005

Gly Gly  Cys Thr Cys Thr Ala  Gly Ala Ala Gly Cys  Thr Cys Thr
    1010                1015                1020

Gly Cys  Thr Ala Cys Ala Cys  Thr Thr Cys Cys Thr  Gly Gly Cys
    1025                1030                1035

Ala Gly  Gly Cys Gly Gly Cys  Gly Gly Ala Gly Ala  Ala Gly Ala
    1040                1045                1050
```

```
Thr Gly Gly Cys Thr Gly Ala Gly Ala Ala Gly Ala Ala Gly Gly
    1055                1060                1065

Cys Gly Gly Cys Ala Gly Cys Cys Thr Ala Thr Cys Thr Cys Thr
    1070                1075                1080

Gly Thr Gly Gly Cys Thr Cys Cys Thr Gly Cys Thr Gly Gly Ala
    1085                1090                1095

Cys Cys Thr Cys Cys Thr Ala Gly Ala Cys Gly Gly Cys Cys Cys
    1100                1105                1110

Ala Ala Cys Cys Ala Gly Ala Ala Gly Cys Cys Thr Ala Ala Thr
    1115                1120                1125

Cys Cys Thr Cys Cys Thr Gly Gly Cys Gly Gly Ala Gly Cys Cys
    1130                1135                1140

Ala Gly Ala Thr Gly Cys Gly Thr Gly Ala Thr Cys Ala Thr Gly
    1145                1150                1155

Ala Gly Gly Cys Cys Thr Ala Cys Ala Thr Gly Gly Cys Cys Thr
    1160                1165                1170

Gly Gly Cys Ala Cys Cys Ala Gly Cys Gly Cys Cys Thr Thr Cys
    1175                1180                1185

Ala Cys Cys Ala Ala Gly Ala Gly Ala Ala Gly Cys Thr Thr Thr
    1190                1195                1200

Gly Cys Cys Gly Thr Gly Ala Cys Cys Gly Ala Gly Cys Gly Gly
    1205                1210                1215

Ala Thr Cys Ala Thr Cys Gly Ala Cys Thr Ala Thr Thr Gly Gly
    1220                1225                1230

Gly Cys Thr Cys Ala Ala Ala Ala Ala Gly Ala Gly Ala Ala Gly
    1235                1240                1245

Gly Gly Cys Ala Gly Cys Ala Gly Cys Ala Gly Cys Thr Thr Cys
    1250                1255                1260

Cys Thr Gly Cys Gly Gly Cys Cys Thr Ala Gly Cys Thr Gly Thr
    1265                1270                1275

Gly Ala Thr Thr Ala Thr Thr Gly Gly Gly Cys Cys Cys Ala Gly
    1280                1285                1290

Ala Ala Ala Gly Ala Ala Ala Ala Gly Ala Thr Cys Ala Gly Cys
    1295                1300                1305

Ala Thr Cys Cys Cys Cys Ala Gly Ala Ala Cys Ala Cys Ala Cys
    1310                1315                1320

Cys Thr Gly Thr Gly Cys Cys Thr Gly Gly Thr Gly Cys Thr Gly
    1325                1330                1335

Gly Gly Ala Gly Thr Gly Cys Thr Gly Thr Cys Thr Gly Gly Ala
    1340                1345                1350

Cys Ala Cys Thr Cys Thr Gly Gly Cys Ala Gly Cys Ala Gly Ala
    1355                1360                1365

Cys Thr Gly Thr Ala Thr Gly Ala Gly Gly Cys Cys Gly Gly Cys
    1370                1375                1380

Ala Thr Gly Ala Cys Ala Cys Thr Cys Gly Gly Cys Gly Gly Cys
    1385                1390                1395

Ala Ala Gly Ala Thr Cys Cys Thr Gly Thr Thr Cys Thr Thr Cys
    1400                1405                1410

Cys Thr Gly Thr Thr Cys Cys Thr Gly Cys Thr Gly Cys Thr Cys
    1415                1420                1425

Cys Cys Thr Cys Thr Gly Ala Gly Cys Cys Cys Cys Thr Thr Cys
    1430                1435                1440

Ala Gly Cys Cys Thr Gly Ala Thr Cys Thr Thr Cys Ala Cys Cys
```

```
    1445                1450                1455

Gly Ala  Gly Ala Thr Cys Ala  Gly Cys Thr Gly Cys  Thr Gly Cys
    1460                1465                1470

Ala Cys  Cys Cys Thr Gly Ala  Gly Cys Ala Gly Cys  Gly Ala Gly
    1475                1480                1485

Gly Ala  Ala Ala Ala Cys Gly  Ala Gly Thr Ala Cys  Cys Thr Gly
    1490                1495                1500

Cys Cys  Thr Ala Gly Ala Cys  Cys Thr Gly Ala Gly  Thr Gly Gly
    1505                1510                1515

Cys Ala  Gly Cys Thr Gly Cys  Ala Gly Gly Thr Cys  Cys Cys Cys
    1520                1525                1530

Thr Thr  Cys Ala Gly Ala Gly  Ala Gly Cys Thr Gly  Ala Ala Gly
    1535                1540                1545

Ala Ala  Cys Gly Thr Thr Thr  Cys Cys Gly Thr Gly  Cys Thr Gly
    1550                1555                1560

Gly Ala  Ala Gly Gly Cys Cys  Thr Gly Ala Gly Ala  Cys Ala Gly
    1565                1570                1575

Gly Gly  Cys Ala Gly Ala Cys  Thr Thr Gly Gly Cys  Gly Gly Cys
    1580                1585                1590

Cys Cys  Thr Thr Gly Thr Ala  Gly Cys Thr Gly Thr  Cys Ala Cys
    1595                1600                1605

Thr Gly  Cys Cys Cys Cys Ala  Gly Ala Cys Cys Thr  Ala Gly Thr
    1610                1615                1620

Cys Ala  Gly Gly Cys Cys Ala  Gly Ala Cys Thr Gly  Ala Cys Ala
    1625                1630                1635

Cys Cys  Thr Gly Thr Gly Gly  Ala Thr Gly Thr Gly  Gly Cys Cys
    1640                1645                1650

Gly Gly  Ala Cys Cys Thr Thr  Thr Cys Cys Thr Gly  Thr Gly Thr
    1655                1660                1665

Cys Thr  Gly Gly Gly Ala Gly  Ala Thr Cys Cys Thr  Gly Gly Cys
    1670                1675                1680

Cys Thr  Gly Thr Thr Thr Cys  Cys Ala Cys Cys Thr  Gly Thr Gly
    1685                1690                1695

Ala Ala  Gly Thr Cys Cys Ala  Gly Cys Ala Thr Cys  Ala Cys Ala
    1700                1705                1710

Gly Gly  Cys Gly Gly Cys Ala  Ala Gly Thr Cys Cys  Ala Cys Ala
    1715                1720                1725

Thr Gly  Thr Thr Cys Thr Gly  Cys Cys Cys Cys Thr  Gly Gly Ala
    1730                1735                1740

Cys Cys  Thr Cys Ala Gly Ala  Gly Cys Cys Thr Gly  Cys Cys Thr
    1745                1750                1755

Ala Gly  Cys Ala Cys Ala Cys  Cys Cys Thr Thr Cys  Ala Gly Cys
    1760                1765                1770

Ala Cys  Ala Thr Ala Cys Cys  Cys Thr Cys Ala Gly  Thr Gly Gly
    1775                1780                1785

Gly Thr  Cys Ala Thr Cys Cys  Thr Gly Ala Thr Cys  Ala Cys Cys
    1790                1795                1800

Gly Ala  Ala Cys Thr Cys Gly  Gly Cys Ala Thr Gly  Gly Ala Ala
    1805                1810                1815

Thr Gly  Cys Ala Cys Cys Cys  Thr Gly Gly Gly Ala  Cys Ala Ala
    1820                1825                1830

Gly Thr  Gly Gly Gly Ala Gly  Cys Cys Cys Cys Ala  Thr Cys Thr
    1835                1840                1845
```

```
Cys Cys  Thr Ala Gly Ala Ala  Gly Ala Gly Ala Ala  Gly Ala Gly
    1850                 1855                 1860

Gly Ala  Thr Gly Gly Cys Thr  Gly Gly Cys Gly Cys  Gly Gly Ala
    1865                 1870                 1875

Gly Gly  Cys Cys Ala Cys Thr  Cys Thr Ala Gly Ala  Thr Thr Cys
    1880                 1885                 1890

Ala Ala  Ala Gly Cys Thr Gly  Ala Thr Gly Thr Gly  Cys Cys Cys
    1895                 1900                 1905

Gly Cys  Thr Cys Cys Thr Cys  Ala Gly Gly Gly Cys  Cys Cys Thr
    1910                 1915                 1920

Thr Gly  Thr Thr Gly Gly Gly  Gly Ala Gly Gly Ala  Cys Ala Ala
    1925                 1930                 1935

Cys Cys  Thr Gly Gly Ala Thr  Cys Thr Gly Cys Cys  Cys Cys Ala
    1940                 1945                 1950

Thr Cys  Thr Thr Cys Thr Gly  Cys Cys Cys Cys Ala  Cys Cys Thr
    1955                 1960                 1965

Gly Ala  Ala Cys Ala Gly Thr  Cys Cys Cys Thr Gly  Cys Thr Gly
    1970                 1975                 1980

Gly Ala  Thr Thr Gly Gly Ala  Ala Gly Thr Thr Cys  Gly Ala Gly
    1985                 1990                 1995

Ala Thr  Gly Ala Gly Cys Thr  Ala Cys Ala Cys Cys  Gly Thr Cys
    2000                 2005                 2010

Gly Gly  Cys Gly Gly Ala Cys  Cys Thr Cys Cys Ala  Cys Cys Thr
    2015                 2020                 2025

Cys Ala  Thr Gly Thr Thr Cys  Ala Thr Gly Cys Cys  Ala Gly Ala
    2030                 2035                 2040

Cys Cys  Thr Cys Gly Gly Cys  Ala Cys Thr Gly Gly  Ala Ala Ala
    2045                 2050                 2055

Ala Cys  Cys Gly Ala Cys Ala  Gly Ala Gly Ala Thr  Gly Gly Cys
    2060                 2065                 2070

Cys Ala  Cys Ala Gly Cys Thr  Ala Cys Ala Cys Cys  Ala Gly Cys
    2075                 2080                 2085

Ala Ala  Ala Gly Thr Gly Ala  Ala Cys Thr Gly Cys  Cys Thr Cys
    2090                 2095                 2100

Cys Thr  Gly Cys Thr Gly Cys  Ala Gly Gly Ala Thr  Gly Gly Cys
    2105                 2110                 2115

Thr Thr  Cys Cys Ala Cys Gly  Gly Cys Thr Gly Thr  Gly Thr Gly
    2120                 2125                 2130

Thr Cys  Thr Ala Thr Thr Ala  Cys Thr Gly Gly Cys  Gly Cys Cys
    2135                 2140                 2145

Gly Cys  Thr Gly Gly Cys Ala  Gly Ala Cys Gly Gly  Ala Ala Cys
    2150                 2155                 2160

Cys Thr  Gly Ala Gly Cys Ala  Thr Cys Thr Thr Thr  Cys Thr Gly
    2165                 2170                 2175

Thr Thr  Thr Cys Thr Gly Ala  Thr Gly Cys Thr Gly  Thr Gly Cys
    2180                 2185                 2190

Ala Ala  Gly Cys Thr Cys Gly  Ala Gly Thr Thr Cys  Cys Ala Cys
    2195                 2200                 2205

Gly Cys  Cys Thr Gly Cys Ala  Ala Gly Ala Thr Cys  Cys Ala Gly
    2210                 2215                 2220

Ala Ala  Cys Ala Ala Gly Ala  Ala Cys Thr Gly Cys  Cys Cys Cys
    2225                 2230                 2235
```

```
Gly Ala  Cys Thr Thr Cys Ala  Ala Gly Ala Ala Gly  Thr Thr Cys
    2240                 2245                 2250

Gly Ala  Cys Gly Gly Cys Cys  Cys Thr Thr Gly Cys  Gly Gly Ala
    2255                 2260                 2265

Gly Ala  Ala Ala Gly Ala Gly  Gly Cys Gly Gly Ala  Gly Gly Cys
    2270                 2275                 2280

Ala Gly  Ala Ala Cys Ala Gly  Cys Thr Ala Gly Ala  Gly Cys Cys
    2285                 2290                 2295

Cys Thr  Thr Thr Gly Gly Gly  Cys Thr Ala Gly Ala  Gly Gly Cys
    2300                 2305                 2310

Gly Ala  Cys Ala Gly Cys Gly  Thr Thr Cys Thr Gly  Ala Cys Ala
    2315                 2320                 2325

Cys Cys  Ala Gly Cys Thr Cys  Thr Gly Gly Ala Cys  Cys Cys Thr
    2330                 2335                 2340

Cys Ala  Gly Ala Cys Ala Cys  Cys Thr Gly Thr Thr  Ala Gly Gly
    2345                 2350                 2355

Gly Cys  Cys Cys Cys Thr Ala  Gly Cys Cys Thr Gly  Ala Cys Ala
    2360                 2365                 2370

Ala Gly  Ala Gly Cys Thr Gly  Cys Cys Gly Cys Cys  Gly Cys Thr
    2375                 2380                 2385

Gly Thr  Gly Cys Ala Cys Thr  Ala Cys Ala Ala Gly  Cys Thr Gly
    2390                 2395                 2400

Ala Thr  Cys Cys Ala Gly Cys  Ala Gly Cys Cys Ala  Ala Thr Cys
    2405                 2410                 2415

Ala Gly  Cys Cys Thr Gly Thr  Thr Cys Ala Gly Cys  Ala Thr Cys
    2420                 2425                 2430

Ala Cys  Cys Gly Ala Cys Cys  Gly Gly Cys Thr Gly  Cys Ala Cys
    2435                 2440                 2445

Ala Ala  Gly Ala Cys Ala Thr  Thr Cys Ala Gly Cys  Cys Ala Gly
    2450                 2455                 2460

Cys Thr  Gly Cys Cys Ala Ala  Gly Cys Gly Thr Gly  Cys Ala Cys
    2465                 2470                 2475

Cys Thr  Gly Thr Gly Cys Thr  Cys Cys Ala Thr Cys  Ala Cys Cys
    2480                 2485                 2490

Thr Thr  Cys Cys Ala Gly Thr  Gly Gly Gly Gly Ala  Cys Ala Cys
    2495                 2500                 2505

Cys Cys  Thr Cys Cys Thr Ala  Thr Cys Thr Thr Thr  Thr Gly Cys
    2510                 2515                 2520

Thr Cys  Cys Ala Cys Cys Ala  Ala Cys Gly Ala Cys  Ala Thr Cys
    2525                 2530                 2535

Thr Gly  Cys Gly Thr Gly Ala  Cys Cys Gly Cys Cys  Ala Ala Cys
    2540                 2545                 2550

Thr Thr  Cys Thr Gly Thr Ala  Thr Cys Ala Gly Cys  Gly Thr Gly
    2555                 2560                 2565

Ala Cys  Cys Thr Thr Cys Cys  Thr Gly Ala Ala Gly  Cys Cys Thr
    2570                 2575                 2580

Thr Gly  Cys Thr Thr Thr Cys  Thr Gly Cys Thr Gly  Cys Ala Cys
    2585                 2590                 2595

Gly Ala  Gly Gly Cys Cys Ala  Gly Cys Gly Cys Cys  Thr Cys Thr
    2600                 2605                 2610

Cys Ala  Gly Thr Gly Cys Cys  Ala Cys Thr Thr Gly  Thr Thr Thr
    2615                 2620                 2625

Cys Thr  Gly Cys Ala Gly Cys  Cys Cys Cys Ala Ala  Gly Thr Gly
```

```
    2630                2635                2640

Gly Gly  Cys Ala Cys Ala Cys  Cys Thr Cys Cys Thr  Cys Cys Ala
    2645                2650                2655

Cys Ala  Thr Ala Cys Ala Gly  Cys Cys Thr Cys Thr  Gly Cys Thr
    2660                2665                2670

Ala Gly  Ala Gly Cys Ala Cys  Cys Thr Ala Gly Cys  Gly Gly Cys
    2675                2680                2685

Cys Cys  Thr Cys Cys Ala Cys  Ala Thr Cys Cys Thr  Cys Ala Cys
    2690                2695                2700

Gly Ala  Ala Thr Cys Thr Thr  Gly Thr Cys Cys Thr  Gly Cys Cys
    2705                2710                2715

Gly Gly  Ala Ala Gly Ala Ala  Gly Gly Cys Cys Thr  Gly Cys Cys
    2720                2725                2730

Ala Gly  Ala Gly Cys Cys Gly  Cys Thr Cys Ala Ala  Ala Cys Ala
    2735                2740                2745

Thr Gly  Thr Gly Cys Cys Ala  Gly Ala Cys Gly Ala  Cys Ala Gly
    2750                2755                2760

Cys Ala  Cys Gly Gly Ala Cys  Thr Gly Cys Cys Thr  Gly Gly Ala
    2765                2770                2775

Thr Gly  Thr Gly Ala Ala Gly  Ala Gly Gly Cys Thr  Gly Gly Ala
    2780                2785                2790

Ala Cys  Ala Gly Cys Cys Ala  Gly Ala Gly Thr Gly  Cys Cys Thr
    2795                2800                2805

Ala Gly  Cys Cys Thr Gly Cys  Ala Cys Cys Thr Cys  Cys Ala Thr
    2810                2815                2820

Cys Thr  Gly Cys Ala Thr Cys  Ala Gly Gly Cys Thr  Gly Cys Thr
    2825                2830                2835

Cys Thr  Thr Gly Gly Ala Gly  Cys Cys Gly Gly Ala  Ala Gly Ala
    2840                2845                2850

Gly Gly  Thr Ala Gly Ala Gly  Gly Ala Thr Gly Gly  Gly Gly Cys
    2855                2860                2865

Gly Ala  Ala Gly Cys Thr Thr  Gly Thr Gly Cys Thr  Cys Ala Gly
    2870                2875                2880

Gly Thr  Gly Cys Cys Ala Cys  Cys Thr Thr Cys Thr  Ala Gly Ala
    2885                2890                2895

Gly Gly  Cys Gly Thr Gly Cys  Thr Gly Ala Gly Ala  Thr Thr Cys
    2900                2905                2910

Cys Thr  Gly Gly Ala Cys Cys  Thr Gly Ala Ala Ala  Gly Thr Gly
    2915                2920                2925

Cys Gly  Cys Thr Ala Cys Cys  Thr Gly Cys Ala Cys  Ala Gly Cys
    2930                2935                2940

Cys Ala  Gly Thr Gly Gly Cys  Ala Gly Cys Ala Cys  Thr Ala Thr
    2945                2950                2955

Cys Ala  Cys Ala Gly Ala Thr  Cys Thr Gly Gly Cys  Gly Ala Ala
    2960                2965                2970

Gly Cys  Cys Gly Cys Cys Gly  Gly Ala Ala Cys Ala  Cys Cys Cys
    2975                2980                2985

Cys Thr  Thr Thr Gly Gly Ala  Gly Gly Cys Cys Ala  Ala Cys Ala
    2990                2995                3000

Ala Gly  Ala Ala Ala Cys Gly  Thr Gly Cys Cys Cys  Thr Thr Cys
    3005                3010                3015

Cys Gly  Gly Gly Ala Ala Cys  Thr Gly Ala Ala Gly  Ala Ala Cys
    3020                3025                3030
```

```
Cys Ala  Gly Ala Gly Ala Ala  Cys Ala Gly Cys Thr  Cys Ala Gly
    3035                 3040                 3045

Gly Gly  Cys Gly Cys Thr Cys  Cys Thr Gly Gly Ala  Ala Thr Cys
    3050                 3055                 3060

Cys Ala  Cys Cys Ala Thr Gly  Cys Thr Gly Cys Thr  Thr Cys Thr
    3065                 3070                 3075

Cys Cys  Ala Gly Thr Gly Gly  Cys Cys Gly Cys Cys  Ala Ala Cys
    3080                 3085                 3090

Cys Thr  Gly Thr Gly Thr Gly  Ala Thr Cys Cys Thr  Gly Cys Cys
    3095                 3100                 3105

Ala Gly  Ala Cys Ala Thr Gly  Cys Cys Cys Ala Gly  Cys Ala Cys
    3110                 3115                 3120

Ala Cys  Cys Ala Gly Gly Ala  Thr Thr Cys Cys Thr  Thr Gly Thr
    3125                 3130                 3135

Gly Gly  Cys Gly Cys Thr Gly  Gly Ala Cys Ala Ala  Gly Thr Gly
    3140                 3145                 3150

Cys Gly  Cys Gly Cys Thr Gly  Gly Ala Ala Gly Ala  Gly Gly Ala
    3155                 3160                 3165

Cys Cys  Thr Gly Ala Ala Gly  Cys Ala Gly Gly Cys  Gly Gly Ala
    3170                 3175                 3180

Gly Gly  Thr Gly Thr Thr Cys  Thr Gly Cys Ala Ala  Cys Cys Thr
    3185                 3190                 3195

Cys Ala  Ala Ala Gly Ala Cys  Cys Cys Gly Cys Thr  Cys Cys Thr
    3200                 3205                 3210

Gly Ala  Gly Ala Ala Gly Cys  Cys Thr Gly Gly Cys  Thr Gly Cys
    3215                 3220                 3225

Cys Cys  Thr Thr Gly Cys Ala  Gly Ala Ala Gly Ala  Gly Gly Ala
    3230                 3235                 3240

Cys Ala  Gly Cys Cys Thr Ala  Gly Ala Cys Thr Gly  Cys Ala Cys
    3245                 3250                 3255

Ala Cys  Cys Gly Thr Gly Ala  Ala Ala Ala Thr Gly  Thr Gly Gly
    3260                 3265                 3270

Cys Gly  Ala Gly Cys Cys Gly  Thr Gly Gly Cys Cys  Ala Thr Gly
    3275                 3280                 3285

Ala Thr  Gly Gly Thr Gly Cys  Cys Cys Gly Ala Thr  Ala Gly Ala
    3290                 3295                 3300

Cys Ala  Gly Gly Thr Cys Cys  Ala Cys Thr Ala Cys  Gly Ala Cys
    3305                 3310                 3315

Thr Thr  Thr Gly Gly Ala Cys  Thr Gly Gly Gly Cys  Gly Thr Gly
    3320                 3325                 3330

Cys Cys  Ala Gly Gly Cys Gly  Ala Thr Ala Gly Cys  Ala Cys Thr
    3335                 3340                 3345

Cys Gly  Gly Ala Gly Ala Gly  Cys Cys Gly Thr Cys  Ala Gly Ala
    3350                 3355                 3360

Cys Gly  Gly Ala Thr Gly Ala  Ala Cys Ala Cys Cys  Thr Thr Thr
    3365                 3370                 3375

Thr Ala  Cys Gly Ala Ala Gly  Cys Cys Gly Gly Gly  Ala Thr Gly
    3380                 3385                 3390

Ala Cys  Cys Cys Thr Gly Gly  Gly Cys Gly Ala Gly  Ala Ala Gly
    3395                 3400                 3405

Thr Thr  Cys Ala Gly Ala Gly  Thr Gly Gly Gly Cys  Ala Ala Cys
    3410                 3415                 3420
```

```
Thr Gly  Cys Ala Ala Gly Cys  Ala Cys Cys Thr Gly  Ala Ala Gly
    3425                 3430                 3435

Ala Thr  Gly Ala Cys Cys Cys  Gly Gly Cys Cys Thr  Ala Ala Cys
    3440                 3445                 3450

Ala Gly  Cys Ala Ala Gly Ala  Thr Gly Gly Cys Cys  Cys Thr Gly
    3455                 3460                 3465

Ala Ala  Thr Ala Gly Cys Gly  Ala Gly Gly Cys Cys  Cys Thr Gly
    3470                 3475                 3480

Thr Cys  Thr Gly Thr Gly Gly  Thr Gly Thr Cys Thr  Gly Ala Ala
    3485                 3490                 3495

Thr Gly  Thr Gly Gly Cys Gly  Cys Cys Thr Cys Thr  Gly Cys Cys
    3500                 3505                 3510

Thr Gly  Thr Gly Ala Cys Gly  Thr Gly Thr Cys Cys  Cys Thr Gly
    3515                 3520                 3525

Ala Thr  Cys Gly Cys Thr Ala  Thr Gly Gly Ala Cys  Thr Cys Cys
    3530                 3535                 3540

Gly Cys  Cys Thr Thr Thr Gly  Thr Gly Cys Ala Gly  Gly Gly Cys
    3545                 3550                 3555

Ala Ala  Ala Gly Ala Cys Thr  Gly Gly Gly Gly Cys  Gly Thr Gly
    3560                 3565                 3570

Ala Ala  Gly Ala Ala Gly Thr  Thr Cys Ala Thr Cys  Cys Gly Gly
    3575                 3580                 3585

Cys Gly  Gly Gly Ala Cys Thr  Thr Cys Thr Ala Cys  Gly Cys Cys
    3590                 3595                 3600

Thr Ala  Cys Ala Ala Gly Gly  Ala Cys Thr Thr Cys  Cys Thr Gly
    3605                 3610                 3615

Thr Gly  Gly Thr Gly Cys Thr  Thr Cys Cys Cys Cys  Thr Thr Cys
    3620                 3625                 3630

Thr Cys  Thr Cys Thr Gly Gly  Thr Gly Thr Thr Cys  Cys Thr Gly
    3635                 3640                 3645

Cys Ala  Ala Gly Ala Gly Ala  Thr Cys Cys Ala Gly  Ala Thr Cys
    3650                 3655                 3660

Thr Gly  Cys Thr Gly Thr Cys  Ala Thr Gly Thr Gly  Thr Cys Cys
    3665                 3670                 3675

Thr Gly  Cys Cys Thr Gly Thr  Gly Cys Thr Gly Cys  Ala Thr Cys
    3680                 3685                 3690

Thr Gly  Cys Thr Gly Thr Ala  Gly Cys Ala Cys Cys  Ala Gly Ala
    3695                 3700                 3705

Ala Thr  Cys Thr Gly Cys Cys  Thr Gly Gly Gly Cys  Thr Gly Thr
    3710                 3715                 3720

Cys Thr  Gly Cys Thr Gly Gly  Ala Ala Cys Thr Gly  Thr Thr Cys
    3725                 3730                 3735

Cys Thr  Gly Ala Gly Cys Ala  Gly Ala Gly Cys Cys  Cys Thr Gly
    3740                 3745                 3750

Ala Gly  Ala Gly Cys Ala Cys  Thr Gly Cys Ala Cys  Gly Thr Gly
    3755                 3760                 3765

Cys Thr  Gly Thr Gly Gly Ala  Ala Cys Gly Gly Ala  Thr Thr Cys
    3770                 3775                 3780

Cys Ala  Gly Cys Thr Gly Cys  Ala Cys Thr Gly Cys  Cys Ala Gly
    3785                 3790                 3795

Ala Cys  Cys Gly Ala Gly Thr  Ala Cys Ala Ala Cys  Cys Ala Gly
    3800                 3805                 3810

Ala Ala  Ala Cys Thr Gly Cys  Ala Ala Gly Thr Gly  Ala Ala Cys
```

-continued 3815 3820 3825

Cys Ala Gly Thr Thr Cys Ala Gly Cys Gly Ala Gly Ala Gly Cys
3830 3835 3840

Ala Ala Gly Ala Gly Cys Cys Thr Gly Thr Ala Cys Cys Ala Cys
3845 3850 3855

Cys Gly Gly Gly Ala Ala Ala Ala Gly Cys Ala Gly Cys Thr Cys
3860 3865 3870

Ala Thr Thr Gly Cys Cys Ala Thr Gly Gly Ala Cys Ala Gly Cys
3875 3880 3885

Gly Cys Cys Ala Thr Cys Thr Gly Cys Gly Ala Ala Gly Ala Gly
3890 3895 3900

Ala Gly Ala Gly Gly Cys Gly Cys Cys Gly Cys Ala Gly Gly Ala
3905 3910 3915

Thr Cys Thr Cys Thr Gly Ala Thr Cys Thr Cys Cys Thr Gly Cys
3920 3925 3930

Gly Ala Ala Ala Cys Ala Ala Thr Gly Cys Cys Cys Gly Cys Cys
3935 3940 3945

Ala Thr Cys Cys Thr Gly Ala Ala Gly Cys Thr Gly Cys Ala Gly
3950 3955 3960

Ala Ala Gly Ala Ala Thr Thr Gly Cys Cys Thr Cys Cys Thr Ala
3965 3970 3975

Ala Gly Cys Cys Thr Gly Cys Gly Ala Ala Cys Cys Gly Cys Thr
3980 3985 3990

Cys Thr Gly Ala Cys Ala Cys Ala Cys Ala Ala Cys Cys Ala Gly
3995 4000 4005

Gly Ala Cys Thr Thr Cys Ala Gly Cys Ala Thr Cys Thr Ala Cys
4010 4015 4020

Ala Gly Ala Cys Thr Gly Thr Gly Thr Thr Gly Cys Ala Ala Gly
4025 4030 4035

Cys Gly Gly Gly Gly Cys Thr Cys Cys Cys Thr Gly Thr Gly Cys
4040 4045 4050

Cys Ala Thr Gly Cys Ala Ala Gly Cys Cys Ala Ala Gly Cys Thr
4055 4060 4065

Ala Gly Ala Ala Gly Cys Cys Cys Cys Gly Cys Cys Thr Thr Thr
4070 4075 4080

Cys Cys Thr Ala Ala Ala Cys Cys Thr Gly Thr Gly Cys Gly Ala
4085 4090 4095

Cys Cys Thr Cys Thr Gly Cys Cys Ala Gly Cys Thr Cys Cys Ala
4100 4105 4110

Ala Thr Cys Ala Cys Cys Ala Gly Ala Ala Thr Thr Ala Cys Cys
4115 4120 4125

Cys Cys Thr Cys Ala Gly Cys Thr Cys Gly Gly Cys Gly Gly Cys
4130 4135 4140

Cys Ala Gly Ala Gly Cys Gly Ala Thr Thr Cys Ala Thr Cys Thr
4145 4150 4155

Cys Ala Ala Cys Cys Thr Cys Thr Gly Cys Thr Gly Ala Cys Cys
4160 4165 4170

Ala Cys Cys Gly Gly Cys Ala Gly Ala Cys Cys Thr Cys Ala Ala
4175 4180 4185

Gly Gly Cys Thr Gly Gly Cys Ala Ala Gly Ala Cys Cys Ala Ala
4190 4195 4200

Gly Cys Thr Cys Thr Gly Ala Gly Ala Cys Ala Cys Ala Cys Cys
4205 4210 4215

Cys Ala Gly Cys Ala Gly Gly Cys Thr Ala Gly Cys Cys Cys Thr
4220 4225 4230

Gly Cys Cys Thr Cys Thr Thr Gly Thr Gly Cys Cys Ala Cys Cys
4235 4240 4245

Ala Thr Cys Ala Cys Ala Ala Thr Cys Cys Cys Cys Ala Thr Cys
4250 4255 4260

Cys Ala Cys Thr Cys Thr Gly Cys Cys Gly Cys Thr Cys Thr Gly
4265 4270 4275

Gly Gly Cys Gly Ala Thr Cys Ala Thr Thr Cys Thr Gly Gly Cys
4280 4285 4290

Gly Ala Thr Cys Cys Thr Gly Gly Ala Cys Cys Ala Gly Cys Cys
4295 4300 4305

Thr Gly Gly Gly Ala Cys Ala Cys Ala Thr Gly Thr Cys Cys Thr
4310 4315 4320

Cys Cys Ala Cys Thr Gly Cys Cys Ala Cys Thr Cys Ala Cys Ala
4325 4330 4335

Ala Cys Ala Cys Thr Gly Ala Thr Cys Cys Cys Thr Ala Gly Gly
4340 4345 4350

Gly Cys Thr Cys Cys Thr Cys Cys Ala Cys Cys Thr Thr Ala Cys
4355 4360 4365

Gly Gly Cys Gly Ala Thr Thr Cys Thr Ala Cys Cys Gly Cys Thr
4370 4375 4380

Ala Gly Ala Ala Gly Cys Thr Gly Gly Cys Cys Cys Ala Gly Cys
4385 4390 4395

Ala Gly Ala Thr Gly Thr Gly Gly Ala Cys Cys Ala Cys Thr Cys
4400 4405 4410

Gly Gly Ala Gly Gly Cys Ala Ala Cys Ala Cys Ala Ala Cys Cys
4415 4420 4425

Cys Thr Cys Cys Ala Gly Cys Ala Ala Cys Thr Gly Gly Gly Ala
4430 4435 4440

Gly Ala Ala Gly Cys Cys Thr Cys Thr Cys Ala Gly Gly Cys Thr
4445 4450 4455

Cys Cys Thr Ala Gly Cys Gly Gly Cys Thr Cys Thr Cys Thr Gly
4460 4465 4470

Ala Thr Cys Cys Cys Thr Cys Thr Cys Ala Gly Ala Cys Thr Gly
4475 4480 4485

Cys Cys Thr Cys Thr Cys Cys Thr Gly Thr Gly Gly Gly Ala Ala
4490 4495 4500

Gly Thr Thr Cys Gly Gly Gly Gly Cys Cys Ala Gly Cys Cys Thr
4505 4510 4515

Gly Ala Thr Thr Cys Thr Thr Thr Thr Gly Cys Cys Gly Cys Ala
4520 4525 4530

Cys Thr Gly Cys Ala Cys Ala Gly Cys Thr Cys Cys Cys Thr Gly
4535 4540 4545

Ala Ala Cys Gly Ala Gly Cys Thr Gly Gly Gly Ala Gly Ala Gly
4550 4555 4560

Ala Thr Cys Gly Cys Thr Ala Gly Ala Gly Ala Gly Cys Thr Gly
4565 4570 4575

Cys Ala Cys Cys Ala Gly Thr Thr Cys Gly Cys Cys Thr Thr Cys
4580 4585 4590

Gly Ala Cys Cys Thr Gly Cys Thr Gly Ala Thr Cys Ala Ala Gly
4595 4600 4605

Ala Gly Cys Cys Ala Cys Thr Thr Cys Gly Thr Gly Cys Ala Ala
4610 4615 4620

Gly Gly Cys Ala Ala Gly Gly Ala Thr Thr Gly Gly Gly Gly Cys
4625 4630 4635

Cys Thr Cys Ala Ala Ala Ala Ala Gly Thr Thr Thr Ala Thr Cys
4640 4645 4650

Cys Gly Cys Ala Gly Ala Gly Ala Cys Thr Thr Cys Thr Gly Gly
4655 4660 4665

Gly Gly Cys Ala Thr Gly Gly Ala Ala Cys Thr Gly Gly Cys Cys
4670 4675 4680

Gly Cys Cys Ala Gly Cys Ala Gly Ala Ala Gly Ala Thr Thr Cys
4685 4690 4695

Ala Gly Cys Thr Gly Gly Gly Ala Thr Cys Ala Thr Cys Ala Thr
4700 4705 4710

Ala Gly Cys Gly Cys Ala Gly Gly Cys Gly Gly Cys Cys Cys Ala
4715 4720 4725

Cys Cys Thr Ala Gly Ala Gly Thr Gly Cys Cys Ala Thr Cys Thr
4730 4735 4740

Gly Thr Thr Ala Gly Ala Ala Gly Cys Gly Gly Ala Gly Cys Thr
4745 4750 4755

Gly Cys Cys Cys Ala Gly Gly Thr Gly Cys Ala Gly Cys Cys Thr
4760 4765 4770

Ala Ala Ala Gly Ala Thr Cys Cys Thr Cys Thr Gly Cys Cys Ala
4775 4780 4785

Cys Thr Gly Ala Gly Ala Ala Cys Ala Cys Thr Gly Gly Cys Cys
4790 4795 4800

Gly Gly Cys Thr Gly Cys Cys Thr Thr Gly Cys Thr Ala Gly Ala
4805 4810 4815

Ala Cys Ala Gly Cys Cys Cys Ala Thr Cys Thr Thr Ala Gly Ala
4820 4825 4830

Cys Cys Thr Gly Gly Cys Gly Cys Cys Gly Ala Gly Thr Cys Thr
4835 4840 4845

Cys Thr Gly Cys Cys Thr Cys Ala Gly Cys Cys Ala Cys Ala Ala
4850 4855 4860

Cys Thr Gly Cys Ala Cys Thr Gly Thr Ala Cys Cys Cys Thr Gly
4865 4870 4875

Thr Gly Gly Thr Thr Cys Cys Ala Gly Thr Cys Cys Ala Gly Cys
4880 4885 4890

Gly Ala Gly Cys Thr Gly Thr Cys Thr Cys Cys Thr Ala Cys Thr
4895 4900 4905

Gly Gly Thr Gly Cys Cys Cys Cys Thr Thr Gly Gly Cys Cys Ala
4910 4915 4920

Thr Cys Thr Ala Gly Ala Cys Gly Cys Cys Cys Thr Ala Cys Thr
4925 4930 4935

Thr Gly Gly Ala Gly Ala Gly Gly Cys Ala Cys Cys Ala Cys Cys
4940 4945 4950

Gly Thr Gly Thr Cys Ala Cys Cys Ala Ala Gly Ala Ala Cys Cys
4955 4960 4965

Gly Cys Cys Ala Cys Ala Ala Gly Cys Ala Gly Cys Gly Cys Cys
4970 4975 4980

Ala Gly Ala Ala Cys Cys Thr Gly Thr Thr Gly Thr Gly Gly Cys
4985 4990 4995

Ala Cys Ala Ala Ala Gly Thr Gly Gly Cys Cys Cys Thr Cys Cys

-continued 5000 5005 5010

Ala Gly Cys Cys Ala Ala Gly Ala Ala Gly Cys Cys Gly Cys Thr
5015 5020 5025

Cys Thr Cys Gly Gly Ala Cys Thr Thr Gly Gly Ala Ala Gly Cys
5030 5035 5040

Gly Gly Ala Cys Thr Gly Cys Thr Gly Ala Gly Gly Thr Thr Cys
5045 5050 5055

Thr Cys Thr Thr Gly Thr Gly Gly Ala Ala Cys Cys Gly Cys Cys
5060 5065 5070

Gly Cys Cys Ala Thr Thr Cys Gly Gly Ala Ala Gly Ala Thr Gly
5075 5080 5085

Cys Ala Cys Thr Thr Thr Ala Gly Cys Cys Thr Gly Ala Ala Ala
5090 5095 5100

Gly Ala Ala Cys Ala Cys Cys Cys Thr Cys Cys Ala Cys Cys Ala
5105 5110 5115

Cys Cys Thr Thr Gly Thr Cys Cys Thr Cys Cys Ala Gly Ala Gly
5120 5125 5130

Gly Cys Thr Thr Thr Cys Cys Ala Ala Ala Gly Ala Gly Cys Thr
5135 5140 5145

Gly Cys Thr Gly Gly Cys Gly Ala Ala Gly Gly Cys Gly Gly Ala
5150 5155 5160

Cys Cys Thr Gly Gly Thr Ala Gly Ala Gly Gly Thr Gly Gly Thr
5165 5170 5175

Gly Cys Thr Ala Gly Ala Ala Gly Ala Gly Gly Thr Gly Cys Thr
5180 5185 5190

Ala Gly Gly Gly Thr Gly Cys Thr Gly Cys Ala Gly Ala Gly Cys
5195 5200 5205

Cys Cys Ala Thr Thr Cys Thr Gly Thr Ala Gly Ala Gly Cys Ala
5210 5215 5220

Gly Gly Cys Gly Cys Ala Gly Gly Cys Gly Ala Ala Thr Gly Gly
5225 5230 5235

Cys Thr Gly Gly Gly Cys Cys Ala Thr Cys Ala Gly Ala Gly Thr
5240 5245 5250

Cys Thr Gly Ala Gly Ala Cys Ala Thr Gly Thr Cys Gly Thr Cys
5255 5260 5265

Gly Gly Cys Thr Ala Cys Gly Gly Cys Cys Ala Cys Cys Thr Gly
5270 5275 5280

Gly Ala Thr Ala Cys Ala Ala Gly Cys Gly Gly Ala Ala Gly Cys
5285 5290 5295

Ala Gly Cys Thr Cys Thr Ala Gly Cys Thr Cys Cys Ala Gly Cys
5300 5305 5310

Thr Gly Gly Cys Cys Thr Ala Ala Cys Thr Cys Ala Ala Ala Ala
5315 5320 5325

Ala Thr Gly Gly Cys Thr Cys Thr Gly Ala Ala Cys Ala Gly Cys
5330 5335 5340

Cys Thr Gly Ala Ala Cys Thr Cys Cys Ala Thr Cys Gly Ala Cys
5345 5350 5355

Gly Ala Cys Gly Cys Cys Cys Ala Gly Cys Thr Gly Ala Cys Ala
5360 5365 5370

Ala Gly Ala Ala Thr Cys Gly Cys Cys Cys Cys Thr Cys Cys Thr
5375 5380 5385

Ala Gly Ala Thr Cys Thr Cys Ala Cys Thr Gly Cys Thr Gly Cys
5390 5395 5400

```
Thr Thr  Thr Thr Gly Gly Gly  Ala Ala Gly Thr Gly  Ala Ala Cys
    5405                 5410                 5415

Gly Cys  Cys Cys Cys Ala Ala  Gly Cys Cys Ala Thr  Cys Ala Cys
    5420                 5425                 5430

Cys Ala  Thr Cys Ala Cys Cys  Ala Cys Cys Ala Thr  Thr Ala Gly
    5435                 5440                 5445

Thr Ala  Ala Ala Gly Gly Cys  Gly Cys Gly Cys Cys  Thr Ala Gly
    5450                 5455                 5460

Cys Gly  Gly Cys Cys Gly Cys  Gly Ala Thr Cys Thr  Gly Cys Thr
    5465                 5470                 5475

Gly Thr  Gly Cys Cys Thr Thr  Cys Thr Ala Gly Thr  Thr Gly Cys
    5480                 5485                 5490

Cys Ala  Gly Cys Cys Ala Thr  Cys Thr Gly Thr Thr  Gly Thr Thr
    5495                 5500                 5505

Thr Gly  Cys Cys Cys Cys Thr  Cys Cys Cys Cys Cys  Gly Thr Gly
    5510                 5515                 5520

Cys Cys  Thr Thr Cys Cys Thr  Thr Gly Ala Cys Cys  Cys Thr Gly
    5525                 5530                 5535

Gly Ala  Ala Gly Gly Thr Gly  Cys Cys Ala Cys Thr  Cys Cys Cys
    5540                 5545                 5550

Ala Cys  Thr Gly Thr Cys Cys  Thr Thr Thr Cys Cys  Thr Ala Ala
    5555                 5560                 5565

Thr Ala  Ala Ala Ala Thr Gly  Ala Gly Gly Ala Ala  Ala Thr Thr
    5570                 5575                 5580

Gly Cys  Ala Thr Cys Gly Cys  Ala Thr Thr Gly Thr  Cys Thr Gly
    5585                 5590                 5595

Ala Gly  Thr Ala Gly Gly Thr  Gly Thr Cys Ala Thr  Thr Cys Thr
    5600                 5605                 5610

Ala Thr  Thr Cys Thr Gly Gly  Gly Gly Gly Gly Thr  Gly Gly Gly
    5615                 5620                 5625

Gly Thr  Gly Gly Gly Gly Cys  Ala Gly Gly Ala Cys  Ala Gly Cys
    5630                 5635                 5640

Ala Ala  Gly Gly Gly Gly Gly  Ala Gly Gly Ala Thr  Thr Gly Gly
    5645                 5650                 5655

Gly Ala  Ala Gly Ala Cys Ala  Ala Thr Ala Gly Cys  Ala Gly Gly
    5660                 5665                 5670

Cys Ala  Thr Gly Cys Thr Gly  Gly Gly Gly Ala Thr  Gly Cys Gly
    5675                 5680                 5685

Gly Thr  Gly Gly Gly Cys Thr  Cys Thr Ala Thr Gly  Gly Cys Cys
    5690                 5695                 5700
```

```
<210> SEQ ID NO 552
<211> LENGTH: 1507
<212> TYPE: PRT
<213> ORGANISM: Artificial seqeunce
<220> FEATURE:
<223> OTHER INFORMATION: Heterologous polypeptide

<400> SEQUENCE: 552

Met Gly Gln Lys Glu Gln Ile His Thr Leu Gln Lys Asn Ser Glu Arg
1               5                   10                  15

Met Ser Lys Gln Leu Thr Arg Ser Ser Gln Ala Val Gln Asn Leu Gln
            20                  25                  30

Asn Gly Gly Gly Ser Arg Ser Ser Ala Thr Leu Pro Gly Arg Arg Arg
        35                  40                  45
```

```
Arg Arg Trp Leu Arg Arg Arg Arg Gln Pro Ile Ser Val Ala Pro Ala
    50                  55                  60

Gly Pro Pro Arg Arg Pro Asn Gln Lys Pro Asn Pro Pro Gly Gly Ala
65                  70                  75                  80

Arg Cys Val Ile Met Arg Pro Thr Trp Pro Gly Thr Ser Ala Phe Thr
                85                  90                  95

Gly Met Glu Cys Thr Leu Gly Gln Val Gly Ala Pro Ser Pro Arg Arg
            100                 105                 110

Glu Glu Asp Gly Trp Arg Gly Gly His Ser Arg Phe Lys Ala Asp Val
        115                 120                 125

Pro Ala Pro Gln Gly Pro Cys Trp Gly Gly Gln Pro Gly Ser Ala Pro
    130                 135                 140

Ser Ser Ala Pro Pro Glu Gln Ser Leu Leu Asp Asp Tyr Trp Ala Gln
145                 150                 155                 160

Lys Glu Lys Ile Ser Ile Pro Arg Thr His Leu Cys Trp Lys Phe Glu
                165                 170                 175

Met Ser Tyr Thr Val Gly Gly Pro Pro Pro His Val His Ala Arg Pro
            180                 185                 190

Arg His Trp Lys Thr Asp Arg Asp Tyr Trp Ala Gln Lys Glu Lys Gly
        195                 200                 205

Ser Ser Ser Phe Leu Arg Pro Ser Cys Val Pro Phe Arg Glu Leu Lys
    210                 215                 220

Asn Val Ser Val Leu Glu Gly Leu Arg Gln Gly Arg Leu Gly Gly Pro
225                 230                 235                 240

Cys Ser Cys His Cys Pro Arg Pro Ser Gln Ala Arg Leu Thr Pro Val
                245                 250                 255

Asp Val Ala Gly Pro Phe Leu Cys Leu Gly Asp Pro Gly Leu Phe Pro
            260                 265                 270

Pro Val Lys Ser Ser Ile Thr Glu Ile Ser Cys Cys Thr Leu Ser Ser
        275                 280                 285

Glu Glu Asn Glu Tyr Leu Pro Arg Pro Glu Trp Gln Leu Gln Tyr Glu
    290                 295                 300

Ala Gly Met Thr Leu Gly Gly Lys Ile Leu Phe Phe Leu Phe Leu Leu
305                 310                 315                 320

Leu Pro Leu Ser Pro Phe Ser Leu Ile Phe Leu Val Leu Gly Val Leu
                325                 330                 335

Ser Gly His Ser Gly Ser Arg Leu Lys Arg Ser Phe Ala Val Thr Glu
            340                 345                 350

Arg Ile Ile Thr Gly Gly Lys Ser Thr Cys Ser Ala Pro Gly Pro Gln
        355                 360                 365

Ser Leu Pro Ser Thr Pro Phe Ser Thr Tyr Pro Gln Trp Val Ile Leu
    370                 375                 380

Ile Thr Glu Leu Asp Gly His Ser Tyr Thr Ser Lys Val Asn Cys Leu
385                 390                 395                 400

Leu Leu Gln Asp Gly Phe His Gly Cys Val Ser Ile Thr Gly Ala Ala
                405                 410                 415

Gly Arg Arg Asn Leu Ser Ile Phe Leu Phe Leu Met Leu Cys Lys Leu
            420                 425                 430

Glu Phe His Ala Cys Gln Trp Gln His Tyr His Arg Ser Gly Glu Ala
        435                 440                 445

Ala Gly Thr Pro Leu Trp Arg Pro Thr Arg Asn Val Ala Met Met Val
    450                 455                 460
```

Pro Asp Arg Gln Val His Tyr Asp Phe Gly Leu Lys Ile Gln Asn Lys
465 470 475 480

Asn Cys Pro Asp Val Leu Arg Phe Leu Asp Leu Lys Val Arg Tyr Leu
485 490 495

His Ser Val Pro Phe Arg Glu Leu Lys Asn Gln Arg Thr Ala Gln Gly
500 505 510

Ala Pro Gly Ile His His Ala Ala Ser Pro Val Ala Ala Asn Leu Cys
515 520 525

Asp Pro Ala Arg His Ala Gln His Thr Arg Ile Pro Cys Gly Ala Gly
530 535 540

Gln Val Arg Ala Gly Arg Gly Pro Glu Ala Gly Gly Gly Val Leu Gln
545 550 555 560

Pro Gln Arg Pro Ala Pro Glu Lys Pro Gly Cys Pro Cys Arg Arg Gly
565 570 575

Gln Pro Arg Leu His Thr Val Lys Met Trp Arg Ala Cys His Leu Phe
580 585 590

Leu Gln Pro Gln Val Gly Thr Pro Pro Pro His Thr Ala Ser Ala Arg
595 600 605

Ala Pro Ser Gly Pro Pro His Pro His Glu Ser Cys Pro Ala Gly Arg
610 615 620

Arg Pro Ala Arg Ala Ala Gln Thr Cys Ala Arg Arg Gln His Gly Leu
625 630 635 640

Pro Gly Cys Glu Glu Ala Gly Thr Ala Arg Val Pro Ser Leu His Leu
645 650 655

His Leu His Gln Ala Ala Leu Gly Ala Gly Arg Gly Arg Gly Trp Gly
660 665 670

Glu Ala Cys Ala Gln Val Pro Pro Ser Arg Gly His Tyr Lys Leu Ile
675 680 685

Gln Gln Pro Ile Ser Leu Phe Ser Ile Thr Asp Arg Leu His Lys Thr
690 695 700

Phe Ser Gln Leu Pro Ser Val His Leu Cys Ser Ile Thr Phe Gln Trp
705 710 715 720

Gly His Pro Pro Ile Phe Cys Ser Thr Asn Asp Ile Cys Val Thr Ala
725 730 735

Asn Phe Cys Ile Ser Val Thr Phe Leu Lys Pro Cys Phe Leu Leu His
740 745 750

Glu Ala Ser Ala Ser Gln Phe Lys Lys Phe Asp Gly Pro Cys Gly Glu
755 760 765

Arg Gly Gly Gly Arg Thr Ala Arg Ala Leu Trp Ala Arg Gly Asp Ser
770 775 780

Val Leu Thr Pro Ala Leu Asp Pro Gln Thr Pro Val Arg Ala Pro Ser
785 790 795 800

Leu Thr Arg Ala Ala Ala Ala Val Gly Val Pro Gly Asp Ser Thr Arg
805 810 815

Arg Ala Val Arg Arg Met Asn Thr Phe Cys Gly Ala Ser Ala Cys Asp
820 825 830

Val Ser Leu Ile Ala Met Asp Ser Ala Cys Glu Glu Arg Gly Ala Ala
835 840 845

Gly Ser Leu Ile Ser Cys Glu Ser Leu Tyr His Arg Glu Lys Gln Leu
850 855 860

Ile Ala Met Asp Ser Ala Ile Phe Val Gln Gly Lys Asp Trp Gly Val
865 870 875 880

Lys Lys Phe Ile Arg Arg Asp Phe Thr Met Pro Ala Ile Leu Lys Leu

-continued

```
                885                 890                 895

Gln Lys Asn Cys Leu Leu Ser Leu Asn Ser Lys Met Ala Leu Asn Ser
            900                 905                 910

Glu Ala Leu Ser Val Val Ser Glu Tyr Glu Ala Gly Met Thr Leu Gly
        915                 920                 925

Glu Lys Phe Arg Val Gly Asn Cys Lys His Leu Lys Met Thr Arg Pro
    930                 935                 940

Thr Glu Tyr Asn Gln Lys Leu Gln Val Asn Gln Phe Ser Glu Ser Lys
945                 950                 955                 960

Arg Thr Ala Leu Thr His Asn Gln Asp Phe Ser Ile Tyr Arg Leu Cys
                965                 970                 975

Cys Lys Arg Gly Ser Leu Cys His Ala Ser Gln Ala Arg Ser Pro Ala
            980                 985                 990

Phe Pro Lys Pro Val Arg Pro Leu  Pro Ala Pro Ile Thr  Arg Ile Thr
        995                 1000                1005

Pro Gln  Leu Gly Gly Gln Ser  Asp Ser Ser Gln Pro  Leu Leu Thr
    1010                1015                1020

Thr Gly  Arg Pro Gln Gly Trp  Gln Asp Gln Ala Leu  Arg His Thr
    1025                1030                1035

Gln Gln  Ala Ser Pro Ala Ser  Cys Ala Thr Ile Thr  Ile Pro Ile
    1040                1045                1050

His Ser  Ala Ala Leu Gly Asp  His Ser Gly Asp Pro  Gly Pro Ala
    1055                1060                1065

Trp Asp  Thr Cys Pro Pro Leu  Pro Leu Thr Thr Leu  Ile Pro Arg
    1070                1075                1080

Ala Pro  Pro Pro Tyr Gly Asp  Ser Thr Ala Arg Ser  Trp Pro Ser
    1085                1090                1095

Arg Cys  Gly Pro Leu Gly Tyr  Ala Tyr Lys Asp Phe  Leu Trp Cys
    1100                1105                1110

Phe Pro  Phe Ser Leu Val Phe  Leu Gln Glu Ile Gln  Ile Cys Cys
    1115                1120                1125

His Val  Ser Cys Leu Cys Cys  Ile Cys Cys Ser Thr  Arg Ile Cys
    1130                1135                1140

Leu Gly  Cys Leu Leu Glu Leu  Phe Leu Ser Arg Ala  Leu Arg Ala
    1145                1150                1155

Leu His  Val Leu Trp Asn Gly  Phe Gln Leu His Cys  Gln Gly Asn
    1160                1165                1170

Thr Thr  Leu Gln Gln Leu Gly  Glu Ala Ser Gln Ala  Pro Ser Gly
    1175                1180                1185

Ser Leu  Ile Pro Leu Arg Leu  Pro Leu Leu Trp Glu  Val Arg Gly
    1190                1195                1200

Asn Ser  Lys Met Ala Leu Asn  Ser Leu Asn Ser Ile  Asp Asp Ala
    1205                1210                1215

Gln Leu  Thr Arg Ile Ala Pro  Pro Arg Ser His Cys  Cys Phe Trp
    1220                1225                1230

Glu Val  Asn Ala Pro Phe Val  Gln Gly Lys Asp Trp  Gly Leu Lys
    1235                1240                1245

Lys Phe  Ile Arg Arg Asp Phe  Glu Ala Phe Gln Arg  Ala Ala Gly
    1250                1255                1260

Glu Gly  Gly Pro Gly Arg Gly  Gly Ala Arg Arg Gly  Ala Arg Val
    1265                1270                1275

Leu Gln  Ser Pro Phe Cys Arg  Ala Gly Ala Gly Glu  Trp Leu Gly
    1280                1285                1290
```

```
His Gln  Ser Leu Arg Trp Gly  Met Glu Leu Ala Ala  Ser Arg Arg
    1295                 1300                 1305

Phe Ser  Trp Asp His His Ser  Ala Gly Gly Pro Pro  Arg Val Pro
    1310                 1315                 1320

Ser Val  Arg Ser Gly Ala Ala  Gln Val Gln Pro Lys  Asp Pro Leu
    1325                 1330                 1335

Pro Leu  Arg Thr Leu Ala Gly  Cys Leu Ala Arg Thr  Ala His Leu
    1340                 1345                 1350

Arg Pro  Gly Ala Glu Ser Leu  Pro Gln Pro Gln Leu  His Cys Thr
    1355                 1360                 1365

Ile Ala  Arg Glu Leu His Gln  Phe Ala Phe Asp Leu  Leu Ile Lys
    1370                 1375                 1380

Ser His  Lys Met His Phe Ser  Leu Lys Glu His Pro  Pro Pro Pro
    1385                 1390                 1395

Cys Pro  Pro His Val Val Gly  Tyr Gly His Leu Asp  Thr Ser Gly
    1400                 1405                 1410

Ser Ser  Ser Ser Ser Ser Trp  Pro Gln Pro Asp Ser  Phe Ala Ala
    1415                 1420                 1425

Leu His  Ser Ser Leu Asn Glu  Leu Gly Glu Leu Trp  Phe Gln Ser
    1430                 1435                 1440

Ser Glu  Leu Ser Pro Thr Gly  Ala Pro Trp Pro Ser  Arg Arg Pro
    1445                 1450                 1455

Thr Trp  Arg Gly Thr Thr Val  Ser Pro Arg Thr Ala  Thr Ser Ser
    1460                 1465                 1470

Ala Arg  Thr Cys Cys Gly Thr  Lys Trp Pro Ser Ser  Gln Glu Ala
    1475                 1480                 1485

Ala Leu  Gly Leu Gly Ser Gly  Leu Leu Arg Phe Ser  Cys Gly Thr
    1490                 1495                 1500

Ala Ala  Ile Arg
    1505
```

<210> SEQ ID NO 553
<211> LENGTH: 4722
<212> TYPE: DNA
<213> ORGANISM: Artificial seqeunce
<220> FEATURE:
<223> OTHER INFORMATION: Heterologous polynucleotide

<400> SEQUENCE: 553

```
gatcactaat tccaaaccca cccgcttttt atagtaagtt tttcacccat aaataataaa     60

tacaataatt aatttctcgt aaaagtagaa aatatattct aatttattgc acggtaagga    120

agtagaatca taaagaacag tgacggatcc cgcgacttcg ccgccatggg ccagaaagag    180

cagatccaca cactgcagaa aaacagcgag cggatgagca agcagctgac cagatcttct    240

caggccgtgc agaacctgca gaacggcgga ggctctagaa gctctgctac acttcctggc    300

aggcggcgga gaagatggct gagaagaagg cggcagccta tctctgtggc tcctgctgga    360

cctcctagac ggcccaacca gaagcctaat cctcctggcg gagccagatg cgtgatcatg    420

aggcctacat ggcctggcac cagcgccttt accggcatgg aatgtacact gggccaagtg    480

ggagccccat ctcctagaag agaagaggat ggctggcgcg gaggccactc tagattcaaa    540

gctgatgtgc ccgctcctca gggcccttgt tggggaggac aacctggatc tgccccatct    600

tctgccccac ctgaacagag cctgctggat gactattggg ctcaaaaaga gaagatcagc    660

atccccagaa cacacctgtg ctggaagttc gagatgagct acaccgttgg cggccctcca    720
```

-continued

```
ccacatgttc acgccagacc tagacactgg aaaaccgaca gagattattg ggcccagaaa    780
gaaaagggca gcagcagctt cctgcggcct agctgtgtgc ccttccggga actgaagaac    840
gtgtccgttc tggaaggcct gaggcagggc agacttggcg gaccttgtag ctgccactgt    900
cctagaccaa gccaggccag actgacccct gtggatgtgg ctggcccatt tctgtgtctg    960
ggcgaccctg gactgttccc tccagtgaag tctagcatca ccgagatcag ctgctgcacc   1020
ctgagcagcg aggaaaacga gtacctgcct agacctgaat ggcagctgca gtacgaggcc   1080
ggcatgacac tcggaggcaa gatcctgttc ttcctgttcc tgctgctccc tctgagcccc   1140
ttcagcctga tctttctggt gctgggcgtg ctgtctggcc actctggaag cagactgaag   1200
agaagcttcg ccgtgaccga gcggatcatc acaggcggca agagcacatg ttctgcccct   1260
ggacctcagt ctctgcccag cacacccttc agcacatacc ctcagtgggt catcctgatc   1320
accgagctgg atggccacag ctacaccagc aaagtgaact gcctcctgct gcaggatggc   1380
ttccacggct gtgtgtctat tactggcgcc gctggcagac ggaacctgag catctttctg   1440
tttctgatgc tgtgcaagct cgagttccac gcctgccaat ggcagcacta ccacagatct   1500
ggcgaagccg ctggaacccc actttggagg cctaccagaa acgtggccat gatggtgccc   1560
gacagacagg tgcactacga cttcggcctg aagatccaga acaagaactg ccccgacgtg   1620
ctgcggttcc tggatctcaa agtgcgctac ctgcacagcg tgcccttcag agagctgaaa   1680
aaccagagaa cagcccaggg cgctcctgga atccatcatg ctgcttctcc agtggccgcc   1740
aatctgtgcg atcctgccag acatgcccag cataccagga ttccttgtgg cgctggacaa   1800
gtgcgcgctg gaagaggacc tgaagctggt ggcggagttc tgcagcctca aagacctgct   1860
cctgagaagc ctggctgccc ctgtagaaga ggacagccta gactgcacac cgtgaagatg   1920
tggcgggcct gccacttgtt tctccagcca caagtgggca cccctccacc tcatacagcc   1980
tctgctagag cacctagcgg cccacctcat cctcacgaat cttgtcctgc cggaagaagg   2040
cctgccagag ccgctcaaac atgtgccaga cgacagcacg gactgcccgg atgtgaagaa   2100
gccggaacag ccagagtgcc tagcctgcac cttcatctgc atcaggccgc tcttggagcc   2160
ggaagaggta gaggatgggg agaagcttgt gcccaggtgc caccttctag aggccactac   2220
aagctgatcc agcagccaat cagcctgttc tccatcaccg accggctgca caagacattc   2280
agccagctgc cttccgtgca tctgtgcagc atcaccttcc agtggggaca ccctcctatc   2340
ttttgctcca ccaacgacat ctgcgtgacc gccaacttct gtatcagcgt gaccttcctg   2400
aagccttgct ttctgctgca cgaggcctcc gccagccagt ttaagaagtt tgacggcccc   2460
tgcggcgaga gaggcggagg aagaactgca agagcccttt gggccagagg cgactctgtt   2520
ctgacaccag ctctggaccc tcagacacct gttagggccc ctagcctgac aagagctgcc   2580
gctgctgttg gagtgcctgg cgattctact agaagggccg tgcggcggat gaacaccttt   2640
tgtggcgcat ctgcctgcga cgtgtccctg atcgctatgg atagcgcctg cgaggaaaga   2700
ggcgcagccg gatctctgat ctcttgcgag agcctgtacc accgggaaaa gcagctcatt   2760
gccatggaca gcgccatctt cgtgcagggc aaagactggg gcgtgaagaa gttcatccgg   2820
cgggacttta ccatgcctgc cattctgaag ctgcagaaga attgtcttct aagcctgaac   2880
agcaagatgg ccctgaatag cgaggccctg tctgtggtgt ccgagtatga ggctggaatg   2940
accctgggcg agaagttcag agtgggcaac tgcaagcacc tgaagatgac ccggcctacc   3000
gagtacaacc agaaactgca agtgaaccag ttcagcgaga gcaagcggac cgctctgacc   3060
```

-continued

```
cacaaccagg acttcagcat ctaccggctg tgctgcaaga ggggctctct gtgtcatgct   3120

agccaggcta gaagccccgc ctttcctaag cctgtcagac ctctgcctgc tcctatcacc   3180

agaatcaccc ctcagctcgg cggccagtct gattcatctc agccactgct gaccaccggc   3240

agacctcaag gatggcaaga ccaggctctg agacacacac agcaggctag cccagcctct   3300

tgcgccacca tcacaatacc aatacattct gccgctctgg gcgatcacag cggagatcct   3360

ggacctgcct gggatacttg tcctcctctg cccctaacta cactgatccc tagggctcct   3420

ccaccttacg gcgatagcac agccagatcc tggcctagca gatgtggccc tctgggctac   3480

gcctacaagg acttcctgtg gtgcttcccc ttctctctgg tgttcctgca agaaatccag   3540

atctgctgtc acgtgtcctg cctgtgctgt atctgctgta gcacccggat ctgtctgggc   3600

tgtctgctgg aactgttcct gagcagagcc ctgagagcac tgcacgtgct gtggaacgga   3660

ttccagctgc actgccaggg caacaccaca ctgcaacagc tgggagaagc ctctcaggcc   3720

ccaagcggtt ctctgatccc tctcagactg cccctcctgt gggaagtgcg gggcaattct   3780

aagatggctc tcaacagcct gaactccatc gacgacgccc agctgacaag aatcgcccct   3840

ccaagaagcc actgttgctt ttgggaagtg aacgcccctt ttgtgcaggg taaagattgg   3900

ggcctcaaaa agtttatcag acgggacttc gaggctttcc agagagcagc tggcgaaggc   3960

ggacctggca gaggtggtgc tagaagaggt gctagagtgc tgcagagccc attctgtaga   4020

gctggcgctg gcgaatggct gggccaccaa tctcttagat ggggaatgga actggccgct   4080

agcaggcggt ttagctggga tcatcattct gccggcggac ctccaagagt gccaagcgtt   4140

agaagcggag cagcccaggt ccagcctaaa gatccactgc cactgagaac actggccggc   4200

tgccttgcca gaacagctca tcttagacct ggcgccgaaa gcctgcctca acctcagctg   4260

cattgcacaa tcgccagaga actgcaccag ttcgccttcg acctgctgat caagagccac   4320

aagatgcact tctcactgaa agagcacccg ccaccgccgt gcccaccgca cgttgtcggc   4380

tatggccacc tggatacaag cggctcctct agcagtagct cctggcctca gcctgacagc   4440

tttgctgccc tgcatagctc cctgaatgag ctgggcgaac tgtggttcca gtccagcgaa   4500

ctgtctccta ctggcgctcc atggccaagc agaaggccta cttggagagg caccaccgtg   4560

tctccaagaa ccgctacaag cagcgccaga acctgttgcg gcacaaaatg gccctccagc   4620

caagaagctg ccctcggact tggaagcgga ctgctgagat tcagctgtgg cacagccgcc   4680

atcagaagcc atcaccatca ccaccattag taaaggcgcg cc                      4722
```

<210> SEQ ID NO 554
<211> LENGTH: 1507
<212> TYPE: PRT
<213> ORGANISM: Artificial seqeunce
<220> FEATURE:
<223> OTHER INFORMATION: Heterologous polypeptide

<400> SEQUENCE: 554

```
Met Gly Gln Lys Glu Gln Ile His Thr Leu Gln Lys Asn Ser Glu Arg
1               5                   10                  15

Met Ser Lys Gln Leu Thr Arg Ser Ser Gln Ala Val Gln Asn Leu Gln
            20                  25                  30

Asn Gly Gly Gly Ser Arg Ser Ser Ala Thr Leu Pro Gly Arg Arg Arg
        35                  40                  45

Arg Arg Trp Leu Arg Arg Arg Arg Gln Pro Ile Ser Val Ala Pro Ala
    50                  55                  60

Gly Pro Pro Arg Arg Pro Asn Gln Lys Pro Asn Pro Pro Gly Gly Ala
```

```
65                  70                  75                  80

Arg Cys Val Ile Met Arg Pro Thr Trp Pro Gly Thr Ser Ala Phe Thr
                85                  90                  95

Lys Arg Ser Phe Ala Val Thr Glu Arg Ile Ile Leu Val Leu Gly Val
            100                 105                 110

Leu Ser Gly His Ser Gly Ser Arg Leu Tyr Glu Ala Gly Met Thr Leu
        115                 120                 125

Gly Gly Lys Ile Leu Phe Phe Leu Phe Leu Leu Leu Pro Leu Ser Pro
    130                 135                 140

Phe Ser Leu Ile Phe Thr Glu Ile Ser Cys Cys Thr Leu Ser Ser Glu
145                 150                 155                 160

Glu Asn Glu Tyr Leu Pro Arg Pro Glu Trp Gln Leu Gln Val Pro Phe
                165                 170                 175

Arg Glu Leu Lys Asn Val Ser Val Leu Glu Gly Leu Arg Gln Gly Arg
            180                 185                 190

Leu Gly Gly Pro Cys Ser Cys His Cys Pro Arg Pro Ser Gln Ala Arg
        195                 200                 205

Leu Thr Pro Val Asp Val Ala Gly Pro Phe Leu Cys Leu Gly Asp Pro
    210                 215                 220

Gly Leu Phe Pro Pro Val Lys Ser Ser Ile Thr Gly Gly Lys Ser Thr
225                 230                 235                 240

Cys Ser Ala Pro Gly Pro Gln Ser Leu Pro Ser Thr Pro Phe Ser Thr
                245                 250                 255

Tyr Pro Gln Trp Val Ile Leu Ile Thr Glu Leu Gly Met Glu Cys Thr
            260                 265                 270

Leu Gly Gln Val Gly Ala Pro Ser Pro Arg Arg Glu Glu Asp Gly Trp
        275                 280                 285

Arg Gly Gly His Ser Arg Phe Lys Ala Asp Val Pro Ala Pro Gln Gly
    290                 295                 300

Pro Cys Trp Gly Gly Gln Pro Gly Ser Ala Pro Ser Ser Ala Pro Pro
305                 310                 315                 320

Glu Gln Ser Leu Leu Asp Asp Tyr Trp Ala Gln Lys Glu Lys Gly Ser
                325                 330                 335

Ser Ser Phe Leu Arg Pro Ser Cys Asp Tyr Trp Ala Gln Lys Glu Lys
            340                 345                 350

Ile Ser Ile Pro Arg Thr His Leu Cys Trp Lys Phe Glu Met Ser Tyr
        355                 360                 365

Thr Val Gly Gly Pro Pro Pro His Val His Ala Arg Pro Arg His Trp
    370                 375                 380

Lys Thr Asp Arg Gly Val Pro Gly Asp Ser Thr Arg Arg Ala Val Arg
385                 390                 395                 400

Arg Met Asn Thr Phe Tyr Glu Ala Gly Met Thr Leu Gly Glu Lys Phe
                405                 410                 415

Arg Val Gly Asn Cys Lys His Leu Lys Met Thr Arg Pro Asn Ser Lys
            420                 425                 430

Met Ala Leu Asn Ser Glu Ala Leu Ser Val Val Ser Glu Cys Gly Ala
        435                 440                 445

Ser Ala Cys Asp Val Ser Leu Ile Ala Met Asp Ser Ala Phe Val Gln
    450                 455                 460

Gly Lys Asp Trp Gly Val Lys Lys Phe Ile Arg Arg Asp Phe Tyr Ala
465                 470                 475                 480

Tyr Lys Asp Phe Leu Trp Cys Phe Pro Phe Ser Leu Val Phe Leu Gln
                485                 490                 495
```

```
Glu Ile Gln Ile Cys Cys His Val Ser Cys Leu Cys Cys Ile Cys Cys
            500                 505                 510

Ser Thr Arg Ile Cys Leu Gly Cys Leu Leu Glu Leu Phe Leu Ser Arg
        515                 520                 525

Ala Leu Arg Ala Leu His Val Leu Trp Asn Gly Phe Gln Leu His Cys
    530                 535                 540

Gln Thr Glu Tyr Asn Gln Lys Leu Gln Val Asn Gln Phe Ser Glu Ser
545                 550                 555                 560

Lys Ser Leu Tyr His Arg Glu Lys Gln Leu Ile Ala Met Asp Ser Ala
                565                 570                 575

Ile Cys Glu Glu Arg Gly Ala Ala Gly Ser Leu Ile Ser Cys Glu Thr
            580                 585                 590

Met Pro Ala Ile Leu Lys Leu Gln Lys Asn Cys Leu Leu Ser Leu Arg
        595                 600                 605

Thr Ala Leu Thr His Asn Gln Asp Phe Ser Ile Tyr Arg Leu Cys Cys
    610                 615                 620

Lys Arg Gly Ser Leu Cys His Ala Ser Gln Ala Arg Ser Pro Ala Phe
625                 630                 635                 640

Pro Lys Pro Val Arg Pro Leu Pro Ala Pro Ile Thr Arg Ile Thr Pro
                645                 650                 655

Gln Leu Gly Gly Gln Ser Asp Ser Ser Gln Pro Leu Leu Thr Thr Gly
            660                 665                 670

Arg Pro Gln Gly Trp Gln Asp Gln Ala Leu Arg His Thr Gln Gln Ala
        675                 680                 685

Ser Pro Ala Ser Cys Ala Thr Ile Thr Ile Pro Ile His Ser Ala Ala
    690                 695                 700

Leu Gly Asp His Ser Gly Asp Pro Gly Pro Ala Trp Asp Thr Cys Pro
705                 710                 715                 720

Pro Leu Pro Leu Thr Thr Leu Ile Pro Arg Ala Pro Pro Pro Tyr Gly
                725                 730                 735

Asp Ser Thr Ala Arg Ser Trp Pro Ser Arg Cys Gly Pro Leu Gly Asp
            740                 745                 750

Gly His Ser Tyr Thr Ser Lys Val Asn Cys Leu Leu Leu Gln Asp Gly
        755                 760                 765

Phe His Gly Cys Val Ser Ile Thr Gly Ala Ala Gly Arg Arg Asn Leu
    770                 775                 780

Ser Ile Phe Leu Phe Leu Met Leu Cys Lys Leu Glu Phe His Ala Cys
785                 790                 795                 800

Lys Ile Gln Asn Lys Asn Cys Pro Asp Phe Lys Lys Phe Asp Gly Pro
                805                 810                 815

Cys Gly Glu Arg Gly Gly Gly Arg Thr Ala Arg Ala Leu Trp Ala Arg
            820                 825                 830

Gly Asp Ser Val Leu Thr Pro Ala Leu Asp Pro Gln Thr Pro Val Arg
        835                 840                 845

Ala Pro Ser Leu Thr Arg Ala Ala Ala Ala Val His Tyr Lys Leu Ile
    850                 855                 860

Gln Gln Pro Ile Ser Leu Phe Ser Ile Thr Asp Arg Leu His Lys Thr
865                 870                 875                 880

Phe Ser Gln Leu Pro Ser Val His Leu Cys Ser Ile Thr Phe Gln Trp
                885                 890                 895

Gly His Pro Pro Ile Phe Cys Ser Thr Asn Asp Ile Cys Val Thr Ala
            900                 905                 910
```

-continued

```
Asn Phe Cys Ile Ser Val Thr Phe Leu Lys Pro Cys Phe Leu Leu His
        915                 920                 925

Glu Ala Ser Ala Ser Gln Cys His Leu Phe Leu Gln Pro Gln Val Gly
    930                 935                 940

Thr Pro Pro Pro His Thr Ala Ser Ala Arg Ala Pro Ser Gly Pro Pro
945                 950                 955                 960

His Pro His Glu Ser Cys Pro Ala Gly Arg Arg Pro Ala Arg Ala Ala
                965                 970                 975

Gln Thr Cys Ala Arg Arg Gln His Gly Leu Pro Gly Cys Glu Glu Ala
            980                 985                 990

Gly Thr Ala Arg Val Pro Ser Leu  His Leu His Leu His  Gln Ala Ala
        995                 1000                 1005

Leu Gly  Ala Gly Arg Gly Arg  Gly Trp Gly Glu Ala  Cys Ala Gln
    1010                 1015                 1020

Val Pro  Pro Ser Arg Gly Val  Leu Arg Phe Leu Asp  Leu Lys Val
    1025                 1030                 1035

Arg Tyr  Leu His Ser Gln Trp  Gln His Tyr His Arg  Ser Gly Glu
    1040                 1045                 1050

Ala Ala  Gly Thr Pro Leu Trp  Arg Pro Thr Arg Asn  Val Pro Phe
    1055                 1060                 1065

Arg Glu  Leu Lys Asn Gln Arg  Thr Ala Gln Gly Ala  Pro Gly Ile
    1070                 1075                 1080

His His  Ala Ala Ser Pro Val  Ala Ala Asn Leu Cys  Asp Pro Ala
    1085                 1090                 1095

Arg His  Ala Gln His Thr Arg  Ile Pro Cys Gly Ala  Gly Gln Val
    1100                 1105                 1110

Arg Ala  Gly Arg Gly Pro Glu  Ala Gly Gly Gly Val  Leu Gln Pro
    1115                 1120                 1125

Gln Arg  Pro Ala Pro Glu Lys  Pro Gly Cys Pro Cys  Arg Arg Gly
    1130                 1135                 1140

Gln Pro  Arg Leu His Thr Val  Lys Met Trp Arg Ala  Val Ala Met
    1145                 1150                 1155

Met Val  Pro Asp Arg Gln Val  His Tyr Asp Phe Gly  Leu Gly Asn
    1160                 1165                 1170

Thr Thr  Leu Gln Gln Leu Gly  Glu Ala Ser Gln Ala  Pro Ser Gly
    1175                 1180                 1185

Ser Leu  Ile Pro Leu Arg Leu  Pro Leu Leu Trp Glu  Val Arg Gly
    1190                 1195                 1200

Gln Pro  Asp Ser Phe Ala Ala  Leu His Ser Ser Leu  Asn Glu Leu
    1205                 1210                 1215

Gly Glu  Ile Ala Arg Glu Leu  His Gln Phe Ala Phe  Asp Leu Leu
    1220                 1225                 1230

Ile Lys  Ser His Phe Val Gln  Gly Lys Asp Trp Gly  Leu Lys Lys
    1235                 1240                 1245

Phe Ile  Arg Arg Asp Phe Trp  Gly Met Glu Leu Ala  Ala Ser Arg
    1250                 1255                 1260

Arg Phe  Ser Trp Asp His His  Ser Ala Gly Gly Pro  Pro Arg Val
    1265                 1270                 1275

Pro Ser  Val Arg Ser Gly Ala  Ala Gln Val Gln Pro  Lys Asp Pro
    1280                 1285                 1290

Leu Pro  Leu Arg Thr Leu Ala  Gly Cys Leu Ala Arg  Thr Ala His
    1295                 1300                 1305

Leu Arg  Pro Gly Ala Glu Ser  Leu Pro Gln Pro Gln  Leu His Cys
```

```
    1310                1315                1320

Thr Leu  Trp Phe Gln Ser Ser  Glu Leu Ser Pro Thr  Gly Ala Pro
    1325                1330                1335

Trp Pro  Ser Arg Arg Pro Thr  Trp Arg Gly Thr Thr  Val Ser Pro
    1340                1345                1350

Arg Thr  Ala Thr Ser Ser Ala  Arg Thr Cys Cys Gly  Thr Lys Trp
    1355                1360                1365

Pro Ser  Ser Gln Glu Ala Ala  Leu Gly Leu Gly Ser  Gly Leu Leu
    1370                1375                1380

Arg Phe  Ser Cys Gly Thr Ala  Ala Ile Arg Lys Met  His Phe Ser
    1385                1390                1395

Leu Lys  Glu His Pro Pro Pro  Pro Cys Pro Pro Glu  Ala Phe Gln
    1400                1405                1410

Arg Ala  Ala Gly Glu Gly Gly  Pro Gly Arg Gly Gly  Ala Arg Arg
    1415                1420                1425

Gly Ala  Arg Val Leu Gln Ser  Pro Phe Cys Arg Ala  Gly Ala Gly
    1430                1435                1440

Glu Trp  Leu Gly His Gln Ser  Leu Arg His Val Val  Gly Tyr Gly
    1445                1450                1455

His Leu  Asp Thr Ser Gly Ser  Ser Ser Ser Ser Ser  Trp Pro Asn
    1460                1465                1470

Ser Lys  Met Ala Leu Asn Ser  Leu Asn Ser Ile Asp  Asp Ala Gln
    1475                1480                1485

Leu Thr  Arg Ile Ala Pro Pro  Arg Ser His Cys Cys  Phe Trp Glu
    1490                1495                1500

Val Asn  Ala Pro
    1505
```

<210> SEQ ID NO 555
<211> LENGTH: 1507
<212> TYPE: PRT
<213> ORGANISM: Artificial seqeunce
<220> FEATURE:
<223> OTHER INFORMATION: Heterologous polypeptide

<400> SEQUENCE: 555

```
Met Gly Gln Lys Glu Gln Ile His Thr Leu Gln Lys Asn Ser Glu Arg
1               5                   10                  15

Met Ser Lys Gln Leu Thr Arg Ser Ser Gln Ala Val Gln Asn Leu Gln
            20                  25                  30

Asn Gly Gly Gly Ser Arg Ser Ser Ala Thr Leu Pro Gly Arg Arg Arg
        35                  40                  45

Arg Arg Trp Leu Arg Arg Arg Arg Gln Pro Ile Ser Val Ala Pro Ala
    50                  55                  60

Gly Pro Pro Arg Arg Pro Asn Gln Lys Pro Asn Pro Pro Gly Gly Ala
65                  70                  75                  80

Arg Cys Val Ile Met Arg Pro Thr Trp Pro Gly Thr Ser Ala Phe Thr
                85                  90                  95

Lys Arg Ser Phe Ala Val Thr Glu Arg Ile Ile Thr Glu Ile Ser Cys
            100                 105                 110

Cys Thr Leu Ser Ser Glu Glu Asn Glu Tyr Leu Pro Arg Pro Glu Trp
        115                 120                 125

Gln Leu Gln Tyr Glu Ala Gly Met Thr Leu Gly Gly Lys Ile Leu Phe
    130                 135                 140

Phe Leu Phe Leu Leu Leu Pro Leu Ser Pro Phe Ser Leu Ile Phe Asp
```

```
145                 150                 155                 160

Tyr Trp Ala Gln Lys Glu Lys Gly Ser Ser Ser Phe Leu Arg Pro Ser
                165                 170                 175

Cys Val Pro Phe Arg Glu Leu Lys Asn Val Ser Val Leu Glu Gly Leu
            180                 185                 190

Arg Gln Gly Arg Leu Gly Gly Pro Cys Ser Cys His Cys Pro Arg Pro
        195                 200                 205

Ser Gln Ala Arg Leu Thr Pro Val Asp Val Ala Gly Pro Phe Leu Cys
    210                 215                 220

Leu Gly Asp Pro Gly Leu Phe Pro Pro Val Lys Ser Ser Ile Thr Gly
225                 230                 235                 240

Gly Lys Ser Thr Cys Ser Ala Pro Gly Pro Gln Ser Leu Pro Ser Thr
                245                 250                 255

Pro Phe Ser Thr Tyr Pro Gln Trp Val Ile Leu Ile Thr Glu Leu Gly
            260                 265                 270

Met Glu Cys Thr Leu Gly Gln Val Gly Ala Pro Ser Pro Arg Arg Glu
        275                 280                 285

Glu Asp Gly Trp Arg Gly Gly His Ser Arg Phe Lys Ala Asp Val Pro
    290                 295                 300

Ala Pro Gln Gly Pro Cys Trp Gly Gly Gln Pro Gly Ser Ala Pro Ser
305                 310                 315                 320

Ser Ala Pro Pro Glu Gln Ser Leu Leu Asp Asp Tyr Trp Ala Gln Lys
                325                 330                 335

Glu Lys Ile Ser Ile Pro Arg Thr His Leu Cys Leu Val Leu Gly Val
            340                 345                 350

Leu Ser Gly His Ser Gly Ser Arg Leu Trp Lys Phe Glu Met Ser Tyr
        355                 360                 365

Thr Val Gly Gly Pro Pro Pro His Val His Ala Arg Pro Arg His Trp
    370                 375                 380

Lys Thr Asp Arg Asp Gly His Ser Tyr Thr Ser Lys Val Asn Cys Leu
385                 390                 395                 400

Leu Leu Gln Asp Gly Phe His Gly Cys Val Ser Ile Thr Gly Ala Ala
                405                 410                 415

Gly Arg Arg Asn Leu Ser Ile Phe Leu Phe Leu Met Leu Cys Lys Leu
            420                 425                 430

Glu Phe His Ala Cys Lys Ile Gln Asn Lys Asn Cys Pro Asp Phe Lys
        435                 440                 445

Lys Phe Asp Gly Pro Cys Gly Glu Arg Gly Gly Gly Arg Thr Ala Arg
    450                 455                 460

Ala Leu Trp Ala Arg Gly Asp Ser Val Leu Thr Pro Ala Leu Asp Pro
465                 470                 475                 480

Gln Thr Pro Val Arg Ala Pro Ser Leu Thr Arg Ala Ala Ala Ala Val
                485                 490                 495

His Tyr Lys Leu Ile Gln Gln Pro Ile Ser Leu Phe Ser Ile Thr Asp
            500                 505                 510

Arg Leu His Lys Thr Phe Ser Gln Leu Pro Ser Val His Leu Cys Ser
        515                 520                 525

Ile Thr Phe Gln Trp Gly His Pro Pro Ile Phe Cys Ser Thr Asn Asp
    530                 535                 540

Ile Cys Val Thr Ala Asn Phe Cys Ile Ser Val Thr Phe Leu Lys Pro
545                 550                 555                 560

Cys Phe Leu Leu His Glu Ala Ser Ala Ser Gln Cys His Leu Phe Leu
                565                 570                 575
```

```
Gln Pro Gln Val Gly Thr Pro Pro Pro His Thr Ala Ser Ala Arg Ala
            580                 585                 590

Pro Ser Gly Pro Pro His Pro His Glu Ser Cys Pro Ala Gly Arg Arg
        595                 600                 605

Pro Ala Arg Ala Ala Gln Thr Cys Ala Arg Arg Gln His Gly Leu Pro
    610                 615                 620

Gly Cys Glu Glu Ala Gly Thr Ala Arg Val Pro Ser Leu His Leu His
625                 630                 635                 640

Leu His Gln Ala Ala Leu Gly Ala Gly Arg Gly Arg Gly Trp Gly Glu
                645                 650                 655

Ala Cys Ala Gln Val Pro Pro Ser Arg Gly Val Leu Arg Phe Leu Asp
            660                 665                 670

Leu Lys Val Arg Tyr Leu His Ser Gln Trp Gln His Tyr His Arg Ser
        675                 680                 685

Gly Glu Ala Ala Gly Thr Pro Leu Trp Arg Pro Thr Arg Asn Val Pro
    690                 695                 700

Phe Arg Glu Leu Lys Asn Gln Arg Thr Ala Gln Gly Ala Pro Gly Ile
705                 710                 715                 720

His His Ala Ala Ser Pro Val Ala Ala Asn Leu Cys Asp Pro Ala Arg
                725                 730                 735

His Ala Gln His Thr Arg Ile Pro Cys Gly Ala Gly Gln Val Arg Ala
            740                 745                 750

Gly Arg Gly Pro Glu Ala Gly Gly Gly Val Leu Gln Pro Gln Arg Pro
        755                 760                 765

Ala Pro Glu Lys Pro Gly Cys Pro Cys Arg Arg Gly Gln Pro Arg Leu
    770                 775                 780

His Thr Val Lys Met Trp Arg Ala Val Ala Met Met Val Pro Asp Arg
785                 790                 795                 800

Gln Val His Tyr Asp Phe Gly Leu Gly Val Pro Gly Asp Ser Thr Arg
                805                 810                 815

Arg Ala Val Arg Arg Met Asn Thr Phe Tyr Glu Ala Gly Met Thr Leu
            820                 825                 830

Gly Glu Lys Phe Arg Val Gly Asn Cys Lys His Leu Lys Met Thr Arg
        835                 840                 845

Pro Asn Ser Lys Met Ala Leu Asn Ser Glu Ala Leu Ser Val Val Ser
    850                 855                 860

Glu Cys Gly Ala Ser Ala Cys Asp Val Ser Leu Ile Ala Met Asp Ser
865                 870                 875                 880

Ala Phe Val Gln Gly Lys Asp Trp Gly Val Lys Lys Phe Ile Arg Arg
                885                 890                 895

Asp Phe Tyr Ala Tyr Lys Asp Phe Leu Trp Cys Phe Pro Phe Ser Leu
            900                 905                 910

Val Phe Leu Gln Glu Ile Gln Ile Cys Cys His Val Ser Cys Leu Cys
        915                 920                 925

Cys Ile Cys Cys Ser Thr Arg Ile Cys Leu Gly Cys Leu Leu Glu Leu
    930                 935                 940

Phe Leu Ser Arg Ala Leu Arg Ala Leu His Val Leu Trp Asn Gly Phe
945                 950                 955                 960

Gln Leu His Cys Gln Thr Glu Tyr Asn Gln Lys Leu Gln Val Asn Gln
                965                 970                 975

Phe Ser Glu Ser Lys Ser Leu Tyr His Arg Glu Lys Gln Leu Ile Ala
            980                 985                 990
```

```
Met Asp Ser Ala Ile Cys Glu Glu  Arg Gly Ala Ala Gly  Ser Leu Ile
        995                  1000                 1005

Ser Cys  Glu Thr Met Pro Ala  Ile Leu Lys Leu Gln  Lys Asn Cys
    1010                 1015                 1020

Leu Leu  Ser Leu Arg Thr Ala  Leu Thr His Asn Gln  Asp Phe Ser
    1025                 1030                 1035

Ile Tyr  Arg Leu Cys Cys Lys  Arg Gly Ser Leu Cys  His Ala Ser
    1040                 1045                 1050

Gln Ala  Arg Ser Pro Ala Phe  Pro Lys Pro Val Arg  Pro Leu Pro
    1055                 1060                 1065

Ala Pro  Ile Thr Arg Ile Thr  Pro Gln Leu Gly Gly  Gln Ser Asp
    1070                 1075                 1080

Ser Ser  Gln Pro Leu Leu Thr  Thr Gly Arg Pro Gln  Gly Trp Gln
    1085                 1090                 1095

Asp Gln  Ala Leu Arg His Thr  Gln Gln Ala Ser Pro  Ala Ser Cys
    1100                 1105                 1110

Ala Thr  Ile Thr Ile Pro Ile  His Ser Ala Ala Leu  Gly Asp His
    1115                 1120                 1125

Ser Gly  Asp Pro Gly Pro Ala  Trp Asp Thr Cys Pro  Pro Leu Pro
    1130                 1135                 1140

Leu Thr  Thr Leu Ile Pro Arg  Ala Pro Pro Pro Tyr  Gly Asp Ser
    1145                 1150                 1155

Thr Ala  Arg Ser Trp Pro Ser  Arg Cys Gly Pro Leu  Gly Gly Asn
    1160                 1165                 1170

Thr Thr  Leu Gln Gln Leu Gly  Glu Ala Ser Gln Ala  Pro Ser Gly
    1175                 1180                 1185

Ser Leu  Ile Pro Leu Arg Leu  Pro Leu Leu Trp Glu  Val Arg Gly
    1190                 1195                 1200

Gln Pro  Asp Ser Phe Ala Ala  Leu His Ser Ser Leu  Asn Glu Leu
    1205                 1210                 1215

Gly Glu  Ile Ala Arg Glu Leu  His Gln Phe Ala Phe  Asp Leu Leu
    1220                 1225                 1230

Ile Lys  Ser His Phe Val Gln  Gly Lys Asp Trp Gly  Leu Lys Lys
    1235                 1240                 1245

Phe Ile  Arg Arg Asp Phe Trp  Gly Met Glu Leu Ala  Ala Ser Arg
    1250                 1255                 1260

Arg Phe  Ser Trp Asp His His  Ser Ala Gly Gly Pro  Pro Arg Val
    1265                 1270                 1275

Pro Ser  Val Arg Ser Gly Ala  Ala Gln Val Gln Pro  Lys Asp Pro
    1280                 1285                 1290

Leu Pro  Leu Arg Thr Leu Ala  Gly Cys Leu Ala Arg  Thr Ala His
    1295                 1300                 1305

Leu Arg  Pro Gly Ala Glu Ser  Leu Pro Gln Pro Gln  Leu His Cys
    1310                 1315                 1320

Thr Leu  Trp Phe Gln Ser Ser  Glu Leu Ser Pro Thr  Gly Ala Pro
    1325                 1330                 1335

Trp Pro  Ser Arg Arg Pro Thr  Trp Arg Gly Thr Thr  Val Ser Pro
    1340                 1345                 1350

Arg Thr  Ala Thr Ser Ser Ala  Arg Thr Cys Cys Gly  Thr Lys Trp
    1355                 1360                 1365

Pro Ser  Ser Gln Glu Ala Ala  Leu Gly Leu Gly Ser  Gly Leu Leu
    1370                 1375                 1380

Arg Phe  Ser Cys Gly Thr Ala  Ala Ile Arg Lys Met  His Phe Ser
```

```
    1385                1390                1395

Leu Lys  Glu His Pro Pro Pro  Pro Cys Pro Pro Glu  Ala Phe Gln
    1400                1405                1410

Arg Ala  Ala Gly Glu Gly Gly  Pro Gly Arg Gly Gly  Ala Arg Arg
    1415                1420                1425

Gly Ala  Arg Val Leu Gln Ser  Pro Phe Cys Arg Ala  Gly Ala Gly
    1430                1435                1440

Glu Trp  Leu Gly His Gln Ser  Leu Arg His Val Val  Gly Tyr Gly
    1445                1450                1455

His Leu  Asp Thr Ser Gly Ser  Ser Ser Ser Ser Ser  Trp Pro Asn
    1460                1465                1470

Ser Lys  Met Ala Leu Asn Ser  Leu Asn Ser Ile Asp  Asp Ala Gln
    1475                1480                1485

Leu Thr  Arg Ile Ala Pro Pro  Arg Ser His Cys Cys  Phe Trp Glu
    1490                1495                1500

Val Asn  Ala Pro
    1505


<210> SEQ ID NO 556
<211> LENGTH: 1507
<212> TYPE: PRT
<213> ORGANISM: Artificial seqeunce
<220> FEATURE:
<223> OTHER INFORMATION: Heterologous polypeptide

<400> SEQUENCE: 556

Met Gly Gln Lys Glu Gln Ile His Thr Leu Gln Lys Asn Ser Glu Arg
1               5                   10                  15

Met Ser Lys Gln Leu Thr Arg Ser Ser Gln Ala Val Gln Asn Leu Gln
            20                  25                  30

Asn Gly Gly Gly Ser Arg Ser Ser Ala Thr Leu Pro Gly Arg Arg Arg
        35                  40                  45

Arg Arg Trp Leu Arg Arg Arg Arg Gln Pro Ile Ser Val Ala Pro Ala
    50                  55                  60

Gly Pro Pro Arg Arg Pro Asn Gln Lys Pro Asn Pro Pro Gly Gly Ala
65                  70                  75                  80

Arg Cys Val Ile Met Arg Pro Thr Trp Pro Gly Thr Ser Ala Phe Thr
                85                  90                  95

Lys Arg Ser Phe Ala Val Thr Glu Arg Ile Ile Asp Tyr Trp Ala Gln
            100                 105                 110

Lys Glu Lys Gly Ser Ser Ser Phe Leu Arg Pro Ser Cys Val Pro Phe
        115                 120                 125

Arg Glu Leu Lys Asn Val Ser Val Leu Glu Gly Leu Arg Gln Gly Arg
    130                 135                 140

Leu Gly Gly Pro Cys Ser Cys His Cys Pro Arg Pro Ser Gln Ala Arg
145                 150                 155                 160

Leu Thr Pro Val Asp Val Ala Gly Pro Phe Leu Cys Leu Gly Asp Pro
                165                 170                 175

Gly Leu Phe Pro Pro Val Lys Ser Ser Ile Leu Val Leu Gly Val Leu
            180                 185                 190

Ser Gly His Ser Gly Ser Arg Leu Tyr Glu Ala Gly Met Thr Leu Gly
        195                 200                 205

Gly Lys Ile Leu Phe Phe Leu Phe Leu Leu Leu Pro Leu Ser Pro Phe
    210                 215                 220

Ser Leu Ile Phe Thr Glu Ile Ser Cys Cys Thr Leu Ser Ser Glu Glu
```

-continued

```
225                 230                 235                 240

Asn Glu Tyr Leu Pro Arg Pro Glu Trp Gln Leu Gln Thr Gly Gly Lys
                245                 250                 255

Ser Thr Cys Ser Ala Pro Gly Pro Gln Ser Leu Pro Ser Thr Pro Phe
            260                 265                 270

Ser Thr Tyr Pro Gln Trp Val Ile Leu Ile Thr Glu Leu Gly Met Glu
        275                 280                 285

Cys Thr Leu Gly Gln Val Gly Ala Pro Ser Pro Arg Arg Glu Glu Asp
    290                 295                 300

Gly Trp Arg Gly Gly His Ser Arg Phe Lys Ala Asp Val Pro Ala Pro
305                 310                 315                 320

Gln Gly Pro Cys Trp Gly Gly Gln Pro Gly Ser Ala Pro Ser Ser Ala
                325                 330                 335

Pro Pro Glu Gln Ser Leu Leu Asp Asp Tyr Trp Ala Gln Lys Glu Lys
            340                 345                 350

Ile Ser Ile Pro Arg Thr His Leu Cys Trp Lys Phe Glu Met Ser Tyr
        355                 360                 365

Thr Val Gly Gly Pro Pro Pro His Val His Ala Arg Pro Arg His Trp
    370                 375                 380

Lys Thr Asp Arg Asp Gly His Ser Tyr Thr Ser Lys Val Asn Cys Leu
385                 390                 395                 400

Leu Leu Gln Asp Gly Phe His Gly Cys Val Ser Ile Thr Gly Ala Ala
                405                 410                 415

Gly Arg Arg Asn Leu Ser Ile Phe Leu Phe Leu Met Leu Cys Lys Leu
            420                 425                 430

Glu Phe His Ala Cys Lys Ile Gln Asn Lys Asn Cys Pro Asp Phe Lys
        435                 440                 445

Lys Phe Asp Gly Pro Cys Gly Glu Arg Gly Gly Gly Arg Thr Ala Arg
    450                 455                 460

Ala Leu Trp Ala Arg Gly Asp Ser Val Leu Thr Pro Ala Leu Asp Pro
465                 470                 475                 480

Gln Thr Pro Val Arg Ala Pro Ser Leu Thr Arg Ala Ala Ala Ala Val
                485                 490                 495

His Tyr Lys Leu Ile Gln Gln Pro Ile Ser Leu Phe Ser Ile Thr Asp
            500                 505                 510

Arg Leu His Lys Thr Phe Ser Gln Leu Pro Ser Val His Leu Cys Ser
        515                 520                 525

Ile Thr Phe Gln Trp Gly His Pro Pro Ile Phe Cys Ser Thr Asn Asp
    530                 535                 540

Ile Cys Val Thr Ala Asn Phe Cys Ile Ser Val Thr Phe Leu Lys Pro
545                 550                 555                 560

Cys Phe Leu Leu His Glu Ala Ser Ala Ser Gln Cys His Leu Phe Leu
                565                 570                 575

Gln Pro Gln Val Gly Thr Pro Pro Pro His Thr Ala Ser Ala Arg Ala
            580                 585                 590

Pro Ser Gly Pro Pro His Pro His Glu Ser Cys Pro Ala Gly Arg Arg
        595                 600                 605

Pro Ala Arg Ala Ala Gln Thr Cys Ala Arg Arg Gln His Gly Leu Pro
    610                 615                 620

Gly Cys Glu Glu Ala Gly Thr Ala Arg Val Pro Ser Leu His Leu His
625                 630                 635                 640

Leu His Gln Ala Ala Leu Gly Ala Gly Arg Gly Arg Gly Trp Gly Glu
                645                 650                 655
```

```
Ala Cys Ala Gln Val Pro Pro Ser Arg Gly Val Leu Arg Phe Leu Asp
            660                 665                 670

Leu Lys Val Arg Tyr Leu His Ser Gln Trp Gln His Tyr His Arg Ser
        675                 680                 685

Gly Glu Ala Ala Gly Thr Pro Leu Trp Arg Pro Thr Arg Asn Val Pro
    690                 695                 700

Phe Arg Glu Leu Lys Asn Gln Arg Thr Ala Gln Gly Ala Pro Gly Ile
705                 710                 715                 720

His His Ala Ala Ser Pro Val Ala Ala Asn Leu Cys Asp Pro Ala Arg
                725                 730                 735

His Ala Gln His Thr Arg Ile Pro Cys Gly Ala Gly Gln Val Arg Ala
            740                 745                 750

Gly Arg Gly Pro Glu Ala Gly Gly Gly Val Leu Gln Pro Gln Arg Pro
        755                 760                 765

Ala Pro Glu Lys Pro Gly Cys Pro Cys Arg Arg Gly Gln Pro Arg Leu
    770                 775                 780

His Thr Val Lys Met Trp Arg Ala Val Ala Met Met Val Pro Asp Arg
785                 790                 795                 800

Gln Val His Tyr Asp Phe Gly Leu Gly Val Pro Gly Asp Ser Thr Arg
                805                 810                 815

Arg Ala Val Arg Arg Met Asn Thr Phe Tyr Glu Ala Gly Met Thr Leu
            820                 825                 830

Gly Glu Lys Phe Arg Val Gly Asn Cys Lys His Leu Lys Met Thr Arg
        835                 840                 845

Pro Asn Ser Lys Met Ala Leu Asn Ser Glu Ala Leu Ser Val Val Ser
    850                 855                 860

Glu Cys Gly Ala Ser Ala Cys Asp Val Ser Leu Ile Ala Met Asp Ser
865                 870                 875                 880

Ala Phe Val Gln Gly Lys Asp Trp Gly Val Lys Lys Phe Ile Arg Arg
                885                 890                 895

Asp Phe Tyr Ala Tyr Lys Asp Phe Leu Trp Cys Phe Pro Phe Ser Leu
            900                 905                 910

Val Phe Leu Gln Glu Ile Gln Ile Cys Cys His Val Ser Cys Leu Cys
        915                 920                 925

Cys Ile Cys Cys Ser Thr Arg Ile Cys Leu Gly Cys Leu Leu Glu Leu
    930                 935                 940

Phe Leu Ser Arg Ala Leu Arg Ala Leu His Val Leu Trp Asn Gly Phe
945                 950                 955                 960

Gln Leu His Cys Gln Thr Glu Tyr Asn Gln Lys Leu Gln Val Asn Gln
                965                 970                 975

Phe Ser Glu Ser Lys Ser Leu Tyr His Arg Glu Lys Gln Leu Ile Ala
            980                 985                 990

Met Asp Ser Ala Ile Cys Glu Glu  Arg Gly Ala Ala Gly  Ser Leu Ile
        995                 1000                1005

Ser Cys  Glu Thr Met Pro Ala  Ile Leu Lys Leu Gln  Lys Asn Cys
    1010                 1015                 1020

Leu Leu  Ser Leu Arg Thr Ala  Leu Thr His Asn Gln  Asp Phe Ser
    1025                 1030                 1035

Ile Tyr  Arg Leu Cys Cys Lys  Arg Gly Ser Leu Cys  His Ala Ser
    1040                 1045                 1050

Gln Ala  Arg Ser Pro Ala Phe  Pro Lys Pro Val Arg  Pro Leu Pro
    1055                 1060                 1065
```

Ala Pro Ile Thr Arg Ile Thr Pro Gln Leu Gly Gly Gln Ser Asp
1070 1075 1080

Ser Ser Gln Pro Leu Leu Thr Thr Gly Arg Pro Gln Gly Trp Gln
1085 1090 1095

Asp Gln Ala Leu Arg His Thr Gln Gln Ala Ser Pro Ala Ser Cys
1100 1105 1110

Ala Thr Ile Thr Ile Pro Ile His Ser Ala Ala Leu Gly Asp His
1115 1120 1125

Ser Gly Asp Pro Gly Pro Ala Trp Asp Thr Cys Pro Pro Leu Pro
1130 1135 1140

Leu Thr Thr Leu Ile Pro Arg Ala Pro Pro Pro Tyr Gly Asp Ser
1145 1150 1155

Thr Ala Arg Ser Trp Pro Ser Arg Cys Gly Pro Leu Gly Gly Asn
1160 1165 1170

Thr Thr Leu Gln Gln Leu Gly Glu Ala Ser Gln Ala Pro Ser Gly
1175 1180 1185

Ser Leu Ile Pro Leu Arg Leu Pro Leu Leu Trp Glu Val Arg Gly
1190 1195 1200

Gln Pro Asp Ser Phe Ala Ala Leu His Ser Ser Leu Asn Glu Leu
1205 1210 1215

Gly Glu Ile Ala Arg Glu Leu His Gln Phe Ala Phe Asp Leu Leu
1220 1225 1230

Ile Lys Ser His Phe Val Gln Gly Lys Asp Trp Gly Leu Lys Lys
1235 1240 1245

Phe Ile Arg Arg Asp Phe Trp Gly Met Glu Leu Ala Ala Ser Arg
1250 1255 1260

Arg Phe Ser Trp Asp His His Ser Ala Gly Gly Pro Pro Arg Val
1265 1270 1275

Pro Ser Val Arg Ser Gly Ala Ala Gln Val Gln Pro Lys Asp Pro
1280 1285 1290

Leu Pro Leu Arg Thr Leu Ala Gly Cys Leu Ala Arg Thr Ala His
1295 1300 1305

Leu Arg Pro Gly Ala Glu Ser Leu Pro Gln Pro Gln Leu His Cys
1310 1315 1320

Thr Leu Trp Phe Gln Ser Ser Glu Leu Ser Pro Thr Gly Ala Pro
1325 1330 1335

Trp Pro Ser Arg Arg Pro Thr Trp Arg Gly Thr Thr Val Ser Pro
1340 1345 1350

Arg Thr Ala Thr Ser Ser Ala Arg Thr Cys Cys Gly Thr Lys Trp
1355 1360 1365

Pro Ser Ser Gln Glu Ala Ala Leu Gly Leu Gly Ser Gly Leu Leu
1370 1375 1380

Arg Phe Ser Cys Gly Thr Ala Ala Ile Arg Lys Met His Phe Ser
1385 1390 1395

Leu Lys Glu His Pro Pro Pro Pro Cys Pro Pro Glu Ala Phe Gln
1400 1405 1410

Arg Ala Ala Gly Glu Gly Gly Pro Gly Arg Gly Gly Ala Arg Arg
1415 1420 1425

Gly Ala Arg Val Leu Gln Ser Pro Phe Cys Arg Ala Gly Ala Gly
1430 1435 1440

Glu Trp Leu Gly His Gln Ser Leu Arg His Val Val Gly Tyr Gly
1445 1450 1455

His Leu Asp Thr Ser Gly Ser Ser Ser Ser Ser Ser Trp Pro Asn

```
    1460                1465                1470

Ser Lys  Met Ala Leu Asn Ser  Leu Asn Ser Ile Asp  Asp Ala Gln
    1475                1480                1485

Leu Thr  Arg Ile Ala Pro Pro  Arg Ser His Cys Cys  Phe Trp Glu
    1490                1495                1500

Val Asn  Ala Pro
    1505


<210> SEQ ID NO 557
<211> LENGTH: 1507
<212> TYPE: PRT
<213> ORGANISM: Artificial seqeunce
<220> FEATURE:
<223> OTHER INFORMATION: Heterologous polypeptide

<400> SEQUENCE: 557

Met Gly Gln Lys Glu Gln Ile His Thr Leu Gln Lys Asn Ser Glu Arg
1               5                   10                  15

Met Ser Lys Gln Leu Thr Arg Ser Ser Gln Ala Val Gln Asn Leu Gln
            20                  25                  30

Asn Gly Gly Gly Ser Arg Ser Ser Ala Thr Leu Pro Gly Arg Arg Arg
        35                  40                  45

Arg Arg Trp Leu Arg Arg Arg Arg Gln Pro Ile Ser Val Ala Pro Ala
    50                  55                  60

Gly Pro Pro Arg Arg Pro Asn Gln Lys Pro Asn Pro Pro Gly Gly Ala
65                  70                  75                  80

Arg Cys Val Ile Met Arg Pro Thr Trp Pro Gly Thr Ser Ala Phe Thr
                85                  90                  95

Gly Met Glu Cys Thr Leu Gly Gln Val Gly Ala Pro Ser Pro Arg Arg
            100                 105                 110

Glu Glu Asp Gly Trp Arg Gly Gly His Ser Arg Phe Lys Ala Asp Val
        115                 120                 125

Pro Ala Pro Gln Gly Pro Cys Trp Gly Gly Gln Pro Gly Ser Ala Pro
    130                 135                 140

Ser Ser Ala Pro Pro Glu Gln Ser Leu Leu Asp Asp Tyr Trp Ala Gln
145                 150                 155                 160

Lys Glu Lys Ile Ser Ile Pro Arg Thr His Leu Cys Trp Lys Phe Glu
                165                 170                 175

Met Ser Tyr Thr Val Gly Gly Pro Pro Pro His Val His Ala Arg Pro
            180                 185                 190

Arg His Trp Lys Thr Asp Arg Asp Tyr Trp Ala Gln Lys Glu Lys Gly
        195                 200                 205

Ser Ser Ser Phe Leu Arg Pro Ser Cys Val Pro Phe Arg Glu Leu Lys
    210                 215                 220

Asn Val Ser Val Leu Glu Gly Leu Arg Gln Gly Arg Leu Gly Gly Pro
225                 230                 235                 240

Cys Ser Cys His Cys Pro Arg Pro Ser Gln Ala Arg Leu Thr Pro Val
                245                 250                 255

Asp Val Ala Gly Pro Phe Leu Cys Leu Gly Asp Pro Gly Leu Phe Pro
            260                 265                 270

Pro Val Lys Ser Ser Ile Thr Glu Ile Ser Cys Cys Thr Leu Ser Ser
        275                 280                 285

Glu Glu Asn Glu Tyr Leu Pro Arg Pro Glu Trp Gln Leu Gln Tyr Glu
    290                 295                 300

Ala Gly Met Thr Leu Gly Gly Lys Ile Leu Phe Phe Leu Phe Leu Leu
```

-continued

```
305                 310                 315                 320

Leu Pro Leu Ser Pro Phe Ser Leu Ile Phe Leu Val Leu Gly Val Leu
                325                 330                 335

Ser Gly His Ser Gly Ser Arg Leu Lys Arg Ser Phe Ala Val Thr Glu
            340                 345                 350

Arg Ile Ile Thr Gly Gly Lys Ser Thr Cys Ser Ala Pro Gly Pro Gln
        355                 360                 365

Ser Leu Pro Ser Thr Pro Phe Ser Thr Tyr Pro Gln Trp Val Ile Leu
    370                 375                 380

Ile Thr Glu Leu Asp Gly His Ser Tyr Thr Ser Lys Val Asn Cys Leu
385                 390                 395                 400

Leu Leu Gln Asp Gly Phe His Gly Cys Val Ser Ile Thr Gly Ala Ala
                405                 410                 415

Gly Arg Arg Asn Leu Ser Ile Phe Leu Phe Leu Met Leu Cys Lys Leu
            420                 425                 430

Glu Phe His Ala Cys Cys His Leu Phe Leu Gln Pro Gln Val Gly Thr
        435                 440                 445

Pro Pro Pro His Thr Ala Ser Ala Arg Ala Pro Ser Gly Pro Pro His
    450                 455                 460

Pro His Glu Ser Cys Pro Ala Gly Arg Arg Pro Ala Arg Ala Ala Gln
465                 470                 475                 480

Thr Cys Ala Arg Arg Gln His Gly Leu Pro Gly Cys Glu Glu Ala Gly
                485                 490                 495

Thr Ala Arg Val Pro Ser Leu His Leu His Leu His Gln Ala Ala Leu
            500                 505                 510

Gly Ala Gly Arg Gly Arg Gly Trp Gly Glu Ala Cys Ala Gln Val Pro
        515                 520                 525

Pro Ser Arg Gly His Tyr Lys Leu Ile Gln Gln Pro Ile Ser Leu Phe
    530                 535                 540

Ser Ile Thr Asp Arg Leu His Lys Thr Phe Ser Gln Leu Pro Ser Val
545                 550                 555                 560

His Leu Cys Ser Ile Thr Phe Gln Trp Gly His Pro Pro Ile Phe Cys
                565                 570                 575

Ser Thr Asn Asp Ile Cys Val Thr Ala Asn Phe Cys Ile Ser Val Thr
            580                 585                 590

Phe Leu Lys Pro Cys Phe Leu Leu His Glu Ala Ser Ala Ser Gln Val
        595                 600                 605

Ala Met Met Val Pro Asp Arg Gln Val His Tyr Asp Phe Gly Leu Lys
    610                 615                 620

Ile Gln Asn Lys Asn Cys Pro Asp Val Leu Arg Phe Leu Asp Leu Lys
625                 630                 635                 640

Val Arg Tyr Leu His Ser Val Pro Phe Arg Glu Leu Lys Asn Gln Arg
                645                 650                 655

Thr Ala Gln Gly Ala Pro Gly Ile His His Ala Ala Ser Pro Val Ala
            660                 665                 670

Ala Asn Leu Cys Asp Pro Ala Arg His Ala Gln His Thr Arg Ile Pro
        675                 680                 685

Cys Gly Ala Gly Gln Val Arg Ala Gly Arg Gly Pro Glu Ala Gly Gly
    690                 695                 700

Gly Val Leu Gln Pro Gln Arg Pro Ala Pro Glu Lys Pro Gly Cys Pro
705                 710                 715                 720

Cys Arg Arg Gly Gln Pro Arg Leu His Thr Val Lys Met Trp Arg Ala
                725                 730                 735
```

-continued

```
Gln Trp Gln His Tyr His Arg Ser Gly Glu Ala Ala Gly Thr Pro Leu
            740                 745                 750

Trp Arg Pro Thr Arg Asn Phe Lys Lys Phe Asp Gly Pro Cys Gly Glu
        755                 760                 765

Arg Gly Gly Gly Arg Thr Ala Arg Ala Leu Trp Ala Arg Gly Asp Ser
    770                 775                 780

Val Leu Thr Pro Ala Leu Asp Pro Gln Thr Pro Val Arg Ala Pro Ser
785                 790                 795                 800

Leu Thr Arg Ala Ala Ala Ala Val Gly Val Pro Gly Asp Ser Thr Arg
                805                 810                 815

Arg Ala Val Arg Arg Met Asn Thr Phe Cys Gly Ala Ser Ala Cys Asp
            820                 825                 830

Val Ser Leu Ile Ala Met Asp Ser Ala Cys Glu Glu Arg Gly Ala Ala
        835                 840                 845

Gly Ser Leu Ile Ser Cys Glu Ser Leu Tyr His Arg Glu Lys Gln Leu
    850                 855                 860

Ile Ala Met Asp Ser Ala Ile Phe Val Gln Gly Lys Asp Trp Gly Val
865                 870                 875                 880

Lys Lys Phe Ile Arg Arg Asp Phe Thr Met Pro Ala Ile Leu Lys Leu
                885                 890                 895

Gln Lys Asn Cys Leu Leu Ser Leu Asn Ser Lys Met Ala Leu Asn Ser
            900                 905                 910

Glu Ala Leu Ser Val Val Ser Glu Tyr Glu Ala Gly Met Thr Leu Gly
        915                 920                 925

Glu Lys Phe Arg Val Gly Asn Cys Lys His Leu Lys Met Thr Arg Pro
    930                 935                 940

Thr Glu Tyr Asn Gln Lys Leu Gln Val Asn Gln Phe Ser Glu Ser Lys
945                 950                 955                 960

Arg Thr Ala Leu Thr His Asn Gln Asp Phe Ser Ile Tyr Arg Leu Cys
                965                 970                 975

Cys Lys Arg Gly Ser Leu Cys His Ala Ser Gln Ala Arg Ser Pro Ala
            980                 985                 990

Phe Pro Lys Pro Val Arg Pro Leu  Pro Ala Pro Ile Thr  Arg Ile Thr
        995                 1000                 1005

Pro Gln  Leu Gly Gly Gln Ser  Asp Ser Ser Gln Pro  Leu Leu Thr
    1010                 1015                 1020

Thr Gly  Arg Pro Gln Gly Trp  Gln Asp Gln Ala Leu  Arg His Thr
    1025                 1030                 1035

Gln Gln  Ala Ser Pro Ala Ser  Cys Ala Thr Ile Thr  Ile Pro Ile
    1040                 1045                 1050

His Ser  Ala Ala Leu Gly Asp  His Ser Gly Asp Pro  Gly Pro Ala
    1055                 1060                 1065

Trp Asp  Thr Cys Pro Pro Leu  Pro Leu Thr Thr Leu  Ile Pro Arg
    1070                 1075                 1080

Ala Pro  Pro Pro Tyr Gly Asp  Ser Thr Ala Arg Ser  Trp Pro Ser
    1085                 1090                 1095

Arg Cys  Gly Pro Leu Gly Tyr  Ala Tyr Lys Asp Phe  Leu Trp Cys
    1100                 1105                 1110

Phe Pro  Phe Ser Leu Val Phe  Leu Gln Glu Ile Gln  Ile Cys Cys
    1115                 1120                 1125

His Val  Ser Cys Leu Cys Cys  Ile Cys Cys Ser Thr  Arg Ile Cys
    1130                 1135                 1140
```

-continued

```
Leu Gly  Cys Leu Leu Glu Leu  Phe Leu Ser Arg Ala  Leu Arg Ala
    1145                 1150                 1155

Leu His  Val Leu Trp Asn Gly  Phe Gln Leu His Cys  Gln Gly Asn
    1160                 1165                 1170

Thr Thr  Leu Gln Gln Leu Gly  Glu Ala Ser Gln Ala  Pro Ser Gly
    1175                 1180                 1185

Ser Leu  Ile Pro Leu Arg Leu  Pro Leu Leu Trp Glu  Val Arg Gly
    1190                 1195                 1200

Asn Ser  Lys Met Ala Leu Asn  Ser Leu Asn Ser Ile  Asp Asp Ala
    1205                 1210                 1215

Gln Leu  Thr Arg Ile Ala Pro  Pro Arg Ser His Cys  Cys Phe Trp
    1220                 1225                 1230

Glu Val  Asn Ala Pro Phe Val  Gln Gly Lys Asp Trp  Gly Leu Lys
    1235                 1240                 1245

Lys Phe  Ile Arg Arg Asp Phe  Glu Ala Phe Gln Arg  Ala Ala Gly
    1250                 1255                 1260

Glu Gly  Gly Pro Gly Arg Gly  Gly Ala Arg Arg Gly  Ala Arg Val
    1265                 1270                 1275

Leu Gln  Ser Pro Phe Cys Arg  Ala Gly Ala Gly Glu  Trp Leu Gly
    1280                 1285                 1290

His Gln  Ser Leu Arg Trp Gly  Met Glu Leu Ala Ala  Ser Arg Arg
    1295                 1300                 1305

Phe Ser  Trp Asp His His Ser  Ala Gly Gly Pro Pro  Arg Val Pro
    1310                 1315                 1320

Ser Val  Arg Ser Gly Ala Ala  Gln Val Gln Pro Lys  Asp Pro Leu
    1325                 1330                 1335

Pro Leu  Arg Thr Leu Ala Gly  Cys Leu Ala Arg Thr  Ala His Leu
    1340                 1345                 1350

Arg Pro  Gly Ala Glu Ser Leu  Pro Gln Pro Gln Leu  His Cys Thr
    1355                 1360                 1365

Ile Ala  Arg Glu Leu His Gln  Phe Ala Phe Asp Leu  Leu Ile Lys
    1370                 1375                 1380

Ser His  Lys Met His Phe Ser  Leu Lys Glu His Pro  Pro Pro Pro
    1385                 1390                 1395

Cys Pro  Pro His Val Val Gly  Tyr Gly His Leu Asp  Thr Ser Gly
    1400                 1405                 1410

Ser Ser  Ser Ser Ser Ser Trp  Pro Gln Pro Asp Ser  Phe Ala Ala
    1415                 1420                 1425

Leu His  Ser Ser Leu Asn Glu  Leu Gly Glu Leu Trp  Phe Gln Ser
    1430                 1435                 1440

Ser Glu  Leu Ser Pro Thr Gly  Ala Pro Trp Pro Ser  Arg Arg Pro
    1445                 1450                 1455

Thr Trp  Arg Gly Thr Thr Val  Ser Pro Arg Thr Ala  Thr Ser Ser
    1460                 1465                 1470

Ala Arg  Thr Cys Cys Gly Thr  Lys Trp Pro Ser Ser  Gln Glu Ala
    1475                 1480                 1485

Ala Leu  Gly Leu Gly Ser Gly  Leu Leu Arg Phe Ser  Cys Gly Thr
    1490                 1495                 1500

Ala Ala  Ile Arg
    1505
```

<210> SEQ ID NO 558
<211> LENGTH: 1507
<212> TYPE: PRT

<213> ORGANISM: Artificial seqeunce
<220> FEATURE:
<223> OTHER INFORMATION: Heterologous polypeptide

<400> SEQUENCE: 558

```
Met Gly Gln Lys Glu Gln Ile His Thr Leu Gln Lys Asn Ser Glu Arg
1               5                   10                  15

Met Ser Lys Gln Leu Thr Arg Ser Ser Gln Ala Val Asp Gly His Ser
            20                  25                  30

Tyr Thr Ser Lys Val Asn Cys Leu Leu Leu Gln Asp Gly Phe His Gly
        35                  40                  45

Cys Val Ser Ile Thr Gly Ala Ala Gly Arg Arg Asn Leu Ser Ile Phe
    50                  55                  60

Leu Phe Leu Met Leu Cys Lys Leu Glu Phe His Ala Cys Gln Trp Gln
65                  70                  75                  80

His Tyr His Arg Ser Gly Glu Ala Ala Gly Thr Pro Leu Trp Arg Pro
                85                  90                  95

Thr Arg Asn Val Ala Met Met Val Pro Asp Arg Gln Val His Tyr Asp
            100                 105                 110

Phe Gly Leu Val Leu Arg Phe Leu Asp Leu Lys Val Arg Tyr Leu His
        115                 120                 125

Ser Lys Ile Gln Asn Lys Asn Cys Pro Asp Val Pro Phe Arg Glu Leu
    130                 135                 140

Lys Asn Gln Arg Thr Ala Gln Gly Ala Pro Gly Ile His His Ala Ala
145                 150                 155                 160

Ser Pro Val Ala Ala Asn Leu Cys Asp Pro Ala Arg His Ala Gln His
                165                 170                 175

Thr Arg Ile Pro Cys Gly Ala Gly Gln Val Arg Ala Gly Arg Gly Pro
            180                 185                 190

Glu Ala Gly Gly Gly Val Leu Gln Pro Gln Arg Pro Ala Pro Glu Lys
        195                 200                 205

Pro Gly Cys Pro Cys Arg Arg Gly Gln Pro Arg Leu His Thr Val Lys
    210                 215                 220

Met Trp Arg Ala Cys His Leu Phe Leu Gln Pro Gln Val Gly Thr Pro
225                 230                 235                 240

Pro Pro His Thr Ala Ser Ala Arg Ala Pro Ser Gly Pro Pro His Pro
                245                 250                 255

His Glu Ser Cys Pro Ala Gly Arg Arg Pro Ala Arg Ala Ala Gln Thr
            260                 265                 270

Cys Ala Arg Arg Gln His Gly Leu Pro Gly Cys Glu Glu Ala Gly Thr
        275                 280                 285

Ala Arg Val Pro Ser Leu His Leu His Leu His Gln Ala Ala Leu Gly
    290                 295                 300

Ala Gly Arg Gly Arg Gly Trp Gly Glu Ala Cys Ala Gln Val Pro Pro
305                 310                 315                 320

Ser Arg Gly His Tyr Lys Leu Ile Gln Gln Pro Ile Ser Leu Phe Ser
                325                 330                 335

Ile Thr Asp Arg Leu His Lys Thr Phe Ser Gln Leu Pro Ser Val His
            340                 345                 350

Leu Cys Ser Ile Thr Phe Gln Trp Gly His Pro Pro Ile Phe Cys Ser
        355                 360                 365

Thr Asn Asp Ile Cys Val Thr Ala Asn Phe Cys Ile Ser Val Thr Phe
    370                 375                 380

Leu Lys Pro Cys Phe Leu Leu His Glu Ala Ser Ala Ser Gln Phe Lys
```

-continued

```
385                 390                 395                 400

Lys Phe Asp Gly Pro Cys Gly Glu Arg Gly Gly Gly Arg Thr Ala Arg
                405                 410                 415

Ala Leu Trp Ala Arg Gly Asp Ser Val Leu Thr Pro Ala Leu Asp Pro
            420                 425                 430

Gln Thr Pro Val Arg Ala Pro Ser Leu Thr Arg Ala Ala Ala Ala Val
        435                 440                 445

Gln Asn Leu Gln Asn Gly Gly Gly Ser Arg Ser Ser Ala Thr Leu Pro
    450                 455                 460

Gly Arg Arg Arg Arg Arg Trp Leu Arg Arg Arg Arg Gln Pro Ile Ser
465                 470                 475                 480

Val Ala Pro Ala Gly Pro Pro Arg Arg Pro Asn Gln Lys Pro Asn Pro
                485                 490                 495

Pro Gly Gly Ala Arg Cys Val Ile Met Arg Pro Thr Trp Pro Gly Thr
            500                 505                 510

Ser Ala Phe Thr Gly Met Glu Cys Thr Leu Gly Gln Val Gly Ala Pro
        515                 520                 525

Ser Pro Arg Arg Glu Glu Asp Gly Trp Arg Gly Gly His Ser Arg Phe
    530                 535                 540

Lys Ala Asp Val Pro Ala Pro Gln Gly Pro Cys Trp Gly Gly Gln Pro
545                 550                 555                 560

Gly Ser Ala Pro Ser Ser Ala Pro Pro Glu Gln Ser Leu Leu Asp Asp
                565                 570                 575

Tyr Trp Ala Gln Lys Glu Lys Ile Ser Ile Pro Arg Thr His Leu Cys
            580                 585                 590

Trp Lys Phe Glu Met Ser Tyr Thr Val Gly Gly Pro Pro Pro His Val
        595                 600                 605

His Ala Arg Pro Arg His Trp Lys Thr Asp Arg Asp Tyr Trp Ala Gln
    610                 615                 620

Lys Glu Lys Gly Ser Ser Ser Phe Leu Arg Pro Ser Cys Val Pro Phe
625                 630                 635                 640

Arg Glu Leu Lys Asn Val Ser Val Leu Glu Gly Leu Arg Gln Gly Arg
                645                 650                 655

Leu Gly Gly Pro Cys Ser Cys His Cys Pro Arg Pro Ser Gln Ala Arg
            660                 665                 670

Leu Thr Pro Val Asp Val Ala Gly Pro Phe Leu Cys Leu Gly Asp Pro
        675                 680                 685

Gly Leu Phe Pro Pro Val Lys Ser Ser Ile Thr Glu Ile Ser Cys Cys
    690                 695                 700

Thr Leu Ser Ser Glu Glu Asn Glu Tyr Leu Pro Arg Pro Glu Trp Gln
705                 710                 715                 720

Leu Gln Tyr Glu Ala Gly Met Thr Leu Gly Gly Lys Ile Leu Phe Phe
                725                 730                 735

Leu Phe Leu Leu Leu Pro Leu Ser Pro Phe Ser Leu Ile Phe Leu Val
            740                 745                 750

Leu Gly Val Leu Ser Gly His Ser Gly Ser Arg Leu Lys Arg Ser Phe
        755                 760                 765

Ala Val Thr Glu Arg Ile Ile Thr Gly Gly Lys Ser Thr Cys Ser Ala
    770                 775                 780

Pro Gly Pro Gln Ser Leu Pro Ser Thr Pro Phe Ser Thr Tyr Pro Gln
785                 790                 795                 800

Trp Val Ile Leu Ile Thr Glu Leu Gly Val Pro Gly Asp Ser Thr Arg
                805                 810                 815
```

```
Arg Ala Val Arg Arg Met Asn Thr Phe Cys Gly Ala Ser Ala Cys Asp
            820                 825                 830

Val Ser Leu Ile Ala Met Asp Ser Ala Cys Glu Glu Arg Gly Ala Ala
        835                 840                 845

Gly Ser Leu Ile Ser Cys Glu Ser Leu Tyr His Arg Glu Lys Gln Leu
    850                 855                 860

Ile Ala Met Asp Ser Ala Ile Phe Val Gln Gly Lys Asp Trp Gly Val
865                 870                 875                 880

Lys Lys Phe Ile Arg Arg Asp Phe Thr Met Pro Ala Ile Leu Lys Leu
                885                 890                 895

Gln Lys Asn Cys Leu Leu Ser Leu Asn Ser Lys Met Ala Leu Asn Ser
            900                 905                 910

Glu Ala Leu Ser Val Val Ser Glu Tyr Glu Ala Gly Met Thr Leu Gly
        915                 920                 925

Glu Lys Phe Arg Val Gly Asn Cys Lys His Leu Lys Met Thr Arg Pro
    930                 935                 940

Thr Glu Tyr Asn Gln Lys Leu Gln Val Asn Gln Phe Ser Glu Ser Lys
945                 950                 955                 960

Arg Thr Ala Leu Thr His Asn Gln Asp Phe Ser Ile Tyr Arg Leu Cys
                965                 970                 975

Cys Lys Arg Gly Ser Leu Cys His Ala Ser Gln Ala Arg Ser Pro Ala
            980                 985                 990

Phe Pro Lys Pro Val Arg Pro Leu  Pro Ala Pro Ile Thr  Arg Ile Thr
        995                 1000                1005

Pro Gln  Leu Gly Gly Gln Ser  Asp Ser Ser Gln Pro  Leu Leu Thr
    1010                 1015                 1020

Thr Gly  Arg Pro Gln Gly Trp  Gln Asp Gln Ala Leu  Arg His Thr
    1025                 1030                 1035

Gln Gln  Ala Ser Pro Ala Ser  Cys Ala Thr Ile Thr  Ile Pro Ile
    1040                 1045                 1050

His Ser  Ala Ala Leu Gly Asp  His Ser Gly Asp Pro  Gly Pro Ala
    1055                 1060                 1065

Trp Asp  Thr Cys Pro Pro Leu  Pro Leu Thr Thr Leu  Ile Pro Arg
    1070                 1075                 1080

Ala Pro  Pro Pro Tyr Gly Asp  Ser Thr Ala Arg Ser  Trp Pro Ser
    1085                 1090                 1095

Arg Cys  Gly Pro Leu Gly Tyr  Ala Tyr Lys Asp Phe  Leu Trp Cys
    1100                 1105                 1110

Phe Pro  Phe Ser Leu Val Phe  Leu Gln Glu Ile Gln  Ile Cys Cys
    1115                 1120                 1125

His Val  Ser Cys Leu Cys Cys  Ile Cys Cys Ser Thr  Arg Ile Cys
    1130                 1135                 1140

Leu Gly  Cys Leu Leu Glu Leu  Phe Leu Ser Arg Ala  Leu Arg Ala
    1145                 1150                 1155

Leu His  Val Leu Trp Asn Gly  Phe Gln Leu His Cys  Gln Gly Asn
    1160                 1165                 1170

Thr Thr  Leu Gln Gln Leu Gly  Glu Ala Ser Gln Ala  Pro Ser Gly
    1175                 1180                 1185

Ser Leu  Ile Pro Leu Arg Leu  Pro Leu Leu Trp Glu  Val Arg Gly
    1190                 1195                 1200

Asn Ser  Lys Met Ala Leu Asn  Ser Leu Asn Ser Ile  Asp Asp Ala
    1205                 1210                 1215
```

-continued

Gln Leu Thr Arg Ile Ala Pro Pro Arg Ser His Cys Cys Phe Trp
1220 1225 1230

Glu Val Asn Ala Pro Phe Val Gln Gly Lys Asp Trp Gly Leu Lys
1235 1240 1245

Lys Phe Ile Arg Arg Asp Phe Glu Ala Phe Gln Arg Ala Ala Gly
1250 1255 1260

Glu Gly Gly Pro Gly Arg Gly Gly Ala Arg Arg Gly Ala Arg Val
1265 1270 1275

Leu Gln Ser Pro Phe Cys Arg Ala Gly Ala Gly Glu Trp Leu Gly
1280 1285 1290

His Gln Ser Leu Arg Trp Gly Met Glu Leu Ala Ala Ser Arg Arg
1295 1300 1305

Phe Ser Trp Asp His His Ser Ala Gly Gly Pro Pro Arg Val Pro
1310 1315 1320

Ser Val Arg Ser Gly Ala Ala Gln Val Gln Pro Lys Asp Pro Leu
1325 1330 1335

Pro Leu Arg Thr Leu Ala Gly Cys Leu Ala Arg Thr Ala His Leu
1340 1345 1350

Arg Pro Gly Ala Glu Ser Leu Pro Gln Pro Gln Leu His Cys Thr
1355 1360 1365

Ile Ala Arg Glu Leu His Gln Phe Ala Phe Asp Leu Leu Ile Lys
1370 1375 1380

Ser His Lys Met His Phe Ser Leu Lys Glu His Pro Pro Pro Pro
1385 1390 1395

Cys Pro Pro His Val Val Gly Tyr Gly His Leu Asp Thr Ser Gly
1400 1405 1410

Ser Ser Ser Ser Ser Ser Trp Pro Gln Pro Asp Ser Phe Ala Ala
1415 1420 1425

Leu His Ser Ser Leu Asn Glu Leu Gly Glu Leu Trp Phe Gln Ser
1430 1435 1440

Ser Glu Leu Ser Pro Thr Gly Ala Pro Trp Pro Ser Arg Arg Pro
1445 1450 1455

Thr Trp Arg Gly Thr Thr Val Ser Pro Arg Thr Ala Thr Ser Ser
1460 1465 1470

Ala Arg Thr Cys Cys Gly Thr Lys Trp Pro Ser Ser Gln Glu Ala
1475 1480 1485

Ala Leu Gly Leu Gly Ser Gly Leu Leu Arg Phe Ser Cys Gly Thr
1490 1495 1500

Ala Ala Ile Arg
1505

<210> SEQ ID NO 559
<211> LENGTH: 1507
<212> TYPE: PRT
<213> ORGANISM: Artificial seqeunce
<220> FEATURE:
<223> OTHER INFORMATION: Heterologous polypeptide

<400> SEQUENCE: 559

Met Gly Gln Lys Glu Gln Ile His Thr Leu Gln Lys Asn Ser Glu Arg
1 5 10 15

Met Ser Lys Gln Leu Thr Arg Ser Ser Gln Ala Val Gly Asn Thr Thr
20 25 30

Leu Gln Gln Leu Gly Glu Ala Ser Gln Ala Pro Ser Gly Ser Leu Ile
35 40 45

-continued

```
Pro Leu Arg Leu Pro Leu Leu Trp Glu Val Arg Gly Asn Ser Lys Met
    50                  55                  60

Ala Leu Asn Ser Leu Asn Ser Ile Asp Asp Ala Gln Leu Thr Arg Ile
65                  70                  75                  80

Ala Pro Pro Arg Ser His Cys Cys Phe Trp Glu Val Asn Ala Pro Phe
                85                  90                  95

Val Gln Gly Lys Asp Trp Gly Leu Lys Lys Phe Ile Arg Arg Asp Phe
            100                 105                 110

Glu Ala Phe Gln Arg Ala Ala Gly Glu Gly Gly Pro Gly Arg Gly Gly
        115                 120                 125

Ala Arg Arg Gly Ala Arg Val Leu Gln Ser Pro Phe Cys Arg Ala Gly
    130                 135                 140

Ala Gly Glu Trp Leu Gly His Gln Ser Leu Arg Trp Gly Met Glu Leu
145                 150                 155                 160

Ala Ala Ser Arg Arg Phe Ser Trp Asp His His Ser Ala Gly Gly Pro
                165                 170                 175

Pro Arg Val Pro Ser Val Arg Ser Gly Ala Ala Gln Val Gln Pro Lys
            180                 185                 190

Asp Pro Leu Pro Leu Arg Thr Leu Ala Gly Cys Leu Ala Arg Thr Ala
        195                 200                 205

His Leu Arg Pro Gly Ala Glu Ser Leu Pro Gln Pro Gln Leu His Cys
    210                 215                 220

Thr Ile Ala Arg Glu Leu His Gln Phe Ala Phe Asp Leu Leu Ile Lys
225                 230                 235                 240

Ser His Lys Met His Phe Ser Leu Lys Glu His Pro Pro Pro Pro Cys
                245                 250                 255

Pro Pro His Val Val Gly Tyr Gly His Leu Asp Thr Ser Gly Ser Ser
            260                 265                 270

Ser Ser Ser Ser Trp Pro Gln Pro Asp Ser Phe Ala Ala Leu His Ser
        275                 280                 285

Ser Leu Asn Glu Leu Gly Glu Leu Trp Phe Gln Ser Ser Glu Leu Ser
    290                 295                 300

Pro Thr Gly Ala Pro Trp Pro Ser Arg Arg Pro Thr Trp Arg Gly Thr
305                 310                 315                 320

Thr Val Ser Pro Arg Thr Ala Thr Ser Ser Ala Arg Thr Cys Cys Gly
                325                 330                 335

Thr Lys Trp Pro Ser Ser Gln Glu Ala Ala Leu Gly Leu Gly Ser Gly
            340                 345                 350

Leu Leu Arg Phe Ser Cys Gly Thr Ala Ala Ile Arg Asp Gly His Ser
        355                 360                 365

Tyr Thr Ser Lys Val Asn Cys Leu Leu Leu Gln Asp Gly Phe His Gly
    370                 375                 380

Cys Val Ser Ile Thr Gly Ala Ala Gly Arg Arg Asn Leu Ser Ile Phe
385                 390                 395                 400

Leu Phe Leu Met Leu Cys Lys Leu Glu Phe His Ala Cys Gln Trp Gln
                405                 410                 415

His Tyr His Arg Ser Gly Glu Ala Ala Gly Thr Pro Leu Trp Arg Pro
            420                 425                 430

Thr Arg Asn Val Ala Met Met Val Pro Asp Arg Gln Val His Tyr Asp
        435                 440                 445

Phe Gly Leu Lys Ile Gln Asn Lys Asn Cys Pro Asp Val Leu Arg Phe
    450                 455                 460

Leu Asp Leu Lys Val Arg Tyr Leu His Ser Val Pro Phe Arg Glu Leu
```

```
465                 470                 475                 480

Lys Asn Gln Arg Thr Ala Gln Gly Ala Pro Gly Ile His His Ala Ala
                485                 490                 495

Ser Pro Val Ala Ala Asn Leu Cys Asp Pro Ala Arg His Ala Gln His
            500                 505                 510

Thr Arg Ile Pro Cys Gly Ala Gly Gln Val Arg Ala Gly Arg Gly Pro
        515                 520                 525

Glu Ala Gly Gly Gly Val Leu Gln Pro Gln Arg Pro Ala Pro Glu Lys
    530                 535                 540

Pro Gly Cys Pro Cys Arg Arg Gly Gln Pro Arg Leu His Thr Val Lys
545                 550                 555                 560

Met Trp Arg Ala Cys His Leu Phe Leu Gln Pro Gln Val Gly Thr Pro
                565                 570                 575

Pro Pro His Thr Ala Ser Ala Arg Ala Pro Ser Gly Pro Pro His Pro
            580                 585                 590

His Glu Ser Cys Pro Ala Gly Arg Arg Pro Ala Arg Ala Ala Gln Thr
        595                 600                 605

Cys Ala Arg Arg Gln His Gly Leu Pro Gly Cys Glu Glu Ala Gly Thr
    610                 615                 620

Ala Arg Val Pro Ser Leu His Leu His Leu His Gln Ala Ala Leu Gly
625                 630                 635                 640

Ala Gly Arg Gly Arg Gly Trp Gly Glu Ala Cys Ala Gln Val Pro Pro
                645                 650                 655

Ser Arg Gly His Tyr Lys Leu Ile Gln Gln Pro Ile Ser Leu Phe Ser
            660                 665                 670

Ile Thr Asp Arg Leu His Lys Thr Phe Ser Gln Leu Pro Ser Val His
        675                 680                 685

Leu Cys Ser Ile Thr Phe Gln Trp Gly His Pro Pro Ile Phe Cys Ser
    690                 695                 700

Thr Asn Asp Ile Cys Val Thr Ala Asn Phe Cys Ile Ser Val Thr Phe
705                 710                 715                 720

Leu Lys Pro Cys Phe Leu Leu His Glu Ala Ser Ala Ser Gln Phe Lys
                725                 730                 735

Lys Phe Asp Gly Pro Cys Gly Glu Arg Gly Gly Gly Arg Thr Ala Arg
            740                 745                 750

Ala Leu Trp Ala Arg Gly Asp Ser Val Leu Thr Pro Ala Leu Asp Pro
        755                 760                 765

Gln Thr Pro Val Arg Ala Pro Ser Leu Thr Arg Ala Ala Ala Ala Val
    770                 775                 780

Gly Val Pro Gly Asp Ser Thr Arg Arg Ala Val Arg Arg Met Asn Thr
785                 790                 795                 800

Phe Cys Gly Ala Ser Ala Cys Asp Val Ser Leu Ile Ala Met Asp Ser
                805                 810                 815

Ala Thr Glu Tyr Asn Gln Lys Leu Gln Val Asn Gln Phe Ser Glu Ser
            820                 825                 830

Lys Tyr Glu Ala Gly Met Thr Leu Gly Glu Lys Phe Arg Val Gly Asn
        835                 840                 845

Cys Lys His Leu Lys Met Thr Arg Pro Thr Met Pro Ala Ile Leu Lys
    850                 855                 860

Leu Gln Lys Asn Cys Leu Leu Ser Leu Asn Ser Lys Met Ala Leu Asn
865                 870                 875                 880

Ser Glu Ala Leu Ser Val Val Ser Glu Cys Glu Glu Arg Gly Ala Ala
                885                 890                 895
```

```
Gly Ser Leu Ile Ser Cys Glu Ser Leu Tyr His Arg Glu Lys Gln Leu
            900                 905                 910

Ile Ala Met Asp Ser Ala Ile Phe Val Gln Gly Lys Asp Trp Gly Val
        915                 920                 925

Lys Lys Phe Ile Arg Arg Asp Phe Arg Thr Ala Leu Thr His Asn Gln
    930                 935                 940

Asp Phe Ser Ile Tyr Arg Leu Cys Cys Lys Arg Gly Ser Leu Cys His
945                 950                 955                 960

Ala Ser Gln Ala Arg Ser Pro Ala Phe Pro Lys Pro Val Arg Pro Leu
                965                 970                 975

Pro Ala Pro Ile Thr Arg Ile Thr Pro Gln Leu Gly Gly Gln Ser Asp
            980                 985                 990

Ser Ser Gln Pro Leu Leu Thr Thr  Gly Arg Pro Gln Gly  Trp Gln Asp
        995                 1000                1005

Gln Ala  Leu Arg His Thr Gln  Gln Ala Ser Pro Ala  Ser Cys Ala
    1010                1015                1020

Thr Ile  Thr Ile Pro Ile His  Ser Ala Ala Leu Gly  Asp His Ser
    1025                1030                1035

Gly Asp  Pro Gly Pro Ala Trp  Asp Thr Cys Pro Pro  Leu Pro Leu
    1040                1045                1050

Thr Thr  Leu Ile Pro Arg Ala  Pro Pro Pro Tyr Gly  Asp Ser Thr
    1055                1060                1065

Ala Arg  Ser Trp Pro Ser Arg  Cys Gly Pro Leu Gly  Tyr Ala Tyr
    1070                1075                1080

Lys Asp  Phe Leu Trp Cys Phe  Pro Phe Ser Leu Val  Phe Leu Gln
    1085                1090                1095

Glu Ile  Gln Ile Cys Cys His  Val Ser Cys Leu Cys  Cys Ile Cys
    1100                1105                1110

Cys Ser  Thr Arg Ile Cys Leu  Gly Cys Leu Leu Glu  Leu Phe Leu
    1115                1120                1125

Ser Arg  Ala Leu Arg Ala Leu  His Val Leu Trp Asn  Gly Phe Gln
    1130                1135                1140

Leu His  Cys Gln Gln Asn Leu  Gln Asn Gly Gly Gly  Ser Arg Ser
    1145                1150                1155

Ser Ala  Thr Leu Pro Gly Arg  Arg Arg Arg Arg Trp  Leu Arg Arg
    1160                1165                1170

Arg Arg  Gln Pro Ile Ser Val  Ala Pro Ala Gly Pro  Pro Arg Arg
    1175                1180                1185

Pro Asn  Gln Lys Pro Asn Pro  Pro Gly Gly Ala Arg  Cys Val Ile
    1190                1195                1200

Met Arg  Pro Thr Trp Pro Gly  Thr Ser Ala Phe Thr  Gly Met Glu
    1205                1210                1215

Cys Thr  Leu Gly Gln Val Gly  Ala Pro Ser Pro Arg  Arg Glu Glu
    1220                1225                1230

Asp Gly  Trp Arg Gly Gly His  Ser Arg Phe Lys Ala  Asp Val Pro
    1235                1240                1245

Ala Pro  Gln Gly Pro Cys Trp  Gly Gly Gln Pro Gly  Ser Ala Pro
    1250                1255                1260

Ser Ser  Ala Pro Pro Glu Gln  Ser Leu Leu Asp Asp  Tyr Trp Ala
    1265                1270                1275

Gln Lys  Glu Lys Ile Ser Ile  Pro Arg Thr His Leu  Cys Trp Lys
    1280                1285                1290
```

-continued

```
Phe Glu  Met Ser Tyr Thr Val  Gly Gly Pro Pro Pro  His Val His
    1295                 1300                 1305

Ala Arg  Pro Arg His Trp Lys  Thr Asp Arg Asp Tyr  Trp Ala Gln
    1310                 1315                 1320

Lys Glu  Lys Gly Ser Ser Ser  Phe Leu Arg Pro Ser  Cys Val Pro
    1325                 1330                 1335

Phe Arg  Glu Leu Lys Asn Val  Ser Val Leu Glu Gly  Leu Arg Gln
    1340                 1345                 1350

Gly Arg  Leu Gly Gly Pro Cys  Ser Cys His Cys Pro  Arg Pro Ser
    1355                 1360                 1365

Gln Ala  Arg Leu Thr Pro Val  Asp Val Ala Gly Pro  Phe Leu Cys
    1370                 1375                 1380

Leu Gly  Asp Pro Gly Leu Phe  Pro Pro Val Lys Ser  Ser Ile Thr
    1385                 1390                 1395

Glu Ile  Ser Cys Cys Thr Leu  Ser Ser Glu Glu Asn  Glu Tyr Leu
    1400                 1405                 1410

Pro Arg  Pro Glu Trp Gln Leu  Gln Tyr Glu Ala Gly  Met Thr Leu
    1415                 1420                 1425

Gly Gly  Lys Ile Leu Phe Phe  Leu Phe Leu Leu Leu  Pro Leu Ser
    1430                 1435                 1440

Pro Phe  Ser Leu Ile Phe Leu  Val Leu Gly Val Leu  Ser Gly His
    1445                 1450                 1455

Ser Gly  Ser Arg Leu Lys Arg  Ser Phe Ala Val Thr  Glu Arg Ile
    1460                 1465                 1470

Ile Thr  Gly Gly Lys Ser Thr  Cys Ser Ala Pro Gly  Pro Gln Ser
    1475                 1480                 1485

Leu Pro  Ser Thr Pro Phe Ser  Thr Tyr Pro Gln Trp  Val Ile Leu
    1490                 1495                 1500

Ile Thr  Glu Leu
    1505
```

<210> SEQ ID NO 560
<211> LENGTH: 15
<212> TYPE: PRT
<213> ORGANISM: Homo sapiens

<400> SEQUENCE: 560

```
Trp Lys Phe Glu Met Ser Tyr Thr Val Gly Gly Pro Pro Pro His
1               5                   10                  15
```

<210> SEQ ID NO 561
<211> LENGTH: 15
<212> TYPE: PRT
<213> ORGANISM: Homo sapiens

<400> SEQUENCE: 561

```
Val Gly Gly Pro Pro Pro His Val His Ala Arg Pro Arg His Trp
1               5                   10                  15
```

<210> SEQ ID NO 562
<211> LENGTH: 14
<212> TYPE: PRT
<213> ORGANISM: Homo sapiens

<400> SEQUENCE: 562

```
Pro Pro His Val His Ala Arg Pro Arg His Trp Lys Thr Asp
1               5                   10
```

<210> SEQ ID NO 563
<211> LENGTH: 15
<212> TYPE: PRT
<213> ORGANISM: Homo sapiens

<400> SEQUENCE: 563

Tyr Glu Ala Gly Met Thr Leu Gly Gly Lys Ile Leu Phe Phe Leu
1 5 10 15

<210> SEQ ID NO 564
<211> LENGTH: 15
<212> TYPE: PRT
<213> ORGANISM: Homo sapiens

<400> SEQUENCE: 564

Gly Lys Ile Leu Phe Phe Leu Phe Leu Leu Leu Pro Leu Ser Pro
1 5 10 15

<210> SEQ ID NO 565
<211> LENGTH: 16
<212> TYPE: PRT
<213> ORGANISM: Homo sapiens

<400> SEQUENCE: 565

Phe Phe Leu Phe Leu Leu Leu Pro Leu Ser Pro Phe Ser Leu Ile Phe
1 5 10 15

<210> SEQ ID NO 566
<211> LENGTH: 15
<212> TYPE: PRT
<213> ORGANISM: Homo sapiens

<400> SEQUENCE: 566

Asp Gly His Ser Tyr Thr Ser Lys Val Asn Cys Leu Leu Leu Gln
1 5 10 15

<210> SEQ ID NO 567
<211> LENGTH: 15
<212> TYPE: PRT
<213> ORGANISM: Homo sapiens

<400> SEQUENCE: 567

Val Asn Cys Leu Leu Leu Gln Asp Gly Phe His Gly Cys Val Ser
1 5 10 15

<210> SEQ ID NO 568
<211> LENGTH: 15
<212> TYPE: PRT
<213> ORGANISM: Homo sapiens

<400> SEQUENCE: 568

Gly Phe His Gly Cys Val Ser Ile Thr Gly Ala Ala Gly Arg Arg
1 5 10 15

<210> SEQ ID NO 569
<211> LENGTH: 15
<212> TYPE: PRT
<213> ORGANISM: Homo sapiens

<400> SEQUENCE: 569

Thr Gly Ala Ala Gly Arg Arg Asn Leu Ser Ile Phe Leu Phe Leu
1 5 10 15

<210> SEQ ID NO 570
<211> LENGTH: 15

<212> TYPE: PRT
<213> ORGANISM: Homo sapiens

<400> SEQUENCE: 570

Leu Ser Ile Phe Leu Phe Leu Met Leu Cys Lys Leu Glu Phe His
1 5 10 15

<210> SEQ ID NO 571
<211> LENGTH: 13
<212> TYPE: PRT
<213> ORGANISM: Homo sapiens

<400> SEQUENCE: 571

Leu Phe Leu Met Leu Cys Lys Leu Glu Phe His Ala Cys
1 5 10

<210> SEQ ID NO 572
<211> LENGTH: 15
<212> TYPE: PRT
<213> ORGANISM: Homo sapiens

<400> SEQUENCE: 572

Thr Gly Gly Lys Ser Thr Cys Ser Ala Pro Gly Pro Gln Ser Leu
1 5 10 15

<210> SEQ ID NO 573
<211> LENGTH: 15
<212> TYPE: PRT
<213> ORGANISM: Homo sapiens

<400> SEQUENCE: 573

Ala Pro Gly Pro Gln Ser Leu Pro Ser Thr Pro Phe Ser Thr Tyr
1 5 10 15

<210> SEQ ID NO 574
<211> LENGTH: 15
<212> TYPE: PRT
<213> ORGANISM: Homo sapiens

<400> SEQUENCE: 574

Ser Thr Pro Phe Ser Thr Tyr Pro Gln Trp Val Ile Leu Ile Thr
1 5 10 15

<210> SEQ ID NO 575
<211> LENGTH: 15
<212> TYPE: PRT
<213> ORGANISM: Homo sapiens

<400> SEQUENCE: 575

Ser Arg Ser Ser Ala Thr Leu Pro Gly Arg Arg Arg Arg Arg Trp
1 5 10 15

<210> SEQ ID NO 576
<211> LENGTH: 15
<212> TYPE: PRT
<213> ORGANISM: Homo sapiens

<400> SEQUENCE: 576

Asp Tyr Trp Ala Gln Lys Glu Lys Gly Ser Ser Ser Phe Leu Arg
1 5 10 15

<210> SEQ ID NO 577
<211> LENGTH: 14
<212> TYPE: PRT
<213> ORGANISM: Homo sapiens

<400> SEQUENCE: 577

Gln Lys Glu Lys Gly Ser Ser Ser Phe Leu Arg Pro Ser Cys
1 5 10

<210> SEQ ID NO 578
<211> LENGTH: 15
<212> TYPE: PRT
<213> ORGANISM: Homo sapiens

<400> SEQUENCE: 578

Val Pro Phe Arg Glu Leu Lys Asn Val Ser Val Leu Glu Gly Leu
1 5 10 15

<210> SEQ ID NO 579
<211> LENGTH: 15
<212> TYPE: PRT
<213> ORGANISM: Homo sapiens

<400> SEQUENCE: 579

Val Ser Val Leu Glu Gly Leu Arg Gln Gly Arg Leu Gly Gly Pro
1 5 10 15

<210> SEQ ID NO 580
<211> LENGTH: 15
<212> TYPE: PRT
<213> ORGANISM: Homo sapiens

<400> SEQUENCE: 580

Gln Gly Arg Leu Gly Gly Pro Cys Ser Cys His Cys Pro Arg Pro
1 5 10 15

<210> SEQ ID NO 581
<211> LENGTH: 15
<212> TYPE: PRT
<213> ORGANISM: Homo sapiens

<400> SEQUENCE: 581

Ser Cys His Cys Pro Arg Pro Ser Gln Ala Arg Leu Thr Pro Val
1 5 10 15

<210> SEQ ID NO 582
<211> LENGTH: 15
<212> TYPE: PRT
<213> ORGANISM: Homo sapiens

<400> SEQUENCE: 582

Gln Ala Arg Leu Thr Pro Val Asp Val Ala Gly Pro Phe Leu Cys
1 5 10 15

<210> SEQ ID NO 583
<211> LENGTH: 15
<212> TYPE: PRT
<213> ORGANISM: Homo sapiens

<400> SEQUENCE: 583

Val Ala Gly Pro Phe Leu Cys Leu Gly Asp Pro Gly Leu Phe Pro
1 5 10 15

<210> SEQ ID NO 584
<211> LENGTH: 13
<212> TYPE: PRT
<213> ORGANISM: Homo sapiens

<400> SEQUENCE: 584

Gly Asp Pro Gly Leu Phe Pro Pro Val Lys Ser Ser Ile
1 5 10

<210> SEQ ID NO 585
<211> LENGTH: 15
<212> TYPE: PRT
<213> ORGANISM: Homo sapiens

<400> SEQUENCE: 585

Gly Met Glu Cys Thr Leu Gly Gln Val Gly Ala Pro Ser Pro Arg
1 5 10 15

<210> SEQ ID NO 586
<211> LENGTH: 15
<212> TYPE: PRT
<213> ORGANISM: Homo sapiens

<400> SEQUENCE: 586

Val Gly Ala Pro Ser Pro Arg Arg Glu Glu Asp Gly Trp Arg Gly
1 5 10 15

<210> SEQ ID NO 587
<211> LENGTH: 15
<212> TYPE: PRT
<213> ORGANISM: Homo sapiens

<400> SEQUENCE: 587

Glu Glu Asp Gly Trp Arg Gly Gly His Ser Arg Phe Lys Ala Asp
1 5 10 15

<210> SEQ ID NO 588
<211> LENGTH: 15
<212> TYPE: PRT
<213> ORGANISM: Homo sapiens

<400> SEQUENCE: 588

His Ser Arg Phe Lys Ala Asp Val Pro Ala Pro Gln Gly Pro Cys
1 5 10 15

<210> SEQ ID NO 589
<211> LENGTH: 15
<212> TYPE: PRT
<213> ORGANISM: Homo sapiens

<400> SEQUENCE: 589

Pro Ala Pro Gln Gly Pro Cys Trp Gly Gly Gln Pro Gly Ser Ala
1 5 10 15

<210> SEQ ID NO 590
<211> LENGTH: 15
<212> TYPE: PRT
<213> ORGANISM: Homo sapiens

<400> SEQUENCE: 590

Gly Gly Gln Pro Gly Ser Ala Pro Ser Ser Ala Pro Pro Glu Gln
1 5 10 15

<210> SEQ ID NO 591
<211> LENGTH: 15
<212> TYPE: PRT
<213> ORGANISM: Homo sapiens

<400> SEQUENCE: 591

Gly Ser Ala Pro Ser Ser Ala Pro Pro Glu Gln Ser Leu Leu Asp 1 5 10 15

<210> SEQ ID NO 592
<211> LENGTH: 15
<212> TYPE: PRT
<213> ORGANISM: Homo sapiens

<400> SEQUENCE: 592

Gly Asn Thr Thr Leu Gln Gln Leu Gly Glu Ala Ser Gln Ala Pro
1 5 10 15

<210> SEQ ID NO 593
<211> LENGTH: 15
<212> TYPE: PRT
<213> ORGANISM: Homo sapiens

<400> SEQUENCE: 593

Gly Glu Ala Ser Gln Ala Pro Ser Gly Ser Leu Ile Pro Leu Arg
1 5 10 15

<210> SEQ ID NO 594
<211> LENGTH: 16
<212> TYPE: PRT
<213> ORGANISM: Homo sapiens

<400> SEQUENCE: 594

Gly Ser Leu Ile Pro Leu Arg Leu Pro Leu Leu Trp Glu Val Arg Gly
1 5 10 15

<210> SEQ ID NO 595
<211> LENGTH: 15
<212> TYPE: PRT
<213> ORGANISM: Homo sapiens

<400> SEQUENCE: 595

Glu Ala Phe Gln Arg Ala Ala Gly Glu Gly Gly Pro Gly Arg Gly
1 5 10 15

<210> SEQ ID NO 596
<211> LENGTH: 15
<212> TYPE: PRT
<213> ORGANISM: Homo sapiens

<400> SEQUENCE: 596

Glu Gly Gly Pro Gly Arg Gly Gly Ala Arg Arg Gly Ala Arg Val
1 5 10 15

<210> SEQ ID NO 597
<211> LENGTH: 15
<212> TYPE: PRT
<213> ORGANISM: Homo sapiens

<400> SEQUENCE: 597

Ala Arg Arg Gly Ala Arg Val Leu Gln Ser Pro Phe Cys Arg Ala
1 5 10 15

<210> SEQ ID NO 598
<211> LENGTH: 15
<212> TYPE: PRT
<213> ORGANISM: Homo sapiens

<400> SEQUENCE: 598

Gln Ser Pro Phe Cys Arg Ala Gly Ala Gly Glu Trp Leu Gly His
1 5 10 15

<210> SEQ ID NO 599
<211> LENGTH: 15
<212> TYPE: PRT
<213> ORGANISM: Homo sapiens

<400> SEQUENCE: 599

Cys Arg Ala Gly Ala Gly Glu Trp Leu Gly His Gln Ser Leu Arg
1 5 10 15

<210> SEQ ID NO 600
<211> LENGTH: 15
<212> TYPE: PRT
<213> ORGANISM: Homo sapiens

<400> SEQUENCE: 600

Asp Tyr Trp Ala Gln Lys Glu Lys Ile Ser Ile Pro Arg Thr His
1 5 10 15

<210> SEQ ID NO 601
<211> LENGTH: 13
<212> TYPE: PRT
<213> ORGANISM: Homo sapiens

<400> SEQUENCE: 601

Gln Lys Glu Lys Ile Ser Ile Pro Arg Thr His Leu Cys
1 5 10

<210> SEQ ID NO 602
<211> LENGTH: 15
<212> TYPE: PRT
<213> ORGANISM: Homo sapiens

<400> SEQUENCE: 602

Val Ala Met Met Val Pro Asp Arg Gln Val His Tyr Asp Phe Gly
1 5 10 15

<210> SEQ ID NO 603
<211> LENGTH: 13
<212> TYPE: PRT
<213> ORGANISM: Homo sapiens

<400> SEQUENCE: 603

Val Pro Asp Arg Gln Val His Tyr Asp Phe Gly Leu Arg
1 5 10

<210> SEQ ID NO 604
<211> LENGTH: 15
<212> TYPE: PRT
<213> ORGANISM: Homo sapiens

<400> SEQUENCE: 604

Phe Lys Lys Phe Asp Gly Pro Cys Gly Glu Arg Gly Gly Gly Arg
1 5 10 15

<210> SEQ ID NO 605
<211> LENGTH: 15
<212> TYPE: PRT
<213> ORGANISM: Homo sapiens

<400> SEQUENCE: 605

Gly Glu Arg Gly Gly Gly Arg Thr Ala Arg Ala Leu Trp Ala Arg
1 5 10 15

<210> SEQ ID NO 606

<211> LENGTH: 15
<212> TYPE: PRT
<213> ORGANISM: Homo sapiens

<400> SEQUENCE: 606

Ala Arg Ala Leu Trp Ala Arg Gly Asp Ser Val Leu Thr Pro Ala
1 5 10 15

<210> SEQ ID NO 607
<211> LENGTH: 15
<212> TYPE: PRT
<213> ORGANISM: Homo sapiens

<400> SEQUENCE: 607

Asp Ser Val Leu Thr Pro Ala Leu Asp Pro Gln Thr Pro Val Arg
1 5 10 15

<210> SEQ ID NO 608
<211> LENGTH: 15
<212> TYPE: PRT
<213> ORGANISM: Homo sapiens

<400> SEQUENCE: 608

Asp Pro Gln Thr Pro Val Arg Ala Pro Ser Leu Thr Arg Ala Ala
1 5 10 15

<210> SEQ ID NO 609
<211> LENGTH: 14
<212> TYPE: PRT
<213> ORGANISM: Homo sapiens

<400> SEQUENCE: 609

Pro Val Arg Ala Pro Ser Leu Thr Arg Ala Ala Ala Ala Val
1 5 10

<210> SEQ ID NO 610
<211> LENGTH: 15
<212> TYPE: PRT
<213> ORGANISM: Homo sapiens

<400> SEQUENCE: 610

Gly Arg Arg Arg Arg Arg Trp Leu Arg Arg Arg Arg Gln Pro Ile
1 5 10 15

<210> SEQ ID NO 611
<211> LENGTH: 15
<212> TYPE: PRT
<213> ORGANISM: Homo sapiens

<400> SEQUENCE: 611

Gly Val Pro Gly Asp Ser Thr Arg Arg Ala Val Arg Arg Met Asn
1 5 10 15

<210> SEQ ID NO 612
<211> LENGTH: 13
<212> TYPE: PRT
<213> ORGANISM: Homo sapiens

<400> SEQUENCE: 612

Asp Ser Thr Arg Arg Ala Val Arg Arg Met Asn Thr Phe
1 5 10

<210> SEQ ID NO 613
<211> LENGTH: 15
<212> TYPE: PRT

<213> ORGANISM: Homo sapiens

<400> SEQUENCE: 613

Arg Arg Arg Arg Gln Pro Ile Ser Val Ala Pro Ala Gly Pro Pro
1 5 10 15

<210> SEQ ID NO 614
<211> LENGTH: 15
<212> TYPE: PRT
<213> ORGANISM: Homo sapiens

<400> SEQUENCE: 614

Val Ala Pro Ala Gly Pro Pro Arg Arg Pro Asn Gln Lys Pro Asn
1 5 10 15

<210> SEQ ID NO 615
<211> LENGTH: 15
<212> TYPE: PRT
<213> ORGANISM: Homo sapiens

<400> SEQUENCE: 615

Thr Glu Ile Ser Cys Cys Thr Leu Ser Ser Glu Glu Asn Glu Tyr
1 5 10 15

<210> SEQ ID NO 616
<211> LENGTH: 16
<212> TYPE: PRT
<213> ORGANISM: Homo sapiens

<400> SEQUENCE: 616

Ser Ser Glu Glu Asn Glu Tyr Leu Pro Arg Pro Glu Trp Gln Leu Gln
1 5 10 15

<210> SEQ ID NO 617
<211> LENGTH: 15
<212> TYPE: PRT
<213> ORGANISM: Homo sapiens

<400> SEQUENCE: 617

Arg Pro Asn Gln Lys Pro Asn Pro Pro Gly Gly Ala Arg Cys Val
1 5 10 15

<210> SEQ ID NO 618
<211> LENGTH: 15
<212> TYPE: PRT
<213> ORGANISM: Homo sapiens

<400> SEQUENCE: 618

Pro Gly Gly Ala Arg Cys Val Ile Met Arg Pro Thr Trp Pro Gly
1 5 10 15

<210> SEQ ID NO 619
<211> LENGTH: 15
<212> TYPE: PRT
<213> ORGANISM: Homo sapiens

<400> SEQUENCE: 619

His Val Val Gly Tyr Gly His Leu Asp Thr Ser Gly Ser Ser Ser
1 5 10 15

<210> SEQ ID NO 620
<211> LENGTH: 16
<212> TYPE: PRT
<213> ORGANISM: Homo sapiens

<400> SEQUENCE: 620

Tyr Gly His Leu Asp Thr Ser Gly Ser Ser Ser Ser Ser Ser Trp Pro
1 5 10 15

<210> SEQ ID NO 621
<211> LENGTH: 12
<212> TYPE: PRT
<213> ORGANISM: Homo sapiens

<400> SEQUENCE: 621

Met Arg Pro Thr Trp Pro Gly Thr Ser Ala Phe Thr
1 5 10

<210> SEQ ID NO 622
<211> LENGTH: 32363
<212> TYPE: DNA
<213> ORGANISM: Artificial sequence
<220> FEATURE:
<223> OTHER INFORMATION: GAd20

<400> SEQUENCE: 622
catcatcaat aatatacctt attttggatt gaggccaata tgataatgag gtgggcgggg 60
cgaggcgggg cgggtgacgt aggacgcgcg agtagggttg ggaggtgtgg cggaagtgtg 120
gcatttgcaa gtgggaggag ctgacatgca atcttccgtc gcggaaaatg tgacgttttt 180
gatgagcgcc gcctacctcc ggaagtgcca attttcgcgc gcttttcacc ggatatcgta 240
gtaattttgg gcgggaccat gtaagatttg gccattttcg cgcgaaaagt gaaacgggga 300
agtgaaaact gaataatagg gcgttagtca tagcgcgtaa tatttaccga gggccgaggg 360
actttgaccg attacgtgga ggactcgccc aggtgttttt tacgtgaatt tccgcgttcc 420
gggtcaaagt ctccgttttt attgtcgccg tcatctgacg cggagggtat ttaaacccgc 480
tgcgctccta aagaggccac tcttgagtgc cagcgagaag agttttctcc tccgctccgt 540
ttcggcgatc gaaaaatgag acatttagcc tgcactccgg gtcttttgtc cggccgggcg 600
gcgtccgagc ttttggacgc tttgctcaat gaggttctga gcgatgattt tccgtctact 660
acccacttta gcccacctac tcttcacgaa ctgtacgatc tggatgtact ggtggatgtg 720
aacgatccca acgaggaggc ggtttctacg ttttttcccg agtctgcgct tttggctgcc 780
caggagggat ttgacctaca cactccgccg ctgcctattt tagagtctcc gctgccggag 840
cccagtggta taccttatat gcctgaactg cttcccgaag tggtagacct gacctgccac 900
gagccgggct ttccgcccag cgacgatgag ggtgagcctt ttgctttaga ctatgctgag 960
atacctgggc tcggttgcag gtcttgtgca tatcatcaga gggttaccgg agaccccgag 1020
gttaagtgtt cgctgtgcta tatgaggctg acctcttcct ttatctacag taagtttttt 1080
tgtgtaggtg ggctttttgg gtaggtgggt tttgtggcag gacaggtgta aatgttgctt 1140
gtgtttttg tacctgcagg tccggtgtcc gagccagacc cggagcccga ccgcgatccc 1200
gagccggatc ccgagcctcc tcgcaggcca aggaaattac cttccatttt gtgcaagcct 1260
aagacacctg tgaggaccag cgaggcggac agcactgact ctggcacttc tacctctcct 1320
cctgaaattc acccagtggt tcctctgggt atacatagac ctgttgctgt tagagtttgc 1380
gggcgacgcc ctgcagtaga gtgcattgag gacttgctta acgatcccga gggacctttg 1440
gacttgagca ttaaacgccc taggcaataa accccaccta agtaataaac cccacctaag 1500
taataaactt taccgccctt ggttattgag atgacgccca atgtttgctt ttgaatgact 1560
tcatgtgtat aataaaagtg agtgtggtca taggtctctt gtttgtctgg gcggggttta 1620
agggtatata agtttctcgg ggctaaactt ggttacactt gaccccaatg gaggcgtggg 1680
ggtgcttgga ggagtttgcg gacgtgcgcc gtttgctgga cgagagctct agcaatacct 1740
atagtatttg gaggtatctg tggggctcta ctcaggccaa gttggtcttc agaattaagc 1800
aggattacaa gtgcgatttt gaagagcttt ttagttcctg tggtgagctt ttgcaatcct 1860
tgaatctggg ccaccaggct atcttccagg aaaaggttct ctcgactttg gatttttcca 1920
ctcccgggcg caccgccgct tgtgtggctt ttgtgtcttt tgtgcaagat aaatggagcg 1980
gggagaccca cctgagtcac ggctacgtgc tggatttcat ggcgatggct ctttggaggg 2040
cttacaacaa atggaagatt cagaaggaac tgtacggttc cgccctacgt cgtccacttc 2100
tgcagcggca ggggctgatg tttcccgacc atcgccagca tcagaatctg gaagacgagc 2160
gagcggagaa gatcagcttg agagccggcc tggaccctcc tcaggaggaa tgaatctccc 2220
gcaggtggtt gagctgtttc ccgaactgag acgggtcctg actatcaggg aggatggtca 2280
gtttgtgaag aagctgaaga gggatcgggg tgagggagat gatgaggcgg ctagcaattt 2340
agcttttagt ctgataactc gccaccgacc ggaatgtatt acctatcagc agattaagga 2400
gagttgtgcc aacgagctgg atcttttggg tcagaagtat agcatagaac agcttaccac 2460
ttactggctt cagcccgggg atgattggga agaggcgatt agggtgtatg caaaggtggc 2520
cctgcggccc gattgcaagt ataagattac taagttggtt aatattagaa actgctgcta 2580
tatttctgga aacggggccg aagtggagat agatactgag gacagggtgg ctattaggtg 2640
ttgcatgata aacatgtggc ccgggatact ggggatggat ggggtgatat ttatgaatgt 2700
gaggttcacg ggccccaact ttaatggtac ggtgttcatg ggcaacacca acttgctcct 2760
gcatggtgcg agtttctatg ggtttaacaa cacctgtata gaggcctgga ccgatgtaaa 2820
ggttcgaggt tgttcctttt atagctgttg gaaggcggtg gtgtgtcgcc ctaaaagcag 2880
gggttctgtg aagaaatgct tgtttgaaag gtgcaccct a ggtatccttt ctgagggcaa 2940
ctccagggtg cgccataatg tggcttcgaa ctgcggttgc ttcatgcaag tgaagggggt 3000
gagcgttatc aagcataact cggtctgtgg aaactgcgag gatcgcgcct ctcagatgct 3060
gacctgcttt gatggcaact gtcacctgtt gaagaccatt catataagca gtcaccccag 3120
aaaggcctgg cccgtgtttg agcataacat tctgacccgc tgttccttgc atctgggggt 3180
caggaggggt atgttcctgc cttaccagtg taactttagc cacactaaaa tcctgctgga 3240
acccgagtgc atgactaagg tcagcctgaa tggtgtgttt gatgtgagtc tgaagatttg 3300
gaaggtgctg aggtatgatg agaccaggac caggtgccga ccctgcgagt gcggcggcaa 3360
gcacatgaga aatcagcctg tgatgttgga tgtgaccgag gagcttaggc ctgaccatct 3420
ggtgctggcc tgcaccaggg ccgagtttgg gtctagcgat gaggataccg attgaggtgg 3480
gtaaggtggg cgtggctagc agggtgggcg tgtataaatt gggggtctaa ggggtctctc 3540
tgtttgtctt gcaacagccg ccgccatgag cgacaccggc aacagctttg atggaagcat 3600
ctttagtccc tatctgacag tgcgcatgcc tcactgggcc ggagtgcgtc agaatgtgat 3660
gggttccaac gtggatggac gtcccgttct gccttcaaat tcgtctacta tggcctacgc 3720
gaccgtggga ggaactccgc tggacgccgc gacctccgcc gccgcctccg ccgccgccgc 3780
gaccgcgcgc agcatggcta cggaccttta cagctctttg gtggcgagca gcgcggcctc 3840
tcgcgcgtct gctcgggatg agaaactgac tgctctgctg cttaaactgg aagacttgac 3900
ccgggagctg ggtcaactga cccagcaggt ttccagcttg cgtgagagca gccttgcctc 3960

-continued

```
cccctaatgg cccataatat aaataaaagc cagtctgttt ggattaagca agtgtatgtt   4020
ctttatttaa ctctccgcgc gcggtaagcc cgggaccagc ggtctcggtc gtttagggtg   4080
cggtggattt tttccaacac gtggtacagg tggctctgga tgtttagata catgggcatg   4140
agtccatccc tggggtggag gtagcaccac tgcagagctt cgtgctcggg ggtggtgttg   4200
tatatgatcc agtcgtagca ggagcgctgg gcgtggtgct gaaaaatgtc cttaagcaag   4260
aggcttatag ctagggggag gcccttggtg taagtgttta caaatctgct tagctgggag   4320
gggtgcatcc gggggggatat gatgtgcatc ttggactgga tttttaggtt ggctatgttc   4380
ccgcccagat cccttctggg attcatgttg tgcaggacca ccagcacggt atatccagtg   4440
cacttgggaa atttatcgtg gagcttagac gggaatgcat ggaagaactt ggagacgccc   4500
ttgtggcctc ccagattttc catacattcg tccatgatga tggcaatggg cccgtgggaa   4560
gctgcctgag caaaaacgtt tctggcatcg ctcacatcgt agttatgttc cagggtgagg   4620
tcatcatagg acatctttac gaatcggggg cgaagggtcc cggactgggg gatgatggta   4680
ccctcgggcc ccgggggcgta gttcccctca cagatctgca tctcccaggc tttcatttca   4740
gagggaggga tcatatccac ctgcggggcg atgaaaaaga cagtttctgg cgcaggggag   4800
attaactggg atgagagcag gtttctgagc agctgtgact ttccacagcc ggtgggccca   4860
tatatcacgc ctatcaccgg ctgcagctgg tagttaagag agctgcagct gccgtcctcc   4920
cggagcaggg gggccacctc gttgagcata tccctgacgt ggatgttctc cctgaccagt   4980
tccgccagaa ggcgctcgcc gcccagcgaa agcagctctt gcaaggaagc aaaatttttc   5040
agcggtttca ggccatcggc cgtgggcatg tttttcagcg tctgggtcag cagctccagc   5100
ctgtcccaga gctcggtgat gtgctctacg gcatctcgat ccagcagatc tcctcgtttc   5160
gcgggttggg gcggctttcg ctgtagggca ccagccgatg ggcgtccagc ggggccagag   5220
tcatgtcctt ccatgggcgc agggtcctcg tcagggtggt ctgggtcacg gtgaaggggt   5280
gcgctccggg ttgggcactg gccagggtgc gcttgaggct ggttctgctg gtgctgaatc   5340
gctgccgctc ttcgccctgc gcgtcggcca ggtagcattt gaccatggtc tcgtagtcga   5400
gaccctcggc ggcgtgcccc ttggcgcgga gctttccctt ggaggtggcg ccgcacgagg   5460
ggcactgcag gctcttcagg gcgtagagct tgggagcgag aaacacggac tctggggagt   5520
aggcgtccgc gccgcaggcc gagcagaccg tctcgcattc caccagccaa gtgagttccg   5580
ggcggtcagg gtcaaaaacc aggttgcccc catgcttttt gatgcgtttc ttaccttggc   5640
tctccatgag gcggtgtccc ttctcggtga cgaagaggct gtccgtgtcc ccgtagaccg   5700
acttcagggg cctgtcttcc agcggagtgc ctctgtcctc ctcgtagaga aactctgacc   5760
actctgagac gaaggcccgc gtccaggcca ggacgaagga ggccacgtgg gaggggtagc   5820
ggtcgttgtc cactagcggg tccaccttct ccagggtgtg caggcacatg tccccctcct   5880
ccgcgtccag aaaagtgatt ggcttgtagg tgtaggacac gtgaccgggg gttcccaacg   5940
gggggtata aaaggggggtg ggtgcccttt catcttcact ctcttccgca tcgctgtctg   6000
cgagagccag ctgctggggt aagtattccc tctcgaaggc gggcatgacc tcagcgctca   6060
ggttgtcagt ttctaaaaat gaggaggatt tgatgttcac ctgtccggag gtgatacctt   6120
tgagggtacc tgggtccatc tggtcagaaa acactatttt tttgttatca agcttggtgg   6180
cgaatgaccc gtagagggcg ttggagagca gcttggcgat ggagcgcagg gtctggtttt   6240
tgtcgcggtc ggctcgctcc ttggccgcga tgttgagttg cacgtactcg cgggccacgc   6300
acttccactc ggggaacacg gtggtgcgct cgtctgggat caggcgcacc ctccagccgc   6360
```

ggttgtgcag ggtgaccatg tcgacgctgg tggcgacctc accgcgcaga cgctcgttgg 6420
tccagcagag gcggccgccc ttgcgcgagc agaagggggg tagggggtcc agctggtcct 6480
cgtttggggg gtccgcgtcg atggtaaaga ccccggggag caggcgcggg tcaaagtagt 6540
cgatcttgca agcttgcatg tccagagccc gctgccattc gcgggcggcg agcgcgcgct 6600
cgtaggggtt gaggggcggg ccccagggca tggggtgggt gagcgcggag gcgtacatgc 6660
cgcagatgtc atacacgtac aggggttccc tgaggatacc gaggtaggtg gggtagcagc 6720 gcccccccgcg gatgctggcg cgcacgtagt catagagctc gtgggagggg gccagcatgt 6780
tgggcccgag gttggtgcgc tgggggcgct cggcgcggaa gacgatctgc ctgaagatgg 6840
cgtgggagtt ggaggagatg gtgggccgct ggaagacgtt gaagcttgct tcttgcaagc 6900
ccacggagtc cctgacgaag gaggcgtagg actcgcgcag cttgtgcacc agctcggcgg 6960
tgacctggac gtcgagcgca cagtagtcga gggtctcgcg gatgatgtca tacctatcct 7020 ccccccttctt tttccacagc tcgcggttga ggacgaactc ttcgcggtct ttccagtact 7080
cttggagggg aaacccgtcc gtgtccgaac ggtaagagcc tagcatgtag aactggttga 7140
cggcctggta ggggcagcag cccttctcca cgggcagcgc gtaggcctgc gccgccttgc 7200
ggagggaggt gtgggtgagg gcgaaagtgt ccctgaccat gactttgagg tattgatgtc 7260
tgaagtctgt gtcatcgcag ccgccctgtt cccacagggt gtagtccgtg cgctttttgg 7320
agcgcgggtt gggcagggag aaggtgaggt cattgaagag gatcttcccc gctcgaggca 7380
tgaagtttct ggtgatgcga aagggccctg ggaccgagga gcggttgttg atgacctggg 7440
cggccaggac gatctcgtca aagccgttta tgttgtgtcc cacgatgtag agctccagga 7500
agcggggctg gcccttgatg gaggggagct ttttaagttc ctcgtaggta agctcctcgg 7560
gcgattccag gccgtgctcc tccagggccc agtcttgcaa gtgagggttg gccgccagga 7620
aggatcgcca gaggtcgcgg gccatgaggg tctgcaggcg gtcgcggaag gttctgaact 7680
gccgccccac ggccattttt tcgggggtga tgcagtagaa ggtgaggggg tctttctccc 7740
aggggtccca tctgagctct cgggcgaggt cgcgcgcggc agcgaccaga gcctcgtcgc 7800
cccccagttt catgaccagc atgaagggca cgagttgctt gccaaaggct cccatccaag 7860
tgtaggtttc tacatcgtag gtgacaaaga ggcgctccgt gcgaggatga gagccgattg 7920
ggaagaactg gatctcccgc caccagttgg aggattggct gttgatgtgg tgaaagtaga 7980
agtcccgtct gcgggccgag cactcgtgct ggcttttgta aaagcgaccg cagtactggc 8040
agcgctgcac gggttgtata tcttgcacga ggtgaacctg gcgacctctg acgaggaagc 8100
gcagcgggaa tctaagtccc ccgcctgggg tcccgtgtgg ctggtggtct tttactttgg 8160
ttgtctggcc gccagcatct gtctcctgga gggcgatggt ggaacagacc accacgccgc 8220
gagagccgca ggtccagatc tcggcgctcg gcgggcggag tttgatgacg acatcgcgca 8280
cattggagct gtccatggtc tccagctccc gcggcggcag gtcagccggg agttcctgga 8340
ggttcacctc gcagagacgg gtcaaggcgc ggacagtgtt gagatggtat ctgatttcaa 8400
ggggcatgtt ggaggcggag tcgatggctt gcaggaggcc gcagccccgg ggggccacga 8460
tggttccccg cggggcgcga ggggaggcgg aagctggggg tgtgttcaga agcggtgacg 8520
cgggcgggcc cccggaggta gggggggttc cggccccaca ggcatgggcg gcaggggcac 8580
gtcttcgccg cgcgcgggca ggggctggtg ctggctccga agagcgcttg cgtgcgcgac 8640
gacgcgacgg ttggtgtcct gtatctggcg cctctgagtg aagaccacgg gtcccgtgac 8700

```
cttgaacctg aaagagagtt cgacagaatc aatctcggca tcgttgacag cggcctggcg   8760
caggatctcc tgcacgtcgc ccgagttgtc ctggtaggcg atttctgcca tgaactgctc   8820
gatctcttcc tcctggagat ctcctcgtcc ggcgcgctcc acggtggccg ccaggtcgtt   8880
ggagatgcga cccatgagct gcgagaaggc gttgagtccg ccctcgttcc agacccggct   8940
gtagaccacg ccccccctcgg cgtcgcgggc gcgcatgacc acctgggcca ggttgagctc   9000
cacgtgtcgc gtgaagacgg cgtagttgcg caggcgctgg aaaaggtagt tcagggtggt   9060
ggcggtgtgc tcggcgacga agaagtacat gacccagcgc cgcaacgtgg attcattgat   9120
gtcccccaag gcctccaggc gctccatggc ctcgtagaag tccacggcga agttgaaaaa   9180
ctgggagttg cgagcggaca cggtcaactc ctcctccaga agacggatga gctcggcgac   9240
agtgtcgcgc acctcgcgct cgaaggccac ggggggcgct tcttcctctt ccacctcttc   9300
ttccatgatt gcttcttctt cttcctcagc cgggacggga gggggcggcg gcgggggagg   9360
ggcgcggcgg cggcggcggc gcaccgggag gcggtcgatg aagcgctcga tcatctcccc   9420
ccgcatgcgg cgcatggtct cggtgacggc gcggccgttc tcccgggggc gcagctcgaa   9480
gacgccgcct ctcatttcgc cgcggggcgg gcggccgtga ggtagcgaga cggcgctgac   9540
tatgcatctt aacaattgct gtgtaggtac gccgccaagg gacctgattg agtccagatc   9600
caccggatcc gaaaaccttt ggaggaaagc gtctatccag tcgcagtcgc aaggtaggct   9660
gagcaccgtg gcgggcgggg gcgggtcggg agagttcctg gcggagatgc tgctgatgat   9720
gtaattaaag taggcggtct tgagaaggcg gatggtggac aggagcacca tgtctttggg   9780
tccggcctgt tggatgcgga ggcggtcggc catgccccag gcctcgttct gacaccggcg   9840
caggtctttg tagtaatctt gcatgagtct ttccaccggc acttcttctc cttcctcttc   9900
ttcatctcgc cggtggtttc tcgcgccgcc catgcgcgtg accccaaagc ccctgagcgg   9960
ctgcagcagg gccaggtcgg cgaccacgcg ctcggccaag atggcctgct gtacctgagt  10020
gagggtcctc tcgaagtcat ccatgtccac gaagcggtgg taggcacccg tgttgatggt  10080
gtaggtgcag ttggccatga cggaccagtt gacggtctgg tgtcccggct gcgagagctc  10140
cgtgtaccgc aggcgcgaga aggcgcggga atcgaacacg tagtcgttgc aagtccgcac  10200
cagatactgg tagcccacca ggaagtgcgg cggaggttgg cgatagaggg gccagcgctg  10260
ggtggcgggg gcgccgggcg ccaggtcttc cagcatgagg cggtggtatc cgtagatgta  10320
cctggacatc caggtgatgc ctgcggcggt ggtggtggcg cgcgcgtagt cgcggacccg  10380
gttccagatg tttcgcaggg gcgagaagtg ttccatggtc ggcacgctct ggccggtgag  10440
gcgcgcgcag tcgttgacgc tctatacaca cacaaaaacg aaagcgttta cagggctttc  10500
gttctgtagc ctggaggaaa gtaaatgggt tgggttgcgg tgtgccccgg ttcgagacca  10560
agctgagctc agccggctga agccgcagct aacgtggtat tggcagtccc gtctcgaccc  10620
aggccctgta tcctccagga tacggtcgag agccctttttg ctttcttggc caagcgcccg  10680
tggcgcgatc tgggatagat ggtcgcgatg agaggacaaa agcggctcgc ttccgtagtc  10740
tggagaaaca atcgccaggg ttgcgttgcg gcgtaccccg gttcgagccc ctatggcggc  10800
ttggatcggc cggaaccgcg gctaacgtgg gctgtggcag ccccgtcctc aggaccccgc  10860
cagccgactt ctccagttac gggagcgagc cccttttgtt tttttatttt ttagatgcat  10920
cccgtgctgc ggcagatgcg cccctcgccc cggcccgatc agcagcagca acagcaggca  10980
tgcagacccc cctctcctct ccccgccccg gtcaccacgg ccgcggcggc cgtgtccggt  11040
gcggggggcg cgctggagtc agatgagcca ccgcggcggc gacctaggca gtatctggac  11100
```

-continued ttggaagagg gcgagggact ggcgcggctg gggcgagct ctccagagcg ccacccgcgg 11160
gtgcagttga aaagggacgc gcgtgaggcg tacctgccgc ggcaaaacct gtttcgcgac 11220
cgcgggggcg aggagcccga ggagatgcgg gactgcaggt tccaagcggg gcgcgagctg 11280
cgccgcggct tggacagaca gcgcctgctg cgcgaggagg actttgagcc cgacacgcag 11340
acgggcatca gccccgcgcg cgcgcacgtg gccgcggccg acctggtgac cgcctacgag 11400
cagacggtga accaggagcg caacttccaa aaaagcttca acaaccacgt gcgcacgctg 11460
gtggcgcgcg aggaggtgac cctgggtctc atgcatctgt gggacctggt ggaggcgatc 11520
gtgcagaacc ccagcagcaa gcccctgacc gcgcagctgt tcctggtggt gcagcacagc 11580
agggacaacg aggccttcag ggaggcgctg ctgaacatca ccgagccgga ggggcgctgg 11640
ctcctggacc tgataaacat cctgcagagc atagtggtgc aggagcgcag cctgagcctg 11700
gccgagaagg tggcggccat taactattct atgctgagcc tgggcaagtt ctacgctcgc 11760
aagatctaca agacccccta cgtgcccata gacaaggagg tgaagataga cagcttctac 11820
atgcgcatgg cgctgaaggt gctaaccctg agcgacgacc tgggagtgta ccgcaacgag 11880
cgcatccaca aggccgtgag cgccagccgg cggcgcgagc tgagcgaccg cgaactgatg 11940
cacagtctgc agcgcgcgct gaccggcgcg ggcgagggcg acagggaggt cgagtcctac 12000
tttgacatgg gggccgacct gcactggcag ccgagccgcc gcgccctgga agcggcgggg 12060
gcgtacggcg gccccctggc ggccgatgac gaggaagagg aggactatga gctagaggag 12120
ggcgagtacc tggaggactg acctggctgg tggtgttttg gtatagatgc aagatccgaa 12180
cgtggcggac ccggcggtcc gggcggcgct gcagagccag ccgtccggca ttaactcctc 12240
tgacgactgg gccgcggcca tgggtcgcat catggccctg accgcgcgca accccgaggc 12300
cttcaggcag cagcctcagg ctaaccggct ggcggccatc ttggaagcgg tagtgcccgc 12360
gcgctccaac ccccacccacg agaaggtgct ggccatagtc aacgcgctgg cggagagcag 12420
ggccatccgg gcagacgagg ccggactggt gtacgatgcg ctgctgcagc gggtggcgcg 12480
gtacaacagc ggcaacgtgc agaccaacct ggaccgcctg gtgacggacg tgcgcgaggc 12540
cgtggcgcag cgcgagcgct tgcatcagga cggcaacctg ggctcgctgg tggcgctaaa 12600
cgccttcctt agcacccagc cggccaacgt accgcggggg caggaggact acaccaactt 12660
cttgagcgcg ctgcggctga tggtgaccga ggtccctcag agcgaggtgt accagtcggg 12720
gcccgactac ttcttccaga ccagcagaca gggcttgcaa accgtgaacc tgagccaggc 12780
tttcaagaac ctgcgggggc tgtggggagt gaaggcgccc accggcgacc gggctacggt 12840
gtccagcctg ctaaccccca actcgcgcct gctgctgctg ctgatcgcgc ccttcacgga 12900
cagcgggagc gtctcgcggg agacctatct gggccacctg ctgacgctgt accgcgaggc 12960
catcgggcag gcgcaggtgg acgagcacac cttccaggag atcaccagcg tgagccacgc 13020
gctggggcag gaggacacgg gcagcctgca ggcgaccctg aactacctgc tgaccaacag 13080
gcggcagaag attcccacgc tgcacagcct gacccaggag gaggagcgca tcttgcgcta 13140
cgtgcagcag agcgtgagcc tgaacctgat gcgcgacggc gtgacgccca gcgtggcgct 13200
ggacatgacc gcgcgcaaca tggaaccggg catgtacgct tcccagcggc cgttcatcaa 13260
ccgcctgatg gactacttgc atcgggcggc ggccgtgaac cccgagtact tcaccaatgc 13320
cattctgaat ccccactgga tgccccctcc gggtttctac aacggggact tcgaggtgcc 13380
tgaggtcaac gatgggttcc tctgggatga catggatgac agtgtgttct cccccaaccc 13440

-continued

```
gctgcgcgcc gcgtctctgc gattgaagga gggctctgac agggaaggac caaggagtct  13500
ggcctcctcc ctggctctgg gggcggtggg cgccacgggc gcggcggcgc ggggcagcag  13560
ccccttcccc agcctggcgg actctctgaa tagcgggcgg gtgagcaggc cccgcttgct  13620
aggcgaggag gagtatctga acaactccct gctgcagccc gtgagggaca aaaacgctca  13680
gcggcagcag tttcccaaca atgggataga gagcctggtg gacaagatgt ccagatggaa  13740
gacgtatgcg caggagtaca aggagtggga ggaccgccag ccgcggcccc tgccgccccc  13800
tagacagcgc tggcagcggc gcgcgtccaa ccgccgctgg aggcaggggc ccgaggacga  13860
tgatgactct gcagatgaca gcagcgtgtt ggacctgggc gggagcggga accccttttc  13920
gcacctgcgc ccacgcctgg gcaagatgtt ttaaaagaga aaaataaaaa ctcaccaagg  13980
ccatggcgac gagcgttggt tttttgttcc cttccttagt atgcggcgcg cggcgatgtt  14040
cgaggagggg cctcccccct cttacgagag cgcgatggga atttctcctg cggcgcccct  14100
gcagcctccc tacgtgcctc ctcggtacct gcaacctaca gggggggagaa atagcatctg  14160
ttactctgag ctgcagcccc tgtacgatac caccagactg tacctggtgg acaacaagtc  14220
cgcggacgtg gcctccctga actaccagaa cgaccacagc gatttttga ccacggtgat  14280
ccaaaacaac gacttcaccc caaccgaggc cagtacccag accataaacc tggacaacag  14340
gtcgaactgg ggcggcgacc tgaagactat cctgcacacc aatatgccca acgtgaacga  14400
gttcatgttc accaactctt ttaaggcgcg ggtgatggtg gcgcgcgagc agggggaggc  14460
gaagtacgag tgggtggact tcacgctgcc cgagggcaac tactcagaga ccatgactct  14520
cgacctgatg aacaatgcga tcgtggaaca ctatctgaaa gtgggcaggc agaacggggt  14580
gaaggagagc gatatcgggg tcaagtttga caccagaaac ttccgtctgg gctgggaccc  14640
tgtgaccggg ctggtcatgc cgggggtcta caccaacgag gcctttcatc ccgatatagt  14700
gctcctgccc ggctgtgggg tggacttcac ccagagccgg ctgagcaacc tgctgggcgt  14760
tcgcaagcgg caacctttcc aggagggttt caagatcacc tatgaggatc tggagggggg  14820
caacattccc gcgctccttg atctggacgc ctacgaggag agcttgaaac ccgaggagag  14880
cgctggcgac agcggcgaga gtggcgagga gcaagccggc ggcggcggca gcgcgtcggt  14940
agaaaacgaa agtactcccg cagtggcggc ggacgctgcg gaggtcgagc cggaggccat  15000
gcagcaggac gcagaggagg gcgcgcagga ggacatgaac aatggggaga tcaggggcga  15060
cactttcgcc acccggggcg aagaaaaaga ggcagaggcg gcggcggcga cggcggaagc  15120
cgaaaccgag gcagaggcag agcccgagac cgaagttatg gaagacatga atgatggaga  15180
acgtaggggt gacacgtttg ccacccgggg cgaagagaag gcggcggagg cagaagccgc  15240
ggctgaggag gcggctgcgg ctgcggccaa ggctgaggct gcggctgagg ctaaggtcga  15300
agccgatgtt gcggttgagg ctcaggctga ggaggaggcg gcggctgaag cagttaagga  15360
aaaggcccag gcagagcagg aagagaaaaa acctgtcatt caacctctaa aagaagatag  15420
caaaaagcgc agttacaacg tcattgaggg cagcaccttt acccaatacc gcagctggta  15480
cctggcttac aactacggcg acccggtcaa gggggtgcgc tcgtggaccc tgctctgcac  15540
gccggacgtc acctgcggct ccgagcagat gtactggtcg ctgccaaaca tgatgcaaga  15600
cccggtgacc ttccgttcca cgcggcaggt tagcaacttt ccggtggtgg gcgccgaact  15660
gctgccagta cactccaaga gtttttacaa cgagcaggcc gtctactccc agctgatccg  15720
ccaggccacc tctctgaccc acgtgttcaa tcgctttccc gagaaccaga ttttggcgcg  15780
cccgccggcc cccaccatca ccaccgtcag tgaaaacgtt cctgccctca cagatcacgg  15840
```

-continued

```
gacgctaccg ctgcgcaaca gcatctcagg agtccagcga gtgaccatta ctgacgccag  15900
acgccggacc tgcccctacg tttacaaggc cttgggcata gtctcgccgc gcgtcctctc  15960
cagtcgcact ttttaaaaca catccaccca cacgctccaa aatcatgtcc gtactcatct  16020
cgcccagcaa caacaccggc tgggggctgc gcgcacccag caagatgttt ggaggggcaa  16080
ggaagcgctc cgaccagcac cccgtgcgcg tgcgcggcca ctaccgcgcg ccctggggtg  16140
cgcacaagcg cgggcgcaca gggcgcacca ctgtggatga tgtcattgac tccgtagtgg  16200
agcaggcgcg ccactacaca cccggcgcgc cgaccgcctc cgccgtgtcc accgtggacc  16260
aggcgatcga aagcgtggta caggggggcgc ggcactatgc caaccttaaa agtcgccgcc  16320
gccgcgtggc gcgccgccat cgccggagac cccgggctac tgccgccgcg cgccttacca  16380
aggctctgct caagcgcgcc aggcgaactg gccaccgggc cgccatgagg gccgcacggc  16440
gggctgccgc tgccgcgagc gccgtggccc cgcgggcacg aaggcgcgcg gccgctgccg  16500
ccgccgccgc catttccagc ttggcctcga cgcggcgcgg taacatatac tgggtgcgcg  16560
actcggtgag cggcacacgt gtgcccgtgc gctttcgccc cccacggaat tagcacaaga  16620
caacatacac actgagtctc ctgctgttgt gtatcccagc ggcgaccgtc agcagcggcg  16680
acatgtccaa gcgcaaaatt aaagaagaga tgctccaggt catcgcgccg gagatctatg  16740
ggccccccgaa gaaggaggag gaggattaca agccccgcaa gctaaagcgg gtcaaaaaga  16800
aaaagaaaga tgatgacgtt gacgaggcgg tggagtttgt ccgccgcatg gcgcccaggc  16860
gccctgtgca gtggaagggt cggcgcgtgc agcgagtcct gcgccccggc accgcggtgg  16920
tctttacgcc cggcgagcgt tccacgcgca ctttcaagcg ggtgtacgat gaggtgtacg  16980
gcgacgagga tctgttggag caggccaacc atcgatttgg ggagtttgca tatgggaaac  17040
ggcctcgcga gagtctaaaa gaggacctgc tggcgctacc gctggacgag ggcaatccca  17100
ccccgagtct gaagccggtg accctgcaac aggtgctgcc tttgagcgcg cccagcgagc  17160
agaagcgagg gttaaagcgc gagggcgggg acctggcacc caccgtgcag ttgatggtgc  17220
ccaagcggca gaagctggag gacgtgctgg agaaaatgaa agtagagccc gggatccagc  17280
ccgagatcaa ggtccgccct atcaagcagg tggcgcccgg cgtgggagtc cagaccgtgg  17340
acgttaggat tcccacggag gagatggaaa cccaaaccgc cactccctct tcggcagcaa  17400
gcgccaccac cggcgccgct tcggtagagg tgcagacgga cccctggcta cccgccgcca  17460
ctatcgccgt cgccgccgcc ccccgttcgc gcggacgcaa gagaaattat ccagcggcca  17520
gcgcgcttat gccccagtat gcgctgcatc catccatcgc gcccaccccc ggctaccgcg  17580
ggtactcgta ccgcccgcgc agatcagccg gcactcgcgg ccgccgccgc cgtgcgacca  17640
caaccagccg ccgccgtcgc cgccgccgcc agccagtgct gacccccgtg tctgtaagga  17700
aggtggctcg ctcggggagc acgctggtgg tgcccagagc gcgctaccac cccagcatcg  17760
tttaaagccg gtctctgtat ggttcttgca gatatggccc tcacttgtcg ccttcgcttc  17820
ccggtgccgg gataccgagg aagaactcac cgccgcaggg gcatggcggg cagcggtctc  17880
cgcggcggcc gtcgccatcg ccggcgcgca aagagcaggc gcatgcgcgg cggtgtgttg  17940
cccctgctgg tcccgctact cgccgcggcg atcggcgccg tgcccgggat cgcctccgtg  18000
gccctgcagg cgtcccagaa acattgactc ttgcaacctt gcaagcttgc atttttggag  18060
gaaaaaataa aaaagtctag actctcacgc tcgcttggtc ctgtgactat tttgtagaaa  18120
aaagatggaa gacatcaact ttgcgtcgct ggccccgcgt cacggctcgc gcccgttcat  18180
```

gggagactgg acagatatcg gcaccagcaa tatgagcggt ggcgccttca gctggggcag 18240
tctgtggagc ggccttaaaa attttggttc caccattaag aactatggca acaaagcgtg 18300
gaacagcagc acgggtcaga tgctgagaga caagttgaaa gagcagaact tccaggagaa 18360
ggtggcgcag ggcctggcct ctggcatcag cggggtggtg gacatagcta accaggccgt 18420
gcagaaaaag ataaacagtc atctggaccc ccgccctcag gtggaggaaa cgcctccagc 18480
catggagacg gtgtctcccg agggcaaagg cgaaaagcgc ccgcggcccg acagggaaga 18540
gaccctggtg tcacacaccg aggagccgcc ctcttacgag gaggcagtca aggccggcct 18600
gcccaccact cgccccatag ctcccatggc caccggtgtg gtgggtcaca ggcaacacac 18660
ccccgcaaca ctagatctgc ccccgccgtc cgagccgact cgccagccaa aggcggtgac 18720
ggtgtccgct ccctccactt ccgccgccaa cagagtgcct ctgcgccgcg ctgcgagcgg 18780
cccccgggcc tcgcgagtca gcggcaactg gcagagcaca ctgaacagca tcgtgggcct 18840
gggagtgagg agtgtgaagc gccgccgttg ctactgaatg agcaagctag ctaacgtgtt 18900
gtatgtgtgt atgcgtccta tgtcgccgcc agaggagctg ttgagccgcc ggcgccgtct 18960
gcactccagc gaatttcaag atggcgaccc catcgatgat gcctcagtgg tcgtacatgc 19020
acatctcggg ccaggacgct tcggagtacc tgagccccgg gctggtgcag ttcgcccgcg 19080
ccacagacac ctacttcaac atgagtaaca agttcaggaa ccccactgtg gcgcccaccc 19140
acgatgtgac cacggaccgg tcgcagcgcc tgacgctgcg gttcatcccc gtggatcggg 19200
aggacaccgc ttactcttac aaggcgcggt tcacgctggc cgtgggcgac aaccgcgtgc 19260
tggacatggc ctccacttac tttgacatcc ggggggtgct ggacaggggc cccactttta 19320
agccctactc gggcactgcc tacaaccccc tggcccccaa gggcgccccc aattcttgtg 19380
agtgggaaca agaggaaaat caggtggtcg ctgcagatga tgaacttgaa gatgaagaag 19440
cgcaagcaca agaggaagcc cctgtgaaaa aaattcatgt atatgctcag gcgcctcttt 19500
ctggcgaaaa gatttccaag gatggtatcc aaataggtac tgaagtcgta ggagatacat 19560
ctaaggacac ttttgcagat aaaacattcc aacccgaacc tcagataggc gagtctcagt 19620
ggaacgaggc tgatgccaca gcagcaggag gtagagtttt gaaaaagact accccctatga 19680
gaccttgcta tggatcctat gccaggccta ccaatgccaa cgggggtcaa ggaattatgg 19740
ttgccaatga acaaggagtg ttggagtcta aagtagaaat gcaatttttc tctaacacca 19800
caacccttaa tgcgcgggat ggaaccggca atcccgaacc aaaggtggtg ttgtacagcg 19860
aagatgtcca cttggaatct cccgatactc atctgtctta caagcccaaa aaggatgatg 19920
ttaatgccaa aatcatgttg ggtcagcaag ccatgcccaa cagacccaac ctcattggat 19980
ttagagataa tttcattggg cttatgtttt acaacagcac cggtaacatg ggagtgctgg 20040
cgggtcaggc ctctcagttg aatgctgtgg tggacttgca ggatagaaac acagaactgt 20100
catatcagct tctgcttgat tcaattgggg atagaaccag atacttctcc atgtggaacc 20160
aggcagtgga tagctatgat ccagatgtca gaattattga aaaccatggg actgaggatg 20220
aactgcccaa ctactgcttc cctttgggcg gcataggagt tactgatact tatcaaggga 20280
taaaaaatac caatggcaat ggtcagtgga ccaaagatga tcagttcgcg gaccgcaacg 20340
aaataggggt gggaaacaac ttcgccatgg agatcaacat ccaggccaac ctttggagaa 20400
acttcctcta tgcaaacgtg gggctctacc tgccagacaa gctcaagtac aaccccacca 20460
acgtggacat ctctgacaac cccaacacct atgactacat gaacaagcgg gtggtggccc 20520
ctggcctggt ggactgcttt gtcaatgtgg gagccaggtg gtccctggac tacatggaca 20580
acgtcaaccc cttcaaccac caccgcaatg cgggtctgcg ctaccgctcc atgatcctgg 20640
gcaacgggcg ctatgtgccc tttcacatcc aggtacccca gaagttcttt gccatcaaga 20700
acctcctgct cctgcccggc tcctacacct acgagtggaa cttcaggaag gatgtgaaca 20760
tggtcctaca gagctctctg ggcaatgacc ttagggtgga tggggccagc atcaagtttg 20820
acagcatcac cctctatgct acatttttcc ccatggccca caacaccgcc tccacgcttg 20880
aggccatgct gagaaacgac accaacgacc agtcctttaa tgactacctc tctggggcca 20940
acatgctcta cccaatccca gccaaggcca ccaacgtgcc catctccatc cctctcgca 21000
actgggccgc ctttagaggc tgggccttta cccgccttaa gaccaaggag acccccctccc 21060
tgggctcggg ttttgatccc tactttgttt actcgggatc catcccctac ctggatggca 21120
ccttctacct caaccacact ttcaagaaga tatccatcat gtatgactcc tccgtcagct 21180
ggccgggcaa cgaccgcttg ctcacccccca atgagttcga ggtcaagcgc gccgtggacg 21240
gcgagggcta caacgtggcc cagtgcaaca tgaccaagga ctggttcctg gtgcagatgc 21300
tggccaacta caacataggc taccagggct tttacatccc agagagctac aaggacagga 21360
tgtactcctt cttcagaaat ttccaaccca tgagccgaca ggtggtggac gagaccaatt 21420
acaaggacta tcaagccatt ggcatcaccc accagcacaa caactcgggt ttcgtgggct 21480
acctggcgcc caccatgcgc gagggtcagg cctaccccgc caacttcccc taccccttga 21540
taggcaagac cgcggtcgac agcgtcaccc agaaaaagtt cctctgcgac cgcaccctct 21600
ggcgcatccc cttctctagc aacttcatgt ccatgggtgc gctcacggac ctgggccaaa 21660
acctgcttta tgccaactct gcccatgcgc tggacatgac ttttgaggtg gaccccatgg 21720
acgagcccac ccttctctat attgtgtttg aagtgttcga cgtggtcaga gtgcaccagc 21780
cgcaccgcgg tgtcatcgag accgtgtacc tgcgtacgcc cttctcagcc ggcaacgcca 21840
ccacctaagg agacagcgcc gccgccgcct gcatgacggg ttccaccgag caagagctca 21900
gggccattgc cagagacctg ggatgcggac cctatttttt gggcacctat gacaaacgct 21960
tcccgggctt tatctcccga gacaagctcg cctgcgccat tgtcaacacg gccgcgcgcg 22020
agaccggggg cgtgcactgg ctggcctttg gctgggaccc gcgctccaaa acttgctacc 22080
tctttgaccc ctttggcttc tccgatcagc gcctcaggca gatttatgag tttgagtacg 22140
aggggctgct gcgccgcagc gcgctcgcct cctcgcccga ccgctgcatc acccttgaga 22200
agtccaccga aaccgtgcag ggccccact cggccgcctg cggtctcttc tgttgcatgt 22260
ttttgcacgc ctttgtgcac tggcctcaga gtcccatgga ttgcaacccc accatgaact 22320
tgctaaaggg agtgcccaac gccatgctcc agagccccca ggtccagccc accctgcgcc 22380
gcaaccagga acagctttac cgcttcctgg agcgccactc cccctacttc cgcagccaca 22440
gcgcgcgcat ccgggggcc acctcttttt gccacttgca agaaaacatg caagacggaa 22500
aatgatgtac agcatgcttt taataaatgt aaagactgtg cactttaatt atacacgggc 22560
tctttctggt tatttattca acaccgccgt cgccatttag aaatcgaaag ggttctgccg 22620
tgcgtcgccg tgcgccacgg gcagagacac gttgcgatac tggaagcggc tcgcccactt 22680
gaactcgggc accaccatgc ggggcagtgg ttcctcgggg aagttctcgc tccacagggt 22740
gcgggtcagc tgcagcgcgc tcaggaggtc gggagccgag atcttgaagt cgcagttggg 22800
gccggaaccc tgcgcgcgcg agttgcggta cacggggttg cagcactgga acaccagcag 22860
ggccggatta ttcacgctgg ccagcaggct ctcgtcgctg atcatgtcgc tgtccagatc 22920

```
ctccgcgttg ctcagggcga atggggtcat cttgcagacc tgcctgccca ggaaaggcgg  22980
gagcccaggc ttgccgttgc agtcgcagcg caggggcatt agcaggtgcc cacggcccga  23040
ctgcgcctgc gggtacaacg cgcgcatgaa ggcttcgatc tgcctaaaag ccacctgggt  23100
cttggctccc tccgaaaaga acatcccaca ggacttgctg gagaactggt tcgcgggaca  23160
gctggcatcg tgcaggcagc agcgcgcgtc agtgttggca atctgcacca cgttgcgacc  23220
ccaccggttt ttcactatct tggccttgga agcctgctcc tttagcgcgc gctggccgtt  23280
ctcgctggtc acatccatct ctatcacctg ttccttgttg atcatgtttg tcccgtgcag  23340
acactttagg tcgccctccg tctgggtgca gcggtgctcc cacagcgcgc aaccggtggg  23400
ctcccaattc ttgtgggtca cccccgcgta ggcctgcagg taggcctgca ggaagcgccc  23460
catcatggtc ataaaggtct tctggctcgt aaaggtcagc tgcaggccgc gatgctcttc  23520
gttcagccag gtcttgcaga tggcggccag cgcctcggtc tgctcgggca gcatcttaaa  23580
atttgtcttc aggtcgttat ccacgtggta cttgtccatc atggcacgcg ccgcctccat  23640
gcccttctcc caggcggaca ccatgggcag gcttaggggg tttatcactt ccagcggcga  23700
ggacaccgta ctttcgattt cttcttcctc cccctcttcc cggcgcgcgc ccccgctgtt  23760
gcgcgctctt accgcctgca ccaaggggtc gtcttcaggc aagcgccgca ccgagcgctt  23820
gccgcccttg acctgcttga tcagtaccgg cgggttgctg aagcccacca tggtcagcgc  23880
cgcctgctct tcttcgtctt cgctgtctac cactatttct ggggaggggc ttctccgctc  23940
tgcggcaaag gcggcggatc gcttcttttt tttcttggga gccgccgcga tggagtccgc  24000
cacggcgacc gaggtcgagg gcgtggggct gggggtgcgc ggtaccaggg cctcgtcgcc  24060
ctcggactct tcctctgact ccaggcggcg gcggagtcgc ttctttgggg gcgcgcgcgt  24120
cagcggcggc ggagacgggg acggggacgg ggacgggacg ccctccacag ggggtggtct  24180
tcgcgcagac ccgcggccgc gctcgggggt cttctcgcgc tggtcttggt cccgactggc  24240
cattgtatcc tcctcctcct aggcagagag acataaggag tctatcatgc aagtcgagaa  24300
ggaggagagc ttaaccaccc cctcagagac cgccgatgcg cccgccgtcg ccgtcgcccc  24360
cgctaccgcc gacgcgcccg ccacaccgag cgacaccccc acggaccccc ccgccgacgc  24420
acccctgttc gaggaagcgg ccgtggagca ggacccgggc tttgtctcgg cagaggagga  24480
tttgcaagag gaggagaata aggaggagaa gccctcagtg ccaaaagatc ataaagagca  24540
agacgagcac gacgcagacg cacaccaggg tgaagtcggg cggggggacg gagggcatgg  24600
cggcgccgac tacctagacg aaggaaacga cgtgctcttg aagcacctgc atcgtcagtg  24660
cgccatcgtc tgcgacgctc tgcaggagcg cagcgaggtg cccctcagcg tggcggaggt  24720
cagccgcgcc tacgagctca gcctcttttc cccccgggtg cccccccgcc gccgcgaaaa  24780
cggcacatgc gagcccaacc cgcgcctcaa cttctacccc gcctttgtgg tgcccgaggt  24840
cctggccacc tatcacatct tctttcaaaa ttgcaagatc cccatctcgt gccgcgccaa  24900
ccgtagccgc gccgataaga tgctggccct gcgccagggc gaccacatac ctgatatcgc  24960
cgctttggaa gatgtgccaa agatcttcga gggtctgggg cgcaacgaga agcgggcagc  25020
aaactctctg caacaggaaa acagcgaaaa tgagagtcac actggagcgc tggtggagct  25080
ggagggcgac aacgcccgcc tggcggtgct caagcgcagc atcgaggtca cccactttgc  25140
ctaccccgcg ctcaacctgc cccccaaagt catgaacgcg gtcatggacg ggctgatcat  25200
gcgccgcggc cggcccctcg ctccagatgc aaacttgcat gaggagaccg aggacggtca  25260
gcccgtggtc agcgacgagc agctgacgcg ctggctggag agcgcggacc ccgccgaact  25320
```

-continued ggaggagcgg cgcaagatga tgatggccgc ggtgctggtc accgtagagc tggagtgtct 25380
gcagcgcttc ttcggtgacc ccgagatgca gagaaaggtc gaggagaccc tacactacac 25440
cttccgccag ggctacgtgc gccaggcttg caagatctcc aacgtggagc tcagcaacct 25500
ggtgtcctac ctgggcatct tgcatgaaaa ccgccttggg cagagcgtgc tacactccac 25560
cctgcgcggg gaggcgcgcc gcgactacgt gcgcgactgc gtttacctct tcctctgcta 25620
cacctggcag acggccatgg gggtctggca gcagtgcctg gaggagcgca acctcaagga 25680
gctggagaag cttctgcagc gcgcgctcaa agacctctgg acgggcttca acgagcgctc 25740
ggtggccgcc gcgctagccg acctcatctt ccccgagcgc ctgctcaaaa ccctccagca 25800
ggggctgccc gacttcacca gccaaagcat gttgcaaaat tttaggaact ttatcctgga 25860
gcgttctggc atcctacccg ccacctgctg cgccctgccc agcgactttg tcccccctcgt 25920 gtaccgcgag tgcccccgc cgctgtgggg ccactgctac ctgttccaac tggccaacta 25980
cctgtcctac cacgcggacc tcatggagga ctccagcggc gaggggctca tggagtgcca 26040
ctgccgctgc aacctctgca cgccccaccg ctccctggtc tgcaacaccc aactgctcag 26100
cgagagtcag attatcggta ccttcgagct acagggtccg tcctcctcag acgagaagtc 26160
cgcggctccg gggctaaaac tcactccggg gctgtggact tccgcctacc tgcgcaaatt 26220
tgtacctgaa gactaccacg cccacgaaat caggttttac gaggaccaat cccgcccgcc 26280
caaggcggag ctgaccgcct gcgtcatcac ccagggcgag atcctaggcc aattgcaagc 26340
catccaaaaa gcccgccaag agtttttgct gaagaggggt cggggggtgt atctggaccc 26400
ccagtcgggt gaggagctca acccggttcc cccgctgcca ccgccgcggg accttgcttc 26460
ccaggataag catcgccatg gctcccagaa agaagcagca gcggccgccg ctgccgccgc 26520
cccacatgct ggaggaagag gaggaatact gggacagtca ggcagaggag gtttcggacg 26580
aggaggagcc ggagacggag atggaagagt gggaggagga cagcttagac gaggaggctt 26640
ccgaagccga agaggcaggc gcaacaccgt caccctcggc cgcagccccc tcgcaggcgc 26700
ccccgaagtc cgctcccagc atcagcagca acagcagcgc tataacctcc gctcctccac 26760
cgccgcgacc cacggccgac cgcagaccca accgtagatg ggacaccacc ggaaccgggg 26820
ccggtaagtc ctccgggaga ggcaagcaag cgcagcgcca aggctaccgc tcgtggcgcg 26880
ctcacaagaa cgccatagtc gcttgcttgc aagactgcgg ggggaacatc tccttcgccc 26940
gccgcttcct gctcttccac cacggtgtgg ccttcccccg taacgtcctg cattactacc 27000
gtcatctcta cagcccctac tgcggcggca gtgagccaga ggcggccagc ggcggcggcg 27060
cccgtttcgg tgcctaggaa gacccagggc aagacttcag ccaagaaact cgcggcgacc 27120
gcggcgaacg cggtcgcggg ggccctgcgc ctgacggtga acgaacccct gtcgacccgc 27180
gaactgagga accgaatctt ccccactctc tatgccatct tccagcagag cagagggcag 27240
gatcaggaac tgaaagtaaa aaacaggtct ctgcgctccc tcacccgcag ctgtctgtat 27300
cacaagagcg aagaccagct tcggcgcacg ctggaggacg ctgaggcact cttcagcaaa 27360
tactgcgcgc tcactcttaa ggactagctc cgcgcccttc tcgaatttag gcgggaacgc 27420
ctacgtcatc gcagcgccgc cgtcatgagc aaggacattc ccacgccata catgtggagc 27480
tatcagccgc agatgggact cgcggcgggc gcctcccaag actactccac ccgcatgaac 27540
tggctcagtg ccggcccaca catgatctca caggttaatg acatccgcac ccatcgaaac 27600
caaatattgg tgaagcaggc ggcaattacc accacgcccc gcaataatcc caaccccagg 27660

-continued

```
gagtggcccg cgtccctggt gtatcaggaa attcccggcc ccaccaccgt actacttccg  27720
cgtgattccc aggccgaagt ccaaatgact aactcagggg cacagctcgc gggcggctgt  27780
cgtcacaggg tgcggcctcc tcgccagggt ataactcacc tggagatccg aggcagaggt  27840
attcagctca acgacgagtc ggtgagctcc tcgctcggtc tcagacctga cgggaccttc  27900
cagatagccg gagccggccg atcttccttc acgccccgcc aggcgtacct gactctgcag  27960
agctcgtcct cggcgccgcg ctcgggcggc atcgggactc tccagttcgt gcaggagttt  28020
gtgccctcgg tctacttcaa ccccttctcg ggctctcccg gtcgctaccc ggaccagttt  28080
atcccgaact ttgacgccgc gagggactcg gtggacggct acgactgaat gtcgggtgga  28140
cccggtgcag agcaacttcg cctgaagcac cttgaccact gccgccgccc tcagtgcttt  28200
gcccgctgtc agaccggtga gttccagtac ttttccctgc ccgactcgca cccggacggc  28260
ccggcgcacg gggtgcgctt tttcatcccg agtcaggtcc gctctaccct aatcagggag  28320
ttcaccgccc gtcccctact ggcggagttg gaaaaggggc cttctatcct aaccattgcc  28380
tgcatttgct ctaaccctgg attacaccaa gatctttgct gtcatttgtg tgctgagtat  28440
aataaaggct gagatcagaa tctactcggg ctcctgtcgc catcctgtca acgccaccgt  28500
ccaagcccgg cccgatcagc ccgaggtgaa cctcacctgt ggtctgcacc ggcgcctgag  28560
gaaataccta gcttggtact acaacagcac tccctttgtg gtttacaaca gctttgacca  28620
ggacggggtc tcactgaggg ataacctctc gaacctgagc tactccatca ggaagaacaa  28680
caccctcgag ctacttcctc cttacctgcc cgggacttac cagtgtgtca ccggcccctg  28740
cacccacacc cacctgttga tcgtaaacga ctctcttccg agaacagacc tcaataactc  28800
ctctccgcag ttccccagaa caggaggtga gctcaggaaa ccccgggtaa agaagggtgg  28860
acaagagtta acacttgtgg ggtttctggt atatgtgacg ctggtggtgg ctcttttgat  28920
taaggctttt ccttccatgt ctgaactatc cctcttcttt tatgaacaac tcgactagtg  28980
ctaacgggac cctacccaac gaatcgggat tgaatatcgg taaccaggtt gcagtttcac  29040
ttttgattac cttcatagtc ctcttcctgc tagtgctgtc gcttctgtgc ctgcggatcg  29100
ggggctgctg catccacgtt tatatctggt gctggctgtt tagaaggttc ggagaccacc  29160
gcaggtagaa taatgctgct taccctcttt gtcctggcgc tggctgccag ctgccaagcc  29220
ttttccgagg ctgacttcat agagccccag tgcaatatca cttataaatc tgaacgtgcc  29280
atctgtacta ttctaatcaa atgtgttact caacacgata aggtgactgt taaatacaaa  29340
gatcaattaa aaaaagacgc actttacagc agctggcaac caggagatga tcaaaaatac  29400
aatgtaaccg tcttccaggg caaactctcc aaaacttaca attacaattt cccatttgag  29460
cagatgtgtg actttgtcat gtacatggaa aagcagtaca agctgtggcc tccaactccc  29520
cagggctgtg tggaaaatcc aggctctttc tgtatgatct ctctctgtgt aactgtgctg  29580
gcactaatac tcacgcttct gtatctcaga tttaaatcaa ggcaaagctt cattgatgaa  29640
aagaaaatgc cataatcgct caacgcttga ttgctaacac cgggtttttta tccgcagaat  29700
gattggaatc accctactaa tcacctccct ccttgcgatt gcccatgggt tggaacgaat  29760
cgaagtccct gtgggggcca atgttaccct ggtggggcct gtcggcaatg ctacattaat  29820
gtgggaaaaa tatactaaaa atcaatgggt ttcttactgc actaacaaaa acagccacaa  29880
gcccagagcc atctgcgatg ggcaaaatct aaccttgatt gatgttcaat tgctggatgc  29940
gggctactat tatgggcagc tgggtacaat gattaattac tggagacccc acagagatta  30000
catgcttcac gtagtaaagg gtcccattag cagcccaacc accacctcta ccacacccac  30060
```

```
taccaccact actcccacca ccagcactgc cgcccagcct cctcatagca gaacaaccac  30120
ttttatcaat tccaagtccc actcccccca cattgccggc gggccctccg cctcagactc  30180
cgagaccacc gagatctgct tctgcaaatg ctctgacgcc attgcccagg atttggaaga  30240
tcacgaggaa gatgagcatg actacgcaga tgcatgccag gcatcagagg cagaagcgct  30300
accggtggcc ctaaaacagt atgcagactc ccacaccacc cccaaccttc ctccaccttc  30360
ccagaagcca agtttcctgg gggaaaatga aactctgcct ctttccatac tagctctgac  30420
atctgttgct attttggccg ctctgctggt gcttctatgc tctatatgct acctgatctg  30480
ctgcagaaag aaaaaatctc acggccatgc tcaccagccc ctcatgcact tcccttaccc  30540
tccagagctg ggcgaccaca aactttaagt ctgcagtagc tatctgccca tcccttgtca  30600
gtcgacagcg atgagcccca ctaatctaac agcctctgga cttacaacat tgtctcttaa  30660
tgagaccacc gctcctcaag acctgtacga tggtgtctcc gcgctggtta accagtggga  30720
tcacctgggc atatggtggc tcctcatagg agcagtgacc ctgtgcctaa tcctggtctg  30780
gatcatctgc tgcatcaaaa gcagaagacc caggcggcgg cccatctaca ggcccttcgt  30840
catcacacct gaagataatg atgatgatga caccacctcc aggctgcaga gcctaaagca  30900
gctactcttc tcttttacag catggtaaat tgaatcatgc cccgcatttt catctacttg  30960
cttctccttc cactttttct gggctcctct acattggcca ctgtgtccca catcgaggta  31020
gactgcctca cgcccttcac agtctacctg cttttcggct ttgtcatctg cacctttgtc  31080
tgcagcgtta tcactgtagt gatctgcttc atacagtgca tcgactacat ctgtgtgcgg  31140
gtggcctact ttagacacca cccccagtat cgcaacaggg acatagcggc tctcctaaga  31200
cttgtttaaa tcatggccaa attacctgtg attggtcttc tgattatctg ctgcgtccta  31260
gccgcgattg ggactcaacc taataccacc accagcgctc ccagaaagag acatgtatcc  31320
tgcagcttca agcgtccctg gaatataccc caatgcttta ctgatgaacc tgaaatctct  31380
ttggcttggt acttcagcgt caccgccctt ctcatcttct gcagtacggt tattgctctt  31440
gccatctacc cttcccttaa cctgggctgg aatgctgtca actctatgga atatcccacc  31500
ttcccagaac cagacctgcc agacctggtt gttctaaacg cgtttcctcc tcctccagtt  31560
caaaatcagt ttcgccctcc gtcccctacg cccactgagg tcagctactt taatctaaca  31620
ggcggagatg actgaaaacc tagacctaga aatggacggt ctctgcagcg agcaacgcac  31680
actagagagg cgccggcaaa aagcagagct cgagcgtctt aaacaagagc tccaagacgc  31740
cgtggccata caccagtgca aaaaagggct cttctgtctg gtaaaacagg ccacgctcac  31800
ctatgaaaaa acaggtgaca cccaccgcct aggatacaag ctgcccacac agcgccaaaa  31860
gtttgccctt atgataggtg aacaacccat caccgtcacc cagcactccg tggagacaga  31920
aggctgcatt catgctccct gcaggggcgc tgactgcctc tacaccttga tcaaaaccct  31980
ctgcggtctc agagacctta tccctttcaa ttgatcataa ctgtaatcaa taaaaaatca  32040
cttacttgaa atctgatagc aagactctgt ccaatttttt cagcaacact tccttcccct  32100
cctcccaact ctggtactct aggcgcctcc tagctgcaaa cttcctccac agtctgaagg  32160
gaatgtcaga ttcctcctcc tgtccctccg cacccacgat cttcatgttg ttacagatga  32220
aacgcgcgag atcgtctgac gagaccttca accccgtgta cccctacgat accgagatcg  32280
ctccgacttc tgtccctttc cttacccctc cctttgtatc atccgcagga atgcaagaaa  32340
atccagctgg ggtgctgtcc ctg                                          32363
```

<210> SEQ ID NO 623
<211> LENGTH: 1507
<212> TYPE: PRT
<213> ORGANISM: Artificial seqeunce
<220> FEATURE:
<223> OTHER INFORMATION: Heterologous polypeptide

<400> SEQUENCE: 623

```
Met Gly Gln Lys Glu Gln Ile His Thr Leu Gln Lys Asn Ser Glu Arg
1               5                   10                  15

Met Ser Lys Gln Leu Thr Arg Ser Ser Gln Ala Val Gly Val Pro Gly
            20                  25                  30

Asp Ser Thr Arg Arg Ala Val Arg Arg Met Asn Thr Phe Tyr Glu Ala
        35                  40                  45

Gly Met Thr Leu Gly Glu Lys Phe Arg Val Gly Asn Cys Lys His Leu
    50                  55                  60

Lys Met Thr Arg Pro Asn Ser Lys Met Ala Leu Asn Ser Glu Ala Leu
65                  70                  75                  80

Ser Val Val Ser Glu Cys Gly Ala Ser Ala Cys Asp Val Ser Leu Ile
                85                  90                  95

Ala Met Asp Ser Ala Phe Val Gln Gly Lys Asp Trp Gly Val Lys Lys
            100                 105                 110

Phe Ile Arg Arg Asp Phe Tyr Ala Tyr Lys Asp Phe Leu Trp Cys Phe
        115                 120                 125

Pro Phe Ser Leu Val Phe Leu Gln Glu Ile Gln Ile Cys Cys His Val
    130                 135                 140

Ser Cys Leu Cys Cys Ile Cys Cys Ser Thr Arg Ile Cys Leu Gly Cys
145                 150                 155                 160

Leu Leu Glu Leu Phe Leu Ser Arg Ala Leu Arg Ala Leu His Val Leu
                165                 170                 175

Trp Asn Gly Phe Gln Leu His Cys Gln Thr Glu Tyr Asn Gln Lys Leu
            180                 185                 190

Gln Val Asn Gln Phe Ser Glu Ser Lys Ser Leu Tyr His Arg Glu Lys
        195                 200                 205

Gln Leu Ile Ala Met Asp Ser Ala Ile Cys Glu Glu Arg Gly Ala Ala
    210                 215                 220

Gly Ser Leu Ile Ser Cys Glu Thr Met Pro Ala Ile Leu Lys Leu Gln
225                 230                 235                 240

Lys Asn Cys Leu Leu Ser Leu Arg Thr Ala Leu Thr His Asn Gln Asp
                245                 250                 255

Phe Ser Ile Tyr Arg Leu Cys Cys Lys Arg Gly Ser Leu Cys His Ala
            260                 265                 270

Ser Gln Ala Arg Ser Pro Ala Phe Pro Lys Pro Val Arg Pro Leu Pro
        275                 280                 285

Ala Pro Ile Thr Arg Ile Thr Pro Gln Leu Gly Gly Gln Ser Asp Ser
    290                 295                 300

Ser Gln Pro Leu Leu Thr Thr Gly Arg Pro Gln Gly Trp Gln Asp Gln
305                 310                 315                 320

Ala Leu Arg His Thr Gln Gln Ala Ser Pro Ala Ser Cys Ala Thr Ile
                325                 330                 335

Thr Ile Pro Ile His Ser Ala Ala Leu Gly Asp His Ser Gly Asp Pro
            340                 345                 350

Gly Pro Ala Trp Asp Thr Cys Pro Pro Leu Pro Leu Thr Thr Leu Ile
        355                 360                 365
```

```
Pro Arg Ala Pro Pro Pro Tyr Gly Asp Ser Thr Ala Arg Ser Trp Pro
    370                 375                 380

Ser Arg Cys Gly Pro Leu Gly Gly Asn Thr Thr Leu Gln Gln Leu Gly
385                 390                 395                 400

Glu Ala Ser Gln Ala Pro Ser Gly Ser Leu Ile Pro Leu Arg Leu Pro
                405                 410                 415

Leu Leu Trp Glu Val Arg Gly Gln Pro Asp Ser Phe Ala Ala Leu His
            420                 425                 430

Ser Ser Leu Asn Glu Leu Gly Glu Ile Ala Arg Glu Leu His Gln Phe
        435                 440                 445

Ala Phe Asp Leu Leu Ile Lys Ser His Phe Val Gln Gly Lys Asp Trp
    450                 455                 460

Gly Leu Lys Lys Phe Ile Arg Arg Asp Phe Trp Gly Met Glu Leu Ala
465                 470                 475                 480

Ala Ser Arg Arg Phe Ser Trp Asp His His Ser Ala Gly Gly Pro Pro
                485                 490                 495

Arg Val Pro Ser Val Arg Ser Gly Ala Ala Gln Val Gln Pro Lys Asp
            500                 505                 510

Pro Leu Pro Leu Arg Thr Leu Ala Gly Cys Leu Ala Arg Thr Ala His
        515                 520                 525

Leu Arg Pro Gly Ala Glu Ser Leu Pro Gln Pro Gln Leu His Cys Thr
    530                 535                 540

Leu Trp Phe Gln Ser Ser Glu Leu Ser Pro Thr Gly Ala Pro Trp Pro
545                 550                 555                 560

Ser Arg Arg Pro Thr Trp Arg Gly Thr Thr Val Ser Pro Arg Thr Ala
                565                 570                 575

Thr Ser Ser Ala Arg Thr Cys Cys Gly Thr Lys Trp Pro Ser Ser Gln
            580                 585                 590

Glu Ala Ala Leu Gly Leu Gly Ser Gly Leu Leu Arg Phe Ser Cys Gly
        595                 600                 605

Thr Ala Ala Ile Arg Lys Met His Phe Ser Leu Lys Glu His Pro Pro
    610                 615                 620

Pro Pro Cys Pro Pro Glu Ala Phe Gln Arg Ala Ala Gly Glu Gly Gly
625                 630                 635                 640

Pro Gly Arg Gly Gly Ala Arg Arg Gly Ala Arg Val Leu Gln Ser Pro
                645                 650                 655

Phe Cys Arg Ala Gly Ala Gly Glu Trp Leu Gly His Gln Ser Leu Arg
            660                 665                 670

His Val Val Gly Tyr Gly His Leu Asp Thr Ser Gly Ser Ser Ser Ser
        675                 680                 685

Ser Ser Trp Pro Asn Ser Lys Met Ala Leu Asn Ser Leu Asn Ser Ile
    690                 695                 700

Asp Asp Ala Gln Leu Thr Arg Ile Ala Pro Pro Arg Ser His Cys Cys
705                 710                 715                 720

Phe Trp Glu Val Asn Ala Pro Asp Gly His Ser Tyr Thr Ser Lys Val
                725                 730                 735

Asn Cys Leu Leu Leu Gln Asp Gly Phe His Gly Cys Val Ser Ile Thr
            740                 745                 750

Gly Ala Ala Gly Arg Arg Asn Leu Ser Ile Phe Leu Phe Leu Met Leu
        755                 760                 765

Cys Lys Leu Glu Phe His Ala Cys Lys Ile Gln Asn Lys Asn Cys Pro
    770                 775                 780

Asp Phe Lys Lys Phe Asp Gly Pro Cys Gly Glu Arg Gly Gly Gly Arg
```

```
785                 790                 795                 800

Thr Ala Arg Ala Leu Trp Ala Arg Gly Asp Ser Val Leu Thr Pro Ala
                805                 810                 815

Leu Asp Pro Gln Thr Pro Val Arg Ala Pro Ser Leu Thr Arg Ala Ala
            820                 825                 830

Ala Ala Val His Tyr Lys Leu Ile Gln Gln Pro Ile Ser Leu Phe Ser
        835                 840                 845

Ile Thr Asp Arg Leu His Lys Thr Phe Ser Gln Leu Pro Ser Val His
    850                 855                 860

Leu Cys Ser Ile Thr Phe Gln Trp Gly His Pro Pro Ile Phe Cys Ser
865                 870                 875                 880

Thr Asn Asp Ile Cys Val Thr Ala Asn Phe Cys Ile Ser Val Thr Phe
                885                 890                 895

Leu Lys Pro Cys Phe Leu Leu His Glu Ala Ser Ala Ser Gln Cys His
            900                 905                 910

Leu Phe Leu Gln Pro Gln Val Gly Thr Pro Pro Pro His Thr Ala Ser
        915                 920                 925

Ala Arg Ala Pro Ser Gly Pro Pro His Pro His Glu Ser Cys Pro Ala
    930                 935                 940

Gly Arg Arg Pro Ala Arg Ala Ala Gln Thr Cys Ala Arg Arg Gln His
945                 950                 955                 960

Gly Leu Pro Gly Cys Glu Glu Ala Gly Thr Ala Arg Val Pro Ser Leu
                965                 970                 975

His Leu His Leu His Gln Ala Ala Leu Gly Ala Gly Arg Gly Arg Gly
            980                 985                 990

Trp Gly Glu Ala Cys Ala Gln Val  Pro Pro Ser Arg Gly  Val Leu Arg
        995                 1000                1005

Phe Leu  Asp Leu Lys Val Arg  Tyr Leu His Ser Gln  Trp Gln His
    1010                 1015                 1020

Tyr His  Arg Ser Gly Glu Ala  Ala Gly Thr Pro Leu  Trp Arg Pro
    1025                 1030                 1035

Thr Arg  Asn Val Pro Phe Arg  Glu Leu Lys Asn Gln  Arg Thr Ala
    1040                 1045                 1050

Gln Gly  Ala Pro Gly Ile His  His Ala Ala Ser Pro  Val Ala Ala
    1055                 1060                 1065

Asn Leu  Cys Asp Pro Ala Arg  His Ala Gln His Thr  Arg Ile Pro
    1070                 1075                 1080

Cys Gly  Ala Gly Gln Val Arg  Ala Gly Arg Gly Pro  Glu Ala Gly
    1085                 1090                 1095

Gly Gly  Val Leu Gln Pro Gln  Arg Pro Ala Pro Glu  Lys Pro Gly
    1100                 1105                 1110

Cys Pro  Cys Arg Arg Gly Gln  Pro Arg Leu His Thr  Val Lys Met
    1115                 1120                 1125

Trp Arg  Ala Val Ala Met Met  Val Pro Asp Arg Gln  Val His Tyr
    1130                 1135                 1140

Asp Phe  Gly Leu Gln Asn Leu  Gln Asn Gly Gly Gly  Ser Arg Ser
    1145                 1150                 1155

Ser Ala  Thr Leu Pro Gly Arg  Arg Arg Arg Arg Trp  Leu Arg Arg
    1160                 1165                 1170

Arg Arg  Gln Pro Ile Ser Val  Ala Pro Ala Gly Pro  Pro Arg Arg
    1175                 1180                 1185

Pro Asn  Gln Lys Pro Asn Pro  Pro Gly Gly Ala Arg  Cys Val Ile
    1190                 1195                 1200
```

Met Arg Pro Thr Trp Pro Gly Thr Ser Ala Phe Thr Lys Arg Ser
1205 1210 1215

Phe Ala Val Thr Glu Arg Ile Ile Leu Val Leu Gly Val Leu Ser
1220 1225 1230

Gly His Ser Gly Ser Arg Leu Tyr Glu Ala Gly Met Thr Leu Gly
1235 1240 1245

Gly Lys Ile Leu Phe Phe Leu Phe Leu Leu Leu Pro Leu Ser Pro
1250 1255 1260

Phe Ser Leu Ile Phe Thr Glu Ile Ser Cys Cys Thr Leu Ser Ser
1265 1270 1275

Glu Glu Asn Glu Tyr Leu Pro Arg Pro Glu Trp Gln Leu Gln Val
1280 1285 1290

Pro Phe Arg Glu Leu Lys Asn Val Ser Val Leu Glu Gly Leu Arg
1295 1300 1305

Gln Gly Arg Leu Gly Gly Pro Cys Ser Cys His Cys Pro Arg Pro
1310 1315 1320

Ser Gln Ala Arg Leu Thr Pro Val Asp Val Ala Gly Pro Phe Leu
1325 1330 1335

Cys Leu Gly Asp Pro Gly Leu Phe Pro Pro Val Lys Ser Ser Ile
1340 1345 1350

Thr Gly Gly Lys Ser Thr Cys Ser Ala Pro Gly Pro Gln Ser Leu
1355 1360 1365

Pro Ser Thr Pro Phe Ser Thr Tyr Pro Gln Trp Val Ile Leu Ile
1370 1375 1380

Thr Glu Leu Gly Met Glu Cys Thr Leu Gly Gln Val Gly Ala Pro
1385 1390 1395

Ser Pro Arg Arg Glu Glu Asp Gly Trp Arg Gly Gly His Ser Arg
1400 1405 1410

Phe Lys Ala Asp Val Pro Ala Pro Gln Gly Pro Cys Trp Gly Gly
1415 1420 1425

Gln Pro Gly Ser Ala Pro Ser Ser Ala Pro Pro Glu Gln Ser Leu
1430 1435 1440

Leu Asp Asp Tyr Trp Ala Gln Lys Glu Lys Gly Ser Ser Ser Phe
1445 1450 1455

Leu Arg Pro Ser Cys Asp Tyr Trp Ala Gln Lys Glu Lys Ile Ser
1460 1465 1470

Ile Pro Arg Thr His Leu Cys Trp Lys Phe Glu Met Ser Tyr Thr
1475 1480 1485

Val Gly Gly Pro Pro Pro His Val His Ala Arg Pro Arg His Trp
1490 1495 1500

Lys Thr Asp Arg
1505

<210> SEQ ID NO 624
<211> LENGTH: 1507
<212> TYPE: PRT
<213> ORGANISM: Artificial seqeunce
<220> FEATURE:
<223> OTHER INFORMATION: Heterologous polypeptide

<400> SEQUENCE: 624

Met Gly Gln Lys Glu Gln Ile His Thr Leu Gln Lys Asn Ser Glu Arg
1 5 10 15

Met Ser Lys Gln Leu Thr Arg Ser Ser Gln Ala Val Gly Asn Thr Thr
20 25 30

```
Leu Gln Gln Leu Gly Glu Ala Ser Gln Ala Pro Ser Gly Ser Leu Ile
        35                  40                  45

Pro Leu Arg Leu Pro Leu Leu Trp Glu Val Arg Gly Gln Pro Asp Ser
    50                  55                  60

Phe Ala Ala Leu His Ser Ser Leu Asn Glu Leu Gly Glu Ile Ala Arg
65                  70                  75                  80

Glu Leu His Gln Phe Ala Phe Asp Leu Leu Ile Lys Ser His Phe Val
                85                  90                  95

Gln Gly Lys Asp Trp Gly Leu Lys Lys Phe Ile Arg Arg Asp Phe Trp
            100                 105                 110

Gly Met Glu Leu Ala Ala Ser Arg Arg Phe Ser Trp Asp His His Ser
        115                 120                 125

Ala Gly Gly Pro Pro Arg Val Pro Ser Val Arg Ser Gly Ala Ala Gln
    130                 135                 140

Val Gln Pro Lys Asp Pro Leu Pro Leu Arg Thr Leu Ala Gly Cys Leu
145                 150                 155                 160

Ala Arg Thr Ala His Leu Arg Pro Gly Ala Glu Ser Leu Pro Gln Pro
                165                 170                 175

Gln Leu His Cys Thr Leu Trp Phe Gln Ser Ser Glu Leu Ser Pro Thr
            180                 185                 190

Gly Ala Pro Trp Pro Ser Arg Arg Pro Thr Trp Arg Gly Thr Thr Val
        195                 200                 205

Ser Pro Arg Thr Ala Thr Ser Ser Ala Arg Thr Cys Cys Gly Thr Lys
    210                 215                 220

Trp Pro Ser Ser Gln Glu Ala Ala Leu Gly Leu Gly Ser Gly Leu Leu
225                 230                 235                 240

Arg Phe Ser Cys Gly Thr Ala Ala Ile Arg Lys Met His Phe Ser Leu
                245                 250                 255

Lys Glu His Pro Pro Pro Pro Cys Pro Pro Glu Ala Phe Gln Arg Ala
            260                 265                 270

Ala Gly Glu Gly Gly Pro Gly Arg Gly Gly Ala Arg Arg Gly Ala Arg
        275                 280                 285

Val Leu Gln Ser Pro Phe Cys Arg Ala Gly Ala Gly Glu Trp Leu Gly
    290                 295                 300

His Gln Ser Leu Arg His Val Val Gly Tyr Gly His Leu Asp Thr Ser
305                 310                 315                 320

Gly Ser Ser Ser Ser Ser Ser Trp Pro Asn Ser Lys Met Ala Leu Asn
                325                 330                 335

Ser Leu Asn Ser Ile Asp Asp Ala Gln Leu Thr Arg Ile Ala Pro Pro
            340                 345                 350

Arg Ser His Cys Cys Phe Trp Glu Val Asn Ala Pro Gly Val Pro Gly
        355                 360                 365

Asp Ser Thr Arg Arg Ala Val Arg Arg Met Asn Thr Phe Tyr Glu Ala
    370                 375                 380

Gly Met Thr Leu Gly Glu Lys Phe Arg Val Gly Asn Cys Lys His Leu
385                 390                 395                 400

Lys Met Thr Arg Pro Asn Ser Lys Met Ala Leu Asn Ser Glu Ala Leu
                405                 410                 415

Ser Val Val Ser Glu Cys Gly Ala Ser Ala Cys Asp Val Ser Leu Ile
            420                 425                 430

Ala Met Asp Ser Ala Phe Val Gln Gly Lys Asp Trp Gly Val Lys Lys
        435                 440                 445
```

-continued

```
Phe Ile Arg Arg Asp Phe Tyr Ala Tyr Lys Asp Phe Leu Trp Cys Phe
    450                 455                 460

Pro Phe Ser Leu Val Phe Leu Gln Glu Ile Gln Ile Cys Cys His Val
465                 470                 475                 480

Ser Cys Leu Cys Cys Ile Cys Cys Ser Thr Arg Ile Cys Leu Gly Cys
                485                 490                 495

Leu Leu Glu Leu Phe Leu Ser Arg Ala Leu Arg Ala Leu His Val Leu
            500                 505                 510

Trp Asn Gly Phe Gln Leu His Cys Gln Thr Glu Tyr Asn Gln Lys Leu
        515                 520                 525

Gln Val Asn Gln Phe Ser Glu Ser Lys Ser Leu Tyr His Arg Glu Lys
    530                 535                 540

Gln Leu Ile Ala Met Asp Ser Ala Ile Cys Glu Glu Arg Gly Ala Ala
545                 550                 555                 560

Gly Ser Leu Ile Ser Cys Glu Thr Met Pro Ala Ile Leu Lys Leu Gln
                565                 570                 575

Lys Asn Cys Leu Leu Ser Leu Arg Thr Ala Leu Thr His Asn Gln Asp
            580                 585                 590

Phe Ser Ile Tyr Arg Leu Cys Cys Lys Arg Gly Ser Leu Cys His Ala
        595                 600                 605

Ser Gln Ala Arg Ser Pro Ala Phe Pro Lys Pro Val Arg Pro Leu Pro
    610                 615                 620

Ala Pro Ile Thr Arg Ile Thr Pro Gln Leu Gly Gly Gln Ser Asp Ser
625                 630                 635                 640

Ser Gln Pro Leu Leu Thr Thr Gly Arg Pro Gln Gly Trp Gln Asp Gln
                645                 650                 655

Ala Leu Arg His Thr Gln Gln Ala Ser Pro Ala Ser Cys Ala Thr Ile
            660                 665                 670

Thr Ile Pro Ile His Ser Ala Ala Leu Gly Asp His Ser Gly Asp Pro
        675                 680                 685

Gly Pro Ala Trp Asp Thr Cys Pro Pro Leu Pro Leu Thr Thr Leu Ile
    690                 695                 700

Pro Arg Ala Pro Pro Pro Tyr Gly Asp Ser Thr Ala Arg Ser Trp Pro
705                 710                 715                 720

Ser Arg Cys Gly Pro Leu Gly Asp Gly His Ser Tyr Thr Ser Lys Val
                725                 730                 735

Asn Cys Leu Leu Leu Gln Asp Gly Phe His Gly Cys Val Ser Ile Thr
            740                 745                 750

Gly Ala Ala Gly Arg Arg Asn Leu Ser Ile Phe Leu Phe Leu Met Leu
        755                 760                 765

Cys Lys Leu Glu Phe His Ala Cys Lys Ile Gln Asn Lys Asn Cys Pro
    770                 775                 780

Asp Phe Lys Lys Phe Asp Gly Pro Cys Gly Glu Arg Gly Gly Gly Arg
785                 790                 795                 800

Thr Ala Arg Ala Leu Trp Ala Arg Gly Asp Ser Val Leu Thr Pro Ala
                805                 810                 815

Leu Asp Pro Gln Thr Pro Val Arg Ala Pro Ser Leu Thr Arg Ala Ala
            820                 825                 830

Ala Ala Val His Tyr Lys Leu Ile Gln Gln Pro Ile Ser Leu Phe Ser
        835                 840                 845

Ile Thr Asp Arg Leu His Lys Thr Phe Ser Gln Leu Pro Ser Val His
    850                 855                 860

Leu Cys Ser Ile Thr Phe Gln Trp Gly His Pro Pro Ile Phe Cys Ser
```

```
865                 870                 875                 880

Thr Asn Asp Ile Cys Val Thr Ala Asn Phe Cys Ile Ser Val Thr Phe
                885                 890                 895

Leu Lys Pro Cys Phe Leu Leu His Glu Ala Ser Ala Ser Gln Cys His
            900                 905                 910

Leu Phe Leu Gln Pro Gln Val Gly Thr Pro Pro Pro His Thr Ala Ser
        915                 920                 925

Ala Arg Ala Pro Ser Gly Pro Pro His Pro His Glu Ser Cys Pro Ala
    930                 935                 940

Gly Arg Arg Pro Ala Arg Ala Ala Gln Thr Cys Ala Arg Arg Gln His
945                 950                 955                 960

Gly Leu Pro Gly Cys Glu Glu Ala Gly Thr Ala Arg Val Pro Ser Leu
                965                 970                 975

His Leu His Leu His Gln Ala Ala Leu Gly Ala Gly Arg Gly Arg Gly
            980                 985                 990

Trp Gly Glu Ala Cys Ala Gln Val  Pro Pro Ser Arg Gly  Val Leu Arg
        995                 1000                1005

Phe Leu  Asp Leu Lys Val Arg  Tyr Leu His Ser Gln  Trp Gln His
    1010                 1015                 1020

Tyr His  Arg Ser Gly Glu Ala  Ala Gly Thr Pro Leu  Trp Arg Pro
    1025                 1030                 1035

Thr Arg  Asn Val Pro Phe Arg  Glu Leu Lys Asn Gln  Arg Thr Ala
    1040                 1045                 1050

Gln Gly  Ala Pro Gly Ile His  His Ala Ala Ser Pro  Val Ala Ala
    1055                 1060                 1065

Asn Leu  Cys Asp Pro Ala Arg  His Ala Gln His Thr  Arg Ile Pro
    1070                 1075                 1080

Cys Gly  Ala Gly Gln Val Arg  Ala Gly Arg Gly Pro  Glu Ala Gly
    1085                 1090                 1095

Gly Gly  Val Leu Gln Pro Gln  Arg Pro Ala Pro Glu  Lys Pro Gly
    1100                 1105                 1110

Cys Pro  Cys Arg Arg Gly Gln  Pro Arg Leu His Thr  Val Lys Met
    1115                 1120                 1125

Trp Arg  Ala Val Ala Met Met  Val Pro Asp Arg Gln  Val His Tyr
    1130                 1135                 1140

Asp Phe  Gly Leu Gln Asn Leu  Gln Asn Gly Gly Gly  Ser Arg Ser
    1145                 1150                 1155

Ser Ala  Thr Leu Pro Gly Arg  Arg Arg Arg Arg Trp  Leu Arg Arg
    1160                 1165                 1170

Arg Arg  Gln Pro Ile Ser Val  Ala Pro Ala Gly Pro  Pro Arg Arg
    1175                 1180                 1185

Pro Asn  Gln Lys Pro Asn Pro  Pro Gly Gly Ala Arg  Cys Val Ile
    1190                 1195                 1200

Met Arg  Pro Thr Trp Pro Gly  Thr Ser Ala Phe Thr  Lys Arg Ser
    1205                 1210                 1215

Phe Ala  Val Thr Glu Arg Ile  Ile Thr Glu Ile Ser  Cys Cys Thr
    1220                 1225                 1230

Leu Ser  Ser Glu Glu Asn Glu  Tyr Leu Pro Arg Pro  Glu Trp Gln
    1235                 1240                 1245

Leu Gln  Tyr Glu Ala Gly Met  Thr Leu Gly Gly Lys  Ile Leu Phe
    1250                 1255                 1260

Phe Leu  Phe Leu Leu Leu Pro  Leu Ser Pro Phe Ser  Leu Ile Phe
    1265                 1270                 1275
```

```
Asp Tyr  Trp Ala Gln Lys Glu  Lys Gly Ser Ser Ser  Phe Leu Arg
    1280                 1285                 1290

Pro Ser  Cys Val Pro Phe Arg  Glu Leu Lys Asn Val  Ser Val Leu
    1295                 1300                 1305

Glu Gly  Leu Arg Gln Gly Arg  Leu Gly Gly Pro Cys  Ser Cys His
    1310                 1315                 1320

Cys Pro  Arg Pro Ser Gln Ala  Arg Leu Thr Pro Val  Asp Val Ala
    1325                 1330                 1335

Gly Pro  Phe Leu Cys Leu Gly  Asp Pro Gly Leu Phe  Pro Pro Val
    1340                 1345                 1350

Lys Ser  Ser Ile Thr Gly Gly  Lys Ser Thr Cys Ser  Ala Pro Gly
    1355                 1360                 1365

Pro Gln  Ser Leu Pro Ser Thr  Pro Phe Ser Thr Tyr  Pro Gln Trp
    1370                 1375                 1380

Val Ile  Leu Ile Thr Glu Leu  Gly Met Glu Cys Thr  Leu Gly Gln
    1385                 1390                 1395

Val Gly  Ala Pro Ser Pro Arg  Arg Glu Glu Asp Gly  Trp Arg Gly
    1400                 1405                 1410

Gly His  Ser Arg Phe Lys Ala  Asp Val Pro Ala Pro  Gln Gly Pro
    1415                 1420                 1425

Cys Trp  Gly Gly Gln Pro Gly  Ser Ala Pro Ser Ser  Ala Pro Pro
    1430                 1435                 1440

Glu Gln  Ser Leu Leu Asp Asp  Tyr Trp Ala Gln Lys  Glu Lys Ile
    1445                 1450                 1455

Ser Ile  Pro Arg Thr His Leu  Cys Leu Val Leu Gly  Val Leu Ser
    1460                 1465                 1470

Gly His  Ser Gly Ser Arg Leu  Trp Lys Phe Glu Met  Ser Tyr Thr
    1475                 1480                 1485

Val Gly  Gly Pro Pro Pro His  Val His Ala Arg Pro  Arg His Trp
    1490                 1495                 1500

Lys Thr  Asp Arg
    1505
```

<210> SEQ ID NO 625
<211> LENGTH: 1507
<212> TYPE: PRT
<213> ORGANISM: Artificial seqeunce
<220> FEATURE:
<223> OTHER INFORMATION: Heterologous polypeptide

<400> SEQUENCE: 625

```
Met Gly Gln Lys Glu Gln Ile His Thr Leu Gln Lys Asn Ser Glu Arg
1               5                   10                  15

Met Ser Lys Gln Leu Thr Arg Ser Ser Gln Ala Val Gly Asn Thr Thr
            20                  25                  30

Leu Gln Gln Leu Gly Glu Ala Ser Gln Ala Pro Ser Gly Ser Leu Ile
        35                  40                  45

Pro Leu Arg Leu Pro Leu Leu Trp Glu Val Arg Gly Asn Ser Lys Met
    50                  55                  60

Ala Leu Asn Ser Leu Asn Ser Ile Asp Asp Ala Gln Leu Thr Arg Ile
65                  70                  75                  80

Ala Pro Pro Arg Ser His Cys Cys Phe Trp Glu Val Asn Ala Pro Phe
                85                  90                  95

Val Gln Gly Lys Asp Trp Gly Leu Lys Lys Phe Ile Arg Arg Asp Phe
            100                 105                 110
```

```
Glu Ala Phe Gln Arg Ala Ala Gly Glu Gly Gly Pro Gly Arg Gly Gly
        115                 120                 125

Ala Arg Arg Gly Ala Arg Val Leu Gln Ser Pro Phe Cys Arg Ala Gly
    130                 135                 140

Ala Gly Glu Trp Leu Gly His Gln Ser Leu Arg Trp Gly Met Glu Leu
145                 150                 155                 160

Ala Ala Ser Arg Arg Phe Ser Trp Asp His His Ser Ala Gly Gly Pro
                165                 170                 175

Pro Arg Val Pro Ser Val Arg Ser Gly Ala Ala Gln Val Gln Pro Lys
            180                 185                 190

Asp Pro Leu Pro Leu Arg Thr Leu Ala Gly Cys Leu Ala Arg Thr Ala
        195                 200                 205

His Leu Arg Pro Gly Ala Glu Ser Leu Pro Gln Pro Gln Leu His Cys
    210                 215                 220

Thr Ile Ala Arg Glu Leu His Gln Phe Ala Phe Asp Leu Leu Ile Lys
225                 230                 235                 240

Ser His Lys Met His Phe Ser Leu Lys Glu His Pro Pro Pro Pro Cys
                245                 250                 255

Pro Pro His Val Val Gly Tyr Gly His Leu Asp Thr Ser Gly Ser Ser
            260                 265                 270

Ser Ser Ser Ser Trp Pro Gln Pro Asp Ser Phe Ala Ala Leu His Ser
        275                 280                 285

Ser Leu Asn Glu Leu Gly Glu Leu Trp Phe Gln Ser Ser Glu Leu Ser
    290                 295                 300

Pro Thr Gly Ala Pro Trp Pro Ser Arg Arg Pro Thr Trp Arg Gly Thr
305                 310                 315                 320

Thr Val Ser Pro Arg Thr Ala Thr Ser Ser Ala Arg Thr Cys Cys Gly
                325                 330                 335

Thr Lys Trp Pro Ser Ser Gln Glu Ala Ala Leu Gly Leu Gly Ser Gly
            340                 345                 350

Leu Leu Arg Phe Ser Cys Gly Thr Ala Ala Ile Arg Gln Asn Leu Gln
        355                 360                 365

Asn Gly Gly Gly Ser Arg Ser Ser Ala Thr Leu Pro Gly Arg Arg Arg
    370                 375                 380

Arg Arg Trp Leu Arg Arg Arg Arg Gln Pro Ile Ser Val Ala Pro Ala
385                 390                 395                 400

Gly Pro Pro Arg Arg Pro Asn Gln Lys Pro Asn Pro Pro Gly Gly Ala
                405                 410                 415

Arg Cys Val Ile Met Arg Pro Thr Trp Pro Gly Thr Ser Ala Phe Thr
            420                 425                 430

Gly Met Glu Cys Thr Leu Gly Gln Val Gly Ala Pro Ser Pro Arg Arg
        435                 440                 445

Glu Glu Asp Gly Trp Arg Gly Gly His Ser Arg Phe Lys Ala Asp Val
    450                 455                 460

Pro Ala Pro Gln Gly Pro Cys Trp Gly Gly Gln Pro Gly Ser Ala Pro
465                 470                 475                 480

Ser Ser Ala Pro Pro Glu Gln Ser Leu Leu Asp Asp Tyr Trp Ala Gln
                485                 490                 495

Lys Glu Lys Ile Ser Ile Pro Arg Thr His Leu Cys Trp Lys Phe Glu
            500                 505                 510

Met Ser Tyr Thr Val Gly Gly Pro Pro Pro His Val His Ala Arg Pro
        515                 520                 525
```

-continued

```
Arg His Trp Lys Thr Asp Arg Asp Tyr Trp Ala Gln Lys Glu Lys Gly
    530                 535                 540

Ser Ser Ser Phe Leu Arg Pro Ser Cys Val Pro Phe Arg Glu Leu Lys
545                 550                 555                 560

Asn Val Ser Val Leu Glu Gly Leu Arg Gln Gly Arg Leu Gly Gly Pro
                565                 570                 575

Cys Ser Cys His Cys Pro Arg Pro Ser Gln Ala Arg Leu Thr Pro Val
            580                 585                 590

Asp Val Ala Gly Pro Phe Leu Cys Leu Gly Asp Pro Gly Leu Phe Pro
        595                 600                 605

Pro Val Lys Ser Ser Ile Thr Glu Ile Ser Cys Cys Thr Leu Ser Ser
    610                 615                 620

Glu Glu Asn Glu Tyr Leu Pro Arg Pro Glu Trp Gln Leu Gln Tyr Glu
625                 630                 635                 640

Ala Gly Met Thr Leu Gly Gly Lys Ile Leu Phe Phe Leu Phe Leu Leu
                645                 650                 655

Leu Pro Leu Ser Pro Phe Ser Leu Ile Phe Leu Val Leu Gly Val Leu
            660                 665                 670

Ser Gly His Ser Gly Ser Arg Leu Lys Arg Ser Phe Ala Val Thr Glu
        675                 680                 685

Arg Ile Ile Thr Gly Gly Lys Ser Thr Cys Ser Ala Pro Gly Pro Gln
    690                 695                 700

Ser Leu Pro Ser Thr Pro Phe Ser Thr Tyr Pro Gln Trp Val Ile Leu
705                 710                 715                 720

Ile Thr Glu Leu Asp Gly His Ser Tyr Thr Ser Lys Val Asn Cys Leu
                725                 730                 735

Leu Leu Gln Asp Gly Phe His Gly Cys Val Ser Ile Thr Gly Ala Ala
            740                 745                 750

Gly Arg Arg Asn Leu Ser Ile Phe Leu Phe Leu Met Leu Cys Lys Leu
        755                 760                 765

Glu Phe His Ala Cys Gln Trp Gln His Tyr His Arg Ser Gly Glu Ala
    770                 775                 780

Ala Gly Thr Pro Leu Trp Arg Pro Thr Arg Asn Val Ala Met Met Val
785                 790                 795                 800

Pro Asp Arg Gln Val His Tyr Asp Phe Gly Leu Val Leu Arg Phe Leu
                805                 810                 815

Asp Leu Lys Val Arg Tyr Leu His Ser Lys Ile Gln Asn Lys Asn Cys
            820                 825                 830

Pro Asp Val Pro Phe Arg Glu Leu Lys Asn Gln Arg Thr Ala Gln Gly
        835                 840                 845

Ala Pro Gly Ile His His Ala Ala Ser Pro Val Ala Ala Asn Leu Cys
    850                 855                 860

Asp Pro Ala Arg His Ala Gln His Thr Arg Ile Pro Cys Gly Ala Gly
865                 870                 875                 880

Gln Val Arg Ala Gly Arg Gly Pro Glu Ala Gly Gly Gly Val Leu Gln
                885                 890                 895

Pro Gln Arg Pro Ala Pro Glu Lys Pro Gly Cys Pro Cys Arg Arg Gly
            900                 905                 910

Gln Pro Arg Leu His Thr Val Lys Met Trp Arg Ala Cys His Leu Phe
        915                 920                 925

Leu Gln Pro Gln Val Gly Thr Pro Pro Pro His Thr Ala Ser Ala Arg
    930                 935                 940

Ala Pro Ser Gly Pro Pro His Pro His Glu Ser Cys Pro Ala Gly Arg
```

-continued

```
945                 950                 955                 960

Arg Pro Ala Arg Ala Ala Gln Thr Cys Ala Arg Arg Gln His Gly Leu
                965                 970                 975

Pro Gly Cys Glu Glu Ala Gly Thr Ala Arg Val Pro Ser Leu His Leu
            980                 985                 990

His Leu His Gln Ala Ala Leu Gly  Ala Gly Arg Gly Arg  Gly Trp Gly
        995                 1000                1005

Glu Ala  Cys Ala Gln Val Pro  Pro Ser Arg Gly His  Tyr Lys Leu
    1010                 1015                 1020

Ile Gln  Gln Pro Ile Ser Leu  Phe Ser Ile Thr Asp  Arg Leu His
    1025                 1030                 1035

Lys Thr  Phe Ser Gln Leu Pro  Ser Val His Leu Cys  Ser Ile Thr
    1040                 1045                 1050

Phe Gln  Trp Gly His Pro Pro  Ile Phe Cys Ser Thr  Asn Asp Ile
    1055                 1060                 1065

Cys Val  Thr Ala Asn Phe Cys  Ile Ser Val Thr Phe  Leu Lys Pro
    1070                 1075                 1080

Cys Phe  Leu Leu His Glu Ala  Ser Ala Ser Gln Phe  Lys Lys Phe
    1085                 1090                 1095

Asp Gly  Pro Cys Gly Glu Arg  Gly Gly Gly Arg Thr  Ala Arg Ala
    1100                 1105                 1110

Leu Trp  Ala Arg Gly Asp Ser  Val Leu Thr Pro Ala  Leu Asp Pro
    1115                 1120                 1125

Gln Thr  Pro Val Arg Ala Pro  Ser Leu Thr Arg Ala  Ala Ala Ala
    1130                 1135                 1140

Val Gly  Val Pro Gly Asp Ser  Thr Arg Arg Ala Val  Arg Arg Met
    1145                 1150                 1155

Asn Thr  Phe Cys Gly Ala Ser  Ala Cys Asp Val Ser  Leu Ile Ala
    1160                 1165                 1170

Met Asp  Ser Ala Cys Glu Glu  Arg Gly Ala Ala Gly  Ser Leu Ile
    1175                 1180                 1185

Ser Cys  Glu Ser Leu Tyr His  Arg Glu Lys Gln Leu  Ile Ala Met
    1190                 1195                 1200

Asp Ser  Ala Ile Phe Val Gln  Gly Lys Asp Trp Gly  Val Lys Lys
    1205                 1210                 1215

Phe Ile  Arg Arg Asp Phe Thr  Met Pro Ala Ile Leu  Lys Leu Gln
    1220                 1225                 1230

Lys Asn  Cys Leu Leu Ser Leu  Asn Ser Lys Met Ala  Leu Asn Ser
    1235                 1240                 1245

Glu Ala  Leu Ser Val Val Ser  Glu Tyr Glu Ala Gly  Met Thr Leu
    1250                 1255                 1260

Gly Glu  Lys Phe Arg Val Gly  Asn Cys Lys His Leu  Lys Met Thr
    1265                 1270                 1275

Arg Pro  Thr Glu Tyr Asn Gln  Lys Leu Gln Val Asn  Gln Phe Ser
    1280                 1285                 1290

Glu Ser  Lys Arg Thr Ala Leu  Thr His Asn Gln Asp  Phe Ser Ile
    1295                 1300                 1305

Tyr Arg  Leu Cys Cys Lys Arg  Gly Ser Leu Cys His  Ala Ser Gln
    1310                 1315                 1320

Ala Arg  Ser Pro Ala Phe Pro  Lys Pro Val Arg Pro  Leu Pro Ala
    1325                 1330                 1335

Pro Ile  Thr Arg Ile Thr Pro  Gln Leu Gly Gly Gln  Ser Asp Ser
    1340                 1345                 1350
```

Ser Gln Pro Leu Leu Thr Thr Gly Arg Pro Gln Gly Trp Gln Asp
1355 1360 1365

Gln Ala Leu Arg His Thr Gln Gln Ala Ser Pro Ala Ser Cys Ala
1370 1375 1380

Thr Ile Thr Ile Pro Ile His Ser Ala Ala Leu Gly Asp His Ser
1385 1390 1395

Gly Asp Pro Gly Pro Ala Trp Asp Thr Cys Pro Pro Leu Pro Leu
1400 1405 1410

Thr Thr Leu Ile Pro Arg Ala Pro Pro Pro Tyr Gly Asp Ser Thr
1415 1420 1425

Ala Arg Ser Trp Pro Ser Arg Cys Gly Pro Leu Gly Tyr Ala Tyr
1430 1435 1440

Lys Asp Phe Leu Trp Cys Phe Pro Phe Ser Leu Val Phe Leu Gln
1445 1450 1455

Glu Ile Gln Ile Cys Cys His Val Ser Cys Leu Cys Cys Ile Cys
1460 1465 1470

Cys Ser Thr Arg Ile Cys Leu Gly Cys Leu Leu Glu Leu Phe Leu
1475 1480 1485

Ser Arg Ala Leu Arg Ala Leu His Val Leu Trp Asn Gly Phe Gln
1490 1495 1500

Leu His Cys Gln
1505

<210> SEQ ID NO 626
<211> LENGTH: 1507
<212> TYPE: PRT
<213> ORGANISM: Artificial seqeunce
<220> FEATURE:
<223> OTHER INFORMATION: Heterologous polypeptide

<400> SEQUENCE: 626

Met Gly Gln Lys Glu Gln Ile His Thr Leu Gln Lys Asn Ser Glu Arg
1 5 10 15

Met Ser Lys Gln Leu Thr Arg Ser Ser Gln Ala Val Asp Gly His Ser
20 25 30

Tyr Thr Ser Lys Val Asn Cys Leu Leu Leu Gln Asp Gly Phe His Gly
35 40 45

Cys Val Ser Ile Thr Gly Ala Ala Gly Arg Arg Asn Leu Ser Ile Phe
50 55 60

Leu Phe Leu Met Leu Cys Lys Leu Glu Phe His Ala Cys Val Pro Phe
65 70 75 80

Arg Glu Leu Lys Asn Gln Arg Thr Ala Gln Gly Ala Pro Gly Ile His
85 90 95

His Ala Ala Ser Pro Val Ala Ala Asn Leu Cys Asp Pro Ala Arg His
100 105 110

Ala Gln His Thr Arg Ile Pro Cys Gly Ala Gly Gln Val Arg Ala Gly
115 120 125

Arg Gly Pro Glu Ala Gly Gly Gly Val Leu Gln Pro Gln Arg Pro Ala
130 135 140

Pro Glu Lys Pro Gly Cys Pro Cys Arg Arg Gly Gln Pro Arg Leu His
145 150 155 160

Thr Val Lys Met Trp Arg Ala Gln Trp Gln His Tyr His Arg Ser Gly
165 170 175

Glu Ala Ala Gly Thr Pro Leu Trp Arg Pro Thr Arg Asn Lys Ile Gln
180 185 190

```
Asn Lys Asn Cys Pro Asp Val Ala Met Met Val Pro Asp Arg Gln Val
        195                 200                 205

His Tyr Asp Phe Gly Leu Val Leu Arg Phe Leu Asp Leu Lys Val Arg
    210                 215                 220

Tyr Leu His Ser Cys His Leu Phe Leu Gln Pro Gln Val Gly Thr Pro
225                 230                 235                 240

Pro Pro His Thr Ala Ser Ala Arg Ala Pro Ser Gly Pro Pro His Pro
                245                 250                 255

His Glu Ser Cys Pro Ala Gly Arg Arg Pro Ala Arg Ala Ala Gln Thr
            260                 265                 270

Cys Ala Arg Arg Gln His Gly Leu Pro Gly Cys Glu Glu Ala Gly Thr
        275                 280                 285

Ala Arg Val Pro Ser Leu His Leu His Leu His Gln Ala Ala Leu Gly
    290                 295                 300

Ala Gly Arg Gly Arg Gly Trp Gly Glu Ala Cys Ala Gln Val Pro Pro
305                 310                 315                 320

Ser Arg Gly His Tyr Lys Leu Ile Gln Gln Pro Ile Ser Leu Phe Ser
                325                 330                 335

Ile Thr Asp Arg Leu His Lys Thr Phe Ser Gln Leu Pro Ser Val His
            340                 345                 350

Leu Cys Ser Ile Thr Phe Gln Trp Gly His Pro Pro Ile Phe Cys Ser
        355                 360                 365

Thr Asn Asp Ile Cys Val Thr Ala Asn Phe Cys Ile Ser Val Thr Phe
    370                 375                 380

Leu Lys Pro Cys Phe Leu Leu His Glu Ala Ser Ala Ser Gln Phe Lys
385                 390                 395                 400

Lys Phe Asp Gly Pro Cys Gly Glu Arg Gly Gly Gly Arg Thr Ala Arg
                405                 410                 415

Ala Leu Trp Ala Arg Gly Asp Ser Val Leu Thr Pro Ala Leu Asp Pro
            420                 425                 430

Gln Thr Pro Val Arg Ala Pro Ser Leu Thr Arg Ala Ala Ala Ala Val
        435                 440                 445

Gln Asn Leu Gln Asn Gly Gly Gly Ser Arg Ser Ser Ala Thr Leu Pro
    450                 455                 460

Gly Arg Arg Arg Arg Arg Trp Leu Arg Arg Arg Arg Gln Pro Ile Ser
465                 470                 475                 480

Val Ala Pro Ala Gly Pro Pro Arg Arg Pro Asn Gln Lys Pro Asn Pro
                485                 490                 495

Pro Gly Gly Ala Arg Cys Val Ile Met Arg Pro Thr Trp Pro Gly Thr
            500                 505                 510

Ser Ala Phe Thr Gly Met Glu Cys Thr Leu Gly Gln Val Gly Ala Pro
        515                 520                 525

Ser Pro Arg Arg Glu Glu Asp Gly Trp Arg Gly Gly His Ser Arg Phe
    530                 535                 540

Lys Ala Asp Val Pro Ala Pro Gln Gly Pro Cys Trp Gly Gly Gln Pro
545                 550                 555                 560

Gly Ser Ala Pro Ser Ser Ala Pro Pro Glu Gln Ser Leu Leu Asp Asp
                565                 570                 575

Tyr Trp Ala Gln Lys Glu Lys Ile Ser Ile Pro Arg Thr His Leu Cys
            580                 585                 590

Trp Lys Phe Glu Met Ser Tyr Thr Val Gly Gly Pro Pro Pro His Val
        595                 600                 605
```

```
His Ala Arg Pro Arg His Trp Lys Thr Asp Arg Asp Tyr Trp Ala Gln
    610                 615                 620

Lys Glu Lys Gly Ser Ser Ser Phe Leu Arg Pro Ser Cys Val Pro Phe
625                 630                 635                 640

Arg Glu Leu Lys Asn Val Ser Val Leu Glu Gly Leu Arg Gln Gly Arg
                645                 650                 655

Leu Gly Gly Pro Cys Ser Cys His Cys Pro Arg Pro Ser Gln Ala Arg
            660                 665                 670

Leu Thr Pro Val Asp Val Ala Gly Pro Phe Leu Cys Leu Gly Asp Pro
        675                 680                 685

Gly Leu Phe Pro Pro Val Lys Ser Ser Ile Thr Glu Ile Ser Cys Cys
    690                 695                 700

Thr Leu Ser Ser Glu Glu Asn Glu Tyr Leu Pro Arg Pro Glu Trp Gln
705                 710                 715                 720

Leu Gln Tyr Glu Ala Gly Met Thr Leu Gly Gly Lys Ile Leu Phe Phe
                725                 730                 735

Leu Phe Leu Leu Leu Pro Leu Ser Pro Phe Ser Leu Ile Phe Leu Val
            740                 745                 750

Leu Gly Val Leu Ser Gly His Ser Gly Ser Arg Leu Lys Arg Ser Phe
        755                 760                 765

Ala Val Thr Glu Arg Ile Ile Thr Gly Gly Lys Ser Thr Cys Ser Ala
    770                 775                 780

Pro Gly Pro Gln Ser Leu Pro Ser Thr Pro Phe Ser Thr Tyr Pro Gln
785                 790                 795                 800

Trp Val Ile Leu Ile Thr Glu Leu Gly Asn Thr Thr Leu Gln Gln Leu
                805                 810                 815

Gly Glu Ala Ser Gln Ala Pro Ser Gly Ser Leu Ile Pro Leu Arg Leu
            820                 825                 830

Pro Leu Leu Trp Glu Val Arg Gly Asn Ser Lys Met Ala Leu Asn Ser
        835                 840                 845

Leu Asn Ser Ile Asp Asp Ala Gln Leu Thr Arg Ile Ala Pro Pro Arg
    850                 855                 860

Ser His Cys Cys Phe Trp Glu Val Asn Ala Pro Phe Val Gln Gly Lys
865                 870                 875                 880

Asp Trp Gly Leu Lys Lys Phe Ile Arg Arg Asp Phe Glu Ala Phe Gln
                885                 890                 895

Arg Ala Ala Gly Glu Gly Gly Pro Gly Arg Gly Gly Ala Arg Arg Gly
            900                 905                 910

Ala Arg Val Leu Gln Ser Pro Phe Cys Arg Ala Gly Ala Gly Glu Trp
        915                 920                 925

Leu Gly His Gln Ser Leu Arg Trp Gly Met Glu Leu Ala Ala Ser Arg
    930                 935                 940

Arg Phe Ser Trp Asp His His Ser Ala Gly Gly Pro Pro Arg Val Pro
945                 950                 955                 960

Ser Val Arg Ser Gly Ala Ala Gln Val Gln Pro Lys Asp Pro Leu Pro
                965                 970                 975

Leu Arg Thr Leu Ala Gly Cys Leu Ala Arg Thr Ala His Leu Arg Pro
            980                 985                 990

Gly Ala Glu Ser Leu Pro Gln Pro  Gln Leu His Cys Thr  Ile Ala Arg
        995                 1000                1005

Glu Leu  His Gln Phe Ala Phe  Asp Leu Leu Ile Lys  Ser His Lys
    1010                1015                1020

Met His  Phe Ser Leu Lys Glu  His Pro Pro Pro Pro  Cys Pro Pro
```

-continued

```
    1025                1030                1035

His Val  Val Gly Tyr Gly His  Leu Asp Thr Ser Gly  Ser Ser Ser
    1040                1045                1050

Ser Ser  Ser Trp Pro Gln Pro  Asp Ser Phe Ala Ala  Leu His Ser
    1055                1060                1065

Ser Leu  Asn Glu Leu Gly Glu  Leu Trp Phe Gln Ser  Ser Glu Leu
    1070                1075                1080

Ser Pro  Thr Gly Ala Pro Trp  Pro Ser Arg Arg Pro  Thr Trp Arg
    1085                1090                1095

Gly Thr  Thr Val Ser Pro Arg  Thr Ala Thr Ser Ser  Ala Arg Thr
    1100                1105                1110

Cys Cys  Gly Thr Lys Trp Pro  Ser Ser Gln Glu Ala  Ala Leu Gly
    1115                1120                1125

Leu Gly  Ser Gly Leu Leu Arg  Phe Ser Cys Gly Thr  Ala Ala Ile
    1130                1135                1140

Arg Gly  Val Pro Gly Asp Ser  Thr Arg Arg Ala Val  Arg Arg Met
    1145                1150                1155

Asn Thr  Phe Cys Gly Ala Ser  Ala Cys Asp Val Ser  Leu Ile Ala
    1160                1165                1170

Met Asp  Ser Ala Cys Glu Glu  Arg Gly Ala Ala Gly  Ser Leu Ile
    1175                1180                1185

Ser Cys  Glu Ser Leu Tyr His  Arg Glu Lys Gln Leu  Ile Ala Met
    1190                1195                1200

Asp Ser  Ala Ile Phe Val Gln  Gly Lys Asp Trp Gly  Val Lys Lys
    1205                1210                1215

Phe Ile  Arg Arg Asp Phe Tyr  Glu Ala Gly Met Thr  Leu Gly Glu
    1220                1225                1230

Lys Phe  Arg Val Gly Asn Cys  Lys His Leu Lys Met  Thr Arg Pro
    1235                1240                1245

Thr Met  Pro Ala Ile Leu Lys  Leu Gln Lys Asn Cys  Leu Leu Ser
    1250                1255                1260

Leu Asn  Ser Lys Met Ala Leu  Asn Ser Glu Ala Leu  Ser Val Val
    1265                1270                1275

Ser Glu  Thr Glu Tyr Asn Gln  Lys Leu Gln Val Asn  Gln Phe Ser
    1280                1285                1290

Glu Ser  Lys Arg Thr Ala Leu  Thr His Asn Gln Asp  Phe Ser Ile
    1295                1300                1305

Tyr Arg  Leu Cys Cys Lys Arg  Gly Ser Leu Cys His  Ala Ser Gln
    1310                1315                1320

Ala Arg  Ser Pro Ala Phe Pro  Lys Pro Val Arg Pro  Leu Pro Ala
    1325                1330                1335

Pro Ile  Thr Arg Ile Thr Pro  Gln Leu Gly Gly Gln  Ser Asp Ser
    1340                1345                1350

Ser Gln  Pro Leu Leu Thr Thr  Gly Arg Pro Gln Gly  Trp Gln Asp
    1355                1360                1365

Gln Ala  Leu Arg His Thr Gln  Gln Ala Ser Pro Ala  Ser Cys Ala
    1370                1375                1380

Thr Ile  Thr Ile Pro Ile His  Ser Ala Ala Leu Gly  Asp His Ser
    1385                1390                1395

Gly Asp  Pro Gly Pro Ala Trp  Asp Thr Cys Pro Pro  Leu Pro Leu
    1400                1405                1410

Thr Thr  Leu Ile Pro Arg Ala  Pro Pro Pro Tyr Gly  Asp Ser Thr
    1415                1420                1425
```

```
Ala Arg  Ser Trp Pro Ser Arg  Cys Gly Pro Leu Gly  Tyr Ala Tyr
    1430                 1435                 1440

Lys Asp  Phe Leu Trp Cys Phe  Pro Phe Ser Leu Val  Phe Leu Gln
    1445                 1450                 1455

Glu Ile  Gln Ile Cys Cys His  Val Ser Cys Leu Cys  Cys Ile Cys
    1460                 1465                 1470

Cys Ser  Thr Arg Ile Cys Leu  Gly Cys Leu Leu Glu  Leu Phe Leu
    1475                 1480                 1485

Ser Arg  Ala Leu Arg Ala Leu  His Val Leu Trp Asn  Gly Phe Gln
    1490                 1495                 1500

Leu His  Cys Gln
    1505


<210> SEQ ID NO 627
<211> LENGTH: 7
<212> TYPE: PRT
<213> ORGANISM: Artificial seqeunce
<220> FEATURE:
<223> OTHER INFORMATION: protein tag

<400> SEQUENCE: 627

Ser His His His His His His
1               5


<210> SEQ ID NO 628
<211> LENGTH: 845
<212> TYPE: DNA
<213> ORGANISM: Artificial sequence
<220> FEATURE:
<223> OTHER INFORMATION: Promoter

<400> SEQUENCE: 628

ccattgcata cgttgtatcc atatcataat atgtacattt atattggctc atgtccaaca     60

ttaccgccat gttgacattg attattgact agttattaat agtaatcaat tacggggtca    120

ttagttcata gcccatatat ggagttccgc gttacataac ttacggtaaa tggcccgcct    180

ggctgaccgc ccaacgaccc ccgcccattg acgtcaataa tgacgtatgt tcccatagta    240

acgccaatag ggactttcca ttgacgtcaa tgggtggagt atttacggta aactgcccac    300

ttggcagtac atcaagtgta tcatatgcca agtacgcccc ctattgacgt caatgacggt    360

aaatggcccg cctggcatta tgcccagtac atgaccttat gggactttcc tacttggcag    420

tacatctacg tattagtcat cgctattacc atggtgatgc ggttttggca gtacatcaat    480

gggcgtggat agcggtttga ctcacgggga tttccaagtc tccaccccat tgacgtcaat    540

gggagtttgt tttggcacca aaatcaacgg gactttccaa aatgtcgtaa caactccgcc    600

ccattgacgc aaatgggcgg taggcgtgta cggtgggagg tctatataag cagagctctc    660

cctatcagtg atagagatct ccctatcagt gatagagatc gtcgacgagc tcgtttagtg    720

aaccgtcaga tcgcctggag acgccatcca cgctgttttg acctccatag aagacaccgg    780

gaccgatcca gcctccgcgg ccgggaacgg tgcattggaa cgcggattcc ccgtgccaag    840

agtga                                                                845


<210> SEQ ID NO 629
<211> LENGTH: 227
<212> TYPE: DNA
<213> ORGANISM: Artificial sequence
<220> FEATURE:
<223> OTHER INFORMATION: polyA site
```

<400> SEQUENCE: 629
ctgtgccttc tagttgccag ccatctgttg tttgcccctc ccccgtgcct tccttgaccc 60
tggaaggtgc cactcccact gtcctttcct aataaaatga ggaaattgca tcgcattgtc 120
tgagtaggtg tcattctatt ctggggggtg gggtggggca ggacagcaag ggggaggatt 180
gggaagacaa tagcaggcat gctggggatg cggtgggctc tatggcc 227

<210> SEQ ID NO 630
<211> LENGTH: 149
<212> TYPE: DNA
<213> ORGANISM: Artificial sequence
<220> FEATURE:
<223> OTHER INFORMATION: Promoter

<400> SEQUENCE: 630
gatcactaat tccaaaccca cccgcttttt atagtaagtt tttcacccat aaataataaa 60
tacaataatt aatttctcgt aaaagtagaa aatatattct aatttattgc acggtaagga 120
agtagaatca taaagaacag tgacggatc 149

<210> SEQ ID NO 631
<211> LENGTH: 15
<212> TYPE: PRT
<213> ORGANISM: Homo sapiens

<400> SEQUENCE: 631

Val Pro Phe Arg Glu Leu Lys Asn Gln Arg Thr Ala Gln Gly Ala
1 5 10 15

<210> SEQ ID NO 632
<211> LENGTH: 15
<212> TYPE: PRT
<213> ORGANISM: Homo sapiens

<400> SEQUENCE: 632

Gln Arg Thr Ala Gln Gly Ala Pro Gly Ile His His Ala Ala Ser
1 5 10 15

<210> SEQ ID NO 633
<211> LENGTH: 15
<212> TYPE: PRT
<213> ORGANISM: Homo sapiens

<400> SEQUENCE: 633

Gly Ile His His Ala Ala Ser Pro Val Ala Ala Asn Leu Cys Asp
1 5 10 15

<210> SEQ ID NO 634
<211> LENGTH: 15
<212> TYPE: PRT
<213> ORGANISM: Homo sapiens

<400> SEQUENCE: 634

Val Ala Ala Asn Leu Cys Asp Pro Ala Arg His Ala Gln His Thr
1 5 10 15

<210> SEQ ID NO 635
<211> LENGTH: 15
<212> TYPE: PRT
<213> ORGANISM: Homo sapiens

<400> SEQUENCE: 635

Ala Arg His Ala Gln His Thr Arg Ile Pro Cys Gly Ala Gly Gln
1 5 10 15

<210> SEQ ID NO 636
<211> LENGTH: 15
<212> TYPE: PRT
<213> ORGANISM: Homo sapiens

<400> SEQUENCE: 636

Ile Pro Cys Gly Ala Gly Gln Val Arg Ala Gly Arg Gly Pro Glu
1 5 10 15

<210> SEQ ID NO 637
<211> LENGTH: 15
<212> TYPE: PRT
<213> ORGANISM: Homo sapiens

<400> SEQUENCE: 637

Arg Ala Gly Arg Gly Pro Glu Ala Gly Gly Gly Val Leu Gln Pro
1 5 10 15

<210> SEQ ID NO 638
<211> LENGTH: 15
<212> TYPE: PRT
<213> ORGANISM: Homo sapiens

<400> SEQUENCE: 638

Gly Gly Gly Val Leu Gln Pro Gln Arg Pro Ala Pro Glu Lys Pro
1 5 10 15

<210> SEQ ID NO 639
<211> LENGTH: 15
<212> TYPE: PRT
<213> ORGANISM: Homo sapiens

<400> SEQUENCE: 639

Arg Pro Ala Pro Glu Lys Pro Gly Cys Pro Cys Arg Arg Gly Gln
1 5 10 15

<210> SEQ ID NO 640
<211> LENGTH: 15
<212> TYPE: PRT
<213> ORGANISM: Homo sapiens

<400> SEQUENCE: 640

Cys Pro Cys Arg Arg Gly Gln Pro Arg Leu His Thr Val Lys Met
1 5 10 15

<210> SEQ ID NO 641
<211> LENGTH: 14
<212> TYPE: PRT
<213> ORGANISM: Homo sapiens

<400> SEQUENCE: 641

Arg Gly Gln Pro Arg Leu His Thr Val Lys Met Trp Arg Ala
1 5 10

<210> SEQ ID NO 642
<211> LENGTH: 15
<212> TYPE: PRT
<213> ORGANISM: Homo sapiens

<400> SEQUENCE: 642

Cys His Leu Phe Leu Gln Pro Gln Val Gly Thr Pro Pro Pro His
1 5 10 15

<210> SEQ ID NO 643
<211> LENGTH: 15
<212> TYPE: PRT
<213> ORGANISM: Homo sapiens

<400> SEQUENCE: 643

Val Gly Thr Pro Pro Pro His Thr Ala Ser Ala Arg Ala Pro Ser
1 5 10 15

<210> SEQ ID NO 644
<211> LENGTH: 15
<212> TYPE: PRT
<213> ORGANISM: Homo sapiens

<400> SEQUENCE: 644

Ala Ser Ala Arg Ala Pro Ser Gly Pro Pro His Pro His Glu Ser
1 5 10 15

<210> SEQ ID NO 645
<211> LENGTH: 15
<212> TYPE: PRT
<213> ORGANISM: Homo sapiens

<400> SEQUENCE: 645

Pro Pro His Pro His Glu Ser Cys Pro Ala Gly Arg Arg Pro Ala
1 5 10 15

<210> SEQ ID NO 646
<211> LENGTH: 15
<212> TYPE: PRT
<213> ORGANISM: Homo sapiens

<400> SEQUENCE: 646

Pro Ala Gly Arg Arg Pro Ala Arg Ala Ala Gln Thr Cys Ala Arg
1 5 10 15

<210> SEQ ID NO 647
<211> LENGTH: 15
<212> TYPE: PRT
<213> ORGANISM: Homo sapiens

<400> SEQUENCE: 647

Ala Ala Gln Thr Cys Ala Arg Arg Gln His Gly Leu Pro Gly Cys
1 5 10 15

<210> SEQ ID NO 648
<211> LENGTH: 15
<212> TYPE: PRT
<213> ORGANISM: Homo sapiens

<400> SEQUENCE: 648

Gln His Gly Leu Pro Gly Cys Glu Glu Ala Gly Thr Ala Arg Val
1 5 10 15

<210> SEQ ID NO 649
<211> LENGTH: 15
<212> TYPE: PRT
<213> ORGANISM: Homo sapiens

<400> SEQUENCE: 649

Glu Ala Gly Thr Ala Arg Val Pro Ser Leu His Leu His Leu His
1 5 10 15

<210> SEQ ID NO 650
<211> LENGTH: 15
<212> TYPE: PRT
<213> ORGANISM: Homo sapiens

<400> SEQUENCE: 650

Ser Leu His Leu His Leu His Gln Ala Ala Leu Gly Ala Gly Arg
1 5 10 15

<210> SEQ ID NO 651
<211> LENGTH: 15
<212> TYPE: PRT
<213> ORGANISM: Homo sapiens

<400> SEQUENCE: 651

Ala Ala Leu Gly Ala Gly Arg Gly Arg Gly Trp Gly Glu Ala Cys
1 5 10 15

<210> SEQ ID NO 652
<211> LENGTH: 15
<212> TYPE: PRT
<213> ORGANISM: Homo sapiens

<400> SEQUENCE: 652

Arg Gly Trp Gly Glu Ala Cys Ala Gln Val Pro Pro Ser Arg Gly
1 5 10 15

<210> SEQ ID NO 653
<211> LENGTH: 15
<212> TYPE: PRT
<213> ORGANISM: Homo sapiens

<400> SEQUENCE: 653

His Tyr Lys Leu Ile Gln Gln Pro Ile Ser Leu Phe Ser Ile Thr
1 5 10 15

<210> SEQ ID NO 654
<211> LENGTH: 15
<212> TYPE: PRT
<213> ORGANISM: Homo sapiens

<400> SEQUENCE: 654

Ile Ser Leu Phe Ser Ile Thr Asp Arg Leu His Lys Thr Phe Ser
1 5 10 15

<210> SEQ ID NO 655
<211> LENGTH: 15
<212> TYPE: PRT
<213> ORGANISM: Homo sapiens

<400> SEQUENCE: 655

Arg Leu His Lys Thr Phe Ser Gln Leu Pro Ser Val His Leu Cys
1 5 10 15

<210> SEQ ID NO 656
<211> LENGTH: 15
<212> TYPE: PRT
<213> ORGANISM: Homo sapiens

<400> SEQUENCE: 656

Leu Pro Ser Val His Leu Cys Ser Ile Thr Phe Gln Trp Gly His
1 5 10 15

<210> SEQ ID NO 657
<211> LENGTH: 15

<212> TYPE: PRT
<213> ORGANISM: Homo sapiens

<400> SEQUENCE: 657

Ile Thr Phe Gln Trp Gly His Pro Pro Ile Phe Cys Ser Thr Asn
1 5 10 15

<210> SEQ ID NO 658
<211> LENGTH: 15
<212> TYPE: PRT
<213> ORGANISM: Homo sapiens

<400> SEQUENCE: 658

Pro Ile Phe Cys Ser Thr Asn Asp Ile Cys Val Thr Ala Asn Phe
1 5 10 15

<210> SEQ ID NO 659
<211> LENGTH: 15
<212> TYPE: PRT
<213> ORGANISM: Homo sapiens

<400> SEQUENCE: 659

Ile Cys Val Thr Ala Asn Phe Cys Ile Ser Val Thr Phe Leu Lys
1 5 10 15

<210> SEQ ID NO 660
<211> LENGTH: 15
<212> TYPE: PRT
<213> ORGANISM: Homo sapiens

<400> SEQUENCE: 660

Ile Ser Val Thr Phe Leu Lys Pro Cys Phe Leu Leu His Glu Ala
1 5 10 15

<210> SEQ ID NO 661
<211> LENGTH: 11
<212> TYPE: PRT
<213> ORGANISM: Homo sapiens

<400> SEQUENCE: 661

Cys Phe Leu Leu His Glu Ala Ser Ala Ser Gln
1 5 10

<210> SEQ ID NO 662
<211> LENGTH: 15
<212> TYPE: PRT
<213> ORGANISM: Homo sapiens

<400> SEQUENCE: 662

Arg Thr Ala Leu Thr His Asn Gln Asp Phe Ser Ile Tyr Arg Leu
1 5 10 15

<210> SEQ ID NO 663
<211> LENGTH: 15
<212> TYPE: PRT
<213> ORGANISM: Homo sapiens

<400> SEQUENCE: 663

Asp Phe Ser Ile Tyr Arg Leu Cys Cys Lys Arg Gly Ser Leu Cys
1 5 10 15

<210> SEQ ID NO 664
<211> LENGTH: 15
<212> TYPE: PRT
<213> ORGANISM: Homo sapiens

<400> SEQUENCE: 664

Cys Lys Arg Gly Ser Leu Cys His Ala Ser Gln Ala Arg Ser Pro
1 5 10 15

<210> SEQ ID NO 665
<211> LENGTH: 15
<212> TYPE: PRT
<213> ORGANISM: Homo sapiens

<400> SEQUENCE: 665

Ala Ser Gln Ala Arg Ser Pro Ala Phe Pro Lys Pro Val Arg Pro
1 5 10 15

<210> SEQ ID NO 666
<211> LENGTH: 15
<212> TYPE: PRT
<213> ORGANISM: Homo sapiens

<400> SEQUENCE: 666

Phe Pro Lys Pro Val Arg Pro Leu Pro Ala Pro Ile Thr Arg Ile
1 5 10 15

<210> SEQ ID NO 667
<211> LENGTH: 15
<212> TYPE: PRT
<213> ORGANISM: Homo sapiens

<400> SEQUENCE: 667

Pro Ala Pro Ile Thr Arg Ile Thr Pro Gln Leu Gly Gly Gln Ser
1 5 10 15

<210> SEQ ID NO 668
<211> LENGTH: 15
<212> TYPE: PRT
<213> ORGANISM: Homo sapiens

<400> SEQUENCE: 668

Pro Gln Leu Gly Gly Gln Ser Asp Ser Ser Gln Pro Leu Leu Thr
1 5 10 15

<210> SEQ ID NO 669
<211> LENGTH: 15
<212> TYPE: PRT
<213> ORGANISM: Homo sapiens

<400> SEQUENCE: 669

Ser Ser Gln Pro Leu Leu Thr Thr Gly Arg Pro Gln Gly Trp Gln
1 5 10 15

<210> SEQ ID NO 670
<211> LENGTH: 15
<212> TYPE: PRT
<213> ORGANISM: Homo sapiens

<400> SEQUENCE: 670

Gly Arg Pro Gln Gly Trp Gln Asp Gln Ala Leu Arg His Thr Gln
1 5 10 15

<210> SEQ ID NO 671
<211> LENGTH: 15
<212> TYPE: PRT
<213> ORGANISM: Homo sapiens

<400> SEQUENCE: 671

Gln Ala Leu Arg His Thr Gln Gln Ala Ser Pro Ala Ser Cys Ala
1 5 10 15

<210> SEQ ID NO 672
<211> LENGTH: 15
<212> TYPE: PRT
<213> ORGANISM: Homo sapiens

<400> SEQUENCE: 672

Ala Ser Pro Ala Ser Cys Ala Thr Ile Thr Ile Pro Ile His Ser
1 5 10 15

<210> SEQ ID NO 673
<211> LENGTH: 15
<212> TYPE: PRT
<213> ORGANISM: Homo sapiens

<400> SEQUENCE: 673

Ile Thr Ile Pro Ile His Ser Ala Ala Leu Gly Asp His Ser Gly
1 5 10 15

<210> SEQ ID NO 674
<211> LENGTH: 15
<212> TYPE: PRT
<213> ORGANISM: Homo sapiens

<400> SEQUENCE: 674

Ala Leu Gly Asp His Ser Gly Asp Pro Gly Pro Ala Trp Asp Thr
1 5 10 15

<210> SEQ ID NO 675
<211> LENGTH: 15
<212> TYPE: PRT
<213> ORGANISM: Homo sapiens

<400> SEQUENCE: 675

Pro Gly Pro Ala Trp Asp Thr Cys Pro Pro Leu Pro Leu Thr Thr
1 5 10 15

<210> SEQ ID NO 676
<211> LENGTH: 15
<212> TYPE: PRT
<213> ORGANISM: Homo sapiens

<400> SEQUENCE: 676

Pro Pro Leu Pro Leu Thr Thr Leu Ile Pro Arg Ala Pro Pro Pro
1 5 10 15

<210> SEQ ID NO 677
<211> LENGTH: 15
<212> TYPE: PRT
<213> ORGANISM: Homo sapiens

<400> SEQUENCE: 677

Ile Pro Arg Ala Pro Pro Pro Tyr Gly Asp Ser Thr Ala Arg Ser
1 5 10 15

<210> SEQ ID NO 678
<211> LENGTH: 16
<212> TYPE: PRT
<213> ORGANISM: Homo sapiens

<400> SEQUENCE: 678

Gly Asp Ser Thr Ala Arg Ser Trp Pro Ser Arg Cys Gly Pro Leu Gly

-continued 1 5 10 15

<210> SEQ ID NO 679
<211> LENGTH: 15
<212> TYPE: PRT
<213> ORGANISM: Homo sapiens

<400> SEQUENCE: 679

Tyr Ala Tyr Lys Asp Phe Leu Trp Cys Phe Pro Phe Ser Leu Val
1 5 10 15

<210> SEQ ID NO 680
<211> LENGTH: 15
<212> TYPE: PRT
<213> ORGANISM: Homo sapiens

<400> SEQUENCE: 680

Cys Phe Pro Phe Ser Leu Val Phe Leu Gln Glu Ile Gln Ile Cys
1 5 10 15

<210> SEQ ID NO 681
<211> LENGTH: 15
<212> TYPE: PRT
<213> ORGANISM: Homo sapiens

<400> SEQUENCE: 681

Leu Gln Glu Ile Gln Ile Cys Cys His Val Ser Cys Leu Cys Cys
1 5 10 15

<210> SEQ ID NO 682
<211> LENGTH: 15
<212> TYPE: PRT
<213> ORGANISM: Homo sapiens

<400> SEQUENCE: 682

His Val Ser Cys Leu Cys Cys Ile Cys Cys Ser Thr Arg Ile Cys
1 5 10 15

<210> SEQ ID NO 683
<211> LENGTH: 15
<212> TYPE: PRT
<213> ORGANISM: Homo sapiens

<400> SEQUENCE: 683

Cys Cys Ser Thr Arg Ile Cys Leu Gly Cys Leu Leu Glu Leu Phe
1 5 10 15

<210> SEQ ID NO 684
<211> LENGTH: 15
<212> TYPE: PRT
<213> ORGANISM: Homo sapiens

<400> SEQUENCE: 684

Gly Cys Leu Leu Glu Leu Phe Leu Ser Arg Ala Leu Arg Ala Leu
1 5 10 15

<210> SEQ ID NO 685
<211> LENGTH: 15
<212> TYPE: PRT
<213> ORGANISM: Homo sapiens

<400> SEQUENCE: 685

Ser Arg Ala Leu Arg Ala Leu His Val Leu Trp Asn Gly Phe Gln
1 5 10 15

<210> SEQ ID NO 686
<211> LENGTH: 11
<212> TYPE: PRT
<213> ORGANISM: Homo sapiens

<400> SEQUENCE: 686

Val Leu Trp Asn Gly Phe Gln Leu His Cys Gln
1               5                   10

<210> SEQ ID NO 687
<211> LENGTH: 15
<212> TYPE: PRT
<213> ORGANISM: Homo sapiens

<400> SEQUENCE: 687

Tyr Glu Ala Gly Met Thr Leu Gly Glu Lys Phe Arg Val Gly Asn
1               5                   10                  15

<210> SEQ ID NO 688
<211> LENGTH: 16
<212> TYPE: PRT
<213> ORGANISM: Homo sapiens

<400> SEQUENCE: 688

Glu Lys Phe Arg Val Gly Asn Cys Lys His Leu Lys Met Thr Arg Pro
1               5                   10                  15

<210> SEQ ID NO 689
<211> LENGTH: 15
<212> TYPE: PRT
<213> ORGANISM: Homo sapiens

<400> SEQUENCE: 689

Trp Gly Met Glu Leu Ala Ala Ser Arg Arg Phe Ser Trp Asp His
1               5                   10                  15

<210> SEQ ID NO 690
<211> LENGTH: 15
<212> TYPE: PRT
<213> ORGANISM: Homo sapiens

<400> SEQUENCE: 690

Arg Arg Phe Ser Trp Asp His His Ser Ala Gly Gly Pro Pro Arg
1               5                   10                  15

<210> SEQ ID NO 691
<211> LENGTH: 15
<212> TYPE: PRT
<213> ORGANISM: Homo sapiens

<400> SEQUENCE: 691

Ser Ala Gly Gly Pro Pro Arg Val Pro Ser Val Arg Ser Gly Ala
1               5                   10                  15

<210> SEQ ID NO 692
<211> LENGTH: 15
<212> TYPE: PRT
<213> ORGANISM: Homo sapiens

<400> SEQUENCE: 692

Pro Ser Val Arg Ser Gly Ala Ala Gln Val Gln Pro Lys Asp Pro
1               5                   10                  15

<210> SEQ ID NO 693

<211> LENGTH: 15
<212> TYPE: PRT
<213> ORGANISM: Homo sapiens

<400> SEQUENCE: 693

Gln Val Gln Pro Lys Asp Pro Leu Pro Leu Arg Thr Leu Ala Gly
1 5 10 15

<210> SEQ ID NO 694
<211> LENGTH: 15
<212> TYPE: PRT
<213> ORGANISM: Homo sapiens

<400> SEQUENCE: 694

Pro Leu Arg Thr Leu Ala Gly Cys Leu Ala Arg Thr Ala His Leu
1 5 10 15

<210> SEQ ID NO 695
<211> LENGTH: 15
<212> TYPE: PRT
<213> ORGANISM: Homo sapiens

<400> SEQUENCE: 695

Leu Ala Arg Thr Ala His Leu Arg Pro Gly Ala Glu Ser Leu Pro
1 5 10 15

<210> SEQ ID NO 696
<211> LENGTH: 14
<212> TYPE: PRT
<213> ORGANISM: Homo sapiens

<400> SEQUENCE: 696

Pro Gly Ala Glu Ser Leu Pro Gln Pro Gln Leu His Cys Thr
1 5 10

<210> SEQ ID NO 697
<211> LENGTH: 15
<212> TYPE: PRT
<213> ORGANISM: Homo sapiens

<400> SEQUENCE: 697

Asn Ser Lys Met Ala Leu Asn Ser Leu Asn Ser Ile Asp Asp Ala
1 5 10 15

<210> SEQ ID NO 698
<211> LENGTH: 15
<212> TYPE: PRT
<213> ORGANISM: Homo sapiens

<400> SEQUENCE: 698

Leu Asn Ser Ile Asp Asp Ala Gln Leu Thr Arg Ile Ala Pro Pro
1 5 10 15

<210> SEQ ID NO 699
<211> LENGTH: 15
<212> TYPE: PRT
<213> ORGANISM: Homo sapiens

<400> SEQUENCE: 699

Leu Thr Arg Ile Ala Pro Pro Arg Ser His Cys Cys Phe Trp Glu
1 5 10 15

<210> SEQ ID NO 700
<211> LENGTH: 15
<212> TYPE: PRT

<213> ORGANISM: Homo sapiens

<400> SEQUENCE: 700

Ala Pro Pro Arg Ser His Cys Cys Phe Trp Glu Val Asn Ala Pro
1 5 10 15

<210> SEQ ID NO 701
<211> LENGTH: 15
<212> TYPE: PRT
<213> ORGANISM: Homo sapiens

<400> SEQUENCE: 701

Leu Trp Phe Gln Ser Ser Glu Leu Ser Pro Thr Gly Ala Pro Trp
1 5 10 15

<210> SEQ ID NO 702
<211> LENGTH: 15
<212> TYPE: PRT
<213> ORGANISM: Homo sapiens

<400> SEQUENCE: 702

Ser Pro Thr Gly Ala Pro Trp Pro Ser Arg Arg Pro Thr Trp Arg
1 5 10 15

<210> SEQ ID NO 703
<211> LENGTH: 15
<212> TYPE: PRT
<213> ORGANISM: Homo sapiens

<400> SEQUENCE: 703

Ser Arg Arg Pro Thr Trp Arg Gly Thr Thr Val Ser Pro Arg Thr
1 5 10 15

<210> SEQ ID NO 704
<211> LENGTH: 15
<212> TYPE: PRT
<213> ORGANISM: Homo sapiens

<400> SEQUENCE: 704

Thr Thr Val Ser Pro Arg Thr Ala Thr Ser Ser Ala Arg Thr Cys
1 5 10 15

<210> SEQ ID NO 705
<211> LENGTH: 15
<212> TYPE: PRT
<213> ORGANISM: Homo sapiens

<400> SEQUENCE: 705

Thr Ser Ser Ala Arg Thr Cys Cys Gly Thr Lys Trp Pro Ser Ser
1 5 10 15

<210> SEQ ID NO 706
<211> LENGTH: 15
<212> TYPE: PRT
<213> ORGANISM: Homo sapiens

<400> SEQUENCE: 706

Gly Thr Lys Trp Pro Ser Ser Gln Glu Ala Ala Leu Gly Leu Gly
1 5 10 15

<210> SEQ ID NO 707
<211> LENGTH: 15
<212> TYPE: PRT
<213> ORGANISM: Homo sapiens

<400> SEQUENCE: 707

Glu Ala Ala Leu Gly Leu Gly Ser Gly Leu Leu Arg Phe Ser Cys
1 5 10 15

<210> SEQ ID NO 708
<211> LENGTH: 13
<212> TYPE: PRT
<213> ORGANISM: Homo sapiens

<400> SEQUENCE: 708

Gly Leu Leu Arg Phe Ser Cys Gly Thr Ala Ala Ile Arg
1 5 10

<210> SEQ ID NO 709
<211> LENGTH: 15
<212> TYPE: PRT
<213> ORGANISM: Homo sapiens

<400> SEQUENCE: 709

Gln Asn Leu Gln Asn Gly Gly Gly Ser Arg Ser Ser Ala Thr Leu
1 5 10 15

<210> SEQ ID NO 710
<211> LENGTH: 15
<212> TYPE: PRT
<213> ORGANISM: Homo sapiens

<400> SEQUENCE: 710

Gln Trp Gln His Tyr His Arg Ser Gly Glu Ala Ala Gly Thr Pro
1 5 10 15

<210> SEQ ID NO 711
<211> LENGTH: 14
<212> TYPE: PRT
<213> ORGANISM: Homo sapiens

<400> SEQUENCE: 711

Gly Glu Ala Ala Gly Thr Pro Leu Trp Arg Pro Thr Arg Asn
1 5 10

<210> SEQ ID NO 712
<211> LENGTH: 16
<212> TYPE: PRT
<213> ORGANISM: Homo sapiens

<400> SEQUENCE: 712

Thr Glu Tyr Asn Gln Lys Leu Gln Val Asn Gln Phe Ser Glu Ser Lys
1 5 10 15

<210> SEQ ID NO 713
<211> LENGTH: 32767
<212> TYPE: DNA
<213> ORGANISM: Artificial sequence
<220> FEATURE:
<223> OTHER INFORMATION: recombinant GAd20

<400> SEQUENCE: 713
catcatcaat aatatacctt attttggatt gaggccaata tgataatgag gtgggcgggg 60
cgaggcgggg cgggtgacgt aggacgcgcg agtagggttg ggaggtgtgg cggaagtgtg 120
gcatttgcaa gtgggaggag ctgacatgca atcttccgtc gcggaaaatg tgacgttttt 180
gatgagcgcc gcctacctcc ggaagtgcca attttcgcgc gcttttcacc ggatatcgta 240
gtaattttgg gcgggaccat gtaagatttg gccattttcg cgcgaaaagt gaaacgggga 300

```
agtgaaaact gaataatagg gcgttagtca tagcgcgtaa tatttaccga gggccgaggg    360
actttgaccg attacgtgga ggactcgccc aggtgttttt tacgtgaatt tccgcgttcc    420
gggtcaaagt ctccgttttt attgtcgccg tcatctgacg ggccgccatt gcatacgttg    480
tatccatatc ataatatgta catttatatt ggctcatgtc caacattacc gccatgttga    540
cattgattat tgactagtta ttaatagtaa tcaattacgg ggtcattagt tcatagccca    600
tatatggagt tccgcgttac ataacttacg gtaaatggcc cgcctggctg accgcccaac    660
gacccccgcc cattgacgtc aataatgacg tatgttccca tagtaacgcc aatagggact    720
ttccattgac gtcaatgggt ggagtattta cggtaaactg cccacttggc agtacatcaa    780
gtgtatcata tgccaagtac gccccctatt gacgtcaatg acggtaaatg gcccgcctgg    840
cattatgccc agtacatgac cttatgggac tttcctactt ggcagtacat ctacgtatta    900
gtcatcgcta ttaccatggt gatgcggttt tggcagtaca tcaatgggcg tggatagcgg    960
tttgactcac ggggatttcc aagtctccac cccattgacg tcaatgggag tttgttttgg   1020
caccaaaatc aacgggactt tccaaaatgt cgtaacaact ccgccccatt gacgcaaatg   1080
ggcggtaggc gtgtacggtg ggaggtctat ataagcagag ctctccctat cagtgataga   1140
gatctcccta tcagtgatag agatcgtcga cgagctcgtt tagtgaaccg tcagatcgcc   1200
tggagacgcc atccacgctg ttttgacctc catagaagac accgggaccg atccagcctc   1260
cgcggccggg aacggtgcat tggaacgcgg attccccgtg ccaagagtga gatcttccgt   1320
ttatctaggt accagatatc agaattcgga tcccgcgact tcgccgccat gggccagaaa   1380
gagcagatcc acacactgca gaaaaacagc gagcggatga gcaagcagct gaccagatct   1440
tctcaggccg tgcagaacct gcagaacggc ggaggctcta gaagctctgc tacacttcct   1500
ggcaggcggc ggagaagatg gctgagaaga aggcggcagc ctatctctgt ggctcctgct   1560
ggacctccta gacggcccaa ccagaagcct aatcctcctg gcggagccag atgcgtgatc   1620
atgaggccta catggcctgg caccagcgcc ttcaccaaga gaagctttgc cgtgaccgag   1680
cggatcatcg actattgggc tcaaaaagag aagggcagca gcagcttcct gcggcctagc   1740
tgtgattatt gggcccagaa agaaaagatc agcatcccca gaacacacct gtgcctggtg   1800
ctgggagtgc tgtctggaca ctctggcagc agactgtatg aggccggcat gacactcggc   1860
ggcaagatcc tgttcttcct gttcctgctg ctccctctga gcccccttcag cctgatcttc   1920
accgagatca gctgctgcac cctgagcagc gaggaaaacg agtacctgcc tagacctgag   1980
tggcagctgc aggtcccctt cagagagctg aagaacgttt ccgtgctgga aggcctgaga   2040
cagggcagac ttggcggccc ttgtagctgt cactgcccca gacctagtca ggccagactg   2100
acacctgtgg atgtggccgg acctttcctg tgtctgggag atcctggcct gtttccacct   2160
gtgaagtcca gcatcacagg cggcaagtcc acatgttctg cccctggacc tcagagcctg   2220
cctagcacac ccttcagcac ataccctcag tgggtcatcc tgatcaccga actcggcatg   2280
gaatgcaccc tgggacaagt gggagcccca tctcctagaa gagaagagga tggctggcgc   2340
ggaggccact ctagattcaa agctgatgtg cccgctcctc agggcccttg ttggggagga   2400
caacctggat ctgccccatc ttctgcccca cctgaacagt ccctgctgga ttggaagttc   2460
gagatgagct acaccgtcgg cggacctcca cctcatgttc atgccagacc tcggcactgg   2520
aaaaccgaca gagatggcca cagctacacc agcaaagtga actgcctcct gctgcaggat   2580
ggcttccacg gctgtgtgtc tattactggc gccgctggca gacggaacct gagcatcttt   2640
```

-continued

```
ctgtttctga tgctgtgcaa gctcgagttc cacgcctgca agatccagaa caagaactgc   2700
cccgacttca agaagttcga cggcccttgc ggagaaagag gcggaggcag aacagctaga   2760
gccctttggg ctagaggcga cagcgttctg acaccagctc tggaccctca gacacctgtt   2820
agggccccta gcctgacaag agctgccgcc gctgtgcact acaagctgat ccagcagcca   2880
atcagcctgt tcagcatcac cgaccggctg cacaagacat tcagccagct gccaagcgtg   2940
cacctgtgct ccatcacctt ccagtgggga caccctccta tcttttgctc caccaacgac   3000
atctgcgtga ccgccaactt ctgtatcagc gtgaccttcc tgaagccttg ctttctgctg   3060
cacgaggcca gcgcctctca gtgccacttg tttctgcagc cccaagtggg cacacctcct   3120
ccacatacag cctctgctag agcacctagc ggccctccac atcctcacga atcttgtcct   3180
gccggaagaa ggcctgccag agccgctcaa acatgtgcca gacgacagca cggactgcct   3240
ggatgtgaag aggctggaac agccagagtg cctagcctgc acctccatct gcatcaggct   3300
gctcttggag ccggaagagg tagaggatgg ggcgaagctt gtgctcaggt gccaccttct   3360
agaggcgtgc tgagattcct ggacctgaaa gtgcgctacc tgcacagcca gtggcagcac   3420
tatcacagat ctggcgaagc cgccggaaca ccccctttgga ggccaacaag aaacgtgccc   3480
ttccgggaac tgaagaacca gagaacagct cagggcgctc ctggaatcca ccatgctgct   3540
tctccagtgg ccgccaacct gtgtgatcct gccagacatg cccagcacac caggattcct   3600
tgtggcgctg gacaagtgcg cgctggaaga ggacctgaag caggcggagg tgttctgcaa   3660
cctcaaagac ccgctcctga gaagcctggc tgcccttgca gaagaggaca gcctagactg   3720
cacaccgtga aaatgtggcg agccgtggcc atgatggtgc ccgatagaca ggtccactac   3780
gactttggac tgggcgtgcc aggcgatagc actcggagag ccgtcagacg gatgaacacc   3840
ttttacgaag ccgggatgac cctgggcgag aagttcagag tgggcaactg caagcacctg   3900
aagatgaccc ggcctaacag caagatggcc ctgaatagcg aggccctgtc tgtggtgtct   3960
gaatgtggcg cctctgcctg tgacgtgtcc ctgatcgcta tggactccgc ctttgtgcag   4020
ggcaaagact ggggcgtgaa gaagttcatc cggcgggact tctacgccta caaggacttc   4080
ctgtggtgct tcccccttctc tctggtgttc ctgcaagaga tccagatctg ctgtcatgtg   4140
tcctgcctgt gctgcatctg ctgtagcacc agaatctgcc tgggctgtct gctggaactg   4200
ttcctgagca gagccctgag agcactgcac gtgctgtgga acggattcca gctgcactgc   4260
cagaccgagt acaaccagaa actgcaagtg aaccagttca gcgagagcaa gagcctgtac   4320
caccgggaaa agcagctcat tgccatggac agcgccatct gcgaagagag aggcgccgca   4380
ggatctctga tctcctgcga aacaatgccc gccatcctga agctgcagaa gaattgcctc   4440
ctaagcctgc gaaccgctct gacacacaac caggacttca gcatctacag actgtgttgc   4500
aagcggggct ccctgtgcca tgcaagccaa gctagaagcc ccgcctttcc taaacctgtg   4560
cgacctctgc cagctccaat caccagaatt acccctcagc tcggcggcca gagcgattca   4620
tctcaacctc tgctgaccac cggcagacct caaggctggc aagaccaagc tctgagacac   4680
acccagcagg ctagccctgc ctcttgtgcc accatcacaa tccccatcca ctctgccgct   4740
ctgggcgatc attctggcga tcctggacca gcctgggaca catgtcctcc actgccactc   4800
acaacactga tccctagggc tcctccacct tacggcgatt ctaccgctag aagctggccc   4860
agcagatgtg gaccactcgg aggcaacaca accctccagc aactgggaga agcctctcag   4920
gctcctagcg gctctctgat ccctctcaga ctgcctctcc tgtgggaagt tcggggccag   4980
cctgattctt ttgccgcact gcacagctcc ctgaacgagc tgggagagat cgctagagag   5040
```

-continued ctgcaccagt tcgccttcga cctgctgatc aagagccact tcgtgcaagg caaggattgg 5100
ggcctcaaaa agtttatccg cagagacttc tggggcatgg aactggccgc cagcagaaga 5160
ttcagctggg atcatcatag cgcaggcggc ccacctagag tgccatctgt tagaagcgga 5220
gctgcccagg tgcagcctaa agatcctctg ccactgagaa cactggccgg ctgccttgct 5280
agaacagccc atcttagacc tggcgccgag tctctgcctc agccacaact gcactgtacc 5340
ctgtggttcc agtccagcga gctgtctcct actggtgccc cttggccatc tagacgccct 5400
acttggagag gcaccaccgt gtcaccaaga accgccacaa gcagcgccag aacctgttgt 5460
ggcacaaagt ggccctccag ccaagaagcc gctctcggac ttggaagcgg actgctgagg 5520
ttctcttgtg gaaccgccgc cattcggaag atgcacttta gcctgaaaga acaccctcca 5580
ccaccttgtc ctccagaggc tttccaaaga gctgctggcg aaggcggacc tggtagaggt 5640
ggtgctagaa gaggtgctag ggtgctgcag agcccattct gtagagcagg cgcaggcgaa 5700
tggctgggcc atcagagtct gagacatgtc gtcggctacg gccacctgga tacaagcgga 5760
agcagctcta gctccagctg gcctaactca aaaatggctc tgaacagcct gaactccatc 5820
gacgacgccc agctgacaag aatcgcccct cctagatctc actgctgctt ttgggaagtg 5880
aacgccccaa gccatcacca tcaccaccat tagtaaaggc gcgcctagcg gccgcgatct 5940
gctgtgcctt ctagttgcca gccatctgtt gtttgcccct cccccgtgcc ttccttgacc 6000
ctggaaggtg ccactcccac tgtcctttcc taataaaatg aggaaattgc atcgcattgt 6060
ctgagtaggt gtcattctat tctggggggt ggggtggggc aggacagcaa gggggaggat 6120
tgggaagaca atagcaggca tgctggggat gcggtgggct ctatggccgg gccgcgatcg 6180
cgcttaggcc tgaccatctg gtgctggcct gcaccagggc cgagtttggg tctagcgatg 6240
aggataccga ttgaggtggg taaggtgggc gtggctagca gggtgggcgt gtataaattg 6300
ggggtctaag ggtctctct gtttgtcttg caacagccgc cgccatgagc gacaccggca 6360
acagctttga tggaagcatc tttagtccct atctgacagt gcgcatgcct cactgggccg 6420
gagtgcgtca gaatgtgatg ggttccaacg tggatggacg tcccgttctg ccttcaaatt 6480
cgtctactat ggcctacgcg accgtgggag gaactccgct ggacgccgcg acctccgccg 6540
ccgcctccgc cgccgccgcg accgcgcgca gcatggctac ggacctttac agctctttgg 6600
tggcgagcag cgcggcctct cgcgcgtctg ctcgggatga gaaactgact gctctgctgc 6660
ttaaactgga agacttgacc cgggagctgg gtcaactgac ccagcaggtt tccagcttgc 6720
gtgagagcag ccttgcctcc ccctaatggc ccataatata aataaaagcc agtctgtttg 6780
gattaagcaa gtgtatgttc tttatttaac tctccgcgcg cggtaagccc gggaccagcg 6840
gtctcggtcg tttagggtgc ggtggatttt ttccaacacg tggtacaggt ggctctggat 6900
gtttagatac atgggcatga gtccatccct ggggtggagg tagcaccact gcagagcttc 6960
gtgctcgggg gtggtgttgt atatgatcca gtcgtagcag gagcgctggg cgtggtgctg 7020
aaaaatgtcc ttaagcaaga ggcttatagc taggggggagg cccttggtgt aagtgtttac 7080
aaatctgctt agctgggagg ggtgcatccg gggggatatg atgtgcatct tggactggat 7140
ttttaggttg gctatgttcc cgcccagatc ccttctggga ttcatgttgt gcaggaccac 7200
cagcacggta tatccagtgc acttgggaaa tttatcgtgg agcttagacg ggaatgcatg 7260
gaagaacttg gagacgccct tgtggcctcc cagattttcc atacattcgt ccatgatgat 7320
ggcaatgggc ccgtgggaag ctgcctgagc aaaaacgttt ctggcatcgc tcacatcgta 7380

```
gttatgttcc agggtgaggt catcatagga catctttacg aatcgggggc gaagggtccc   7440
ggactggggg atgatggtac cctcgggccc cggggcgtag ttcccctcac agatctgcat   7500
ctcccaggct ttcatttcag agggagggat catatccacc tgcggggcga tgaaaaagac   7560
agtttctggc gcaggggaga ttaactggga tgagagcagg tttctgagca gctgtgactt   7620
tccacagccg gtgggcccat atatcacgcc tatcaccggc tgcagctggt agttaagaga   7680
gctgcagctg ccgtcctccc ggagcagggg ggccacctcg ttgagcatat ccctgacgtg   7740
gatgttctcc ctgaccagtt ccgccagaag gcgctcgccg cccagcgaaa gcagctcttg   7800
caaggaagca aaatttttca gcggtttcag gccatcggcc gtgggcatgt tttcagcgt    7860
ctgggtcagc agctccagcc tgtcccagag ctcggtgatg tgctctacgg catctcgatc   7920
cagcagatct cctcgtttcg cgggttgggg cggctttcgc tgtagggcac cagccgatgg   7980
gcgtccagcg gggccagagt catgtccttc catgggcgca gggtcctcgt cagggtggtc   8040
tgggtcacgg tgaaggggtg cgctccgggt tgggcactgg ccagggtgcg cttgaggctg   8100
gttctgctgg tgctgaatcg ctgccgctct tcgccctgcg cgtcggccag gtagcatttg   8160
accatggtct cgtagtcgag accctcggcg gcgtgcccct tggcgcggag ctttcccttg   8220
gaggtggcgc cgcacgaggg gcactgcagg ctcttcaggg cgtagagctt gggagcgaga   8280
aacacggact ctggggagta ggcgtccgcg ccgcaggccg agcagaccgt ctcgcattcc   8340
accagccaag tgagttccgg gcggtcaggg tcaaaaacca ggttgccccc atgctttttg   8400
atgcgtttct taccttggct ctccatgagg cggtgtccct tctcggtgac gaagaggctg   8460
tccgtgtccc cgtagaccga cttcaggggc ctgtcttcca gcggagtgcc tctgtcctcc   8520
tcgtagagaa actctgacca ctctgagacg aaggcccgcg tccaggccag gacgaaggag   8580
gccacgtggg aggggtagcg gtcgttgtcc actagcgggt ccaccttctc cagggtgtgc   8640
aggcacatgt ccccctcctc cgcgtccaga aaagtgattg gcttgtaggt gtaggacacg   8700
tgaccggggg ttcccaacgg gggggtataa aagggggtgg gtgccctttc atcttcactc   8760
tcttccgcat cgctgtctgc gagagccagc tgctggggta agtattccct ctcgaaggcg   8820
ggcatgacct cagcgctcag gttgtcagtt tctaaaaatg aggaggattt gatgttcacc   8880
tgtccggagg tgataccttt gagggtacct gggtccatct ggtcagaaaa cactattttt   8940
ttgttatcaa gcttggtggc gaatgacccg tagagggcgt tggagagcag cttggcgatg   9000
gagcgcaggg tctggttttt gtcgcggtcg gctcgctcct tggccgcgat gttgagttgc   9060
acgtactcgc gggccacgca cttccactcg gggaacacgg tggtgcgctc gtctgggatc   9120
aggcgcaccc tccagccgcg gttgtgcagg gtgaccatgt cgacgctggt ggcgacctca   9180
ccgcgcagac gctcgttggt ccagcagagg cggccgccct tgcgcgagca gaagggggt    9240
agggggtcca gctggtcctc gtttgggggg tccgcgtcga tggtaaagac cccggggagc   9300
aggcgcgggt caaagtagtc gatcttgcaa gcttgcatgt ccagagcccg ctgccattcg   9360
cgggcggcga gcgcgcgctc gtaggggttg aggggcgggc cccagggcat ggggtgggtg   9420
agcgcggagg cgtacatgcc gcagatgtca tacacgtaca ggggttccct gaggataccg   9480
aggtaggtgg ggtagcagcg ccccccgcgg atgctggcgc gcacgtagtc atagagctcg   9540
tgggaggggg ccagcatgtt gggcccgagg ttggtgcgct gggggcgctc ggcgcggaag   9600
acgatctgcc tgaagatggc gtgggagttg gaggagatgg tgggccgctg gaagacgttg   9660
aagcttgctt cttgcaagcc cacggagtcc ctgacgaagg aggcgtagga ctcgcgcagc   9720
ttgtgcacca gctcggcggt gacctggacg tcgagcgcac agtagtcgag ggtctcgcgg   9780
```

-continued

```
atgatgtcat acctatcctc ccccttcttt ttccacagct cgcggttgag gacgaactct   9840
tcgcggtctt tccagtactc ttggagggga aacccgtccg tgtccgaacg gtaagagcct   9900
agcatgtaga actggttgac ggcctggtag gggcagcagc ccttctccac gggcagcgcg   9960
taggcctgcg ccgccttgcg gagggaggtg tgggtgaggg cgaaagtgtc cctgaccatg  10020
actttgaggt attgatgtct gaagtctgtg tcatcgcagc cgccctgttc ccacagggtg  10080
tagtccgtgc gctttttgga gcgcgggttg ggcagggaga aggtgaggtc attgaagagg  10140
atcttccccg ctcgaggcat gaagtttctg gtgatgcgaa agggccctgg gaccgaggag  10200
cggttgttga tgacctgggc ggccaggacg atctcgtcaa agccgtttat gttgtgtccc  10260
acgatgtaga gctccaggaa gcggggctgg cccttgatgg aggggagctt tttaagttcc  10320
tcgtaggtaa gctcctcggg cgattccagg ccgtgctcct ccagggccca gtcttgcaag  10380
tgagggttgg ccgccaggaa ggatcgccag aggtcgcggg ccatgagggt ctgcaggcgg  10440
tcgcggaagg ttctgaactg ccgccccacg gccatttttt cggggggtgat gcagtagaag  10500
gtgagggggt ctttctccca ggggtcccat ctgagctctc gggcgaggtc gcgcgcggca  10560
gcgaccagag cctcgtcgcc ccccagtttc atgaccagca tgaagggcac gagttgcttg  10620
ccaaaggctc ccatccaagt gtaggtttct acatcgtagg tgacaaagag gcgctccgtg  10680
cgaggatgag agccgattgg gaagaactgg atctcccgcc accagttgga ggattggctg  10740
ttgatgtggt gaaagtagaa gtcccgtctg cgggccgagc actcgtgctg gcttttgtaa  10800
aagcgaccgc agtactggca gcgctgcacg ggttgtatat cttgcacgag gtgaacctgg  10860
cgacctctga cgaggaagcg cagcgggaat ctaagtcccc cgcctggggt cccgtgtggc  10920
tggtggtctt ttactttggt tgtctggccg ccagcatctg tctcctggag ggcgatggtg  10980
gaacagacca ccacgccgcg agagccgcag gtccagatct cggcgctcgg cgggcggagt  11040
ttgatgacga catcgcgcac attggagctg tccatggtct ccagctcccg cggcggcagg  11100
tcagccggga gttccctgga ggttcacctc gcagagacgg gtcaaggcgc ggacagtgtt  11160
gagatggtat ctgatttcaa ggggcatgtt ggaggcggag tcgatggctt gcaggaggcc  11220
gcagccccgg ggggccacga tggttccccg cggggcgcga ggggaggcgg aagctggggg  11280
tgtgttcaga agcggtgacg cgggcgggcc cccggaggta ggggggggttc cggccccaca  11340
ggcatgggcg gcaggggcac gtcttcgccg cgcgcgggca ggggctggtg ctggctccga  11400
agagcgcttg cgtgcgcgac gacgcgacgg ttggtgttcc tgtatctggc gcctctgagt  11460
gaagaccacg ggtcccgtga ccttgaacct gaaagagagt tcgacagaat caatctcggc  11520
atcgttgaca gcggcctggc gcaggatctc ctgcacgtcg cccgagttgt cctggtaggc  11580
gatttctgcc atgaactgct cgatctcttc ctcctggaga tctcctcgtc cggcgcgctc  11640
cacggtggcc gccaggtcgt tggagatgcg acccatgagc tgcgagaagg cgttgagtcc  11700
gccctcgttc cagacccggc tgtagaccac gccccccctcg gcgtcgcggg cgcgcatgac  11760
cacctgggcc aggttgagct ccacgtgtcg cgtgaagacg gcgtagttgc gcaggcgctg  11820
gaaaaggtag ttcagggtgg tggcggtgtg ctcggcgacg aagaagtaca tgacccagcg  11880
ccgcaacgtg gattcattga tgtcccccaa ggcctccagg cgctccatgg cctcgtagaa  11940
gtccacggcg aagttgaaaa actgggagtt gcgagcggac acggtcaact cctcctccag  12000
aagaacggat gagctcggcg acagtgtcgc gcacctcgcg ctcgaaggcc acggggggcg  12060
cttcttcctc ttccacctct tcttccatga ttgcttcttc ttcttcctca gccgggacgg  12120
```

-continued

```
gagggggcgg cggcggggga ggggcgcggc ggcggcggcg gcgcaccggg aggcggtcga  12180
tgaagcgctc gatcatctcc ccccgcatgc ggcgcatggt ctcggtgacg gcgcggccgt  12240
tctcccgggg gcgcagctcg aagacgccgc ctctcatttc gccgcggggc gggcggccgt  12300
gaggtagcga gacggcgctg actatgcatc ttaacaattg ctgtgtaggt acgccgccaa  12360
gggacctgat tgagtccaga tccaccggat ccgaaaacct ttggaggaaa gcgtctatcc  12420
agtcgcagtc gcaaggtagg ctgagcaccg tggcgggcgg gggcgggtcg ggagagttcc  12480
tggcggagat gctgctgatg atgtaattaa agtaggcggt cttgagaagg cggatggtgg  12540
acaggagcac catgtctttg ggtccggcct gttggatgcg gaggcggtcg gccatgcccc  12600
aggcctcgtt ctgacaccgg cgcaggtctt tgtagtaatc ttgcatgagt ctttccaccg  12660
gcacttcttc tccttcctct tcttcatctc gccggtggtt tctcgcgccg cccatgcgcg  12720
tgaccccaaa gcccctgagc ggctgcagca gggccaggtc ggcgaccacg cgctcggcca  12780
agatggcctg ctgtacctga gtgagggtcc tctcgaagtc atccatgtcc acgaagcggt  12840
ggtaggcacc cgtgttgatg gtgtaggtgc agttggccat gacggaccag ttgacggtct  12900
ggtgtcccgg ctgcgagagc tccgtgtacc gcaggcgcga gaaggcgcgg gaatcgaaca  12960
cgtagtcgtt gcaagtccgc accagatact ggtagcccac caggaagtgc ggcggaggtt  13020
ggcgatagag gggccagcgc tgggtggcgg gggcgccggg cgccaggtct tccagcatga  13080
ggcggtggta tccgtagatg tacctggaca tccaggtgat gcctgcggcg gtggtggtgg  13140
cgcgcgcgta gtcgcggacc cggttccaga tgtttcgcag ggcgagaaag tgttccatgg  13200
tcggcacgct ctggccggtg aggcgcgcgc agtcgttgac gctctataca cacacaaaaa  13260
cgaaagcgtt tacagggctt tcgttctgta gcctggagga aagtaaatgg gttgggttgc  13320
ggtgtgcccc ggttcgagac caagctgagc tcagccggct gaagccgcag ctaacgtggt  13380
attggcagtc ccgtctcgac ccaggccctg tatcctccag gatacggtcg agagcccttt  13440
tgctttcttg gccaagcgcc cgtggcgcga tctgggatag atggtcgcga tgagaggaca  13500
aaagcggctc gcttccgtag tctggagaaa caatcgccag ggttgcgttg cggcgtaccc  13560
cggttcgagc ccctatggcg gcttggatcg gccggaaccg cggctaacgt gggctgtggc  13620
agccccgtcc tcaggacccc gccagccgac ttctccagtt acgggagcga gccccttttg  13680
tttttttatt ttttagatgc atcccgtgct gcggcagatg cgcccctcgc cccggcccga  13740
tcagcagcag caacagcagg catgcagacc cccctctcct ctccccgccc cggtcaccac  13800
ggccgcggcg gccgtgtccg gtgcgggggg cgcgctggag tcagatgagc caccgcggcg  13860
gcgacctagg cagtatctgg acttggaaga gggcgaggga ctggcgcggc tgggggcgag  13920
ctctccagag cgccacccgc gggtgcagtt gaaaagggac gcgcgtgagg cgtacctgcc  13980
gcggcaaaac ctgtttcgcg accgcggggg cgaggagccc gaggagatgc gggactgcag  14040
gttccaagcg gggcgcgagc tgcgccgcgg cttggacaga cagcgcctgc tgcgcgagga  14100
ggactttgag cccgacacgc agacgggcat cagccccgcg cgcgcgcacg tggccgcggc  14160
cgacctggtg accgcctacg agcagacggt gaaccaggag cgcaacttcc aaaaaagctt  14220
caacaaccac gtgcgcacgc tggtggcgcg cgaggaggtg accctgggtc tcatgcatct  14280
gtgggacctg gtggaggcga tcgtgcagaa ccccagcagc aagcccctga ccgcgcagct  14340
gttcctggtg gtgcagcaca gcagggacaa cgaggccttc agggaggcgc tgctgaacat  14400
caccgagccg gaggggcgct ggctcctgga cctgataaac atcctgcaga gcatagtggt  14460
gcaggagcgc agcctgagcc tggccgagaa ggtggcggcc attaactatt ctatgctgag  14520
```

-continued

```
cctgggcaag ttctacgctc gcaagatcta caagaccccc tacgtgccca tagacaagga  14580
ggtgaagata gacagcttct acatgcgcat ggcgctgaag gtgctaaccc tgagcgacga  14640
cctgggagtg taccgcaacg agcgcatcca caaggccgtg agcgccagcc ggcggcgcga  14700
gctgagcgac cgcgaactga tgcacagtct gcagcgcgcg ctgaccggcg cgggcgaggg  14760
cgacagggag gtcgagtcct actttgacat gggggccgac ctgcactggc agccgagccg  14820
ccgcgccctg gaagcggcgg gggcgtacgg cggccccctg gcggccgatg acgaggaaga  14880
ggaggactat gagctagagg agggcgagta cctggaggac tgacctggct ggtggtgttt  14940
tggtatagat gcaagatccg aacgtggcgg acccggcggt ccgggcggcg ctgcagagcc  15000
agccgtccgg cattaactcc tctgacgact gggccgcggc catgggtcgc atcatggccc  15060
tgaccgcgcg caaccccgag gccttcaggc agcagcctca ggctaaccgg ctggcggcca  15120
tcttggaagc ggtagtgccc gcgcgctcca accccaccca cgagaaggtg ctggccatag  15180
tcaacgcgct ggcggagagc agggccatcc gggcagacga ggccggactg gtgtacgatg  15240
cgctgctgca gcgggtggcg cggtacaaca gcggcaacgt gcagaccaac ctggaccgcc  15300
tggtgacgga cgtgcgcgag gccgtggcgc agcgcgagcg cttgcatcag gacggcaacc  15360
tgggctcgct ggtggcgcta aacgccttcc ttagcaccca gccggccaac gtaccgcggg  15420
ggcaggagga ctacaccaac ttcttgagcg cgctgcggct gatggtgacc gaggtccctc  15480
agagcgaggt gtaccagtcg gggcccgact acttcttcca gaccagcaga cagggcttgc  15540
aaaccgtgaa cctgagccag gctttcaaga acctgcgggg gctgtgggga gtgaaggcgc  15600
ccaccggcga ccgggctacg gtgtccagcc tgctaacccc caactcgcgc ctgctgctgc  15660
tgctgatcgc gcccttcacg gacagcggga gcgtctcgcg ggagacctat ctgggccacc  15720
tgctgacgct gtaccgcgag gccatcgggc aggcgcaggt ggacgagcac accttccagg  15780
agatcaccag cgtgagccac gcgctggggc aggaggacac gggcagcctg caggcgaccc  15840
tgaactacct gctgaccaac aggcggcaga agattcccac gctgcacagc ctgacccagg  15900
aggaggagcg catcttgcgc tacgtgcagc agagcgtgag cctgaacctg atgcgcgacg  15960
gcgtgacgcc cagcgtggcg ctggacatga ccgcgcgcaa catggaaccg ggcatgtacg  16020
cttcccagcg gccgttcatc aaccgcctga tggactactt gcatcgggcg gcggccgtga  16080
accccgagta cttcaccaat gccattctga atccccactg gatgccccct ccgggtttct  16140
acaacgggga cttcgaggtg cctgaggtca acgatgggtt cctctgggat gacatggatg  16200
acagtgtgtt ctcccccaac ccgctgcgcg ccgcgtctct gcgattgaag gagggctctg  16260
acagggaagg accaaggagt ctggcctcct ccctggctct gggggcggtg ggcgccacgg  16320
gcgcggcggc gcggggcagc agccccttcc ccagcctggc ggactctctg aatagcgggc  16380
gggtgagcag gccccgcttg ctaggcgagg aggagtatct gaacaactcc ctgctgcagc  16440
ccgtgaggga caaaaacgct cagcggcagc agtttcccaa caatgggata gagagcctgg  16500
tggacaagat gtccagatgg aagacgtatg cgcaggagta caaggagtgg gaggaccgcc  16560
agccgcggcc cctgccgccc cctagacagc gctggcagcg gcgcgcgtcc aaccgccgct  16620
ggaggcaggg gcccgaggac gatgatgact ctgcagatga cagcagcgtg ttggacctgg  16680
gcgggagcgg gaacccettt tcgcacctgc gcccacgcct gggcaagatg ttttaaaaga  16740
gaaaaataaa aactcaccaa ggccatggcg acgagcgttg gtttttttgtt cccttcctta  16800
gtatgcggcg cgcggcgatg ttcgaggagg ggcctccccc ctcttacgag agcgcgatgg  16860
```

-continued

```
gaatttctcc tgcggcgccc ctgcagcctc cctacgtgcc tcctcggtac ctgcaaccta  16920
caggggggag aaatagcatc tgttactctg agctgcagcc cctgtacgat accaccagac  16980
tgtacctggt ggacaacaag tccgcggacg tggcctccct gaactaccag aacgaccaca  17040
gcgatttttt gaccacggtg atccaaaaca acgacttcac ccaaccgag gccagtaccc  17100
agaccataaa cctggacaac aggtcgaact ggggcggcga cctgaagact atcctgcaca  17160
ccaatatgcc caacgtgaac gagttcatgt tcaccaactc ttttaaggcg cgggtgatgg  17220
tggcgcgcga gcagggggag gcgaagtacg agtgggtgga cttcacgctg cccgagggca  17280
actactcaga gaccatgact ctcgacctga tgaacaatgc gatcgtggaa cactatctga  17340
aagtgggcag gcagaacggg gtgaaggaga gcgatatcgg ggtcaagttt gacaccagaa  17400
acttccgtct gggctgggac cctgtgaccg ggctggtcat gccgggggtc tacaccaacg  17460
aggcctttca tcccgatata gtgctcctgc ccggctgtgg ggtggacttc acccagagcc  17520
ggctgagcaa cctgctgggc gttcgcaagc ggcaaccttt ccaggagggt ttcaagatca  17580
cctatgagga tctggagggg ggcaacattc ccgcgctcct tgatctggac gcctacgagg  17640
agagcttgaa acccgaggag agcgctggcg acagcggcga gagtggcgag gagcaagccg  17700
gcggcggcgg cagcgcgtcg gtagaaaacg aaagtactcc cgcagtggcg gcggacgctg  17760
cggaggtcga gccggaggcc atgcagcagg acgcagagga gggcgcgcag gaggacatga  17820
acaatgggga gatcaggggc gacactttcg ccacccgggg cgaagaaaaa gaggcagagg  17880
cggcggcggc gacggcggaa gccgaaaccg aggcagaggc agagcccgag accgaagtta  17940
tggaagacat gaatgatgga gaacgtaggg gtgacacgtt tgccacccgg ggcgaagaga  18000
aggcggcgga ggcagaagcc gcggctgagg aggcggctgc ggctgcggcc aaggctgagg  18060
ctgcggctga ggctaaggtc gaagccgatg ttgcggttga ggctcaggct gaggaggagg  18120
cggcggctga agcagttaag gaaaaggccc aggcagagca ggaagagaaa aaacctgtca  18180
ttcaacctct aaaagaagat agcaaaaagc gcagttacaa cgtcattgag ggcagcacct  18240
ttacccaata ccgcagctgg tacctggctt acaactacgg cgacccggtc aagggggtgc  18300
gctcgtggac cctgctctgc acgccggacg tcacctgcgg ctccgagcag atgtactggt  18360
cgctgccaaa catgatgcaa gacccggtga ccttccgttc cacgcggcag gttagcaact  18420
ttccggtggt gggcgccgaa ctgctgccag tacactccaa gagtttttac aacgagcagg  18480
ccgtctactc ccagctgatc cgccaggcca cctctctgac ccacgtgttc aatcgctttc  18540
ccgagaacca gattttggcg cgcccgccgg cccccaccat caccaccgtc agtgaaaacg  18600
ttcctgccct cacagatcac gggacgctac cgctgcgcaa cagcatctca ggagtccagc  18660
gagtgaccat tactgacgcc agacgccgga cctgccccta cgtttacaag gccttgggca  18720
tagtctcgcc gcgcgtcctc tccagtcgca ctttttaaaa cacatccacc cacacgctcc  18780
aaaatcatgt ccgtactcat ctcgcccagc aacaacaccg gctgggggct gcgcgcaccc  18840
agcaagatgt ttggaggggc aaggaagcgc tccgaccagc accccgtgcg cgtgcgcggc  18900
cactaccgcg cgccctgggg tgcgcacaag cgcgggcgca cagggcgcac cactgtggat  18960
gatgtcattg actccgtagt ggagcaggcg cgccactaca cacccggcgc gccgaccgcc  19020
tccgccgtgt ccaccgtgga ccaggcgatc gaaagcgtgg tacagggggc gcggcactat  19080
gccaacctta aaagtcgccg ccgccgcgtg gcgcgccgcc atcgccggag accccgggct  19140
actgccgccg cgcgccttac caaggctctg ctcaagcgcg ccaggcgaac tggccaccgg  19200
gccgccatga gggccgcacg gcgggctgcc gctgccgcga gcgccgtggc cccgcgggca  19260
```

```
cgaaggcgcg cggccgctgc cgccgccgcc gccatttcca gcttggcctc gacgcggcgc  19320
ggtaacatat actgggtgcg cgactcggtg agcggcacac gtgtgcccgt gcgctttcgc  19380
cccccacgga attagcacaa gacaacatac acactgagtc tcctgctgtt gtgtatccca  19440
gcggcgaccg tcagcagcgg cgacatgtcc aagcgcaaaa ttaaagaaga gatgctccag  19500
gtcatcgcgc cggagatcta tgggcccccg aagaaggagg aggaggatta caagccccgc  19560
aagctaaagc gggtcaaaaa gaaaaagaaa gatgatgacg ttgacgaggc ggtggagttt  19620
gtccgccgca tggcgcccag gcgccctgtg cagtggaagg gtcggcgcgt gcagcgagtc  19680
ctgcgccccg gcaccgcggt ggtctttacg cccggcgagc gttccacgcg cactttcaag  19740
cgggtgtacg atgaggtgta cggcgacgag gatctgttgg agcaggccaa ccatcgattt  19800
ggggagtttg catatgggaa acggcctcgc gagagtctaa aagaggacct gctggcgcta  19860
ccgctggacg agggcaatcc caccccgagt ctgaagccgg tgaccctgca acaggtgctg  19920
cctttgagcg cgcccagcga gcagaagcga gggttaaagc gcgagggcgg ggacctggca  19980
cccaccgtgc agttgatggt gcccaagcgg cagaagctgg aggacgtgct ggagaaaatg  20040
aaagtagagc ccgggatcca gcccgagatc aaggtccgcc ctatcaagca ggtggcgccc  20100
ggcgtgggag tccagaccgt ggacgttagg attcccacgg aggagatgga aacccaaacc  20160
gccactccct cttcggcagc aagcgccacc accggcgccg cttcggtaga ggtgcagacg  20220
gacccctggc tacccgccgc cactatcgcc gtcgccgccg ccccccgttc gcgcggacgc  20280
aagagaaatt atccagcggc cagcgcgctt atgccccagt atgcgctgca tccatccatc  20340
gcgcccaccc ccggctaccg cggtactcg taccgcccgc gcagatcagc cggcactcgc  20400
ggccgccgcc gccgtgcgac cacaaccagc cgccgccgtc gccgccgccg ccagccagtg  20460
ctgacccccg tgtctgtaag gaaggtggct cgctcgggga gcacgctggt ggtgcccaga  20520
gcgcgctacc accccagcat cgtttaaagc cggtctctgt atggttcttg cagatatggc  20580
cctcacttgt cgccttcgct tcccggtgcc gggataccga ggaagaactc accgccgcag  20640
gggcatggcg ggcagcggtc tccgcggcgg ccgtcgccat cgccggcgcg caaagagcag  20700
gcgcatgcgc ggcggtgtgt tgcccctgct ggtcccgcta ctcgccgcgg cgatcggcgc  20760
cgtgcccggg atcgcctccg tggccctgca ggcgtcccag aaacattgac tcttgcaacc  20820
ttgcaagctt gcatttttgg aggaaaaaat aaaaaagtct agactctcac gctcgcttgg  20880
tcctgtgact attttgtaga aaaaagatgg aagacatcaa ctttgcgtcg ctggccccgc  20940
gtcacggctc gcgcccgttc atgggagact ggacagatat cggcaccagc aatatgagcg  21000
gtggcgcctt cagctggggc agtctgtgga gcggccttaa aaattttggt tccaccatta  21060
agaactatgg caacaaagcg tggaacagca gcacgggtca gatgctgaga gacaagttga  21120
aagagcagaa cttccaggag aaggtggcgc agggcctggc ctctggcatc agcggggtgg  21180
tggacatagc taaccaggcc gtgcagaaaa agataaacag tcatctggac ccccgccctc  21240
aggtggagga aacgcctcca gccatggaga cggtgtctcc cgagggcaaa ggcgaaaagc  21300
gcccgcggcc cgacagggaa gagaccctgg tgtcacacac cgaggagccg ccctcttacg  21360
aggaggcagt caaggccggc ctgcccacca ctcgccccat agctcccatg gccaccggtg  21420
tggtgggtca caggcaacac acccccgcaa cactagatct gcccccgccg tccgagccga  21480
ctcgccagcc aaaggcggtg acggtgtccg ctccctccac ttccgccgcc aacagagtgc  21540
ctctgcgccg cgctgcgagc ggcccccggg cctcgcgagt cagcggcaac tggcagagca  21600
```

-continued cactgaacag catcgtgggc ctgggagtga ggagtgtgaa gcgccgccgt tgctactgaa 21660
tgagcaagct agctaacgtg ttgtatgtgt gtatgcgtcc tatgtcgccg ccagaggagc 21720
tgttgagccg ccggcgccgt ctgcactcca gcgaatttca agatggcgac cccatcgatg 21780
atgcctcagt ggtcgtacat gcacatctcg ggccaggacg cttcggagta cctgagcccc 21840
gggctggtgc agttcgcccg cgccacagac acctacttca acatgagtaa caagttcagg 21900
aaccccactg tggcgcccac ccacgatgtg accacggacc ggtcgcagcg cctgacgctg 21960
cggttcatcc ccgtggatcg ggaggacacc gcttactctt acaaggcgcg gttcacgctg 22020
gccgtgggcg acaaccgcgt gctggacatg gcctccactt actttgacat ccgggggggtg 22080
ctggacaggg gccccacttt taagccctac tcgggcactg cctacaaccc cctggccccc 22140
aagggcgccc ccaattcttg tgagtgggaa caagaggaaa atcaggtggt cgctgcagat 22200
gatgaacttg aagatgaaga agcgcaagca caagaggaag cccctgtgaa aaaaattcat 22260
gtatatgctc aggcgcctct ttctggcgaa aagatttcca aggatggtat ccaaataggt 22320
actgaagtcg taggagatac atctaaggac acttttgcag ataaaaacatt ccaacccgaa 22380
cctcagatag gcgagtctca gtggaacgag gctgatgcca cagcagcagg aggtagagtt 22440
ttgaaaaaga ctacccctat gagaccttgc tatggatcct atgccaggcc taccaatgcc 22500
aacgggggtc aaggaattat ggttgccaat gaacaaggag tgttggagtc taaagtagaa 22560
atgcaatttt tctctaacac cacaaccctt aatgcgcggg atggaaccgg caatcccgaa 22620
ccaaaggtgg tgttgtacag cgaagatgtc cacttggaat ctcccgatac tcatctgtct 22680
tacaagccca aaaaggatga tgttaatgcc aaaatcatgt tgggtcagca agccatgccc 22740
aacagaccca acctcattgg atttagagat aatttcattg ggcttatgtt ttacaacagc 22800
accggtaaca tgggagtgct ggcgggtcag gcctctcagt tgaatgctgt ggtggacttg 22860
caggatagaa acacagaact gtcatatcag cttctgcttg attcaattgg ggatagaacc 22920
agatacttct ccatgtggaa ccaggcagtg gatagctatg atccagatgt cagaattatt 22980
gaaaaccatg ggactgagga tgaactgccc aactactgct tccctttggg cggcatagga 23040
gttactgata cttatcaagg gataaaaaat accaatggca atggtcagtg gaccaaagat 23100
gatcagttcg cggaccgcaa cgaaataggg gtgggaaaca acttcgccat ggagatcaac 23160
atccaggcca acctttggag aaacttcctc tatgcaaacg tggggctcta cctgccagac 23220
aagctcaagt acaaccccac caacgtggac atctctgaca accccaacac ctatgactac 23280
atgaacaagc gggtggtggc ccctggcctg gtggactgct ttgtcaatgt gggagccagg 23340
tggtccctgg actacatgga caacgtcaac cccttcaacc accaccgcaa tgcgggtctg 23400
cgctaccgct ccatgatcct gggcaacggg cgctatgtgc cctttcacat ccaggtaccc 23460
cagaagttct ttgccatcaa gaacctcctg ctcctgcccg gctcctacac ctacgagtgg 23520
aacttcagga aggatgtgaa catggtccta cagagctctc tgggcaatga ccttagggtg 23580
gatggggcca gcatcaagtt tgacagcatc accctctatg ctacattttt ccccatggcc 23640
cacaacaccg cctccacgct tgaggccatg ctgagaaacg acaccaacga ccagtccttt 23700
aatgactacc tctctggggc caacatgctc tacccaatcc cagccaaggc caccaacgtg 23760
cccatctcca tcccctctcg caactgggcc gcctttagag gctgggcctt tacccgcctt 23820
aagaccaagg agaccccctc cctgggctcg ggttttgatc cctactttgt ttactcggga 23880
tccatcccct acctggatgg caccttctac ctcaaccaca ctttcaagaa gatatccatc 23940
atgtatgact cctccgtcag ctggccgggc aacgaccgct tgctcacccc caatgagttc 24000

-continued gaggtcaagc gcgccgtgga cggcgagggc tacaacgtgg cccagtgcaa catgaccaag 24060
gactggttcc tggtgcagat gctggccaac tacaacatag gctaccaggg cttttacatc 24120
ccagagagct acaaggacag gatgtactcc ttcttcagaa atttccaacc catgagccga 24180
caggtggtgg acgagaccaa ttacaaggac tatcaagcca ttggcatcac ccaccagcac 24240
aacaactcgg gtttcgtggg ctacctggcg cccaccatgc gcgagggtca ggcctacccc 24300
gccaacttcc cctacccctt gataggcaag accgcggtcg acagcgtcac ccagaaaaag 24360
ttcctctgcg accgcaccct ctggcgcatc cccttctcta gcaacttcat gtccatgggt 24420
gcgctcacgg acctgggcca aaacctgctt tatgccaact ctgcccatgc gctggacatg 24480
acttttgagg tggaccccat ggacgagccc acccttctct atattgtgtt tgaagtgttc 24540
gacgtggtca gagtgcacca gccgcaccgc ggtgtcatcg agaccgtgta cctgcgtacg 24600
cccttctcag ccggcaacgc caccacctaa ggagacagcg ccgccgccgc ctgcatgacg 24660
ggttccaccg agcaagagct cagggccatt gccagagacc tgggatgcgg accctatttt 24720
ttgggcacct atgacaaacg cttcccgggc tttatctccc gagacaagct cgcctgcgcc 24780
attgtcaaca cggccgcgcg cgagaccggg ggcgtgcact ggctggcctt tggctgggac 24840
ccgcgctcca aaacttgcta cctctttgac ccctttggct tctccgatca gcgcctcagg 24900
cagatttatg agtttgagta cgaggggctg ctgcgccgca gcgcgctcgc ctcctcgccc 24960
gaccgctgca tcacccttga gaagtccacc gaaaccgtgc aggggcccca ctcggccgcc 25020
tgcggtctct tctgttgcat gtttttgcac gcctttgtgc actggcctca gagtcccatg 25080
gattgcaacc ccaccatgaa cttgctaaag ggagtgccca acgccatgct ccagagcccc 25140
caggtccagc ccaccctgcg ccgcaaccag gaacagcttt accgcttcct ggagcgccac 25200
tccccctact tccgcagcca cagcgcgcgc atccgggggg ccacctcttt ttgccacttg 25260
caagaaaaca tgcaagacgg aaaatgatgt acagcatgct tttaataaat gtaaagactg 25320
tgcactttaa ttatacacgg gctctttctg gttatttatt caacaccgcc gtcgccattt 25380
agaaatcgaa agggttctgc cgtgcgtcgc cgtgcgccac gggcagagac acgttgcgat 25440
actggaagcg gctcgcccac ttgaactcgg gcaccaccat gcggggcagt ggttcctcgg 25500
ggaagttctc gctccacagg gtgcgggtca gctgcagcgc gctcaggagg tcgggagccg 25560
agatcttgaa gtcgcagttg gggccggaac cctgcgcgcg cgagttgcgg tacacggggt 25620
tgcagcactg gaacaccagc agggccggat tattcacgct ggccagcagg ctctcgtcgc 25680
tgatcatgtc gctgtccaga tcctccgcgt tgctcagggc gaatggggtc atcttgcaga 25740
cctgcctgcc caggaaaggc gggagcccag gcttgccgtt gcagtcgcag cgcaggggca 25800
ttagcaggtg cccacggccc gactgcgcct gcgggtacaa cgcgcgcatg aaggcttcga 25860
tctgcctaaa agccacctgg gtcttggctc cctccgaaaa gaacatccca caggacttgc 25920
tggagaactg gttcgcggga cagctggcat cgtgcaggca gcagcgcgcg tcagtgttgg 25980
caatctgcac cacgttgcga ccccaccggt ttttcactat cttggccttg gaagcctgct 26040
cctttagcgc gcgctggccg ttctcgctgg tcacatccat ctctatcacc tgttccttgt 26100
tgatcatgtt tgtcccgtgc agacacttta ggtcgccctc cgtctgggtg cagcggtgct 26160
cccacagcgc gcaaccggtg ggctcccaat tcttgtgggt cacccccgcg taggcctgca 26220
ggtaggcctg caggaagcgc cccatcatgg tcataaaggt cttctggctc gtaaaggtca 26280
gctgcaggcc gcgatgctct tcgttcagcc aggtcttgca gatggcggcc agcgcctcgg 26340

```
tctgctcggg cagcatctta aaatttgtct tcaggtcgtt atccacgtgg tacttgtcca  26400
tcatggcacg cgccgcctcc atgcccttct cccaggcgga caccatgggc aggcttaggg  26460
ggtttatcac ttccagcggc gaggacaccg tactttcgat ttcttcttcc tccccctctt  26520
cccggcgcgc gcccccgctg ttgcgcgctc ttaccgcctg caccaagggg tcgtcttcag  26580
gcaagcgccg caccgagcgc ttgccgccct tgacctgctt gatcagtacc ggcgggttgc  26640
tgaagcccac catggtcagc gccgcctgct cttcttcgtc ttcgctgtct accactattt  26700
ctggggaggg gcttctccgc tctgcggcaa aggcggcgga tcgcttcttt tttttcttgg  26760
gagccgccgc gatggagtcc gccacggcga ccgaggtcga gggcgtgggg ctgggggtgc  26820
gcggtaccag ggcctcgtcg ccctcggact cttcctctga ctccaggcgg cggcggagtc  26880
gcttctttgg gggcgcgcgc gtcagcggcg gcggagacgg ggacggggac ggggacggga  26940
cgccctccac agggggtggt cttcgcgcag acccgcggcc gcgctcgggg gtcttctcgc  27000
gctggtcttg gtcccgactg gccattgtat cctcctcctc ctaggcagag agacataagg  27060
agtctatcat gcaagtcgag aaggaggaga gcttaaccac cccctcagag accgccgatg  27120
cgcccgccgt cgccgtcgcc cccgctaccg ccgacgcgcc cgccacaccg agcgacaccc  27180
ccacggaccc ccccgccgac gcacccctgt tcgaggaagc ggccgtggag caggacccgg  27240
gctttgtctc ggcagaggag gatttgcaag aggaggagaa taaggaggag aagccctcag  27300
tgccaaaaga tcataaagag caagacgagc acgacgcaga cgcacaccag ggtgaagtcg  27360
ggcgggggga cggagggcat ggcggcgccg actacctaga cgaaggaaac gacgtgctct  27420
tgaagcacct gcatcgtcag tgcgccatcg tctgcgacgc tctgcaggag cgcagcgagg  27480
tgcccctcag cgtggcggag gtcagccgcg cctacgagct cagcctcttt tccccccggg  27540
tgcccccccg ccgccgcgaa aacggcacat gcgagcccaa cccgcgcctc aacttctacc  27600
ccgcctttgt ggtgcccgag gtcctggcca cctatcacat cttctttcaa aattgcaaga  27660
tccccatctc gtgccgcgcc aaccgtagcc gcgccgataa gatgctggcc ctgcgccagg  27720
gcgaccacat acctgatatc gccgctttgg aagatgtgcc aaagatcttc gagggtctgg  27780
ggcgcaacga gaagcgggca gcaaactctc tgcaacagga aaacagcgaa aatgagagtc  27840
acactggagc gctggtggag ctggagggcg acaacgcccg cctggcggtg ctcaagcgca  27900
gcatcgaggt cacccacttt gcctaccccg cgctcaacct gccccccaaa gtcatgaacg  27960
cggtcatgga cgggctgatc atgcgccgcg gccggcccct cgctccagat gcaaacttgc  28020
atgaggagac cgaggacggt cagcccgtgg tcagcgacga gcagctgacg cgctggctgg  28080
agagcgcgga ccccgccgaa ctggaggagc ggcgcaagat gatgatggcc gcggtgctgg  28140
tcaccgtaga gctggagtgt ctgcagcgct tcttcggtga ccccgagatg cagagaaagg  28200
tcgaggagac cctacactac accttccgcc agggctacgt gcgccaggct tgcaagatct  28260
ccaacgtgga gctcagcaac ctggtgtcct acctgggcat cttgcatgaa aaccgccttg  28320
ggcagagcgt gctacactcc accctgcgcg gggaggcgcg ccgcgactac gtgcgcgact  28380
gcgtttacct cttcctctgc tacacctggc agacggccat gggggtctgg cagcagtgcc  28440
tggaggagcg caacctcaag gagctggaga agcttctgca gcgcgcgctc aaagacctct  28500
ggacgggctt caacgagcgc tcggtggccg ccgcgctagc cgacctcatc ttccccgagc  28560
gcctgctcaa aaccctccag caggggctgc ccgacttcac cagccaaagc atgttgcaaa  28620
attttaggaa ctttatcctg gagcgttctg gcatcctacc cgccacctgc tgcgccctgc  28680
ccagcgactt tgtcccccctc gtgtaccgcg agtgcccccc gccgctgtgg ggccactgct  28740
```

acctgttcca actggccaac tacctgtcct accacgcgga cctcatggag gactccagcg 28800
gcgaggggct catggagtgc cactgccgct gcaacctctg cacgccccac cgctccctgg 28860
tctgcaacac ccaactgctc agcgagagtc agattatcgg taccttcgag ctacagggtc 28920
cgtcctcctc agacgagaag tccgcggctc cggggctaaa actcactccg ggctgtgga 28980
cttccgccta cctgcgcaaa tttgtacctg aagactacca cgcccacgaa atcaggtttt 29040
acgaggacca atcccgcccg cccaaggcgg agctgaccgc ctgcgtcatc acccagggcg 29100
agatcctagg ccaattgcaa gccatccaaa aagcccgcca agagtttttg ctgaagaggg 29160
gtcggggggt gtatctggac ccccagtcgg gtgaggagct caacccggtt cccccgctgc 29220
caccgccgcg ggaccttgct tcccaggata agcatcgcca tggctcccag aaagaagcag 29280
cagcggccgc cgctgccgcc gccccacatg ctggaggaag aggaggaata ctgggacagt 29340
caggcagagg aggtttcgga cgaggaggag ccggagacgg agatggaaga gtgggaggag 29400
gacagcttag acgaggaggc ttccgaagcc gaagaggcag gcgcaacacc gtcaccctcg 29460
gccgcagccc cctcgcaggc gcccccgaag tccgctccca gcatcagcag caacagcagc 29520
gctataacct ccgctcctcc accgccgcga cccacggccg accgcagacc caaccgtaga 29580
tgggacacca ccggaaccgg ggccggtaag tcctccggga gaggcaagca agcgcagcgc 29640
caaggctacc gctcgtggcg cgctcacaag aacgccatag tcgcttgctt gcaagactgc 29700
ggggggaaca tctccttcgc ccgccgcttc ctgctcttcc accacggtgt ggccttcccc 29760
cgtaacgtcc tgcattacta ccgtcatctc tacagcccct actgcggcgg cagtgagcca 29820
gaggcggcca gcggcggcgg cgcccgtttc ggtgcctagg aagacccagg gcaagacttc 29880
agccaagaaa ctcgcggcga ccgcggcgaa cgcggtcgcg ggggccctgc gcctgacggt 29940
gaacgaaccc ctgtcgaccc gcgaactgag gaaccgaatc ttccccactc tctatgccat 30000
cttccagcag agcagagggc aggatcagga actgaaagta aaaaacaggt ctctgcgctc 30060
cctcacccgc agctgtctgt atcacaagag cgaagaccag cttcggcgca cgctggagga 30120
cgctgaggca ctcttcagca aatactgcgc gctcactctt aaggactagc tccgcgccct 30180
tctcgaattt aggcgggaac gcctacgtca tcgcagcgcc gccgtcatga gcaaggacat 30240
tcccacgcca tacatgtgga gctatcagcc gcagatggga ctcgcggcgg gcgcctccca 30300
agactactcc acccgcatga actggctcag tgccggccca cacatgatct cacaggttaa 30360
tgacatccgc acccatcgaa accaaatatt ggtgaagcag gcggcaatta ccaccacgcc 30420
ccgcaataat cccaacccca gggagtggcc cgcgtccctg gtgtatcagg aaattcccgg 30480
ccccaccacc gtactacttc cgcgtgattc ccaggccgaa gtccaaatga ctaactcagg 30540
ggcacagctc gcgggcggct gtcgtcacag ggtgcggcct cctcgccagg gtataactca 30600
cctggagatc cgaggcagag gtattcagct caacgacgag tcggtgagct cctcgctcgg 30660
tctcagacct gacgggacct tccagatagc cggagccggc cgatcttcct tcacgccccg 30720
ccaggcgtac ctgactctgc agagctcgtc ctcggcgccg cgctcgggcg gcatcgggac 30780
tctccagttc gtgcaggagt ttgtgccctc ggtctacttc aacccccttct cgggctctcc 30840
cggtcgctac ccggaccagt ttatcccgaa ctttgacgcc gcgagggact cggtggacgg 30900
ctacgactga atgtcgggtg gacccggtgc agagcaactt cgcctgaagc accttgacca 30960
ctgccgccgc cctcagtgct ttgcccgctg tcagaccggt gagttccagt acttttccct 31020
gcccgactcg cacccggacg gcccggcgca cggggtgcgc tttttcatcc cgagtcaggt 31080

-continued

```
ccgctctacc ctaatcaggg agttcaccgc ccgtccccta ctggcggagt tggaaaaggg  31140

gccttctatc ctaaccattg cctgcatttg ctctaaccct ggattacacc aagatctttg  31200

ctgtcatttg tgtgctgagt ataataaagg ctgagatcag aatctactcg gaccttatcc  31260

ctttcaattg atcataactg taatcaataa aaaatcactt acttgaaatc tgatagcaag  31320

actctgtcca attttttcag caacacttcc ttcccctcct cccaactctg gtactctagg  31380

cgcctcctag ctgcaaactt cctccacagt ctgaagggaa tgtcagattc ctcctcctgt  31440

ccctccgcac ccacgatctt catgttgtta cagatgaaac gcgcgagatc gtctgacgag  31500

accttcaacc ccgtgtaccc ctacgatacc gagatcgctc cgacttctgt ccctttcctt  31560

acccctccct ttgtatcatc cgcaggaatg caagaaaatc cagctggggt gctgtccctg  31620

cacctgtcag agccccttac cacccacaat ggggccctga ctctaaaaat ggggggcggc  31680

ctgaccctgg acaaggaagg gaatctcact tcccaaaaca tcaccagtgt cgatccccct  31740

ctcaaaaaaa gcaagaacaa catcagcctt cagaccgccg cacccctcgc cgtcagctcc  31800

ggggccctaa cccttttttgc cactccccc ctagcggtca gtggcgacaa ccttactgtg  31860

cagtctcagg cccctcttac tttggaagac tcaaaactaa ctctggccac caaaggaccc  31920

ctaactgtgt ccgaaggcaa acttgtccta gaaacagagc ctcccctgca tgcaagtgac  31980

agcagtagcc tgggccttag cgtcacggcc ccacttagca ttaacaatga cagcctagga  32040

ctagacatgc aagcgcccat cagctctcga gatggaaaac tggctctaac agtggcggcc  32100

cccctaactg tggccgaggg tatcaatgct ttggcagtag ccacaggtaa tggtattgga  32160

ctaaatgaaa ccaacacaca cctgcaggca aaactggtcg cgcccctagg ctttgatacc  32220

aacggcaaca ttaagctaag cgtcgcagga ggcatgaggc taaacaataa cacactgata  32280

ctagatgtaa actacccatt tgaggctcaa ggccaactga gcctaagagt gggctcgggc  32340

ccactatatg tagattctag tagtcataac ctaaccatta gatgccttag ggatattgtat  32400

gtaacatctt ctaacaacca aaacggtcta gaggccaaca ttaaactaac aaaaggcctt  32460

gtgtatgacg gaaatgccat agcagttaat gttggcaaag ggctggaata cagccctact  32520

ggcacaacag aaaaacctat acagactaaa ataggtctag gcatggagta tgacactgag  32580

ggagccatga tgacaaaact aggctctgga ctaagctttg acaattcagg agccattgtg  32640

gtgggaaaca aaaatgatga caggcttact ttgtggacca caccggaccc atcgcccaac  32700

tgtcagattt actctgaaaa agatgctaaa ctaaccttgg tactgactaa atgtggcagt  32760

caggttg                                                            32767
```

<210> SEQ ID NO 714
<211> LENGTH: 16
<212> TYPE: PRT
<213> ORGANISM: Homo sapiens

<400> SEQUENCE: 714

```
Gly Ser Thr Gly Cys Leu Thr Cys Arg His His Gln Thr Ser His Glu
1               5                   10                  15
```

<210> SEQ ID NO 715
<211> LENGTH: 15
<212> TYPE: PRT
<213> ORGANISM: Homo sapiens

<400> SEQUENCE: 715

```
Val Val Gly Arg Arg His Glu Thr Ala Pro Gln Pro Leu Leu Val
1               5                   10                  15
```

<210> SEQ ID NO 716
<211> LENGTH: 15
<212> TYPE: PRT
<213> ORGANISM: Homo sapiens

<400> SEQUENCE: 716

Ala Pro Gln Pro Leu Leu Val Pro Asp Arg Ala Gly Gly Glu Gly
1 5 10 15

<210> SEQ ID NO 717
<211> LENGTH: 9
<212> TYPE: PRT
<213> ORGANISM: Homo sapiens

<400> SEQUENCE: 717

Asp Arg Ala Gly Gly Glu Gly Gly Ala
1 5

<210> SEQ ID NO 718
<211> LENGTH: 15
<212> TYPE: PRT
<213> ORGANISM: Homo sapiens

<400> SEQUENCE: 718

Pro Val Pro Thr Ala Thr Pro Gly Val Arg Ser Val Thr Ser Pro
1 5 10 15

<210> SEQ ID NO 719
<211> LENGTH: 15
<212> TYPE: PRT
<213> ORGANISM: Homo sapiens

<400> SEQUENCE: 719

Val Arg Ser Val Thr Ser Pro Gln Gly Leu Gly Leu Phe Leu Lys
1 5 10 15

<210> SEQ ID NO 720
<211> LENGTH: 9
<212> TYPE: PRT
<213> ORGANISM: Homo sapiens

<400> SEQUENCE: 720

Gly Leu Gly Leu Phe Leu Lys Phe Ile
1 5

<210> SEQ ID NO 721
<211> LENGTH: 15
<212> TYPE: PRT
<213> ORGANISM: Homo sapiens

<400> SEQUENCE: 721

Lys Glu Asn Asp Val Arg Glu Val Cys Asp Val Tyr Leu Gln Met
1 5 10 15

<210> SEQ ID NO 722
<211> LENGTH: 15
<212> TYPE: PRT
<213> ORGANISM: Homo sapiens

<400> SEQUENCE: 722

Cys Asp Val Tyr Leu Gln Met Gln Ile Phe Phe His Phe Lys Phe
1 5 10 15

<210> SEQ ID NO 723
<211> LENGTH: 12
<212> TYPE: PRT
<213> ORGANISM: Homo sapiens

<400> SEQUENCE: 723

Ile Phe Phe His Phe Lys Phe Arg Ser Tyr Phe His
1 5 10

<210> SEQ ID NO 724
<211> LENGTH: 15
<212> TYPE: PRT
<213> ORGANISM: Homo sapiens

<400> SEQUENCE: 724

Phe Ala Arg Lys Met Leu Glu Lys Val His Arg Gln His Leu Gln
1 5 10 15

<210> SEQ ID NO 725
<211> LENGTH: 14
<212> TYPE: PRT
<213> ORGANISM: Homo sapiens

<400> SEQUENCE: 725

Val His Arg Gln His Leu Gln Leu Ser His Asn Ser Gln Glu
1 5 10

<210> SEQ ID NO 726
<211> LENGTH: 15
<212> TYPE: PRT
<213> ORGANISM: Homo sapiens

<400> SEQUENCE: 726

Met Phe Leu Arg Lys Glu Gln Gln Val Gly Pro His Ser Phe Ser
1 5 10 15

<210> SEQ ID NO 727
<211> LENGTH: 9
<212> TYPE: PRT
<213> ORGANISM: Homo sapiens

<400> SEQUENCE: 727

Val Gly Pro His Ser Phe Ser Met Leu
1 5

<210> SEQ ID NO 728
<211> LENGTH: 15
<212> TYPE: PRT
<213> ORGANISM: Homo sapiens

<400> SEQUENCE: 728

Gly Leu Asn Leu Asn Thr Asp Arg Pro Gly Gly Tyr Ser Tyr Ser
1 5 10 15

<210> SEQ ID NO 729
<211> LENGTH: 15
<212> TYPE: PRT
<213> ORGANISM: Homo sapiens

<400> SEQUENCE: 729

Pro Gly Gly Tyr Ser Tyr Ser Ile Trp Trp Lys Asn Asn Ala Lys
1 5 10 15

<210> SEQ ID NO 730
<211> LENGTH: 9

<212> TYPE: PRT
<213> ORGANISM: Homo sapiens

<400> SEQUENCE: 730

Trp Trp Lys Asn Asn Ala Lys Asn Arg
1 5

<210> SEQ ID NO 731
<211> LENGTH: 15
<212> TYPE: PRT
<213> ORGANISM: Homo sapiens

<400> SEQUENCE: 731

Lys Val Leu Asn Glu Ile Asp Ala Val Val Thr Val Pro Pro Ser
1 5 10 15

<210> SEQ ID NO 732
<211> LENGTH: 15
<212> TYPE: PRT
<213> ORGANISM: Homo sapiens

<400> SEQUENCE: 732

Val Val Thr Val Pro Pro Ser Leu Ser Thr Ser Gln Ile Pro Gln
1 5 10 15

<210> SEQ ID NO 733
<211> LENGTH: 13
<212> TYPE: PRT
<213> ORGANISM: Homo sapiens

<400> SEQUENCE: 733

Ser Thr Ser Gln Ile Pro Gln Gly Cys Cys Ile Ile Leu
1 5 10

<210> SEQ ID NO 734
<211> LENGTH: 15
<212> TYPE: PRT
<213> ORGANISM: Homo sapiens

<400> SEQUENCE: 734

Ala Asn Leu Lys Gly Thr Leu Gln Val Arg Ser Gly Gln Ala Val
1 5 10 15

<210> SEQ ID NO 735
<211> LENGTH: 10
<212> TYPE: PRT
<213> ORGANISM: Homo sapiens

<400> SEQUENCE: 735

Val Arg Ser Gly Gln Ala Val Ser Pro Arg
1 5 10

<210> SEQ ID NO 736
<211> LENGTH: 15
<212> TYPE: PRT
<213> ORGANISM: Homo sapiens

<400> SEQUENCE: 736

Leu Gln Ala Ala Ala Ser Gly Gln Gly Lys Gln Gly Val Pro Cys
1 5 10 15

<210> SEQ ID NO 737
<211> LENGTH: 15
<212> TYPE: PRT
<213> ORGANISM: Homo sapiens

<400> SEQUENCE: 737

Gly Lys Gln Gly Val Pro Cys Pro Trp Gly Cys Cys Ala Tyr Ala
1 5 10 15

<210> SEQ ID NO 738
<211> LENGTH: 15
<212> TYPE: PRT
<213> ORGANISM: Homo sapiens

<400> SEQUENCE: 738

Trp Gly Cys Cys Ala Tyr Ala Glu Ser Pro Arg Ala Leu Ile Ser
1 5 10 15

<210> SEQ ID NO 739
<211> LENGTH: 15
<212> TYPE: PRT
<213> ORGANISM: Homo sapiens

<400> SEQUENCE: 739

Ser Pro Arg Ala Leu Ile Ser Gly Asp Ala Pro Ser Gln Val Glu
1 5 10 15

<210> SEQ ID NO 740
<211> LENGTH: 15
<212> TYPE: PRT
<213> ORGANISM: Homo sapiens

<400> SEQUENCE: 740

Asp Ala Pro Ser Gln Val Glu Arg Glu Val Pro Gly Pro Cys Leu
1 5 10 15

<210> SEQ ID NO 741
<211> LENGTH: 15
<212> TYPE: PRT
<213> ORGANISM: Homo sapiens

<400> SEQUENCE: 741

Glu Val Pro Gly Pro Cys Leu Asn Thr His Ser Leu Ser His Arg
1 5 10 15

<210> SEQ ID NO 742
<211> LENGTH: 15
<212> TYPE: PRT
<213> ORGANISM: Homo sapiens

<400> SEQUENCE: 742

Thr His Ser Leu Ser His Arg Ser Pro Gln Leu Pro Gly Leu Pro
1 5 10 15

<210> SEQ ID NO 743
<211> LENGTH: 14
<212> TYPE: PRT
<213> ORGANISM: Homo sapiens

<400> SEQUENCE: 743

Pro Gln Leu Pro Gly Leu Pro His Pro Lys Gln Pro Ser Val
1 5 10

<210> SEQ ID NO 744
<211> LENGTH: 15
<212> TYPE: PRT
<213> ORGANISM: Homo sapiens

<400> SEQUENCE: 744

Gly Glu Val Glu Leu Ser Glu Gly Gly Glu Gly Gln Arg His Leu
1 5 10 15

<210> SEQ ID NO 745
<211> LENGTH: 15
<212> TYPE: PRT
<213> ORGANISM: Homo sapiens

<400> SEQUENCE: 745

Gly Glu Gly Gln Arg His Leu Ala Phe Pro Trp Ala Cys Ser Gly
1 5 10 15

<210> SEQ ID NO 746
<211> LENGTH: 15
<212> TYPE: PRT
<213> ORGANISM: Homo sapiens

<400> SEQUENCE: 746

Phe Pro Trp Ala Cys Ser Gly Pro Gly Trp Arg Gly Val Cys Cys
1 5 10 15

<210> SEQ ID NO 747
<211> LENGTH: 15
<212> TYPE: PRT
<213> ORGANISM: Homo sapiens

<400> SEQUENCE: 747

Lys Met Arg Ala Ile Gln Ala Glu Gly Gly His Gly Gln Ala Cys
1 5 10 15

<210> SEQ ID NO 748
<211> LENGTH: 15
<212> TYPE: PRT
<213> ORGANISM: Homo sapiens

<400> SEQUENCE: 748

Gly Gly His Gly Gln Ala Cys Cys Gly Gly Ala Trp Gly Trp Ala
1 5 10 15

<210> SEQ ID NO 749
<211> LENGTH: 15
<212> TYPE: PRT
<213> ORGANISM: Homo sapiens

<400> SEQUENCE: 749

Gly Gly Ala Trp Gly Trp Ala Pro Gly Asp Gly Gly Pro Gln Gly
1 5 10 15

<210> SEQ ID NO 750
<211> LENGTH: 15
<212> TYPE: PRT
<213> ORGANISM: Homo sapiens

<400> SEQUENCE: 750

Gly Asp Gly Gly Pro Gln Gly Met Leu Thr His Thr Leu Pro Thr
1 5 10 15

<210> SEQ ID NO 751
<211> LENGTH: 15
<212> TYPE: PRT
<213> ORGANISM: Homo sapiens

<400> SEQUENCE: 751

Leu Thr His Thr Leu Pro Thr Leu Gly Phe Gln Ser Ala Trp Thr 1 5 10 15

<210> SEQ ID NO 752
<211> LENGTH: 15
<212> TYPE: PRT
<213> ORGANISM: Homo sapiens

<400> SEQUENCE: 752

Gly Phe Gln Ser Ala Trp Thr Trp Arg Arg Glu Asp Ala Asp Arg
1 5 10 15

<210> SEQ ID NO 753
<211> LENGTH: 15
<212> TYPE: PRT
<213> ORGANISM: Homo sapiens

<400> SEQUENCE: 753

Arg Arg Glu Asp Ala Asp Arg Ala Trp Arg Thr Pro Lys Ala Cys
1 5 10 15

<210> SEQ ID NO 754
<211> LENGTH: 14
<212> TYPE: PRT
<213> ORGANISM: Homo sapiens

<400> SEQUENCE: 754

Trp Arg Thr Pro Lys Ala Cys Ala Ser Arg Arg Trp Ser Ile
1 5 10

<210> SEQ ID NO 755
<211> LENGTH: 15
<212> TYPE: PRT
<213> ORGANISM: Homo sapiens

<400> SEQUENCE: 755

Leu Leu Glu Pro Phe Arg Arg Gly Glu Pro Gly Pro Arg Gly Leu
1 5 10 15

<210> SEQ ID NO 756
<211> LENGTH: 15
<212> TYPE: PRT
<213> ORGANISM: Homo sapiens

<400> SEQUENCE: 756

Glu Pro Gly Pro Arg Gly Leu Leu Ser Gly Ser Ser Arg Gly Gly
1 5 10 15

<210> SEQ ID NO 757
<211> LENGTH: 15
<212> TYPE: PRT
<213> ORGANISM: Homo sapiens

<400> SEQUENCE: 757

Ser Gly Ser Ser Arg Gly Gly Glu Gly Pro Gly Arg Ser Ile Glu
1 5 10 15

<210> SEQ ID NO 758
<211> LENGTH: 15
<212> TYPE: PRT
<213> ORGANISM: Homo sapiens

<400> SEQUENCE: 758

Gly Pro Gly Arg Ser Ile Glu Ala Ala Pro Ala Thr Pro Leu Pro
1 5 10 15

<210> SEQ ID NO 759
<211> LENGTH: 15
<212> TYPE: PRT
<213> ORGANISM: Homo sapiens

<400> SEQUENCE: 759

Ala Pro Ala Thr Pro Leu Pro Cys Cys Arg Lys Asn Pro Cys Arg
1 5 10 15

<210> SEQ ID NO 760
<211> LENGTH: 15
<212> TYPE: PRT
<213> ORGANISM: Homo sapiens

<400> SEQUENCE: 760

Cys Arg Lys Asn Pro Cys Arg Pro Gln Pro Ser Arg Phe Leu Pro
1 5 10 15

<210> SEQ ID NO 761
<211> LENGTH: 15
<212> TYPE: PRT
<213> ORGANISM: Homo sapiens

<400> SEQUENCE: 761

Gln Pro Ser Arg Phe Leu Pro Pro Arg Val Leu Leu Val Ile Ile
1 5 10 15

<210> SEQ ID NO 762
<211> LENGTH: 15
<212> TYPE: PRT
<213> ORGANISM: Homo sapiens

<400> SEQUENCE: 762

Arg Val Leu Leu Val Ile Ile Leu Pro Lys Leu Asp Cys Pro Lys
1 5 10 15

<210> SEQ ID NO 763
<211> LENGTH: 10
<212> TYPE: PRT
<213> ORGANISM: Homo sapiens

<400> SEQUENCE: 763

Pro Lys Leu Asp Cys Pro Lys Leu Gly Phe
1 5 10

<210> SEQ ID NO 764
<211> LENGTH: 15
<212> TYPE: PRT
<213> ORGANISM: Homo sapiens

<400> SEQUENCE: 764

Pro Ser Gly Arg Arg Thr Lys Arg Leu Val Thr Leu Arg Ser Gly
1 5 10 15

<210> SEQ ID NO 765
<211> LENGTH: 15
<212> TYPE: PRT
<213> ORGANISM: Homo sapiens

<400> SEQUENCE: 765

Leu Val Thr Leu Arg Ser Gly Cys Ala Ile Gln Cys Trp His Pro
1 5 10 15

<210> SEQ ID NO 766

<211> LENGTH: 15
<212> TYPE: PRT
<213> ORGANISM: Homo sapiens

<400> SEQUENCE: 766

Ala Ile Gln Cys Trp His Pro Arg Ala Gly Pro Val Pro Ser Ala
1 5 10 15

<210> SEQ ID NO 767
<211> LENGTH: 15
<212> TYPE: PRT
<213> ORGANISM: Homo sapiens

<400> SEQUENCE: 767

Ala Gly Pro Val Pro Ser Ala Leu Pro His Thr Glu Arg Pro Pro
1 5 10 15

<210> SEQ ID NO 768
<211> LENGTH: 15
<212> TYPE: PRT
<213> ORGANISM: Homo sapiens

<400> SEQUENCE: 768

Pro His Thr Glu Arg Pro Pro Arg Leu Val Arg Gly Ala Ala Asp
1 5 10 15

<210> SEQ ID NO 769
<211> LENGTH: 15
<212> TYPE: PRT
<213> ORGANISM: Homo sapiens

<400> SEQUENCE: 769

Leu Val Arg Gly Ala Ala Asp Pro Arg Thr Val Thr Leu Gly Arg
1 5 10 15

<210> SEQ ID NO 770
<211> LENGTH: 15
<212> TYPE: PRT
<213> ORGANISM: Homo sapiens

<400> SEQUENCE: 770

Arg Thr Val Thr Leu Gly Arg Ser Pro Ala Val Met Pro Arg Ala
1 5 10 15

<210> SEQ ID NO 771
<211> LENGTH: 9
<212> TYPE: PRT
<213> ORGANISM: Homo sapiens

<400> SEQUENCE: 771

Pro Ala Val Met Pro Arg Ala Pro Ala
1 5

<210> SEQ ID NO 772
<211> LENGTH: 15
<212> TYPE: PRT
<213> ORGANISM: Homo sapiens

<400> SEQUENCE: 772

Asp Cys Met Leu Ser Glu Glu Gly Gly Gln Ala Arg Arg Gly Gly
1 5 10 15

<210> SEQ ID NO 773
<211> LENGTH: 15
<212> TYPE: PRT

<213> ORGANISM: Homo sapiens

<400> SEQUENCE: 773

Gly Gln Ala Arg Arg Gly Gly Ser Leu Cys Ser Leu Ala Ala His
1 5 10 15

<210> SEQ ID NO 774
<211> LENGTH: 15
<212> TYPE: PRT
<213> ORGANISM: Homo sapiens

<400> SEQUENCE: 774

Leu Cys Ser Leu Ala Ala His Thr Ile Ala Ser Ala Ala Arg Gly
1 5 10 15

<210> SEQ ID NO 775
<211> LENGTH: 15
<212> TYPE: PRT
<213> ORGANISM: Homo sapiens

<400> SEQUENCE: 775

Ile Ala Ser Ala Ala Arg Gly Arg Phe Leu Ser Arg Leu Ser Asn
1 5 10 15

<210> SEQ ID NO 776
<211> LENGTH: 15
<212> TYPE: PRT
<213> ORGANISM: Homo sapiens

<400> SEQUENCE: 776

Phe Leu Ser Arg Leu Ser Asn Phe Cys Ala Val Val Lys Ala Ser
1 5 10 15

<210> SEQ ID NO 777
<211> LENGTH: 16
<212> TYPE: PRT
<213> ORGANISM: Homo sapiens

<400> SEQUENCE: 777

Cys Ala Val Val Lys Ala Ser Arg Gly Ala Pro Ser Cys Thr Trp Glu
1 5 10 15

<210> SEQ ID NO 778
<211> LENGTH: 15
<212> TYPE: PRT
<213> ORGANISM: Homo sapiens

<400> SEQUENCE: 778

Pro Glu Pro Arg Arg Leu Ser Pro Gly Glu Pro Arg Gly Arg Pro
1 5 10 15

<210> SEQ ID NO 779
<211> LENGTH: 15
<212> TYPE: PRT
<213> ORGANISM: Homo sapiens

<400> SEQUENCE: 779

Gly Glu Pro Arg Gly Arg Pro Arg Lys Gly Trp Gly Ile Trp Gly
1 5 10 15

<210> SEQ ID NO 780
<211> LENGTH: 15
<212> TYPE: PRT
<213> ORGANISM: Homo sapiens

<400> SEQUENCE: 780

Lys Gly Trp Gly Ile Trp Gly Leu Cys Gly Ala Arg Val Gly Pro
1 5 10 15

<210> SEQ ID NO 781
<211> LENGTH: 11
<212> TYPE: PRT
<213> ORGANISM: Homo sapiens

<400> SEQUENCE: 781

Cys Gly Ala Arg Val Gly Pro Lys Ala Trp Arg
1 5 10

<210> SEQ ID NO 782
<211> LENGTH: 15
<212> TYPE: PRT
<213> ORGANISM: Homo sapiens

<400> SEQUENCE: 782

Phe Val Ser Leu Thr Ala Ile Gln Met Ala Ser Ser Ala Thr Pro
1 5 10 15

<210> SEQ ID NO 783
<211> LENGTH: 15
<212> TYPE: PRT
<213> ORGANISM: Homo sapiens

<400> SEQUENCE: 783

Met Ala Ser Ser Ala Thr Pro Trp Gly Arg Trp Pro Val Ala Thr
1 5 10 15

<210> SEQ ID NO 784
<211> LENGTH: 15
<212> TYPE: PRT
<213> ORGANISM: Homo sapiens

<400> SEQUENCE: 784

Gly Arg Trp Pro Val Ala Thr Pro Thr Ala Ala Cys Pro Arg Arg
1 5 10 15

<210> SEQ ID NO 785
<211> LENGTH: 15
<212> TYPE: PRT
<213> ORGANISM: Homo sapiens

<400> SEQUENCE: 785

Thr Ala Ala Cys Pro Arg Arg Arg Pro Ser Ser Leu Pro Thr Gly
1 5 10 15

<210> SEQ ID NO 786
<211> LENGTH: 15
<212> TYPE: PRT
<213> ORGANISM: Homo sapiens

<400> SEQUENCE: 786

Pro Ser Ser Leu Pro Thr Gly Gly Asp Ser Ala Ser Lys Lys Pro
1 5 10 15

<210> SEQ ID NO 787
<211> LENGTH: 15
<212> TYPE: PRT
<213> ORGANISM: Homo sapiens

<400> SEQUENCE: 787

Asp Ser Ala Ser Lys Lys Pro Ile Ser Arg Arg Ala Pro Trp Gln
1 5 10 15

<210> SEQ ID NO 788
<211> LENGTH: 15
<212> TYPE: PRT
<213> ORGANISM: Homo sapiens

<400> SEQUENCE: 788

Ser Arg Arg Ala Pro Trp Gln Pro Trp Ala Cys Pro Gly Arg Ser
1 5 10 15

<210> SEQ ID NO 789
<211> LENGTH: 15
<212> TYPE: PRT
<213> ORGANISM: Homo sapiens

<400> SEQUENCE: 789

Trp Ala Cys Pro Gly Arg Ser Val Asn Ser Ala Ala Pro Arg Ala
1 5 10 15

<210> SEQ ID NO 790
<211> LENGTH: 15
<212> TYPE: PRT
<213> ORGANISM: Homo sapiens

<400> SEQUENCE: 790

Asn Ser Ala Ala Pro Arg Ala Trp Cys Pro Pro Ala Thr Thr Pro
1 5 10 15

<210> SEQ ID NO 791
<211> LENGTH: 15
<212> TYPE: PRT
<213> ORGANISM: Homo sapiens

<400> SEQUENCE: 791

Cys Pro Pro Ala Thr Thr Pro Arg Thr Gln Ser Pro Ser Arg Asp
1 5 10 15

<210> SEQ ID NO 792
<211> LENGTH: 15
<212> TYPE: PRT
<213> ORGANISM: Homo sapiens

<400> SEQUENCE: 792

Thr Gln Ser Pro Ser Arg Asp Leu Arg Pro Arg Cys Leu Ser Ser
1 5 10 15

<210> SEQ ID NO 793
<211> LENGTH: 10
<212> TYPE: PRT
<213> ORGANISM: Homo sapiens

<400> SEQUENCE: 793

Arg Pro Arg Cys Leu Ser Ser Trp Ser Ser
1 5 10

<210> SEQ ID NO 794
<211> LENGTH: 15
<212> TYPE: PRT
<213> ORGANISM: Homo sapiens

<400> SEQUENCE: 794

Pro Val Ala Ile Lys Pro Gly Thr Gly Pro Pro Asn Asn Ser Ser
1 5 10 15

<210> SEQ ID NO 795
<211> LENGTH: 15
<212> TYPE: PRT
<213> ORGANISM: Homo sapiens

<400> SEQUENCE: 795

Gly Pro Pro Asn Asn Ser Ser Ile His Gly Gly Ser Lys Arg Ser
1 5 10 15

<210> SEQ ID NO 796
<211> LENGTH: 15
<212> TYPE: PRT
<213> ORGANISM: Homo sapiens

<400> SEQUENCE: 796

His Gly Gly Ser Lys Arg Ser Glu Asn Ser Tyr Cys Arg Asp Leu
1 5 10 15

<210> SEQ ID NO 797
<211> LENGTH: 15
<212> TYPE: PRT
<213> ORGANISM: Homo sapiens

<400> SEQUENCE: 797

Asn Ser Tyr Cys Arg Asp Leu Arg Gly Gln Leu Arg Ala Ile Cys
1 5 10 15

<210> SEQ ID NO 798
<211> LENGTH: 15
<212> TYPE: PRT
<213> ORGANISM: Homo sapiens

<400> SEQUENCE: 798

Gly Gln Leu Arg Ala Ile Cys Cys Ser Ser Tyr Ser His Asp Arg
1 5 10 15

<210> SEQ ID NO 799
<211> LENGTH: 15
<212> TYPE: PRT
<213> ORGANISM: Homo sapiens

<400> SEQUENCE: 799

Ser Ser Tyr Ser His Asp Arg His Thr Thr Glu Glu Arg Gly Ser
1 5 10 15

<210> SEQ ID NO 800
<211> LENGTH: 15
<212> TYPE: PRT
<213> ORGANISM: Homo sapiens

<400> SEQUENCE: 800

Thr Thr Glu Glu Arg Gly Ser Arg Gly Arg His Val Trp Arg Ile
1 5 10 15

<210> SEQ ID NO 801
<211> LENGTH: 15
<212> TYPE: PRT
<213> ORGANISM: Homo sapiens

<400> SEQUENCE: 801

Gly Arg His Val Trp Arg Ile Arg Arg Leu His Thr Ser Gly Leu
1 5 10 15

<210> SEQ ID NO 802
<211> LENGTH: 15
<212> TYPE: PRT
<213> ORGANISM: Homo sapiens

<400> SEQUENCE: 802

Arg Leu His Thr Ser Gly Leu Pro Cys Cys Cys His Ser Gly Pro
1 5 10 15

<210> SEQ ID NO 803
<211> LENGTH: 15
<212> TYPE: PRT
<213> ORGANISM: Homo sapiens

<400> SEQUENCE: 803

Cys Cys Cys His Ser Gly Pro His Pro Arg Arg Leu Pro Asp Ile
1 5 10 15

<210> SEQ ID NO 804
<211> LENGTH: 15
<212> TYPE: PRT
<213> ORGANISM: Homo sapiens

<400> SEQUENCE: 804

Pro Arg Arg Leu Pro Asp Ile Leu Arg Leu Val Thr Ser Thr Lys
1 5 10 15

<210> SEQ ID NO 805
<211> LENGTH: 15
<212> TYPE: PRT
<213> ORGANISM: Homo sapiens

<400> SEQUENCE: 805

Arg Leu Val Thr Ser Thr Lys Thr Asp His Thr Asn Thr Thr Glu
1 5 10 15

<210> SEQ ID NO 806
<211> LENGTH: 13
<212> TYPE: PRT
<213> ORGANISM: Homo sapiens

<400> SEQUENCE: 806

Asp His Thr Asn Thr Thr Glu Gly Thr Leu Asp Tyr Leu
1 5 10

<210> SEQ ID NO 807
<211> LENGTH: 15
<212> TYPE: PRT
<213> ORGANISM: Homo sapiens

<400> SEQUENCE: 807

Lys Trp Asn Lys Asn Trp Thr Ala Thr Leu Gly Ala Leu Thr Ile
1 5 10 15

<210> SEQ ID NO 808
<211> LENGTH: 15
<212> TYPE: PRT
<213> ORGANISM: Homo sapiens

<400> SEQUENCE: 808

Thr Leu Gly Ala Leu Thr Ile Arg Gly His Lys Leu Leu Cys His
1 5 10 15

<210> SEQ ID NO 809
<211> LENGTH: 15

<212> TYPE: PRT
<213> ORGANISM: Homo sapiens

<400> SEQUENCE: 809

Gly His Lys Leu Leu Cys His Leu Pro His Leu Leu Ser Ser Val
1 5 10 15

<210> SEQ ID NO 810
<211> LENGTH: 16
<212> TYPE: PRT
<213> ORGANISM: Homo sapiens

<400> SEQUENCE: 810

Pro His Leu Leu Ser Ser Val Gln Gln Thr Cys Arg Ser Ser Ser Arg
1 5 10 15

<210> SEQ ID NO 811
<211> LENGTH: 15
<212> TYPE: PRT
<213> ORGANISM: Homo sapiens

<400> SEQUENCE: 811

Glu Asn Ala Ser Leu Val Phe Thr Gly Ser Asn Ser Pro Ile Pro
1 5 10 15

<210> SEQ ID NO 812
<211> LENGTH: 15
<212> TYPE: PRT
<213> ORGANISM: Homo sapiens

<400> SEQUENCE: 812

Gly Ser Asn Ser Pro Ile Pro Ala Cys Glu Leu Ser Ser His Pro
1 5 10 15

<210> SEQ ID NO 813
<211> LENGTH: 15
<212> TYPE: PRT
<213> ORGANISM: Homo sapiens

<400> SEQUENCE: 813

Cys Glu Leu Ser Ser His Pro Ala His Gly Ile Ser Pro Trp Ile
1 5 10 15

<210> SEQ ID NO 814
<211> LENGTH: 15
<212> TYPE: PRT
<213> ORGANISM: Homo sapiens

<400> SEQUENCE: 814

His Gly Ile Ser Pro Trp Ile Pro Ser Pro Gly Asn Glu His Phe
1 5 10 15

<210> SEQ ID NO 815
<211> LENGTH: 15
<212> TYPE: PRT
<213> ORGANISM: Homo sapiens

<400> SEQUENCE: 815

Ser Pro Gly Asn Glu His Phe His Gly Ile Lys Lys Gln Val Lys
1 5 10 15

<210> SEQ ID NO 816
<211> LENGTH: 12
<212> TYPE: PRT
<213> ORGANISM: Homo sapiens

<400> SEQUENCE: 816

Gly Ile Lys Lys Gln Val Lys Ala Ile Lys Val Glu
1 5 10

<210> SEQ ID NO 817
<211> LENGTH: 15
<212> TYPE: PRT
<213> ORGANISM: Homo sapiens

<400> SEQUENCE: 817

Arg Leu Thr Gln Arg Leu Val Gln Gly Trp Thr Pro Met Glu Asn
1 5 10 15

<210> SEQ ID NO 818
<211> LENGTH: 15
<212> TYPE: PRT
<213> ORGANISM: Homo sapiens

<400> SEQUENCE: 818

Gly Trp Thr Pro Met Glu Asn Arg Trp Cys Gly Arg Arg Ala Gly
1 5 10 15

<210> SEQ ID NO 819
<211> LENGTH: 15
<212> TYPE: PRT
<213> ORGANISM: Homo sapiens

<400> SEQUENCE: 819

Trp Cys Gly Arg Arg Ala Gly Gly Gln Pro Ala Ser Ser Ser Thr
1 5 10 15

<210> SEQ ID NO 820
<211> LENGTH: 15
<212> TYPE: PRT
<213> ORGANISM: Homo sapiens

<400> SEQUENCE: 820

Gln Pro Ala Ser Ser Ser Thr Arg Trp Thr Thr Cys Arg Ala Ala
1 5 10 15

<210> SEQ ID NO 821
<211> LENGTH: 15
<212> TYPE: PRT
<213> ORGANISM: Homo sapiens

<400> SEQUENCE: 821

Trp Thr Thr Cys Arg Ala Ala Cys Leu Leu Thr Lys Trp Thr Ala
1 5 10 15

<210> SEQ ID NO 822
<211> LENGTH: 15
<212> TYPE: PRT
<213> ORGANISM: Homo sapiens

<400> SEQUENCE: 822

Leu Leu Thr Lys Trp Thr Ala Gly Arg Ser Gln Thr Ser Ile Gly
1 5 10 15

<210> SEQ ID NO 823
<211> LENGTH: 15
<212> TYPE: PRT
<213> ORGANISM: Homo sapiens

<400> SEQUENCE: 823

Glu Asn Ser Gly Asn Ala Ser Arg Trp Leu His Val Pro Ser Ser
1 5 10 15

<210> SEQ ID NO 824
<211> LENGTH: 15
<212> TYPE: PRT
<213> ORGANISM: Homo sapiens

<400> SEQUENCE: 824

Trp Leu His Val Pro Ser Ser Ser Asp Asp Trp Leu Gly Trp Lys
1 5 10 15

<210> SEQ ID NO 825
<211> LENGTH: 16
<212> TYPE: PRT
<213> ORGANISM: Homo sapiens

<400> SEQUENCE: 825

Asp Asp Trp Leu Gly Trp Lys Lys Ser Ser Ala Ile Thr Ser Asn Ser
1 5 10 15

<210> SEQ ID NO 826
<211> LENGTH: 15
<212> TYPE: PRT
<213> ORGANISM: Homo sapiens

<400> SEQUENCE: 826

Lys Gly Ser Val Glu Arg Arg Ser Val Ser Leu Gly His Pro Ala
1 5 10 15

<210> SEQ ID NO 827
<211> LENGTH: 15
<212> TYPE: PRT
<213> ORGANISM: Homo sapiens

<400> SEQUENCE: 827

Val Ser Leu Gly His Pro Ala Glu Gly Trp Ala Trp Ala Glu Arg
1 5 10 15

<210> SEQ ID NO 828
<211> LENGTH: 15
<212> TYPE: PRT
<213> ORGANISM: Homo sapiens

<400> SEQUENCE: 828

Gly Trp Ala Trp Ala Glu Arg Ser Leu Gln Pro Gly Met Thr Thr
1 5 10 15

<210> SEQ ID NO 829
<211> LENGTH: 15
<212> TYPE: PRT
<213> ORGANISM: Homo sapiens

<400> SEQUENCE: 829

Leu Gln Pro Gly Met Thr Thr Ala Asn Thr Gly Cys Leu Ser Phe
1 5 10 15

<210> SEQ ID NO 830
<211> LENGTH: 15
<212> TYPE: PRT
<213> ORGANISM: Homo sapiens

<400> SEQUENCE: 830

Asn Thr Gly Cys Leu Ser Phe His His Arg Gly Cys Leu Leu Pro 1 5 10 15

<210> SEQ ID NO 831
<211> LENGTH: 15
<212> TYPE: PRT
<213> ORGANISM: Homo sapiens

<400> SEQUENCE: 831

His Arg Gly Cys Leu Leu Pro Val Leu Pro Lys Leu His Cys Gly
1 5 10 15

<210> SEQ ID NO 832
<211> LENGTH: 15
<212> TYPE: PRT
<213> ORGANISM: Homo sapiens

<400> SEQUENCE: 832

Leu Pro Lys Leu His Cys Gly Leu Gly Gly Leu Pro Leu Val Arg
1 5 10 15

<210> SEQ ID NO 833
<211> LENGTH: 15
<212> TYPE: PRT
<213> ORGANISM: Homo sapiens

<400> SEQUENCE: 833

Gly Gly Leu Pro Leu Val Arg Ala Lys Glu Ile Lys Arg Val Gln
1 5 10 15

<210> SEQ ID NO 834
<211> LENGTH: 15
<212> TYPE: PRT
<213> ORGANISM: Homo sapiens

<400> SEQUENCE: 834

Lys Glu Ile Lys Arg Val Gln Arg Ala Gly Glu Ser Ser Leu Pro
1 5 10 15

<210> SEQ ID NO 835
<211> LENGTH: 15
<212> TYPE: PRT
<213> ORGANISM: Homo sapiens

<400> SEQUENCE: 835

Ala Gly Glu Ser Ser Leu Pro Val Lys Gly Leu Leu Thr Val Ala
1 5 10 15

<210> SEQ ID NO 836
<211> LENGTH: 15
<212> TYPE: PRT
<213> ORGANISM: Homo sapiens

<400> SEQUENCE: 836

Lys Gly Leu Leu Thr Val Ala Ser Ala Val Ile Ala Val Leu Trp
1 5 10 15

<210> SEQ ID NO 837
<211> LENGTH: 15
<212> TYPE: PRT
<213> ORGANISM: Homo sapiens

<400> SEQUENCE: 837

Ala Val Ile Ala Val Leu Trp Gly Arg Pro Ser Glu Val Thr Gly
1 5 10 15

<210> SEQ ID NO 838
<211> LENGTH: 14
<212> TYPE: PRT
<213> ORGANISM: Homo sapiens

<400> SEQUENCE: 838

Arg Pro Ser Glu Val Thr Gly Glu Asn Glu Ala Gln His Asp
1 5 10

<210> SEQ ID NO 839
<211> LENGTH: 15
<212> TYPE: PRT
<213> ORGANISM: Homo sapiens

<400> SEQUENCE: 839

Phe Gly Leu Thr Thr Leu Ala Gly Arg Ser Ser His Gly Thr Ser
1 5 10 15

<210> SEQ ID NO 840
<211> LENGTH: 15
<212> TYPE: PRT
<213> ORGANISM: Homo sapiens

<400> SEQUENCE: 840

Arg Ser Ser His Gly Thr Ser Gly Leu Arg Ala Ala Thr His Thr
1 5 10 15

<210> SEQ ID NO 841
<211> LENGTH: 15
<212> TYPE: PRT
<213> ORGANISM: Homo sapiens

<400> SEQUENCE: 841

Leu Arg Ala Ala Thr His Thr Lys Ser Gly Asp Gly Gly Gln Gly
1 5 10 15

<210> SEQ ID NO 842
<211> LENGTH: 15
<212> TYPE: PRT
<213> ORGANISM: Homo sapiens

<400> SEQUENCE: 842

Ser Gly Asp Gly Gly Gln Gly Ala Ala Arg Gln Cys Glu Lys Leu
1 5 10 15

<210> SEQ ID NO 843
<211> LENGTH: 15
<212> TYPE: PRT
<213> ORGANISM: Homo sapiens

<400> SEQUENCE: 843

Ala Arg Gln Cys Glu Lys Leu Leu Glu Leu Ala Arg Ala Thr Arg
1 5 10 15

<210> SEQ ID NO 844
<211> LENGTH: 15
<212> TYPE: PRT
<213> ORGANISM: Homo sapiens

<400> SEQUENCE: 844

Glu Leu Ala Arg Ala Thr Arg Pro Trp Gly Arg Ser Thr Ser Ala
1 5 10 15

<210> SEQ ID NO 845

<211> LENGTH: 15
<212> TYPE: PRT
<213> ORGANISM: Homo sapiens

<400> SEQUENCE: 845

Trp Gly Arg Ser Thr Ser Ala Ser Ser Arg Trp Thr His Arg Gly
1 5 10 15

<210> SEQ ID NO 846
<211> LENGTH: 15
<212> TYPE: PRT
<213> ORGANISM: Homo sapiens

<400> SEQUENCE: 846

Ser Arg Trp Thr His Arg Gly Tyr Met Cys Pro Pro Arg Cys Ala
1 5 10 15

<210> SEQ ID NO 847
<211> LENGTH: 11
<212> TYPE: PRT
<213> ORGANISM: Homo sapiens

<400> SEQUENCE: 847

Met Cys Pro Pro Arg Cys Ala Val Ala Cys Trp
1 5 10

<210> SEQ ID NO 848
<211> LENGTH: 15
<212> TYPE: PRT
<213> ORGANISM: Homo sapiens

<400> SEQUENCE: 848

Ile Ile Asp Ser Asp Lys Ile Met Ala Val Cys Met Gly Cys Leu
1 5 10 15

<210> SEQ ID NO 849
<211> LENGTH: 15
<212> TYPE: PRT
<213> ORGANISM: Homo sapiens

<400> SEQUENCE: 849

Asp Lys Ile Met Ala Val Cys Met Gly Cys Leu Leu Thr Arg His
1 5 10 15

<210> SEQ ID NO 850
<211> LENGTH: 15
<212> TYPE: PRT
<213> ORGANISM: Homo sapiens

<400> SEQUENCE: 850

Ala Val Cys Met Gly Cys Leu Leu Thr Arg His Val Gln Cys Gln
1 5 10 15

<210> SEQ ID NO 851
<211> LENGTH: 15
<212> TYPE: PRT
<213> ORGANISM: Homo sapiens

<400> SEQUENCE: 851

Gly Cys Leu Leu Thr Arg His Val Gln Cys Gln Ala Met Glu Met
1 5 10 15

<210> SEQ ID NO 852
<211> LENGTH: 13
<212> TYPE: PRT

<213> ORGANISM: Homo sapiens

<400> SEQUENCE: 852

Thr Arg His Val Gln Cys Gln Ala Met Glu Met Gln Gln
1 5 10

<210> SEQ ID NO 853
<211> LENGTH: 16
<212> TYPE: PRT
<213> ORGANISM: Homo sapiens

<400> SEQUENCE: 853

Leu Ser Ile Phe Leu Phe Leu Met Leu Cys Lys Leu Glu Phe His Ala
1 5 10 15

<210> SEQ ID NO 854
<211> LENGTH: 15
<212> TYPE: PRT
<213> ORGANISM: Homo sapiens

<400> SEQUENCE: 854

Leu Leu Asn Ala Glu Asp Tyr Arg Cys Ala Ile His Ser Lys Glu
1 5 10 15

<210> SEQ ID NO 855
<211> LENGTH: 15
<212> TYPE: PRT
<213> ORGANISM: Homo sapiens

<400> SEQUENCE: 855

Cys Ala Ile His Ser Lys Glu Ile Tyr Leu Leu Ser Pro Ser Pro
1 5 10 15

<210> SEQ ID NO 856
<211> LENGTH: 15
<212> TYPE: PRT
<213> ORGANISM: Homo sapiens

<400> SEQUENCE: 856

Tyr Leu Leu Ser Pro Ser Pro His Gln Ala Met Asp Lys Phe Ser
1 5 10 15

<210> SEQ ID NO 857
<211> LENGTH: 15
<212> TYPE: PRT
<213> ORGANISM: Homo sapiens

<400> SEQUENCE: 857

Gln Ala Met Asp Lys Phe Ser Leu Cys Cys Ile Asn Cys Asn Leu
1 5 10 15

<210> SEQ ID NO 858
<211> LENGTH: 15
<212> TYPE: PRT
<213> ORGANISM: Homo sapiens

<400> SEQUENCE: 858

Cys Cys Ile Asn Cys Asn Leu Cys Leu His Val Phe Leu Leu Leu
1 5 10 15

<210> SEQ ID NO 859
<211> LENGTH: 15
<212> TYPE: PRT
<213> ORGANISM: Homo sapiens

<400> SEQUENCE: 859

Leu His Val Phe Leu Leu Leu Leu Phe Phe Gln Asn Lys Asp Val
1 5 10 15

<210> SEQ ID NO 860
<211> LENGTH: 15
<212> TYPE: PRT
<213> ORGANISM: Homo sapiens

<400> SEQUENCE: 860

Phe Phe Gln Asn Lys Asp Val Trp Leu Ile Ser Asn Ile Ile Leu
1 5 10 15

<210> SEQ ID NO 861
<211> LENGTH: 14
<212> TYPE: PRT
<213> ORGANISM: Homo sapiens

<400> SEQUENCE: 861

Leu Ile Ser Asn Ile Ile Leu Leu Trp Ile Tyr Gly Gly Ile
1 5 10

<210> SEQ ID NO 862
<211> LENGTH: 15
<212> TYPE: PRT
<213> ORGANISM: Homo sapiens

<400> SEQUENCE: 862

Val Glu Thr Leu Glu Asn Ala Asn Ser Phe Ser Ser Gly Ile Gln
1 5 10 15

<210> SEQ ID NO 863
<211> LENGTH: 15
<212> TYPE: PRT
<213> ORGANISM: Homo sapiens

<400> SEQUENCE: 863

Ser Phe Ser Ser Gly Ile Gln Pro Leu Leu Cys Ser Leu Ile Gly
1 5 10 15

<210> SEQ ID NO 864
<211> LENGTH: 12
<212> TYPE: PRT
<213> ORGANISM: Homo sapiens

<400> SEQUENCE: 864

Leu Leu Cys Ser Leu Ile Gly Leu Glu Asn Pro Thr
1 5 10

<210> SEQ ID NO 865
<211> LENGTH: 15
<212> TYPE: PRT
<213> ORGANISM: Homo sapiens

<400> SEQUENCE: 865

Ala Gly Ala Gly Thr Ile Ser Glu Gly Ser Val Leu His Gly Gln
1 5 10 15

<210> SEQ ID NO 866
<211> LENGTH: 15
<212> TYPE: PRT
<213> ORGANISM: Homo sapiens

<400> SEQUENCE: 866

Gly Ser Val Leu His Gly Gln Arg Leu Glu Cys Asp Ala Arg Arg
1 5 10 15

<210> SEQ ID NO 867
<211> LENGTH: 15
<212> TYPE: PRT
<213> ORGANISM: Homo sapiens

<400> SEQUENCE: 867

Leu Glu Cys Asp Ala Arg Arg Phe Phe Gly Cys Gly Thr Thr Ile
1 5 10 15

<210> SEQ ID NO 868
<211> LENGTH: 14
<212> TYPE: PRT
<213> ORGANISM: Homo sapiens

<400> SEQUENCE: 868

Phe Gly Cys Gly Thr Thr Ile Leu Ala Glu Trp Glu His His
1 5 10

<210> SEQ ID NO 869
<211> LENGTH: 15
<212> TYPE: PRT
<213> ORGANISM: Homo sapiens

<400> SEQUENCE: 869

Lys Glu Gln Ile Leu Ala Val Ala Ser Leu Val Ser Ser Gln Ser
1 5 10 15

<210> SEQ ID NO 870
<211> LENGTH: 15
<212> TYPE: PRT
<213> ORGANISM: Homo sapiens

<400> SEQUENCE: 870

Ser Leu Val Ser Ser Gln Ser Ile His Pro Ser Trp Gly Gln Ser
1 5 10 15

<210> SEQ ID NO 871
<211> LENGTH: 12
<212> TYPE: PRT
<213> ORGANISM: Homo sapiens

<400> SEQUENCE: 871

His Pro Ser Trp Gly Gln Ser Pro Leu Ser Arg Ile
1 5 10

<210> SEQ ID NO 872
<211> LENGTH: 15
<212> TYPE: PRT
<213> ORGANISM: Homo sapiens

<400> SEQUENCE: 872

Gln Gln Leu Arg Ile Phe Cys Ala Ala Met Ala Ser Asn Glu Asp
1 5 10 15

<210> SEQ ID NO 873
<211> LENGTH: 9
<212> TYPE: PRT
<213> ORGANISM: Homo sapiens

<400> SEQUENCE: 873

Ala Met Ala Ser Asn Glu Asp Phe Ser
1 5

<210> SEQ ID NO 874
<211> LENGTH: 15
<212> TYPE: PRT
<213> ORGANISM: Homo sapiens

<400> SEQUENCE: 874

Asp Gly Phe Ser Gly Ser Leu Phe Ala Val Val Thr Arg Arg Cys
1 5 10 15

<210> SEQ ID NO 875
<211> LENGTH: 15
<212> TYPE: PRT
<213> ORGANISM: Homo sapiens

<400> SEQUENCE: 875

Ala Val Val Thr Arg Arg Cys Tyr Phe Leu Lys Trp Arg Thr Ile
1 5 10 15

<210> SEQ ID NO 876
<211> LENGTH: 15
<212> TYPE: PRT
<213> ORGANISM: Homo sapiens

<400> SEQUENCE: 876

Phe Leu Lys Trp Arg Thr Ile Phe Pro Gln Ser Leu Met Trp Leu
1 5 10 15

<210> SEQ ID NO 877
<211> LENGTH: 15
<212> TYPE: PRT
<213> ORGANISM: Homo sapiens

<400> SEQUENCE: 877

Asp Leu Arg Arg Val Ala Thr Tyr Cys Ala Pro Leu Pro Ser Ser
1 5 10 15

<210> SEQ ID NO 878
<211> LENGTH: 15
<212> TYPE: PRT
<213> ORGANISM: Homo sapiens

<400> SEQUENCE: 878

Cys Ala Pro Leu Pro Ser Ser Trp Arg Pro Gly Thr Gly Thr Thr
1 5 10 15

<210> SEQ ID NO 879
<211> LENGTH: 15
<212> TYPE: PRT
<213> ORGANISM: Homo sapiens

<400> SEQUENCE: 879

Arg Pro Gly Thr Gly Thr Thr Ile Pro Pro Arg Met Arg Ser Cys
1 5 10 15

<210> SEQ ID NO 880
<211> LENGTH: 15
<212> TYPE: PRT
<213> ORGANISM: Homo sapiens

<400> SEQUENCE: 880

Leu Gln Glu Arg Met Glu Leu Leu Ala Cys Gly Ala Glu Arg Gly
1 5 10 15

<210> SEQ ID NO 881
<211> LENGTH: 15
<212> TYPE: PRT
<213> ORGANISM: Homo sapiens

<400> SEQUENCE: 881

Ala Cys Gly Ala Glu Arg Gly Ala Gly Gly Trp Gly Gly Gly Gly
1 5 10 15

<210> SEQ ID NO 882
<211> LENGTH: 15
<212> TYPE: PRT
<213> ORGANISM: Homo sapiens

<400> SEQUENCE: 882

Gly Gly Trp Gly Gly Gly Gly Gly Gly Gly Gly Gly Asp Arg Arg
1 5 10 15

<210> SEQ ID NO 883
<211> LENGTH: 15
<212> TYPE: PRT
<213> ORGANISM: Homo sapiens

<400> SEQUENCE: 883

Gly Gly Gly Gly Asp Arg Arg Gly Gly Gly Gly Ser Ala Pro Ala
1 5 10 15

<210> SEQ ID NO 884
<211> LENGTH: 16
<212> TYPE: PRT
<213> ORGANISM: Homo sapiens

<400> SEQUENCE: 884

Gly Gly Gly Ser Ala Pro Ala Leu Ala Asp Phe Ala Gly Gly Arg Gly
1 5 10 15

<210> SEQ ID NO 885
<211> LENGTH: 15
<212> TYPE: PRT
<213> ORGANISM: Homo sapiens

<400> SEQUENCE: 885

Trp Thr Asp Ile Val Lys Gln Ser Val Ser Thr Asn Cys Ile Ser
1 5 10 15

<210> SEQ ID NO 886
<211> LENGTH: 15
<212> TYPE: PRT
<213> ORGANISM: Homo sapiens

<400> SEQUENCE: 886

Val Ser Thr Asn Cys Ile Ser Ile Lys Lys Gly Ser Tyr Thr Lys
1 5 10 15

<210> SEQ ID NO 887
<211> LENGTH: 15
<212> TYPE: PRT
<213> ORGANISM: Homo sapiens

<400> SEQUENCE: 887

Lys Lys Gly Ser Tyr Thr Lys Leu Phe Ser Leu Val Phe Leu Ile
1 5 10 15

<210> SEQ ID NO 888
<211> LENGTH: 16

<212> TYPE: PRT
<213> ORGANISM: Homo sapiens

<400> SEQUENCE: 888

Phe Ser Leu Val Phe Leu Ile Phe Cys Trp Pro Leu Ile Ile Gln Leu
1 5 10 15

<210> SEQ ID NO 889
<211> LENGTH: 15
<212> TYPE: PRT
<213> ORGANISM: Homo sapiens

<400> SEQUENCE: 889

Leu Arg Tyr Gly Ala Leu Cys Asn Val Ser Arg Ile Ser Tyr Phe
1 5 10 15

<210> SEQ ID NO 890
<211> LENGTH: 15
<212> TYPE: PRT
<213> ORGANISM: Homo sapiens

<400> SEQUENCE: 890

Val Ser Arg Ile Ser Tyr Phe Ser Leu Thr Asn Ile Phe Asn Phe
1 5 10 15

<210> SEQ ID NO 891
<211> LENGTH: 15
<212> TYPE: PRT
<213> ORGANISM: Homo sapiens

<400> SEQUENCE: 891

Leu Thr Asn Ile Phe Asn Phe Val Ile Lys Ser Leu Thr Ala Ile
1 5 10 15

<210> SEQ ID NO 892
<211> LENGTH: 15
<212> TYPE: PRT
<213> ORGANISM: Homo sapiens

<400> SEQUENCE: 892

Arg Lys Glu Arg Asn Ile Arg Lys Ser Glu Ser Thr Leu Arg Leu
1 5 10 15

<210> SEQ ID NO 893
<211> LENGTH: 15
<212> TYPE: PRT
<213> ORGANISM: Homo sapiens

<400> SEQUENCE: 893

Ser Glu Ser Thr Leu Arg Leu Ser Pro Phe Pro Thr Pro Ala Pro
1 5 10 15

<210> SEQ ID NO 894
<211> LENGTH: 15
<212> TYPE: PRT
<213> ORGANISM: Homo sapiens

<400> SEQUENCE: 894

Pro Phe Pro Thr Pro Ala Pro Ser Gly Ala Pro Ala Ala Ala Gln
1 5 10 15

<210> SEQ ID NO 895
<211> LENGTH: 15
<212> TYPE: PRT
<213> ORGANISM: Homo sapiens

<400> SEQUENCE: 895

Gly Ala Pro Ala Ala Ala Gln Gly Lys Val Val Arg Val Pro Gly
1 5 10 15

<210> SEQ ID NO 896
<211> LENGTH: 15
<212> TYPE: PRT
<213> ORGANISM: Homo sapiens

<400> SEQUENCE: 896

Lys Val Val Arg Val Pro Gly Pro Ala Gly Gly Leu Val Pro Arg
1 5 10 15

<210> SEQ ID NO 897
<211> LENGTH: 15
<212> TYPE: PRT
<213> ORGANISM: Homo sapiens

<400> SEQUENCE: 897

Ala Gly Gly Leu Val Pro Arg Asp Ala Gly Ala Arg Leu Leu Pro
1 5 10 15

<210> SEQ ID NO 898
<211> LENGTH: 15
<212> TYPE: PRT
<213> ORGANISM: Homo sapiens

<400> SEQUENCE: 898

Ala Gly Ala Arg Leu Leu Pro Pro Ala Gly Gly Pro Gly Gly Gly
1 5 10 15

<210> SEQ ID NO 899
<211> LENGTH: 15
<212> TYPE: PRT
<213> ORGANISM: Homo sapiens

<400> SEQUENCE: 899

Ala Gly Gly Pro Gly Gly Gly Ala Ala Ala Gly Glu Gly Arg Ala
1 5 10 15

<210> SEQ ID NO 900
<211> LENGTH: 15
<212> TYPE: PRT
<213> ORGANISM: Homo sapiens

<400> SEQUENCE: 900

Ala Ala Gly Glu Gly Arg Ala Gly Arg Gly Arg Phe Pro Ser Ile
1 5 10 15

<210> SEQ ID NO 901
<211> LENGTH: 15
<212> TYPE: PRT
<213> ORGANISM: Homo sapiens

<400> SEQUENCE: 901

Arg Gly Arg Phe Pro Ser Ile Thr Glu Pro Arg Pro Arg Asp Leu
1 5 10 15

<210> SEQ ID NO 902
<211> LENGTH: 15
<212> TYPE: PRT
<213> ORGANISM: Homo sapiens

<400> SEQUENCE: 902

```
Glu Pro Arg Pro Arg Asp Leu Pro Pro Arg Val Ala Thr Gly Arg
1               5                   10                  15


<210> SEQ ID NO 903
<211> LENGTH: 15
<212> TYPE: PRT
<213> ORGANISM: Homo sapiens

<400> SEQUENCE: 903

Pro Arg Val Ala Thr Gly Arg Arg Ala Gly Gly Arg Arg Lys Gly
1               5                   10                  15


<210> SEQ ID NO 904
<211> LENGTH: 15
<212> TYPE: PRT
<213> ORGANISM: Homo sapiens

<400> SEQUENCE: 904

Ala Gly Gly Arg Arg Lys Gly Ala Gly Gln Gly Val Arg Thr Arg
1               5                   10                  15


<210> SEQ ID NO 905
<211> LENGTH: 15
<212> TYPE: PRT
<213> ORGANISM: Homo sapiens

<400> SEQUENCE: 905

Gly Gln Gly Val Arg Thr Arg Pro Leu Pro Ala Ser Trp Pro Gly
1               5                   10                  15


<210> SEQ ID NO 906
<211> LENGTH: 15
<212> TYPE: PRT
<213> ORGANISM: Homo sapiens

<400> SEQUENCE: 906

Leu Pro Ala Ser Trp Pro Gly Gly Arg Gly Pro Phe Arg Lys Gly
1               5                   10                  15


<210> SEQ ID NO 907
<211> LENGTH: 15
<212> TYPE: PRT
<213> ORGANISM: Homo sapiens

<400> SEQUENCE: 907

Arg Gly Pro Phe Arg Lys Gly Pro Arg Arg Leu Pro Leu Gly Ser
1               5                   10                  15


<210> SEQ ID NO 908
<211> LENGTH: 15
<212> TYPE: PRT
<213> ORGANISM: Homo sapiens

<400> SEQUENCE: 908

Arg Arg Leu Pro Leu Gly Ser Gly Pro Pro Ala Ala Gly Val Gln
1               5                   10                  15


<210> SEQ ID NO 909
<211> LENGTH: 15
<212> TYPE: PRT
<213> ORGANISM: Homo sapiens

<400> SEQUENCE: 909

Pro Pro Ala Ala Gly Val Gln Arg Leu Arg Cys Ser His Leu Ser
```

1 5 10 15

<210> SEQ ID NO 910
<211> LENGTH: 15
<212> TYPE: PRT
<213> ORGANISM: Homo sapiens

<400> SEQUENCE: 910

Leu Arg Cys Ser His Leu Ser Arg Gly Pro Arg Arg Arg Arg Gly
1 5 10 15

<210> SEQ ID NO 911
<211> LENGTH: 15
<212> TYPE: PRT
<213> ORGANISM: Homo sapiens

<400> SEQUENCE: 911

Gly Pro Arg Arg Arg Arg Gly Arg Val Cys Gly Arg Ala Cys Val
1 5 10 15

<210> SEQ ID NO 912
<211> LENGTH: 15
<212> TYPE: PRT
<213> ORGANISM: Homo sapiens

<400> SEQUENCE: 912

Val Cys Gly Arg Ala Cys Val Ser Pro Pro Leu Pro Pro Arg Pro
1 5 10 15

<210> SEQ ID NO 913
<211> LENGTH: 15
<212> TYPE: PRT
<213> ORGANISM: Homo sapiens

<400> SEQUENCE: 913

Pro Pro Leu Pro Pro Arg Pro Pro Pro Val Gly Leu Ser Ala Glu
1 5 10 15

<210> SEQ ID NO 914
<211> LENGTH: 15
<212> TYPE: PRT
<213> ORGANISM: Homo sapiens

<400> SEQUENCE: 914

Pro Val Gly Leu Ser Ala Glu Asn Leu Ser Trp Leu Ser Ser Gly
1 5 10 15

<210> SEQ ID NO 915
<211> LENGTH: 15
<212> TYPE: PRT
<213> ORGANISM: Homo sapiens

<400> SEQUENCE: 915

Leu Ser Trp Leu Ser Ser Gly Leu Pro Arg Ala Cys Ser Trp Arg
1 5 10 15

<210> SEQ ID NO 916
<211> LENGTH: 15
<212> TYPE: PRT
<213> ORGANISM: Homo sapiens

<400> SEQUENCE: 916

Pro Arg Ala Cys Ser Trp Arg Glu Phe Ser Pro Glu Thr Cys Ala
1 5 10 15

<210> SEQ ID NO 917
<211> LENGTH: 15
<212> TYPE: PRT
<213> ORGANISM: Homo sapiens

<400> SEQUENCE: 917

Phe Ser Pro Glu Thr Cys Ala Phe Arg Leu Ser Gly Leu Asp Ser
1 5 10 15

<210> SEQ ID NO 918
<211> LENGTH: 15
<212> TYPE: PRT
<213> ORGANISM: Homo sapiens

<400> SEQUENCE: 918

Arg Leu Ser Gly Leu Asp Ser Lys Leu Ser Ala Arg Val Glu Arg
1 5 10 15

<210> SEQ ID NO 919
<211> LENGTH: 15
<212> TYPE: PRT
<213> ORGANISM: Homo sapiens

<400> SEQUENCE: 919

Leu Ser Ala Arg Val Glu Arg Asp Leu Gly Ala Leu Arg Ala Pro
1 5 10 15

<210> SEQ ID NO 920
<211> LENGTH: 15
<212> TYPE: PRT
<213> ORGANISM: Homo sapiens

<400> SEQUENCE: 920

Leu Gly Ala Leu Arg Ala Pro Gly Ser Arg Ala Ala Gln Gly Gly
1 5 10 15

<210> SEQ ID NO 921
<211> LENGTH: 15
<212> TYPE: PRT
<213> ORGANISM: Homo sapiens

<400> SEQUENCE: 921

Ser Arg Ala Ala Gln Gly Gly Gly Arg Val Arg Gly Ser Arg Ser
1 5 10 15

<210> SEQ ID NO 922
<211> LENGTH: 15
<212> TYPE: PRT
<213> ORGANISM: Homo sapiens

<400> SEQUENCE: 922

Arg Val Arg Gly Ser Arg Ser Glu Trp Lys Thr Arg Pro Trp Arg
1 5 10 15

<210> SEQ ID NO 923
<211> LENGTH: 15
<212> TYPE: PRT
<213> ORGANISM: Homo sapiens

<400> SEQUENCE: 923

Trp Lys Thr Arg Pro Trp Arg Pro Pro Pro Ala Trp Pro Leu Thr
1 5 10 15

<210> SEQ ID NO 924

<211> LENGTH: 15
<212> TYPE: PRT
<213> ORGANISM: Homo sapiens

<400> SEQUENCE: 924

Pro Pro Ala Trp Pro Leu Thr Arg Ala Gly Gly Pro Leu Pro Lys
1 5 10 15

<210> SEQ ID NO 925
<211> LENGTH: 15
<212> TYPE: PRT
<213> ORGANISM: Homo sapiens

<400> SEQUENCE: 925

Ala Gly Gly Pro Leu Pro Lys Asn Pro Phe Leu Glu Ser Cys Ser
1 5 10 15

<210> SEQ ID NO 926
<211> LENGTH: 15
<212> TYPE: PRT
<213> ORGANISM: Homo sapiens

<400> SEQUENCE: 926

Pro Phe Leu Glu Ser Cys Ser Glu Thr Ala Gln Arg Arg Arg Val
1 5 10 15

<210> SEQ ID NO 927
<211> LENGTH: 15
<212> TYPE: PRT
<213> ORGANISM: Homo sapiens

<400> SEQUENCE: 927

Thr Ala Gln Arg Arg Arg Val Phe Ser Phe Ser Thr Pro Leu Ser
1 5 10 15

<210> SEQ ID NO 928
<211> LENGTH: 15
<212> TYPE: PRT
<213> ORGANISM: Homo sapiens

<400> SEQUENCE: 928

Ser Ile Asn Lys Ala Thr Ile Thr Gly Lys Lys Asp Leu Glu Leu
1 5 10 15

<210> SEQ ID NO 929
<211> LENGTH: 15
<212> TYPE: PRT
<213> ORGANISM: Homo sapiens

<400> SEQUENCE: 929

Gly Lys Lys Asp Leu Glu Leu Ile Leu His Val Ser Arg Lys Lys
1 5 10 15

<210> SEQ ID NO 930
<211> LENGTH: 15
<212> TYPE: PRT
<213> ORGANISM: Homo sapiens

<400> SEQUENCE: 930

Leu His Val Ser Arg Lys Lys Pro Phe Leu Pro Arg Val Asn Ile
1 5 10 15

<210> SEQ ID NO 931
<211> LENGTH: 15
<212> TYPE: PRT

<213> ORGANISM: Homo sapiens

<400> SEQUENCE: 931

Phe Leu Pro Arg Val Asn Ile Thr Pro Thr Pro Ile Ser Cys Cys
1 5 10 15

<210> SEQ ID NO 932
<211> LENGTH: 15
<212> TYPE: PRT
<213> ORGANISM: Homo sapiens

<400> SEQUENCE: 932

Pro Thr Pro Ile Ser Cys Cys Asn Leu Lys Met Leu Lys Lys Phe
1 5 10 15

<210> SEQ ID NO 933
<211> LENGTH: 15
<212> TYPE: PRT
<213> ORGANISM: Homo sapiens

<400> SEQUENCE: 933

Leu Lys Met Leu Lys Lys Phe Phe Leu Leu Tyr Ile Ile Ile Ser
1 5 10 15

<210> SEQ ID NO 934
<211> LENGTH: 15
<212> TYPE: PRT
<213> ORGANISM: Homo sapiens

<400> SEQUENCE: 934

Leu Leu Tyr Ile Ile Ile Ser Ile Ile Asp Leu Thr Asn Cys Leu
1 5 10 15

<210> SEQ ID NO 935
<211> LENGTH: 15
<212> TYPE: PRT
<213> ORGANISM: Homo sapiens

<400> SEQUENCE: 935

Ile Asp Leu Thr Asn Cys Leu Ser Cys Tyr Leu Glu His Phe Tyr
1 5 10 15

<210> SEQ ID NO 936
<211> LENGTH: 15
<212> TYPE: PRT
<213> ORGANISM: Homo sapiens

<400> SEQUENCE: 936

Cys Tyr Leu Glu His Phe Tyr Arg Phe Thr Phe Phe Thr Asp Val
1 5 10 15

<210> SEQ ID NO 937
<211> LENGTH: 10
<212> TYPE: PRT
<213> ORGANISM: Homo sapiens

<400> SEQUENCE: 937

Phe Thr Phe Phe Thr Asp Val His Tyr Phe
1 5 10

<210> SEQ ID NO 938
<211> LENGTH: 15
<212> TYPE: PRT
<213> ORGANISM: Homo sapiens

<400> SEQUENCE: 938

Pro Tyr Tyr Ser Ala Leu Ser Gly Asn Ser Trp Val Pro Ser Thr
1 5 10 15

<210> SEQ ID NO 939
<211> LENGTH: 15
<212> TYPE: PRT
<213> ORGANISM: Homo sapiens

<400> SEQUENCE: 939

Asn Ser Trp Val Pro Ser Thr Leu Glu Ser Asp Pro Phe Gly Tyr
1 5 10 15

<210> SEQ ID NO 940
<211> LENGTH: 15
<212> TYPE: PRT
<213> ORGANISM: Homo sapiens

<400> SEQUENCE: 940

Glu Ser Asp Pro Phe Gly Tyr Val Phe Ser Pro Leu Ala Thr Arg
1 5 10 15

<210> SEQ ID NO 941
<211> LENGTH: 15
<212> TYPE: PRT
<213> ORGANISM: Homo sapiens

<400> SEQUENCE: 941

Phe Ser Pro Leu Ala Thr Arg Pro Ala Leu Asn Asp Gln Glu Ser
1 5 10 15

<210> SEQ ID NO 942
<211> LENGTH: 15
<212> TYPE: PRT
<213> ORGANISM: Homo sapiens

<400> SEQUENCE: 942

Ala Leu Asn Asp Gln Glu Ser Ile Leu Trp Pro Thr Leu Thr Ser
1 5 10 15

<210> SEQ ID NO 943
<211> LENGTH: 15
<212> TYPE: PRT
<213> ORGANISM: Homo sapiens

<400> SEQUENCE: 943

Leu Trp Pro Thr Leu Thr Ser Val Val Ser Cys Ala Leu Ser Cys
1 5 10 15

<210> SEQ ID NO 944
<211> LENGTH: 15
<212> TYPE: PRT
<213> ORGANISM: Homo sapiens

<400> SEQUENCE: 944

Val Ser Cys Ala Leu Ser Cys Pro Ser Leu Asn Leu Pro Glu Asn
1 5 10 15

<210> SEQ ID NO 945
<211> LENGTH: 15
<212> TYPE: PRT
<213> ORGANISM: Homo sapiens

<400> SEQUENCE: 945

Ser Leu Asn Leu Pro Glu Asn Trp Leu Thr Leu Ile Thr Gly Gly
1 5 10 15

<210> SEQ ID NO 946
<211> LENGTH: 15
<212> TYPE: PRT
<213> ORGANISM: Homo sapiens

<400> SEQUENCE: 946

Leu Thr Leu Ile Thr Gly Gly Met Lys Gly Gly Lys Lys Met Lys
1 5 10 15

<210> SEQ ID NO 947
<211> LENGTH: 12
<212> TYPE: PRT
<213> ORGANISM: Homo sapiens

<400> SEQUENCE: 947

Lys Gly Gly Lys Lys Met Lys Phe Thr Phe Arg His
1 5 10

<210> SEQ ID NO 948
<211> LENGTH: 15
<212> TYPE: PRT
<213> ORGANISM: Homo sapiens

<400> SEQUENCE: 948

Gly Leu Arg Asn Leu Gly Asn Thr Val Arg Ala Ile Leu Leu Ser
1 5 10 15

<210> SEQ ID NO 949
<211> LENGTH: 15
<212> TYPE: PRT
<213> ORGANISM: Homo sapiens

<400> SEQUENCE: 949

Val Arg Ala Ile Leu Leu Ser Phe Leu Ser Lys Arg Asn Val Lys
1 5 10 15

<210> SEQ ID NO 950
<211> LENGTH: 15
<212> TYPE: PRT
<213> ORGANISM: Homo sapiens

<400> SEQUENCE: 950

Leu Ser Lys Arg Asn Val Lys Trp Cys Trp Gly Trp Gly Lys Pro
1 5 10 15

<210> SEQ ID NO 951
<211> LENGTH: 15
<212> TYPE: PRT
<213> ORGANISM: Homo sapiens

<400> SEQUENCE: 951

Cys Trp Gly Trp Gly Lys Pro Thr Ser Leu Gly Lys Ala Cys Gly
1 5 10 15

<210> SEQ ID NO 952
<211> LENGTH: 14
<212> TYPE: PRT
<213> ORGANISM: Homo sapiens

<400> SEQUENCE: 952

Ser Leu Gly Lys Ala Cys Gly Arg Arg Ala Leu Lys Leu Phe
1 5 10

<210> SEQ ID NO 953
<211> LENGTH: 15
<212> TYPE: PRT
<213> ORGANISM: Homo sapiens

<400> SEQUENCE: 953

Met Glu Ala Glu Asn Ala Gly Ser Leu His Phe His Glu Val Leu
1 5 10 15

<210> SEQ ID NO 954
<211> LENGTH: 14
<212> TYPE: PRT
<213> ORGANISM: Homo sapiens

<400> SEQUENCE: 954

Leu His Phe His Glu Val Leu Lys Met Gly His Val Lys Phe
1 5 10

<210> SEQ ID NO 955
<211> LENGTH: 15
<212> TYPE: PRT
<213> ORGANISM: Homo sapiens

<400> SEQUENCE: 955

Trp Thr Pro Ile Pro Val Leu Thr Arg Trp Pro Leu Pro His Pro
1 5 10 15

<210> SEQ ID NO 956
<211> LENGTH: 15
<212> TYPE: PRT
<213> ORGANISM: Homo sapiens

<400> SEQUENCE: 956

Arg Trp Pro Leu Pro His Pro Pro Pro Trp Arg Arg Ala Thr Ser
1 5 10 15

<210> SEQ ID NO 957
<211> LENGTH: 15
<212> TYPE: PRT
<213> ORGANISM: Homo sapiens

<400> SEQUENCE: 957

Pro Trp Arg Arg Ala Thr Ser Cys Arg Met Ala Arg Ser Ser Pro
1 5 10 15

<210> SEQ ID NO 958
<211> LENGTH: 15
<212> TYPE: PRT
<213> ORGANISM: Homo sapiens

<400> SEQUENCE: 958

Arg Met Ala Arg Ser Ser Pro Ser Ala Thr Ser Gly Ser Ser Val
1 5 10 15

<210> SEQ ID NO 959
<211> LENGTH: 15
<212> TYPE: PRT
<213> ORGANISM: Homo sapiens

<400> SEQUENCE: 959

Ala Thr Ser Gly Ser Ser Val Arg Arg Arg Cys Ser Ser Leu Pro
1 5 10 15

-continued

<210> SEQ ID NO 960
<211> LENGTH: 15
<212> TYPE: PRT
<213> ORGANISM: Homo sapiens

<400> SEQUENCE: 960

Arg Arg Cys Ser Ser Leu Pro Ser Trp Val Trp Asn Leu Ala Ala
1 5 10 15

<210> SEQ ID NO 961
<211> LENGTH: 16
<212> TYPE: PRT
<213> ORGANISM: Homo sapiens

<400> SEQUENCE: 961

Trp Val Trp Asn Leu Ala Ala Ser Thr Arg Pro Arg Ser Thr Pro Ser
1 5 10 15

<210> SEQ ID NO 962
<211> LENGTH: 15
<212> TYPE: PRT
<213> ORGANISM: Homo sapiens

<400> SEQUENCE: 962

Leu His Pro Gln Arg Glu Thr Phe Thr Pro Arg Trp Ser Gly Ala
1 5 10 15

<210> SEQ ID NO 963
<211> LENGTH: 15
<212> TYPE: PRT
<213> ORGANISM: Homo sapiens

<400> SEQUENCE: 963

Thr Pro Arg Trp Ser Gly Ala Asn Tyr Trp Lys Leu Ala Phe Pro
1 5 10 15

<210> SEQ ID NO 964
<211> LENGTH: 15
<212> TYPE: PRT
<213> ORGANISM: Homo sapiens

<400> SEQUENCE: 964

Tyr Trp Lys Leu Ala Phe Pro Val Gly Ala Glu Gly Thr Phe Pro
1 5 10 15

<210> SEQ ID NO 965
<211> LENGTH: 15
<212> TYPE: PRT
<213> ORGANISM: Homo sapiens

<400> SEQUENCE: 965

Gly Ala Glu Gly Thr Phe Pro Ala Ala Ala Thr Gln Arg Gly Val
1 5 10 15

<210> SEQ ID NO 966
<211> LENGTH: 11
<212> TYPE: PRT
<213> ORGANISM: Homo sapiens

<400> SEQUENCE: 966

Ala Ala Thr Gln Arg Gly Val Val Arg Pro Ala
1 5 10

<210> SEQ ID NO 967
<211> LENGTH: 15

<212> TYPE: PRT
<213> ORGANISM: Homo sapiens

<400> SEQUENCE: 967

Met Ala Gly Gly Val Leu Arg Arg Leu Leu Cys Arg Glu Pro Asp
1 5 10 15

<210> SEQ ID NO 968
<211> LENGTH: 15
<212> TYPE: PRT
<213> ORGANISM: Homo sapiens

<400> SEQUENCE: 968

Leu Leu Cys Arg Glu Pro Asp Arg Asp Gly Asp Lys Gly Ala Ser
1 5 10 15

<210> SEQ ID NO 969
<211> LENGTH: 15
<212> TYPE: PRT
<213> ORGANISM: Homo sapiens

<400> SEQUENCE: 969

Asp Gly Asp Lys Gly Ala Ser Arg Glu Glu Thr Val Val Pro Leu
1 5 10 15

<210> SEQ ID NO 970
<211> LENGTH: 15
<212> TYPE: PRT
<213> ORGANISM: Homo sapiens

<400> SEQUENCE: 970

Glu Glu Thr Val Val Pro Leu His Ile Gly Asp Pro Val Val Leu
1 5 10 15

<210> SEQ ID NO 971
<211> LENGTH: 15
<212> TYPE: PRT
<213> ORGANISM: Homo sapiens

<400> SEQUENCE: 971

Ile Gly Asp Pro Val Val Leu Pro Gly Ile Gly Gln Cys Tyr Ser
1 5 10 15

<210> SEQ ID NO 972
<211> LENGTH: 10
<212> TYPE: PRT
<213> ORGANISM: Homo sapiens

<400> SEQUENCE: 972

Gly Ile Gly Gln Cys Tyr Ser Ala Leu Phe
1 5 10

<210> SEQ ID NO 973
<211> LENGTH: 15
<212> TYPE: PRT
<213> ORGANISM: Homo sapiens

<400> SEQUENCE: 973

Val Phe Phe Lys Arg Ala Ala Glu Gly Phe Phe Arg Met Asn Lys
1 5 10 15

<210> SEQ ID NO 974
<211> LENGTH: 15
<212> TYPE: PRT
<213> ORGANISM: Homo sapiens

<400> SEQUENCE: 974

Gly Phe Phe Arg Met Asn Lys Leu Lys Glu Ser Ser Asp Thr Asn
1 5 10 15

<210> SEQ ID NO 975
<211> LENGTH: 15
<212> TYPE: PRT
<213> ORGANISM: Homo sapiens

<400> SEQUENCE: 975

Lys Glu Ser Ser Asp Thr Asn Pro Lys Pro Tyr Cys Met Ala Ala
1 5 10 15

<210> SEQ ID NO 976
<211> LENGTH: 15
<212> TYPE: PRT
<213> ORGANISM: Homo sapiens

<400> SEQUENCE: 976

Lys Pro Tyr Cys Met Ala Ala Pro Met Gly Leu Thr Glu Asn Asn
1 5 10 15

<210> SEQ ID NO 977
<211> LENGTH: 15
<212> TYPE: PRT
<213> ORGANISM: Homo sapiens

<400> SEQUENCE: 977

Met Gly Leu Thr Glu Asn Asn Arg Asn Arg Lys Lys Ser Tyr Arg
1 5 10 15

<210> SEQ ID NO 978
<211> LENGTH: 15
<212> TYPE: PRT
<213> ORGANISM: Homo sapiens

<400> SEQUENCE: 978

Asn Arg Lys Lys Ser Tyr Arg Glu Thr Asn Leu Lys Ala Val Ser
1 5 10 15

<210> SEQ ID NO 979
<211> LENGTH: 13
<212> TYPE: PRT
<213> ORGANISM: Homo sapiens

<400> SEQUENCE: 979

Thr Asn Leu Lys Ala Val Ser Trp Pro Leu Asn His Thr
1 5 10

<210> SEQ ID NO 980
<211> LENGTH: 13
<212> TYPE: PRT
<213> ORGANISM: Homo sapiens

<400> SEQUENCE: 980

Gly Trp Arg Gly Val Cys Cys Ala Ala Val Glu Pro Ala
1 5 10

PROSTATE NEOANTIGENS AND THEIR USES

CROSS-REFERENCE TO RELATED APPLICATIONS

This application claims the benefit of U.S. Provisional Application Ser. No. 62/913,969, filed 11 Oct. 2019, U.S. Provisional Application Ser. No. 62/883,786, filed 7 Aug. 2019, U.S. Provisional Application Ser. No. 62/851,273, filed 22 May 2019, and U.S. Provisional Application Ser. No. 62/790,673, filed 10 Jan. 2019, the entire content of the aforementioned applications are incorporated herein by reference in its entirety.

SEQUENCE LISTING

This application contains a Sequence Listing submitted via EFS-Web, the entire content of which incorporated herein by reference in its entirety. The ASCII text file, created on Jun. 25 2021, is named 103693.002401_SL.txt and is 554 kilobytes in size.

BACKGROUND

Prostate cancer is the most common non-cutaneous malignancy in men and the second leading cause of death in men from cancer in the western world. Prostate cancer results from the uncontrolled growth of abnormal cells in the prostate gland. Once a prostate cancer tumor develops, androgens such as testosterone promote prostate cancer growth. At its early stages, localized prostate cancer is often curable with local therapy including, for example, surgical removal of the prostate gland and radiotherapy. However, when local therapy fails to cure prostate cancer, as it does in up to a third of men, the disease progresses into incurable metastatic disease.

For many years, the established standard of care for men with malignant castration-resistant prostate cancer (mCRPC) was docetaxel chemotherapy. More recently, abiraterone acetate (ZYTIGA®) in combination with prednisone has been approved for treating metastatic castrate resistant prostate cancer. Androgen receptor (AR)-targeted agents, such as enzalutamide (XTANDI®) have also entered the market for treating metastatic castrate resistant prostate cancer. Platinum-based chemotherapy has been tested in a number of clinical studies in molecularly unselected prostate cancer patients with limited results and significant toxicities. However, there remains a subset of patients who either do not respond initially or become refractory (or resistant) to these treatments. No approved therapeutic options are available for such patients.

Therefore, a need remains for therapies against a prostate cancer, including hormone sensitive, hormone naive high risk, and castration-resistant prostate cancers.

BRIEF SUMMARY

The disclosure provides an isolated polynucleotide encoding a polypeptide of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 or 447, or fragments thereof.

The disclosure also provides an isolated polynucleotide comprising a polynucleotide sequence of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 503, 504, 505, 506, 507, 508, 509, 510, 511, 512, 513, 514, 515, 516, 517, 519, 520, 521, 522, 523, 524, 525, 528, 529, 530, 531, 532, 533, 534, 535, 536, 537, 538, 539 or 540, or fragments thereof.

The disclosure also provides an isolated heterologous polynucleotide comprising two or more polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide encoding a heterologous polypeptide comprising two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated polypeptide comprising an amino acid sequence of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 or 447, or fragments thereof.

The disclosure also provides an isolated heterologous polypeptide comprising two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides a vector comprising a polynucleotide encoding one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 or 447, or fragments thereof;

one or more polynucleotides of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 or 458, or fragments thereof;

a heterologous polynucleotide encoding a heterologous polypeptide comprising two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof; or a heterologous polynucleotide comprising two or more polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a recombinant human adenovirus (rAd) comprising the vector of the disclosure.

The disclosure also provides a recombinant modified vaccinia Ankara (rMVA) comprising the vector of the disclosure.

The disclosure also provides a recombinant great ape adenovirus (rGAd) comprising the vector of the disclosure.

The disclosure also provides a cell comprising or transduced with the vector of the disclosure or the recombinant virus of the disclosure.

The disclosure also provides a vaccine comprising the polynucleotide of the disclosure.

The disclosure also provides a vaccine comprising the heterologous polynucleotide of the disclosure.

The disclosure also provides a vaccine comprising the polypeptide of the disclosure.

The disclosure also provides a vaccine comprising the heterologous polypeptide of the disclosure.

The disclosure also provides a vaccine comprising the vector of the disclosure.

The disclosure also provides a vaccine comprising the rAd of the disclosure.

The disclosure also provides a vaccine comprising the rMVA of the disclosure.

The disclosure also provides a vaccine comprising the rGAd of the disclosure.

The disclosure also provides a vaccine comprising the cell of the disclosure.

The disclosure also provides a pharmaceutical composition comprising the vaccine of the disclosure and a pharmaceutically acceptable carrier or adjuvant.

The disclosure also provides a kit comprising one or more vaccines of the disclosure or the pharmaceutical composition of the disclosure.

The disclosure also provides a method of preventing or treating a prostate cancer in a subject, comprising administering to the subject a therapeutically effective amount of one or more vaccines of the disclosure or one or more pharmaceutical composition of the disclosure.

The disclosure also provides a method of inducing an immune response against one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 or 447, or fragments thereof in a subject, comprising administering to the subject one or more vaccines of the disclosure.

The disclosure also provides an isolated heterologous polynucleotide encoding two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides a vector comprising:

a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;

a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24, 178, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 503, 504, 505, 506, 507, 508, 509, 510, 511, 512, 513, 514, 515, 516, 517, 519, 520, 521, 522, 523, 524, 525, 528, 529, 530, 531, 532, 533, 534, 535, 536, 537, 538, 539 and 540, and fragments thereof;

a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof;

a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof;

a heterologous polynucleotide encoding the heterologous polypeptide of SEQ ID NOs: 541, 550, 554, 555, 556, 623 or 624;

- a heterologous polynucleotide encoding the heterologous polypeptide of SEQ ID NOs: 543, 552, 557, 558, 559, 625 or 626;
- a heterologous polynucleotide comprising a polynucleotide sequence of SEQ ID NO: 542 or SEQ ID NO: 551; or
- a heterologous polynucleotide comprising the polynucleotide sequence of SEQ ID NO: 544 or SEQ ID NO: 553.

The disclosure also provides a recombinant human adenovirus (rAd), comprising: a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;

a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof;

a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499 and fragments thereof; or a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a recombinant great ape adenovirus (rGAd), comprising:

- a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;
- a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof;
- a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof; or
- a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a recombinant modified vaccinia Ankara (rMVA), comprising:

- a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;
- a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof;
- a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof; or
- a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a vaccine comprising a rAd, comprising a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;

a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof;

a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof; or a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a vaccine comprising rGAd20, comprising a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;

a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof;

a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof; or a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a vaccine comprising rMVA comprising a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;

a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof;

a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof; or a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a vaccine comprising a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides a method of treating or preventing a prostate cancer in a subject, comprising: administering to the subject a therapeutically effective amount of a vaccine comprising a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof as a prime; and administering to the subject a therapeutically effective amount of a vaccine comprising a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof as a boost; thereby treating or preventing the prostate cancer in the subject.

The disclosure also provides a vaccine comprising a heterologous polynucleotide encoding a heterologous polypeptide of SEQ ID NOs: 541, 550, 554, 555, 556, 623 or 624.

The disclosure also provides a vaccine comprising a heterologous polynucleotide encoding a heterologous polypeptide of SEQ ID NOs: 543, 552, 557, 558, 559, 625 or 626.

The disclosure also provides a method of treating or preventing a prostate cancer in a subject, comprising administering to the subject

- a first vaccine comprising a first heterologous polynucleotide encoding a first heterologous polypeptide, wherein the first heterologous polypeptide comprises two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177; and
- a second vaccine comprising a second heterologous polynucleotide encoding a second heterologous polypeptide, wherein the second heterologous polypeptide comprises two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177; wherein the first heterologous polypeptide and the second heterologous polypeptide have distinct amino acid sequences.

The disclosure also provides a method of inducing an immune response in a subject, comprising administering to the subject

- a first vaccine comprising a first heterologous polynucleotide encoding a first heterologous polypeptide, wherein the first heterologous polypeptide comprises two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177; and
- a second vaccine comprising a second heterologous polynucleotide encoding a second heterologous polypeptide, wherein the second heterologous polypeptide comprises two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177; wherein the first heterologous polypeptide and the second heterologous polypeptide have distinct amino acid sequences.

The disclosure also provides an isolated proteinaceous molecule that specifically binds the polypeptide of the disclosure.

The disclosure also provides a method of preventing or treating a prostate cancer in a subject, comprising administering to the subject the proteinaceous molecule of the disclosure.

It is to be understood, that the above embodiments of the invention encompass polypeptides comprising, in addition to the specifically recited polypeptides and fragments thereof, also additional polypeptide sequences, including one or more polypeptides different from those specifically recited. Similarly, the above embodiments of the invention also encompass polynucleotides comprising, in addition to the specifically recited polynucleotides and fragments thereof, also additional polynucleotide sequences, including one or more polynucleotides different from those specifically recited.

DETAILED DESCRIPTION

Definitions

Figure 1:
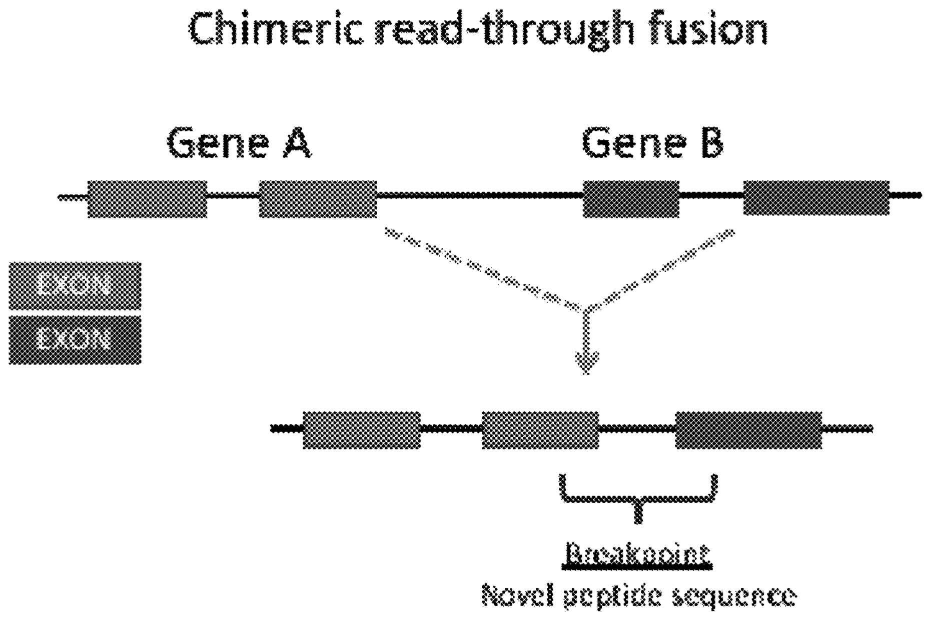
FIG. 1 shows a cartoon of chimeric read-through fusions between Gene A and Gene B. Neoantigenic peptide sequences arise at the breakpoint junction.

All publications, including but not limited to patents and patent applications, cited in this specification are herein incorporated by reference as though fully set forth.

It is to be understood that the terminology used herein is for describing particular embodiments only and is not intended to be limiting. Unless defined otherwise, all technical and scientific terms used herein have the same meaning as commonly understood by one of ordinary skill in the art to which the disclosure pertains.

Although any methods and materials similar or equivalent to those described herein may be used in the practice for testing of the present disclosure, exemplary materials and methods are described herein. In describing and claiming the present disclosure, the following terminology will be used.

As used in this specification and the appended claims, the singular forms "a," "an," and "the" include plural referents unless the content clearly dictates otherwise. Thus, for example, reference to "a cell" includes a combination of two or more cells, and the like.

The transitional terms "comprising," "consisting essentially of," and "consisting of" are intended to connote their generally accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed disclosure. Embodiments described in terms of the phrase "comprising" (or its equivalents) also provide as embodiments those independently described in terms of "consisting of" and "consisting essentially of."

As used in this specification and the appended claims, the phrase "and fragments thereof" when appended to a list includes fragments of one or more members of the associated list. The list may comprise a Markush group so that, as an example, the phrase "the group consisting of peptides A, B, and C, and fragments thereof" specifies or recites a Markush group including A, B, C, fragments of A, fragments of B, and/or fragments of C.

"Isolated" refers to a homogenous population of molecules (such as synthetic polynucleotides or polypeptides) which have been substantially separated and/or purified away from other components of the system the molecules are produced in, such as a recombinant cell, as well as a protein that has been subjected to at least one purification or isolation step. "Isolated" refers to a molecule that is substantially free of other cellular material and/or chemicals and encompasses molecules that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"Polynucleotide" refers to a synthetic molecule comprising a chain of nucleotides covalently linked by a sugar-phosphate backbone or other equivalent covalent chemistry. cDNA is a typical example of a polynucleotide.

"Polypeptide" or "protein" refers to a molecule that comprises at least two amino acid residues linked by a peptide bond to form a polypeptide Small polypeptides of less than 50 amino acids may be referred to as "peptides".

"Immunogenic fragment" refers to a polypeptide that is recognized by cytotoxic T lymphocytes, helper T lymphocytes or B cells when the fragment is in complex with MHC class I or MHC class II molecules.

"In-frame" refers to the reading frame of codons in a first polynucleotide being the same as the reading frame of codons in a second polynucleotide which are joined together to form a heterologous polynucleotide. In-frame heterologous polynucleotide encodes a heterologous polypeptide encoded by both the first polynucleotide and the second polynucleotide.

"Immunogenic" refers to a polypeptide that comprises one or more immunogenic fragments.

"Heterologous" refers to two or more polynucleotides or two or more polypeptides that are not found in the same relationship to each other in nature.

"Heterologous polynucleotide" refers to a non-naturally occurring polynucleotide that encodes two or more neoantigens as described herein.

"Heterologous polypeptide" refers to a non-naturally occurring polypeptide comprising two or more neoantigen polypeptides as described herein.

"Non-naturally occurring" refers to a molecule that does not exist in nature.

"Vector" refers to a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

"Expression vector" refers to a vector that can be utilized in a biological system or in a reconstituted biological system to direct the translation of a polypeptide encoded by a polynucleotide sequence present in the expression vector.

"Viral vector" refers to a vector construct that includes at least one polynucleotide element of viral origin and has the capacity to be packaged into a viral vector particle.

"Neoantigen" refers to a polypeptide that is present in prostate tumor tissue that has at least one alteration that makes it distinct from the corresponding wild-type polypeptide present in non-malignant tissue, e.g., via mutation in a tumor cell or post-translational modification specific to a tumor cell. A mutation can include a frameshift or nonframeshift insertion or deletion, missense or nonsense substitution, splice site alteration, aberrant splice variants, genomic rearrangement or gene fusion, or any genomic or expression alteration giving rise to the neoantigen.

"Prevalence" refers to a percentage of a population studied harboring a prostate neoantigen.

"Recombinant" refers to polynucleotides, polypeptides, vectors, viruses and other macromolecules that are prepared, expressed, created or isolated by recombinant means.

"Vaccine" refers to a composition that comprises one or more immunogenic polypeptides, immunogenic polynucleotides or fragments, or any combination thereof intentionally administered to induce acquired immunity in the recipient (e.g. subject).

"Treat", "treating" or "treatment" of a disease or disorder such as cancer refers to accomplishing one or more of the following: reducing the severity and/or duration of the disorder, inhibiting worsening of symptoms characteristic of the disorder being treated, limiting or preventing recurrence of the disorder in subjects that have previously had the disorder, or limiting or preventing recurrence of symptoms in subjects that were previously symptomatic for the disorder.

"Prevent", "preventing", "prevention", or "prophylaxis" of a disease or disorder means preventing that a disorder occurs in subject.

"Therapeutically effective amount" refers to an amount effective, at doses and for periods of time necessary, to achieve a desired therapeutic result. A therapeutically effective amount may vary depending on factors such as the disease state, age, sex, and weight of the individual, and the ability of a therapeutic or a combination of therapeutics to elicit a desired response in the individual. Exemplary indicators of an effective therapeutic or combination of therapeutics that include, for example, improved well-being of the patient.

"Relapsed" refers to the return of a disease or the signs and symptoms of a disease after a period of improvement after prior treatment with a therapeutic.

"Refractory" refers to a disease that does not respond to a treatment. A refractory disease can be resistant to a treatment before or at the beginning of the treatment, or a refractory disease can become resistant during a treatment.

"Subject" includes any human or nonhuman animal "Nonhuman animal" includes all vertebrates, e.g., mammals and non-mammals, such as nonhuman primates, sheep, dogs, cats, horses, cows, chickens, amphibians, reptiles, etc. The terms "subject" and "patient" can be used interchangeably herein.

"In combination with" means that two or more therapeutic agents are be administered to a subject together in a mixture, concurrently as single agents or sequentially as single agents in any order.

"Enhance" or "induce" when in reference to an immune response refers to increasing the scale and/or efficiency of an immune response or extending the duration of the immune response. The terms are used interchangeably with "augment".

"Immune response" refers to any response to an immunogenic polypeptide or polynucleotide or fragment by the immune system of a vertebrate subject. Exemplary immune responses include local and systemic cellular as well as humoral immunity, such as cytotoxic T lymphocyte (CTL) responses, including antigen-specific induction of $CD8^+$ CTLs, helper T-cell responses including T-cell proliferative responses and cytokine release, and B-cell responses including antibody response.

"Specifically binds", "specific binding", "specifically binding" or "binds" refer to a proteinaceous molecule binding to an antigen or an epitope within the antigen (e.g. to prostate neoantigen) with greater affinity than for other antigens. Typically, the proteinaceous molecule binds to the antigen or the epitope within the antigen with an equilibrium dissociation constant ($K_D$) of about $1\times10^{-7}$ M or less, for example about $5\times10^{-8}$ M or less, about $1\times10^{-8}$ M or less, about $1\times10^{-9}$ M or less, about $1\times10^{-10}$ M or less, about $1\times10^{-11}$ M or less, or about $1\times10^{-12}$ M or less, typically with the $K_D$ that is at least one hundred fold less than its $K_D$ for binding to a non-specific antigen (e.g., BSA, casein). In the context of the prostate neoantigens described here, "specific binding" refers to binding of the proteinaceous molecule to the prostate neoantigen without detectable binding to a wild-type protein the neoantigen is a variant of.

"Variant", "mutant" or "altered" refers to a polypeptide or a polynucleotide that differs from a reference polypeptide or a reference polynucleotide by one or more modifications, for example one or more substitutions, insertions or deletions.

"Antibody" refers to an immunoglobulin molecule including monoclonal antibodies including murine, human, humanized and chimeric monoclonal antibodies, antigen-binding fragments, bispecific or multispecific antibodies, dimeric, tetrameric or multimeric antibodies, single chain antibodies, domain antibodies and any other modified configuration of the immunoglobulin molecule that comprises an antigen binding site of the required specificity.

"Full length antibody" is comprised of two heavy chains (HC) and two light chains (LC) inter-connected by disulfide bonds as well as multimers thereof (e.g. IgM). Each heavy chain is comprised of a heavy chain variable domain (VH) and a heavy chain constant domain, the heavy chain constant domain comprised of subdomains CH1, hinge, CH2 and CH3. Each light chain is comprised of a light chain variable domain (VL) and a light chain constant domain (CL). The VH and the VL may be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4.

"Complementarity determining regions (CDR)" are antibody regions that bind an antigen. There are three CDRs in the VH (HCDR1, HCDR2, HCDR3) and three CDRs in the VL (LCDR1, LCDR2, LCDR3). CDRs may be defined using various delineations such as Kabat (Wu et al. (1970) J Exp Med 132: 211-50; Kabat et al., Sequences of Proteins of Immunological Interest, 5th Ed. Public Health Service, National Institutes of Health, Bethesda, Md., 1991), Chothia (Chothia et al. (1987) J Mol Biol 196: 901-17), IMGT (Lefranc et al. (2003) Dev Comp Immunol 27: 55-77) and AbM (Martin and Thornton J Bmol Biol 263: 800-15, 1996). The correspondence between the various delineations and variable region numbering are described (see e.g. Lefranc et al. (2003) Dev Comp Immunol 27: 55-77; Honegger and Pluckthun, J Mol Biol (2001) 309:657-70; International ImMunoGeneTics (IMGT) database; Web resources, http://www_jmgt_org). Available programs such as abYsis by UCL Business PLC may be used to delineate CDRs. The term "CDR", "HCDR1", "HCDR2", "HCDR3", "LCDR1", "LCDR2" and "LCDR3" as used herein includes CDRs defined by any of the methods described supra, Kabat, Chothia, IMGT or AbM, unless otherwise explicitly stated in the specification.

Immunoglobulins may be assigned to five major classes, IgA, IgD, IgE, IgG and IgM, depending on the heavy chain constant region amino acid sequence. IgA and IgG are further sub-classified as isotypes IgA1, IgA2, IgG1, IgG2, IgG3 and IgG4. Antibody light chains of any vertebrate species may be assigned to one of two clearly distinct types, namely kappa (κ) and lambda (i), based on the amino acid sequences of their constant domains.

"Antigen-binding fragment" refers to a portion of an immunoglobulin molecule that retains the antigen binding properties of the parental full length antibody. Exemplary antigen-binding fragments are heavy chain complementarity determining regions (HCDR) 1, 2 and/or 3, light chain complementarity determining regions (LCDR) 1, 2 and/or 3, the VH, the VL, the VH and the VL, Fab, F(ab')2, Fd and Fv fragments as well as domain antibodies (dAb) consisting of either one VH domain or one VL domain. The VH and the VL domains may be linked together via a synthetic linker to form various types of single chain antibody designs in which the VH/VL domains pair intramolecularly, or intermolecularly in those cases when the VH and VL domains are expressed by separate chains, to form a monovalent antigen binding site, such as single chain Fv (scFv) or diabody; described for example in Int. Pat. Publ. No. WO1998/44001, Int. Pat. Publ. No. WO1988/01649, Int. Pat. Publ. No. WO1994/13804 or Int. Pat. Publ. No. WO1992/01047.

"Monoclonal antibody" refers to an antibody obtained from a substantially homogenous population of antibody molecules, i.e., the individual antibodies comprising the population are identical except for possible well-known alterations such as removal of C-terminal lysine from the antibody heavy chain or post-translational modifications such as amino acid isomerization or deamidation, methionine oxidation or asparagine or glutamine deamidation. Monoclonal antibodies typically bind one antigenic epitope. A bispecific monoclonal antibody binds two distinct antigenic epitopes. Monoclonal antibodies may have heterogeneous glycosylation within the antibody population. Monoclonal antibody may be monospecific or multispecific such as bispecific, monovalent, bivalent or multivalent.

"Humanized antibody" refers to an antibody in which at least one CDR is derived from non-human species and at least one framework is derived from human immunoglobulin sequences. Humanized antibody may include substitutions in the frameworks so that the frameworks may not be exact copies of expressed human immunoglobulin or human immunoglobulin germline gene sequences.

"Human antibody" refers to an antibody that is optimized to have minimal immune response when administered to a human subject. Variable regions of human antibody are derived from human immunoglobulin sequences. If human antibody contains a constant region or a portion of the constant region, the constant region is also derived from human immunoglobulin sequences. Human antibody comprises heavy and light chain variable regions that are "derived from" sequences of human origin if the variable regions of the human antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci. "Human antibody" typically contains amino acid differences when compared to the immunoglobulins expressed in humans due to differences between the systems used to obtain the human antibody and human immunoglobulin loci, introduction of somatic mutations or intentional introduction of substitutions into the frameworks or CDRs, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin or rearranged immunoglobulin genes. In some cases, "human antibody" may contain consensus framework sequences derived from human framework sequence analyses, for example as described in Knappik et al., (2000) J Mol Biol 296:57-86, or a synthetic HCDR3 incorporated into human immunoglobulin gene libraries displayed on phage, for example as described in Shi et al., (2010) J Mol Biol 397:385-96, and in Int. Patent Publ. No. WO2009/085462. Antibodies in which at least one CDR is derived from a non-human species are not included in the definition of "human antibody".

"Alternative scaffold" refers to a single chain protein framework that contains a structured core associated with variable domains of high conformational tolerance. The variable domains tolerate variation to be introduced without compromising scaffold integrity, and hence the variable domains can be engineered and selected for binding to a specific antigen.

"Chimeric antigen receptor" or "CAR" refers to engineered T cell receptors which graft a ligand or antigen specificity onto T cells (for example naïve T cells central memory T cells effector memory T cells or combinations thereof). CARs are also known as artificial T-cell receptors, chimeric T-cell receptors or chimeric immunoreceptors. CARs comprise an extracellular domain capable of binding to an antigen, a transmembrane domain and at least one intracellular domain. CAR intracellular domain comprises a polypeptide known to function as a domain that transmits a signal to cause activation or inhibition of a biological process in a cell. The transmembrane domain comprises any peptide or polypeptide known to span the cell membrane and that can function to link the extracellular and signaling domains. A chimeric antigen receptor may optionally comprise a hinge domain which serves as a linker between the extracellular and transmembrane domains.

"T cell receptor" or "TCR" refers to a molecule capable of recognizing a peptide when presented by an MHC molecule. Naturally-occurring TCR heterodimer consists of an alpha (cc) and beta (β) chain in around 95% of T-cells, whereas around 5% of T-cells have TCRs consisting of gamma (γ) and delta (δ) chains. Each chain of a natural TCR is a member of the immunoglobulin superfamily and possesses one N-terminal immunoglobulin (Ig)-variable (V) domain, one Ig-constant (C) domain, a transmembrane/cell membrane-spanning region, and a short cytoplasmic tail at the C-terminal end. The variable domain of both the TCR α chain and β chain have three hypervariable or complementarity determining regions (CDRs), CDR1, CDR2 and CDR3, which are responsible for recognizing processed antigens presented on MHC.

TCR may be a full length α/β or γ/δ heterodimer or a soluble molecule comprising a portion of the extracellular domain of the TCR that retains binding the peptide/MHC complex. TCR may be engineered into a single chain TCR.

"T cell receptor complex" or "TCR complex" refers to a known TCR complex comprising of a TCRα and TCRβ chains, CD3ε, CD3γ, CD3δ and CD3ζ molecules. In some instances, TCRα and TCRβ chains are replaced by TCRγ and TCRδ chains. The amino acid sequences of the various proteins forming the TCR complex are well-known.

"T cell" and "T lymphocyte" are interchangeable and used synonymously herein. T cell includes thymocytes, naïve T lymphocytes, memory T cells, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; $CD4^+$ T cell) $CD4^+$ T cell, a cytotoxic T cell (CTL; $CD8^+$ T cell), a tumor infiltrating cytotoxic T cell (TIL; $CD8^+$ T cell), $CD4^+CD8^+$ T cell, or any other subset of T cells. Also included are "NKT cells", which refer to a specialized population of T cells that express a semi-invariant αβ T-cell receptor, but also express a variety of molecular markers that are typically associated with NK cells, such as NK1.1. NKT cells include $NK1.1^+$ and NK1.1$^-$, as well as CD4$^+$, CD4$^-$, CD8+ and CD8$^-$ cells. The TCR on NKT cells is unique in that it recognizes glycolipid antigens presented by the MHC I-like molecule CD Id. NKT cells can have either protective or deleterious effects due to their abilities to produce cytokines that promote either inflammation or immune tolerance. Also included are "gamma-delta T cells (γδ T cells)," which refer to a specialized population that to a small subset of T cells possessing a distinct TCR on their surface, and unlike the majority of T cells in which the TCR is composed of two glycoprotein chains designated α- and β-TCR chains, the TCR in γδ T cells is made up of a_γ-chain and a δ-chain. γδ T cells can play a role in immunosurveillance and immunoregulation, and were found to be an important source of IL-17 and to induce robust CD8$^+$ cytotoxic T cell response. Also included are "regulatory T cells" or "Tregs" which refer to T cells that suppress an abnormal or excessive immune response and play a role in immune tolerance. Tregs are typically transcription factor Foxp3-positive CD4$^+$ T cells and can also include transcription factor Foxp3-negative regulatory T cells that are IL-10-producing CD4$^+$ T cells.

"Natural killer cell" or "NK cell" refers to a differentiated lymphocyte with a CD 16$^+$ CD56$^+$ and/or CD57$^+$ TCR$^-$ phenotype. NKs are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

"About" means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, "about" means within one standard deviation per the practice in the art, or a range of up to 5%, whichever is larger.

"Antigen presenting cell" (APC) refers to any cell that presents on its surface an antigen in association with a major histocompatibility complex molecule, either MHC class I or MHC class II molecule, or both.

"Prime-boost" or "prime-boost regimen" refers to a method of treating a subject involving priming a T-cell response with a first vaccine followed by boosting the immune response with a second vaccine. The first vaccine and the second vaccine are typically distinct. These prime-boost immunizations elicit immune responses of greater height and breadth than can be achieved by priming and boosting with the same vaccine. The priming step initiates memory cells and the boost step expands the memory response. Boosting can occur once or multiple times.

"Facilitator element" refers to any polynucleotide or polypeptide element that is operably linked to a polynucleotide or a polypeptide, and include promoters, enhancers, polyadenylation signals, stop codons, protein tags, such as histidine tag, and the like. Facilitator elements herein include regulatory elements.

"Distinct" in the context of polypeptide or polynucleotide sequences refers to polypeptide or polynucleotide sequences that are not identical.

Compositions of Matter

The disclosure relates to prostate neoantigens, polynucleotides encoding them, vectors, host cells, vaccines comprising the neoantigens or polynucleotides encoding the neoantigens, proteinaceous molecules binding the prostate neoantigens, and methods of making and using them. The disclosure also provides vaccines comprising the prostate neoantigens of the disclosure that are prevalent in a population of prostate cancer patients, thereby providing a pan-vaccine that may be useful to treating a broad population of patients having diagnosed with various stages of prostate cancer, such as localized or metastasized prostate cancer.

Cancer cells produce neoantigens that result from genomic alterations and aberrant transcriptional programs. Neoantigen burden in patients has been associated with response to immunotherapy (Snyder et al., N Engl J Med. 2014 Dec. 4; 371(23):2189-2199. doi: 10.1056/NEJMoa1406498. Epub 2014 Nov. 19; Le et al., N Engl J Med. 2015 Jun. 25; 372(26):2509-20. doi: 10.1056/NEJMoa1500596. Epub 2015 May 30; Rizvi et al., Science. 2015 Apr. 3; 348(6230):124-8. doi: 10.1126/science.aaa1348. Epub 2015 Mar. 12; Van Allen et al., Science. 2015 Oct. 9; 350(6257):207-211. doi: 10.1126/science.aad0095. Epub 2015 Sep. 10). The disclosure is based, at least in part, on the identification of prostate neoantigens that are common in prostate cancer patients and hence can be utilized to develop a therapy amenable to treatment of a spectrum of prostate cancer patients. One or more neoantigens or polynucleotides encoding the neoantigens of the disclosure may also be used for diagnostic or prognostic purposes.

Polypeptides and Polynucleotides of the Disclosure

The disclosure provides an isolated polynucleotide encoding a polypeptide of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

The disclosure also provides an isolated polynucleotide comprising a polynucleotide sequence of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 or 458, or fragments thereof.

The disclosure also provides an isolated polynucleotide comprising a polynucleotide sequence of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 or 540, or fragments thereof.

The disclosure also provides an isolated heterologous polynucleotide comprising two or more polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide encoding a heterologous polypeptide comprising two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the fragments comprise at least 18 nucleotides. In some embodiments, the fragments comprise at least 21 nucleotides. In some embodiments, the fragments comprise at least 24 nucleotides. In some embodiments, the fragments comprise at least 27 nucleotides. In some embodiments, the fragments comprise at least 30 nucleotides. In some embodiments, the fragments comprise at least 33 nucleotides. In some embodiments, the fragments comprise at least 36 nucleotides. In some embodiments, the fragments comprise at least 39 nucleotides. In some embodiments, the fragments comprise at least 42 nucleotides. In some embodiments, the fragments comprise at least 45 nucleotides. In some embodiments, the fragments comprise at least 48 nucleotides. In some embodiments, the fragments comprise at least 51 nucleotides. In some embodiments, the fragments comprise at least 54 nucleotides. In some embodiments, the fragments comprise at least 57 nucleotides. In some embodiments, the fragments comprise at least 60 nucleotides. In some embodiments, the fragments comprise at least 63 nucleotides. In some embodiments, the fragments comprise at least 66 nucleotides. In some embodiments, the fragments comprise at least 69 nucleotides. In some embodiments, the fragments comprise at least 72 nucleotides. In some embodiments, the fragments comprise at least 75 nucleotides. In some embodiments, the fragments comprise about 18 nucleotides. In some embodiments, the fragments comprise about 21 nucleotides. In some embodiments, the fragments comprise about 24 nucleotides. In some embodiments, the fragments comprise about 27 nucleotides. In some embodiments, the fragments comprise about 30 nucleotides. In some embodiments, the fragments comprise about 33 nucleotides. In some embodiments, the fragments comprise about 36 nucleotides. In some embodiments, the fragments comprise about 39 nucleotides. In some embodiments, the fragments comprise about 42 nucleotides. In some embodiments, the fragments comprise about 45 nucleotides. In some embodiments, the fragments comprise about 48 nucleotides. In some embodiments, the fragments comprise about 51 nucleotides. In some embodiments, the fragments comprise about 54 nucleotides. In some embodiments, the fragments comprise about 57 nucleotides. In some embodiments, the fragments comprise about 60 nucleotides. In some embodiments, the fragments comprise about 63 nucleotides. In some embodiments, the fragments comprise about 66 nucleotides. In some embodiments, the fragments comprise about 69 nucleotides. In some embodiments, the fragments comprise about 72 nucleotides. In some embodiments, the fragments comprise about 75 nucleotides. In some embodiments, the fragments comprise about 18-75 nucleotides. In some embodiments, the fragments comprise about 21-75 nucleotides. In some embodiments, the fragments comprise about 24-75 nucleotides. In some embodiments, the fragments comprise about 24-72 nucleotides. In some embodiments, the fragments comprise about 24-69 nucleotides. In some embodiments, the fragments comprise about 24-66 nucleotides. In some embodiments, the fragments comprise about 24-63 nucleotides. In some embodiments, the fragments comprise about 24-60 nucleotides. In some embodiments, the fragments comprise about 24-57 nucleotides. In some embodiments, the fragments comprise about 24-54 nucleotides. In some embodiments, the fragments comprise about 24-51 nucleotides. In some embodiments, the fragments comprise about 24-48 nucleotides. In some embodiments, the fragments comprise about 24-45 nucleotides. In some embodiments, the fragments comprise about 24-42 nucleotides. In some embodiments, the fragments comprise about 27-42 nucleotides. In some embodiments, the fragments comprise about 27-39 nucleotides. In some embodiments, the fragments comprise about 27-36 nucleotides. In some embodiments, the fragments comprise about 27-33 nucleotides. In some embodiments, the fragments comprise about 27-30 nucleotides.

The polynucleotides and the heterologous polynucleotides of the disclosure encode the prostate neoantigens and heterologous polypeptides comprising two or more prostate neoantigens described herein. The polynucleotides and the heterologous polynucleotides of the disclosure are useful in generating the polypeptides, the heterologous polypeptides, the vectors, the recombinant viruses, the cells and the vaccines of the disclosure. The polynucleotides and the heterologous polynucleotides of the disclosure may be utilized as therapeutics by delivering them to a subject having a prostate cancer using various technologies, including viral vectors as described herein or other delivery technologies as also described herein.

The disclosure also provides an isolated polynucleotide encoding the polypeptide of SEQ ID NO: 1 or a fragment thereof. In some embodiments, the polypeptide of SEQ ID NO: 1, or a fragment thereof, is encoded by the polynucleotide of SEQ ID NO: 2 or a fragment thereof.

The disclosure also provides an isolated polynucleotide encoding the polypeptide of SEQ ID NO: 3 or a fragment thereof. In some embodiments, the polypeptide of SEQ ID NO: 3, or a fragment thereof, is encoded by the polynucleotide of SEQ ID NO: 4 or a fragment thereof.

The disclosure also provides an isolated polynucleotide encoding the polypeptide of SEQ ID NO: 5 or a fragment thereof. In some embodiments, the polypeptide of SEQ ID NO: 5, or a fragment thereof, is encoded by the polynucleotide of SEQ ID NO: 6 or a fragment thereof.

The disclosure also provides an isolated polynucleotide encoding the polypeptide of SEQ ID NO: 7 or a fragment thereof. In some embodiments, the polypeptide of SEQ ID NO: 7, or a fragment thereof, is encoded by the polynucleotide of SEQ ID NO: 8 or a fragment thereof.

The disclosure also provides an isolated polynucleotide encoding the polypeptide of SEQ ID NO: 9 or a fragment thereof. In some embodiments, the polypeptide of SEQ ID NO: 9, or a fragment thereof, is encoded by the polynucleotide of SEQ ID NO: 10 or a fragment thereof.

The disclosure also provides an isolated polynucleotide encoding the polypeptide of SEQ ID NO: 11 or a fragment thereof. In some embodiments, the polypeptide of SEQ ID NO: 11, or a fragment thereof, is encoded by the polynucleotide of SEQ ID NO: 12 or a fragment thereof.

The disclosure also provides an isolated polynucleotide encoding the polypeptide of SEQ ID NO: 13 or a fragment thereof. In some embodiments, the polypeptide of SEQ ID NO: 13, or a fragment thereof, is encoded by the polynucleotide of SEQ ID NO: 14 or a fragment thereof.

The disclosure also provides an isolated polynucleotide encoding the polypeptide of SEQ ID NO: 15 or a fragment thereof. In some embodiments, the polypeptide of SEQ ID NO: 15, or a fragment thereof, is encoded by the polynucleotide of SEQ ID NO: 16 or a fragment thereof.

The disclosure also provides an isolated polynucleotide encoding the polypeptide of SEQ ID NO: 17 or a fragment thereof. In some embodiments, the polypeptide of SEQ ID NO: 17, or a fragment thereof, is encoded by the polynucleotide of SEQ ID NO: 18 or a fragment thereof.

The disclosure also provides an isolated polynucleotide encoding the polypeptide of SEQ ID NO: 19 or a fragment thereof. In some embodiments, the polypeptide of SEQ ID NO: 19, or a fragment thereof, is encoded by the polynucleotide of SEQ ID NO: 20 or a fragment thereof. In some embodiments, the polypeptide of SEQ ID NO: 19, or a fragment thereof, is encoded by the polynucleotide of SEQ ID NO: 497 or a fragment thereof. In some embodiments, the polypeptide of SEQ ID NO: 19, or a fragment thereof, is encoded by the polynucleotide of SEQ ID NO: 538 or a fragment thereof.

The disclosure also provides an isolated polynucleotide encoding the polypeptide of SEQ ID NO: 21 or a fragment thereof. In some embodiments, the polypeptide of SEQ ID NO: 21, or a fragment thereof, is encoded by the polynucleotide of SEQ ID NO: 22 or a fragment thereof.

The disclosure also provides an isolated polynucleotide encoding the polypeptide of SEQ ID NO: 23 or a fragment thereof. In some embodiments, the polypeptide of SEQ ID NO: 23, or a fragment thereof, is encoded by the polynucleotide of SEQ ID NO: 24 or a fragment thereof. In some embodiments, the polypeptide of SEQ ID NO: 23, or a fragment thereof, is encoded by the polynucleotide of SEQ ID NO: 498 or a fragment thereof. In some embodiments, the polypeptide of SEQ ID NO: 23, or a fragment thereof, is encoded by the polynucleotide of SEQ ID NO: 539 or a fragment thereof.

The disclosure also provides an isolated polynucleotide encoding the polypeptide of SEQ ID NO: 25 or a fragment thereof. In some embodiments, the polypeptide of SEQ ID NO: 25, or a fragment thereof, is encoded by the polynucleotide of SEQ ID NO: 26 or a fragment thereof.

The disclosure also provides an isolated polynucleotide encoding the polypeptide of SEQ ID NO: 27 or a fragment thereof. In some embodiments, the polypeptide of SEQ ID NO: 27, or a fragment thereof, is encoded by the polynucleotide of SEQ ID NO: 28 or a fragment thereof.

The disclosure also provides an isolated polynucleotide encoding the polypeptide of SEQ ID NO: 29 or a fragment thereof. In some embodiments, the polypeptide of SEQ ID NO: 29, or a fragment thereof, is encoded by the polynucleotide of SEQ ID NO: 30 or a fragment thereof.

The disclosure also provides an isolated polynucleotide encoding the polypeptide of SEQ ID NO: 31 or a fragment thereof. In some embodiments, the polypeptide of SEQ ID NO: 31, or a fragment thereof, is encoded by the polynucleotide of SEQ ID NO: 32 or a fragment thereof.

The disclosure also provides an isolated polynucleotide encoding the polypeptide of SEQ ID NO: 33 or a fragment thereof. In some embodiments, the polypeptide of SEQ ID NO: 33, or a fragment thereof, is encoded by the polynucleotide of SEQ ID NO: 34 or a fragment thereof.

The disclosure also provides an isolated polynucleotide encoding the polypeptide of SEQ ID NO: 35 or a fragment thereof. In some embodiments, the polypeptide of SEQ ID NO: 35, or a fragment thereof, is encoded by the polynucleotide of SEQ ID NO: 36 or a fragment thereof.

The disclosure also provides an isolated polynucleotide encoding the polypeptide of SEQ ID NO: 37 or a fragment thereof. In some embodiments, the polypeptide of SEQ ID NO: 37, or a fragment thereof, is encoded by the polynucleotide of SEQ ID NO: 38 or a fragment thereof.

The disclosure also provides an isolated polynucleotide encoding the polypeptide of SEQ ID NO: 39 or a fragment thereof. In some embodiments, the polypeptide of SEQ ID NO: 39, or a fragment thereof, is encoded by the polynucleotide of SEQ ID NO: 40 or a fragment thereof.

The disclosure also provides an isolated polynucleotide encoding the polypeptide of SEQ ID NO: 41 or a fragment thereof. In some embodiments, the polypeptide of SEQ ID NO: 41, or a fragment thereof, is encoded by the polynucleotide of SEQ ID NO: 42 or a fragment thereof.

The disclosure also provides an isolated polynucleotide encoding the polypeptide of SEQ ID NO: 43 or a fragment thereof. In some embodiments, the polypeptide of SEQ ID NO: 43, or a fragment thereof, is encoded by the polynucleotide of SEQ ID NO: 44 or a fragment thereof.

The disclosure also provides an isolated polynucleotide encoding the polypeptide of SEQ ID NO: 45 or a fragment thereof. In some embodiments, the polypeptide of SEQ ID NO: 45, or a fragment thereof, is encoded by the polynucleotide of SEQ ID NO: 46 or a fragment thereof.

The disclosure also provides an isolated polynucleotide encoding the polypeptide of SEQ ID NO: 47 or a fragment thereof. In some embodiments, the polypeptide of SEQ ID NO: 47, or a fragment thereof, is encoded by the polynucleotide of SEQ ID NO: 48 or a fragment thereof.

The disclosure also provides an isolated polynucleotide encoding the polypeptide of SEQ ID NO: 49 or a fragment thereof. In some embodiments, the polypeptide of SEQ ID NO: 49, or a fragment thereof, is encoded by the polynucleotide of SEQ ID NO: 50 or a fragment thereof.

The disclosure also provides an isolated polynucleotide encoding the polypeptide of SEQ ID NO: 51 or a fragment thereof. In some embodiments, the polypeptide of SEQ ID NO: 51, or a fragment thereof, is encoded by the polynucleotide of SEQ ID NO: 52 or a fragment thereof.

The disclosure also provides an isolated polynucleotide encoding the polypeptide of SEQ ID NO: 53 or a fragment thereof. In some embodiments, the polypeptide of SEQ ID NO: 53, or a fragment thereof, is encoded by the polynucleotide of SEQ ID NO: 54 or a fragment thereof.

The disclosure also provides an isolated polynucleotide encoding the polypeptide of SEQ ID NO: 55 or a fragment thereof. In some embodiments, the polypeptide of SEQ ID NO: 55, or a fragment thereof, is encoded by the polynucleotide of SEQ ID NO: 56 or a fragment thereof.

The disclosure also provides an isolated polynucleotide encoding the polypeptide of SEQ ID NO: 57 or a fragment thereof. In some embodiments, the polypeptide of SEQ ID NO: 57, or a fragment thereof, is encoded by the polynucleotide of SEQ ID NO: 58 or a fragment thereof.

The disclosure also provides an isolated polynucleotide encoding the polypeptide of SEQ ID NO: 59 or a fragment thereof. In some embodiments, the polypeptide of SEQ ID NO: 59, or a fragment thereof, is encoded by the polynucleotide of SEQ ID NO: 60 or a fragment thereof.

The disclosure also provides an isolated polynucleotide encoding the polypeptide of SEQ ID NO: 61 or a fragment thereof. In some embodiments, the polypeptide of SEQ ID NO: 61, or a fragment thereof, is encoded by the polynucleotide of SEQ ID NO: 62 or a fragment thereof.

The disclosure also provides an isolated polynucleotide encoding the polypeptide of SEQ ID NO: 63 or a fragment thereof. In some embodiments, the polypeptide of SEQ ID NO: 63, or a fragment thereof, is encoded by the polynucleotide of SEQ ID NO: 64 or a fragment thereof.

The disclosure also provides an isolated polynucleotide encoding the polypeptide of SEQ ID NO: 65 or a fragment thereof. In some embodiments, the polypeptide of SEQ ID NO: 65, or a fragment thereof, is encoded by the polynucleotide of SEQ ID NO: 66 or a fragment thereof.

The disclosure also provides an isolated polynucleotide encoding the polypeptide of SEQ ID NO: 67 or a fragment thereof. In some embodiments, the polypeptide of SEQ ID NO: 67, or a fragment thereof, is encoded by the polynucleotide of SEQ ID NO: 68 or a fragment thereof.

The disclosure also provides an isolated polynucleotide encoding the polypeptide of SEQ ID NO: 69 or a fragment thereof. In some embodiments, the polypeptide of SEQ ID NO: 69, or a fragment thereof, is encoded by the polynucleotide of SEQ ID NO: 70 or a fragment thereof.

The disclosure also provides an isolated polynucleotide encoding the polypeptide of SEQ ID NO: 71 or a fragment thereof. In some embodiments, the polypeptide of SEQ ID NO: 71, or a fragment thereof, is encoded by the polynucleotide of SEQ ID NO: 72 or a fragment thereof.

The disclosure also provides an isolated polynucleotide encoding the polypeptide of SEQ ID NO: 73 or a fragment thereof. In some embodiments, the polypeptide of SEQ ID NO: 73, or a fragment thereof, is encoded by the polynucleotide of SEQ ID NO: 74 or a fragment thereof.

The disclosure also provides an isolated polynucleotide encoding the polypeptide of SEQ ID NO: 75 or a fragment thereof. In some embodiments, the polypeptide of SEQ ID NO: 75, or a fragment thereof, is encoded by the polynucleotide of SEQ ID NO: 76 or a fragment thereof.

The disclosure also provides an isolated polynucleotide encoding the polypeptide of SEQ ID NO: 77 or a fragment thereof. In some embodiments, the polypeptide of SEQ ID NO: 77, or a fragment thereof, is encoded by the polynucleotide of SEQ ID NO: 78 or a fragment thereof.

The disclosure also provides an isolated polynucleotide encoding the polypeptide of SEQ ID NO: 79 or a fragment thereof. In some embodiments, the polypeptide of SEQ ID NO: 79, or a fragment thereof, is encoded by the polynucleotide of SEQ ID NO: 80 or a fragment thereof.

The disclosure also provides an isolated polynucleotide encoding the polypeptide of SEQ ID NO: 81 or a fragment thereof. In some embodiments, the polypeptide of SEQ ID NO: 81, or a fragment thereof, is encoded by the polynucleotide of SEQ ID NO: 82 or a fragment thereof.

The disclosure also provides an isolated polynucleotide encoding the polypeptide of SEQ ID NO: 83 or a fragment thereof. In some embodiments, the polypeptide of SEQ ID NO: 83, or a fragment thereof, is encoded by the polynucleotide of SEQ ID NO: 84 or a fragment thereof.

The disclosure also provides an isolated polynucleotide encoding the polypeptide of SEQ ID NO: 85 or a fragment thereof. In some embodiments, the polypeptide of SEQ ID NO: 85, or a fragment thereof, is encoded by the polynucleotide of SEQ ID NO: 86 or a fragment thereof.

The disclosure also provides an isolated polynucleotide encoding the polypeptide of SEQ ID NO: 87 or a fragment thereof. In some embodiments, the polypeptide of SEQ ID NO: 87, or a fragment thereof, is encoded by the polynucleotide of SEQ ID NO: 88 or a fragment thereof.

The disclosure also provides an isolated polynucleotide encoding the polypeptide of SEQ ID NO: 89 or a fragment thereof. In some embodiments, the polypeptide of SEQ ID NO: 89, or a fragment thereof, is encoded by the polynucleotide of SEQ ID NO: 90 or a fragment thereof.

The disclosure also provides an isolated polynucleotide encoding the polypeptide of SEQ ID NO: 91 or a fragment thereof. In some embodiments, the polypeptide of SEQ ID NO: 91, or a fragment thereof, is encoded by the polynucleotide of SEQ ID NO: 92 or a fragment thereof.

The disclosure also provides an isolated polynucleotide encoding the polypeptide of SEQ ID NO: 93 or a fragment thereof. In some embodiments, the polypeptide of SEQ ID NO: 93, or a fragment thereof, is encoded by the polynucleotide of SEQ ID NO: 94 or a fragment thereof.

The disclosure also provides an isolated polynucleotide encoding the polypeptide of SEQ ID NO: 95 or a fragment thereof. In some embodiments, the polypeptide of SEQ ID NO: 95, or a fragment thereof, is encoded by the polynucleotide of SEQ ID NO: 96 or a fragment thereof.

The disclosure also provides an isolated polynucleotide encoding the polypeptide of SEQ ID NO: 97 or a fragment thereof. In some embodiments, the polypeptide of SEQ ID NO: 97, or a fragment thereof, is encoded by the polynucleotide of SEQ ID NO: 98 or a fragment thereof.

The disclosure also provides an isolated polynucleotide encoding the polypeptide of SEQ ID NO: 99 or a fragment thereof. In some embodiments, the polypeptide of SEQ ID NO: 99, or a fragment thereof, is encoded by the polynucleotide of SEQ ID NO: 100 or a fragment thereof.

The disclosure also provides an isolated polynucleotide encoding the polypeptide of SEQ ID NO: 101 or a fragment thereof. In some embodiments, the polypeptide of SEQ ID NO: 101, or a fragment thereof, is encoded by the polynucleotide of SEQ ID NO: 102 or a fragment thereof.

The disclosure also provides an isolated polynucleotide encoding the polypeptide of SEQ ID NO: 103 or a fragment thereof. In some embodiments, the polypeptide of SEQ ID NO: 103, or a fragment thereof, is encoded by the polynucleotide of SEQ ID NO: 104 or a fragment thereof.

The disclosure also provides an isolated polynucleotide encoding the polypeptide of SEQ ID NO: 105 or a fragment thereof. In some embodiments, the polypeptide of SEQ ID NO: 105, or a fragment thereof, is encoded by the polynucleotide of SEQ ID NO: 106 or a fragment thereof.

The disclosure also provides an isolated polynucleotide encoding the polypeptide of SEQ ID NO: 107 or a fragment thereof. In some embodiments, the polypeptide of SEQ ID NO: 107, or a fragment thereof, is encoded by the polynucleotide of SEQ ID NO: 108 or a fragment thereof.

The disclosure also provides an isolated polynucleotide encoding the polypeptide of SEQ ID NO: 109 or a fragment thereof. In some embodiments, the polypeptide of SEQ ID NO: 109, or a fragment thereof, is encoded by the polynucleotide of SEQ ID NO: 110 or a fragment thereof.

The disclosure also provides an isolated polynucleotide encoding the polypeptide of SEQ ID NO: 111 or a fragment thereof. In some embodiments, the polypeptide of SEQ ID NO: 111, or a fragment thereof, is encoded by the polynucleotide of SEQ ID NO: 112 or a fragment thereof.

The disclosure also provides an isolated polynucleotide encoding the polypeptide of SEQ ID NO: 113 or a fragment thereof. In some embodiments, the polypeptide of SEQ ID NO: 113, or a fragment thereof, is encoded by the polynucleotide of SEQ ID NO: 114 or a fragment thereof.

The disclosure also provides an isolated polynucleotide encoding the polypeptide of SEQ ID NO: 115 or a fragment thereof. In some embodiments, the polypeptide of SEQ ID NO: 115, or a fragment thereof, is encoded by the polynucleotide of SEQ ID NO: 116 or a fragment thereof.

The disclosure also provides an isolated polynucleotide encoding the polypeptide of SEQ ID NO: 117 or a fragment thereof. In some embodiments, the polypeptide of SEQ ID NO: 117, or a fragment thereof, is encoded by the polynucleotide of SEQ ID NO: 118 or a fragment thereof.

The disclosure also provides an isolated polynucleotide encoding the polypeptide of SEQ ID NO: 119 or a fragment thereof. In some embodiments, the polypeptide of SEQ ID NO: 119, or a fragment thereof, is encoded by the polynucleotide of SEQ ID NO: 120 or a fragment thereof.

The disclosure also provides an isolated polynucleotide encoding the polypeptide of SEQ ID NO: 121 or a fragment thereof. In some embodiments, the polypeptide of SEQ ID NO: 121, or a fragment thereof, is encoded by the polynucleotide of SEQ ID NO: 122 or a fragment thereof.

The disclosure also provides an isolated polynucleotide encoding the polypeptide of SEQ ID NO: 123 or a fragment thereof. In some embodiments, the polypeptide of SEQ ID NO: 123, or a fragment thereof, is encoded by the polynucleotide of SEQ ID NO: 124 or a fragment thereof.

The disclosure also provides an isolated polynucleotide encoding the polypeptide of SEQ ID NO: 125 or a fragment thereof. In some embodiments, the polypeptide of SEQ ID NO: 125, or a fragment thereof, is encoded by the polynucleotide of SEQ ID NO: 126 or a fragment thereof.

The disclosure also provides an isolated polynucleotide encoding the polypeptide of SEQ ID NO: 127 or a fragment thereof. In some embodiments, the polypeptide of SEQ ID NO: 127, or a fragment thereof, is encoded by the polynucleotide of SEQ ID NO: 128 or a fragment thereof.

The disclosure also provides an isolated polynucleotide encoding the polypeptide of SEQ ID NO: 129 or a fragment thereof. In some embodiments, the polypeptide of SEQ ID NO: 129, or a fragment thereof, is encoded by the polynucleotide of SEQ ID NO: 130 or a fragment thereof.

The disclosure also provides an isolated polynucleotide encoding the polypeptide of SEQ ID NO: 131 or a fragment thereof. In some embodiments, the polypeptide of SEQ ID NO: 131, or a fragment thereof, is encoded by the polynucleotide of SEQ ID NO: 132 or a fragment thereof.

The disclosure also provides an isolated polynucleotide encoding the polypeptide of SEQ ID NO: 133 or a fragment thereof. In some embodiments, the polypeptide of SEQ ID NO: 133, or a fragment thereof, is encoded by the polynucleotide of SEQ ID NO: 134 or a fragment thereof.

The disclosure also provides an isolated polynucleotide encoding the polypeptide of SEQ ID NO: 135 or a fragment thereof. In some embodiments, the polypeptide of SEQ ID NO: 135, or a fragment thereof, is encoded by the polynucleotide of SEQ ID NO: 136 or a fragment thereof.

The disclosure also provides an isolated polynucleotide encoding the polypeptide of SEQ ID NO: 137 or a fragment thereof. In some embodiments, the polypeptide of SEQ ID NO: 137, or a fragment thereof, is encoded by the polynucleotide of SEQ ID NO: 138 or a fragment thereof.

The disclosure also provides an isolated polynucleotide encoding the polypeptide of SEQ ID NO: 139 or a fragment thereof. In some embodiments, the polypeptide of SEQ ID NO: 139, or a fragment thereof, is encoded by the polynucleotide of SEQ ID NO: 140 or a fragment thereof.

The disclosure also provides an isolated polynucleotide encoding the polypeptide of SEQ ID NO: 141 or a fragment thereof. In some embodiments, the polypeptide of SEQ ID NO: 141, or a fragment thereof, is encoded by the polynucleotide of SEQ ID NO: 142 or a fragment thereof.

The disclosure also provides an isolated polynucleotide encoding the polypeptide of SEQ ID NO: 143 or a fragment thereof. In some embodiments, the polypeptide of SEQ ID NO: 143, or a fragment thereof, is encoded by the polynucleotide of SEQ ID NO: 144 or a fragment thereof.

The disclosure also provides an isolated polynucleotide encoding the polypeptide of SEQ ID NO: 145 or a fragment thereof. In some embodiments, the polypeptide of SEQ ID NO: 145, or a fragment thereof, is encoded by the polynucleotide of SEQ ID NO: 146 or a fragment thereof.

The disclosure also provides an isolated polynucleotide encoding the polypeptide of SEQ ID NO: 147 or a fragment thereof. In some embodiments, the polypeptide of SEQ ID NO: 147, or a fragment thereof, is encoded by the polynucleotide of SEQ ID NO: 148 or a fragment thereof.

The disclosure also provides an isolated polynucleotide encoding the polypeptide of SEQ ID NO: 149 or a fragment thereof. In some embodiments, the polypeptide of SEQ ID NO: 149, or a fragment thereof, is encoded by the polynucleotide of SEQ ID NO: 150 or a fragment thereof.

The disclosure also provides an isolated polynucleotide encoding the polypeptide of SEQ ID NO: 151 or a fragment thereof. In some embodiments, the polypeptide of SEQ ID NO: 151, or a fragment thereof, is encoded by the polynucleotide of SEQ ID NO: 152 or a fragment thereof.

The disclosure also provides an isolated polynucleotide encoding the polypeptide of SEQ ID NO: 153 or a fragment thereof. In some embodiments, the polypeptide of SEQ ID NO: 153, or a fragment thereof, is encoded by the polynucleotide of SEQ ID NO: 154 or a fragment thereof.

The disclosure also provides an isolated polynucleotide encoding the polypeptide of SEQ ID NO: 155 or a fragment thereof. In some embodiments, the polypeptide of SEQ ID NO: 155, or a fragment thereof, is encoded by the polynucleotide of SEQ ID NO: 156 or a fragment thereof.

The disclosure also provides an isolated polynucleotide encoding the polypeptide of SEQ ID NO: 157 or a fragment thereof. In some embodiments, the polypeptide of SEQ ID NO: 157, or a fragment thereof, is encoded by the polynucleotide of SEQ ID NO: 158 or a fragment thereof.

The disclosure also provides an isolated polynucleotide encoding the polypeptide of SEQ ID NO: 159 or a fragment thereof. In some embodiments, the polypeptide of SEQ ID NO: 159, or a fragment thereof, is encoded by the polynucleotide of SEQ ID NO: 160 or a fragment thereof.

The disclosure also provides an isolated polynucleotide encoding the polypeptide of SEQ ID NO: 161 or a fragment thereof. In some embodiments, the polypeptide of SEQ ID NO: 161, or a fragment thereof, is encoded by the polynucleotide of SEQ ID NO: 162 or a fragment thereof.

The disclosure also provides an isolated polynucleotide encoding the polypeptide of SEQ ID NO: 163 or a fragment thereof. In some embodiments, the polypeptide of SEQ ID NO: 163, or a fragment thereof, is encoded by the polynucleotide of SEQ ID NO: 164 or a fragment thereof.

The disclosure also provides an isolated polynucleotide encoding the polypeptide of SEQ ID NO: 165 or a fragment thereof. In some embodiments, the polypeptide of SEQ ID NO: 165, or a fragment thereof, is encoded by the polynucleotide of SEQ ID NO: 166 or a fragment thereof.

The disclosure also provides an isolated polynucleotide encoding the polypeptide of SEQ ID NO: 167 or a fragment thereof. In some embodiments, the polypeptide of SEQ ID NO: 167, or a fragment thereof, is encoded by the polynucleotide of SEQ ID NO: 168 or a fragment thereof. In some embodiments, the polypeptide of SEQ ID NO: 167, or a fragment thereof, is encoded by the polynucleotide of SEQ ID NO: 495 or a fragment thereof. In some embodiments, the polypeptide of SEQ ID NO: 167, or a fragment thereof, is encoded by the polynucleotide of SEQ ID NO: 536 or a fragment thereof.

The disclosure also provides an isolated polynucleotide encoding the polypeptide of SEQ ID NO: 169 or a fragment thereof. In some embodiments, the polypeptide of SEQ ID NO: 169, or a fragment thereof, is encoded by the polynucleotide of SEQ ID NO: 170 or a fragment thereof.

The disclosure also provides an isolated polynucleotide encoding the polypeptide of SEQ ID NO: 171 or a fragment thereof. In some embodiments, the polypeptide of SEQ ID NO: 171, or a fragment thereof, is encoded by the polynucleotide of SEQ ID NO: 172 or a fragment thereof. In some embodiments, the polypeptide of SEQ ID NO: 171, or a fragment thereof, is encoded by the polynucleotide of SEQ ID NO: 496 or a fragment thereof. In some embodiments, the polypeptide of SEQ ID NO: 171, or a fragment thereof, is encoded by the polynucleotide of SEQ ID NO: 537 or a fragment thereof.

The disclosure also provides an isolated polynucleotide encoding the polypeptide of SEQ ID NO: 173 or a fragment thereof. In some embodiments, the polypeptide of SEQ ID NO: 173, or a fragment thereof, is encoded by the polynucleotide of SEQ ID NO: 174 or a fragment thereof.

The disclosure also provides an isolated polynucleotide encoding the polypeptide of SEQ ID NO: 175 or a fragment thereof. In some embodiments, the polypeptide of SEQ ID NO: 175, or a fragment thereof, is encoded by the polynucleotide of SEQ ID NO: 176 or a fragment thereof.

The disclosure also provides an isolated polynucleotide encoding the polypeptide of SEQ ID NO: 177 or a fragment thereof. In some embodiments, the polypeptide of SEQ ID NO: 177, or a fragment thereof, is encoded by the polynucleotide of SEQ ID NO: 178 or a fragment thereof. In some embodiments, the polypeptide of SEQ ID NO: 177, or a fragment thereof, is encoded by the polynucleotide of SEQ ID NO: 499 or a fragment thereof. In some embodiments, the polypeptide of SEQ ID NO: 177, or a fragment thereof, is encoded by the polynucleotide of SEQ ID NO: 540 or a fragment thereof.

The disclosure also provides an isolated polynucleotide encoding the polypeptide of SEQ ID NO: 179 or a fragment thereof. In some embodiments, the polypeptide of SEQ ID NO: 179, or a fragment thereof, is encoded by the polynucleotide of SEQ ID NO: 180 or a fragment thereof.

The disclosure also provides an isolated polynucleotide encoding the polypeptide of SEQ ID NO: 181 or a fragment thereof. In some embodiments, the polypeptide of SEQ ID NO: 181, or a fragment thereof, is encoded by the polynucleotide of SEQ ID NO: 182 or a fragment thereof.

The disclosure also provides an isolated polynucleotide encoding the polypeptide of SEQ ID NO: 183 or a fragment thereof. In some embodiments, the polypeptide of SEQ ID NO: 183, or a fragment thereof, is encoded by the polynucleotide of SEQ ID NO: 184 or a fragment thereof.

The disclosure also provides an isolated polynucleotide encoding the polypeptide of SEQ ID NO: 185 or a fragment thereof. In some embodiments, the polypeptide of SEQ ID NO: 185, or a fragment thereof, is encoded by the polynucleotide of SEQ ID NO: 186 or a fragment thereof.

The disclosure also provides an isolated polynucleotide encoding the polypeptide of SEQ ID NO: 187 or a fragment thereof. In some embodiments, the polypeptide of SEQ ID NO: 187, or a fragment thereof, is encoded by the polynucleotide of SEQ ID NO: 188 or a fragment thereof.

The disclosure also provides an isolated polynucleotide encoding the polypeptide of SEQ ID NO: 189 or a fragment thereof. In some embodiments, the polypeptide of SEQ ID NO: 189, or a fragment thereof, is encoded by the polynucleotide of SEQ ID NO: 190 or a fragment thereof.

The disclosure also provides an isolated polynucleotide encoding the polypeptide of SEQ ID NO: 191 or a fragment thereof. In some embodiments, the polypeptide of SEQ ID NO: 191, or a fragment thereof, is encoded by the polynucleotide of SEQ ID NO: 192 or a fragment thereof.

The disclosure also provides an isolated polynucleotide encoding the polypeptide of SEQ ID NO: 193 or a fragment thereof. In some embodiments, the polypeptide of SEQ ID NO: 193, or a fragment thereof, is encoded by the polynucleotide of SEQ ID NO: 194 or a fragment thereof.

The disclosure also provides an isolated polynucleotide encoding the polypeptide of SEQ ID NO: 195 or a fragment thereof. In some embodiments, the polypeptide of SEQ ID NO: 195, or a fragment thereof, is encoded by the polynucleotide of SEQ ID NO: 196 or a fragment thereof.

The disclosure also provides an isolated polynucleotide encoding the polypeptide of SEQ ID NO: 197 or a fragment thereof. In some embodiments, the polypeptide of SEQ ID NO: 197, or a fragment thereof, is encoded by the polynucleotide of SEQ ID NO: 198 or a fragment thereof.

The disclosure also provides an isolated polynucleotide encoding the polypeptide of SEQ ID NO: 199 or a fragment thereof. In some embodiments, the polypeptide of SEQ ID NO: 199, or a fragment thereof, is encoded by the polynucleotide of SEQ ID NO: 200 or a fragment thereof.

The disclosure also provides an isolated polynucleotide encoding the polypeptide of SEQ ID NO: 201 or a fragment thereof. In some embodiments, the polypeptide of SEQ ID NO: 201, or a fragment thereof, is encoded by the polynucleotide of SEQ ID NO: 202 or a fragment thereof.

The disclosure also provides an isolated polynucleotide encoding the polypeptide of SEQ ID NO: 203 or a fragment thereof. In some embodiments, the polypeptide of SEQ ID NO: 203, or a fragment thereof, is encoded by the polynucleotide of SEQ ID NO: 204 or a fragment thereof.

The disclosure also provides an isolated polynucleotide encoding the polypeptide of SEQ ID NO: 205 or a fragment thereof. In some embodiments, the polypeptide of SEQ ID NO: 205, or a fragment thereof, is encoded by the polynucleotide of SEQ ID NO: 206 or a fragment thereof.

The disclosure also provides an isolated polynucleotide encoding the polypeptide of SEQ ID NO: 207 or a fragment thereof. In some embodiments, the polypeptide of SEQ ID NO: 207, or a fragment thereof, is encoded by the polynucleotide of SEQ ID NO: 208 or a fragment thereof.

The disclosure also provides an isolated polynucleotide encoding the polypeptide of SEQ ID NO: 209 or a fragment thereof. In some embodiments, the polypeptide of SEQ ID NO: 209, or a fragment thereof, is encoded by the polynucleotide of SEQ ID NO: 210 or a fragment thereof.

The disclosure also provides an isolated polynucleotide encoding the polypeptide of SEQ ID NO: 211 or a fragment thereof. In some embodiments, the polypeptide of SEQ ID NO: 211, or a fragment thereof, is encoded by the polynucleotide of SEQ ID NO: 212 or a fragment thereof. In some embodiments, the polypeptide of SEQ ID NO: 211, or a fragment thereof, is encoded by the polynucleotide of SEQ ID NO: 484 or a fragment thereof. In some embodiments, the polypeptide of SEQ ID NO: 211, or a fragment thereof, is encoded by the polynucleotide of SEQ ID NO: 525 or a fragment thereof.

The disclosure also provides an isolated polynucleotide encoding the polypeptide of SEQ ID NO: 213 or a fragment thereof. In some embodiments, the polypeptide of SEQ ID NO: 213, or a fragment thereof, is encoded by the polynucleotide of SEQ ID NO: 214 or a fragment thereof. In some embodiments, the polypeptide of SEQ ID NO: 213, or a fragment thereof, is encoded by the polynucleotide of SEQ ID NO: 486 or a fragment thereof.

The disclosure also provides an isolated polynucleotide encoding the polypeptide of SEQ ID NO: 215 or a fragment thereof. In some embodiments, the polypeptide of SEQ ID NO: 215, or a fragment thereof, is encoded by the polynucleotide of SEQ ID NO: 216 or a fragment thereof. In some embodiments, the polypeptide of SEQ ID NO: 215, or a fragment thereof, is encoded by the polynucleotide of SEQ ID NO: 487 or a fragment thereof. In some embodiments, the polypeptide of SEQ ID NO: 215, or a fragment thereof, is encoded by the polynucleotide of SEQ ID NO: 528 or a fragment thereof.

The disclosure also provides an isolated polynucleotide encoding the polypeptide of SEQ ID NO: 217 or a fragment thereof. In some embodiments, the polypeptide of SEQ ID NO: 217, or a fragment thereof, is encoded by the polynucleotide of SEQ ID NO: 218 or a fragment thereof.

The disclosure also provides an isolated polynucleotide encoding the polypeptide of SEQ ID NO: 219 or a fragment thereof. In some embodiments, the polypeptide of SEQ ID NO: 219, or a fragment thereof, is encoded by the polynucleotide of SEQ ID NO: 220 or a fragment thereof. In some embodiments, the polypeptide of SEQ ID NO: 219, or a fragment thereof, is encoded by the polynucleotide of SEQ ID NO: 489 or a fragment thereof. In some embodiments, the polypeptide of SEQ ID NO: 219, or a fragment thereof, is encoded by the polynucleotide of SEQ ID NO: 530 or a fragment thereof.

The disclosure also provides an isolated polynucleotide encoding the polypeptide of SEQ ID NO: 221 or a fragment thereof. In some embodiments, the polypeptide of SEQ ID NO: 221, or a fragment thereof, is encoded by the polynucleotide of SEQ ID NO: 222 or a fragment thereof. In some embodiments, the polypeptide of SEQ ID NO: 221, or a fragment thereof, is encoded by the polynucleotide of SEQ ID NO: 488 or a fragment thereof. In some embodiments, the polypeptide of SEQ ID NO: 221, or a fragment thereof, is encoded by the polynucleotide of SEQ ID NO: 529 or a fragment thereof.

The disclosure also provides an isolated polynucleotide encoding the polypeptide of SEQ ID NO: 223 or a fragment thereof. In some embodiments, the polypeptide of SEQ ID NO: 223, or a fragment thereof, is encoded by the polynucleotide of SEQ ID NO: 224 or a fragment thereof. In some embodiments, the polypeptide of SEQ ID NO: 223, or a fragment thereof, is encoded by the polynucleotide of SEQ ID NO: 494 or a fragment thereof. In some embodiments, the polypeptide of SEQ ID NO: 223, or a fragment thereof, is encoded by the polynucleotide of SEQ ID NO: 535 or a fragment thereof.

The disclosure also provides an isolated polynucleotide encoding the polypeptide of SEQ ID NO: 225 or a fragment thereof. In some embodiments, the polypeptide of SEQ ID NO: 225, or a fragment thereof, is encoded by the polynucleotide of SEQ ID NO: 226 or a fragment thereof. In some embodiments, the polypeptide of SEQ ID NO: 225, or a fragment thereof, is encoded by the polynucleotide of SEQ ID NO: 490 or a fragment thereof. In some embodiments, the polypeptide of SEQ ID NO: 225, or a fragment thereof, is encoded by the polynucleotide of SEQ ID NO: 531 or a fragment thereof.

The disclosure also provides an isolated polynucleotide encoding the polypeptide of SEQ ID NO: 227 or a fragment thereof. In some embodiments, the polypeptide of SEQ ID NO: 227, or a fragment thereof, is encoded by the polynucleotide of SEQ ID NO: 228 or a fragment thereof.

The disclosure also provides an isolated polynucleotide encoding the polypeptide of SEQ ID NO: 229 or a fragment thereof. In some embodiments, the polypeptide of SEQ ID NO: 229, or a fragment thereof, is encoded by the polynucleotide of SEQ ID NO: 230 or a fragment thereof.

The disclosure also provides an isolated polynucleotide encoding the polypeptide of SEQ ID NO: 231 or a fragment thereof. In some embodiments, the polypeptide of SEQ ID NO: 231, or a fragment thereof, is encoded by the polynucleotide of SEQ ID NO: 232 or a fragment thereof.

The disclosure also provides an isolated polynucleotide encoding the polypeptide of SEQ ID NO: 233 or a fragment thereof. In some embodiments, the polypeptide of SEQ ID NO: 233, or a fragment thereof, is encoded by the polynucleotide of SEQ ID NO: 234 or a fragment thereof.

The disclosure also provides an isolated polynucleotide encoding the polypeptide of SEQ ID NO: 235 or a fragment thereof. In some embodiments, the polypeptide of SEQ ID NO: 235, or a fragment thereof, is encoded by the polynucleotide of SEQ ID NO: 236 or a fragment thereof. In some embodiments, the polypeptide of SEQ ID NO: 235, or a fragment thereof, is encoded by the polynucleotide of SEQ ID NO: 493 or a fragment thereof. In some embodiments, the polypeptide of SEQ ID NO: 235, or a fragment thereof, is encoded by the polynucleotide of SEQ ID NO: 534 or a fragment thereof.

The disclosure also provides an isolated polynucleotide encoding the polypeptide of SEQ ID NO: 237 or a fragment thereof. In some embodiments, the polypeptide of SEQ ID NO: 237, or a fragment thereof, is encoded by the polynucleotide of SEQ ID NO: 238 or a fragment thereof.

The disclosure also provides an isolated polynucleotide encoding the polypeptide of SEQ ID NO: 239 or a fragment thereof. In some embodiments, the polypeptide of SEQ ID NO: 239, or a fragment thereof, is encoded by the polynucleotide of SEQ ID NO: 240 or a fragment thereof.

The disclosure also provides an isolated polynucleotide encoding the polypeptide of SEQ ID NO: 241 or a fragment thereof. In some embodiments, the polypeptide of SEQ ID NO: 241, or a fragment thereof, is encoded by the polynucleotide of SEQ ID NO: 242 or a fragment thereof.

The disclosure also provides an isolated polynucleotide encoding the polypeptide of SEQ ID NO: 243 or a fragment thereof. In some embodiments, the polypeptide of SEQ ID NO: 243, or a fragment thereof, is encoded by the polynucleotide of SEQ ID NO: 244 or a fragment thereof.

The disclosure also provides an isolated polynucleotide encoding the polypeptide of SEQ ID NO: 245 or a fragment thereof. In some embodiments, the polypeptide of SEQ ID NO: 245, or a fragment thereof, is encoded by the polynucleotide of SEQ ID NO: 246 or a fragment thereof. In some embodiments, the polypeptide of SEQ ID NO: 245, or a fragment thereof, is encoded by the polynucleotide of SEQ ID NO: 470 or a fragment thereof. In some embodiments, the polypeptide of SEQ ID NO: 245, or a fragment thereof, is encoded by the polynucleotide of SEQ ID NO: 511 or a fragment thereof.

The disclosure also provides an isolated polynucleotide encoding the polypeptide of SEQ ID NO: 247 or a fragment thereof. In some embodiments, the polypeptide of SEQ ID NO: 247, or a fragment thereof, is encoded by the polynucleotide of SEQ ID NO: 248 or a fragment thereof.

The disclosure also provides an isolated polynucleotide encoding the polypeptide of SEQ ID NO: 249 or a fragment thereof. In some embodiments, the polypeptide of SEQ ID NO: 249, or a fragment thereof, is encoded by the polynucleotide of SEQ ID NO: 250 or a fragment thereof.

The disclosure also provides an isolated polynucleotide encoding the polypeptide of SEQ ID NO: 251 or a fragment thereof. In some embodiments, the polypeptide of SEQ ID NO: 251, or a fragment thereof, is encoded by the polynucleotide of SEQ ID NO: 252 or a fragment thereof. In some embodiments, the polypeptide of SEQ ID NO: 251, or a fragment thereof, is encoded by the polynucleotide of SEQ ID NO: 469 or a fragment thereof. In some embodiments, the polypeptide of SEQ ID NO: 251, or a fragment thereof, is encoded by the polynucleotide of SEQ ID NO: 510 or a fragment thereof.

The disclosure also provides an isolated polynucleotide encoding the polypeptide of SEQ ID NO: 253 or a fragment thereof. In some embodiments, the polypeptide of SEQ ID NO: 253, or a fragment thereof, is encoded by the polynucleotide of SEQ ID NO: 254 or a fragment thereof. In some embodiments, the polypeptide of SEQ ID NO: 253, or a fragment thereof, is encoded by the polynucleotide of SEQ ID NO: 464 or a fragment thereof. In some embodiments, the polypeptide of SEQ ID NO: 253, or a fragment thereof, is encoded by the polynucleotide of SEQ ID NO: 505 or a fragment thereof.

The disclosure also provides an isolated polynucleotide encoding the polypeptide of SEQ ID NO: 255 or a fragment thereof. In some embodiments, the polypeptide of SEQ ID NO: 255, or a fragment thereof, is encoded by the polynucleotide of SEQ ID NO: 256 or a fragment thereof. In some embodiments, the polypeptide of SEQ ID NO: 255, or a fragment thereof, is encoded by the polynucleotide of SEQ ID NO: 474 or a fragment thereof. In some embodiments, the polypeptide of SEQ ID NO: 255, or a fragment thereof, is encoded by the polynucleotide of SEQ ID NO: 515 or a fragment thereof.

The disclosure also provides an isolated polynucleotide encoding the polypeptide of SEQ ID NO: 257 or a fragment thereof. In some embodiments, the polypeptide of SEQ ID NO: 257, or a fragment thereof, is encoded by the polynucleotide of SEQ ID NO: 258 or a fragment thereof.

The disclosure also provides an isolated polynucleotide encoding the polypeptide of SEQ ID NO: 259 or a fragment thereof. In some embodiments, the polypeptide of SEQ ID NO: 259, or a fragment thereof, is encoded by the polynucleotide of SEQ ID NO: 260 or a fragment thereof.

The disclosure also provides an isolated polynucleotide encoding the polypeptide of SEQ ID NO: 261 or a fragment thereof. In some embodiments, the polypeptide of SEQ ID NO: 261, or a fragment thereof, is encoded by the polynucleotide of SEQ ID NO: 262 or a fragment thereof. In some embodiments, the polypeptide of SEQ ID NO: 261, or a fragment thereof, is encoded by the polynucleotide of SEQ ID NO: 471 or a fragment thereof. In some embodiments, the polypeptide of SEQ ID NO: 261, or a fragment thereof, is encoded by the polynucleotide of SEQ ID NO: 512 or a fragment thereof.

The disclosure also provides an isolated polynucleotide encoding the polypeptide of SEQ ID NO: 263 or a fragment thereof. In some embodiments, the polypeptide of SEQ ID NO: 263, or a fragment thereof, is encoded by the polynucleotide of SEQ ID NO: 264 or a fragment thereof.

The disclosure also provides an isolated polynucleotide encoding the polypeptide of SEQ ID NO: 265 or a fragment thereof. In some embodiments, the polypeptide of SEQ ID NO: 265, or a fragment thereof, is encoded by the polynucleotide of SEQ ID NO: 266 or a fragment thereof. In some embodiments, the polypeptide of SEQ ID NO: 265, or a fragment thereof, is encoded by the polynucleotide of SEQ ID NO: 472 or a fragment thereof. In some embodiments, the polypeptide of SEQ ID NO: 265, or a fragment thereof, is encoded by the polynucleotide of SEQ ID NO: 513 or a fragment thereof.

The disclosure also provides an isolated polynucleotide encoding the polypeptide of SEQ ID NO: 267 or a fragment thereof. In some embodiments, the polypeptide of SEQ ID NO: 267, or a fragment thereof, is encoded by the polynucleotide of SEQ ID NO: 268 or a fragment thereof.

The disclosure also provides an isolated polynucleotide encoding the polypeptide of SEQ ID NO: 269 or a fragment thereof. In some embodiments, the polypeptide of SEQ ID NO: 269, or a fragment thereof, is encoded by the polynucleotide of SEQ ID NO: 270 or a fragment thereof. In some embodiments, the polypeptide of SEQ ID NO: 269, or a fragment thereof, is encoded by the polynucleotide of SEQ ID NO: 463 or a fragment thereof. In some embodiments, the polypeptide of SEQ ID NO: 269, or a fragment thereof, is encoded by the polynucleotide of SEQ ID NO: 504 or a fragment thereof.

The disclosure also provides an isolated polynucleotide encoding the polypeptide of SEQ ID NO: 271 or a fragment thereof. In some embodiments, the polypeptide of SEQ ID NO: 271, or a fragment thereof, is encoded by the polynucleotide of SEQ ID NO: 272 or a fragment thereof. In some embodiments, the polypeptide of SEQ ID NO: 271, or a fragment thereof, is encoded by the polynucleotide of SEQ ID NO: 465 or a fragment thereof. In some embodiments, the polypeptide of SEQ ID NO: 271, or a fragment thereof, is encoded by the polynucleotide of SEQ ID NO: 508 or a fragment thereof.

The disclosure also provides an isolated polynucleotide encoding the polypeptide of SEQ ID NO: 273 or a fragment thereof. In some embodiments, the polypeptide of SEQ ID NO: 273, or a fragment thereof, is encoded by the polynucleotide of SEQ ID NO: 274 or a fragment thereof.

The disclosure also provides an isolated polynucleotide encoding the polypeptide of SEQ ID NO: 275 or a fragment thereof. In some embodiments, the polypeptide of SEQ ID NO: 275, or a fragment thereof, is encoded by the polynucleotide of SEQ ID NO: 276 or a fragment thereof. In some embodiments, the polypeptide of SEQ ID NO: 275, or a fragment thereof, is encoded by the polynucleotide of SEQ ID NO: 459 or a fragment thereof. In some embodiments, the polypeptide of SEQ ID NO: 275, or a fragment thereof, is encoded by the polynucleotide of SEQ ID NO: 500 or a fragment thereof.

The disclosure also provides an isolated polynucleotide encoding the polypeptide of SEQ ID NO: 277 or a fragment thereof. In some embodiments, the polypeptide of SEQ ID NO: 277, or a fragment thereof, is encoded by the polynucleotide of SEQ ID NO: 278 or a fragment thereof. In some embodiments, the polypeptide of SEQ ID NO: 277, or a fragment thereof, is encoded by the polynucleotide of SEQ ID NO: 475 or a fragment thereof. In some embodiments, the polypeptide of SEQ ID NO: 277, or a fragment thereof, is encoded by the polynucleotide of SEQ ID NO: 516 or a fragment thereof.

The disclosure also provides an isolated polynucleotide encoding the polypeptide of SEQ ID NO: 279 or a fragment thereof. In some embodiments, the polypeptide of SEQ ID NO: 279, or a fragment thereof, is encoded by the polynucleotide of SEQ ID NO: 280 or a fragment thereof.

The disclosure also provides an isolated polynucleotide encoding the polypeptide of SEQ ID NO: 281 or a fragment thereof. In some embodiments, the polypeptide of SEQ ID NO: 281, or a fragment thereof, is encoded by the polynucleotide of SEQ ID NO: 282 or a fragment thereof.

The disclosure also provides an isolated polynucleotide encoding the polypeptide of SEQ ID NO: 283 or a fragment thereof. In some embodiments, the polypeptide of SEQ ID NO: 283, or a fragment thereof, is encoded by the polynucleotide of SEQ ID NO: 284 or a fragment thereof.

The disclosure also provides an isolated polynucleotide encoding the polypeptide of SEQ ID NO: 285 or a fragment thereof. In some embodiments, the polypeptide of SEQ ID NO: 285, or a fragment thereof, is encoded by the polynucleotide of SEQ ID NO: 286 or a fragment thereof. In some embodiments, the polypeptide of SEQ ID NO: 285, or a fragment thereof, is encoded by the polynucleotide of SEQ ID NO: 477 or a fragment thereof.

The disclosure also provides an isolated polynucleotide encoding the polypeptide of SEQ ID NO: 287 or a fragment thereof. In some embodiments, the polypeptide of SEQ ID NO: 287, or a fragment thereof, is encoded by the polynucleotide of SEQ ID NO: 288 or a fragment thereof.

The disclosure also provides an isolated polynucleotide encoding the polypeptide of SEQ ID NO: 289 or a fragment thereof. In some embodiments, the polypeptide of SEQ ID NO: 289, or a fragment thereof, is encoded by the polynucleotide of SEQ ID NO: 290 or a fragment thereof.

The disclosure also provides an isolated polynucleotide encoding the polypeptide of SEQ ID NO: 291 or a fragment thereof. In some embodiments, the polypeptide of SEQ ID NO: 291, or a fragment thereof, is encoded by the polynucleotide of SEQ ID NO: 292 or a fragment thereof.

The disclosure also provides an isolated polynucleotide encoding the polypeptide of SEQ ID NO: 293 or a fragment thereof. In some embodiments, the polypeptide of SEQ ID NO: 293, or a fragment thereof, is encoded by the polynucleotide of SEQ ID NO: 294 or a fragment thereof.

The disclosure also provides an isolated polynucleotide encoding the polypeptide of SEQ ID NO: 295 or a fragment thereof. In some embodiments, the polypeptide of SEQ ID NO: 295, or a fragment thereof, is encoded by the polynucleotide of SEQ ID NO: 296 or a fragment thereof.

The disclosure also provides an isolated polynucleotide encoding the polypeptide of SEQ ID NO: 297 or a fragment thereof. In some embodiments, the polypeptide of SEQ ID NO: 297, or a fragment thereof, is encoded by the polynucleotide of SEQ ID NO: 298 or a fragment thereof. In some embodiments, the polypeptide of SEQ ID NO: 297, or a fragment thereof, is encoded by the polynucleotide of SEQ ID NO: 476 or a fragment thereof. In some embodiments, the polypeptide of SEQ ID NO: 297, or a fragment thereof, is encoded by the polynucleotide of SEQ ID NO: 517 or a fragment thereof.

The disclosure also provides an isolated polynucleotide encoding the polypeptide of SEQ ID NO: 299 or a fragment thereof. In some embodiments, the polypeptide of SEQ ID NO: 299, or a fragment thereof, is encoded by the polynucleotide of SEQ ID NO: 300 or a fragment thereof.

The disclosure also provides an isolated polynucleotide encoding the polypeptide of SEQ ID NO: 301 or a fragment thereof. In some embodiments, the polypeptide of SEQ ID NO: 301, or a fragment thereof, is encoded by the polynucleotide of SEQ ID NO: 302 or a fragment thereof.

The disclosure also provides an isolated polynucleotide encoding the polypeptide of SEQ ID NO: 303 or a fragment thereof. In some embodiments, the polypeptide of SEQ ID NO: 303, or a fragment thereof, is encoded by the polynucleotide of SEQ ID NO: 304 or a fragment thereof.

The disclosure also provides an isolated polynucleotide encoding the polypeptide of SEQ ID NO: 305 or a fragment thereof. In some embodiments, the polypeptide of SEQ ID NO: 305, or a fragment thereof, is encoded by the polynucleotide of SEQ ID NO: 306 or a fragment thereof. In some embodiments, the polypeptide of SEQ ID NO: 305, or a fragment thereof, is encoded by the polynucleotide of SEQ ID NO: 468 or a fragment thereof. In some embodiments, the polypeptide of SEQ ID NO: 305, or a fragment thereof, is encoded by the polynucleotide of SEQ ID NO: 509 or a fragment thereof.

The disclosure also provides an isolated polynucleotide encoding the polypeptide of SEQ ID NO: 307 or a fragment thereof. In some embodiments, the polypeptide of SEQ ID NO: 307, or a fragment thereof, is encoded by the polynucleotide of SEQ ID NO: 308 or a fragment thereof.

The disclosure also provides an isolated polynucleotide encoding the polypeptide of SEQ ID NO: 309 or a fragment thereof. In some embodiments, the polypeptide of SEQ ID NO: 309, or a fragment thereof, is encoded by the polynucleotide of SEQ ID NO: 310 or a fragment thereof. In some embodiments, the polypeptide of SEQ ID NO: 309, or a fragment thereof, is encoded by the polynucleotide of SEQ ID NO: 465 or a fragment thereof. In some embodiments, the polypeptide of SEQ ID NO: 309, or a fragment thereof, is encoded by the polynucleotide of SEQ ID NO: 506 or a fragment thereof.

The disclosure also provides an isolated polynucleotide encoding the polypeptide of SEQ ID NO: 311 or a fragment thereof. In some embodiments, the polypeptide of SEQ ID NO: 311, or a fragment thereof, is encoded by the polynucleotide of SEQ ID NO: 312 or a fragment thereof.

The disclosure also provides an isolated polynucleotide encoding the polypeptide of SEQ ID NO: 313 or a fragment thereof. In some embodiments, the polypeptide of SEQ ID NO: 313, or a fragment thereof, is encoded by the polynucleotide of SEQ ID NO: 314 or a fragment thereof.

The disclosure also provides an isolated polynucleotide encoding the polypeptide of SEQ ID NO: 315 or a fragment thereof. In some embodiments, the polypeptide of SEQ ID NO: 315, or a fragment thereof, is encoded by the polynucleotide of SEQ ID NO: 316 or a fragment thereof.

The disclosure also provides an isolated polynucleotide encoding the polypeptide of SEQ ID NO: 317 or a fragment thereof. In some embodiments, the polypeptide of SEQ ID NO: 317, or a fragment thereof, is encoded by the polynucleotide of SEQ ID NO: 318 or a fragment thereof. In some embodiments, the polypeptide of SEQ ID NO: 317, or a fragment thereof, is encoded by the polynucleotide of SEQ ID NO: 473 or a fragment thereof. In some embodiments, the polypeptide of SEQ ID NO: 317, or a fragment thereof, is encoded by the polynucleotide of SEQ ID NO: 514 or a fragment thereof.

The disclosure also provides an isolated polynucleotide encoding the polypeptide of SEQ ID NO: 319 or a fragment thereof. In some embodiments, the polypeptide of SEQ ID NO: 319, or a fragment thereof, is encoded by the polynucleotide of SEQ ID NO: 320 or a fragment thereof.

The disclosure also provides an isolated polynucleotide encoding the polypeptide of SEQ ID NO: 321 or a fragment thereof. In some embodiments, the polypeptide of SEQ ID NO: 321, or a fragment thereof, is encoded by the polynucleotide of SEQ ID NO: 322 or a fragment thereof.

The disclosure also provides an isolated polynucleotide encoding the polypeptide of SEQ ID NO: 323 or a fragment thereof. In some embodiments, the polypeptide of SEQ ID NO: 323, or a fragment thereof, is encoded by the polynucleotide of SEQ ID NO: 324 or a fragment thereof.

The disclosure also provides an isolated polynucleotide encoding the polypeptide of SEQ ID NO: 325 or a fragment thereof. In some embodiments, the polypeptide of SEQ ID NO: 325, or a fragment thereof, is encoded by the polynucleotide of SEQ ID NO: 326 or a fragment thereof. In some embodiments, the polypeptide of SEQ ID NO: 325, or a fragment thereof, is encoded by the polynucleotide of SEQ ID NO: 466 or a fragment thereof. In some embodiments, the polypeptide of SEQ ID NO: 325, or a fragment thereof, is encoded by the polynucleotide of SEQ ID NO: 507 or a fragment thereof.

The disclosure also provides an isolated polynucleotide encoding the polypeptide of SEQ ID NO: 327 or a fragment thereof. In some embodiments, the polypeptide of SEQ ID NO: 327, or a fragment thereof, is encoded by the polynucleotide of SEQ ID NO: 328 or a fragment thereof.

The disclosure also provides an isolated polynucleotide encoding the polypeptide of SEQ ID NO: 329 or a fragment thereof. In some embodiments, the polypeptide of SEQ ID NO: 329, or a fragment thereof, is encoded by the polynucleotide of SEQ ID NO: 330 or a fragment thereof.

The disclosure also provides an isolated polynucleotide encoding the polypeptide of SEQ ID NO: 331 or a fragment thereof. In some embodiments, the polypeptide of SEQ ID NO: 331, or a fragment thereof, is encoded by the polynucleotide of SEQ ID NO: 332 or a fragment thereof.

The disclosure also provides an isolated polynucleotide encoding the polypeptide of SEQ ID NO: 333 or a fragment thereof. In some embodiments, the polypeptide of SEQ ID NO: 333, or a fragment thereof, is encoded by the polynucleotide of SEQ ID NO: 334 or a fragment thereof. In some embodiments, the polypeptide of SEQ ID NO: 333, or a fragment thereof, is encoded by the polynucleotide of SEQ ID NO: 461 or a fragment thereof.

The disclosure also provides an isolated polynucleotide encoding the polypeptide of SEQ ID NO: 335 or a fragment thereof. In some embodiments, the polypeptide of SEQ ID NO: 335, or a fragment thereof, is encoded by the polynucleotide of SEQ ID NO: 336 or a fragment thereof.

The disclosure also provides an isolated polynucleotide encoding the polypeptide of SEQ ID NO: 337 or a fragment thereof. In some embodiments, the polypeptide of SEQ ID NO: 337, or a fragment thereof, is encoded by the polynucleotide of SEQ ID NO: 338 or a fragment thereof. In some embodiments, the polypeptide of SEQ ID NO: 337, or a fragment thereof, is encoded by the polynucleotide of SEQ ID NO: 462 or a fragment thereof. In some embodiments, the polypeptide of SEQ ID NO: 337, or a fragment thereof, is encoded by the polynucleotide of SEQ ID NO: 503 or a fragment thereof.

The disclosure also provides an isolated polynucleotide encoding the polypeptide of SEQ ID NO: 339 or a fragment thereof. In some embodiments, the polypeptide of SEQ ID NO: 339, or a fragment thereof, is encoded by the polynucleotide of SEQ ID NO: 340 or a fragment thereof.

The disclosure also provides an isolated polynucleotide encoding the polypeptide of SEQ ID NO: 341 or a fragment thereof. In some embodiments, the polypeptide of SEQ ID NO: 341, or a fragment thereof, is encoded by the polynucleotide of SEQ ID NO: 342 or a fragment thereof.

The disclosure also provides an isolated polynucleotide encoding the polypeptide of SEQ ID NO: 343 or a fragment thereof. In some embodiments, the polypeptide of SEQ ID NO: 343, or a fragment thereof, is encoded by the polynucleotide of SEQ ID NO: 344 or a fragment thereof. In some embodiments, the polypeptide of SEQ ID NO: 343, or a fragment thereof, is encoded by the polynucleotide of SEQ ID NO: 483 or a fragment thereof. In some embodiments, the polypeptide of SEQ ID NO: 343, or a fragment thereof, is encoded by the polynucleotide of SEQ ID NO: 524 or a fragment thereof.

The disclosure also provides an isolated polynucleotide encoding the polypeptide of SEQ ID NO: 345 or a fragment thereof. In some embodiments, the polypeptide of SEQ ID NO: 345, or a fragment thereof, is encoded by the polynucleotide of SEQ ID NO: 346 or a fragment thereof. In some embodiments, the polypeptide of SEQ ID NO: 345, or a fragment thereof, is encoded by the polynucleotide of SEQ ID NO: 491 or a fragment thereof. In some embodiments, the polypeptide of SEQ ID NO: 345, or a fragment thereof, is encoded by the polynucleotide of SEQ ID NO: 532 or a fragment thereof.

The disclosure also provides an isolated polynucleotide encoding the polypeptide of SEQ ID NO: 347 or a fragment thereof. In some embodiments, the polypeptide of SEQ ID NO: 347, or a fragment thereof, is encoded by the polynucleotide of SEQ ID NO: 348 or a fragment thereof.

The disclosure also provides an isolated polynucleotide encoding the polypeptide of SEQ ID NO: 349 or a fragment thereof. In some embodiments, the polypeptide of SEQ ID NO: 349, or a fragment thereof, is encoded by the polynucleotide of SEQ ID NO: 350 or a fragment thereof. In some embodiments, the polypeptide of SEQ ID NO: 349, or a fragment thereof, is encoded by the polynucleotide of SEQ ID NO: 485 or a fragment thereof.

The disclosure also provides an isolated polynucleotide encoding the polypeptide of SEQ ID NO: 351 or a fragment thereof. In some embodiments, the polypeptide of SEQ ID NO: 351, or a fragment thereof, is encoded by the polynucleotide of SEQ ID NO: 352 or a fragment thereof.

The disclosure also provides an isolated polynucleotide encoding the polypeptide of SEQ ID NO: 353 or a fragment thereof. In some embodiments, the polypeptide of SEQ ID NO: 353, or a fragment thereof, is encoded by the polynucleotide of SEQ ID NO: 354 or a fragment thereof. In some embodiments, the polypeptide of SEQ ID NO: 353, or a fragment thereof, is encoded by the polynucleotide of SEQ ID NO: 492 or a fragment thereof. In some embodiments, the polypeptide of SEQ ID NO: 353, or a fragment thereof, is encoded by the polynucleotide of SEQ ID NO: 533 or a fragment thereof.

The disclosure also provides an isolated polynucleotide encoding the polypeptide of SEQ ID NO: 355 or a fragment thereof. In some embodiments, the polypeptide of SEQ ID NO: 355, or a fragment thereof, is encoded by the polynucleotide of SEQ ID NO: 356 or a fragment thereof.

The disclosure also provides an isolated polynucleotide encoding the polypeptide of SEQ ID NO: 357 or a fragment thereof. In some embodiments, the polypeptide of SEQ ID NO: 357, or a fragment thereof, is encoded by the polynucleotide of SEQ ID NO: 358 or a fragment thereof.

The disclosure also provides an isolated polynucleotide encoding the polypeptide of SEQ ID NO: 359 or a fragment thereof. In some embodiments, the polypeptide of SEQ ID NO: 359, or a fragment thereof, is encoded by the polynucleotide of SEQ ID NO: 360 or a fragment thereof.

The disclosure also provides an isolated polynucleotide encoding the polypeptide of SEQ ID NO: 361 or a fragment thereof. In some embodiments, the polypeptide of SEQ ID NO: 361, or a fragment thereof, is encoded by the polynucleotide of SEQ ID NO: 362 or a fragment thereof.

The disclosure also provides an isolated polynucleotide encoding the polypeptide of SEQ ID NO: 363 or a fragment thereof. In some embodiments, the polypeptide of SEQ ID NO: 363, or a fragment thereof, is encoded by the polynucleotide of SEQ ID NO: 364 or a fragment thereof.

The disclosure also provides an isolated polynucleotide encoding the polypeptide of SEQ ID NO: 365 or a fragment thereof. In some embodiments, the polypeptide of SEQ ID NO: 365, or a fragment thereof, is encoded by the polynucleotide of SEQ ID NO: 366 or a fragment thereof.

The disclosure also provides an isolated polynucleotide encoding the polypeptide of SEQ ID NO: 367 or a fragment thereof. In some embodiments, the polypeptide of SEQ ID NO: 367, or a fragment thereof, is encoded by the polynucleotide of SEQ ID NO: 368 or a fragment thereof.

The disclosure also provides an isolated polynucleotide encoding the polypeptide of SEQ ID NO: 369 or a fragment thereof. In some embodiments, the polypeptide of SEQ ID NO: 369, or a fragment thereof, is encoded by the polynucleotide of SEQ ID NO: 370 or a fragment thereof.

The disclosure also provides an isolated polynucleotide encoding the polypeptide of SEQ ID NO: 371 or a fragment thereof. In some embodiments, the polypeptide of SEQ ID NO: 371, or a fragment thereof, is encoded by the polynucleotide of SEQ ID NO: 372 or a fragment thereof.

The disclosure also provides an isolated polynucleotide encoding the polypeptide of SEQ ID NO: 373 or a fragment thereof. In some embodiments, the polypeptide of SEQ ID NO: 373, or a fragment thereof, is encoded by the polynucleotide of SEQ ID NO: 374 or a fragment thereof.

The disclosure also provides an isolated polynucleotide encoding the polypeptide of SEQ ID NO: 375 or a fragment thereof. In some embodiments, the polypeptide of SEQ ID NO: 375, or a fragment thereof, is encoded by the polynucleotide of SEQ ID NO: 376 or a fragment thereof.

The disclosure also provides an isolated polynucleotide encoding the polypeptide of SEQ ID NO: 379 or a fragment thereof. In some embodiments, the polypeptide of SEQ ID NO: 379, or a fragment thereof, is encoded by the polynucleotide of SEQ ID NO: 380 or a fragment thereof. In some embodiments, the polypeptide of SEQ ID NO: 379, or a fragment thereof, is encoded by the polynucleotide of SEQ ID NO: 482 or a fragment thereof. In some embodiments, the polypeptide of SEQ ID NO: 379, or a fragment thereof, is encoded by the polynucleotide of SEQ ID NO: 523 or a fragment thereof.

The disclosure also provides an isolated polynucleotide encoding the polypeptide of SEQ ID NO: 381 or a fragment thereof. In some embodiments, the polypeptide of SEQ ID NO: 381, or a fragment thereof, is encoded by the polynucleotide of SEQ ID NO: 382 or a fragment thereof. In some embodiments, the polypeptide of SEQ ID NO: 381, or a fragment thereof, is encoded by the polynucleotide of SEQ ID NO: 460 or a fragment thereof. In some embodiments, the polypeptide of SEQ ID NO: 381, or a fragment thereof, is encoded by the polynucleotide of SEQ ID NO: 501 or a fragment thereof.

The disclosure also provides an isolated polynucleotide encoding the polypeptide of SEQ ID NO: 383 or a fragment thereof. In some embodiments, the polypeptide of SEQ ID NO: 383, or a fragment thereof, is encoded by the polynucleotide of SEQ ID NO: 384 or a fragment thereof.

The disclosure also provides an isolated polynucleotide encoding the polypeptide of SEQ ID NO: 385 or a fragment thereof. In some embodiments, the polypeptide of SEQ ID NO: 385, or a fragment thereof, is encoded by the polynucleotide of SEQ ID NO: 386 or a fragment thereof.

The disclosure also provides an isolated polynucleotide encoding the polypeptide of SEQ ID NO: 387 or a fragment thereof.

The disclosure also provides an isolated polynucleotide encoding the polypeptide of SEQ ID NO: 388 or a fragment thereof.

The disclosure also provides an isolated polynucleotide encoding the polypeptide of SEQ ID NO: 389 or a fragment thereof.

The disclosure also provides an isolated polynucleotide encoding the polypeptide of SEQ ID NO: 390 or a fragment thereof.

The disclosure also provides an isolated polynucleotide encoding the polypeptide of SEQ ID NO: 391 or a fragment thereof.

The disclosure also provides an isolated polynucleotide encoding the polypeptide of SEQ ID NO: 392 or a fragment thereof.

The disclosure also provides an isolated polynucleotide encoding the polypeptide of SEQ ID NO: 393 or a fragment thereof.

The disclosure also provides an isolated polynucleotide encoding the polypeptide of SEQ ID NO: 394 or a fragment thereof.

The disclosure also provides an isolated polynucleotide encoding the polypeptide of SEQ ID NO: 395 or a fragment thereof.

The disclosure also provides an isolated polynucleotide encoding the polypeptide of SEQ ID NO: 396 or a fragment thereof.

The disclosure also provides an isolated polynucleotide encoding the polypeptide of SEQ ID NO: 397 or a fragment thereof.

The disclosure also provides an isolated polynucleotide encoding the polypeptide of SEQ ID NO: 398 or a fragment thereof.

The disclosure also provides an isolated polynucleotide encoding the polypeptide of SEQ ID NO: 399 or a fragment thereof.

The disclosure also provides an isolated polynucleotide encoding the polypeptide of SEQ ID NO: 400 or a fragment thereof.

The disclosure also provides an isolated polynucleotide encoding the polypeptide of SEQ ID NO: 401 or a fragment thereof.

The disclosure also provides an isolated polynucleotide encoding the polypeptide of SEQ ID NO: 402 or a fragment thereof.

The disclosure also provides an isolated polynucleotide encoding the polypeptide of SEQ ID NO: 403 or a fragment thereof.

The disclosure also provides an isolated polynucleotide encoding the polypeptide of SEQ ID NO: 404 or a fragment thereof.

The disclosure also provides an isolated polynucleotide encoding the polypeptide of SEQ ID NO: 405 or a fragment thereof.

The disclosure also provides an isolated polynucleotide encoding the polypeptide of SEQ ID NO: 406 or a fragment thereof.

The disclosure also provides an isolated polynucleotide encoding the polypeptide of SEQ ID NO: 407 or a fragment thereof.

The disclosure also provides an isolated polynucleotide encoding the polypeptide of SEQ ID NO: 408 or a fragment thereof.

The disclosure also provides an isolated polynucleotide encoding the polypeptide of SEQ ID NO: 426 or a fragment thereof.

The disclosure also provides an isolated polynucleotide encoding the polypeptide of SEQ ID NO: 427 or a fragment thereof.

The disclosure also provides an isolated polynucleotide encoding the polypeptide of SEQ ID NO: 428 or a fragment thereof.

The disclosure also provides an isolated polynucleotide encoding the polypeptide of SEQ ID NO: 429 or a fragment thereof.

The disclosure also provides an isolated polynucleotide encoding the polypeptide of SEQ ID NO: 430 or a fragment thereof.

The disclosure also provides an isolated polynucleotide encoding the polypeptide of SEQ ID NO: 431 or a fragment thereof.

The disclosure also provides an isolated polynucleotide encoding the polypeptide of SEQ ID NO: 432 or a fragment thereof.

The disclosure also provides an isolated polynucleotide encoding the polypeptide of SEQ ID NO: 433 or a fragment thereof.

The disclosure also provides an isolated polynucleotide encoding the polypeptide of SEQ ID NO: 434 or a fragment thereof.

The disclosure also provides an isolated polynucleotide encoding the polypeptide of SEQ ID NO: 435 or a fragment thereof.

The disclosure also provides an isolated polynucleotide encoding the polypeptide of SEQ ID NO: 436 or a fragment thereof.

The disclosure also provides an isolated polynucleotide encoding the polypeptide of SEQ ID NO: 437 or a fragment thereof. In some embodiments, the polypeptide of SEQ ID NO: 437, or a fragment thereof, is encoded by the polynucleotide of SEQ ID NO: 448 or a fragment thereof. In some embodiments, the polypeptide of SEQ ID NO: 437, or a fragment thereof, is encoded by the polynucleotide of SEQ ID NO: 478 or a fragment thereof. In some embodiments, the polypeptide of SEQ ID NO: 437, or a fragment thereof, is encoded by the polynucleotide of SEQ ID NO: 519 or a fragment thereof.

The disclosure also provides an isolated polynucleotide encoding the polypeptide of SEQ ID NO: 438 or a fragment thereof. In some embodiments, the polypeptide of SEQ ID NO: 438, or a fragment thereof, is encoded by the polynucleotide of SEQ ID NO: 449 or a fragment thereof.

The disclosure also provides an isolated polynucleotide encoding the polypeptide of SEQ ID NO: 439 or a fragment thereof. In some embodiments, the polypeptide of SEQ ID NO: 439, or a fragment thereof, is encoded by the polynucleotide of SEQ ID NO: 450 or a fragment thereof. In some embodiments, the polypeptide of SEQ ID NO: 439, or a fragment thereof, is encoded by the polynucleotide of SEQ ID NO: 479 or a fragment thereof. In some embodiments, the polypeptide of SEQ ID NO: 439, or a fragment thereof, is encoded by the polynucleotide of SEQ ID NO: 520 or a fragment thereof.

The disclosure also provides an isolated polynucleotide encoding the polypeptide of SEQ ID NO: 440 or a fragment thereof. In some embodiments, the polypeptide of SEQ ID NO: 440, or a fragment thereof, is encoded by the polynucleotide of SEQ ID NO: 451 or a fragment thereof.

The disclosure also provides an isolated polynucleotide encoding the polypeptide of SEQ ID NO: 441 or a fragment thereof. In some embodiments, the polypeptide of SEQ ID NO: 441, or a fragment thereof, is encoded by the polynucleotide of SEQ ID NO: 452 or a fragment thereof.

The disclosure also provides an isolated polynucleotide encoding the polypeptide of SEQ ID NO: 442 or a fragment thereof. In some embodiments, the polypeptide of SEQ ID NO: 442, or a fragment thereof, is encoded by the polynucleotide of SEQ ID NO: 453 or a fragment thereof. In some embodiments, the polypeptide of SEQ ID NO: 442, or a fragment thereof, is encoded by the polynucleotide of SEQ ID NO: 480 or a fragment thereof. In some embodiments, the polypeptide of SEQ ID NO: 442, or a fragment thereof, is encoded by the polynucleotide of SEQ ID NO: 521 or a fragment thereof.

The disclosure also provides an isolated polynucleotide encoding the polypeptide of SEQ ID NO: 443 or a fragment thereof. In some embodiments, the polypeptide of SEQ ID NO: 443, or a fragment thereof, is encoded by the polynucleotide of SEQ ID NO: 454 or a fragment thereof.

The disclosure also provides an isolated polynucleotide encoding the polypeptide of SEQ ID NO: 444 or a fragment thereof. In some embodiments, the polypeptide of SEQ ID NO: 444, or a fragment thereof, is encoded by the polynucleotide of SEQ ID NO: 455 or a fragment thereof. In some embodiments, the polypeptide of SEQ ID NO: 444, or a fragment thereof, is encoded by the polynucleotide of SEQ ID NO: 481 or a fragment thereof. In some embodiments, the polypeptide of SEQ ID NO: 444, or a fragment thereof, is encoded by the polynucleotide of SEQ ID NO: 522 or a fragment thereof.

The disclosure also provides an isolated polynucleotide encoding the polypeptide of SEQ ID NO: 445 or a fragment thereof. In some embodiments, the polypeptide of SEQ ID NO: 445, or a fragment thereof, is encoded by the polynucleotide of SEQ ID NO: 456 or a fragment thereof.

The disclosure also provides an isolated polynucleotide encoding the polypeptide of SEQ ID NO: 446 or a fragment thereof. In some embodiments, the polypeptide of SEQ ID NO: 446, or a fragment thereof, is encoded by the polynucleotide of SEQ ID NO: 457 or a fragment thereof.

The disclosure also provides an isolated polynucleotide encoding the polypeptide of SEQ ID NO: 447 or a fragment thereof. In some embodiments, the polypeptide of SEQ ID NO: 447, or a fragment thereof, is encoded by the polynucleotide of SEQ ID NO: 458 or a fragment thereof.

In some embodiments, the heterologous polynucleotide is an in-frame heterologous polynucleotide.

The disclosure also provides an isolated heterologous polynucleotide comprising 3 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 4 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 5 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 6 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 7 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 8 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 9 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 10 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 11 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 12 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 13 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 14 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 15 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 16 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 17 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 18 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 19 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 20 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 21 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 22 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 23 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 24 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 25 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 26 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 27 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 28 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 29 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 30 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 31 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 32 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 33 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 34 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 35 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 36 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 37 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 38 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 39 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 40 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 41 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 42 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 43 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 44 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 45 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 46 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 47 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 48 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 49 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 50 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 51 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 52 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 53 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 54 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 55 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 56 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 57 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 58 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 59 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 60 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 61 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 62 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 63 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 64 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 65 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 66 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 67 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 68 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 69 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 70 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 71 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 72 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 73 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 74 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 75 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 76 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 77 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 78 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 79 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 80 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 81 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 82 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 83 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 84 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 85 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 86 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 87 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 88 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 89 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 90 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 91 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 92 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 93 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 94 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 95 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 96 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 97 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 98 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 99 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 100 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 101 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 102 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 103 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 104 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 105 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 106 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 107 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 108 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 109 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 110 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 111 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 112 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 113 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 114 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 115 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 116 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 117 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 118 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 119 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 120 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 121 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 122 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof. The disclosure also provides an isolated heterologous polynucleotide comprising 123 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 124 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 125 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 126 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 127 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 128 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 129 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 130 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 131 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 132 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 133 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 134 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 135 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 136 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 137 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 138 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 139 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 140 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 141 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 142 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 143 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 144 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 145 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 146 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 147 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 148 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 149 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 150 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 151 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 152 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 153 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 154 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 155 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 156 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 157 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 158 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 159 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 160 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 161 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 162 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 163 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 164 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 165 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 166 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 167 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 168 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 169 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 170 polynucleotides selected from the group consisting of SEQ ID NOs: 2, 4, 6, 8, 10, 12, 14, 16, 18, 386, 448, 449, 450, 451, 452, 453, 454, 455, 456, 457 and 458, and fragments thereof.

The disclosure also provides an isolated heterologous polynucleotide comprising 171 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 172 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 173 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 174 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 175 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 176 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 177 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 178 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 179 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 180 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 181 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 182 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 183 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 184 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 185 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 186 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 187 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 188 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 189 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 190 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 191 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 192 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 193 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 194 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 195 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 196 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 197 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 198 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 199 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 200 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 201 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 202 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 203 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 204 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 3 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 4 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 5 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 6 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 7 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 8 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 9 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 10 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 11 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 12 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 13 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 14 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 15 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 16 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 17 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 18 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 19 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 20 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 21 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 22 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 23 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 24 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 25 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 26 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 27 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 28 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 29 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 30 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 31 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 32 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 33 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 34 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 35 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 36 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 37 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 38 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 39 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 40 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

For expression in various hosts, the polynucleotides may be codon-optimized utilizing known methods. For example, for adenoviral expression, a heterologous polynucleotide comprising at least one of the polynucleotides of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 or 499 may be used. For expression in a modified vaccinia Ankara (MVA), a heterologous polynucleotide comprising at least one of the polynucleotides of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 or 540 may be used.

The disclosure also provides an isolated heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 3 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 4 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 5 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 6 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 7 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and thereof.

The disclosure also provides an isolated heterologous polynucleotide comprising 8 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 9 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and thereof.

The disclosure also provides an isolated heterologous polynucleotide comprising 10 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 11 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 12 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 13 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 14 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 15 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 16 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 17 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 18 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 19 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 20 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 21 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 22 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 23 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 24 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 25 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 26 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 27 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 28 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 29 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 30 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 31 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 32 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 33 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 34 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 35 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 36 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 37 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 38 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 39 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 40 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 3 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 4 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 5 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 6 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 7 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 8 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 9 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 10 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 11 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 12 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 13 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 14 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 15 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 16 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 17 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 18 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 19 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 20 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 21 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 22 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 23 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 24 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 25 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 26 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 27 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 28 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 29 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 30 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 31 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 32 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 33 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 34 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 35 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 36 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 37 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 38 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 39 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 40 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

In some embodiments, the isolated heterologous polynucleotide is an in-frame heterologous polynucleotide.

The disclosure also provides an isolated heterologous polynucleotide encoding a heterologous polypeptide comprising 3 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 4 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 5 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 6 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 7 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 8 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 9 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 10 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 11 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 12 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 13 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 14 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 15 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 16 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 17 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 18 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 19 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 20 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 21 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 22 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 23 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 24 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 25 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 26 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 27 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 28 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 29 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 30 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 31 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 32 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 33 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 34 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 35 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 36 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 37 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 38 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 39 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 40 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 41 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 42 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 43 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 44 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 45 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 46 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 47 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 48 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 49 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 50 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 51 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 52 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 53 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 54 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 55 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 56 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 57 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 58 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 59 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 60 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 61 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 62 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 63 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 64 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 65 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 66 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 67 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 68 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 69 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 70 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 71 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 72 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 73 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 74 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 75 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 76 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 77 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 78 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 79 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 80 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 81 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 82 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 83 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 84 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 85 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 86 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 87 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 88 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 89 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 90 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 91 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 92 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 93 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 94 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 95 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 96 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 97 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 98 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 99 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 100 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 101 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 102 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 103 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 104 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 105 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 106 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 107 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 108 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 109 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 110 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 111 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 112 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 113 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 114 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 115 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 116 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 117 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 118 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 119 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 120 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 121 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 122 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 123 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293,295, 297, 299, 301, 303, 305, 307, 309, 311, 313,315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 124 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293,295, 297, 299, 301, 303, 305, 307, 309, 311, 313,315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 125 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 126 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 127 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 128 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 129 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 130 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 131 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 132 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 133 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 134 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 135 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 136 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 137 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 138 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 139 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 140 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 141 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 142 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235,237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 143 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235,237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 144 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 145 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 146 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293,295, 297, 299, 301, 303, 305, 307, 309, 311, 313,315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 147 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 148 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 149 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 150 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 151 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 152 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 153 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 154 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 155 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 156 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 157 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 158 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 159 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 160 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 161 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 162 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 163 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 164 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 165 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 166 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 167 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 168 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 169 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 170 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 171 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 172 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 173 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 174 polypeptides selected from the group consisting of 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 175 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 176 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381,
383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 177 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 178 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 179 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 180 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 181 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 182 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 183 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 184 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 185 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 186 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 187 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 188 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 189 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 190 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 191 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 192 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 193 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 194 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 195 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 196 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 197 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 198 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 199 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 200 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 201 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 202 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 203 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 204 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 205 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 206 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 207 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 208 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 209 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 210 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 211 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 212 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 213 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 214 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 215 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235,237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 216 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 217 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 218 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 219 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293,295, 297, 299, 301, 303, 305, 307, 309, 311, 313,315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 220 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293,295, 297, 299, 301, 303, 305, 307, 309, 311, 313,315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 221 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 222 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 223 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 224 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 225 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 226 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 227 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 228 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 229 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 230 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 231 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 232 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 233 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 234 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 235 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polynucleotide encoding a heterologous polypeptide comprising 236 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 237 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 2 polypeptides selected from the group consisting of SEQ ID NOs: 275, 381,333, 337, 269, 253, 309, 325,271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 3 polypeptides selected from the group consisting of SEQ ID NOs: 275, 381,333, 337, 269, 253, 309, 325,271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 4 polypeptides selected from the group consisting of SEQ ID NOs: 275, 381,333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 5 polypeptides selected from the group consisting of SEQ ID NOs: 275, 381,333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 6 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 7 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 8 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 9 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 10 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 11 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 12 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 13 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 14 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 15 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 16 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 17 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 18 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 19 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 20 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 21 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 22 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 23 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 24 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 25 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 26 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 27 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 28 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 29 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 30 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 31 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 32 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 33 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 34 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 35 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 36 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 37 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 38 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 39 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 40 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the fragments comprise about 6-24 amino acids in length.

In some embodiments, the fragments comprise at least 6 amino acids. In some embodiments, the fragments comprise at least 7 amino acids In some embodiments, the fragments comprise at least 8 amino acids. In some embodiments, the fragments comprise at least 9 amino acids. In some embodiments, the fragments comprise at least 10 amino acids. In some embodiments, the fragments comprise at least 11 amino acids. In some embodiments, the fragments comprise at least 12 amino acids. In some embodiments, the fragments comprise at least 13 amino acids. In some embodiments, the fragments comprise at least 14 amino acids. In some embodiments, the fragments comprise at least 15 amino acids. In some embodiments, the fragments comprise at least 16 amino acids. In some embodiments, the fragments comprise at least 17 amino acids. In some embodiments, the fragments comprise at least 18 amino acids. In some embodiments, the fragments comprise at least 19 amino acids. In some embodiments, the fragments comprise at least 20 amino acids. In some embodiments, the fragments comprise at least 21 amino acids. In some embodiments, the fragments comprise at least 22 amino acids. In some embodiments, the fragments comprise at least 23 amino acids. In some embodiments, the fragments comprise at least 24 amino acids. In some embodiments, the fragments comprise at least 25 amino acids. In some embodiments, the fragments comprise about 6 amino acids. In some embodiments, the fragments comprise about 7 amino acids. In some embodiments, the fragments comprise about 8 amino acids. In some embodiments, the fragments comprise about 9 amino acids. In some embodiments, the fragments comprise about 10 amino acids. In some embodiments, the fragments comprise about 11 amino acids. In some embodiments, the fragments comprise about 12 amino acids. In some embodiments, the fragments comprise about 13 amino acids. In some embodiments, the fragments comprise about 14 amino acids. In some embodiments, the fragments comprise about 15 amino acids. In some embodiments, the fragments comprise about 16 amino acids. In some embodiments, the fragments comprise about 17 amino acids. In some embodiments, the fragments comprise about 18 amino acids. In some embodiments, the fragments comprise about 19 amino acids. In some embodiments, the fragments comprise about 20 amino acids. In some embodiments, the fragments comprise about 21 amino acids. In some embodiments, the fragments comprise about 22 amino acids. In some embodiments, the fragments comprise about 23 amino acids. In some embodiments, the fragments comprise about 24 amino acids. In some embodiments, the fragments comprise about 25 amino acids. In some embodiments, the fragments comprise about 6-25 amino acids. In some embodiments, the fragments comprise about 7-25 amino acids. In some embodiments, the fragments comprise about 8-25 amino acids. In some embodiments, the fragments comprise about 8-24 amino acids. In some embodiments, the fragments comprise about 8-23 amino acids.

In some embodiments, the fragments comprise about 8-22 amino acids. In some embodiments, the fragments comprise about 8-21 amino acids. In some embodiments, the fragments comprise about 8-20 amino acids. In some embodiments, the fragments comprise about 8-19 amino acids.

In some embodiments, the fragments comprise about 8-18 amino acids. In some embodiments, the fragments comprise about 8-17 amino acids. In some embodiments, the fragments comprise about 8-16 amino acids. In some embodiments, the fragments comprise about 8-15 amino acids.

In some embodiments, the fragments comprise about 8-14 amino acids. In some embodiments, the fragments comprise about 9-14 amino acids. In some embodiments, the fragments comprise about 9-13 amino acids. In some embodiments, the fragments comprise about 9-12 amino acids.

In some embodiments, the fragments comprise about 9-11 amino acids. In some embodiments, the fragments comprise about 9-10 amino acids.

In some embodiments, the fragments comprise SEQ ID NOs: 387, 388, 389, 390, 391, 392, 393, 394, 395, 396, 397, 398, 399, 400, 401, 402, 403, 404, 405, 406, 407, 408, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620 or 621.

In some embodiments, the fragments comprise SEQ ID NOs: 377, 378, 415,417, 418, 420, 502, 518, 526, 527, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 74, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 487, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980 or 548.

In some embodiments, the fragments are immunogenic fragments.

Immunogenic fragments in general are peptides that activate T cells, for example those that induce cytotoxic T cells when presented on MHC. Methods for assessing activation of T cells and/or induction of cytotoxic T lymphocytes are well known. In an exemplary assay, PBMCs isolated from a prostate cancer patient are cultured in vitro in the presence of a test neoantigen or fragments thereof and IL-25. The cultures may be replenished periodically with IL-15 and IL-2 and cultured for an additional 12 days. On day 12, the cultures are re-stimulated with the test neoantigen or fragments thereof and the following day T cell activation may be assessed by measuring a percentage of IFN$\gamma^+$ TNA$\alpha^+$ $CD8^+$ cells when compared to a control culture.

The disclosure also provides an isolated polypeptide comprising an amino acid sequence of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215,217, 219, 221, 223, 225, 227, 229, 231, 233, 235, 237, 239, 241, 243, 245,247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 or 447, or fragments thereof.

In some embodiments, the polypeptide is encoded by a polynucleotide sequence of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 or 458, or fragments thereof.

In some embodiments, the polypeptide is encoded by a polynucleotide sequence of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 or 499, or fragments thereof.

In some embodiments, the polypeptide is encoded by a polynucleotide sequence of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 or 540, or fragments thereof.

The polypeptides and the heterologous polypeptides of the disclosure comprise one or more prostate neoantigens described herein. The polypeptides and the heterologous polypeptides of the disclosure are useful in generating the recombinant viruses, the cells and the vaccines of the disclosure and proteinaceous molecules that specifically bind the one or more prostate neoantigens of the disclosure or may be used directly as therapeutic agents by delivering them to a subject having a prostate cancer using various technologies. The two or more neoantigens (e.g. polypeptides) may be incorporated into the vaccine in any order using standard cloning methods.

The disclosure also provides an isolated polypeptide comprising an amino acid sequence of SEQ ID NO: 1 or fragments thereof.

The disclosure also provides an isolated polypeptide comprising an amino acid sequence of SEQ ID NO: 3 or fragments thereof.

The disclosure also provides an isolated polypeptide comprising an amino acid sequence of SEQ ID NO: 5 or fragments thereof.

The disclosure also provides an isolated polypeptide comprising an amino acid sequence of SEQ ID NO: 7 or fragments thereof.

The disclosure also provides an isolated polypeptide comprising an amino acid sequence of SEQ ID NO: 9 or fragments thereof.

The disclosure also provides an isolated polypeptide comprising an amino acid sequence of SEQ ID NO: 11 or fragments thereof.

The disclosure also provides an isolated polypeptide comprising an amino acid sequence of SEQ ID NO: 13 or fragments thereof.

The disclosure also provides an isolated polypeptide comprising an amino acid sequence of SEQ ID NO: 15 or fragments thereof.

The disclosure also provides an isolated polypeptide comprising an amino acid sequence of SEQ ID NO: 17 or fragments thereof.

The disclosure also provides an isolated polypeptide comprising an amino acid sequence of SEQ ID NO: 19 or fragments thereof.

The disclosure also provides an isolated polypeptide comprising an amino acid sequence of SEQ ID NO: 21 or fragments thereof.

The disclosure also provides an isolated polypeptide comprising an amino acid sequence of SEQ ID NO: 23 or fragments thereof.

The disclosure also provides an isolated polypeptide comprising an amino acid sequence of SEQ ID NO: 25 or fragments thereof.

The disclosure also provides an isolated polypeptide comprising an amino acid sequence of SEQ ID NO: 27 or fragments thereof.

The disclosure also provides an isolated polypeptide comprising an amino acid sequence of SEQ ID NO: 29 or fragments thereof.

The disclosure also provides an isolated polypeptide comprising an amino acid sequence of SEQ ID NO: 31 or fragments thereof.

The disclosure also provides an isolated polypeptide comprising an amino acid sequence of SEQ ID NO: 33 or fragments thereof.

The disclosure also provides an isolated polypeptide comprising an amino acid sequence of SEQ ID NO: 35 or fragments thereof.

The disclosure also provides an isolated polypeptide comprising an amino acid sequence of SEQ ID NO: 37 or fragments thereof.

The disclosure also provides an isolated polypeptide comprising an amino acid sequence of SEQ ID NO: 39 or fragments thereof.

The disclosure also provides an isolated polypeptide comprising an amino acid sequence of SEQ ID NO: 41 or fragments thereof.

The disclosure also provides an isolated polypeptide comprising an amino acid sequence of SEQ ID NO: 43 or fragments thereof.

The disclosure also provides an isolated polypeptide comprising an amino acid sequence of SEQ ID NO: 45 or fragments thereof.

The disclosure also provides an isolated polypeptide comprising an amino acid sequence of SEQ ID NO: 47 or fragments thereof.

The disclosure also provides an isolated polypeptide comprising an amino acid sequence of SEQ ID NO: 49 or fragments thereof.

The disclosure also provides an isolated polypeptide comprising an amino acid sequence of SEQ ID NO: 51 or fragments thereof.

The disclosure also provides an isolated polypeptide comprising an amino acid sequence of SEQ ID NO: 53 or fragments thereof.

The disclosure also provides an isolated polypeptide comprising an amino acid sequence of SEQ ID NO: 55 or fragments thereof.

The disclosure also provides an isolated polypeptide comprising an amino acid sequence of SEQ ID NO: 57 or fragments thereof.

The disclosure also provides an isolated polypeptide comprising an amino acid sequence of SEQ ID NO: 59 or fragments thereof.

The disclosure also provides an isolated polypeptide comprising an amino acid sequence of SEQ ID NO: 61 or fragments thereof.

The disclosure also provides an isolated polypeptide comprising an amino acid sequence of SEQ ID NO: 63 or fragments thereof.

The disclosure also provides an isolated polypeptide comprising an amino acid sequence of SEQ ID NO: 65 or fragments thereof.

The disclosure also provides an isolated polypeptide comprising an amino acid sequence of SEQ ID NO: 67 or fragments thereof.

The disclosure also provides an isolated polypeptide comprising an amino acid sequence of SEQ ID NO: 69 or fragments thereof.

The disclosure also provides an isolated polypeptide comprising an amino acid sequence of SEQ ID NO: 71 or fragments thereof.

The disclosure also provides an isolated polypeptide comprising an amino acid sequence of SEQ ID NO: 73 or fragments thereof.

The disclosure also provides an isolated polypeptide comprising an amino acid sequence of SEQ ID NO: 75 or fragments thereof.

The disclosure also provides an isolated polypeptide comprising an amino acid sequence of SEQ ID NO: 77 or fragments thereof.

The disclosure also provides an isolated polypeptide comprising an amino acid sequence of SEQ ID NO: 79 or fragments thereof.

The disclosure also provides an isolated polypeptide comprising an amino acid sequence of SEQ ID NO: 81 or fragments thereof.

The disclosure also provides an isolated polypeptide comprising an amino acid sequence of SEQ ID NO: 83 or fragments thereof.

The disclosure also provides an isolated polypeptide comprising an amino acid sequence of SEQ ID NO: 85 or fragments thereof.

The disclosure also provides an isolated polypeptide comprising an amino acid sequence of SEQ ID NO: 87 or fragments thereof.

The disclosure also provides an isolated polypeptide comprising an amino acid sequence of SEQ ID NO: 89 or fragments thereof.

The disclosure also provides an isolated polypeptide comprising an amino acid sequence of SEQ ID NO: 91 or fragments thereof.

The disclosure also provides an isolated polypeptide comprising an amino acid sequence of SEQ ID NO: 93 or fragments thereof.

The disclosure also provides an isolated polypeptide comprising an amino acid sequence of SEQ ID NO: 95 or fragments thereof.

The disclosure also provides an isolated polypeptide comprising an amino acid sequence of SEQ ID NO: 97 or fragments thereof.

The disclosure also provides an isolated polypeptide comprising an amino acid sequence of SEQ ID NO: 99 or fragments thereof.

The disclosure also provides an isolated polypeptide comprising an amino acid sequence of SEQ ID NO: 101 or fragments thereof.

The disclosure also provides an isolated polypeptide comprising an amino acid sequence of SEQ ID NO: 103 or fragments thereof.

The disclosure also provides an isolated polypeptide comprising an amino acid sequence of SEQ ID NO: 105 or fragments thereof.

The disclosure also provides an isolated polypeptide comprising an amino acid sequence of SEQ ID NO: 107 or fragments thereof.

The disclosure also provides an isolated polypeptide comprising an amino acid sequence of SEQ ID NO: 109 or fragments thereof.

The disclosure also provides an isolated polypeptide comprising an amino acid sequence of SEQ ID NO: 111 or fragments thereof.

The disclosure also provides an isolated polypeptide comprising an amino acid sequence of SEQ ID NO: 113 or fragments thereof.

The disclosure also provides an isolated polypeptide comprising an amino acid sequence of SEQ ID NO: 115 or fragments thereof.

The disclosure also provides an isolated polypeptide comprising an amino acid sequence of SEQ ID NO: 117 or fragments thereof.

The disclosure also provides an isolated polypeptide comprising an amino acid sequence of SEQ ID NO: 119 or fragments thereof.

The disclosure also provides an isolated polypeptide comprising an amino acid sequence of SEQ ID NO: 121 or fragments thereof.

The disclosure also provides an isolated polypeptide comprising an amino acid sequence of SEQ ID NO: 123 or fragments thereof.

The disclosure also provides an isolated polypeptide comprising an amino acid sequence of SEQ ID NO: 125 or fragments thereof.

The disclosure also provides an isolated polypeptide comprising an amino acid sequence of SEQ ID NO: 127 or fragments thereof.

The disclosure also provides an isolated polypeptide comprising an amino acid sequence of SEQ ID NO: 129 or fragments thereof.

The disclosure also provides an isolated polypeptide comprising an amino acid sequence of SEQ ID NO: 131 or fragments thereof.

The disclosure also provides an isolated polypeptide comprising an amino acid sequence of SEQ ID NO: 133 or fragments thereof.

The disclosure also provides an isolated polypeptide comprising an amino acid sequence of SEQ ID NO: 135 or fragments thereof.

The disclosure also provides an isolated polypeptide comprising an amino acid sequence of SEQ ID NO: 137 or fragments thereof.

The disclosure also provides an isolated polypeptide comprising an amino acid sequence of SEQ ID NO: 139 or fragments thereof.

The disclosure also provides an isolated polypeptide comprising an amino acid sequence of SEQ ID NO: 141 or fragments thereof.

The disclosure also provides an isolated polypeptide comprising an amino acid sequence of SEQ ID NO: 143 or fragments thereof.

The disclosure also provides an isolated polypeptide comprising an amino acid sequence of SEQ ID NO: 145 or fragments thereof.

The disclosure also provides an isolated polypeptide comprising an amino acid sequence of SEQ ID NO: 147 or fragments thereof.

The disclosure also provides an isolated polypeptide comprising an amino acid sequence of SEQ ID NO: 149 or fragments thereof.

The disclosure also provides an isolated polypeptide comprising an amino acid sequence of SEQ ID NO: 151 or fragments thereof.

The disclosure also provides an isolated polypeptide comprising an amino acid sequence of SEQ ID NO: 153 or fragments thereof.

The disclosure also provides an isolated polypeptide comprising an amino acid sequence of SEQ ID NO: 155 or fragments thereof.

The disclosure also provides an isolated polypeptide comprising an amino acid sequence of SEQ ID NO: 157 or fragments thereof.

The disclosure also provides an isolated polypeptide comprising an amino acid sequence of SEQ ID NO: 159 or fragments thereof.

The disclosure also provides an isolated polypeptide comprising an amino acid sequence of SEQ ID NO: 161 or fragments thereof.

The disclosure also provides an isolated polypeptide comprising an amino acid sequence of SEQ ID NO: 163 or fragments thereof.

The disclosure also provides an isolated polypeptide comprising an amino acid sequence of SEQ ID NO: 165 or fragments thereof.

The disclosure also provides an isolated polypeptide comprising an amino acid sequence of SEQ ID NO: 167 or fragments thereof.

The disclosure also provides an isolated polypeptide comprising an amino acid sequence of SEQ ID NO: 169 or fragments thereof.

The disclosure also provides an isolated polypeptide comprising an amino acid sequence of SEQ ID NO: 171 or fragments thereof.

The disclosure also provides an isolated polypeptide comprising an amino acid sequence of SEQ ID NO: 173 or fragments thereof.

The disclosure also provides an isolated polypeptide comprising an amino acid sequence of SEQ ID NO: 175 or fragments thereof.

The disclosure also provides an isolated polypeptide comprising an amino acid sequence of SEQ ID NO: 177 or fragments thereof.

The disclosure also provides an isolated polypeptide comprising an amino acid sequence of SEQ ID NO: 179 or fragments thereof.

The disclosure also provides an isolated polypeptide comprising an amino acid sequence of SEQ ID NO: 181 or fragments thereof.

The disclosure also provides an isolated polypeptide comprising an amino acid sequence of SEQ ID NO: 183 or fragments thereof.

The disclosure also provides an isolated polypeptide comprising an amino acid sequence of SEQ ID NO: 185 or fragments thereof.

The disclosure also provides an isolated polypeptide comprising an amino acid sequence of SEQ ID NO: 187 or fragments thereof.

The disclosure also provides an isolated polypeptide comprising an amino acid sequence of SEQ ID NO: 189 or fragments thereof.

The disclosure also provides an isolated polypeptide comprising an amino acid sequence of SEQ ID NO: 191 or fragments thereof.

The disclosure also provides an isolated polypeptide comprising an amino acid sequence of SEQ ID NO: 193 or fragments thereof.

The disclosure also provides an isolated polypeptide comprising an amino acid sequence of SEQ ID NO: 195 or fragments thereof.

The disclosure also provides an isolated polypeptide comprising an amino acid sequence of SEQ ID NO: 197 or fragments thereof.

The disclosure also provides an isolated polypeptide comprising an amino acid sequence of SEQ ID NO: 199 or fragments thereof.

The disclosure also provides an isolated polypeptide comprising an amino acid sequence of SEQ ID NO: 201 or fragments thereof.

The disclosure also provides an isolated polypeptide comprising an amino acid sequence of SEQ ID NO: 203 or fragments thereof.

The disclosure also provides an isolated polypeptide comprising an amino acid sequence of SEQ ID NO: 205 or fragments thereof.

The disclosure also provides an isolated polypeptide comprising an amino acid sequence of SEQ ID NO: 207 or fragments thereof.

The disclosure also provides an isolated polypeptide comprising an amino acid sequence of SEQ ID NO: 209 or fragments thereof.

The disclosure also provides an isolated polypeptide comprising an amino acid sequence of SEQ ID NO: 211 or fragments thereof.

The disclosure also provides an isolated polypeptide comprising an amino acid sequence of SEQ ID NO: 213 or fragments thereof.

The disclosure also provides an isolated polypeptide comprising an amino acid sequence of SEQ ID NO: 215 or fragments thereof.

The disclosure also provides an isolated polypeptide comprising an amino acid sequence of SEQ ID NO: 217 or fragments thereof.

The disclosure also provides an isolated polypeptide comprising an amino acid sequence of SEQ ID NO: 219 or fragments thereof.

The disclosure also provides an isolated polypeptide comprising an amino acid sequence of SEQ ID NO: 221 or fragments thereof.

The disclosure also provides an isolated polypeptide comprising an amino acid sequence of SEQ ID NO: 223 or fragments thereof.

The disclosure also provides an isolated polypeptide comprising an amino acid sequence of SEQ ID NO: 225 or fragments thereof.

The disclosure also provides an isolated polypeptide comprising an amino acid sequence of SEQ ID NO: 227 or fragments thereof.

The disclosure also provides an isolated polypeptide comprising an amino acid sequence of SEQ ID NO: 229 or fragments thereof.

The disclosure also provides an isolated polypeptide comprising an amino acid sequence of SEQ ID NO: 231 or fragments thereof.

The disclosure also provides an isolated polypeptide comprising an amino acid sequence of SEQ ID NO: 233 or fragments thereof.

The disclosure also provides an isolated polypeptide comprising an amino acid sequence of SEQ ID NO: 235 or fragments thereof.

The disclosure also provides an isolated polypeptide comprising an amino acid sequence of SEQ ID NO: 237 or fragments thereof.

The disclosure also provides an isolated polypeptide comprising an amino acid sequence of SEQ ID NO: 239 or fragments thereof.

The disclosure also provides an isolated polypeptide comprising an amino acid sequence of SEQ ID NO: 241 or fragments thereof.

The disclosure also provides an isolated polypeptide comprising an amino acid sequence of SEQ ID NO: 243 or fragments thereof.

The disclosure also provides an isolated polypeptide comprising an amino acid sequence of SEQ ID NO: 245 or fragments thereof.

The disclosure also provides an isolated polypeptide comprising an amino acid sequence of SEQ ID NO: 247 or fragments thereof.

The disclosure also provides an isolated polypeptide comprising an amino acid sequence of SEQ ID NO: 249 or fragments thereof.

The disclosure also provides an isolated polypeptide comprising an amino acid sequence of SEQ ID NO: 251 or fragments thereof.

The disclosure also provides an isolated polypeptide comprising an amino acid sequence of SEQ ID NO: 253 or fragments thereof.

The disclosure also provides an isolated polypeptide comprising an amino acid sequence of SEQ ID NO: 255 or fragments thereof.

The disclosure also provides an isolated polypeptide comprising an amino acid sequence of SEQ ID NO: 257 or fragments thereof.

The disclosure also provides an isolated polypeptide comprising an amino acid sequence of SEQ ID NO: 259 or fragments thereof.

The disclosure also provides an isolated polypeptide comprising an amino acid sequence of SEQ ID NO: 261 or fragments thereof.

The disclosure also provides an isolated polypeptide comprising an amino acid sequence of SEQ ID NO: 263 or fragments thereof.

The disclosure also provides an isolated polypeptide comprising an amino acid sequence of SEQ ID NO: 265 or fragments thereof.

The disclosure also provides an isolated polypeptide comprising an amino acid sequence of SEQ ID NO: 267 or fragments thereof.

The disclosure also provides an isolated polypeptide comprising an amino acid sequence of SEQ ID NO: 269 or fragments thereof.

The disclosure also provides an isolated polypeptide comprising an amino acid sequence of SEQ ID NO: 271 or fragments thereof.

The disclosure also provides an isolated polypeptide comprising an amino acid sequence of SEQ ID NO: 273 or fragments thereof.

The disclosure also provides an isolated polypeptide comprising an amino acid sequence of SEQ ID NO: 275 or fragments thereof.

The disclosure also provides an isolated polypeptide comprising an amino acid sequence of SEQ ID NO: 277 or fragments thereof.

The disclosure also provides an isolated polypeptide comprising an amino acid sequence of SEQ ID NO: 279 or fragments thereof.

The disclosure also provides an isolated polypeptide comprising an amino acid sequence of SEQ ID NO: 281 or fragments thereof.

The disclosure also provides an isolated polypeptide comprising an amino acid sequence of SEQ ID NO: 283 or fragments thereof.

The disclosure also provides an isolated polypeptide comprising an amino acid sequence of SEQ ID NO: 285 or fragments thereof.

The disclosure also provides an isolated polypeptide comprising an amino acid sequence of SEQ ID NO: 287 or fragments thereof.

The disclosure also provides an isolated polypeptide comprising an amino acid sequence of SEQ ID NO: 289 or fragments thereof.

The disclosure also provides an isolated polypeptide comprising an amino acid sequence of SEQ ID NO: 291 or fragments thereof.

The disclosure also provides an isolated polypeptide comprising an amino acid sequence of SEQ ID NO: 293 or fragments thereof.

The disclosure also provides an isolated polypeptide comprising an amino acid sequence of SEQ ID NO: 295 or fragments thereof.

The disclosure also provides an isolated polypeptide comprising an amino acid sequence of SEQ ID NO: 297 or fragments thereof.

The disclosure also provides an isolated polypeptide comprising an amino acid sequence of SEQ ID NO: 299 or fragments thereof.

The disclosure also provides an isolated polypeptide comprising an amino acid sequence of SEQ ID NO: 301 or fragments thereof.

The disclosure also provides an isolated polypeptide comprising an amino acid sequence of SEQ ID NO: 303 or fragments thereof.

The disclosure also provides an isolated polypeptide comprising an amino acid sequence of SEQ ID NO: 305 or fragments thereof.

The disclosure also provides an isolated polypeptide comprising an amino acid sequence of SEQ ID NO: 307 or fragments thereof.

The disclosure also provides an isolated polypeptide comprising an amino acid sequence of SEQ ID NO: 309 or fragments thereof.

The disclosure also provides an isolated polypeptide comprising an amino acid sequence of SEQ ID NO: 311 or fragments thereof.

The disclosure also provides an isolated polypeptide comprising an amino acid sequence of SEQ ID NO: 313 or fragments thereof.

The disclosure also provides an isolated polypeptide comprising an amino acid sequence of SEQ ID NO: 315 or fragments thereof.

The disclosure also provides an isolated polypeptide comprising an amino acid sequence of SEQ ID NO: 317 or fragments thereof.

The disclosure also provides an isolated polypeptide comprising an amino acid sequence of SEQ ID NO: 319 or fragments thereof.

The disclosure also provides an isolated polypeptide comprising an amino acid sequence of SEQ ID NO: 321 or fragments thereof.

The disclosure also provides an isolated polypeptide comprising an amino acid sequence of SEQ ID NO: 323 or fragments thereof.

The disclosure also provides an isolated polypeptide comprising an amino acid sequence of SEQ ID NO: 325 or fragments thereof.

The disclosure also provides an isolated polypeptide comprising an amino acid sequence of SEQ ID NO: 327 or fragments thereof.

The disclosure also provides an isolated polypeptide comprising an amino acid sequence of SEQ ID NO: 329 or fragments thereof.

The disclosure also provides an isolated polypeptide comprising an amino acid sequence of SEQ ID NO: 331 or fragments thereof.

The disclosure also provides an isolated polypeptide comprising an amino acid sequence of SEQ ID NO: 333 or fragments thereof.

The disclosure also provides an isolated polypeptide comprising an amino acid sequence of SEQ ID NO: 335 or fragments thereof.

The disclosure also provides an isolated polypeptide comprising an amino acid sequence of SEQ ID NO: 337 or fragments thereof.

The disclosure also provides an isolated polypeptide comprising an amino acid sequence of SEQ ID NO: 339 or fragments thereof.

The disclosure also provides an isolated polypeptide comprising an amino acid sequence of SEQ ID NO: 341 or fragments thereof.

The disclosure also provides an isolated polypeptide comprising an amino acid sequence of SEQ ID NO: 343 or fragments thereof.

The disclosure also provides an isolated polypeptide comprising an amino acid sequence of SEQ ID NO: 345 or fragments thereof.

The disclosure also provides an isolated polypeptide comprising an amino acid sequence of SEQ ID NO: 347 or fragments thereof.

The disclosure also provides an isolated polypeptide comprising an amino acid sequence of SEQ ID NO: 349 or fragments thereof.

The disclosure also provides an isolated polypeptide comprising an amino acid sequence of SEQ ID NO: 351 or fragments thereof.

The disclosure also provides an isolated polypeptide comprising an amino acid sequence of SEQ ID NO: 353 or fragments thereof.

The disclosure also provides an isolated polypeptide comprising an amino acid sequence of SEQ ID NO: 355 or fragments thereof.

The disclosure also provides an isolated polypeptide comprising an amino acid sequence of SEQ ID NO: 357 or fragments thereof.

The disclosure also provides an isolated polypeptide comprising an amino acid sequence of SEQ ID NO: 359 or fragments thereof.

The disclosure also provides an isolated polypeptide comprising an amino acid sequence of SEQ ID NO: 361 or fragments thereof.

The disclosure also provides an isolated polypeptide comprising an amino acid sequence of SEQ ID NO: 363 or fragments thereof.

The disclosure also provides an isolated polypeptide comprising an amino acid sequence of SEQ ID NO: 365 or fragments thereof.

The disclosure also provides an isolated polypeptide comprising an amino acid sequence of SEQ ID NO: 367 or fragments thereof.

The disclosure also provides an isolated polypeptide comprising an amino acid sequence of SEQ ID NO: 369 or fragments thereof.

The disclosure also provides an isolated polypeptide comprising an amino acid sequence of SEQ ID NO: 371 or fragments thereof.

The disclosure also provides an isolated polypeptide comprising an amino acid sequence of SEQ ID NO: 373 or fragments thereof.

The disclosure also provides an isolated polypeptide comprising an amino acid sequence of SEQ ID NO: 375 or fragments thereof.

The disclosure also provides an isolated polypeptide comprising an amino acid sequence of SEQ ID NO: 379 or fragments thereof.

The disclosure also provides an isolated polypeptide comprising an amino acid sequence of SEQ ID NO: 381 or fragments thereof.

The disclosure also provides an isolated polypeptide comprising an amino acid sequence of SEQ ID NO: 383 or fragments thereof.

The disclosure also provides an isolated polypeptide comprising an amino acid sequence of SEQ ID NO: 385 or fragments thereof.

The disclosure also provides an isolated polypeptide comprising an amino acid sequence of SEQ ID NO: 387 or fragments thereof.

The disclosure also provides an isolated polypeptide comprising an amino acid sequence of SEQ ID NO: 388 or fragments thereof.

The disclosure also provides an isolated polypeptide comprising an amino acid sequence of SEQ ID NO: 389 or fragments thereof.

The disclosure also provides an isolated polypeptide comprising an amino acid sequence of SEQ ID NO: 390 or fragments thereof.

The disclosure also provides an isolated polypeptide comprising an amino acid sequence of SEQ ID NO: 391 or fragments thereof.

The disclosure also provides an isolated polypeptide comprising an amino acid sequence of SEQ ID NO: 392 or fragments thereof.

The disclosure also provides an isolated polypeptide comprising an amino acid sequence of SEQ ID NO: 393 or fragments thereof.

The disclosure also provides an isolated polypeptide comprising an amino acid sequence of SEQ ID NO: 394 or fragments thereof.

The disclosure also provides an isolated polypeptide comprising an amino acid sequence of SEQ ID NO: 395 or fragments thereof.

The disclosure also provides an isolated polypeptide comprising an amino acid sequence of SEQ ID NO: 396 or fragments thereof.

The disclosure also provides an isolated polypeptide comprising an amino acid sequence of SEQ ID NO: 397 or fragments thereof.

The disclosure also provides an isolated polypeptide comprising an amino acid sequence of SEQ ID NO: 398 or fragments thereof.

The disclosure also provides an isolated polypeptide comprising an amino acid sequence of SEQ ID NO: 399 or fragments thereof.

The disclosure also provides an isolated polypeptide comprising an amino acid sequence of SEQ ID NO: 400 or fragments thereof.

The disclosure also provides an isolated polypeptide comprising an amino acid sequence of SEQ ID NO: 401 or fragments thereof.

The disclosure also provides an isolated polypeptide comprising an amino acid sequence of SEQ ID NO: 402 or fragments thereof.

The disclosure also provides an isolated polypeptide comprising an amino acid sequence of SEQ ID NO: 403 or fragments thereof.

The disclosure also provides an isolated polypeptide comprising an amino acid sequence of SEQ ID NO: 404 or fragments thereof.

The disclosure also provides an isolated polypeptide comprising an amino acid sequence of SEQ ID NO: 405 or fragments thereof.

The disclosure also provides an isolated polypeptide comprising an amino acid sequence of SEQ ID NO: 406 or fragments thereof.

The disclosure also provides an isolated polypeptide comprising an amino acid sequence of SEQ ID NO: 407 or fragments thereof.

The disclosure also provides an isolated polypeptide comprising an amino acid sequence of SEQ ID NO: 408 or fragments thereof.

The disclosure also provides an isolated polypeptide comprising an amino acid sequence of SEQ ID NO: 426 or fragments thereof.

The disclosure also provides an isolated polypeptide comprising an amino acid sequence of SEQ ID NO: 427 or fragments thereof.

The disclosure also provides an isolated polypeptide comprising an amino acid sequence of SEQ ID NO: 428 or fragments thereof.

The disclosure also provides an isolated polypeptide comprising an amino acid sequence of SEQ ID NO: 429 or fragments thereof.

The disclosure also provides an isolated polypeptide comprising an amino acid sequence of SEQ ID NO: 430 or fragments thereof.

The disclosure also provides an isolated polypeptide comprising an amino acid sequence of SEQ ID NO: 431 or fragments thereof.

The disclosure also provides an isolated polypeptide comprising an amino acid sequence of SEQ ID NO: 432 or fragments thereof.

The disclosure also provides an isolated polypeptide comprising an amino acid sequence of SEQ ID NO: 433 or fragments thereof.

The disclosure also provides an isolated polypeptide comprising an amino acid sequence of SEQ ID NO: 434 or fragments thereof.

The disclosure also provides an isolated polypeptide comprising an amino acid sequence of SEQ ID NO: 435 or fragments thereof.

The disclosure also provides an isolated polypeptide comprising an amino acid sequence of SEQ ID NO: 436 or fragments thereof.

The disclosure also provides an isolated polypeptide comprising an amino acid sequence of SEQ ID NO: 437 or fragments thereof.

The disclosure also provides an isolated polypeptide comprising an amino acid sequence of SEQ ID NO: 438 or fragments thereof.

The disclosure also provides an isolated polypeptide comprising an amino acid sequence of SEQ ID NO: 439 or fragments thereof.

The disclosure also provides an isolated polypeptide comprising an amino acid sequence of SEQ ID NO: 440 or fragments thereof.

The disclosure also provides an isolated polypeptide comprising an amino acid sequence of SEQ ID NO: 441 or fragments thereof.

The disclosure also provides an isolated polypeptide comprising an amino acid sequence of SEQ ID NO: 442 or fragments thereof.

The disclosure also provides an isolated polypeptide comprising an amino acid sequence of SEQ ID NO: 443 or fragments thereof.

The disclosure also provides an isolated polypeptide comprising an amino acid sequence of SEQ ID NO: 444 or fragments thereof.

The disclosure also provides an isolated polypeptide comprising an amino acid sequence of SEQ ID NO: 445 or fragments thereof.

The disclosure also provides an isolated polypeptide comprising an amino acid sequence of SEQ ID NO: 446 or fragments thereof.

The disclosure also provides an isolated polypeptide comprising an amino acid sequence of SEQ ID NO: 447 or fragments thereof.

The disclosure also provides an isolated polypeptide comprising an amino acid sequence of SEQ ID NO: 560 or fragments thereof.

The disclosure also provides an isolated polypeptide comprising an amino acid sequence of SEQ ID NO: 561 or fragments thereof.

The disclosure also provides an isolated polypeptide comprising an amino acid sequence of SEQ ID NO: 562 or fragments thereof.

The disclosure also provides an isolated polypeptide comprising an amino acid sequence of SEQ ID NO: 563 or fragments thereof.

The disclosure also provides an isolated polypeptide comprising an amino acid sequence of SEQ ID NO: 564 or fragments thereof.

The disclosure also provides an isolated polypeptide comprising an amino acid sequence of SEQ ID NO: 565 or fragments thereof.

The disclosure also provides an isolated polypeptide comprising an amino acid sequence of SEQ ID NO: 566 or fragments thereof.

The disclosure also provides an isolated polypeptide comprising an amino acid sequence of SEQ ID NO: 567 or fragments thereof.

The disclosure also provides an isolated polypeptide comprising an amino acid sequence of SEQ ID NO: 568 or fragments thereof.

The disclosure also provides an isolated polypeptide comprising an amino acid sequence of SEQ ID NO: 569 or fragments thereof.

The disclosure also provides an isolated polypeptide comprising an amino acid sequence of SEQ ID NO: 570 or fragments thereof.

The disclosure also provides an isolated polypeptide comprising an amino acid sequence of SEQ ID NO: 571 or fragments thereof.

The disclosure also provides an isolated polypeptide comprising an amino acid sequence of SEQ ID NO: 572 or fragments thereof.

The disclosure also provides an isolated polypeptide comprising an amino acid sequence of SEQ ID NO: 573 or fragments thereof.

The disclosure also provides an isolated polypeptide comprising an amino acid sequence of SEQ ID NO: 574 or fragments thereof.

The disclosure also provides an isolated polypeptide comprising an amino acid sequence of SEQ ID NO: 575 or fragments thereof.

The disclosure also provides an isolated polypeptide comprising an amino acid sequence of SEQ ID NO: 576 or fragments thereof.

The disclosure also provides an isolated polypeptide comprising an amino acid sequence of SEQ ID NO: 577 or fragments thereof.

The disclosure also provides an isolated polypeptide comprising an amino acid sequence of SEQ ID NO: 578 or fragments thereof.

The disclosure also provides an isolated polypeptide comprising an amino acid sequence of SEQ ID NO: 579 or fragments thereof.

The disclosure also provides an isolated polypeptide comprising an amino acid sequence of SEQ ID NO: 580 or fragments thereof.

The disclosure also provides an isolated polypeptide comprising an amino acid sequence of SEQ ID NO: 581 or fragments thereof.

The disclosure also provides an isolated polypeptide comprising an amino acid sequence of SEQ ID NO: 582 or fragments thereof.

The disclosure also provides an isolated polypeptide comprising an amino acid sequence of SEQ ID NO: 583 or fragments thereof.

The disclosure also provides an isolated polypeptide comprising an amino acid sequence of SEQ ID NO: 584 or fragments thereof.

The disclosure also provides an isolated polypeptide comprising an amino acid sequence of SEQ ID NO: 585 or fragments thereof.

The disclosure also provides an isolated polypeptide comprising an amino acid sequence of SEQ ID NO: 586 or fragments thereof.

The disclosure also provides an isolated polypeptide comprising an amino acid sequence of SEQ ID NO: 587 or fragments thereof.

The disclosure also provides an isolated polypeptide comprising an amino acid sequence of SEQ ID NO: 588 or fragments thereof.

The disclosure also provides an isolated polypeptide comprising an amino acid sequence of SEQ ID NO: 589 or fragments thereof.

The disclosure also provides an isolated polypeptide comprising an amino acid sequence of SEQ ID NO: 590 or fragments thereof.

The disclosure also provides an isolated polypeptide comprising an amino acid sequence of SEQ ID NO: 591 or fragments thereof.

The disclosure also provides an isolated polypeptide comprising an amino acid sequence of SEQ ID NO: 592 or fragments thereof.

The disclosure also provides an isolated polypeptide comprising an amino acid sequence of SEQ ID NO: 593 or fragments thereof.

The disclosure also provides an isolated polypeptide comprising an amino acid sequence of SEQ ID NO: 594 or fragments thereof.

The disclosure also provides an isolated polypeptide comprising an amino acid sequence of SEQ ID NO: 595 or fragments thereof.

The disclosure also provides an isolated polypeptide comprising an amino acid sequence of SEQ ID NO: 596 or fragments thereof.

The disclosure also provides an isolated polypeptide comprising an amino acid sequence of SEQ ID NO: 597 or fragments thereof.

The disclosure also provides an isolated polypeptide comprising an amino acid sequence of SEQ ID NO: 598 or fragments thereof.

The disclosure also provides an isolated polypeptide comprising an amino acid sequence of SEQ ID NO: 599 or fragments thereof.

The disclosure also provides an isolated polypeptide comprising an amino acid sequence of SEQ ID NO: 600 or fragments thereof.

The disclosure also provides an isolated polypeptide comprising an amino acid sequence of SEQ ID NO: 601 or fragments thereof.

The disclosure also provides an isolated polypeptide comprising an amino acid sequence of SEQ ID NO:602 or fragments thereof.

The disclosure also provides an isolated polypeptide comprising an amino acid sequence of SEQ ID NO: 603 or fragments thereof.

The disclosure also provides an isolated polypeptide comprising an amino acid sequence of SEQ ID NO: 604 or fragments thereof.

The disclosure also provides an isolated polypeptide comprising an amino acid sequence of SEQ ID NO: 605 or fragments thereof.

The disclosure also provides an isolated polypeptide comprising an amino acid sequence of SEQ ID NO: 606 or fragments thereof.

The disclosure also provides an isolated polypeptide comprising an amino acid sequence of SEQ ID NO: 607 or fragments thereof.

The disclosure also provides an isolated polypeptide comprising an amino acid sequence of SEQ ID NO: 608 or fragments thereof.

The disclosure also provides an isolated polypeptide comprising an amino acid sequence of SEQ ID NO: 609 or fragments thereof.

The disclosure also provides an isolated polypeptide comprising an amino acid sequence of SEQ ID NO: 610 or fragments thereof.

The disclosure also provides an isolated polypeptide comprising an amino acid sequence of SEQ ID NO: 611 or fragments thereof.

The disclosure also provides an isolated polypeptide comprising an amino acid sequence of SEQ ID NO: 612 or fragments thereof.

The disclosure also provides an isolated polypeptide comprising an amino acid sequence of SEQ ID NO: 613 or fragments thereof.

The disclosure also provides an isolated polypeptide comprising an amino acid sequence of SEQ ID NO: 614 or fragments thereof.

The disclosure also provides an isolated polypeptide comprising an amino acid sequence of SEQ ID NO: 615 or fragments thereof.

The disclosure also provides an isolated polypeptide comprising an amino acid sequence of SEQ ID NO: 616 or fragments thereof.

The disclosure also provides an isolated polypeptide comprising an amino acid sequence of SEQ ID NO: 617 or fragments thereof.

The disclosure also provides an isolated polypeptide comprising an amino acid sequence of SEQ ID NO: 618 or fragments thereof.

The disclosure also provides an isolated polypeptide comprising an amino acid sequence of SEQ ID NO: 619 or fragments thereof.

The disclosure also provides an isolated polypeptide comprising an amino acid sequence of SEQ ID NO: 620 or fragments thereof.

The disclosure also provides an isolated polypeptide comprising an amino acid sequence of SEQ ID NO: 621 or fragments thereof.

The disclosure also provides an isolated heterologous polypeptide comprising two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231,233, 235, 237, 239, 241, 243,245, 247, 249, 251,253, 255, 257, 259, 261,263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the heterologous polypeptide is encoded by two or more polynucleotides selected from the group consisting of 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

In some embodiments, the fragments are about 6-25 amino acids in length, such as about 8-25 amino acids in length.

In some embodiments, the fragments comprise polypeptides of SEQ ID NOs: 387, 388, 389, 390, 391, 392, 393, 394, 395, 396, 397, 398, 399, 400, 401, 402, 403, 404, 405, 406, 407, 408, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620 or 621.

In some embodiments, the fragments comprise polypeptides of SEQ ID NOs: 377, 378, 415, 417, 418, 420, 502, 518, 526, 527, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 74, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 487, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980 or 548.

The disclosure also provides an isolated heterologous polypeptide comprising 3 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 4 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 5 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 6 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 7 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 8 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 9 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 10 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 11 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 12 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 13 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 14 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 15 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 16 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 17 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 18 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 19 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 20 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 21 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 22 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 23 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 24 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 25 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 26 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 27 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 28 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 29 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 30 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 31 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 32 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 33 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 34 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 35 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 36 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 37 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 38 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 39 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 40 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 41 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 42 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 43 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 44 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 45 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 46 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 47 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 48 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 49 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 50 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 51 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 52 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 53 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 54 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 55 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 56 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 57 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 58 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 59 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 60 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 61 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 62 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 63 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 64 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 65 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 66 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 67 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 68 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 69 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 70 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 71 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 72 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 73 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 74 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 75 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 76 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 77 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 78 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 79 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 80 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 81 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 82 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 83 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 84 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 85 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 86 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 87 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 88 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 89 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 90 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 91 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 92 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 93 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 94 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 95 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 96 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 97 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 98 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 99 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 100 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 101 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 102 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 103 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 104 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 105 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 106 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 107 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 108 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 109 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 110 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 111 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 112 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 113 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 114 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 115 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 116 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 117 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 118 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 119 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 120 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 121 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 122 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 123 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 124 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 125 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 126 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 127 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 128 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 129 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 130 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 131 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 132 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 133 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 134 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 135 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 136 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 137 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 138 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 139 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 140 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 141 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 142 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 143 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 144 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 145 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 146 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 147 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 148 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 149 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 150 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 151 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 152 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 153 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 154 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 155 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 156 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 157 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 158 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 159 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 160 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 161 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 162 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 163 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 164 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 165 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 166 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 167 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 168 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 169 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 170 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 171 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 172 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 173 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 174 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 175 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 176 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 177 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 178 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 179 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 180 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 181 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 182 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 183 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 184 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 185 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 186 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 187 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 188 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 189 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 190 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 191 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 192 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 193 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 194 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 195 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 196 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 197 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 198 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 199 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 200 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 201 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 202 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 203 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 204 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 205 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 206 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 207 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 208 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 209 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 210 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 211 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 212 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 213 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 214 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 215 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 216 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 217 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 218 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 219 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 220 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 221 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 222 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 223 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 224 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 225 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 226 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 227 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341,343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 228 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341,343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 229 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 230 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 231 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 232 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 233 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 234 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 235 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 236 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising 237 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides an isolated heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211,349, 213, 215, 221,219, 225, 345, 353, 235, 223, 167, 171, 19, 23 and 177, and fragments thereof.

In some embodiments, the isolated heterologous polypeptide is encoded by a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 3 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 3 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 3 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 3 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 4 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 4 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded byaa heterologous polynucleotides comprising 4 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 4 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 5 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 5 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 5 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 5 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 6 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 6 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 6 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 6 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 7 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 7 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 7 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 7 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 8 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 8 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 8 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 8 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 9 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 9 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 9 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 9 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 10 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 10 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 10 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 10 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 11 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 11 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 11 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 11 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 12 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 12 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 12 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 12 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 13 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 13 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 13 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 13 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 14 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 14 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 14 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 14 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 15 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 15 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 15 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 15 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 16 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 16 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 16 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 16 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 17 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 17 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 17 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 17 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 18 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 18 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 18 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 18 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 19 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 19 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 19 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 19 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 20 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 20 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 20 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 20 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 21 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 21 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 21 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 21 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 22 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 22 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 22 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 22 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 23 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 23 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 23 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 23 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 24 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 24 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 24 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 24 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 25 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 25 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 25 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 25 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 26 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 26 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 26 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 26 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 27 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 27 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 27 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 27 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 28 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 28 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 28 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 28 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 29 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 29 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 29 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 29 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 30 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 30 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 30 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 30 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 31 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 31 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 31 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 31 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 32 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 32 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 32 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 32 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 33 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 33 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 33 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 33 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 34 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 34 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 34 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 34 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 35 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 35 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 35 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 35 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 36 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 36 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 36 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 36 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 37 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 37 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 37 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 37 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 38 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 38 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 38 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 38 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 39 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 39 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 39 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 39 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 40 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 40 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 40 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 40 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

Variants of Engineered Polynucleotides, Polypeptides, Heterologous Polynucleotides and Heterologous Polypeptides of the Disclosure Variants of the polynucleotides, polypeptides, heterologous polynucleotides and heterologous polypeptides or fragments thereof are within the scope of the disclosure. For example, variants may comprise one or more substitutions, deletions or insertions, as long as the variants retain or have improved characteristics (such as immunogenicity or stability) when compared to the parent. In some embodiments, the sequence identity may be about 80%, 81%, 82%, 83%, 84%, 85%, 86%, 87%, 88%, 89%, 90%, 91%, 92%, 93%, 94%, 95%, 96%, 97%, 98% or 99% between the parent and the variant. In some embodiments, variants are generated by conservative substitutions.

In some embodiments, the identity is about 80%. In some embodiments, the identity is about 85%. In some embodiments, the identity is about 90%. In some embodiments, the identity is about 91%. In some embodiments, the identity is about 91%. In some embodiments, the identity is about 92%. In some embodiments, the identity is about 93%. In some embodiments, the identity is about 94%. In some embodiments, the identity is 94%. In some embodiments, the identity is about 95%. In some embodiments, the identity is about 96%. In some embodiments, the identity is about 97%. In some embodiments, the identity is about 98%. In some embodiments, the identity is about 99%.

In some embodiments, variants may comprise 1, 2, 3, 4, 5, 6, 7, 8, 9, 10, 11, 12, 13, 14, 15, 16, 17, 18, 19 or 20 substitutions, deletions or insertions, as long as the variants retain or have improved characteristics (such as immunogenicity or stability) when compared to the parent.

The percent identity between the two sequences is a function of the number of identical positions shared by the sequences (i.e., % identity=number of identical positions/total number of positions×100), taking into account the number of gaps, and the length of each gap, which need to be introduced for optimal alignment of the two sequences. The percent identity between two amino acid sequences may be determined using the algorithm of E. Meyers and W. Miller (*Comput Appl Biosci* 4:11-17 (1988)) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch (*J Mol Biol* 48:444-453 (1970)) algorithm which has been incorporated into the GAP program in the GCG software package (available at http_//_www_gcg_com), using either a Blossum 62 matrix or a PAM250 matrix, and a gap weight of 16, 14, 12, 10, 8, 6, or 4 and a length weight of 1, 2, 3, 4, 5, or 6. The variants of the polypeptides or the heterologous polypeptides or fragments thereof containing one ammo acid alteration generally retain similar tertiary structure and antigenicity relative to the parent. In some instances, the variant may also contain at least one amino acid alteration that causes the variant to have increased antigenicity, increased binding affinity to TCR or to antibody, or both. The variants of the polypeptides or the heterologous polypeptides may also have improved ability to bind to a HLA molecule.

The variants of the disclosure may be engineered to contain conservative substitutions. Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gin); Group 3-polar, positively charged residues (His, Arg, Lys); Group 4-large, aliphatic, nonpolar residues (Met, Leu, lie, Val, Cys); and Group 5-large, aromatic residues (Phe, Tyr, Trp).

The variants of the disclosure may be engineered to contain less conservative substitutions, such as the replacement of one amino acid by another that has similar characteristics but is somewhat different in size, such as replacement of an alanine by an isoleucine residue. The variants of the disclosure may also be engineered to contain highly non-conservative substitutions which may involve substituting an acidic amino acid for one that is polar, or even for one that is basic in character.

Additional substitutions that may be made to generate variants of the disclosure include substitutions may involve structures other than the common L-amino acids. Thus, D-amino and non-standard amino acids (i.e., other than the common naturally occurring proteinogenic amino acids) may also be used for substitution purposes to produce variants with enhanced immunogenicity when compared to the parent.

If substitutions at more than one position are found to result in polypeptides or heterologous polypeptides with substantially equivalent or greater immunogenicity, then combinations of those substitutions may be tested to determine if the combined substitutions result in additive or synergistic effects on the immunogenicity of the variant.

The amino acid residues that do not substantially contribute to interactions with the TCR may be modified by replacement with other amino acid whose incorporation does not substantially affect T-cell reactivity and does not eliminate binding to the relevant MHC. The amino acid residues that do not substantially contribute to interactions with the TCR may also be deleted as long as the deletion does not substantially affect T-cell reactivity and does not eliminate binding to the relevant MHC.

In addition, the polypeptides or the heterologous polypeptides or fragments thereof or variants may be further modified to improve stability and/or binding to MHC molecules in order to elicit a stronger immune response. Methods for such an optimization of a peptide sequence are well known in the art and include, for example, the introduction of reverse peptide bonds or non-peptide bonds. In a reverse peptide bond amino acid residues are not joined by peptide (—CO—NH—) linkages but the peptide bond is reversed. Such retro-inverso peptidomimetics may be made using methods known in the art. This approach involves making pseudopeptides containing changes involving the backbone, and not the orientation of side chains. Retro-inverse peptides, which contain NH—CO bonds instead of CO—NH peptide bonds are much more resistant to proteolysis. Additional non-peptide bond that may be used are, for example, $—CH_2—NH$, $—CH_2S—$, $—CH_2CH_2—$, —CH=CH—, $—COCH_2—$, $—CH(OH)CH_2—$, and $—CH_2SO—$.

The polypeptides or the heterologous polypeptides or fragments thereof, or variants of the disclosure may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the amino terminus. Likewise, an acetyl group or a 9-fluorenyl-methoxy-carbonyl group may be placed at the amino termini. Additionally, the hydrophobic group, t-butyloxycarbonyl, or an amido group may be added to the carboxy termini.

Further, the polypeptides or the heterologous polypeptides or fragments thereof, or variants of the disclosure may be synthesized to alter their steric configuration. For example, the D-isomer of one or more of the amino acid residues of the peptide may be used, rather than the usual L-isomer.

Similarly, the polypeptides or the heterologous polypeptides or fragments thereof, or variants of the disclosure may be modified chemically by reacting specific amino acids either before or after synthesis of the polypeptides or the heterologous polypeptides or fragments thereof, or variants of the disclosure. Examples for such modifications are well known in the art and are summarized e.g. in R. Lundblad, Chemical Reagents for Protein Modification, 3rd ed. CRC Press, 2004 (Lundblad, 2004). Chemical modifications of amino acids include modification by acylation, amidation, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) (Coligan et al., 1995) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich (http_://www_sigma-aldrich.com) provide information on specific reagents. Selective reduction of disulfide bonds in proteins is also common. Disulfide bonds can be formed and oxidized during the heat treatment of biopharmaceuticals. Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue. For example, diethylpyrocarbonate is a reagent for the modification of histidyl residues in proteins. Histidine can also be modified using 4-hydroxy-2-nonenal. The reaction of lysine residues and other α-amino groups is, for example, useful in binding of peptides to surfaces or the cross-linking of proteins/peptides. Lysine is the site of attachment of poly(ethylene)glycol and the major site of modification in the glycosylation of proteins. Methionine residues in proteins can be modified with e.g. iodoacetamide, bromoethylamine, and chloramine T. Tetranitromethane and N-acetylimidazole can be used for the modification of tyrosyl residues. Cross-linking via the formation of dityrosine can be accomplished with hydrogen peroxide/copper ions. Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole). Successful modification of therapeutic proteins and peptides with PEG is often associated with an extension of circulatory half-life while cross-linking of proteins with glutaraldehyde, polyethylene glycol diacrylate and formaldehyde is used for the preparation of hydrogels. Chemical modification of allergens for immunotherapy is often achieved by carbamylation with potassium cyanate.

The disclosure provides an isolated polypeptide that is about 80%, 81%, 82%, 83%, 84%, 85%, 86%, 87%, 88%, 89%, 90%, 91%, 92%, 93%, 94%, 95%, 96%, 97%, 98% or 99% identical to the polypeptide of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 or 447.

The disclosure also provides an isolated polypeptide comprising a polypeptide sequence having 1, 2, 3, 4, 5, 6, 7, 8, 9, 10, 11, 12, 13, 14, 15, 16, 17, 18, 19 or 20 substitutions, deletions or insertions when compared to the polypeptide of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 or 447.

The disclosure also provides an isolated polynucleotide that is about 80%, 81%, 82%, 83%, 84%, 85%, 86%, 87%, 88%, 89%, 90%, 91%, 92%, 93%, 94%, 95%, 96%, 97%, 98% or 99% identical to the polynucleotide of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 or 458.

The disclosure also provides an isolated polypeptide that is about 80%, 81%, 82%, 83%, 84%, 85%, 86%, 87%, 88%, 89%, 90%, 91%, 92%, 93%, 94%, 95%, 96%, 97%, 98% or 99% identical to the polypeptide of SEQ ID NOs: 387, 388, 389, 390, 391, 392, 393, 394, 395, 396, 397, 398, 399, 400, 401, 402, 403, 404, 405, 406, 407, 408, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620 or 621.

The disclosure also provides an isolated polypeptide that is about 80%, 81%, 82%, 83%, 84%, 85%, 86%, 87%, 88%, 89%, 90%, 91%, 92%, 93%, 94%, 95%, 96%, 97%, 98% or 99% identical to the polypeptide of SEQ ID NOs: 377, 378, 415,417, 418, 420, 502, 518, 526, 527, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 74, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 487, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980 or 548.

The disclosure also provides an isolated polypeptide that is about 80%, 81%, 82%, 83%, 84%, 85%, 86%, 87%, 88%, 89%, 90%, 91%, 92%, 93%, 94%, 95%, 96%, 97%, 98% or 99% identical to the polypeptide of SEQ ID NOs: 541, 550, 554, 555, 556, 623 or 624.

The disclosure also provides an isolated polynucleotide that is about 80%, 81%, 82%, 83%, 84%, 85%, 86%, 87%, 88%, 89%, 90%, 91%, 92%, 93%, 94%, 95%, 96%, 97%, 98% or 99% identical to the polypeptide of SEQ ID NOs: 542 or SEQ ID NO: 551.

The disclosure also provides an isolated polypeptide that is about 80%, 81%, 82%, 83%, 84%, 85%, 86%, 87%, 88%, 89%, 90%, 91%, 92%, 93%, 94%, 95%, 96%, 97%, 98% or 99% identical to the polypeptide of SEQ ID NOs: 543, 552, 557, 558, 559, 625 or 626.

The disclosure also provides an isolated polynucleotide that is about 80%, 81%, 82%, 83%, 84%, 85%, 86%, 87%, 88%, 89%, 90%, 91%, 92%, 93%, 94%, 95%, 96%, 97%, 98% or 99% identical to the polypeptide of SEQ ID NOs: 544 or SEQ ID NO: 553.

The disclosure also provides an isolated polypeptide comprising an amino acid sequence of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231,233, 235, 237, 239, 241,243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof, wherein the polypeptide comprises one or more reverse peptide bonds.

The disclosure also provides an isolated polypeptide comprising an amino acid sequence of SEQ ID NOs: 387, 388, 389, 390, 391, 392, 393, 394, 395, 396, 397, 398, 399, 400, 401, 402, 403, 404, 405, 406, 407, 408, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620 or 621, wherein the polypeptide comprises one or more reverse peptide bonds.

The disclosure also provides an isolated polypeptide comprising an amino acid sequence of SEQ ID NOs: 377, 378, 415,417, 418, 420, 502, 518, 526, 527, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 74, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 487, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931,932, 933, 934, 935, 936, 937, 938, 939, 940, 941,942, 943, 944, 945,946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980 or 548, wherein the polypeptide comprises one or more reverse peptide bonds.

The disclosure also provides an isolated heterologous polypeptide comprising an amino acid sequence of SEQ ID NOs: 541, 550, 554, 555, 556, 623 or 624, wherein the heterologous polypeptide comprises one or more reverse peptide bonds.

The disclosure also provides an isolated heterologous polypeptide comprising an amino acid sequence of SEQ ID NOs: SEQ ID NOs: 543, 552, 557, 558, 559, 625 or 626, wherein the heterologous polypeptide comprises one or more reverse peptide bonds.

In some embodiments, the reverse peptide bond comprises NH—CO bond.

In some embodiments, the reverse peptide bond comprises $CH_2$—NH, —$CH_2$S—, —$CH_2CH_2$—, —CH═CH—, —$COCH_2$—, —CH(OH)$CH_2$—, or —$CH_2$SO— bond.

The disclosure also provides an isolated polypeptide comprising an amino acid sequence of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof, wherein the polypeptide comprises one or more chemical modifications.

The disclosure also provides an isolated polypeptide comprising an amino acid sequence of SEQ ID NOs: 387, 388, 389, 390, 391, 392, 393, 394, 395, 396, 397, 398, 399, 400, 401, 402, 403, 404, 405, 406, 407, 408, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620 or 621, wherein the polypeptide comprises one or more chemical modifications.

The disclosure also provides an isolated polypeptide comprising an amino acid sequence of SEQ ID NOs: 377, 378, 415,417, 418, 420, 502, 518, 526, 527, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 74, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 487, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980 or 548, wherein the polypeptide comprises one or more chemical modifications.

The disclosure also provides an isolated heterologous polypeptide comprising an amino acid sequence of SEQ ID NOs: 541, 550, 554, 555, 556, 623 or 624, wherein the heterologous polypeptide comprises one or more chemical modifications.

The disclosure also provides an isolated heterologous polypeptide comprising an amino acid sequence of SEQ ID NOs: SEQ ID NOs: 543, 552, 557, 558, 559, 625 or 626, wherein the heterologous polypeptide comprises one or more chemical modifications.

In some embodiments, the one or more chemical modification comprises modification with carbobenzoxyl, dansyl, t-butyloxycarbonyl, 9-fluorenylmethoxy-carbonyl or D-isomer of an amino acid.

Methods of Making Polynucleotides and Polypeptides of the Disclosure

The polynucleotides of the disclosure or variants may be in the form of RNA or in the form of DNA obtained by cloning or produced synthetically. The DNA may be double-stranded or single-stranded.

Methods of generating polynucleotides and heterologous polynucleotides of the disclosure or variants are known in the art and include chemical synthesis, enzymatic synthesis (e.g. in vitro transcription), enzymatic or chemical cleavage of a longer precursor, chemical synthesis of smaller fragments of the polynucleotides followed by ligation of the fragments or known PCR methods. The polynucleotide sequence to be synthesized may be designed with the appropriate codons for the desired amino acid sequence. In general, preferred codons may be selected for the intended host in which the sequence will be used for expression.

Methods of making polypeptides and heterologous polypeptides of the disclosure are known in the art and include standard molecular biology techniques for cloning and expression of the polypeptides and chemical synthesis of the polypeptides.

Peptides may be synthesized by the Fmoc-polyamide mode of solid-phase peptide synthesis as disclosed by Lukas et al. (Lukas et al., 1981) and by references as cited therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1 hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, (Bruckdorfer et al., 2004), and the references as cited therein).

U.S. Pat. No. 4,897,445 provides a method for the solid phase synthesis of non-peptide bonds (—$CH_2$—NH) in polypeptide chains which involves polypeptides synthesized by standard procedures and the non-peptide bond synthesized by reacting an amino aldehyde and an amino acid in the presence of $NaCNBH_3$.

Vectors and Recombinant Viruses of the Disclosure

The disclosure also provides a vector comprising a polynucleotide or a heterologous polynucleotide of the disclosure, or fragments or variants thereof.

In some embodiments, the vector is an expression vector. In some embodiments, the vector is a viral vector. The vectors of the disclosure may be utilized to generate recombinant viruses comprising the vectors of the disclosure or to express the polypeptides of the disclosure.

The disclosure also provides a vector comprising a polynucleotide encoding one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 or 447, or fragments thereof.

The disclosure also provides a vector comprising a polynucleotide encoding a polypeptide that is about 80%, 81%, 82%, 83%, 84%, 85%, 86%, 87%, 88%, 89%, 90%, 91%, 92%, 93%, 94%, 95%, 96%, 97%, 98% or 99% identical to the polypeptide of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 or 447, or fragments thereof.

The disclosure also provides a vector comprising one or more polynucleotides of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 or 458, or fragments thereof.

The disclosure also provides a vector comprising a polynucleotide that is about 80%, 81%, 82%, 83%, 84%, 85%, 86%, 87%, 88%, 89%, 90%, 91%, 92%, 93%, 94%, 95%, 96%, 97%, 98% or 99% identical to the polynucleotide of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 or 458, or fragments thereof.

The disclosure also provides a vector comprising a heterologous polynucleotide encoding a heterologous polypeptide comprising two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241,243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

The disclosure also provides a vector comprising a heterologous polynucleotide comprising two or more polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a vector comprising a heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides a vector comprising a heterologous polynucleotide encoding a heterologous polypeptide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides a vector comprising a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides a vector comprising a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides a vector comprising a heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a vector comprising a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a recombinant virus comprising the vector of the disclosure.

The disclosure also provides a recombinant adenovirus comprising the vector of the disclosure.

The disclosure also provides a recombinant human adenovirus (rAd) comprising the vector of the disclosure.

The disclosure also provides a recombinant human adenovirus derived from serotype 26 (rAd26) comprising the vector of the disclosure.

The disclosure also provides a recombinant great ape adenovirus (rGAd) comprising the vector of the disclosure.

In some embodiments, the rGAd is derived from GAd20. In some embodiments, the rGAd is derived from GAd19. In some embodiments, the rGAd is derived from GAd21. In some embodiments, the rGAd is derived from GAd25. In some embodiments, the rGAd is derived from GAd26. In some embodiments, the rGAd is derived from GAd27, In some embodiments, the rGAd is derived from GAd28. In some embodiments, the rGAd is derived from GAd29. In some embodiments, the rGAd is derived from GAd30. In some embodiments, the rGAd is derived from GAd31. GAd19-21 and GAd25-31 are described in Int. Pat. Publ. No. WO2019/008111 and represent strains with high immunogenicity and no pre-existing immunity in the general human population. The polynucleotide sequence of GAd20 genome is shown in SEQ ID NO: 622 as disclosed in WO2019/008111.

SEQ ID NO: 622

```
CATCATCAATAATATACCTTATTTTGGATTGAGGCCAATATGATAATGAGGTGGGCG

GGGCGAGGCGGGGCGGGTGACGTAGGACGCGCGAGTAGGGTTGGGAGGTGTGGCG

GAAGTGTGGCATTTGCAAGTGGGAGGAGCTGACATGCAATCTTCCGTCGCGGAAAA

TGTGACGTTTTTGATGAGCGCCGCCTACCTCCGGAAGTGCCAATTTTCGCGCGCTTTT

CACCGGATATCGTAGTAATTTTGGGCGGGACCATGTAAGATTTGGCCATTTTCGCGC

GAAAAGTGAAACGGGGAAGTGAAAACTGAATAATAGGGCGTTAGTCATAGCGCGTA

ATATTTACCGAGGGCCGAGGGACTTTGACCGATTACGTGGAGGACTCGCCCAGGTGT

TTTTTACGTGAATTTCCGCGTTCCGGGTCAAAGTCTCCGTTTTTATTGTCGCCGTCAT
```

-continued

```
CTGACGCGGAGGGTATTTAAACCCGCTGCGCTCCTAAAGAGGCCACTCTTGAGTGCC

AGCGAGAAGAGTTTTCTCCTCCGCTCCGTTTCGGCGATCGAAAAATGAGACATTTAG

CCTGCACTCCGGGTCTTTTGTCCGGCCGGGCGGCGTCCGAGCTTTTGGACGCTTTGCT

CAATGAGGTTCTGAGCGATGATTTTCCGTCTACTACCCACTTTAGCCCACCTACTCTT

CACGAACTGTACGATCTGGATGTACTGGTGGATGTGAACGATCCCAACGAGGAGGC

GGTTTCTACGTTTTTTCCCGAGTCTGCGCTTTTGGCTGCCCAGGAGGGATTTGACCTA

CACACTCCGCCGCTGCCTATTTTAGAGTCTCCGCTGCCGGAGCCCAGTGGTATACCTT

ATATGCCTGAACTGCTTCCCGAAGTGGTAGACCTGACCTGCCACGAGCCGGGCTTTC

CGCCCAGCGACGATGAGGGTGAGCCTTTTGCTTTAGACTATGCTGAGATACCTGGGC

TCGGTTGCAGGTCTTGTGCATATCATCAGAGGGTTACCGGAGACCCCGAGGTTAAGT

GTTCGCTGTGCTATATGAGGCTGACCTCTTCCTTTATCTACAGTAAGTTTTTTTGTGT

AGGTGGGCTTTTTGGGTAGGTGGGTTTTGTGGCAGGACAGGTGTAAATGTTGCTTGT

GTTTTTTGTACCTGCAGGTCCGGTGTCCGAGCCAGACCCGGAGCCCGACCGCGATCC

CGAGCCGGATCCCGAGCCTCCTCGCAGGCCAAGGAAATTACCTTCCATTTTGTGCAA

GCCTAAGACACCTGTGAGGACCAGCGAGGCGGACAGCACTGACTCTGGCACTTCTA

CCTCTCCTCCTGAAATTCACCCAGTGGTTCCTCTGGGTATACATAGACCTGTTGCTGT

TAGAGTTTGCGGGCGACGCCCTGCAGTAGAGTGCATTGAGGACTTGCTTAACGATCC

CGAGGGACCTTTGGACTTGAGCATTAAACGCCCTAGGCAATAAACCCCACCTAAGTA

ATAAACCCCACCTAAGTAATAAACTTTACCGCCCTTGGTTATTGAGATGACGCCCAA

TGTTTGCTTTTGAATGACTTCATGTGTATAATAAAAGTGAGTGTGGTCATAGGTCTCT

TGTTTGTCTGGGCGGGGTTTAAGGGTATATAAGTTTCTCGGGGCTAAACTTGGTTAC

ACTTGACCCCAATGGAGGCGTGGGGGTGCTTGGAGGAGTTTGCGGACGTGCGCCGTT

TGCTGGACGAGAGCTCTAGCAATACCTATAGTATTTGGAGGTATCTGTGGGGCTCTA

CTCAGGCCAAGTTGGTCTTCAGAATTAAGCAGGATTACAAGTGCGATTTTGAAGAGC

TTTTTAGTTCCTGTGGTGAGCTTTTGCAATCCTTGAATCTGGGCCACCAGGCTATCTT

CCAGGAAAAGGTTCTCTCGACTTTGGATTTTTCCACTCCCGGGCGCACCGCCGCTTGT

GTGGCTTTTGTGTCTTTTGTGCAAGATAAATGGAGCGGGGAGACCCACCTGAGTCAC

GGCTACGTGCTGGATTTCATGGCGATGGCTCTTTGGAGGGCTTACAACAAATGGAAG

ATTCAGAAGGAACTGTACGGTTCCGCCCTACGTCGTCCACTTCTGCAGCGGCAGGGG

CTGATGTTTCCCGACCATCGCCAGCATCAGAATCTGGAAGACGAGCGAGCGGAGAA

GATCAGCTTGAGAGCCGGCCTGGACCCTCCTCAGGAGGAATGAATCTCCCGCAGGT

GGTTGAGCTGTTTCCCGAACTGAGACGGGTCCTGACTATCAGGGAGGATGGTCAGTT

TGTGAAGAAGCTGAAGAGGGATCGGGGTGAGGGAGATGATGAGGCGGCTAGCAATT

TAGCTTTTAGTCTGATAACTCGCCACCGACCGGAATGTATTACCTATCAGCAGATTA

AGGAGAGTTGTGCCAACGAGCTGGATCTTTTGGGTCAGAAGTATAGCATAGAACAG

CTTACCACTTACTGGCTTCAGCCCGGGGATGATTGGGAAGAGGCGATTAGGGTGTAT

GCAAAGGTGGCCCTGCGGCCCGATTGCAAGTATAAGATTACTAAGTTGGTTAATATT

AGAAACTGCTGCTATATTTCTGGAAACGGGGCCGAAGTGGAGATAGATACTGAGGA

CAGGGTGGCTATTAGGTGTTGCATGATAAACATGTGGCCCGGGATACTGGGGATGG

ATGGGGTGATATTTATGAATGTGAGGTTCACGGGCCCCAACTTTAATGGTACGGTGT

TCATGGGCAACACCAACTTGCTCCTGCATGGTGCGAGTTTCTATGGGTTTAACAACA
```

-continued

CCTGTATAGAGGCCTGGACCGATGTAAAGGTTCGAGGTTGTTCCTTTTATAGCTGTT

GGAAGGCGGTGGTGTGTCGCCCTAAAAGCAGGGGTTCTGTGAAGAAATGCTTGTTTG

AAAGGTGCACCCTAGGTATCCTTTCTGAGGGCAACTCCAGGGTGCGCCATAATGTGG

CTTCGAACTGCGGTTGCTTCATGCAAGTGAAGGGGGTGAGCGTTATCAAGCATAACT

CGGTCTGTGGAAACTGCGAGGATCGCGCCTCTCAGATGCTGACCTGCTTTGATGGCA

ACTGTCACCTGTTGAAGACCATTCATATAAGCAGTCACCCCAGAAAGGCCTGGCCCG

TGTTTGAGCATAACATTCTGACCCGCTGTTCCTTGCATCTGGGGGTCAGGAGGGGTA

TGTTCCTGCCTTACCAGTGTAACTTTAGCCACACTAAAATCCTGCTGGAACCCGAGT

GCATGACTAAGGTCAGCCTGAATGGTGTGTTTGATGTGAGTCTGAAGATTTGGAAGG

TGCTGAGGTATGATGAGACCAGGACCAGGTGCCGACCCTGCGAGTGCGGCGGCAAG

CACATGAGAAATCAGCCTGTGATGTTGGATGTGACCGAGGAGCTTAGGCCTGACCAT

CTGGTGCTGGCCTGCACCAGGGCCGAGTTTGGGTCTAGCGATGAGGATACCGATTGA

GGTGGGTAAGGTGGGCGTGGCTAGCAGGGTGGGCGTGTATAAATTGGGGGTCTAAG

GGGTCTCTCTGTTTGTCTTGCAACAGCCGCCGCCATGAGCGACACCGGCAACAGCTT

TGATGGAAGCATCTTTAGTCCCTATCTGACAGTGCGCATGCCTCACTGGGCCGGAGT

GCGTCAGAATGTGATGGGTTCCAACGTGGATGGACGTCCCGTTCTGCCTTCAAATTC

GTCTACTATGGCCTACGCGACCGTGGGAGGAACTCCGCTGGACGCCGCGACCTCCGC

CGCCGCCTCCGCCGCCGCCGCGACCGCGCGCAGCATGGCTACGGACCTTTACAGCTC

TTTGGTGGCGAGCAGCGCGGCCTCTCGCGCGTCTGCTCGGGATGAGAAACTGACTGC

TCTGCTGCTTAAACTGGAAGACTTGACCCGGGAGCTGGGTCAACTGACCCAGCAGGT

TTCCAGCTTGCGTGAGAGCAGCCTTGCCTCCCCCTAATGGCCCATAATATAAATAAA

AGCCAGTCTGTTTGGATTAAGCAAGTGTATGTTCTTTATTTAACTCTCCGCGCGCGGT

AAGCCCGGGACCAGCGGTCTCGGTCGTTTAGGGTGCGGTGGATTTTTTCCAACACGT

GGTACAGGTGGCTCTGGATGTTTAGATACATGGGCATGAGTCCATCCCTGGGGTGGA

GGTAGCACCACTGCAGAGCTTCGTGCTCGGGGGTGGTGTTGTATATGATCCAGTCGT

AGCAGGAGCGCTGGGCGTGGTGCTGAAAAATGTCCTTAAGCAAGAGGCTTATAGCT

AGGGGGAGGCCCTTGGTGTAAGTGTTTACAAATCTGCTTAGCTGGGAGGGGTGCATC

CGGGGGGATATGATGTGCATCTTGGACTGGATTTTTAGGTTGGCTATGTTCCCGCCC

AGATCCCTTCTGGGATTCATGTTGTGCAGGACCACCAGCACGGTATATCCAGTGCAC

TTGGGAAATTTATCGTGGAGCTTAGACGGGAATGCATGGAAGAACTTGGAGACGCC

CTTGTGGCCTCCCAGATTTTCCATACATTCGTCCATGATGATGGCAATGGGCCCGTG

GGAAGCTGCCTGAGCAAAAACGTTTCTGGCATCGCTCACATCGTAGTTATGTTCCAG

GGTGAGGTCATCATAGGACATCTTTACGAATCGGGGGCGAAGGGTCCCGGACTGGG

GGATGATGGTACCCTCGGGCCCCGGGGCGTAGTTCCCCTCACAGATCTGCATCTCCC

AGGCTTTCATTTCAGAGGGAGGGATCATATCCACCTGCGGGGCGATGAAAAAGACA

GTTTCTGGCGCAGGGGAGATTAACTGGGATGAGAGCAGGTTTCTGAGCAGCTGTGA

CTTTCCACAGCCGGTGGGCCCATATATCACGCCTATCACCGGCTGCAGCTGGTAGTT

AAGAGAGCTGCAGCTGCCGTCCTCCCGGAGCAGGGGGGCCACCTCGTTGAGCATAT

CCCTGACGTGGATGTTCTCCCTGACCAGTTCCGCCAGAAGGCGCTCGCCGCCCAGCG

AAAGCAGCTCTTGCAAGGAAGCAAAATTTTTCAGCGGTTTCAGGCCATCGGCCGTGG

-continued

GCATGTTTTTCAGCGTCTGGGTCAGCAGCTCCAGCCTGTCCCAGAGCTCGGTGATGT

GCTCTACGGCATCTCGATCCAGCAGATCTCCTCGTTTCGCGGGTTGGGGCGGCTTTC

GCTGTAGGGCACCAGCCGATGGGCGTCCAGCGGGGCCAGAGTCATGTCCTTCCATG

GGCGCAGGGTCCTCGTCAGGGTGGTCTGGGTCACGGTGAAGGGGTGCGCTCCGGGT

TGGGCACTGGCCAGGGTGCGCTTGAGGCTGGTTCTGCTGGTGCTGAATCGCTGCCGC

TCTTCGCCCTGCGCGTCGGCCAGGTAGCATTTGACCATGGTCTCGTAGTCGAGACCC

TCGGCGGCGTGCCCCTTGGCGCGGAGCTTTCCCTTGGAGGTGGCGCCGCACGAGGGG

CACTGCAGGCTCTTCAGGGCGTAGAGCTTGGGAGCGAGAAACACGGACTCTGGGGA

GTAGGCGTCCGCGCCGCAGGCCGAGCAGACCGTCTCGCATTCCACCAGCCAAGTGA

GTTCCGGGCGGTCAGGGTCAAAAACCAGGTTGCCCCCATGCTTTTTGATGCGTTTCTT

ACCTTGGCTCTCCATGAGGCGGTGTCCCTTCTCGGTGACGAAGAGGCTGTCCGTGTC

CCCGTAGACCGACTTCAGGGGCCTGTCTTCCAGCGGAGTGCCTCTGTCCTCCTCGTA

GAGAAACTCTGACCACTCTGAGACGAAGGCCCGCGTCCAGGCCAGGACGAAGGAGG

CCACGTGGGAGGGGTAGCGGTCGTTGTCCACTAGCGGGTCCACCTTCTCCAGGGTGT

GCAGGCACATGTCCCCCTCCTCCGCGTCCAGAAAAGTGATTGGCTTGTAGGTGTAGG

ACACGTGACCGGGGGTTCCCAACGGGGGGGTATAAAAGGGGGTGGGTGCCCTTTCA

TCTTCACTCTCTTCCGCATCGCTGTCTGCGAGAGCCAGCTGCTGGGGTAAGTATTCCC

TCTCGAAGGCGGGCATGACCTCAGCGCTCAGGTTGTCAGTTTCTAAAAATGAGGAGG

ATTTGATGTTCACCTGTCCGGAGGTGATACCTTTGAGGGTACCTGGGTCCATCTGGTC

AGAAAACACTATTTTTTTGTTATCAAGCTTGGTGGCGAATGACCCGTAGAGGGCGTT

GGAGAGCAGCTTGGCGATGGAGCGCAGGGTCTGGTTTTTGTCGCGGTCGGCTCGCTC

CTTGGCCGCGATGTTGAGTTGCACGTACTCGCGGGCCACGCACTTCCACTCGGGGAA

CACGGTGGTGCGCTCGTCTGGGATCAGGCGCACCCTCCAGCCGCGGTTGTGCAGGGT

GACCATGTCGACGCTGGTGGCGACCTCACCGCGCAGACGCTCGTTGGTCCAGCAGA

GGCGGCCGCCCTTGCGCGAGCAGAAGGGGGGTAGGGGGTCCAGCTGGTCCTCGTTT

GGGGGGTCCGCGTCGATGGTAAAGACCCCGGGGAGCAGGCGCGGGTCAAAGTAGTC

GATCTTGCAAGCTTGCATGTCCAGAGCCCGCTGCCATTCGCGGGCGGCGAGCGCGCG

CTCGTAGGGGTTGAGGGGCGGGCCCCAGGGCATGGGGTGGGTGAGCGCGGAGGCGT

ACATGCCGCAGATGTCATACACGTACAGGGGTTCCCTGAGGATACCGAGGTAGGTG

GGGTAGCAGCGCCCCCCGCGGATGCTGGCGCGCACGTAGTCATAGAGCTCGTGGGA

GGGGGCCAGCATGTTGGGCCCGAGGTTGGTGCGCTGGGGGCGCTCGGCGCGGAAGA

CGATCTGCCTGAAGATGGCGTGGGAGTTGGAGGAGATGGTGGGCCGCTGGAAGACG

TTGAAGCTTGCTTCTTGCAAGCCCACGGAGTCCCTGACGAAGGAGGCGTAGGACTCG

CGCAGCTTGTGCACCAGCTCGGCGGTGACCTGGACGTCGAGCGCACAGTAGTCGAG

GGTCTCGCGGATGATGTCATACCTATCCTCCCCCTTCTTTTTCCACAGCTCGCGGTTG

AGGACGAACTCTTCGCGGTCTTTCCAGTACTCTTGGAGGGGAAACCCGTCCGTGTCC

GAACGGTAAGAGCCTAGCATGTAGAACTGGTTGACGGCCTGGTAGGGGCAGCAGCC

CTTCTCCACGGGCAGCGCGTAGGCCTGCGCCGCCTTGCGGAGGGAGGTGTGGGTGA

GGGCGAAAGTGTCCCTGACCATGACTTTGAGGTATTGATGTCTGAAGTCTGTGTCAT

CGCAGCCGCCCTGTTCCCACAGGGTGTAGTCCGTGCGCTTTTTGGAGCGCGGGTTGG

GCAGGGAGAAGGTGAGGTCATTGAAGAGGATCTTCCCCGCTCGAGGCATGAAGTTT

-continued

CTGGTGATGCGAAAGGGCCCTGGGACCGAGGAGCGGTTGTTGATGACCTGGGCGGC

CAGGACGATCTCGTCAAAGCCGTTTATGTTGTGTCCCACGATGTAGAGCTCCAGGAA

GCGGGGCTGGCCCTTGATGGAGGGGAGCTTTTTAAGTTCCTCGTAGGTAAGCTCCTC

GGGCGATTCCAGGCCGTGCTCCTCCAGGGCCCAGTCTTGCAAGTGAGGGTTGGCCGC

CAGGAAGGATCGCCAGAGGTCGCGGGCCATGAGGGTCTGCAGGCGGTCGCGGAAGG

TTCTGAACTGCCGCCCCACGGCCATTTTTTCGGGGGTGATGCAGTAGAAGGTGAGGG

GGTCTTTCTCCCAGGGGTCCCATCTGAGCTCTCGGGCGAGGTCGCGCGCGGCAGCGA

CCAGAGCCTCGTCGCCCCCCAGTTTCATGACCAGCATGAAGGGCACGAGTTGCTTGC

CAAAGGCTCCCATCCAAGTGTAGGTTTCTACATCGTAGGTGACAAAGAGGCGCTCCG

TGCGAGGATGAGAGCCGATTGGGAAGAACTGGATCTCCCGCCACCAGTTGGAGGAT

TGGCTGTTGATGTGGTGAAAGTAGAAGTCCCGTCTGCGGGCCGAGCACTCGTGCTGG

CTTTTGTAAAAGCGACCGCAGTACTGGCAGCGCTGCACGGGTTGTATATCTTGCACG

AGGTGAACCTGGCGACCTCTGACGAGGAAGCGCAGCGGGAATCTAAGTCCCCCGCC

TGGGGTCCCGTGTGGCTGGTGGTCTTTTACTTTGGTTGTCTGGCCGCCAGCATCTGTC

TCCTGGAGGGCGATGGTGGAACAGACCACCACGCCGCGAGAGCCGCAGGTCCAGAT

CTCGGCGCTCGGCGGGCGGAGTTTGATGACGACATCGCGCACATTGGAGCTGTCCAT

GGTCTCCAGCTCCCGCGGCGGCAGGTCAGCCGGGAGTTCCTGGAGGTTCACCTCGCA

GAGACGGGTCAAGGCGCGGACAGTGTTGAGATGGTATCTGATTTCAAGGGGCATGT

TGGAGGCGGAGTCGATGGCTTGCAGGAGGCCGCAGCCCCGGGGGGCCACGATGGTT

CCCCGCGGGGCGCGAGGGGAGGCGGAAGCTGGGGGTGTGTTCAGAAGCGGTGACGC

GGGCGGGCCCCCGGAGGTAGGGGGGGTTCCGGCCCCACAGGCATGGGCGGCAGGG

GCACGTCTTCGCCGCGCGCGGGCAGGGGCTGGTGCTGGCTCCGAAGAGCGCTTGCGT

GCGCGACGACGCGACGGTTGGTGTCCTGTATCTGGCGCCTCTGAGTGAAGACCACGG

GTCCCGTGACCTTGAACCTGAAAGAGAGTTCGACAGAATCAATCTCGGCATCGTTGA

CAGCGGCCTGGCGCAGGATCTCCTGCACGTCGCCCGAGTTGTCCTGGTAGGCGATTT

CTGCCATGAACTGCTCGATCTCTTCCTCCTGGAGATCTCCTCGTCCGGCGCGCTCCAC

GGTGGCCGCCAGGTCGTTGGAGATGCGACCCATGAGCTGCGAGAAGGCGTTGAGTC

CGCCCTCGTTCCAGACCCGGCTGTAGACCACGCCCCCCTCGGCGTCGCGGGCGCGCA

TGACCACCTGGGCCAGGTTGAGCTCCACGTGTCGCGTGAAGACGGCGTAGTTGCGCA

GGCGCTGGAAAAGGTAGTTCAGGGTGGTGGCGGTGTGCTCGGCGACGAAGAAGTAC

ATGACCCAGCGCCGCAACGTGGATTCATTGATGTCCCCCAAGGCCTCCAGGCGCTCC

ATGGCCTCGTAGAAGTCCACGGCGAAGTTGAAAAACTGGGAGTTGCGAGCGGACAC

GGTCAACTCCTCCTCCAGAAGACGGATGAGCTCGGCGACAGTGTCGCGCACCTCGCG

CTCGAAGGCCACGGGGGGCGCTTCTTCCTCTTCCACCTCTTCTTCCATGATTGCTTCT

TCTTCTTCCTCAGCCGGGACGGGAGGGGGCGGCGGCGGGGGAGGGGCGCGGCGGCG

GCGGCGGCGCACCGGGAGGCGGTCGATGAAGCGCTCGATCATCTCCCCCCGCATGC

GGCGCATGGTCTCGGTGACGGCGCGGCCGTTCTCCCGGGGGCGCAGCTCGAAGACG

CCGCCTCTCATTTCGCCGCGGGGCGGGCGGCCGTGAGGTAGCGAGACGGCGCTGAC

TATGCATCTTAACAATTGCTGTGTAGGTACGCCGCCAAGGGACCTGATTGAGTCCAG

ATCCACCGGATCCGAAAACCTTTGGAGGAAAGCGTCTATCCAGTCGCAGTCGCAAG

-continued

GTAGGCTGAGCACCGTGGCGGGCGGGGGCGGGTCGGGAGAGTTCCTGGCGGAGATG

CTGCTGATGATGTAATTAAAGTAGGCGGTCTTGAGAAGGCGGATGGTGGACAGGAG

CACCATGTCTTTGGGTCCGGCCTGTTGGATGCGGAGGCGGTCGGCCATGCCCCAGGC

CTCGTTCTGACACCGGCGCAGGTCTTTGTAGTAATCTTGCATGAGTCTTTCCACCGGC

ACTTCTTCTCCTTCCTCTTCTTCATCTCGCCGGTGGTTTCTCGCGCCGCCCATGCGCGT

GACCCCAAAGCCCCTGAGCGGCTGCAGCAGGGCCAGGTCGGCGACCACGCGCTCGG

CCAAGATGGCCTGCTGTACCTGAGTGAGGGTCCTCTCGAAGTCATCCATGTCCACGA

AGCGGTGGTAGGCACCCGTGTTGATGGTGTAGGTGCAGTTGGCCATGACGGACCAG

TTGACGGTCTGGTGTCCCGGCTGCGAGAGCTCCGTGTACCGCAGGCGCGAGAAGGC

GCGGGAATCGAACACGTAGTCGTTGCAAGTCCGCACCAGATACTGGTAGCCCACCA

GGAAGTGCGGCGGAGGTTGGCGATAGAGGGGCCAGCGCTGGGTGGCGGGGGCGCC

GGGCGCCAGGTCTTCCAGCATGAGGCGGTGGTATCCGTAGATGTACCTGGACATCCA

GGTGATGCCTGCGGCGGTGGTGGTGGCGCGCGCGTAGTCGCGGACCCGGTTCCAGA

TGTTTCGCAGGGGCGAGAAGTGTTCCATGGTCGGCACGCTCTGGCCGGTGAGGCGCG

CGCAGTCGTTGACGCTCTATACACACACAAAAACGAAAGCGTTTACAGGGCTTTCGT

TCTGTAGCCTGGAGGAAAGTAAATGGGTTGGGTTGCGGTGTGCCCCGGTTCGAGACC

AAGCTGAGCTCAGCCGGCTGAAGCCGCAGCTAACGTGGTATTGGCAGTCCCGTCTCG

ACCCAGGCCCTGTATCCTCCAGGATACGGTCGAGAGCCCTTTTGCTTTCTTGGCCAA

GCGCCCGTGGCGCGATCTGGGATAGATGGTCGCGATGAGAGGACAAAAGCGGCTCG

CTTCCGTAGTCTGGAGAAACAATCGCCAGGGTTGCGTTGCGGCGTACCCCGGTTCGA

GCCCCTATGGCGGCTTGGATCGGCCGGAACCGCGGCTAACGTGGGCTGTGGCAGCC

CCGTCCTCAGGACCCCGCCAGCCGACTTCTCCAGTTACGGGAGCGAGCCCCTTTTGT

TTTTTTATTTTTTAGATGCATCCCGTGCTGCGGCAGATGCGCCCCTCGCCCCGGCCCG

ATCAGCAGCAGCAACAGCAGGCATGCAGACCCCCCTCTCCTCTCCCCGCCCCGGTCA

CCACGGCCGCGGCGGCCGTGTCCGGTGCGGGGGCGCGCTGGAGTCAGATGAGCCA

CCGCGGCGGCGACCTAGGCAGTATCTGGACTTGGAAGAGGGCGAGGGACTGGCGCG

GCTGGGGGCGAGCTCTCCAGAGCGCCACCCGCGGGTGCAGTTGAAAAGGGACGCGC

GTGAGGCGTACCTGCCGCGGCAAAACCTGTTTCGCGACCGCGGGGGCGAGGAGCCC

GAGGAGATGCGGGACTGCAGGTTCCAAGCGGGGCGCGAGCTGCGCCCGCGGCTTGGA

CAGACAGCGCCTGCTGCGCGAGGAGGACTTTGAGCCCGACACGCAGACGGGCATCA

GCCCCGCGCGCGCGCACGTGGCCGCGGCCGACCTGGTGACCGCCTACGAGCAGACG

GTGAACCAGGAGCGCAACTTCCAAAAAAGCTTCAACAACCACGTGCGCACGCTGGT

GGCGCGCGAGGAGGTGACCCTGGGTCTCATGCATCTGTGGGACCTGGTGGAGGCGA

TCGTGCAGAACCCCAGCAGCAAGCCCCTGACCGCGCAGCTGTTCCTGGTGGTGCAGC

ACAGCAGGGACAACGAGGCCTTCAGGGAGGCGCTGCTGAACATCACCGAGCCGGAG

GGGCGCTGGCTCCTGGACCTGATAAACATCCTGCAGAGCATAGTGGTGCAGGAGCG

CAGCCTGAGCCTGGCCGAGAAGGTGGCGGCCATTAACTATTCTATGCTGAGCCTGGG

CAAGTTCTACGCTCGCAAGATCTACAAGACCCCCTACGTGCCCATAGACAAGGAGGT

GAAGATAGACAGCTTCTACATGCGCATGGCGCTGAAGGTGCTAACCCTGAGCGACG

ACCTGGGAGTGTACCGCAACGAGCGCATCCACAAGGCCGTGAGCGCCAGCCGGCGG

CGCGAGCTGAGCGACCGCGAACTGATGCACAGTCTGCAGCGCGCGCTGACCGGCGC

-continued

GGGCGAGGGCGACAGGGAGGTCGAGTCCTACTTTGACATGGGGGCCGACCTGCACT

GGCAGCCGAGCCGCCGCGCCCTGGAAGCGGCGGGGGCGTACGGCGGCCCCCTGGCG

GCCGATGACGAGGAAGAGGAGGACTATGAGCTAGAGGAGGGCGAGTACCTGGAGG

ACTGACCTGGCTGGTGGTGTTTTGGTATAGATGCAAGATCCGAACGTGGCGGACCCG

GCGGTCCGGGCGGCGCTGCAGAGCCAGCCGTCCGGCATTAACTCCTCTGACGACTGG

GCCGCGGCCATGGGTCGCATCATGGCCCTGACCGCGCGCAACCCCGAGGCCTTCAG

GCAGCAGCCTCAGGCTAACCGGCTGGCGGCCATCTTGGAAGCGGTAGTGCCCGCGC

GCTCCAACCCCACCCACGAGAAGGTGCTGGCCATAGTCAACGCGCTGGCGGAGAGC

AGGGCCATCCGGGCAGACGAGGCCGGACTGGTGTACGATGCGCTGCTGCAGCGGGT

GGCGCGGTACAACAGCGGCAACGTGCAGACCAACCTGGACCGCCTGGTGACGGACG

TGCGCGAGGCCGTGGCGCAGCGCGAGCGCTTGCATCAGGACGGCAACCTGGGCTCG

CTGGTGGCGCTAAACGCCTTCCTTAGCACCCAGCCGGCCAACGTACCGCGGGGGCA

GGAGGACTACACCAACTTCTTGAGCGCGCTGCGGCTGATGGTGACCGAGGTCCCTCA

GAGCGAGGTGTACCAGTCGGGGCCCGACTACTTCTTCCAGACCAGCAGACAGGGCT

TGCAAACCGTGAACCTGAGCCAGGCTTTCAAGAACCTGCGGGGGCTGTGGGGAGTG

AAGGCGCCCACCGGCGACCGGGCTACGGTGTCCAGCCTGCTAACCCCCAACTCGCG

CCTGCTGCTGCTGCTGATCGCGCCCTTCACGGACAGCGGGAGCGTCTCGCGGGAGAC

CTATCTGGGCCACCTGCTGACGCTGTACCGCGAGGCCATCGGGCAGGCGCAGGTGG

ACGAGCACACCTTCCAGGAGATCACCAGCGTGAGCCACGCGCTGGGGCAGGAGGAC

ACGGGCAGCCTGCAGGCGACCCTGAACTACCTGCTGACCAACAGGCGGCAGAAGAT

TCCCACGCTGCACAGCCTGACCCAGGAGGAGGAGCGCATCTTGCGCTACGTGCAGC

AGAGCGTGAGCCTGAACCTGATGCGCGACGGCGTGACGCCCAGCGTGGCGCTGGAC

ATGACCGCGCGCAACATGGAACCGGGCATGTACGCTTCCCAGCGGCCGTTCATCAAC

CGCCTGATGGACTACTTGCATCGGGCGGCGGCCGTGAACCCCGAGTACTTCACCAAT

GCCATTCTGAATCCCCACTGGATGCCCCCTCCGGGTTTCTACAACGGGGACTTCGAG

GTGCCTGAGGTCAACGATGGGTTCCTCTGGGATGACATGGATGACAGTGTGTTCTCC

CCCAACCCGCTGCGCGCCGCGTCTCTGCGATTGAAGGAGGGCTCTGACAGGGAAGG

ACCAAGGAGTCTGGCCTCCTCCCTGGCTCTGGGGGCGGTGGGCGCCACGGGCGCGG

CGGCGCGGGGCAGCAGCCCCTTCCCCAGCCTGGCGGACTCTCTGAATAGCGGGCGG

GTGAGCAGGCCCCGCTTGCTAGGCGAGGAGGAGTATCTGAACAACTCCCTGCTGCA

GCCCGTGAGGGACAAAAACGCTCAGCGGCAGCAGTTTCCCAACAATGGGATAGAGA

GCCTGGTGGACAAGATGTCCAGATGGAAGACGTATGCGCAGGAGTACAAGGAGTGG

GAGGACCGCCAGCCGCGGCCCCTGCCGCCCCCTAGACAGCGCTGGCAGCGGCGCGC

GTCCAACCGCCGCTGGAGGCAGGGGCCCGAGGACGATGATGACTCTGCAGATGACA

GCAGCGTGTTGGACCTGGGCGGGAGCGGGAACCCCTTTTCGCACCTGCGCCCACGCC

TGGGCAAGATGTTTTAAAAGAGAAAAATAAAAACTCACCAAGGCCATGGCGACGAG

CGTTGGTTTTTTGTTCCCTTCCTTAGTATGCGGCGCGCGGCGATGTTCGAGGAGGGGC

CTCCCCCCTCTTACGAGAGCGCGATGGGAATTTCTCCTGCGGCGCCCCTGCAGCCTC

CCTACGTGCCTCCTCGGTACCTGCAACCTACAGGGGGGAGAAATAGCATCTGTTACT

CTGAGCTGCAGCCCCTGTACGATACCACCAGACTGTACCTGGTGGACAACAAGTCCG

-continued

CGGACGTGGCCTCCCTGAACTACCAGAACGACCACAGCGATTTTTTGACCACGGTGA

TCCAAAACAACGACTTCACCCCAACCGAGGCCAGTACCCAGACCATAAACCTGGAC

AACAGGTCGAACTGGGGCGGCGACCTGAAGACTATCCTGCACACCAATATGCCCAA

CGTGAACGAGTTCATGTTCACCAACTCTTTTAAGGCGCGGGTGATGGTGGCGCGCGA

GCAGGGGGAGGCGAAGTACGAGTGGGTGGACTTCACGCTGCCCGAGGGCAACTACT

CAGAGACCATGACTCTCGACCTGATGAACAATGCGATCGTGGAACACTATCTGAAA

GTGGGCAGGCAGAACGGGGTGAAGGAGAGCGATATCGGGGTCAAGTTTGACACCAG

AAACTTCCGTCTGGGCTGGGACCCTGTGACCGGGCTGGTCATGCCGGGGGTCTACAC

CAACGAGGCCTTTCATCCCGATATAGTGCTCCTGCCCGGCTGTGGGGTGGACTTCAC

CCAGAGCCGGCTGAGCAACCTGCTGGGCGTTCGCAAGCGGCAACCTTTCCAGGAGG

GTTTCAAGATCACCTATGAGGATCTGGAGGGGGGCAACATTCCCGCGCTCCTTGATC

TGGACGCCTACGAGGAGAGCTTGAAACCCGAGGAGAGCGCTGGCGACAGCGGCGA

GAGTGGCGAGGAGCAAGCCGGCGGCGGCGGCAGCGCGTCGGTAGAAAACGAAAGT

ACTCCCGCAGTGGCGGCGGACGCTGCGGAGGTCGAGCCGGAGGCCATGCAGCAGGA

CGCAGAGGAGGGCGCGCAGGAGGACATGAACAATGGGGAGATCAGGGGCGACACT

TTCGCCACCCGGGGCGAAGAAAAAGAGGCAGAGGCGGCGGCGGCGACGGCGGAAG

CCGAAACCGAGGCAGAGGCAGAGCCCGAGACCGAAGTTATGGAAGACATGAATGA

TGGAGAACGTAGGGGTGACACGTTTGCCACCCGGGGCGAAGAGAAGGCGGCGGAG

GCAGAAGCCGCGGCTGAGGAGGCGGCTGCGGCTGCGGCCAAGGCTGAGGCTGCGGC

TGAGGCTAAGGTCGAAGCCGATGTTGCGGTTGAGGCTCAGGCTGAGGAGGAGGCGG

CGGCTGAAGCAGTTAAGGAAAAGGCCCAGGCAGAGCAGGAAGAGAAAAAACCTGT

CATTCAACCTCTAAAAGAAGATAGCAAAAAGCGCAGTTACAACGTCATTGAGGGCA

GCACCTTTACCCAATACCGCAGCTGGTACCTGGCTTACAACTACGGCGACCCGGTCA

AGGGGGTGCGCTCGTGGACCCTGCTCTGCACGCCGGACGTCACCTGCGGCTCCGAGC

AGATGTACTGGTCGCTGCCAAACATGATGCAAGACCCGGTGACCTTCCGTTCCACGC

GGCAGGTTAGCAACTTTCCGGTGGTGGGCGCCGAACTGCTGCCAGTACACTCCAAGA

GTTTTTACAACGAGCAGGCCGTCTACTCCCAGCTGATCCGCCAGGCCACCTCTCTGA

CCCACGTGTTCAATCGCTTTCCCGAGAACCAGATTTTGGCGCGCCCGCCGGCCCCCA

CCATCACCACCGTCAGTGAAAACGTTCCTGCCCTCACAGATCACGGGACGCTACCGC

TGCGCAACAGCATCTCAGGAGTCCAGCGAGTGACCATTACTGACGCCAGACGCCGG

ACCTGCCCCTACGTTTACAAGGCCTTGGGCATAGTCTCGCCGCGCGTCCTCTCCAGTC

GCACTTTTTAAAACACATCCACCCACACGCTCCAAAATCATGTCCGTACTCATCTCG

CCCAGCAACAACACCGGCTGGGGGCTGCGCGCACCCAGCAAGATGTTTGGAGGGGC

AAGGAAGCGCTCCGACCAGCACCCCGTGCGCGTGCGCGGCCACTACCGCGCGCCCT

GGGGTGCGCACAAGCGCGGGCGCACAGGGCGCACCACTGTGGATGATGTCATTGAC

TCCGTAGTGGAGCAGGCGCGCCACTACACACCCGGCGCGCCGACCGCCTCCGCCGT

GTCCACCGTGGACCAGGCGATCGAAAGCGTGGTACAGGGGGCGCGGCACTATGCCA

ACCTTAAAAGTCGCCGCCGCCGCGTGGCGCGCCGCCATCGCCGGAGACCCCGGGCT

ACTGCCGCCGCGCGCCTTACCAAGGCTCTGCTCAAGCGCGCCAGGCGAACTGGCCAC

CGGGCCGCCATGAGGGCCGCACGGCGGGCTGCCGCTGCCGCGAGCGCCGTGGCCCC

GCGGGCACGAAGGCGCGCGGCCGCTGCCGCCGCCGCCGCCATTTCCAGCTTGGCCTC

-continued

GACGCGGCGCGGTAACATATACTGGGTGCGCGACTCGGTGAGCGGCACACGTGTGC

CCGTGCGCTTTCGCCCCCCACGGAATTAGCACAAGACAACATACACACTGAGTCTCC

TGCTGTTGTGTATCCCAGCGGCGACCGTCAGCAGCGGCGACATGTCCAAGCGCAAA

ATTAAAGAAGAGATGCTCCAGGTCATCGCGCCGGAGATCTATGGGCCCCCGAAGAA

GGAGGAGGAGGATTACAAGCCCCGCAAGCTAAAGCGGGTCAAAAAGAAAAAGAAA

GATGATGACGTTGACGAGGCGGTGGAGTTTGTCCGCCGCATGGCGCCCAGGCGCCCT

GTGCAGTGGAAGGGTCGGCGCGTGCAGCGAGTCCTGCGCCCCGGCACCGCGGTGGT

CTTTACGCCCGGCGAGCGTTCCACGCGCACTTTCAAGCGGGTGTACGATGAGGTGTA

CGGCGACGAGGATCTGTTGGAGCAGGCCAACCATCGATTTGGGGAGTTTGCATATG

GGAAACGGCCTCGCGAGAGTCTAAAAGAGGACCTGCTGGCGCTACCGCTGGACGAG

GGCAATCCCACCCCGAGTCTGAAGCCGGTGACCCTGCAACAGGTGCTGCCTTTGAGC

GCGCCCAGCGAGCAGAAGCGAGGGTTAAAGCGCGAGGGCGGGGACCTGGCACCCA

CCGTGCAGTTGATGGTGCCCAAGCGGCAGAAGCTGGAGGACGTGCTGGAGAAAATG

AAAGTAGAGCCCGGGATCCAGCCCGAGATCAAGGTCCGCCCTATCAAGCAGGTGGC

GCCCGGCGTGGGAGTCCAGACCGTGGACGTTAGGATTCCCACGGAGGAGATGGAAA

CCCAAACCGCCACTCCCTCTTCGGCAGCAAGCGCCACCACCGGCGCCGCTTCGGTAG

AGGTGCAGACGGACCCCTGGCTACCCGCCGCCACTATCGCCGTCGCCGCCGCCCCC

GTTCGCGCGGACGCAAGAGAAATTATCCAGCGGCCAGCGCGCTTATGCCCCAGTAT

GCGCTGCATCCATCCATCGCGCCCACCCCCGGCTACCGCGGGTACTCGTACCGCCCG

CGCAGATCAGCCGGCACTCGCGGCCGCCGCCGCCGTGCGACCACAACCAGCCGCCG

CCGTCGCCGCCGCCGCCAGCCAGTGCTGACCCCCGTGTCTGTAAGGAAGGTGGCTCG

CTCGGGGAGCACGCTGGTGGTGCCCAGAGCGCGCTACCACCCCAGCATCGTTTAAA

GCCGGTCTCTGTATGGTTCTTGCAGATATGGCCCTCACTTGTCGCCTTCGCTTCCCGG

TGCCGGGATACCGAGGAAGAACTCACCGCCGCAGGGGCATGGCGGGCAGCGGTCTC

CGCGGCGGCCGTCGCCATCGCCGGCGCGCAAAGAGCAGGCGCATGCGCGGCGGTGT

GTTGCCCCTGCTGGTCCCGCTACTCGCCGCGGCGATCGGCGCCGTGCCCGGGATCGC

CTCCGTGGCCCTGCAGGCGTCCCAGAAACATTGACTCTTGCAACCTTGCAAGCTTGC

ATTTTTGGAGGAAAAAATAAAAAAGTCTAGACTCTCACGCTCGCTTGGTCCTGTGAC

TATTTTGTAGAAAAAAGATGGAAGACATCAACTTTGCGTCGCTGGCCCCGCGTCACG

GCTCGCGCCCGTTCATGGGAGACTGGACAGATATCGGCACCAGCAATATGAGCGGT

GGCGCCTTCAGCTGGGGCAGTCTGTGGAGCGGCCTTAAAAATTTTGGTTCCACCATT

AAGAACTATGGCAACAAAGCGTGGAACAGCAGCACGGGTCAGATGCTGAGAGACA

AGTTGAAAGAGCAGAACTTCCAGGAGAAGGTGGCGCAGGGCCTGGCCTCTGGCATC

AGCGGGGTGGTGGACATAGCTAACCAGGCCGTGCAGAAAAAGATAAACAGTCATCT

GGACCCCCGCCCTCAGGTGGAGGAAACGCCTCCAGCCATGGAGACGGTGTCTCCCG

AGGGCAAAGGCGAAAAGCGCCCGCGGCCCGACAGGGAAGAGACCCTGGTGTCACA

CACCGAGGAGCCGCCCTCTTACGAGGAGGCAGTCAAGGCCGGCCTGCCCACCACTC

GCCCCATAGCTCCCATGGCCACCGGTGTGGTGGGTCACAGGCAACACACCCCCGCA

ACACTAGATCTGCCCCCGCCGTCCGAGCCGACTCGCCAGCCAAAGGCGGTGACGGT

GTCCGCTCCCTCCACTTCCGCCGCCAACAGAGTGCCTCTGCGCCGCGCTGCGAGCGG

-continued
CCCCCGGGCCTCGCGAGTCAGCGGCAACTGGCAGAGCACACTGAACAGCATCGTGG

GCCTGGGAGTGAGGAGTGTGAAGCGCCGCCGTTGCTACTGAATGAGCAAGCTAGCT

AACGTGTTGTATGTGTGTATGCGTCCTATGTCGCCGCCAGAGGAGCTGTTGAGCCGC

CGGCGCCGTCTGCACTCCAGCGAATTTCAAGATGGCGACCCCATCGATGATGCCTCA

GTGGTCGTACATGCACATCTCGGGCCAGGACGCTTCGGAGTACCTGAGCCCCGGGCT

GGTGCAGTTCGCCCGCGCCACAGACACCTACTTCAACATGAGTAACAAGTTCAGGA

ACCCCACTGTGGCGCCCACCCACGATGTGACCACGGACCGGTCGCAGCGCCTGACG

CTGCGGTTCATCCCCGTGGATCGGGAGGACACCGCTTACTCTTACAAGGCGCGGTTC

ACGCTGGCCGTGGGCGACAACCGCGTGCTGGACATGGCCTCCACTTACTTTGACATC

CGGGGGGTGCTGGACAGGGGCCCCACTTTTAAGCCCTACTCGGGCACTGCCTACAAC

CCCCTGGCCCCCAAGGGCGCCCCCAATTCTTGTGAGTGGGAACAAGAGGAAAATCA

GGTGGTCGCTGCAGATGATGAACTTGAAGATGAAGAAGCGCAAGCACAAGAGGAA

GCCCCTGTGAAAAAAATTCATGTATATGCTCAGGCGCCTCTTTCTGGCGAAAAGATT

TCCAAGGATGGTATCCAAATAGGTACTGAAGTCGTAGGAGATACATCTAAGGACAC

TTTTGCAGATAAAACATTCCAACCCGAACCTCAGATAGGCGAGTCTCAGTGGAACGA

GGCTGATGCCACAGCAGCAGGAGGTAGAGTTTTGAAAAAGACTACCCCTATGAGAC

CTTGCTATGGATCCTATGCCAGGCCTACCAATGCCAACGGGGGTCAAGGAATTATGG

TTGCCAATGAACAAGGAGTGTTGGAGTCTAAAGTAGAAATGCAATTTTTCTCTAACA

CCACAACCCTTAATGCGCGGGATGGAACCGGCAATCCCGAACCAAAGGTGGTGTTG

TACAGCGAAGATGTCCACTTGGAATCTCCCGATACTCATCTGTCTTACAAGCCCAAA

AAGGATGATGTTAATGCCAAAATCATGTTGGGTCAGCAAGCCATGCCCAACAGACC

CAACCTCATTGGATTTAGAGATAATTTCATTGGGCTTATGTTTTACAACAGCACCGGT

AACATGGGAGTGCTGGCGGGTCAGGCCTCTCAGTTGAATGCTGTGGTGGACTTGCAG

GATAGAAACACAGAACTGTCATATCAGCTTCTGCTTGATTCAATTGGGGATAGAACC

AGATACTTCTCCATGTGGAACCAGGCAGTGGATAGCTATGATCCAGATGTCAGAATT

ATTGAAAACCATGGGACTGAGGATGAACTGCCCAACTACTGCTTCCCTTTGGGCGGC

ATAGGAGTTACTGATACTTATCAAGGGATAAAAAATACCAATGGCAATGGTCAGTG

GACCAAAGATGATCAGTTCGCGGACCGCAACGAAATAGGGGTGGGAAACAACTTCG

CCATGGAGATCAACATCCAGGCCAACCTTTGGAGAAACTTCCTCTATGCAAACGTGG

GGCTCTACCTGCCAGACAAGCTCAAGTACAACCCCACCAACGTGGACATCTCTGACA

ACCCCAACACCTATGACTACATGAACAAGCGGGTGGTGGCCCCTGGCCTGGTGGACT

GCTTTGTCAATGTGGGAGCCAGGTGGTCCCTGGACTACATGGACAACGTCAACCCCT

TCAACCACCACCGCAATGCGGGTCTGCGCTACCGCTCCATGATCCTGGGCAACGGGC

GCTATGTGCCCTTTCACATCCAGGTACCCCAGAAGTTCTTTGCCATCAAGAACCTCCT

GCTCCTGCCCGGCTCCTACACCTACGAGTGGAACTTCAGGAAGGATGTGAACATGGT

CCTACAGAGCTCTCTGGGCAATGACCTTAGGGTGGATGGGGCCAGCATCAAGTTTGA

CAGCATCACCCTCTATGCTACATTTTTCCCCATGGCCCACAACACCGCCTCCACGCTT

GAGGCCATGCTGAGAAACGACACCAACGACCAGTCCTTTAATGACTACCTCTCTGGG

GCCAACATGCTCTACCCAATCCCAGCCAAGGCCACCAACGTGCCCATCTCCATCCCC

TCTCGCAACTGGGCCGCCTTTAGAGGCTGGGCCTTTACCCGCCTTAAGACCAAGGAG

ACCCCCTCCCTGGGCTCGGGTTTTGATCCCTACTTTGTTTACTCGGGATCCATCCCCT

-continued

ACCTGGATGGCACCTTCTACCTCAACCACACTTTCAAGAAGATATCCATCATGTATG

ACTCCTCCGTCAGCTGGCCGGGCAACGACCGCTTGCTCACCCCCAATGAGTTCGAGG

TCAAGCGCGCCGTGGACGGCGAGGGCTACAACGTGGCCCAGTGCAACATGACCAAG

GACTGGTTCCTGGTGCAGATGCTGGCCAACTACAACATAGGCTACCAGGGCTTTTAC

ATCCCAGAGAGCTACAAGGACAGGATGTACTCCTTCTTCAGAAATTTCCAACCCATG

AGCCGACAGGTGGTGGACGAGACCAATTACAAGGACTATCAAGCCATTGGCATCAC

CCACCAGCACAACAACTCGGGTTTCGTGGGCTACCTGGCGCCCACCATGCGCGAGG

GTCAGGCCTACCCCGCCAACTTCCCCTACCCCTTGATAGGCAAGACCGCGGTCGACA

GCGTCACCCAGAAAAAGTTCCTCTGCGACCGCACCCTCTGGCGCATCCCCTTCTCTA

GCAACTTCATGTCCATGGGTGCGCTCACGGACCTGGGCCAAAACCTGCTTTATGCCA

ACTCTGCCCATGCGCTGGACATGACTTTTGAGGTGGACCCCATGGACGAGCCCACCC

TTCTCTATATTGTGTTTGAAGTGTTCGACGTGGTCAGAGTGCACCAGCCGCACCGCG

GTGTCATCGAGACCGTGTACCTGCGTACGCCCTTCTCAGCCGGCAACGCCACCACCT

AAGGAGACAGCGCCGCCGCCGCCTGCATGACGGGTTCCACCGAGCAAGAGCTCAGG

GCCATTGCCAGAGACCTGGGATGCGGACCCTATTTTTTGGGCACCTATGACAAACGC

TTCCCGGGCTTTATCTCCCGAGACAAGCTCGCCTGCGCCATTGTCAACACGGCCGCG

CGCGAGACCGGGGGCGTGCACTGGCTGGCCTTTGGCTGGGACCCGCGCTCCAAAAC

TTGCTACCTCTTTGACCCCTTTGGCTTCTCCGATCAGCGCCTCAGGCAGATTTATGAG

TTTGAGTACGAGGGGCTGCTGCGCCGCAGCGCGCTCGCCTCCTCGCCCGACCGCTGC

ATCACCCTTGAGAAGTCCACCGAAACCGTGCAGGGGCCCCACTCGGCCGCCTGCGGT

CTCTTCTGTTGCATGTTTTTGCACGCCTTTGTGCACTGGCCTCAGAGTCCCATGGATT

GCAACCCCACCATGAACTTGCTAAAGGGAGTGCCCAACGCCATGCTCCAGAGCCCC

CAGGTCCAGCCCACCCTGCGCCGCAACCAGGAACAGCTTTACCGCTTCCTGGAGCGC

CACTCCCCCTACTTCCGCAGCCACAGCGCGCGCATCCGGGGGGCCACCTCTTTTTGC

CACTTGCAAGAAAACATGCAAGACGGAAAATGATGTACAGCATGCTTTTAATAAAT

GTAAAGACTGTGCACTTTAATTATACACGGGCTCTTTCTGGTTATTTATTCAACACCG

CCGTCGCCATTTAGAAATCGAAAGGGTTCTGCCGTGCGTCGCCGTGCGCCACGGGCA

GAGACACGTTGCGATACTGGAAGCGGCTCGCCCACTTGAACTCGGGCACCACCATG

CGGGGCAGTGGTTCCTCGGGGAAGTTCTCGCTCCACAGGGTGCGGGTCAGCTGCAGC

GCGCTCAGGAGGTCGGGAGCCGAGATCTTGAAGTCGCAGTTGGGGCCGGAACCCTG

CGCGCGCGAGTTGCGGTACACGGGGTTGCAGCACTGGAACACCAGCAGGGCCGGAT

TATTCACGCTGGCCAGCAGGCTCTCGTCGCTGATCATGTCGCTGTCCAGATCCTCCGC

GTTGCTCAGGGCGAATGGGGTCATCTTGCAGACCTGCCTGCCCAGGAAAGGCGGGA

GCCCAGGCTTGCCGTTGCAGTCGCAGCGCAGGGGCATTAGCAGGTGCCCACGGCCC

GACTGCGCCTGCGGGTACAACGCGCGCATGAAGGCTTCGATCTGCCTAAAAGCCAC

CTGGGTCTTGGCTCCCTCCGAAAAGAACATCCCACAGGACTTGCTGGAGAACTGGTT

CGCGGGACAGCTGGCATCGTGCAGGCAGCAGCGCGCGTCAGTGTTGGCAATCTGCA

CCACGTTGCGACCCCACCGGTTTTTCACTATCTTGGCCTTGGAAGCCTGCTCCTTTAG

CGCGCGCTGGCCGTTCTCGCTGGTCACATCCATCTCTATCACCTGTTCCTTGTTGATC

ATGTTTGTCCCGTGCAGACACTTTAGGTCGCCCTCCGTCTGGGTGCAGCGGTGCTCCC

-continued

ACAGCGCGCAACCGGTGGGCTCCCAATTCTTGTGGGTCACCCCCGCGTAGGCCTGCA

GGTAGGCCTGCAGGAAGCGCCCCATCATGGTCATAAAGGTCTTCTGGCTCGTAAAGG

TCAGCTGCAGGCCGCGATGCTCTTCGTTCAGCCAGGTCTTGCAGATGGCGGCCAGCG

CCTCGGTCTGCTCGGGCAGCATCTTAAAATTTGTCTTCAGGTCGTTATCCACGTGGTA

CTTGTCCATCATGGCACGCGCCGCCTCCATGCCCTTCTCCCAGGCGGACACCATGGG

CAGGCTTAGGGGGTTTATCACTTCCAGCGGCGAGGACACCGTACTTTCGATTTCTTCT

TCCTCCCCCTCTTCCCGGCGCGCGCCCCCGCTGTTGCGCGCTCTTACCGCCTGCACCA

AGGGGTCGTCTTCAGGCAAGCGCCGCACCGAGCGCTTGCCGCCCTTGACCTGCTTGA

TCAGTACCGGCGGGTTGCTGAAGCCCACCATGGTCAGCGCCGCCTGCTCTTCTTCGT

CTTCGCTGTCTACCACTATTTCTGGGGAGGGGCTTCTCCGCTCTGCGGCAAAGGCGG

CGGATCGCTTCTTTTTTTTCTTGGGAGCCGCCGCGATGGAGTCCGCCACGGCGACCG

AGGTCGAGGGCGTGGGGCTGGGGGTGCGCGGTACCAGGGCCTCGTCGCCCTCGGAC

TCTTCCTCTGACTCCAGGCGGCGGCGGAGTCGCTTCTTTGGGGGCGCGCGCGTCAGC

GGCGGCGGAGACGGGGACGGGGACGGGGACGGGACGCCCTCCACAGGGGGTGGTC

TTCGCGCAGACCCGCGGCCGCGCTCGGGGGTCTTCTCGCGCTGGTCTTGGTCCCGAC

TGGCCATTGTATCCTCCTCCTCCTAGGCAGAGAGACATAAGGAGTCTATCATGCAAG

TCGAGAAGGAGGAGAGCTTAACCACCCCCTCAGAGACCGCCGATGCGCCCGCCGTC

GCCGTCGCCCCCGCTACCGCCGACGCGCCCGCCACACCGAGCGACACCCCCACGGA

CCCCCCCGCCGACGCACCCCTGTTCGAGGAAGCGGCCGTGGAGCAGGACCCGGGCT

TTGTCTCGGCAGAGGAGGATTTGCAAGAGGAGGAGAATAAGGAGGAGAAGCCCTCA

GTGCCAAAAGATCATAAAGAGCAAGACGAGCACGACGCAGACGCACACCAGGGTG

AAGTCGGGCGGGGGGACGGAGGGCATGGCGGCGCCGACTACCTAGACGAAGGAAA

CGACGTGCTCTTGAAGCACCTGCATCGTCAGTGCGCCATCGTCTGCGACGCTCTGCA

GGAGCGCAGCGAGGTGCCCCTCAGCGTGGCGGAGGTCAGCCGCGCCTACGAGCTCA

GCCTCTTTTCCCCCCGGGTGCCCCCCCGCCGCCGCGAAAACGGCACATGCGAGCCCA

ACCCGCGCCTCAACTTCTACCCCGCCTTTGTGGTGCCCGAGGTCCTGGCCACCTATCA

CATCTTCTTTCAAAATTGCAAGATCCCCATCTCGTGCCGCGCCAACCGTAGCCGCGC

CGATAAGATGCTGGCCCTGCGCCAGGGCGACCACATACCTGATATCGCCGCTTTGGA

AGATGTGCCAAAGATCTTCGAGGGTCTGGGGCGCAACGAGAAGCGGGCAGCAAACT

CTCTGCAACAGGAAAACAGCGAAAATGAGAGTCACACTGGAGCGCTGGTGGAGCTG

GAGGGCGACAACGCCCGCCTGGCGGTGCTCAAGCGCAGCATCGAGGTCACCCACTT

TGCCTACCCCGCGCTCAACCTGCCCCCCAAAGTCATGAACGCGGTCATGGACGGGCT

GATCATGCGCCGCGGCCGGCCCCTCGCTCCAGATGCAAACTTGCATGAGGAGACCG

AGGACGGTCAGCCCGTGGTCAGCGACGAGCAGCTGACGCGCTGGCTGGAGAGCGCG

GACCCCGCCGAACTGGAGGAGCGGCGCAAGATGATGATGGCCGCGGTGCTGGTCAC

CGTAGAGCTGGAGTGTCTGCAGCGCTTCTTCGGTGACCCCGAGATGCAGAGAAAGG

TCGAGGAGACCCTACACTACACCTTCCGCCAGGGCTACGTGCGCCAGGCTTGCAAGA

TCTCCAACGTGGAGCTCAGCAACCTGGTGTCCTACCTGGGCATCTTGCATGAAAACC

GCCTTGGGCAGAGCGTGCTACACTCCACCCTGCGCGGGGAGGCGCGCCGCGACTAC

GTGCGCGACTGCGTTTACCTCTTCCTCTGCTACACCTGGCAGACGGCCATGGGGGTC

TGGCAGCAGTGCCTGGAGGAGCGCAACCTCAAGGAGCTGGAGAAGCTTCTGCAGCG

-continued

CGCGCTCAAAGACCTCTGGACGGGCTTCAACGAGCGCTCGGTGGCCGCCGCGCTAG

CCGACCTCATCTTCCCCGAGCGCCTGCTCAAAACCCTCCAGCAGGGGCTGCCCGACT

TCACCAGCCAAAGCATGTTGCAAAATTTTAGGAACTTTATCCTGGAGCGTTCTGGCA

TCCTACCCGCCACCTGCTGCGCCCTGCCCAGCGACTTTGTCCCCCTCGTGTACCGCGA

GTGCCCCCCGCCGCTGTGGGGCCACTGCTACCTGTTCCAACTGGCCAACTACCTGTC

CTACCACGCGGACCTCATGGAGGACTCCAGCGGCGAGGGGCTCATGGAGTGCCACT

GCCGCTGCAACCTCTGCACGCCCCACCGCTCCCTGGTCTGCAACACCCAACTGCTCA

GCGAGAGTCAGATTATCGGTACCTTCGAGCTACAGGGTCCGTCCTCCTCAGACGAGA

AGTCCGCGGCTCCGGGGCTAAAACTCACTCCGGGGCTGTGGACTTCCGCCTACCTGC

GCAAATTTGTACCTGAAGACTACCACGCCCACGAAATCAGGTTTTACGAGGACCAAT

CCCGCCCGCCCAAGGCGGAGCTGACCGCCTGCGTCATCACCCAGGGCGAGATCCTA

GGCCAATTGCAAGCCATCCAAAAAGCCCGCCAAGAGTTTTTGCTGAAGAGGGGTCG

GGGGGTGTATCTGGACCCCCAGTCGGGTGAGGAGCTCAACCCGGTTCCCCCGCTGCC

ACCGCCGCGGGACCTTGCTTCCCAGGATAAGCATCGCCATGGCTCCCAGAAAGAAG

CAGCAGCGGCCGCCGCTGCCGCCGCCCCACATGCTGGAGGAAGAGGAGGAATACTG

GGACAGTCAGGCAGAGGAGGTTTCGGACGAGGAGGAGCCGGAGACGGAGATGGAA

GAGTGGGAGGAGGACAGCTTAGACGAGGAGGCTTCCGAAGCCGAAGAGGCAGGCG

CAACACCGTCACCCTCGGCCGCAGCCCCCTCGCAGGCGCCCCCGAAGTCCGCTCCCA

GCATCAGCAGCAACAGCAGCGCTATAACCTCCGCTCCTCCACCGCCGCGACCCACGG

CCGACCGCAGACCCAACCGTAGATGGGACACCACCGGAACCGGGGCCGGTAAGTCC

TCCGGGAGAGGCAAGCAAGCGCAGCGCCAAGGCTACCGCTCGTGGCGCGCTCACAA

GAACGCCATAGTCGCTTGCTTGCAAGACTGCGGGGGGAACATCTCCTTCGCCCGCCG

CTTCCTGCTCTTCCACCACGGTGTGGCCTTCCCCCGTAACGTCCTGCATTACTACCGT

CATCTCTACAGCCCCTACTGCGGCGGCAGTGAGCCAGAGGCGGCCAGCGGCGGCGG

CGCCCGTTTCGGTGCCTAGGAAGACCCAGGGCAAGACTTCAGCCAAGAAACTCGCG

GCGACCGCGGCGAACGCGGTCGCGGGGGCCCTGCGCCTGACGGTGAACGAACCCCT

GTCGACCCGCGAACTGAGGAACCGAATCTTCCCCACTCTCTATGCCATCTTCCAGCA

GAGCAGAGGGCAGGATCAGGAACTGAAAGTAAAAAACAGGTCTCTGCGCTCCCTCA

CCCGCAGCTGTCTGTATCACAAGAGCGAAGACCAGCTTCGGCGCACGCTGGAGGAC

GCTGAGGCACTCTTCAGCAAATACTGCGCGCTCACTCTTAAGGACTAGCTCCGCGCC

CTTCTCGAATTTAGGCGGGAACGCCTACGTCATCGCAGCGCCGCCGTCATGAGCAAG

GACATTCCCACGCCATACATGTGGAGCTATCAGCCGCAGATGGGACTCGCGGCGGG

CGCCTCCCAAGACTACTCCACCCGCATGAACTGGCTCAGTGCCGGCCCACACATGAT

CTCACAGGTTAATGACATCCGCACCCATCGAAACCAAATATTGGTGAAGCAGGCGG

CAATTACCACCACGCCCCGCAATAATCCCAACCCCAGGGAGTGGCCCGCGTCCCTGG

TGTATCAGGAAATTCCCGGCCCCACCACCGTACTACTTCCGCGTGATTCCCAGGCCG

AAGTCCAAATGACTAACTCAGGGGCACAGCTCGCGGGCGGCTGTCGTCACAGGGTG

CGGCCTCCTCGCCAGGGTATAACTCACCTGGAGATCCGAGGCAGAGGTATTCAGCTC

AACGACGAGTCGGTGAGCTCCTCGCTCGGTCTCAGACCTGACGGGACCTTCCAGATA

GCCGGAGCCGGCCGATCTTCCTTCACGCCCCGCCAGGCGTACCTGACTCTGCAGAGC

-continued

TCGTCCTCGGCGCCGCGCTCGGGCGGCATCGGGACTCTCCAGTTCGTGCAGGAGTTT

GTGCCCTCGGTCTACTTCAACCCCTTCTCGGGCTCTCCCGGTCGCTACCCGGACCAGT

TTATCCCGAACTTTGACGCCGCGAGGGACTCGGTGGACGGCTACGACTGAATGTCGG

GTGGACCCGGTGCAGAGCAACTTCGCCTGAAGCACCTTGACCACTGCCGCCGCCCTC

AGTGCTTTGCCCGCTGTCAGACCGGTGAGTTCCAGTACTTTTCCCTGCCCGACTCGCA

CCCGGACGGCCCGGCGCACGGGGTGCGCTTTTTCATCCCGAGTCAGGTCCGCTCTAC

CCTAATCAGGGAGTTCACCGCCCGTCCCCTACTGGCGGAGTTGGAAAAGGGGCCTTC

TATCCTAACCATTGCCTGCATTTGCTCTAACCCTGGATTACACCAAGATCTTTGCTGT

CATTTGTGTGCTGAGTATAATAAAGGCTGAGATCAGAATCTACTCGGGCTCCTGTCG

CCATCCTGTCAACGCCACCGTCCAAGCCCGGCCCGATCAGCCCGAGGTGAACCTCAC

CTGTGGTCTGCACCGGCGCCTGAGGAAATACCTAGCTTGGTACTACAACAGCACTCC

CTTTGTGGTTTACAACAGCTTTGACCAGGACGGGGTCTCACTGAGGGATAACCTCTC

GAACCTGAGCTACTCCATCAGGAAGAACAACACCCTCGAGCTACTTCCTCCTTACCT

GCCCGGGACTTACCAGTGTGTCACCGGCCCCTGCACCCACACCCACCTGTTGATCGT

AAACGACTCTCTTCCGAGAACAGACCTCAATAACTCCTCTCCGCAGTTCCCCAGAAC

AGGAGGTGAGCTCAGGAAACCCCGGGTAAAGAAGGGTGGACAAGAGTTAACACTTG

TGGGGTTTCTGGTATATGTGACGCTGGTGGTGGCTCTTTTGATTAAGGCTTTTCCTTC

CATGTCTGAACTATCCCTCTTCTTTTATGAACAACTCGACTAGTGCTAACGGGACCCT

ACCCAACGAATCGGGATTGAATATCGGTAACCAGGTTGCAGTTTCACTTTTGATTAC

CTTCATAGTCCTCTTCCTGCTAGTGCTGTCGCTTCTGTGCCTGCGGATCGGGGGCTGC

TGCATCCACGTTTATATCTGGTGCTGGCTGTTTAGAAGGTTCGGAGACCACCGCAGG

TAGAATAATGCTGCTTACCCTCTTTGTCCTGGCGCTGGCTGCCAGCTGCCAAGCCTTT

TCCGAGGCTGACTTCATAGAGCCCCAGTGCAATATCACTTATAAATCTGAACGTGCC

ATCTGTACTATTCTAATCAAATGTGTTACTCAACACGATAAGGTGACTGTTAAATAC

AAAGATCAATTAAAAAAAGACGCACTTTACAGCAGCTGGCAACCAGGAGATGATCA

AAAATACAATGTAACCGTCTTCCAGGGCAAACTCTCCAAAACTTACAATTACAATTT

CCCATTTGAGCAGATGTGTGACTTTGTCATGTACATGGAAAAGCAGTACAAGCTGTG

GCCTCCAACTCCCCAGGGCTGTGTGGAAAATCCAGGCTCTTTCTGTATGATCTCTCTC

TGTGTAACTGTGCTGGCACTAATACTCACGCTTCTGTATCTCAGATTTAAATCAAGGC

AAAGCTTCATTGATGAAAAGAAAATGCCATAATCGCTCAACGCTTGATTGCTAACAC

CGGGTTTTTATCCGCAGAATGATTGGAATCACCCTACTAATCACCTCCCTCCTTGCGA

TTGCCCATGGGTTGGAACGAATCGAAGTCCCTGTGGGGGCCAATGTTACCCTGGTGG

GGCCTGTCGGCAATGCTACATTAATGTGGGAAAAATATACTAAAAATCAATGGGTTT

CTTACTGCACTAACAAAAACAGCCACAAGCCCAGAGCCATCTGCGATGGGCAAAAT

CTAACCTTGATTGATGTTCAATTGCTGGATGCGGGCTACTATTATGGGCAGCTGGGT

ACAATGATTAATTACTGGAGACCCCACAGAGATTACATGCTTCACGTAGTAAAGGGT

CCCATTAGCAGCCCAACCACCACCTCTACCACACCCACTACCACCACTACTCCCACC

ACCAGCACTGCCGCCCAGCCTCCTCATAGCAGAACAACCACTTTTATCAATTCCAAG

TCCCACTCCCCCCACATTGCCGGCGGGCCCTCCGCCTCAGACTCCGAGACCACCGAG

ATCTGCTTCTGCAAATGCTCTGACGCCATTGCCCAGGATTTGGAAGATCACGAGGAA

GATGAGCATGACTACGCAGATGCATGCCAGGCATCAGAGGCAGAAGCGCTACCGGT

-continued

GGCCCTAAAACAGTATGCAGACTCCCACACCACCCCCAACCTTCCTCCACCTTCCCA

GAAGCCAAGTTTCCTGGGGGAAAATGAAACTCTGCCTCTTTCCATACTAGCTCTGAC

ATCTGTTGCTATTTTGGCCGCTCTGCTGGTGCTTCTATGCTCTATATGCTACCTGATCT

GCTGCAGAAAGAAAAAATCTCACGGCCATGCTCACCAGCCCCTCATGCACTTCCCTT

ACCCTCCAGAGCTGGGCGACCACAAACTTTAAGTCTGCAGTAGCTATCTGCCCATCC

CTTGTCAGTCGACAGCGATGAGCCCCACTAATCTAACAGCCTCTGGACTTACAACAT

TGTCTCTTAATGAGACCACCGCTCCTCAAGACCTGTACGATGGTGTCTCCGCGCTGG

TTAACCAGTGGGATCACCTGGGCATATGGTGGCTCCTCATAGGAGCAGTGACCCTGT

GCCTAATCCTGGTCTGGATCATCTGCTGCATCAAAAGCAGAAGACCCAGGCGGCGG

CCCATCTACAGGCCCTTCGTCATCACACCTGAAGATAATGATGATGATGACACCACC

TCCAGGCTGCAGAGCCTAAAGCAGCTACTCTTCTCTTTTACAGCATGGTAAATTGAA

TCATGCCCCGCATTTTCATCTACTTGCTTCTCCTTCCACTTTTTCTGGGCTCCTCTACA

TTGGCCACTGTGTCCCACATCGAGGTAGACTGCCTCACGCCCTTCACAGTCTACCTG

CTTTTCGGCTTTGTCATCTGCACCTTTGTCTGCAGCGTTATCACTGTAGTGATCTGCTT

CATACAGTGCATCGACTACATCTGTGTGCGGGTGGCCTACTTTAGACACCACCCCCA

GTATCGCAACAGGGACATAGCGGCTCTCCTAAGACTTGTTTAAATCATGGCCAAATT

ACCTGTGATTGGTCTTCTGATTATCTGCTGCGTCCTAGCCGCGATTGGGACTCAACCT

AATACCACCACCAGCGCTCCCAGAAAGAGACATGTATCCTGCAGCTTCAAGCGTCCC

TGGAATATACCCCAATGCTTTACTGATGAACCTGAAATCTCTTTGGCTTGGTACTTCA

GCGTCACCGCCCTTCTCATCTTCTGCAGTACGGTTATTGCTCTTGCCATCTACCCTTC

CCTTAACCTGGGCTGGAATGCTGTCAACTCTATGGAATATCCCACCTTCCCAGAACC

AGACCTGCCAGACCTGGTTGTTCTAAACGCGTTTCCTCCTCCTCCAGTTCAAAATCAG

TTTCGCCCTCCGTCCCCTACGCCCACTGAGGTCAGCTACTTTAATCTAACAGGCGGA

GATGACTGAAAACCTAGACCTAGAAATGGACGGTCTCTGCAGCGAGCAACGCACAC

TAGAGAGGCGCCGGCAAAAAGCAGAGCTCGAGCGTCTTAAACAAGAGCTCCAAGAC

GCCGTGGCCATACACCAGTGCAAAAAAGGGCTCTTCTGTCTGGTAAAACAGGCCAC

GCTCACCTATGAAAAAACAGGTGACACCCACCGCCTAGGATACAAGCTGCCCACAC

AGCGCCAAAAGTTTGCCCTTATGATAGGTGAACAACCCATCACCGTCACCCAGCACT

CCGTGGAGACAGAAGGCTGCATTCATGCTCCCTGCAGGGGCGCTGACTGCCTCTACA

CCTTGATCAAAACCCTCTGCGGTCTCAGAGACCTTATCCCTTTCAATTGATCATAACT

GTAATCAATAAAAAATCACTTACTTGAAATCTGATAGCAAGACTCTGTCCAATTTTT

TCAGCAACACTTCCTTCCCCTCCTCCCAACTCTGGTACTCTAGGCGCCTCCTAGCTGC

AAACTTCCTCCACAGTCTGAAGGGAATGTCAGATTCCTCCTCCTGTCCCTCCGCACCC

ACGATCTTCATGTTGTTACAGATGAAACGCGCGAGATCGTCTGACGAGACCTTCAAC

CCCGTGTACCCCTACGATACCGAGATCGCTCCGACTTCTGTCCCTTTCCTTACCCCTC

CCTTTGTATCATCCGCAGGAATGCAAGAAAATCCAGCTGGGGTGCTGTCCCTGCACC

TGTCAGAGCCCCTTACCACCCACAATGGGGCCCTGACTCTAAAAATGGGGGGCGGC

CTGACCCTGGACAAGGAAGGGAATCTCACTTCCCAAAACATCACCAGTGTCGATCCC

CCTCTCAAAAAAAGCAAGAACAACATCAGCCTTCAGACCGCCGCACCCCTCGCCGTC

AGCTCCGGGGCCCTAACCCTTTTTGCCACTCCCCCCCTAGCGGTCAGTGGCGACAAC

-continued

CTTACTGTGCAGTCTCAGGCCCCTCTTACTTTGGAAGACTCAAAACTAACTCTGGCC

ACCAAAGGACCCCTAACTGTGTCCGAAGGCAAACTTGTCCTAGAAACAGAGCCTCC

CCTGCATGCAAGTGACAGCAGTAGCCTGGGCCTTAGCGTCACGGCCCCACTTAGCAT

TAACAATGACAGCCTAGGACTAGACATGCAAGCGCCCATCAGCTCTCGAGATGGAA

AACTGGCTCTAACAGTGGCGGCCCCCCTAACTGTGGCCGAGGGTATCAATGCTTTGG

CAGTAGCCACAGGTAATGGTATTGGACTAAATGAAACCAACACACACCTGCAGGCA

AAACTGGTCGCGCCCCTAGGCTTTGATACCAACGGCAACATTAAGCTAAGCGTCGCA

GGAGGCATGAGGCTAAACAATAACACACTGATACTAGATGTAAACTACCCATTTGA

GGCTCAAGGCCAACTGAGCCTAAGAGTGGGCTCGGGCCCACTATATGTAGATTCTAG

TAGTCATAACCTAACCATTAGATGCCTTAGGGGATTGTATGTAACATCTTCTAACAA

CCAAAACGGTCTAGAGGCCAACATTAAACTAACAAAAGGCCTTGTGTATGACGGAA

ATGCCATAGCAGTTAATGTTGGCAAAGGGCTGGAATACAGCCCTACTGGCACAACA

GAAAAACCTATACAGACTAAAATAGGTCTAGGCATGGAGTATGACACTGAGGGAGC

CATGATGACAAAACTAGGCTCTGGACTAAGCTTTGACAATTCAGGAGCCATTGTGGT

GGGAAACAAAAATGATGACAGGCTTACTTTGTGGACCACACCGGACCCATCGCCCA

ACTGTCAGATTTACTCTGAAAAAGATGCTAAACTAACCTTGGTACTGACTAAATGTG

GCAGTCAGGTTGTAGGCACAGTATCTATTGCCGCTCTTAAAGGTAGCCTTGTGCCAA

TCACTAGTGCAATCAGTGTGGTTCAGATATACCTAAGGTTTGATGAAAATGGGGTGC

TGATGAGTAACTCTTCACTTAATGGCGAATACTGGAATTTTAGAAACGGAGACTCAA

CTAATGGCACACCATATACAAACGCAGTGGGTTTTATGCCTAATCTACTGGCCTATC

CTAAAGGTCAAACTACAACTGCAAAAAGTAACATTGTCAGCCAGGTCTACATGAAC

GGGGACGATACTAAACCCATGACATTTACAATCAACTTCAATGGCCTTAGTGAAACA

GGGGATACCCCTGTCAGTAAATATTCCATGACATTCTCATGGAGGTGGCCAAATGGA

AGCTACATAGGGCACAATTTTGTAACAAACTCCTTTACTTTCTCCTACATCGCCCAAG

AATAAAGAAAGCACAGAGATGCTTGTTTTTGATTTCAAAATTGTGTGCTTTTATTTAT

TTTCAAGCTTACAGTATTTCCAGTAGTCATTAGAATAGAGCTTAATTAAACTGCATG

AGAACCCTTCCACATAGCTTAAATTATCACCAGTGCAAATGGAAAAAAATCAACAT

ACCTTTTTATCCAGATATCAAAGAACTCTAGTGGTCAGTTTTCCCCCACCCTCCCAGC

TCACAGAATACACAGTCCTTTCCCCCCGGCTGGCTTTAAACAACACTATCTCATTGGT

AACAGACATATTTTTAGGTGTAATAATCCACACGGTCTCTTGGCGGGCCAAACGCTG

GTCTGTGATGTTAATAAACTCCCCAGGCAGCTCTTTCAAGTTCACGTCGCTGTCCAAC

TGCTGAAGCGCTCGCGGCTCCGACTGCGCCTCTAGCGGAGGCAACGGCAGCACCCG

ATCCTTGATCTATAAAGGAGTAGAGTCATAATCCCCCATAAGAATAGGGCGGTGATG

CAGCAACAAGGCGCGCAGCAACTCCTGCCGCCGCCTCTCCGTACGACAGGAATGCA

ACGGGGTGGTGGTCTCCTCCGCGATAATCCGCACCGCTCGCAGCATCAGCATCCTCG

TCCTCCGGGCACAGCAGCGCATCCTGATCTCACTGAGATCGGCGCAGTAAGTGCAGC

ACAACACCAAGATGTTATTTAAGATCCCACAGTGCAAAGCACTGTACCCAAAGCTCA

TGGCGGGAAGGACAGCCCCCACGTGACCATCGTACCAGATCCTCAGGTAAATCAAA

TGACGACCTCTCATAAACACGCTGGACATATACATCACCTCCTTGGGCATGAGCTGA

TTCACCACCTCTCGATACCACAGGCATCGCTGATTAATTAAAGACCCCTCGAGCACC

ATCCTGAACCAGGAAGCCAGCACCTGACCCCCCGCCAGGCACTGCAGGGACCCCGG

-continued

TGAATCGCAGTGGCAGTGAAGACTCCAGCGCTCGTAGCCGTGAACCATAGAGCTGG

TCATTATATCCACATTGGCACAACACAGACACACTTTCATACACTTTTTCATGATTAG

CAGCTCCTCTCTAGTCAAGACCATATCCCAAGGAATCACCCACTCTTGAATCAAGGT

AAATCCCACACAGCAGGGCAGGCCTCTCACATAACTCACGTTATGCATAGTGAGCGT

GTCGCAATCTGGAAATACCGGATGATCTTCCATCACCGAAGCCCGGGTCTCCGTCTC

AAAGGGAGGTAAACGGTCCCTCGTGTAGGGACAGTGGCGGGATAATCGAGATCGTG

TTGAACGTAGAGTCATGCCAAAGGGAACAGCGGACGTACTCATATTTCCTCCAGCAG

AACCAAGTGCGCGCGTGGCAGCTATCCCTGCGTCTTCTGTCTCGCCGCCTGCCCCGC

TCGGTGTAGTAGTTGTAATACAGCCACTCCCTCAGACCGTCAAGGCGCTCCCTGGCG

TCCGGATCTATAACAACACCGTCCTGCAGCGCCGCCCTGATGACATCCACCACCGTA

GAGTATGCCAAGCCCAGCCACGAAATGCACTCACTTTGACAGCGAGAGATAGGAGG

AGCGGGAAGAGATGGAAGAACCATGATAGTAAAAGAACTTTTATTCCAATCGATCC

TCTACAATGTCAAAGTGTAGATCTATCAGATGGCACTGGTCTCCTCCGCTGAGTCGA

TCAAAAATAACAGCTAAACCACAAACAACACGATTGGTCAAATGCTGCACAAGGGC

TTGCAGCATAAAATCGCCTCGAAAGTCCACCGCAAGCATAACATCAAAGCCACCGC

CCCTATCATGATCTATGATAAAAACCCCACAGCTATCCACCAGACCCATATAGTTTT

CATCTCTCCATCGTGAAAAAATATTTACAAGCTCCTCCTTTAAATCACCTCCAACCAA

TTCAAAAAGTTGAGCCAGACCGCCCTCCACCTTCATTTTCAGCATGCGCATCATGAT

TGCAAAAATTCAGGCTCCTCAGACACCTGTATAAGATTGAGAAGCGGAACGTTAAC

ATCAATGTTTCGCTCGCGAAGATCGCGCCTCAGTGCAAGCATGATATAATCCCACAG

GTCGGAGCGGATCAGCGAGGACATCTCCCCGCCAGGAACCAACTCAACGGAGCCTA

TGCTGATTATAATACGCATATTCGGGGCTATGCTAACCAGCACGGCCCCCAAATAGG

CGTACTGCATAGGCGGCGACAAAAAGTGAACAGTTTGGGTTAAAAAATCAGGCAAA

CACTCGCGCAAAAAAGCAAGAACATCATAACCATGCTCATGCAAATAGATGCAAGT

AAGCTCAGGAACGACCACAGAAAAATGCACAATTTTTCTCTCAAACATGACTGCGA

GCCCTGCAAAAAATAAAAAAGAAACATTACACAAGAGTAGCCTGTCTTACAATGGG

ATAGACTACTCTAACCAACATAAGACGGGCCACGACATCGCCCGCGTGGCCATAAA

AAAAATTATCCGTGTGATTAAAAAGAAGCACAGATAGCTGGCCAGTCATATCCGGA

GTCATCACGTGCGAACCCGTGTAGACCCCCGGGTTGGACACATCGGCCAAACAAAG

AAAGCGGCCAATGTATCCCGGAGGAATGATAACACTAAGACGAAGATACAACAGAA

TAACCCCATGGGGGGGAATAACAAAGTTAGTAGGTGAATAAAAACGATAAACACCC

GAAACTCCCTCCTGCGTAGGCAAAATAGCGCCCTCCCCTTCCAAAACAACATACAGC

GCTTCCACAGCAGCCATGACAAAAGACTCAAAACACTCAAAAGACTCAGTCTTACC

AGGAAAATAAAAGCACTCTCACAGCACCAGCACTAATCAGAGTGTGAAGAGGGCCA

AGTGCCGAACGAGTATATATAGGAATTAAAAATGACGTAAATGTGTAAAGGTCAAA

AAACGCCCAGAAAAATACACAGACCAACGCCCGAAACGAAAACCCGCGAAAAAAT

ACCCAGAAGTTCCTCAACAACCGCCACTTCCGCTTTCCCACGATACGTCACTTCCTCA

AAAATAGCAAACTACATTTCCCACATGTACAAAACCAAAACCCCTCCCCTTGTCACC

-continued

GCCCACAACTTACATAATCACAAACGTCAAAGCCTACGTCACCCGCCCCGCCTCGCC

CCGCCCACCTCATTATCATATTGGCCTCAATCCAAAATAAGGTATATTATTGATGAT

G

The disclosure also provides a recombinant chimpanzee adenovirus derived from serotype 20 (rChAd20) comprising the vector of the disclosure.

The disclosure also provides a recombinant modified vaccinia Ankara (rMVA) comprising the vector of the disclosure.

The vector may be a vector intended for expression of the polynucleotide or the heterologous polynucleotide of the disclosure in any host, such as bacteria, yeast or a mammal. Suitable expression vectors are typically replicable in the host organisms either as episomes or as an integral part of the host chromosomal DNA. Commonly, expression vectors contain selection markers such as ampicillin-resistance, hygromycin-resistance, tetracycline resistance, kanamycin resistance or neomycin resistance to permit detection of those cells transformed or transduced with the desired DNA sequences. Exemplary vectors are plasmids, cosmids, phages, viral vectors, transposons or artificial chromosomes.

Vectors of the disclosure may be circular or linear. They may be prepared to contain a replication system functional in a prokaryotic or eukaryotic host cell. Replication systems can be derived, e.g., from ColE1, SV40, 2μ plasmid, λ, bovine papilloma virus, and the like.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. "Suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine deaminase, purine nucleoside phosphorylase, and nitroreductase.

The vectors may also comprise selection markers, which are well known in the art. Selection markers include positive and negative selection marker. Marker genes include biocide resistance, e.g., resistance to antibiotics, heavy metals, etc., complementation in an auxotrophic host to provide prototrophy, and the like. Exemplary marker genes include antibiotic resistance genes (e.g., neomycin resistance gene, a hygromycin resistance gene, a kanamycin resistance gene, a tetracycline resistance gene, a penicillin resistance gene, histidinol resistance gene, histidinol x resistance gene), glutamine synthase genes, HSV-TK, HSV-TK derivatives for ganciclovir selection, or bacterial purine nucleoside phosphorylase gene for 6-methylpurine selection (Gadi et al., 7 *Gene Ther.* 1738-1743 (2000)). A nucleic acid sequence encoding a selection marker or the cloning site may be upstream or downstream of a nucleic acid sequence encoding a polypeptide of interest or cloning site.

Suitable vectors are known; many are commercially available for generating recombinant constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene), pSVK3, pBPV, pMSG and pSVL (Pharmacia). Transposon vectors: Sleeping Beauty transposon and PiggyBac transposon.

In some embodiments, the vector is a viral vector. Viral vectors are derived from naturally occurring virus genomes, which typically are modified to be replication incompetent, e.g. non-replicating. Non-replicating viruses require the provision of proteins in trans for replication. Typically, those proteins are stably or transiently expressed in a viral producer cell line, thereby allowing replication of the virus. The viral vectors are, thus, typically infectious and non-replicating. Viral vectors may be adenovirus vectors, adeno-associated virus (AAV) vectors (e.g., AAV type 5 and type 2), alphavirus vectors (e.g., Venezuelan equine encephalitis virus (VEE), Sindbis virus (SIN), Semliki forest virus (SFV), and VEE-SIN chimeras), herpes virus vectors (e.g. vectors derived from cytomegaloviruses, like rhesus cytomegalovirus (RhCMV)), arena virus vectors (e.g. lymphocytic choriomeningitis virus (LCMV) vectors), measles virus vectors, pox virus vectors (e.g., vaccinia virus, modified vaccinia virus Ankara (MVA), NYVAC (derived from the Copenhagen strain of vaccinia), and avipox vectors: canarypox (ALVAC) and fowlpox (FPV) vectors), vesicular stomatitis virus vectors, retrovirus vectors, lentivirus vectors, viral like particles, baculoviral vectors and bacterial spores.

Adenovirus Vectors

Adenovirus vectors may be derived from human adenovirus (Ad) but also from adenoviruses that infect other species, such as bovine adenovirus (e.g. bovine adenovirus 3, BAdV3), a canine adenovirus (e.g. CAdV2), a porcine adenovirus (e.g. PAdV3 or 5), or great apes, such as Chimpanzee (Pan), Gorilla (Gorilla), Orangutan (Pongo), Bonobo (Pan paniscus) and common chimpanzee (Pan troglodytes). Typically, naturally occurring great ape adenoviruses are isolated from stool samples of the respective great ape.

Human adenovirus vectors may be derived from various adenovirus serotypes, for example from human adenovirus serotypes hAd5, hAd7, hAd11, hAd26, hAd34, hAd35, hAd48, hAd49 or hAd50 (the serotypes are also referred to as Ad5, Ad7, Ad11, Ad26, Ad34, Ad35, Ad48, Ad49 or Ad50).

Great ape adenovirus vectors may be derived from various adenovirus serotypes, for example from great ape adenovirus serotypes GAd20, Gad19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, or PanAd3.

Adenovirus vectors are known in the art. The sequences of most of the human and non-human adenoviruses are known, and for others can be obtained using routine procedures. An exemplary genome sequence of Ad26 is found in GenBank Accession number EF153474 and in SEQ ID NO:

1 of Int. Pat. Publ. No. WO2007/104792. An exemplary genome sequence of Ad35 is found in FIG. 6 of Int. Pat. Publ. No. WO2000/70071. Vectors based on Ad26 are described for example, in Int. Pat. Publ. No. WO2007/104792. Vectors based on Ad35 are described for example in U.S. Pat. No. 7,270,811 and Int. Pat. Publ. No. WO2000/70071. Vectors based on ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd63 and ChAd82 are described in WO2005/071093. Vectors based on PanAd1, PanAd2, PanAd3, ChAd55, ChAd73, ChAd83, ChAd146, and ChAd147 are described in Int. Pat. Publ. No. WO2010/086189.

Adenovirus vectors are engineered to comprise at least one functional deletion or a complete removal of a gene product that is essential for viral replication, such as one or more of the adenoviral regions E1, E2 and E4, therefore rendering the adenovirus to be incapable of replication. The deletion of the E1 region may comprise deletion of EIA, EIB 55K or EIB 21K, or any combination thereof. Replication deficient adenoviruses are propagated by providing the proteins encoded by the deleted region(s) in trans by the producer cell by utilizing helper plasmids or engineering the produce cell to express the required proteins. Adenovirus vectors may also have a deletion in the E3 region, which is dispensable for replication, and hence such a deletion does not have to be complemented. The adenovirus vector of the disclosure may comprise a functional deletion or a complete removal of the E1 region and at least part of the E3 region. The adenovirus vector of the disclosure may further comprise a functional deletion or a complete removal of the E4 region and/or the E2 region. Suitable producer cells that can be utilized are human retina cells immortalized by E1, e.g. 911 or PER.C6 cells (see, e.g., U.S. Pat. No. 5,994,128), E1-transformed amniocytes (See, e.g., EP 1230354), E 1-transformed A549 cells (see e.g. Int. Pat. Publ. No. WO1998/39411, U.S. Pat. No. 5,891,690). Exemplary vectors that may be used are Ad26 comprising a functional E1 coding region that is sufficient for viral replication, a deletion in the E3 coding region and a deletion in the E4 coding region, provided that E4 open reading frame 6/7 is not deleted (see e.g. U.S. Pat. No. 9,750,801) In some embodiments, the adenovirus vector is a human adenovirus (Ad) vector. In some embodiments, the Ad vector is derived from Ad5. In some embodiments, the Ad vector is derived from Ad11. In some embodiments, the Ad vector is derived from Ad26. In some embodiments, the Ad vector is derived from Ad34. In some embodiments, the Ad vector is derived from Ad35. In some embodiments, the Ad vector is derived from Ad48. In some embodiments, the Ad vector is derived from Ad49. In some embodiments, the Ad vector is derived from Ad50.

In some embodiments, the adenovirus vector is a great ape adenovirus (GAd) vector. In some embodiments, the GAd vector is derived from GAd20. In some embodiments, the GAd vector is derived from GAd19. In some embodiments, the GAd vector is derived from GAd21.

In some embodiments, the GAd vector is derived from GAd25. In some embodiments, the GAd vector is derived from GAd26. In some embodiments, the GAd vector is derived from GAd27.

In some embodiments, the GAd vector is derived from GAd28. In some embodiments, the GAd vector is derived from GAd29. In some embodiments, the GAd vector is derived from GAd30.

In some embodiments, the GAd vector is derived from GAd31. In some embodiments, the GAd vector is derived from ChAd4. In some embodiments, the GAd vector is derived from ChAd5.

In some embodiments, the GAd vector is derived from ChAd6. In some embodiments, the GAd vector is derived from ChAd7. In some embodiments, the GAd vector is derived from ChAd8.

In some embodiments, the GAd vector is derived from ChAd9. In some embodiments, the GAd vector is derived from ChAd20. In some embodiments, the GAd vector is derived from ChAd22.

In some embodiments, the GAd vector is derived from ChAd24. In some embodiments, the GAd vector is derived from ChAd26. In some embodiments, the GAd vector is derived from ChAd30. In some embodiments, the GAd vector is derived from ChAd31. In some embodiments, the GAd vector is derived from ChAd32. In some embodiments, the GAd vector is derived from ChAd33. In some embodiments, the GAd vector is derived from ChAd37. In some embodiments, the GAd vector is derived from ChAd38. In some embodiments, the GAd vector is derived from ChAd44. In some embodiments, the GAd vector is derived from ChAd55. In some embodiments, the GAd vector is derived from ChAd63. In some embodiments, the GAd vector is derived from ChAd68. In some embodiments, the GAd vector is derived from ChAd73. In some embodiments, the GAd vector is derived from ChAd82. In some embodiments, the GAd vector is derived from ChAd83.

The polypeptide or the heterologous polypeptide of the disclosure may be inserted into a site or region (insertion region) in the vector that does not affect virus viability of the resultant recombinant virus. The polypeptide or the heterologous polypeptide of the disclosure may be inserted into the deleted E1 region in parallel (transcribed 5' to 3') or anti-parallel (transcribed in a 3' to 5' direction relative to the vector backbone) orientation. In addition, appropriate transcriptional regulatory elements that are capable of directing expression of the polypeptide or the heterologous polypeptide of the disclosure in the mammalian host cells that the vector is being prepared for use may be operatively linked to the polypeptide or the heterologous polypeptide of the disclosure. “Operatively linked” sequences include both expression control sequences that are contiguous with the nucleic acid sequences that they regulate and regulatory sequences that act in trans, or at a distance to control the regulated nucleic acid sequence.

Recombinant adenoviral particles may be prepared and propagated according to any conventional technique in the field of the art (e.g., Int. Pat. Publ. No. WO1996/17070) using a complementation cell line or a helper virus, which supplies in trans the missing viral genes necessary for viral replication. The cell lines 293 (Graham et al., 1977, J. Gen. Virol. 36: 59-72), PER.C6 (see e.g. U.S. Pat. No. 5,994,128), E1 A549 and 911 are commonly used to complement E1 deletions. Other cell lines have been engineered to complement defective vectors (Yeh, et al., 1996, J. Virol. 70: 559-565; Kroughak and Graham, 1995, Human Gene Ther. 6: 1575-1586; Wang, et al., 1995, Gene Ther. 2: 775-783; Lusky, et al., 1998, J. Virol. 72: 2022-203; EP 919627 and Int. Pat. Publ. No. WO1997/04119). The adenoviral particles may be recovered from the culture supernatant but also from the cells after lysis and optionally further purified according to standard techniques (e.g., chromatography, ultracentrifugation, as described in Int. Pat. Publ. No. WO1996/27677, Int. Pat. Publ. No. WO1998/00524, Int. Pat. Publ. No. WO1998/26048 and Int. Pat. Publ. No. WO2000/50573).

The construction and methods for propagating adenoviral vectors are also described in for example, U.S. Pat. Nos. 5,559,099, 5,837,511, 5,846,782, 5,851,806, 5,994,106, 5,994,128, 5,965,541, 5,981,225, 6,040,174, 6,020,191, and 6,113,913.

Poxvirus Vectors

Poxvirus (Poxviridae) vectors may be derived from smallpox virus (variola), vaccinia virus, cowpox virus or monkeypox virus. Exemplary vaccinia viruses are the Copenhagen vaccinia virus (W), New York Attenuated Vaccinia Virus (NYVAC), ALVAC, TROVAC and Modified Vaccinia Ankara (MVA).

MVA originates from the dermal vaccinia strain Ankara (Chorioallantois vaccinia Ankara (CVA) virus) that was maintained in the Vaccination Institute, Ankara, Turkey for many years and used as the basis for vaccination of humans. However, due to the often severe post-vaccinal complications associated with vaccinia viruses (VACV), there were several attempts to generate a more attenuated, safer smallpox vaccine.

MVA has been generated by 516 serial passages on chicken embryo fibroblasts of the CVA virus (see Meyer et al., *J. Gen. Virol.,* 72: 1031-1038 (1991) and U.S. Pat. No. 10,035,832). As a consequence of these long-term passages the resulting MVA virus deleted about 31 kilobases of its genomic sequence and, therefore, was described as highly host cell restricted to avian cells (Meyer, H. et al., Mapping of deletions in the genome of the highly attenuated vaccinia virus MVA and their influence on virulence, J. Gen. Virol. 72, 1031-1038, 1991; Meisinger-Henschel et al., Genomic sequence of chorioallantois vaccinia virus Ankara, the ancestor of modified vaccinia virus Ankara, J. Gen. Virol. 88, 3249-3259, 2007). Comparison of the MVA genome to its parent, CVA, revealed 6 major deletions of genomic DNA (deletion I, II, III, IV, V, and VI), totaling 31,000 basepairs. (Meyer et al., J. Gen. Virol. 72:1031-8 (1991)). It was shown in a variety of animal models that the resulting MVA was significantly avirulent (Mayr, A. & Danner, K. Vaccination against pox diseases under immunosuppressive conditions, Dev. Biol. Stand. 41: 225-34, 1978). Being that many passages were used to attenuate MVA, there are a number of different strains or isolates, depending on the passage number in CEF cells, such as MVA 476 MG/14/78, MVA-571, MVA-572, MVA-574, MVA-575 and MVA-BN. MVA 476 MG/14/78 is described for example in Int. Pat. Publ. No. WO2019/115816A1. MVA-572 strain was deposited at the European Collection of Animal Cell Cultures ("ECACC"), Health Protection Agency, Microbiology Services, Porton Down, Salisbury SP4 OJG, United Kingdom ("UK"), under the deposit number ECACC 94012707 on Jan. 27, 1994. MVA-575 strain was deposited at the ECACC under deposit number ECACC 00120707 on Dec. 7, 2000; MVA-Bavarian Nordic ("MVA-BN") strain was deposited at the ECACC under deposit number V00080038 on Aug. 30, 2000. The genome sequences of MVA-BN and MVA-572 are available at GenBank (Accession numbers DQ983238 and DQ983237, respectively). The genome sequences of other MVA strains can be obtained using standard sequencing methods.

Vectors and viruses of the disclosure may be derived from any MVA strain or further derivatives of the MVA strain. A further exemplary MVA strain is deposit VR-1508, deposited at the American Type Culture collection (ATCC), Manassas, Va. 20108, USA.

"Derivatives" of MVA refer to viruses exhibiting essentially the same characteristics as the parent MVA, but exhibiting differences in one or more parts of their genomes. In some embodiments, the MVA vector is derived from MVA 476 MG/14/78. In some embodiments, the MVA vector is derived from MVA-571. In some embodiments, the MVA vector is derived from MVA-572. In some embodiments, the MVA vector is derived from MVA-574. In some embodiments, the MVA vector is derived from MVA-575. In some embodiments, the MVA vector is derived from MVA-BN.

The polynucleotide or the heterologous polynucleotide of the disclosure may be inserted into a site or region (insertion region) in the MVA vector that does not affect virus viability of the resultant recombinant virus. Such regions can be readily identified by testing segments of virus DNA for regions that allow recombinant formation without seriously affecting virus viability of the recombinant virus. The thymidine kinase (TK) gene is an insertion region that may be used and is present in many viruses, such as in all examined poxvirus genomes. Additionally, MVA contains 6 natural deletion sites, each of which may be used as insertion sites (e.g. deletion I, II, III, IV, V, and VI; see e.g. U.S. Pat. Nos. 5,185,146 and 6,440,442). One or more intergenic regions (IGR) of the MVA may also be used as an insertion site, such as IGRs IGR07/08, IGR 44/45, IGR 64/65, IGR 88/89, IGR 136/137, and IGR 148/149 (see e.g. U.S. Pat. Publ. No. 2018/0064803). Additional suitable insertion sites are described in Int. Pat. Publ. No. WO2005/048957.

Recombinant poxviral particles such as rMVA are prepared as described in the art (Piccini, et al., 1987, Methods of Enzymology 153: 545-563; U.S. Pat. Nos. 4,769,330; 4,772,848; 4,603,112; 5,100,587 and 5,179,993). In an exemplary method, the DNA sequence to be inserted into the virus can be placed into an *E. coli* plasmid construct into which DNA homologous to a section of DNA of the MVA has been inserted. Separately, the DNA sequence to be inserted can be ligated to a promoter. The promoter-gene linkage can be positioned in the plasmid construct so that the promoter-gene linkage is flanked on both ends by DNA homologous to a DNA sequence flanking a region of MVA DNA containing a non-essential locus. The resulting plasmid construct can be amplified by propagation within *E. coli* bacteria and isolated. The isolated plasmid containing the DNA gene sequence to be inserted can be transfected into a cell culture, e.g., of chicken embryo fibroblasts (CEFs), at the same time the culture is infected with MVA. Recombination between homologous MVA DNA in the plasmid and the viral genome, respectively, can generate an MVA modified by the presence of foreign DNA sequences. rMVA particles may be recovered from the culture supernatant or from the cultured cells after a lysis step (e.g., chemical lysis, freezing/thawing, osmotic shock, sonication and the like). Consecutive rounds of plaque purification can be used to remove contaminating wild type virus. Viral particles can then be purified using the techniques known in the art (e.g., chromatographic methods or ultracentrifugation on cesium chloride or sucrose gradients).

Other Viral Vectors and Recombinant Viruses

Other viral vectors include vectors derived from human adeno-associated viruses, such as AAV-2 (adeno-associated virus type 2). An attractive feature of AAV vectors is that they do not express any viral genes. The only viral DNA sequences included in the AAV vectors are the 145 bp inverted terminal repeats (ITR). Thus, as in immunization with naked DNA, the only gene expressed is that of the antigen, or antigen chimera. Additionally, AAV vectors are known to transduce both dividing and non-dividing cells, such as human peripheral blood monocyte-derived dendritic cells, with persistent transgene expression, and with the possibility of oral and intranasal delivery for generation of mucosal immunity. Moreover, the amount of DNA required appears to be much less by several orders of magnitude, with maximum responses at doses of $10^{10}$ to $10^{11}$ particles or copies of DNA in contrast to naked DNA doses of 50 μg or about 1015 copies. AAV vectors are packaged by co-transfection of a suitable cell line (e.g., human 293 cells) with the DNA contained in the AAV ITR chimeric protein encoding constructs and an AAV helper plasmid ACG2 containing the AAV coding region (AAV rep and cap genes) without the ITRs. The cells are subsequently infected with the adenovirus Ad5. Vectors can be purified from cell lysates using methods known in the art (e.g., such as cesium chloride density gradient ultracentrifugation) and are validated to ensure that they are free of detectable replication-competent AAV or adenovirus (e.g., by a cytopathic effect bioassay).

Retroviral vectors may also be used. Retroviruses are a class of integrative viruses which replicate using a virus-encoded reverse transcriptase, to replicate the viral RNA genome into double stranded DNA which is integrated into chromosomal DNA of the infected cells (e.g., target cells). Such vectors include those derived from murine leukemia viruses, especially Moloney (Gilboa, et al., 1988, Adv. Exp. Med. Biol. 241: 29) or Friend's FB29 strains (Int. Pat. Publ. No. WO1995/01447). Generally, a retroviral vector is deleted of all or part of the viral genes gag, pol and env and retains 5' and 3' LTRs and an encapsidation sequence. These elements may be modified to increase expression level or stability of the retroviral vector. Such modifications include the replacement of the retroviral encapsidation sequence by one of a retrotransposon such as VL30 (see, e.g., U.S. Pat. No. 5,747,323). The polynucleotides of the disclosure may be inserted downstream of the encapsidation sequence, such as in opposite direction relative to the retroviral genome. Retroviral particles are prepared in the presence of a helper virus or in an appropriate complementation (packaging) cell line which contains integrated into its genome the retroviral genes for which the retroviral vector is defective (e.g. gag/pol and env). Such cell lines are described in the prior art (Miller and Rosman, 1989, BioTechniques 7: 980; Danos and Mulligan, 1988, Proc. Natl. Acad. Sci. USA 85: 6460; Markowitz, et al., 1988, Virol. 167: 400). The product of the env gene is responsible for the binding of the viral particle to the viral receptors present on the surface of the target cell and, therefore determines the host range of the retroviral particle. Packaging cell line, such as the PA317 cells (ATCC CRL 9078) or 293EI6 (WO97/35996) containing an amphotropic envelope protein may therefore be used to allow infection of human and other species' target cells. The retroviral particles are recovered from the culture supernatant and may optionally be further purified according to standard techniques (e.g. chromatography, ultracentrifugation).

Regulatory Elements

The polynucleotide or the heterologous polynucleotide of the disclosure may be operably linked to one or more regulatory elements in the vector. The regulatory elements may comprise promoters, enhancers, polyadenylation signals, repressors and the like.

Some of the commonly used enhancer and promoter sequences in expression vectors and viral vectors are, for example, human cytomegalovirus (hCMV), vaccinia P7.5 early/late promoter, CAG, SV40, mouse CMV (mCMV), EF-1 and hPGK promoters. Due to its high potency and moderate size of ca. 0.8 kB, the hCMV promoter is one of the most commonly used of these promoters. The hPGK promoter is characterized by a small size (ca. 0.4 kB), but it is less potent than the hCMV promoter. On the other hand, the CAG promoter consisting of a cytomegalovirus early enhancer element, promoter, first exon and intron of chicken beta-actin gene, and splice acceptor of the rabbit beta-globin gene, can direct very potent gene expression that is comparable to the hCMV promoter, but its large size makes it less suitable in viral vectors where space constraints can be a significant concern, e.g., in adenoviral vectors (AdV), adeno-associated viral vectors (AAV) or lentiviral vectors (LVs).

Additional promoters that may be used are Aotine Herpesvirus 1 major immediate early promoter (AoHV-1 promoter) described in Int. Pat. Publ. No. WO2018/146205. The promoter may be operably coupled to a repressor operator sequence, to which a repressor protein can bind in order to repress expression of the promoter in the presence of the repressor protein. In certain embodiments, the repressor operator sequence is a TetO sequence or a CuO sequence (see e.g. U.S. Pat. No. 9,790,256).

In certain cases, it may be desirable to express at least two separate polypeptides from the same vector. In this case each polynucleotide may be operably linked to the same or different promoter and/or enhancer sequences, or well-known bicistronic expression systems for example by utilizing internal ribosome entry site (IRES) from encephalomyocarditis virus may be used. Alternatively, bidirectional synthetic promoters may be used, such as a hCMV-rhCMV promoter and other promoters described in Int. Pat. Publ. No. WO2017/220499.

Polyadenylation signals may be derived from SV40 or bovine growth hormone (BGH).

The vectors of the disclosure may be generated using known techniques.

Exemplary regulatory elements that may be included into the vector comprise vaccinia P7.5 early/late promoter (SEQ ID NO: 630), TetOCMV promoter (SEQ ID NO: 628), BGH poly A site (SEQ ID NO: 629), T cell enhancer (SEQ ID NO: 546).

The disclosure also provides an isolated viral vector comprising a heterologous polynucleotide encoding a heterologous polypeptide comprising two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising two or more polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

In some embodiments, the viral vector is an adenovirus vector.

In some embodiments, the viral vector is derived from a human adenovirus.

In some embodiments, the viral vector is derived from Ad26.

In some embodiments, the viral vector is derived from a great ape adenovirus.

In some embodiments, the vial vector is derived from GAd20.

In some embodiments, the viral vector is derived from ChAd20.

In some embodiments, the viral vector is a poxvirus vector.

In some embodiments, the viral vector is derived from modified virus Ankara (MVA).

The disclosure also provides an isolated viral vector comprising a heterologous polynucleotide encoding a heterologous polypeptide comprising 3 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 3 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 4 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293,295, 297, 299, 301, 303,305, 307, 309, 311, 313,315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 4 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336,338, 340, 342, 344, 346, 348, 350, 352, 354, 356, 358, 360, 362,364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 5 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293,295, 297, 299, 301, 303,305, 307, 309, 311, 313,315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 5 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 6 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303,305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 6 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 7 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241,243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 7 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 8 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317,319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 8 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 9 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293,295, 297, 299, 301, 303,305, 307, 309, 311, 313,315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 9 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336,338, 340, 342, 344, 346, 348, 350, 352, 354, 356, 358, 360, 362,364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 10 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 10 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336,338, 340, 342, 344,346, 348, 350, 352, 354, 356, 358, 360, 362,364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 11 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 11 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 12 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 12 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 13 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 13 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 14 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 14 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 15 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 15 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 16 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 16 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 17 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 17 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 18 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 18 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 19 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 19 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 20 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 20 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 21 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 21 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 22 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 22 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 23 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 23 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 24 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 24 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 25 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 25 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 26 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 26 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 27 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 27 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362,364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 28 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 28 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 29 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 29 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 30 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 30 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 31 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 31 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 32 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 32 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 33 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 33 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 34 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 34 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 35 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 35 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 36 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 36 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 37 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 37 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 38 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 38 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 39 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 39 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 40 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 40 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 41 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 41 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 42 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 42 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 43 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 43 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 44 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 44 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 45 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 45 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 46 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 46 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 47 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 47 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 48 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 48 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 49 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 49 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 50 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 50 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 51 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 51 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 52 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 52 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 53 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 53 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 54 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 54 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 55 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 55 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 56 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 56 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 57 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 57 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 58 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 58 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 59 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 59 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 60 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 60 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 61 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 61 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 62 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 62 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 63 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 63 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 64 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 64 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 65 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 65 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 66 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 66 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 67 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 67 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 68 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 68 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 69 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 69 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 70 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 70 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 71 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 71 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 72 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 72 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 73 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 73 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 74 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 74 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 75 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 75 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 76 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 76 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 77 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 77 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 78 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 78 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 79 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 79 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 80 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 80 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 81 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 81 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 82 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 82 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 83 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 83 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 84 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 84 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 85 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 85 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 86 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 86 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 87 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 87 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 88 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 88 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 89 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 89 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 90 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 90 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 91 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 91 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 92 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313,315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 92 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 93 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313,315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 93 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 94 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 94 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 95 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 95 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 96 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 96 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 97 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 97 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302,304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 98 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 98 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 99 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 99 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 100 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 100 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 101 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 101 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 102 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 102 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 103 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 103 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 104 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 104 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 105 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 105 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 106 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 106 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 107 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 107 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 108 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 108 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 109 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 109 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 110 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 110 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 111 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 111 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 112 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 112 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 113 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 113 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 114 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 114 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 115 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 115 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 116 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 116 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 117 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 117 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 118 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 118 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 119 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 119 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 120 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 120 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 121 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 121 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 122 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 122 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 123 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 123 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 124 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 124 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 125 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 125 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 126 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 126 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 127 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 127 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 128 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 128 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 129 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 129 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 130 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 130 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 131 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211,213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 131 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 132 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285,287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the viral vector comprises a heterologous polynucleotide comprising 132 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 133 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 133 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 134 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 134 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 135 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 135 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 136 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 136 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 137 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 137 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 138 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 138 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 139 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 139 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 140 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 140 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 141 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 141 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 142 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 142 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 143 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 143 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 144 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 144 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 145 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 145 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 146 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 146 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 147 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 147 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 148 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 148 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 149 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 149 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 150 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 150 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 151 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 151 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 152 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 152 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 153 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 153 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 154 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 154 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 155 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 155 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 156 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 156 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 157 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 157 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 158 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 158 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 159 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 159 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 160 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 160 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 161 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 161 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 162 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 162 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 163 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 163 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 164 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 164 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 165 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 165 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 166 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 166 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 167 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 167 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 168 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 168 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 169 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 169 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 170 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 170 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 171 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 171 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 172 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 172 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 173 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 173 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 174 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 174 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 175 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 175 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 176 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 176 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 177 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 177 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 178 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 178 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 179 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 179 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 180 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 180 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 181 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 181 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 182 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 182 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 183 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 183 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 184 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 184 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 185 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 185 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 186 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 186 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 187 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 187 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 188 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 188 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 189 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 189 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 190 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 190 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 191 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 191 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 192 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 192 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 193 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 193 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 194 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 194 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 195 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 195 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 196 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 196 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 197 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 197 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 198 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 198 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 199 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 199 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 200 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 200 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 201 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 201 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 202 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 202 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 203 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 203 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 204 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 204 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 205 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 206 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 207 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 208 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 209 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 210 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 211 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 212 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 213 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 214 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 215 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 216 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 217 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 218 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 219 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 220 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 221 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 222 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 223 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 224 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 225 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 226 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 227 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 228 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 229 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 230 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 231 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 232 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 233 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 234 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 235 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 236 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 237 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499.

In some embodiments, the viral vector comprises a heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540.

The disclosure also provides an isolated viral vector comprising a heterologous polynucleotide encoding a heterologous polypeptide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499.

In some embodiments, the viral vector comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540.

The disclosure also provides an isolated viral vector comprising a heterologous polynucleotide encoding a heterologous polypeptide comprising 2 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 2 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 2 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 2 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 3 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 3 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 3 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 3 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 4 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 4 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 4 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 4 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 5 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 5 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 5 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 5 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 6 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 6 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 6 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 6 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 7 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 7 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 7 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 7 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 8 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 8 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 8 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 8 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 9 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 9 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 9 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 9 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 10 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 10 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 10 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 10 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 11 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 11 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 11 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 11 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 12 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 12 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 12 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 12 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 13 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 13 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 13 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 13 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 14 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 14 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 14 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 14 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 15 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 15 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 15 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 15 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 16 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 16 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 16 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 16 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 17 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 17 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 17 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 17 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 18 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 18 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 18 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 18 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 19 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 19 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 19 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 19 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 20 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 20 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 20 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 20 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 21 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 21 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 21 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 21 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 22 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 22 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 22 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 22 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 23 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 23 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 23 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 23 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 24 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 24 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 24 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 24 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 25 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 25 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 25 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 25 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 26 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 26 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 26 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 26 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 27 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 27 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 27 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 27 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 28 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 28 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 28 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 28 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 29 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 29 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 29 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 29 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 30 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 30 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 30 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 30 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 31 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 31 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 31 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 31 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 32 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 32 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 32 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 32 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 33 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 33 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 33 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 33 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 34 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 34 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 34 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 34 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 35 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 35 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 35 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 35 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 36 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 36 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 36 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 36 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 37 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 37 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 37 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 37 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 38 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 38 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 38 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 38 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 39 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 39 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 39 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 39 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 40 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 40 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 40 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 40 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540.

In some embodiments, the viral vector comprises a heterologous polynucleotide comprising 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

In some embodiments, the viral vector is an adenovirus vector.

In some embodiments, the viral vector is derived from a human adenovirus.

In some embodiments, the viral vector is derived from Ad26.

In some embodiments, the viral vector is derived from a great ape adenovirus.

In some embodiments, the viral vector is derived from GAd20.

In some embodiments, the viral vector is derived from GAd19.

In some embodiments, the viral vector is derived from GAd21.

In some embodiments, the viral vector is derived from GAd25.

In some embodiments, the viral vector is derived from GAd26.

In some embodiments, the viral vector is derived from GAd27.

In some embodiments, the viral vector is derived from GAd28.

In some embodiments, the viral vector is derived from GAd29.

In some embodiments, the viral vector is derived from GAd30.

In some embodiments, the viral vector is derived from GAd31.

In some embodiments, the viral vector is derived from ChAd20.

In some embodiments, the viral vector is a poxvirus vector.

In some embodiments, the viral vector is derived from Modified Vaccinia Ankara (MVA).

The disclosure also provides a recombinant human adenovirus serotype 26 (rAd26) comprising a viral vector comprising a heterologous polynucleotide encoding a heterologous polypeptide comprising two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a viral vector comprising two or more polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 3 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 3 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 4 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 4 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 5 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 5 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 6 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 6 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 7 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 7 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 8 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 8 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 9 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 9 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 10 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 10 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 11 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 11 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 12 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 12 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 13 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 13 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 14 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 14 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 15 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 15 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 16 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 16 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 17 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 17 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 18 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 18 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 19 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 19 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 20 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 20 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 21 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 21 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 22 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 22 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 23 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 23 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 24 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 24 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 25 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 25 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 26 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 26 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 27 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 27 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 28 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 28 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 29 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 29 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 30 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 30 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 31 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 31 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 32 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 32 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 33 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 33 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 34 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 34 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 35 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 35 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 36 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 36 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 37 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 37 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 38 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 38 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 39 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 39 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 40 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 40 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 41 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 41 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 42 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 42 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 43 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 43 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 44 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 44 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 45 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 45 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 46 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 46 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 47 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 47 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 48 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 48 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 49 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 49 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 50 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 50 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 51 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 51 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 52 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 52 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 53 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 53 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 54 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 54 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 55 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 55 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 56 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 56 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 57 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 57 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 58 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 58 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 59 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 59 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 60 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 60 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 61 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 61 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 62 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 62 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 63 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 63 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 64 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 64 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 65 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 65 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 66 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 66 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 67 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 67 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 68 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 68 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 69 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 69 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 70 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 70 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 71 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 71 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 72 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 72 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 73 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 73 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 74 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 74 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 75 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 75 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 76 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 76 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 77 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 77 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 78 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 78 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 79 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 79 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 80 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 80 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

In some embodiments, the rAd26 comprises a heterologous polynucleotide comprising 81 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 81 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 82 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 82 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 83 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 83 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 84 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 84 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 85 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 85 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 86 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 86 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 87 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 87 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 88 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 88 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 89 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 89 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 90 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 90 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 91 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 91 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 92 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 92 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 93 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 93 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 94 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 94 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 95 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 95 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 96 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 96 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 97 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 97 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 98 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 98 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 99 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 99 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 100 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 100 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 101 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 101 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 102 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 102 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 103 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 103 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 104 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 104 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 105 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 105 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 106 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 106 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 107 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 107 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 108 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 108 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 109 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 109 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 110 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 110 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 111 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 111 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 112 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 112 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 113 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 113 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 114 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 114 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 115 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 115 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 116 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 116 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 117 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 117 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 118 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 118 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 119 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 119 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 120 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 120 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 121 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 121 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 122 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 122 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 123 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 123 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 124 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 124 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 125 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299,301, 303, 305, 307,309, 311, 313, 315, 317,319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the rAd26 comprises a heterologous polynucleotide comprising 125 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306,308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 126 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 126 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 127 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 127 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 128 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 128 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 129 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 129 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 130 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 130 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 131 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 131 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 132 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 132 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 133 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 133 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 134 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 134 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 135 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 135 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 136 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 136 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 137 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 137 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 138 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 138 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 139 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 139 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 140 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 140 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 141 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 141 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 142 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 142 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 143 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 143 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 144 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 144 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 145 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 145 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 146 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 146 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 147 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 147 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 148 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 148 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 149 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 149 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 150 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 150 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 151 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 151 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 152 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 152 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 153 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 153 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 154 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 154 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 155 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 155 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 156 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 156 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 157 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 157 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 158 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 158 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 159 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 159 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 160 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 160 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 161 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 161 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 162 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 162 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 163 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 163 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 164 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 164 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 165 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 165 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 166 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 166 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 167 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 167 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 168 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 168 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 169 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 169 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 170 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 170 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 171 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 171 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 172 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 172 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 173 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 173 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 174 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 174 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 175 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 175 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 176 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 176 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 177 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 177 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 178 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 178 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 179 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 179 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 180 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 180 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 181 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 181 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 182 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 182 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 183 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 183 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 184 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 184 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 185 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 185 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 186 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 186 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 187 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 187 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 188 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 188 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 189 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 189 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 190 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 190 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 191 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 191 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 192 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 192 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 193 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 193 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 194 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 194 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 195 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 195 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 196 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 196 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 197 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 197 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 198 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 198 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 199 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 199 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 200 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 200 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 201 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 201 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 202 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 202 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 203 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 203 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 204 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 204 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 205 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 206 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 207 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 208 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 209 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 210 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 211 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 212 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 213 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 214 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 215 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 216 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 217 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 218 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 219 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 220 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 221 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 222 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 223 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 224 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 225 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 226 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 227 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 228 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 229 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 230 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 231 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 232 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 233 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 234 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 235 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 236 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 237 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 2 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 2 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 2 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 2 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 3 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 3 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 3 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 3 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 4 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 4 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 4 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 4 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 5 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 5 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 5 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 5 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 6 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 6 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 6 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 6 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 7 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 7 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 7 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 7 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 8 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 8 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 8 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 8 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 9 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 9 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 9 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 9 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 10 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 10 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 10 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 10 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 11 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 11 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 11 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 11 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 12 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 12 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 12 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 12 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 13 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 13 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 13 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 13 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 14 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 14 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 14 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 14 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 15 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 15 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 15 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 15 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 16 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 16 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 16 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 16 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 17 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 17 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 17 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 17 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 18 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 18 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 18 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 18 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 19 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 19 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 19 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 19 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 20 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 20 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 20 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 20 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 21 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 21 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 21 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 21 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 22 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 22 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 22 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 22 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 23 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 23 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 23 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 23 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 24 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 24 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 24 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 24 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 25 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 25 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 25 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 25 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 26 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 26 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 26 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 26 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 27 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 27 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 27 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 27 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 28 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 28 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 28 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 28 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 29 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 29 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 29 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 29 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 30 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 30 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 30 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 30 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 31 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 31 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 31 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 31 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 32 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 32 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 32 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 32 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 33 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 33 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 33 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 33 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 34 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 34 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 34 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 34 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 35 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 35 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 35 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 35 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 36 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 36 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 36 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 36 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 37 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 37 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 37 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 37 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 38 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 38 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 38 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 38 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 39 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 39 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 39 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 39 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 40 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 40 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 40 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 40 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a recombinant great ape adenovirus (rGAd) comprising a viral vector comprising a heterologous polynucleotide encoding a heterologous polypeptide comprising two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a viral vector comprising a heterologous polynucleotide comprising two or more polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 3 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 3 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 4 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 4 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 5 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 5 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 6 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 6 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 7 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 7 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 8 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 8 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 9 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 9 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 10 polypeptides selected from the group consisting of ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 10 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 11 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 11 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 12 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 12 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 13 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 13 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 14 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 14 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 15 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 15 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 16 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 16 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 17 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 17 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 18 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 18 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 19 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 19 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 20 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 20 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 21 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 21 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 22 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 22 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 23 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 23 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 24 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 24 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 25 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 25 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 26 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 26 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 27 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 27 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 28 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 28 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 29 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 29 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 30 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 30 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 31 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 31 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 32 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 32 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 33 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 33 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 34 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 34 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 35 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 35 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 36 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 36 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 37 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 37 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 38 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 38 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 39 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 39 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 40 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 40 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 41 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 41 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 42 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 42 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 43 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 43 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 44 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 44 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 45 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 45 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 46 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 46 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 47 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 47 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 48 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 48 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 49 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 49 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 50 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 50 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 51 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 51 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 52 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 52 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 53 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 53 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 54 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 54 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 55 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 55 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 56 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 56 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 57 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 57 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 58 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 58 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 59 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 59 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 60 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 60 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 61 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 61 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 62 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 62 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 63 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 63 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 64 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 64 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 65 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 65 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 66 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 66 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 67 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 67 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 68 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 68 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 69 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 69 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 70 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 70 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 71 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 71 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 72 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 72 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 73 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 73 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 74 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 74 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 75 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 75 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 76 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 76 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 77 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 77 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 78 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 78 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 79 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 79 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 80 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 80 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 81 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 81 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 82 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 82 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 83 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 83 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 84 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 84 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 85 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 85 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 86 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 86 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 87 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 87 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 88 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 88 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 89 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 89 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 90 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 90 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 91 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 91 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 92 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 92 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 93 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 93 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 94 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 94 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 95 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 95 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 96 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 96 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 97 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 97 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 98 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 98 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 99 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 99 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 100 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 100 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 101 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 101 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 102 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 102 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 103 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 103 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 104 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 104 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 105 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 105 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 106 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 106 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 107 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 107 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 108 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 108 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 109 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 109 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 110 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 110 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 111 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 111 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 112 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 112 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 113 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 113 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 114 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 114 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 115 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 115 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 116 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 116 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 117 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 117 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 118 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 118 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 119 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 119 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 120 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 120 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 121 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 121 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 122 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 122 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 123 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 123 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 124 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 124 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 125 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 125 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 126 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 126 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 127 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 127 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 128 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 128 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 129 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 129 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 130 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 130 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 131 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 131 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 132 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 132 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 133 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 133 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 134 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 134 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 135 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 135 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 136 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 136 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 137 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 137 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 138 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 138 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 139 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 139 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 140 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 140 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 141 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 141 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 142 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 142 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 143 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 143 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 144 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 144 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 145 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 145 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 146 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 146 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 147 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 147 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 148 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 148 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 149 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 149 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 150 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 150 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 151 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 151 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 152 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 152 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 153 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 153 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 154 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 154 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 155 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 155 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 156 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 156 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 157 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 157 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 158 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 158 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 159 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 159 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 160 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 160 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 161 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 161 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 162 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 162 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 163 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 163 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 164 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 164 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 165 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 165 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 166 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 166 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 167 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 167 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 168 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 168 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 169 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 169 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 170 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 170 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 171 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 171 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 172 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 172 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 173 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 173 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 174 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 174 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 175 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 175 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 176 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 176 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 177 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 177 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 178 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 178 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 179 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 179 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 180 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 180 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 181 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 181 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 182 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 182 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 183 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 183 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 184 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 184 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 185 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 185 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 186 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 186 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 187 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 187 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 188 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 188 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 189 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 189 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 190 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 190 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 191 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 191 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 192 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 192 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 193 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 193 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 194 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 194 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 195 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 195 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 196 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 196 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 197 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 197 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 198 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 198 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 199 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 199 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 200 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 200 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 201 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 201 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 202 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 202 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 203 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 203 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 204 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 204 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 205 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 206 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 207 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 208 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 209 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 210 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 211 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 212 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 213 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 214 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 215 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 216 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 217 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 218 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 219 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 220 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 221 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 222 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 223 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 224 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 225 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 226 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 227 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 228 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 229 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 230 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 231 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 232 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 233 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 234 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 235 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 236 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 237 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 2 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 2 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 2 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 2 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 3 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 3 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 3 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 3 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 4 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 4 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 4 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 4 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 5 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 5 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 5 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 5 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 6 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 6 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 6 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 6 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 7 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 7 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 7 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 7 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 8 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 8 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 8 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 8 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 9 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 9 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 9 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 9 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 10 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 10 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 10 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 10 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 11 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 11 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 11 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 11 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 12 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 12 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 12 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 12 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 13 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 13 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 13 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 13 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 14 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 14 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 14 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 14 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 15 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 15 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 15 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 15 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 16 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 16 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 16 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 16 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 17 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 17 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 17 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 17 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 18 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 18 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 18 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 18 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 19 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 19 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 19 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 19 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 20 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 20 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 20 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 20 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 21 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 21 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 21 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 21 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 22 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 22 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 22 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 22 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 23 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 23 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 23 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 23 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 24 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 24 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 24 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 24 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 25 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 25 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 25 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 25 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 26 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 26 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 26 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 26 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 27 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 27 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 27 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 27 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 28 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 28 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 28 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 28 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 29 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 29 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 29 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 29 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 30 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 30 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 30 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 30 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 31 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 31 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 31 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 31 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 32 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 32 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 32 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 32 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 33 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 33 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 33 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 33 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 34 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 34 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 34 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 34 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 35 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 35 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 35 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 35 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 36 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 36 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 36 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 36 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 37 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 37 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 37 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 37 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 38 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 38 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 38 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 38 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 39 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 39 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 39 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 39 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 40 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 40 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 40 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 40 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising two or more polynucleotides selected from the group consisting of SEQ ID NOs: 500, 501, 461, 503, 504, 505,506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 2 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 2 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 2 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 2 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 3 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 3 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 3 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 3 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 4 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 4 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 4 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 4 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 5 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 5 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 5 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 5 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 6 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 6 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 6 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 6 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 7 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 7 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 7 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 7 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521,522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 8 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 8 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 8 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 8 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 9 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 9 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 9 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 9 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 10 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 10 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 10 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 10 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 11 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 11 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 11 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 11 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 12 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 12 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 12 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 12 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 13 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 13 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 13 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 13 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 14 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 14 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 14 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 14 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 15 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 15 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 15 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 15 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 16 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 16 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 16 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 16 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 17 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 17 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 17 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 17 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 18 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 18 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 18 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 18 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 19 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 19 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 19 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 19 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 20 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 20 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 20 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 20 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 21 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 21 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 21 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 21 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 22 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 22 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 22 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 22 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 23 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 23 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 23 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 23 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 24 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 24 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 24 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 24 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 25 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 25 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 25 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 25 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 26 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 26 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 26 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 26 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 27 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 27 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 27 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 27 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 28 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 28 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 28 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 28 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 29 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 29 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 29 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 29 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 30 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 30 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 30 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 30 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 31 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 31 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 31 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 31 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 32 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 32 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 32 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 32 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 33 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 33 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 33 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 33 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 34 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 34 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 34 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 34 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 35 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 35 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 35 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 35 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 36 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 36 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 36 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 36 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 37 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 37 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 37 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 37 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 38 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 38 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 38 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 38 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 39 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 39 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 39 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 39 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 40 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 40 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 40 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 40 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a recombinant modified vaccinia Ankara (rMVA) comprising a viral vector comprising a heterologous polynucleotide encoding a heterologous polypeptide comprising two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a viral vector comprisinga heterologous polypeptide comprising two or more polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 3 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 3 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 4 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 4 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 5 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 5 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 6 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 6 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 7 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 7 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 8 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 8 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 9 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 9 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 10 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 10 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 11 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 11 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 12 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 12 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 13 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 13 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 14 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 14 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 15 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 15 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 16 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 16 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 17 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 17 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 18 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 18 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 19 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 19 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 20 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 20 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 21 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 21 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 22 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 22 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 23 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 23 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 24 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 24 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 25 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 25 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 26 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 26 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 27 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 27 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 28 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 28 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 29 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 29 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 30 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 30 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 31 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 31 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 32 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 32 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 33 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 33 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 34 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 34 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 35 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 35 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 36 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 36 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 37 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 37 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 38 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 38 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 39 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 39 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 40 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 40 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 41 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 41 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 42 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 42 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 43 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 43 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 44 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 44 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 45 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 45 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 46 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 46 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 47 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 47 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 48 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 48 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 49 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 49 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 50 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 50 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 51 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 51 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 52 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 52 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 53 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 53 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 54 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 54 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 55 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 55 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 56 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 56 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 57 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 57 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 58 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 58 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 59 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 59 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 60 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 60 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 61 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 61 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 62 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 62 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 63 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 63 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 64 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 64 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 65 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 65 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 66 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 66 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 67 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 67 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 68 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 68 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 69 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 69 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 70 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 70 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 71 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 71 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 72 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 72 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 73 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 73 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 74 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 74 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 75 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 75 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 76 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 76 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 77 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 77 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 78 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 78 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 79 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 79 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 80 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 80 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 81 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 81 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 82 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 82 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 83 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 83 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 84 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 84 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 85 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 85 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 86 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 86 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 87 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 87 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 88 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 88 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 89 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 89 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 90 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 90 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 91 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 91 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 92 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 92 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 93 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 93 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 94 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 94 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 95 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 95 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 96 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 96 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 97 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 97 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 98 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 98 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 99 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 99 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 100 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 100 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 101 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 101 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 102 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 102 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 103 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 103 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 104 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 104 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 105 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 105 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 106 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 106 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 107 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 107 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 108 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 108 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 109 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 109 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 110 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 110 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 111 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 111 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 112 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 112 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 113 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 113 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 114 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 114 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 115 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 115 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 116 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 116 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 117 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 117 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 118 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 118 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 119 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 119 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 120 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 120 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 121 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 121 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 122 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 122 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 123 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 123 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 124 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 124 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 125 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 125 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 126 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 126 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 127 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 127 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 128 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 128 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 129 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 129 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 130 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 130 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 131 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 131 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 132 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 132 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 133 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 133 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 134 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 134 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 135 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 135 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 136 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 136 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 137 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 137 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 138 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 138 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 139 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 139 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 140 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 140 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 141 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 141 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 142 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 142 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 143 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 143 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 144 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 144 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 145 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 145 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 146 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 146 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 147 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 147 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 148 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 148 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 149 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 149 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 150 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 150 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 151 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 151 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 152 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 152 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 153 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 153 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 154 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 154 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 155 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 155 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 156 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 156 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 157 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 157 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 158 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 158 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 159 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 159 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 160 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 160 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 161 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 161 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 162 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 162 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 163 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 163 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 164 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 164 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 165 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 165 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 166 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 166 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 167 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 167 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 168 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 168 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 169 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 169 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 170 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 170 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 171 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 171 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 172 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 172 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 173 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 173 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 174 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 174 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 175 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 175 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 176 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 176 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 177 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 177 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 178 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 178 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 179 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 179 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 180 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 180 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 181 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 181 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 182 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 182 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 183 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 183 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 184 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 184 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 185 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 185 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 186 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 186 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 187 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 187 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 188 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 188 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 189 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 189 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 190 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 190 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 191 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 191 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 192 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 192 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 193 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 193 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 194 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 194 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 195 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 195 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 196 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 196 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 197 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 197 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 198 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 198 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 199 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 199 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 200 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 200 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 201 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 201 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 202 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 202 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 203 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 203 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 204 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 204 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 205 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 206 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 207 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 208 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 209 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 210 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 211 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 212 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 213 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 214 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 215 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 216 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 217 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 218 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 219 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 220 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 221 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 222 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 223 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 224 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 225 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 226 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 227 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 228 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 229 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 230 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 231 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 232 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 233 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 234 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 235 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 236 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 237 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising two or more polynucleotides selected from the group consisting of SEQ ID NOs: 500, 501, 461, 503, 504, 505,506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 2 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 2 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 3 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 3 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 3 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 3 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 4 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 4 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 4 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 4 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 5 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 5 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 5 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 5 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 6 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 6 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 6 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 6 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 7 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 7 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 7 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 7 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 8 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 8 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 8 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 8 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 9 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 9 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 9 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 9 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 10 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 10 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 10 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 10 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 11 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 11 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 11 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 11 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 12 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 12 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 12 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 12 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 13 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 13 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 13 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 13 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 14 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 14 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 14 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 14 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 15 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 15 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 15 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 15 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 16 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 16 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 16 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 16 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 17 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 17 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 17 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 17 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 18 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 18 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 18 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 18 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 19 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 19 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 19 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 19 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 20 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 20 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 20 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 20 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 21 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 21 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 21 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 21 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 22 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 22 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 22 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 22 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 23 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 23 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 23 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 23 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 24 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 24 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 24 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 24 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 25 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 25 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 25 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 25 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 26 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 26 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 26 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 26 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 27 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 27 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 27 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 27 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 28 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 28 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 28 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 28 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 29 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 29 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 29 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 29 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 30 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 30 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 30 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 30 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 31 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 31 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 31 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 31 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 32 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 32 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 32 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 32 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 33 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 33 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 33 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 33 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 34 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 34 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 34 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 34 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 35 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 35 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 35 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 35 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 36 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 36 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 36 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 36 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 37 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 37 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 37 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 37 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 38 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 38 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 38 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 38 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 39 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 39 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 39 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 39 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 40 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 40 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 40 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 40 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

Cells of the Disclosure

The disclosure also provides a cell comprising or transduced with one or more vectors of the disclosure or one or more recombinant viruses of the disclosure. In some embodiments, the cell is a host cell.

Suitable cells include prokaryotic and eukaryotic cells, e.g., mammalian cells, yeast, fungi and bacteria (such as *E. coli*), such as Hek 293, CHO, PER.C6, PER.C6 TetO or chicken embryonic fibroblast (CEF) cells. The cell can be used in vitro, such as for research or for production of the polypeptides or viruses, or the cell can be used in vivo. In some embodiments, the cell is a muscle cell. In some embodiments, the cell is an antigen presenting cell (APC). Suitable antigen presenting cells include dendritic cells, B lymphocytes, monocytes and macrophages.

"Transduced", "transformed", or "transfected" refers to introduction of polynucleotides, heterologous polynucleotides or vectors of the disclosure inside a cell. The introduced polynucleotide may or may not be integrated into chromosomal DNA making up the genome of the cell.

"Cell" refers to the original cell and any progeny or clonal cell line established from the original cell.

The cells that are transfected with the polynucleotides or vectors of the disclosure may typically be obtained through cell culture repositories such as ATCC. APCs may be obtained from the peripheral blood using leukopheresis and "FICOLL/HYPAQUE" density gradient centrifugation (stepwise centrifugation through Ficoll and discontinuous Percoll density gradients). APCs may be isolated, cultured and engineered using known methods. For example, immature and mature dendritic cells may be generated from peripheral blood mononuclear cells (PBMCs) using known methods. In an exemplary method, isolated PBMCs are pre-treated to deplete T- and B-cells by means of an immunomagnetic technique. Lymphocyte-depleted PBMC are then cultured for in RPMI medium 9 e.g., about 7 days), supplemented with human plasma (preferably autologous plasma) and GM-CSF/IL-4, to generate dendritic cells. Dendritic cells are nonadherent when compared to their monocyte progenitors. Thus, on approximately day 7, non-adherent cells are harvested for further processing. The dendritic cells derived from PBMC in the presence of GM-CSF and IL-4 are immature, in that they can lose the nonadherence property and revert back to macrophage cell fate if the cytokine stimuli are removed from the culture. The dendritic cells in an immature state are effective in processing native protein antigens for the MHC class II restricted pathway (Romani, et al., J. Exp. Med. 169: 1169, 1989). Further maturation of cultured dendritic cells is accomplished by culturing for 3 days in a macrophage-conditioned medium (CM), which contains the necessary maturation factors. Mature dendritic cells are less able to capture new proteins for presentation but are much better at stimulating resting T cells (both CD4 and CD8) to grow and differentiate. Mature dendritic cells can be identified by their change in morphology, such as the formation of more motile cytoplasmic processes; by their nonadherence; by the presence of at least one of the following markers: CD83, CD68, HLA-DR or CD86; or by the loss of Fc receptors such as CD115 (reviewed in Steinman, Annu. Rev. Immunol. 9: 271, 1991). Mature dendritic cells can be collected and analyzed using typical cytofluorography and cell sorting techniques and devices, such as FACScan and FACStar. Primary antibodies used for flow cytometry are those specific to cell surface antigens of mature dendritic cells and are commercially available. Secondary antibodies can be biotinylated Igs followed by FITC- or PE-conjugated streptavidin. The vectors and recombinant viruses of the disclosure can be introduced into cells including APCs using the methods known in the art, including, but not limited to, transfection, electroporation, fusion, microinjection, viral-based delivery, or cell-based delivery.

Vaccines and Pharmaceutical Compositions of the Disclosure

The polypeptides or the heterologous polypeptides or fragments thereof, or the polynucleotides encoding them may be delivered into the subject utilizing any known delivery vehicle suitable for administering to the subject. It is expected that the polypeptides, the heterologous polypeptides or fragments thereof will be immunogenic in the subject regardless of the delivery vehicle used. It is expected that the various viral strains will be equally effective in mediating delivery of the polypeptides or the heterologous polypeptides in human subjects and therefore can be interchangeable. For example, it is expected that the various MVA strains disclosed herein would be equally efficient in potentiating immune responses against antigens encoded by the same transgene cassette. Similarly, it is expected that the various adenovirus strains would be interchangeable with no or minimal changes in their ability to potentiate immune responses against antigens encoded by the same transgene cassette. The polynucleotide may be DNA or RNA, or derivatives thereof. RNA may be in the form of oligonucleotide RNA, tRNA (transfer RNA), snRNA (small nuclear RNA), rRNA (ribosomal RNA), mRNA (messenger RNA), antisense RNA, siRNA (small interfering RNA), self-replicating RNA, ribozymes, chimeric sequences, or derivatives of these groups.

The disclosure also provides a vaccine comprising the polynucleotide of the disclosure.

In some embodiments, the polynucleotide is DNA.

In some embodiments, the polynucleotides is RNA.

In some embodiments, RNA is mRNA, or self-replicating RNA.

In some embodiments, RNA is self-replicating RNA.

The disclosure also provides a vaccine comprising the heterologous polynucleotide of the disclosure.

In some embodiments, the heterologous polynucleotide is DNA.

In some embodiments, the heterologous polynucleotides is RNA.

In some embodiments, RNA is mRNA, or self-replicating RNA.

In some embodiments, RNA is self-replicating RNA.

The disclosure also provides a vaccine comprising the polypeptide of the disclosure.

The disclosure also provides a vaccine comprising the heterologous polypeptide of the disclosure.

The disclosure also provides a vaccine comprising the vector of the disclosure.

The disclosure also provides a vaccine comprising the rAd26 of the disclosure.

The disclosure also provides a vaccine comprising the rMVA of the disclosure.

The disclosure also provides a vaccine comprising the rGAd of the disclosure.

The disclosure also provides a vaccine comprising the rGAd20 of the disclosure.

The disclosure also provides a vaccine comprising the ChAd20 of the disclosure.

The disclosure also provides a vaccine comprising the cell of the disclosure.

The preparation of vaccine compositions is well known. Vaccines may comprise or may be formulated into a pharmaceutical composition comprising the vaccine and a pharmaceutically acceptable excipient. "Pharmaceutically acceptable" refers to the excipient that at the dosages and concentrations employed, will not cause unwanted or harmful effects in the subjects to which they are administered and include carrier, buffers, stabilizers or other materials well known to those skilled in the art. The precise nature of the carrier or other material may depend on the route of administration, e.g., intramuscular, subcutaneous, oral, intravenous, cutaneous, intramucosal (e.g., gut), intranasal or intraperitoneal routes. Liquid carriers such as water, petroleum, animal or vegetable oils, mineral oil or synthetic oil may be included. Physiological saline solution, dextrose or other saccharide solution or glycols such as ethylene glycol, propylene glycol or polyethylene glycol may be included. Exemplary viral formulation are the Adenovirus World Standard (Hoganson et al, 2002): 20 mM Tris pH 8, 25 mM NaCl, 2.5% glycerol; or 20 mM Tris, 2 mM MgCl2, 25 mM NaCl, sucrose 10% w/v, polysorbate-80 0.02% w/v; or 10-25 mM citrate buffer pH 5.9-6.2, 4-6% (w/w) hydroxypropylbeta-cyclodextrin (HBCD), 70-100 mM NaCl, 0.018-0.035% (w/w) polysorbate-80, and optionally 0.3-0.45% (w/w) ethanol. Many other buffers can be used, and examples of suitable formulations for the storage and for pharmaceutical administration of purified pharmaceutical preparations are known.

The vaccine may comprise one or more adjuvants. Suitable adjuvants include QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Alum, and MF59. Other adjuvants that may be used include lectins, growth factors, cytokines and lymphokines such as alpha-interferon, gamma interferon, platelet derived growth factor (PDGF), granulocyte-colony stimulating factor (gCSF), granulocyte macrophage colony stimulating factor (gMCSF), tumor necrosis factor (TNF), epidermal growth factor (EGF), IL-1, IL-2, IL-4, IL-6, IL-8, IL-10, IL-12 or TLR agonists.

"Adjuvant" and "immune stimulant" are used interchangeably herein and are defined as one or more substances that cause stimulation of the immune system. In this context, an adjuvant is used to enhance an immune response to the vaccines or viral vectors described herein.

A pharmaceutical composition according to the disclosure may in certain embodiments be the vaccine of the disclosure.

Similarly, the polynucleotides, the heterologous polynucleotides, the polypeptides and the heterologous polypeptides of the disclosure may be formulated into pharmaceutical compositions comprising the polynucleotides, the heterologous polynucleotides, the polypeptides and the heterologous polypeptides and the pharmaceutically acceptable excipients.

Kits

The disclosure also provides a kit comprising one or more vaccines of the disclosure. The disclosure also provides a kit comprising one or more recombinant viruses of the disclosure. The kits may be used to facilitate performing the methods described herein. In some embodiments, the kit further comprises reagents to facilitate entry of the vaccines of the disclosure into a cell, such as lipid-based formulations or viral packaging materials.

In some embodiments, the kit comprises the rAd26 of the disclosure. In some embodiments, the kit comprises the rMVA of the disclosure. In some embodiments, the kit comprises the rGAd of the disclosure. In some embodiments, the kit comprises the rAd26 of the disclosure and the rMVA of the disclosure. In some embodiments, the kit comprises the rGAd of the disclosure and the rMVA of the disclosure. In some embodiments, the kit comprises the rAd26 of the disclosure and the rGAd of the disclosure. In some embodiments, the kit comprises one or more polynucleotides of the disclosure. In some embodiments, the kit comprises one or more heterologous polynucleotides of the disclosure. In some embodiments, the kit comprises one or more polypeptides of the disclosure. In some embodiments, the kit comprises one or more heterologous polypeptides of the disclosure. In some embodiments, the kit comprises one or more vectors of the disclosure. In some embodiment, the kit comprises one or more cells of the disclosure.

Non-Viral Delivery Vehicles

Nanoparticles

The polypeptides or the heterologous polypeptides or fragments thereof, the polynucleotides encoding them or vectors comprising the polynucleotides of the disclosure may be attached to nanoparticles for delivery to a subject. Delivery of the polypeptides or the heterologous polypeptides or fragments thereof, the polynucleotides encoding them or the vectors comprising the polynucleotides using nanoparticles may eliminate the need to include a virus or an adjuvant in the vaccine composition. The polynucleotide may be DNA or RNA. The nanoparticles may contain immune danger signals that help to effectively induce an immune response to the peptides. The nanoparticles may induce dendritic cell (DC) activation and maturation, required for a robust immune response. The nanoparticles may contain non-self components that improve uptake of the nanoparticles and thus the peptides by cells, such as antigen presenting cells.

The nanoparticles are typically from about 1 nm to about 100 nm in diameter, such as about 20 nm to about 40 nm. Nanoparticles with a mean diameter of 20 to 40 nm may facilitate uptake of the nanoparticle to the cytosol (see. e.g. WO2019/135086). Exemplary nanoparticles are polymeric nanoparticles, inorganic nanoparticles, liposomes, lipid nanoparticles (LNP), an immune stimulating complex (ISCOM), a virus-like particle (VLP), or a self-assembling protein. The nanoparticles may be calcium phosphate nanoparticles, silicon nanoparticles or gold nanoparticles. The polymeric nanoparticles may comprise one or more synthetic polymers, such as poly(d,l-lactide-co-glycolide) (PLG), poly(d,l-lactic-coglycolic acid) (PLGA), poly(g-glutamic acid) (g-PGA)m poly(ethylene glycol) (PEG), or polystyrene or one or more natural polymers such as a polysaccharide, for example pullulan, alginate, inulin, and chitosan. The use of a polymeric nanoparticles may be advantageous due to the properties of the polymers that may be include in the nanoparticle. For instance, the natural and synthetic polymers recited above may have good biocompatibility and biodegradability, a non-toxic nature and/or the ability to be manipulated into desired shapes and sizes. The polymeric nanoparticle may also form hydrogel nanoparticles, hydrophilic three-dimensional polymer networks with favorable properties including flexible mesh size, large surface area for multivalent conjugation, high water content, and high loading capacity for antigens. Polymers such as Poly(L-lactic acid) (PLA), PLGA, PEG, and polysaccharides are suitable for forming hydrogel nanoparticles. Inorganic nanoparticles typically have a rigid structure and comprise a shell in which an antigen is encapsulated or a core to which the antigen may be covalently attached. The core may comprise one or more atoms such as gold (Au), silver (Ag), copper (Cu) atoms, Au/Ag, Au/Cu, Au/Ag/Cu, Au/Pt, Au/Pd or Au/Ag/Cu/Pd or calcium phosphate (CaP).

The nanoparticles may be liposomes. Liposomes are typically formed from biodegradable, non-toxic phospholipids and comprise a self-assembling phospholipid bilayer shell with an aqueous core. Liposomes may be an unilamellar vesicle comprising a single phospholipid bilayer, or a multilamellar vesicle that comprises several concentric phospholipid shells separated by layers of water. As a consequence, liposomes may be tailored to incorporate either hydrophilic molecules into the aqueous core or hydrophobic molecules within the phospholipid bilayers. Liposomes may encapsulate antigens such as the polypeptides or the heterologous polypeptides or fragments thereof of the disclosure within the core for delivery. Liposomes and liposomal formulations can be prepared according to standard methods and are well known in the art, see, e.g., Remington's; Akimaru, 1995, Cytokines Mol. Ther. 1: 197-210; Alving, 1995, Immunol. Rev. 145: 5-31; Szoka, 1980, Ann. Rev. Biophys. Bioeng. 9: 467; U.S. Pat. Nos. 4,235,871; 4,501,728; and 4,837,028. The liposomes may comprise a targeting molecule for targeting liposome complexes to a particular cell type. Targeting molecule may comprise a binding partner (e.g., a ligand or receptor) for a biomolecule (e.g., a receptor or ligand) on the surface of a blood vessel or a cell found in a target tissue. Liposome charge is an important determinant in liposome clearance from the blood, with negatively charged liposomes being taken up more rapidly by the reticuloendothelial system (Juliano, 1975, Biochem. Biophys. Res. Commun. 63: 651) and thus having shorter half-lives in the bloodstream. Incorporating phosphatidylethanolamine derivatives enhances the circulation time by preventing liposomal aggregation. For example, incorporation of N-(omega-carboxy)acylamidophosphatidylethanolamines into large unilamellar vesicles of L-alpha-distearoylphosphatidylcholine dramatically increases the in vivo liposomal circulation lifetime (see, e.g., Ahl, 1997, Biochim. Biophys. Acta 1329: 370-382). Typically, liposomes are prepared with about 5 to 15 mole percent negatively charged phospholipids, such as phosphatidylglycerol, phosphatidylserine or phosphatidyl-inositol. Added negatively charged phospholipids, such as phosphatidylglycerol, also serve to prevent spontaneous liposome aggregation, and thus minimize the risk of undersized liposomal aggregate formation. Membrane-rigidifying agents, such as sphingomyelin or a saturated neutral phospholipid, at a concentration of at least about 50 mole percent, and 5 to 15 mole percent of monosialylganglioside can also impart desirably liposome properties, such as rigidity (see, e.g., U.S. Pat. No. 4,837,028). Additionally, the liposome suspension can include lipid-protective agents which protect lipids against free-radical and lipid-peroxidative damages on storage. Lipophilic free-radical quenchers, such as alpha-tocopherol and water-soluble iron-specific chelators, such as ferrioxianine, are preferred.

The nanoparticles may be lipid nanoparticles (LNP). LNPs are similar to liposomes but have slightly different function and composition. LNPs are designed toward encapsulating polynucleotides, such as DNA, mRNA, siRNA and sRNA. Traditional liposomes contain an aqueous core surrounded by one or more lipid bilayers. LNPs may assume a micelle-like structure, encapsulating drug molecules in a non-aqueous core. LNPs typically contain a cationic lipid, a non-cationic lipid, and a lipid that prevents aggregation of the particle (e.g., a PEG-lipid conjugate). LNPs are useful for systemic applications, as they exhibit extended circulation lifetimes following intravenous (i.e.) injection and accumulate at distal sites (e.g., sites physically separated from the administration site). The LNPs may have a mean diameter of about 50 nm to about 150 nm, such as about 60 nm to about 130 nm, or about 70 nm to about 110 nm, or about 70 nm to about 90 nm, and are substantially nontoxic. Preparation of polynucleotide loaded LNPs are disclosed in, e.g., U.S. Pat. Nos. 5,976,567; 5,981,501; 6,534,484; 6,586,410; 6,815,432; and PCT Publication No. WO 96/40964. Polynucleotide containing LNPs are described for example in WO2019/191780.

The polynucleotides, the heterologous polynucleotides, the polypeptides and the heterologous polypeptides of the disclosure can include multilamellar vesicles of heterogeneous sizes. For example, vesicle-forming lipids can be dissolved in a suitable organic solvent or solvent system and dried under vacuum or an inert gas to form a thin lipid film. If desired, the film can be redissolved in a suitable solvent, such as tertiary butanol, and then lyophilized to form a more homogeneous lipid mixture which is in a more easily hydrated powder like form. This film is covered with an aqueous solution of the polypeptide complex and allowed to hydrate, typically over a 15 to 60 minute period with agitation. The size distribution of the resulting multilamellar vesicles can be shifted toward smaller sizes by hydrating the lipids under more vigorous agitation conditions or by adding solubilizing detergents such as deoxycholate. The hydration medium may comprise the nucleic acid at a concentration which is desired in the interior volume of the liposomes in the final liposome suspension. Suitable lipids that may be used to form multilamellar vesicles include DOTMA (Feigner, et al., 1987, Proc. Natl. Acad. Sci. USA 84: 7413-7417), DOGS or Transfectain™ (Behr, et al., 1989, Proc. Natl. Acad. Sci. USA 86: 6982-6986), DNERIE or DORIE (Feigner, et al., Methods 5: 67-75), DC-CHOL (Gao and Huang, 1991, BBRC 179: 280-285), DOTAP™ (McLachlan, et al., 1995, Gene Therapy 2: 674-622), Lipofectamine™. and glycerolipid compounds (see, e.g., EP901463 and WO98/37916).

The nanoparticle may be an immune-stimulating complex (ISCOM). ISCOMs are cage-like particles which are typically formed from colloidal saponin-containing micelles. ISCOMs may comprise cholesterol, phospholipid (such as phosphatidylethanolamine or phosphatidylcholine) and saponin (such as Quil A from the tree *Quillaia saponaria*).

The nanoparticle may be a virus-like particle (VLP). VLPs are self-assembling nanoparticles that lack infectious nucleic acid, which are formed by self-assembly of biocompatible capsid protein. VLPs are typically about 20 to about 150 nm, such as about 20 to about 40 nm, about 30 to about 140 nm, about 40 to about 130 nm, about 50 to about 120 nm, about 60 to about 110 nm, about 70 to about 100 nm, or about 80 to about 90 nm in diameter. VLPs advantageously harness the power of evolved viral structure, which is naturally optimized for interaction with the immune system. The naturally-optimized nanoparticle size and repetitive structural order means that VLPs induce potent immune responses, even in the absence of adjuvant.

The nanoparticles may contain replicons that encode the polypeptides or the heterologous polypeptides of the disclosure. The replicons may be DNA or RNA.

"Replicon" refers to a viral nucleic acid that is capable of directing the generation of copies of itself and includes RNA as well as DNA. For example, double-stranded DNA versions of arterivirus genomes can be used to generate a single-stranded RNA transcript that constitutes an arterivirus replicon. Generally, a viral replicon contains the complete genome of the virus. "Sub-genomic replicon" refers to a viral nucleic acid that contains something less than the full complement of genes and other features of the viral genome, yet is still capable of directing the generation of copies of itself. For example, the sub-genomic replicons of arterivirus may contain most of the genes for the non-structural proteins of the virus, but are missing most of the genes coding for the structural proteins. Sub-genomic replicons are capable of directing the expression of all of the viral genes necessary for the replication of the viral sub-genome (replication of the sub-genomic replicon), without the production of viral particles.

"RNA replicon" (or "self-replication RNA") refer to RNA which contains all of the genetic information required for directing its own amplification or self-replication within a permissive cell. To direct its own replication, the RNA molecule 1) encodes polymerase, replicase, or other proteins which may interact with viral or host cell-derived proteins, nucleic acids or ribonucleoproteins to catalyze the RNA amplification process; and 2) contain cis-acting RNA sequences required for replication and transcription of the replicon-encoded RNA. Self-replicating RNA is typically derived from the genomes of positive strand RNA viruses and can be used as basis of introducing foreign sequences to host cells by replacing viral sequences encoding structural or non-structural genes or inserting the foreign sequences 5' or 3' of the sequences encoding the structural or non-structural genes. Foreign sequences may also be introduced into the subgenomic regions of alphaviruses. Self-replicating RNA may be packaged into recombinant virus particles, such as recombinant alphavirus particles or alternatively delivered to the host using lipid nanoparticles (LNP). Self-replicating RNA may be at least 1 kb or at least 2 kb or at least 3 kb or at least 4 kb or at least 5 kb or at least 6 kb or at least 7 kb or at least 8 kb or at least 10 kb or at least 12 kb or at least 15 kb or at least 17 kb or at least 19 kb or at least 20 kb in size, or can be 100 bp-8 kb or 500 bp-8 kb or 500 bp-7 kb or 1-7 kb or 1-8 kb or 2-15 kb or 2-20 kb or 5-15 kb or 5-20 kb or 7-15 kb or 7-18 kb or 7-20 kb in size. Self-replicating RNAs are described, for example, in WO2017/180770, WO2018/075235, WO2019143949A2, Other molecules suitable for complexing with the polynucleotides, the heterologous polynucleotides, the polypeptides and the heterologous polypeptides of the disclosure include cationic molecules, such as, polyamidoamine (Haensler and Szoka, 1993, Bioconjugate Chem. 4: 372-379), dendritic polylysine (Int. Pat. Publ. No. WO1995/24221), polyethylene irinine or polypropylene h-nine (Int. Pat. Publ. No. WO1996/02655), polylysine (U.S. Pat. No. 5,595,897), chitosan (U.S. Pat. No. 5,744,166), DNA-gelatin coarcervates (see, e.g., U.S. Pat. Nos. 6,207,195; 6,025,337; 5,972,707) or DEAE dextran (Lopata, et al., 1984, Nucleic Acid Res. 12: 5707-5717), dendrimers (see, e.g., WO1996/19240), or polyethylenimine (PEI) (see, e.g., Sun et al., 2014, Mol Med Rep. 10(5):2657-2662).

Prostate Neoantigen/HLA Complexes

The disclosure also provides a protein complex comprising a prostate neoantigen and HLA. The disclosure also provides a protein complex comprising a fragment of the prostate neoantigen and HLA. The disclosure also provides a protein complex comprising a variant of the prostate neoantigen and HLA. The disclosure also provides a protein complex comprising a variant of a fragment of the prostate neoantigen and HLA.

In some embodiments, the prostate neoantigen comprises the polypeptide of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447.

In some embodiments, the fragment of the prostate neoantigen comprises an amino acid sequences of SEQ ID NOs: 387, 388, 389, 390, 391, 392, 393, 394, 395, 396, 397, 398, 399, 400, 401, 402, 403, 404, 405, 406, 407, 408, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620 and 621.

In some embodiments, the fragment of the prostate neoantigen comprises an amino acid sequence of SEQ ID NOs: 377, 378, 415, 417, 418, 420, 502, 518, 526, 527, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 74, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 487, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931,932, 933, 934, 935,936, 937, 938, 939, 940, 941,942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980 or 548.

In some embodiments, HLA is class I HLA. In some embodiments, HLA is class II HLA. In some embodiments, HLA is HLA-A. In some embodiments, HLA is HLA-B. In some embodiments, HLA is HLA-C. In some embodiments, HLA is HLA-DP. In some embodiments, HLA is HLA-DQ. In some embodiments, HLA is HLA-DR. In some embodiments, HLA is HLA-A*01:01, A*02:01, A*03:01, A*24:02, B*07:02 or B*08:01.

The complex of the prostate neoantigen and HLA may be used to for example isolate cognate T cells in vitro or in vivo. The complex of the prostate neoantigen and HLA may also be conjugated to a detectable label and used as a detection agent to detect, visualize or isolate cognate TCR or T cells expressing the cognate TCR. The complex of the prostate neoantigen and HLA may also be conjugated to a cytotoxic agent and used to deplete or reduce the number of cells expressing the cognate TCR. The complex may be in its native configuration or alternatively the prostate neoantigen and/or the HLA may be engineered.

Engineering concepts include covalent coupling of the peptide to the HLA, for example by using covalent linkers that may be cleavable. The prostate neoantigen and HLA complex may be a monomer or a multimer. The prostate neoantigen and HLA complex may be coupled to a toxin or a detection agent. Various engineering concepts include expressing the complex as a covalent prostate neoantigen-$\beta$2-$\alpha$2-$\alpha$1-$\mu$1 chain or prostate neoantigen-f chain, e.g. as a soluble complex. Linkers which are at least 15 amino acids long may be used between the prostate neoantigen and the HLA. Alternatively, the complex may be expressed as covalently coupled prostate neoantigen-single chain $\beta$1-$\alpha$1. The prostate neoantigen/HLA complex may also be expressed as a full length HLAP chains to which the prostate neoantigen is covalently coupled to the N-terminus of the $\alpha$ chain or alternatively the prostate neoantigen is associated with the $\alpha\beta$ chain via non-covalent interactions. Various expression formats are disclosed in U.S. Pat. Nos. 5,976, 551, 5,734,023, 5,820,866, 7,141,656B2, U.S. Pat. No. 6,270,772B1 and U.S. Pat. No. 7,074,905B2. Additionally the HLA may be expressed as a single chain construct which is mutated at a1 chain or stabilized via disulfide bonds via a2 and P2 domains as described in U.S. Pat. No. 8,377,447B2 and U.S. Pat. No. 8,828,379B2. The prostate neoantigen or fragment thereof may be coupled to the HLA via light sensitive or periodate sensitive cleavable linkers as described in U.S. Pat. No. 9,079,941B2. The prostate neoantigen/HLA complexes may be engineered into multimeric format. Multimeric formats may be generated by incorporating a reactive side chain to the C-terminus of the HLA a or P3 chain to facilitate cross-linking of two or more prostate neoantigen/HLA complexes, as described in U.S. Pat. No. 7,074,904B2. Alternatively, a biotinylation recognition sequence BirA may be incorporated to the C-terminus of the HLA a or P3 chain which is subsequently biotinylated and the multimer is formed by binding to avidin/streptavidin as described in US563536. Multimeric prostate neoantigen/HLA complexes may further be generated utilizing Fc fusions, coupling the prostate neoantigen/HLA complexes in dextran carriers, oligomerizing the via coiled-coil domains, utilizing additional biotinylation peptides or conjugating the prostate neoantigen/HLA complexes onto nanoparticles or chelate carrier as is described in U.S. Pat. No. 6,197,302B1, U.S. Pat. No. 6,268,411B1, US20150329617A1, EP1670823B1, EP1882700B1, EP2061807B1, US20120093934A1, US20130289253A1, US20170095544A1, US20170003288A1 and WO2017015064A1.

Proteinaceous Molecules that Bind the Prostate Neoantigens or Prostate Neoantigen/HLA Complexes The disclosure also provides a proteinaceous molecule comprising an antigen binding domain that specifically binds the polypeptide of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragment thereof. The proteinaceous molecule has insubstantial binding to a wild-type protein the neoantigen is derived from.

The disclosure also provides a proteinaceous molecule comprising an antigen binding domain that specifically binds a prostate neoantigen/HLA complex, wherein the prostate neoantigen comprises a polypeptide of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

Exemplary fragments comprise amino acid sequences of SEQ ID NOs: 387, 388, 389, 390, 391, 392, 393, 394, 395, 396, 397, 398, 399, 400, 401, 402, 403, 404, 405, 406, 407, 408, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620 or 621.

Other exemplary fragments comprise amino acid sequences of SEQ ID NOs: 377, 378, 415, 417, 418, 420, 502, 518, 526, 527, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 74, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 487, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980 or 548.

HLA may comprise class I or class II.

HLA may comprise HLA-A, HLA-B or HLA-C.

HLA may comprise HLA-DP, HLA-DQ or HLA-DR.

HLA may comprise class I alleles HLA-A*01:01, A*02:01, A*03:01, A*24:02, B*07:02 or B*08:01.

In some embodiments, the proteinaceous molecule is an antigen binding fragment of an antibody.

In some embodiments, the proteinaceous molecule is a multispecific molecule. In some embodiments, the proteinaceous molecule is a bispecific molecule. In some embodiments, the proteinaceous molecule is a trispecific molecule. In some embodiments, the multispecific molecule binds two or more distinct prostate neoantigens. In some embodiments, the multispecific molecule binds a prostate neoantigen and a T cell receptor (TCR) complex. In some embodiments, the multispecific molecule binds two or more distinct prostate neoantigens and a T cell receptor (TCR) complex.

In some embodiments, the proteinaceous molecule is an antibody.

In some embodiments, the proteinaceous molecule is a multispecific antibody. In some embodiments, the proteinaceous molecule is a bispecific antibody. In some embodiments, the proteinaceous molecule is a trispecific antibody. In some embodiments, the proteinaceous molecule is a T cell redirecting molecule.

In instances where the prostate neoantigen of the disclosure is part of an extracellular domain of a protein, the prostate neoantigen may be used as a tumor associated antigen for recruiting T cells to tumors or targeting CAR-T and other cellular therapies to tumor utilizing antigen binding domains that selectively bind the prostate neoantigen on tumor cells.

In instances in which the prostate neoantigen is part of an intracellular domain, antigen binding domains having the ability to be delivered into intracellular compartments conjugated to cytotoxic agent or a therapeutic agent may be used as therapeutics. Alternatively, cells engineered to express cognate TCR which bind the prostate neoantigen/HLA complex may be used as therapeutics.

In some embodiments, the proteinaceous molecule is an alternative scaffold.

In some embodiments, the proteinaceous molecule is a chimeric antigen receptor (CAR).

In some embodiments, the proteinaceous molecule is a T cell receptor (TCR).

Binding of the proteinaceous molecule to the prostate neoantigen or the prostate neoantigen/HLA complex of the disclosure may be determined experimentally using any suitable method. Such methods may utilize ProteOn XPR36, Biacore 3000 or KinExA instrumentation, ELISA or competitive binding assays known to those skilled in the art. The measured binding may vary if measured under different conditions (e.g., osmolarity, pH). Thus, measurements of affinity and other binding parameters (e.g., $K_D$, $K_{on}$, $K_{off}$) are typically made with standardized conditions and a standardized buffer, such as the buffer described herein. Skilled in the art will appreciate that the internal error for affinity measurements for example using Biacore 3000 or ProteOn (measured as standard deviation, SD) may typically be within 5-33% for measurements within the typical limits of detection. "Insubstantial" refers to binding that is 100-fold less when compared to the measured binding of the proteinaceous molecule to the prostate neoantigen of the disclosure. The proteinaceous molecule of the disclosure may further be characterized for their activity and function using know methods and those described herein, such as ability of the proteinaceous molecules to kill cells expressing the prostate neoantigens or prostate neoantigen/HLA complexes.

Antibodies and Antigen Binding Domains

Antibodies and antigen binding domains that specifically bind the prostate neoantigens or the prostate neoantigen/HLA complexes may be generated using known methods. Such antibodies may include immunoglobulin molecules of any type (e.g., IgG, IgE, IgM, IgD, IgA and IgY), class (e.g., IgG1, IgG2, IgG3, IgG4, IgA1, and IgA2) or subclass.

For example, the hybridoma method of Kohler and Milstein, *Nature* 256:495, 1975 may be used to generate monoclonal antibodies. In the hybridoma method, a mouse or other host animal, such as a hamster, rat or monkey, is immunized with one or more prostate neoantigens, or prostate neoantigen/HLA complexes followed by fusion of spleen cells from immunized animals with myeloma cells using standard methods to form hybridoma cells (Goding, Monoclonal Antibodies: Principles and Practice, pp. 59-103 (Academic Press, 1986)). Colonies arising from single immortalized hybridoma cells are screened for production of antibodies with desired properties, such as specificity of binding and affinity for the prostate neoantigen of the disclosure.

Various host animals may be used to produce the antibodies. For example, Balb/c mice, rats or chickens may be used to generate antibodies containing the VH/VL pair, and llama and alpaca may be used to generated heavy chain only (VHH) antibodies using standard immunization protocols. The antibodies made in non-human animals may be humanized using various technologies to generate more human-like sequences.

Exemplary humanization techniques including selection of human acceptor frameworks are known and include CDR grafting (U.S. Pat. No. 5,225,539), SDR grafting (U.S. Pat. No. 6,818,749), resurfacing (Padlan, (1991) *Mol Immunol* 28:489-499), Specificity Determining Residues Resurfacing (U.S. Patent Publ. No. 2010/0261620), human framework adaptation (U.S. Pat. No. 8,748,356) and superhumanization (U.S. Pat. No. 7,709,226). In these methods, CDRs of parental antibodies are transferred onto human frameworks that may be selected based on their overall homology to the parental frameworks, based on similarity in CDR length, or canonical structure identity, or any combination thereof.

Humanized antibodies may be further optimized to improve their selectivity or affinity to a desired antigen by incorporating altered framework support residues to preserve binding affinity (backmutations) by techniques such as those described in Int. Patent Publ. Nos. WO1090/007861 and WO1992/22653, or by introducing variation at any of the CDRs for example to improve affinity of the antibody.

Transgenic animals, such as mice or rats carrying human immunoglobulin (Ig) loci in their genome may be used to generate human antibodies against the prostate neoantigens or the prostate neoantigen/HLA complexes, and are described in for example U.S. Pat. No. 6,150,584, Int. Patent Publ. No. WO99/45962, Int. Patent Publ. Nos. WO2002/066630, WO2002/43478, WO2002/043478 and WO1990/04036, Lonberg et al (1994) *Nature* 368:856-9; Green et al (1994) *Nature Genet.* 7:13-21; Green & Jakobovits (1998) *Exp. Med.* 188:483-95; Lonberg and Huszar (1995) *Int Rev Immunol* 13:65-93; Bruggemann et al., (1991) *Eur J Immunol* 21:1323-1326; Fishwild et al., (1996) *Nat Biotechnol* 14:845-851; Mendez et al., (1997) *Nat Genet* 15:146-156; Green (1999) *J Immunol Methods* 231:11-23; Yang et al., (1999) *Cancer Res* 59:1236-1243; Brüggemann and Taussig (1997) *Curr Opin Biotechnol* 8:455-458. The endogenous immunoglobulin loci in such animal may be disrupted or deleted, and at least one complete or partial human immunoglobulin locus may be inserted into the genome of the animal using homologous or non-homologous recombination, using transchromosomes, or using minigenes. Companies such as Regeneron (http://_www_regeneron_com), Harbour Antibodies (http://_www_harbourantibodies_com), Open Monoclonal Technology, Inc. (OMT) (http://_www_omtinc_net), KyMab (http://_www_kymab_com), Trianni (http://_www.trianni_com) and Ablexis (http://_www_ablexis_com) may be engaged to provide human antibodies directed against a selected antigen using technologies as described above.

Human antibodies may be selected from a phage display library, where the phage is engineered to express human immunoglobulins or portions thereof such as Fabs, single chain antibodies (scFv), domain antibodies or unpaired or paired antibody variable regions (Knappik et al., (2000) *J Mol Biol* 296:57-86; Krebs et al., (2001) *J Immunol Meth* 254:67-84; Vaughan et al., (1996) *Nature Biotechnology*

14:309-314; Sheets et al., (1998) *PITAS* (*USA*) 95:6157-6162; Hoogenboom and Winter (1991) *J Mol Biol* 227:381; Marks et al., (1991) *J Mol Biol* 222:581). The antibodies of the disclosure may be isolated for example from phage display library expressing antibody heavy and light chain variable regions as heterologous polypeptides with bacteriophage pIX coat protein as described in Shi et al., (2010) *J Mol Biol* 397:385-96, and Int. Patent Publ. No. WO09/085462). The libraries may be screened for phage binding to the prostate neoantigen or the prostate neoantigen/HLA complex and the obtained positive clones may be further characterized, the Fabs isolated from the clone lysates, and expressed as full length IgGs. Such phage display methods for isolating human antibodies are described in for example: U.S. Pat. Nos. 5,223,409, 5,403,484, 5,571,698, 5,427,908, 5,580,717, 5,969,108, 6,172,197, 5,885,793; 6,521,404; 6,544,731; 6,555,313; 6,582,915 and 6,593,081. The antibodies may further be tested for their binding to the HLA/neoantigen complex or to the neoantigen alone.

Preparation of immunogenic antigens and monoclonal antibody production may be performed using any suitable technique, such as recombinant protein production or by chemical synthesis of peptides. The immunogenic antigens may be administered to an animal in the form of purified protein, or protein mixtures including whole cells or cell or tissue extracts, or the antigen may be formed de novo in the animal's body from nucleic acids encoding said antigen or a portion thereof.

Antigen binding domains that specifically bind the prostate neoantigen or prostate neoantigen/HLA complexes may also be derived from the antibodies described herein. Antigen binding domains include single chain antibodies, Fab fragments, Fv fragments, single-chain Fv fragments (scFv), VHH domains, VH, VL, alternative scaffolds (e.g. non-antibody antigen binding domains), a divalent antibody fragment such as an (Fab)2'-fragment, F(ab') fragments, disulfide-linked Fvs (sdFv), intrabodies, minibodies, diabodies, triabodies and decabodies.

Bispecific and multispecific antibodies that specifically bind the prostate neoantigen or prostate neoantigen/HLA complexes and a second antigen may be generated using known methods. The second antigen may be a T cell receptor complex (TCR complex). The second antigen may be CD3 within the TCR complex. The bispecific and multispecific antibodies that specifically bind the prostate neoantigen or prostate neoantigen/HLA complexes of the disclosure and the second antigen may be engineered into any multivalent format using any known antigen binding domains format that specifically bind the prostate neoantigens or prostate neoantigen/HLA complexes and the second antigen. The antigen binding domain that specifically bind the prostate neoantigen or prostate neoantigen/HLA complex may be conjugated to one or more Fc domains or fragment thereof, or optionally to other scaffolds such as half-life extending moieties including albumin, PEG or transferrin.

Multispecific antibodies that specifically bind two or more prostate neoantigens may provide a benefit in terms of improved specificity in targeting tumor cells expressing the prostate neoantigens.

The antigen binding domains that specifically bind the prostate neoantigen or prostate neoantigen/HLA complexes may be engineered into full length multispecific antibodies which are generated using Fab arm exchange, in which substitutions are introduced into two monospecific bivalent antibodies within the Ig constant region CH3 domain which promote Fab arm exchange in vitro. In the methods, two monospecific bivalent antibodies are engineered to have certain substitutions at the CH3 domain that promote heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl)phosphine (TCEP), L-cysteine and beta-mercaptoethanol, preferably a reducing agent selected from the group consisting of: 2-mercaptoethylamine, dithiothreitol and tris(2-carboxyethyl)phosphine. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

CH3 mutations that may be used include technologies such as Knob-in-Hole mutations (Genentech), electrostatically-matched mutations (Chugai, Amgen, NovoNordisk, Oncomed), the Strand Exchange Engineered Domain body (SEEDbody) (EMD Serono), Duobody® mutations (Genmab), and other asymmetric mutations (e.g. Zymeworks).

Knob-in-hole mutations are disclosed for example in WO1996/027011 and include mutations on the interface of CH3 region in which an amino acid with a small side chain (hole) is introduced into the first CH3 region and an amino acid with a large side chain (knob) is introduced into the second CH3 region, resulting in preferential interaction between the first CH3 region and the second CH3 region. Exemplary CH3 region mutations forming a knob and a hole are T366Y/F405A, T366W/F405W, F405W/Y407A, T394W/Y407T, T394S/Y407A, T366W/T394S, F405W/T394S and T366W/T366S_L368A_Y407V.

Heavy chain heterodimer formation may be promoted by using electrostatic interactions by substituting positively charged residues on the first CH3 region and negatively charged residues on the second CH3 region as described in US2010/0015133, US2009/0182127, US2010/028637 or US2011/0123532.

Other asymmetric mutations that can be used to promote heavy chain heterodimerization are L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F, or T350V_L351Y_F405A_Y407V/T350V_T366L_K392L_T394W as described in US2012/0149876 or US2013/0195849 (Zymeworks).

SEEDbody mutations involve substituting select IgG residues with IgA residues to promote heavy chai heterodimerization as described in US20070287170.

Other exemplary mutations that may be used are R409D_K370E/D399K_E357K, S354C_T366W/Y349C_T366S_L368A_Y407V, Y349C_T366W/S354C_T366S_L368A_Y407V, T366K/L351D, L351K/Y349E, L351K/Y349D, L351K/L368E, L351Y_Y407A/T366A_K409F, L351Y_Y407A/T366V_K409F, K392D/D399K, K392D/E356K, K253E_D282K_K322D/D239K_E240K_K292D, K392D_K409D/D356K D399K as described in WO2007/147901, WO 2011/143545, WO2013157954, WO2013096291 and US2018/0118849.

Duobody® mutations (Genmab) are disclosed for example in U.S. Pat. No. 9,150,663 and US2014/0303356 and include mutations F405L/K409R, wild-type/F405L_R409K, T350I_K370T_F405L/K409R, K370W/

K409R, D399AFGHILMNRSTVWY/K409R, T366ADEFGHILMQVY/K409R, L368ADEGHNRSTVQ/K409AGRH, D399FHKRQ/K409AGRH, F405IKLSTVW/K409AGRH and Y407LWQ/K409AGRH.

Additional bispecific or multispecific structures into which the antigen binding domains that specifically bind the prostate neoantigen or prostate neoantigen/HLA complexes can be incorporated include Dual Variable Domain Immunoglobulins (DVD) (Int. Pat. Publ. No. WO2009/134776; DVDs are full length antibodies comprising the heavy chain having a structure VH1-linker-VH2-CH and the light chain having the structure VL1-linker-VL2-CL; linker being optional), structures that include various dimerization domains to connect the two antibody arms with different specificity, such as leucine zipper or collagen dimerization domains (Int. Pat. Publ. No. WO2012/022811, U.S. Pat. Nos. 5,932,448; 6,833,441), two or more domain antibodies (dAbs) conjugated together, diabodies, heavy chain only antibodies such as camelid antibodies and engineered camelid antibodies, Dual Targeting (DT)-Ig (GSK/Domantis), Two-in-one Antibody (Genentech), Cross-linked Mabs (Karmanos Cancer Center), mAb2 (F-Star) and CovX-body (CovX/Pfizer), IgG-like Bispecific (InnClone/Eli Lilly), Ts2Ab (Medlmmune/AZ) and BsAb (Zymogenetics), HERCULES (Biogen Idec) and TvAb (Roche), ScFv/Fc Fusions (Academic Institution), SCORPION (Emergent BioSolutions/Trubion, Zymogenetics/BMS), Dual Affinity Retargeting Technology (Fc-DART) (MacroGenics) and Dual(ScFv)$_2$-Fab (National Research Center for Antibody Medicine—China), Dual-Action or Bis-Fab (Genentech), Dock-and-Lock (DNL) (ImmunoMedics), Bivalent Bispecific (Biotecnol) and Fab-Fv (UCB-Celltech). ScFv-, diabody-based, and domain antibodies, include but are not limited to, Bispecific T Cell Engager (BiTE) (Micromet), Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies.

Alternative Scaffolds

Alternative scaffolds (also referred to as antibody mimetics) that specifically bind the prostate neoantigen or prostate neoantigen/HLA complexes may be generated using various scaffolds known in the art and described herein. Alternative scaffolds may be monobodies, designed to incorporate the fibronectin type III domain (Fn3) of fibronectin or tenascin as a protein scaffold (U.S. Pat. Nos. 6,673,901; 6,348,584) or synthetic FN3 domains such as tencon as described in U.S. Pat. Publ. No. 2010/0216708 and U.S. Pat. Pub. No. 2010/0255056. Additional alternative scaffolds comprise Adnectin™, an iMab, an Anticalin®, an EETI-II/AGRP, a Kunitz domain, a thioredoxin peptide aptamer, an Affibody®, a DARPin, an Affilin, a Tetranectin, a Fynomer, and an Avimer. Alternative scaffolds are single chain polypeptidic frameworks that contains a highly structured core associated with variable domains of high conformational tolerance allowing insertions, deletions, or other substitutions within the variable domains. Libraries introducing diversity to one or more variable domains, and in some instances to the structured core, may be generated using known protocols and the resulting libraries may be screened for binding to the neoantigen of the disclosure, and the identified binders may be further characterized for their specificity using known methods. Alternative scaffold may be derived from Protein A, in particular, the Z-domain thereof (affibodies), ImmE7 (immunity proteins), BPTI/APPI (Kunitz domains), Ras-binding protein AF-6 (PDZ-domains), charybdotoxin (Scorpion toxin), CTLA-4, Min-23 (knottins), lipocalins (anticalins), neokarzinostatin, a fibronectin domain, an ankyrin consensus repeat domain, or thioredoxin (Skerra, A., "Alternative Non-Antibody Scaffolds for Molecular Recognition," *Curr. Opin. Biotechnol.* 18:295-304 (2005); Hosse et al., "A New Generation of Protein Display Scaffolds for Molecular Recognition," Protein Sci. 15:14-27 (2006); Nicaise et al., "Affinity Transfer by CDR Grafting on a Nonimmunoglobulin Scaffold," Protein Sci. 13:1882-1891 (2004); Nygren and Uhlen, "Scaffolds for Engineering Novel Binding Sites in Proteins," *Curr. Opin. Struc. Biol.* 7:463-469 (1997).

Chimeric Antigen Receptors (CAR)

CARs may be generated that bind the prostate neoantigens or the prostate neoantigen/HLA complex by incorporating an antigen binding domain that specifically binds the prostate neoantigens or the prostate neoantigen/HLA complex to the extracellular domain of the CAR. CARs are genetically engineered receptors. These engineered receptors can be readily inserted into and expressed by immune cells, including T cells in accordance with techniques known in the art. With a CAR, a single receptor can be programmed to both recognize a specific antigen and, when bound to that antigen, activate the immune cell to attack and destroy the cell bearing that antigen. When these antigens exist on tumor cells, an immune cell that expresses the CAR can target and kill the tumor cell.

The CAR typically comprises an extracellular domain that binds the antigen (e.g. the prostate neoantigen or the prostate neoantigen/HLA complex), an optional linker, a transmembrane domain, and a cytosolic domain comprising a costimulatory domain and/or a signaling domain.

The extracellular domain of the CAR may contain any polypeptide that specifically binds the desired antigen (e.g. prostate neoantigen). The extracellular domain may comprise a scFv, a portion of an antibody or an alternative scaffold. The CARs may also be engineered to bind two or more desired antigens that may be arranged in tandem and separated by linker sequences. For example, one or more domain antibodies, scFvs, llama VHH antibodies or other VH only antibody fragments may be organized in tandem via a linker to provide bispecificity or multispecificity to the CAR.

The transmembrane domain of the CAR may be derived from the transmembrane domain of CD8, an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CDI la, CD18), ICOS (CD278), 4-1 BB (CD137), 4-1 BBL, GITR, CD40, BAFFR, HVEM (LIGHTR), SLAMF7, NKp80 (KLRFI), CD160, CD19, IL2R beta, IL2R gamma, IL7R a, ITGA1, VLA1, CD49a, ITGA4, IA4, CD49D, ITGA6, VLA-6, CD49f, ITGAD, CDI Id, ITGAE, CD103, ITGAL, CDI la, LFA-1, ITGAM, CDI lb, ITGAX, CDI lc, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), SLAMF6 (NTB-A, Lyl08), SLAM (SLAMF1, CD150, IPO-3), BLAME (SLAMF8), SELPLG (CD162), LTBR, PAG/Cbp, NKp44, NKp30, NKp46, NKG2D, and/or NKG2C.

The intracellular costimulatory domain of CAR may be derived from the intracellular domains of one or more co-stimulatory molecules. Co-stimulatory molecules are well-known cell surface molecules other than antigen receptors or Fc receptors that provide a second signal required for efficient activation and function of T lymphocytes upon binding to antigen. Exemplary co-stimulatory domains that can be used in CARs are intracellular domains of 4-1BB, CD2, CD7, CD27, CD28, CD30, CD40, CD54 (ICAM), CD83, CD134 (OX40), CD150 (SLAMF1), CD152 (CTLA4), CD223 (LAG3), CD270 (HVEM), CD278 (ICOS), DAP10, LAT, NKD2C SLP76, TRIM, BTLA, GITR, CD226, HVEM, and ZAP70.

The intracellular signaling domain of the CAR may be derived from the signaling domains of for example CD3, CD3s, CD22, CD79a, CD66d, CD39 DAP10, DAP12, Fc epsilon receptor I gamma chain (FCER1G), FcR f3, CD36, CD3γ, CD5, CD226, or CD79B. "Intracellular signaling domain" refers to the part of the CAR polypeptide that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited following antigen binding to the extracellular CAR domain.

The optional linker of the CAR positioned between the extracellular domain and the transmembrane domain may be a polypeptide of about 2 to 100 amino acids in length. The linker may include or be composed of flexible residues such as glycine and serine so that the adjacent protein domains are free to move relative to one another. Longer linkers may be used when it is desirable to ensure that two adjacent domains do not sterically interfere with one another. Linkers may be cleavable or non-cleavable. Examples of cleavable linkers include 2A linkers (for example T2A), 2A-like linkers or functional equivalents thereof and combinations thereof. The linker may also be derived from a hinge region or portion of the hinge region of any immunoglobulin. Non-limiting examples of linkers include a part of human CD8a chain, partial extracellular domain of CD28, FcyRIIIa receptor, IgG, IgM, IgA, IgD, IgE, an Ig hinge, or functional fragment thereof.

Exemplary CARs that may be used are for example CAR that contains an extracellular domain that binds the prostate neoantigen of the disclosure, CD8 transmembrane domain and CD3ζ signaling domain. Other exemplary CARs contain an extracellular domain that binds the prostate neoantigen of the disclosure, CD8 or CD28 transmembrane domain, CD28, 41BB or OX40 costimulatory domain and CD3ζ signaling domain.

The CARs are generated by standard molecular biology techniques. The extracellular domain that binds the desired antigen may be derived from antibodies or their antigen binding fragments generated using the technologies described herein.

T cell receptor (TCR)

TCRs may be generated that bind the prostate neoantigen/HLA complexes. The TCRs may be identified based on T cell binding to the prostate neoantigen/HLA complex, isolating the T cell and sequencing the TCR expressed in the T cells. The identified TCRs may be identified from αβ T cells or γδ T cells. The identified TCRs may be further engineered to improve their affinity, stability, solubility or the like. TCRs may be affinity matured utilizing the same technologies utilized to affinity mature immunoglobulins. TCRs may be expressed as soluble TCRs which have been cysteine stabilized, they can be stabilized by engineering mutations onto α/β interaction surface, for example G192R on α chain and R208G on P3 chain. TCRs may also be stabilized by engineering cysteine residues which form disulfide bonds into TCR constant domain, by introducing mutations into the hydrophobic core, such as at positions 11, 13, 19, 21, 53, 76, 89, 91 or 94 of α chain, utilizing domain swaps including swaps between a and P3 chain V domains, transmembrane domains or constant domains as described in U.S. Pat. Nos. 7,329,731, 7,871,817B2, 7,569,664, 9,133,264, 9,624,292, US20120252742A1, US2016/0130319, EP3215164A1, EP3286210A1, WO2017091905A1 or U.S. Pat. No. 9,884,075.

Cells Expressing the CARs or the TCRs of the Disclosure

Cells expressing the CARs or the TCRs that specifically bind the prostate neoantigens of the disclosure of the prostate neoantigen/HLA complexes of the disclosure are within the scope of the disclosure. The disclosure also provides isolated cells comprising the CAR of the disclosure or the TCR of the disclosure. In some embodiments, the isolated cells are transduced with the CAR or the TCR of the disclosure, resulting in constitutive expression of the CAR or the TCR of the disclosure on the surface of the cell. The cells expressing the CAR or the TCR of the disclosure may further be engineered to express one or more co-stimulatory molecules. Exemplary co-stimulatory molecules are CD28, ICOS, LIGHT, GITR, 4-1BB and OX40. The cells expressing the CAR or the TCR of the disclosure may further be engineered to produce one or more cytokines or chemokines or proinflammatory mediators, such as TNFα, IFNγ, IL-2, IL-3, IL-6, IL-7, IL-11, IL-12, IL-15, IL-17 or IL-21. The cells may have their endogenous TCR locus and/or HLA locus inactivated using known gene editing technologies. In some embodiment, the cell comprising the CAR or the TCR of the disclosure is a T cell, a natural killer (NK) cell, a cytotoxic T lymphocyte (CTL), a regulatory T cell (Treg), a human embryonic stem cell, a lymphoid progenitor cell, a T cell-precursor cell, a pluripotent stem cell or induced pluripotent stem cell (iPSC) from which lymphoid cells may be differentiated.

In some embodiments, the isolated cell comprising the CAR or the TCR of the disclosure is a T cell. The T cell may be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from any source, including to bone marrow, blood, lymph node, thymus, or other tissues or fluids. T cells may also be enriched for or purified. The T cell may be a human T cell. The T cell may be a T cell isolated from a human. The T cell can be any type of T cell and may be of any developmental stage, including, $CD4^+$ $CD8^+$ double positive T cells, $CD8^+$ T cells (e.g., cytotoxic T cells), $CD4^+$ helper T cells, e.g., Th1 and Th2 cells, peripheral blood mononuclear cells (PBMCs), peripheral blood leukocytes (PBLs), tumor infiltrating cells, memory T cells, naïve T cells, and the like. The T cell may be a $CD8^+$ T cell or a $CD4^+$ T cell. The T cell may be an αβ T cell or a γδ T cell.

In some embodiments, the isolated cell comprising the CAR of the disclosure or the TCR of the disclosure is a NK cell.

In some embodiments, the isolated cell comprising the CAR of the disclosure or the TCR of the disclosure is a αβ T cell.

In some embodiments, the isolated cell comprising the CAR of the disclosure or the TCR of the disclosure is a γδ T cell.

In some embodiments, the isolated cell comprising the CAR of the disclosure or the TCR of the disclosure is a $CD8^+$ cytotoxic T lymphocyte In some embodiments, the isolated cell comprising the CAR of the disclosure or the TCR of the disclosure is a human embryonic stem cell.

In some embodiments, the isolated cell comprising the CAR of the disclosure or the TCR of the disclosure is a lymphoid progenitor cell.

In some embodiments, the isolated cell comprising the CAR of the disclosure or the TCR of the disclosure is a pluripotent stem cell.

In some embodiments, the isolated cell comprising the CAR of the disclosure or the TCR of the disclosure is an induced pluripotent stem cell (iPSC).

The cells of the disclosure may be generated by introducing a lentiviral vector comprising a desired CAR or TCR into the cells using known methods. The cells of the disclosure are able to replicate in vivo resulting in long-term persistence that can lead to sustained tumor control.

Conjugates with cytotoxic agents, drugs, detectable labels, and the like

The polypeptides, the heterologous polypeptide and the proteinaceous molecules binding them may be conjugated to a cytotoxic agent, therapeutics, detectable labels and the like. These molecules are referred herein to immunoconjugates. The immunoconjugates comprising the prostate neoantigens may be used to detect, deliver payload or kill cells expressing a HLA molecule that binds the prostate neoantigen. The immunoconjugates comprising the antibodies, antigen binding fragments or alternative scaffolds which specifically bind the prostate neoantigen or the prostate neoantigen/HLA complex may be used to detect, deliver payload or kill cells that express the prostate neoantigen on their surface in the context or a larger protein or in complex with HLA, or detect intracellular prostate neoantigens after lysis of the cells.

In some embodiments, the immunoconjugate comprises a detectable label.

In some embodiments, the immunoconjugate comprises a cytotoxic agent.

In some embodiments, the immunoconjugate comprises a therapeutic.

Detectable labels include compositions that can be visualized via spectroscopic, photochemical, biochemical, immunochemical, or chemical means. Detectable labels may also include cytotoxic agents, an cytotoxic agents may include detectable labels.

Exemplary detectable labels include radioactive isotopes, magnetic beads, metallic beads, colloidal particles, fluorescent dyes, electron-dense reagents, enzymes (for example, as commonly used in an ELISA), biotin, digoxigenin, haptens, luminescent molecules, chemiluminescent molecules, fluorochromes, fluorophores, fluorescent quenching agents, colored molecules, radioactive isotopes, scintillates, avidin, streptavidin, protein A, protein G, antibodies or fragments thereof, polyhistidine, $Ni^{2+}$, Flag tags, myc tags, heavy metals, enzymes, alkaline phosphatase, peroxidase, luciferase, electron donors/acceptors, acridinium esters, and colorimetric substrates.

A detectable label may emit a signal spontaneously, such as when the detectable label is a radioactive isotope. In other cases, the detectable label emits a signal as a result of being stimulated by an external field.

Exemplary radioactive isotopes may be γ-emitting, Auger-emitting, a3-emitting, an alpha-emitting or positron-emitting radioactive isotope. Exemplary radioactive isotopes include $^{3}H$, $^{11}C$, $^{13}C$, $^{15}N$, $^{18}F$, $^{19}F$, $^{55}Co$, $^{57}Co$, $^{60}Co$, $^{61}Cu$, $^{62}Cu$ $^{64}Cu$, $^{67}Cu$, $^{68}Ga$, $^{72}As$, $^{75}Br$, $^{86}Y$, $^{89}Zr$, $^{90}Sr$, $^{94m}Tc$, $^{99m}Tc$, $^{115}In$, $^{123}I$, $^{124}I$, $^{125}I$, $^{131}I$, $^{211}At$, $^{212}Bi$, $^{213}Bi$, $^{223}Ra$, $^{226}Ra$, $^{225}Ac$ and $^{227}Ac$.

Exemplary metal atoms are metals with an atomic number greater than 20, such as calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, lead atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, neptunium atoms, plutonium atoms, americium atoms, curium atoms, berkelium atoms, californium atoms, einsteinium atoms, fermium atoms, mendelevium atoms, nobelium atoms, or lawrencium atoms.

In some embodiments, the metal atoms may be alkaline earth metals with an atomic number greater than twenty.

In some embodiments, the metal atoms may be lanthanides.

In some embodiments, the metal atoms may be actinides.

In some embodiments, the metal atoms may be transition metals.

In some embodiments, the metal atoms may be poor metals.

In some embodiments, the metal atoms may be gold atoms, bismuth atoms, tantalum atoms, and gadolinium atoms.

In some embodiments, the metal atoms may be metals with an atomic number of 53 (i.e. iodine) to 83 (i.e. bismuth).

In some embodiments, the metal atoms may be atoms suitable for magnetic resonance imaging.

The metal atoms may be metal ions in the form of +1, +2, or +3 oxidation states, such as $Ba^{2+}$, $Bi^{3+}$, $Cs^{+}$, $Ca^{2+}$, $Cr^{2+}$, $Cr^{3+}$, $Cr^{6+}$, $Co^{2+}$, $Co^{3+}$, $Cu^{+}$, $Cu^{2+}$, $Cu^{3+}$, $Ga^{3+}$, $Gd^{3+}$, $Au^{+}$, $Au^{3+}$, $Fe^{2+}$, $Fe^{3+}$, $F^{3+}$, $Pb^{2+}$, $Mn^{2+}$, $Mn^{3+}$, $Mn^{4+}$, $Mn^{7+}$, $Hg^{2+}$, $Ni^{2+}$, $Ni^{3+}$, $Ag^{+}$, $Sr^{2+}$, $Sn^{2+}$, $Sn^{4+}$, and $Zn^{2+}$. The metal atoms may comprise a metal oxide, such as iron oxide, manganese oxide, or gadolinium oxide.

Suitable dyes include any commercially available dyes such as, for example, 5(6)-carboxyfluorescein, IRDye 680RD maleimide or IRDye 800CW, ruthenium polypyridyl dyes, and the like.

Suitable fluorophores are fluorescein isothiocyanate (FITC), fluorescein thiosemicarbazide, rhodamine, Texas Red, CyDyes (e.g., Cy3, Cy5, Cy5.5), Alexa Fluors (e.g., Alexa488, Alexa555, Alexa594; Alexa647), near infrared (NIR) (700-900 nm) fluorescent dyes, and carbocyanine and aminostyryl dyes.

The immunoconjugates comprising a detectable label may be used as an imaging agent.

In some embodiments, the cytotoxic agent is a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

In some embodiments, the cytotoxic agent is daunomycin, doxorubicin, methotrexate, vindesine, bacterial toxins such as diphtheria toxin, ricin, geldanamycin, maytansinoids or calicheamicin. The cytotoxic agent may elicit their cytotoxic and cytostatic effects by mechanisms including tubulin binding, DNA binding, or topoisomerase inhibition.

In some embodiments, the cytotoxic agent is an enzymatically active toxin such as diphtheria A chain, nonbinding active fragments of diphtheria toxin, exotoxin A chain (from *Pseudomonas aeruginosa*), ricin A chain, abrin A chain, modeccin A chain, alpha-sarcin, Aleuritesfordii proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In some embodiments, the cytotoxic agent is a radionuclide, such as $^{212}$Bi, $^{131}$, $^{131}$In, $^{90}$Y, and $^{186}$Re.

In some embodiments, the cytotoxic agent is dolastatins or dolostatin peptidic analogs and derivatives, auristatin or monomethyl auristatin phenylalanine. Exemplary molecules are disclosed in U.S. Pat. Nos. 5,635,483 and 5,780,588. Dolastatins and auristatins have been shown to interfere with microtubule dynamics, GTP hydrolysis, and nuclear and cellular division (Woyke et al (2001) Antimicrob Agents and Chemother. 45(12):3580-3584) and have anticancer and antifungal activity. The dolastatin or auristatin drug moiety may be attached to the antibody of the invention through the N (amino) terminus or the C (carboxyl) terminus of the peptidic drug moiety (WO002/088172), or via any cysteine engineered into the antibody.

The immunoconjugates may be made using known methods.

In some embodiments, the detectable label is complexed with a chelating agent.

The detectable label, cytotoxic agent or therapeutic may be linked directly, or indirectly via a linker, to the polypeptides, the heterologous polypeptides or the proteinaceous molecules that bind the polypeptides or the heterologous polypeptides. Suitable linkers are known in the art and include, for example, prosthetic groups, non-phenolic linkers (derivatives of N-succimidyl-benzoates; dodecaborate), chelating moieties of both macrocyclics and acyclic chelators, such as derivatives of 1,4,7,10-tetraazacyclododecane-1,4,7,10,tetraacetic acid (DOTA), derivatives of diethylenetriaminepentaacetic avid (DTPA), derivatives of S-2-(4-Isothiocyanatobenzyl)-1,4,7-triazacyclononane-1,4,7-triacetic acid (NOTA) and derivatives of 1,4,8,11-tetraazacyclodocedan-1,4,8,11-tetraacetic acid (TETA), N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene) and other chelating moieties. Suitable peptide linkers are well known.

Methods of Treatment, Uses and Administration

The various molecules of the disclosure that can be used to introduce the prostate neoantigens of the disclosure into a subject, e.g. the polynucleotides, the heterologous polynucleotides, the polypeptides, the heterologous polypeptides, the vectors, the recombinant viruses and vaccines of the disclosure may be used to treat prostate cancer in a subject. The various molecules of the disclosure that may be used to introduce the prostate neoantigens of the disclosure into a subject, e.g. the polynucleotides, the heterologous polynucleotides, the polypeptides, the heterologous polypeptides, the vectors, the recombinant viruses and vaccines of the disclosure may also be used to prevent prostate cancer in a subject. The proteinaceous molecules that specifically bind the prostate neoantigens of the disclosure or the prostate neoantigen/HLA complexes of the disclosure can be used to treat or prevent prostate cancer in the subject.

The prostate cancer neoantigens identified herein are present at a frequency of at least about 1% or more, about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 16% or more about 17% or more, about 18% or more, about 19% or more, about 20% or more, about 21% or more, about 22% or more, about 23% or more, about 24% or more, about 25% or more, about 26% or more, about 27% or more, about 28% or more, about 29% or more, about 30% or more, about 35% or more, about 40% or more, about 45% or more, about 50% or more, about 55% or more, about 60% or more, about 65% or more or about 70% or more in a population of subjects having the prostate cancer.

The disclosure provides a method of treating or preventing a prostate cancer in a subject, comprising administering to the subject a therapeutically effective amount of one or more vaccines of the disclosure.

The disclosure also provides a method of treating or preventing a prostate cancer in a subject, comprising administering to the subject a therapeutically effective amount of one or more pharmaceutical compositions of the disclosure.

In some embodiments, the vaccine comprises the rAd26 of the disclosure.

In some embodiments, the vaccine comprises the rMVA of the disclosure.

In some embodiments, the vaccine comprises the rGAd of the disclosure.

In some embodiments, the vaccine comprises the rGAd20 of the disclosure.

In some embodiments, the vaccine comprises the rCh20 of the disclosure.

In some embodiments, the vaccine comprises the rAd26 of the disclosure and rMVA of the disclosure.

In some embodiments, the vaccine comprises the rGAd20 of the disclosure and rMVA of the disclosure.

In some embodiments, the vaccine comprises the heterologous polypeptide of the disclosure.

In some embodiments, the vaccine comprises the heterologous polynucleotide of the disclosure.

In some embodiments, the vaccine comprises the polynucleotide of the disclosure.

In some embodiments, the vaccine comprises the polypeptide of the disclosure.

"Prostate cancer" is meant to include all types of cancerous growths within prostate or oncogenic processes, metastatic tissues or malignantly transformed cells, tissues, or organs, irrespective of histopathology type or stage of invasiveness.

In some embodiments, the prostate cancer is an adenocarcinoma.

In some embodiments, the prostate cancer is a metastatic prostate cancer. In some embodiments, the prostate cancer has metastasized to rectum, lymph node or bone, or any combination thereof.

In some embodiments, the prostate cancer is a relapsed or a refractory prostate cancer.

In some embodiments, the prostate cancer is a castration resistant prostate cancer.

In some embodiments, the prostate cancer is sensitive to an androgen deprivation therapy.

In some embodiments, the prostate cancer is insensitive to the androgen deprivation therapy.

In some embodiments, the subject is treatment naïve.

In some embodiments, the subject has received androgen deprivation therapy.

In some embodiments, the subject has an elevated level of prostate specific antigen (PSA). PSA is elevated in a subject when the level is typically about >4.0 ng/mL. In some instances, elevated PSA may refer to level off>3.0 ng/mL. PSA levels may also be compared to post-androgen deprivation therapy levels.

Androgen deprivation therapies include abiraterone, ketoconazole, enzalutamide, galeterone, ARN-509 and orteronel (TAK-700), or prostatectomy.

The disclosure also provides a method of treating prostate cancer in a subject, comprising administering to the subject a therapeutically effective amount of a first vaccine comprising the rAd26 of the disclosure for priming the immune response; and administering to the subject a therapeutically effective amount of a second vaccine comprising the rMVA of the disclosure for boosting the immune response; thereby treating the prostate cancer in the subject.

The disclosure also provides a method of treating prostate cancer in a subject, comprising administering to the subject a therapeutically effective amount of a first vaccine comprising the rGAd of the disclosure for priming the immune response; and administering to the subject a therapeutically effective amount of a second vaccine comprising the rMVA of the disclosure for boosting the immune response; thereby treating the prostate cancer in the subject.

The disclosure also provides a method of treating prostate cancer in a subject, comprising administering to the subject a therapeutically effective amount of a first vaccine comprising the rGAd20 of the disclosure for priming the immune response; and administering to the subject a therapeutically effective amount of a second vaccine comprising the rMVA of the disclosure for boosting the immune response; thereby treating the prostate cancer in the subject.

The disclosure also provides a method of preventing prostate cancer in a subject, comprising administering to the subject a therapeutically effective amount of a first vaccine comprising the rAd26 of the disclosure for priming the immune response; and administering to the subject a therapeutically effective amount of a second vaccine comprising the rMVA of the disclosure for boosting the immune response; thereby preventing the prostate cancer in the subject.

The disclosure also provides a method of preventing prostate cancer in a subject, comprising administering to the subject a therapeutically effective amount of a first vaccine comprising the rGAd of the disclosure for priming the immune response; and administering to the subject a therapeutically effective amount of a second vaccine comprising the rMVA of the disclosure for boosting the immune response; thereby preventing the prostate cancer in the subject.

The disclosure also provides a method of preventing prostate cancer in a subject, comprising administering to the subject a therapeutically effective amount of a first vaccine comprising the rGAd20 of the disclosure for priming the immune response; and administering to the subject a therapeutically effective amount of a second vaccine comprising the rMVA of the disclosure for boosting the immune response; thereby preventing the prostate cancer in the subject.

The disclosure also provides a method of enhancing an immune response in a subject, comprising administering to the subject an immunologically effective amount of a first vaccine comprising the rAd26 of the disclosure for priming the immune response; and administering to the subject an immunologically effective amount of a second vaccine comprising the rMVA of the disclosure for boosting the immune response; thereby enhancing the immune response in the subject.

The disclosure also provides a method of enhancing an immune response in a subject, comprising administering to the subject an immunologically effective amount of a first vaccine comprising the rGAd of the disclosure for priming the immune response; and administering to the subject an immunologically effective amount of a second vaccine comprising the rMVA of the disclosure for boosting the immune response; thereby enhancing the immune response in the subject.

The disclosure also provides a method of enhancing an immune response in a subject, comprising administering to the subject an immunologically effective amount of a first vaccine comprising the rGAd20 of the disclosure for priming the immune response; and administering to the subject an immunologically effective amount of a second vaccine comprising the rMVA of the disclosure for boosting the immune response; thereby enhancing the immune response in the subject.

The disclosure also provides a method of treating prostate cancer in a subject, comprising administering to the subject a therapeutically effective amount of a first vaccine comprising the rAd26 of the disclosure for priming the immune response; and administering to the subject a therapeutically effective amount of a second vaccine comprising the rMVA of the disclosure for boosting the immune response; thereby treating the prostate cancer in the subject, wherein the rAd26 and the rMVA comprise a heterologous polynucleotide encoding one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

The disclosure also provides a method of treating prostate cancer in a subject, comprising administering to the subject a therapeutically effective amount of a first vaccine comprising the rGAd of the disclosure for priming the immune response; and administering to the subject a therapeutically effective amount of a second vaccine comprising the rMVA of the disclosure for boosting the immune response; thereby treating the prostate cancer in the subject, wherein the rGAd and the rMVA comprise a heterologous polynucleotide encoding one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

The disclosure also provides a method of treating prostate cancer in a subject, comprising administering to the subject a therapeutically effective amount of a first vaccine comprising the rGAd20 of the disclosure for priming the immune response; and administering to the subject a therapeutically effective amount of a second vaccine comprising the rMVA of the disclosure for boosting the immune response; thereby treating the prostate cancer in the subject, wherein the rGAd20 and the rMVA comprise a heterologous polynucleotide encoding one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

The disclosure also provides a method of preventing prostate cancer in a subject, comprising administering to the subject a therapeutically effective amount of a first vaccine comprising the rAd26 of the disclosure for priming the immune response; and administering to the subject a therapeutically effective amount of a second vaccine comprising the rMVA of the disclosure for boosting the immune response; thereby preventing the prostate cancer in the subject, wherein the rAd26 and the rMVA comprise a heterologous polynucleotide encoding one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

The disclosure also provides a method of preventing prostate cancer in a subject, comprising administering to the subject a therapeutically effective amount of a first vaccine comprising the rGAd of the disclosure for priming the immune response; and administering to the subject a therapeutically effective amount of a second vaccine comprising the rMVA of the disclosure for boosting the immune response; thereby preventing the prostate cancer in the subject, wherein the rGAd and the rMVA comprise a heterologous polynucleotide encoding one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

The disclosure also provides a method of preventing prostate cancer in a subject, comprising administering to the subject a therapeutically effective amount of a first vaccine comprising the rGAd20 of the disclosure for priming the immune response; and administering to the subject a therapeutically effective amount of a second vaccine comprising the rMVA of the disclosure for boosting the immune response; thereby preventing the prostate cancer in the subject, wherein the rGAd20 and the rMVA comprise a heterologous polynucleotide encoding one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

The disclosure also provides a method of enhancing an immune response in a subject, comprising administering to the subject an immunologically effective amount of a first vaccine comprising the rAd26 of the disclosure for priming the immune response; and administering to the subject an immunologically effective amount of a second vaccine comprising the rMVA of the disclosure for boosting the immune response; thereby enhancing the immune response in the subject, wherein the rAd26 and the rMVA comprise a heterologous polynucleotide encoding one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

The disclosure also provides a method of enhancing an immune response in a subject, comprising administering to the subject an immunologically effective amount of a first vaccine comprising the rGAd of the disclosure for priming the immune response; and administering to the subject an immunologically effective amount of a second vaccine comprising the rMVA of the disclosure for boosting the immune response; thereby enhancing the immune response in the subject, wherein the rGAd and the rMVA comprise a heterologous polynucleotide encoding one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

The disclosure also provides a method of enhancing an immune response in a subject, comprising administering to the subject an immunologically effective amount of a first vaccine comprising the rGAd20 of the disclosure for priming the immune response; and administering to the subject an immunologically effective amount of a second vaccine comprising the rMVA of the disclosure for boosting the immune response; thereby enhancing the immune response in the subject, wherein the rGAd20 and the rMVA comprise a heterologous polynucleotide encoding one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

In some embodiments, the subject is suspected to have or is suspected to develop prostate cancer.

The vaccines of the disclosure may be typically administered by intramuscular or subcutaneous injection. However other modes of administration such as intravenous, cutaneous, intradermal or nasal can be envisaged as well. Intramuscular administration of the vaccines can be achieved by using a needle. An alternative is the use of a needleless injection device to administer the composition (using, e.g., Biojector™) or a freeze-dried powder containing the vaccine.

For intravenous, cutaneous or subcutaneous injection, or injection at the site of affliction, the vector may be the form of a parenterally acceptable aqueous solution which is pyrogen-free and has suitable pH, isotonicity and stability. Those of skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required. A slow-release formulation may also be employed.

Typically, administration will have a prophylactic aim to generate an immune response against the prostate neoantigens before development of symptoms of prostate cancer.

The vaccines of the disclosure are administered to a subject, giving rise to an immune response in the subject. An amount of the vaccine to in induce a detectable immune response is defined to be an "immunologically effective dose." The vaccines of the disclosure may induce a humoral as well as a cell-mediated immune response. In a typical embodiment the immune response is a protective immune response.

The actual amount administered, and rate and time-course of administration, will depend on the nature and severity of what is being treated. Prescription of treatment, e.g., decisions on dosage etc., is within the responsibility of general practitioners and other medical doctors, and typically takes account of the disorder to be treated, the condition of the individual patient, the site of delivery, the method of administration and other factors known to practitioners.

In one exemplary regimen, the adenovirus vector is administered (e.g., intramuscularly) in a volume ranging between about 100 μL to about 10 ml containing concentrations of about $10^4$ to $10^{12}$ virus particles/ml. The adenovirus vector may be administered in a volume ranging between 0.25 and 1.0 ml, such as in a volume of 0.5 ml.

The adenovirus may be administered in an amount of about $10^9$ to about $10^{12}$ viral particles (vp) to a human subject during one administration, more typically in an amount of about $10^{10}$ to about 1012 vp.

In one exemplary regimen, the rMVA of the disclosure is administered (e.g., intramuscularly) in a volume ranging between about 100 μl to about 10 ml of saline solution containing a dose of about $1\times10^7$ $TCID_{50}$ to $1\times10^9$ $TCID_{50}$ (50% Tissue Culture Infective Dose) or Inf.U. (Infectious Unit). The rMVA may be administered in a volume ranging between 0.25 and 1.0 ml.

Boosting compositions may be administered two or more times, weeks or months after administration of the priming composition, for example, about 1 or 2 weeks or 3 weeks, or 4 weeks, or 6 weeks, or 8 weeks, or 12 weeks, or 16 weeks, or 20 weeks, or 24 weeks, or 28 weeks, or 32 weeks or one to two years after administration of the priming composition. Additional boosting compositions may be administered 6 weeks to 5 years after the boosting step (b), such as 6, 7, 8, 9, 10, 11, 12, 13, 14, 15, 16, 17, 18, 19, 20, 21, 22, 23, 24 or 25 weeks, or 7, 8, 9, 10, 11 or 12 months, or 2, 3, 4 or 5 years, after the initial boosting inoculation. Optionally, the further boosting step (c) can be repeated one or more times as needed.

Prostate Neoantigen Combinations for Vaccine Therapy

The identified neoantigens described herein can be further validated and prioritized for their inclusion into a universal prostate cancer vaccine. The considerations for inclusion are, for example, higher expression in prostate cancer tissues vs. normal prostate tissue and other normal tissues (such as liver, kidney, pancreas, ovary, prostate, mammary gland, colon, stomach, skeletal muscle and lung), or undetectable expression in normal tissues, ability of the neoantigens or their fragments to mediate activation of $CD8^+$ T cells in known assays, binding to HLA, demonstrated in vivo processing and presentation to HLA of peptide fragments derived from the neoantigens and sufficient prevalence in prostate cancer subjects.

Through the validation process, 41 neoantigens (SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177) were identified as particularly useful to be included into a prostate cancer vaccine based on their expression profile, prevalence and in vitro immunogenicity. It is expected that any combination of the 41 neoantigens can be utilized to generate a prostate cancer vaccine that can be delivered to a subject utilizing any available delivery vehicles and any form available, such as peptides, DNA, RNA, replicons, or using viral delivery. The 41 neoantigens may be assembled into heterologous polynucleotides encoding heterologous polypeptides in any neoantigen order, and the neoantigen order may differ between the various delivery options. In general, assembly of the neoantigens into a particular order may be based on generating a minimum number of junctional epitopes utilizing known algorithms. Exemplary orders of the neoantigens are orders providing heterologous polypeptides of SEQ ID NOs: 541, 550, 554, 555, 556, 623, 624, 543, 552, 557, 558, 559, 625 or 626 as described herein and throughout the examples.

The disclosure provides a vaccine comprising a heterologous polynucleotide encoding a heterologous polypeptide, wherein the heterologous polypeptide comprises two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides a vaccine comprising a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the fragments comprise polypeptides of SEQ ID NOs: 387, 388, 390, 392, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710 or 711.

In some embodiments, the vaccine is capable of eliciting a cellular immune response in a subject administered the vaccine.

In some embodiments, the cellular immune response is specific against a fragment of one or more polypeptides of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 or 177.

In some embodiments, the cellular immune response is activation of vaccine-specific $CD8^+$ T cells, $CD4^+$ T cells, or $CD8^+$ T cells and $CD4^+$ T cells, wherein activation is assessed by increased production of TNFα, IFNγ, or TNFα and IFNγ by $CD8^+$ T cells, $CD4^+$ T cells, or $CD8^+$ T cells and $CD4^+$ T cells.

In some embodiments, the heterologous polynucleotide comprises a promoter, an enhancer, a polyadenylation site, a Kozak sequence, a stop codon, a T cell enhancer (TCE), or any combination thereof.

In some embodiments, the promoter comprises a CMV promoter or a vaccinia P7.5 promoter.

In some embodiments, the TCE is encoded by a polynucleotide of SEQ ID NO: 546, the CMV promoter comprises a polynucleotide of SEQ ID NO: 628, the vaccinia P7.5 promoter comprises a polynucleotide of SEQ ID NO: 630 and the polyadenylation site comprises a bovine growth hormone polyadenylation site of SEQ ID NO: 629.

In some embodiments, the heterologous polypeptide comprises an amino acid sequence of SEQ ID NOs: 541, 550, 554, 555, 556, 623 or 624.

In some embodiments, the heterologous polynucleotide comprises a polynucleotide sequence of SEQ ID NO: 542 or SEQ ID NO: 551.

In some embodiments, the heterologous polypeptide comprises the amino acid sequence of SEQ ID NOs: 543, 552, 557, 558, 559, 625 or 626.

In some embodiments, the heterologous polynucleotide comprises the polynucleotide sequence of SEQ ID NO: 544 or SEQ ID NO: 553.

In some embodiments, the heterologous polynucleotide is DNA or RNA.

In some embodiments, RNA is mRNA or self-replicating RNA.

The disclosure also provides a vaccine comprising a heterologous polynucleotide encoding a heterologous polypeptide of SEQ ID NO: 541.

The disclosure also provides a vaccine comprising a heterologous polynucleotide encoding a heterologous polypeptide of SEQ ID NO: 550.

The disclosure also provides a vaccine comprising a heterologous polynucleotide encoding a heterologous polypeptide of SEQ ID NO: 554.

The disclosure also provides a vaccine comprising a heterologous polynucleotide encoding a heterologous polypeptide of SEQ ID NO: 555.

The disclosure also provides a vaccine comprising a heterologous polynucleotide encoding a heterologous polypeptide of SEQ ID NO: 556.

The disclosure also provides a vaccine comprising a heterologous polynucleotide encoding a heterologous polypeptide of SEQ ID NO: 623.

The disclosure also provides a vaccine comprising a heterologous polynucleotide encoding a heterologous polypeptide of SEQ ID NO: 624.

The disclosure also provides a vaccine comprising a heterologous polynucleotide of SEQ ID NO: 542.

The disclosure also provides a vaccine comprising a heterologous polynucleotide of SEQ ID NO: 551.

The disclosure also provides a vaccine comprising a heterologous polynucleotide encoding a heterologous polypeptide of SEQ ID NO: 543.

The disclosure also provides a vaccine comprising a heterologous polynucleotide encoding a heterologous polypeptide of SEQ ID NO: 552.

The disclosure also provides a vaccine comprising a heterologous polynucleotide encoding a heterologous polypeptide of SEQ ID NO: 557.

The disclosure also provides a vaccine comprising a heterologous polynucleotide encoding a heterologous polypeptide of SEQ ID NO: 558.

The disclosure also provides a vaccine comprising a heterologous polynucleotide encoding a heterologous polypeptide of SEQ ID NO: 559.

The disclosure also provides a vaccine comprising a heterologous polynucleotide encoding a heterologous polypeptide of SEQ ID NO: 625.

The disclosure also provides a vaccine comprising a heterologous polynucleotide encoding a heterologous polypeptide of SEQ ID NO: 626.

The disclosure also provides a vaccine comprising a heterologous polynucleotide of SEQ ID NOs: 544.

The disclosure also provides a vaccine comprising a heterologous polynucleotide of SEQ ID NOs: 553.

In some embodiments, the vaccine is a recombinant virus.

In some embodiments, the recombinant virus is derived from adenovirus (Ad), poxvirus, adeno-associated virus (AAV) or retrovirus.

In some embodiments, the recombinant virus is derived from hAd5, hAd7, hAd11, hAd26, hAd34, hAd35, hAd48, hAd49, hAd50, GAd20, Gad19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, PanAd3, Copenhagen vaccinia virus (W), New York Attenuated Vaccinia Virus (NYVAC), ALVAC, TROVAC, or modified vaccinia Ankara (MVA).

In some embodiments, the recombinant virus is derived from GAd20.

In some embodiments, the recombinant virus derived from GAd20 comprises a polynucleotide sequence of SEQ ID NO: 713.

In some embodiments, the recombinant virus is derived from MVA.

In some embodiments, the recombinant virus is derived from hAd26.

The disclosure also provides a vaccine comprising a heterologous polynucleotide encoding a heterologous polypeptide of SEQ ID NO: 541, wherein the vaccine is a recombinant virus derived from GAd20.

The disclosure also provides a vaccine comprising a heterologous polynucleotide encoding a heterologous polypeptide of SEQ ID NO: 550, wherein the vaccine is a recombinant virus derived from GAd20.

The disclosure also provides a vaccine comprising a heterologous polynucleotide encoding a heterologous polypeptide of SEQ ID NO: 554, wherein the vaccine is a recombinant virus derived from GAd20.

The disclosure also provides a vaccine comprising a heterologous polynucleotide encoding a heterologous polypeptide of SEQ ID NO: 555, wherein the vaccine is a recombinant virus derived from GAd20.

The disclosure also provides a vaccine comprising a heterologous polynucleotide encoding a heterologous polypeptide of SEQ ID NO: 556, wherein the vaccine is a recombinant virus derived from GAd20.

The disclosure also provides a vaccine comprising a heterologous polynucleotide encoding a heterologous polypeptide of SEQ ID NO: 623, wherein the vaccine is a recombinant virus derived from GAd20.

The disclosure also provides a vaccine comprising a heterologous polynucleotide encoding a heterologous polypeptide of SEQ ID NO: 624, wherein the vaccine is a recombinant virus derived from GAd20.

The disclosure also provides a vaccine comprising a polynucleotide sequence of SEQ ID NO: 713, wherein the vaccine is a recombinant virus derived from GAd20.

The disclosure also provides a vaccine comprising a heterologous polynucleotide of SEQ ID NOs: 542, wherein the vaccine is a recombinant virus derived from GAd20.

The disclosure also provides a vaccine comprising a heterologous polynucleotide of SEQ ID NOs: 551, wherein the vaccine is a recombinant virus derived from GAd20.

The disclosure also provides a vaccine comprising a heterologous polynucleotide encoding a heterologous polypeptide of SEQ ID NO: 543, wherein the vaccine is a recombinant virus derived from MVA.

The disclosure also provides a vaccine comprising a heterologous polynucleotide encoding a heterologous polypeptide of SEQ ID NO: 552, wherein the vaccine is a recombinant virus derived from MVA.

The disclosure also provides a vaccine comprising a heterologous polynucleotide encoding a heterologous polypeptide of SEQ ID NO: 557, wherein the vaccine is a recombinant virus derived from MVA.

The disclosure also provides a vaccine comprising a heterologous polynucleotide encoding a heterologous polypeptide of SEQ ID NO: 558, wherein the vaccine is a recombinant virus derived from MVA.

The disclosure also provides a vaccine comprising a heterologous polynucleotide encoding a heterologous polypeptide of SEQ ID NO: 559, wherein the vaccine is a recombinant virus derived from MVA.

The disclosure also provides a vaccine comprising a heterologous polynucleotide encoding a heterologous polypeptide of SEQ ID NO: 625, wherein the vaccine is a recombinant virus derived from MVA.

The disclosure also provides a vaccine comprising a heterologous polynucleotide encoding a heterologous polypeptide of SEQ ID NO: 626, wherein the vaccine is a recombinant virus derived from MVA.

The disclosure also provides a vaccine comprising a heterologous polynucleotide of SEQ ID NOs: 544, wherein the vaccine is a recombinant virus derived from MVA.

The disclosure also provides a vaccine comprising a heterologous polynucleotide of SEQ ID NOs: 553, wherein the vaccine is a recombinant virus derived from MVA.

The disclosure also provides a method of treating or preventing a prostate cancer in a subject, comprising administering to the subject a therapeutically effective amount of a vaccine comprising a recombinant virus derived from GAd20 comprising a heterologous polynucleotide encoding a heterologous polypeptide of SEQ ID NOs: 541, 550, 554, 555, 556, 623 or 624.

The disclosure also provides a method of treating or preventing a prostate cancer in a subject, comprising administering to the subject a therapeutically effective amount of a vaccine comprising a recombinant virus derived from GAd20 comprising a heterologous polynucleotide encoding a heterologous polypeptide of SEQ ID NO: 541.

The disclosure also provides a method of treating or preventing a prostate cancer in a subject, comprising administering to the subject a therapeutically effective amount of a vaccine comprising a recombinant virus derived from GAd20 comprising a heterologous polynucleotide encoding a heterologous polypeptide of SEQ ID NO: 550.

The disclosure also provides a method of treating or preventing a prostate cancer in a subject, comprising administering to the subject a therapeutically effective amount of a vaccine comprising a recombinant virus derived from GAd20 comprising a heterologous polynucleotide encoding a heterologous polypeptide of SEQ ID NO: 554.

The disclosure also provides a method of treating or preventing a prostate cancer in a subject, comprising administering to the subject a therapeutically effective amount of a vaccine comprising a recombinant virus derived from GAd20 comprising a heterologous polynucleotide encoding a heterologous polypeptide of SEQ ID NO: 555.

The disclosure also provides a method of treating or preventing a prostate cancer in a subject, comprising administering to the subject a therapeutically effective amount of a vaccine comprising a recombinant virus derived from GAd20 comprising a heterologous polynucleotide encoding a heterologous polypeptide of SEQ ID NO: 556.

The disclosure also provides a method of treating or preventing a prostate cancer in a subject, comprising administering to the subject a therapeutically effective amount of a vaccine comprising a recombinant virus derived from GAd20 comprising a heterologous polynucleotide encoding a heterologous polypeptide of SEQ ID NO: 623.

The disclosure also provides a method of treating or preventing a prostate cancer in a subject, comprising administering to the subject a therapeutically effective amount of a vaccine comprising a recombinant virus derived from GAd20 comprising a heterologous polynucleotide encoding a heterologous polypeptide of SEQ ID NO: 624.

The disclosure also provides a method of treating or preventing a prostate cancer in a subject, comprising administering to the subject a therapeutically effective amount of a vaccine comprising a recombinant virus derived from MVA comprising a heterologous polynucleotide encoding a heterologous polypeptide of SEQ ID NOs: 543, 552, 557, 558, 559, 625 or 626.

The disclosure also provides a method of treating or preventing a prostate cancer in a subject, comprising administering to the subject a therapeutically effective amount of a vaccine comprising a recombinant virus derived from MVA comprising a heterologous polynucleotide encoding a heterologous polypeptide of SEQ ID NO: 543.

The disclosure also provides a method of treating or preventing a prostate cancer in a subject, comprising administering to the subject a therapeutically effective amount of a vaccine comprising a recombinant virus derived from MVA comprising a heterologous polynucleotide encoding a heterologous polypeptide of SEQ ID NO: 552.

The disclosure also provides a method of treating or preventing a prostate cancer in a subject, comprising administering to the subject a therapeutically effective amount of a vaccine comprising a recombinant virus derived from MVA comprising a heterologous polynucleotide encoding a heterologous polypeptide of SEQ ID NO: 557.

The disclosure also provides a method of treating or preventing a prostate cancer in a subject, comprising administering to the subject a therapeutically effective amount of a vaccine comprising a recombinant virus derived from MVA comprising a heterologous polynucleotide encoding a heterologous polypeptide of SEQ ID NO: 558.

The disclosure also provides a method of treating or preventing a prostate cancer in a subject, comprising administering to the subject a therapeutically effective amount of a vaccine comprising a recombinant virus derived from MVA comprising a heterologous polynucleotide encoding a heterologous polypeptide of SEQ ID NO: 559.

The disclosure also provides a method of treating or preventing a prostate cancer in a subject, comprising administering to the subject a therapeutically effective amount of a vaccine comprising a recombinant virus derived from MVA comprising a heterologous polynucleotide encoding a heterologous polypeptide of SEQ ID NO: 625.

The disclosure also provides a method of treating or preventing a prostate cancer in a subject, comprising administering to the subject a therapeutically effective amount of a vaccine comprising a recombinant virus derived from MVA comprising a heterologous polynucleotide encoding a heterologous polypeptide of SEQ ID NO: 626.

In some embodiments, the vaccine comprising a recombinant virus derived from GAd20 is administered as a prime.

In some embodiments, the vaccine comprising a recombinant virus derived from MVA is administered as a boost.

In some embodiments, the vaccine comprising the heterologous polynucleotide sequence encoding a heterologous polypeptide of SEQ ID NOs: 541 or 550 is administered as a prime.

In some embodiments, the vaccine comprising the heterologous polynucleotide sequence encoding a heterologous polypeptide of SEQ ID NOs 543 or 552 is administered as a boost.

The disclosure also provides a method of treating or preventing a prostate cancer in a subject, comprising administering to the subject a therapeutically effective amount of a vaccine comprising a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof as a prime; and administering to the subject a therapeutically effective amount of a vaccine comprising a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof as a boost; thereby treating or preventing the prostate cancer in the subject.

The disclosure also provides a method of treating or preventing a prostate cancer in a subject, comprising administering to the subject a first vaccine comprising a first heterologous polynucleotide encoding a first heterologous polypeptide, wherein the first heterologous polypeptide comprises two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177; and a second vaccine comprising a second heterologous polynucleotide encoding a second heterologous polypeptide, wherein the second heterologous polypeptide comprises two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177.

The disclosure also provides a method of treating or preventing a prostate cancer in a subject, comprising administering to the subject a first vaccine comprising a first heterologous polynucleotide encoding a first heterologous polypeptide, wherein the first heterologous polypeptide comprises two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177; and a second vaccine comprising a second heterologous polynucleotide encoding a second heterologous polypeptide, wherein the second heterologous polypeptide comprises two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177; wherein the first heterologous polypeptide and the second heterologous polypeptide have distinct amino acid sequences.

In some embodiments, the polypeptides are organized in a first order and in a second order.

In some embodiments, the polypeptides organized in the first order comprises a heterologous polypeptide of SEQ ID NO: 541 or SEQ ID NO: 550.

In some embodiments, the polypeptides organized in the second order comprises a heterologous polypeptide of SEQ ID NO: 543 or SEQ ID NO: 552.

In some embodiments, the heterologous polynucleotide is DNA or RNA.

In some embodiments, RNA is mRNA or self-replicating RNA.

In some embodiments, the vaccine is a recombinant virus.

In some embodiments, the recombinant virus is derived from adenovirus, poxvirus, adeno-associated virus or retrovirus.

In some embodiments, the polypeptides organized in the first order are encoded by a polynucleotide of SEQ ID NO: 542 or SEQ ID NO: 551.

In some embodiments, the polypeptides organized in the second order are encoded by a polynucleotide of SEQ ID NO: 544 or SEQ ID NO: 553.

In some embodiments, the prime comprises the recombinant virus derived from GAd20 comprising a heterologous polypeptide of SEQ ID NO: 541 or SEQ ID NO: 550.

In some embodiments, the boost comprises the recombinant virus derived from MVA comprising the heterologous polypeptide of SEQ ID NO: 543 or SEQ ID NO: 552.

The disclosure also provides a method of treating or preventing a prostate cancer in a subject, comprising administering to the subject a first vaccine comprising a first heterologous polynucleotide encoding a first heterologous polypeptide, wherein the first heterologous polypeptide comprises an amino acid sequence of SEQ ID NOs: 541, 550, 554, 555, 556, 623 or 624; and a second vaccine comprising a second heterologous polynucleotide encoding a second heterologous polypeptide, wherein the second heterologous polypeptide comprises the amino acid sequence of SEQ ID NOs: 543, 552, 557, 558, 559, 625 or 626.

The disclosure also provides a method of treating or preventing a prostate cancer in a subject, comprising administering to the subject a first vaccine comprising a first heterologous polynucleotide encoding a first heterologous polypeptide, wherein the first heterologous polypeptide comprises an amino acid sequence of SEQ ID NO: 541; and a second vaccine comprising a second heterologous polynucleotide encoding a second heterologous polypeptide, wherein the second heterologous polypeptide comprises the amino acid sequence of SEQ ID NO: 543.

The disclosure also provides a method of treating or preventing a prostate cancer in a subject, comprising administering to the subject a first vaccine comprising a first heterologous polynucleotide encoding a first heterologous polypeptide, wherein the first heterologous polypeptide comprises an amino acid sequence of SEQ ID NO: 550; and a second vaccine comprising a second heterologous polynucleotide encoding a second heterologous polypeptide, wherein the second heterologous polypeptide comprises the amino acid sequence of SEQ ID NO: 552.

The disclosure also provides a method of treating or preventing a prostate cancer in a subject, comprising administering to the subject a first vaccine comprising a first heterologous polynucleotide encoding a first heterologous polypeptide, wherein the first heterologous polypeptide comprises an amino acid sequence of SEQ ID NO: 541, wherein the first vaccine is a recombinant Gad20; and a second vaccine comprising a second heterologous polynucleotide encoding a second heterologous polypeptide, wherein the second heterologous polypeptide comprises the amino acid sequence of SEQ ID NO: 543, wherein the second vaccine is a recombinant MVA.

The disclosure also provides a method of treating or preventing a prostate cancer in a subject, comprising administering to the subject a first vaccine comprising a first heterologous polynucleotide encoding a first heterologous polypeptide, wherein the first heterologous polypeptide comprises an amino acid sequence of SEQ ID NO: 550, wherein the first vaccine is a recombinant GAd20; and a second vaccine comprising a second heterologous polynucleotide encoding a second heterologous polypeptide, wherein the second heterologous polypeptide comprises the amino acid sequence of SEQ ID NO: 552, wherein the second vaccine is a recombinant MVA.

The disclosure also provides a method of inducing an immune response in a subject, comprising administering to the subject a vaccine comprising a recombinant virus derived from GAd20 comprising a heterologous polynucleotide encoding a heterologous polypeptide of SEQ ID NOs: 541, 550, 554, 555, 556, 623 or 624.

The disclosure also provides a method of inducing an immune response in a subject, comprising administering to the subject a vaccine comprising a recombinant virus derived from GAd20 comprising a heterologous polynucleotide encoding a heterologous polypeptide of SEQ ID NO: 541.

The disclosure also provides a method of inducing an immune response in a subject, comprising administering to the subject a vaccine comprising a recombinant virus derived from GAd20 comprising a heterologous polynucleotide encoding a heterologous polypeptide of SEQ ID NO: 550.

The disclosure also provides a method of inducing an immune response in a subject, comprising administering to the subject a vaccine comprising a recombinant virus derived from GAd20 comprising a heterologous polynucleotide encoding a heterologous polypeptide of SEQ ID NO: 554.

The disclosure also provides a method of inducing an immune response in a subject, comprising administering to the subject a vaccine comprising a recombinant virus derived from GAd20 comprising a heterologous polynucleotide encoding a heterologous polypeptide of SEQ ID NO: 555.

The disclosure also provides a method of inducing an immune response in a subject, comprising administering to the subject a vaccine comprising a recombinant virus derived from GAd20 comprising a heterologous polynucleotide encoding a heterologous polypeptide of SEQ ID NO: 556.

The disclosure also provides a method of inducing an immune response in a subject, comprising administering to the subject a vaccine comprising a recombinant virus derived from GAd20 comprising a heterologous polynucleotide encoding a heterologous polypeptide of SEQ ID NO: 623.

The disclosure also provides a method of inducing an immune response in a subject, comprising administering to the subject a vaccine comprising a recombinant virus derived from GAd20 comprising a heterologous polynucleotide encoding a heterologous polypeptide of SEQ ID NO: 624.

The disclosure also provides a method of inducing an immune response in a subject, comprising administering to the subject a vaccine comprising a recombinant virus derived from MVA comprising a heterologous polynucleotide encoding a heterologous polypeptide of SEQ ID NOs: 543, 552, 557, 558, 559, 625 or 626.

The disclosure also provides a method of inducing an immune response in a subject, comprising administering to the subject a vaccine comprising a recombinant virus derived from MVA comprising a heterologous polynucleotide encoding a heterologous polypeptide of SEQ ID NO: 543.

The disclosure also provides a method of inducing an immune response in a subject, comprising administering to the subject a vaccine comprising a recombinant virus derived from MVA comprising a heterologous polynucleotide encoding a heterologous polypeptide of SEQ ID NO: 552.

The disclosure also provides a method of inducing an immune response in a subject, comprising administering to the subject a vaccine comprising a recombinant virus derived from MVA comprising a heterologous polynucleotide encoding a heterologous polypeptide of SEQ ID NO: 557.

The disclosure also provides a method of inducing an immune response in a subject, comprising administering to the subject a vaccine comprising a recombinant virus derived from MVA comprising a heterologous polynucleotide encoding a heterologous polypeptide of SEQ ID NO: 558.

The disclosure also provides a method of inducing an immune response in a subject, comprising administering to the subject a vaccine comprising a recombinant virus derived from MVA comprising a heterologous polynucleotide encoding a heterologous polypeptide of SEQ ID NO: 559.

The disclosure also provides a method of inducing an immune response in a subject, comprising administering to the subject a vaccine comprising a recombinant virus derived from MVA comprising a heterologous polynucleotide encoding a heterologous polypeptide of SEQ ID NO: 625.

The disclosure also provides a method of inducing an immune response in a subject, comprising administering to the subject a vaccine comprising a recombinant virus derived from MVA comprising a heterologous polynucleotide encoding a heterologous polypeptide of SEQ ID NO: 626.

The disclosure also provides a method of inducing an immune response in a subject, comprising administering to the subject a first vaccine comprising a first heterologous polynucleotide encoding a first heterologous polypeptide, wherein the first heterologous polypeptide comprises an amino acid sequence of SEQ ID NOs: 541, 550, 554, 555, 556, 623 or 624; and a second vaccine comprising a second heterologous polynucleotide encoding a second heterologous polypeptide, wherein the second heterologous polypeptide comprises the amino acid sequence of SEQ ID NOs: 543, 552, 557, 558, 559, 625 or 626.

The disclosure also provides a method of inducing an immune response in a subject, comprising administering to the subject a first vaccine comprising a first heterologous polynucleotide encoding a first heterologous polypeptide, wherein the first heterologous polypeptide comprises an amino acid sequence of SEQ ID NO: 541; and a second vaccine comprising a second heterologous polynucleotide encoding a second heterologous polypeptide, wherein the second heterologous polypeptide comprises the amino acid sequence of SEQ ID NO: 543.

The disclosure also provides a method of inducing an immune response in a subject, comprising administering to the subject a first vaccine comprising a first heterologous polynucleotide encoding a first heterologous polypeptide, wherein the first heterologous polypeptide comprises an amino acid sequence of SEQ ID NO: 550; and a second vaccine comprising a second heterologous polynucleotide encoding a second heterologous polypeptide, wherein the second heterologous polypeptide comprises the amino acid sequence of SEQ ID NO: 552.

The disclosure also provides a method of inducing an immune response in a subject, comprising administering to the subject a first vaccine comprising a first heterologous polynucleotide encoding a first heterologous polypeptide, wherein the first heterologous polypeptide comprises an amino acid sequence of SEQ ID NO: 541, wherein the first vaccine is a recombinant Gad20; and a second vaccine comprising a second heterologous polynucleotide encoding a second heterologous polypeptide, wherein the second heterologous polypeptide comprises the amino acid sequence of SEQ ID NO: 543, wherein the second vaccine is a recombinant MVA.

The disclosure also provides a method of inducing an immune response in a subject, comprising administering to the subject a first vaccine comprising a first heterologous polynucleotide encoding a first heterologous polypeptide, wherein the first heterologous polypeptide comprises an amino acid sequence of SEQ ID NO: 550, wherein the first vaccine is a recombinant GAd20; and a second vaccine comprising a second heterologous polynucleotide encoding a second heterologous polypeptide, wherein the second heterologous polypeptide comprises the amino acid sequence of SEQ ID NO: 552, wherein the second vaccine is a recombinant MVA.

In some embodiments, the subject has, is suspected to have or is suspected to develop prostate cancer. Prostate cancer diagnosis performed by a licensed physician.

In some embodiments, prostate cancer is a relapsed prostate cancer, a refractory prostate cancer, a metastatic prostate cancer or a castration resistant prostate cancer, or any combination thereof.

In some embodiments, the subject is treatment naïve.

In some embodiments, the subject has received androgen deprivation therapy.

In some embodiments, the first vaccine is administered one or more times to the subject.

In some embodiments, the second vaccine is administered one or more times to the subject.

In some embodiments, the first vaccine is administered between about 1-16 weeks prior to administering the second vaccine. In some embodiments, the first vaccine is administered about 1 week prior to administering the second vaccine. In some embodiments, the first vaccine is administered about 2 weeks prior to administering the second vaccine. In some embodiments, the first vaccine is administered about 3 weeks prior to administering the second vaccine. In some embodiments, the first vaccine is administered about 4 weeks prior to administering the second vaccine. In some embodiments, the first vaccine is administered about 5 weeks prior to administering the second vaccine. In some embodiments, the first vaccine is administered about 6 weeks prior to administering the second vaccine. In some embodiments, the first vaccine is administered about 7 weeks prior to administering the second vaccine. In some embodiments, the first vaccine is administered about 8 weeks prior to administering the second vaccine. In some embodiments, the first vaccine is administered about 9 weeks prior to administering the second vaccine. In some embodiments, the first vaccine is administered about 10 weeks prior to administering the second vaccine. In some embodiments, the first vaccine is administered about 11 weeks prior to administering the second vaccine. In some embodiments, the first vaccine is administered about 12 weeks prior to administering the second vaccine. In some embodiments, the first vaccine is administered about 13 weeks prior to administering the second vaccine. In some embodiments, the first vaccine is administered about 14 weeks prior to administering the second vaccine. In some embodiments, the first vaccine is administered about 16 weeks prior to administering the second vaccine.

In some embodiments, the prostate cancer is a relapsed prostate cancer, a refractory prostate cancer, a metastatic prostate cancer, or a castration resistant prostate cancer, or any combination thereof.

In some embodiments, the method comprises further administering an additional cancer therapeutic agent to the subject.

Combination Therapies

The vaccines of the disclosure may be used in combination with at least one additional cancer therapeutic agent for treating prostate cancer.

The additional cancer therapeutic agent may be a surgery, a chemotherapy, an androgen deprivation therapy, radiation therapy, targeted therapy or a checkpoint inhibitor, or any combination thereof.

Exemplary chemotherapeutic agents are alkylating agents; nitrosoureas; antimetabolites; antitumor antibiotics; plant alkyloids; taxanes; hormonal agents; and miscellaneous agents, such as busulfan, carboplatin, chlorambucil, cisplatin, cyclophosphamide, dacarbazine, ifosfamide, mechlorethamine hydrochloride, melphalan, procarbazine, thiotepa, uracil mustard, 5-fluorouracil, 6-mercaptopurine, capecitabine, cytosine arabinoside, floxuridine, fludarabine, gemcitabine, methotrexate, thioguanine, dactinomycin, daunorubicin, doxorubicin, idarubicin, mitomycin-C, and mitoxantrone, vinblastine, vincristine, vindesine, vinorelbine, paclitaxel, docetaxel.

Exemplary androgen deprivation therapies include abiraterone acetate, ketoconazole, enzalutamide, galeterone, ARN-509 and orteronel (TAK-700) and surgical removal of the testicles.

Radiation therapy may be administered using various methods, including external-beam therapy, internal radiation therapy, implant radiation, stereotactic radiosurgery, systemic radiation therapy, radiotherapy and permanent or temporary interstitial brachytherapy. External-beam therapy involves three-dimensional, conformal radiation therapy where the field of radiation is designed, local radiation (e.g., radiation directed to a preselected target or organ), or focused radiation. Focused radiation may be selected from stereotactic radiosurgery, fractionated stereotactic radiosurgery or intensity-modulated radiation therapy. Focused radiation may have particle beam (proton), cobalt-60 (photon) linear accelerator (x-ray) as a radiation source (see e.g. WO 2012/177624). "Brachytherapy," refers to radiation therapy delivered by a spatially confined radioactive material inserted into the body at or near a tumor or other proliferative tissue disease site, and includes exposure to radioactive isotopes (e.g., At-211, 1-131, 1-125, Y-90, Re-186, Re-188, Sm-153, Bi-212, P-32, and radioactive isotopes of Lu). Suitable radiation sources for use as a cell conditioner include both solids and liquids. The radiation source can be a radionuclide, such as 1-125, 1-131, Yb-169, Ir-192 as a solid source, 1-125 as a solid source, or other radionuclides that emit photons, beta particles, gamma radiation, or other therapeutic rays. The radioactive material may also be a fluid made from any solution of radionuclide(s), e.g., a solution of I-125 or 1-131, or a radioactive fluid can be produced using a slurry of a suitable fluid containing small particles of solid radionuclides, such as Au-198, Y-90. The radionuclide(s) may be embodied in a gel or radioactive micro spheres.

Targeted therapies include anti-androgen therapies, inhibitors of angiogenesis such as bevacizumab, anti-PSA or anti-PSMA antibodies or vaccines enhancing immune responses to PSA or PSMA.

Exemplary checkpoint inhibitors are antagonists of PD-1, PD-L1, PD-L2, VISTA, BTNL2, B7-H3, B7-H4, HVEM, HHLA2, CTLA-4, LAG-3, TIM-3, BTLA, CD160, CEACAM-1, LAIR1, TGF3, IL-10, Siglec family protein, KIR, CD96, TIGIT, NKG2A, CD112, CD47, SIRPA or CD244. "Antagonist" refers to a molecule that, when bound to a cellular protein, suppresses at least one reaction or activity that is induced by a natural ligand of the protein. A molecule is an antagonist when the at least one reaction or activity is suppressed by at least about 30%, 40%, 45%, 50%, 55%, 60%, 65%, 70%, 75%, 80%, 85%, 90%, 95%, or 100% more than the at least one reaction or activity suppressed in the absence of the antagonist (e.g., negative control), or when the suppression is statistically significant when compared to the suppression in the absence of the antagonist. Antagonist may be an antibody, a soluble ligand, a small molecule, a DNA or RNA such as siRNA. Exemplary antagonists of checkpoint inhibitors are described in U.S. Pat. Publ. No. 2017/0121409.

In some embodiments, one or more vaccines or the disclosure is administered in combination with a CTLA-4 antibody, a CTLA4 ligand, a PD-1 axis inhibitor, a PD-L1 axis inhibitor, a TLR agonist, a CD40 agonist, an OX40 agonist, hydroxyurea, ruxolitinib, fedratinib, a 41BB agonist, aa CD28 agonist, a STING antagonist, a RIG-1 antagonist, TCR-T therapy, CAR-T therapy, FLT3 ligand, aluminum sulfate, BTK inhibitor, CD38 antibody, CDK inhibitor, CD33 antibody, CD37 antibody, CD25 antibody, GM-CSF inhibitor, IL-2, IL-15, IL-7, CD3 redirection molecules, pomalimib, IFNγ, IFNα, TNFα, VEGF antibody, CD70 antibody, CD27 antibody, BCMA antibody or GPRC5D antibody, any combination thereof.

In some embodiments, the checkpoint inhibitor is ipilimumab, cetrelimab, pembrolizumab, nivolumab, sintilimab. cemiplimab, toripalimab, camrelizumab, tislelizumab, dostralimab, spartalizumab, prolgolimab, AK-105, HLX-10, balstilimab, MEDI-0680, HX-008, GLS-010, BI-754091, genolimzumab, AK-104, MGA-012, F-520, 609A, LY-3434172, AMG-404, SL-279252, SCT-I10A, RO-7121661, ICTCAR-014, MEDI-5752, CS-1003, XmAb-23104, Sym-021, LZM-009, hAB21, BAT-1306, MGD-019, JTX-4014, budigalimab, XmAb-20717, AK-103, MGD-013, IBI-318, sasanlimab, CC-90006, avelumab, atezolizumab, durvalumab, CS-1001, bintrafusp alpha, envafolimab, CX-072, GEN-1046, GS-4224, KL-A167, BGB-A333, SHR-1316, CBT-502, IL-103, KN-046, ZKAB-001, CA-170, TG 1501, LP-002, INCB-86550, ADG-104, SHR-1701, BCD-135, IMC-001, MSB-2311, FPT-155, FAZ-053, HLX-20, iodapolimab, FS-118, BMS-986189, AK-106, MCLA-145, IBI-318 or CK-301, or any combination thereof.

In some embodiments, one or more vaccines of the disclosure are administered in combination with ipilimumab, cetrelimab, pembrolizumab, nivolumab, sintilimab. cemiplimab, toripalimab, camrelizumab, tislelizumab, dostralimab, spartalizumab, prolgolimab, balstilimab, budigalimab, sasanlimab, avelumab, atezolizumab, durvalumab, envafolimab or iodapolimab, or any combination thereof.

Kits

The disclosure also provides a kit comprising:

a first vaccine comprising a recombinant virus derived from GAd20 comprising a heterologous polynucleotide encoding a heterologous polypeptide of SEQ ID NOs: 541, 550, 554, 555, 556, 623 or 624; and a second vaccine comprising a recombinant virus derived from MVA comprising a heterologous polynucleotide encoding a heterologous polypeptide of SEQ ID NOs: 543, 552, 557, 558, 559, 625 or 626.

The disclosure also provides a kit comprising:

a first vaccine comprising a recombinant virus derived from GAd20 comprising a heterologous polynucleotide encoding a heterologous polypeptide of SEQ ID NO: 541; and a second vaccine comprising a recombinant virus derived from MVA comprising a heterologous polynucleotide encoding a heterologous polypeptide of SEQ ID NO: 543.

The disclosure also provides a kit comprising:

a first vaccine comprising a recombinant virus derived from GAd20 comprising a heterologous polynucleotide encoding a heterologous polypeptide of SEQ ID NO: 550; and a second vaccine comprising a recombinant virus derived from MVA comprising a heterologous polynucleotide encoding a heterologous polypeptide of SEQ ID NO: 552.

Heterologous Polypeptides Encoding or Heterologous Polypeptides Comprising a Combination of Select Prostate Neoantigens The disclosure also provides an isolated heterologous polypeptide comprising two or more polypeptides selected from the group consisting of

```
AS18 comprising the amino acid sequence
                                    (SEQ ID NO: 275)
WKFEMSYTVGGPPPHVHARPRHWKTDR;

P87 comprising the amino acid sequence
                                    (SEQ ID NO: 381)
YEAGMTLGGKILFFLFLLLPLSPFSLIF;

A555 comprising the amino acid sequence
                                    (SEQ ID NO: 333)
DGHSYTSKVNCLLLQDGFHGCVSITGAAGRRNLSIFLFLMLCKLEFHAC;

A557 comprising the amino acid sequence
                                    (SEQ ID NO: 337)
TGGKSTCSAPGPQSLPSTPFSTYPQWVILITEL;
```

A515 comprising the amino acid sequence
(SEQ ID NO: 269)
VLRFLDLKVRYLHS;

A57 comprising the amino acid sequence
(SEQ ID NO: 253)
DYWAQKEKGSSSFLRPSC;

A543 comprising the amino acid sequence
(SEQ ID NO: 309)
VPFRELKNVSVLEGLRQGRLGGPCSCHCPRPSQARLTPVDVAGPFLCLGDP

GLFPPVKSSI;

AS51 comprising the amino acid sequence
(SEQ ID NO: 325)
GMECTLGQVGAPSPRREEDGWRGGHSRFKADVPAPQGPCWGGQPGSAPSS

APPEQSLLD;

AS16 comprising the amino acid sequence
(SEQ ID NO: 271)
GNTTLQQLGEASQAPSGSLIPLRLPLLWEVRG;

A541 comprising the amino acid sequence
(SEQ ID NO: 305)
EAFQRAAGEGGPGRGGARRGARVLQSPFCRAGAGEWLGHQSLR;

A56 comprising the amino acid sequence
(SEQ ID NO: 251)
DYWAQKEKISIPRTHLC;

A53 comprising the amino acid sequence
(SEQ ID NO: 245)
VAMMVPDRQVHYDFGL;

AS11 comprising the amino acid sequence
(SEQ ID NO: 261)
VPFRELKNQRTAQGAPGIHHAASPVAANLCDPARHAQHTRIPCGAGQVRA

GRGPEAGGGVLQPQRPAPEKPGCPCRRGQPRLHTVKMWRA;

A513 comprising the amino acid sequence
(SEQ ID NO: 265)
KRSFAVTERII;

A547 comprising the amino acid sequence
(SEQ ID NO: 317)
FKKFDGPCGERGGGRTARALWARGDSVLTPALDPQTPVRAPSLTRAAAAV;

A58 comprising the amino acid sequence
(SEQ ID NO: 255)
LVLGVLSGHSGSRL;

AS19 comprising the amino acid sequence
(SEQ ID NO: 277)
QWQHYHRSGEAAGTPLWRPTRN;

A537 comprising the amino acid sequence
(SEQ ID NO: 297)
CHLFLQPQVGTPPPHTASARAPSGPPHPHESCPAGRRPARAAQTCARRQH

GLPGCEEAGTARVPSLHLHLHQAALGAGRGRGWGEACAQVPPSRG;

A523 comprising the amino acid sequence
(SEQ ID NO: 285)
KIQNKNCPD;

MS1 comprising the amino acid sequence
(SEQ ID NO: 437)
HYKLIQQPISLFSITDRLHKTFSQLPSVHLCSITFQWGHPPIFCSTND

ICVTANFCISVTFLKPCFLLHEASASQ;

M53 comprising the amino acid sequence
(SEQ ID NO: 439)
RTALTHNQDFSIYRLCCKRGSLCHASQARSPAFPKPVRPLPAPITRI

TPQLGGQSDSSQPLLTTGRPQGWQDQALRHTQQASPASCATITIPIH

SAALGDHSGDPGPAWDTCPPLPLTTLIPRAPPPYGDSTARSWPSRCGPLG;

M56 comprising the amino acid sequence
(SEQ ID NO: 442)
YAYKDFLWCFPFSLVFLQEIQICCHVSCLCCICCSTRICLGCLLELFLSR

ALRALHVLWNGFQLHCQ;

M58 comprising the amino acid sequence
(SEQ ID NO: 444)
TMPAILKLQKNCLLSL;

and

P82 comprising the amino acid sequence
(SEQ ID NO: 379)
YEAGMTLGEKFRVGNCKHLKMTRP, and fragments thereof.

In some embodiments, the isolated heterologous polypeptide further comprises one or more polypeptides selected from the group consisting of P16 comprising the amino acid sequence
(SEQ ID NO: 343)
GVPGDSTRRAVRRMNTF;

FUS1 comprising the amino acid sequence
(SEQ ID NO: 211)
CGASACDVSLIAMDSA;

P22 comprising the amino acid sequence
(SEQ ID NO: 349)
SLYHREKQLIAMDSAI;

FUS2 comprising the amino acid sequence
(SEQ ID NO: 213)
TEYNQKLQVNQFSESK;

FUS3 comprising the amino acid sequence
(SEQ ID NO: 215)
TEISCCTLSSEENEYLPRPEWQLQ;

FUS6 comprising the amino acid sequence
(SEQ ID NO: 221)
CEERGAAGSLISCE;

FUS5 comprising the amino acid sequence
(SEQ ID NO: 219)
NSKMALNSEALSVVSE;

FUS8 comprising the amino acid sequence
(SEQ ID NO: 225)
WGMELAASRRFSWDHHSAGGPPRVPSVRSGAAQVQPKDPLPLRTLAGC

LARTAHLRPGAESLPQPQLHCT;

FUS15 comprising the amino acid sequence
(SEQ ID NO: 345)
HVVGYGHLDTSGSSSSSSWP;

P35 comprising the amino acid sequence
(SEQ ID NO: 353)
NSKMALNSLNSIDDAQLTRIAPPRSHCCFWEVNAP;

FUS19 comprising the amino acid sequence
(SEQ ID NO: 235)
KMHFSLKEHPPPPCPP;
and

FUS7 comprising the amino acid sequence
(SEQ ID NO: 223)
LWFQSSELSPTGAPWPSRRPTWRGTTVSPRTATSSARTCCGTKWPSSQE

AALGLGSGLLRFSCGTAAIR, and fragments thereof.

The disclosure also provides an isolated heterologous polypeptide comprising one or more polypeptides selected from the group consisting of P16 comprising the amino acid sequence (SEQ ID NO: 343)
GVPGDSTRRAVRRMNTF;

FUS1 comprising the amino acid sequence (SEQ ID NO: 211)
CGASACDVSLIAMDSA;

P22 comprising the amino acid sequence (SEQ ID NO: 349)
SLYHREKQLIAMDSAI;

FUS2 comprising the amino acid sequence (SEQ ID NO: 213)
TEYNQKLQVNQFSESK;

FUS3 comprising the amino acid sequence (SEQ ID NO: 215)
TEISCCTLSSEENEYLPRPEWQLQ;

FUS6 comprising the amino acid sequence (SEQ ID NO: 221)
CEERGAAGSLISCE;

FUSS comprising the amino acid sequence (SEQ ID NO: 219)
NSKMALNSEALSVVSE;

FUS8 comprising the amino acid sequence (SEQ ID NO: 225)
WGMELAASRRFSWDHHSAGGPPRVPSVRSGAAQVQPKDPLPLRTLAGC

LARTAHLRPGAESLPQPQLHCT;

FUS15 comprising the amino acid sequence (SEQ ID NO: 345)
HVVGYGHLDTSGSSSSSSWP;

P35 comprising the amino acid sequence (SEQ ID NO: 353)
NSKMALNSLNSIDDAQLTRIAPPRSHCCFWEVNAP;

FUS19 comprising the amino acid sequence (SEQ ID NO: 235)
KMHFSLKEHPPPPCPP;
and

FUS7 comprising the amino acid sequence (SEQ ID NO: 223)
LWFQSSELSPTGAPWPSRRPTWRGTTVSPRTATSSARTCCGTKWPSSQ

EAALGLGSGLLRFSCGTAAIR, and fragments thereof.

In some embodiments, the isolated heterologous polypeptide further comprises one or more polypeptides selected from the group consisting of AS18 comprising the amino acid sequence (SEQ ID NO: 275)
WKFEMSYTVGGPPPHVHARPRHWKTDR;

P87 comprising the amino acid sequence (SEQ ID NO: 381)
YEAGMTLGGKILFFLFLLLPLSPFSLIF;

AS55 comprising the amino acid sequence (SEQ ID NO: 333)
DGHSYTSKVNCLLLQDGFHGCVSITGAAGRRNLSIFLFLMLCKLEFHAC;

AS57 comprising the amino acid sequence (SEQ ID NO: 337)
TGGKSTCSAPGPQSLPSTPFSTYPQWVILITEL;

AS15 comprising the amino acid sequence (SEQ ID NO: 269)
VLRFLDLKVRYLHS;

-continued

AS7 comprising the amino acid sequence (SEQ ID NO: 253)
DYWAQKEKGSSSFLRPSC;

AS43 comprising the amino acid sequence (SEQ ID NO: 309)
VPFRELKNVSVLEGLRQGRLGGPCSCHCPRPSQARLTPVDVAGPFLCLG

DPGLFPPVKSSI;

AS51 comprising the amino acid sequence (SEQ ID NO: 325)
GMECTLGQVGAPSPRREEDGWRGGHSRFKADVPAPQGPCWGGQPGSAPS

SAPPEQSLLD;

AS16 comprising the amino acid sequence (SEQ ID NO: 271)
GNTTLQQLGEASQAPSGSLIPLRLPLLWEVRG;

AS41 comprising the amino acid sequence (SEQ ID NO: 305)
EAFQRAAGEGGPGRGGARRGARVLQSPFCRAGAGEWLGHQSLR;

AS6 comprising the amino acid sequence (SEQ ID NO: 251)
DYWAQKEKISIPRTHLC;

AS3 comprising the amino acid sequence (SEQ ID NO: 245)
VAMMVPDRQVHYDFGL;

AS11 comprising the amino acid sequence (SEQ ID NO: 261)
VPFRELKNQRTAQGAPGIHHAASPVAANLCDPARHAQHTRIPCGAGQVRA

GRGPEAGGGVLQPQRPAPEKPGCPCRRGQPRLHTVKMWRA;

AS13 comprising the amino acid sequence (SEQ ID NO: 265)
KRSFAVTERII;

AS47 comprising the amino acid sequence (SEQ ID NO: 317)
FKKFDGPCGERGGGRTARALWARGDSVLTPALDPQTPVRAPSLTRAAAAV;

A58 comprising the amino acid sequence (SEQ ID NO: 255)
LVLGVLSGHSGSRL;

AS19 comprising the amino acid sequence (SEQ ID NO: 277)
QWQHYHRSGEAAGTPLWRPTRN;

A537 comprising the amino acid sequence (SEQ ID NO: 297)
CHLFLQPQVGTPPPHTASARAPSGPPHPHESCPAGRRPARAAQTCARRQ

HGLPGCEEAGTARVPSLHLHLHQAALGAGRGRGWGEACAQVPPSRG;

A523 comprising the amino acid sequence (SEQ ID NO: 285)
KIQNKNCPD;

MS1 comprising the amino acid sequence (SEQ ID NO: 437)
HYKLIQQPISLFSITDRLHKTFSQLPSVHLCSITFQWGHPPIFCSTNDICV

TANFCISVTFLKPCFLLHEASASQ;

MS3 comprising the amino acid sequence (SEQ ID NO: 439)
RTALTHNQDFSIYRLCCKRGSLCHASQARSPAFPKPVRPLPAPITRITP

QLGGQSDSSQPLLTTGRPQGWQDQALRHTQQASPASCATITIPIHSAAL

GDHSGDPGPAWDTCPPLPLTTLIPRAPPPYGDSTARSWPSRCGPLG;

-continued

M56 comprising the amino acid sequence
(SEQ ID NO: 442)
YAYKDFLWCFPFSLVFLQEIQICCHVSCLCCICCSTRICLGCLLELFLS

RALRALHVLWNGFQLHCQ;

M58 comprising the amino acid sequence
(SEQ ID NO: 444)
TMPAILKLQKNCLLSL;
and

P82 comprising the amino acid sequence
(SEQ ID NO: 379)
YEAGMTLGEKFRVGNCKHLKMTRP, and fragments thereof.

In some embodiments, the isolated heterologous polypeptide further comprises one or more polypeptides selected from the group consisting of M84 comprising the amino acid sequence
(SEQ ID NO: 167)
IARELHQFAFDLLIKSH;

M86 comprising the amino acid sequence
(SEQ ID NO: 171)
QPDSFAALHSSLNELGE;

M10 comprising the amino acid sequence
(SEQ ID NO: 19)
FVQGKDWGLKKFIRRDF;

M12 comprising the amino acid sequence
(SEQ ID NO: 23)
FVQGKDWGVKKFIRRDF;
and

FR1 comprising the amino acid sequence
(SEQ ID NO: 177)
QNLQNGGGSRSSATLPGRRRRRWLRRRRQPISVAPAGPPRRPNQKPNPPGG

ARCVIMRPTWPGTSAFT, and fragments thereof.

The disclosure also provides a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide comprising two or more polynucleotides selected from the group consisting of the polynucleotide sequence of the polynucleotide sequence of
(SEQ ID NO: 276)
TGGAAATTCGAGATGAGCTACACGGTGGGTGGCCCGCCTCCCCATGTTC ATGCTAGACCCAGGCATTGGAAAACTGATAGA (encoding AS18);

the polynucleotide sequence of
(SEQ ID NO: 382)
TATGAAGCAGGGATGACTCTGGGAGGTAAGATACTTTTCTTTCTCTTCC TCCTCCTTCCTCTCTCCCCCTTCTCCCTCATTTTC (encoding

P87);

-continued the polynucleotide sequence of
(SEQ ID NO: 334)
GATGGCCACTCCTACACATCCAAGGTGAATTGTTTACTCCTTCAAGATG

GGTTCCATGGCTGTGTGAGCATCACCGGGGCAGCTGGAAGAAGAAACCT

GAGCATCTTCCTGTTCTTGATGCTGTGCAAATTGGAGTTCCATGCTTGT (encoding AS55);

the polynucleotide sequence of
(SEQ ID NO: 338)
ACAGGGGGCAAAAGCACCTGCTCGGCTCCTGGCCCTCAGTCTCTCCCCT

CCACTCCATTCTCCACCTACCCACAGTGGGTCATTCTGATCACCGAACT

G (encoding AS57);

the polynucleotide sequence of
(SEQ ID NO: 270)
GTGCTGCGCTTTCTGGACTTAAAGGTGAGATACCTGCACTCT (encoding AS15);

the polynucleotide sequence of
(SEQ ID NO: 254)
GACTACTGGGCTCAAAAGGAGAAGGGATCATCTTCATTCCTGCGACCAT CCTGT (encoding AS7);

the polynucleotide sequence of
(SEQ ID NO: 310)
GTGCCCTTCCGGGAGCTCAAGAACGTGAGTGTCCTGGAGGGGCTCCGTC

AAGGCCGGCTTGGGGGTCCCTGTTCATGTCACTGCCCAAGACCTTCCCA

GGCCAGGCTCACGCCAGTGGATGTGGCAGGTCCCTTCTTGTGTCTGGGG

GATCCTGGGCTGTTCCCCCCAGTCAAGAGCAGTATC (encoding

AS43);

the polynucleotide sequence of
(SEQ ID NO: 326)
GGCATGGAGTGCACCCTGGGGCAGGTGGGTGCCCCGTCCCCTCGGAGGG

AGGAGGACGGTTGGCGTGGGGGCCACAGCCGATTCAAGGCTGATGTACC

AGCACCGCAGGGACCCTGCTGGGGTGGCCAACCTGGCTCTGCCCCCTCC

TCAGCTCCTCCTGAACAGTCATTATTAGAT (encoding AS51);

the polynucleotide sequence of
(SEQ ID NO: 272)
GGCAACACCACCCTCCAGCAGCTGGGTGAGGCCTCCCAGGCGCCCTCAG

GCTCCCTCATCCCTCTGAGGCTGCCTCTGCTCTGGGAAGTGAGGGGC (encoding AS16);

the polynucleotide sequence of
(SEQ ID NO: 306)
GAGGCCTTCCAGAGGGCCGCTGGTGAGGGCGGCCCGGGCCGCGGTGGGG

CACGGCGCGGTGCCAGGGTGTTGCAGAGCCCCTTTTGCAGGGCAGGAGC

TGGGGAGTGGTTAGGACATCAGTCCCTCAGG (encoding AS41);

the polynucleotide sequence of
(SEQ ID NO: 252)
GACTACTGGGCTCAAAAGGAGAAGATCAGCATCCCCAGAACACACCTGT GT (encoding AS6);

the polynucleotide sequence of
(SEQ ID NO: 246)
GTTGCTATGATGGTTCCTGATAGACAGGTTCATTATGACTTTGGATTG (encoding AS3);

-continued the polynucleotide sequence of (SEQ ID NO: 262)
GTGCCCTTCCGGGAGCTCAAGAACCAGAGAACAGCACAAGGGGCTCCTG
GGATCCACCACGCGGCTTCCCCCGTTGCTGCCAACCTCTGCGACCCGGC
GAGACACGCACAGCACACACGCATCCCCTGCGGCGCTGGCCAAGTGCGT
GCTGGCCGAGGTCCCGAAGCAGGTGGTGGAGTACTACAGCCACAGAGGC
CTGCCCCCGAGAAGCCTGGGTGTCCCTGCCGGAGAGGCCAGCCCAGGCT
GCACACCGTGAAGATGTGGAGGGCG (encoding AS11);

the polynucleotide sequence of (SEQ ID NO: 266)
AAGAGAAGTTTTGCTGTCACGGAGAGGATCATC (encoding AS13);

the polynucleotide sequence of (SEQ ID NO: 318)
TTCAAGAAGTTCGACGGCCCTTGTGGTGAGCGCGGCGGCGGGCGCACGG
CTCGAGCTCTGTGGGCGCGCGGCGACAGCGTCCTGACTCCTGCCCTCGA
CCCCCAGACCCCTGTCAGGGCGCCCTCCCTGACCCGAGCCGCAGCTGCC
GTG (encoding AS47);

the polynucleotide sequence of (SEQ ID NO: 256)
CTTGTACTTGGTGTATTGAGCGGGCACAGTGGCTCACGCCTA
(encoding AS8);

the polynucleotide sequence of (SEQ ID NO: 278)
CAGTGGCAGCACTACCACCGGTCAGGTGAGGCCGCAGGGACTCCCCTCT
GGAGACCCACAAGAAAC (encoding AS19);

the polynucleotide sequence of (SEQ ID NO: 298)
TGCCACCTCTTCCTGCAGCCCCAGGTTGGCACCCCCCCCCCCCACACTG
CCAGTGCTCGAGCCCCCAGTGGTCCACCCCACCCTCATGAAAGTTGCCC
TGCAGGGCGAAGACCTGCGAGAGCTGCGCAGACATGTGCACGCCGACAG
CACGGACTTCCTGGCTGTGAAGAGGCTGGTACAGCGCGTGTTCCCAGCC
TGCACCTGCACCTGCACCAGGCCGCCCTCGGAGCAGGAAGGGGCCGTGG
GTGGGGAGAGGCCTGTGCCCAAGTACCCCCCTCAAGAGGC
(encoding AS37);

the polynucleotide sequence of (SEQ ID NO: 286)
AAAATTCAGAATAAAAATTGTCCAGAC (encoding AS23);

the polynucleotide sequence of (SEQ ID NO: 448)
CACTACAAATTAATTCAACAACCCATATCCCTCTTCTCCATCACTGATA
GGCTCCATAAGACGTTCAGTCAGCTGCCCTCGGTCCATCTCTGCTCAAT
CACCTTCCAGTGGGGACACCCGCCCATTTTCTGCTCAACAAATGATATC
TGTGTCACGGCCAACTTCTGCATCTCGGTCACATTCCTTAAACCGTGCT
TCCTCCTACATGAGGCATCTGCCTCACAG (encoding MS1);

the polynucleotide sequence of (SEQ ID NO: 450)
AGGACCGCCCTGACACACAATCAGGACTTCTCTATCTACAGGCTCTGTT
GCAAGAGGGGGTCCCTCTGCCACGCTTCCCAGGCCAGATCCCCGGCTTT
CCCGAAGCCGGTCAGACCTCTTCCTGCCCCCATCACCAGAATCACCCCC
CAACTGGGGGGACAATCTGACTCGAGTCAACCCCTTCTCACTACGGGAA -continued GACCTCAGGGGTGGCAAGATCAAGCTCTTAGACACACCCAGCAAGCCAG
TCCTGCCTCTTGTGCCACCATCACCATTCCCATCCACTCAGCTGCCCTT
GGTGACCACTCCGGAGACCCTGGTCCAGCCTGGGACACCTGCCCGCCGC
TGCCGCTCACTACCCTCATCCCCCGAGCTCCCCCGCCGTATGGAGACAG
CACTGCCAGGTCCTGGCCCTCCCGCTGTGGGCCCCTCGGC
(encoding MS3);

the polynucleotide sequence of (SEQ ID NO: 453)
TATGCTTACAAGGACTTTCTCTGGTGTTTTCCTTTTTCTTTAGTTTTTC
TCCAAGAGATTCAAATCTGCTGCCATGTTAGCTGTCTTTGCTGTATCTG
CTGTAGTACACGAATATGCCTTGGCTGTTTGCTTGAGCTTTTTCTATCC
CGTGCTCTTCGTGCTCTTCATGTTCTTTGGAATGGCTTTCAACTTCATT
GTCAA (encoding MS6);

the polynucleotide sequence of (SEQ ID NO: 455)
ACCATGCCTGCTATTTTAAAGTTACAGAAGAATTGTCTTCTCTCCTTA
(encoding MS8);
and the polynucleotide sequence of (SEQ ID NO: 380)
TATGAAGCAGGGATGACTCTGGGAGAAAAATTCCGGGTTGGCAATTGCA
AGCATCTCAAAATGACCAGACCC (encoding P82);

and fragments thereof.

In some embodiments, the isolated heterologous polynucleotide further comprises one or more polynucleotides selected from the group consisting of the polynucleotide sequence of (SEQ ID NO: 344)
GGAGTTCCAGGAGATTCAACCAGGAGAGCAGTGAGGAGAATGAATACCT
TC (encoding P16);

the polynucleotide sequence of (SEQ ID NO: 212)
TGCGGGGCCTCTGCCTGTGATGTCTCCCTCATTGCTATGGACAGTGCT
(encoding FUS1);

the polynucleotide sequence of (SEQ ID NO: 350)
TCCCTCTACCACCGGGAGAAGCAGCTCATTGCTATGGACAGTGCTATC
(encoding P22);

the polynucleotide sequence of (SEQ ID NO: 214)
ACCGAATACAACCAGAAATTACAAGTGAATCAATTTAGTGAATCCAAA
(encoding FUS2);

the polynucleotide sequence of (SEQ ID NO: 216)
ACAGAAATTTCATGTTGCACCCTGAGCAGTGAGGAGAATGAATACCTTC
CAAGACCAGAGTGGCAGCTCCAG (encoding FUS3);

the polynucleotide sequence of (SEQ ID NO: 222)
TGTGAGGAGCGCGGCGCGGCAGGAAGCCTTATCAGTTGTGAG
(encoding FUS6);

-continued the polynucleotide sequence of (SEQ ID NO: 220) AACAGCAAGATGGCTTTGAACTCAGAAGCCTTATCAGTTGTGAGTGAG (encoding FUS5);

the polynucleotide sequence of (SEQ ID NO: 226) TGGGGGATGGAGTTGGCAGCGTCTCGGAGGTTCTCCTGGGACCACCACT CCGCCGGGGGGCCGCCCAGAGTGCCAAGCGTCCGATCCGGCGCCGCCCA AGTGCAGCCCAAGGACCCGCTCCCGCTCCGCACCCTGGCAGGCTGCCTA GCCAGGACTGCGCACCTGCGCCCTGGGGCGGAGTCCTTACCCCAACCCC AGCTTCACTGCACA (encoding FUS8);

the polynucleotide sequence of (SEQ ID NO: 346) CACGTGGTGGGCTATGGCCACCTTGATACTTCCGGGTCATCCTCCTCCT CCTCCTGGCCC (encoding FUS15);

the polynucleotide sequence of (SEQ ID NO: 354) AACAGCAAGATGGCTTTGAACTCATTAAACTCCATTGATGATGCACAGT TGACAAGAATTGCCCCTCCAAGATCTCATTGCTGTTTCTGGGAAGTAAA CGCTCCT (encoding P35);

the polynucleotide sequence of (SEQ ID NO: 236) AAAATGCACTTCTCCCTCAAGGAGCACCCACCGCCCCCTTGCCCGCCT (encoding FUS19);
and the polynucleotide sequence of (SEQ ID NO: 224) CTGTGGTTCCAGAGCAGTGAGCTGTCCCCGACGGGAGCGCCATGGCCCA GCCGCCGCCCGACGTGGAGGGGGACGACTGTCTCCCCGCGTACCGCCAC CTCTTCTGCCCGGACCTGCTGCGGGACAAAGTGGCCTTCATCACAGGAG GCGGCTCTGGGATTGGGTTCCGGATTGCTGAGATTTTCATGCGGCACGG CTGCCATACGG (encoding FUS7), and fragments thereof.

The disclosure also provides an isolated heterologous polynucleotide comprising two or more polynucleotides selected from the group consisting of the polynucleotide sequence of (SEQ ID NO: 344) GGAGTTCCAGGAGATTCAACCAGGAGAGCAGTGAGGAGAATGAATACCTT C(encoding P16);

the polynucleotide sequence of (SEQ ID NO: 212) TGCGGGGCCTCTGCCTGTGATGTCTCCCTCATTGCTATGGACAGTGC T(encoding FUS1);

the polynucleotide sequence of (SEQ ID NO: 350) TCCCTCTACCACCGGGAGAAGCAGCTCATTGCTATGGACAGTGCTAT C(encoding P22);

the polynucleotide sequence of (SEQ ID NO: 214) ACCGAATACAACCAGAAATTACAAGTGAATCAATTTAGTGAATCCAA A(encoding FUS2);

-continued the polynucleotide sequence of (SEQ ID NO: 216) ACAGAAATTTCATGTTGCACCCTGAGCAGTGAGGAGAATGAATACCTTCC AAGACCAGAGTGGCAGCTCCAG(encoding FUS3);

the polynucleotide sequence of (SEQ ID NO: 222) TGTGAGGAGCGCGGCGCGGCAGGAAGCCTTATCAGTTGTGA G(encoding FUS6);

the polynucleotide sequence of (SEQ ID NO: 220) AACAGCAAGATGGCTTTGAACTCAGAAGCCTTATCAGTTGTGAGTGA G(encoding FUS5);

the polynucleotide sequence of (SEQ ID NO: 226) TGGGGGATGGAGTTGGCAGCGTCTCGGAGGTTCTCCTGGGACCACCACTC CGCCGGGGGGCCGCCCAGAGTGCCAAGCGTCCGATCCGGCGCCGCCCAAG TGCAGCCCAAGGACCCGCTCCCGCTCCGCACCCTGGCAGGCTGCCTAGCC AGGACTGCGCACCTGCGCCCTGGGGCGGAGTCCTTACCCCAACCCCAGCT TCACTGCACA(encoding FUS8);

the polynucleotide sequence of (SEQ ID NO: 346) CACGTGGTGGGCTATGGCCACCTTGATACTTCCGGGTCATCCTCCTCCTC CTCCTGGCCC(encoding FUS15);

the polynucleotide sequence of (SEQ ID NO: 354) AACAGCAAGATGGCTTTGAACTCATTAAACTCCATTGATGATGCACAGTT GACAAGAATTGCCCCTCCAAGATCTCATTGCTGTTTCTGGGAAGTAAACG CTCCT(encoding P35);

the polynucleotide sequence of (SEQ ID NO: 236) AAAATGCACTTCTCCCTCAAGGAGCACCCACCGCCCCCTTGCCCGCC T(encoding FUS19);
and the polynucleotide sequence of (SEQ ID NO: 224) CTGTGGTTCCAGAGCAGTGAGCTGTCCCCGACGGGAGCGCCATGGCCCAG CCGCCGCCCGACGTGGAGGGGGACGACTGTCTCCCCGCGTACCGCCACCT CTTCTGCCCGGACCTGCTGCGGGACAAAGTGGCCTTCATCACAGGAGGCG GCTCTGGGATTGGGTTCCGGATTGCTGAGATTTTCATGCGGCACGGCTGC CATACGG(encoding FUS7).

In some embodiments, the isolated heterologous polynucleotide further comprises one or more polynucleotides or one or more at least 24 nucleotide long contiguous fragments of the one or more polynucleotides, wherein the polynucleotides comprise the polynucleotide sequence of (SEQ ID NO: 276) TGGAAATTCGAGATGAGCTACACGGTGGGTGGCCCGCCTCCCCATGTTCA TGCTAGACCCAGGCATTGGAAAACTGATAGA(encoding AS18);

-continued the polynucleotide sequence of
(SEQ ID NO: 382)
TATGAAGCAGGGATGACTCTGGGAGGTAAGATACTTTTCTTTCTCTTCCT
CCTCCTTCCTCTCTCCCCCTTCTCCCTCATTTTC(encoding P87);

the polynucleotide sequence of
(SEQ ID NO: 334)
GATGGCCACTCCTACACATCCAAGGTGAATTGTTTACTCCTTCAAGATGG
GTTCCATGGCTGTGTGAGCATCACCGGGGCAGCTGGAAGAAGAAACCTGA
GCATCTTCCTGTTCTTGATGCTGTGCAAATTGGAGTTCCATGCTTG
T(encoding AS55);

the polynucleotide sequence of
(SEQ ID NO: 338)
ACAGGGGGCAAAAGCACCTGCTCGGCTCCTGGCCCTCAGTCTCTCCCCTC
CACTCCATTCTCCACCTACCCACAGTGGGTCATTCTGATCACCGAACT
G(encoding AS57);

the polynucleotide sequence of
(SEQ ID NO: 270)
GTGCTGCGCTTTCTGGACTTAAAGGTGAGATACCTGCACTC
T(encoding AS15);

the polynucleotide sequence of
(SEQ ID NO: 254)
GACTACTGGGCTCAAAAGGAGAAGGGATCATCTTCATTCCTGCGACCATC
CTGT(encoding AS7);

the polynucleotide sequence of
(SEQ ID NO: 310)
GTGCCCTTCCGGGAGCTCAAGAACGTGAGTGTCCTGGAGGGGCTCCGTCA
AGGCCGGCTTGGGGGTCCCTGTTCATGTCACTGCCCAAGACCTTCCCAGG
CCAGGCTCACGCCAGTGGATGTGGCAGGTCCCTTCTTGTGTCTGGGGGAT
CCTGGGCTGTTCCCCCCAGTCAAGAGCAGTATC(encoding AS43);

the polynucleotide sequence of
(SEQ ID NO: 326)
GGCATGGAGTGCACCCTGGGGCAGGTGGGTGCCCCGTCCCCTCGGAGGGA
GGAGGACGGTTGGCGTGGGGGCCACAGCCGATTCAAGGCTGATGTACCAG
CACCGCAGGGACCCTGCTGGGGTGGCCAACCTGGCTCTGCCCCCTCCTCA
GCTCCTCCTGAACAGTCATTATTAGAT(encoding AS51);

the polynucleotide sequence of
((SEQ ID NO: 272)
GGCAACACCACCCTCCAGCAGCTGGGTGAGGCCTCCCAGGCGCCCTCAGG
CTCCCTCATCCCTCTGAGGCTGCCTCTGCTCTGGGAAGTGAGGGG
C(encoding AS16);

the polynucleotide sequence of
(SEQ ID NO: 306)
GAGGCCTTCCAGAGGGCCGCTGGTGAGGGCGGCCCGGGCCGCGGTGGGGC
ACGGCGCGGTGCCAGGGTGTTGCAGAGCCCCTTTTGCAGGGCAGGAGCTG
GGGAGTGGTTAGGACATCAGTCCCTCAGG(encoding AS41);

the polynucleotide sequence of
(SEQ ID NO: 252)
GACTACTGGGCTCAAAAGGAGAAGATCAGCATCCCCAGAACACACCTGTG
T(encoding AS6);

the polynucleotide sequence of
(SEQ ID NO: 246)
GTTGCTATGATGGTTCCTGATAGACAGGTTCATTATGACTTTGGATT
G(encoding AS3);

the polynucleotide sequence of
(SEQ ID NO: 262)
GTGCCCTTCCGGGAGCTCAAGAACCAGAGAACAGCACAAGGGGCTCCTGG
GATCCACCACGCGGCTTCCCCCGTTGCTGCCAACCTCTGCGACCCGGCGA
GACACGCACAGCACACACGCATCCCCTGCGGCGCTGGCCAAGTGCGTGCT
GGCCGAGGTCCCGAAGCAGGTGGTGGAGTACTACAGCCACAGAGGCCTGC
CCCCGAGAAGCCTGGGTGTCCCTGCCGGAGAGGCCAGCCCAGGCTGCACA
CCGTGAAGATGTGGAGGGCG(encoding AS11);

the polynucleotide sequence of
(SEQ ID NO: 266)
AAGAGAAGTTTTGCTGTCACGGAGAGGATCATC(encoding AS13);

the polynucleotide sequence of
(SEQ ID NO: 318)
TTCAAGAAGTTCGACGGCCCTTGTGGTGAGCGCGGCGGCGGGCGCACGGC
TCGAGCTCTGTGGGCGCGCGGCGACAGCGTCCTGACTCCTGCCCTCGACC
CCCAGACCCCTGTCAGGGCGCCCTCCCTGACCCGAGCCGCAGCTGCCGT
G(encoding AS47);

the polynucleotide sequence of
(SEQ ID NO: 256)
CTTGTACTTGGTGTATTGAGCGGGCACAGTGGCTCACGCCT
A(encoding AS8);

the polynucleotide sequence of
(SEQ ID NO: 278)
CAGTGGCAGCACTACCACCGGTCAGGTGAGGCCGCAGGGACTCCCCTCTG
GAGACCCACAAGAAAC(encoding AS19);

the polynucleotide sequence of
(SEQ ID NO: 298)
TGCCACCTCTTCCTGCAGCCCCAGGTTGGCACCCCCCCCCCCCACACTGC
CAGTGCTCGAGCCCCCAGTGGTCCACCCCACCCTCATGAAAGTTGCCCTG
CAGGGCGAAGACCTGCGAGAGCTGCGCAGACATGTGCACGCCGACAGCAC
GGACTTCCTGGCTGTGAAGAGGCTGGTACAGCGCGTGTTCCCAGCCTGCA
CCTGCACCTGCACCAGGCCGCCCTCGGAGCAGGAAGGGGCCGTGGGTGGG
GAGAGGCCTGTGCCCAAGTACCCCCCTCAAGAGGC(encoding
AS37);

the polynucleotide sequence of
(SEQ ID NO: 286)
AAAATTCAGAATAAAAATTGTCCAGAC(encoding AS23);

the polynucleotide sequence of
(SEQ ID NO: 448)
CACTACAAATTAATTCAACAACCCATATCCCTCTTCTCCATCACTGATAG
GCTCCATAAGACGTTCAGTCAGCTGCCCTCGGTCCATCTCTGCTCAATCA
CCTTCCAGTGGGGACACCCGCCCATTTTCTGCTCAACAAATGATATCTGT
GTCACGGCCAACTTCTGCATCTCGGTCACATTCCTTAAACCGTGCTTCCT
CCTACATGAGGCATCTGCCTCACAG(encoding MS1);

-continued the polynucleotide sequence of (SEQ ID NO: 450)
AGGACCGCCCTGACACACAATCAGGACTTCTCTATCTACAGGCTCTGTTG
CAAGAGGGGGTCCCTCTGCCACGCTTCCCAGGCCAGATCCCCGGCTTTCC
CGAAGCCGGTCAGACCTCTTCCTGCCCCCATCACCAGAATCACCCCCCAA
CTGGGGGGACAATCTGACTCGAGTCAACCCCTTCTCACTACGGGAAGACC
TCAGGGGTGGCAAGATCAAGCTCTTAGACACACCCAGCAAGCCAGTCCTG
CCTCTTGTGCCACCATCACCATTCCCATCCACTCAGCTGCCCTTGGTGAC
CACTCCGGAGACCCTGGTCCAGCCTGGGACACCTGCCCGCCGCTGCCGCT
CACTACCCTCATCCCCCGAGCTCCCCCGCCGTATGGAGACAGCACTGCCA
GGTCCTGGCCCTCCCGCTGTGGGCCCCTCGGC (encoding MS3);

the polynucleotide sequence of (SEQ ID NO: 453)
TATGCTTACAAGGACTTTCTCTGGTGTTTTCCTTTTTCTTTAGTTTTTCT
CCAAGAGATTCAAATCTGCTGCCATGTTAGCTGTCTTTGCTGTATCTGCT
GTAGTACACGAATATGCCTTGGCTGTTTGCTTGAGCTTTTTCTATCCCGT
GCTCTTCGTGCTCTTCATGTTCTTTGGAATGGCTTTCAACTTCATTGTCA
A (encoding MS6);

the polynucleotide sequence of (SEQ ID NO: 455)
ACCATGCCTGCTATTTTAAAGTTACAGAAGAATTGTCTTCTCTCCTT
A (encoding MS8);
and the polynucleotide sequence of (SEQ ID NO: 380)
TATGAAGCAGGGATGACTCTGGGAGAAAAATTCCGGGTTGGCAATTGCAA
GCATCTCAAAATGACCAGACCC (encoding P82), and fragments thereof.

In some embodiments, the isolated heterologous polynucleotide further comprises one or more polynucleotides selected from the group consisting of the polynucleotide sequence of (SEQ ID NO: 168)
ATTGCGAGAGAGCTGCATCAGTTCGCTTTTGACCTGCTAATCAAGTCAC
AC (encoding M84);

the polynucleotide sequence of (SEQ ID NO: 172)
CAGCCCGACTCCTTTGCAGCCTTGCACTCTAGCCTCAATGAACTGGGAG
AG (encoding M86);

the polynucleotide sequence of (SEQ ID NO: 20)
TTTGTGCAAGGCAAAGACTGGGGATTAAAGAAATTCATCCGTAGAGATT
TT (encoding M10);

the polynucleotide sequence of (SEQ ID NO: 24)
TTTGTGCAAGGCAAAGACTGGGGAGTCAAGAAATTCATCCGTAGAGATT
TT (encoding M12);
and -continued the polynucleotide sequence of (SEQ ID NO: 178)
CAGAACCTGCAGAATGGAGGGGGGAGCAGGTCTTCAGCCACACTGCCGG
GGCGGCGGCGGCGGCGGTGGCTGCGGCGGCGGCGGCAGCCAATATCAGT
AGCTCCTGCGGGGCCCCCTCGCCGACCAAACCAAAAACCAAACCCACCT
GGCGGTGCGAGGTGTGTGATTATGAGACCAACGTGGCCAGGAACCTCCG
CATTCACA (encoding FR1);

The disclosure also provides a heterologous polynucleotide encoding two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof. The polynucleotides are useful in expression in adenovirus.

The disclosure also provides a heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof. The polynucleotides are useful in expression in MVA.

For example, a heterologous polynucleotide of SEQ ID NO: 542 encoding a heterologous polypeptide of SEQ ID NO: 541 by may be used to generate adenovirus-based prostate cancer vaccines, such as those based on rGAd20. Alternatively, heterologous polynucleotides encoding heterologous polypeptides of SEQ ID NOs: 550, 554, 555, 556, 623 or 624 may also be used in adenovirus-based vaccines. In addition to the heterologous polynucleotide encoding the combination of the 41 neoantigens, additional facilitator elements may be included to the 5' or 3' of the heterologous polynucleotide, such as regulatory sequences, tags, and the like. Exemplary facilitator elements include CMV promoter, vaccinia P7.5 promoter, TetO repressor, Kozak sequence, a polynucleotide encoding a T cell enhancer (TCE), a polynucleotide encoding a histidine tag, one or more stop codons, a polyadenylation signal or a promoter sequence. Exemplary polynucleotide sequences of the facilitator elements comprise CMVTetO promoter comprising SEQ ID NO: 628, Kozak sequence comprising SEQ ID NO: 545, the polynucleotide encoding the TCE comprising SEQ ID NO: 546, the polynucleotide encoding the histidine tag comprising SEQ ID NO: 547, a BGH polyadenylation site comprising SEQ ID NO: 629, the one or more stop codons comprising the polynucleotide sequence of TAGTAA, the CMV promoter comprising a polynucleotide of SEQ ID NO: 628 or the vaccinia P7.5 promoter comprising a polynucleotide of SEQ ID NO: 630. Thus the heterologous polynucleotide comprising one or more additional facilitator sequences comprises the polynucleotide sequence of SEQ ID NO: 551, encoding the polypeptide of SEQ ID NO: 550.

In some embodiments, the isolated heterologous polypeptide comprises the amino acid sequence of SEQ ID NO: 541.

In some embodiments, the heterologous polypeptide is encoded by the heterologous polynucleotide of SEQ ID NO: 542.

In some embodiments, the heterologous polynucleotide further comprises one or more facilitator elements.

In some embodiments, the facilitator elements comprises a promoter, an enhancer, a polyadenylation site, a Kozak sequence, a stop codon, a T cell enhancer (TCE), or any combination thereof.

In some embodiments, the Kozak sequence comprises SEQ ID NO: 545, the polynucleotide encoding the TCE comprises SEQ ID NO: 546, the polynucleotide encoding the histidine tag comprises SEQ ID NO: 547 and the one or more stop codons comprises the polynucleotide sequence of TAGTAA.

In some embodiments, the TCE is encoded by a polynucleotide of SEQ ID NO: 546, the CMV promoter comprises a polynucleotide of SEQ ID NO: 628, the vaccinia P7.5 promoter comprises a polynucleotide of SEQ ID NO: 630 and the polyadenylation site comprises a bovine growth hormone polyadenylation site of SEQ ID NO: 629.

The disclosure also provides an isolated heterologous polypeptide comprising the amino acid sequence of SEQ ID NO: 550.

In some embodiments, the heterologous polypeptide is encoded by the heterologous polynucleotide of SEQ ID NO: 551.

The disclosure also provides an isolated heterologous polypeptide comprising the amino acid sequence of SEQ ID NO: 554.

In some embodiments, the isolated heterologous polypeptide comprises the amino acid sequence of SEQ ID NO: 555.

The disclosure also provides an isolated heterologous polypeptide comprising the amino acid sequence of SEQ ID NO: 556.

In some embodiments, the isolated heterologous polypeptide comprises the amino acid sequence of SEQ ID NO: 623.

The disclosure also provides an isolated heterologous polypeptide comprising the amino acid sequence of SEQ ID NO: 624.

In some embodiments, the heterologous polynucleotide is DNA. In some embodiments, the heterologous polynucleotide is RNA. In some embodiments, the heterologous polynucleotide is mRNA. In some embodiments, the heterologous polynucleotide is self-replicating RNA.

The heterologous polynucleotide of SEQ ID NO: 544 encoding the heterologous polypeptide of SEQ ID NO: 543 may be used to engineer MVA-based prostate cancer vaccines. Alternatively, the heterologous polypeptides of SEQ ID NOs: 557, 558, 559, 625 or 626 may also be used. In addition to the heterologous polynucleotide encoding the combination of the 41 neoantigens, additional facilitator elements may be included to the 5' or 3' of the heterologous polynucleotide, such as regulatory sequences, tags, and the like. Exemplary facilitator sequences include Kozak sequence, a polynucleotide encoding a T cell enhancer (TCE), a polynucleotide encoding a histidine tag, one or more stop codons, a polyadenylation signal or a promoter sequence. Exemplary polynucleotide sequences of the facilitator elements comprise Kozak sequence comprising SEQ ID NO: 545, the polynucleotide encoding the TCE comprising SEQ ID NO: 546, the polynucleotide encoding the histidine tag comprising SEQ ID NO: 547 and the one or more stop codons comprising the polynucleotide sequence of TAGTAA. Thus a heterologous polynucleotide comprising one or more additional facilitator elements comprises the polynucleotide sequence of SEQ ID NO: 553, encoding the polypeptide of SEQ ID NO: 552.

The disclosure also provides an isolated heterologous polypeptide comprising the amino acid sequence of SEQ ID NO: 543.

In some embodiments, the heterologous polypeptide is encoded by the heterologous polynucleotide of SEQ ID NO: 544.

In some embodiments, the heterologous polynucleotide further comprises one or more facilitator elements.

In some embodiments, the facilitator elements comprises a promoter, an enhancer, a polyadenylation site, a Kozak sequence, a stop codon, a T cell enhancer (TCE), or any combination thereof.

In some embodiments, the Kozak sequence comprises SEQ ID NO: 545, the polynucleotide encoding the TCE comprises SEQ ID NO: 546, the polynucleotide encoding the histidine tag comprises SEQ ID NO: 547 and the one or more stop codons comprises the polynucleotide sequence of TAGTAA.

In some embodiments, the TCE is encoded by a polynucleotide of SEQ ID NO: 546, the CMV promoter comprises a polynucleotide of SEQ ID NO: 628, the vaccinia P7.5 promoter comprises a polynucleotide of SEQ ID NO: 630 and the polyadenylation site comprises a bovine growth hormone polyadenylation site of SEQ ID NO: 629. In some embodiments, the isolated heterologous polypeptide comprises the amino acid sequence of SEQ ID NO: 552.

In some embodiments, the heterologous polypeptide is encoded by the heterologous polynucleotide of SEQ ID NO: 553.

The disclosure also provides an isolated heterologous polypeptide comprising the amino acid sequence of SEQ ID NO: 557.

The disclosure also provides an isolated heterologous polypeptide comprising the amino acid sequence of SEQ ID NO: 558.

The disclosure also provides an isolated heterologous polypeptide comprising the amino acid sequence of SEQ ID NO: 559.

The disclosure also provides an isolated heterologous polypeptide comprising the amino acid sequence of SEQ ID NO: 625.

The disclosure also provides an isolated heterologous polypeptide comprising the amino acid sequence of SEQ ID NO: 626.

In some embodiments, the heterologous polynucleotide is DNA. In some embodiments, the heterologous polynucleotide is RNA. In some embodiments, the heterologous polynucleotide is mRNA. In some embodiments, the heterologous polynucleotide is self-replicating RNA.

One or more fragments of the 41 prostate neoantigens (SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177) may also be used to generate a prostate cancer vaccine, as long as the one or more fragments are immunogenic. Exemplary such fragments that may be used are polypeptides of SEQ ID NOs: 387, 388, 390, 392, 405, 406, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709. Immunogenicity of the fragments can be tested using assays described herein.

In some embodiments, the first N-terminal amino acid residue of the fragment is absent.

The disclosure also provides an isolated heterologous polynucleotide encoding the heterologous polypeptide of the disclosure.

In some embodiments, the first 5' codon of the fragment is absent.

The disclosure also provides a vector comprising a heterologous polynucleotide encoding two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides a vector comprising a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides a vector comprising a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof. The polynucleotides are useful in expression in adenovirus.

The disclosure also provides a vector comprising a heterologous polynucleotide encoding the heterologous polypeptide of SEQ ID NO: 541. In some embodiments, the heterologous polynucleotide comprises the polynucleotide of SEQ ID NO: 542.

The disclosure also provides a vector comprising the heterologous polynucleotide of SEQ ID NO: 542.

The disclosure also provides a vector comprising a heterologous polynucleotide encoding the heterologous polypeptide of SEQ ID NO: 550. In some embodiments, the heterologous polynucleotide comprises the polynucleotide of SEQ ID NO: 551.

The disclosure also provides a vector comprising the heterologous polynucleotide of SEQ ID NO: 551.

The disclosure also provides a vector comprising a heterologous polynucleotide encoding the heterologous polypeptide of SEQ ID NO: 554.

The disclosure also provides a vector comprising a heterologous polynucleotide encoding the heterologous polypeptide of SEQ ID NO: 555.

The disclosure also provides a vector comprising a heterologous polynucleotide encoding the heterologous polypeptide of SEQ ID NO: 556.

The disclosure also provides a vector comprising a heterologous polynucleotide encoding the heterologous polypeptide of SEQ ID NO: 623.

The disclosure also provides a vector comprising a heterologous polynucleotide encoding the heterologous polypeptide of SEQ ID NO: 624.

In some embodiments, the vector is a viral vector.

In some embodiments, the viral vector is an adenovirus vector.

In some embodiments, the adenovirus vector is derived from a human adenovirus, optionally from Ad5, Ad7, Ad11, Ad26, Ad34, Ad35, Ad48, Ad49 or Ad50.

In some embodiments, the adenovirus vector is derived from Ad26.

In some embodiments, the adenovirus vector is derived from a great ape adenovirus, optionally from GAd20, GAd19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd1, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2 or PanAd3.

In some embodiments, the adenovirus vector is derived from GAd20.

The disclosure also provides a rGAd20 comprising a heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides a rGAd20 comprising a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides a rGAd20 comprising a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof. The polynucleotides are useful in expression in adenovirus.

The disclosure also provides a rGAd20 comprising a heterologous polynucleotide encoding the heterologous polypeptide of SEQ ID NO: 541. In some embodiments, the heterologous polynucleotide comprises SEQ ID NO: 542.

The disclosure also provides a rGAd20 comprising the heterologous polynucleotide of SEQ ID NO: 542.

The disclosure also provides a rGAd20 comprising a heterologous polynucleotide encoding the heterologous polypeptide of SEQ ID NO: 550. In some embodiments, the heterologous polynucleotide comprises SEQ ID NO: 551.

The disclosure also provides a rGAd20 comprising the heterologous polynucleotide of SEQ ID NO: 551.

The disclosure also provides a rGAd20 comprising a heterologous polynucleotide encoding the heterologous polypeptide of SEQ ID NO: 554.

The disclosure also provides a rGAd20 comprising a heterologous polynucleotide encoding the heterologous polypeptide of SEQ ID NO: 555.

The disclosure also provides a rGAd20 comprising a heterologous polynucleotide encoding the heterologous polypeptide of SEQ ID NO: 556.

The disclosure also provides a rGAd20 comprising a heterologous polynucleotide encoding the heterologous polypeptide of SEQ ID NO: 623.

The disclosure also provides a rGAd20 comprising a heterologous polynucleotide encoding the heterologous polypeptide of SEQ ID NO: 624.

The disclosure also provides a cell comprising or transduced with the rGAd20, wherein the rGAd20 comprises:

a heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;

a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof;

a heterologous polynucleotide encoding the heterologous polypeptide of SEQ ID NO: 541;

heterologous polynucleotide of SEQ ID NO: 542;

a heterologous polynucleotide encoding the heterologous polypeptide of SEQ ID NO: 550;

a heterologous polynucleotide of SEQ ID NO: 551;

a heterologous polynucleotide encoding the heterologous polypeptide of SEQ ID NO: 554;

a heterologous polynucleotide encoding the heterologous polypeptide of SEQ ID NO: 555;

a heterologous polynucleotide encoding the heterologous polypeptide of SEQ ID NO: 556;

a heterologous polynucleotide encoding the heterologous polypeptide of SEQ ID NO: 623; or a heterologous polynucleotide encoding the heterologous polypeptide of SEQ ID NO: 624.

The disclosure also provides a vaccine comprising the rGAd20, wherein the rGAd20 comprises:

a heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;

a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof;

a heterologous polynucleotide encoding the heterologous polypeptide of SEQ ID NO: 541;

a heterologous polynucleotide of SEQ ID NO: 542;

a heterologous polynucleotide encoding the heterologous polypeptide of SEQ ID NO: 550;

a heterologous polynucleotide of SEQ ID NO: 551;

a heterologous polynucleotide encoding the heterologous polypeptide of SEQ ID NO: 554;

a heterologous polynucleotide encoding the heterologous polypeptide of SEQ ID NO: 555;

a heterologous polynucleotide encoding the heterologous polypeptide of SEQ ID NO: 556;

a heterologous polynucleotide encoding the heterologous polypeptide of SEQ ID NO: 623; or a heterologous polynucleotide encoding the heterologous polypeptide of SEQ ID NO: 624.

The disclosure also provides a vector comprising a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides a vector comprising a heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof. The polynucleotides are useful in expression in MVA.

The disclosure also provides a vector comprising a heterologous polynucleotide encoding the heterologous polypeptide of SEQ ID NO: 543. In some embodiments, the heterologous polynucleotide comprises SEQ ID NO: 544.

The disclosure also provides a vector comprising a heterologous polynucleotide of SEQ ID NO: 544.

The disclosure also provides a vector comprising a heterologous polynucleotide encoding the heterologous polypeptide of SEQ ID NO: 552. In some embodiments, the heterologous polynucleotide comprises SEQ ID NO: 553.

The disclosure also provides a vector comprising a heterologous polynucleotide of SEQ ID NO: 553.

The disclosure also provides a vector comprising a heterologous polynucleotide encoding the heterologous polypeptide of SEQ ID NO: 557.

The disclosure also provides a vector comprising a heterologous polynucleotide encoding the heterologous polypeptide of SEQ ID NO: 558.

The disclosure also provides a vector comprising a heterologous polynucleotide encoding the heterologous polypeptide of SEQ ID NO: 559.

The disclosure also provides a vector comprising a heterologous polynucleotide encoding the heterologous polypeptide of SEQ ID NO: 625.

The disclosure also provides a vector comprising a heterologous polynucleotide encoding the heterologous polypeptide of SEQ ID NO: 626.

In some embodiments, the vector is a viral vector.

In some embodiments, the viral vector is MVA.

In some embodiments, the MVA vector is derived from MVA 476 MG/14/78, MVA-571, MVA-572, MVA-574, MVA-575 or MVA-BN.

The disclosure also provides a rMVA comprising a heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;

The disclosure also provides a rMVA comprising a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides a rMVA comprising a heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof. The polynucleotides are useful in expression in MVA.

The disclosure also provides a rMVA comprising a heterologous polynucleotide encoding the heterologous polypeptide of SEQ ID NO: 543. In some embodiments, the heterologous polynucleotide comprises SEQ ID NO: 544.

The disclosure also provides a rMVA comprising the heterologous polynucleotide of SEQ ID NO: 544.

The disclosure also provides a rMVA comprising a heterologous polynucleotide encoding the heterologous polypeptide of SEQ ID NO: 552. In some embodiments, the heterologous polynucleotide comprises SEQ ID NO: 553.

The disclosure also provides a rMVA comprising the heterologous polynucleotide of SEQ ID NO: 553.

The disclosure also provides a rMVA comprising a heterologous polynucleotide encoding the heterologous polypeptide of SEQ ID NO: 557.

The disclosure also provides a rMVA comprising a heterologous polynucleotide encoding the heterologous polypeptide of SEQ ID NO: 558.

The disclosure also provides a rMVA comprising a heterologous polynucleotide encoding the heterologous polypeptide of SEQ ID NO: 559.

The disclosure also provides a rMVA comprising a heterologous polynucleotide encoding the heterologous polypeptide of SEQ ID NO: 625.

The disclosure also provides a rMVA comprising a heterologous polynucleotide encoding the heterologous polypeptide of SEQ ID NO: 626.

The disclosure also provides a cell comprising or transduced with the rMVA, wherein the rMVA comprises:

- a heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;
- a heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540;
- a heterologous polynucleotide encoding the heterologous polypeptide of SEQ ID NO: 543;
- a heterologous polynucleotide of SEQ ID NO: 544;
- a heterologous polynucleotide encoding the heterologous polypeptide of SEQ ID NO: 552;
- a heterologous polynucleotide of SEQ ID NO: 553;
- a heterologous polynucleotide encoding the heterologous polypeptide of SEQ ID NO: 557;
- a heterologous polynucleotide encoding the heterologous polypeptide of SEQ ID NO: 558;
- a heterologous polynucleotide encoding the heterologous polypeptide of SEQ ID NO: 559;
- a heterologous polynucleotide encoding the heterologous polypeptide of SEQ ID NO: 625; or
- a heterologous polynucleotide encoding the heterologous polypeptide of SEQ ID NO: 626.

The disclosure also provides a vaccine comprising the rMVA, wherein the MVA comprises:

- a heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;
- a heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540;
- a heterologous polynucleotide encoding the heterologous polypeptide of SEQ ID NO: 543;
- a heterologous polynucleotide of SEQ ID NO: 544;
- a heterologous polynucleotide encoding the heterologous polypeptide of SEQ ID NO: 552;
- a heterologous polynucleotide of SEQ ID NO: 553;
- a heterologous polynucleotide encoding the heterologous polypeptide of SEQ ID NO: 557;
- a heterologous polynucleotide encoding the heterologous polypeptide of SEQ ID NO: 558;
- a heterologous polynucleotide encoding the heterologous polypeptide of SEQ ID NO: 559;
- a heterologous polynucleotide encoding the heterologous polypeptide of SEQ ID NO: 625; or
- a heterologous polynucleotide encoding the heterologous polypeptide of SEQ ID NO: 626.

The disclosure also provides a vaccine comprising a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polynucleotide comprises two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the fragments comprise peptides of SEQ ID NOs: 387, 388, 390, 392, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620 or 621.

In some embodiments, the heterologous polypeptide comprises SEQ ID NOs: 541, 550, 554, 555, 556, 623 or 624.

In some embodiments, the heterologous polynucleotide comprises SEQ ID NO: 542 or SEQ ID NO: 551.

In some embodiments, the heterologous polypeptide comprises SEQ ID NOs: 543, 552, 557, 558, 559, 625 or 626.

In some embodiments, the heterologous polynucleotide comprises SEQ ID NO: 544 or SEQ ID NO: 553.

In some embodiments, the heterologous polynucleotide is DNA or RNA.

In some embodiments, RNA is mRNA or self-replicating RNA.

In some embodiments, the vaccine is a recombinant virus.

In some embodiments, the recombinant virus is derived from adenovirus, poxvirus, adeno-associated virus or retrovirus.

In some embodiments, the recombinant virus is derived from hAd5, hAd7, hAd1, hAd26, hAd34, hAd35, hAd48, hAd49, hAd50, GAd20, Gad19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, PanAd3, Copenhagen vaccinia virus (W), New York Attenuated Vaccinia Virus (NYVAC), ALVAC, TROVAC, or modified vaccinia Ankara (MVA).

In some embodiments, the recombinant virus is derived from GAd20.

In some embodiments, the recombinant virus is derived from MVA.

In some embodiments, the recombinant virus is derived from Ad26.

The disclosure also provides a vaccine comprising a heterologous polynucleotide sequence encoding a heterologous polypeptide of SEQ ID NO: 541 or 550.

In some embodiments, the heterologous polynucleotide comprises SEQ ID NO: 542 or 551.

In some embodiments, the vaccine is a recombinant virus derived from GAd20.

The disclosure also provides a vaccine comprising a heterologous polynucleotide sequence encoding a heterologous polypeptide of SEQ ID NO: 543 or 552.

In some embodiments, the heterologous polynucleotide comprises SEQ ID NO: 544 or 553.

In some embodiments, the vaccine is a recombinant virus derived from MVA.

The following examples are provided to further describe some of the embodiments disclosed herein. The examples are intended to illustrate, not to limit, the disclosed embodiments.

Example 1 General Methods

Peptide Synthesis

Peptides were synthesized by New England Peptide with purity >80%. The lyophilized peptides were solubilized in 100% DMSO.

In Vitro Immunogenicity Assessment of Neoantigens ("Patient PBMC Restimulation Assay")

PBMCs from human patients with metastatic castrate-resistant prostate cancer were thawed using media (RPMI 1640 supplemented with Glutamax, 10% HI FBS, and 1× Sodium Pyruvate). Cells were counted and plated in a 96 well round bottom microplate at a concentration of 250,000 viable cells per well. Lyophilized peptides were solubilized in 100% DMSO and diluted in media to 10 μg/mL. Neoantigen peptides were added in equal volume to PBMCs for a final concentration of 5 μg/mL. CEF Peptide Pool "Plus" (Cellular Technologies, Ltd.) was utilized as a positive control and DMSO at the same final concentration as the experimental peptides was utilized as a negative control. Human IL-15 (Peprotech) was added to all wells at final concentration of 10 ng/mL.

Plates were incubated at 37° C. (5% $CO_2$) for a total of 13 days. Media was refreshed every 2 days with IL-15 (10 ng/mL final concentration) and IL-2 (R&D systems, 10 IU/mL final concentration). On day 12, PBMCs were re-stimulated with identical experimental peptides or controls, at same concentration as peptide stimulation on Day 1. After 1-hour incubation, protein Inhibitor Cocktail (eBioscience) was added to every well and plate was incubated overnight.

On day 13, cells were stained for intracellular flow cytometry analysis. The cells were washed with PBS and stained with Live/Dead Fixable Aqua Dead Cell stain (Thermo-Fisher). Following the live/dead stain, cells were blocked using Biotin-Free Fc Receptor Blocker (Accurate Chemical & Scientific Corp). Extracellular cellular flow panel (1 μL/antibody per well in 50 μL) consisted of CD3 PerCP-Cy5.5 (Biolegend), CD4 BV421 (Biolegend), and CD8 APC-Cy7 (Biolegend). After extracellular staining, cells were fixed using Foxp3/Transcription Factor Staining Buffer Set (eBioscience) and stained for intracellular proteins (1:50 dilution) using TNFα FITC (R&D Systems) and IFNγ BV785 (Biolegend). Cells were washed and resuspended in stain buffer and analyzed using a BD Celesta flow cytometer.

Flow cytometry cell staining analysis was completed using FlowJo v10. Cells were gated on live, singlet, CD3+ cells. The CD8+ T cells were analyzed for TNFα/IFNγ expression and the frequency of double positive TNFα/IFNγ CD8+ T cells was recorded. Responses were assessed to be positive when the frequency of double positive TNFα/IFNγ CD8+ T cells due to stimulation with an experimental peptide was increased greater than or equal to 2-fold over the DMSO only negative control for that patient. Peptides were analyzed in 1 to 7 patient samples.

In Vitro Immunogenicity Assessment of Neoantigens ("Exogenous Autologous Normal Donor Restimulation Assay")

CD1c+ Dendritic Cells (DC) isolated from human normal PBMCs were thawed using media (IMDM (Gibco) supplemented with glutamine, HEPES, 5% human serum (Sigma), and 1× Pen-Strep). DC cells were resuspended in media supplemented with IL-4 (Peprotech, 80 ng/mL) and GM-CSF (Gibco, 80 ng/mL), plated in 6 well microplates, and rested overnight at 37° C. (5% $CO_2$). The following day, DC cells were counted and plated in a 96 well round bottom microplate at a concentration of 30,000 viable cells per well. Lyophilized peptides (15-mer overlapping peptides) were solubilized in 100% DMSO and pooled by neoantigen to between 5 mg/mL and 20 mg/mL. Neoantigen peptides pools were added to DCs for a final concentration of 2.5 μg/mL to 10 μg/mL and rested for 2 hours at 37° C. (5% $CO_2$). CEF Peptide Pool "Plus" (Cellular Technologies, Ltd.) was utilized as a positive control and DMSO at the same final concentration as the experimental peptides was utilized as a negative control. After 2 hours, DC cells were irradiated with 50 gray of ionizing radiation. Autologous CD3+ Pan-T cells isolated from human normal PBMCs were thawed using media. Following irradiation, autologous Pan-T cells were added to the irradiated DCs at 300,000 viable cells per well. Human IL-15 (Peprotech) was added to all wells at final concentration of 10 ng/mL. Plates were incubated at 37° C. (5% $CO_2$) for a total of 12 days. Media was refreshed every 2-3 days with IL-15 (10 ng/mL final concentration) and IL-2 (R&D systems, 10 IU/mL final concentration). On day 11 cells were re-stimulated with identical experimental peptide pools or controls, at same concentration as peptide stimulation on Day 1. Protein Inhibitor Cocktail (eBioscience) was added to every well and plate was incubated overnight at 37° C. (5% $CO_2$).

On day 12, cells were stained for intracellular flow cytometry analysis. The cells were washed with PBS and stained with Live/Dead Fixable Aqua Dead Cell stain (Thermo-Fisher). Following the live/dead stain, cells were blocked using Biotin-Free Fc Receptor Blocker (Accurate Chemical & Scientific Corp). Extracellular cellular flow panel (1 μL/antibody per well in 50 μL) consisted of CD3 PerCP-Cy5.5 (Biolegend), CD4 BV421 (Biolegend), and CD8 APC-Cy7 (Biolegend). After extracellular staining, cells were fixed using Foxp3/Transcription Factor Staining Buffer Set (eBioscience) and stained for intracellular proteins (1:50 dilution) using TNFα FITC (R&D Systems) and IFNγ BV785 (Biolegend). Cells were washed and resuspended in stain buffer and analyzed using a BD Celesta flow cytometer.

Flow cytometry cell staining analysis was completed using FlowJo v10. Cells were gated on live, singlet, CD3+ cells. The CD8+ and CD4+ T cells were analyzed for TNFα/IFNγ expression and the frequency of double positive TNFα/IFNγ CD8+ and the frequency of double positive TNFα/IFNγ CD4+ T cells were recorded. Responses were assessed to be positive when the frequency of double positive TNFα/IFNγ CD8+ or TNFα/IFNγ CD4+ T cells due to stimulation with an experimental peptide pool was increased greater than or equal to 3-fold over the DMSO only negative control for that donor and at least 0.01%.

In Vitro Endogenous Immunogenicity Assessment of Neoantigens ("Endogenous Autologous Normal Donor Restimulation Assay")

CD1c+ Dendritic Cells (DC) isolated from human normal PBMCs were thawed using media (IMDM (Gibco) supplemented with glutamine, HEPES, 5% human serum (Sigma), and 1× Pen-Strep). DC cells were resuspended in media supplemented with IL-4 (Peprotech, 80 ng/mL) and GM-CSF (Gibco, 80 ng/mL), plated in 6 well microplates, and rested overnight at 37° C. (5% $CO_2$). The following day, DC cells were counted and plated in a 96 well round bottom microplate at a concentration of 30,000 viable cells per well. Ad5 vectors (Vector Biolabs) were dilute in media to an MOI (Multiplicity Of Infection) of 5000 based on Plaque Forming Units. Ad5 vectors for the CEF pool and a "null" were used as controls. DCs were transduced with Ad5 vectors overnight at 37° C. (5% $CO_2$). The following day, the Ad5 vectors were washed off the plate by three sequential centrifugation/aspiration steps using sterile Phosphate Buffered Saline. After the final wash, transduced DCs were resuspended in 100 μL media. Autologous CD3+ Pan-T cells isolated from human normal PBMCs were thawed using media. Pan-T cells were added to the irradiated DCs at 300,000 viable cells per well (100 μL/well). Human IL-15 (Peprotech) was added to all wells at final concentration of 10 ng/mL.

Plates were incubated at 37° C. (5% $CO_2$) for a total of 12 days. Media was refreshed every 2-3 days with IL-15 (10 ng/mL final concentration) and IL-2 (R&D systems, 10 IU/mL final concentration). On day 11 lyophilized peptides (15-mer overlapping peptides) were solubilized in 100% DMSO and pooled by neoantigen to between 5 mg/mL and 20 mg/mL. Neoantigen peptides pools were added to cells for a final concentration of 2.5 μg/mL to 10 μg/mL. CEF Peptide Pool "Plus" (Cellular Technologies, Ltd.) was utilized as a positive control and DMSO at the same final concentration as the experimental peptides was utilized as a negative control. Protein Inhibitor Cocktail (eBioscience) was added to every well and plate was incubated overnight at 37° C. (5% $CO_2$).

On day 12, cells were stained for intracellular flow cytometry analysis. The cells were washed with PBS and stained with Live/Dead Fixable Aqua Dead Cell stain (Thermo-Fisher). Following the live/dead stain, cells were blocked using Biotin-Free Fc Receptor Blocker (Accurate Chemical & Scientific Corp). Extracellular cellular flow panel (1 μL/antibody per well in 50 μL) consisted of CD3 PerCP-Cy5.5 (Biolegend), CD4 BV421 (Biolegend), and CD8 APC-Cy7 (Biolegend). After extracellular staining, cells were fixed using Foxp3/Transcription Factor Staining Buffer Set (eBioscience) and stained for intracellular proteins (1:50 dilution) using TNFα FITC (R&D Systems) and IFNγ BV785 (Biolegend). Cells were washed and resuspended in stain buffer and analyzed using a BD Celesta flow cytometer.

Flow cytometry cell staining analysis was completed using FlowJo v10. Cells were gated on live, singlet, CD3+ cells. The CD8+ and CD4+ T cells were analyzed for TNFα/IFNγ expression and the frequency of double positive TNFα/IFNγ CD8+ and the frequency of double positive TNFα/IFNγ CD4+ T cells were recorded. Responses were assessed to be positive when the frequency of double positive TNFα/IFNγ CD8+ or TNFα/IFNγ CD4+ T cells due to stimulation with an experimental peptide pool was increased greater than or equal to 3-fold over the DMSO only negative control for that donor and at least 0.01%.

In Vitro Binding of Neoantigens to Class I MHC

The 9 mer peptides identified by bioinformatics analysis were analyzed for their binding propensities to 6 common HLA class I alleles (HLA-A*01:01, A*02:01, A*03:01, A*24:02, B*07:02, B*08:01). The principle of the method is briefly described below and consists of two parts, one involving exchange of peptide with a positive control induced by Ultraviolet (UV) radiation, and the second is an enzyme immunoassay to detect stable HLA-peptide and empty HLA complexes.

HLA-bound peptides are critical for the stability of the HLA complex. A conditional HLA class I complex was stabilized by an UV-labile peptide utilizing a different peptide (Pos) for each HLA (Pos: HLA-A*01:01: CTELKLSDY(SEQ ID NO: 409), HLA-A*02:01: NLVPMVATV (SEQ ID NO: 410), HLA-A*03:01: LIYRRRLMK (SEQ ID NO: 411), HLA-A*24:02: LYSACFWWL (SEQ ID NO: 412), HLA-B*07:02: NPKASLLSL (SEQ ID NO: 413), HLA-B*08:01: ELRSRYWAI (SEQ ID NO: 414), which could be cleaved by UV irradiation when bound to the HLA molecule. Upon cleavage, the resulting peptide fragments dissociated from the HLA class I complex since their length was insufficient to bind stably to HLA. Under the conditions in which peptide cleavage was performed (neutral pH, on melting ice), the peptide-free HLA complex remained stable. Thus, when cleavage was performed in the presence of another HLA class I peptide of choice, this reaction resulted in net exchange of the cleaved UV-labile peptide Pos with the chosen peptide (Rodenko, B et al. (2006) Nature Protocols 1: 1120-32, Toebes, M et al. (2006) Nat Med 12: 246-51, Bakker, A H et al. (2008) Proc Natl Acad Sci USA 105: 3825-30).

The exchange efficiency between the peptide of interest and Pos was analyzed using an HLA class I ELISA. The combined technologies allowed the identification of ligands for an HLA molecule of interest which are potentially immunogenic.

Exchange control peptide Pos was a high affinity binder to the relevant HLA class I allele while exchange control peptide Neg was a non-binder. The UV control represented UV-irradiation of conditional HLA class I complex in the absence of a rescue peptide. The binding of exchange control peptide Neg (HLA-A*01:01: NPKASLLSL (SEQ ID NO: 413), HLA-A*02-01: IVTDFSVIK (SEQ ID NO: 416), HLA-A*03:01: NPKASLLSL (SEQ ID NO: 413), HLA-A*24:02: NLVPMVATV (SEQ ID NO: 410), HLA-B*07:02: LIYRRRLMK (SEQ ID NO: 411), HLA-B*08:01: NLVPMVATV (SEQ ID NO: 410) and all experimental peptides were evaluated relative to that of exchange control peptide Pos. The absorption of the latter peptide was set at 100%. This procedure resulted in a range of different exchange percentages that reflected the affinities of the different experimental peptides for the HLA allele used.

The HLA class I ELISA is an enzyme immunoassay based on the detection of beta2-microglobulin (B2M) of (peptide-stabilized) HLA class I complexes. To this end streptavidin was bound onto polystyrene microtiter wells. After washing and blocking, HLA complex present in exchange reaction mixtures or ELISA controls was captured by the streptavidin on the microtiter plate via its biotinylated heavy chain. Non-bound material was removed by washing. Subsequently, horseradish peroxidase (HRP)-conjugated antibody to human B2M was added. The HRP-conjugated antibody binds only to an intact HLA complex present in the microtiter well because unsuccessful peptide exchange results in disintegration of the original UV-sensitive HLA complex upon UV illumination. In the latter case B2M was removed during the washing step. After removal of non-bound HRP conjugate by washing, a substrate solution was added to the wells. A coloured product formed in proportion to the amount of intact HLA complex present in the samples. After the reaction was terminated by the addition of a stop solution, absorbance was measured in a microtiter plate reader. The absorbance was normalized to the absorbance of an exchange control peptide (represents 100%). Suboptimal HLA binding of peptides with a moderate to low affinity for HLA class I molecules can also be detected by this ELISA technique (Rodenko, B et al. (2006) Nature Protocols 1: 1120-32).

Peptides that had 10% or greater exchange efficiency in one of the 6 HLA alleles were considered for further immunogenicity testing and analysis.

Example 2. Identification of Neoantigens by Bioinformatics

A computational framework was developed to analyze various prostate cancer RNA-seq datasets by bioinformatics means to identify common prostate cancer neoantigens resulting from aberrant transcriptional programs such as gene fusion events, intron retention, alternatively spliced variants and aberrant expression of developmentally silenced genes. The datasets queried were:

The Genotype-Tissue Expression (GTEx) Consortium. This dataset encompasses 6137 RNA-seq datasets from 49 normal tissues and was used to annotate RNA features in normal tissues and assess frequency of potential prostate neoantigen candidates in normal tissue.

The Cancer Genome Atlas Prostate Adenocarcinoma (TCGA PRAD) (Cancer Genome Atlas Research Network. Cell. 2015 Nov. 5; 163(4):1011-25. doi: 10.1016/j.cell.2015.10.025). This dataset encompasses RNA-seq datasets from 508 prostate cancer subjects and was used to identify neoantigen candidates in localized prostate adenocarcinoma.

Stand Up To Cancer (SU2C) (Robinson D et al., Cell. 2015 May 21; 161(5): 1215-1228. doi: 10.1016/j.cell.2015.05.001). This dataset encompasses RNA-seq datasets from 43 mCRPC subjects.

Quality control (QC) of raw data was conducted prior to analysis. Sequencing reads were first trimmed to remove Illumina's adapter sequences and reads mapping to human tRNA and rRNA were removed from downstream analysis. Reads were also trimmed of bases with poor base quality score (<10, PHRED scale; indicating a base with a 1 in 10 probability of being incorrect) at either ends. PHRED quality score measures the quality of the identification of the bases generated by automated DNA sequencing instruments. Trimmed reads with less than 25 bps were removed from the datasets. Additionally, following QC steps were considered to remove poor quality reads: remove reads having maximal base quality PHRED score of <15, remove reads with average base quality PHRED score of <10, remove reads having polyATCG rate >80%, remove RNA sequences in which one of the two reads failed.

Reads that passed the QC criteria were mapped to Human Genome Build 38 using ArrayStudio ((https_//www_omicsoft_com/array-studio/) platform. Refseq gene model (release date Jun. 6, 2017) was used for annotation of novel RNA features.

The results published here are in whole or part based upon data generated by The Cancer Genome Atlas managed by the NCI and NHGRI. Information about TCGA can be found at http://_cancergenme_nih_gov.

Identification of Gene Fusion Events

FusionMap algorithm (Ge H et al., Bioinformatics. 2011 Jul. 15; 27(14):1922-8. doi: 10.1093/bioinformatics/btr310. Epub 2011 May 18) was used to identify gene fusion events in the prostate cancer datasets described above. FusionMap detects fusion junctions based on seed reads which contain the fusion breakpoint position in the middle region of the reads. The algorithm dynamically creates a pseudo fusion transcript/sequence library based on the consensus of mapped fusion junctions from the seed reads. FusionMap then aligns unmapped possible fusion reads to the pseudo fusion reference to further identify rescued reads. The program reports a list of detected fusion junctions, statistics of supporting reads, fusion gene pairs, as well as genomic locations of breakpoints and junction sequences, which characterize fusion genes comprehensively at base-pair resolution.

Figure 2:
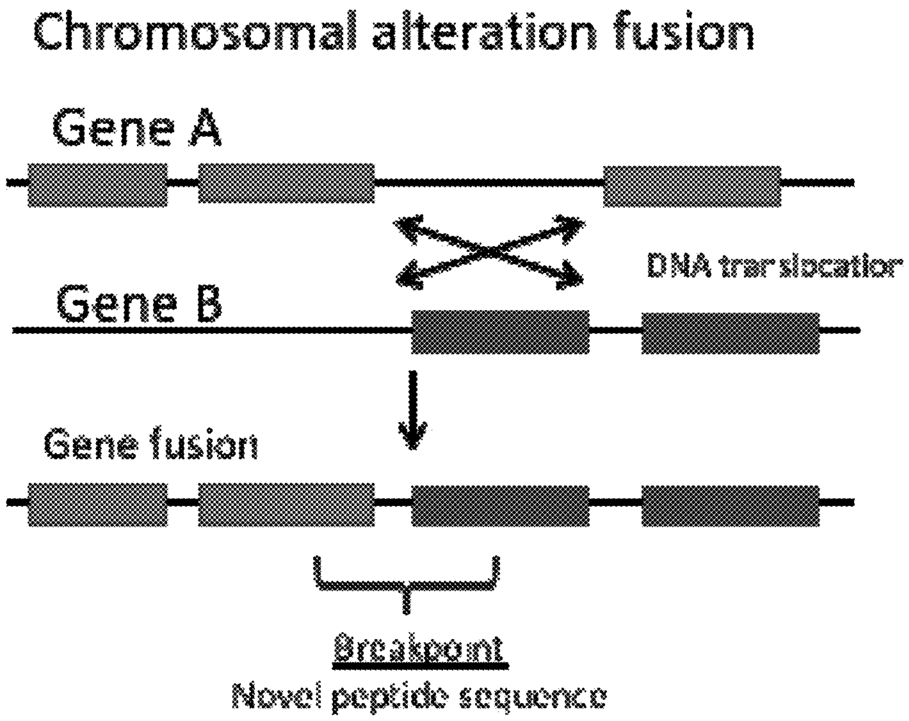
FIG. 2 shows a cartoon of gene fusions resulting from chromosomal alteration, such as DNA translocations.

Neoantigens originating from chimeric read-through fusions as shown in FIG. 1 and fusions resulting from chromosomal alterations as shown in FIG. 2 were identified using FusionMap. Neoantigens were classified as originating from gene fusion events when following criteria were met: fusion junction was supported by at least two seed reads with different mapping positions in the genome, at least 4 sequencing reads (seed and rescued reads) parsing the junction, and at least one junction spanning read. The prevalence of neoantigens were queried in tumor tissue and normal tissue using the datasets mentioned above. Neoantigens were identified as common when the prevalence was identified to be >10% in at least one disease cohort (TCGA and SU2C) and <2% in normal tissue (6137 RNA-seq datasets from 49 normal tissues). Gene fusion events with less than 10% prevalence in disease cohort were included if they generated long stretches of novel peptide sequences or were present in genes of interest.

Identification of Splice Variants

Figure 3:
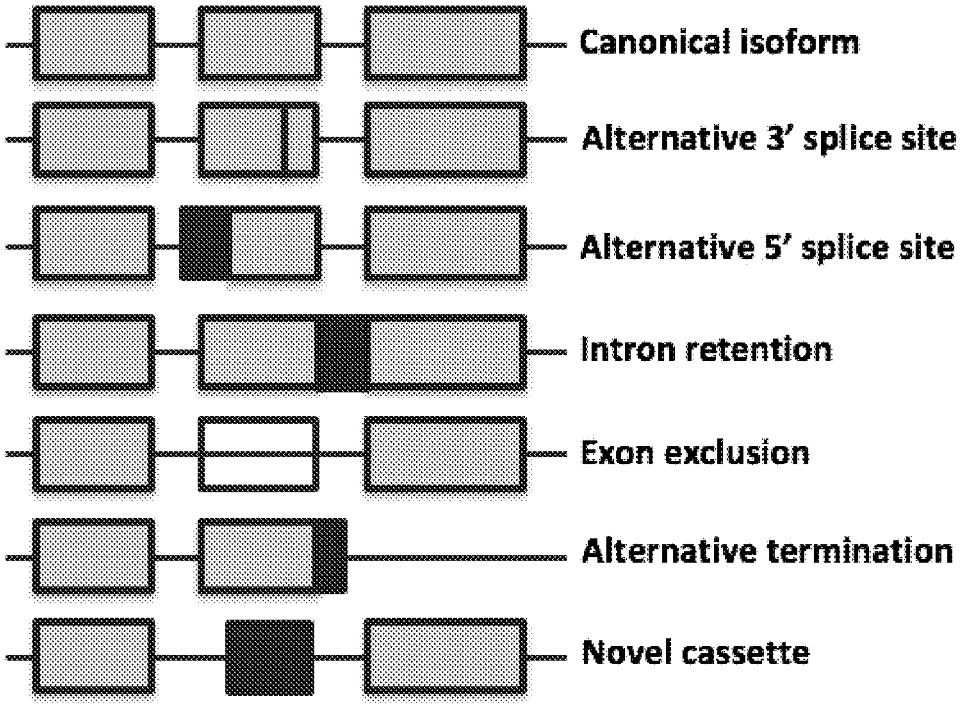
FIG. 3 shows a cartoon of splice variants with alternative 5' or 3' splice sites, retained introns, excluded exons or alternative terminations or insertions.
Figure 4:
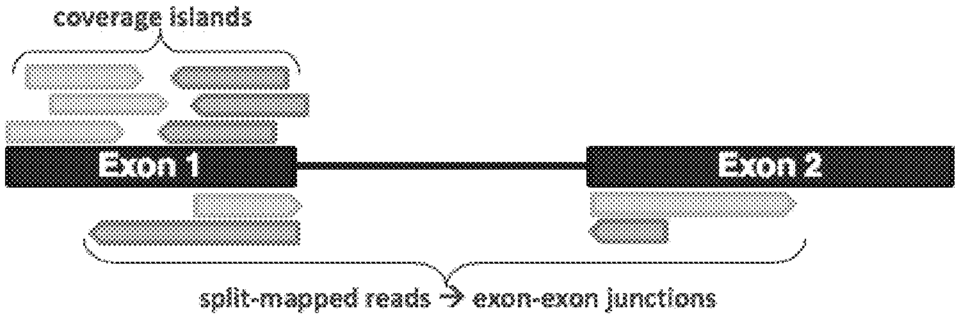
FIG. 4 shows the cartoon for approach of identification of splice variants.

A custom bioinformatic software was developed to analyze paired-end RNA-seq data to identify potential neoantigens arising from alternative splicing events. Utilizing the developed process, splice variants with alternative 5' or 3' splice sites, retained introns, excluded exons, alternative terminations or insertion(s) of novel cassettes as show in in FIG. 3 were identified. The process identified splice variants that were not present in the RefSeq gene model through two main functionalities: 1) Identification of novel junctions based on reads with gaps of 6 or more bp and sequences of at least 15 bp aligned on each side of the gap, henceforth referred to as split-mapped reads. Novel junctions were reported if they were represented by at least 5 split-mapped reads and one mate pair of reads flanking the junction on each end. 2) Identification of islands of aligned reads, henceforth referred to as coverage islands. Further details on parameters used for determining island boundaries are described below. FIG. 4 shows the cartoon of the approach.

In order to differentiate reads mapping to intronic regions due to true splicing variation as opposed to genomic DNA and/or pre-mRNA contamination, two parameters were developed to establish the distribution of contamination across 200 highly expressed housekeeping genes. The tail ends of these distributions were then used as cut-offs for discovery of novel splice variants where relevant.

1. Intron depth of coverage (IDC): $90^{th}$ percentile depth of coverage for all housekeeping intronic bases. If the coverage of a particular region fell below this value, the first base where this occurred was defined as a coverage island boundary.
2. Intron/exon coverage ratio (IECR): $90^{th}$ percentile of the ratio between median intron coverage and median coverage of the nearest upstream exon of all housekeeping gene introns All Reported Splice Variants were Required to Meet the Following Criteria:

Alternative 3'/5' Splice Site Identification:

Novel splice site was supported by at least 5 split-mapped reads and one mate pair of reads flanking the junction Intronic region resulting from using the splice site (if applicable) exceeded IECR and entire region exceeded IDC Novel Cassette Identification:

Two novel splice sites in an intronic region were supported by at least 5 split-mapped reads and one mate pair of reads flanking the junction Region between the two splice sites exceeded IECR and entire region exceeded IDC Intron Retention Identification:

Intronic region exceeded IECR and entire region exceeded IDC

At least 5 reads span both intron-exon boundaries, with at least 15 bp aligned on each side of the boundaries Alternative Termination Identification:

3' boundary defined as the edge of a coverage island that did not fall within 60 bp of the 3' end of a canonical exon Any intronic regions between 5' end of a canonical exon and the 3' boundary exceeded IECR and entire region exceeded IDC Exon Exclusion Identification:

Novel junction was supported by at least 5 split-mapped reads and one mate pair of reads flanking the junction where one or more canonical exons were skipped Neoantigens derived from aberrant splicing events were identified as common when the incidence was identified to be about >10% in disease cohort (TCGA and SU2C datasets) and about <1% in normal tissue (GTEx Consortium dataset).

Identification of DNA Mutations (Point and Frameshift) Based Neoantigens

The TCGA, SU2C and the integrated DFCI/Sloane Kettering datasets (Integrated DFCI/Sloane Kettering dataset (Armenia et al., Nat Genet. 2018 May; 50(5):645-651. doi: 10.1038/s41588-018-0078-z. Epub 2018 Apr. 2) as described above containing exome sequencing data from patients with prostate cancer were examined. Mutation calls published by the consortia that generated these datasets were downloaded, and gene mutations that were present in >10% of the patient population or in genes known to be drivers of prostate cancer (such as AR) were identified. For each single point mutation chosen, a 17 mer peptide with the mutated amino acid at its center was identified for further validation studies.

Splicing Isoform Prediction

In certain cases, there were multiple reading frames and exons upstream of the identified splicing events that could impact the canonical peptide sequence preceding the neoepitope sequence. In these genes, it was determined which canonical exons neighbored each neoepitope feature based on the split-mapped reads present at the exon boundaries. The most highly expressed isoform with the highest average expression in the disease cohort with the highest prevalence of the event that could contain the predicted neoepitope was chosen for translation into the corresponding protein by choice of the open reading frame associated with the isoform. The neoepitope portion of the protein sequence was extracted, with an additional 8 amino acid residues upstream of the first altered amino acid included and used for subsequent validation studies. A similar procedure was followed to identify putative immunogenic antigens from DNA frameshift alterations. For both frameshift deletions and insertions, the resulting DNA sequence was translated into the corresponding protein by choice of the appropriate open reading frame, and the frameshift altered portion of the protein sequence was extracted, with an additional 8 amino acid residues upstream of the first altered amino acid included.

Table 1 shows the gene origin, the specific mutation, the amino acid sequences of identified neoantigens with single amino acid mutations (M) and frequency in patients. Each mutation is bolded in Table 1. Table 2 shows their corresponding polynucleotide sequences. The mutant sequences are capitalized in Table 2. Patient frequency (%) in Table 1 was obtained from Armenia et al., *Nat Genet* 50(5): 645-651, 2018.

TABLE 1

| Neo-epitope ID | Gene | Mutation | Patient Frequency (%) | Amino acid sequence | SEQ ID NO: |
|---|---|---|---|---|---|
| M1 | TP53 | R248Q | 1.0859 | SSCMGGMN**Q**RPILTIIT | 1 |
| M2 | TP53 | R248W | 0.0987 | SSCMGGMN**W**RPILTIIT | 3 |
| M3 | TP53 | R273C | 0.6910 | LGRNSFEV**C**VCACPGRD | 5 |
| M4 | TP53 | R273L | 0.3949 | LGRNSFEV**L**VCACPGRD | 7 |
| M5 | TP53 | G245S | 0.6910 | MCNSSCMG**S**MNRRPILT | 9 |
| M6 | TP53 | Y220C | 0.4936 | FRHSVVVP**C**EPPEVGSD | 11 |

TABLE 1-continued

| Neo-epitope ID | Gene | Mutation | Patient Frequency (%) | Amino acid sequence | SEQ ID NO: |
|---|---|---|---|---|---|
| M7 | TP53 | R282W | 0.4936 | VCACPGRD**W**RTEEENLR | 13 |
| M8 | SPOP | F133C | 0.5923 | FVQGKDWG**C**KKFIRRDF | 15 |
| M9 | SPOP | F133I | 0.3949 | FVQGKDWG**I**KKFIRRDF | 17 |
| M10 | SPOP | F133L | 1.1846 | FVQGKDWG**L**KKFIRRDF | 19 |
| M11 | SPOP | F1335 | 0.3949 | FVQGKDWG**S**KKFIRRDF | 21 |
| M12 | SPOP | F133V | 0.9872 | FVQGKDWG**V**KKFIRRDF | 23 |
| M13 | SPOP | W131C | 0.0987 | YRFVQGKD**C**GFKKFIRR | 25 |
| M14 | SPOP | W131G | 1.2833 | YRFVQGKD**G**GFKKFIRR | 27 |
| M15 | SPOP | W131L | 0.1974 | YRFVQGKD**L**GFKKFIRR | 29 |
| M16 | SPOP | W131R | 0.1974 | YRFVQGKD**R**GFKKFIRR | 31 |
| M17 | SPOP | W131S | 0.0987 | YRFVQGKD**S**GFKKFIRR | 33 |
| M18 | KMT2D | R5214H | 0.1974 | YPVGYEAT**H**IYWSLRTN | 35 |
| M19 | FOXA1 | R261C | 0.1974 | MFENGCYL**C**RQKRFKCE | 37 |
| M20 | FOXA1 | H247Q | 0.1974 | GKGSYWTL**Q**PDSGNMFE | 39 |
| M21 | FOXA1 | H247L | 0.0987 | GKGSYWTL**L**PDSGNMFE | 41 |
| M22 | FOXA1 | H247N | 0.0987 | GKGSYWTL**N**PDSGNMFE | 43 |
| M23 | FOXA1 | H247Y | 0.0987 | GKGSYWTL**Y**PDSGNMFE | 45 |
| M24 | FOXA1 | F266C | 0.0987 | CYLRRQKR**C**KCEKQPGA | 47 |
| M25 | FOXA1 | F266S | 0.0987 | CYLRRQKR**S**KCEKQPGA | 49 |
| M26 | FOXA1 | D226G | 0.0987 | IRHSLSFN**G**CFVKVARS | 51 |
| M27 | FOXA1 | D226N | 0.1974 | IRHSLSFN**N**CFVKVARS | 53 |
| M28 | FOXA1 | R219C | 0.0987 | QQRWQNSI**C**HSLSFNDC | 55 |
| M29 | FOXA1 | R219S | 0.1974 | QQRWQNSI**S**HSLSFNDC | 57 |
| M30 | FOXA1 | M253K | 0.1974 | TLHPDSGN**K**FENGCYLR | 59 |
| M31 | FOXA1 | M253R | 0.0987 | TLHPDSGN**R**FENGCYLR | 61 |
| M32 | CDK12 | R858W | 0.1974 | CHKKNFLH**W**DIKCSNIL | 63 |
| M33 | PTEN | R130Q | 0.2962 | IHCKAGKG**Q**TGVMICAY | 65 |
| M34 | PTEN | V119F | 0.1974 | WLSEDDNH**F**AAIHCKAG | 67 |
| M35 | ATM | N2875S | 0.0987 | GLGDRHVQ**S**ILINEQSA | 69 |
| M36 | ATM | N2875K | 0.0987 | GLGDRHVQ**K**ILINEQSA | 71 |
| M37 | KDM6A | C1164S | 0.0987 | NINIGPGD**S**EWFVVPEG | 73 |
| M38 | KDM6A | C1164Y | 0.0987 | NINIGPGD**Y**EWFVVPEG | 75 |
| M39 | PIK3CA | H1047R | 0.4936 | FMKQMNDA**R**HGGWTTKM | 77 |
| M40 | PIK3CA | E545K | 0.2962 | RDPLSEIT**K**QEKDFLWS | 79 |
| M41 | PIK3CA | E545G | 0.0987 | RDPLSEIT**G**QEKDFLWS | 81 |
| M42 | PIK3CA | E545A | 0.0987 | RDPLSEIT**A**QEKDFLWS | 83 |
| M43 | CTNNB1 | T41A | 0.4936 | SGIHSGAT**A**TAPSLSGK | 85 |
| M44 | CTNNB1 | D32A | 0.0987 | HWQQQSYL**A**SGIHSGAT | 87 |
| M45 | CTNNB1 | D32H | 0.0987 | HWQQQSYL**H**SGIHSGAT | 89 |
| M46 | CTNNB1 | D32V | 0.0987 | HWQQQSYL**V**SGIHSGAT | 91 |
| M47 | CTNNB1 | D32Y | 0.1974 | HWQQQSYL**Y**SGIHSGAT | 93 |
| M48 | CTNNB1 | S37A | 0.0987 | SYLDSGIH**A**GATTTAPS | 95 |
| M49 | CTNNB1 | S37C | 0.0987 | SYLDSGIH**C**GATTTAPS | 97 |
| M50 | CTNNB1 | S37F | 0.0987 | SYLDSGIH**F**GATTTAPS | 99 |
| M51 | CTNNB1 | S37Y | 0.0987 | SYLDSGIH**Y**GATTTAPS | 101 |
| M52 | CTNNB1 | S45C | 0.0987 | SGATTTAP**C**LSGKGNPE | 103 |
| M53 | CTNNB1 | S45F | 0.0987 | SGATTTAP**F**LSGKGNPE | 105 |
| M54 | CTNNB1 | S45P | 0.0987 | SGATTTAP**P**LSGKGNPE | 107 |
| M55 | COL5A1 | T348K | 0.1974 | YVPSEDYY**K**PSPYDDLT | 109 |
| M56 | TAF1L | A869T | 0.1974 | IRKRLKLC**T**DFKRTGMD | 111 |

TABLE 1-continued

| Neo-epitope ID | Gene | Mutation | Patient Frequency (%) | Amino acid sequence | SEQ ID NO: |
|---|---|---|---|---|---|
| M57 | MED12 | L1224F | 0.7897 | VDGAVFAV**F**KAVF VLGD | 113 |
| M58 | MED12 | V1223G | 0.0987 | IVDGAVFA**G**LKAV FVLG | 115 |
| M59 | MED12 | V1223L | 0.0987 | IVDGAVFA**L**LKAV FVLG | 117 |
| M60 | MGA | R2435W | 0.1974 | THTANERR**W**RGEM RDLF | 119 |
| M61 | ARID1A | P1756R | 0.1974 | GRFSKVSS**R**APME GGEE | 121 |
| M62 | CUL3 | M299R | 0.4936 | GKTEDLGC**R**YKLF SRVP | 123 |
| M63 | USP7 | Q4H | 0.4936 | MNH**H**QQQQQQKA | 125 |
| M64 | SF3B1 | K700E | 0.1974 | HGLVDEQQ**E**VRTI SALA | 127 |
| M65 | U2AF1 | S34F | 0.2962 | VCRHGDRC**F**RLHN KPTF | 129 |
| M66 | CDC27 | Y73C | 0.1974 | SCTTPQCK**C**LLAK CCVD | 131 |
| M67 | CDC27 | N260H | 0.1974 | SILSKQVQ**H**KPKT GRSL | 133 |
| M68 | BRAF | G469A | 0.2962 | QRIGSGSF**A**TVYK GKWH | 135 |
| M69 | BRAF | K601E | 0.1974 | GDFGLATV**E**SRWS GSHQ | 137 |
| M70 | RAG1 | R112C | 0.0987 | QANLRHLC**C**ICGN SFRA | 139 |
| M71 | RAG1 | R112H | 0.1974 | QANLRHLC**H**ICGN SFRA | 141 |
| M72 | CNOT3 | E20K | 0.3949 | DRCLKKVS**K**GVEQ FEDI | 143 |

TABLE 1-continued

| Neo-epitope ID | Gene | Mutation | Patient Frequency (%) | Amino acid sequence | SEQ ID NO: |
|---|---|---|---|---|---|
| M73 | CNOT3 | E70K | 0.2962 | IKTWVASN**K**IKDK RQLI | 145 |
| M74 | PIK3CB | E1051K | 0.2962 | QKFDEALR**K**SWTT KVNW | 147 |
| M75 | IDH1 | R132C | 0.1974 | WVKPIIIG**C**HAYG DQYR | 149 |
| M76 | IDH1 | R132G | 0.0987 | WVKPIIIG**G**HAYG DQYR | 151 |
| M77 | IDH1 | R132H | 0.4936 | WVKPIIIG**H**HAYG DQYR | 153 |
| M78 | KRAS | G12D | 0.1974 | YKLVVVGA**D**GVGK SALT | 155 |
| M79 | KRAS | G12R | 0.2962 | YKLVVVGA**R**GVGK SALT | 157 |
| M80 | KRAS | Q61K | 0.2962 | LDILDTAG**K**EEYS AMRD | 159 |
| M81 | KRAS | Q61L | 0.0987 | LDILDTAG**L**EEYS AMRD | 161 |
| M82 | KRAS | Q61R | 0.0987 | LDILDTAG**R**EEYS AMRD | 163 |
| M83 | AKT1 | E17K | 0.4936 | EGWLHKRG**K**YIKT WRPR | 165 |
| M84 | AR | T878A | 1.2833 | IARELHQF**A**FDLL IKSH | 167 |
| M85 | AR | T878G | 0.0987 | IARELHQF**G**FDLL IKSH | 169 |
| M86 | AR | L702H | 1.0859 | QPDSFAAL**H**SSLN ELGE | 171 |
| M87 | AR | W742L | 0.1974 | QMAVIQYS**L**MGLM VFAM | 173 |
| M88 | AR | W742F | 0.0987 | QMAVIQYS**F**MGL MVFAM | 175 |

TABLE 2

| Neoepitope ID | Polynucleotide sequence | SEQ ID NO: |
|---|---|---|
| M1 | agttcctgcatgggcggcatgaaccAgaggcccatcctcaccatcatcaca | 2 |
| M2 | agttcctgcatgggcggcatgaaTTggaggcccatcctcaccatcatcaca | 4 |
| M3 | ctgggacggaacagctttgaggtgTgtgtttgtgcctgtcctgggagagac | 6 |
| M4 | ctgggacggaacagctttgaggtgcTtgtttgtgcctgtcctgggagagac | 8 |
| M5 | atgtgtaacagttcctgcatgggcAgcatgaaccggaggcccatcctcacc | 10 |
| M6 | tttcgacatagtgtggtggtgccctGtgagccgcctgaggttggctctgac | 12 |
| M7 | gtttgtgcctgtcctgggagagaTTggcgcacagaggaagagaatctccgc | 14 |
| M8 | tttgtgcaaggcaaagactggggatGcaagaaattcatccgtagagatttt | 16 |
| M9 | tttgtgcaaggcaaagactggggaAtcaagaaattcatccgtagagatttt | 18 |
| M10 | tttgtgcaaggcaaagactggggattAaagaaattcatccgtagagatttt | 20 |

TABLE 2-continued

| Neoepitope ID | Polynucleotide sequence | SEQ ID NO: |
|---|---|---|
| M11 | tttgtgcaaggcaaagactggggatCcaagaaattcatccgtagagatttt | 22 |
| M12 | tttgtgcaaggcaaagactggggaGtcaagaaattcatccgtagagatttt | 24 |
| M13 | tataggtttgtgcaaggcaaagactgTggattcaagaaattcatccgtaga | 26 |
| M14 | tataggtttgtgcaaggcaaagacGggggattcaagaaattcatccgtaga | 28 |
| M15 | tataggtttgtgcaaggcaaagactggggattcaagaaattcatccgtaga | 30 |
| M16 | tataggtttgtgcaaggcaaagacCggggattcaagaaattcatccgtaga | 32 |
| M17 | tataggtttgtgcaaggcaaagactCgggattcaagaaattcatccgtaga | 34 |
| M18 | tatcccgtgggctacgaggccacgcAcatctattggagcctccgcaccaac | 36 |
| M19 | atgttcgagaacggctgctacttgTgccgccagaagcgcttcaagtgcgag | 38 |
| M20 | ggcaagggctcctactggacgctgcaGccggactccggcaacatgttcgag | 40 |
| M21 | ggcaagggctcctactggacgctgcTcccggactccggcaacatgttcgag | 42 |
| M22 | ggcaagggctcctactggacgctgAacccggactccggcaacatgttcgag | 44 |
| M23 | ggcaagggctcctactggacgctgTacccggactccggcaacatgttcgag | 46 |
| M24 | tgctacttgcgccgccagaagcgctGcaagtgcgagaagcagccgggggcc | 48 |
| M25 | tgctacttgcgccgccagaagcgctCcaagtgcgagaagcagccgggggcc | 50 |
| M26 | atccgccactcgctgtccttcaatgGctgcttcgtcaaggtggcacgctcc | 52 |
| M27 | atccgccactcgctgtccttcaatAactgcttcgtcaaggtggcacgctcc | 54 |
| M28 | cagcagcgctggcagaactccatcTgccactcgctgtccttcaatgactgc | 56 |
| M29 | cagcagcgctggcagaactccatcAgccactcgctgtccttcaatgactgc | 58 |
| M30 | acgctgcacccggactccggcaacaAgttcgagaacggctgctacttgcgc | 60 |
| M31 | acgctgcacccggactccggcaacaGgttcgagaacggctgctacttgcgc | 62 |
| M32 | tgtcacaaaaagaatttcctgcatTgggatattaagtgttctaacattttg | 64 |
| M33 | attcactgtaaagctggaaagggacAaactggtgtaatgatatgtgcatat | 66 |
| M34 | tggctaagtgaagatgacaatcatTttgcagcaattcactgtaaagctgga | 68 |
| M35 | ggacttggtgatagacatgtacagaGtatcttgataaatgagcagtcagca | 70 |
| M36 | ggacttggtgatagacatgtacagaaAatcttgataaatgagcagtcagca | 72 |
| M37 | aacataaatattggcccaggtgactCtgaatggtttgttgttcctgaaggt | 74 |
| M38 | aacataaatattggcccaggtgactAtgaatggtttgtttcctgaaggt | 76 |
| M39 | ttcatgaaacaaatgaatgatgcacGtcatggtggctggacaacaaaaatg | 78 |
| M40 | cgagatcctctctctgaaatcactAagcaggagaaagattttctatggagt | 80 |
| M41 | cgagatcctctctctgaaatcactgGgcaggagaaagattttctatggagt | 82 |
| M42 | cgagatcctctctctgaaatcactgCgcaggagaaagattttctatggagt | 84 |
| M43 | tctggaatccattctggtgccactGccacagctccttctctgagtggtaaa | 86 |
| M44 | cactggcagcaacagtcttacctggCctctggaatccattctggtgccact | 88 |
| M45 | cactggcagcaacagtcttacctgCactctggaatccattctggtgccact | 90 |
| M46 | cactggcagcaacagtcttacctggTctctggaatccattctggtgccact | 92 |
| M47 | cactggcagcaacagtcttacctgTactctggaatccattctggtgccact | 94 |
| M48 | tcttacctggactctggaatccatGctggtgccactaccacagctccttct | 96 |

TABLE 2-continued

| Neoepitope ID | Polynucleotide sequence | SEQ ID NO: |
|---|---|---|
| M49 | tcttacctggactctggaatccattGtggtgccactaccacagctccttct | 98 |
| M50 | tcttacctggactctggaatccattTtggtgccactaccacagctccttct | 100 |
| M51 | tcttacctggactctggaatccattAtggtgccactaccacagctccttct | 102 |
| M52 | tctggtgccactaccacagctccttGtctgagtggtaaaggcaatcctgag | 104 |
| M53 | tctggtgccactaccacagctccttTtctgagtggtaaaggcaatcctgag | 106 |
| M54 | tctggtgccactaccacagctcctCctctgagtggtaaaggcaatcctgag | 108 |
| M55 | tacgtgcccagtgaggactactacaAgccctcaccgtatgatgacctcacc | 110 |
| M56 | atccggaagaggctaaagctctgcActgacttcaaacgcacagggatggat | 112 |
| M57 | gtggatggagccgtgtttgctgttTtcaaggctgtgtttgtacttggggat | 114 |
| M58 | atcgtggatggagccgtgtttgctgGtctcaaggctgtgtttgtacttggg | 116 |
| M59 | atcgtggatggagccgtgtttgctCttctcaaggctgtgtttgtacttggg | 118 |
| M60 | acacacactgccaatgagcggcggTggcgtggtgaaatgagggatctcttt | 120 |
| M61 | gggaggttcagcaaggtgtctagtcGagctcccatggagggtggggaagaa | 122 |
| M62 | ggaaagacagaagaccttggttgcaGgtacaagttatttagtcgtgtgcca | 124 |
| M63 | atgaaccaccaCcagcagcagcagcagcagaaagcg | 126 |
| M64 | catggtcttgtggatgagcagcagGaagttcggaccatcagtgctttggcc | 128 |
| M65 | gcatgtcgtcatggagacaggtgctTtcggttgcacaataaaccgacgttt | 130 |
| M66 | agttgtactacaccgcaatgcaaatGcctgcttgcaaaatgttgtgttgat | 132 |
| M67 | tccatattatctaaacaggttcaaCataaaccaaaaactggtcgaagttta | 134 |
| M68 | caaagaattggatctggatcatttgCaacagtctacaagggaaagtggcat | 136 |
| M69 | ggtgattttggtctagctacagtgGaatctcgatggagtgggtcccatcag | 138 |
| M70 | caagccaaccttcgacatctctgcTgcatctgtgggaattcttttagagct | 140 |
| M71 | caagccaaccttcgacatctctgccAcatctgtgggaattcttttagagct | 142 |
| M72 | gatcgctgcctcaagaaggtgtccAagggcgtggagcagtttgaagatatt | 144 |
| M73 | atcaagacatgggtagcgtccaacAagatcaaggacaagaggcagcttata | 146 |
| M74 | caaaaatttgatgaggcgctcaggAaaagctggactactaaagtgaactgg | 148 |
| M75 | tgggtaaaacctatcatcataggtTgtcatgcttatggggatcaatacaga | 150 |
| M76 | tgggtaaaacctatcatcataggtGgtcatgcttatggggatcaatacaga | 152 |
| M77 | tgggtaaaacctatcatcataggtcAtcatgcttatggggatcaatacaga | 154 |
| M78 | tataagctggtggtggtgggcgccgAcggtgtgggcaagagtgcgctgacc | 156 |
| M79 | tataagctggtggtggtgggcgccCgcggtgtgggcaagagtgcgctgacc | 158 |
| M80 | ttggacatcctggataccgccggAAaggaggagtacagcgccatgcgggac | 160 |
| M81 | ttggacatcctggataccgccggccTggaggagtacagcgccatgcgggac | 162 |
| M82 | ttggacatcctggataccgccggccGggaggagtacagcgccatgcgggac | 164 |
| M83 | gagggttggctgcacaaacgagggAagtacatcaagacctggcggccacgc | 166 |
| M84 | attgcgagagagctgcatcagttcGcttttgacctgctaatcaagtcacac | 168 |
| M85 | attgcgagagagctgcatcagttcGGttttgacctgctaatcaagtcacac | 170 |
| M86 | cagcccgactcctttgcagccttgcActctagcctcaatgaactgggagag | 172 |

TABLE 2-continued

| Neoepitope ID | Polynucleotide sequence | SEQ ID NO: |
|---|---|---|
| M87 | cagatggctgtcattcagtactcctTgatggggctcatggtgtttgccatg | 174 |
| M88 | cagatggctgtcattcagtactcctTTatggggctcatggtgtttgccatg | 176 |

Table 3 shows the gene origin, the specific frameshift mutation (FR), the amino acid sequences of the identified neoantigens that arose from frameshift events and frequency of the mutation in patients. The wild-type sequence is bolded in Table 3, followed by the novel sequence due to frameshift. Table 4 shows their corresponding polynucleotide sequences. The mutant sequences are capitalized in Table 4. Patient frequency (%) in Table 3 was obtained from Armenia et al., *Nat Genet* 50(5): 645-651, 2018.

TABLE 3

| Neoepitope ID | Gene | Frameshift | Patient Frequency (%) | Amino acid sequence | SEQ ID NO: |
|---|---|---|---|---|---|
| FR1 | ZFHX3 | E763Sfs*61 | 0.2962 | **QNLQNGGG**SRSSATLPGRRRRRRWLRRRRQPISVAPAGPPRPNQKPNPPGGARCVIMRPTWPGTSAFT | 177 |
| FR2 | ZFHX3 | E763Gfs*26 | 0.0987 | **QNLQNGGG**GAGLQPHCRGGGGGGCGGGGSQYQ | 179 |
| FR3 | APC | T1556Nfs*3 | 0.3949 | **NQEKEAEK**NY | 181 |
| FR4 | SPEN | A2105Lfs*33 | 0.1974 | **DAAVSPRG**LQHRQGRGNLGWWQSPLRKVRVPKRRMVYHPS | 183 |
| FR5 | BRCA2 | T3085Nfs*26 | 0.1974 | **FVVSVVKK**NRTCPFRLFVRRMLQFTGNKVLDRP | 185 |
| FR6 | BRCA2 | K2674Rfs*2 | 0.1974 | **RSRRSAIK**R | 187 |
| FR7 | ARID4A | S1067Rfs*16 | 0.2962 | **SIIVQERE**RAERRVRRGQVMEIVD | 189 |
| FR8 | SMARCAD1 | N770Kfs*28 | 0.1974 | **NNLVTEKK**HRNVQCHDAVEENGQSSFITSPILHS | 191 |
| FR9 | RNF43 | G659Vfs*41 | 0.3949 | **HPQRKRRG**VPPSPPLALGPRMQLCTQLARFFPITPPVWHILGPQRHTP | 193 |
| FR10 | AXIN2 | G665Afs*24 | 0.1974 | **ASRHHLWG**ATAGTPAPPPVPTCSPRTLRCLP | 195 |
| FR11 | ERF | L525Sfs*6 | 0.2962 | **GPGEAGGP**SPQGG | 197 |
| FR12 | ERF | G299Efs*12 | 0.2962 | **GGGPSGSG**EAPTSPSALRT | 199 |
| FR13 | CHD3 | R599Vfs*16 | 0.3949 | **GNPDVPPP**VLFKADQSESSLSSG | 201 |
| FR14 | KMT2C | S143Vfs*3 | 0.2962 | **AFCYCGEK**VP | 203 |
| FR15 | FOXA1 | M253_N256del | 0.0987 | **TLHPDSGN**GCYLRRQK | 205 |
| FR16 | FOXA1 | F254_N256delinsY | 0.2962 | **LHPDSGNM**YGCYLRRQ | 207 |
| FR17 | FOXA1 | F254_G257delinsC | 0.0987 | **LHPDSGNM**CCYLRRQKR | 209 |

TABLE 4

| Neoantigen ID | Polynucleotide sequence | SEQ ID NO: |
|---|---|---|
| FR1 | Cagaacctgcagaatggagggggagcaggtcttcagccacactgccggggcggcggcggcg<br>gcggtggctgcggcggcggcggcagccaatatcagtagctcctgcggggccccctcgccgac<br>caaaccaaaaaccaaacccacctggcggtgcgaggtgtgtgattatgagaccaacgtggcca<br>ggaacctccgcattcaca | 178 |
| FR2 | cagaacctgcagaatggagggggGgagcaggtcttcagccacactgccggggcggcggcgg<br>cggcggtggctgcggcggcggcggcagccaatatcagtag | 180 |
| FR3 | aaccaagagaaagaggcagAaaaaaactattga | 182 |
| FR4 | gatgctgctgtcagtcccaggggctgcagcacaggcaggggagagggaatctggggtggtg<br>gcagtctcccctgagaaaagtgagagtccccaaaaggaggatggtttatcatcccagttga | 184 |
| FR5 | tttgtcgtttctgttgtgaAaaaaaacaggacttgcccctttcgtctatttgtcagacgaat<br>gttacaatttactggcaataaagttttggatagaccttaa | 186 |
| FR6 | agaagcagaagatcggctataaaaagataatg | 188 |
| FR7 | agtataattgtacaAGagagagagagagcagagagaagggtcagaagaggccaagtgatgga<br>aatagtggattaa | 190 |
| FR8 | aataacttggtcacagAaaaaaaacacagaaatgtgcaatgtcatgatgcagttgaggaaaa<br>tggccaatcatcctttattacatcgccaatattacacagctgaaa | 192 |
| FR9 | cacccacagaggaaaaggcgggggtccctccgagcccacccctggctctcggccccaggat<br>gcaactgtgcacccagcttgccagattttccccattacacccccagtgtggcatatccttg<br>gtccccagaggcacaccccttgatc | 194 |
| FR10 | gccagccggcaccatctgtgggggcaacagcgggcacccccgcaccacccccccgtgcccac<br>ctgttcacccaggaccctgcgatgcctcccctgacc | 196 |
| FR11 | gggcctggggaggctgggggcccctcaccccaaggcgggtgagc | 198 |
| FR12 | ggcgggggcccagcggctcaggggaggctcccacttctccttcagccctgaggacatgaaa | 200 |
| FR13 | ggaaatccagatgtcccaccccccgtcctcttcaaggcagatcagagcgagagttctttgtc<br>aagtgggtag | 202 |
| FR14 | gctttttgttactgtggggaaaaagttccttagga | 204 |
| FR15 | acgctgcacccggactccggcaacggctgctacttgcgccgccagaagcg | 206 |
| FR16 | acgctgcacccggactccggcaacatgtacggctgctacttgcgccgccagaa | 208 |
| FR17 | ctgcacccggactccggcaacatgtgctgctacttgcgccgccagaagcgc | 210 |

Table 5 shows the gene origin and amino acid sequences of the identified neoantigens that arose from gene fusion (FUS) events. Table 6 shows their corresponding polynucleotide sequences. Table 7 shows the prevalence of the FUS neoantigens in analyzed databases.

TABLE 5

| Neoantigen ID | Fusion Gene | Amino acid sequence | SEQ ID NO: |
|---|---|---|---|
| FUS1 | SLC45A3->ELK4 | CGASACDVSLIAMDSA | 211 |
| FUS2 | ARHGEF38->ARHGEF38-IT1 | TEYNQKLQVNQFSESK | 213 |
| FUS3 | MSMB->NCOA4 | TEISCCTLSSEENEYLPRPEWQLQ | 215 |
| FUS4 | LIPE->CNFN | GLVSFGEHFCLPCALC | 217 |
| FUS5 | TMPRSS2->ERG | NSKMALNSEALSVVSE | 219 |
| FUS6 | TMPRSS2->ERG | CEERGAAGSLISCE | 221 |
| FUS7 | NME4->DECR2 | LWFQSSELSPTGAPWPSRRPTWRGTTVSPRT<br>ATSSARTCCGTKWPSSQEAALGLGSGLLRFS<br>CGTAAIR | 223 |

TABLE 5-continued

| Neoantigen ID | Fusion Gene | Amino acid sequence | SEQ ID NO: |
|---|---|---|---|
| FUS8 | INCA1->CAMTA2 | WGMELAASRRFSWDHHSAGGPPRVPSVRSG AAQVQPKDPLPLRTLAGCLARTAHLRPGAES LPQPQLHCT | 225 |
| FUS9 | AP5S1->MAVS | KEQILAVASLVSSQSIHPSWGQSPLSRI | 227 |
| FUS10 | DIP2A->DIP2A-IT1 | LELELSEGVCFRLR | 229 |
| FUS11 | MBTPS2->YY2 | QQLRIFCAAMASNEDFS | 231 |
| FUS15 | D2HGDH->GAL3ST2 | HVVGYGHLDTSGSSSSSSWP | 345 |
| FUS18 | OPN3->CHML | DGFSGSLFAVVTRRCYFLKWRTIFPQSLMWL | 233 |
| FUS19 | GTF2F1->PSPN | KMHFSLKEHPPPPCPP | 235 |
| FUS23 | NUDT14->JAG2 | DLRRVATYCAPLPSSWRPGTGTTIPPRMRSC | 237 |
| FUS24 | DMPK->SIX5 | LQERMELLACGAERGAGGWGGGGGGGGD RRGGGGSAPALADFAGGRG | 239 |

TABLE 6

| Neo-antigen ID | Polynucleotide sequence | SEQ ID NO: |
|---|---|---|
| FUS1 | TGCGGGGCCTCTGCCTGTGATGTCTCCCTCATTGCT ATGGACAGTGCT | 212 |
| FUS2 | ACCGAATACAACCAGAAATTACAAGTGAATCAATTT AGTGAATCCAAA | 214 |
| FUS3 | ACAGAAATTTCATGTTGCACCCTGAGCAGTGAGGAG AATGAATACCTTCCAAGACCAGAGTGGCAGCTCCAG | 216 |
| FUS4 | GGGCTGGTGTCCTTCGGGGAGCACTTTTGTCTGCCC TGCGCCCTCTGCCA | 218 |
| FUS5 | AACAGCAAGATGGCTTTGAACTCAGAAGCCTTATCA GTTGTGAGTGAG | 220 |
| FUS6 | TGTGAGGAGCGCGGCGCGGCAGGAAGCCTTATCAGT TGTGAG | 222 |
| FUS7 | CTGTGGTTCCAGAGCAGTGAGCTGTCCCCGACGGGA GCGCCATGGCCCAGCCGCCGCCCGACGTGGAGGGGG ACGACTGTCTCCCCGCGTACCGCCACCTCTTCTGCC CGGACCTGCTGCGGGACAAAGTGGCCTTCATCACAG GAGGCGGCTCTGGGATTGGGTTCCGGATTGCTGAGA TTTTCATGCGGCACGGCTGCCATACGG | 224 |
| FUS8 | TGGGGGATGGAGTTGGCAGCGTCTCGGAGGTTCTCC TGGGACCACCACTCCGCCGGGGGGCCGCCCAGAGTG CCAAGCGTCCGATCCGGCGCCGCCCAAGTGCAGCCC AAGGACCCGCTCCCGCTCCGCACCCTGGCAGGCTGC CTAGCCAGGACTGCGCACCTGCGCCCTGGGGCGGAG TCCTTACCCCAACCCCAGCTTCACTGCACA | 226 |
| FUS9 | AAGGAACAGATTTTAGCTGTGGCCAGTCTCGTTTCC TCTCAGTCCATCCACCCTTCATGGGGCCAGAGCCCT CTCTCCAGAATC | 228 |
| FUS10 | CTGGAGCTGGAGCTGTCGGAAGGAGTCTGCTTCAGA TTAAGA | 230 |
| FUS11 | CAGCAGCTAAGGATATTTTGTGCAGCCATGGCCTCC AACGAAGATTTCTCCA | 232 |
| FUS15 | CACGTGGTGGGCTATGGCCACCTTGATACTTCCGGG TCATCCTCCTCCTCCTCCTGGCCC | 346 |
| FUS18 | GACGGGTTTAGCGGCAGCCTCTTCGCAGTTGTCACC AGACGCTGTTACTTCCTAAAATGGCGGACAATCTTC CCACAGAGTTTGATGTGGTTA | 234 |
| FUS19 | AAAATGCACTTCTCCCTCAAGGAGCACCCACCGCCC CCTTGCCCGCCT | 236 |
| FUS23 | GATCTGCGCCGGGTCGCCACATACTGCGCTCCTTTA CCCTCATCGTGGAGGCCTGGGACTGGGACAACGATA CCACCCCGAATGAGGAGCTGC | 238 |
| FUS24 | TTGCAGGAGCGGATGGAGTTGCTTGCCTGCGGAGCC GAGCGCGGGGCCGGCGGCTGGGGGGGAGGCGGTGGC GGCGGCGGCGGCGACCGAAGAGGAGGAGGAGGAAGC GCGCCAGCTCTTGCAGACTTTGCAGGCGGCCGAGGG | 240 |

TABLE 7

| Neoantigen ID | TCGA (%) | SU2C (%) |
|---|---|---|
| FUS1 | 30.51 | 23.26 |
| FUS2 | 63.58 | 46.51 |
| FUS3 | 35.04 | 23.26 |
| FUS4 | 12.20 | 11.63 |
| FUSS | 12.40 | 18.60 |
| FUS6 | 21.46 | 32.56 |
| FUS7 | 3.35 | 16.28 |
| FUS8 | 1.18 | 32.56 |
| FUS9 | N.O. | 18.60 |
| FUS10 | N.O. | 13.95 |
| FUS11 | 1.57 | 13.95 |
| FUS15 | 0.39 | 9.30 |
| FUS18 | 0.39 | 9.30 |
| FUS19 | 8.86 | 30.23 |
| FUS23 | N.O. | 9.30 |
| FUS24 | N.O. | 9.30 |

N.O. not observed

Table 8 shows the gene origin and amino acid sequences of the identified neoantigens that arose from alternative splicing (AS) events. Table 9 shows their corresponding polynucleotide sequences. Table 10 shows the prevalence of the AS neoantigens in analyzed databases.

TABLE 8

| Neo epitope ID | Gene | Amino acid sequence | SEQ ID NO: |
|---|---|---|---|
| AS1 | ABCC4 | **LTFLDFIQ**VTLRVMSGSQMENGSSYFFKPFSWGLGVGLSAWLCVMLT | 241 |
| AS2 | SLC30A4 | **FMIGELVG**ELCCQLTFRLPFLESLCQAVVTQALRFNPSFQEVCIYQDTDLM | 243 |
| AS3 | DNAH8 | **VAMMVPDR**QVHYDFGL | 245 |
| AS4 | NCAPD3 | **WCPLDLRL**GSTGCLTCRHHQTSHE | 247 |
| AS5 | DHDH | **VVGRRHET**APQPLLVPDRAGGEGGA | 249 |
| AS6 | ACSM1 | **DYWAQKEK**ISIPRTHLC | 251 |
| AS7 | ACSM1 | **DYWAQKEK**GSSSFLRPSC | 253 |
| AS8 | CACNA1D | **LVLGVLSG**HSGSRL | 255 |
| AS9 | CACNA1D | **PVPTATPG**VRSVTSPQGLGLFLKFI | 257 |
| AS10 | CHRNA5 | **KENDVREV**CDVYLQMQIFFHFKFRSYFH | 259 |
| AS11, AS33 | CPNE7 | **VPFRELKN**QRTAQGAPGIHHAASPVAANLCDPARHAQHTRIPCGAGQVRAGRGPEAGGGVLQPQRPAPEKPGCPCRRGQPRLHTVKMWRA | 261 |
| AS12 | EVPL | **FARKMLEK**VHRQHLQLSHNSQE | 263 |
| AS13 | GRIN3A | **KRSFAVTE**RII | 265 |
| AS14 | IQCG | **MFLRKEQQ**VGPHSFSML | 267 |
| AS15 | LRRC45 | **VLRFLDLK**VRYLHS | 269 |
| AS16 | LRRC45 | **GNTTLQQL**GEASQAPSGSLIPLRLPLLWEVRG | 271 |
| AS17 | MPHOSPH9 | **GLNLNTDR**PGGYSYSIWWKNNAKNR | 273 |
| AS18 | NWD1 | **WKFEMSYT**VGGPPPHVHARPRHWKTDR | 275 |
| AS19 | NWD1 | **QWQHYHRS**GEAAGTPLWRPTRN | 277 |
| AS20 | PFKFB4 | **KVLNEIDA**VVTVPPSLSTSQIPQGCCIIL | 279 |
| AS21 | RECQL4 | **ANLKGTLQ**VRSGQAVSPR | 281 |
| AS22 | TONSL | **LQAAASGQ**GKQGVPCPWGCCAYAESPRALISGDAPSQVEREVPGPCLNTHSLSHRSPQLPGLPHPKQPSV | 283 |
| AS23 | ZNF614 | **KIQNKNCPD** | 285 |
| AS32 | TONSL | **GEVELSEG**GEGQRHLAFPWACSGPGWRGVCCAAVEPA | 287 |
| AS63 | TDRD1 | **IEMKKLLKS** | 289 |
| AS34 | LRRC45 | **KMRAIQAE**GGHGQACCGGAWGWAPGDGGPQGMLTHTLPTLGFQSAWTWRREDADRAWRTPKACASRRWSI | 291 |
| AS35 | AMACR | **LLEPFRR**GEPGPRGLLSGSSRGGEGPGRSIEAAPATPLPCCRKNPCRPQPSRFLPPRVLLVIILPKLDCPKLGF | 293 |
| AS36 | CCNF | **PSGRRTKR**LVTLRSGCAIQCWHPRAGPVPSALPHTERPPRLVRGAADPRTVTLGRSPAVMPRAPA | 295 |

TABLE 8-continued

| Neo epitope ID | Gene | Amino acid sequence | SEQ ID NO: |
|---|---|---|---|
| AS37 | RECQL4 | **CHLFLQPQ**VGTPPPHTASARAPSGPPHPHESCPAGRRPARAAQTCARRQHGLPGCEEAGTARVPSLHLHLHQAALGAGRGRGWGEACAQVPPSRG | 297 |
| AS38 | LRRC45 | **KELKLEQQ**VGGQGLRGVGQGVRGGFVTLTTHTPFPSQ**EAAERESK** | 299 |
| AS39 | CCNF | **GEISQEEV**PPSRHLGVSWGAGVWAGLTLGASAPPNSSFPSGAELQPVVCCIRSDTRQPRPPDFPQHRGDPRLPQLSLGAENQTVSYPAFWLRHTMLASSCRPSSLSASSHREAPKACQGSSRSQDSDPGTEPCSHASGPCVTSTVSSPGLLPQRLLPLALTGLPVEEDGFEHAGA | 301 |
| AS40 | LRRC45 | **DCMLSEEG**GQARRGGSLCSLAAHTIASAARGRFLSRLSNFCAVVKASRGAPSCTWE | 303 |
| AS41 | RHPN1 | **EAFQRAAG**EGGPGRGGARRGARVLQSPFCRAGAGEWLGHQSLR | 305 |
| AS42 | 5LC39A4 | **PEPRRLSP**GEPRGRPRKGWGIWGLCGARVGPKAWR | 307 |
| AS43 | CPNE7 | **VPFRELKN**VSVLEGLRQGRLGGPCSCHCPRPSQARLTPVDVAGPFLCLGDPGLFPPVKSSI | 309 |
| AS44 | FASN | **FVSLTAIQ**MASSATPWGRWPVATPTAACPRRRPSSLPTGGDSASKKPISRRAPWQPWACPGRSVNSAAPRAWCPPATTPRTQSPSRDLRPRCLSSWSS | 311 |
| AS45 | RBM47 | **PVAIKPGT**GPPNNSSIHGGSKRSENSYCRDLRGQLRAICCSSYSHDRHTTEERGSRGRHVWRIRRLHTSGLPCCCHSGPHPRRLPDILRLVTSTKTDHTNTTEGTLDYL | 313 |
| AS46 | SERINC5 | **KWNKNWTA**TLGALTIRGHKLLCHLPHLLSSVQQTCRSSSR | 315 |
| AS47 | AGRN | **FKKFDGPC**GERGGGRTARALWARGDSVLTPALDPQTPVRAPSLTRAAAAV | 317 |
| AS48 | SYT17 | **ENASLVFT**GSNSPIPACELSSHPAHGISPWIPSPGNEHFHGIKKQVKAIKVE | 319 |
| AS49 | PDF | **RLTQRLVQ**GWTPMENRWCGRRAGGQPASSSTRWTTCRAACLLTKWTAGRSQTSIG | 321 |
| AS50 | LRIF1 | **ENSGNASR**WLHVPSSSDDWLGWKKSSAITSNS | 323 |
| AS51 | CPNE7 | **GMECTLGQ**VGAPSPRREEDGWRGGHSRFKADVPAPQGPCWGGQPGSAPSSAPPEQSLLD | 325 |
| AS52 | ILDR1 | **KGSVERRS**VSLGHPAEGWAWAERSLQPGMTTANTGCLSFHHRGCLLPVLPKLHCGLGGLPLVRAKEIKRVQRAGESSLPVKGLLTVASAVIAVLWGRPSEVTGENEAQHD | 327 |
| AS53 | PEX10 | **FGLTTLAG**RSSHGTSGLRAATHTKSGDGGQGAARQCEKLLELARATRPWGRSTSASSRWTHRGYMCPPRCAVACW | 329 |
| AS54 | ABCC4 | **IIDSDKIM**AVCMGCLLTRHVQCQAMEMQQ | 331 |
| AS55 | SPOCK1 | **DGHSYTSK**VNCLLLQDGFHGCVSITGAAGRRNLSIFLFL**MLCKLEFHAC** | 333 |

TABLE 8-continued

| Neo epitope ID | Gene | Amino acid sequence | SEQ ID NO: |
|---|---|---|---|
| AS56 | TM9SF3 | **LLNAEDYR**CAIHSKEIYLLSPSPHQAMDKFSLCCINCNLCLHVFLLLLFFQNKDVWLISNIILLWIYGGI | 335 |
| AS57 | KLK3 | **TGGKSTCS**APGPQSLPSTPFSTYPQ**WVILITEL** | 337 |
| AS58 | CREB3L1 | **VETLENAN**SFSSGIQPLLCSLIGLENPT | 339 |
| AS59 | ACSL3 | **AGAGTISE**GSVLHGQRLECDARRFFGCGTTILAEWEHH | 341 |
| AS55.1 | SPOCK1 | **DGHSYTSK**VNCLLLQDGFHGCVSITGAAGRRNLSIFLFLMLCKLEFHA | 385 |

TABLE 9

| Neo-epi-tope ID | Polynucleotide sequence | SEQ ID NO: |
|---|---|---|
| AS1 | CTGACGTTTTTAGATTTCATCCAGGTAACGTTGAGAGTAATGTCAGGATCTCAAATGGAAAACGGAAGTTCCTATTTTTTCAAGCCCTTTTCATGGGGTCTGGGGGTGGGACTCTCGGCCTGGCTGTGTGTAATGTTAACT | 242 |
| AS2 | TTCATGATTGGAGAACTTGTAGGTGAGTTGTGTTGCCAACTCACTTTCCGTTTACCTTTCCTCGAGAGTCTTTGTCAAGCTGTAGTTACACAGGCTTTGAGGTTTAACCCATCTTTTCAGGAAGTTTGTATTTATCAAGACACTGATCTCATG | 244 |
| AS3 | GTTGCTATGATGGTTCCTGATAGACAGGTTCATTATGACTTTGGATTG | 246 |
| AS4 | TGGTGTCCGCTGGATCTTAGACTCGGTTCCACTGGATGTCTCACATGCAGACATCATCAAACGTCACATGAG | 248 |
| AS5 | GTCGTGGGAAGGCGTCATGAAACAGCTCCTCAACCCCTGCTGGTGCCCGACCGAGCTGGTGGTGAAGGGGGAGCA | 250 |
| AS6 | GACTACTGGGCTCAAAAGGAGAAGATCAGCATCCCCAGAACACACCTGTGT | 252 |
| AS7 | GACTACTGGGCTCAAAAGGAGAAGGGATCATCTTCATTCCTGCGACCATCCTGT | 254 |
| AS8 | CTTGTACTTGGTGTATTGAGCGGGCACAGTGGCTCACGCCTA | 256 |
| AS9 | CCTGTCCCAACTGCTACACCTGGGGTAAGATCAGTGACTAGTCCCCAGGGGCTGGGCCTTTTCCTTAAGTTTATT | 258 |
| AS10 | AAGGAAAATGATGTCCGTGAGGTCTGTGATGTGTATTTACAAATGCAGATCTTCTTCCATTTTAAGTTCAGAAGTTACTTTCAT | 260 |
| AS11, AS33 | GTGCCCTTCCGGGAGCTCAAGAACCAGAGAACAGCACAAGGGGCTCCTGGGATCCACCACGCGGCTTCCCCCGTTGCTGCCAACCTCTGCGACCCGGCGAGACACGCACAGCACACACGCATCCCCTGCGGCGCTGGCCAAGTGCGTGCTGGCCGAGGTCCCGAAGCAGGTGGTGGAGTACTACAGCCACAGAGGCCTGCCCCCGAGAAGCCTGGGTGTCCCTGCCGGAGAGGCCAGCCCAGGCTGCACACCGTGAAGATGTGGAGGGCG | 262 |
| AS12 | TTTGCTAGAAAAATGCTGGAGAAGGTACACAGACAACACCTACAGCTTTCCCACAATAGCCAGGAA | 264 |
| AS13 | AAGAGAAGTTTTGCTGTCACGGAGAGGATCATC | 266 |
| AS14 | ATGTTCCTTAGAAAGGAGCAGCAGGTGGGTCCCCACAGCTTTTCTATGCTT | 268 |

TABLE 9-continued

| Neo-epi-tope ID | Polynucleotide sequence | SEQ ID NO: |
|---|---|---|
| AS15 | GTGCTGCGCTTTCTGGACTTAAAGGTGAGATACCTGCACTCT | 270 |
| AS16 | GGCAACACCACCCTCCAGCAGCTGGGTGAGGCCTCCCAGGCGCCCTCAGGCTCCCTCATCCCTCTGAGGCTGCCTCTGCTCTGGGAAGTGAGGGGC | 272 |
| AS17 | GGACTGAACTTAAATACTGATAGACCAGGTGGTTACAGCTATTCAATTTGGTGGAAAAACAATGCCAAGAACAGA | 274 |
| AS18 | TGGAAATTCGAGATGAGCTACACGGTGGGTGGCCCGCCTCCCCATGTTCATGCTAGACCCAGGCATTGGAAAACTGATAGA | 276 |
| AS19 | CAGTGGCAGCACTACCACCGGTCAGGTGAGGCCGCAGGGACTCCCCTCTGGAGACCCACAAGAAAC | 278 |
| AS20 | AAGGTCCTCAACGAGATCGATGCGGTAGTTACCGTCCCTCCCTCCCTGTCTACCTCCCAGATACCGCAGGGCTGCTGCATCATATTG | 280 |
| AS21 | GCCAATCTGAAAGGCACCCTGCAGGTGAGGAGTGGGCAGGCAGTGAGTCCACGC | 282 |
| AS22 | CTCCAGGCGGCTGCCTCGGGCCAAGGCAAGCAGGGCGTCCCTTGTCCCTGGGGTTGCTGTGCCTACGCTGAGAGTCCCCGGGCCCTGATTTCGGGAGATGCTCCATCACAGGTGGAGCGGGAGGTGCCGGGCCCCTGCCTCAACACGCATTCTCTCTCCCACAGATCCCCACAGCTCCCAGGCCTTCCACACCCCAAGCAGCCTTCTGTT | 284 |
| AS23 | AAAATTCAGAATAAAAATTGTCCAGAC | 286 |
| AS32 | GGCGAGGTGGAGCTCTCAGAGGGCGGTGAGGGCCAGCGGCACCTTGCATTTCCCTGGGCCTGCTCTGGGCCGGGCTGGAGAGGGGTGTGCTGTGCTGCTGTGGAGCCTGCT | 288 |
| AS63 | ATTGAAATGAAAAAACTGTTAAAAAGT | 290 |
| AS34 | AAGATGCGGGCCATCCAGGCCGAGGGTGGGCACGGGCAGGCCTGCTGTGGAGGGGCCTGGGGATGGGCACCGGGGGACGGGGGCCCCCAGGGGATGCTCACGCATACTCTGCCCACCCTGGGCTTCCAGAGCGCCTGGACATGGAGAAGAGAAGATGCAGACAGAGCCTGGAGGACTCCGAAAGCCTGCGCATCAAGGAGGTGGAGCATA | 292 |
| AS35 | CTGCTGGAGCCCTTCCGCCGCGGTGAGCCCGGGCCCCGCGGGCTGCTCTCGGGAAGTTCCCGCGGAGGGGAGGGGCCTGGCCGTTCGATCGAGGCTGCACCCGCCACACCTTTGCCCTGTTGCCGCAAGAACCCTTGTCGGCCCCAGCCTTCCAGATTTTTGCCTCCTAGGGTATTGTTAGTGATCATTCTTCCCAAACTGGATTGTCCAAAACTTGGGTTC | 294 |
| AS36 | CCCTCGGGGCGGAGAACCAAACGGTTAGTTACCCTGCGTTCTGGCTGCGCCATACAATGCTGGCATCCTCGTGCCGGCCCAGTTCCCTCAGCGCTTCCTCACACAGAGAGGCCCCCAAGGCTTGTCAGGGGAGCAGCAGATCCCAGGACAGTGACCCTGGGACGGAGCCCTGCAGTCATGCCTCGGGCCCCTGCG | 296 |
| AS37 | TGCCACCTCTTCCTGCAGCCCCAGGTTGGCACCCCCCCCCCCCACACTGCCAGTGCTCGAGCCCCCAGTGGTCCACCCCACCCTCATGAAAGTTGCCCTGCAGGGCGAAGACCTGCGAGAGCTGCGCAGACATGTGCACGCCGACAGCACGGACTTCCTGGCTGTGAAGAGGCTGGTACAGCGCGTGTTCCCAGCCTGCACCTGCACCTGCACCAGGCCGCCCTCGGAGCAGGAAGGGGCCGTGGGTGGGGAGAGGCCTGTGCCCAAGTACCCCCCTCAAGAGGC | 298 |
| AS38 | AAGGAGCTCAAGCTGGAGCAGCAGGTGGGTGGGCAGGGCTTGAGAGGGGTGGGCCAAGGGGTGCGTGGCGGCTTCGTGACCCTCACTACCCATACCCCGTTCCCCTCCCAGGAAGCTGCAGAGCGGGAGTCTAAA | 300 |

TABLE 9-continued

| Neo-epi-tope ID | Polynucleotide sequence | SEQ ID NO: |
|---|---|---|
| AS39 | GGAGAAATCAGCCAGGAAGAGGTGCCTCCCTCCCGCCACCTGGGCGTCTCATGGGGTGCTGGGGTGTGGGCGGGCCTCACCCTCGGGGCCTCTGCACCCCCTAACTCTAGCTTCCCCTCAGGTGCTGAGCTACAGCCAGTTGTGTGCTGCATTAGGAGTGACACAAGACAGCCCCGACCCCCCGACTTTCCTCAGCACAGGGGAGATCCACGCCTTCCTCAGCTCTCCCTCGGGGCGGAGAACCAAACGGTTAGTTACCCTGCGTTCTGGCTGCGCCATACAATGCTGGCATCCTCGTGCCGGCCCAGTTCCCTCAGCGCTTCCTCACACAGAGAGGCCCCCAAGGCTTGTCAGGGGAGCAGCAGATCCCAGGACAGTGACCCTGGGACGGAGCCCTGCAGTCATGCCTCGGGCCCCTGCGTAACCTCCACTGTCTCCAGCCCAGGTCTCCTTCCTCAGAGGCTATTGCCTCTCGCTCTGACTGGGCTCCCTGTGGAGGAAGATGGTTTCGAGCACGCGGGAGCC | 302 |
| AS40 | GACTGCATGCTCAGCGAGGAAGGTGGGCAGGCGCGGCGGGGTGGATCCCTCTGCTCCTTAGCTGCCCACACCATTGCCTCGGCAGCCCGAGGTCGCTTCCTCTCCAGGCTCTCCAATTTCTGTGCCGTAGTTAAAGCGAGCAGGGGCGCCCCTTCCTGCACCTGGGAG | 304 |
| AS41 | GAGGCCTTCCAGAGGGCCGCTGGTGAGGGCGGCCCGGGCCGCGGTGGGGCACGGCGCGGTGCCAGGGTGTTGCAGAGCCCCTTTTGCAGGGCAGGAGCTGGGGAGTGGTTAGGACATCAGTCCCTCAGG | 306 |
| AS42 | CCTGAGCCCAGGAGACTGAGCCCAGGTGAGCCCAGGGGGCGACCCCGGAAGGGCTGGGGATCTGGGGTTTGTGTGGAGCGCGGGTGGGGCCCAAGGCTTGGCGG | 308 |
| AS43 | GTGCCCTTCCGGGAGCTCAAGAACGTGAGTGTCCTGGAGGGGCTCCGTCAAGGCCGGCTTGGGGGTCCCTGTTCATGTCACTGCCCAAGACCTTCCCAGGCCAGGCTCACGCCAGTGGATGTGGCAGGTCCCTTCTTGTGTCTGGGGGATCCTGGGCTGTTCCCCCCAGTCAAGAGCAGTATC | 310 |
| AS44 | TTTGTGAGCCTGACTGCCATCCAGATGGCATCGTCGGCCACTCCCTGGGGGAGGTGGCCTGTGGCTACGCCGACGGCTGCCTGTCCCAGGAGGAGGCCGTCCTCGCTGCCTACTGGAGGGGACAGTGCATCAAAGAAGCCCATCTCCCGCCGGGCGCCATGGCAGCCGTGGGCTTGTCCTGGGAGGAGTGTAAACAGCGCTGCCCCCCGGGCGTGGTGCCCGCCTGCCACAACTCCAAGGACACAGTCACCATCTCGGGACCTCAGGCCCCGGTGTTTGAGTTCGTGGAGCAGC | 312 |
| AS45 | CCAGTTGCCATTAAACCTGGTACAGGGCCGCCCAATAACTCCAGTATACACGGTGGCTCCAAACGTTCAGAGAATTCCTACTGCCGGGATCTACGGGGCCAGTTACGTGCCATTTGCTGCTCCAGCTACAGCCACGATCGCCACACTACAGAAGAACGCGGCAGCCCGCGGCCGCCATGTATGGAGGATACGCAGGCTACATACCTCAGGCCTTCCCTGCTGCTGCCATTCAGGTCCCCATCCCCGACGTCTACCAGACATACTGAGGCTGGTGACCAGCACGAAGACAGACCACACAAACACCACTGAAGGAACGCTTGACTATTTA | 314 |
| AS46 | AAGTGGAACAAGAACTGGACAGCCACACTCGGGGCTCTTACAATCAGGGGTCATAAGCTGCTATGTCACCTACCTCACCTTCTCAGCTCTGTCCAGCAAACCTGCAGAAGTAGTTCTAGA | 316 |
| AS47 | TTCAAGAAGTTCGACGGCCCTTGTGGTGAGCGCGGCGGCGGGCGCACGGCTCGAGCTCTGTGGGCGCGCGGCGACAGCGTCCTGACTCCTGCCCTCGACCCCCAGACCCCTGTCAGGGCGCCCTCCCTGACCCGAGCCGCAGCTGCCGTG | 318 |
| AS48 | GAAAATGCCAGCCTAGTGTTTACAGGATCCAACAGCCCCATACCAGCCTGCGAACTGAGTAGTCACCCAGCTCATGGTATCAGTCCTTGGATACCCTCACCTGGAAATGAACATTTCCATGGCATAAAGAAGCAAGTAAAGGCAATAAAAGTAGAA | 320 |
| AS49 | CGGCTGACGCAACGGCTGGTCCAGGGCTGGACCCCAATGGAGAACAGGTGGTGTGGCAGGCGAGCGGGTGGCAGCCCGCATCATCCAGCACGAGATGGACCACCTGCAGGGCTGCCTGTTTATTGACAAAATGGACAGCAGGACGTTCACAAACGTCTATTGGA | 322 |
| AS50 | GAAAATTCAGGCAACGCCTCGCGTTGGCTGCATGTACCAAGTAGTTCAGACGATTGGCTCGGATGGAAAAAATCTTCTGCAATTACTTCCAATTCC | 324 |
| AS51 | GGCATGGAGTGCACCCTGGGGCAGGTGGGTGCCCCGTCCCCTCGGAGGGAGGAGGACGGTTGGCGTGGGGGCCACAGCCGATTCAAGGCTGATGTACCAGCACCGCAGGGACCCTGCTGGGGTGGCCAACCTGGCTCTGCCCCCTCCTCAGCTCCTCCTGAACAGTCATTATTAGAT | 326 |
| AS52 | AAAGGGAGTGTGGAGAGGCGCTCGGTGAGCCTGGGGCATCCTGCTGAGGGTTGGGCATGGGCAGAGAGGAGCCTCCAGCCAGGCATGACCACAGCCAACACAGGCTGCCTCTCATTCCACCACAGAGGGTGCCTCCTCCCTGTTTTGCCCAAATTACACTGTGGGCTAGGTGGACTACCTCTTGTCAGAGCTAAAGAAATCAAGCGAGTGCAGAGGGCAGGGGAGAGTTCGCTGCCTGTGAAGGGCCTTCTCACCGTCGCTTCGGCTGTCATCGCAGTCCTGTGGGGTAGGCCAAGCGAGGTCACAGGAGAAAATGAGGCTCAGCATGAT | 328 |
| AS53 | TTTGGCCTCACCACACTTGCAGGTAGAAGCTCCCACGGGACCTCAGGACTGAGGGCAGCCACACACACCAAGTCTGGGGACGGTGGCCAGGGGGCTGCCAGGCAGTGTGAGAAGCTCCTGGAGCTGGCCCGGGCTACCAGACCCTGGGGGAGGAGTACGTCAGCATCATCCAGGTGGACCCATCGCGGATACATGTGCCCTCCTCGCTGCGCCGTGGCGTGCTGG | 330 |
| AS54 | ATTATTGACAGCGACAAGATAATGGCAGTGTGCATGGGGTGCCTGCTCACACGTCATGTGCAATGCCAGGCCATGGAGATGCAACAG | 332 |
| AS55 | GATGGCCACTCCTACACATCCAAGGTGAATTGTTTACTCCTTCAAGATGGGTTCCATGGCTGTGTGAGCATCACCGGGGCAGCTGGAAGAAGAAACCTGAGCATCTTCCTGTTCTTGATGCTGTGCAAATTGGAGTTCCATGCTTGT | 334 |
| AS56 | CTACTAAATGCAGAAGATTACCGGTGTGCCATTCATTCAAAAGAGATTTATCTTCTTTCCCCCTCCCCCCACCAGGCAATGGACAAGTTTTCTCTCTGCTGCATCAACTGCAATCTATGTTTACATGTATTCCTTTTACTACTATTTTTTCAAAACAAAGATGTATGGCTTATTTCAAACATCATTTTACTTTGGATATATGGCGGTATT | 336 |
| AS57 | ACAGGGGGCAAAAGCACCTGCTCGGCTCCTGGCCCTCAGTCTCTCCCCTCCACTCCATTCTCCACCTACCCACAGTGGGTCATTCTGATCACCGAACTG | 338 |
| AS58 | GTGGAGACCCTGGAGAATGCCAACAGCTTCTCCAGCGGGATCCAGCCACTCCTCTGTTCCCTGATTGGCCTGGAGAATCCCACC | 340 |
| AS59 | GCTGGGGCTGGAACAATTTCCGAAGGTAGTGTTCTCCATGGTCAGAGGCTGGAGTGTGATGCCAGACGTTTTTTTGGGTGTGGGACTACAATACTGGCAGAGTGGGAGCACCAT | 342 |
| AS55.1 | GATGGCCACTCCTACACATCCAAGGTGAATTGTTTACTCCTTCAAGATGGGTTCCATGGCTGTGTGAGCATCACCGGGGCAGCTGGAAGAAGAAACCTGAGCATCTTCCTGTTCTTGATGCTGTGCAAATTGGAGTTCCATGCT | 386 |

TABLE 10

| Neoepitope ID | TCGA (%) | SU2C (%) |
|---|---|---|
| AS1 | 28.5 | 2.3 |
| AS2 | 18.5 | N.O. |
| AS3 | 10.4 | 25.6 |
| AS4 | 27.4 | 41.9 |
| AS5 | 18.7 | 9.3 |
| AS6 | 5.1 | 16.3 |

TABLE 10-continued

| Neoepitope ID | TCGA (%) | SU2C (%) |
|---|---|---|
| AS7 | 5.1 | 16.3 |
| AS8 | N.O. | 14.0 |
| AS9 | 1.2 | 18.6 |
| AS10 | 8.9 | 27.9 |
| AS11 | 1.2 | 48.8 |
| AS12 | 0.4 | 34.9 |
| AS13 | 5.7 | 32.6 |
| AS14 | N.O. | 30.2 |
| AS15 | 4.5 | 46.5 |
| AS16 | 0.6 | 18.6 |
| AS17 | N.O. | 37.2 |
| AS18 | 12.6 | 20.9 |
| AS19 | 12.6 | 20.9 |
| AS20 | 0.2 | 16.3 |
| AS21 | N.O. | 11.6 |
| AS22 | 0.2 | 20.9 |
| AS23 | 3.1 | 18.6 |
| AS32 | 57.1 | N.O. |
| AS33 | 47.6 | N.O. |
| AS34 | N.O. | 42.9 |
| AS35 | N.O. | 42.9 |
| AS36 | N.O. | 40.5 |
| AS37 | N.O. | 38.1 |
| AS38 | N.O. | 35.7 |
| AS39 | N.O. | 33.3 |
| AS40 | N.O. | 33.3 |
| AS41 | N.O. | 33.3 |
| AS42 | N.O. | 33.3 |
| AS43 | N.O. | 31 |
| AS44 | N.O. | 28.6 |
| AS45 | N.O. | 26.2 |
| AS46 | N.O. | 26.2 |
| AS47 | N.O. | 23.8 |
| AS48 | N.O. | 23.8 |
| AS49 | N.O. | 23.8 |
| AS50 | N.O. | 23.8 |
| AS51 | N.O. | 23.8 |
| AS52 | 15.9 | 38.1 |
| AS53 | 16 | 9.5 |
| AS54 | 11.9 | N.O. |
| AS55 | 12.1 | N.O. |
| AS56 | 14.7 | N.O. |
| AS57 | 14.9 | N.O. |
| AS58 | 16.6 | N.O. |
| AS59 | 17.6 | N.O. |
| AS63 | 18.0 | |

N.O. not observed

Example 3: Identification of Additional Neoantigens Using Bioinformatics

Additional neoantigen sequences were identified by further queries as described in Example 2. Table 11 shows the amino acid sequences of the additional neoantigens. Table 12 shows the corresponding polynucleotide sequences.

TABLE 11

| Neoantigen ID | Gene(s) | Amino acid sequence | SEQ ID NO: |
|---|---|---|---|
| P16 | MSMB-NCOA4 | GVPGD**STRRAVRRM**NTF | 343 |
| P17 | MSMB-NOCA4 | GVPGDSTR**RAVRRMNTF** | 343 |
| P19 | TMEM222-LOC644961 | WTP**IPVLTRWPL**PHPPPWRRATSCRMARSSPSATSGSSVRRRCSSLPSWVWNLAASTRPRSTPS | 347 |
| P22 | 5LC45A3-ELK4 | SLYHREK**QLIAMDSAI** | 349 |
| P27 | FAM126B-ORC2 | LHPQRETFTPRWSGANYWKLA**FPVGAEGTF**PAAATQRGVVRPA | 351 |
| P35 | TMPRSS2-ERG | **NSKMALNS**LNSIDDAQLTRIAPPRSHCCFWEVNAP | 353 |
| P37 | TSTD1-F11R | MAG**GVLRRLLCR**EPDRDGDKGASREETVVPLHIGDPVVLPGIGQCYSALF | 355 |
| P46 | TP53 (R213D) | DDRNTFDIVWW**CPMSRLRLAL**TVPPSTTTTCVTVPAWAA | 357 |
| P48 | AR.p.H875Y | VQPIAREL**YQFTFDLLI** | 359 |
| P50 | AR (W742C) | QMAV**IQYSCMGLM**VFAM | 361 |
| P56 | SPOP (F102C) | PKSEV**RAKCKFSIL**NAK | 363 |
| P58 | AR (Q903H) | MMAEHSV**HVPKILSGK** | 365 |
| P59 | FOXA1 (F254V) | LHPDSG**NMVENGCYL**RR | 367 |
| P60 | FOXA1.p. F266L | C**YLRRQKRLK**CEKQPGA | 369 |
| P61 | FOXA1.p. R261G | MFENG**CYLGRQKRF**KCE | 371 |
| P73 | TP53 (G266E) | DSSGN**LLERNSFEV**RV | 373 |
| P76 | AR-V3 | VFFKRAAEGFFRMNKLKESSDTNPKP**YCMAAPMGL**TENNRNRKKSYRETNLKAVSWPLNHT | 375 |
| P77 | AR-V3 | V**FFKRAAEGF**FRMNKLKESSDTNPKPYCMAAPMGLTENNRNRKKSYRETNLKAVSWPLNHT | 375 |
| P82 | AR-V7 | YEAGMTLGEKF**RVGNCKHLK**MTRP | 379 |
| P87 | AR-Intron | YEAGMTLGGKILF**FLFLLLPLS**PFSLIF | 381 |
| P97 | FOXRED2-TXN2 | GYLRMQG**LMAQRLLLR** | 383 |
| P98 | TP53 (R213D) | DDRNTFD**IVWWCPMSR**LRLALTVPPSTTTTCVTVPAWAA | 357 |

TABLE 12

| Neoantigen ID | Gene(s) | Nucleotide sequence | SEQ ID NO: |
|---|---|---|---|
| P16 | MSMB-NCOA4 | GGAGTTCCAGGAGATTCAACCAGGAGAGCAGTGAGGAGAATGAATACCTTC | 344 |
| P17 | MSMB-NOCA4 | GGAGTTCCAGGAGATTCAACCAGGAGAGCAGTGAGGAGAATGAATACCTTC | 344 |
| P19 | TMEM222-LOC644961 | TGGACGCCCATCCCGGTGCTCACGAGATGGCCACTACCACATCCTCCTCCCTGGAGAAGAGCTACAAGCTGCCGGATGGCCAGGTCATCACCATCAGCAACAAGCGGTTCCAGTGTCCGGAGGCGCTGTTCCAGCCTTCCTTCCTGGGTATGGAATCTTGCGGCATCCACGAGACCACGTTCAACTCCATCATGAA | 348 |

TABLE 12-continued

| Neo-anti-gen ID | Gene(s) | Nucleotide sequence | SEQ ID NO: |
|---|---|---|---|
| P22 | 5LC45A3-ELK4 | TCCCTCTACCACCGGGAGAAGCAGCTCATTGCTATGGACAGTGCTATC | 350 |
| P27 ORC2 | FAM126B- | CTTCATCCTCAGAGGGAAACATTCACTCCCCGGTGGTCGGGCGCGAATTACTGGAAATTGGCTTTTCCCGTTGGGGCCGAAGGTACCTTCCCTGCGGCGGCGACTCAGCGGGGTGTCGTTCGGCCGGCGTG | 352 |
| P35 | TMPRSS2-ERG | AACAGCAAGATGGCTTTGAACTCATTAAACTCCATTGATGATGCACAGTTGACAAGAATTGCCCCTCCAAGATCTCATTGCTGTTTCTGGGAAGTAAACGCTCCT | 354 |
| P37 | TSTD1-F11R | ATGGCTGGAGGAGTCCTTCGGCGGCTGTTGTGTCGGGAGCCTGATCGCGATGGGGACAAAGGCGCAAGTCGAGAGGAAACTGTTGTGCCTCTTCATATTGGCGATCCTGTTGTGCTCCCTGGCATTGGGCAGTGTTACAGTGCACTCTTCT | 356 |
| P46 | TP53 (R213D) | GATGACAGAAACACTTTCGACATAGTGTGGTGGTGCCCTATGAGCCGCCTGAGGTTGGCTCTGACTGTACCACCATCCACTACAACTACATGTGTAACAGTTCCTGCATGGGCGGCATGA | 358 |
| P48 | AR.p.H875Y | GTGCAGCCTATTGCGAGAGAGCTGCATCAGTTCACTTTTGACCTGCTAATC | 360 |
| P50 | AR (W742C) | CAGATGGCTGTCATTCAGTACTCCTGCATGGGGCTCATGGTGTTTGCCATG | 362 |
| P56 | SPOP (F102C) | CAAAGAGTGAAGTTCGGGCAAAATTCAAATGCTCCATCCTGAATGCCAAG | 364 |
| P58 | AR (Q903H) | ATGATGGCAGAGATCATCTCTGTGCACGTGCCCAAGATCCTTTCTGGGAAA | 366 |
| P59 | FOXA1 (F254V) | CTGCACCCGGACTCCGGCAACATGGTCGAGAACGGCTGCTACTTGCGCCGC | 368 |
| P60 | FOXA1.p.F266L | TGCTACTTGCGCCGCCAGAAGCGCTTGAAGTGCGAGAAGCAGCCGGGGGCC | 370 |
| P61 | FOXA1.p.R261G | ATGTTCGAGAACGGCTGCTACTTGGGCCGCCAGAAGCGCTTCAAGTGCGAG | 372 |
| P73 | TP53 (G266E) | GACTCCAGTGGTAATCTACTGGAACGGAACAGCTTTGAGGTGCGTGTT | 374 |
| P76 | AR-V3 | GTCTTCTTCAAAAGAGCCGCTGAAGGATTTTTCAGAATGAACAAATTAAAAGAATCATCAGACACTAACCCCAAGCCATACTGCATGGCAGCACCAATGGGACTGACAGAAAACAACAGAAATAGGAAGAAATCCTACAGAGAAACAAACTTGAAAGCTGTCTCATGGCCTTTGAATCATACT | 376 |
| P77 | AR-V3 | GTCTTCTTCAAAAGAGCCGCTGAAGGATTTTTCAGAATGAACAAATTAAAAGAATCATCAGACACTAACCCCAAGCCATACTGCATGGCAGCACCAATGGGACTGACAGAAAACAACAGAAATAGGAAGAAATCCTACAGAGAAACAAACTTGAAAGCTGTCTCATGGCCTTTGAATCATACT | 376 |
| P82 | AR-V7 | TATGAAGCAGGGATGACTCTGGGAGAAAAATTCCGGGTTGGCAATTGCAAGCATCTCAAAATGACCAGACCC | 380 |
| P87 | AR-Intron | TATGAAGCAGGGATGACTCTGGGAGGTAAGATACTTTTCTTTCTCTTCCTCCTCCTTCCTCTCTCCCCCTTCTCCCTCATTTTC | 382 |
| P97 | FOXRED2-TXN2 | GGGTACCTGAGGATGCAGGGACTCATGGCTCAGCGACTTCTTCTGAGG | 384 |
| P98 | TP53 (R213D) | GATGACAGAAACACTTTCGACATAGTGTGGTGGTGCCCTATGAGCCGCCTGAGGTTGGCTCTGACTGTACCACCATCCACTACAACTACATGTGTAACAGTTCCTGCATGGGCGGCATGA | 358 |

Example 4: HLA Binding Predictions

The amino acid sequences of the neoantigens identified using the various approaches as described in Example 3 were split into all possible unique, contiguous 9 mer amino acid fragments and HLA binding predictions to six common HLA alleles (HLA-A*01:01, HLA-A*02:01, HLA-A*03:01, HLA-A*24:02, HLA-B*07:02, HLA-B*08:01) were performed for each of these 9mers using netMHCpan4.0. Several 9 mer fragments were selected for further analysis based on ranking by likelihood of binding to one or more of the tested HLA alleles and their prevalence in prostate cancer patients.

Table 13 shows the amino acid sequences of select 9 mer fragments and their neoantigen origin. Table 14 shows the prevalence of neoantigens in the analyzed cohorts.

TABLE 13

| Neoantigen ID | Gene(s) | Type | Amino acid sequence or 9-mer | SEQ ID NO: of the 9 mer |
|---|---|---|---|---|
| P16 | MSMB-NCOA4 | Fusion | STRRAVRRM | 387 |
| P17 | MSMB-NOCA4 | Fusion | RAVRRMNTF | 388 |
| P19 | TMEM222- | Fusion | IPVLTRWPL | 389 |
| P22 | SLC45A3-ELK4 | Fusion | QLIAMDSAI | 390 |
| P27 | FAM126B-ORC2 | Fusion | FPVGAEGTF | 391 |
| P35 | TMPRSS2-ERG | Fusion | NSKMALNSL | 392 |

TABLE 13-continued

| Neoantigen ID | Gene(s) | Type | Amino acid sequence or 9-mer | SEQ ID NO: of the 9 mer |
|---|---|---|---|---|
| P37 | TSTD1-F11R | Fusion | GVLRRLLCR | 393 |
| P46 | TP53 (R213D) | Frameshift | CPMSRLRLA | 394 |
| P48 | AR.p.H875Y | Missense | YQFTFDLLI | 395 |
| P50 | AR (W742C) | Missense | IQYSCMGLM | 396 |
| P56 | SPOP(F102C) | Missense | RAKCKFSIL | 397 |
| P58 | AR (Q903H) | Missense | HVPKILSGK | 398 |
| P59 | FOXA1 (F254V) | Missense | NMVENGCYL | 399 |
| P60 | FOXA1.p.F266L | Missense | YLRRQKRLK | 400 |
| P61 | FOXA1.p.R261G | Missense | CYLGRQKRF | 401 |
| P73 | TP53 (G266E) | Missense | LLERNSFEV | 402 |
| P76 | AR-V3 | Splice Variant | YCMAAPMGL | 403 |
| P77 | AR-V3 | Splice Variant | FFKRAAEGF | 404 |
| P82 | AR-V7 | Splice Variant | RVGNCKHLK | 405 |
| P87 | AR-Intron | Splice Variant | FLFLLLPLS | 406 |
| P97 | FOXRED2-TXN2 | Fusion | LMAQRLLLR | 407 |
| P98 | TP53 (R213D) | Frameshift | IVWWCPMSR | 408 |

TABLE 14

| Neoantigen | | Prevalence | |
|---|---|---|---|
| ID | Gene | TCGA | SU2C |
| P16 | MSMB-NCOA4 | 27.16% | 23.25% |
| P17 | MSMB-NOCA4 | 27.16% | 23.25% |
| P19 | TMEM222-LOC644961 | N.O. | 13.95% |
| P22 | SLC45A3-ELK4 | 17.71% | 13.95% |
| P27 | FAM126B-ORC2 | 5.11% | 18.60% |
| P35 | TMPRSS2-ERG | 2.75% | 11.62% |
| P37 | TSTD1-F11R | 16.33% | 9.30% |
| P46 | TP53 (R213D) | N.O. | 1% |
| P48 | AR.p.H875Y | N.O. | 1% |
| P50 | AR (W742C) | N.O. | 1.25% |
| P56 | SPOP (F102C) | 0.40% | 2.00% |
| P58 | AR (Q903H) | N.O. | 1.00% |
| P59 | FOXA1 (F254V) | 0.20% | 1.00% |
| P60 | FOXA1.p.F266L | 0.20% | 1% |
| P61 | FOXA1.p.R261G | 0.20% | 1% |
| P73 | TP53 (G266E) | N.O. | 1% |
| P76 | AR-V3 | Present | Present |
| P77 | AR-V3 | Present | Present |
| P82 | AR-V7 | Present | Present |
| P87 | AR-Intron | Present | Present |
| P97 | FOXRED2-TXN2 | 3.74% | 11.62% |
| P98 | TP53 (R213D) | 0.00% | 1.00% |

N.O: not observed;

Present: AR splice variants were expressed at variable levels and hence prevalence was not determined

Example 5: Immunogenicity Assessment of Neoantigens

Figure 5A:
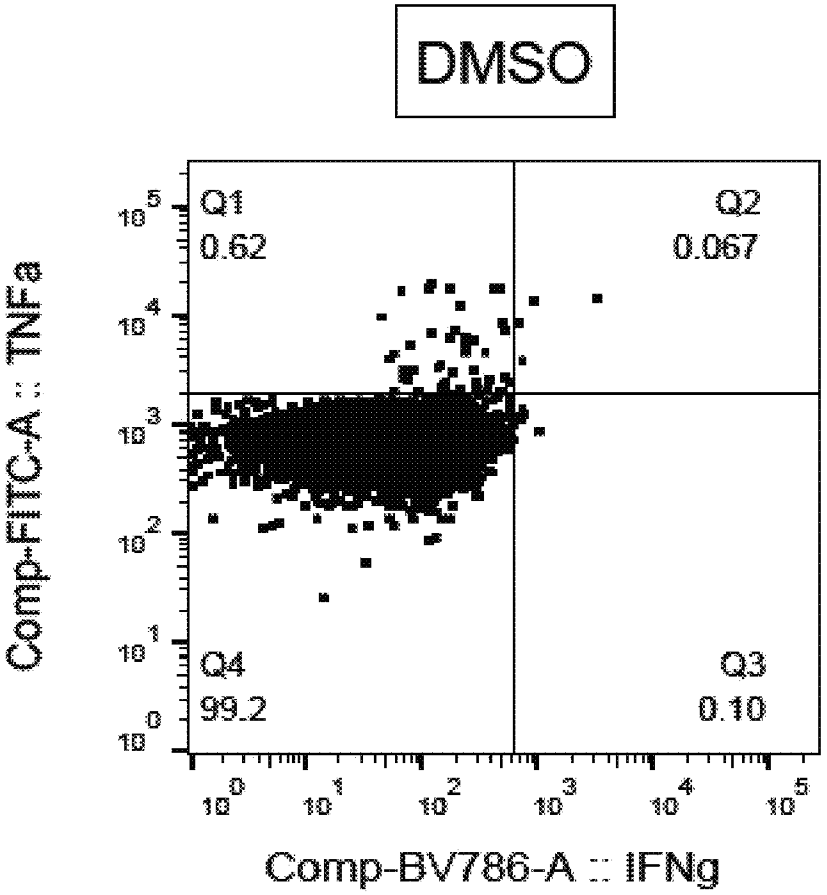
FIG. 5A shows a flow cytometry dot plot depicting $TNF\alpha^+IFN\gamma^+CD8^+$ T cell frequencies in PBMC samples after no stimulation (DMSO).
Figure 5B:
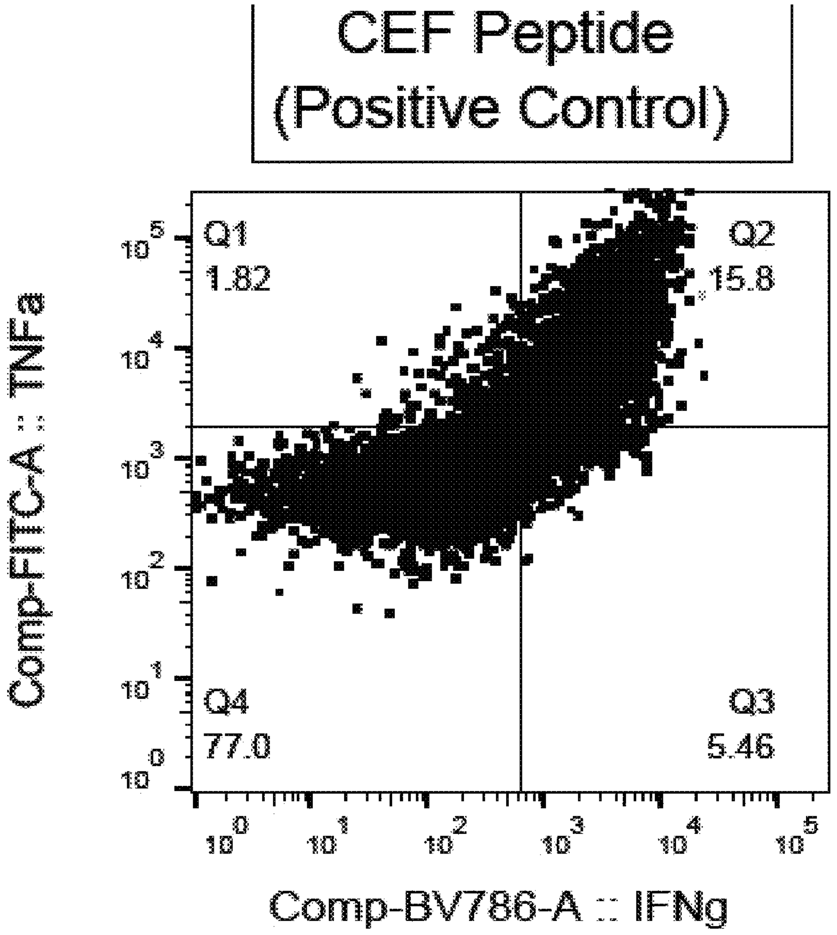
FIG. 5B shows a flow cytometry dot plot depicting $TNF\alpha^+IFN\gamma^+CD8^+$ T cell frequencies in PBMC samples after stimulating with CEF peptide.
Figure 5C:
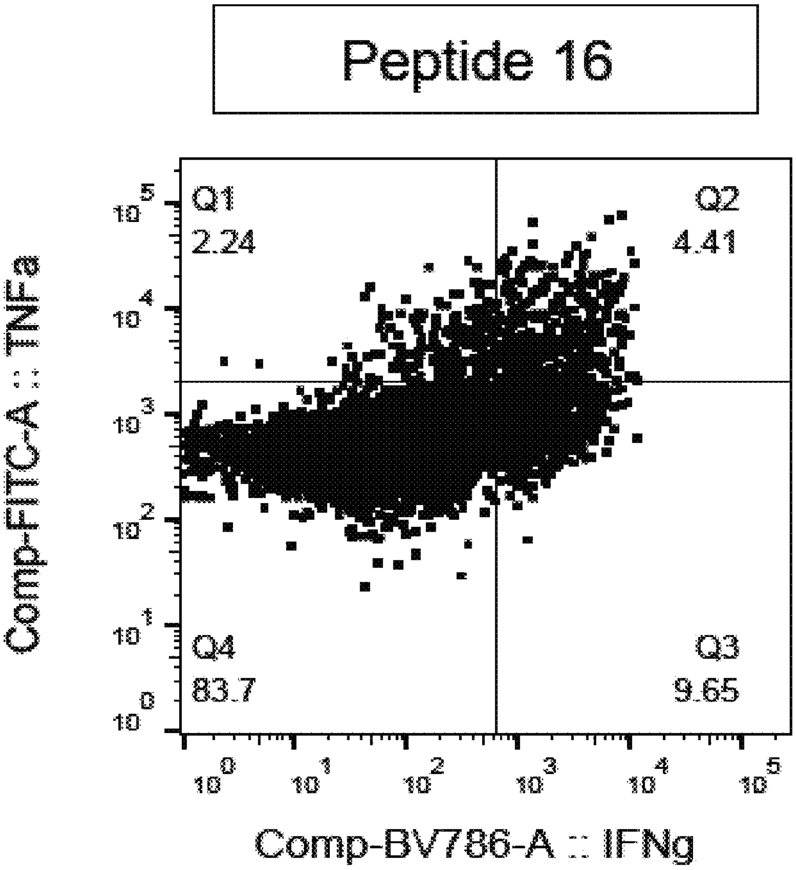
FIG. 5C shows a flow cytometry dot plot depicting $TNF\alpha^+IFN\gamma^+CD8^+$ T cell frequencies in PBMC samples after stimulation with P16.
Figure 5D:
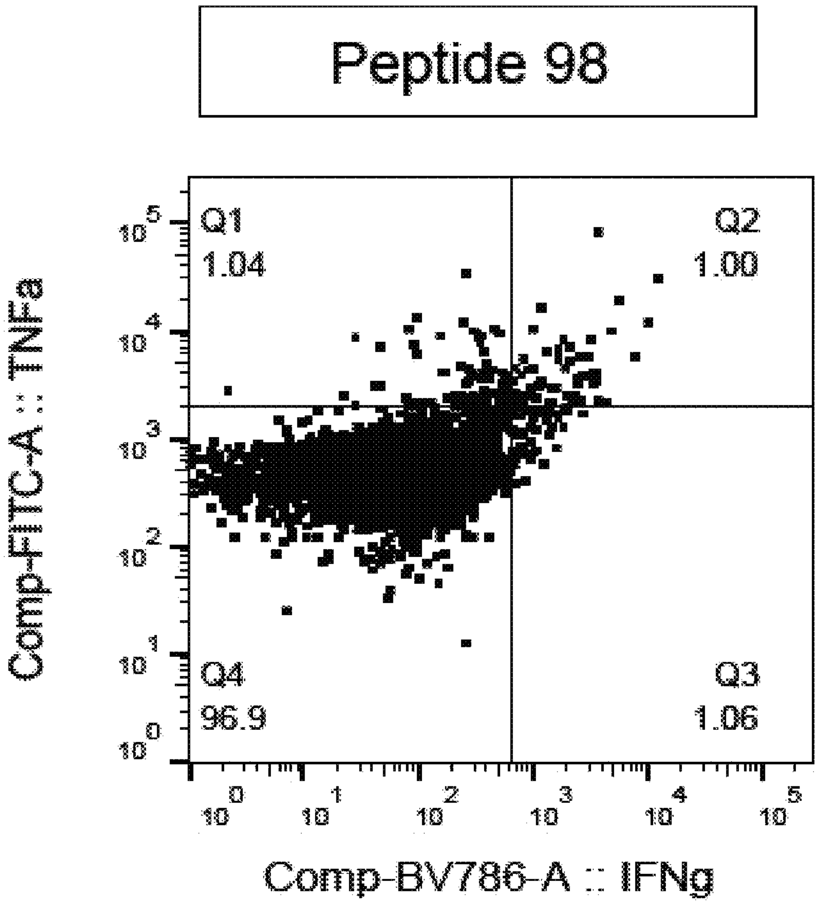
FIG. 5D shows a flow cytometry dot plot depicting $TNF\alpha^+IFN\gamma^+CD8^+$ T cell frequencies in PBMC samples after stimulation with P98.
Figure 5E:
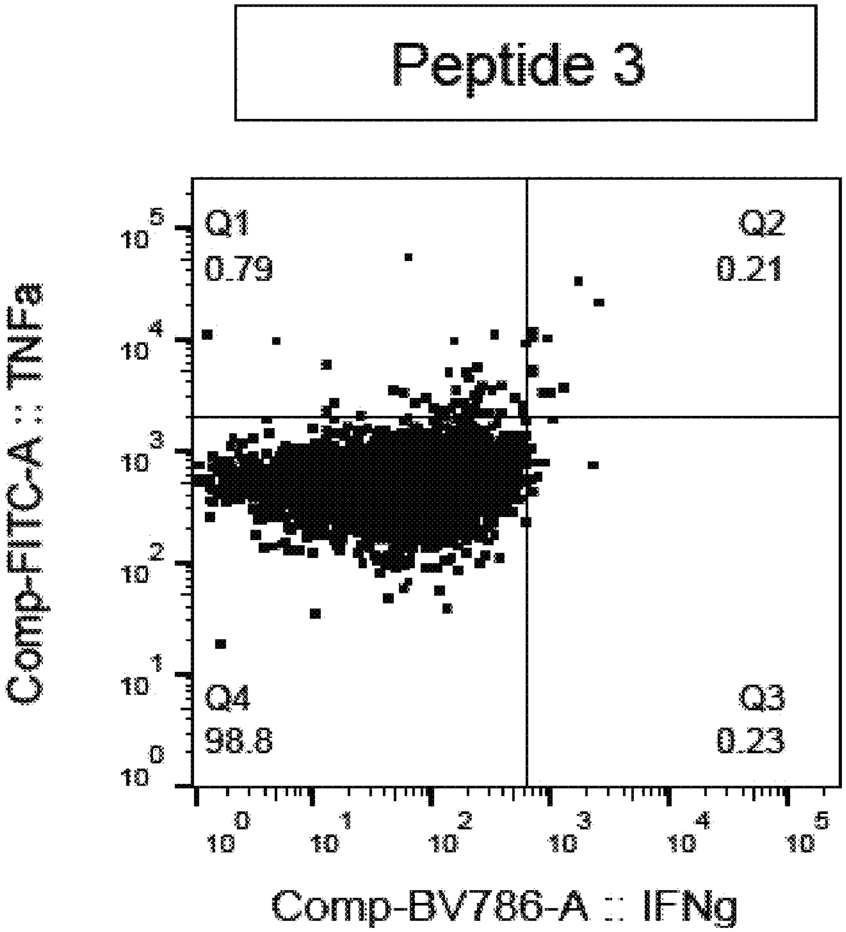
FIG. 5E shows a flow cytometry dot plot depicting $TNF\alpha^+IFN\gamma^+CD8^+$ T cell frequencies in PBMC samples after stimulation with P3 self-antigen.
Figure 6:
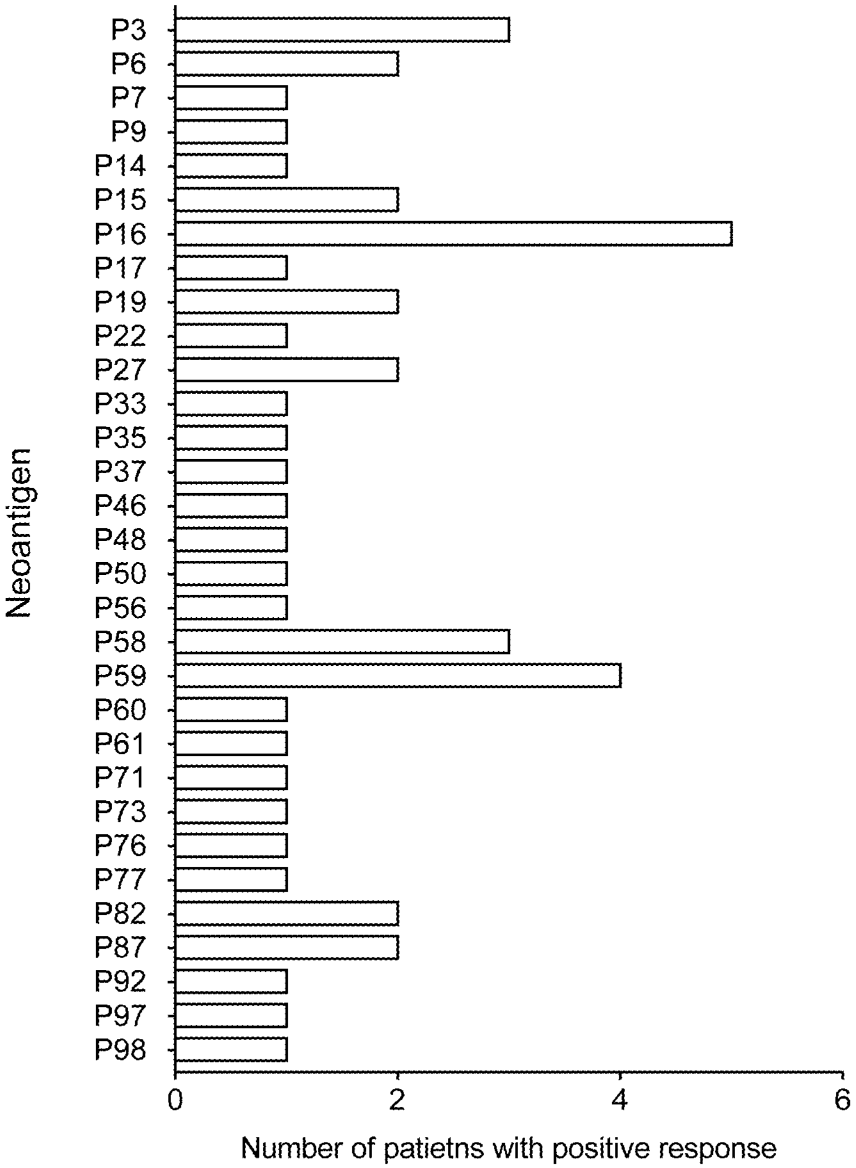
FIG. 6 shows the number of prostate cancer patients whose PBMC samples demonstrated a positive immune response to the specified neoantigens. P3, P6, P7, P9 and P92 represent self-antigens.

The 9 mer fragments shown in Table 13 were assessed for their ability to activate T cells using the Patient PBMC restimulation assay described in Example 1 using TNFα and IFNγ production by $CD8^+$ T cells as a readout. Self-antigens shown in Table 15 were also used in the assays. FIG. 5A, FIG. 5B, FIG. 5C, FIG. 5D and FIG. 5E show flow cytometry dot plots depicting $TNF\alpha^+IFN\gamma^+CD8^+$ T cell frequencies in PBMC samples after no stimulation (DMSO negative control) (FIG. 5A), after stimulation with CEF peptide (positive control (FIG. 5B), after stimulation with P16 (FIG. 5C), after stimulation with P98 (FIG. 5D), and after stimulation with P3 (FIG. 5E). Table 16 shows the maximum frequency of $TNF\alpha^+$ $IFN\gamma^+$ $CD8^+$ T cells and maximum fold change over negative control for each peptide analyzed, indicating the highest frequency of $TNF\alpha^+IFN\gamma^+CD8^+$ T cells and resulting fold change across the PBMC donors evaluated for the peptide. All neoantigens evaluated were found to stimulate $CD8^+$ T cells. FIG. 6 shows the number of prostate cancer patients whose PBMC samples demonstrated a positive immune response to the specified neoantigens. PBMCs from ten patients were evaluated.

TABLE 15

| Peptide ID | Gene name | Amino Acid Sequence of the 9-mer | SEQ ID NO: |
|---|---|---|---|
| P3 | ERG | KLSRALRYY | 421 |
| P6 | FOLH1 | MVFELANSI | 422 |
| P7 | ERG | ILFQNIDGK | 423 |
| P9 | FOLH1 | KIVIARYGK | 424 |
| P92 | ERG | FLLELLSDS | 425 |

TABLE 16

| Peptide Name | Maximum fold change over | Maximum frequency of $TNF\alpha^{+}IFN\gamma^{+}CD8^{+}$ T cells | Immuno-genic |
|---|---|---|---|
| Negative control | n/a | 0.011-0.8 (depending on | n/a |
| P16 | 65.82 | 4.620 | Yes |
| P17 | 2.17 | 0.130 | Yes |
| P19 | 5.00 | 0.480 | Yes |
| P22 | 5.00 | 0.120 | Yes |
| P27 | 3.43 | 0.430 | Yes |

TABLE 16-continued

| Peptide Name | Maximum fold change over | Maximum frequency of $TNF\alpha^{+}IFN\gamma^{+}CD8^{+}$ T cells | Immuno-genic |
|---|---|---|---|
| P35 | 2.67 | 0.064 | Yes |
| P37 | 3.13 | 1.160 | Yes |
| P46 | 2.33 | 0.140 | Yes |
| P48 | 2.33 | 0.220 | Yes |
| P50 | 5.14 | 0.190 | Yes |
| P56 | 11.57 | 1.620 | Yes |
| P58 | 19.18 | 5.370 | Yes |
| P59 | 10.75 | 3.010 | Yes |
| P60 | 2.08 | 0.340 | Yes |
| P61 | 2.27 | 0.084 | Yes |
| P73 | 2.97 | 0.110 | Yes |
| P76 | 2.30 | 0.170 | Yes |
| P77 | 3.24 | 0.160 | Yes |
| P82 | 3.46 | 0.970 | Yes |
| P87 | 3.24 | 0.120 | Yes |
| P97 | 4.55 | 0.160 | Yes |
| P98 | 14.93 | 1.000 | Yes |

Maximum frequency refers to the greatest frequency of $TNF\alpha^{+}IFN\gamma^{+}CD8^{+}$ T cells among all tested PBMC donors Example 6: Binding of Neoantigens to HLA Binding of select neoepitopes to HLA-A*01:01, HLA-A*02:01, HLA-A*03:01, HLA-A*24:02, HLA-B*07:02 and HLA-B*08:01 was evaluated using the assay described in Example 1. The results of binding the various neoantigens to HLA is shown in Table 17. Each HLA allele tested had a corresponding positive control (Pos) and a negative control (Neg) peptide against which the peptide of interest was exchanged. An exchange rate of 100% with Pos, thus means that the peptide of interest has the same binding affinity to the HLA allele as the positive control peptide. As a criterion for further evaluation, peptides with an exchange rate of at least 10% with the corresponding Pos peptide for at least one of the 6 HLA alleles that we considered for further evaluation. The exchange rates with the allele specific Pos peptides, of the 24 neoantigens so identified are summarized below in Table 17. Higher percentages correspond to stronger binding to the HLA allele.

TABLE 17

| Peptide Name | HLA-A*01:01 | HLA-A*02:01 | HLA-A*03:01 | HLA-A*24:02 | HLA-B*07:02 | HLA-B*08:01 |
|---|---|---|---|---|---|---|
| P16 | 5.5 | 10.4 | 6.1 | 0.8 | 13.7 | 6.2 |
| P17 | 4.9 | 9.3 | 3.8 | 0.1 | 38.7 | 9 |
| P19 | 5.2 | 8.2 | 4.1 | 0.1 | 91.3 | 14.5 |
| P22 | 4.4 | 46.9 | 4.8 | 0 | 8.3 | 3.9 |
| P27 | 4.8 | 10 | 4.5 | 0.7 | 7.8 | 6.4 |
| P35 | 2.5 | 12.5 | 4.2 | 0.2 | 12.1 | 13.7 |
| P37 | 1.4 | 12.5 | 6.4 | −0.1 | 9.4 | 3.3 |
| P46 | 2.4 | 14.4 | 10.3 | −0.4 | 64.8 | 14.5 |
| P48 | 4.3 | 99.3 | 4.4 | 0.1 | 12.8 | 8.9 |
| P50 | 2.3 | 8.8 | 5.5 | 0.1 | 10.4 | 4.7 |
| P56 | 2.6 | 8.4 | 6.8 | 0.5 | 82.5 | 38 |
| P58 | 2.5 | 11.8 | 32.5 | 0.2 | 9.7 | 5.3 |
| P59 | 2.2 | 11.9 | 4.5 | −0.5 | 7.5 | 5.5 |
| P60 | 3.1 | 7.9 | 36.6 | 0.9 | 6.1 | 10.2 |
| P61 | 1.7 | 5.8 | 2.1 | 90.3 | 9.6 | 3.6 |
| P73 | 2.1 | 89.2 | 3.5 | 0.5 | 8.7 | 2.6 |
| P76 | 0.1 | 85.9 | 6 | −0.5 | 91.5 | 8.5 |
| P77 | 1.9 | 9.6 | 2.8 | 1.7 | 14.2 | 3.4 |
| P82 | 1.5 | 6.3 | 58.1 | −0.1 | 12.9 | 1.4 |
| P87 | 1.1 | 64 | 2.4 | 0.2 | 5 | 3.1 |
| P97 | 2.5 | 4.6 | 39 | 0.1 | 7 | 2.7 |
| P98 | 2.5 | 7.9 | 51.1 | −0.1 | 6.7 | 2.4 |

Example 7: MHC I-Peptide Complex Profiling of Prostate Cancer Tissues Identified Unique MHC I-Presented Peptides in Prostate Cancer MHC I-peptide complexes were isolated from samples of 11 human prostate cancer and peptides presented by MHC I were identified using unbiased mass spectrometry. At collection, the subjects were diagnosed with grade 7 adenocarcinoma or stromal sarcoma with two subject having invasive adenocarcinoma.

Frozen human prostate cancer tissues with HLA-A*02:01, HLA-A*03:03, HLA-B*27:0 and HLA-B*08:01 haplotypes were mechanically disrupted in non-ionic detergent including protease inhibitors and processed. A pan-MHC allele monoclonal antibody was used to immunopurify MHC I-peptide complexes from the samples. After acid elution, recovery of the MHC I-peptide complexes was assessed by ELISA and recovered peptides desalted and subjected to LC-MS/MS analyses.

The raw LC-MS/MS data files from prostate tumors were analyzed to search against the neoantigen database that was created from corresponding RNAseq data obtained from the 11 human prostate cancer samples. These peptides had a theoretical mass for parent ions (MS1) and a list of theoretical fragment ions (MS2). A list of MS1 ions that had triggered MS2 scans were searched against the theoretical list of peptides and matched by mass. All theoretical peptides within a set MS1 ppm mass accuracy (5 ppm) then had their in silico MS2 spectrum compared to the empirical MS2 for that parent ion (peptide spectral matches or PSMs). A score was computed based on how closely the empirical spectrum matched the theoretical spectrum. Each LC-MS/MS run (one file per tumor sample) produced thousands of PSMs. However, the vast majority of these peptides were canonical sequences that were found in the human reference database (Swissprot). These were filtered out and peptides of interest (putative neoantigens) were compiled. From this list, peptides that had sufficient evidence for being positive were selected.

Table 18 shows the amino acid sequences of the peptides identified in complex with MHC I using LC-MS/MS and the gene origin of the peptides.

Table 19 shows the amino acid sequences of the corresponding longer neoantigens of the peptides identified in complex with MHC I using LC/MS/MS.

Table 20 shows the polynucleotide sequences encoding the corresponding longer neoantigens.

The MHC I complexed peptides described herein confirmed the expression, processing, and presentation of immunogenic epitopes specific to prostate cancer aberrant gene alterations. Evaluation of RNAseq databases mapped the identified MHC I complexed peptides within longer aberrant transcripts present in prostate cancer. Hence, these data identified prostate cancer neoantigens that contained at least one MHC class I epitope that is immunologically relevant and capable of eliciting an adaptive T cell response.

TABLE 18

| Neoantigen ID | Amino acid sequence | SEQ ID NO: | Gene | type |
|---|---|---|---|---|
| MS1 | VTFLKPCFLL | 426 | TTLL7 | Alternative 5' SS |
| MS2 | TDIVKQSV | 427 | CHD7 | Alternative Last Exon |
| MS3 | SPAFPKPVRP | 428 | TESK1 | Alternative Last Exon |
| MS4 | SYFSLTNIFNFV | 429 | PPIP5K2 | Alternative Last Exon |
| MS5 | EFSPETCAFRLS | 430 | SRPK2 | Alternative Last Exon |
| MS6 | FLSRALRAL | 431 | SOAT1 | Alternative 5' SS |
| MS7 | KKDLELIL | 432 | PDE4D | Alternative Last Exon |
| MS8 | KLQKNCLL | 433 | ZYG11A | Exon Skip |
| MS9 | SALSGNSWV | 434 | SYNE2 | Alternative Last Exon |
| MS10 | TVRAILL | 435 | USP21 | Intron Retention |
| MS11 | GSLHFHEVLK | 436 | TDG | Novel Cassette |

TABLE 19

| Neoantigen ID | Gene ID | Peptide Sequence | Peptide SEQ ID |
|---|---|---|---|
| MS1 | TTLL7 | **HYKLIQQP**ISLFSITDRLHKTFSQLPSVHLCSIT FQWGHPPIFCSTNDICVTANFCISVTFLKPCFLL HEASASQ | 437 |
| MS2 | CHD7 | **WTDIVKQS**VSTNCISIKKGSYTKLFSLVFLIFC WPLIIQL | 438 |
| MS3 | TESK1 | **RTALTHNQ**DFSIYRLCCKRGSLCHASQARSP AFPKPVRPLPAPITRITPQLGGQSDSSQPLLTTG RPQGWQDQALRHTQQASPASCATITIPIHSAA LGDHSGDPGPAWDTCPPLPLTTLIPRAPPPYG DSTARSWPSRCGPLG | 439 |
| MS4 | PPIP5K2 | **LRYGALCN**VSRISYFSLTNIFNFVIKSLTAIFTV KF | 440 |
| MS5 | SRPK2 | **RKERNIRK**SESTLRLSPFPTPAPSGAPAAAQG KVVRVPGPAGGLVPRDAGARLLPPAGGPGGG AAAGEGRAGRGRFPSITEPRPRDLPPRVATGR RAGGRRKGAGQGVRTRPLPASWPGGRGPFRK GPRRLPLGSGPPAAGVQRLRCSHLSRGPRRRR GRVCGRACVSPPLPPRPPPVGLSAENLSWLSS GLPRACSWREFSPETCAFRLSGLDSKLSARVE RDLGALRAPGSRAAQGGGRVRGSRSEWKTRP WRPPPAWPLTRAGGPLPKNPFLESCSETAQRR RVFSFSTPLS | 441 |
| MS6 | SOAT1 | **YAYKDFLW**CFPFSLVFLQEIQICCHVSCLCCIC CSTRICLGCLLELFLSRALRALHVLWNGFQLH CQ | 442 |

TABLE 19-continued

| Neoantigen ID | Gene ID | Peptide Sequence | Peptide SEQ ID |
|---|---|---|---|
| MS7 | PDE4D | **SINKATIT**GKKDLELILHVSRKKPFLPRVNITP TPISCCNLKMLKKFFLLYIIISIIDLTNCLSCYLE HFYRFTFFTDVHYF | 443 |
| MS8 | ZYG11A | **TMPAILKL**QKNCLLSL | 444 |
| MS9 | SYNE2 | **PYYSALSG**NSWVPSTLESDPFGYVFSPLATRP ALNDQESILWPTLTSVVSCALSCPSLNLPENW LTLITGGMKGGKKMKFTFRH | 445 |
| MS10 | USP21 | **GLRNLGNT**VRAILLSFLSKRNVKWCWGWGK PTSLGKACGRRALKLF | 446 |
| MS11 | TDG | **MEAENAGS**LHFHEVLKMGHVKF | 447 |

TABLE 20

| Neoantigen ID | Gene ID | Polynucleotide sequence | DNA SEQ ID NO: |
|---|---|---|---|
| MS1 | TTLL7 | **CACTACAAATTAATTCAACAACCCA**TATCCCTCTT CTCCATCACTGATAGGCTCCATAAGACGTTCAGTC AGCTGCCCTCGGTCCATCTCTGCTCAATCACCTTCC AGTGGGGACACCCGCCCATTTTCTGCTCAACAAAT GATATCTGTGTCACGGCCAACTTCTGCATCTCGGTC ACATTCCTTAAACCGTGCTTCCTCCTACATGAGGCA TCTGCCTCACAG | 448 |
| MS2 | CHD7 | **TGGACTGATATAGTTAAGCAGTCT**GTAAGTACAA ACTGCATTTCTATCAAGAAAGGTAGCTATACAAAA CTGTTTTCCTTAGTCTTTCTTATTTTCTGTTGGCCAT TAATTATTCAGTTG | 449 |
| MS3 | TESK1 | **AGGACCGCCCTGACACACAATCAGG**ACTTCTCTA TCTACAGGCTCTGTTGCAAGAGGGGGTCCCTCTGC CACGCTTCCCAGGCCAGATCCCCGGCTTTCCCGAA GCCGGTCAGACCTCTTCCTGCCCCCATCACCAGAAT CACCCCCCAACTGGGGGGACAATCTGACTCGAGTC AACCCCTTCTCACTACGGGAAGACCTCAGGGGTGG CAAGATCAAGCTCTTAGACACACCCAGCAAGCCAG TCCTGCCTCTTGTGCCACCATCACCATTCCCATCCA CTCAGCTGCCCTTGGTGACCACTCCGGAGACCCTG GTCCAGCCTGGGACACCTGCCCGCCGCTGCCGCTC ACTACCCTCATCCCCCGAGCTCCCCCGCCGTATGGA GACAGCACTGCCAGGTCCTGGCCCTCCCGCTGTGG GCCCCTCGGC | 450 |
| MS4 | PPIP5 K2 | **CTTCGCTATGGTGCCTTATGCAAT**GTAAGTAGAA TAAGTTATTTCAGTCTAACAAATATATTTAATTTTG TAATTAAATCACTAACTGCTATTTTTACTGTGAAAT TT | 451 |
| MS5 | SRPK2 | **CGAAAAGAGAGAAACATCCGAAAAA**GTGAGTCC ACGCTGCGCCTGTCCCCGTTCCCCACCCCCGCCCCG TCGGGGGCGCCCGCGGCCGCGCAGGGGAAAGTTGT CCGGGTCCCCGGGCCGGCGGGCGGGCTGGTCCCCC GGGACGCTGGCGCTCGGCTCCTGCCCCCGGCGGGC GGCCCGGGGGGAGGGGCGGCGGCGGGGGAGGGGC GCGCGGGCCGCGGCCGGTTCCCTAGCATCACGGAG CCTCGACCCCGCGACCTCCCGCCCCGGGTCGCCAC CGGCCGGCGGGCGGGAGGCCGGCGGAAAGGCGCC GGGCAGGGCGTGCGCACCCGTCCCTTGCCCGCGAG CTGGCCCGGGGGTCGCGGCCCTTTCCGGAAGGGGC CCCGGCGTCTGCCGCTGGGCTCCGGCCCGCCCGCT GCGGGAGTGCAGCGGCTGCGTTGCTCCCACCTGAG CCGCGGGCCGAGGAGGCGGAGGGGCCGAGTGTGC GGGAGGGCGTGTGTCTCGCCTCCCCTTCCTCCCCGG CCCCCGCCTGTCGGCCTTTCTGCTGAGAACCTAAGC TGGTTGTCAAGTGGTTTGCCTCGGGCGTGTTCCTGG CGCGAGTTCAGCCCCGAGACCTGTGCGTTTCGGCT CTCGGGTTTGGATTCGAAACTTTCCGCTCGGGTTGA GCGTGACTTGGGTGCGCTGCGGGCGCCGGGGTCGC | 452 |

TABLE 20-continued

| Neoantigen ID | Gene ID | Polynucleotide sequence | DNA SEQ ID NO: |
|---|---|---|---|
| | | GGGCTGCGCAGGGCGGTGGGCGTGTGCGCGGGAG CCGGTCGGAGTGGAAAACGCGCCCGTGGCGGCCAC CTCCAGCCTGGCCGCTCACCCGAGCAGGGGGGCCG CTGCCCAAGAACCCTTTCCTGGAGAGCTGCTCCGA GACCGCACAGCGCCGCCGCGTCTTCTCCTTTTCCAC TCCTCTCTCC | |
| MS6 | SOAT 1 | **TATGCTTACAAGGACTTTCTCTGG**TGTTTTCCTTT TTCTTTAGTTTTTCTCCAAGAGATTCAAATCTGCTG CCATGTTAGCTGTCTTTGCTGTATCTGCTGTAGTAC ACGAATATGCCTTGGCTGTTTGCTTGAGCTTTTTCT ATCCCGTGCTCTTCGTGCTCTTCATGTTCTTTGGAA TGGCTTTCAACTTCATTGTCAA | 453 |
| MS7 | PDE4 D | **TCCATCAACAAAGCCACCATAACAG**GTAAGAAA GATCTGGAGCTTATTCTTCATGTGTCTAGGAAGAA ACCATTTCTGCCAAGAGTCAATATAACACCAACAC CAATTTCATGCTGCAATTTGAAAATGTTAAAGAAA TTCTTTCTTCTCTACATTATCATTTCTATCATTGATC TCACAAATTGTCTAAGCTGTTATTTGGAACATTTTT ACCGATTTACGTTTTTTACTGATGTACATTATTTT | 454 |
| MS8 | ZYG11 A | **ACCATGCCTGCTATTTTAAAG**TTACAGAAGAATT GTCTTCTCTCCTTA | 455 |
| MS9 | SYNE 2 | **CCATACTACAGCGCACTGTCAG**GTAACAGCTGGG TTCCCAGCACCCTGGAAAGTGACCCGTTTGGCTAT GTTTTTAGCCCCTTAGCAACACGGCCAGCTCTCAAT GACCAAGAGTCCATCTTGTGGCCGACCCTGACTTCT GTGGTTTCCTGTGCTCTATCCTGCCCATCTCTTAAC TTACCTGAGAATTGGCTCACTCTCATCACAGGTGG AATGAAAGGGGGAAAAAAAATGAAATTCACATTC AGACAC | 456 |
| MS10 | USP21 | **GGCCTTCGAAACCTGGGAAACACG**GTGAGAGCT ATTCTCCTATCTTTCCTCTCTAAAAGGAATGTGAAA TGGTGCTGGGGGTGGGGAAAACCCACGAGCTTGGG GAAGGCATGTGGAAGGAGAGCTCTGAAGCTCTTC | 457 |
| MS11 | TDG | **ATGGAAGCGGAGAACGCGGGCAGT**TTGCATTTTC ATGAAGTGCTCAAAATGGGACATGTGAAATTC | 458 |

Example 8 Expression Profiling of Prostate Neoantigens in Tumor and Normal Tissues The identified prostate neoantigens were profiled for their expression in about 90 FFPE tissue samples from prostate cancer (adenocarcinoma, clinical stages II-IV, Gleason score 8-9, subjects were treatment naïve or treated with CASODEX® (bicalutamide), LUPRON DEPOT® (leuprolide acetate for depot suspension) or FIRMAGON® (degarelix)) and a panel of normal tissues including liver, kidney, pancreas, ovary, prostate, mammary gland, colon, stomach, skeletal muscle and lung, in PBMCs obtained from healthy subjects and in prostate cancer cell lines including DU145-1, MDA-MB-436-1, LREX-1, 22RV1-1, H660-1. And other tissue cell lines including NCI-H2106-1, L-363-1, HCl-N87-1, OCI-AML5-1, MDA-PCa-2b-1 and GDM-1-1. Total RNA was extracted from formalin fixed paraffin embedded tissue samples using CELLDATA's RNAstorm-RNA isolation kit following kit protocol. RNA from cultured cell lines and PBMCs were isolated using Qiagen RNA isolation kits using standard methods. 200 ng of Total RNA from FFPE samples was used to prepare cDNA using High-capacity cDNA reverse transcription kit (ABI) and standard protocols. 37.5 ng cDNA was preamplified with gene markers in 15 µl preamplification mix using TaqMan preamplification kit (ThermoFisher Scientific) and standard protocols. To test gene expression of the identified neoantigens in the various samples, primers spanning the breakpoint sequences were designed for each of the identified prostate neoantigens and expression was assessed using Fluidigm Biomark™ HD. Percent (%) of expression positive FFPE prostate cancer samples were recorded for each neoantigen with relative average CT calculated in the prostate cancer samples. The results of the expression profiling of select neoantigens is shown in Table 21. The prevalence of each neoantigen in TCGA, SU2C and GTEx database is shown in Table 22.

TABLE 21

| Neo-antigen ID | Amino acid SEQ ID NO: | Poly-nucleotide SEQ ID NO: | qPCR % Positive FFPE | qPCR Relative Average Ct | qPCR Normal Tissue Expression |
|---|---|---|---|---|---|
| AS18 | 275 | 276 | 95.6 | 6.3 | Ovary, Prostate |
| P87 | 381 | 382 | 85.6 | 8.3 | Ovary, Prostate |
| AS55 | 333 | 334 | 83.3 | 8.2 | Prostate |
| AS57 | 337 | 338 | 83.3 | 7.9 | Prostate |
| AS15 | 269 | 270 | 68.9 | 11.4 | Ovary, Mammary Gland |
| AS7 | 253 | 254 | 57.8 | 11.0 | None |
| AS43 | 309 | 310 | 52.2 | 11.2 | Mammary Gland |
| AS51 | 325 | 326 | 47.8 | 10.5 | Ovary |
| AS16 | 271 | 272 | 47.8 | 10.8 | Ovary |

TABLE 21-continued

| Neo-antigen ID | Amino acid SEQ ID NO: | Poly-nucleotide SEQ ID NO: | qPCR % Positive FFPE | Relative Average Ct | Normal Tissue Expression |
|---|---|---|---|---|---|
| AS41 | 305 | 306 | 45.6 | 11.6 | Ovary |
| AS6 | 251 | 252 | 33.3 | 10.0 | None |
| AS3 | 245 | 246 | 26.7 | 10.8 | None |
| AS11 | 261 | 262 | 25.6 | 12.1 | None |
| AS13 | 265 | 266 | 21.1 | 11.1 | None |
| AS47 | 317 | 318 | 16.7 | 12.3 | Ovary |
| AS8 | 255 | 256 | 13.3 | 12.5 | None |
| AS19 | 277 | 278 | 95.6 | 6.3 | Ovary, Prostate |
| AS37 | 297 | 298 | 0.0 | N/A | None |
| AS23 | 285 | 286 | 22.0 | 13.0 | Ovary, Prostate, Mammary Gland |
| MS1 | 437 | 448 | N/A | N/A | None |
| MS3 | 439 | 450 | N/A | N/A | None |
| MS6 | 442 | 453 | N/A | N/A | None |
| MS8 | 444 | 455 | N/A | N/A | None |
| P82 | 379 | 380 | 37.0 | 11 | |
| P16 | 343 | 344 | 76 | 9 | Prostate |
| FUS1 | 211 | 212 | 72 | 9 | Prostate |
| P22 | 349 | 350 | 70 | 9 | Prostate |
| FUS2 | 213 | 214 | 55 | 11 | Mammary Gland |
| FUS3 | 215 | 216 | 43 | 11 | Prostate |
| FUS6 | 221 | 222 | 19 | 11 | None |
| FUS5 | 219 | 220 | 14 | 7 | None |
| FUS8 | 225 | 226 | 11 | 14 | None |
| FUS15 | 345 | 346 | 8 | 13 | None |
| P35 | 353 | 354 | 5 | 13 | None |
| FUS19 | 235 | 236 | 4 | 13 | None |
| FUS7 | 223 | 224 | 0 | N/A | None |
| M84 | 167 | 168 | N/A | N/A | N/A |
| M86 | 171 | 172 | N/A | N/A | N/A |
| M10 | 19 | 20 | N/A | N/A | N/A |
| M12 | 23 | 24 | N/A | N/A | N/A |
| FR1 | 177 | 178 | N/A | N/A | N/A |

TABLE 22

| Neo-antigen ID | Amino acid SEQ ID NO: | Frozen prostate cancer tissues* (n = 11) | TCGA % | SU2C % | GTEx % |
|---|---|---|---|---|---|
| AS18 | 275 | 54.5 | 12.6 | 20.9 | 0.03 |
| P87 | 381 | 0.0 | 0 | 20.9 | 0 |
| AS55 | 333 | 18.2 | 12.1 | 0 | 0 |
| AS57 | 337 | 36.4 | 14.9 | 0 | 0 |
| AS15 | 269 | 36.4 | 4.5 | 46.5 | 0 |
| AS7 | 253 | 27.3 | 5.1 | 16.3 | 0 |
| AS43 | 309 | 0.0 | 0 | 31 | 0.4 |
| AS51 | 325 | 9.1 | 0 | 23.8 | 0.52 |
| AS16 | 271 | 45.5 | 0.6 | 18.6 | 0 |
| AS41 | 305 | 0.0 | 0 | 33.3 | 0.16 |
| AS6 | 251 | 27.3 | 5.1 | 16.3 | 0 |
| AS3 | 245 | 27.3 | 10.4 | 25.6 | 0.03 |
| AS11 | 261 | 9.1 | 1.2 | 48.8 | 0.07 |
| AS13 | 265 | 27.3 | 5.7 | 32.6 | 0 |
| AS47 | 317 | 0.0 | 0 | 23.8 | 0.05 |
| AS8 | 255 | 0.0 | 0 | 14 | 0 |
| AS19 | 277 | 54.5 | 12.6 | 20.9 | 0.03 |
| AS37 | 297 | 0.0 | 0 | 38.1 | 0 |
| AS23 | 285 | 45.5 | 3.1 | 18.6 | 0.09 |
| MS1 | 437 | 18.2 | 0 | 0 | 0 |
| MS3 | 439 | 9.1 | 0.197 | 0 | 0.13 |
| MS6 | 442 | 9.1 | 0.197 | 0 | 0 |
| MS8 | 444 | 18.2 | 0 | 0 | 0.016 |
| P82 | 379 | | Varied Expression | | |
| P16 | 343 | | 27.17 | 2.33 | 0.02 |
| FUS1 | 211 | | 17.72 | 13.95 | #N/A |
| P22 | 349 | | 30.51 | 23.26 | 0.03 |
| FUS2 | 213 | | 63.58 | 46.51 | 1.78 |
| FUS3 | 215 | | 35.04 | 23.26 | 0.02 |
| FUS6 | 221 | | 21.46 | 32.56 | #N/A |
| FUS5 | 219 | | 12.40 | 18.60 | #N/A |
| FUS8 | 225 | | 1.18 | 32.56 | 0.54 |
| FUS15 | 345 | | 0.39 | 9.30 | 0.11 |
| P35 | 353 | | 1.38 | 6.98 | #N/A |
| FUS19 | 235 | | 8.86 | 30.23 | 1.04 |
| FUS7 | 223 | | 3.35 | 16.28 | 0.51 |
| M84 | 167 | | | 1.28 | |
| M86 | 171 | | | 1.09 | |
| M10 | 19 | | | 1.18 | |
| M12 | 23 | | | 0.99 | |
| FR1 | 177 | | | 0.30 | |

Example 10 Generation of Viral Vectors Encoding the Identified Neoantigens

The identified neoantigens were validated and prioritized for their inclusion into a universal prostate cancer vaccine. 41 of the identified neoantigens were selected to be included into the expression cassettes based on their expression across prostate cancer samples, low expression in normal tissues, binding to HLA, and immunogenicity. The selected 41 neoantigens are shown in Table 21 and Table 22 and include

AS18
(WKFEMSYTVGGPPPHVHARPRHWKTDR; SEQ ID NO: 275),

P87
(YEAGMTLGGKILFFLFLLLPLSPFSLIF; SEQ ID NO: 381),

AS55
(DGHSYTSKVNCLLLQDGFHGCVSITGAAGRRNLSIFLFLMLCKLEFHA

C; SEQ ID NO: 333),

AS57
(TGGKSTCSAPGPQSLPSTPFSTYPQWVILITEL; SEQ ID NO:

337),

AS15
(VLRFLDLKVRYLHS; SEQ ID NO: 269),

AS7
(DYWAQKEKGSSSFLRPSC; SEQ ID NO: 253),

AS43
(VPFRELKNVSVLEGLRQGRLGGPCSCHCPRPSQARLTPVDVAGPFLCLG

DPGLFPPVKSSI; SEQ ID NO: 309),

AS51
(GMECTLGQVGAPSPRREEDGWRGGHSRFKADVPAPQGPCWGGQPGSAPS

SAPPEQSLLD; SEQ ID NO: 325),

AS16
(GNTTLQQLGEASQAPSGSLIPLRLPLLWEVRG; SEQ ID NO: 271),

AS41
(EAFQRAAGEGGPGRGGARRGARVLQSPFCRAGAGEWLGHQSLR; SEQ

ID NO: 305),

AS6
(DYWAQKEKISIPRTHLC(SEQ ID NO: 251),

AS3
(VAMMVPDRQVHYDFGL(SEQ ID NO: 245),

-continued

AS11
(VPFRELKNQRTAQGAPGIHHAASPVAANLCDPARHAQHTRIPCGAGQVR AGRGPEAGGGVLQPQRPAPEKPGCPCRRGQPRLHTVKMWRA; SEQ ID NO: 261),

AS13
(KRSFAVTERII; SEQ ID NO: 265),

AS47
(FKKFDGPCGERGGGRTARALWARGDSVLTPALDPQTPVRAPSLTRAAAA V; SEQ ID NO: 317),

AS8
(LVLGVLSGHSGSRL; SEQ ID NO: 255),

AS19
(QWQHYHRSGEAAGTPLWRPTRN; SEQ ID NO: 277),

AS37
(CHLFLQPQVGTPPPHTASARAPSGPPHPHESCPAGRRPARAAQTCARRQ HGLPGCEEAGTARVPSLHLHLHQAALGAGRGRGWGEACAQVPPSRG; SEQ ID NO: 297),

AS23
(KIQNKNCPD; SEQ ID NO: 285),

MS1
(HYKLIQQPISLFSITDRLHKTFSQLPSVHLCSITFQWGHPPIFCSTNDI CVTANFCISVTFLKPCFLLHEASASQ; SEQ ID NO: 437),

MS3
(RTALTHNQDFSIYRLCCKRGSLCHASQARSPAFPKPVRPLPAPITRITP QLGGQSDSSQPLLTTGRPQGWQDQALRHTQQASPASCATITIPIHSAALG DHSGDPGPAWDTCPPLPLTTLIPRAPPPYGDSTARSWPSRCGPLG; SEQ ID NO: 439),

MS6
(YAYKDFLWCFPFSLVFLQEIQICCHVSCLCCICCSTRICLGCLLELFLS RALRALHVLWNGFQLHCQ; SEQ ID NO: 442),

MS8
(TMPAILKLQKNCLLSL; SEQ ID NO: 444),

P82
(YEAGMTLGEKFRVGNCKHLKMTRP; SEQ ID NO: 379).

P16
(GVPGDSTRRAVRRMNTF; SEQ ID NO: 343),

FUS1
(CGASACDVSLIAMDSA; SEQ ID NO: 211),

-continued

P22
(SLYHREKQLIAMDSAI; SEQ ID NO: 349),

FUS2
(TEYNQKLQVNQFSESK; SEQ ID NO: 213),

FUS3
(TEISCCTLSSEENEYLPRPEWQLQ; SEQ ID NO: 215),

FUS6
(CEERGAAGSLISCE; SEQ ID NO: 221),

FUS6
(NSKMALNSEALSVVSE; SEQ ID NO: 219),

FUS8
(WGMELAASRRFSWDHHSAGGPPRVPSVRSGAAQVQPKDPLPLRTLAGCL ARTAHLRPGAESLPQPQLHCT; SEQ ID NO: 225),

FUS15
(HVVGYGHLDTSGSSSSSSWP; SEQ ID NO: 345),

P35
(NSKMALNSLNSIDDAQLTRIAPPRSHCCFWEVNAP; SEQ ID NO: 353),

FUS19
(KMHFSLKEHPPPPCPP; SEQ ID NO: 235),
and

FUS7
(LWFQSSELSPTGAPWPSRRPTWRGTTVSPRTATSSARTCCGTKWPSSQE AALGLGSGLLRFSCGTAAIR; SEQ ID NO: 223),

M84
(IARELHQFAFDLLIKSH; SEQ ID NO: 167),

M86
(QPDSFAALHSSLNELGE; SEQ ID NO: 171),

M10
(FVQGKDWGLKKFIRRDF; SEQ ID NO: 19),

M12
(FVQGKDWGVKKFIRRDF; SEQ ID NO: 23),
and

FR1
(QNLQNGGGSRSSATLPGRRRRRWLRRRRQPISVAPAGPPRRPNQKPNPP GGARCVIMRPTWPGTSAFT; SEQ ID NO: 177).

Expression cassettes were designed for cloning into viral backbones Modified Vaccinia Ankara (MVA) and Great Ape Adenovirus 20 (GAd20) by joining the 41 neoantigen sequences one after the other without any linker. Each neoantigen sequences was codon-optimized for expression in either MVA or GAd20. The optimized polynucleotide sequences are shown in Table 23 for GAd20 and Table 24 for MVA expression.

TABLE 23

| Neoantigen ID | Gene ID | Amino acid SEQ ID NO: | Codon-optimized polynucleotide for GAd20 expression; SEQ ID NO: | Codon-optimized polynucleotide sequence for GAd20 expression |
|---|---|---|---|---|
| AS18 | NWD1 | 275 | 459 | TGGAAGTTCGAGATGAGCTACACCGTCGGC GGACCTCCACCTCATGTTCATGCCAGACCTC GGCACTGGAAAACCGACAGA |

TABLE 23-continued

| Neoantigen ID | Gene ID | Amino acid SEQ ID NO: | Codon-optimized polynucleotide for GAd20 expression; SEQ ID NO: | Codon-optimized polynucleotide sequence for GAd20 expression |
|---|---|---|---|---|
| P87 | AR-Intron | 381 | 460 | TATGAGGCCGGCATGACACTCGGCGGCAAGATCCTGTTCTTCCTGTTCCTGCTGCTCCCTCTGAGCCCCTTCAGCCTGATCTTC |
| AS55 | SPOC | 333 | 461 | GATGGCCACAGCTACACCAGCAAAGTGAACTGCCTCCTGCTGCAGGATGGCTTCCACGGCTGTGTGTCTATTACTGGCGCCGCTGGCAGACGGAACCTGAGCATCTTTCTGTTTCTGATGCTGTGCAAGCTCGAGTTCCACGCCTGC |
| AS57 | KLK3 | 337 | 462 | ACAGGCGGCAAGTCCACATGTTCTGCCCCTGGACCTCAGAGCCTGCCTAGCACACCCTTCAGCACATACCCTCAGTGGGTCATCCTGATCACCGAACTC |
| AS15 | LRRC45 | 269 | 463 | GTGCTGAGATTCCTGGACCTGAAAGTGCGCTACCTGCACAGC |
| AS7 | ACSM1 | 253 | 464 | GACTATTGGGCTCAAAAAGAGAAGGGCAGCAGCAGCTTCCTGCGGCCTAGCTGT |
| AS43 | CPNE7 | 309 | 465 | GTCCCCTTCAGAGAGCTGAAGAACGTTTCCGTGCTGGAAGGCCTGAGACAGGGCAGACTTGGCGGCCCTTGTAGCTGTCACTGCCCCAGACCTAGTCAGGCCAGACTGACACCTGTGGATGTGGCCGGACCTTTCCTGTGTCTGGGAGATCCTGGCCTGTTTCCACCTGTGAAGTCCAGCATC |
| AS51 | CPNE7 | 325 | 466 | GGCATGGAATGCACCCTGGGACAAGTGGGAGCCCCATCTCCTAGAAGAGAAGAGGATGGCTGGCGCGGAGGCCACTCTAGATTCAAAGCTGATGTGCCCGCTCCTCAGGGCCCTTGTTGGGGAGGACAACCTGGATCTGCCCCATCTTCTGCCCCACCTGAACAGTCCCTGCTGGAT |
| AS16 | LRRC45 | 271 | 467 | GGCAACACAACCCTCCAGCAACTGGGAGAAGCCTCTCAGGCTCCTAGCGGCTCTCTGATCCCTCTCAGACTGCCTCTCCTGTGGGAAGTTCGGGGC |
| AS41 | RHPN1 | 305 | 468 | GAGGCTTTCCAAAGAGCTGCTGGCGAAGGCGGACCTGGTAGAGGTGGTGCTAGAAGAGGTGCTAGGGTGCTGCAGAGCCCATTCTGTAGAGCAGGCGCAGGCGAATGGCTGGGCCATCAGAGTCTGAGA |
| AS6 | ACSM1 | 251 | 469 | GATTATTGGGCCCAGAAAGAAAAGATCAGCATCCCCAGAACACACCTGTGC |
| AS3 | DNAH8 | 245 | 470 | GTGGCCATGATGGTGCCCGATAGACAGGTCCACTACGACTTTGGACTG |
| AS11 | CPNE7 | 261 | 471 | GTGCCCTTCCGGGAACTGAAGAACCAGAGAACAGCTCAGGGCGCTCCTGGAATCCACCATGCTGCTTCTCCAGTGGCCGCCAACCTGTGTGATCCTGCCAGACATGCCCAGCACACCAGGATTCCTTGTGGCGCTGGACAAGTGCGCGCTGGAAGAGGACCTGAAGCAGGCGGAGGTGTTCTGCAACCTCAAAGACCCGCTCCTGAGAAGCCTGGCTGCCCTTGCAGAAGAGGACAGCCTAGACTGCACACCGTGAAAATGTGGCGAGCC |
| AS13 | GRIN3A | 265 | 472 | AAGAGAAGCTTTGCCGTGACCGAGCGGATCATC |
| AS47 | AGRN | 317 | 473 | TTCAAGAAGTTCGACGGCCCTTGCGGAGAAAGAGGCGGAGGCAGAACAGCTAGAGCCCTTTGGGCTAGAGGCGACAGCGTTCTGACACCAGCTCTGGACCCTCAGACACCTGTTAGGGCCCCTAGCCTGACAAGAGCTGCCGCCGCTGTG |

TABLE 23-continued

| Neoantigen ID | Gene ID | Amino acid SEQ ID NO: | Codon-optimized polynucleotide for GAd20 expression; SEQ ID NO: | Codon-optimized polynucleotide sequence for GAd20 expression |
|---|---|---|---|---|
| AS8 | CACNA1 D | 255 | 474 | CTGGTGCTGGGAGTGCTGTCTGGACACTCTG GCAGCAGACTG |
| AS19 | NWD1 | 277 | 475 | CAGTGGCAGCACTATCACAGATCTGGCGAA GCCGCCGGAACACCCCTTTGGAGGCCAACA AGAAAC |
| AS37 | RECQL4 | 297 | 476 | TGCCACTTGTTTCTGCAGCCCCAAGTGGGCA CACCTCCTCCACATACAGCCTCTGCTAGAGC ACCTAGCGGCCCTCCACATCCTCACGAATCT TGTCCTGCCGGAAGAAGGCCTGCCAGAGCC GCTCAAACATGTGCCAGACGACAGCACGGA CTGCCTGGATGTGAAGAGGCTGGAACAGCC AGAGTGCCTAGCCTGCACCTCCATCTGCATC AGGCTGCTCTTGGAGCCGGAAGAGGTAGAG GATGGGGCGAAGCTTGTGCTCAGGTGCCAC CTTCTAGAGGC |
| AS23 | ZNF614 | 285 | 477 | AAGATCCAGAACAAGAACTGCCCCGAC |
| MS1 | TTLL7 | 437 | 478 | CACTACAAGCTGATCCAGCAGCCAATCAGC CTGTTCAGCATCACCGACCGGCTGCACAAG ACATTCAGCCAGCTGCCAAGCGTGCACCTG TGCTCCATCACCTTCCAGTGGGGACACCCTC CTATCTTTTGCTCCACCAACGACATCTGCGT GACCGCCAACTTCTGTATCAGCGTGACCTTC CTGAAGCCTTGCTTTCTGCTGCACGAGGCCA GCGCCTCTCAG |
| MS3 | TESK1 | 439 | 479 | CGAACCGCTCTGACACACAACCAGGACTTC AGCATCTACAGACTGTGTTGCAAGCGGGGC TCCCTGTGCCATGCAAGCCAAGCTAGAAGC CCCGCCTTTCCTAAACCTGTGCGACCTCTGC CAGCTCCAATCACCAGAATTACCCCTCAGCT CGGCGGCCAGAGCGATTCATCTCAACCTCT GCTGACCACCGGCAGACCTCAAGGCTGGCA AGACCAAGCTCTGAGACACACCCAGCAGGC TAGCCCTGCCTCTTGTGCCACCATCACAATC CCCATCCACTCTGCCGCTCTGGGCGATCATT CTGGCGATCCTGGACCAGCCTGGGACACAT GTCCTCCACTGCCACTCACAACACTGATCCC TAGGGCTCCTCCACCTTACGGCGATTCTACC GCTAGAAGCTGGCCCAGCAGATGTGGACCA CTCGGA |
| MS6 | SOAT1 | 442 | 480 | TACGCCTACAAGGACTTCCTGTGGTGCTTCC CCTTCTCTCTGGTGTTCCTGCAAGAGATCCA GATCTGCTGTCATGTGTCCTGCCTGTGCTGC ATCTGCTGTAGCACCAGAATCTGCCTGGGCT GTCTGCTGGAACTGTTCCTGAGCAGAGCCCT GAGAGCACTGCACGTGCTGTGGAACGGATT CCAGCTGCACTGCCAG |
| MS8 | ZYG11A | 444 | 481 | ACAATGCCCGCCATCCTGAAGCTGCAGAAG AATTGCCTCCTAAGCCTG |
| P82 | AR-V7 | 379 | 482 | TACGAAGCCGGGATGACCCTGGGCGAGAAG TTCAGAGTGGGCAACTGCAAGCACCTGAAG ATGACCCGGCCT |
| P16 | MSMB-NCOA4-1 | 343 | 483 | GGCGTGCCAGGCGATAGCACTCGGAGAGCC GTCAGACGGATGAACACCTTT |
| FUS1 | SLC45A3 → ELK4 -1 | 211 | 484 | TGTGGCGCCTCTGCCTGTGACGTGTCCCTGA TCGCTATGGACTCCGCC |
| P22 | SLC45A3 -ELK4 - | 349 | 485 | AGCCTGTACCACCGGGAAAAGCAGCTCATT GCCATGGACAGCGCCATC |

TABLE 23-continued

| Neoantigen ID | Gene ID | Amino acid SEQ ID NO: | Codon-optimized polynucleotide for GAd20 expression; SEQ ID NO: | Codon-optimized polynucleotide sequence for GAd20 expression |
|---|---|---|---|---|
| | 2 | | | |
| FUS2 | ARHGEF 38→ ARHGEF 38-IT1 | 213 | 486 | ACCGAGTACAACCAGAAACTGCAAGTGAACCAGTTCAGCGAGAGCAAG |
| FUS3 | MSMB→ NCOA4-2 | 215 | 487 | ACCGAGATCAGCTGCTGCACCCTGAGCAGCGAGGAAAACGAGTACCTGCCTAGACCTGAGTGGCAGCTGCAG |
| FUS6 | TMPRSS 2→ ERG | 221 | 488 | TGCGAAGAGAGAGGCGCCGCAGGATCTCTGATCTCCTGCGAA |
| FUS5 | TMPRSS 2→ ERG | 219 | 489 | AACAGCAAGATGGCCCTGAATAGCGAGGCCCTGTCTGTGGTGTCTGAA |
| FUS8 | INCA1→ CAMTA 2 | 225 | 490 | TGGGGCATGGAACTGGCCGCCAGCAGAAGATTCAGCTGGGATCATCATAGCGCAGGCGGCCCACCTAGAGTGCCATCTGTTAGAAGCGGAGCTGCCCAGGTGCAGCCTAAAGATCCTCTGCCACTGAGAACACTGGCCGGCTGCCTTGCTAGAACAGCCCATCTTAGACCTGGCGCCGAGTCTCTGCCTCAGCCACAACTGCACTGTACC |
| FUS15 | D2HGD H→ GAL3ST 2 | 345 | 491 | CATGTCGTCGGCTACGGCCACCTGGATACAAGCGGAAGCAGCTCTAGCTCCAGCTGGCCT |
| P35 | TMPRSS 2-ERG | 353 | 492 | AACTCAAAAATGGCTCTGAACAGCCTGAACTCCATCGACGACGCCCAGCTGACAAGAATCGCCCCTCCTAGATCTCACTGCTGCTTTTGGGAAGTGAACGCCCCA |
| FUS19 | GTF2F1→ PSPN | 235 | 493 | AAGATGCACTTTAGCCTGAAAGAACACCCTCCACCACCTTGTCCTCCA |
| FUS7 | NME4→ DECR2 | 223 | 494 | CTGTGGTTCCAGTCCAGCGAGCTGTCTCCTACTGGTGCCCCTTGGCCATCTAGACGCCCTACTTGGAGAGGCACCACCGTGTCACCAAGAACCGCCACAAGCAGCGCCAGAACCTGTTGTGGCACAAAGTGGCCCTCCAGCCAAGAAGCCGCTCTCGGACTTGGAAGCGGACTGCTGAGGTTCTCTTGTGGAACCGCCGCCATTCGG |
| M84 | AR-T878A | 167 | 495 | ATCGCTAGAGAGCTGCACCAGTTCGCCTTCGACCTGCTGATCAAGAGCCAC |
| M86 | AR-L702H | 171 | 496 | CAGCCTGATTCTTTTGCCGCACTGCACAGCTCCCTGAACGAGCTGGGAGAG |
| M10 | SPOP-F133L | 19 | 497 | TTCGTGCAAGGCAAGGATTGGGGCCTCAAAAAGTTTATCCGCAGAGACTTC |
| M12 | SPOP-W133V | 23 | 498 | TTTGTGCAGGGCAAAGACTGGGGCGTGAAGAAGTTCATCCGGCGGGACTTC |
| FR1 | ZFHX3 | 177 | 499 | CAGAACCTGCAGAACGGCGGAGGCTCTAGAAGCTCTGCTACACTTCCTGGCAGGCGGCGGAGAAGATGGCTGAGAAGAAGGCGGCAGCCTATCTCTGTGGCTCCTGCTGGACCTCCTAGACGGCCCAACCAGAAGCCTAATCCTCCTGGCGGAGCCAGATGCGTGATCATGAGGCCTACATGGCCTGGCACCAGCGCCTTCACC |

TABLE 24

| Neoantigen ID | Gene ID | Amino acid optimized SEQ ID NO: | Codon-MVAexpression polynucleotide for MVA expression; SEQ ID NO: | Codon-optimized polynucleotide sequence for |
|---|---|---|---|---|
| AS18 | NWD1 | 275 | 500 | TGGAAGTTCGAGATGAGCTACACCGTTGG CGGCCCTCCACCACATGTTCACGCCAGAC CTAGACACTGGAAAACCGACAGA |
| P87 | AR-Intron | 381 | 501 | TACGAGGCCGGCATGACACTCGGAGGCAA GATCCTGTTCTTCCTGTTCCTGCTGCTCCCT CTGAGCCCCTTCAGCCTGATCTTT |
| AS55 | SPOC | 333 | 461 | GATGGCCACAGCTACACCAGCAAAGTGAA CTGCCTCCTGCTGCAGGATGGCTTCCACGG CTGTGTGTCTATTACTGGCGCCGCTGGCAG ACGGAACCTGAGCATCTTTCTGTTTCTGAT GCTGTGCAAGCTCGAGTTCCACGCCTGC |
| AS57 | KLK3 | 337 | 503 | ACAGGCGGCAAGAGCACATGTTCTGCCCC TGGACCTCAGTCTCTGCCCAGCACACCCTT CAGCACATACCCTCAGTGGGTCATCCTGA TCACCGAGCTG |
| AS15 | LRRC45 | 269 | 504 | GTGCTGCGGTTCCTGGATCTCAAAGTGCG CTACCTGCACAGC |
| AS7 | ACSM1 | 253 | 505 | GATTATTGGGCCCAGAAAGAAAAGGGCAG CAGCAGCTTCCTGCGGCCTAGCTGT |
| AS43 | CPNE7 | 309 | 506 | GTGCCCTTCCGGGAACTGAAGAACGTGTC CGTTCTGGAAGGCCTGAGGCAGGGCAGAC TTGGCGGACCTTGTAGCTGCCACTGTCCTA GACCAAGCCAGGCCAGACTGACCCCTGTG GATGTGGCTGGCCCATTTCTGTGTCTGGGC GACCCTGGACTGTTCCCTCCAGTGAAGTCT AGCATC |
| AS51 | CPNE7 | 325 | 507 | GGCATGGAATGTACACTGGGCCAAGTGGG AGCCCCATCTCCTAGAAGAGAAGAGGATG GCTGGCGCGGAGGCCACTCTAGATTCAAA GCTGATGTGCCCGCTCCTCAGGGCCCTTGT TGGGGAGGACAACCTGGATCTGCCCCATC TTCTGCCCCACCTGAACAGAGCCTGCTGG AT |
| AS16 | LRRC45 | 271 | 508 | GGCAACACCACACTGCAACAGCTGGGAGA AGCCTCTCAGGCCCCAAGCGGTTCTCTGAT CCCTCTCAGACTGCCCCTCCTGTGGGAAGT GCGGGGC |
| AS41 | RHPN1 | 305 | 509 | GAGGCTTTCCAGAGAGCAGCTGGCGAAGG CGGACCTGGCAGAGGTGGTGCTAGAAGAG GTGCTAGAGTGCTGCAGAGCCCATTCTGT AGAGCTGGCGCTGGCGAATGGCTGGGCCA CCAATCTCTTAGA |
| AS6 | ACSM1 | 251 | 510 | GACTATTGGGCTCAAAAAGAGAAGATCAG CATCCCCAGAACACACCTGTGC |
| AS3 | DNAH8 | 245 | 511 | GTGGCCATGATGGTGCCCGACAGACAGGT GCACTACGACTTCGGCCTG |
| AS11 | CPNE7 | 261 | 512 | GTGCCCTTCAGAGAGCTGAAAAACCAGAG AACAGCCCAGGGCGCTCCTGGAATCCATC ATGCTGCTTCTCCAGTGGCCGCCAATCTGT GCGATCCTGCCAGACATGCCCAGCATACC AGGATTCCTTGTGGCGCTGGACAAGTGCG CGCTGGAAGAGGACCTGAAGCTGGTGGCG GAGTTCTGCAGCCTCAAAGACCTGCTCCT GAGAAGCCTGGCTGCCCCTGTAGAAGAGG ACAGCCTAGACTGCACACCGTGAAGATGT GGCGGGCC |
| AS13 | GRIN3A | 265 | 513 | AAGAGAAGCTTCGCCGTGACCGAGCGGAT CATC |

TABLE 24-continued

| Neoantigen ID | Gene ID | Amino acid optimized SEQ ID NO: | Codon-MVAexpression polynucleotide for MVA expression; SEQ ID NO: | Codon-optimized polynucleotide sequence for |
|---|---|---|---|---|
| AS47 | AGRN | 317 | 514 | TTTAAGAAGTTTGACGGCCCCTGCGGCGA GAGAGGCGGAGGAAGAACTGCAAGAGCC CTTTGGGCCAGAGGCGACTCTGTTCTGAC ACCAGCTCTGGACCCTCAGACACCTGTTA GGGCCCCTAGCCTGACAAGAGCTGCCGCT GCTGTT |
| AS8 | CACNA1 D | 255 | 515 | CTGGTGCTGGGCGTGCTGTCTGGCCACTCT GGAAGCAGACTG |
| AS19 | NWD1 | 277 | 516 | CAATGGCAGCACTACCACAGATCTGGCGA AGCCGCTGGAACCCCACTTTGGAGGCCTA CCAGAAAC |
| AS37 | RECQL4 | 297 | 517 | TGCCACTTGTTTCTCCAGCCACAAGTGGGC ACCCCTCCACCTCATACAGCCTCTGCTAGA GCACCTAGCGGCCCACCTCATCCTCACGA ATCTTGTCCTGCCGGAAGAAGGCCTGCCA GAGCCGCTCAAACATGTGCCAGACGACAG CACGGACTGCCCGGATGTGAAGAAGCCGG AACAGCCAGAGTGCCTAGCCTGCACCTTC ATCTGCATCAGGCCGCTCTTGGAGCCGGA AGAGGTAGAGGATGGGGAGAAGCTTGTGC CCAGGTGCCACCTTCTAGAGGC |
| AS23 | ZNF614 | 285 | 477 | AAGATCCAGAACAAGAACTGCCCCGAC |
| MS1 | TTLL7 | 437 | 519 | CACTACAAGCTGATCCAGCAGCCAATCAG CCTGTTCTCCATCACCGACCGGCTGCACAA GACATTCAGCCAGCTGCCTTCCGTGCATCT GTGCAGCATCACCTTCCAGTGGGGACACC CTCCTATCTTTTGCTCCACCAACGACATCT GCGTGACCGCCAACTTCTGTATCAGCGTG ACCTTCCTGAAGCCTTGCTTTCTGCTGCAC GAGGCCTCCGCCAGCCAG |
| MS3 | TESK1 | 439 | 520 | CGGACCGCTCTGACCCACAACCAGGACTT CAGCATCTACCGGCTGTGCTGCAAGAGGG GCTCTCTGTGTCATGCTAGCCAGGCTAGA AGCCCCGCCTTTCCTAAGCCTGTCAGACCT CTGCCTGCTCCTATCACCAGAATCACCCCT CAGCTCGGCGGCCAGTCTGATTCATCTCA GCCACTGCTGACCACCGGCAGACCTCAAG GATGGCAAGACCAGGCTCTGAGACACACA CAGCAGGCTAGCCCAGCCTCTTGCGCCAC CATCACAATACCAATACATTCTGCCGCTCT GGGCGATCACAGCGGAGATCCTGGACCTG CCTGGGATACTTGTCCTCCTCTGCCCCTAA CTACACTGATCCCTAGGGCTCCTCCACCTT ACGGCGATAGCACAGCCAGATCCTGGCCT AGCAGATGTGGCCCTCTGGGC |
| MS6 | SOAT1 | 442 | 521 | TACGCCTACAAGGACTTCCTGTGGTGCTTC CCCTTCTCTCTGGTGTTCCTGCAAGAAATC CAGATCTGCTGTCACGTGTCCTGCCTGTGC TGTATCTGCTGTAGCACCCGGATCTGTCTG GGCTGTCTGCTGGAACTGTTCCTGAGCAG AGCCCTGAGAGCACTGCACGTGCTGTGGA ACGGATTCCAGCTGCACTGCCAG |
| MS8 | ZYG11A | 444 | 522 | ACCATGCCTGCCATTCTGAAGCTGCAGAA GAATTGTCTTCTAAGCCTG |
| P82 | AR-V7 | 379 | 523 | TATGAGGCTGGAATGACCCTGGGCGAGAA GTTCAGAGTGGGCAACTGCAAGCACCTGA AGATGACCCGGCCT |
| P16 | MSMB-NCOA4-1 | 343 | 524 | GGAGTGCCTGGCGATTCTACTAGAAGGGC CGTGCGGCGGATGAACACCTTT |

TABLE 24-continued

| Neoantigen ID | Gene ID | Amino acid optimized SEQ ID NO: | Codon-MVAexpression polynucleotide for MVA expression; SEQ ID NO: | Codon-optimized polynucleotide sequence for |
|---|---|---|---|---|
| FUS1 | SLC45A3→ ELK4 - 1 | 211 | 525 | TGTGGCGCATCTGCCTGCGACGTGTCCCTG ATCGCTATGGATAGCGCC |
| P22 | SLC45A3- ELK4 -2 | 349 | 485 | AGCCTGTACCACCGGGAAAAGCAGCTCAT TGCCATGGACAGCGCCATC |
| FUS2 | ARHGEF3 8→ ARHGEF3 8-IT1 | 213 | 486 | ACCGAGTACAACCAGAAACTGCAAGTGAA CCAGTTCAGCGAGAGCAAG |
| FUS3 | MSMB→ NCOA4-2 | 215 | 528 | ACCGAGATCAGCTGCTGCACCCTGAGCAG CGAGGAAAACGAGTACCTGCCTAGACCTG AATGGCAGCTGCAG |
| FUS6 | TMPRSS2 → ERG | 221 | 529 | TGCGAGGAAAGAGGCGCAGCCGGATCTCT GATCTCTTGCGAG |
| FUS8 | TMPRSS2 → ERG | 219 | 530 | AACAGCAAGATGGCCCTGAATAGCGAGGC CCTGTCTGTGGTGTCCGAG |
| FUS8 | INCA1→ CAMTA2 | 225 | 531 | TGGGGAATGGAACTGGCCGCTAGCAGGCG GTTTAGCTGGGATCATCATTCTGCCGGCGG ACCTCCAAGAGTGCCAAGCGTTAGAAGCG GAGCAGCCCAGGTCCAGCCTAAAGATCCA CTGCCACTGAGAACACTGGCCGGCTGCCT TGCCAGAACAGCTCATCTTAGACCTGGCG CCGAAAGCCTGCCTCAACCTCAGCTGCAT TGCACA |
| FUS15 | D2HGDH→ GAL3ST2 | 345 | 532 | CACGTTGTCGGCTATGGCCACCTGGATAC AAGCGGCTCCTCTAGCAGTAGCTCCTGGC CT |
| P35 | TMPRSS2 -ERG | 353 | 533 | AATTCTAAGATGGCTCTCAACAGCCTGAA CTCCATCGACGACGCCCAGCTGACAAGAA TCGCCCCTCCAAGAAGCCACTGTTGCTTTT GGGAAGTGAACGCCCCT |
| FUS19 | GTF2F1→ PSPN | 235 | 534 | AAGATGCACTTCTCACTGAAAGAGCACCC GCCACCGCCGTGCCCACCG |
| FUS7 | NME4→ DECR2 | 223 | 535 | CTGTGGTTCCAGTCCAGCGAACTGTCTCCT ACTGGCGCTCCATGGCCAAGCAGAAGGCC TACTTGGAGAGGCACCACCGTGTCTCCAA GAACCGCTACAAGCAGCGCCAGAACCTGT TGCGGCACAAAATGGCCCTCCAGCCAAGA AGCTGCCCTCGGACTTGGAAGCGGACTGC TGAGATTCAGCTGTGGCACAGCCGCCATC AGA |
| M84 | AR-T878A | 167 | 536 | ATCGCCAGAGAACTGCACCAGTTCGCCTT CGACCTGCTGATCAAGAGCCAC |
| M86 | AR-L702H | 171 | 537 | CAGCCTGACAGCTTTGCTGCCCTGCATAGC TCCCTGAATGAGCTGGGCGAA |
| M10 | SPOP- F133L | 19 | 538 | TTTGTGCAGGGTAAAGATTGGGGCCTCAA AAAGTTTATCAGACGGGACTTC |
| M12 | SPOP- W133V | 23 | 539 | TTCGTGCAGGGCAAAGACTGGGGCGTGAA GAAGTTCATCCGGCGGGACTTT |
| FR1 | ZFHX3 | 177 | 540 | CAGAACCTGCAGAACGGCGGAGGCTCTAG AAGCTCTGCTACACTTCCTGGCAGGCGGC GGAGAAGATGGCTGAGAAGAAGGCGGCA GCCTATCTCTGTGGCTCCTGCTGGACCTCC TAGACGGCCCAACCAGAAGCCTAATCCTC CTGGCGGAGCCAGATGCGTGATCATGAGG CCTACATGGCCTGGCACCAGCGCCTTTACC |

Synthetic Gene Design

The 41 neoantigen amino acidic sequences were joined head to tail. The order of the neoantigens sequences was determined according to a strategy that minimized the formation of predicted junctional epitopes that may be generated by the juxtaposition of two adjacent neoantigen peptides.

To this purpose, custom tools were developed to split the 41 neoantigens into 4 smaller lists (sublists) of similar cumulative length and to generate, for each sublist, 2 million scrambled layouts of the synthetic gene with a different neoantigen order. The tool proceeded iteratively. At each loop a scrambled layout was generated and compared to the layouts already generated. If the number of predicted junctional epitopes in the new layout was lower than the number of the previously best layout, the new layout was considered as the best. Each scrambled layout was analyzed estimating the number of potential junctional epitopes predicted to bind one out of a subset of 9 class I HLA haplotypes with an $IC_{50}$<=1500 nM (considering only 9mer epitopes predicted by the IEDB_recommended method included in the IEDB 2.17 software). The 9 class I HLA haplotypes cumulatively cover 82% of the world population as estimated by analyzing haplotypes annotated for subjects in the 1000 genomes project. Scrambled layouts with neoantigens that formed predicted junctional epitopes with the N-terminal T-cell enhancer or the C-terminal TAG sequence were excluded. As an additional constraint, in each layout junctions that contained a 9mer peptide that matched a protein annotated in the human wildtype proteome were also excluded.

The best layouts obtained after scrambling 2 million times each of the 4 sublists were then joined to generate an overall layout comprising all 41 neoantigens. Out of all possible combinations of the best 4 layouts the one with the minimal number of predicted epitopes formed by the newly formed junctions was selected.

The whole procedure described was applied two times independently to generate two artificial genes to be encoded alternatively by the GAd20 or MVA vector. For the MVA vector the scrambled layouts were designed with the additional constraint of avoiding the junctions with predicted junctional epitopes that were already present in the layout selected for the Adenoviral transgene.

Amino acid sequences of the optimized layout for the GAd20 is shown in SEQ ID NO: 541 and for MVA SEQ ID NO: 543. Neoantigens in the GAd20 insert of SEQ ID NO: 541 were in the following order: FR1-AS13-AS7-AS6-AS8-P87-FUS3-AS43-AS57-AS51-AS18-AS55-AS23-AS47-MS 1-AS37-AS15-AS19-AS11-AS3-P16-P82-FUS5-FUS1-M12-MS6-FUS2-P22-FUS6-MS8-MS3-AS16-M86-M84-M10-FUS8-FUS7-FUS19-AS41-FUS15-P35. Neoantigens in the MVA insert of SEQ DID NO: 543 were in the following order: FR1-AS51-AS6-AS18-AS7-AS43-FUS3-P87-AS8-AS13-AS57-AS55-AS19-AS3-AS23-AS15-AS11-AS37-MS1-AS47-P16-FUS1-FUS6-P22-M12-MS8-FUS5-P82-FUS2-MS3-MS6-AS16-P35-M10-AS41-FUS8-M84-FUS19-FUS15-M86-FUS7

Five additional alternative optimized layouts of scrambled neoantigens were assessed for each vector. The five alternative layouts had the same number of predicted junctional epitopes compared to SEQ ID NO: 541 and SEQ ID NO: 543. The five alternative layouts for Gad20 are shown in SEQ ID NO: 554, SEQ ID NO; 555, SEQ ID NO: 556, SEQ ID NO: 623 and SEQ ID NO: 624. The five alternative layouts for MVA are shown in SEQ ID NO: 557, SEQ ID NO: 558, SEQ ID NO: 559, SEQ ID NO: 625 and SEQ ID NO: 626. The neoantigens in the alternative optimized layouts were in the following order:

SEQ ID NO: 554: FR1-AS13-AS8-P87-FUS3-AS43-AS57-AS51-AS7-AS6-AS18-P16-P82-FUS5-FUS1-M12-MS6-FUS2-P22-FUS6-MS8-MS3-AS55-AS23-AS47-MS1-AS37-AS15-AS19-AS11-AS3-AS16-M86-M84-M10-FUS8-FUS7-FUS19-AS41-FUS15-P35

SEQ ID NO: 555: FR1-AS13-FUS3-P87-AS7-AS43-AS57-AS51-AS6-AS8-AS18-AS55-AS23-AS47-MS1-AS37-AS15-AS19-AS11-AS3-P16-P82-FUS5-FUS1-M12-MS6-FUS2-P22-FUS6-MS8-MS3-AS16-M86-M84-M10-FUS8-FUS7-FUS19-AS41-FUS15-P35

SEQ ID NO: 556: FR1-AS13-AS7-AS43-AS8-P87-FUS3-AS57-AS51-AS6-AS18-AS55-AS23-AS47-MS1-AS37-AS15-AS19-AS11-AS3-P16-P82-FUS5-FUS1-M12-MS6-FUS2-P22-FUS6-MS8-MS3-AS16-M86-M84-M10-FUS8-FUS7-FUS19-AS41-FUS15-P35

ID NO: 623: P16-P82-FUS5-FUS1-M12-MS6-FUS2-P22-FUS6-MS8-MS3-AS16-M86-M84-M10-FUS8-FUS7-FUS19-AS41-FUS15-P35-AS55-AS23-AS47-MS1-AS37-AS15-AS19-AS11-AS3-FR1-AS13-AS8-P87-FUS3-AS43-AS57-AS51-AS7-AS6-AS18

SEQ ID NO: 624: AS16-M86-M84-M10-FUS8-FUS7-FUS19-AS41-FUS15-P35-P16-P82-FUS5-FUS1-M12-MS6-FUS2-P22-FUS6-MS8-MS3-AS55-AS23-AS47-MS1-AS37-AS15-AS19-AS11-AS3-FR1-AS13-FUS3-P87-A7-S7-AS43-AS57-AS51-AS6-AS8-AS18

SEQ ID NO: 557: FR1-AS51-AS6-AS18-AS7-AS43-FUS3-P87-AS8-AS13-AS57-AS55-AS37-MS1-AS3-AS23-AS15-AS11-AS19-AS47-P16-FUS1-FUS6-P22-M12-MS8-FUS5-P82-FUS2-MS3-MS6-AS16-P35-M10-AS41-FUS8-M84-FUS19-FUS15-M86-FUS7

SEQ ID NO: 558: AS55-AS19-AS3-AS15-AS23-AS11-AS37-MS1-AS47-FR1-AS51-AS6-AS18-AS7-AS43-FUS3-P87-AS8-AS13-AS57-P16-FUS1-FUS6-P22-M12-MS8-FUS5-P82-FUS2-MS3-MS6-AS16-P35-M10-AS41-FUS8-M84-FUS19-FUS15-M86-FUS7

ID NO: 559: AS16-P35-M10-AS41-FUS8-M84-FUS19-FUS15-M86-FUS7-AS55-AS19-AS3-AS23-AS15-AS11-AS37-MS1-AS47-P16-FUS1-FUS2-P82-MS8-FUS5-FUS6-P22-M12-MS3-MS6-FR1-AS51-AS6-AS18-AS7-AS43-FUS3-P87-AS8-AS13-AS57

ID NO: 625: AS16-P35-M10-AS41-FUS8-M84-FUS19-FUS15-M86-FUS7-FR1-AS51-AS6-AS18-AS7-AS43-FUS3-P87-AS8-AS13-AS57-AS55-AS19-AS3-AS15-AS23-AS11-AS37-MS1-AS47-P16-FUS1-FUS6-P22-M12-MS8-FUS5-P82-FUS2-MS3-MS6

SEQ ID NO: 626: AS55-AS11-AS19-AS23-AS3-AS15-AS37-MS1-AS47-FR1-AS51-AS6-AS18-AS7-AS43-FUS3-P87-AS8-AS13-AS57-AS16-P35-M10-AS41-FUS8-M84-FUS19-FUS15-M86-FUS7-P16-FUS1-FUS6-P22-M12-P82-MS8-FUS5-FUS2-MS3-MS6

Insertion of T-Cell Enhancer and TAG Sequences

A small peptide fragment with length of 28aa from the mandarin fish invariant chain (MGQKEQIHTLQKNSERMSKQLTRSSQAV; SEQ ID NO: 549) was placed at the N-terminus of each transgene encoding the 41 neoantigens. Preclinical data has shown this sequence to increase the immunological response of the viral vector. A small segment of 7 amino acids (TAG sequence; seq: SHHHHHH; SEQ ID NO: 627) was added at the C-terminus of the transgene for the purpose of monitoring the expression of the encoded transgene.

Amino acid sequences of the optimized layout for the GAd20 that includes the TCE sequence and omits the tag sequence are shown in SEQ ID NO: 550 and for MVA SEQ ID NO: 551.

Conversion into Nucleotide Sequence and Optimization to Remove Predicted miRNA Binding Sites.

The conversion from amino acid sequence into nucleotide sequence was performed using codon optimizing according to the human codon usage applying additional constraints to avoid as much as possible the following features:

- internal TATA-boxes, chi-sites and ribosomal entry sites
- AT-rich or GC-rich sequence stretches
- RNA instability motifs
- repeat sequences and RNA secondary structures
- (cryptic) splice donor and acceptor sites in higher eukaryotes
- TTTTTnT termination motifs for the MVA vector EcoR1, BamH1 restriction sites and a KOZAK sequence were then added upstream the optimized nucleotide sequence. 2 STOP codons followed by Asc1 and Not1 restriction sites were added downstream the optimized nucleotide sequence.

The optimized nucleotide sequence of each transgene was then further analyzed with the PITA and miranda software to detect predicted miRNA target sites that might downregulate the expression of the synthetic transgene. 9 miRNA binding sites detected by both methods were removed by modifying the nucleotide sequence of the regions that are predicted to bind the miRNA "seed" by introducing synonymous changes in the corresponding codons. The synthesis of GAd20 and MVA transgenes, was performed using standard methods.

The codon optimized polynucleotide sequence encoding the GAd20 neoantigen layout of SEQ ID NO: 541 is shown in SEQ ID NO: 542.

The codon optimized polynucleotide sequence encoding the MVA (neoMVA) neoantigen layout of SEQ ID NO: 543 is shown in SEQ ID NO: 544.

The codon optimized polynucleotide sequence encoding the GAd20 neoantigen layout including the TCE sequence and excluding the TAG sequence of SEQ ID NO: 550 is shown in SEQ ID NO: 551.

The codon optimized polynucleotide sequence encoding the MVA neoantigen layout including the TCE sequence and excluding the TAG sequence of SEQ ID NO: 552 is shown in SEQ ID NO: 553.

```
Kozak sequence:
                                        SEQ ID NO: 545
CGCGACTTCGCCGCC;

Polynucleotide encoding the TCE:
                                        SEQ ID NO: 546
ATGGGCCAGAAAGAGCAGATCCACACACTGCAGAAAAACAGCGAGCGGAT

GAGCAAGCAGCTGACCAGATCTTCTCAGGCCGTG;

Polynucleotide encoding the serine-histidine tag:
                                        SEQ ID NO: 547
AGCCATCACCATCACCACCAT;

Two stop codons (TAGTAA)
Polypeptide sequence of the TCE:
                                        SEQ ID NO: 549
MGQKEQIHTLQKNSERMSKQLTRSSQAV;
```

Viral Vector Production

GAd20 Viral Vector Production

The GAd20 transgene was subcloned into a shuttle plasmid between CMV promoter with two TetO repeats and a BGH polyA via ECOR1-NOT1 restriction sites.

The resulting expression cassette was transferred into the GAd20 genome by homologous recombination in suitable *E. coli* strains, transformed with the CMV-transgene-BGH DNA fragment and with a construct carrying the GAd20 genome.

Recombination involved CMV and BGH as homology arms, that were already present in the GAd20 construct in place of the E1 deletion (insertion site of the transgene). Recombinant GAd20 vectors were then rescued by transfection of the E1 complementing, TetR expressing M9 cells and amplified by subsequent re-infection of fresh M9 cells.

```
CMV promoter with TetO sites:
                                        SEQ ID NO: 628
Ccattgcatacgttgtatccatatcataatatgtacatttatattggctc

atgtccaacattaccgccatgttgacattgattattgactagttattaat

agtaatcaattacggggtcattagttcatagcccatatatggagttccgc

gttacataacttacggtaaatggcccgcctggctgaccgcccaacgaccc

ccgcccattgacgtcaataatgacgtatgttcccatagtaacgccaatag

ggactttccattgacgtcaatgggtggagtatttacggtaaactgcccac

ttggcagtacatcaagtgtatcatatgccaagtacgccccctattgacgt

caatgacggtaaatggcccgcctggcattatgcccagtacatgaccttat

gggactttcctacttggcagtacatctacgtattagtcatcgctattacc

atggtgatgcggttttggcagtacatcaatgggcgtggatagcggtttga

ctcacggggatttccaagtctccaccccattgacgtcaatgggagtttgt

tttggcaccaaaatcaacgggactttccaaaatgtcgtaacaactccgcc

ccattgacgcaaatgggcggtaggcgtgtacggtgggaggtctatataag

cagagctctccctatcagtgatagagatctccctatcagtgatagagatc

gtcgacgagctcgtttagtgaaccgtcagatcgcctggagacgccatcca

cgctgttttgacctccatagaagacaccgggaccgatccagcctccgcgg

ccgggaacggtgcattggaacgcggattccccgtgccaagagtga

BGH poly A
                                        SEQ ID NO: 629
ctgtgccttctagttgccagccatctgttgtttgcccctcccccgtgcct

tccttgaccctggaaggtgccactcccactgtcctttcctaataaaatga

ggaaattgcatcgcattgtctgagtaggtgtcattctattctggggggtg

gggtggggcaggacagcaagggggaggattgggaagacaatagcaggcat

gctggggatgcggtgggctctatggcc
```

MVA Viral Vector Production

The MVA transgene was subcloned into the p94 shuttle plasmid via BAMH1-ASC1 restriction sites, under the control of the vaccinia P7.5 early/late promoter (SEQ ID NO: 630), between sequences homologous to the deletion III locus of MVA (FlankIII-1 and -2 regions). An additional expression cassette for eGFP protein, flanked by a repeated sequence named "Z", was present in the p94 shuttle plasmid, between Flank III regions.

The parental MVA vector used for recombinant vaccine viruses' generation carried the HcRed1-1 fluorescent protein transgene at the Deletion III locus and was indicated as MVA-RED 476 MG.

Recombinant MVA, with transgene insertion at the Deletion III locus, were generated by two events of in vivo recombination in Chicken embryo fibroblasts (CEF) cells. The first recombination event occurred in cells infected with MVA-RED 476 MG and transfected with the p94 shuttle plasmid, and resulted in replacement of the HcRed protein gene with the transgene/eGFP cassette. Infected cells containing MVA-Green intermediate were isolated by FACS sorting of green cells. The intermediate recombinant MVA resulting from first recombination carried both the transgene and the eGFP cassette but was unstable due to the presence of repeated Z regions. Thus, a spontaneous second recombination event occurred involving Z regions and removed the eGFP cassette. The resulting recombinant MVA was colorless and carried the transgene cassette at the Deletion III locus (insertion site) of MVA-RED 476 MG. This was isolated by FACS sorting of colorless infected cells and amplified by re-infection of fresh CEF cells. The obtained lysate was used to infect Age1 cells to produce the research batch.

P7.5 early/late promoter
SEQ ID NO: 630

GATCACTAATTCCAAACCCACCCGCTTTTTATAGTAAGTTTTTCACCCATAAATAATA

AATACAATAATTAATTTCTCGTAAAAGTAGAAAATATATTCTAATTTATTGCACGGT

AAGGAAGTAGAATCATAAAGAACAGTGACGGATC neoGAd20 protein (no TCE, no HIS tag)
SEQ ID NO: 541

QNLQNGGGSRSSATLPGRRRRRWLRRRRQPISVAPAGPPRRPNQKPNPPGGARCVIMRP

TWPGTSAFTKRSFAVTERIIDYWAQKEKGSSSFLRPSCDYWAQKEKISIPRTHLCLVLGV

LSGHSGSRLYEAGMTLGGKILFFLFLLLPLSPFSLIFTEISCCTLSSEENEYLPRPEWQLQVP

FRELKNVSVLEGLRQGRLGGPCSCHCPRPSQARLTPVDVAGPFLCLGDPGLFPPVKSSIT

GGKSTCSAPGPQSLPSTPFSTYPQWVILITELGMECTLGQVGAPSPRREEDGWRGGHSRF

KADVPAPQGPCWGGQPGSAPSSAPPEQSLLDWKFEMSYTVGGPPPHVHARPRHWKTDR

DGHSYTSKVNCLLLQDGFHGCVSITGAAGRRNLSIFLFLMLCKLEFHACKIQNKNCPDFK

KFDGPCGERGGGRTARALWARGDSVLTPALDPQTPVRAPSLTRAAAAVHYKLIQQPISL

FSITDRLHKTFSQLPSVHLCSITFQWGHPPIFCSTNDICVTANFCISVTFLKPCFLLHEASAS

QCHLFLQPQVGTPPPHTASARAPSGPPHPHESCPAGRRPARAAQTCARRQHGLPGCEEA

GTARVPSLHLHLHQAALGAGRGRGWGEACAQVPPSRGVLRFLDLKVRYLHSQWQHYH

RSGEAAGTPLWRPTRNVPFRELKNQRTAQGAPGIHHAASPVAANLCDPARHAQHTRIPC

GAGQVRAGRGPEAGGGVLQPQRPAPEKPGCPCRRGQPRLHTVKMWRAVAMMVPDRQ

VHYDFGLGVPGDSTRRAVRRMNTFYEAGMTLGEKFRVGNCKHLKMTRPNSKMALNSE

ALSVVSECGASACDVSLIAMDSAFVQGKDWGVKKFIRRDFYAYKDFLWCFPFSLVFLQE

IQICCHVSCLCCICCSTRICLGCLLELFLSRALRALHVLWNGFQLHCQTEYNQKLQVNQF

SESKSLYHREKQLIAMDSAICEERGAAGSLISCETMPAILKLQKNCLLSLRTALTHNQDFS

IYRLCCKRGSLCHASQARSPAFPKPVRPLPAPITRITPQLGGQSDSSQPLLTTGRPQGWQD

QALRHTQQASPASCATITIPIHSAALGDHSGDPGPAWDTCPPLPLTTLIPRAPPPYGDSTA

RSWPSRCGPLGGNTTLQQLGEASQAPSGSLIPLRLPLLWEVRGQPDSFAALHSSLNELGEI

ARELHQFAFDLLIKSHFVQGKDWGLKKFIRRDFWGMELAASRRFSWDHHSAGGPPRVP

SVRSGAAQVQPKDPLPLRTLAGCLARTAHLRPGAESLPQPQLHCTLWFQSSELSPTGAP

WPSRRPTWRGTTVSPRTATSSARTCCGTKWPSSQEAALGLGSGLLRFSCGTAAIRKMHF

SLKEHPPPPCPPEAFQRAAGEGGPGRGGARRGARVLQSPFCRAGAGEWLGHQSLRHVV

GYGHLDTSGSSSSSSWPNSKMALNSLNSIDDAQLTRIAPPRSHCCFWEVNAP neoGAd20 polynucleotide (no TCE, no HIS tag)
SEQ ID NO: 542

CAGAACCTGCAGAACGGCGGAGGCTCTAGAAGCTCTGCTACACTTCCTGGCAGGCG

GCGGAGAAGATGGCTGAGAAGAAGGCGGCAGCCTATCTCTGTGGCTCCTGCTGGAC

CTCCTAGACGGCCCAACCAGAAGCCTAATCCTCCTGGCGGAGCCAGATGCGTGATCA

-continued

TGAGGCCTACATGGCCTGGCACCAGCGCCTTCACCAAGAGAAGCTTTGCCGTGACCG

AGCGGATCATCGACTATTGGGCTCAAAAAGAGAAGGGCAGCAGCAGCTTCCTGCGG

CCTAGCTGTGATTATTGGGCCCAGAAAGAAAAGATCAGCATCCCCAGAACACACCT

GTGCCTGGTGCTGGGAGTGCTGTCTGGACACTCTGGCAGCAGACTGTATGAGGCCGG

CATGACACTCGGCGGCAAGATCCTGTTCTTCCTGTTCCTGCTGCTCCCTCTGAGCCCC

TTCAGCCTGATCTTCACCGAGATCAGCTGCTGCACCCTGAGCAGCGAGGAAAACGA

GTACCTGCCTAGACCTGAGTGGCAGCTGCAGGTCCCCTTCAGAGAGCTGAAGAACGT

TTCCGTGCTGGAAGGCCTGAGACAGGGCAGACTTGGCGGCCCTTGTAGCTGTCACTG

CCCCAGACCTAGTCAGGCCAGACTGACACCTGTGGATGTGGCCGGACCTTTCCTGTG

TCTGGGAGATCCTGGCCTGTTTCCACCTGTGAAGTCCAGCATCACAGGCGGCAAGTC

CACATGTTCTGCCCCTGGACCTCAGAGCCTGCCTAGCACACCCTTCAGCACATACCC

TCAGTGGGTCATCCTGATCACCGAACTCGGCATGGAATGCACCCTGGGACAAGTGG

GAGCCCCATCTCCTAGAAGAGAAGAGGATGGCTGGCGCGGAGGCCACTCTAGATTC

AAAGCTGATGTGCCCGCTCCTCAGGGCCCTTGTTGGGGAGGACAACCTGGATCTGCC

CCATCTTCTGCCCCACCTGAACAGTCCCTGCTGGATTGGAAGTTCGAGATGAGCTAC

ACCGTCGGCGGACCTCCACCTCATGTTCATGCCAGACCTCGGCACTGGAAAACCGAC

AGAGATGGCCACAGCTACACCAGCAAAGTGAACTGCCTCCTGCTGCAGGATGGCTT

CCACGGCTGTGTGTCTATTACTGGCGCCGCTGGCAGACGGAACCTGAGCATCTTTCT

GTTTCTGATGCTGTGCAAGCTCGAGTTCCACGCCTGCAAGATCCAGAACAAGAACTG

CCCCGACTTCAAGAAGTTCGACGGCCCTTGCGGAGAAAGAGGCGGAGGCAGAACAG

CTAGAGCCCTTTGGGCTAGAGGCGACAGCGTTCTGACACCAGCTCTGGACCCTCAGA

CACCTGTTAGGGCCCCTAGCCTGACAAGAGCTGCCGCCGCTGTGCACTACAAGCTGA

TCCAGCAGCCAATCAGCCTGTTCAGCATCACCGACCGGCTGCACAAGACATTCAGCC

AGCTGCCAAGCGTGCACCTGTGCTCCATCACCTTCCAGTGGGGACACCCTCCTATCT

TTTGCTCCACCAACGACATCTGCGTGACCGCCAACTTCTGTATCAGCGTGACCTTCCT

GAAGCCTTGCTTTCTGCTGCACGAGGCCAGCGCCTCTCAGTGCCACTTGTTTCTGCAG

CCCCAAGTGGGCACACCTCCTCCACATACAGCCTCTGCTAGAGCACCTAGCGGCCCT

CCACATCCTCACGAATCTTGTCCTGCCGGAAGAAGGCCTGCCAGAGCCGCTCAAACA

TGTGCCAGACGACAGCACGGACTGCCTGGATGTGAAGAGGCTGGAACAGCCAGAGT

GCCTAGCCTGCACCTCCATCTGCATCAGGCTGCTCTTGGAGCCGGAAGAGGTAGAGG

ATGGGGCGAAGCTTGTGCTCAGGTGCCACCTTCTAGAGGCGTGCTGAGATTCCTGGA

CCTGAAAGTGCGCTACCTGCACAGCCAGTGGCAGCACTATCACAGATCTGGCGAAG

CCGCCGGAACACCCCTTTGGAGGCCAACAAGAAACGTGCCCTTCCGGGAACTGAAG

AACCAGAGAACAGCTCAGGGCGCTCCTGGAATCCACCATGCTGCTTCTCCAGTGGCC

GCCAACCTGTGTGATCCTGCCAGACATGCCCAGCACACCAGGATTCCTTGTGGCGCT

GGACAAGTGCGCGCTGGAAGAGGACCTGAAGCAGGCGGAGGTGTTCTGCAACCTCA

AAGACCCGCTCCTGAGAAGCCTGGCTGCCCTTGCAGAAGAGGACAGCCTAGACTGC

ACACCGTGAAAATGTGGCGAGCCGTGGCCATGATGGTGCCCGATAGACAGGTCCAC

TACGACTTTGGACTGGGCGTGCCAGGCGATAGCACTCGGAGAGCCGTCAGACGGAT

GAACACCTTTTACGAAGCCGGGATGACCCTGGGCGAGAAGTTCAGAGTGGGCAACT

GCAAGCACCTGAAGATGACCCGGCCTAACAGCAAGATGGCCCTGAATAGCGAGGCC

-continued

CTGTCTGTGGTGTCTGAATGTGGCGCCTCTGCCTGTGACGTGTCCCTGATCGCTATGG

ACTCCGCCTTTGTGCAGGGCAAAGACTGGGGCGTGAAGAAGTTCATCCGGCGGGAC

TTCTACGCCTACAAGGACTTCCTGTGGTGCTTCCCCTTCTCTCTGGTGTTCCTGCAAG

AGATCCAGATCTGCTGTCATGTGTCCTGCCTGTGCTGCATCTGCTGTAGCACCAGAA

TCTGCCTGGGCTGTCTGCTGGAACTGTTCCTGAGCAGAGCCCTGAGAGCACTGCACG

TGCTGTGGAACGGATTCCAGCTGCACTGCCAGACCGAGTACAACCAGAAACTGCAA

GTGAACCAGTTCAGCGAGAGCAAGAGCCTGTACCACCGGGAAAAGCAGCTCATTGC

CATGGACAGCGCCATCTGCGAAGAGAGAGGCGCCGCAGGATCTCTGATCTCCTGCG

AAACAATGCCCGCCATCCTGAAGCTGCAGAAGAATTGCCTCCTAAGCCTGCGAACC

GCTCTGACACACAACCAGGACTTCAGCATCTACAGACTGTGTTGCAAGCGGGGCTCC

CTGTGCCATGCAAGCCAAGCTAGAAGCCCCGCCTTTCCTAAACCTGTGCGACCTCTG

CCAGCTCCAATCACCAGAATTACCCCTCAGCTCGGCGGCCAGAGCGATTCATCTCAA

CCTCTGCTGACCACCGGCAGACCTCAAGGCTGGCAAGACCAAGCTCTGAGACACAC

CCAGCAGGCTAGCCCTGCCTCTTGTGCCACCATCACAATCCCCATCCACTCTGCCGCT

CTGGGCGATCATTCTGGCGATCCTGGACCAGCCTGGGACACATGTCCTCCACTGCCA

CTCACAACACTGATCCCTAGGGCTCCTCCACCTTACGGCGATTCTACCGCTAGAAGC

TGGCCCAGCAGATGTGGACCACTCGGAGGCAACACAACCCTCCAGCAACTGGGAGA

AGCCTCTCAGGCTCCTAGCGGCTCTCTGATCCCTCTCAGACTGCCTCTCCTGTGGGAA

GTTCGGGGCCAGCCTGATTCTTTTGCCGCACTGCACAGCTCCCTGAACGAGCTGGGA

GAGATCGCTAGAGAGCTGCACCAGTTCGCCTTCGACCTGCTGATCAAGAGCCACTTC

GTGCAAGGCAAGGATTGGGGCCTCAAAAAGTTTATCCGCAGAGACTTCTGGGGCAT

GGAACTGGCCGCCAGCAGAAGATTCAGCTGGGATCATCATAGCGCAGGCGGCCCAC

CTAGAGTGCCATCTGTTAGAAGCGGAGCTGCCCAGGTGCAGCCTAAAGATCCTCTGC

CACTGAGAACACTGGCCGGCTGCCTTGCTAGAACAGCCCATCTTAGACCTGGCGCCG

AGTCTCTGCCTCAGCCACAACTGCACTGTACCCTGTGGTTCCAGTCCAGCGAGCTGT

CTCCTACTGGTGCCCCTTGGCCATCTAGACGCCCTACTTGGAGAGGCACCACCGTGT

CACCAAGAACCGCCACAAGCAGCGCCAGAACCTGTTGTGGCACAAAGTGGCCCTCC

AGCCAAGAAGCCGCTCTCGGACTTGGAAGCGGACTGCTGAGGTTCTCTTGTGGAACC

GCCGCCATTCGGAAGATGCACTTTAGCCTGAAAGAACACCCTCCACCACCTTGTCCT

CCAGAGGCTTTCCAAAGAGCTGCTGGCGAAGGCGGACCTGGTAGAGGTGGTGCTAG

AAGAGGTGCTAGGGTGCTGCAGAGCCCATTCTGTAGAGCAGGCGCAGGCGAATGGC

TGGGCCATCAGAGTCTGAGACATGTCGTCGGCTACGGCCACCTGGATACAAGCGGA

AGCAGCTCTAGCTCCAGCTGGCCTAACTCAAAAATGGCTCTGAACAGCCTGAACTCC

ATCGACGACGCCCAGCTGACAAGAATCGCCCCTCCTAGATCTCACTGCTGCTTTTGG

GAAGTGAACGCCCCA neoMVA protein (no TCE, no HIS Tag)

SEQ ID NO: 543

QNLQNGGGSRSSATLPGRRRRRWLRRRRQPISVAPAGPPRRPNQKPNPPGGARCVIMRP

TWPGTSAFTGMECTLGQVGAPSPRREEDGWRGGHSRFKADVPAPQGPCWGGQPGSAPS

SAPPEQSLLDDYWAQKEKISIPRTHLCWKFEMSYTVGGPPPHVHARPRHWKTDRDYWA

QKEKGSSSFLRPSCVPFRELKNVSVLEGLRQGRLGGPCSCHCPRPSQARLTPVDVAGPFL

-continued

CLGDPGLFPPVKSSITEISCCTLSSEENEYLPRPEWQLQYEAGMTLGGKILFFLFLLLPLSP

FSLIFLVLGVLSGHSGSRLKRSFAVTERIITGGKSTCSAPGPQSLPSTPFSTYPQWVILITEL

DGHSYTSKVNCLLLQDGFHGCVSITGAAGRRNLSIFLFLMLCKLEFHACQWQHYHRSGE

AAGTPLWRPTRNVAMMVPDRQVHYDFGLKIQNKNCPDVLRFLDLKVRYLHSVPFRELK

NQRTAQGAPGIHHAASPVAANLCDPARHAQHTRIPCGAGQVRAGRGPEAGGGVLQPQR

PAPEKPGCPCRRGQPRLHTVKMWRACHLFLQPQVGTPPPHTASARAPSGPPHPHESCPA

GRRPARAAQTCARRQHGLPGCEEAGTARVPSLHLHLHQAALGAGRGRGWGEACAQVP

PSRGHYKLIQQPISLFSITDRLHKTFSQLPSVHLCSITFQWGHPPIFCSTNDICVTANFCISV

TFLKPCFLLHEASASQFKKFDGPCGERGGGRTARALWARGDSVLTPALDPQTPVRAPSL

TRAAAAVGVPGDSTRRAVRRMNTFCGASACDVSLIAMDSACEERGAAGSLISCESLYHR

EKQLIAMDSAIFVQGKDWGVKKFIRRDFTMPAILKLQKNCLLSLNSKMALNSEALSVVS

EYEAGMTLGEKFRVGNCKHLKMTRPTEYNQKLQVNQFSESKRTALTHNQDFSIYRLCC

KRGSLCHASQARSPAFPKPVRPLPAPITRITPQLGGQSDSSQPLLTTGRPQGWQDQALRH

TQQASPASCATITIPIHSAALGDHSGDPGPAWDTCPPLPLTTLIPRAPPPYGDSTARSWPSR

CGPLGYAYKDFLWCFPFSLVFLQEIQICCHVSCLCCICCSTRICLGCLLELFLSRALRALH

VLWNGFQLHCQGNTTLQQLGEASQAPSGSLIPLRLPLLWEVRGNSKMALNSLNSIDDAQ

LTRIAPPRSHCCFWEVNAPFVQGKDWGLKKFIRRDFEAFQRAAGEGGPGRGGARRGAR

VLQSPFCRAGAGEWLGHQSLRWGMELAASRRFSWDHHSAGGPPRVPSVRSGAAQVQP

KDPLPLRTLAGCLARTAHLRPGAESLPQPQLHCTIARELHQFAFDLLIKSHKMHFSLKEH

PPPPCPPHVVGYGHLDTSGSSSSSSWPQPDSFAALHSSLNELGELWFQSSELSPTGAPWPS

RRPTWRGTTVSPRTATSSARTCCGTKWPSSQEAALGLGSGLLRFSCGTAAIR neoMVA polynucleotide

SEQ ID NO: 544

CAGAACCTGCAGAACGGCGGAGGCTCTAGAAGCTCTGCTACACTTCCTGGCAGGCG

GCGGAGAAGATGGCTGAGAAGAAGGCGGCAGCCTATCTCTGTGGCTCCTGCTGGAC

CTCCTAGACGGCCCAACCAGAAGCCTAATCCTCCTGGCGGAGCCAGATGCGTGATCA

TGAGGCCTACATGGCCTGGCACCAGCGCCTTTACCGGCATGGAATGTACACTGGGCC

AAGTGGGAGCCCCATCTCCTAGAAGAGAAGAGGATGGCTGGCGCGGAGGCCACTCT

AGATTCAAAGCTGATGTGCCCGCTCCTCAGGGCCCTTGTTGGGGAGGACAACCTGGA

TCTGCCCCATCTTCTGCCCCACCTGAACAGAGCCTGCTGGATGACTATTGGGCTCAA

AAAGAGAAGATCAGCATCCCCAGAACACACCTGTGCTGGAAGTTCGAGATGAGCTA

CACCGTTGGCGGCCCTCCACCACATGTTCACGCCAGACCTAGACACTGGAAAACCGA

CAGAGATTATTGGGCCCAGAAAGAAAAGGGCAGCAGCAGCTTCCTGCGGCCTAGCT

GTGTGCCCTTCCGGGAACTGAAGAACGTGTCCGTTCTGGAAGGCCTGAGGCAGGGC

AGACTTGGCGGACCTTGTAGCTGCCACTGTCCTAGACCAAGCCAGGCCAGACTGACC

CCTGTGGATGTGGCTGGCCCATTTCTGTGTCTGGGCGACCCTGGACTGTTCCCTCCAG

TGAAGTCTAGCATCACCGAGATCAGCTGCTGCACCCTGAGCAGCGAGGAAAACGAG

TACCTGCCTAGACCTGAATGGCAGCTGCAGTACGAGGCCGGCATGACACTCGGAGG

CAAGATCCTGTTCTTCCTGTTCCTGCTGCTCCCTCTGAGCCCCTTCAGCCTGATCTTTC

TGGTGCTGGGCGTGCTGTCTGGCCACTCTGGAAGCAGACTGAAGAGAAGCTTCGCCG

TGACCGAGCGGATCATCACAGGCGGCAAGAGCACATGTTCTGCCCCTGGACCTCAGT

CTCTGCCCAGCACACCCTTCAGCACATACCCTCAGTGGGTCATCCTGATCACCGAGC

-continued

TGGATGGCCACAGCTACACCAGCAAAGTGAACTGCCTCCTGCTGCAGGATGGCTTCC
ACGGCTGTGTGTCTATTACTGGCGCCGCTGGCAGACGGAACCTGAGCATCTTTCTGT
TTCTGATGCTGTGCAAGCTCGAGTTCCACGCCTGCCAATGGCAGCACTACCACAGAT
CTGGCGAAGCCGCTGGAACCCCACTTTGGAGGCCTACCAGAAACGTGGCCATGATG
GTGCCCGACAGACAGGTGCACTACGACTTCGGCCTGAAGATCCAGAACAAGAACTG
CCCCGACGTGCTGCGGTTCCTGGATCTCAAAGTGCGCTACCTGCACAGCGTGCCCTT
CAGAGAGCTGAAAAACCAGAGAACAGCCCAGGGCGCTCCTGGAATCCATCATGCTG
CTTCTCCAGTGGCCGCCAATCTGTGCGATCCTGCCAGACATGCCCAGCATACCAGGA
TTCCTTGTGGCGCTGGACAAGTGCGCGCTGGAAGAGGACCTGAAGCTGGTGGCGGA
GTTCTGCAGCCTCAAAGACCTGCTCCTGAGAAGCCTGGCTGCCCCTGTAGAAGAGGA
CAGCCTAGACTGCACACCGTGAAGATGTGGCGGGCCTGCCACTTGTTTCTCCAGCCA
CAAGTGGGCACCCCTCCACCTCATACAGCCTCTGCTAGAGCACCTAGCGGCCCACCT
CATCCTCACGAATCTTGTCCTGCCGGAAGAAGGCCTGCCAGAGCCGCTCAAACATGT
GCCAGACGACAGCACGGACTGCCCGGATGTGAAGAAGCCGGAACAGCCAGAGTGCC
TAGCCTGCACCTTCATCTGCATCAGGCCGCTCTTGGAGCCGGAAGAGGTAGAGGATG
GGGAGAAGCTTGTGCCCAGGTGCCACCTTCTAGAGGCCACTACAAGCTGATCCAGC
AGCCAATCAGCCTGTTCTCCATCACCGACCGGCTGCACAAGACATTCAGCCAGCTGC
CTTCCGTGCATCTGTGCAGCATCACCTTCCAGTGGGGACACCCTCCTATCTTTTGCTC
CACCAACGACATCTGCGTGACCGCCAACTTCTGTATCAGCGTGACCTTCCTGAAGCC
TTGCTTTCTGCTGCACGAGGCCTCCGCCAGCCAGTTTAAGAAGTTTGACGGCCCCTG
CGGCGAGAGAGGCGGAGGAAGAACTGCAAGAGCCCTTTGGGCCAGAGGCGACTCTG
TTCTGACACCAGCTCTGGACCCTCAGACACCTGTTAGGGCCCCTAGCCTGACAAGAG
CTGCCGCTGCTGTTGGAGTGCCTGGCGATTCTACTAGAAGGGCCGTGCGGCGGATGA
ACACCTTTTGTGGCGCATCTGCCTGCGACGTGTCCCTGATCGCTATGGATAGCGCCT
GCGAGGAAAGAGGCGCAGCCGGATCTCTGATCTCTTGCGAGAGCCTGTACCACCGG
GAAAAGCAGCTCATTGCCATGGACAGCGCCATCTTCGTGCAGGGCAAAGACTGGGG
CGTGAAGAAGTTCATCCGGCGGGACTTTACCATGCCTGCCATTCTGAAGCTGCAGAA
GAATTGTCTTCTAAGCCTGAACAGCAAGATGGCCCTGAATAGCGAGGCCCTGTCTGT
GGTGTCCGAGTATGAGGCTGGAATGACCCTGGGCGAGAAGTTCAGAGTGGGCAACT
GCAAGCACCTGAAGATGACCCGGCCTACCGAGTACAACCAGAAACTGCAAGTGAAC
CAGTTCAGCGAGAGCAAGCGGACCGCTCTGACCCACAACCAGGACTTCAGCATCTA
CCGGCTGTGCTGCAAGAGGGGCTCTCTGTGTCATGCTAGCCAGGCTAGAAGCCCCGC
CTTTCCTAAGCCTGTCAGACCTCTGCCTGCTCCTATCACCAGAATCACCCCTCAGCTC
GGCGGCCAGTCTGATTCATCTCAGCCACTGCTGACCACCGGCAGACCTCAAGGATGG
CAAGACCAGGCTCTGAGACACACACAGCAGGCTAGCCCAGCCTCTTGCGCCACCAT
CACAATACCAATACATTCTGCCGCTCTGGGCGATCACAGCGGAGATCCTGGACCTGC
CTGGGATACTTGTCCTCCTCTGCCCCTAACTACACTGATCCCTAGGGCTCCTCCACCT
TACGGCGATAGCACAGCCAGATCCTGGCCTAGCAGATGTGGCCCTCTGGGCTACGCC
TACAAGGACTTCCTGTGGTGCTTCCCCTTCTCTCTGGTGTTCCTGCAAGAAATCCAGA
TCTGCTGTCACGTGTCCTGCCTGTGCTGTATCTGCTGTAGCACCCGGATCTGTCTGGG

-continued

CTGTCTGCTGGAACTGTTCCTGAGCAGAGCCCTGAGAGCACTGCACGTGCTGTGGAA

CGGATTCCAGCTGCACTGCCAGGGCAACACCACACTGCAACAGCTGGGAGAAGCCT

CTCAGGCCCCAAGCGGTTCTCTGATCCCTCTCAGACTGCCCCTCCTGTGGGAAGTGC

GGGGCAATTCTAAGATGGCTCTCAACAGCCTGAACTCCATCGACGACGCCCAGCTGA

CAAGAATCGCCCCTCCAAGAAGCCACTGTTGCTTTTGGGAAGTGAACGCCCCTTTTG

TGCAGGGTAAAGATTGGGGCCTCAAAAAGTTTATCAGACGGGACTTCGAGGCTTTCC

AGAGAGCAGCTGGCGAAGGCGGACCTGGCAGAGGTGGTGCTAGAAGAGGTGCTAG

AGTGCTGCAGAGCCCATTCTGTAGAGCTGGCGCTGGCGAATGGCTGGGCCACCAATC

TCTTAGATGGGGAATGGAACTGGCCGCTAGCAGGCGGTTTAGCTGGGATCATCATTC

TGCCGGCGGACCTCCAAGAGTGCCAAGCGTTAGAAGCGGAGCAGCCCAGGTCCAGC

CTAAAGATCCACTGCCACTGAGAACACTGGCCGGCTGCCTTGCCAGAACAGCTCATC

TTAGACCTGGCGCCGAAAGCCTGCCTCAACCTCAGCTGCATTGCACAATCGCCAGAG

AACTGCACCAGTTCGCCTTCGACCTGCTGATCAAGAGCCACAAGATGCACTTCTCAC

TGAAAGAGCACCCGCCACCGCCGTGCCCACCGCACGTTGTCGGCTATGGCCACCTGG

ATACAAGCGGCTCCTCTAGCAGTAGCTCCTGGCCTCAGCCTGACAGCTTTGCTGCCC

TGCATAGCTCCCTGAATGAGCTGGGCGAACTGTGGTTCCAGTCCAGCGAACTGTCTC

CTACTGGCGCTCCATGGCCAAGCAGAAGGCCTACTTGGAGAGGCACCACCGTGTCTC

CAAGAACCGCTACAAGCAGCGCCAGAACCTGTTGCGGCACAAAATGGCCCTCCAGC

CAAGAAGCTGCCCTCGGACTTGGAAGCGGACTGCTGAGATTCAGCTGTGGCACAGC

CGCCATCAGA neoGAd20 expression cassette protein

SEQ ID NO: 550

MGQKEQIHTLQKNSERMSKQLTRSSQAVQNLQNGGGSRSSATLPGRRRRRWLRRRRQP

ISVAPAGPPRRPNQKPNPPGGARCVIMRPTWPGTSAFTKRSFAVTERIIDYWAQKEKGSS

SFLRPSCDYWAQKEKISIPRTHLCLVLGVLSGHSGSRLYEAGMTLGGKILFFLFLLLPLSP

FSLIFTEISCCTLSSEENEYLPRPEWQLQVPFRELKNVSVLEGLRQGRLGGPCSCHCPRPS

QARLTPVDVAGPFLCLGDPGLFPPVKSSITGGKSTCSAPGPQSLPSTPFSTYPQWVILITEL

GMECTLGQVGAPSPRREEDGWRGGHSRFKADVPAPQGPCWGGQPGSAPSSAPPEQSLL

DWKFEMSYTVGGPPPHVHARPRHWKTDRDGHSYTSKVNCLLLQDGFHGCVSITGAAG

RRNLSIFLFLMLCKLEFHACKIQNKNCPDFKKFDGPCGERGGGRTARALWARGDSVLTP

ALDPQTPVRAPSLTRAAAAVHYKLIQQPISLFSITDRLHKTFSQLPSVHLCSITFQWGHPPI

FCSTNDICVTANFCISVTFLKPCFLLHEASASQCHLFLQPQVGTPPPHTASARAPSGPPHP

HESCPAGRRPARAAQTCARRQHGLPGCEEAGTARVPSLHLHLHQAALGAGRGRGWGE

ACAQVPPSRGVLRFLDLKVRYLHSQWQHYHRSGEAAGTPLWRPTRNVPFRELKNQRTA

QGAPGIHHAASPVAANLCDPARHAQHTRIPCGAGQVRAGRGPEAGGGVLQPQRPAPEK

PGCPCRRGQPRLHTVKMWRAVAMMVPDRQVHYDFGLGVPGDSTRRAVRRMNTFYEA

GMTLGEKFRVGNCKHLKMTRPNSKMALNSEALSVVSECGASACDVSLIAMDSAFVQG

KDWGVKKFIRRDFYAYKDFLWCFPFSLVFLQEIQICCHVSCLCCICCSTRICLGCLLELFL

SRALRALHVLWNGFQLHCQTEYNQKLQVNQFSESKSLYHREKQLIAMDSAICEERGAA

GSLISCETMPAILKLQKNCLLSLRTALTHNQDFSIYRLCCKRGSLCHASQARSPAFPKPVR

PLPAPITRITPQLGGQSDSSQPLLTTGRPQGWQDQALRHTQQASPASCATITIPIHSAALGD

HSGDPGPAWDTCPPLPLTTLIPRAPPPYGDSTARSWPSRCGPLGGNTTLQQLGEASQAPS

-continued

GSLIPLRLPLLWEVRGQPDSFAALHSSLNELGEIARELHQFAFDLLIKSHFVQGKDWGLK

KFIRRDFWGMELAASRRFSWDHHSAGGPPRVPSVRSGAAQVQPKDPLPLRTLAGCLAR

TAHLRPGAESLPQPQLHCTLWFQSSELSPTGAPWPSRRPTWRGTTVSPRTATSSARTCCG

TKWPSSQEAALGLGSGLLRFSCGTAAIRKMHFSLKEHPPPPCPPEAFQRAAGEGGPGRG

GARRGARVLQSPFCRAGAGEWLGHQSLRHVVGYGHLDTSGSSSSSSWPNSKMALNSLN

SIDDAQLTRIAPPRSHCCFWEVNAP neoGAd20 expression cassette polynucleotide

SEQ ID NO: 551

Ccattgcatacgttgtatccatatcataatatgtacatttatattggctcatgtccaacattaccgccatgttgacattgattattgactagttattaat agtaatcaattacggggtcattagttcatagcccatatatggagttccgcgttacataacttacggtaaatggcccgcctggctgaccgcccaa cgacccccgcccattgacgtcaataatgacgtatgttcccatagtaacgccaatagggactttccattgacgtcaatgggtggagtatttacgg taaactgcccacttggcagtacatcaagtgtatcatatgccaagtacgccccctattgacgtcaatgacggtaaatggcccgcctggcattatg cccagtacatgaccttatgggactttcctacttggcagtacatctacgtattagtcatcgctattaccatggtgatgcggttttggcagtacatcaa tgggcgtggatagcggtttgactcacggggatttccaagtctccaccccattgacgtcaatgggagtttgttttggcaccaaaatcaacggga ctttccaaaatgtcgtaacaactccgccccattgacgcaaatgggcggtaggcgtgtacggtgggaggtctatataagcagagctctccctat cagtgatagagatctccctatcagtgatagagatcgtcgacgagctcgtttagtgaaccgtcagatcgcctggagacgccatccacgctgttt tgacctccatagaagacaccgggaccgatccagcctccgcggccgggaacggtgcattggaacgcggattccccgtgccaagagtgag atcttccgtttatctaggtaccagatatcaGAATTCGGATCCCGCGACTTCGCCGCCATGGGCCAGAAA

GAGCAGATCCACACACTGCAGAAAAACAGCGAGCGGATGAGCAAGCAGCTGACCA

GATCTTCTCAGGCCGTGCAGAACCTGCAGAACGGCGGAGGCTCTAGAAGCTCTGCTA

CACTTCCTGGCAGGCGGCGGAGAAGATGGCTGAGAAGAAGGCGGCAGCCTATCTCT

GTGGCTCCTGCTGGACCTCCTAGACGGCCCAACCAGAAGCCTAATCCTCCTGGCGGA

GCCAGATGCGTGATCATGAGGCCTACATGGCCTGGCACCAGCGCCTTCACCAAGAG

AAGCTTTGCCGTGACCGAGCGGATCATCGACTATTGGGCTCAAAAAGAGAAGGGCA

GCAGCAGCTTCCTGCGGCCTAGCTGTGATTATTGGGCCCAGAAAGAAAAGATCAGC

ATCCCCAGAACACACCTGTGCCTGGTGCTGGGAGTGCTGTCTGGACACTCTGGCAGC

AGACTGTATGAGGCCGGCATGACACTCGGCGGCAAGATCCTGTTCTTCCTGTTCCTG

CTGCTCCCTCTGAGCCCCTTCAGCCTGATCTTCACCGAGATCAGCTGCTGCACCCTGA

GCAGCGAGGAAAACGAGTACCTGCCTAGACCTGAGTGGCAGCTGCAGGTCCCCTTC

AGAGAGCTGAAGAACGTTTCCGTGCTGGAAGGCCTGAGACAGGGCAGACTTGGCGG

CCCTTGTAGCTGTCACTGCCCCAGACCTAGTCAGGCCAGACTGACACCTGTGGATGT

GGCCGGACCTTTCCTGTGTCTGGGAGATCCTGGCCTGTTTCCACCTGTGAAGTCCAG

CATCACAGGCGGCAAGTCCACATGTTCTGCCCCTGGACCTCAGAGCCTGCCTAGCAC

ACCCTTCAGCACATACCCTCAGTGGGTCATCCTGATCACCGAACTCGGCATGGAATG

CACCCTGGGACAAGTGGGAGCCCCATCTCCTAGAAGAGAAGAGGATGGCTGGCGCG

GAGGCCACTCTAGATTCAAAGCTGATGTGCCCGCTCCTCAGGGCCCTTGTTGGGGAG

GACAACCTGGATCTGCCCCATCTTCTGCCCCACCTGAACAGTCCCTGCTGGATTGGA

AGTTCGAGATGAGCTACACCGTCGGCGGACCTCCACCTCATGTTCATGCCAGACCTC

GGCACTGGAAAACCGACAGAGATGGCCACAGCTACACCAGCAAAGTGAACTGCCTC

CTGCTGCAGGATGGCTTCCACGGCTGTGTGTCTATTACTGGCGCCGCTGGCAGACGG

AACCTGAGCATCTTTCTGTTTCTGATGCTGTGCAAGCTCGAGTTCCACGCCTGCAAG

-continued

ATCCAGAACAAGAACTGCCCCGACTTCAAGAAGTTCGACGGCCCTTGCGGAGAAAG

AGGCGGAGGCAGAACAGCTAGAGCCCTTTGGGCTAGAGGCGACAGCGTTCTGACAC

CAGCTCTGGACCCTCAGACACCTGTTAGGGCCCCTAGCCTGACAAGAGCTGCCGCCG

CTGTGCACTACAAGCTGATCCAGCAGCCAATCAGCCTGTTCAGCATCACCGACCGGC

TGCACAAGACATTCAGCCAGCTGCCAAGCGTGCACCTGTGCTCCATCACCTTCCAGT

GGGGACACCCTCCTATCTTTTGCTCCACCAACGACATCTGCGTGACCGCCAACTTCT

GTATCAGCGTGACCTTCCTGAAGCCTTGCTTTCTGCTGCACGAGGCCAGCGCCTCTC

AGTGCCACTTGTTTCTGCAGCCCCAAGTGGGCACACCTCCTCCACATACAGCCTCTG

CTAGAGCACCTAGCGGCCCTCCACATCCTCACGAATCTTGTCCTGCCGGAAGAAGGC

CTGCCAGAGCCGCTCAAACATGTGCCAGACGACAGCACGGACTGCCTGGATGTGAA

GAGGCTGGAACAGCCAGAGTGCCTAGCCTGCACCTCCATCTGCATCAGGCTGCTCTT

GGAGCCGGAAGAGGTAGAGGATGGGGCGAAGCTTGTGCTCAGGTGCCACCTTCTAG

AGGCGTGCTGAGATTCCTGGACCTGAAAGTGCGCTACCTGCACAGCCAGTGGCAGC

ACTATCACAGATCTGGCGAAGCCGCCGGAACACCCCTTTGGAGGCCAACAAGAAAC

GTGCCCTTCCGGGAACTGAAGAACCAGAGAACAGCTCAGGGCGCTCCTGGAATCCA

CCATGCTGCTTCTCCAGTGGCCGCCAACCTGTGTGATCCTGCCAGACATGCCCAGCA

CACCAGGATTCCTTGTGGCGCTGGACAAGTGCGCGCTGGAAGAGGACCTGAAGCAG

GCGGAGGTGTTCTGCAACCTCAAAGACCCGCTCCTGAGAAGCCTGGCTGCCCTTGCA

GAAGAGGACAGCCTAGACTGCACACCGTGAAAATGTGGCGAGCCGTGGCCATGATG

GTGCCCGATAGACAGGTCCACTACGACTTTGGACTGGGCGTGCCAGGCGATAGCACT

CGGAGAGCCGTCAGACGGATGAACACCTTTTACGAAGCCGGGATGACCCTGGGCGA

GAAGTTCAGAGTGGGCAACTGCAAGCACCTGAAGATGACCCGGCCTAACAGCAAGA

TGGCCCTGAATAGCGAGGCCCTGTCTGTGGTGTCTGAATGTGGCGCCTCTGCCTGTG

ACGTGTCCCTGATCGCTATGGACTCCGCCTTTGTGCAGGGCAAAGACTGGGGCGTGA

AGAAGTTCATCCGGCGGGACTTCTACGCCTACAAGGACTTCCTGTGGTGCTTCCCCT

TCTCTCTGGTGTTCCTGCAAGAGATCCAGATCTGCTGTCATGTGTCCTGCCTGTGCTG

CATCTGCTGTAGCACCAGAATCTGCCTGGGCTGTCTGCTGGAACTGTTCCTGAGCAG

AGCCCTGAGAGCACTGCACGTGCTGTGGAACGGATTCCAGCTGCACTGCCAGACCG

AGTACAACCAGAAACTGCAAGTGAACCAGTTCAGCGAGAGCAAGAGCCTGTACCAC

CGGGAAAAGCAGCTCATTGCCATGGACAGCGCCATCTGCGAAGAGAGAGGCGCCGC

AGGATCTCTGATCTCCTGCGAAACAATGCCCGCCATCCTGAAGCTGCAGAAGAATTG

CCTCCTAAGCCTGCGAACCGCTCTGACACACAACCAGGACTTCAGCATCTACAGACT

GTGTTGCAAGCGGGGCTCCCTGTGCCATGCAAGCCAAGCTAGAAGCCCCGCCTTTCC

TAAACCTGTGCGACCTCTGCCAGCTCCAATCACCAGAATTACCCCTCAGCTCGGCGG

CCAGAGCGATTCATCTCAACCTCTGCTGACCACCGGCAGACCTCAAGGCTGGCAAGA

CCAAGCTCTGAGACACACCCAGCAGGCTAGCCCTGCCTCTTGTGCCACCATCACAAT

CCCCATCCACTCTGCCGCTCTGGGCGATCATTCTGGCGATCCTGGACCAGCCTGGGA

CACATGTCCTCCACTGCCACTCACAACACTGATCCCTAGGGCTCCTCCACCTTACGG

CGATTCTACCGCTAGAAGCTGGCCCAGCAGATGTGGACCACTCGGAGGCAACACAA

CCCTCCAGCAACTGGGAGAAGCCTCTCAGGCTCCTAGCGGCTCTCTGATCCCTCTCA

GACTGCCTCTCCTGTGGGAAGTTCGGGGCCAGCCTGATTCTTTTGCCGCACTGCACA

-continued

GCTCCCTGAACGAGCTGGGAGAGATCGCTAGAGAGCTGCACCAGTTCGCCTTCGACC

TGCTGATCAAGAGCCACTTCGTGCAAGGCAAGGATTGGGGCCTCAAAAAGTTTATCC

GCAGAGACTTCTGGGGCATGGAACTGGCCGCCAGCAGAAGATTCAGCTGGGATCAT

CATAGCGCAGGCGGCCCACCTAGAGTGCCATCTGTTAGAAGCGGAGCTGCCCAGGT

GCAGCCTAAAGATCCTCTGCCACTGAGAACACTGGCCGGCTGCCTTGCTAGAACAGC

CCATCTTAGACCTGGCGCCGAGTCTCTGCCTCAGCCACAACTGCACTGTACCCTGTG

GTTCCAGTCCAGCGAGCTGTCTCCTACTGGTGCCCCTTGGCCATCTAGACGCCCTACT

TGGAGAGGCACCACCGTGTCACCAAGAACCGCCACAAGCAGCGCCAGAACCTGTTG

TGGCACAAAGTGGCCCTCCAGCCAAGAAGCCGCTCTCGGACTTGGAAGCGGACTGC

TGAGGTTCTCTTGTGGAACCGCCGCCATTCGGAAGATGCACTTTAGCCTGAAAGAAC

ACCCTCCACCACCTTGTCCTCCAGAGGCTTTCCAAAGAGCTGCTGGCGAAGGCGGAC

CTGGTAGAGGTGGTGCTAGAAGAGGTGCTAGGGTGCTGCAGAGCCCATTCTGTAGA

GCAGGCGCAGGCGAATGGCTGGGCCATCAGAGTCTGAGACATGTCGTCGGCTACGG

CCACCTGGATACAAGCGGAAGCAGCTCTAGCTCCAGCTGGCCTAACTCAAAAATGG

CTCTGAACAGCCTGAACTCCATCGACGACGCCCAGCTGACAAGAATCGCCCCTCCTA

GATCTCACTGCTGCTTTTGGGAAGTGAACGCCCCAAGCCATCACCATCACCACCATT

AGTAAAGGCGCGCCTAGCGGCCGCgatctgctgtgccttctagttgccagccatctgttgtttgcccctcccccgtgcct tccttgaccctggaaggtgccactcccactgtcctttcctaataaaatgaggaaattgcatcgcattgtctgagtaggtgtcattctattctgggg ggtggggtggggcaggacagcaagggggaggattgggaagacaatagcaggcatgctggggatgcggtgggctctatggcc neoMVA expression cassette protein

SEQ ID NO: 552

MGQKEQIHTLQKNSERMSKQLTRSSQAVQNLQNGGGSRSSATLPGRRRRRWLRRRRQP

ISVAPAGPPRRPNQKPNPPGGARCVIMRPTWPGTSAFTGMECTLGQVGAPSPRREEDGW

RGGHSRFKADVPAPQGPCWGGQPGSAPSSAPPEQSLLDDYWAQKEKISIPRTHLCWKFE

MSYTVGGPPPHVHARPRHWKTDRDYWAQKEKGSSSFLRPSCVPFRELKNVSVLEGLRQ

GRLGGPCSCHCPRPSQARLTPVDVAGPFLCLGDPGLFPPVKSSITEISCCTLSSEENEYLPR

PEWQLQYEAGMTLGGKILFFLFLLLPLSPFSLIFLVLGVLSGHSGSRLKRSFAVTERIITGG

KSTCSAPGPQSLPSTPFSTYPQWVILITELDGHSYTSKVNCLLLQDGFHGCVSITGAAGRR

NLSIFLFLMLCKLEFHACQWQHYHRSGEAAGTPLWRPTRNVAMMVPDRQVHYDFGLKI

QNKNCPDVLRFLDLKVRYLHSVPFRELKNQRTAQGAPGIHHAASPVAANLCDPARHAQ

HTRIPCGAGQVRAGRGPEAGGGVLQPQRPAPEKPGCPCRRGQPRLHTVKMWRACHLFL

QPQVGTPPPHTASARAPSGPPHPHESCPAGRRPARAAQTCARRQHGLPGCEEAGTARVP

SLHLHLHQAALGAGRGRGWGEACAQVPPSRGHYKLIQQPISLFSITDRLHKTFSQLPSVH

LCSITFQWGHPPIFCSTNDICVTANFCISVTFLKPCFLLHEASASQFKKFDGPCGERGGGR

TARALWARGDSVLTPALDPQTPVRAPSLTRAAAAVGVPGDSTRRAVRRMNTFCGASAC

DVSLIAMDSACEERGAAGSLISCESLYHREKQLIAMDSAIFVQGKDWGVKKFIRRDFTM

PAILKLQKNCLLSLNSKMALNSEALSVVSEYEAGMTLGEKFRVGNCKHLKMTRPTEYN

QKLQVNQFSESKRTALTHNQDFSIYRLCCKRGSLCHASQARSPAFPKPVRPLPAPITRITP

QLGGQSDSSQPLLTTGRPQGWQDQALRHTQQASPASCATITIPIHSAALGDHSGDPGPA

WDTCPPLPLTTLIPRAPPPYGDSTARSWPSRCGPLGYAYKDFLWCFPFSLVFLQEIQICCH

VSCLCCICCSTRICLGCLLELFLSRALRALHVLWNGFQLHCQGNTTLQQLGEASQAPSGS

-continued

LIPLRLPLLWEVRGNSKMALNSLNSIDDAQLTRIAPPRSHCCFWEVNAPFVQGKDWGLK

KFIRRDFEAFQRAAGEGGPGRGGARRGARVLQSPFCRAGAGEWLGHQSLRWGMELAA

SRRFSWDHHSAGGPPRVPSVRSGAAQVQPKDPLPLRTLAGCLARTAHLRPGAESLPQPQ

LHCTIARELHQFAFDLLIKSHKMHFSLKEHPPPPCPPHVVGYGHLDTSGSSSSSSWPQPDS

FAALHSSLNELGELWFQSSELSPTGAPWPSRRPTWRGTTVSPRTATSSARTCCGTKWPSS

QEAALGLGSGLLRFSCGTAAIR neoMVA expression cassette polynucleotide

SEQ ID NO: 553 gatcactaattccaaacccacccgctttttatagtaagtttttcacccataaataataaatacaataattaatttctcgtaaaagtagaaaatatattc taatttattgcacggtaaggaagtagaatcataaagaacagtgacGGATCCCGCGACTTCGCCGCCATGGGCCA

GAAAGAGCAGATCCACACACTGCAGAAAAACAGCGAGCGGATGAGCAAGCAGCTG

ACCAGATCTTCTCAGGCCGTGCAGAACCTGCAGAACGGCGGAGGCTCTAGAAGCTC

TGCTACACTTCCTGGCAGGCGGCGGAGAAGATGGCTGAGAAGAAGGCGGCAGCCTA

TCTCTGTGGCTCCTGCTGGACCTCCTAGACGGCCCAACCAGAAGCCTAATCCTCCTG

GCGGAGCCAGATGCGTGATCATGAGGCCTACATGGCCTGGCACCAGCGCCTTTACCG

GCATGGAATGTACACTGGGCCAAGTGGGAGCCCCATCTCCTAGAAGAGAAGAGGAT

GGCTGGCGCGGAGGCCACTCTAGATTCAAAGCTGATGTGCCCGCTCCTCAGGGCCCT

TGTTGGGGAGGACAACCTGGATCTGCCCCATCTTCTGCCCCACCTGAACAGAGCCTG

CTGGATGACTATTGGGCTCAAAAAGAGAAGATCAGCATCCCCAGAACACACCTGTG

CTGGAAGTTCGAGATGAGCTACACCGTTGGCGGCCCTCCACCACATGTTCACGCCAG

ACCTAGACACTGGAAAACCGACAGAGATTATTGGGCCCAGAAAGAAAAGGGCAGC

AGCAGCTTCCTGCGGCCTAGCTGTGTGCCCTTCCGGGAACTGAAGAACGTGTCCGTT

CTGGAAGGCCTGAGGCAGGGCAGACTTGGCGGACCTTGTAGCTGCCACTGTCCTAG

ACCAAGCCAGGCCAGACTGACCCCTGTGGATGTGGCTGGCCCATTTCTGTGTCTGGG

CGACCCTGGACTGTTCCCTCCAGTGAAGTCTAGCATCACCGAGATCAGCTGCTGCAC

CCTGAGCAGCGAGGAAAACGAGTACCTGCCTAGACCTGAATGGCAGCTGCAGTACG

AGGCCGGCATGACACTCGGAGGCAAGATCCTGTTCTTCCTGTTCCTGCTGCTCCCTCT

GAGCCCCTTCAGCCTGATCTTTCTGGTGCTGGGCGTGCTGTCTGGCCACTCTGGAAG

CAGACTGAAGAGAAGCTTCGCCGTGACCGAGCGGATCATCACAGGCGGCAAGAGCA

CATGTTCTGCCCCTGGACCTCAGTCTCTGCCCAGCACACCCTTCAGCACATACCCTCA

GTGGGTCATCCTGATCACCGAGCTGGATGGCCACAGCTACACCAGCAAAGTGAACT

GCCTCCTGCTGCAGGATGGCTTCCACGGCTGTGTGTCTATTACTGGCGCCGCTGGCA

GACGGAACCTGAGCATCTTTCTGTTTCTGATGCTGTGCAAGCTCGAGTTCCACGCCT

GCCAATGGCAGCACTACCACAGATCTGGCGAAGCCGCTGGAACCCCACTTTGGAGG

CCTACCAGAAACGTGGCCATGATGGTGCCCGACAGACAGGTGCACTACGACTTCGG

CCTGAAGATCCAGAACAAGAACTGCCCCGACGTGCTGCGGTTCCTGGATCTCAAAGT

GCGCTACCTGCACAGCGTGCCCTTCAGAGAGCTGAAAAACCAGAGAACAGCCCAGG

GCGCTCCTGGAATCCATCATGCTGCTTCTCCAGTGGCCGCCAATCTGTGCGATCCTGC

CAGACATGCCCAGCATACCAGGATTCCTTGTGGCGCTGGACAAGTGCGCGCTGGAA

GAGGACCTGAAGCTGGTGGCGGAGTTCTGCAGCCTCAAAGACCTGCTCCTGAGAAG

CCTGGCTGCCCCTGTAGAAGAGGACAGCCTAGACTGCACACCGTGAAGATGTGGCG

GGCCTGCCACTTGTTTCTCCAGCCACAAGTGGGCACCCCTCCACCTCATACAGCCTCT

-continued

GCTAGAGCACCTAGCGGCCCACCTCATCCTCACGAATCTTGTCCTGCCGGAAGAAGG

CCTGCCAGAGCCGCTCAAACATGTGCCAGACGACAGCACGGACTGCCCGGATGTGA

AGAAGCCGGAACAGCCAGAGTGCCTAGCCTGCACCTTCATCTGCATCAGGCCGCTCT

TGGAGCCGGAAGAGGTAGAGGATGGGGAGAAGCTTGTGCCCAGGTGCCACCTTCTA

GAGGCCACTACAAGCTGATCCAGCAGCCAATCAGCCTGTTCTCCATCACCGACCGGC

TGCACAAGACATTCAGCCAGCTGCCTTCCGTGCATCTGTGCAGCATCACCTTCCAGT

GGGGACACCCTCCTATCTTTTGCTCCACCAACGACATCTGCGTGACCGCCAACTTCT

GTATCAGCGTGACCTTCCTGAAGCCTTGCTTTCTGCTGCACGAGGCCTCCGCCAGCC

AGTTTAAGAAGTTTGACGGCCCCTGCGGCGAGAGAGGCGGAGGAAGAACTGCAAGA

GCCCTTTGGGCCAGAGGCGACTCTGTTCTGACACCAGCTCTGGACCCTCAGACACCT

GTTAGGGCCCCTAGCCTGACAAGAGCTGCCGCTGCTGTTGGAGTGCCTGGCGATTCT

ACTAGAAGGGCCGTGCGGCGGATGAACACCTTTTGTGGCGCATCTGCCTGCGACGTG

TCCCTGATCGCTATGGATAGCGCCTGCGAGGAAAGAGGCGCAGCCGGATCTCTGATC

TCTTGCGAGAGCCTGTACCACCGGGAAAAGCAGCTCATTGCCATGGACAGCGCCATC

TTCGTGCAGGGCAAAGACTGGGGCGTGAAGAAGTTCATCCGGCGGGACTTTACCAT

GCCTGCCATTCTGAAGCTGCAGAAGAATTGTCTTCTAAGCCTGAACAGCAAGATGGC

CCTGAATAGCGAGGCCCTGTCTGTGGTGTCCGAGTATGAGGCTGGAATGACCCTGGG

CGAGAAGTTCAGAGTGGGCAACTGCAAGCACCTGAAGATGACCCGGCCTACCGAGT

ACAACCAGAAACTGCAAGTGAACCAGTTCAGCGAGAGCAAGCGGACCGCTCTGACC

CACAACCAGGACTTCAGCATCTACCGGCTGTGCTGCAAGAGGGGCTCTCTGTGTCAT

GCTAGCCAGGCTAGAAGCCCCGCCTTTCCTAAGCCTGTCAGACCTCTGCCTGCTCCT

ATCACCAGAATCACCCCTCAGCTCGGCGGCCAGTCTGATTCATCTCAGCCACTGCTG

ACCACCGGCAGACCTCAAGGATGGCAAGACCAGGCTCTGAGACACACACAGCAGGC

TAGCCCAGCCTCTTGCGCCACCATCACAATACCAATACATTCTGCCGCTCTGGGCGA

TCACAGCGGAGATCCTGGACCTGCCTGGGATACTTGTCCTCCTCTGCCCCTAACTAC

ACTGATCCCTAGGGCTCCTCCACCTTACGGCGATAGCACAGCCAGATCCTGGCCTAG

CAGATGTGGCCCTCTGGGCTACGCCTACAAGGACTTCCTGTGGTGCTTCCCCTTCTCT

CTGGTGTTCCTGCAAGAAATCCAGATCTGCTGTCACGTGTCCTGCCTGTGCTGTATCT

GCTGTAGCACCCGGATCTGTCTGGGCTGTCTGCTGGAACTGTTCCTGAGCAGAGCCC

TGAGAGCACTGCACGTGCTGTGGAACGGATTCCAGCTGCACTGCCAGGGCAACACC

ACACTGCAACAGCTGGGAGAAGCCTCTCAGGCCCCAAGCGGTTCTCTGATCCCTCTC

AGACTGCCCCTCCTGTGGGAAGTGCGGGGCAATTCTAAGATGGCTCTCAACAGCCTG

AACTCCATCGACGACGCCCAGCTGACAAGAATCGCCCCTCCAAGAAGCCACTGTTGC

TTTTGGGAAGTGAACGCCCCTTTTGTGCAGGGTAAAGATTGGGGCCTCAAAAAGTTT

ATCAGACGGGACTTCGAGGCTTTCCAGAGAGCAGCTGGCGAAGGCGGACCTGGCAG

AGGTGGTGCTAGAAGAGGTGCTAGAGTGCTGCAGAGCCCATTCTGTAGAGCTGGCG

CTGGCGAATGGCTGGGCCACCAATCTCTTAGATGGGGAATGGAACTGGCCGCTAGC

AGGCGGTTTAGCTGGGATCATCATTCTGCCGGCGGACCTCCAAGAGTGCCAAGCGTT

AGAAGCGGAGCAGCCCAGGTCCAGCCTAAAGATCCACTGCCACTGAGAACACTGGC

CGGCTGCCTTGCCAGAACAGCTCATCTTAGACCTGGCGCCGAAAGCCTGCCTCAACC

-continued

TCAGCTGCATTGCACAATCGCCAGAGAACTGCACCAGTTCGCCTTCGACCTGCTGAT

CAAGAGCCACAAGATGCACTTCTCACTGAAAGAGCACCCGCCACCGCCGTGCCCAC

CGCACGTTGTCGGCTATGGCCACCTGGATACAAGCGGCTCCTCTAGCAGTAGCTCCT

GGCCTCAGCCTGACAGCTTTGCTGCCCTGCATAGCTCCCTGAATGAGCTGGGCGAAC

TGTGGTTCCAGTCCAGCGAACTGTCTCCTACTGGCGCTCCATGGCCAAGCAGAAGGC

CTACTTGGAGAGGCACCACCGTGTCTCCAAGAACCGCTACAAGCAGCGCCAGAACC

TGTTGCGGCACAAAATGGCCCTCCAGCCAAGAAGCTGCCCTCGGACTTGGAAGCGG

ACTGCTGAGATTCAGCTGTGGCACAGCCGCCATCAGAAGCCATCACCATCACCACCA

TTAGTAAAGGCGCGCC

The amino acid sequence of additional five neoantigen layouts for GAd20 expression are shown in SEQ ID NOs: 554, 555, 556, 623 and 624.

SEQ ID NO: 554

MGQKEQIHTLQKNSERMSKQLTRSSQAVQNLQNGGGSRSSATLPGRRRRRWLRRRRQP

ISVAPAGPPRRPNQKPNPPGGARCVIMRPTWPGTSAFTKRSFAVTERIILVLGVLSGHSGS

RLYEAGMTLGGKILFFLFLLLPLSPFSLIFTEISCCTLSSEENEYLPRPEWQLQVPFRELKN

VSVLEGLRQGRLGGPCSCHCPRPSQARLTPVDVAGPFLCLGDPGLFPPVKSSITGGKSTC

SAPGPQSLPSTPFSTYPQWVILITELGMECTLGQVGAPSPRREEDGWRGGHSRFKADVPA

PQGPCWGGQPGSAPSSAPPEQSLLDDYWAQKEKGSSSFLRPSCDYWAQKEKISIPRTHLC

WKFEMSYTVGGPPPHVHARPRHWKTDRGVPGDSTRRAVRRMNTFYEAGMTLGEKFRV

GNCKHLKMTRPNSKMALNSEALSVVSECGASACDVSLIAMDSAFVQGKDWGVKKFIRR

DFYAYKDFLWCFPFSLVFLQEIQICCHVSCLCCICCSTRICLGCLLELFLSRALRALHVLW

NGFQLHCQTEYNQKLQVNQFSESKSLYHREKQLIAMDSAICEERGAAGSLISCETMPAIL

KLQKNCLLSLRTALTHNQDFSIYRLCCKRGSLCHASQARSPAFPKPVRPLPAPITRITPQL

GGQSDSSQPLLTTGRPQGWQDQALRHTQQASPASCATITIPIHSAALGDHSGDPGPAWD

TCPPLPLTTLIPRAPPPYGDSTARSWPSRCGPLGDGHSYTSKVNCLLLQDGFHGCVSITGA

AGRRNLSIFLFLMLCKLEFHACKIQNKNCPDFKKFDGPCGERGGGRTARALWARGDSVL

TPALDPQTPVRAPSLTRAAAAVHYKLIQQPISLFSITDRLHKTFSQLPSVHLCSITFQWGH

PPIFCSTNDICVTANFCISVTFLKPCFLLHEASASQCHLFLQPQVGTPPPHTASARAPSGPP

HPHESCPAGRRPARAAQTCARRQHGLPGCEEAGTARVPSLHLHLHQAALGAGRGRGW

GEACAQVPPSRGVLRFLDLKVRYLHSQWQHYHRSGEAAGTPLWRPTRNVPFRELKNQR

TAQGAPGIHHAASPVAANLCDPARHAQHTRIPCGAGQVRAGRGPEAGGGVLQPQRPAP

EKPGCPCRRGQPRLHTVKMWRAVAMMVPDRQVHYDFGLGNTTLQQLGEASQAPSGSL

IPLRLPLLWEVRGQPDSFAALHSSLNELGEIARELHQFAFDLLIKSHFVQGKDWGLKKFIR

RDFWGMELAASRRFSWDHHSAGGPPRVPSVRSGAAQVQPKDPLPLRTLAGCLARTAHL

RPGAESLPQPQLHCTLWFQSSELSPTGAPWPSRRPTWRGTTVSPRTATSSARTCCGTKWP

SSQEAALGLGSGLLRFSCGTAAIRKMHFSLKEHPPPPCPPEAFQRAAGEGGPGRGGARRG

ARVLQSPFCRAGAGEWLGHQSLRHVVGYGHLDTSGSSSSSSWPNSKMALNSLNSIDDA

QLTRIAPPRSHCCFWEVNAP

-continued

SEQ ID NO: 555

MGQKEQIHTLQKNSERMSKQLTRSSQAVQNLQNGGGSRSSATLPGRRRRRWLRRRRQP
ISVAPAGPPRRPNQKPNPPGGARCVIMRPTWPGTSAFTKRSFAVTERIITEISCCTLSSEEN
EYLPRPEWQLQYEAGMTLGGKILFFLFLLLPLSPFSLIFDYWAQKEKGSSSFLRPSCVPFR
ELKNVSVLEGLRQGRLGGPCSCHCPRPSQARLTPVDVAGPFLCLGDPGLFPPVKSSITGG
KSTCSAPGPQSLPSTPFSTYPQWVILITELGMECTLGQVGAPSPRREEDGWRGGHSRFKA
DVPAPQGPCWGGQPGSAPSSAPPEQSLLDDYWAQKEKISIPRTHLCLVLGVLSGHSGSRL
WKFEMSYTVGGPPPHVHARPRHWKTDRDGHSYTSKVNCLLLQDGFHGCVSITGAAGR
RNLSIFLFLMLCKLEFHACKIQNKNCPDFKKFDGPCGERGGGRTARALWARGDSVLTPA
LDPQTPVRAPSLTRAAAAVHYKLIQQPISLFSITDRLHKTFSQLPSVHLCSITFQWGHPPIF
CSTNDICVTANFCISVTFLKPCFLLHEASASQCHLFLQPQVGTPPPHTASARAPSGPPHPH
ESCPAGRRPARAAQTCARRQHGLPGCEEAGTARVPSLHLHLHQAALGAGRGRGWGEA
CAQVPPSRGVLRFLDLKVRYLHSQWQHYHRSGEAAGTPLWRPTRNVPFRELKNQRTAQ
GAPGIHHAASPVAANLCDPARHAQHTRIPCGAGQVRAGRGPEAGGGVLQPQRPAPEKP
GCPCRRGQPRLHTVKMWRAVAMMVPDRQVHYDFGLGVPGDSTRRAVRRMNTFYEAG
MTLGEKFRVGNCKHLKMTRPNSKMALNSEALSVVSECGASACDVSLIAMDSAFVQGK
DWGVKKFIRRDFYAYKDFLWCFPFSLVFLQEIQICCHVSCLCCICCSTRICLGCLLELFLS
RALRALHVLWNGFQLHCQTEYNQKLQVNQFSESKSLYHREKQLIAMDSAICEERGAAG
SLISCETMPAILKLQKNCLLSLRTALTHNQDFSIYRLCCKRGSLCHASQARSPAFPKPVRP
LPAPITRITPQLGGQSDSSQPLLTTGRPQGWQDQALRHTQQASPASCATITIPIHSAALGD
HSGDPGPAWDTCPPLPLTTLIPRAPPPYGDSTARSWPSRCGPLGGNTTLQQLGEASQAPS
GSLIPLRLPLLWEVRGQPDSFAALHSSLNELGEIARELHQFAFDLLIKSHFVQGKDWGLK
KFIRRDFWGMELAASRRFSWDHHSAGGPPRVPSVRSGAAQVQPKDPLPLRTLAGCLAR
TAHLRPGAESLPQPQLHCTLWFQSSELSPTGAPWPSRRPTWRGTTVSPRTATSSARTCCG
TKWPSSQEAALGLGSGLLRFSCGTAAIRKMHFSLKEHPPPPCPPEAFQRAAGEGGPGRG
GARRGARVLQSPFCRAGAGEWLGHQSLRHVVGYGHLDTSGSSSSSSWPNSKMALNSLN
SIDDAQLTRIAPPRSHCCFWEVNAP

SEQ ID NO: 556

MGQKEQIHTLQKNSERMSKQLTRSSQAVQNLQNGGGSRSSATLPGRRRRRWLRRRRQP
ISVAPAGPPRRPNQKPNPPGGARCVIMRPTWPGTSAFTKRSFAVTERIIDYWAQKEKGSS
SFLRPSCVPFRELKNVSVLEGLRQGRLGGPCSCHCPRPSQARLTPVDVAGPFLCLGDPGL
FPPVKSSILVLGVLSGHSGSRLYEAGMTLGGKILFFLFLLLPLSPFSLIFTEISCCTLSSEENE
YLPRPEWQLQTGGKSTCSAPGPQSLPSTPFSTYPQWVILITELGMECTLGQVGAPSPRREE
DGWRGGHSRFKADVPAPQGPCWGGQPGSAPSSAPPEQSLLDDYWAQKEKISIPRTHLC
WKFEMSYTVGGPPPHVHARPRHWKTDRDGHSYTSKVNCLLLQDGFHGCVSITGAAGR
RNLSIFLFLMLCKLEFHACKIQNKNCPDFKKFDGPCGERGGGRTARALWARGDSVLTPA
LDPQTPVRAPSLTRAAAAVHYKLIQQPISLFSITDRLHKTFSQLPSVHLCSITFQWGHPPIF
CSTNDICVTANFCISVTFLKPCFLLHEASASQCHLFLQPQVGTPPPHTASARAPSGPPHPH
ESCPAGRRPARAAQTCARRQHGLPGCEEAGTARVPSLHLHLHQAALGAGRGRGWGEA
CAQVPPSRGVLRFLDLKVRYLHSQWQHYHRSGEAAGTPLWRPTRNVPFRELKNQRTAQ
GAPGIHHAASPVAANLCDPARHAQHTRIPCGAGQVRAGRGPEAGGGVLQPQRPAPEKP

-continued

GCPCRRGQPRLHTVKMWRAVAMMVPDRQVHYDFGLGVPGDSTRRAVRRMNTFYEAG

MTLGEKFRVGNCKHLKMTRPNSKMALNSEALSVVSECGASACDVSLIAMDSAFVQGK

DWGVKKFIRRDFYAYKDFLWCFPFSLVFLQEIQICCHVSCLCCICCSTRICLGCLLELFLS

RALRALHVLWNGFQLHCQTEYNQKLQVNQFSESKSLYHREKQLIAMDSAICEERGAAG

SLISCETMPAILKLQKNCLLSLRTALTHNQDFSIYRLCCKRGSLCHASQARSPAFPKPVRP

LPAPITRITPQLGGQSDSSQPLLTTGRPQGWQDQALRHTQQASPASCATITIPIHSAALGD

HSGDPGPAWDTCPPLPLTTLIPRAPPPYGDSTARSWPSRCGPLGGNTTLQQLGEASQAPS

GSLIPLRLPLLWEVRGQPDSFAALHSSLNELGEIARELHQFAFDLLIKSHFVQGKDWGLK

KFIRRDFWGMELAASRRFSWDHHSAGGPPRVPSVRSGAAQVQPKDPLPLRTLAGCLAR

TAHLRPGAESLPQPQLHCTLWFQSSELSPTGAPWPSRRPTWRGTTVSPRTATSSARTCCG

TKWPSSQEAALGLGSGLLRFSCGTAAIRKMHFSLKEHPPPPCPPEAFQRAAGEGGPGRG

GARRGARVLQSPFCRAGAGEWLGHQSLRHVVGYGHLDTSGSSSSSSWPNSKMALNSLN

SIDDAQLTRIAPPRSHCCFWEVNAP

SEQ ID NO: 623

MGQKEQIHTLQKNSERMSKQLTRSSQAVGVPGDSTRRAVRRMNTFYEAGMTLGEKFR

VGNCKHLKMTRPNSKMALNSEALSVVSECGASACDVSLIAMDSAFVQGKDWGVKKFI

RRDFYAYKDFLWCFPFSLVFLQEIQICCHVSCLCCICCSTRICLGCLLELFLSRALRALHV

LWNGFQLHCQTEYNQKLQVNQFSESKSLYHREKQLIAMDSAICEERGAAGSLISCETMP

AILKLQKNCLLSLRTALTHNQDFSIYRLCCKRGSLCHASQARSPAFPKPVRPLPAPITRITP

QLGGQSDSSQPLLTTGRPQGWQDQALRHTQQASPASCATITIPIHSAALGDHSGDPGPA

WDTCPPLPLTTLIPRAPPPYGDSTARSWPSRCGPLGGNTTLQQLGEASQAPSGSLIPLRLP

LLWEVRGQPDSFAALHSSLNELGEIARELHQFAFDLLIKSHFVQGKDWGLKKFIRRDFW

GMELAASRRFSWDHHSAGGPPRVPSVRSGAAQVQPKDPLPLRTLAGCLARTAHLRPGA

ESLPQPQLHCTLWFQSSELSPTGAPWPSRRPTWRGTTVSPRTATSSARTCCGTKWPSSQE

AALGLGSGLLRFSCGTAAIRKMHFSLKEHPPPPCPPEAFQRAAGEGGPGRGGARRGARV

LQSPFCRAGAGEWLGHQSLRHVVGYGHLDTSGSSSSSSWPNSKMALNSLNSIDDAQLTR

IAPPRSHCCFWEVNAPDGHSYTSKVNCLLLQDGFHGCVSITGAAGRRNLSIFLFLMLCKL

EFHACKIQNKNCPDFKKFDGPCGERGGGRTARALWARGDSVLTPALDPQTPVRAPSLTR

AAAAVHYKLIQQPISLFSITDRLHKTFSQLPSVHLCSITFQWGHPPIFCSTNDICVTANFCIS

VTFLKPCFLLHEASASQCHLFLQPQVGTPPPHTASARAPSGPPHPHESCPAGRRPARAAQ

TCARRQHGLPGCEEAGTARVPSLHLHLHQAALGAGRGRGWGEACAQVPPSRGVLRFLD

LKVRYLHSQWQHYHRSGEAAGTPLWRPTRNVPFRELKNQRTAQGAPGIHHAASPVAA

NLCDPARHAQHTRIPCGAGQVRAGRGPEAGGGVLQPQRPAPEKPGCPCRRGQPRLHTV

KMWRAVAMMVPDRQVHYDFGLQNLQNGGGSRSSATLPGRRRRRWLRRRRQPISVAPA

GPPRRPNQKPNPPGGARCVIMRPTWPGTSAFTKRSFAVTERIILVLGVLSGHSGSRLYEA

GMTLGGKILFFLFLLLPLSPFSLIFTEISCCTLSSEENEYLPRPEWQLQVPFRELKNVSVLE

GLRQGRLGGPCSCHCPRPSQARLTPVDVAGPFLCLGDPGLFPPVKSSITGGKSTCSAPGP

QSLPSTPFSTYPQWVILITELGMECTLGQVGAPSPRREEDGWRGGHSRFKADVPAPQGPC

WGGQPGSAPSSAPPEQSLLDDYWAQKEKGSSSFLRPSCDYWAQKEKISIPRTHLCWKFE

MSYTVGGPPPHVHARPRHWKTDR

-continued

SEQ ID NO: 624

MGQKEQIHTLQKNSERMSKQLTRSSQAVGNTTLQQLGEASQAPSGSLIPLRLPLLWEVR
GQPDSFAALHSSLNELGEIARELHQFAFDLLIKSHFVQGKDWGLKKFIRRDFWGMELAA
SRRFSWDHHSAGGPPRVPSVRSGAAQVQPKDPLPLRTLAGCLARTAHLRPGAESLPQPQ
LHCTLWFQSSELSPTGAPWPSRRPTWRGTTVSPRTATSSARTCCGTKWPSSQEAALGLG
SGLLRFSCGTAAIRKMHFSLKEHPPPPCPPEAFQRAAGEGGPGRGGARRGARVLQSPFCR
AGAGEWLGHQSLRHVVGYGHLDTSGSSSSSSWPNSKMALNSLNSIDDAQLTRIAPPRSH
CCFWEVNAPGVPGDSTRRAVRRMNTFYEAGMTLGEKFRVGNCKHLKMTRPNSKMAL
NSEALSVVSECGASACDVSLIAMDSAFVQGKDWGVKKFIRRDFYAYKDFLWCFPFSLVF
LQEIQICCHVSCLCCICCSTRICLGCLLELFLSRALRALHVLWNGFQLHCQTEYNQKLQV
NQFSESKSLYHREKQLIAMDSAICEERGAAGSLISCETMPAILKLQKNCLLSLRTALTHN
QDFSIYRLCCKRGSLCHASQARSPAFPKPVRPLPAPITRITPQLGGQSDSSQPLLTTGRPQG
WQDQALRHTQQASPASCATITIPIHSAALGDHSGDPGPAWDTCPPLPLTTLIPRAPPPYGD
STARSWPSRCGPLGDGHSYTSKVNCLLLQDGFHGCVSITGAAGRRNLSIFLFLMLCKLEF
HACKIQNKNCPDFKKFDGPCGERGGGRTARALWARGDSVLTPALDPQTPVRAPSLTRA
AAAVHYKLIQQPISLFSITDRLHKTFSQLPSVHLCSITFQWGHPPIFCSTNDICVTANFCISV
TFLKPCFLLHEASASQCHLFLQPQVGTPPPHTASARAPSGPPHPHESCPAGRRPARAAQT
CARRQHGLPGCEEAGTARVPSLHLHLHQAALGAGRGRGWGEACAQVPPSRGVLRFLDL
KVRYLHSQWQHYHRSGEAAGTPLWRPTRNVPFRELKNQRTAQGAPGIHHAASPVAAN
LCDPARHAQHTRIPCGAGQVRAGRGPEAGGGVLQPQRPAPEKPGCPCRRGQPRLHTVK
MWRAVAMMVPDRQVHYDFGLQNLQNGGGSRSSATLPGRRRRRWLRRRRQPISVAPAG
PPRRPNQKPNPPGGARCVIMRPTWPGTSAFTKRSFAVTERIITEISCCTLSSEENEYLPRPE
WQLQYEAGMTLGGKILFFLFLLLPLSPFSLIFDYWAQKEKGSSSFLRPSCVPFRELKNVSV
LEGLRQGRLGGPCSCHCPRPSQARLTPVDVAGPFLCLGDPGLFPPVKSSITGGKSTCSAP
GPQSLPSTPFSTYPQWVILITELGMECTLGQVGAPSPRREEDGWRGGHSRFKADVPAPQG
PCWGGQPGSAPSSAPPEQSLLDDYWAQKEKISIPRTHLCLVLGVLSGHSGSRLWKFEMS
YTVGGPPPHVHARPRHWKTDR

The amino acid sequence of additional five neoantigen layouts for MVA expression are shown in SEQ ID NOs: 557, 558, 559, 625 and 626.

SEQ ID NO: 557

MGQKEQIHTLQKNSERMSKQLTRSSQAVQNLQNGGGSRSSATLPGRRRRRWLRRRRQP
ISVAPAGPPRRPNQKPNPPGGARCVIMRPTWPGTSAFTGMECTLGQVGAPSPRREEDGW
RGGHSRFKADVPAPQGPCWGGQPGSAPSSAPPEQSLLDDYWAQKEKISIPRTHLCWKFE
MSYTVGGPPPHVHARPRHWKTDRDYWAQKEKGSSSFLRPSCVPFRELKNVSVLEGLRQ
GRLGGPCSCHCPRPSQARLTPVDVAGPFLCLGDPGLFPPVKSSITEISCCTLSSEENEYLPR
PEWQLQYEAGMTLGGKILFFLFLLLPLSPFSLIFLVLGVLSGHSGSRLKRSFAVTERIITGG
KSTCSAPGPQSLPSTPFSTYPQWVILITELDGHSYTSKVNCLLLQDGFHGCVSITGAAGRR
NLSIFLFLMLCKLEFHACCHLFLQPQVGTPPPHTASARAPSGPPHPHESCPAGRRPARAA
QTCARRQHGLPGCEEAGTARVPSLHLHLHQAALGAGRGRGWGEACAQVPPSRGHYKLI
QQPISLFSITDRLHKTFSQLPSVHLCSITFQWGHPPIFCSTNDICVTANFCISVTFLKPCFLL

-continued

HEASASQVAMMVPDRQVHYDFGLKIQNKNCPDVLRFLDLKVRYLHSVPFRELKNQRTA
QGAPGIHHAASPVAANLCDPARHAQHTRIPCGAGQVRAGRGPEAGGGVLQPQRPAPEK
PGCPCRRGQPRLHTVKMWRAQWQHYHRSGEAAGTPLWRPTRNFKKFDGPCGERGGGR
TARALWARGDSVLTPALDPQTPVRAPSLTRAAAAVGVPGDSTRRAVRRMNTFCGASAC
DVSLIAMDSACEERGAAGSLISCESLYHREKQLIAMDSAIFVQGKDWGVKKFIRRDFTM
PAILKLQKNCLLSLNSKMALNSEALSVVSEYEAGMTLGEKFRVGNCKHLKMTRPTEYN
QKLQVNQFSESKRTALTHNQDFSIYRLCCKRGSLCHASQARSPAFPKPVRPLPAPITRITP
QLGGQSDSSQPLLTTGRPQGWQDQALRHTQQASPASCATITIPIHSAALGDHSGDPGPA
WDTCPPLPLTTLIPRAPPPYGDSTARSWPSRCGPLGYAYKDFLWCFPFSLVFLQEIQICCH
VSCLCCICCSTRICLGCLLELFLSRALRALHVLWNGFQLHCQGNTTLQQLGEASQAPSGS
LIPLRLPLLWEVRGNSKMALNSLNSIDDAQLTRIAPPRSHCCFWEVNAPFVQGKDWGLK
KFIRRDFEAFQRAAGEGGPGRGGARRGARVLQSPFCRAGAGEWLGHQSLRWGMELAA
SRRFSWDHHSAGGPPRVPSVRSGAAQVQPKDPLPLRTLAGCLARTAHLRPGAESLPQPQ
LHCTIARELHQFAFDLLIKSHKMHFSLKEHPPPPCPPHVVGYGHLDTSGSSSSSSWPQPDS
FAALHSSLNELGELWFQSSELSPTGAPWPSRRPTWRGTTVSPRTATSSARTCCGTKWPSS
QEAALGLGSGLLRFSCGTAAIR

SEQ ID NO: 558

MGQKEQIHTLQKNSERMSKQLTRSSQAVDGHSYTSKVNCLLLQDGFHGCVSITGAAGR
RNLSIFLFLMLCKLEFHACQWQHYHRSGEAAGTPLWRPTRNVAMMVPDRQVHYDFGL
VLRFLDLKVRYLHSKIQNKNCPDVPFRELKNQRTAQGAPGIHHAASPVAANLCDPARHA
QHTRIPCGAGQVRAGRGPEAGGGVLQPQRPAPEKPGCPCRRGQPRLHTVKMWRACHLF
LQPQVGTPPPHTASARAPSGPPHPHESCPAGRRPARAAQTCARRQHGLPGCEEAGTARV
PSLHLHLHQAALGAGRGRGWGEACAQVPPSRGHYKLIQQPISLFSITDRLHKTFSQLPSV
HLCSITFQWGHPPIFCSTNDICVTANFCISVTFLKPCFLLHEASASQFKKFDGPCGERGGG
RTARALWARGDSVLTPALDPQTPVRAPSLTRAAAAVQNLQNGGGSRSSATLPGRRRRR
WLRRRRQPISVAPAGPPRRPNQKPNPPGGARCVIMRPTWPGTSAFTGMECTLGQVGAPS
PRREEDGWRGGHSRFKADVPAPQGPCWGGQPGSAPSSAPPEQSLLDDYWAQKEKISIPR
THLCWKFEMSYTVGGPPPHVHARPRHWKTDRDYWAQKEKGSSSFLRPSCVPFRELKNV
SVLEGLRQGRLGGPCSCHCPRPSQARLTPVDVAGPFLCLGDPGLFPPVKSSITEISCCTLSS
EENEYLPRPEWQLQYEAGMTLGGKILFFLFLLLPLSPFSLIFLVLGVLSGHSGSRLKRSFA
VTERIITGGKSTCSAPGPQSLPSTPFSTYPQWVILITELGVPGDSTRRAVRRMNTFCGASA
CDVSLIAMDSACEERGAAGSLISCESLYHREKQLIAMDSAIFVQGKDWGVKKFIRRDFT
MPAILKLQKNCLLSLNSKMALNSEALSVVSEYEAGMTLGEKFRVGNCKHLKMTRPTEY
NQKLQVNQFSESKRTALTHNQDFSIYRLCCKRGSLCHASQARSPAFPKPVRPLPAPITRIT
PQLGGQSDSSQPLLTTGRPQGWQDQALRHTQQASPASCATITIPIHSAALGDHSGDPGPA
WDTCPPLPLTTLIPRAPPPYGDSTARSWPSRCGPLGYAYKDFLWCFPFSLVFLQEIQICCH
VSCLCCICCSTRICLGCLLELFLSRALRALHVLWNGFQLHCQGNTTLQQLGEASQAPSGS
LIPLRLPLLWEVRGNSKMALNSLNSIDDAQLTRIAPPRSHCCFWEVNAPFVQGKDWGLK
KFIRRDFEAFQRAAGEGGPGRGGARRGARVLQSPFCRAGAGEWLGHQSLRWGMELAA
SRRFSWDHHSAGGPPRVPSVRSGAAQVQPKDPLPLRTLAGCLARTAHLRPGAESLPQPQ
LHCTIARELHQFAFDLLIKSHKMHFSLKEHPPPPCPPHVVGYGHLDTSGSSSSSSWPQPDS

-continued

FAALHSSLNELGELWFQSSELSPTGAPWPSRRPTWRGTTVSPRTATSSARTCCGTKWPSS
QEAALGLGSGLLRFSCGTAAIR

SEQ ID NO: 559

MGQKEQIHTLQKNSERMSKQLTRSSQAVGNTTLQQLGEASQAPSGSLIPLRLPLLWEVR
GNSKMALNSLNSIDDAQLTRIAPPRSHCCFWEVNAPFVQGKDWGLKKFIRRDFEAFQRA
AGEGGPGRGGARRGARVLQSPFCRAGAGEWLGHQSLRWGMELAASRRFSWDHHSAG
GPPRVPSVRSGAAQVQPKDPLPLRTLAGCLARTAHLRPGAESLPQPQLHCTIARELHQFA
FDLLIKSHKMHFSLKEHPPPPCPPHVVGYGHLDTSGSSSSSSWPQPDSFAALHSSLNELGE
LWFQSSELSPTGAPWPSRRPTWRGTTVSPRTATSSARTCCGTKWPSSQEAALGLGSGLL
RFSCGTAAIRDGHSYTSKVNCLLLQDGFHGCVSITGAAGRRNLSIFLFLMLCKLEFHACQ
WQHYHRSGEAAGTPLWRPTRNVAMMVPDRQVHYDFGLKIQNKNCPDVLRFLDLKVR
YLHSVPFRELKNQRTAQGAPGIHHAASPVAANLCDPARHAQHTRIPCGAGQVRAGRGP
EAGGGVLQPQRPAPEKPGCPCRRGQPRLHTVKMWRACHLFLQPQVGTPPPHTASARAP
SGPPHPHESCPAGRRPARAAQTCARRQHGLPGCEEAGTARVPSLHLHLHQAALGAGRG
RGWGEACAQVPPSRGHYKLIQQPISLFSITDRLHKTFSQLPSVHLCSITFQWGHPPIFCSTN
DICVTANFCISVTFLKPCFLLHEASASQFKKFDGPCGERGGGRTARALWARGDSVLTPAL
DPQTPVRAPSLTRAAAAVGVPGDSTRRAVRRMNTFCGASACDVSLIAMDSATEYNQKL
QVNQFSESKYEAGMTLGEKFRVGNCKHLKMTRPTMPAILKLQKNCLLSLNSKMALNSE
ALSVVSECEERGAAGSLISCESLYHREKQLIAMDSAIFVQGKDWGVKKFIRRDFRTALTH
NQDFSIYRLCCKRGSLCHASQARSPAFPKPVRPLPAPITRITPQLGGQSDSSQPLLTTGRPQ
GWQDQALRHTQQASPASCATITIPIHSAALGDHSGDPGPAWDTCPPLPLTTLIPRAPPPYG
DSTARSWPSRCGPLGYAYKDFLWCFPFSLVFLQEIQICCHVSCLCCICCSTRICLGCLLEL
FLSRALRALHVLWNGFQLHCQQNLQNGGGSRSSATLPGRRRRRWLRRRRQPISVAPAG
PPRRPNQKPNPPGGARCVIMRPTWPGTSAFTGMECTLGQVGAPSPRREEDGWRGGHSRF
KADVPAPQGPCWGGQPGSAPSSAPPEQSLLDDYWAQKEKISIPRTHLCWKFEMSYTVG
GPPPHVHARPRHWKTDRDYWAQKEKGSSSFLRPSCVPFRELKNVSVLEGLRQGRLGGP
CSCHCPRPSQARLTPVDVAGPFLCLGDPGLFPPVKSSITEISCCTLSSEENEYLPRPEWQLQ
YEAGMTLGGKILFFLFLLLPLSPFSLIFLVLGVLSGHSGSRLKRSFAVTERIITGGKSTCSAP
GPQSLPSTPFSTYPQWVILITEL

SEQ ID NO: 625

MGQKEQIHTLQKNSERMSKQLTRSSQAVGNTTLQQLGEASQAPSGSLIPLRLPLLWEVR
GNSKMALNSLNSIDDAQLTRIAPPRSHCCFWEVNAPFVQGKDWGLKKFIRRDFEAFQRA
AGEGGPGRGGARRGARVLQSPFCRAGAGEWLGHQSLRWGMELAASRRFSWDHHSAG
GPPRVPSVRSGAAQVQPKDPLPLRTLAGCLARTAHLRPGAESLPQPQLHCTIARELHQFA
FDLLIKSHKMHFSLKEHPPPPCPPHVVGYGHLDTSGSSSSSSWPQPDSFAALHSSLNELGE
LWFQSSELSPTGAPWPSRRPTWRGTTVSPRTATSSARTCCGTKWPSSQEAALGLGSGLL
RFSCGTAAIRQNLQNGGGSRSSATLPGRRRRRWLRRRRQPISVAPAGPPRRPNQKPNPPG
GARCVIMRPTWPGTSAFTGMECTLGQVGAPSPRREEDGWRGGHSRFKADVPAPQGPC
WGGQPGSAPSSAPPEQSLLDDYWAQKEKISIPRTHLCWKFEMSYTVGGPPPHVHARPRH
WKTDRDYWAQKEKGSSSFLRPSCVPFRELKNVSVLEGLRQGRLGGPCSCHCPRPSQARL
TPVDVAGPFLCLGDPGLFPPVKSSITEISCCTLSSEENEYLPRPEWQLQYEAGMTLGGKIL
FFLFLLLPLSPFSLIFLVLGVLSGHSGSRLKRSFAVTERIITGGKSTCSAPGPQSLPSTPFSTY

-continued

PQWVILITELDGHSYTSKVNCLLLQDGFHGCVSITGAAGRRNLSIFLFLMLCKLEFHACQ
WQHYHRSGEAAGTPLWRPTRNVAMMVPDRQVHYDFGLVLRFLDLKVRYLHSKIQNKN
CPDVPFRELKNQRTAQGAPGIHHAASPVAANLCDPARHAQHTRIPCGAGQVRAGRGPE
AGGGVLQPQRPAPEKPGCPCRRGQPRLHTVKMWRACHLFLQPQVGTPPPHTASARAPS
GPPHPHESCPAGRRPARAAQTCARRQHGLPGCEEAGTARVPSLHLHLHQAALGAGRGR
GWGEACAQVPPSRGHYKLIQQPISLFSITDRLHKTFSQLPSVHLCSITFQWGHPPIFCSTND
ICVTANFCISVTFLKPCFLLHEASASQFKKFDGPCGERGGGRTARALWARGDSVLTPALD
PQTPVRAPSLTRAAAAVGVPGDSTRRAVRRMNTFCGASACDVSLIAMDSACEERGAAG
SLISCESLYHREKQLIAMDSAIFVQGKDWGVKKFIRRDFTMPAILKLQKNCLLSLNSKMA
LNSEALSVVSEYEAGMTLGEKFRVGNCKHLKMTRPTEYNQKLQVNQFSESKRTALTHN
QDFSIYRLCCKRGSLCHASQARSPAFPKPVRPLPAPITRITPQLGGQSDSSQPLLTTGRPQG
WQDQALRHTQQASPASCATITIPIHSAALGDHSGDPGPAWDTCPPLPLTTLIPRAPPPYGD
STARSWPSRCGPLGYAYKDFLWCFPFSLVFLQEIQICCHVSCLCCICCSTRICLGCLLELFL
SRALRALHVLWNGFQLHCQ

SEQ ID NO: 626

MGQKEQIHTLQKNSERMSKQLTRSSQAVDGHSYTSKVNCLLLQDGFHGCVSITGAAGR
RNLSIFLFLMLCKLEFHACVPFRELKNQRTAQGAPGIHHAASPVAANLCDPARHAQHTRI
PCGAGQVRAGRGPEAGGGVLQPQRPAPEKPGCPCRRGQPRLHTVKMWRAQWQHYHR
SGEAAGTPLWRPTRNKIQNKNCPDVAMMVPDRQVHYDFGLVLRFLDLKVRYLHSCHLF
LQPQVGTPPPHTASARAPSGPPHPHESCPAGRRPARAAQTCARRQHGLPGCEEAGTARV
PSLHLHLHQAALGAGRGRGWGEACAQVPPSRGHYKLIQQPISLFSITDRLHKTFSQLPSV
HLCSITFQWGHPPIFCSTNDICVTANFCISVTFLKPCFLLHEASASQFKKFDGPCGERGGG
RTARALWARGDSVLTPALDPQTPVRAPSLTRAAAAVQNLQNGGGSRSSATLPGRRRRR
WLRRRRQPISVAPAGPPRRPNQKPNPPGGARCVIMRPTWPGTSAFTGMECTLGQVGAPS
PRREEDGWRGGHSRFKADVPAPQGPCWGGQPGSAPSSAPPEQSLLDDYWAQKEKISIPR
THLCWKFEMSYTVGGPPPHVHARPRHWKTDRDYWAQKEKGSSSFLRPSCVPFRELKNV
SVLEGLRQGRLGGPCSCHCPRPSQARLTPVDVAGPFLCLGDPGLFPPVKSSITEISCCTLSS
EENEYLPRPEWQLQYEAGMTLGGKILFFLFLLLPLSPFSLIFLVLGVLSGHSGSRLKRSFA
VTERIITGGKSTCSAPGPQSLPSTPFSTYPQWVILITELGNTTLQQLGEASQAPSGSLIPLRL
PLLWEVRGNSKMALNSLNSIDDAQLTRIAPPRSHCCFWEVNAPFVQGKDWGLKKFIRRD
FEAFQRAAGEGGPGRGGARRGARVLQSPFCRAGAGEWLGHQSLRWGMELAASRRFSW
DHHSAGGPPRVPSVRSGAAQVQPKDPLPLRTLAGCLARTAHLRPGAESLPQPQLHCTIA
RELHQFAFDLLIKSHKMHFSLKEHPPPPCPPHVVGYGHLDTSGSSSSSSWPQPDSFAALH
SSLNELGELWFQSSELSPTGAPWPSRRPTWRGTTVSPRTATSSARTCCGTKWPSSQEAAL
GLGSGLLRFSCGTAAIRGVPGDSTRRAVRRMNTFCGASACDVSLIAMDSACEERGAAGS
LISCESLYHREKQLIAMDSAIFVQGKDWGVKKFIRRDFYEAGMTLGEKFRVGNCKHLK
MTRPTMPAILKLQKNCLLSLNSKMALNSEALSVVSETEYNQKLQVNQFSESKRTALTHN
QDFSIYRLCCKRGSLCHASQARSPAFPKPVRPLPAPITRITPQLGGQSDSSQPLLTTGRPQG
WQDQALRHTQQASPASCATITIPIHSAALGDHSGDPGPAWDTCPPLPLTTLIPRAPPPYGD
STARSWPSRCGPLGYAYKDFLWCFPFSLVFLQEIQICCHVSCLCCICCSTRICLGCLLELFL
SRALRALHVLWNGFQLHCQ

-continued

SEQ ID NO: 713

The polynucleotide sequence of the full GAd20 incorporating the GAd20 expression cassette catcatcaataatataccttattttggattgaggccaatatgataatgaggtgggcggggcgaggcggggcgggtgacgtagga cgcgcgagtagggttgggaggtgtggcggaagtgtggcatttgcaagtgggaggagctgacatgcaatcttccgtcgcggaa aatgtgacgcgtttttgatgagcgccgcctacctccggaagtgccaattttcgcgcgcttttcaccggatatcgtagtaattttgggcg ggaccatgtaagatttggccattttcgcgcgaaaagtgaaacggggaagtgaaaactgaataatagggcgttagtcatagcgcg taatatttaccgagggccgagggactttgaccgattacgtggaggactcgcccaggtgtttttttacgtgaatttccgcgttccgggt caaagtctccgtttttattgtcgccgtcatctgacgggccgccattgcatacgttgtatccatatcataatatgtacatttatattggctc atgtccaacattaccgccatgttgacattgattattgactagttattaatagtaatcaattacggggtcattagttcatagcccatatat ggagttccgcgttacataacttacggtaaatggcccgcctggctgaccgcccaacgacccccgcccattgacgtcaataatgac gtatgttcccatagtaacgccaatagggactttccattgacgtcaatgggtggagtatttacggtaaactgcccacttggcagtaca tcaagtgtatcatatgccaagtacgccccctattgacgtcaatgacggtaaatggcccgcctggcattatgcccagtacatgacct tatgggactttcctacttggcagtacatctacgtattagtcatcgctattaccatggtgatgcggttttggcagtacatcaatgggcgt ggatagcggtttgactcacggggatttccaagtctccaccccattgacgtcaatgggagtttgttttggcaccaaaatcaacggga ctttccaaaatgtcgtaacaactccgccccattgacgcaaatgggcggtaggcgtgtacggtgggaggtctatataagcagagc tctccctatcagtgatagagatctccctatcagtgatagagatcgtcgacgagctcgtttagtgaaccgtcagatcgcctggagac gccatccacgctgttttgacctccatagaagacaccgggaccgatccagcctccgcggccgggaacggtgcattggaacgcg gattccccgtgccaagagtgagatcttccgtttatctaggtaccagatatcagaattcggatcccgcgacttcgccgccatgggc cagaaagagcagatccacacactgcagaaaaacagcgagcggatgagcaagcagctgaccagatcttctcaggccgtgcag aacctgcagaacggcggaggctctagaagctctgctacacttcctggcaggcggcggagaagatggctgagaagaaggcgg cagcctatctctgtggctcctgctggacctcctagacggcccaaccagaagcctaatcctcctggcggagccagatgcgtgatc atgaggcctacatggcctggcaccagcgccttcaccaagagaagctttgccgtgaccgagcggatcatcgactattgggctca aaaagagaagggcagcagcagcttcctgcggcctagctgtgattattgggcccagaaagaaaagatcagcatccccagaaca cacctgtgcctggtgctgggagtgctgtctggacactctggcagcagactgtatgaggccggcatgacactcggcggcaagat cctgttcttcctgttcctgctgctccctctgagccccttcagcctgatcttcaccgagatcagctgctgcaccctgagcagcgagg aaaacgagtacctgcctagacctgagtggcagctgcaggtccccttcagagagctgaagaacgtttccgtgctggaaggcctg agacagggcagacttggcggcccttgtagctgtcactgccccagacctagtcaggccagactgacacctgtggatgtggccg gacctttcctgtgtctgggagatcctggcctgtttccacctgtgaagtccagcatcacaggcggcaagtccacatgttctgcccct ggacctcagagcctgcctagcacacccttcagcacataccctcagtgggtcatcctgatcaccgaactcggcatggaatgcacc ctgggacaagtgggagccccatctcctagaagagaagaggatggctggcgcggaggccactctagattcaaagctgatgtgc ccgctcctcagggcccttgttggggaggacaacctggatctgccccatcttctgccccacctgaacagtccctgctggattggaa gttcgagatgagctacaccgtcggcggacctccacctcatgttcatgccagacctcggcactggaaaaccgacagagatggcc acagctacaccagcaaagtgaactgcctcctgctgcaggatggcttccacggctgtgtgtctattactggcgccgctggcagac ggaacctgagcatctttctgtactgatgctgtgcaagctcgagttccacgcctgcaagatccagaacaagaactgccccgacttc aagaagttcgacggcccttgcggagaaagaggcggaggcagaacagctagagccctttgggctagaggcgacagcgttctg acaccagctctggaccctcagacacctgttagggcccctagcctgacaagagctgccgccgctgtgcactacaagctgatcca gcagccaatcagcctgttcagcatcaccgaccggctgcacaagacattcagccagctgccaagcgtgcacctgtgctccatca ccttccagtggggacaccctcctatcttttgctccaccaacgacatctgcgtgaccgccaacttctgtatcagcgtgaccttcctga agccttgctttctgctgcacgaggccagcgcctctcagtgccacttgtttctgcagccccaagtgggcacacctcctccacatac agcctctgctagagcacctagcggccctccacatcctcacgaatcttgtcctgccggaagaaggcctgccagagccgctcaaa catgtgccagacgacagcacggactgcctggatgtgaagaggctggaacagccagagtgcctagcctgcacctccatctgca -continued tcaggctgctcttggagccggaagaggtagaggatggggcgaagcttgtgctcaggtgccaccttctagaggcgtgctgagat tcctggacctgaaagtgcgctacctgcacagccagtggcagcactatcacagatctggcgaagccgccggaacacccctttgg aggccaacaagaaacgtgcccttccgggaactgaagaaccagagaacagctcagggcgctcctggaatccaccatgctgctt ctccagtggccgccaacctgtgtgatcctgccagacatgcccagcacaccaggattccttgtggcgctggacaagtgcgcgct ggaagaggacctgaagcaggcggaggtgttctgcaacctcaaagacccgctcctgagaagcctggctgcccttgcagaaga ggacagcctagactgcacaccgtgaaaatgtggcgagccgtggccatgatggtgcccgatagacaggtccactacgactttgg actgggcgtgccaggcgatagcactcggagagccgtcagacggatgaacaccttttacgaagccgggatgaccctgggcga gaagttcagagtgggcaactgcaagcacctgaagatgacccggcctaacagcaagatggccctgaatagcgaggccctgtct gtggtgtctgaatgtggcgcctctgcctgtgacgtgtccctgatcgctatggactccgcctttgtgcagggcaaagactggggcg tgaagaagttcatccggcgggacttctacgcctacaaggacttcctgtggtgcttccccttctctctggtgttcctgcaagagatcc agatctgctgtcatgtgtcctgcctgtgctgcatctgctgtagcaccagaatctgcctgggctgtctgctggaactgttcctgagca gagccctgagagcactgcacgtgctgtggaacggattccagctgcactgccagaccgagtacaaccagaaactgcaagtgaa ccagttcagcgagagcaagagcctgtaccaccgggaaaagcagctcattgccatggacagcgccatctgcgaagagagagg cgccgcaggatctctgatctcctgcgaaacaatgcccgccatcctgaagctgcagaagaattgcctcctaagcctgcgaaccg ctctgacacacaaccaggacttcagcatctacagactgtgttgcaagcggggctccctgtgccatgcaagccaagctagaagc cccgcctttcctaaacctgtgcgacctctgccagctccaatcaccagaattacccctcagctcggcggccagagcgattcatctc aacctctgctgaccaccggcagacctcaaggctggcaagaccaagctctgagacacacccagcaggctagccctgcctcttgt gccaccatcacaatccccatccactctgccgctctgggcgatcattctggcgatcctggaccagcctgggacacatgtcctcca ctgccactcacaacactgatccctagggctcctccaccttacggcgattctaccgctagaagctggcccagcagatgtggacca ctcggaggcaacacaaccctccagcaactgggagaagcctctcaggctcctagcggctctctgatccctctcagactgcctctc ctgtgggaagttcggggccagcctgattcttttgccgcactgcacagctccctgaacgagctgggagagatcgctagagagct gcaccagttcgccttcgacctgctgatcaagagccacttcgtgcaaggcaaggattggggcctcaaaaagtttatccgcagaga cttctggggcatggaactggccgccagcagaagattcagctgggatcatcatagcgcaggcggcccacctagagtgccatctg ttagaagcggagctgcccaggtgcagcctaaagatcctctgccactgagaacactggccggctgccttgctagaacagcccat cttagacctggcgccgagtctctgcctcagccacaactgcactgtaccctgtggttccagtccagcgagctgtctcctactggtg ccccttggccatctagacgccctacttggagaggcaccaccgtgtcaccaagaaccgccacaagcagcgccagaacctgttgt ggcacaaagtggccctccagccaagaagccgctctcggacttggaagcggactgctgaggttctcttgtggaaccgccgccat tcggaagatgcactttagcctgaaagaacaccctccaccaccttgtcctccagaggctttccaaagagctgctggcgaaggcgg acctggtagaggtggtgctagaagaggtgctagggtgctgcagagcccattctgtagagcaggcgcaggcgaatggctgggc catcagagtctgagacatgtcgtcggctacggccacctggatacaagcggaagcagctctagctccagctggcctaactcaaa aatggctctgaacagcctgaactccatcgacgacgcccagctgacaagaatcgcccctcctagatctcactgctgcttttgggaa gtgaacgccccaagccatcaccatcaccaccattagtaaaggcgcgcctagcggccgcgatctgctgtgccttctagttgccag ccatctgttgtttgcccctcccccgtgccttccttgaccctggaaggtgccactcccactgtcctttcctaataaaatgaggaaattg catcgcattgtctgagtaggtgtcattctattctggggggtggggtggggcaggacagcaagggggaggattgggaagacaat agcaggcatgctggggatgcggtgggctctatggccgggccgcgatcgcgcttaggcctgaccatctggtgctggcctgcac cagggccgagtttgggtctagcgatgaggataccgattgaggtgggtaaggtgggcgtggctagcagggtgggcgtgtataa attggggtctaaggggtctctctgtttgtcttgcaacagccgccgccatgagcgacaccggcaacagctttgatggaagcatct ttagtccctatctgacagtgcgcatgcctcactgggccggagtgcgtcagaatgtgatgggttccaacgtggatggacgtcccgt tctgccttcaaattcgtctactatggcctacgcgaccgtgggaggaactccgctggacgccgcgacctccgccgccgcctccg ccgccgccgcgaccgcgcgcagcatggctacggacctttacagctctttggtggcgagcagcgcggcctctcgcgcgtctgc -continued tcgggatgagaaactgactgctctgctgcttaaactggaagacttgacccgggagctgggtcaactgacccagcaggtttccag
cttgcgtgagagcagccttgcctcccccctaatggcccataatataaataaaagccagtctgtttggattaagcaagtgtatgttcttt
atttaactctccgcgcgcggtaagcccgggaccagcggtctcggtcgtttagggtgcggtggatttttttccaacacgtggtacag
gtggctctggatgtttagatacatgggcatgagtccatccctggggtggaggtagcaccactgcagagcttcgtgctcgggggt
ggtgttgtatatgatccagtcgtagcaggagcgctgggcgtggtgctgaaaaatgtccttaagcaagaggcttatagctagggg
gaggcccttggtgtaagtgtttacaaatctgcttagctgggaggggtgcatccgggggggatatgatgtgcatcttggactggattt
ttaggttggctatgttcccgcccagatcccttctgggattcatgttgtgcaggaccaccagcacggtatatccagtgcacttggga
aatttatcgtggagcttagacgggaatgcatggaagaacttggagacgcccttgtggcctcccagattttccatacattcgtccat
gatgatggcaatgggcccgtgggaagctgcctgagcaaaaacgtttctggcatcgctcacatcgtagttatgttccagggtgag
gtcatcataggacatctttacgaatcgggggcgaagggtcccggactgggggatgatggtaccctcgggccccggggcgtag
ttcccctcacagatctgcatctcccaggctttcatttcagagggagggatcatatccacctgcggggcgatgaaaaagacagtttc
tggcgcaggggagattaactgggatgagagcaggtttctgagcagctgtgactttccacagccggtgggcccatatatcacgc
ctatcaccggctgcagctggtagttaagagagctgcagctgccgtcctcccggagcaggggggccacctcgttgagcatatcc
ctgacgtggatgttctccctgaccagttccgccagaaggcgctcgccgcccagcgaaagcagctcttgcaaggaagcaaaatt
tttcagcggtttcaggccatcggccgtgggcatgtttttcagcgtctgggtcagcagctccagcctgtcccagagctcggtgatgt
gctctacggcatctcgatccagcagatctcctcgtttcgcgggttggggcggctttcgctgtagggcaccagccgatgggcgtc
cagcggggccagagtcatgtccttccatgggcgcagggtcctcgtcagggtggtctgggtcacggtgaaggggtgcgctccg
ggttgggcactggccagggtgcgcttgaggctggttctgctggtgctgaatcgctgccgctcttcgccctgcgcgtcggccagg
tagcatttgaccatggtctcgtagtcgagaccctcggcggcgtgccccttggcgcggagctttcccttggaggtggcgccgcac
gaggggcactgcaggctcttcagggcgtagagcttgggagcgagaaacacggactctggggagtaggcgtccgcgccgca
ggccgagcagaccgtctcgcattccaccagccaagtgagttccgggcggtcagggtcaaaaaccaggttgcccccatgcttttt
gatgcgtttcttaccttggctctccatgaggcggtgtcccttctcggtgacgaagaggctgtccgtgtccccgtagaccgacttca
ggggcctgtcttccagcggagtgcctctgtcctcctcgtagagaaactctgaccactctgagacgaaggcccgcgtccaggcc
aggacgaaggaggccacgtgggaggggtagcggtcgttgtccactagcgggtccaccttctccagggtgtgcaggcacatgt
ccccctcctccgcgtccagaaaagtgattggcttgtaggtgtaggacacgtgaccggggggttcccaacgggggggtataaaag
ggggtgggtgccctttcatcttcactctcttccgcatcgctgtctgcgagagccagctgctggggtaagtattccctctcgaaggc
gggcatgacctcagcgctcaggttgtcagtttctaaaaatgaggaggatttgatgttcacctgtccggaggtgatacctttgaggg
tacctgggtccatctggtcagaaaacactatttttttgttatcaagcttggtggcgaatgacccgtagagggcgttggagagcagc
ttggcgatggagcgcagggtctggtttttgtcgcggtcggctcgctccttggccgcgatgttgagttgcacgtactcgcgggcca
cgcacttccactcggggaacacggtggtgcgctcgtctgggatcaggcgcaccctccagccgcggttgtgcagggtgaccat
gtcgacgctggtggcgacctcaccgcgcagacgctcgttggtccagcagaggcggccgcccttgcgcgagcagaaggggg
gtagggggtccagctggtcctcgtttgggggggtccgcgtcgatggtaaagaccccggggagcaggcgcgggtcaaagtagt
cgatcttgcaagcttgcatgtccagagcccgctgccattcgcgggcggcgagcgcgcgctcgtaggggttgaggggcgggc
cccagggcatggggtgggtgagcgcggaggcgtacatgccgcagatgtcatacacgtacaggggttccctgaggataccga
ggtaggtggggtagcagcgcccccgcggatgctggcgcgcacgtagtcatagagctcgtgggagggggccagcatgttgg
gcccgaggttggtgcgctgggggcgctcggcgcggaagacgatctgcctgaagatggcgtgggagttggaggagatggtg
ggccgctggaagacgttgaagcttgcttcttgcaagcccacggagtccctgacgaaggaggcgtaggactcgcgcagcttgtg
caccagctcggcggtgacctggacgtcgagcgcacagtagtcgagggtctcgcggatgatgtcatacctatcctccccccttcttt
ttccacagctcgcggttgaggacgaactcttcgcggtctttccagtactcttggaggggaaacccgtccgtgtccgaacggtaag
agcctagcatgtagaactggttgacggcctggtaggggcagcagcccttctccacgggcagcgcgtaggcctgcgccgcctt
gcggagggaggtgtgggtgagggcgaaagtgtccctgaccatgactttgaggtattgatgtctgaagtctgtgtcatcgcagcc -continued gccctgttcccacagggtgtagtccgtgcgctttttggagcgcgggttgggcagggagaaggtgaggtcattgaagaggatctt ccccgctcgaggcatgaagtttctggtgatgcgaaagggccctgggaccgaggagcggttgttgatgacctgggcggccagg acgatctcgtcaaagccgtttatgttgtgtcccacgatgtagagctccaggaagcggggctggcccttgatggaggggagctttt taagttcctcgtaggtaagctcctcgggcgattccaggccgtgctcctccagggcccagtcttgcaagtgagggttggccgcca ggaaggatcgccagaggtcgcgggccatgagggtctgcaggcggtcgcggaaggttctgaactgccgccccacggccatttt ttcgggggtgatgcagtagaaggtgagggggtctttctcccaggggtcccatctgagctctcgggcgaggtcgcgcgcggca gcgaccagagcctcgtcgcccccccagtttcatgaccagcatgaagggcacgagttgcttgccaaaggctcccatccaagtgta ggtttctacatcgtaggtgacaaagaggcgctccgtgcgaggatgagagccgattgggaagaactggatctcccgccaccagt tggaggattggctgttgatgtggtgaaagtagaagtcccgtctgcgggccgagcactcgtgctggcttttgtaaaagcgaccgc agtactggcagcgctgcacgggttgtatatcttgcacgaggtgaacctggcgacctctgacgaggaagcgcagcgggaatcta agtcccccgcctggggtcccgtgtggctggtggtcttttactttggttgtctggccgccagcatctgtctcctggagggcgatggt ggaacagaccaccacgccgcgagagccgcaggtccagatctcggcgctcggcgggcggagtttgatgacgacatcgcgca cattggagctgtccatggtctccagctcccgcggcggcaggtcagccgggagttccctggaggttcacctcgcagagacgggt caaggcgcggacagtgttgagatggtatctgatttcaaggggcatgttggaggcggagtcgatggcttgcaggaggccgcag ccccgggggggccacgatggttccccgcggggcgcgaggggaggcggaagctgggggtgtgttcagaagcggtgacgcgg gcgggcccccggaggtagggggggttccggccccacaggcatgggcggcaggggcacgtcttcgccgcgcgcgggcag gggctggtgctggctccgaagagcgcttgcgtgcgcgacgacgcgacggttggtgttcctgtatctggcgcctctgagtgaag accacgggtcccgtgaccttgaacctgaaagagagttcgacagaatcaatctcggcatcgttgacagcggcctggcgcaggat ctcctgcacgtcgcccgagttgtcctggtaggcgatttctgccatgaactgctcgatctcttcctcctggagatctcctcgtccggc gcgctccacggtggccgccaggtcgttggagatgcgacccatgagctgcgagaaggcgttgagtccgccctcgttccagacc cggctgtagaccacgccccccctcggcgtcgcgggcgcgcatgaccacctgggccaggttgagctccacgtgtcgcgtgaag acggcgtagttgcgcaggcgctggaaaaggtagttcagggtggtggcggtgtgctcggcgacgaagaagtacatgacccag cgccgcaacgtggattcattgatgtcccccaaggcctccaggcgctccatggcctcgtagaagtccacggcgaagttgaaaaa ctgggagttgcgagcggacacggtcaactcctcctccagaagaacggatgagctcggcgacagtgtcgcgcacctcgcgctc gaaggccacggggggcgcttcttcctcttccacctcttcttccatgattgcttcttcttcttcctcagccgggacgggagggggcg gcggcgggggaggggcgcggcggcggcggcggcgcaccgggaggcggtcgatgaagcgctcgatcatctccccccgca tgcggcgcatggtctcggtgacggcgcggccgttctcccgggggcgcagctcgaagacgccgcctctcatttcgccgcggg gcgggcggccgtgaggtagcgagacggcgctgactatgcatcttaacaattgctgtgtaggtacgccgccaagggacctgatt gagtccagatccaccggatccgaaaacctttggaggaaagcgtctatccagtcgcagtcgcaaggtaggctgagcaccgtgg cgggcgggggcgggtcgggagagttcctggcggagatgctgctgatgatgtaattaaagtaggcggtcttgagaaggcggat ggtggacaggagcaccatgtctttgggtccggcctgttggatgcggaggcggtcggccatgccccaggcctcgttctgacacc ggcgcaggtctttgtagtaatcttgcatgagtctttccaccggcacttcttctccttcctcttcttcatctcgccggtggtttctcgcgc cgcccatgcgcgtgaccccaaagcccctgagcggctgcagcagggccaggtcggcgaccacgcgctcggccaagatggc ctgctgtacctgagtgagggtcctctcgaagtcatccatgtccacgaagcggtggtaggcacccgtgttgatggtgtaggtgca gttggccatgacggaccagttgacggtctggtgtcccggctgcgagagctccgtgtaccgcaggcgcgagaaggcgcggga atcgaacacgtagtcgttgcaagtccgcaccagatactggtagcccaccaggaagtgcggcggaggttggcgatagagggg ccagcgctgggtggcgggggcgccgggcgccaggtcttccagcatgaggcggtggtatccgtagatgtacctggacatcca ggtgatgcctgcggcggtggtggtggcgcgcgcgtagtcgcggacccggttccagatgtttcgcaggggcgagaagtgttcc atggtcggcacgctctggccggtgaggcgcgcgcagtcgttgacgctctatacacacacaaaaacgaaagcgtttacagggct ttcgttctgtagcctggaggaaagtaaatgggttgggttgcggtgtgccccggttcgagaccaagctgagctcagccggctgaa -continued gccgcagctaacgtggtattggcagtcccgtctcgacccaggccctgtatcctccaggatacggtcgagagccctttgctttctt ggccaagcgcccgtggcgcgatctgggatagatggtcgcgatgagaggacaaaagcggctcgcttccgtagtctggagaaa caatcgccagggttgcgttgcggcgtaccccggttcgagcccctatggcggcttggatcggccggaaccgcggctaacgtgg gctgtggcagccccgtcctcaggaccccgccagccgacttctccagttacgggagcgagccccttttgtttttatttttagatgc atcccgtgctgcggcagatgcgcccctcgccccggcccgatcagcagcagcaacagcaggcatgcagaccccctctcctct ccccgccccggtcaccacggccgcggcggccgtgtccggtgcgggggcgcgctggagtcagatgagccaccgcggcgg cgacctaggcagtatctggacttggaagagggcgagggactggcgcggctgggggcgagctctccagagcgccacccgcg ggtgcagttgaaaagggacgcgcgtgaggcgtacctgccgcggcaaaacctgtttcgcgaccgcgggggcgaggagcccg aggagatgcgggactgcaggttccaagcggggcgcgagctgcgccgcggcttggacagacagcgcctgctgcgcgagga ggactttgagcccgacacgcagacgggcatcagccccgcgcgcgcgcacgtggccgcggccgacctggtgaccgcctacg agcagacggtgaaccaggagcgcaacttccaaaaaagcttcaacaaccacgtgcgcacgctggtggcgcgcgaggaggtg accctgggtctcatgcatctgtgggacctggtggaggcgatcgtgcagaaccccagcagcaagcccctgaccgcgcagctgtt cctggtggtgcagcacagcagggacaacgaggccttcagggaggcgctgctgaacatcaccgagccggagggggcgctggc tcctggacctgataaacatcctgcagagcatagtggtgcaggagcgcagcctgagcctggccgagaaggtggcggccattaa ctattctatgctgagcctgggcaagttctacgctcgcaagatctacaagacccccctacgtgcccatagacaaggaggtgaagat agacagcttctacatgcgcatggcgctgaaggtgctaaccctgagcgacgacctgggagtgtaccgcaacgagcgcatccac aaggccgtgagcgccagccggcggcgcgagctgagcgaccgcgaactgatgcacagtctgcagcgcgcgctgaccggcg cgggcgagggcgacagggaggtcgagtcctactttgacatgggggccgacctgcactggcagccgagccgccgcgccctg gaagcggcgggggcgtacggcggcccccctggcggccgatgacgaggaagaggaggactatgagctagaggagggcgag tacctggaggactgacctggctggtggtgttttggtatagatgcaagatccgaacgtggcggacccggcggtccgggcggcg ctgcagagccagccgtccggcattaactcctctgacgactgggccgcggccatgggtcgcatcatggccctgaccgcgcgca accccgaggccttcaggcagcagcctcaggctaaccggctggcggccatcttggaagcggtagtgcccgcgcgctccaacc ccacccacgagaaggtgctggccatagtcaacgcgctggcggagagcagggccatccgggcagacgaggccggactggt gtacgatgcgctgctgcagcgggtggcgcggtacaacagcggcaacgtgcagaccaacctggaccgcctggtgacggacgt gcgcgaggccgtggcgcagcgcgagcgcttgcatcaggacggcaacctgggctcgctggtggcgctaaacgccttccttag cacccagccggccaacgtaccgcgggggcaggaggactacaccaacttcttgagcgcgctgcggctgatggtgaccgaggt ccctcagagcgaggtgtaccagtcggggcccgactacttcttccagaccagcagacagggcttgcaaaccgtgaacctgagc caggctttcaagaacctgcgggggctgtggggagtgaaggcgcccaccggcgaccgggctacggtgtccagcctgctaacc cccaactcgcgcctgctgctgctgctgatcgcgcccttcacggacagcgggagcgtctcgcgggagacctatctgggccacct gctgacgctgtaccgcgaggccatcgggcaggcgcaggtggacgagcacaccttccaggagatcaccagcgtgagccacg cgctggggcaggaggacacgggcagcctgcaggcgaccctgaactacctgctgaccaacaggcggcagaagattcccacg ctgcacagcctgacccaggaggaggagcgcatcttgcgctacgtgcagcagagcgtgagcctgaacctgatgcgcgacggc gtgacgcccagcgtggcgctggacatgaccgcgcgcaacatggaaccgggcatgtacgcttcccagcggccgttcatcaacc gcctgatggactacttgcatcgggcggcggccgtgaaccccgagtacttcaccaatgccattctgaatccccactggatgcccc ctccgggtttctacaacggggacttcgaggtgcctgaggtcaacgatgggttcctctgggatgacatggatgacagtgtgttctc ccccaacccgctgcgcgccgcgtctctgcgattgaaggagggctctgacagggaaggaccaaggagtctggcctcctccctg gctctgggggcggtgggcgccacgggcgcggcggcgcggggcagcagccccttccccagcctggcggactctctgaatag cgggcgggtgagcaggccccgcttgctaggcgaggaggagtatctgaacaactccctgctgcagcccgtgagggacaaaaa cgctcagcggcagcagtttcccaacaatgggatagagagcctggtggacaagatgtccagatggaagacgtatgcgcaggag tacaaggagtgggaggaccgccagccgcggcccctgccgcccctagacagcgctggcagcggcgcgcgtccaaccgcc gctggaggcaggggcccgaggacgatgatgactctgcagatgacagcagcgtgttggacctgggcgggagcgggaacccc -continued ttttcgcacctgcgcccacgcctgggcaagatgttttaaaagagaaaaataaaaactcaccaaggccatggcgacgagcgttgg
ttttttgttcccttccttagtatgcggcgcgcggcgatgttcgaggaggggcctccccccctcttacgagagcgcgatgggaatttct
cctgcggcgccccctgcagcctccctacgtgcctcctcggtacctgcaacctacagggggggagaaatagcatctgttactctgag
ctgcagcccctgtacgataccaccagactgtacctggtggacaacaagtccgcggacgtggcctccctgaactaccagaacga
ccacagcgatttttttgaccacggtgatccaaaacaacgacttcaccccaaccgaggccagtacccagaccataaacctggaca
acaggtcgaactggggcggcgacctgaagactatcctgcacaccaatatgcccaacgtgaacgagttcatgttcaccaactcttt
taaggcgcgggtgatggtggcgcgcgagcagggggaggcgaagtacgagtgggtggacttcacgctgcccgagggcaact
actcagagaccatgactctcgacctgatgaacaatgcgatcgtggaacactatctgaaagtgggcaggcagaacggggtgaa
ggagagcgatatcggggtcaagtttgacaccagaaacttccgtctgggctgggaccctgtgaccgggctggtcatgccgggg
gtctacaccaacgaggcctttcatcccgatatagtgctcctgcccggctgtggggtggacttcacccagagccggctgagcaac
ctgctgggcgttcgcaagcggcaacctttccaggagggtttcaagatcacctatgaggatctggagggggggcaacattcccgc
gctccttgatctggacgcctacgaggagagcttgaaacccgaggagagcgctggcgacagcggcgagagtggcgaggagc
aagccggcggcggcggcagcgcgtcggtagaaaacgaaagtactcccgcagtggcggcggacgctgcggaggtcgagcc
ggaggccatgcagcaggacgcagaggagggcgcgcaggaggacatgaacaatggggagatcaggggcgacactttcgcc
acccggggcgaagaaaaagaggcagaggcggcggcggcgacggcggaagccgaaaccgaggcagaggcagagcccg
agaccgaagttatggaagacatgaatgatggagaacgtaggggtgacacgtttgccacccggggcgaagagaaggcggcg
gaggcagaagccgcggctgaggaggcggctgcggctgcggccaaggctgaggctgcggctgaggctaaggtcgaagccg
atgttgcggttgaggctcaggctgaggaggaggcggcggctgaagcagttaaggaaaaggcccaggcagagcaggaagag
aaaaaacctgtcattcaacctctaaaagaagatagcaaaaagcgcagttacaacgtcattgagggcagcacctttacccaatacc
gcagctggtacctggcttacaactacggcgacccggtcaagggggtgcgctcgtggaccctgctctgcacgccggacgtcac
ctgcggctccgagcagatgtactggtcgctgccaaacatgatgcaagacccggtgaccttccgttccacgcggcaggttagca
actttccggtggtgggcgccgaactgctgccagtacactccaagagtttttacaacgagcaggccgtctactcccagctgatccg
ccaggccacctctctgacccacgtgttcaatcgctttcccgagaaccagattttggcgcgcccgccggcccccaccatcaccac
cgtcagtgaaaacgttcctgccctcacagatcacgggacgctaccgctgcgcaacagcatctcaggagtccagcgagtgacc
attactgacgccagacgccggacctgcccctacgtttacaaggccttgggcatagtctcgccgcgcgtcctctccagtcgcactt
tttaaaacacatccacccacacgctccaaaatcatgtccgtactcatctcgcccagcaacaacaccggctgggggctgcgcgca
cccagcaagatgtttggaggggcaaggaagcgctccgaccagcaccccgtgcgcgtgcgcggccactaccgcgcgccctg
ggtgcgcacaagcgcgggcgcacagggcgcaccactgtggatgatgtcattgactccgtagtggagcaggcgcgccacta
cacacccggcgcgccgaccgcctccgccgtgtccaccgtggaccaggcgatcgaaagcgtggtacagggggcgcggcact
atgccaaccttaaaagtcgccgccgccgcgtggcgcgccgccatcgccggagaccccgggctactgccgccgcgcgcctta
ccaaggctctgctcaagcgcgccaggcgaactggccaccgggccgccatgagggccgcacggcgggctgccgctgccgc
gagcgccgtggccccgcgggcacgaaggcgcgcggccgctgccgccgccgccgccatttccagcttggcctcgacgcgg
cgcggtaacatatactgggtgcgcgactcggtgagcggcacacgtgtgcccgtgcgctttcgcccccccacggaattagcacaa
gacaacatacacactgagtctcctgctgttgtgtatcccagcggcgaccgtcagcagcggcgacatgtccaagcgcaaaattaa
agaagagatgctccaggtcatcgcgccggagatctatgggcccccgaagaaggaggaggaggattacaagccccgcaagct
aaagcgggtcaaaaagaaaaagaaagatgatgacgttgacgaggcggtggagtttgtccgccgcatggcgcccaggcgccc
tgtgcagtggaagggtcggcgcgtgcagcgagtcctgcgccccggcaccgcggtggtctttacgcccggcgagcgttccac
gcgcactttcaagcgggtgtacgatgaggtgtacggcgacgaggatctgttggagcaggccaaccatcgatttggggagtttg
catatgggaaacggcctcgcgagagtctaaaagaggacctgctggcgctaccgctggacgagggcaatcccaccccgagtct
gaagccggtgaccctgcaacaggtgctgcctttgagcgcgcccagcgagcagaagcgagggttaaagcgcgagggcggg -continued gacctggcacccaccgtgcagttgatggtgcccaagcggcagaagctggaggacgtgctggagaaaatgaaagtagagccc
gggatccagcccgagatcaaggtccgccctatcaagcaggtggcgcccggcgtgggagtccagaccgtggacgttaggatt
cccacggaggagatggaaacccaaaccgccactccctcttcggcagcaagcgccaccaccggcgccgcttcggtagaggtg
cagacggacccctggctacccgccgccactatcgccgtcgccgccgcccccgttcgcgcggacgcaagagaaattatcca
gcggccagcgcgcttatgccccagtatgcgctgcatccatccatcgcgcccacccccggctaccgcgggtactcgtaccgcc
cgcgcagatcagccggcactcgcggccgccgccgccgtgcgaccacaaccagccgccgccgtcgccgccgccgccagcc
agtgctgacccccgtgtctgtaaggaaggtggctcgctcggggagcacgctggtggtgcccagagcgcgctaccaccccag
catcgtttaaagccggtctctgtatggttcttgcagatatggccctcacttgtcgccttcgcttcccggtgccgggataccgaggaa
gaactcaccgccgcaggggcatggcgggcagcggtctccgcggcggccgtcgccatcgccggcgcgcaaagagcaggc
gcatgcgcggcggtgtgttgcccctgctggtcccgctactcgccgcggcgatcggcgccgtgcccgggatcgcctccgtggc
cctgcaggcgtcccagaaacattgactcttgcaaccttgcaagcttgcatttttggaggaaaaaataaaaaagtctagactctcac
gctcgcttggtcctgtgactattttgtagaaaaaagatggaagacatcaactttgcgtcgctggccccgcgtcacggctcgcgcc
cgttcatgggagactggacagatatcggcaccagcaatatgagcggtggcgccttcagctggggcagtctgtggagcggcctt
aaaaattttggttccaccattaagaactatggcaacaaagcgtggaacagcagcacgggtcagatgctgagagacaagttgaaa
gagcagaacttccaggagaaggtggcgcagggcctggcctctggcatcagcggggtggtggacatagctaaccaggccgtg
cagaaaaagataaacagtcatctggaccccccgccctcaggtggaggaaacgcctccagccatggagacggtgtctcccgag
ggcaaaggcgaaaagcgcccgcggcccgacagggaagagaccctggtgtcacacaccgaggagccgccctcttacgagg
aggcagtcaaggccggcctgcccaccactcgccccatagctcccatggccaccggtgtggtgggtcacaggcaacacaccc
ccgcaacactagatctgccccccgccgtccgagccgactcgccagccaaaggcggtgacggtgtccgctccctccacttccgc
cgccaacagagtgcctctgcgccgcgctgcgagcggcccccgggcctcgcgagtcagcggcaactggcagagcacactga
acagcatcgtgggcctgggagtgaggagtgtgaagcgccgccgttgctactgaatgagcaagctagctaacgtgttgtatgtgt
gtatgcgtcctatgtcgccgccagaggagctgttgagccgccggcgccgtctgcactccagcgaatttcaagatggcgacccc
atcgatgatgcctcagtggtcgtacatgcacatctcgggccaggacgcttcggagtacctgagccccgggctggtgcagttcgc
ccgcgccacagacacctacttcaacatgagtaacaagttcaggaaccccactgtggcgcccacccacgatgtgaccacggac
cggtcgcagcgcctgacgctgcggttcatccccgtggatcgggaggacaccgcttactcttacaaggcgcggttcacgctggc
cgtgggcgacaaccgcgtgctggacatggcctccacttactttgacatccggggggtgctggacaggggccccacttttaagc
cctactcgggcactgcctacaaccccctggcccccaagggcgcccccaattcttgtgagtgggaacaagaggaaaatcaggt
ggtcgctgcagatgatgaacttgaagatgaagaagcgcaagcacaagaggaagcccctgtgaaaaaaaattcatgtatatgctc
aggcgcctctttctggcgaaaagatttccaaggatggtatccaaataggtactgaagtcgtaggagatacatctaaggacactttt
gcagataaaacattccaacccgaacctcagataggcgagtctcagtggaacgaggctgatgccacagcagcaggaggtaga
gttttgaaaaagactaccccctatgagaccttgctatggatcctatgccaggcctaccaatgccaacgggggtcaaggaattatgg
ttgccaatgaacaaggagtgttggagtctaaagtagaaatgcaatttttctctaacaccacaaccccttaatgcgcgggatggaacc
ggcaatcccgaaccaaaggtggtgttgtacagcgaagatgtccacttggaatctcccgatactcatctgtcttacaagcccaaaa
aggatgatgttaatgccaaaatcatgttgggtcagcaagccatgcccaacagacccaacctcattggatttagagataatttcattg
ggcttatgttttacaacagcaccggtaacatgggagtgctggcgggtcaggcctctcagttgaatgctgtggtggacttgcagga
tagaaacacagaactgtcatatcagcttctgcttgattcaattggggatagaaccagatacttctccatgtggaaccaggcagtgg
atagctatgatccagatgtcagaattattgaaaaccatgggactgaggatgaactgcccaactactgcttccctttgggcggcata
ggagttactgatacttatcaagggataaaaaataccaatggcaatggtcagtggaccaaagatgatcagttcgcggaccgcaac
gaaataggggtgggaaacaacttcgccatggagatcaacatccaggccaacctttggagaaacttcctctatgcaaacgtggg
gctctacctgccagacaagctcaagtacaaccccaccaacgtggacatctctgacaaccccaacacctatgactacatgaacaa
gcgggtggtggcccctggcctggtggactgctttgtcaatgtgggagccaggtggtccctggactacatggacaacgtcaacc -continued ccttcaaccaccaccgcaatgcgggtctgcgctaccgctccatgatcctgggcaacgggcgctatgtgccctttcacatccagg
taccccagaagttctttgccatcaagaacctcctgctcctgcccggctcctacacctacgagtggaacttcaggaaggatgtgaa
catggtcctacagagctctctgggcaatgaccttagggtggatggggccagcatcaagtttgacagcatcaccctctatgctaca
tttttccccatggcccacaacaccgcctccacgcttgaggccatgctgagaaacgacaccaacgaccagtcctttaatgactacc
tctctggggccaacatgctctacccaatcccagccaaggccaccaacgtgcccatctccatcccctctcgcaactgggccgcct
ttagaggctgggcctttacccgccttaagaccaaggagacccccctccctgggctcgggttttgatccctactttgtttactcgggat
ccatcccctacctggatggcaccttctacctcaaccacactttcaagaagatatccatcatgtatgactcctccgtcagctggccg
ggcaacgaccgcttgctcacccccaatgagttcgaggtcaagcgcgccgtggacggcgagggctacaacgtggcccagtgc
aacatgaccaaggactggttcctggtgcagatgctggccaactacaacataggctaccagggcttttacatcccagagagctac
aaggacaggatgtactccttcttcagaaatttccaacccatgagccgacaggtggtggacgagaccaattacaaggactatcaa
gccattggcatcacccaccagcacaacaactcgggtttcgtgggctacctggcgcccaccatgcgcgagggtcaggcctacc
ccgccaacttccccctaccccttgataggcaagaccgcggtcgacagcgtcacccagaaaaagttcctctgcgaccgcaccctc
tggcgcatccccttctctagcaacttcatgtccatgggtgcgctcacggacctgggccaaaacctgctttatgccaactctgccca
tgcgctggacatgacttttgaggtggaccccatggacgagcccacccttctctatattgtgtttgaagtgttcgacgtggtcagagt
gcaccagccgcaccgcggtgtcatcgagaccgtgtacctgcgtacgcccttctcagccggcaacgccaccacctaaggagac
agcgccgccgccgcctgcatgacgggttccaccgagcaagagctcagggccattgccagagacctgggatgcggaccctat
tttttgggcacctatgacaaacgcttcccgggctttatctcccgagacaagctcgcctgcgccattgtcaacacggccgcgcgcg
agaccgggggcgtgcactggctggcctttggctgggacccgcgctccaaaacttgctacctctttgacccctttggcttctccga
tcagcgcctcaggcagatttatgagtttgagtacgaggggctgctgcgccgcagcgcgctcgcctcctcgcccgaccgctgca
tcacccttgagaagtccaccgaaaccgtgcaggggcccccactcggccgcctgcggtctcttctgttgcatgtttttgcacgccttt
gtgcactggcctcagagtcccatggattgcaaccccaccatgaacttgctaaagggagtgcccaacgccatgctccagagccc
ccaggtccagcccaccctgcgccgcaaccaggaacagctttaccgcttcctggagcgccactcccccctacttccgcagccaca
gcgcgcgcatccgggggggccacctctttttgccacttgcaagaaaacatgcaagacggaaaatgatgtacagcatgcttttaata
aatgtaaagactgtgcactttaattatacacgggctctttctggttatttattcaacaccgccgtcgccatttagaaatcgaaagggtt
ctgccgtgcgtcgccgtgcgccacgggcagagacacgttgcgatactggaagcggctcgcccacttgaactcgggcaccac
catgcggggcagtggttcctcggggaagttctcgctccacagggtgcgggtcagctgcagcgcgctcaggaggtcgggagc
cgagatcttgaagtcgcagttggggccggaaccctgcgcgcgcgagttgcggtacacggggttgcagcactggaacaccag
cagggccggattattcacgctggccagcaggctctcgtcgctgatcatgtcgctgtccagatcctccgcgttgctcagggcgaat
ggggtcatcttgcagacctgcctgcccaggaaaggcgggagcccaggcttgccgttgcagtcgcagcgcaggggcattagc
aggtgcccacggcccgactgcgcctgcgggtacaacgcgcgcatgaaggcttcgatctgcctaaaagccacctgggtcttgg
ctccctccgaaaagaacatcccacaggacttgctggagaactggttcgcgggacagctggcatcgtgcaggcagcagcgcgc
gtcagtgttggcaatctgcaccacgttgcgaccccaccggtttttcactatcttggccttggaagcctgctcctttagcgcgcgctg
gccgttctcgctggtcacatccatctctatcacctgttccttgttgatcatgtttgtcccgtgcagacactttaggtcgccctccgtctg
ggtgcagcggtgctcccacagcgcgcaaccggtgggctcccaattcttgtgggtcacccccgcgtaggcctgcaggtaggcc
tgcaggaagcgccccatcatggtcataaaggtcttctggctcgtaaaggtcagctgcaggccgcgatgctcttcgttcagccag
gtcttgcagatggcggccagcgcctcggtctgctcgggcagcatcttaaaatttgtcttcaggtcgttatccacgtggtacttgtcc
atcatggcacgcgccgcctccatgcccttctcccaggcggacaccatgggcaggcttagggggtttatcacttccagcggcga
ggacaccgtactttcgatacttcttcctccccctcttcccggcgcgcgccccccgctgttgcgcgctcttaccgcctgcaccaagg
ggtcgtcttcaggcaagcgccgcaccgagcgcttgccgcccttgacctgcttgatcagtaccggcgggttgctgaagcccacc
atggtcagcgccgcctgctcttcttcgtcttcgctgtctaccactatttctggggaggggcttctccgctctgcggcaaaggcggc -continued ggatcgcttcttttttttcttgggagccgccgcgatggagtccgccacggcgaccgaggtcgagggcgtggggctgggggtgc
gcggtaccagggcctcgtcgccctcggactcttcctctgactccaggcggcggcggagtcgcttctttgggggcgcgcgcgtc
agcggcggcggagacggggacggggacggggacgggacgccctccacagggggtggtcttcgcgcagacccgcggcc
gcgctcgggggtcttctcgcgctggtcttggtcccgactggccattgtatcctcctcctcctaggcagagagacataaggagtct
atcatgcaagtcgagaaggaggagagcttaaccacccccctcagagaccgccgatgcgcccgccgtcgccgtcgccccccgct
accgccgacgcgcccgccacaccgagcgacacccccacggacccccccgccgacgcacccctgttcgaggaagcggccg
tggagcaggacccgggctttgtctcggcagaggaggatttgcaagaggaggagaataaggaggagaagccctcagtgccaa
aagatcataaagagcaagacgagcacgacgcagacgcacaccagggtgaagtcgggcgggggacggagggcatggcg
gcgccgactacctagacgaaggaaacgacgtgctcttgaagcacctgcatcgtcagtgcgccatcgtctgcgacgctctgcag
gagcgcagcgaggtgcccctcagcgtggcggaggtcagccgcgcctacgagctcagcctcttttcccccgggtgcccccc
cgccgccgcgaaaacggcacatgcgagcccaacccgcgcctcaacttctaccccgcctttgtggtgcccgaggtcctggcca
cctatcacatcttctttcaaaattgcaagatccccatctcgtgccgcgccaaccgtagccgcgccgataagatgctggccctgcg
ccagggcgaccacatacctgatatcgccgctttggaagatgtgccaaagatcttcgagggtctggggcgcaacgagaagcgg
gcagcaaactctctgcaacaggaaaacagcgaaaatgagagtcacactggagcgctggtggagctggagggcgacaacgc
ccgcctggcggtgctcaagcgcagcatcgaggtcacccactttgcctaccccgcgctcaacctgccccccaaagtcatgaacg
cggtcatggacgggctgatcatgcgccgcggccggcccctcgctccagatgcaaacttgcatgaggagaccgaggacggtc
agcccgtggtcagcgacgagcagctgacgcgctggctggagagcgcggaccccgccgaactggaggagcggcgcaagat
gatgatggccgcggtgctggtcaccgtagagctggagtgtctgcagcgcttcttcggtgaccccgagatgcagagaaaggtcg
aggagaccctacactacaccttccgccagggctacgtgcgccaggcttgcaagatctccaacgtggagctcagcaacctggtg
tcctacctgggcatcttgcatgaaaaccgccttgggcagagcgtgctacactccaccctgcgcggggaggcgcgccgcgact
acgtgcgcgactgcgtttacctcttcctctgctacacctggcagacggccatgggggtctggcagcagtgcctggaggagcgc
aacctcaaggagctggagaagcttctgcagcgcgcgctcaaagacctctggacgggcttcaacgagcgctcggtggccgcc
gcgctagccgacctcatcttccccgagcgcctgctcaaaaccctccagcaggggctgcccgacttcaccagccaaagcatgtt
gcaaaattttaggaactttatcctggagcgttctggcatcctacccgccacctgctgcgccctgcccagcgactttgtcccccctcgt
gtaccgcgagtgcccccccgccgctgtggggccactgctacctgttccaactggccaactacctgtcctaccacgcggacctcat
ggaggactccagcggcgaggggctcatggagtgccactgccgctgcaacctctgcacgccccaccgctccctggtctgcaac
acccaactgctcagcgagagtcagattatcggtaccttcgagctacagggtccgtcctcctcagacgagaagtccgcggctcc
ggggctaaaactcactccggggctgtggacttccgcctacctgcgcaaatttgtacctgaagactaccacgcccacgaaatcag
gttttacgaggaccaatcccgcccgcccaaggcggagctgaccgcctgcgtcatcacccagggcgagatcctaggccaattg
caagccatccaaaaagcccgccaagagtttttgctgaagaggggtcggggggtgtatctggacccccagtcgggtgaggagc
tcaacccggttcccccgctgccaccgccgcgggaccttgcttcccaggataagcatcgccatggctcccagaaagaagcagc
agcggccgccgctgccgccgccccacatgctggaggaagaggaggaatactgggacagtcaggcagaggaggtttcggac
gaggaggagccggagacggagatggaagagtgggaggaggacagcttagacgaggaggcttccgaagccgaagaggca
ggcgcaacaccgtcaccctcggccgcagccccctcgcaggcgcccccgaagtccgctcccagcatcagcagcaacagcag
cgctataacctccgctcctccaccgccgcgacccacggccgaccgcagacccaaccgtagatgggacaccaccggaaccg
gggccggtaagtcctccgggagaggcaagcaagcgcagcgccaaggctaccgctcgtggcgcgctcacaagaacgccata
gtcgcttgcttgcaagactgcgggggggaacatctccttcgcccgccgcttcctgctcttccaccacggtgtggccttcccccgta
acgtcctgcattactaccgtcatctctacagcccctactgcggcggcagtgagccagaggcggccagcggcggcggcgccc
gtttcggtgcctaggaagacccagggcaagacttcagccaagaaactcgcggcgaccgcggcgaacgcggtcgcgggggc
cctgcgcctgacggtgaacgaacccctgtcgacccgcgaactgaggaaccgaatcttccccactctctatgccatcttccagca
gagcagagggcaggatcaggaactgaaagtaaaaaacaggtctctgcgctccctcacccgcagctgtctgtatcacaagagc -continued gaagaccagcttcggcgcacgctggaggacgctgaggcactcttcagcaaatactgcgcgctcactcttaaggactagctccg
cgcccttctcgaatttaggcgggaacgcctacgtcatcgcagcgccgccgtcatgagcaaggacattcccacgccatacatgtg
gagctatcagccgcagatgggactcgcggcgggcgcctcccaagactactccacccgcatgaactggctcagtgccggccc
acacatgatctcacaggttaatgacatccgcacccatcgaaaccaaatattggtgaagcaggcggcaattaccaccacgcccc
gcaataatcccaaccccagggagtggcccgcgtccctggtgtatcaggaaattcccggccccaccaccgtactacttccgcgt
gattcccaggccgaagtccaaatgactaactcaggggcacagctcgcgggcggctgtcgtcacagggtgcggcctcctcgcc
agggtataactcacctggagatccgaggcagaggtattcagctcaacgacgagtcggtgagctcctcgctcggtctcagacct
gacgggaccttccagatagccggagccggccgatcttccttcacgccccgccaggcgtacctgactctgcagagctcgtcctc
ggcgccgcgctcgggcggcatcgggactctccagttcgtgcaggagtttgtgccctcggtctacttcaaccccttctcgggctct
cccggtcgctacccggaccagtttatcccgaactttgacgccgcgagggactcggtggacggctacgactgaatgtcgggtgg
acccggtgcagagcaacttcgcctgaagcaccttgaccactgccgccgccctcagtgctttgcccgctgtcagaccggtgagtt
ccagtacttttccctgcccgactcgcacccggacggcccggcgcacggggtgcgctttttcatcccgagtcaggtccgctctac
cctaatcagggagttcaccgcccgtcccctactggcggagttggaaaaggggccttctatcctaaccattgcctgcatttgctcta
accctggattacaccaagatctttgctgtcatttgtgtgctgagtataataaaggctgagatcagaatctactcggaccttatcccttt
caattgatcataactgtaatcaataaaaaatcacttacttgaaatctgatagcaagactctgtccaatttttttcagcaacacttccttcc
cctcctcccaactctggtactctaggcgcctcctagctgcaaacttcctccacagtctgaagggaatgtcagattcctcctcctgtc
cctccgcacccacgatcttcatgttgttacagatgaaacgcgcgagatcgtctgacgagaccttcaaccccgtgtacccctacga
taccgagatcgctccgacttctgtccctttccttacccctccctttgtatcatccgcaggaatgcaagaaaatccagctggggtgct
gtccctgcacctgtcagagccccttaccacccacaatggggccctgactctaaaaatggggggcggcctgaccctggacaag
gaagggaatctcacttcccaaaacatcaccagtgtcgatcccccctctcaaaaaaagcaagaacaacatcagccttcagaccgcc
gcacccctcgccgtcagctccggggccctaaccctttttgccactcccccccctagcggtcagtggcgacaaccttactgtgcagt
ctcaggcccctcttactttggaagactcaaaactaactctggccaccaaaggacccctaactgtgtccgaaggcaaacttgtcct
agaaacagagcctcccctgcatgcaagtgacagcagtagcctgggccttagcgtcacggccccacttagcattaacaatgaca
gcctaggactagacatgcaagcgcccatcagctctcgagatggaaaactggctctaacagtggcggccccccctaactgtggcc
gagggtatcaatgctttggcagtagccacaggtaatggtattggactaaatgaaaccaacacacacctgcaggcaaaactggtc
gcgcccctaggctttgataccaacggcaacattaagctaagcgtcgcaggaggcatgaggctaaacaataacacactgatact
agatgtaaactacccatttgaggctcaaggccaactgagcctaagagtgggctcgggcccactatatgtagattctagtagtcat
aacctaaccattagatgccttaggggattgtatgtaacatcttctaacaaccaaaacggtctagaggccaacattaaactaacaaa
aggccttgtgtatgacggaaatgccatagcagttaatgttggcaaagggctggaatacagccctactggcacaacagaaaaac
ctatacagactaaaataggtctaggcatggagtatgacactgagggagccatgatgacaaaactaggctctggactaagctttga
caattcaggagccattgtggtgggaaacaaaaatgatgacaggcttactttgtggaccacaccggacccatcgcccaactgtca
gatttactctgaaaaagatgctaaactaaccttggtactgactaaatgtggcagtcaggttgtaggcacagtatctattgccgctctt
aaaggtagccttgtgccaatcactagtgcaatcagtgtggttcagatatacctaaggtttgatgaaaatggggtgctgatgagtaa
ctcttcacttaatggcgaatactggaattttagaaacggagactcaactaatggcacaccatatacaaacgcagtgggttttatgcc
taatctactggcctatcctaaaggtcaaactacaactgcaaaaagtaacattgtcagccaggtctacatgaacggggacgatact
aaacccatgacatttacaatcaacttcaatggccttagtgaaacaggggatacccctgtcagtaaatattccatgacattctcatgg
aggtggccaaatggaagctacatagggcacaattttgtaacaaactcctttactttctcctacatcgcccaagaataaagaaagca
cagagatgcttgttttgatttcaaaattgtgtgcttttatttattttcaagcttacagtatttccagtagtcattagaatagagcttaattaa
actgcatgagaacccttccacatagcttaaatactagtggagaagtactcgcctacatgggggtagagtcataatcgtgcatcag
gatagggcggtggtgctgcagcagcgcgaataaactgctgccgccgccgctccgtcctgcaggaatacaacatggcagtg -continued

```
gtctcctcagcgatgattcgcaccgcccgcagcataaggcgccttgtcctccgggcacagcagcgcaccctgatctcacttaa

tcagcacagtaactgcagcacagcaccacaatattgttcaaaatcccacagtgcaaggcgctgtatccaaagctcatggcggg

gaccacagaacccacgtggccatcataccacaagcgcaggtagattaagtggcgacccctcataaacacgctggacataaac

attacctcttttggcatgttgtaattcaccacctcccggtaccatataaacctctgattaaacatggcgccatccaccaccatcctaa

accagctggccaaaacctgcccgccggctatacactgcagggaaccgggactggaacaatgacagtggagagcccaggact

cgtaaccatggatcatcatgctcgtcatgatatcaatgttggcacaacacaggcacacgtgcatacacttcctcaggattacaagc

tcctcccgcgttagaaccatatcccagggaacaacccattcctgaatcagcgtaaatcccacactgcagggaagacctcgcac

gtaactcacgttgtgcattgtcaaagtgttacattcgggcagcagcggatgatcctccagtatggtagcgcgggtttctgtctcaaa

aggaggtagacgatccctactgtacggagtgcgccgagacaaccgagatcgtgttggtcgtagtgtcatgccaaatggaacgc

cggacgtagtcatatttcctgaagtcttcactctcacagcaccagcactaatcagagtgtgaagagggccaagtgccgaacgag

tatatataggaattaaaaatgacgtaaatgtgtaaaggtcaaaaaacgcccagaaaaatacacagaccaacgcccgaaacgaa

aacccgcgaaaaaatacccagaagttcctcaacaaccgccacttccgctttcccacgatacgtcacttcctcaaaaatagcaaac

tacatttcccacatgtacaaaaccaaaacccctccccttgtcaccgcccacaacttacataatcacaaacgtcaaagcctacgtca

cccgccccgcctcgccccgcccacctcattatcatattggcctcaatccaaaataaggtatattattgatgatg
```

Figure 7:
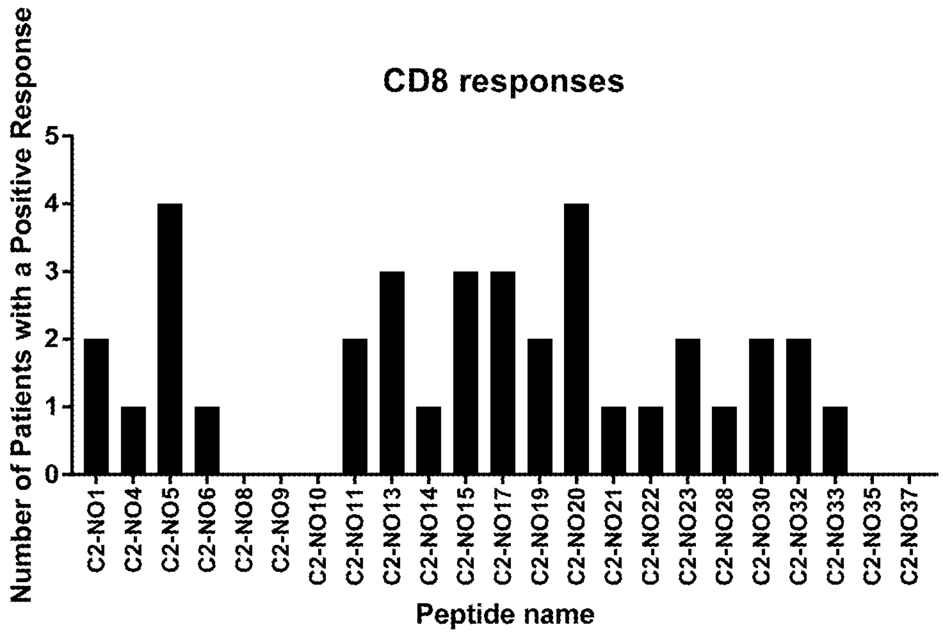
FIG. 7 shows the number of prostate cancer patients whose PBMC samples demonstrated a positive $CD4^+$ immune response to the specified neoantigens.
Figure 8:
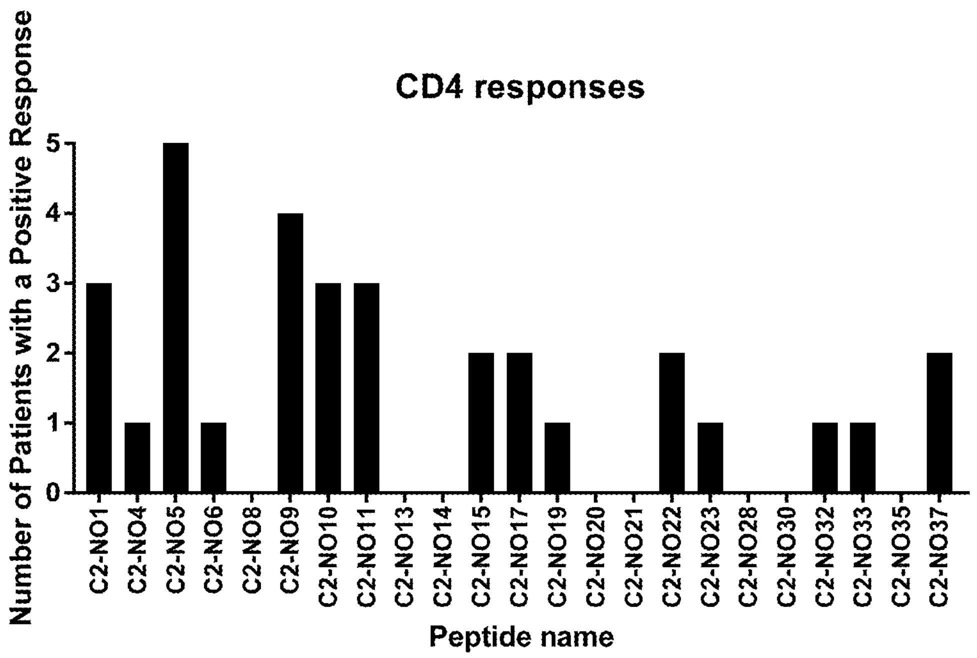
FIG. 8 shows the number of prostate cancer patients whose PBMC samples demonstrated a positive $CD8^+$ immune response to the specified neoantigens.

Example 11 Neoantigens Incorporated into NeoGAd20 and NeoMVA are Immunogenic In Vitro Overlapping 15-mer peptides were designed to span each neoantigen incorporated into NeoGAd20 and NeoMVA to assess their ability to activate T cells using the exogenous autologous normal donor restimulation assay described in Example 1 as pools using TNFα and IFNγ production by $CD8^+$ and $CD4^+$ T cells as a readout. Table 25 shows the maximum frequency of $TNF\alpha^+IFN\gamma^+CD8^+$ and $TNF\alpha^+IFN\gamma^+CD4^+$ T cells and maximum fold change over negative control for the pool of peptides analyzed, indicating the highest frequency of $TNF\alpha^+IFN\gamma^+CD8^+$ and $TNF\alpha^+IFN\gamma^+CD4^+$ T cells and resulting fold change across the normal donors evaluated for the peptide. Table 26 shows the peptide sequences used. FIG. 7 shows the number of patients with a positive CD8+ response for each tested peptide pool for select neoantigens. FIG. 8 shows the number of patients with a positive CD4+ response for each tested peptide pool for select neoantigens.

TABLE 25

| Neoantigen ID (Alternative name) | Maximum Fold Change Over Back-ground CD8+ cells | Maximum Frequency of TNFα/IFNγ Double Positive CD8+ T cells | Maximum Fold Change Over Back-ground CD4+ cells | Maximum Frequency of TNFα/IFNγ Double Positive CD4+ T cells |
|---|---|---|---|---|
| AS18 (C2-NO1) | 9.17 | 0.110 | 7.51 | 0.053 |
| P87 (C2-NO4) | 9.20 | 0.460 | 7.86 | 0.110 |
| AS55 (C2-NO5) | 1354.17 | 32.500 | 19.38 | 0.310 |
| AS57 (C2-NO6) | 4.67 | 0.056 | 11.00 | 0.110 |
| AS15 (C2-NO11) | 4.36 | 0.061 | 9.17 | 0.110 |
| AS7 (C2-NO13) | 52.60 | 2.630 | 2.50 | 0.045 |
| AS43 (C2-NO15) | 28.75 | 0.460 | 5.67 | 0.040 |
| AS51 (C2-NO17) | 33.13 | 0.530 | 8.75 | 0.140 |
| AS16 (C2-NO19) | 24.17 | 0.290 | 7.78 | 0.140 |
| AS41 (C2-NO20) | 190.60 | 9.530 | 2.20 | 0.022 |
| AS6 (C2-NO22) | 6.50 | 0.078 | 31.67 | 0.380 |
| AS3 (C2-NO23) | 7.92 | 0.095 | 3.86 | 0.054 |
| AS11 | 5.11 | 0.07 | 2.98 | 0.03 |

TABLE 25-continued

| Neoantigen ID (Alternative name) | Maximum Fold Change Over Back-ground CD8+ cells | Maximum Frequency of TNFα/IFNγ Double Positive CD8+ T cells | Maximum Fold Change Over Back-ground CD4+ cells | Maximum Frequency of TNFα/IFNγ Double Positive CD4+ T cells |
|---|---|---|---|---|
| AS13 | 1.67 | 0.10 | 1.96 | 0.05 |
| AS47 (C2-NO30) | 4.80 | 0.240 | 2.58 | 0.031 |
| AS8 (C2-NO33) | 54.55 | 0.600 | 4.08 | 0.049 |
| AS19 | 5.87 | 0.63 | 2.59 | 0.1 |
| AS37 | 19.47 | 0.74 | 7.51 | 0.04 |
| AS23 | 3.24 | 0.07 | 5.08 | 0.01 |
| MS1 | 5.56 | 0.1 | 50.19 | 0.39 |
| MS3 | 36.15 | 0.47 | 13.61 | 0.09 |
| MS6 | 4.17 | 0.08 | 111.97 | 0.87 |
| MS8 | 4.44 | 0.14 | 15.60 | 0.40 |
| P82 | 2.92 | 0.09 | 4.44 | 0.17 |
| P16 (C2-NO8) | 2.44 | 0.039 | 2.44 | 0.039 |
| FUS1 (C2-NO9) | 1.94 | 0.031 | 8.33 | 0.100 |
| P22 (C2-NO10) | 1.56 | 0.025 | 18.16 | 0.075 |
| FUS2 (C2-NO14) | 3.13 | 0.05 | 2.14 | 0.03 |
| FUS3 (C2-NO21) | 3.94 | 0.063 | 2.75 | 0.033 |
| FUS6 (C2-NO28) | 3.50 | 0.056 | 2.27 | 0.016 |
| FUS5 (C2-NO32) | 32.50 | 0.390 | 3.43 | 0.048 |
| FUS8 | 1.89 | 0.08 | 7.15 | 0.04 |
| FUS15 (C2-NO35) | 1.75 | 0.028 | 2.79 | 0.039 |
| P35 | 14.44 | 0.26 | 3.47 | 0.03 |
| FUS19(C2-NO37) | 1.88 | 0.030 | 3.15 | 0.013 |
| FUS7 | 8.89 | 0.16 | 36.13 | 0.04 |
| M84 | 1.39 | 0.03 | 35.84 | 0.31 |
| M86 | 4.22 | 0.08 | 6.18 | 0.05 |
| M10 | 1.89 | 0.09 | 14.14 | 0.1 |
| M12 | 6.67 | 0.12 | 8.94 | 0.05 |
| FR1 | 7.92 | 0.38 | 4.89 | 0.04 |

TABLE 26

| Neoantigen ID (alternative name) | Overlapping Peptide Sequences* (SEQ ID NO:) |
|---|---|
| AS18 (C2-NO1) | WKFEMSYTVGGPPPH (560)<br>VGGPPPHVHARPRHW (561)<br>PPHVHARPRHWKTD (562) |

TABLE 26-continued

| Neoantigen ID (alternative name) | Overlapping Peptide Sequences* (SEQ ID NO:) |
|---|---|
| P87 (C2-NO4) | YEAGMTLGGKILFFL (563)<br>GKILFFLFLLLPLSP (564)<br>FFLFLLLPLSPFSLIF (565) |
| AS55 (C2-NO5) | DGHSYTSKVNCLLLQ (566)<br>VNCLLLQDGFHGCVS (567)<br>GFHGCVSITGAAGRR (568)<br>TGAAGRRNLSIFLFL (569)<br>LSIFLFLMLCKLEFH (570)<br>LFLMLCKLEFHAC (571) |
| AS57 (C2-NO6) | TGGKSTCSAPGPQSL (572)<br>APGPQSLPSTPFSTY (573)<br>STPFSTYPQWVILIT (574) |
| AS15 (C2-NO11) | VLRFLDLKVRYLHS (269) |
| AS7 (C2-NO13) | DYWAQKEKGSSSFLR (576)<br>QKEKGSSSFLRPSC (577) |
| AS43 (C2-NO15) | VPFRELKNVSVLEGL (578)<br>VSVLEGLRQGRLGGP (579)<br>QGRLGGPCSCHCPRP (580)<br>SCHCPRPSQARLTPV (581)<br>QARLTPVDVAGPFLC (582)<br>VAGPFLCLGDPGLFP (583)<br>GDPGLFPPVKSSI (584) |
| AS51 (C2-NO17) | GMECTLGQVGAPSPR (585)<br>VGAPSPRREEDGWRG (586)<br>EEDGWRGGHSRFKAD (587)<br>HSRFKADVPAPQGPC (588)<br>PAPQGPCWGGQPGSA (589)<br>GGQPGSAPSSAPPEQ (590)<br>GSAPSSAPPEQSLLD (591) |
| AS16 (C2-NO19) | GNTTLQQLGEASQAP (592)<br>GEASQAPSGSLIPLR (593)<br>GSLIPLRLPLLWEVRG (594) |
| AS41 (C2-NO20) | EAFQRAAGEGGPGRG (595)<br>EGGPGRGGARRGARV (596)<br>ARRGARVLQSPFCRA (597)<br>QSPFCRAGAGEWLGH (598)<br>CRAGAGEWLGHQSLR (599) |
| AS6 (C2-NO22) | DYWAQKEKISIPRTH (600)<br>QKEKISIPRTHLC (601) |
| AS3 (C2-NO23) | VAMMVPDRQVHYDFG (602)<br>VPDRQVHYDFGLR (603) |
| AS11 | VPFRELKNQRTAQGA (631)<br>QRTAQGAPGIHHAAS (632)<br>GIHHAASPVAANLCD (633)<br>VAANLCDPARHAQHT (634)<br>ARHAQHTRIPCGAGQ (635)<br>IPCGAGQVRAGRGPE (636)<br>RAGRGPEAGGGVLQP (637)<br>GGGVLQPQRPAPEKP (638)<br>RPAPEKPGCPCRRGQ (639)<br>CPCRRGQPRLHTVKM (640)<br>RGQPRLHTVKMWRA (641) |
| AS13 | KRSFAVTERII (265) |
| AS47 (C2-NO30) | FKKFDGPCGERGGGR (604)<br>GERGGGRTARALWAR (605)<br>ARALWARGDSVLTPA (606)<br>DSVLTPALDPQTPVR (607)<br>DPQTPVRAPSLTRAA (608)<br>PVRAPSLTRAAAAV (609) |
| AS8 (C2-NO33) | LVLGVLSGHSGSRL (255) |
| AS19 | QWQHYHRSGEAAGTP (710)<br>GEAAGTPLWRPTRN (711) |

TABLE 26-continued

| Neoantigen ID (alternative name) | Overlapping Peptide Sequences* (SEQ ID NO:) |
|---|---|
| AS37 | CHLFLQPQVGTPPPH (642)<br>VGTPPPHTASARAPS (643)<br>ASARAPSGPPHPHES (644)<br>PPHPHESCPAGRRPA (645)<br>PAGRRPARAAQTCAR (646)<br>AAQTCARRQHGLPGC (647)<br>QHGLPGCEEAGTARV (648)<br>EAGTARVPSLHLHLH (649)<br>SLHLHLHQAALGAGR (650)<br>AALGAGRGRGWGEAC (651)<br>RGWGEACAQVPPSRG (652) |
| AS23 | KIQNKNCPD (285) |
| MS1 | HYKLIQQPISLFSIT (653)<br>ISLFSITDRLHKTFS (654)<br>RLHKTFSQLPSVHLC (655)<br>LPSVHLCSITFQWGH (656)<br>ITFQWGHPPIFCSTN (657)<br>PIFCSTNDICVTANF (658)<br>ICVTANFCISVTFLK (659)<br>ISVTFLKPCFLLHEA (660)<br>CFLLHEASASQ (661) |
| MS3 | RTALTHNQDFSIYRL (662)<br>DFSIYRLCCKRGSLC (663)<br>CKRGSLCHASQARSP (664)<br>ASQARSPAFPKPVRP (665)<br>FPKPVRPLPAPITRI (666)<br>PAPITRITPQLGGQS (667)<br>PQLGGQSDSSQPLLT (668)<br>SSQPLLTTGRPQGWQ (669)<br>GRPQGWQDQALRHTQ (670)<br>QALRHTQQASPASCA (671)<br>ASPASCATITIPIHS (672)<br>ITIPIHSAALGDHSG (673)<br>ALGDHSGDPGPAWDT (674)<br>PGPAWDTCPPLPLTT (675)<br>PPLPLTTLIPRAPPP (676)<br>IPRAPPPYGDSTARS (677)<br>GDSTARSWPSRCGPLG (678) |
| MS6 | YAYKDFLWCFPFSLV (679)<br>CFPFSLVFLQEIQIC (680)<br>LQEIQICCHVSCLCC (681)<br>HVSCLCCICCSTRIC (682)<br>CCSTRICLGCLLELF (683)<br>GCLLELFLSRALRAL (684)<br>SRALRALHVLWNGFQ (685)<br>VLWNGFQLHCQ (686) |
| MS8 | TMPAILKLQKNCLLSL (444) |
| P82 | YEAGMTLGEKFRVGN (687)<br>EKFRVGNCKHLKMTRP (688) |
| P16 (C2-NO8) | GVPGDSTRRAVRRMN (611)<br>DSTRRAVRRMNTF (612) |
| FUS1 (C2-NO9) | CGASACDVSLIAMDSA (211) |
| P22 (C2-NO10) | SLYHREKQLIAMDSAI (349) |
| FUS2 | TEYNQKLQVNQFSESK (712) |
| FUS3 (C2-NO21) | TEISCCTLSSEENEY (615)<br>SSEENEYLPRPEWQLQ (616) |
| FUS6 (C2-NO28) | CEERGAAGSLISCE (221) |
| FUS5 (C2-NO32) | NSKMALNSEALSVVSE (219) |
| FUS8 | WGMELAASRRFSWDH (689)<br>RRFSWDHHSAGGPPR (690)<br>SAGGPPRVPSVRSGA (691)<br>PSVRSGAAQVQPKDP (692) |

TABLE 26-continued

| Neoantigen ID (alternative name) | Overlapping Peptide Sequences* (SEQ ID NO:) |
|---|---|
| | QVQPKDPLPLRTLAG (693)<br>PLRTLAGCLARTAHL (694)<br>LARTAHLRPGAESLP (695)<br>PGAESLPQPQLHCT (696) |
| FUS15 (C2-NO35) | HVVGYGHLDTSGSSS (619)<br>YGHLDTSGSSSSSSWP (620) |
| P35 | NSKMALNSLNSIDDA (697)<br>LNSIDDAQLTRIAPP (698)<br>LTRIAPPRSHCCFWE (699)<br>APPRSHCCFWEVNAP (700) |
| FUS19 (C2-NO37) | KMHFSLKEHPPPPCPP (235) |
| FUS7 | LWFQSSELSPTGAPW (701)<br>SPTGAPWPSRRPTWR (702)<br>SRRPTWRGTTVSPRT (703)<br>TTVSPRTATSSARTC (704)<br>TSSARTCCGTKWPSS (705)<br>GTKWPSSQEAALGLG (706)<br>EAALGLGSGLLRFSC(707)<br>GLLRFSCGTAAIR (708) |
| M84 | IARELHQFAFDLLIKSH (167) |

Example 12 Neoantigens Incorporated into NeoGAd20 and NeoMVA are Immunogenic when Expressed Endogenously In Vitro For three of the neoantigens, an Ad5 vector was designed to transduce normal Dendritic cells with the neoantigens. This assay assessed the ability of the endogenously expressed and presented neoantigens to activate autologous T cells following overlapping 15-mer peptide pools restimulation using the endogenous autologous normal donor restimulation assay described in Example 1 utilizing TNFα and IFNγ production by $CD8^+$ and $CD4^+$ T cells as a readout. Table 27 shows the maximum frequency of $TNF\alpha^+IFN\gamma^+$ $CD8^+$ and $TNF\alpha^+IFN\gamma^+CD4^+$ T cells and maximum fold change over negative control for the pool of peptides analyzed, indicating the highest frequency of $TNF\alpha^+IFN\gamma^+$ $CD8^+$ and $TNF\alpha^+IFN\gamma^+CD4^+$ T cells and resulting fold change across the normal donors evaluated for the peptide. Sixteen donors were used to assess endogenous immunogenicity.

TABLE 27

| Neoantigen ID | Overlapping Peptide Sequences* (SEQ ID NO:) | Maximum Fold Change Over Background CD8+ cells | Maximum Frequency of TNFα/IFNγ Double Positive CD8+ T cells | Maximum Fold Change Over Background CD4+ cells | Maximum Frequency of TNFα/IFNγ Double Positive CD4+30 T cells |
|---|---|---|---|---|---|
| AS18 (C2-NO1) | WKFEMSYTVGGPPPH (560)<br>VGGPPPHVHARPRHW (561)<br>PPHVHARPRHWKTD (562) | 4.09 | 0.36 | 1.90 | 0.046 |
| P87 (C2-NO4) | YEAGMTLGGKILFFL (563)<br>GKILFFLFLLLPLSP (564)<br>FFLFLLLPLSPFSLIF (565) | 2.47 | 0.39 | 2.41 | 0.079 |
| AS55 (C2-NO5) | DGHSYTSKVNCLLLQ (566)<br>VNCLLLQDGFHGCVS (567)<br>GFHGCVSITGAAGRR (568)<br>TGAAGRRNLSIFLFL (569)<br>LSIFLFLMLCKLEFH (570)<br>LFLMLCKLEFHAC (571) | 213.88 | 2.05 | 3.50 | 0.063 |

*All generated peptides had NH2 group at N-terminus and -OH group at C-terminus

TABLE 26-continued

| Neoantigen ID (alternative name) | Overlapping Peptide Sequences* (SEQ ID NO:) |
|---|---|
| M86 | QPDSFAALHSSLNELGE (171) |
| M10 | FVQGKDWGLKKFIRRDF (19) |
| M12 | FVQGKDWGVKKFIRRDF (23) |
| FR1 | QNLQNGGGSRSSATL (709)<br>SRSSATLPGRRRRRW (575)<br>GRRRRRWLRRRRQPI (610)<br>RRRRQPISVAPAGPP (613)<br>VAPAGPPRRPNQKPN (614)<br>RPNQKPNPPGGARCV (617)<br>PGGARCVIMRPTWPG (618)<br>MRPTWPGTSAFT (621) |

Example 13: Neoantigens are Immunogenic In Vitro

Immunogenicity of various additional identified neoantigens was assessed. Overlapping 15-mer peptides were designed to span each neoantigen similarly to what was done in Example 11 to assess their ability to activate T cells using the exogenous autologous normal donor restimulation assay described in Example 1 as pools using TNFα and IFNγ production by $CD8^+$ and $CD4^+$ T cells as a readout. Table 28 shows the maximum frequency of $TNF\alpha^+IFN\gamma^+CD8^+$ and $TNF\alpha^+IFN\gamma^+CD4^+$ T cells and maximum fold change over negative control for the pool of peptides analyzed, indicating the highest frequency of $TNF\alpha^+$ $IFN\gamma^+CD8^+$ and $TNF\alpha^+$ $IFN\gamma^+CD4^+$ T cells and resulting fold change across the normal donors evaluated for the peptide. Table 29 shows the amino acid sequences of the peptides used in the assays for each neoantigen.

TABLE 28

| Neoantigen ID (Alternative name) | Max. Fold Change over background CD8+ TNFαINFγ double positive DP | Max. Frequency of CD8+ TNFαINFγ DP | Max. Fold Change over background CD4+ TNFαINFγ double positive DP | Max. Frequency of CD4+ TNFαINFγ DP |
|---|---|---|---|---|
| AS1 (Misc1-NO12) | 8.15 | 0.11 | 3.57 | 0.02 |
| AS2 (Misc1-NO13) | 5.06 | 0.09 | 110.68 | 0.86 |
| AS4 (Misc1-NO14) | 5.4 | 0.17 | 37.38 | 1.43 |
| AS5 (Misc1-NO15) | 2.13 | 0.16 | 8.71 | 0.1 |
| AS9 (Misc1-NO16) | 3.81 | 0.12 | 4.18 | 0.16 |
| AS10 (Misc1-NO17) | 4.33 | 0.08 | 3.97 | 0.23 |
| AS12 (Misc1-NO18) | 6.03 | 0.19 | 7.32 | 0.28 |
| AS14 (Misc1-NO19) | 3.81 | 0.12 | 1.49 | 0.06 |
| AS17 (Misc1-NO20) | 2.38 | 0.07 | 3.18 | 0.01 |
| AS20 (Misc1-NO21) | 3.81 | 0.12 | 1.36 | 0.05 |
| AS21 (Misc1-NO22) | 3.81 | 0.12 | 1.7 | 0.07 |
| AS22 (Misc1-NO23) | 2.61 | 0.1 | 7.86 | 0.11 |
| AS32 (Misc1-NO24) | 3.81 | 0.12 | 2.04 | 0.08 |
| AS34 (Misc1-NO26) | 16.25 | 0.26 | 9.48 | 0.01 |
| AS35 (Misc1-NO27) | 11.32 | 0.43 | 60.93 | 0.23 |
| AS36 (Misc2-NO1) | 1544.74 | 58.7 | 129.8 | 0.49 |
| AS40 (Misc2-NO3) | 178.52 | 2.41 | 15.34 | 0.89 |
| AS42 (Misc2-NO4) | 4.65 | 0.69 | 24.58 | 0.59 |
| AS44 (Misc2-NO5) | 4.72 | 0.09 | 293.94 | 1.48 |
| AS45 (Misc2-NO6) | 4.96 | 0.07 | 78.51 | 0.61 |
| AS46 (Misc2-NO7) | 11.6 | 0.87 | 157.98 | 0.29 |
| AS48 (Misc2-NO8) | 9.21 | 0.29 | 13.45 | 0.13 |
| AS49 (Misc2-NO9) | 8.67 | 0.65 | 184.87 | 0.14 |
| AS50 (Misc2-NO10) | 1.6 | 0.12 | 17.22 | 0.07 |
| AS52 (Misc2-NO11) | 6.85 | 0.1 | 184.87 | 0.63 |
| AS53 (Misc2-NO12) | 4.02 | 0.35 | 113.91 | 0.43 |
| AS54 | 88.15 | 8.33 | 17.87 | 0.18 |
| AS55.1 (Misc2-NO14) | 25.26 | 1.47 | 20.66 | 0.08 |
| AS56 | 6.35 | 0.6 | 128.76 | 0.18 |
| AS58 (Misc2-NO16) | 4.54 | 0.6 | 6.27 | 0.24 |
| AS59 (Misc2-NO17) | 4.22 | 0.08 | 59.58 | 0.3 |
| FUS9 (Misc1-NO2) | 1.82 | 0.07 | 203.97 | 0.77 |
| FUS10 (Misc1-NO3) | 2.42 | 0.09 | 10.86 | 0.04 |
| FUS11 (Misc1-NO4) | 2.63 | 0.1 | 28.57 | 0.16 |
| FUS18 | 42.33 | 0.91 | 31.76 | 0.04 |
| FUS23 (Misc1-NO6) | 11.05 | 0.62 | 12.77 | 0.12 |
| FUS24 (Misc1-NO7) | 8.53 | 0.64 | 4.4 | 0.05 |
| MS2 (Exc1-NO6) | 36.92 | 0.48 | 15.12 | 0.1 |
| MS4 (Exc1-NO8) | 24.13 | 0.76 | 367.35 | 2.43 |
| MS5 (Exc1-NO9) | 32.89 | 1.95 | 126.05 | 0.2 |
| MS7 (Exc1-NO11) | 6.67 | 0.12 | 10.52 | 0.09 |
| MS9 (Exc1-NO13) | 1.38 | 0.1 | 455.63 | 1.72 |
| MS10 (Exc1-NO14) | 3.42 | 0.13 | 74.17 | 0.28 |
| MS11 (Exc1-NO15) | 3.81 | 0.12 | 3.4 | 0.13 |
| P97 (Misc1-NO11) | 7.47 | 1.11 | 3.14 | 0.12 |
| P19 (Misc1-NO8) | 4.76 | 0.15 | 6.67 | 0.16 |
| P27 (Misc1-NO9) | 7.87 | 0.59 | 45.38 | 0.05 |
| P37 (Misc1-NO10) | 2.05 | 0.13 | 22.78 | 0.09 |
| P76, P77 (Misc2-NO18) | 4.56 | 0.08 | 53.18 | 0.36 |

TABLE 29

| Neoantigen ID (Alternative name) | Peptide sequences |
|---|---|
| AS1 (Misc1-NO12) | LTFLDFIQVTLRVMS (SEQ ID NO: 377) |
| | VTLRVMSGSQMENGS (SEQ ID NO: 378) |
| | SQMENGSSYFFKPFS (SEQ ID NO: 415) |
| | YFFKPFSWGLGVGLS (SEQ ID NO: 417) |
| AS2 (Misc1-NO13) | FMIGELVGELCCQLT (SEQ ID NO: 418) |
| | ELCCQLTFRLPFLES (SEQ ID NO: 419) |
| | RLPFLESLCQAVVTQ (SEQ ID NO: 420) |
| | CQAVVTQALRFNPSF (SEQ ID NO: 502) |
| | LRFNPSFQEVCIYQD (SEQ ID NO: 518) |
| | EVCIYQDTDLM (SEQ ID NO: 526) |

TABLE 29-continued

| Neoantigen ID (Alternative name) | Peptide sequences |
|---|---|
| AS4 (Misc1-NO14) | WCPLDLRLGSTGCLT (SEQ ID NO: 527) |
| | GSTGCLTCRHHQTSHE (SEQ ID NO: 714) |
| AS5 (Misc1-NO15) | VVGRRHETAPQPLLV (SEQ ID NO: 715) |
| | APQPLLVPDRAGGEG (SEQ ID NO: 716) |
| | DRAGGEGGA (SEQ ID NO: 717) |
| AS9 (Misc1-NO16) | PVPTATPGVRSVTSP (SEQ ID NO: 718) |
| | VRSVTSPQGLGLFLK (SEQ ID NO: 719) |
| | GLGLFLKFI (SEQ ID NO: 720) |

TABLE 29-continued

| Neoantigen ID (Alternative name) | Peptide sequences |
|---|---|
| AS10 (Misc 1-NO17) | KENDVREVCDVYLQM (SEQ ID NO: 721)<br>CDVYLQMQIFFHFKF (SEQ ID NO: 722)<br>IFFHFKFRSYFH (SEQ ID NO: 723) |
| AS12 (Misc1-NO18) | FARKMLEKVHRQHLQ (SEQ ID NO: 724)<br>VHRQHLQLSHNSQE (SEQ ID NO: 725) |
| AS14 (Misc1-NO19) | MFLRKEQQVGPHSFS (SEQ ID NO: 726)<br>VGPHSFSML (SEQ ID NO: 727) |
| AS17 (Misc1-NO20) | GLNLNTDRPGGYSYS (SEQ ID NO: 728)<br>PGGYSYSIWWKNNAK (SEQ ID NO: 729)<br>WWKNNAKNR (SEQ ID NO: 730) |
| AS20 (Misc1-NO21) | KVLNEIDAVVTVPPS (SEQ ID NO: 731)<br>VVTVPPSLSTSQIPQ (SEQ ID NO: 732)<br>STSQIPQGCCIIL (SEQ ID NO: 733) |
| AS21 (Misc1-NO22) | ANLKGTLQVRSGQAV (SEQ ID NO: 734)<br>VRSGQAVSPR (SEQ ID NO: 735) |
| AS22 (Misc1-NO23) | LQAAASGQGKQGVPC (SEQ ID NO: 736)<br>GKQGVPCPWGCCAYA (SEQ ID NO: 737)<br>WGCCAYAESPRALIS (SEQ ID NO: 738)<br>SPRALISGDAPSQVE (SEQ ID NO: 739)<br>DAPSQVEREVPGPCL (SEQ ID NO: 740)<br>EVPGPCLNTHSLSHR (SEQ ID NO: 741)<br>THSLSHRSPQLPGLP (SEQ ID NO: 742)<br>PQLPGLPHPKQPSV (SEQ ID NO: 743) |
| AS32 (Misc1-NO24) | GEVELSEGGEGQRHL (SEQ ID NO: 744)<br>GEGQRHLAFPWACSG (SEQ ID NO: 745)<br>FPWACSGPGWRGVCC (SEQ ID NO: 746)<br>GWRGVCCAAVEPA (SEQ ID NO: 980) |
| AS34 (Misc1-NO26) | KMRAIQAEGGHGQAC (SEQ ID NO: 747)<br>GGHGQACCGGAWGWA (SEQ ID NO: 748)<br>GGAWGWAPGDGGPQG (SEQ ID NO: 749)<br>GDGGPQGMLTHTLPT (SEQ ID NO: 750)<br>LTHTLPTLGFQSAWT (SEQ ID NO: 751)<br>GFQSAWTWRREDADR (SEQ ID NO: 752)<br>RREDADRAWRTPKAC (SEQ ID NO: 753)<br>WRTPKACASRRWSI (SEQ ID NO: 754) |
| AS35 (Misc1-NO27) | LLEPFRRGEPGPRGL (SEQ ID NO: 755)<br>EPGPRGLLSGSSRGG (SEQ ID NO: 756)<br>SGSSRGGEGPGRSIE (SEQ ID NO: 757)<br>GPGRSIEAAPATPLP (SEQ ID NO: 758)<br>APATPLPCCRKNPCR (SEQ ID NO: 759)<br>CRKNPCRPQPSRFLP (SEQ ID NO: 760)<br>QPSRFLPPRVLLVII (SEQ ID NO: 761)<br>RVLLVIILPKLDCPK (SEQ ID NO: 762)<br>PKLDCPKLGF (SEQ ID NO: 763) |
| AS36 (Misc2-NO1) | PSGRRTKRLVTLRSG (SEQ ID NO: 764)<br>LVTLRSGCAIQCWHP (SEQ ID NO: 765)<br>AIQCWHPRAGPVPSA (SEQ ID NO: 766)<br>AGPVPSALPHTERPP (SEQ ID NO: 767)<br>PHTERPPRLVRGAAD (SEQ ID NO: 768)<br>LVRGAADPRTVTLGR (SEQ ID NO: 769)<br>RTVTLGRSPAVMPRA (SEQ ID NO: 770)<br>PAVMPRAPA (SEQ ID NO: 771) |
| AS40 (Misc2-NO3) | DCMLSEEGGQARRGG (SEQ ID NO: 772)<br>GQARRGGSLCSLAAH (SEQ ID NO: 773)<br>LCSLAAHTIASAARG (SEQ ID NO: 774)<br>IASAARGRFLSRLSN (SEQ ID NO: 775)<br>FLSRLSNFCAVVKAS (SEQ ID NO: 776)<br>CAVVKASRGAPSCTWE (SEQ ID NO: 777) |
| AS42 (Misc2-NO4) | PEPRRLSPGEPRGRP (SEQ ID NO: 778)<br>GEPRGRPRKGWGIWG (SEQ ID NO: 779)<br>KGWGIWGLCGARVGP (SEQ ID NO: 780)<br>CGARVGPKAWR (SEQ ID NO: 781) |

TABLE 29-continued

| Neoantigen ID (Alternative name) | Peptide sequences |
|---|---|
| AS44 (Misc2-NO5) | FVSLTAIQMASSATP (SEQ ID NO: 782)<br>MASSATPWGRWPVAT (SEQ ID NO: 783)<br>GRWPVATPTAACPRR (SEQ ID NO: 784)<br>TAACPRRRPSSLPTG (SEQ ID NO: 785)<br>PSSLPTGGDSASKKP (SEQ ID NO: 786)<br>DSASKKPISRRAPWQ (SEQ ID NO: 787)<br>SRRAPWQPWACPGRS (SEQ ID NO: 788)<br>WACPGRSVNSAAPRA (SEQ ID NO: 789)<br>NSAAPRAWCPPATTP (SEQ ID NO: 790)<br>CPPATTPRTQSPSRD (SEQ ID NO: 791)<br>TQSPSRDLRPRCLSS (SEQ ID NO: 792)<br>RPRCLSSWSS (SEQ ID NO: 793) |
| AS45 (Misc2-NO6) | PVAIKPGTGPPNNSS (SEQ ID NO: 794)<br>GPPNNSSIHGGSKRS (SEQ ID NO: 795)<br>HGGSKRSENSYCRDL (SEQ ID NO: 796)<br>NSYCRDLRGQLRAIC (SEQ ID NO: 797)<br>GQLRAICCSSYSHDR (SEQ ID NO: 798)<br>SSYSHDRHTTEERGS (SEQ ID NO: 799)<br>TTEERGSRGRHVWRI (SEQ ID NO: 800)<br>GRHVWRIRRLHTSGL (SEQ ID NO: 801)<br>RLHTSGLPCCCHSGP (SEQ ID NO: 802)<br>CCCHSGPHPRRLPDI (SEQ ID NO: 803)<br>PRRLPDILRLVTSTK (SEQ ID NO: 804)<br>RLVTSTKTDHTNTTE (SEQ ID NO: 805)<br>DHTNTTEGTLDYL (SEQ ID NO: 806) |
| AS46 (Misc2-NO7) | KWNKNWTATLGALTI (SEQ ID NO: 807)<br>TLGALTIRGHKLLCH (SEQ ID NO: 808)<br>GHKLLCHLPHLLSSV (SEQ ID NO: 809)<br>PHLLSSVQQTCRSSSR (SEQ ID NO: 810) |
| AS48 (Misc2-NO8) | ENASLVFTGSNSPIP (SEQ ID NO: 811)<br>GSNSPIPACELSSHP (SEQ ID NO: 812)<br>CELSSHPAHGISPWI (SEQ ID NO: 813)<br>HGISPWIPSPGNEHF (SEQ ID NO: 814)<br>SPGNEHFHGIKKQVK (SEQ ID NO: 815)<br>GIKKQVKAIKVE (SEQ ID NO: 816) |
| AS49 (Misc2-NO9) | RLTQRLVQGWTPMEN (SEQ ID NO: 817)<br>GWTPMENRWCGRRAG (SEQ ID NO: 818)<br>WCGRRAGGQPASSST (SEQ ID NO: 819)<br>QPASSSTRWTTCRAA (SEQ ID NO: 820)<br>WTTCRAACLLTKWTA (SEQ ID NO: 821)<br>LLTKWTAGRSQTSIG (SEQ ID NO: 822) |
| AS50 (Misc2-NO10) | ENSGNASRWLHVPSS (SEQ ID NO: 823)<br>WLHVPSSSDDWLGWK (SEQ ID NO: 824)<br>DDWLGWKKSSAITSNS (SEQ ID NO: 825) |
| AS52 (Misc2-NO11) | KGSVERRSVSLGHPA (SEQ ID NO: 826)<br>VSLGHPAEGWAWAER (SEQ ID NO: 827)<br>GWAWAERSLQPGMTT (SEQ ID NO: 828)<br>LQPGMTTANTGCLSF (SEQ ID NO: 829)<br>NTGCLSFHHRGCLLP (SEQ ID NO: 830)<br>HRGCLLPVLPKLHCG (SEQ ID NO: 831)<br>LPKLHCGLGGLPLVR (SEQ ID NO: 832)<br>GGLPLVRAKEIKRVQ (SEQ ID NO: 833)<br>KEIKRVQRAGESSLP (SEQ ID NO: 834)<br>AGESSLPVKGLLTVA (SEQ ID NO: 835)<br>KGLLTVASAVIAVLW (SEQ ID NO: 836)<br>AVIAVLWGRPSEVTG (SEQ ID NO: 837)<br>RPSEVTGENEAQHD (SEQ ID NO: 838) |
| AS53 (Misc2-NO12) | FGLTTLAGRSSHGTS (SEQ ID NO: 839)<br>RSSHGTSGLRAATHT (SEQ ID NO: 840)<br>LRAATHTKSGDGGQG (SEQ ID NO: 841)<br>SGDGGQGAARQCEKL (SEQ ID NO: 842)<br>ARQCEKLLELARATR (SEQ ID NO: 843)<br>ELARATRPWGRSTSA (SEQ ID NO: 844)<br>WGRSTSASSRWTHRG (SEQ ID NO: 845)<br>SRWTHRGYMCPPRCA (SEQ ID NO: 846)<br>MCPPRCAVACW (SEQ ID NO: 847) |
| AS54 | IIDSDKIMAVCMGCL (SEQ ID NO: 848)<br>DKIMAVCMGCLLTRH (SEQ ID NO: 849) |

TABLE 29-continued

| Neoantigen ID (Alternative name) | Peptide sequences |
|---|---|
| | AVCMGCLLTRHVQCQ (SEQ ID NO: 850)<br>GCLLTRHVQCQAMEM (SEQ ID NO: 851)<br>TRHVQCQAMEMQQ (SEQ ID NO: 852) |
| AS55.1 (Misc2-NO14) | DGHSYTSKVNCLLLQ (SEQ ID NO: 566)<br>VNCLLLQDGFHGCVS (SEQ ID NO: 567)<br>GFHGCVSITGAAGRR (SEQ ID NO: 568)<br>TGAAGRRNLSIFLFL (SEQ ID NO: 569)<br>LSIFLFLMLCKLEFHA (SEQ ID NO: 853) |
| AS56 | LLNAEDYRCAIHSKE (SEQ ID NO: 854)<br>CAIHSKEIYLLSPSP (SEQ ID NO: 855)<br>YLLSPSPHQAMDKFS (SEQ ID NO: 856)<br>QAMDKFSLCCINCNL (SEQ ID NO: 857)<br>CCINCNLCLHVFLLL (SEQ ID NO: 858)<br>LHVFLLLLFFQNKDV (SEQ ID NO: 859)<br>FFQNKDVWLISNIIL (SEQ ID NO: 860)<br>LISNIILLWIYGGI (SEQ ID NO: 861) |
| AS58 (Misc2-NO16) | VETLENANSFSSGIQ (SEQ ID NO: 862)<br>SFSSGIQPLLCSLIG (SEQ ID NO: 863)<br>LLCSLIGLENPT (SEQ ID NO: 864) |
| AS59 (Misc2-NO17) | AGAGTISEGSVLHGQ (SEQ ID NO: 865)<br>GSVLHGQRLECDARR (SEQ ID NO: 866)<br>LECDARRFFGCGTTI (SEQ ID NO: 867)<br>FGCGTTILAEWEHH (SEQ ID NO: 868) |
| FUS9 (Misc1-NO2) | KEQILAVASLVSSQS (SEQ ID NO: 869)<br>SLVSSQSIHPSWGQS (SEQ ID NO: 870)<br>HPSWGQSPLSRI (SEQ ID NO: 871) |
| FUS10 (Misc1-NO3) | LELELSEGVCFRLR (SEQ ID NO: 229) |
| FUS11 (Misc1-NO4) | QQLRIFCAAMASNED (SEQ ID NO: 872)<br>AMASNEDFS (SEQ ID NO: 873) |
| FUS18 | DGFSGSLFAVVTRRC (SEQ ID NO: 874)<br>AVVTRRCYFLKWRTI (SEQ ID NO: 875)<br>FLKWRTIFPQSLMWL (SEQ ID NO: 876) |
| FUS23 (Misc1-NO6) | DLRRVATYCAPLPSS (SEQ ID NO: 877)<br>CAPLPSSWRPGTGTT (SEQ ID NO: 878)<br>RPGTGTTIPPRMRSC (SEQ ID NO: 879) |
| FUS24 (Misc1-NO7) | LQERMELLACGAERG (SEQ ID NO: 880)<br>ACGAERGAGGWGGGG (SEQ ID NO: 881)<br>GGWGGGGGGGGDRR (SEQ ID NO: 882)<br>GGGGDRRGGGGSAPA (SEQ ID NO: 883)<br>GGGSAPALADFAGGRG (SEQ ID NO: 884) |
| MS2 (Exc1-NO6) | WTDIVKQSVSTNCIS (SEQ ID NO: 885)<br>VSTNCISIKKGSYTK (SEQ ID NO: 886)<br>KKGSYTKLFSLVFLI (SEQ ID NO: 887)<br>FSLVFLIFCWPLIIQL (SEQ ID NO: 888) |
| MS4 (Exc1-NO8) | LRYGALCNVSRISYF (SEQ ID NO: 889)<br>VSRISYFSLTNIFNF (SEQ ID NO: 890)<br>LTNIFNFVIKSLTAI (SEQ ID NO: 891)<br>IKSLTAIFTVKF (SEQ ID NO: 548) |
| MS5 (Exc1-NO9) | RKERNIRKSESTLRL (SEQ ID NO: 892)<br>SESTLRLSPFPTPAP (SEQ ID NO: 893)<br>PFPTPAPSGAPAAAQ (SEQ ID NO: 894)<br>GAPAAAQGKVVRVPG (SEQ ID NO: 895)<br>KVVRVPGPAGGLVPR (SEQ ID NO: 896)<br>AGGLVPRDAGARLLP (SEQ ID NO: 897)<br>AGARLLPPAGGPGGG (SEQ ID NO: 898)<br>AGGPGGGAAAGEGRA (SEQ ID NO: 899)<br>AAGEGRAGRGRFPSI (SEQ ID NO: 900)<br>RGRFPSITEPRPRDL (SEQ ID NO: 901)<br>EPRPRDLPPRVATGR (SEQ ID NO: 902)<br>PRVATGRRAGGRRKG (SEQ ID NO: 903)<br>AGGRRKGAGQGVRTR (SEQ ID NO: 904)<br>GQGVRTRPLPASWPG (SEQ ID NO: 905) |

TABLE 29-continued

| Neoantigen ID (Alternative name) | Peptide sequences |
|---|---|
| | LPASWPGGRGPFRKG (SEQ ID NO: 906)<br>RGPFRKGPRRLPLGS (SEQ ID NO: 907)<br>RRLPLGSGPPAAGVQ (SEQ ID NO: 908)<br>PPAAGVQRLRCSHLS (SEQ ID NO: 909)<br>LRCSHLSRGPRRRRG (SEQ ID NO: 910)<br>GPRRRRGRVCGRACV (SEQ ID NO: 911)<br>VCGRACVSPPLPPRP (SEQ ID NO: 912)<br>PPLPPRPPPVGLSAE (SEQ ID NO: 913)<br>PVGLSAENLSWLSSG (SEQ ID NO: 914)<br>LSWLSSGLPRACSWR (SEQ ID NO: 915)<br>PRACSWREFSPETCA (SEQ ID NO: 916)<br>FSPETCAFRLSGLDS (SEQ ID NO: 917)<br>RLSGLDSKLSARVER (SEQ ID NO: 918)<br>LSARVERDLGALRAP (SEQ ID NO: 919)<br>LGALRAPGSRAAQGG (SEQ ID NO: 920)<br>SRAAQGGGRVRGSRS (SEQ ID NO: 921)<br>RVRGSRSEWKTRPWR (SEQ ID NO: 922)<br>WKTRPWRPPPAWPLT (SEQ ID NO: 923)<br>PPAWPLTRAGGPLPK (SEQ ID NO: 924)<br>AGGPLPKNPFLESCS (SEQ ID NO: 925)<br>PFLESCSETAQRRRV (SEQ ID NO: 926)<br>TAQRRRVFSFSTPLS (SEQ ID NO: 927) |
| MS7 (Exc1-NO11) | SINKATITGKKDLEL (SEQ ID NO: 928)<br>GKKDLELILHVSRKK (SEQ ID NO: 929)<br>LHVSRKKPFLPRVNI (SEQ ID NO: 930)<br>FLPRVNITPTPISCC (SEQ ID NO: 931)<br>PTPISCCNLKMLKKF (SEQ ID NO: 932)<br>LKMLKKFFLLYIIIS (SEQ ID NO: 933)<br>LLYIIISIIDLTNCL (SEQ ID NO: 934)<br>IDLTNCLSCYLEHFY (SEQ ID NO: 935)<br>CYLEHFYRFTFFTDV (SEQ ID NO: 936)<br>FTFFTDVHYF (SEQ ID NO: 937) |
| MS9 (Exc1-NO13) | PYYSALSGNSWVPST (SEQ ID NO: 938)<br>NSWVPSTLESDPFGY (SEQ ID NO: 939)<br>ESDPFGYVFSPLATR (SEQ ID NO: 940)<br>FSPLATRPALNDQES (SEQ ID NO: 941)<br>ALNDQESILWPTLTS (SEQ ID NO: 942)<br>LWPTLTSVVSCALSC (SEQ ID NO: 943)<br>VSCALSCPSLNLPEN (SEQ ID NO: 944)<br>SLNLPENWLTLITGG (SEQ ID NO: 945)<br>LTLITGGMKGGKKMK (SEQ ID NO: 946)<br>KGGKKMKFTFRH (SEQ ID NO: 947) |
| MS10 (Exc1-NO14) | GLRNLGNTVRAILLS (SEQ ID NO: 948)<br>VRAILLSFLSKRNVK (SEQ ID NO: 949)<br>LSKRNVKWCWGWGKP (SEQ ID NO: 950)<br>CWGWGKPTSLGKACG (SEQ ID NO: 951)<br>SLGKACGRRALKLF (SEQ ID NO: 952) |
| MS11 (Exc1-NO15) | MEAENAGSLHFHEVL (SEQ ID NO: 953)<br>LHFHEVLKMGHVKF (SEQ ID NO: 954) |
| P97 (Misc1-NO11) | GYLRMQGLMAQRLLLR (SEQ ID NO: 383) |
| P19 (Misc1-NO8) | WTPIPVLTRWPLPHP (SEQ ID NO: 955)<br>RWPLPHPPPWRRATS (SEQ ID NO: 956)<br>PWRRATSCRMARSSP (SEQ ID NO: 957)<br>RMARSSPSATSGSSV (SEQ ID NO: 958)<br>ATSGSSVRRRCSSLP (SEQ ID NO: 959)<br>RRCSSLPSWVWNLAA (SEQ ID NO: 960)<br>WVWNLAASTRPRSTPS (SEQ ID NO: 961) |
| P27 (Misc1-NO9) | LHPQRETFTPRWSGA (SEQ ID NO: 962)<br>TPRWSGANYWKLAFP (SEQ ID NO: 963)<br>YWKLAFPVGAEGTFP (SEQ ID NO: 964)<br>GAEGTFPAAATQRGV (SEQ ID NO: 965)<br>AATQRGVVRPA (SEQ ID NO: 966) |
| P37 (Misc1-NO10) | MAGGVLRRLLCREPD (SEQ ID NO: 967)<br>LLCREPDRDGDKGAS (SEQ ID NO: 968)<br>DGDKGASREETVVPL (SEQ ID NO: 969)<br>EETVVPLHIGDPVVL (SEQ ID NO: 970)<br>IGDPVVLPGIGQCYS (SEQ ID NO: 971)<br>GIGQCYSALF (SEQ ID NO: 972) |

TABLE 29-continued

| Neoantigen ID (Alternative name) | Peptide sequences |
|---|---|
| P76, P77 (Misc2-NO18) | VFFKRAAEGFFRMNK (SEQ ID NO: 973) |
| | GFFRMNKLKESSDTN (SEQ ID NO: 974) |
| | KESSDTNPKPYCMAA (SEQ ID NO: 975) |
| | KPYCMAAPMGLTENN (SEQ ID NO: 976) |
| | MGLTENNRNRKKSYR (SEQ ID NO: 977) |
| | NRKKSYRETNLKAVS (SEQ ID NO: 978) |
| | TNLKAVSWPLNHT (SEQ ID NO: 979) |

We claim:

1. A vaccine comprising a heterologous polynucleotide encoding a heterologous polypeptide, wherein the heterologous polypeptide comprises the amino acid sequence of SEQ ID NOs: 541, 543, 550, 554, 555, 556, 623, 624, 552, 557, 558, 559, 625, or 626.

2. The vaccine of claim 1, wherein the vaccine is capable of eliciting a cellular immune response in a subject administered the vaccine.

3. The vaccine of claim 2, wherein the cellular immune response is activation of vaccine-specific $CD8^+$ T cells, $CD4^+$ T cells, or $CD8^+$ T cells and $CD4^+$ T cells, wherein activation is assessed by increased production of TNFα, IFNγ, or TNFα and IFNγ by the $CD8^+$ T cells, the $CD4^+$ T cells, or the $CD8^+$ T cells and $CD4^+$ T cells.

4. The vaccine of claim 1, wherein the heterologous polynucleotide comprises a promoter, an enhancer, a polyadenylation site, a Kozak sequence, a stop codon, a T cell enhancer (TCE), or any combination thereof.

5. The vaccine of claim 4, wherein the promoter comprises a CMV promoter or a vaccinia P7.5 promoter.

6. The vaccine of claim 5, wherein the TCE is encoded by a polynucleotide of SEQ ID NO: 546, the CMV promoter comprises a polynucleotide of SEQ ID NO: 628, the vaccinia P7.5 promoter comprises a polynucleotide of SEQ ID NO: 630 and the polyadenylation site comprises a bovine growth hormone polyadenylation site of SEQ ID NO: 629.

7. The vaccine of claim 1, wherein the heterologous polynucleotide comprises the polynucleotide sequence of SEQ ID NO: 542, SEQ ID NO: 544, SEQ ID NO: 551, or SEQ ID NO: 553.

8. The vaccine of claim 1, wherein the heterologous polynucleotide is DNA or RNA.

9. The vaccine of claim 8, wherein RNA is mRNA or self-replicating RNA.

10. The vaccine of claim 7, wherein the heterologous polynucleotide is DNA or RNA.

11. The vaccine of claim 10, wherein RNA is mRNA or self-replicating RNA.

12. The vaccine of claim 1, wherein the vaccine is a recombinant virus.

13. The vaccine of claim 12, wherein the recombinant virus is derived from adenovirus (Ad), poxvirus, adeno-associated virus (AAV) or retrovirus.

14. The vaccine of claim 13, wherein the recombinant virus is derived from hAd5, hAd7, hAd11, hAd26, hAd34, hAd35, hAd48, hAd49, hAd50, GAd20, GAd19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAdl, PanAd2, PanAd3, Copenhagen vaccinia virus (W), New York Attenuated Vaccinia Virus (NYVAC), ALVAC, TROVAC, or modified vaccinia ankara (MVA).

15. The vaccine of claim 14, wherein the recombinant virus is derived from GAd20.

16. The vaccine of claim 14, wherein the recombinant virus is derived from MVA.

17. The vaccine of claim 14, wherein the recombinant virus is derived from hAd26.

18. A vaccine comprising a heterologous polynucleotide encoding a heterologous polypeptide, wherein the heterologous polypeptide comprises the amino acid sequence of SEQ ID NOs: 541, 550, 554, 555, 556, 623, or 624.

19. The vaccine of claim 18, wherein the heterologous polynucleotide comprises the polynucleotide sequence of SEQ ID NOs: 542 or 551.

20. The vaccine of claim 18, wherein the vaccine is a recombinant virus derived from GAd20.

21. A vaccine comprising a heterologous polynucleotide encoding a heterologous polypeptide, wherein the heterologous polypeptide comprises the amino acid sequence of SEQ ID NOs: 543, 552, 557, 558, 559, 625, or 626.

22. The vaccine of claim 21, wherein the heterologous polynucleotide comprises the polynucleotide sequence of SEQ ID NO: 544 or 553.

23. The vaccine of claim 21, wherein the vaccine is a recombinant virus derived from MVA.

24. The vaccine of claim 18, wherein the heterologous polypeptide comprises the amino acid sequence of SEQ ID NO: 541.

25. The vaccine of claim 24, wherein the vaccine is self-replicating RNA or a recombinant virus derived from GAd20, MVA, or hAd26.

26. The vaccine of claim 25, wherein the vaccine is a recombinant virus derived from GAd20.

27. The vaccine of claim 21, wherein the heterologous polypeptide comprises the amino acid sequence of SEQ ID NO: 543.

28. The vaccine of claim 27, wherein the vaccine is self-replicating RNA or a recombinant virus derived from GAd20, MVA, or hAd26.

29. The vaccine of claim 28, wherein the vaccine is a recombinant virus derived from MVA.

* * * * *